US012799113B2

(12) United States Patent
Armstrong et al.

(10) Patent No.: US 12,799,113 B2
(45) Date of Patent: Nov. 17, 2026

21
(54) PRMT5 INHIBITORS AND USES THEREOF

(71) Applicant: Gilead Sciences, Inc., Foster City, CA (US)

(72) Inventors: Megan K. Armstrong, San Francisco, CA (US); Elbert Chin, San Mateo, CA (US); Chienhung Chou, Dublin, CA (US); Laurent P. Debien, San Francisco, CA (US); Joshua D. Farr, Mountain View, CA (US); Pancham Lal Gupta, Foster City, CA (US); Chao-I Hung, San Mateo, CA (US); Michael L. Mitchell, Castro Valley, CA (US); Prasenjit K. Mukherjee, South San Francisco, CA (US); Shaina V. Nguyen, Yorba Linda, CA (US); Gregory T. Notte, Redwood City, CA (US); Daniel Roa, Foster City, CA (US); Adam J. Schrier, Redwood City, CA (US); Zheng-Yu Yang, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 396 days.

(21) Appl. No.: 18/391,258

(22) Filed: Dec. 20, 2023

(65) Prior Publication Data

US 2024/0254118 A1 Aug. 1, 2024

Related U.S. Application Data

(60) Provisional application No. 63/518,001, filed on Aug. 7, 2023, provisional application No. 63/476,905, filed on Dec. 22, 2022.

(51) Int. Cl.

| | |
|---|---|
| ***C07D 471/04*** | (2006.01) |
| ***A61K 31/473*** | (2006.01) |
| ***A61K 31/4741*** | (2006.01) |
| ***A61K 31/4743*** | (2006.01) |
| ***A61K 31/4745*** | (2006.01) |
| ***A61K 31/4748*** | (2006.01) |
| ***A61K 31/496*** | (2006.01) |
| ***A61K 31/501*** | (2006.01) |
| ***A61K 31/506*** | (2006.01) |
| ***A61K 31/5355*** | (2006.01) |
| ***A61K 31/5377*** | (2006.01) |
| ***A61K 31/5386*** | (2006.01) |
| ***A61K 31/541*** | (2006.01) |
| ***A61K 31/55*** | (2006.01) |
| ***C07D 401/12*** | (2006.01) |
| ***C07D 491/048*** | (2006.01) |
| ***C07D 513/04*** | (2006.01) |
| ***C07D 519/00*** | (2006.01) |

(52) U.S. Cl.

CPC .......... *C07D 471/04* (2013.01); *A61K 31/473* (2013.01); *A61K 31/4741* (2013.01); *A61K 31/4743* (2013.01); *A61K 31/4745* (2013.01); *A61K 31/4748* (2013.01); *A61K 31/496* (2013.01); *A61K 31/501* (2013.01); *A61K 31/506* (2013.01); *A61K 31/5355* (2013.01); *A61K 31/5377* (2013.01); *A61K 31/5386* (2013.01); *A61K 31/541* (2013.01); *A61K 31/55* (2013.01); *C07D 401/12* (2013.01); *C07D 491/048* (2013.01); *C07D 513/04* (2013.01); *C07D 519/00* (2013.01)

(58) Field of Classification Search

CPC ........................... C07D 471/04; C07D 401/12; C07D 491/048; C07D 513/04; C07D 519/00; A61K 31/55; A61K 31/541; A61K 31/473; A61K 31/4741; A61K 31/4743; A61K 31/4745; A61K 31/4748; A61K 31/496; A61K 31/501; A61K 31/506; A61K 31/5377; A61K 31/5386

See application file for complete search history.

(56) References Cited

U.S. PATENT DOCUMENTS

| | | | |
|---|---|---|---|
| 2024/0376110 A1 | 11/2024 | Armstrong et al. | |
| 2025/0154172 A1 | 5/2025 | Armstrong et al. | |
| 2025/0376484 A1 | 12/2025 | Debien et al. | |
| 2025/0388585 A1 | 12/2025 | Armstrong et al. | |

FOREIGN PATENT DOCUMENTS

| | | |
|---|---|---|
| CN | 116178347 A | 5/2023 |
| CN | 116462676 A | 7/2023 |
| CN | 116462677 A | 7/2023 |
| CN | 116854668 A | 10/2023 |
| CN | 117924277 A | 4/2024 |
| CN | 117986248 A | 5/2024 |
| CN | 117986262 A | 5/2024 |

(Continued)

OTHER PUBLICATIONS

Intl. Search Report-Written Opinion dated Apr. 26, 2024 for Intl. Appl. No. PCT/US2023/085207.

*Primary Examiner* — Erich A Leeser

(57) ABSTRACT

The present disclosure relates generally to compounds that inhibit PRMT5. The disclosure further relates to the use of the compounds for the preparation of a medicament for the treatment of diseases and/or conditions through inhibiting PRMT5. The disclosure further relates to the use of the compounds for the treatment of a disease or condition associated with chromosome 9p21 deletion or MTAP null. The disclosure further relates to the use of the compounds for the treatment of cancers.

17 Claims, No Drawings

(56) References Cited

FOREIGN PATENT DOCUMENTS

CN 118047776 A 5/2024
CN 118103373 A 5/2024
CN 118221579 A 6/2024
CN 118221682 A 6/2024
CN 118359603 A 7/2024
CN 118359604 A 7/2024
CN 118359617 A 7/2024
CN 118580225 A 9/2024
CN 118619959 A 9/2024
CN 118772164 A 10/2024
CN 118908939 A 11/2024
CN 118930582 A 11/2024
CN 119060035 A 12/2024
CN 119143752 A 12/2024
CN 119176814 A 12/2024
CN 119219608 A 12/2024
CN 119306742 A 1/2025
CN 119431378 A 2/2025
CN 119462695 A 2/2025
CN 119490500 A 2/2025
CN 119504710 A 2/2025
CN 119552151 A 3/2025
CN 119552167 A 3/2025
CN 119552175 A 3/2025
CN 119661432 A 3/2025
CN 119661516 A 3/2025
CN 119684280 A 3/2025
CN 119707931 A 3/2025
CN 119751486 A 4/2025
CN 119823103 A 4/2025
CN 119823149 A 4/2025
CN 119859155 A 4/2025
CN 119977947 A 5/2025
WO WO-2021050915 A1 3/2021
WO WO-2021086879 A1 5/2021
WO WO-2021163344 A1 8/2021
WO WO-2022115377 A1 6/2022
WO WO-2022132914 A1 6/2022
WO WO-2022169948 A1 8/2022
WO WO-2022192745 A1 9/2022
WO WO-2023025540 A1 3/2023
WO WO-2023036974 A1 3/2023
WO WO-2023046873 A1 3/2023
WO WO-2023081367 A2 5/2023
WO WO-2023098439 A1 6/2023
WO WO-2023125540 A1 7/2023
WO WO-2023143210 A1 8/2023
WO WO-2023146987 A1 8/2023
WO WO-2023146989 A1 8/2023
WO WO-2023146991 A1 8/2023
WO WO-2023174250 A1 9/2023
WO WO-2023202626 A1 10/2023
WO WO-2023207556 A1 11/2023
WO WO-2023246873 A1 12/2023
WO WO 2024/012308 * 1/2024 ........... C07D 471/04
WO WO-2024002263 A1 1/2024
WO WO-2024002376 A1 1/2024
WO WO-2024002377 A1 1/2024
WO WO-2024008113 A1 1/2024
WO WO-2024008176 A1 1/2024
WO WO-2024012308 A1 1/2024
WO WO-2024021957 A1 2/2024
WO WO-2024027370 A1 2/2024
WO WO-2024027703 A1 2/2024
WO WO-2024032572 A1 2/2024
WO WO-2024037459 A1 2/2024
WO WO-2024037607 A1 2/2024
WO WO-2024037608 A1 2/2024
WO WO-2024038004 A1 2/2024
WO WO-2024051816 A1 3/2024
WO WO-2024067433 A1 4/2024
WO WO-2024067445 A1 4/2024
WO WO-2024123740 A1 6/2024
WO WO-2024131901 A1 6/2024
WO WO-2024140923 A1 7/2024
WO WO-2024153128 A1 7/2024
WO WO-2024174980 A1 8/2024
WO WO-2024177416 A1 8/2024
WO WO-2024182466 A1 9/2024
WO WO-2024188999 A1 9/2024
WO WO-2024199255 A1 10/2024
WO WO-2024213044 A1 10/2024
WO WO-2024220917 A1 10/2024
WO WO-2024222660 A1 10/2024
WO WO-2024222914 A2 10/2024
WO WO-2024234821 A1 11/2024
WO WO-2024238628 A1 11/2024
WO WO-2024240894 A1 11/2024
WO WO-2024245412 A1 12/2024
WO WO-2024249763 A2 12/2024
WO WO-2024249931 A1 12/2024
WO WO-2024255863 A1 12/2024
WO WO-2025011574 A1 1/2025
WO WO-2025016323 A1 1/2025
WO WO-2025026381 A1 2/2025
WO WO-2025031468 A1 2/2025
WO WO-2025034640 A1 2/2025
WO WO-2025036472 A1 2/2025
WO WO-2025039979 A1 2/2025
WO WO-2025051157 A1 3/2025
WO WO-2025061102 A1 3/2025
WO WO-2025064286 A1 3/2025
WO WO-2025068985 A1 4/2025
WO WO-2025076500 A1 4/2025
WO WO-2025077856 A1 4/2025
WO WO-2025077857 A1 4/2025
WO WO-2025092818 A1 5/2025
WO WO-2025098450 A1 5/2025
WO WO-2025113499 A1 6/2025
WO WO-2025113703 A1 6/2025
WO WO-2025119326 A1 6/2025
WO WO-2025149009 A1 7/2025
WO WO-2025149020 A1 7/2025
WO WO-2025157284 A1 7/2025
WO WO-2025157286 A1 7/2025
WO WO-2025157287 A1 7/2025
WO WO-2025157288 A1 7/2025
WO WO-2025157289 A1 7/2025
WO WO-2025166215 A1 8/2025
WO WO-2025166229 A1 8/2025
WO WO-2025166257 A1 8/2025
WO WO-2025166260 A1 8/2025
WO WO-2025166274 A1 8/2025

* cited by examiner

PRMT5 INHIBITORS AND USES THEREOF

CROSS REFERENCE TO RELATED APPLICATIONS

This application claims priority to U.S. Provisional Application No. 63/476,905, filed Dec. 22, 2022, and U.S. Provisional Application No. 63/518,001, filed Aug. 7, 2023, both of which are incorporated herein in their entireties for all purposes.

FIELD

The present disclosure relates to compounds that inhibit PRMT5. The disclosure further relates to the use of the compounds for the treatment and/or prophylaxis of diseases and/or conditions responsive to PRMT5 inhibition.

BACKGROUND

Protein arginine methyltransferase (PRMT) enzymes catalyze methylation of arginine residues on proteins involved in chromatin organization, gene expression, RNA splicing, protein translation, and signal transduction. Diverse substrates for PRMTs localize to various subcellular compartments including nucleus, nucleolus, cytosol and enable many biological processes critical to mammalian cell function and survival.

Among the nine members of the PRMT family, PRMT5 is responsible for generating the majority of symmetric dimethyl arginines on protein substrates. Methylation by PRMT5 is distributive, implying that PRMT5 produces and releases mono-methyl arginines before the second methylation event. PRMT5 functions as a homo-tetramer in complex with a homo-tetramer of MEP50/WDR77 protein. MEP50/WDR77 is indispensable for PRMT5 enzymatic activity, substrate recognition and interaction with numerous binding partners (S. Antonysamy, et al. PNAS 109, 2012).

PRMT5 expression is frequently upregulated in leukemia, lymphoma, and solid tumors and its expression may inversely correlate with patient survival. (Greenblatt, et al. Exp. Hematol. 2016, Chen, H., et al. Oncogene 2016, Lattouf, et al. Oncotarget, 2019). In normal tissues, PRMT5 is required for hematopoiesis and potentiates both hematopoietic stem cell pluripotency and progenitor expansion, suggesting that its inhibition could have myelosuppressive effects (Liu et al. J. Clin. Invest., 2015).

During past few years, several PRMT5 inhibitors have entered clinical trials with the goal of treating tumors addicted to PRMT5 activity and/or particularly sensitive to PRMT5 inhibition. A narrow therapeutic window and myelosuppression were consistently observed in patients enrolled in these trials, suggesting that inhibition of PRMT5 in normal tissues was undesirable. The inhibition of PRMT5 activity in tumors, while sparing normal cells, can presumably mitigate adverse effects of these first generation PRMT5 inhibitors.

Human cancers frequently acquire homozygous deletion of chromosome 9p21 locus carrying tumor suppressor CDKN2A (cyclin dependent kinase inhibitor 2A). MTAP (methylthioadenosine phosphorylase) gene, located in close proximity to CDKN2A, co-deleted in 90% of tumors with CDKN2A loss. It is estimated that 10-15% of all cancers carry homozygous deletion of the MTAP gene. Pancreatic, bladder, NSCLC, head and neck, esophageal cancer, and glioblastoma are among cancers having a significant portion of patients with MTAP loss.

MTAP loss/null/deletion leads to accumulation of its substrate methylthioadenosine (MTA), which is structurally similar to SAM (S-adenosyl-L-methionine) utilized by PRMT5 as a methyl donating cofactor for catalyzing arginine di-methylation. MTA accumulating in MTAP-deleted cancer cells competes with SAM for binding to the catalytic site of PRMT5 and partially suppresses its enzymatic activity. Tumor cells growing under the pressure of reduced PRMT5 activity become especially vulnerable to further PRMT5 loss, such as knockdown with shRNA or siRNA.

Accumulation of PRMT5-MTA complexes in MTAP deleted cancer can be exploited therapeutically. It is attractive to design MTA-cooperative small molecule inhibitors of PRMT5, which would selectively elicit their inhibitory effects in cancer cells with elevated MTA levels and accumulation of MTA-bound PRMT5.

A need remains for PRMT5 inhibitors with desirable selectivity, potency, metabolic stability, or reduced detrimental effects.

SUMMARY

The present disclosure provides compounds useful as PRMT5 inhibitors. The disclosure further relates to the use of the compounds for the treatment and/or prophylaxis of diseases and/or conditions through inhibiting PRMT5 by said compounds. The disclosure further relates to the use of the compounds for the treatment and/or prophylaxis of diseases and/or conditions through inhibiting PRMT5 in tumors associated with MTAP null or chromosome 9p21 deletion by said compounds.

In one embodiment, provided herein is a compound of Formula (I), (I)

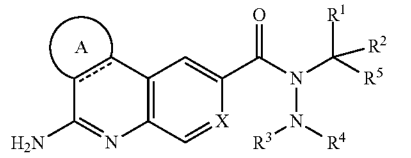

or a pharmaceutically acceptable salt thereof, wherein

--- is a single or double bond;

ring A is $C_{5-7}$ cycloalkyl, phenyl, 5 to 7 membered heterocyclyl, or 5 or 6 membered heteroaryl; the cycloalkyl, phenyl, heterocyclyl, or heteroaryl of ring A is optionally substituted with one to four $R^6$, which may be the same or different;

X is N or $CR^7$;

$R^1$ is H, $C_{1-6}$ alkyl, $C_{1-6}$ haloalkyl, $C_{6-10}$ aryl, $C_{3-10}$ cycloalkyl, 3 to 10 membered heterocyclyl, or 5 to 10 membered heteroaryl; wherein the alkyl, haloalkyl, aryl, cycloalkyl, heterocyclyl, or heteroaryl of $R^1$ is each optionally substituted with one to four $Z^1$, which may be the same or different;

$R^2$ is H, —CN, $C_{1-5}$ alkyl, $C_{1-5}$ haloalkyl, $C_{2-6}$ alkynyl, cyclopropyl, cyclobutyl, or oxetanyl; wherein the alkyl, haloalkyl, alkoxyalkyl, alkynyl, cyclopropyl, or cyclobutyl of $R^2$ is each optionally substituted with one to four $Z^2$, which may be the same or different; each $Z^2$ is independently $C_{2-6}$ alkynyl, halo, —CN, —$OR^{2a}$, cyclopropyl, cyclobutyl, or oxetanyl; $R^{2a}$ is H, $C_{1-3}$ haloalkyl, $C_{3-6}$ cycloalkyl, or $C_{1-3}$ alkyl;

$R^5$ is H, $C_{1-3}$ alkyl, or $C_{1-3}$ haloalkyl;

or $R^1$ and $R^2$ together with the carbon to which they are attached form $C_{3-10}$ cycloalkyl, 3 to 10 membered heterocyclyl; the cycloalkyl or heterocyclyl formed from $R^1$ and $R^2$ is optionally substituted with one to four $Z^5$, which may be the same or different;

or $R^2$ and $R^5$ together with the carbon to which they are attached form cyclopropyl, cyclobutyl, or oxetanyl; the cyclopropyl, or cyclobutyl formed from $R^2$ and $R^5$ is optionally substituted with one to four halo;

$R^3$ is H, $C_{1-6}$ alkyl, $C_{1-6}$ haloalkyl, —$COR^{3a}$, —$COOR^{3a}$, —$CONR^{3a}R^{3b}$, —$SO_2R^{3a}$, —$SO_2NR^{3a}R^{3b}$, $C_{6-10}$ aryl, $C_{3-10}$ cycloalkyl, 3 to 10 membered heterocyclyl, or 5 to 10 membered heteroaryl; wherein the alkyl, aryl, cycloalkyl, heterocyclyl, or heteroaryl of $R^3$ is each optionally substituted with one to four $Z^3$, which may be the same or different, $R^4$ is H, $C_{1-6}$ alkyl, $C_{1-6}$ haloalkyl, $C_{6-10}$ aryl, $C_{3-10}$ cycloalkyl, 3 to 10 membered heterocyclyl, or 5 to 10 membered heteroaryl; wherein the alkyl, aryl, cycloalkyl, heterocyclyl, or heteroaryl of $R^4$ is each optionally substituted with one to four $Z^4$, which may be the same or different, or $R^3$ and $R^4$ together with the nitrogen to which they are attached form a 3 to 10 membered heterocyclyl, or 5 to 10 membered heteroaryl; wherein the heterocyclyl or heteroaryl formed from $R^3$ and $R^4$ is optionally substituted with one to four $Z^9$, which may be the same or different, wherein the heterocyclyl formed from $R^3$ and $R^4$ is a heterocyclyl having 0 to 3 additional heteroatoms each independently N, O, or S, wherein the heteroaryl formed from $R^3$ and $R^4$ is a heteroaryl having 0 to 3 additional heteroatoms each independently N, O, or S, or $R^2$ and $R^4$ together with the atoms to which they are attached form a 5 to 10 membered heterocyclyl; wherein the heterocyclyl formed from $R^2$ and $R^4$ is optionally substituted with one to four $Z^8$, which may be the same or different;

each $R^6$ is independently halo, —OH, —$OCH_3$, oxo, —CN, $C_{1-3}$ alkyl, $C_{1-3}$ haloalkyl, or cyclopropyl;

$R^7$ is H, halo, CN, halomethyl, —$CH_3$, or —$OCH_3$;

each $Z^1$, $Z^3$, $Z^4$, $Z^5$, $Z^8$, or $Z^9$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, 3 to 10 membered heterocyclyl, $C_{6-10}$ aryl, 5 to 10 membered heteroaryl, oxo, —$NO_2$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12a}$)$_2$ ($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —$NR^{12a}$S(O)$_2$N($R^{12b}$)($R^{12c}$), —$NR^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2R^{12a}$, —S(O)$_2$N($R^{12a}$)($R^{12b}$), —S(O)(N$R^{12a}$)$R^{12b}$, or —Si($R^{12a}$)$_3$; wherein the alkyl, haloalkyl, alkenyl, alkynyl, cycloalkyl, heterocyclyl, aryl, or heteroaryl of each $Z^1$, $Z^3$, $Z^4$, $Z^5$, $Z^8$, or $Z^9$ is each optionally substituted with one to four $Z^{1a}$, which may be the same or different;

each $Z^{1a}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, 3 to 10 membered heterocyclyl, $C_{6-10}$ aryl, 5 to 10 membered heteroaryl, oxo, —$NO_2$, —CN, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$)$^+$, —N($R^{12a}$)—C(O)$R^{12b}$, —N($R^{12a}$)C(O)O($R^{12b}$), —N($R^{12a}$)C(O)N($R^{12b}$)($R^{12c}$), —N($R^{12a}$)S(O)$_2$($R^{12b}$), —N($R^{12a}$)S(O)$_2$—N($R^{12b}$)($R^{12c}$), —N($R^{12a}$)S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$ $R^{12a}$, —S(O)$_2$N($R^{12a}$)($R^{12b}$), —S(O)(N$R^{12a}$)$R^{12b}$, or —Si($R^{12a}$)$_3$; wherein the alkyl, haloalkyl, alkenyl, alkynyl, cycloalkyl, heterocyclyl, aryl, or heteroaryl of $Z^{1a}$ is each optionally substituted with one to four $Z^{1b}$, which may be the same or different;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$; wherein the alkyl, cycloalkyl, heterocyclyl, aryl, or heteroaryl of $Z^{1b}$ is optionally substituted with one to three $C_{1-9}$ alkyl, $C_{1-8}$ haloalkyl, halogen, —OH, —$NH_2$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH (aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O) ($C_{3-15}$ cycloalkyl), —NHC(O)(heterocyclyl), —NHC (O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O (heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$, wherein the heteroaryl of $Z^{1b}$ is 5 to 10 membered heteroaryl, the heterocyclyl of $Z^{1b}$ is 3 to 10 membered heterocyclyl; and each $R^{3a}$, $R^{3b}$, $R^{12a}$, $R^{12b}$, or $R^{12c}$ is independently H, $C_{1-6}$ alkyl, $C_{3-10}$ cycloalkyl, 3 to 10 membered heterocyclyl, $C_{6-10}$ aryl, or 5 to 10 heteroaryl, wherein the alkyl, cycloalkyl, heterocyclyl, aryl, or heteroaryl of each $R^{3a}$, $R^{3b}$, $R^{12a}$, $R^{12b}$, or $R^{12c}$ is each optionally substituted with one to four $Z^{1b}$, which may be the same or different;

wherein each heteroaryl or heterocyclyl of the compound of Formula (I) unless otherwise specified has one to three heteroatoms each independently N, O, or S.

In some embodiments, provided herein are pharmaceutical compositions comprising a compound provided herein, or pharmaceutically acceptable salt thereof, and a pharmaceutically acceptable excipient or carrier. In some embodiments, the pharmaceutical compositions comprise a therapeutically effective amount of a compound provided herein, or pharmaceutically acceptable salt thereof, and a pharmaceutically acceptable excipient or carrier.

In some embodiments, the pharmaceutical compositions provided herein further comprise one or more (e.g., one, two, three, four, one or two, one to three, or one to four) additional therapeutic agents, or pharmaceutically acceptable salts thereof. In some embodiments, the pharmaceutical compositions further comprise a therapeutically effective amount of the one or more (e.g., one, two, three, four, one or two, one to three, or one to four) additional therapeutic agents, or pharmaceutically acceptable salts thereof.

In some embodiments, the present disclosure provides methods of inhibiting PRMT5 in a subject in need thereof, comprising administering to the subject a therapeutically effective amount of a compound provided herein (e.g., a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13)), or pharmaceutically acceptable salt thereof, or a pharmaceutical composition provided herein.

In some embodiments, the present disclosure provides methods of treating a patient having a condition associated with chromosome 9p21 deletion or MTAP-null, comprising administering to the patient a therapeutically effective amount of a compound provided herein (e.g., a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13)), or pharmaceutically acceptable salt thereof, or a pharmaceutical composition provided herein.

DETAILED DESCRIPTION

The present disclosure relates to inhibitors of PRMT5. The disclosure also relates to compositions and methods relating to PRMT5 inhibitors and the use of such compounds for treatment and/or prophylaxis of diseases and conditions. The disclosure also relates to compositions and methods of treating and/or preventing cancer or viral infections that include a PRMT5 inhibitor in combination with one or more additional therapeutic agents.

Definitions and General Parameters

The description below is made with the understanding that the present disclosure is to be considered as an exemplification of the claimed subject matter and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

As used in the present specification, the following terms and phrases are generally intended to have the meanings as set forth below, except to the extent that the context in which they are used indicates otherwise.

A dash ("-") that is not between two letters or symbols is used to indicate a point of attachment for a substituent. For example, —$CONH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named. A solid line coming out of the center of a ring indicates that the point of attachment for a substituent on the ring can be at any ring atom. For example, $R^a$ in the below structure can be attached to any of the five carbon ring atoms or $R^a$ can replace the hydrogen attached to the nitrogen ring atom:

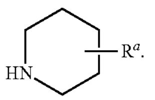

The prefix "$C_{u-v}$" indicates that the following group has from u to v carbon atoms. For example, "$C_{1-6}$ alkyl" indicates that the alkyl group has from 1 to 6 carbon atoms. Likewise, the term "x-y membered" rings, wherein x and y are numerical ranges, such as "3 to 12-membered heterocyclyl", refers to a ring containing x-y atoms (e.g., 3-12), of which up to 80% may be heteroatoms, such as N, O, S, P, and the remaining atoms are carbon.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"A compound disclosed herein" or "a compound of the present disclosure" or "a compound provided herein" or "a compound described herein" refers to the compounds of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13). Also included are the specific compounds of Examples 1 to 52 provided herein.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), 1 to 4 carbon atoms (i.e., $C_{1-4}$ alkyl), or 1 to 3 carbon atoms (i.e., $C_{1-3}$ alkyl). Examples of alkyl groups include methyl, ethyl, n-propyl, isopropyl, n-butyl, sec-butyl, iso-butyl, tert-butyl, n-pentyl, 2-pentyl, isopentyl, neopentyl, n-hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., $-(CH_2)_3CH_3$), sec-butyl (i.e., $-CH(CH_3)CH_2CH_3$), isobutyl (i.e., $-CH_2CH(CH_3)_2$) and tert-butyl (i.e., $-C(CH_3)_3$); and "propyl" includes n-propyl (i.e., $-(CH_2)_2CH_3$) and isopropyl (i.e., $-CH(CH_3)_2$).

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Acyl" refers to a group $-C(=O)R$, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Alkoxy" refers to an alkyl group having an oxygen atom that connects the alkyl group to the point of attachment: alkyl-O—. As for alkyl group, alkoxy groups will have any suitable number of carbon atoms, such as $C_{1-6}$. Alkoxy groups include, for example, methoxy, ethoxy, propoxy, iso-propoxy, butoxy, 2-butoxy, iso-butoxy, see-butoxy, tert-butoxy, pentoxy, hexoxy, etc. The alkoxy groups can be further substituted with a variety of substituents described within. Alkoxy groups can be substituted or unsubstituted.

"Alkoxyalkyl" refers an alkoxy group linked to an alkyl group which is linked to the remainder of the compound. Alkoxyalkyl have any suitable number of carbon, such as from 2 to 6 ($C_{2-6}$ alkoxyalkyl), 2 to 5 ($C_{2-5}$ alkoxyalkyl), 2 to 4 ($C_{2-4}$ alkoxyalkyl), or 2 to 3 ($C_{2-3}$ alkoxyalkyl). The number of carbons refers to the total number of carbons in the alkoxy and the alkyl group. For example, in some embodiments, $C_6$ alkoxyalkyl refers to ethoxy ($C_2$ alkoxy) linked to a butyl ($C_4$ alkyl), and in other embodiments, n-propoxy ($C_3$ alkoxy) linked to isopropyl ($C_3$ alkyl). Alkoxy and alkyl are as defined above where the alkyl is divalent, and can include, but is not limited to, methoxymethyl ($CH_3OCH_2-$), methoxyethyl ($CH_3OCH_2CH_2-$) and others.

"Amino" refers to the group $-NR^yR^z$ wherein $R^y$ and $R^z$ are independently selected from the group consisting of hydrogen, alkyl, haloalkyl, aryl, heteroaryl, cycloalkyl, or heterocyclyl; each of which may be optionally substituted.

"Aryl" as used herein refers to a single all carbon aromatic ring or a multicyclic all carbon ring system wherein at least one of the rings is aromatic. For example, in some embodiments, an aryl group has 6 to 20 carbon atoms, 6 to 14 carbon atoms, or 6 to 12 carbon atoms. Aryl includes a phenyl radical. Aryl also includes multicyclic ring systems (e.g., ring systems comprising 2, 3 or 4 rings) having 9 to 20 carbon atoms, e.g., 9 to 16 carbon atoms, in which at least one ring is aromatic and wherein the other rings may be aromatic or not aromatic (i.e., carbocycle). Such multicyclic ring systems are optionally substituted with one or more (e.g., 1, 2 or 3) oxo groups on any carbocycle portion of the multicyclic ring system. The rings of the multicyclic ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1,2,3,4-tetrahydronaphthyl. Non-limiting examples of aryl groups include, but are not limited to, phenyl, indenyl, naphthyl, 1,2,3,4-tetrahydronaphthyl, anthracenyl, and the like.

"Cyano" or "carbonitrile" refers to the group $-CN$.

"Cycloalkyl" refers to a saturated or partially saturated cyclic alkyl group having a single ring or multiple rings including fused, bridged, and spiro ring systems. The term "cycloalkyl" includes cycloalkenyl groups (i.e., the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Fused" refers to a ring which is bound to an adjacent ring. In some embodiments the fused ring system is a heterocyclyl. In some embodiments the fused ring system is a oxabicyclohexanyl. In some embodiments, the fused ring system is

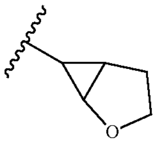 or 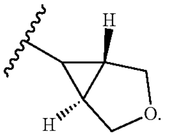

"Bridged" refers to a ring fusion wherein non-adjacent atoms on a ring are joined by a divalent substituent, such as alkylenyl group, an alkylenyl group containing one or two heteroatoms, or a single heteroatom. Quinuclidinyl and admantanyl are examples of bridged ring systems. In some embodiments the bridged ring is a bicyclopentyl (e.g., bicyclo[1.1.1]pentyl), bicycloheptyl (e.g., bicyclo[2.2.1] heptyl, bicyclo[3.1.1]heptyl), or bicyclooctyl (e.g., bicyclo [2.2.2]octyl). In some embodiments, the bridged ring

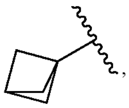, 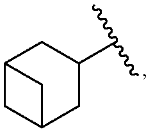, 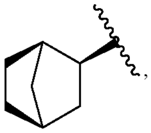,

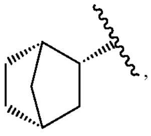, or 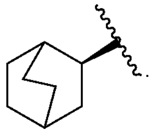.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents. In some embodiments the spiro substituent is a spiropentanyl (spiro [a.b]pentanyl), spirohexanyl, spiroheptanyl, spirooctyl (e.g., spiro[2.5]octyl), spirononanyl (e.g., spiro[3.5]nonanyl), spirodecanyl (e.g., spiro[4.5]decanyl), or spiroundecanyl (e.g., spiro[5.5]undecanyl). In some embodiments the spiro substituent is

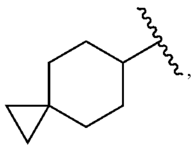, 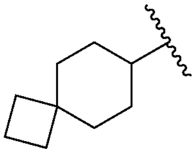,

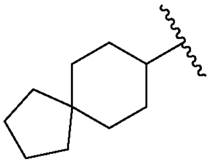, or 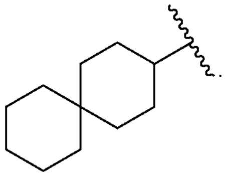.

"Halogen" or "halo" includes fluoro, chloro, bromo, and iodo.

"Haloalkyl" as used herein refers to an alkyl as defined herein, wherein one or more hydrogen atoms of the alkyl are independently replaced by a halo substituent, which may be the same or different. For example, $C_{1-4}$ haloalkyl is a $C_{1-4}$ alkyl wherein one or more of the hydrogen atoms of the $C_{1-4}$ alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

The term "heteroaryl" as used herein refers to a single aromatic ring or a multicyclic ring. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multicyclic ring systems (e.g., ring systems comprising 2 or 3 rings) wherein a heteroaryl group, as defined above, can be fused with one or more heteroaryls (e.g., naphthyridinyl), carbocycles (e.g., 5,6,7,8-tetrahydroquinolyl) or aryls (e.g., indazolyl) to form a multicyclic ring. Such multicyclic rings may be optionally substituted with one or more (e.g., 1, 2 or 3) oxo groups on the carbocycle portions of the multicyclic ring. It is to be understood that the point of attachment of a heteroaryl multicyclic ring, as defined above, can be at any position of the ring including a heteroaryl, aryl or a carbocycle portion of the ring. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thianaphthenyl.

"Heterocyclyl" or "heterocyclic ring" or "heterocycle" as used herein refers to a single saturated or partially unsaturated ring or a multicyclic ring. The term includes single saturated or partially unsaturated ring (e.g., 3, 4, 5, 6 or 7-membered ring) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. The term also includes multicyclic ring systems (e.g., ring systems comprising 2 or 3 rings) wherein a heterocycle group (as defined above) can be connected to two adjacent atoms (fused heterocycle) with one or more heterocycles (e.g., decahydronapthyridinyl), heteroaryls (e.g., 1,2,3,4-tetrahydronaphthyridinyl), carbocycles (e.g., decahydroquinolyl) or aryls. It is to be understood that the point of attachment of a heterocycle multicyclic ring, as defined above, can be at any position of the ring including a heterocyle, heteroaryl, aryl or a carbocycle portion of the ring. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl and 1,4-benzodioxanyl. Exemplary fused bicyclic heterocycles include, but are not limited to

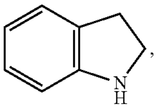, 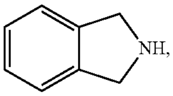, 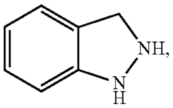, 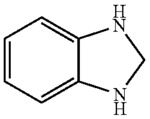, 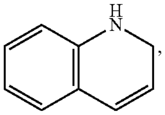, 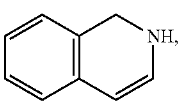, 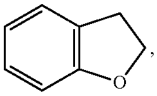, 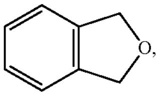, 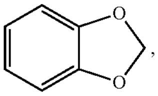, 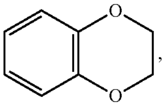, 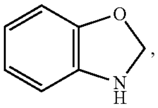, 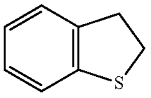, 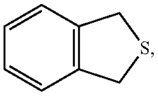, 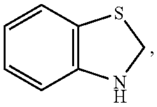, 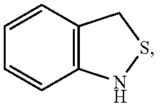, 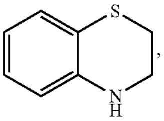, 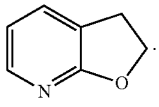.

"Hydroxy" or "hydroxyl" refers to the group —OH.

"Oxo" refers to the group (=O) or (O).

"Sulfonyl" refers to the group $—S(O)_2R^c$, where $R^c$ is alkyl, heterocyclyl, cycloalkyl, heteroaryl, or aryl. Examples of sulfonyl are methylsulfonyl, ethylsulfonyl, phenylsulfonyl, and toluenesulfonyl.

Whenever the graphical representation of a group terminates in a singly bonded nitrogen atom, that group represents an $—NH_2$ group unless otherwise indicated. Similarly, unless otherwise expressed, hydrogen atom(s) are implied and deemed present where necessary in view of the knowledge of one of skill in the art to complete valency or provide stability.

The terms "optional" or "optionally" mean that the subsequently described event or circumstance may or may not occur, and that the description includes instances where said event or circumstance occurs and instances in which it does not. Also, the term "optionally substituted" means that any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, CN, halo, amino, alkoxy, cycloalkyl, heterocyclyl, aryl, and heteroaryl. In additional embodiments, "substituted cycloalkyl" refers to a cycloalkyl group having one or more substituents including alkyl, haloalkyl, CN, cycloalkyl, heterocyclyl, aryl, heteroaryl, amino, alkoxy, halo, oxo, and hydroxyl; "substituted heterocyclyl" refers to a heterocyclyl group having one or more substituents including alkyl, amino, haloalkyl, CN, heterocyclyl, cycloalkyl, aryl, heteroaryl, alkoxy, halo, oxo, and hydroxyl; "substituted aryl" refers to an aryl group having one or more substituents including halo, alkyl, amino, haloalkyl, cycloalkyl, heterocyclyl, heteroaryl, alkoxy, and cyano; "substituted heteroaryl" refers to an heteroaryl group having one or more substituents including halo, amino, alkyl, haloalkyl, cycloalkyl, aryl, heterocyclyl, heteroaryl, alkoxy, and cyano and "substituted sulfonyl" refers to a group $—S(O)_2R$, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

In some embodiments, a substituted cycloalkyl, a substituted heterocyclyl, a substituted aryl, and/or a substituted heteroaryl includes a cycloalkyl, a heterocyclyl, an aryl, and/or a heteroaryl that has a substituent on the ring atom to which the cycloalkyl, heterocyclyl, aryl, and/or heteroaryl is attached to the rest of the compound. For example, in the below moiety, the cyclopropyl is substituted with a methyl group:

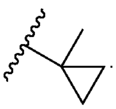.

The disclosures illustratively described herein may suitably be practiced in the absence of any element or elements, limitation or limitations, not specifically disclosed herein. Thus, for example, the terms "comprising," "including," "containing," etc., shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

The compounds of the present disclosure can be in the form of a pharmaceutically acceptable salt. The term "pharmaceutically acceptable salts" refers to salts prepared from pharmaceutically acceptable non-toxic bases or acids, including inorganic bases or acids and organic bases or acids. The compounds of the present disclosure can be in the form of a pharmaceutically acceptable salt. The term "pharmaceutically acceptable salts" refers to salts prepared from pharmaceutically acceptable non-toxic bases or acids, including inorganic bases or acids and organic bases or acids. In case the compounds of the present disclosure contain one or more acidic or basic groups, the disclosure also comprises their corresponding pharmaceutically or toxicologically acceptable salts, in particular their pharmaceutically utilizable salts. Thus, the compounds of the present disclosure which contain acidic groups can be present on these groups and can be used according to the disclosure, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine, amino acids, or other bases known to persons skilled in the art. The compounds of the present disclosure which contain one or more basic groups, i.e., groups which can be protonated, can be present and can be used according to the disclosure in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to persons skilled in the art.

If the compounds of the present disclosure simultaneously contain acidic and basic groups in the molecule, the disclosure also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts.

The present disclosure also includes all salts of the compounds of the present disclosure which, owing to low physiological compatibility, are not directly suitable for use in pharmaceuticals but which can be used, for example, as intermediates for chemical reactions or for the preparation of pharmaceutically acceptable salts. Acids and bases useful for reaction with an underlying compound to form pharmaceutically acceptable salts (acid addition or base addition salts respectively) are known to one of skill in the art. Similarly, methods of preparing pharmaceutically acceptable salts from an underlying compound (upon disclosure) are known to one of skill in the art and are disclosed in for example, Berge, at al. Journal of Pharmaceutical Science, January 1977 vol. 66, No. 1, and other sources.

Furthermore, compounds disclosed herein may be subject to tautomerism. Where tautomerism, e.g., keto-enol tautomerism, of compounds or their prodrugs may occur, the individual forms, like, e.g., the keto and enol form, are each within the scope of the disclosure as well as their mixtures in any ratio. The same applies for stereoisomers, like, e.g., enantiomers, cis/trans isomers, diastereomers, conformers, and the like.

The term "protecting group" refers to a moiety of a compound that masks or alters the properties of a functional group or the properties of the compound as a whole. Chemical protecting groups and strategies for protection/deprotection are well known in the art. See e.g., Protective Groups in Organic Chemistry, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. The term "deprotecting" refers to removing the protecting group.

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

Further the compounds of the present disclosure may be present in the form of solvates, such as those which include as solvate water, or pharmaceutically acceptable solvates, such as alcohols, in particular ethanol. A "solvate" is formed by the interaction of a solvent and a compound.

In certain embodiments, provided are optical isomers, racemates, or other mixtures thereof (e.g., scalemic mixtures) of the compounds described herein or a pharmaceutically acceptable salt or a mixture thereof. If desired, isomers can be separated by methods well known in the art, e.g., by liquid chromatography. In those situations, the single enantiomer or diastereomer, i.e., optically active form, can be obtained by asymmetric synthesis or by resolution. Resolution can be accomplished, for example, by conventional methods such as crystallization in the presence of a resolving agent, or chromatography, using for example, a chiral high-pressure liquid chromatography (HPLC) column.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposeable mirror images of one another. "Diastereomers" are stereoisomers that have at least two asymmetric atoms, but which are not mirror-images of each other. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

Compounds disclosed herein and their pharmaceutically acceptable salts may, in some embodiments, include an asymmetric center and may thus give rise to enantiomers, diastereomers, and other stereoisomeric forms that may be defined, in terms of absolute stereochemistry, as (R)- or (S)- or, as (D)- or (L)- for amino acids. Some embodiments include all such possible isomers, as well as their racemic, scalemic, and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1.1.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

Any formula or structure given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphoros, fluorine and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^{3}H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

The disclosure also includes "deuterated analogs" of compounds disclosed herein, in which from 1 to n hydrogens attached to a carbon atom is/are replaced by deuterium, in which n is the number of hydrogens in the molecule. Such compounds may exhibit increased resistance to metabolism and thus be useful for increasing the half-life of any compound of Formula (I) when administered to a mammal, e.g., a human. See, e.g., Foster, "Deuterium Isotope Effects in Studies of Drug Metabolism," Trends Pharmacol. Sci. 5(12): 524-527 (1984). Such compounds are synthesized by means well known in the art, for example by employing starting materials in which one or more hydrogens have been replaced by deuterium.

Deuterium labelled or substituted therapeutic compounds of the disclosure may have beneficial DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Furthermore, the present disclosure provides pharmaceutical compositions comprising a compound of the present disclosure, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure can encompass any composition made by admixing at least one compound of the present disclosure and a pharmaceutically acceptable carrier.

As used herein, "pharmaceutically acceptable carrier" includes excipients or agents such as solvents, diluents, dispersion media, coatings, antibacterial and antifungal agents, isotonic and absorption delaying agents and the like that are not deleterious to the disclosed compound or use thereof. The use of such carriers and agents to prepare compositions of pharmaceutically active substances is well known in the art (see, e.g., Remington's Pharmaceutical Sciences, Mace Publishing Co., Philadelphia, PA 17th Ed. (1985); and Modern Pharmaceutics, Marcel Dekker, Inc. 3rd Ed. (G. S. Banker & C. T. Rhodes, Eds.).

"$IC_{50}$" or "$EC_{50}$" refers to the inhibitory concentration required to achieve 50% of the maximum desired effect.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival. In some embodiments, the term "treatment" or "treating" means administering a compound or pharmaceutically acceptable salt of Formula (I) for the purpose of: (i) delaying the onset of a disease, that is, causing the clinical symptoms of the disease not to develop or delaying the development thereof; (ii) inhibiting the disease, that is, arresting the development of clinical symptoms; and/or (iii) relieving the disease, that is, causing the regression of clinical symptoms or the severity thereof.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In some embodiments, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to PRMT5 inhibitors. The therapeutically effective amount may vary depending on the subject, and disease or condition being treated, the weight and age of the subject, the severity of the disease or condition, and the manner of administering, which can readily be determined by one or ordinary skill in the art.

List of Abbreviations and Acronyms

| Abbreviation | Meaning |
|---|---|
| ° C. | degrees Celsius |
| Ac | acetate |
| AcOH | acetic acid |
| Boc | tert-butoxycarbonyl |
| CBz | benzyloxycarbonyl |
| d | doublet |
| DCE | 1,2-dichloroethane |
| DCM | dichloromethane |
| dd | doublet of doublets |
| DMAc | dimethylacetoamide |
| DMF | Dimethylformamide |
| DMSO | Dimethylsulfoxide |
| equiv or eq. | equivalents |
| ES/MS | electron spray mass spectrometry |
| Et | ethyl |
| EtOH | ethanol |
| g | gram |
| glyme | 1,2-dimethoxyethane |
| H NMR | proton nuclear magnetic resonance |
| h or hr | hour |
| LC/MS | liquid chromatography/mass spectrometry |
| M | molar |
| m | milli |
| m/z | mass to charge ratio |
| M+ | mass peak |
| M + H | mass peak plus hydrogen |
| Me | methyl |
| MeCN or ACN | acetonitrile |
| MeOH | methanol |
| mg | milligram |
| MHz | megahertz |
| mL or ml | milliliter |
| mol | mole |
| mw | microwave |
| nM | nanomolar |
| $Pd(PPh_3)_4$ | Tetrakis(triphenylphosphine)palladium(0) |
| Pg | protecting group |
| Ph | phenyl |
| r.t. | room temperature |
| RP-HPLC | reversed-phase high perfomance liquid chromatography |
| s | singlet |
| SFC | For chiral separation |
| t | triplet |
| tBu | tert-butyl |
| TEA | triethylamine |
| Tf | trifluoromethanesulfonate |
| TFA | trifluoroacetic acid |
| THF | tetrahydrofuran |
| Ts | toluenesufonyl |
| δ | parts per million referenced to residual solvent peak |
| μL | microliter |
| μmol | micromole |

-continued

Compounds

In one embodiment, the present disclosure provides a compound of Formula (I),

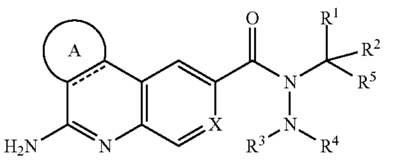

or a pharmaceutically acceptable salt thereof, wherein

 is a single or double bond;

ring A is $C_{5-7}$ cycloalkyl, phenyl, 5 to 7 membered heterocyclyl, or 5 or 6 membered heteroaryl; the cycloalkyl, phenyl, heterocyclyl, or heteroaryl of ring A is optionally substituted with one to four $R^6$, which may be the same or different;

X is N or $CR^7$;

$R^1$ is H, $C_{1-6}$ alkyl, $C_{1-6}$ haloalkyl, $C_{6-10}$ aryl, $C_{3-10}$ cycloalkyl, 3 to 10 membered heterocyclyl, or 5 to 10 membered heteroaryl; wherein the alkyl, haloalkyl, aryl, cycloalkyl, heterocyclyl, or heteroaryl of $R^1$ is each optionally substituted with one to four $Z^1$, which may be the same or different;

$R^2$ is H, —CN, $C_{1-5}$ alkyl, $C_{1-5}$ haloalkyl, $C_{2-6}$ alkynyl, cyclopropyl, cyclobutyl, or oxetanyl; wherein the alkyl, haloalkyl, alkoxyalkyl, alkynyl, cyclopropyl, or cyclobutyl of $R^2$ is each optionally substituted with one to four $Z^2$, which may be the same or different; each $Z^2$ is independently $C_{2-6}$ alkynyl, halo, —CN, —$OR^{2a}$, cyclopropyl, cyclobutyl, or oxetanyl; $R^{2a}$ is H, $C_{1-3}$ haloalkyl, $C_{3-6}$ cycloalkyl, or $C_{1-3}$ alkyl;

$R^5$ is H, $C_{1-3}$ alkyl, or $C_{1-3}$ haloalkyl;

or $R^1$ and $R^2$ together with the carbon to which they are attached form $C_{3-10}$ cycloalkyl, 3 to 10 membered heterocyclyl; the cycloalkyl or heterocyclyl formed from $R^1$ and $R^2$ is optionally substituted with one to four $Z^5$, which may be the same or different;

or $R^2$ and $R^5$ together with the carbon to which they are attached form cyclopropyl, cyclobutyl, or oxetanyl; the cyclopropyl, or cyclobutyl formed from $R^2$ and $R^5$ is optionally substituted with one to four halo;

$R^3$ is H, $C_{1-6}$ alkyl, $C_{1-6}$ haloalkyl, —$COR^{3a}$, —$COOR^{3a}$, —$CONR^{3a}R^{3b}$, —$SO_2R^{3a}$, —$SO_2NR^{3a}R^{3b}$, $C_{6-10}$ aryl, $C_{3-10}$ cycloalkyl, 3 to 10 membered heterocyclyl, or 5 to 10 membered heteroaryl; wherein the alkyl, aryl, cycloalkyl, heterocyclyl, or heteroaryl of $R^3$ is each optionally substituted with one to four $Z^3$, which may be the same or different, $R^4$ is H, $C_{1-6}$ alkyl, $C_{1-6}$ haloalkyl, $C_{6-10}$ aryl, $C_{3-10}$ cycloalkyl, 3 to 10 membered heterocyclyl, or 5 to 10 membered heteroaryl; wherein the alkyl, aryl, cycloalkyl, heterocyclyl, or heteroaryl of $R^4$ is each optionally substituted with one to four $Z^4$, which may be the same or different, or $R^3$ and $R^4$ together with the nitrogen to which they are attached form a 3 to 10 membered heterocyclyl, or 5 to 10 membered heteroaryl; wherein the heterocyclyl or heteroaryl formed from $R^3$ and $R^4$ is optionally substituted with one to four $Z^9$, which may be the same or different, or $R^2$ and $R^4$ together with the atoms to which they are attached form a 5 to 10 membered heterocyclyl; wherein the heterocyclyl formed from $R^2$ and $R^4$ is optionally substituted with one to four $Z^8$, which may be the same or different;

each $R^6$ is independently halo, —OH, —$OCH_3$, oxo, —CN, $C_{1-3}$ alkyl, $C_{1-3}$ haloalkyl, or cyclopropyl;

$R^7$ is H, halo, CN, halomethyl, —$CH_3$, or —$OCH_3$;

each $Z^1$, $Z^3$, $Z^4$, $Z^5$, $Z^8$, or $Z^9$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, 3 to 10 membered heterocyclyl, $C_{6-10}$ aryl, 5 to 10 membered heteroaryl, oxo, —$NO_2$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12a}$)$_2$ ($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —N$R^{12a}$S(O)$_2$N($R^{12b}$)($R^{12c}$), —N$R^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2R^{12a}$, —S(O)$_2$N($R^{12a}$)($R^{12b}$), —S(O)(N$R^{12a}$)$R^{12b}$, or —Si($R^{12a}$)$_3$; wherein the alkyl, haloalkyl, alkenyl, alkynyl, cycloalkyl, heterocyclyl, aryl, or heteroaryl of each $Z^1$, $Z^3$, $Z^4$, $Z^5$, $Z^8$, or $Z^9$ is each optionally substituted with one to four $Z^{1a}$, which may be the same or different;

each $Z^{1a}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, 3 to 10 membered heterocyclyl, $C_{6-10}$ aryl, 5 to 10 membered heteroaryl, oxo, —$NO_2$, —CN, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$)$^+$, —N($R^{12a}$)—C(O)$R^{12b}$, —N($R^{12a}$)C(O)O($R^{12b}$), —N($R^{12a}$)C(O)N($R^{12b}$)($R^{12c}$), —N($R^{12a}$)S(O)$_2$($R^{12b}$), —N($R^{12a}$)S(O)$_2$—N($R^{12b}$)($R^{12c}$), —N($R^{12a}$)S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$ $R^{12a}$, —S(O)$_2$N($R^{12a}$)($R^{12b}$), —S(O)(N$R^{12a}$)$R^{12b}$, or —Si($R^{12a}$)$_3$; wherein the alkyl, haloalkyl, alkenyl, alkynyl, cycloalkyl, heterocyclyl, aryl, or heteroaryl of $Z^{1a}$ is each optionally substituted with one to four $Z^{1b}$, which may be the same or different;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$; wherein the alkyl, cycloalkyl, heterocyclyl, aryl, or heteroaryl of $Z^{1b}$ is optionally substituted with one to three $C_{1-9}$ alkyl, $C_{1-8}$ haloalkyl, halogen, —OH, —$NH_2$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —$S(O)_2NH(C_{1-9}$ alkyl), or —$S(O)_2N(C_{1-9}$ alkyl)$_2$, wherein the heteroaryl of $Z^{1b}$ is 5 to 10 membered heteroaryl, the heterocyclyl of $Z^{1b}$ is 3 to 10 membered heterocyclyl; and each $R^{3a}$, $R^{3b}$, $R^{12a}$, $R^{12b}$, or $R^{12c}$ is independently H, $C_{1-6}$ alkyl, $C_{3-10}$ cycloalkyl, 3 to 10 membered heterocyclyl, $C_{6-10}$ aryl, or 5 to 10 heteroaryl, wherein the alkyl, cycloalkyl, heterocyclyl, aryl, or heteroaryl of each $R^{3a}$, $R^{3b}$, $R^{12a}$, $R^{12b}$, or $R^{12c}$ is each optionally substituted with one to four $Z^{1b}$, which may be the same or different;

wherein each heteroaryl or heterocyclyl has one to three heteroatoms each independently N, O, or S.

In one embodiment, the compound of Formula (I), or a pharmaceutically acceptable salt thereof, is the compound wherein

 is a single or double bond;

ring A is $C_{5-7}$ cycloalkyl, phenyl, 5 to 7 membered heterocyclyl, or 5 or 6 membered heteroaryl; the cycloalkyl, phenyl, heterocyclyl, or heteroaryl of ring A is optionally substituted with one to four $R^6$, which may be the same or different;

X is N or $CR^7$;

$R^1$ is H, $C_{1-6}$ alkyl, $C_{1-6}$ haloalkyl, $C_{6-10}$ aryl, $C_{3-10}$ cycloalkyl, 3 to 10 membered heterocyclyl, or 5 to 10 membered heteroaryl; wherein the alkyl, haloalkyl, aryl, cycloalkyl, heterocyclyl, or heteroaryl of $R^1$ is each optionally substituted with one to four $Z^1$, which may be the same or different;

$R^2$ is H, —CN, $C_{1-5}$ alkyl, $C_{1-5}$ haloalkyl, $C_{2-6}$ alkynyl, cyclopropyl, cyclobutyl, or oxetanyl; wherein the alkyl, haloalkyl, alkoxyalkyl, alkynyl, cyclopropyl, or cyclobutyl of $R^2$ is each optionally substituted with one to four $Z^2$, which may be the same or different; each $Z^2$ is independently $C_{2-6}$ alkynyl, halo, —CN, —$OR^{2a}$, cyclopropyl, cyclobutyl, or oxetanyl; $R^{2a}$ is H, $C_{1-3}$ haloalkyl, $C_{3-6}$ cycloalkyl, or $C_{1-3}$ alkyl;

$R^5$ is H, $C_{1-3}$ alkyl, or $C_{1-3}$ haloalkyl;

or $R^1$ and $R^2$ together with the carbon to which they are attached form $C_{3-10}$ cycloalkyl, 3 to 10 membered heterocyclyl; the cycloalkyl or heterocyclyl formed from $R^1$ and $R^2$ is optionally substituted with one to four $Z^5$, which may be the same or different;

or $R^2$ and $R^5$ together with the carbon to which they are attached form cyclopropyl, cyclobutyl, or oxetanyl; the cyclopropyl, or cyclobutyl formed from $R^2$ and $R^5$ is optionally substituted with one to four halo;

$R^3$ is H, $C_{1-6}$ alkyl, $C_{1-6}$ haloalkyl, —$COR^{3a}$, —$COOR^{3a}$, —$CONR^{3a}R^{3b}$, —$SO_2R^{3a}$, —$SO_2NR^{3a}R^{3b}$, $C_{6-10}$ aryl, $C_{3-10}$ cycloalkyl, 3 to 10 membered heterocyclyl, or 5 to 10 membered heteroaryl; wherein the alkyl, aryl, cycloalkyl, heterocyclyl, or heteroaryl of $R^3$ is each optionally substituted with one to four $Z^3$, which may be the same or different, $R^4$ is H, $C_{1-6}$ alkyl, $C_{1-6}$ haloalkyl, $C_{6-10}$ aryl, $C_{3-10}$ cycloalkyl, 3 to 10 membered heterocyclyl, or 5 to 10 membered heteroaryl; wherein the alkyl, aryl, cycloalkyl, heterocyclyl, or heteroaryl of $R^4$ is each optionally substituted with one to four $Z^4$, which may be the same or different, or $R^3$ and $R^4$ together with the nitrogen to which they are attached form a 3 to 10 membered heterocyclyl, or 5 to 10 membered heteroaryl; wherein the heterocyclyl or heteroaryl formed from $R^3$ and $R^4$ is optionally substituted with one to four $Z^9$, which may be the same or different, wherein the heterocyclyl formed from $R^3$ and $R^4$ is a heterocyclyl having 0 to 3 additional heteroatoms each independently N, O, or S, wherein the heteroaryl formed from $R^3$ and $R^4$ is a heteroaryl having 0 to 3 additional heteroatoms each independently N, O, or S, or $R^2$ and $R^4$ together with the atoms to which they are attached form a 5 to 10 membered heterocyclyl; wherein the heterocyclyl formed from $R^2$ and $R^4$ is optionally substituted with one to four $Z^8$, which may be the same or different;

each $R^6$ is independently halo, —OH, —$OCH_3$, oxo, —CN, $C_{1-3}$ alkyl, $C_{1-3}$ haloalkyl, or cyclopropyl;

$R^7$ is H, halo, CN, halomethyl, —$CH_3$, or —$OCH_3$;

each $Z^1$, $Z^3$, $Z^4$, $Z^5$, $Z^8$, or $Z^9$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, 3 to 10 membered heterocyclyl, $C_{6-10}$ aryl, 5 to 10 membered heteroaryl, oxo, —$NO_2$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12a}$)$_2$ ($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —$NR^{12a}$S(O)$_2$N($R^{12b}$)($R^{12c}$), —$NR^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2R^{12a}$, —S(O)$_2$N($R^{12a}$)($R^{12b}$), —S(O)(N$R^{12a}$)$R^{12b}$, or —Si($R^{12a}$)$_3$; wherein the alkyl, haloalkyl, alkenyl, alkynyl, cycloalkyl, heterocyclyl, aryl, or heteroaryl of each $Z^1$, $Z^3$, $Z^4$, $Z^3$, $Z^8$, or $Z^9$ is each optionally substituted with one to four $Z^{1a}$, which may be the same or different;

each $Z^{1a}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, 3 to 10 membered heterocyclyl, $C_{6-10}$ aryl, 5 to 10 membered heteroaryl, oxo, —$NO_2$, —CN, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$), —N($R^{12a}$)—C(O)$R^{12b}$, —N($R^{12a}$)C(O)O($R^{12b}$), —N($R^{12a}$)C(O)N($R^{12b}$)($R^{12c}$), —N($R^{12a}$)S(O)$_2$($R^{12b}$), —N($R^{12a}$)S(O)$_2$—N($R^{12b}$)($R^{12c}$), —N($R^{12a}$)S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2R^{12a}$, —S(O)$_2$N($R^{12a}$)($R^{12b}$), —S(O)(N$R^{12a}$)$R^{12b}$, or —Si($R^{12a}$)$_3$; wherein the alkyl, haloalkyl, alkenyl, alkynyl, cycloalkyl, heterocyclyl, aryl, or heteroaryl of $Z^{1a}$ is each optionally substituted with one to four $Z^{1b}$, which may be the same or different;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$; wherein the alkyl, cycloalkyl, heterocyclyl, aryl, or heteroaryl of $Z^{1b}$ is optionally substituted with one to three $C_{1-9}$ alkyl, $C_{1-8}$ haloalkyl, halogen, —OH, —$NH_2$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$, wherein the heteroaryl of $Z^{1b}$ is 5 to 10 membered heteroaryl, the heterocyclyl of $Z^{1b}$ is 3 to 10 membered heterocyclyl; and each $R^{3a}$, $R^{3b}$, $R^{12a}$, $R^{12b}$, or $R^{12c}$ is independently H, $C_{1-6}$ alkyl, $C_{3-10}$ cycloalkyl, 3 to 10 membered heterocyclyl, $C_{6-10}$ aryl, or 5 to 10 heteroaryl, wherein the alkyl, cycloalkyl, heterocyclyl, aryl, or heteroaryl of each $R^{3a}$, $R^{3b}$, $R^{12a}$, $R^{12b}$, or $R^{12c}$ is each optionally substituted with one to four $Z^{1b}$, which may be the same or different;

wherein each heteroaryl or heterocyclyl of the compound of Formula (I) unless otherwise specified has one to three heteroatoms each independently N, O, or S.

In some embodiments, the compound of formula (I) or a pharmaceutically acceptable salt thereof, is a compound of Formula (Ia), (Ia)

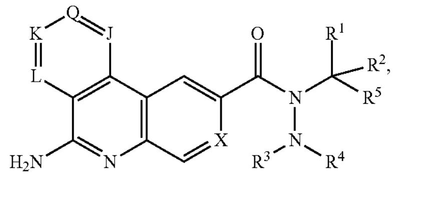

wherein each K, and Q is independently N, CH, or $CR^6$; and each J, and L is independently CH or $CR^6$.

In some embodiments, the compound of formula (I) or a pharmaceutically acceptable salt thereof, is a compound of Formula (Ia-1), (Ia-1)

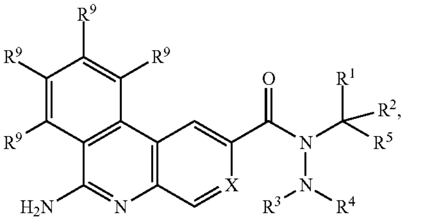

wherein each $R^9$ is independently H or $R^6$.

In some embodiments, the compound of formula (I) or a pharmaceutically acceptable salt thereof, is a compound of Formula (Ia-2), (Ia-2)

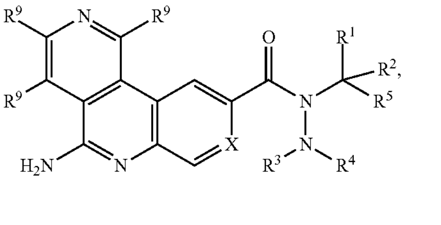

wherein each $R^9$ is independently H or $R^6$.

In some embodiments, the compound of formula (I) or a pharmaceutically acceptable salt thereof, is a compound of Formula (Ia-3), (Ia-3)

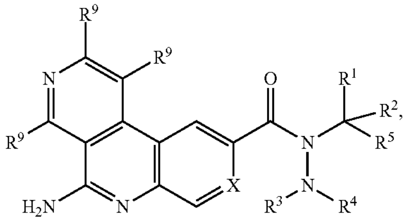

wherein $R^9$ is H or $R^6$.

In some embodiments, the compound of formula (I) or a pharmaceutically acceptable salt thereof, is a compound of Formula (Ib), (Ib)

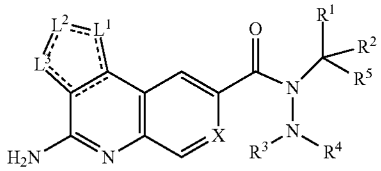

wherein each $L^1$, $L^2$, and $L^3$ is independently $CR^9$, $CR^9R^9$, O, S, N, $NR^9$, or CO;

each dashed line represents an optional bond to complete valency requirements of each $L^1$, $L^2$, $L^3$, and the two C attached to $L^1$ and $L^3$; and each $R^9$ is independently H or $R^6$.

In some embodiments, the compound of formula (I) or a pharmaceutically acceptable salt thereof, is a compound of Formula (Ib-1), (Ib-1)

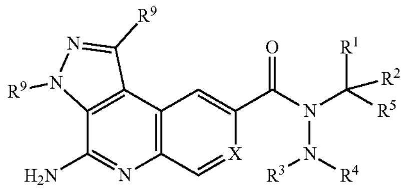

wherein each $R^9$ is independently H or $R^6$.

In some embodiments, the compound of formula (I) or a pharmaceutically acceptable salt thereof, is a compound of Formula (Ib-2), (Ib-2)

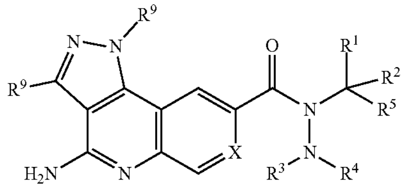

wherein each $R^9$ is independently H or $R^6$.

In some embodiments, the compound of formula (I) or a pharmaceutically acceptable salt thereof, is a compound of Formula (Ib-3), (Ib-3)

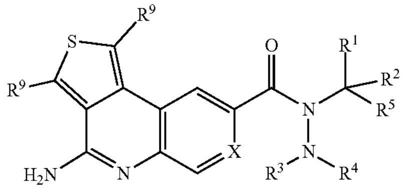

wherein each $R^9$ is independently H or $R^6$.

In some embodiments, the compound of formula (I) or a pharmaceutically acceptable salt thereof, is a compound of Formula (Ib-4), (Ib-4)

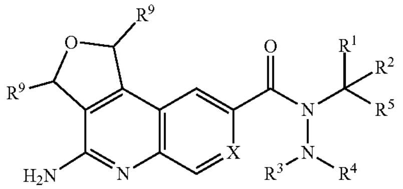

wherein each $R^9$ is independently H or $R^6$.

In some embodiments, the compound of formula (I) or a pharmaceutically acceptable salt thereof, is a compound of Formula (Ib-5), (Ib-5)

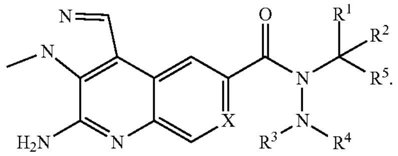

In some embodiments, the compound of formula (I) or a pharmaceutically acceptable salt thereof, is a compound of Formula (Ib-6), (Ib-6)

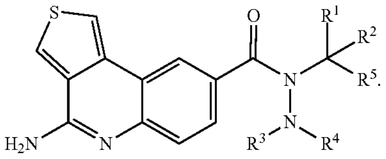

In some embodiments, the compound of formula (I) or a pharmaceutically acceptable salt thereof, is a compound of Formula (Ib-7), (Ib-7)

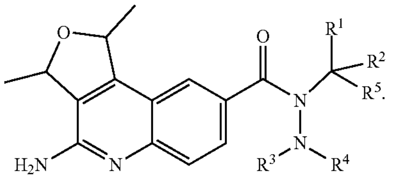

In some embodiments, the compound of formula (I) or a pharmaceutically acceptable salt thereof, is a compound of Formula (Ib-8)

(Ib-8)

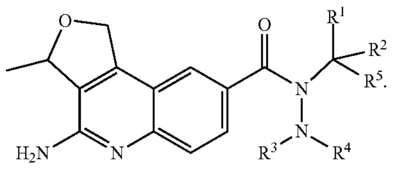

In some embodiments, the compound of formula (I) or a pharmaceutically acceptable salt thereof, is a compound of Formula (Ib-9), (Ib-9)

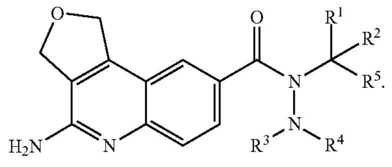

In some embodiments, the compound of formula (I) or a pharmaceutically acceptable salt thereof, is a compound of Formula (Ib-10), (Ib-10)

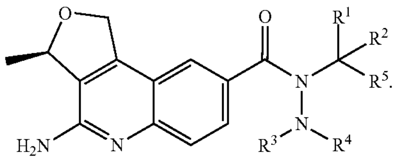

In some embodiments, the compound of formula (I) or a pharmaceutically acceptable salt thereof, is a compound of Formula (Ib-11), (Ib-11)

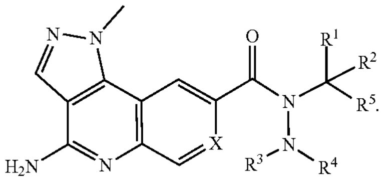

In some embodiments, the compound of formula (I) or a pharmaceutically acceptable salt thereof, is a compound of Formula (Ib-12)

(Ib-12)

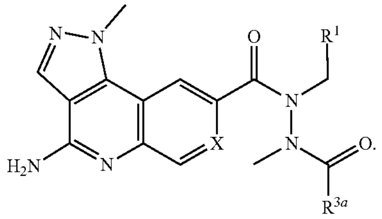

In some embodiments, the compound of formula (I) or a pharmaceutically acceptable salt thereof, is a compound of Formula (Ib-13)

(Ib-13)

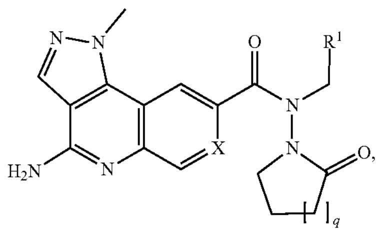

wherein q is 1 or 2. In some embodiments, q is 1. In some embodiments, q is 2.

In some embodiments, the compound of Formula (I), (Ia), (Ia-1), (Ia-2), (Ia-3), (Ib), (Ib-1), (Ib-2), (Ib-3), (Ib-4), (Ib-5), or (Ib-11), or a pharmaceutically acceptable salt thereof, is the compound wherein X is N. In some embodiments, X is $CR^7$. In some embodiments, $R^7$ is H, halo, CN, —$CH_3$, or halomethyl. In some embodiments, $R^7$ is halo. In some embodiments, $R^7$ is F. In some embodiments, $R^7$ is H.

In some embodiments, the compound of Formula (I), or a pharmaceutically acceptable salt thereof, is the compound wherein ring A is phenyl optionally substituted with one to three $R^6$, which may be the same or different. In some embodiments, ring A is 5 or 6 membered heterocyclyl optionally substituted with one to three $R^6$, which may be the same or different. In some embodiments, ring A is 5 to 7 membered heteroaryl optionally substituted with one to three $R^6$, which may be the same or different. In some embodiments, ring A is 5 membered heteroaryl optionally substituted with one to three $R^6$, which may be the same or different. In some embodiments, ring A is 6 membered heteroaryl optionally substituted with one to three $R^6$, which may be the same or different.

In some embodiments, the compound of Formula (I), (Ia), (Ia-1), (Ia-2), (Ia-3), (Ib), (Ib-1), (Ib-2), (Ib-3), or (Ib-4), or a pharmaceutically acceptable salt thereof, is the compound wherein each $R^6$ is independently halo, —OH, —CN, $C_{1-3}$ alkyl, or $C_{1-3}$ haloalkyl. In some embodiments, each $R^6$ is independently F or Cl. In some embodiments, $R^6$ is —$CH_3$.

In some embodiments, the compound of Formula (Ia-1), (Ia-2), (Ia-3), (Ib), (Ib-1), (Ib-2), (Ib-3), or (Ib-4), or a pharmaceutically acceptable salt thereof, is the compound wherein $R^9$ is H.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^5$ is H.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^2$ is H, $C_{1-3}$ alkyl, or $C_{1-3}$ haloalkyl. In some embodiments, $R^2$ is H.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13), or a pharmaceutically acceptable salt thereof, is the compound wherein $R^1$ is 5-10 membered heteroaryl including one to three heteroatoms each independently N, O, or S; the heteroaryl of $R^1$ is optionally substituted with one to three $Z^1$, which may be the same or different. In some embodiments, $R^1$ is monocyclic heteroaryl optionally substituted with one to three $Z^1$, which may be the same or different. In some embodiments, $R^1$ is bicyclic heteroaryl, optionally substituted with one to three $Z^1$, which may be the same or different. In some embodiments, $R^1$ is 5-6 membered heteroaryl including one or two N; the heteroaryl of $R^1$ is optionally substituted with one to three $Z^1$, which may be the same or different. In some embodiments, $R^1$ is

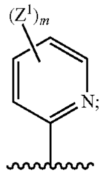

and m is 0, 1, or 2. In some embodiments, m is 0. In some embodiments, m is 1. In some embodiments, m is 2. In some embodiments, $R^1$ is

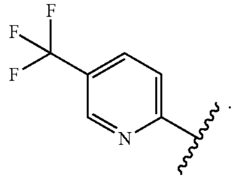

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13), or a pharmaceutically acceptable salt thereof, is the compound wherein $R^1$ is fused bicyclic heteroaryl, optionally substituted with one to three $Z^1$, which may be the same or different. In some embodiments, $R^1$ is [5,6] or [6,5]-fused bicyclic heteroaryl including one to three heteroatoms each independently N, O, or S; the heteroaryl of $R^1$ is optionally substituted with one to three $Z^1$, which may be the same or different. In some embodiments, $R^1$ is imidazopyridinyl, benzoimidazolyl, pyrazolopyridinyl, benzothiazolyl, benzoxazolyl, benzothiophene, or benzothiadiazole, wherein the imidazopyridinyl, benzoimidazolyl, pyrazolopyridinyl, benzothiazolyl, benzoxazolyl, benzothiophene, or benzothiadiazole of $R^1$ is optionally substituted with one to three $Z^1$, which may be the same or different. In some embodiments, $R^1$ is

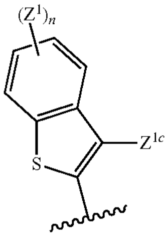 , 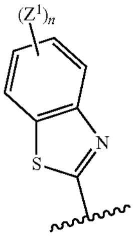 , 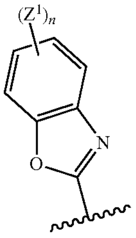 ,

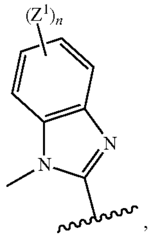 , 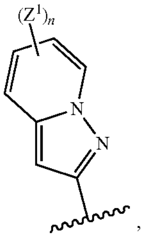 , 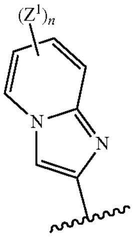 ,

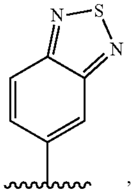 , or 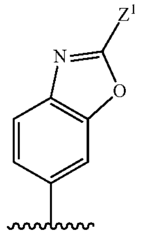 ;

n is 0, 1, or 2; and $Z^{1c}$ is H or $Z^1$. In some embodiments, n is 0. In some embodiments, n is 1. In some embodiments, n is 2. In some embodiments, $Z^{1c}$ is H.

In some embodiments, each $Z^1$ is independently halo, —CN, $C_{1-6}$ alkyl, $C_{3-6}$ cycloalkyl, $C_{1-6}$ haloalkyl, $C_{1-6}$ alkoxy, or $C_{1-6}$ haloalkoxy. In some embodiments, each $Z^1$ is independently halo, —CN, $C_{1-6}$ alkyl, or $C_{1-6}$ haloalkyl. In some embodiments, each $Z^1$ is independently halo or $C_{1-3}$ haloalkyl. In some embodiments, $Z^1$ is —$CF_3$.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13), or a pharmaceutically acceptable salt thereof, is the compound wherein $R^1$ is

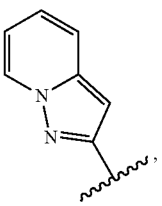 , 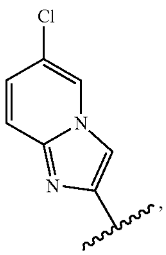 , 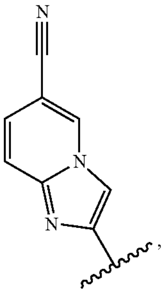 ,

-continued

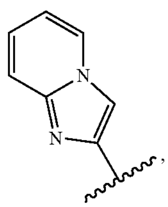,

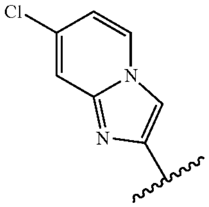,

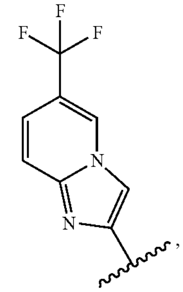,

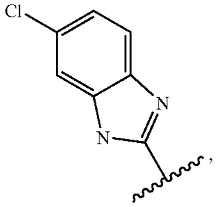,

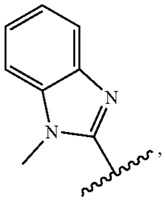,

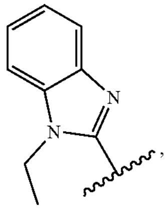,

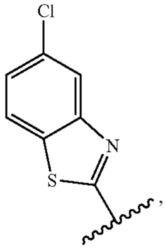,

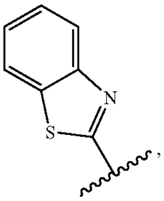,

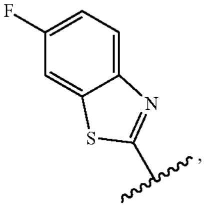,

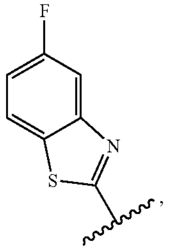,

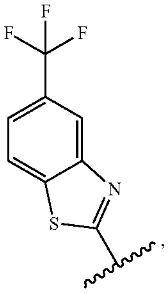, or

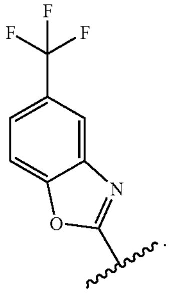.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^3$ is H, $C_{1-6}$ alkyl, $C_{1-6}$ haloalkyl, —$COR^{3a}$, —$COOR^{3a}$, —$CONR^{3b}R^{3b}$, —$SO_2R^{3a}$, —$SO_2NR^{3b}R^{3b}$, $C_{6-10}$ aryl, $C_{3-10}$ cycloalkyl, heterocyclyl, or heteroaryl; wherein the alkyl, aryl, cycloalkyl, heterocyclyl, or heteroaryl of $R^3$ is each optionally substituted with one to four $Z^3$, which may be the same or different; and $R^4$ is H, $C_{1-6}$ alkyl, $C_{1-6}$ haloalkyl, $C_{6-10}$ aryl, $C_{3-10}$ cycloalkyl, heterocyclyl, or heteroaryl; wherein the alkyl, aryl, cycloalkyl, heterocyclyl, or heteroaryl of $R^4$ is each optionally substituted with one to four $Z^4$, which may be the same or different.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^3$ is H, $C_{1-6}$ alkyl, $C_{1-6}$ haloalkyl, —$COR^{3a}$, —$COOR^{3a}$, —$CONR^{3b}R^{3b}$, $C_{6-10}$ aryl, $C_{3-6}$ cycloalkyl, heterocyclyl, or heteroaryl; wherein the aryl, cycloalkyl, heterocyclyl, or heteroaryl of $R^3$ is each optionally substituted with one to four $Z^3$, which may be the same or different; and each $R^{3a}$ and $R^{3b}$ is $C_{1-6}$ alkyl, $C_{6-10}$ aryl, or heteroaryl, wherein the alkyl, aryl, or heteroaryl of $R^{3a}$ is each optionally substituted with one to four $Z^{1b}$, each $Z^{1b}$ is independently halo, —CN, $C_{1-6}$ alkyl, $C_{1-6}$ haloalkyl, $C_{1-6}$ alkoxy, or $C_{1-6}$ haloalkoxy. In some embodiments, each $R^{3a}$ and $R^{3b}$ is independently $C_{1-6}$ alkyl, $C_{3-8}$ cycloalkyl, $C_{6-10}$ aryl, or heteroaryl, wherein the alkyl, cycloalkyl, aryl, or heteroaryl of $R^{3a}$ is each optionally substituted with one to four $Z^{1b}$; each $Z^{1b}$ is independently halo, —CN, $C_{1-6}$ alkyl, $C_{1-6}$ haloalkyl, $C_{1-6}$ alkoxy, or $C_{1-6}$ haloalkoxy.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^3$ is H, $C_{1-6}$ alkyl, $C_{1-6}$ haloalkyl, —$COR^{3a}$, —$COOR^{3a}$, $C_{6-10}$ aryl, or heteroaryl; wherein the aryl or heteroaryl of $R^3$ is each optionally substituted with one to four $Z^3$, which may be the same or different; and $R^{3a}$ is $C_{1-6}$ alkyl, $C_{6-10}$ aryl, or heteroaryl, wherein the alkyl, aryl, or heteroaryl of $R^{3a}$ is each optionally substituted with one to four $Z^{1b}$, each $Z^{1b}$ is independently halo, —CN, $C_{1-6}$ alkyl, $C_{1-6}$ haloalkyl, $C_{1-6}$ alkoxy, or $C_{1-6}$ haloalkoxy. In some embodiments, $R^{3a}$ is $C_{1-6}$ alkyl, $C_{3-8}$ cycloalkyl, $C_{6-10}$ aryl, or heteroaryl, wherein the alkyl, cycloalkyl, aryl, or heteroaryl of $R^{3a}$ is each optionally substituted with one to four $Z^{1b}$, each $Z^{1b}$ is independently halo, —CN, $C_{1-6}$ alkyl, $C_{1-6}$ haloalkyl, $C_{1-6}$ alkoxy, or $C_{1-6}$ haloalkoxy.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^3$ is —$COR^{3a}$, or —$COOR^{3a}$, and $R^{3a}$ is $C_{1-6}$ alkyl, $C_{3-8}$ cycloalkyl, phenyl, 5 or 6 membered heteroaryl, wherein the alkyl, cycloalkyl, phenyl, or heteroaryl of $R^{3a}$ is each optionally substituted with one to three $Z^{1b}$, which may be the same or different.

In some embodiments, $R^{3a}$ is $C_{1-6}$ alkyl or $C_{3-8}$ cycloalkyl, wherein the alkyl or cycloalkyl of $R^{3a}$ is each optionally substituted with one to three $Z^{1b}$, which may be the same or different.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^3$ is —$COR^{3a}$, $R^{3a}$ is $C_{1-3}$ alkyl or $C_{3-6}$ cycloalkyl, wherein the alkyl or cycloalkyl of each $R^{3a}$ is each optionally substituted with one to three $Z^{1b}$, which may be the same or different. In some embodiments, $R^3$ is —$COR^{3a}$; $R^{3a}$ is $C_{3-6}$ cycloalkyl; the cycloalkyl of $R^{3a}$ is fused bicyclic, bridged bicyclic, or spiro bicyclic, optionally substituted with one to three $Z^{1b}$, which may be the same or different. In some embodiments, the cycloalkyl of $R^{3a}$ is monocyclic, optionally substituted with one to four $Z^{1b}$, which may be the same or different.

In some embodiments, each $Z^{1b}$ is independently halo, —CN, $C_{1-6}$ alkyl, $C_{1-6}$ haloalkyl, $C_{1-6}$ haloalkoxy, or $C_{1-6}$ alkoxy.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein each $Z^3$ is independently halo, —CN, $C_{1-6}$ alkyl, $C_{1-6}$ haloalkyl, $C_{1-6}$ haloalkoxy, or $C_{1-6}$ alkoxy.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^3$ is —$COCH_3$, —$COC_2H_5$, —$COOC_2H_5$,

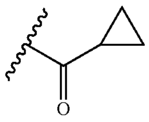, or 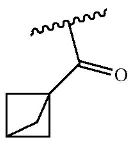.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^4$ is H, $C_{1-3}$ alkyl, $C_{1-3}$ haloalkyl, $C_{6-10}$ aryl, $C_{3-8}$ cycloalkyl, 5 to 8 membered heterocyclyl, or 5 or 6 membered heteroaryl; wherein the aryl, cycloalkyl, heterocyclyl, or heteroaryl of $R^4$ is each optionally substituted with one to four $Z^4$, which may be the same or different.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^4$ is H, $C_{1-3}$ alkyl, $C_{1-3}$ haloalkyl, phenyl, $C_{3-8}$ cycloalkyl, or 5 or 6 membered heteroaryl; wherein the phenyl, cycloalkyl, or heteroaryl of $R^4$ is each optionally substituted with one to four $Z^4$, which may be the same or different.

In some embodiments, $Z^4$ is halo, —OH, —CN, $C_{1-6}$ alkyl, $C_{1-6}$ haloalkyl, $C_{1-6}$ haloalkoxy, or $C_{1-6}$ alkoxy.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^4$ is H, or $C_{1-3}$ alkyl.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^4$ is $CD_3$.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein

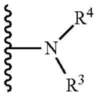 is 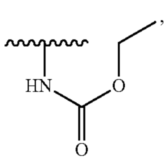,

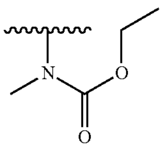, 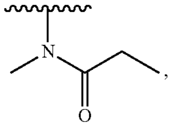, 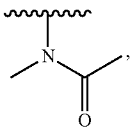,

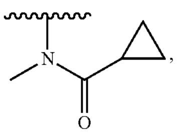, or 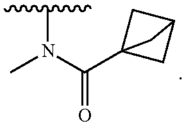.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^3$ and $R^4$ together with the nitrogen to which they are attached form a 5 to 7 membered heterocyclyl; wherein the heterocyclyl formed from $R^3$ and $R^4$ is optionally substituted with one to four $Z^9$, which may be the same or different. In some embodiments, the heterocyclyl formed from $R^3$ and $R^4$ is monocyclic, optionally substituted with one to four $Z^9$, which may be the same or different.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein

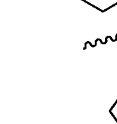 is 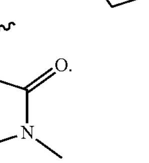, ring D is a heterocyclyl optionally additionally substituted with one to three $Z^9$, which may be the same or different. In some embodiments, ring D is monocyclic, optionally additionally substituted with one to three $Z^9$, which may be the same or different.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^3$ and $R^4$ together with the nitrogen to which they are attached form a 5-7 membered heterocyclyl; the heterocyclyl formed from $R^3$ and $R^4$ has optionally an additional heteroatom N; the heterocyclyl formed from $R^3$ and $R^4$ is optionally substituted with one to three $Z^9$, which may be the same or different.

In some embodiments, each Z' is independently oxo, halo, —CN, $C_{1-6}$ alkyl, $C_{1-6}$ haloalkyl, $C_{1-6}$ haloalkoxy, or $C_{1-6}$ alkoxy. In some embodiments, at least one $Z^9$ is oxo.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein

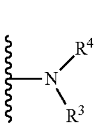 is 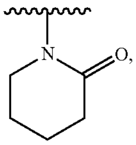, 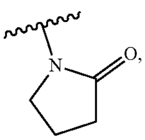, or

.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^1$ is H, $C_{1-6}$ alkyl, $C_{1-6}$ haloalkyl, $C_{6-10}$ aryl, $C_{3-10}$ cycloalkyl, 3 to 10 membered heterocyclyl, or 5 to 10 membered heteroaryl; wherein the alkyl, haloalkyl, aryl, cycloalkyl, heterocyclyl, or heteroaryl of $R^1$ is each optionally substituted with one to four $Z^1$, which may be the same or different;

$R^2$ is H, —CN, $C_{1-5}$ alkyl, $C_{1-5}$ haloalkyl, $C_{2-6}$ alkynyl, cyclopropyl, cyclobutyl, or oxetanyl; wherein the alkyl, haloalkyl, alkoxyalkyl, alkynyl, cyclopropyl, or cyclobutyl of $R^2$ is each optionally substituted with one to four $Z^2$, which may be the same or different; each $Z^2$ is independently $C_{2-6}$ alkynyl, halo, —CN, —$OR^{2a}$, cyclopropyl, cyclobutyl, or oxetanyl; $R^{2a}$ is H, $C_{1-3}$ haloalkyl, $C_{3-6}$ cycloalkyl, or $C_{1-3}$ alkyl; and $R^5$ is H, $C_{1-3}$ alkyl, or $C_{1-3}$ haloalkyl.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^1$ is H, $C_{1-6}$ alkyl, $C_{1-6}$ haloalkyl, $C_{6-10}$ aryl, $C_{3-10}$ cycloalkyl, 3 to 10 membered heterocyclyl, or 5 to 10 membered heteroaryl; wherein the alkyl, haloalkyl, aryl, cycloalkyl, heterocyclyl, or heteroaryl of $R^1$ is each optionally substituted with one to four $Z^1$, which may be the same or different; and $R^2$ and $R^5$ together with the carbon to which they are attached form cyclopropyl, cyclobutyl, or oxetanyl; the cyclopropyl, or cyclobutyl formed from $R^2$ and $R^5$ is optionally substituted with one to four halo.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^1$ and $R^2$ together with the carbon to which they are attached form $C_{3-10}$ cycloalkyl, 3 to 10 membered heterocyclyl; the cycloalkyl or heterocyclyl formed from $R^1$ and $R^2$ is optionally substituted with one to four $Z^5$, which may be the same or different; and $R^5$ is H, $C_{1-3}$ alkyl, or $C_{1-3}$ haloalkyl.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^3$ is H, $C_{1-6}$ alkyl, $C_{1-6}$ haloalkyl, —$COR^{3a}$, —$COOR^{3a}$, —$CONR^{3a}R^{3b}$, —$SO_2R^{3a}$, —$SO_2NR^{3a}R^{3b}$, $C_{6-10}$ aryl, $C_{3-10}$ cycloalkyl, 3 to 10 membered heterocyclyl, or 5 to 10 membered heteroaryl; wherein the alkyl, aryl, cycloalkyl, heterocyclyl, or heteroaryl of $R^3$ is each optionally substituted with one to four $Z^3$, which may be the same or different; and $R^4$ is H, $C_{1-6}$ alkyl, $C_{1-6}$ haloalkyl, $C_{6-10}$ aryl, $C_{3-10}$ cycloalkyl, 3 to 10 membered heterocyclyl, or 5 to 10 membered heteroaryl; wherein the alkyl, aryl, cycloalkyl, heterocyclyl, or heteroaryl of $R^4$ is each optionally substituted with one to four $Z^4$, which may be the same or different.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^3$ and $R^4$ together with the nitrogen to which they are attached form a 3 to 10 membered heterocyclyl, or 5 to 10 membered heteroaryl; wherein the heterocyclyl or heteroaryl formed from $R^3$ and $R^4$ is optionally substituted with one to four $Z^9$, which may be the same or different, wherein the heterocyclyl formed from $R^3$ and $R^4$ is a heterocyclyl having 0 to 2 additional heteroatoms each independently N, O, or S, wherein the heteroaryl formed from $R^3$ and $R^4$ is a heteroaryl having 0 to 2 additional heteroatoms each independently N, O, or S.

In some embodiments, the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), or (Ib-11), or a pharmaceutically acceptable salt thereof, is the compound wherein $R^1$ is H, $C_{1-6}$ alkyl, $C_{1-6}$ haloalkyl, $C_{6-10}$ aryl, $C_{3-10}$ cycloalkyl, 3 to 10 membered heterocyclyl, or 5 to 10 membered heteroaryl; wherein the alkyl, haloalkyl, aryl, cycloalkyl, heterocyclyl, or heteroaryl of $R^1$ is each optionally substituted with one to four $Z^1$, which may be the same or different;

$R^5$ is H, $C_{1-3}$ alkyl, or $C_{1-3}$ haloalkyl;

$R^3$ is H, $C_{1-6}$ alkyl, $C_{1-6}$ haloalkyl, —$COR^{3a}$, —$COOR^{3a}$, —$CONR^{3a}R^{3b}$, —$SO_2R^{3a}$, —$SO_2NR^{3a}R^{3b}$, $C_{6-10}$ aryl, $C_{3-10}$ cycloalkyl, 3 to 10 membered heterocyclyl, or 5 to 10 membered heteroaryl; wherein the alkyl, aryl, cycloalkyl, heterocyclyl, or heteroaryl of $R^3$ is each optionally substituted with one to four $Z^3$, which may be the same or different; and $R^2$ and $R^4$ together with the atoms to which they are attached form a 5 to 10 membered heterocyclyl; wherein the heterocyclyl formed from $R^2$ and $R^4$ is optionally substituted with one to four $Z^8$, which may be the same or different.

In some embodiments, the present disclosure provides a compound in Table 1 or a pharmaceutically acceptable salt thereof.

In some embodiments, the present disclosure provides a racemic mixture comprising the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13), or a pharmaceutically acceptable salt thereof. In some embodiments, the present disclosure provides a racemic mixture comprising the compound disclosed herein, or a pharmaceutically acceptable salt thereof. In some embodiments, the present disclosure provides a scalemic mixture comprising the compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13), or a pharmaceutically acceptable salt thereof. In some embodiments, the present disclosure provides a scalemic mixture comprising the compound disclosed herein, or a pharmaceutically acceptable salt thereof.

One of skill in the art is aware that each and every embodiment of a group (e.g., $R^1$) disclosed herein may be combined with any other embodiment of each of the remaining groups (e.g., $R^2$, $R^3$, $Z^1$, $Z^3$, etc.) to generate a complete compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13), or any Formula described herein or a pharmaceutically acceptable salt, stereoisomer, mixture of stereoisomers, or tautomer thereof, each of which is deemed within the ambit of the present disclosure.

Pharmaceutical Compositions and Modes of Administration

Furthermore, the present disclosure provides pharmaceutical compositions comprising at least one compound of the present disclosure, or a prodrug compound thereof, or a pharmaceutically acceptable salt or solvate thereof as active ingredient together with a pharmaceutically acceptable carrier.

In some embodiments, the pharmaceutical composition of the present disclosure may additionally comprise one or more other compounds as active ingredients like a prodrug compound or other enzyme inhibitors.

In some embodiments, the pharmaceutical composition of the present disclosure may comprise an additional therapeutic agent or therapeutic modality. In some embodiments, the additional therapeutic agent comprises one, two, three, or four additional therapeutic agents and/or therapeutic modalities. In some embodiments, the additional therapeutic agent or therapeutic modalities are selected from an immune checkpoint modulator, an antibody-drug conjugate (ADC), an antiapoptotic agent, a targeted anticancer therapeutic, a chemotherapeutic agent, surgery, or radiation therapy. In some embodiments, the immune checkpoint modulator is selected from an anti-PD-(L)1 antibody, an anti-TIGIT antibody, an anti-CTLA4 antibody, an anti-CCR8 antibody, an anti-TREM1 antibody, an anti-TREM2 antibody, a CD47 inhibitor, a DGKα inhibitor, an HPK1 inhibitor, a FLT3 agonist, an adenosine pathway inhibitor, and a CAR-T cell therapy.

The compositions are suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of the present disclosure can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

In some embodiments, the compounds of the present disclosure may also be used as salts with various countercations to yield an orally available formulation.

The compounds of the present disclosure may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present disclosure. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In some embodiments, compounds of the present disclosure are administered orally.

Kits

Provided herein are also kits that include a compound of the disclosure, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

Treatment Methods and Uses

The disclosure further relates to the use of compounds disclosed herein for the treatment and/or prophylaxis of diseases and/or conditions through inhibiting PRMT5 by said compounds. The disclosure further relates to the use of compounds disclosed herein for the treatment and/or prophylaxis of diseases and/or conditions through inhibiting PRMT5 by said compounds. The disclosure further relates to the use of compounds disclosed herein for the treatment and/or prophylaxis of diseases and/or conditions through inhibiting PRMT5 in MTAP-null cells by said compounds. Further, the present disclosure relates to the use of said compounds for the preparation of a medicament for the treatment and/or prophylaxis of a chromosome 9p21 deletion or MTAP-null associated disease and/or condition through inhibiting PRMT5 in MTAP-null cells by said compounds. In some embodiments the chromosome 9p21 deletion or MTAP-null associated disease or condition is alleviated by inhibition of PRMT5 in MTAP-null cells.

Medicaments as referred to herein can be prepared by conventional processes, including the combination of a compound according to the present disclosure and a pharmaceutically acceptable carrier.

In some embodiments, provided herein is a method of treating and/or preventing a MTAP-null or chromosome 9p21 deletion associated disease or condition in a patient in need thereof, comprising administering to the patient a therapeutically effective amount of a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13), or pharmaceutically acceptable salt thereof, or a composition comprising a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13), or a pharmaceutically acceptable salt thereof.

In some embodiments, the chromosome 9p21 deletion or MTAP-null associated disease or condition includes a solid tumor in or arising from a tissue or organ, such as:

- bone (e.g., adamantinoma, aneurysmal bone cysts, angiosarcoma, chondroblastoma, chondroma, chondromyxoid fibroma, chondrosarcoma, chordoma, dedifferentiated chondrosarcoma, enchondroma, epithelioid hemangioendothelioma, fibrous dysplasia of the bone, giant cell tumour of bone, haemangiomas and related lesions, osteoblastoma, osteochondroma, osteosarcoma, osteoid osteoma, osteoma, periosteal chondroma, Desmoid tumor, Ewing sarcoma);
- lips and oral cavity (e.g., odontogenic ameloblastoma, oral leukoplakia, oral squamous cell carcinoma, primary oral mucosal melanoma); salivary glands (e.g., pleomorphic salivary gland adenoma, salivary gland adenoid cystic carcinoma, salivary gland mucoepidermoid carcinoma, salivary gland Warthin's tumors);
- esophagus (e.g., Barrett's esophagus, dysplasia and adenocarcinoma);
- gastrointestinal tract, including stomach (e.g., gastric adenocarcinoma, primary gastric lymphoma, gastrointestinal stromal tumors (GISTs), metastatic deposits, gastric carcinoids, gastric sarcomas, neuroendocrine carcinoma, gastric primary squamous cell carcinoma, gastric adenoacanthomas), intestines and smooth muscle (e.g., intravenous leiomyomatosis), colon (e.g., colorectal adenocarcinoma), rectum, anus;
- pancreas (e.g., serous neoplasms, including microcystic or macrocystic serous cystadenoma, solid serous cystadenoma, Von Hippel-Landau (VHL)-associated serous cystic neoplasm, serous cystadenocarcinoma; mucinous cystic neoplasms (MCN), intraductal papillary mucinous neoplasms (IPMN), intraductal oncocytic papillary neoplasms (IOPN), intraductal tubular neoplasms, cystic acinar neoplasms, including acinar cell cystadenoma, acinar cell cystadenocarcinoma, pancreatic adenocarcinoma, invasive pancreatic ductal adenocarcinomas, including tubular adenocarcinoma, adenosquamous carcinoma, colloid carcinoma, medullary carcinoma, hepatoid carcinoma, signet ring cell carcinoma, undifferentiated carcinoma, undifferentiated carcinoma with osteoclast-like giant cells, acinar cell carcinoma, neuroendocrine neoplasms, neuroendocrine microadenoma, neuroendocrine tumors (NET), neuroendocrine carcinoma (NEC), including small cell or large cell NEC, insulinoma, gastrinoma, glucagonoma, serotonin-producing NET, somatostatinoma, VIPoma, solid-pseudopapillary neoplasms (SPN), pancreatoblastoma);
- gall bladder (e.g. carcinoma of the gallbladder and extrahepatic bile ducts, intrahepatic cholangiocarcinoma);
- neuro-endocrine (e.g., adrenal cortical carcinoma, carcinoid tumors, phaeochromocytoma, pituitary adenomas);
- thyroid (e.g., anaplastic (undifferentiated) carcinoma, medullary carcinoma, oncocytic tumors, papillary carcinoma, adenocarcinoma);
- liver (e.g., adenoma, combined hepatocellular and cholangiocarcinoma, fibrolamellar carcinoma, hepatoblastoma, hepatocellular carcinoma, mesenchymal, nested stromal epithelial tumor, undifferentiated carcinoma; hepatocellular carcinoma, intrahepatic cholangiocarcinoma, bile duct cystadenocarcinoma, epithelioid hemangioendothelioma, angiosarcoma, embryonal sarcoma, rhabdomyosarcoma, solitary fibrous tumor, teratoma, York sac tumor, carcinosarcoma, rhabdoid tumor);
- kidney (e.g., ALK-rearranged renal cell carcinoma, chromophobe renal cell carcinoma, clear cell renal cell carcinoma, clear cell sarcoma, metanephric adenoma, metanephric adenofibroma, mucinous tubular and spindle cell carcinoma, nephroma, nephroblastoma (Wilms tumor), papillary adenoma, papillary renal cell carcinoma, renal oncocytoma, renal cell carcinoma, succinate dehydrogenase-deficient renal cell carcinoma, collecting duct carcinoma);
- breast (e.g., invasive ductal carcinoma, including without limitation, acinic cell carcinoma, adenoid cystic carcinoma, apocrine carcinoma, cribriform carcinoma, glycogen-rich/clear cell, inflammatory carcinoma, lipid-rich carcinoma, medullary carcinoma, metaplastic carcinoma, micropapillary carcinoma, mucinous carcinoma, neuroendocrine carcinoma, oncocytic carcinoma, papillary carcinoma, sebaceous carcinoma, secretory breast carcinoma, tubular carcinoma; lobular carcinoma, including without limitation, pleomorphic carcinoma, signet ring cell carcinoma;
- peritoneum (e.g., mesothelioma; primary peritoneal cancer);
- female sex organ tissues, including ovary (e.g., choriocarcinoma, epithelial tumors, germ cell tumors, sex cord-stromal tumors), Fallopian tubes (e.g., serous adenocarcinoma, mucinous adenocarcinoma, endometrioid adenocarcinoma, clear cell adenocarcinoma, transitional cell carcinoma, squamous cell carcinoma, undifferentiated carcinoma, Müllerian tumors, adenosarcoma, leiomyosarcoma, teratoma, germ cell tumors, choriocarcinoma, trophoblastic tumors), uterus (e.g., carcinoma of the cervix, endometrial polyps, endometrial hyperplasia, intraepithelial carcinoma (EIC), endometrial carcinoma (e.g., endometrioid carcinoma, serous carcinoma, clear cell carcinoma, mucinous carcinoma, squamous cell carcinoma, transitional carcinoma, small cell carcinoma, undifferentiated carcinoma, mesenchymal neoplasia), leiomyoma (e.g., endometrial stromal nodule, leiomyosarcoma, endometrial stromal sarcoma (ESS), mesenchymal tumors), mixed epithelial and mesenchymal tumors (e.g., adenofibroma, carcinofibroma, adenosarcoma, carcinosarcoma (malignant mixed mesodermal sarcoma—MMMT)), endometrial stromal tumors, endometrial malignant mullerian mixed tumours, gestational trophoblastic tumors (partial hydatiform mole, complete hydatiform mole, invasive hydatiform mole, placental site tumour)), vulva, vagina;

male sex organ tissues, including prostate, testis (e.g., germ cell tumors, spermatocytic seminoma), penis;

bladder (e.g., squamous cell carcinoma, urothelial carcinoma, bladder urothelial carcinoma);

brain, (e.g., gliomas (e.g., astrocytomas, including non-infiltrating, low-grade, anaplastic, glioblastomas; oligodendrogliomas, ependymomas), meningiomas, gangliogliomas, schwannomas (neurilemmomas), craniopharyngiomas, chordomas, Non-Hodgkin lymphomas (NHLs), indolent non-Hodgkin's lymphoma (iNHL), refractory iNHL, pituitary tumors;

eye (e.g., retinoma, retinoblastoma, ocular melanoma, posterior uveal melanoma, iris hamartoma);

head and neck (e.g., nasopharyngeal carcinoma, Endolymphatic Sac Tumor (ELST), epidermoid carcinoma, laryngeal cancers including squamous cell carcinoma (SCC) (e.g., glottic carcinoma, supraglottic carcinoma, subglottic carcinoma, transglottic carcinoma), carcinoma in situ, verrucous, spindle cell and basaloid SCC, undifferentiated carcinoma, laryngeal adenocarcinoma, adenoid cystic carcinoma, neuroendocrine carcinomas, laryngeal sarcoma), head and neck paragangliomas (e.g., carotid body, jugulotympanic, vagal);

thymus (e.g., thymoma);

heart (e.g., cardiac myxoma);

lung (e.g., small cell carcinoma (SCLC), non-small cell lung carcinoma (NSCLC), including squamous cell carcinoma (SCC), adenocarcinoma and large cell carcinoma, carcinoids (typical or atypical), carcinosarcomas, pulmonary blastomas, giant cell carcinomas, spindle cell carcinomas, pleuropulmonary blastoma);

lymph (e.g., lymphomas, including Hodgkin's lymphoma, non-Hodgkin's lymphoma (NHL), indolent non-Hodgkin's lymphoma (iNHL), refractory iNHL, Epstein-Barr virus (EBV)-associated lymphoproliferative diseases, including B cell lymphomas and T cell lymphomas (e.g., Burkitt lymphoma; large B cell lymphoma, diffuse large B-cell lymphoma (DLBCL), mantle cell lymphoma, indolent B-cell lymphoma, low grade B cell lymphoma, fibrin-associated diffuse large cell lymphoma; primary effusion lymphoma; plasmablastic lymphoma; extranodal NK/T cell lymphoma, nasal type;

peripheral T cell lymphoma, cutaneous T cell lymphoma, angioimmunoblastic T cell lymphoma; follicular T cell lymphoma; systemic T cell lymphoma), lymphangioleiomyomatosis);

central nervous system (CNS) (e.g., gliomas including astrocytic tumors (e.g., pilocytic astrocytoma, pilomyxoid astrocytoma, subependymal giant cell astrocytoma, pleomorphic xanthoastrocytoma, diffuse astrocytoma, fibrillary astrocytoma, gemistocytic astrocytoma, protoplasmic astrocytoma, anaplastic astrocytoma, glioblastoma (e.g., giant cell glioblastoma, gliosarcoma, glioblastoma multiforme) and gliomatosis cerebri), oligodendroglial tumors (e.g., oligodendroglioma, anaplastic oligodendroglioma), oligoastrocytic tumors (e.g., oligoastrocytoma, anaplastic oligoastrocytoma), ependymal tumors (e.g., subependymom, myxopapillary ependymoma, ependymomas (e.g., cellular, papillary, clear cell, tanycytic), anaplastic ependymoma), optic nerve glioma, and non-gliomas (e.g., choroid plexus tumors, neuronal and mixed neuronal-glial tumors, pineal region tumors, embryonal tumors, medulloblastoma, meningeal tumors, primary CNS lymphomas, germ cell tumors, Pituitary adenomas, cranial and paraspinal nerve tumors, stellar region tumors); neurofibroma, meningioma, peripheral nerve sheath tumors, peripheral neuroblastic tumours (including without limitation neuroblastoma, ganglioneuroblastoma, ganglioneuroma), trisomy 19 ependymoma);

neuroendocrine tissues (e.g., paraganglionic system including adrenal medulla (pheochromocytomas) and extra-adrenal paraganglia ((extra-adrenal) paragangliomas);

skin (e.g., clear cell hidradenoma, cutaneous benign fibrous histiocytomas, cylindroma, hidradenoma, melanoma (including cutaneous melanoma, mucosal melanoma), pilomatricoma, Spitz tumors); and soft tissues (e.g., aggressive angiomyxoma, alveolar rhabdomyosarcoma, alveolar soft part sarcoma, angiofibroma, angiomatoid fibrous histiocytoma, synovial sarcoma, biphasic synovial sarcoma, clear cell sarcoma, dermatofibrosarcoma protuberans, desmoid-type fibromatosis, small round cell tumor, desmoplastic small round cell tumor, elastofibroma, embryonal rhabdomyosarcoma, Ewing's tumors/primitive neurectodermal tumors (PNET), extraskeletal myxoid chondrosarcoma, extraskeletal osteosarcoma, paraspinal sarcoma, inflammatory myofibroblastic tumor, lipoblastoma, lipoma, chondroid lipoma, liposarcoma/malignant lipomatous tumors, liposarcoma, myxoid liposarcoma, fibromyxoid sarcoma, lymphangioleiomyoma, malignant myoepithelioma, malignant melanoma of soft parts, myoepithelial carcinoma, myoepithelioma, myxoinflammatory fibroblastic sarcoma, undifferentiated sarcoma, pericytoma, rhabdomyosarcoma, non-rhabdomyosarcoma soft tissue sarcoma (NRSTS), soft tissue leiomyosarcoma, undifferentiated sarcoma, well-differentiated liposarcoma.

In some embodiments, the chromosome 9p21 deletion or MTAP-null associated disease or condition is a cancer selected from lung cancer, urothelial cancer, pancreatic cancer, esophageal cancer, bladder cancer, melanoma, mature B-cell neoplasms, head and neck cancer, bile duct cancer, esophagus cancer, glioblastoma, stomach cancer, adrenal cancer, breast cancer, ovarian cancer, thymic epithelial tumor, liver cancer, renal cancer, colorectal cancer, prostate cancer, leukemia, and cervical cancer.

In some embodiments, the chromosome 9p21 deletion or MTAP-null associated disease or condition is a cancer is selected from ovarian, lung, lymphoid, glioblastoma, colon, melanoma, gastric, pancreatic, and bladder cancer.

Dosage

The effective dosage of active ingredient employed may vary depending on the particular compound employed, the mode of administration, the condition being treated and the severity of the condition being treated. Such dosage may be ascertained readily by a person skilled in the art.

When treating or preventing a chromosome 9p21 deletion or MTAP-null associated disease or condition for which compounds of the present disclosure are indicated, generally satisfactory results are obtained when the compounds of the present disclosure are administered at a daily dosage of from about 0.1 milligram to about 300 milligram per kilogram of animal body weight. In some embodiments, the compounds of the present disclosure are given as a single daily dose or in divided doses two to six times a day, or in sustained release form. For most large mammals, the total daily dosage is from about 1 milligram to about 1000 milligrams, or from about 1 milligram to about 50 milligrams. In the case of a 70 kg adult human, the total daily dose will generally be from about 0.1 milligrams to about 200 milligrams. This dosage regimen may be adjusted to provide the optimal therapeutic response. In some embodiments, the total daily dosage is from about 1 milligram to about 900 milligrams, about 1 milligram to about 800 milligrams, about 1 milligram to about 700 milligrams, about 1 milligram to about 600 milligrams, about 1 milligram to about 400 milligrams, about 1 milligram to about 300 milligrams, about 1 milligram to about 200 milligrams, about 1 milligram to about 100 milligrams, about 1 milligram to about 50 milligrams, about 1 milligram to about 20 milligram, or about 1 milligram to about 10 milligrams.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are frequently alternated with resting periods of about 1 to 28 days, commonly about 7 days or about 14 days, between cycles. The treatment cycles, in other embodiments, may also be continuous.

In some embodiments, the methods provided herein comprise administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Combinations

In some embodiments, a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13), provided herein, or pharmaceutically acceptable salt thereof, is administered in combination with one or more additional therapeutic agents to treat or prevent a disease or condition disclosed herein. In some embodiments, the one or more additional therapeutic agents are one, two, three, or four additional therapeutic agents. In some embodiments, the one or more additional therapeutic agents are one additional therapeutic agent. In some embodiments, the one or more additional therapeutic agents are two additional therapeutic agents. In some embodiments, the one or more additional therapeutic agents are three additional therapeutic agents. In some embodiments, the one or more additional therapeutic agents are four additional therapeutic agents.

In some embodiments, the pharmaceutical compositions provided herein have a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, and one or more additional therapeutic agents. In some embodiments, the one or more additional therapeutic agents are one, two, three, or four additional therapeutic agents. In some embodiments, the one or more additional therapeutic agents are one additional therapeutic agent. In some embodiments, the one or more additional therapeutic agents are two additional therapeutic agents. In some embodiments, the one or more additional therapeutic agents are three additional therapeutic agents. In some embodiments, the one or more additional therapeutic agents are four additional therapeutic agents.

In some embodiments the one or more additional therapeutic agents include, e.g., an inhibitory immune checkpoint blocker or inhibitor, a stimulatory immune checkpoint stimulator, agonist or activator, a chemotherapeutic agent, an anti-cancer agent, a radiotherapeutic agent, an anti-neoplastic agent, an anti-proliferation agent, an anti-angiogenic agent, an anti-inflammatory agent, an immunotherapeutic agent, a therapeutic antigen-binding molecule (e.g., a mono- and multi-specific antibody, or fragment thereof, in any format, such as DART®, Duobody®, BiTE®, BIKE, TriKE, XmAb®, TandAb®, scFv, Fab, Fab derivative), a bi-specific antibody, a non-immunoglobulin antibody mimetic (e.g., including adnectin, affibody, affilin, affimer, affitin, alphabody, anticalin, peptide aptamer, armadillo repeat protein (ARM), atrimer, avimer, designed ankyrin repeat protein (DARPin®), fynomer, knottin, Kunitz domain peptide, monobody, and nanoCLAMPs), an antibody-drug conjugate (ADC), antibody-peptide conjugate), an oncolytic virus, a gene modifier or editor, a cell comprising a chimeric antigen receptor (CAR), e.g., including a T-cell immunotherapeutic agent, an NK-cell immunotherapeutic agent, or a macrophage immunotherapeutic agent, a cell comprising an engineered T-cell receptor (TCR-T), or any combination thereof.

Illustrative Targets

In some embodiments, the one or more additional therapeutic agents include, e.g., an inhibitor, agonist, antagonist, ligand, modulator, stimulator, blocker, activator or suppressor of a target (e.g., polypeptide or polynucleotide), such as: 2'-5'-oligoadenylate synthetase (OAS1; NCBI Gene ID: 4938); 5'-3' exoribonuclease 1 (XRN1; NCBI Gene ID: 54464); 5'-nucleotidase ecto (NT5E, CD73; NCBI Gene ID: 4907); ABL proto-oncogene 1, non-receptor tyrosine kinase (ABL1, BCR-ABL, c-ABL, v-ABL; NCBI Gene ID: 25); absent in melanoma 2 (AIM2; NCBI Gene ID: 9447); acetyl-CoA acyltransferase 2 (ACAA2; NCBI Gene ID: 10499); acid phosphatase 3 (ACP3; NCBI Gene ID: 55); adenosine deaminase (ADA, ADA1; NCBI Gene ID: 100); adenosine receptors (e.g., ADORA1 (A1), ADORA2A (A2a, A2AR), ADORA2B (A2b, A2BR), ADORA3 (A3); NCBI Gene IDs: 134, 135, 136, 137); AKT serine/threonine kinase 1 (AKT1, AKT, PKB; NCBI Gene ID: 207); alanyl aminopeptidase, membrane (ANPEP, CD13; NCBI Gene ID: 290); ALK receptor tyrosine kinase (ALK, CD242; NCBI Gene ID: 238); alpha fetoprotein (AFP; NCBI Gene ID: 174); amine oxidase copper containing (e.g., AOC1 (DAO1), AOC2, AOC3 (VAP1); NCBI Gene IDs: 26, 314, 8639); androgen receptor (AR; NCBI Gene ID: 367); angiopoietins (ANGPT1, ANGPT2; NCBI Gene IDs: 284, 285); angiotensin II receptor type 1 (AGTR1; NCBI Gene ID: 185); angiotensinogen (AGT; NCBI Gene ID: 183); apolipoprotein A1 (APOA1; NCBI Gene ID: 335); apoptosis inducing factor mitochondria associated 1 (AIFM1, AIF; NCBI Gene ID: 9131); arachidonate 5-lipoxygenase (ALOX5; NCBI Gene ID: 240); asparaginase (ASPG; NCBI Gene ID: 374569); asteroid homolog 1 (ASTE1; NCBI Gene ID: 28990); ATM serine/threonine kinase (ATM; NCBI Gene ID: 472); ATP binding cassette subfamily B member 1 (ABCB1, CD243, GP170; NCBI Gene ID: 5243); ATP-dependent Clp-protease (CLPP; NCBI Gene ID: 8192); ATR serine/threonine kinase (ATR; NCBI Gene ID: 545); AXL receptor tyrosine kinase (AXL; NCBI Gene ID: 558); B and T lymphocyte associated (BTLA, CD272; NCBI Gene ID:

151888); baculoviral IAP repeat containing proteins (BIRC2 (cIAP1), BIRC3 (cIAP2), XIAP (BIRC4, IAP3), BIRC5 (survivin); NCBI Gene IDs: 329, 330, 331, 332); basigin (Ok blood group) (BSG, CD147; NCBI Gene ID: 682); B-cell lymphoma 2 (BCL2; NCBI Gene ID: 596); BCL2 binding component 3 (BBC3, PUMA; NCBI Gene ID: 27113); BCL2 like (e.g., BCL2L1 (Bcl-x), BCL2L2 (BIM); Bcl-x; NCBI Gene IDs: 598, 10018); beta 3-adrenergic receptor (ADRB3; NCBI Gene ID: 155); bone gamma-carboxyglutamate protein (BGLAP; NCBI Gene ID: 632); bone morphogenetic protein-10 ligand (BMP10; NCBI Gene ID: 27302); bradykinin receptors (e.g., BDKRB1, BDKRB2; NCBI Gene IDs: 623, 624); B-RAF (BRAF; NCBI Gene ID: 273); breakpoint cluster region (BCR; NCBI Gene ID: 613); bromodomain and external domain (BET) bromodomain containing proteins (e.g., BRD2, BRD3, BRD4, BRDT; NCBI Gene IDs: 6046, 8019, 23476, 676); Bruton's tyrosine kinase (BTK; NCBI Gene ID: 695); cadherins (e.g., CDH3 (p-cadherin), CDH6 (k-cadherin); NCBI Gene IDs: 1001, 1004); cancer/testis antigens (e.g., CTAG1A, CTAG1B, CTAG2; NCBI Gene IDs: 1485, 30848, 246100); cannabinoid receptors (e.g., CNR1 (CB1), CNR2 (CB2); NCBI Gene IDs: 1268, 1269); carbohydrate sulfotransferase 15 (CHST15; NCBI Gene ID: 51363); carbonic anhydrases (e.g., CA1, CA2, CA3, CA4, CASA, CA5B, CA6, CA7, CA8, CA9, CA10, CA11, CA12, CA13, CA14; NCBI Gene IDs: 759, 760, 761, 762, 763, 765, 766, 767, 768, 770, 771, 11238, 23632, 56934, 377677); carcinoembryonic antigen related cell adhesion molecules (e.g., CEACAM3 (CD66d), CEACAM5 (CD66e), CEACAM6 (CD66c); NCBI Gene IDs: 1048, 1084, 4680); casein kinases (e.g., CSNK1A1 (CK1), CSNK2A1 (CK2); NCBI Gene IDs: 1452, 1457); caspases (e.g., CASP3, CASP7, CASP8; NCBI Gene IDs: 836, 840, 841, 864); catenin beta 1 (CTNNB1; NCBI Gene ID: 1499); cathepsin G (CTSG; NCBI Gene ID: 1511); Cbl proto-oncogene B (CBLB, Cbl-b; NCBI Gene ID: 868); C—C motif chemokine ligand 21 (CCL21; NCBI Gene ID: 6366); C—C motif chemokine receptor 2 (CCR2; NCBI Gene ID: 729230); C—C motif chemokine receptors (e.g., CCR3 (CD193), CCR4 (CD194), CCR5 (CD195), CCR8 (CDw198); NCBI Gene IDs: 1232, 1233, 1234, 1237); CCAAT enhancer binding protein alpha (CEBPA, CEBP; NCBI Gene ID: 1050); cell adhesion molecule 1 (CADM1; NCBI Gene ID: 23705); cell division cycle 7 (CDC7; NCBI Gene ID: 8317); cellular communication network factor 2 (CCN2; NCBI Gene ID: 1490); cereblon (CRBN; NCBI Gene ID: 51185); checkpoint kinases (e.g., CHEK1 (CHK1), CHEK2 (CHK2); NCBI Gene IDs: 1111, 11200); cholecystokinin B receptor (CCKBR; NCBI Gene ID: 887); chorionic somatomammotropin hormone 1 (CSH1; NCBI Gene ID: 1442); claudins (e.g., CLDN6, CLDN18; NCBI Gene IDs: 9074, 51208); cluster of differentiation markers (e.g., CD1A, CD1C, CD1D, CD1E, CD2, CD3 alpha (TRA), CD beta (TRB), CD gamma (TRG), CD delta (TRD), CD4, CD8A, CD8B, CD19, CD20 (MS4A1), CD22, CD24, CD25 (IL2RA, TCGFR), CD28, CD33 (SIGLEC3), CD37, CD38, CD39 (ENTPD1), CD40 (TNFRSF5), CD44 (MIC4, PGP1), CD47 (IAP), CD48 (BLAST1), CD52, CD55 (DAF), CD58 (LFA3), CD74, CD79a, CD79b, CD80 (B7-1), CD84, CD86 (B7-2), CD96 (TACTILE), CD99 (MIC2), CD115 (CSF1R), CD116 (GMCSFR, CSF2RA), CD122 (IL2RB), CD123 (IL3RA), CD128 (IL8R1), CD132 (IL2RG), CD135 (FLT3), CD137 (TNFRSF9, 4-1BB), CD142 (TF, TFA), CD152 (CTLA4), CD160, CD182 (IL8R2), CD193 (CCR3), CD194 (CCR4), CD195 (CCR5), CD207, CD221 (IGF1R), CD222 (IGF2R), CD223 (LAG3), CD226 (DNAM1), CD244, CD247, CD248, CD276 (B7-H3), CD331 (FGFR1), CD332 (FGFR2), CD333 (FGFR3), CD334 (FGFR4); NCBI Gene IDs: 909, 911, 912, 913, 914, 919, 920, 923, 925, 926, 930, 931, 933, 940, 941, 942, 945, 951, 952, 953, 958,960, 961, 962, 965, 972, 973, 974, 1043, 1232, 1233, 1234, 1237, 1436, 1438, 1493, 1604, 2152, 2260, 2261, 2263, 2322, 3480, 3482, 3559, 3560, 3561, 3563, 3577, 3579, 3604, 3902, 4267, 6955, 6957, 6964, 6965, 8832, 10666, 11126, 50489, 51744, 80381, 100133941); clusterin (CLU; NCBI Gene ID: 1191); coagulation factors (e.g., F7, FXA, NCBI Gene IDs: 2155, 2159); collagen type IV alpha chains (e.g., COL4A1, COL4A2, COL4A3, COL4A4, COL4A5; NCBI Gene IDs: 1282, 1284, 1285, 1286, 1287); collectin subfamily member 10 (COLEC10; NCBI Gene ID: 10584); colony stimulating factors (e.g., CSF1 (MCSF), CSF2 (GMCSF), CSF3 (GCSF); NCBI Gene IDs: 1435, 1437, 1440); complement factors (e.g., C3, C5; NCBI Gene IDs: 718, 727); COP9 signalosome subunit 5 (COPS5; NCBI Gene ID: 10987); C-type lectin domain family member (e.g., CLEC4C (CD303), CLEC9A (CD370), CLEC12A (CD371); CD371; NCBI Gene ID: 160364, 170482, 283420); C—X—C motif chemokine ligand 12 (CXCL12; NCBI Gene ID: 6387); C—X—C motif chemokine receptors (CXCR1 (IL8R1, CD128), CXCR2 (IL8R2, CD182), CXCR3 (CD182, CD183, IP-10R), CXCR4 (CD184); NCBI Gene ID: 2833, 3577, 3579, 7852); cyclin D1 (CCND1, BCL1; NCBI Gene ID: 595); cyclin dependent kinases (e.g., CDK1, CDK2, CDK3, CDK4, CDK5, CDK6, CDK7, CDK8, CDK9, CDK10, CDK12; NCBI Gene ID: 983, 1017, 1018, 1019, 1020, 1021, 1022, 1024, 1025, 8558, 51755); cyclin G1 (CCNG1; NCBI Gene ID: 900); cytochrome P450 family members (e.g., CYP2D6, CYP3A4, CYP11A1, CYP11B2, CYP17A1, CYP19A1, CYP51A1; NCBI Gene IDs: 1565, 1576, 1583, 1585, 1586, 1588, 1595); cytochrome P450 oxidoreductase (POR; NCBI Gene ID: 5447); cytokine inducible SH2 containing protein (CISH; NCBI Gene ID: 1154); cytotoxic T-lymphocyte associated protein 4 (CTLA4, CD152; NCBI Gene ID: 1493); DEAD-box helicases (e.g., DDX5, DDX6, DDX58; NCBI Gene IDs: 1655, 1656, 23586); delta like canonical Notch ligands (e.g., DLL3, DLL4; NCBI Gene IDs: 10683, 54567); diablo IAP-binding mitochondrial protein (DIABLO, SMAC; NCBI Gene ID: 56616); diacylglycerol kinases (e.g., DGKA, DGKZ; NCBI Gene IDs: 1606, 8525); dickkopf WNT signaling pathway inhibitors (e.g., DKK1, DKK3; NCBI Gene ID: 22943, 27122); dihydrofolate reductase (DHFR; NCBI Gene ID: 1719); dihydropyrimidine dehydrogenase (DPYD; NCBI Gene ID: 1806); dipeptidyl peptidase 4 (DPP4; NCBI Gene ID: 1803); discoidin domain receptor tyrosine kinases (e.g., DDR1 (CD167), DDR2; CD167; NCBI Gene ID: 780, 4921); DNA dependent protein kinase (PRKDC; NCBI Gene ID: 5591); DNA topoisomerases (e.g., TOP1, TOP2A, TOP2B, TOP3A, TOP3B; NCBI Gene ID: 7150, 7153, 7155, 7156, 8940); dopachrome tautomerase (DCT; NCBI Gene ID: 1638); dopamine receptor D2 (DRD2; NCBI Gene ID: 1318); DOT1 like histone lysine methyltransferase (DOT1L; NCBI Gene ID: 84444); ectonucleotide pyrophosphatase/phosphodiesterase 3 (ENPP3, CD203c; NCBI Gene ID: 5169); EMAP like 4 (EML4; NCBI Gene ID: 27436); endoglin (ENG; NCBI Gene ID: 2022); endoplasmic reticulum aminopeptidases (e.g., ERAP1, ERAP2; NCBI Gene ID: 51752, 64167); enhancer of zeste 2 polycomb repressive complex 2 subunit (EZH2; NCBI Gene ID: 2146); ephrin receptors (e.g., EPHA1, EPHA2EPHA3, EPHA4, EPHA5, EPHA7, EPHB4; NCBI Gene ID: 1969, 2041, 2042, 2043, 2044, 2045, 2050); ephrins (e.g., EFNA1, EFNA4, EFNB2; NCBI Gene ID: 1942, 1945, 1948); epidermal growth factor receptors (e.g., ERBB1 (HER1, EGFR), ERBB1 variant III (EGFRvIII), ERBB2 (HER2, NEU, CD340), ERBB3 (HER3), ERBB4 (HER4); NCBI Gene ID: 1956, 2064, 2065, 2066); epithelial cell adhesion molecule (EPCAM; NCBI Gene ID: 4072); epithelial mitogen (EPGN; NCBI Gene ID: 255324); eukaryotic translation elongation factors (e.g., EEF1A2, EEF2; NCBI Gene ID: 1917, 1938); eukaryotic translation initiation factors (e.g., EIF4A1, EIF5A; NCBI Gene ID: 1973, 1984); exportin-1 (XPO1; NCBI Gene ID: 7514); farnesoid X receptor (NR1H4, FXR; NCBI Gene ID: 9971); Fas ligand (FASLG, FASL, CD95L, CD178, TNFSF6; NCBI Gene ID: 356); fatty acid amide hydrolase (FAAH; NCBI Gene ID: 2166); fatty acid synthase (FASN; FAS; NCBI Gene ID: 2194); Fc fragment of Ig receptors (e.g., FCER1A, FCGRT, FCGR3A (CD16); NCBI Gene IDs: 2205, 2214, 2217); Fc receptor like 5 (FCRL5, CD307; NCBI Gene ID: 83416); fibroblast activation protein alpha (FAP; NCBI Gene ID: 2191); fibroblast growth factor receptors (e.g., FGFR1 (CD331), FGFR2 (CD332), FGFR3 (CD333), FGFR4 (CD334); NCBI Gene IDs: 2260, 2261, 2263, 2264); fibroblast growth factors (e.g., FGF1 (FGF alpha), FGF2 (FGF beta), FGF4, FGF5; NCBI Gene IDs: 2246, 2247, 2249, 2250); fibronectin 1 (FN1, MSF; NCBI Gene ID: 2335); fms related receptor tyrosine kinases (e.g., FLT1 (VEGFR1), FLT3 (STK1, CD135), FLT4 (VEGFR2); NCBI Gene IDs: 2321, 2322, 2324); fms related receptor tyrosine kinase 3 ligand (FLT3LG; NCBI Gene ID: 2323); focal adhesion kinase 2 (PTK2, FAK1; NCBI Gene ID: 5747); folate hydrolase 1 (FOLH1, PSMA; NCBI Gene ID: 2346); folate receptor 1 (FOLR1; NCBI Gene ID: 2348); forkhead box protein MI (FOXM1; NCBI Gene ID: 2305); FURIN (FURIN, PACE; NCBI Gene ID: 5045); FYN tyrosine kinase (FYN, SYN; NCBI Gene ID: 2534); galectins (e.g., LGALS3, LGALS8 (PCTA1), LGALS9; NCBI Gene ID: 3958, 3964, 3965); glucocorticoid receptor (NR3C1, GR; NCBI Gene ID: 2908); glucuronidase beta (GUSB; NCBI Gene ID: 2990); glutamate metabotropic receptor 1 (GRM1; NCBI Gene ID: 2911); glutaminase (GLS; NCBI Gene ID: 2744); glutathione S-transferase Pi (GSTP1; NCBI Gene ID: 2950); glycogen synthase kinase 3 beta (GSK3B; NCBI Gene ID: 2932); glypican 3 (GPC3; NCBI Gene ID: 2719); gonadotropin releasing hormone 1 (GNRH1; NCBI Gene ID: 2796); gonadotropin releasing hormone receptor (GNRHR; NCBI Gene ID: 2798); GPNMB glycoprotein nmb (GPNMB, osteoactivin; NCBI Gene ID: 10457); growth differentiation factor 2 (GDF2, BMP9; NCBI Gene ID: 2658); growth factor receptor-bound protein 2 (GRB2, ASH; NCBI Gene ID: 2885); guanylate cyclase 2C (GUCY2C, STAR, MECIL, MUCIL, NCBI Gene ID: 2984); H19 imprinted maternally expressed transcript (H19; NCBI Gene ID: 283120); HCK proto-oncogene, Src family tyrosine kinase (HCK; NCBI Gene ID: 3055); heat shock proteins (e.g., HSPA5 (HSP70, BIP, GRP78), HSPB1 (HSP27), HSP90B1 (GP96); NCBI Gene IDs: 3309, 3315, 7184); heme oxygenases (e.g., HMOX1 (HO1), HMOX2 (HO1); NCBI Gene ID: 3162, 3163); heparanase (HPSE; NCBI Gene ID: 10855); hepatitis A virus cellular receptor 2 (HAVCR2, TIM3, CD366; NCBI Gene ID: 84868); hepatocyte growth factor (HGF; NCBI Gene ID: 3082); HERV-H LTR-associating 2 (HHLA2, B7-H7; NCBI Gene ID: 11148); histamine receptor H2 (HRH2; NCBI Gene ID: 3274); histone deacetylases (e.g., HDAC1, HDAC7, HDAC9; NCBI Gene ID: 3065, 9734, 51564); HRas proto-oncogene, GTPase (HRAS; NCBI Gene ID: 3265); hypoxia-inducible factors (e.g., HIF1A, HIF2A (EPAS1); NCBI Gene IDs: 2034, 3091); I-Kappa-B kinase (IKK beta; NCBI Gene IDs: 3551, 3553); IKAROS family zinc fingers (IKZF1 (LYF1), IKZF3; NCBI Gene ID: 10320, 22806); immunoglobulin superfamily member 11 (IGSF11; NCBI Gene ID: 152404); indoleamine 2,3-dioxygenases (e.g., IDO1, IDO2; NCBI Gene IDs: 3620, 169355); inducible T cell costimulator (ICOS, CD278; NCBI Gene ID: 29851); inducible T cell costimulator ligand (ICOSLG, B7-H2; NCBI Gene ID: 23308); insulin like growth factor receptors (e.g., IGF1R, IGF2R; NCBI Gene ID: 3480, 3482); insulin like growth factors (e.g., IGF1, IGF2; NCBI Gene IDs: 3479, 3481); insulin receptor (INSR, CD220; NCBI Gene ID: 3643); integrin subunits (e.g., ITGA5 (CD49e), ITGAV (CD51), ITGB1 (CD29), ITGB2 (CD18, LFA1, MAC1), ITGB7; NCBI Gene IDs: 3678, 3685, 3688, 3695, 3698); intercellular adhesion molecule 1 (ICAM1, CD54; NCBI Gene ID: 3383); interleukin 1 receptor associated kinase 4 (IRAK4; NCBI Gene ID: 51135); interleukin receptors (e.g., IL2RA (TCGFR, CD25), IL2RB (CD122), IL2RG (CD132), IL3RA, IL6R, IL 13RA2 (CD213A2), IL22RA1; NCBI Gene IDs: 3598, 3559, 3560, 3561, 3563, 3570, 58985); interleukins (e.g., IL1A, IL1B, IL2, IL3, IL6 (HGF), IL7, IL8 (CXCL8), IL10 (TGIF), IL12A, IL12B, IL15, IL17A (CTLA8), IL18, IL23A, IL24, IL-29 (IFNL1); NCBI Gene IDs: 3552, 3553, 3558, 3562, 3565, 3569, 3574, 3586, 3592, 3593, 3600, 3605, 3606, 11009, 51561, 282618); isocitrate dehydrogenases (NADP(+)1) (e.g., IDH1, IDH2; NCBI Gene IDs: 3417, 3418); Janus kinases (e.g., JAK1, JAK2, JAK3; NCBI Gene IDs: 3716, 3717, 3718); kallikrein related peptidase 3 (KLK3; NCBI Gene ID: 354); killer cell immunoglobulin like receptor, Ig domains and long cytoplasmic tails (e.g., KIR2DL1 (CD158A), KIR2DL2 (CD158B1), KIR2DL3 (CD158B), KIR2DL4 (CD158D), KIR2DL5A (CD158F), KIR2DL5B, KIR3DL1 (CD158E1), KIR3DL2 (CD158K), KIR3 DPI (CD158c), KIR2DS2 (CD158J); NCBI Gene IDs: 3802, 3803, 3804, 3805, 3811, 3812, 57292, 553128, 548594, 100132285); killer cell lectin like receptors (e.g., KLRC1 (CD159A), KLRC2 (CD159c), KLRC3, KLRRC4, KLRD1 (CD94), KLRG1, KLRK1 (NKG2D, CD314); NCBI Gene IDs: 3821, 3822, 3823, 3824, 8302, 10219, 22914); kinase insert domain receptor (KDR, CD309, VEGFR2; NCBI Gene ID: 3791); kinesin family member 11 (KIF11; NCBI Gene ID: 3832); KiSS-1 metastasis suppressor (KISS1; NCBI Gene ID: 3814); KIT proto-oncogene, receptor tyrosine kinase (KIT, C-KIT, CD117; NCBI Gene ID: 3815); KRAS proto-oncogene, GTPase (KRAS; NCBI Gene ID: 3845); lactotransferrin (LTF; NCBI Gene ID: 4057); LCK proto-oncogene, Src family tyrosine kinase (LCK; NCBI Gene ID: 3932); LDL receptor related protein 1 (LRP1, CD91, IGFBP3R; NCBI Gene ID: 4035); leucine rich repeat containing 15 (LRRC15; NCBI Gene ID: 131578); leukocyte immunoglobulin like receptors (e.g., LILRB1 (ILT2, CD85J), LILRB2 (ILT4, CD85D); NCBI Gene ID: 10288, 10859); leukotriene A4 hydrolase (LTA4H; NCBI Gene ID: 4048); linker for activation of T-cells (LAT; NCBI Gene ID: 27040); luteinizing hormone/choriogonadotropin receptor (LHCGR; NCBI Gene ID: 3973); LY6/PLAUR domain containing 3 (LYPD3; NCBI Gene ID: 27076); lymphocyte activating 3 (LAG3; CD223; NCBI Gene ID: 3902); lymphocyte antigens (e.g., LY9 (CD229), LY75 (CD205); NCBI Gene IDs: 4063, 17076); LYN proto-oncogene, Src family tyrosine kinase (LYN; NCBI Gene ID: 4067); lymphocyte cytosolic protein 2 (LCP2; NCBI Gene ID: 3937); lysine demethylase 1A (KDM1A; NCBI Gene ID: 23028); lysophosphatidic acid receptor 1 (LPAR1, EDG2, LPA1, GPR26; NCBI Gene ID: 1902); lysyl oxidase (LOX; NCBI Gene ID: 4015); lysyl oxidase like 2 (LOXL2; NCBI Gene ID: 4017); macrophage migration inhibitory factor (MIF, GIF; NCBI Gene ID: 4282); macrophage stimulating 1 receptor (MST1R, CD136; NCBI Gene ID: 4486); MAGE family members (e.g., MAGEA1, MAGEA2, MAGEA2B, MAGEA3, MAGEA4, MAGEA5, MAGEA6, MAGEA10, MAGEA11, MAGEC1, MAGEC2, MAGED1, MAGED2; NCBI Gene IDs: 4100, 4101, 4102, 4103, 4104, 4105, 4109, 4110, 9500, 9947, 10916, 51438, 266740); major histocompatibility complexes (e.g., HLA-A, HLA-E, HLA-F, HLA-G; NCBI Gene IDs: 3105, 3133, 3134, 3135); major vault protein (MVP, VAULT1; NCBI Gene ID: 9961); MALT1 paracaspase (MALT1; NCBI Gene ID: 10892); MAPK activated protein kinase 2 (MAPKAPK2; NCBI Gene ID: 9261); MAPK interacting serine/threonine kinases (e.g., MKNK1, MKNK2; NCBI Gene IDs: 2872, 8569); matrix metallopeptidases (e.g., MMP1, MMP2, MMP3, MMP7, MMP8, MMP9, MMP10, MMP11, MMP12, MMP13, MMP14, MMP15, MMP16, MMP17, MMP19, MMP20, MMP21, MMP24, MMP25, MMP26, MMP27, MMP28; NCBI Gene IDs: 4312, 4313, 4314, 4316, 4317, 4318, 4319, 4320, 4321, 4322, 4323, 4324, 4325, 4326, 4327, 9313, 10893, 56547, 64066, 64386, 79148, 118856); MCL1 apoptosis regulator, BCL2 family member (MCL1; NCBI Gene ID: 4170); MDM2 proto-oncogene (MDM2; NCBI Gene ID: 4193); MDM4 regulator of p53 (MDM4; BMFS6; NCBI Gene ID: 4194); mechanistic target of rapamycin kinase (MTOR, FRAP1; NCBI Gene ID: 2475); melan-A (MLANA; NCBI Gene ID: 2315); melanocortin receptors (MC1R, MC2R; NCBI Gene IDs: 4157, 4148); MER proto-oncogene, tyrosine kinase (MERTK; NCBI Gene ID: 10461); mesothelin (MSLN; NCBI Gene ID: 10232); MET proto-oncogene, receptor tyrosine kinase (MET, c-Met, HGFR; NCBI Gene ID: 4233); methionyl aminopeptidase 2 (METAP2, MAP2; NCBI Gene ID: 10988); MHC class I polypeptide-related sequences (e.g., MICA, MICB; NCBI Gene IDs: 4277, 100507436); mitogen activated protein kinases (e.g., MAPKI (ERK2), MAPK3 (ERK1), MAPK8 (JNK1), MAPK9 (JNK2), MAPK10 (JNK3), MAPK11 (p38 beta), MAPK12; NCBI Gene IDs: 5594, 5595, 5599, 5600, 5601, 5602, 819251); mitogen-activated protein kinase kinase kinases (e.g., MAP3K5 (ASK1), MAP3K8 (TPL2, AURA2); NCBI Gene IDs: 4217, 1326); mitogen-activated protein kinase kinase kinase kinase 1 (MAP4K1, HPK1; NCBI Gene ID: 11184); mitogen-activated protein kinase kinases (e.g., MAP2K1 (MEK1), MAP2K2 (MEK2), MAP2K7 (MEK7); NCBI Gene IDs: 5604, 5605, 5609); MPL proto-oncogene, thrombopoietin receptor (MPL; NCBI Gene ID: 4352); mucins (e.g., MUC1 (including splice variants thereof (e.g., including MUC1/A, C, D, X, Y, Z and REP)), MUC5AC, MUC16 (CA125); NCBI Gene IDs: 4582, 4586, 94025); MYC proto-oncogene, bHLH transcription factor (MYC; NCBI Gene ID: 4609); myostatin (MSTN, GDF8; NCBI Gene ID: 2660); myristoylated alanine rich protein kinase C substrate (MARCKS; NCBI Gene ID: 4082); natriuretic peptide receptor 3 (NPR3; NCBI Gene ID: 4883); natural killer cell cytotoxicity receptor 3 ligand 1 (NCR3LG1, B7-H6; NCBI Gene ID: 374383); necdin, MAGE family member (NDN; NCBI Gene ID: 4692); nectin cell adhesion molecules (e.g., NECTIN2 (CD112, PVRL2), NECTIN4 (PVRL4); NCBI Gene IDs: 5819, 81607); neural cell adhesion molecule 1 (NCAM1, CD56; NCBI Gene ID: 4684); neuropilins (e.g., NRP1 (CD304, VEGF165R), NRP2 (VEGF165R2); NCBI Gene IDs: 8828, 8829); neurotrophic receptor tyrosine kinases (e.g., NTRK1 (TRKA), NTRK2 (TRKB), NTRK3 (TRKC); NCBI Gene IDs: 4914, 4915, 4916); NFKB activating protein (NKAP; NCBI Gene ID: 79576); NIMA related kinase 9 (NEK9; NCBI Gene ID: 91754); NLR family pyrin domain containing 3 (NLRP3, NALP3; NCBI Gene ID: 114548); notch receptors (e.g., NOTCH1, NOTCH2, NOTCH3, NOTCH4; NCBI Gene IDs: 4851, 4853, 4854, 4855); NRAS proto-oncogene, GTPase (NRAS; NCBI Gene ID: 4893); nuclear factor kappa B (NFKB1, NFKB2; NCBI Gene IDs: 4790, 4791); nuclear factor, erythroid 2 like 2 (NFE2L2; NRF2; NCBI Gene ID: 4780); nuclear receptor subfamily 4 group A member 1 (NR4A1; NCBI Gene ID: 3164); nucleolin (NCL; NCBI Gene ID: 4691); nucleophosmin 1 (NPM1; NCBI Gene ID: 4869); nucleotide binding oligomerization domain containing 2 (NOD2; NCBI Gene ID: 64127); nudix hydrolase 1 (NUDT1; NCBI Gene ID: 4521); O-6-methylguanine-DNA methyltransferase (MGMT; NCBI Gene ID: 4255); opioid receptor delta 1 (OPRD1; NCBI Gene ID: 4985); ornithine decarboxylase 1 (ODC1; NCBI Gene ID: 4953); oxoglutarate dehydrogenase (OGDH; NCBI Gene ID: 4967); parathyroid hormone (PTH; NCBI Gene ID: 5741); PD-L1 (CD274; NCBI Gene ID: 29126); periostin (POSTN; NCBI Gene ID: 10631); peroxisome proliferator activated receptors (e.g., PPARA (PPAR alpha), PPARD (PPAR delta), PPARG (PPAR gamma); NCBI Gene IDs: 5465, 5467, 5468); phosphatase and tensin homolog (PTEN; NCBI Gene ID: 5728); phosphatidylinositol-4,5-bisphosphate 3-kinases (PIK3CA (PI3K alpha), PIK3CB (PI3K beta), PIK3CD (PI3K delta), PIK3CG (PI3K gamma); NCBI Gene IDs: 5290, 5291, 5293, 5294); phospholipases (e.g., PLA2G1B, PLA2G2A, PLA2G2D, PLA2G3, PLA2G4A, PLA2G5, PLA2G7, PLA2G10, PLA2G12A, PLA2G12B, PLA2G15; NCBI Gene IDs: 5319, 5320, 5321, 5322, 7941, 8399, 50487, 23659, 26279, 81579, 84647); Pim proto-oncogene, serine/threonine kinases (e.g., PIM1, PIM2, PIM3; NCBI Gene IDs: 5292, 11040, 415116); placenta growth factor (PGF; NCBI Gene ID: 5228); plasminogen activator, urokinase (PLAU, u-PA, ATF; NCBI Gene ID: 5328); platelet derived growth factor receptors (e.g., PDGFRA (CD140A, PDGFR2), FDGFRB (CD140B, PDGFR1); NCBI Gene IDs: 5156, 5159); plexin B1 (PLXNB1; NCBI Gene ID: 5364); poliovirus receptor (PVR) cell adhesion molecule (PVR, CD155; NCBI Gene ID: 5817); polo like kinase 1 (PLK1; NCBI Gene ID: 5347); poly(ADP-ribose) polymerases (e.g., PARP1, PARP2, PARP3; NCBI Gene IDs: 142, 10038, 10039); polycomb protein EED (EED; NCBI Gene ID: 8726); porcupine O-acyltransferase (PORCN; NCBI Gene ID: 64840); PRAME nuclear receptor transcriptional regulator (PRAME; NCBI Gene ID: 23532); premelanosome protein (PMEL; NCBI Gene ID: 6490); progesterone receptor (PGR; NCBI Gene ID: 5241); programmed cell death 1 (PDCD1, PD-1, CD279; NCBI Gene ID: 5133); programmed cell death 1 ligand 2 (PDCD1LG2, CD273, PD-L2; NCBI Gene ID: 80380); prominin 1 (PROM1, CD133; NCBI Gene ID: 8842); promyelocytic leukemia (PML; NCBI Gene ID: 5371); prosaposin (PSAP; NCBI Gene ID: 5660); prostaglandin E receptor 4 (PTGER4; NCBI Gene ID: 5734); prostaglandin E synthase (PTGES; NCBI Gene ID: 9536); prostaglandin-endoperoxide synthases (PTGS1 (COX1), PTGS2 (COX2); NCBI Gene ID: 5742, 5743); proteasome 20S subunit beta 9 (PSMB9; NCBI Gene ID: 5698); protein arginine methyltransferases (e.g., PRMT1; NCBI Gene ID: 3276); protein kinase N3 (PKN3; NCBI Gene ID: 29941); protein phosphatase 2A (PPP2CA; NCBI Gene ID: 5515); protein tyrosine kinase 7 (inactive) (PTK7; NCBI Gene ID: 5754); protein tyrosine phosphatase receptors (PTPRB (PTPB), PTPRC (CD45R); NCBI Gene ID: 5787, 5788); prothymosin alpha (PTMA; NCBI Gene ID: 5757); purine nucleoside phosphorylase (PNP; NCBI Gene ID: 4860); purinergic receptor P2X 7 (P2RX7; NCBI Gene ID: 5027); PVR related immunoglobulin domain containing (PVRIG, CD112R; NCBI Gene ID: 79037); Raf-1 proto-oncogene, serine/threonine kinase (RAF1, c-Raf; NCBI Gene ID: 5894); RAR-related orphan receptor gamma (RORC; NCBI Gene ID: 6097); ras homolog family member C (RHOC); NCBI Gene ID: 389); Ras homolog, mTORC1 binding (RHEB; NCBI Gene ID: 6009); RB transcriptional corepressor 1 (RB1; NCBI Gene ID: 5925); receptor-interacting serine/threonine protein kinase 1 (RIPK1; NCBI Gene ID: 8737); ret proto-oncogene (RET; NCBI Gene ID: 5979); retinoic acid early transcripts (e.g., RAET1E, RAET1G, RAET1L; NCBI Gene IDs: 135250, 154064, 353091); retinoic acid receptors alpha (e.g., RARA, RARG; NCBI Gene IDs: 5914, 5916); retinoid X receptors (e.g., RXRA, RXRB, RXRG; NCBI Gene IDs: 6256, 6257, 6258); Rho associated coiled-coil containing protein kinases (e.g., ROCK1, ROCK2; NCBI Gene IDs: 6093, 9475); ribosomal protein S6 kinase B1 (RPS6KB1, S6K-beta 1; NCBI Gene ID: 6198); ring finger protein 128 (RNF128, GRAIL; NCBI Gene ID: 79589); ROS proto-oncogene 1, receptor tyrosine kinase (ROS1; NCBI Gene ID: 6098); roundabout guidance receptor 4 (ROBO4; NCBI Gene ID: 54538); RUNX family transcription factor 3 (RUNX3; NCBI Gene ID: 864); S100 calcium binding protein A9 (S100A9; NCBI Gene ID: 6280); secreted frizzled related protein 2 (SFRP2; NCBI Gene ID: 6423); secreted phosphoprotein 1 (SPP1; NCBI Gene ID: 6696); secretoglobin family 1A member 1 (SCGB1A1; NCBI Gene ID: 7356); selectins (e.g., SELE, SELL (CD62L), SELP (CD62); NCBI Gene IDs: 6401, 6402, 6403); semaphorin 4D (SEMA4D; CD100; NCBI Gene ID: 10507); sialic acid binding Ig like lectins (SIGLEC7 (CD328), SIGLEC9 (CD329), SIGLEC10; NCBI Gene ID: 27036, 27180, 89790); signal regulatory protein alpha (SIRPA, CD172A; NCBI Gene ID: 140885); signal transducer and activator of transcription (e.g., STAT1, STAT3, STAT5A, STAT5B; NCBI Gene IDs: 6772, 6774, 6776, 6777); sirtuin-3 (SIRT3; NCBI Gene ID: 23410); signaling lymphocytic activation molecule (SLAM) family members (e.g., SLAMF1 (CD150), SLAMF6 (CD352), SLAMF7 (CD319), SLAMF8 (CD353), SLAMF9; NCBI Gene IDs: 56833, 57823, 89886, 114836); SLIT and NTRK like family member 6 (SLITRK6; NCBI Gene ID: 84189); smoothened, frizzled class receptor (SMO; NCBI Gene ID: 6608); soluble epoxide hydrolase 2 (EPHX2; NCBI Gene ID: 2053); solute carrier family members (e.g., SLC3A2 (CD98), SLC5A5, SLC6A2, SLC10A3, SLC34A2, SLC39A6, SLC43A2 (LAT4), SLC44A4; NCBI Gene IDs: 6520, 6528, 6530, 8273, 10568, 25800, 80736, 124935); somatostatin receptors (e.g., SSTR1, SSTR2, SSTR3, SSTR4, SSTR5; NCBI Gene IDs: 6751, 6752, 6753, 6754, 6755); sonic hedgehog signaling molecule (SHH; NCBI Gene ID: 6469); Spl transcription factor (SP1; NCBI Gene ID: 6667); sphingosine kinases (e.g., SPHK1, SPHK2; NCBI Gene IDs: 8877, 56848); sphingosine-1-phosphate receptor 1 (S1PR1, CD363; NCBI Gene ID: 1901); spleen associated tyrosine kinase (SYK; NCBI Gene ID: 6850); splicing factor 3B factor 1 (SF3B1; NCBI Gene ID: 23451); SRC proto-oncogene, non-receptor tyrosine kinase (SRC; NCBI Gene ID: 6714); stabilin 1 (STAB1, CLEVER-1; NCBI Gene ID: 23166); STEAP family member 1 (STEAP1; NCBI Gene ID: 26872); steroid sulfatase (STS; NCBI Gene ID: 412); stimulator of interferon response cGAMP interactor 1 (STING1; NCBI Gene ID: 340061); superoxide dismutase 1 (SOD1, ALS1; NCBI Gene ID: 6647); suppressors of cytokine signaling (SOCS1 (CISH1), SOCS3 (CISH3); NCBI Gene ID: 8651, 9021); synapsin 3 (SYN3; NCBI Gene ID: 8224); syndecan 1 (SDC1, CD138, syndecan; NCBI Gene ID: 6382); synuclein alpha (SNCA, PARK1; NCBI Gene ID: 6622); T cell immunoglobulin and mucin domain containing 4 (TIMD4, SMUCKLER; NCBI Gene ID: 91937); T cell immunoreceptor with Ig and ITIM domains (TIGIT; NCBI Gene ID: 201633); tachykinin receptors (e.g., TACR1, TACR3; NCBI Gene ID: 6869, 6870); TANK binding kinase 1 (TBK1; NCBI Gene ID: 29110); tankyrase (TNKS; NCBI Gene ID: 8658); TATA-box binding protein associated factor, RNA polymerase I subunit B (TAF1B; NCBI Gene ID: 9014); T-box transcription factor T (TBXT; NCBI Gene ID: 6862); TCDD inducible poly(ADP-ribose) polymerase (TIPARP, PAPR7; NCBI Gene ID: 25976); tec protein tyrosine kinase (TEC; NCBI Gene ID: 7006); TEK receptor tyrosine kinase (TEK, CD202B, TIE2; NCBI Gene ID: 7010); telomerase reverse transcriptase (TERT; NCBI Gene ID: 7015); tenascin C (TNC; NCBI Gene ID: 3371); three prime repair exonucleases (e.g., TREX1, TREX2; NCBI Gene ID: 11277, 11219); thrombomodulin (THBD, CD141; NCBI Gene ID: 7056); thymidine kinases (e.g., TK1, TK2; NCBI Gene IDs: 7083, 7084); thymidine phosphorylase (TYMP; NCBI Gene ID: 1890); thymidylate synthase (TYMS; NCBI Gene ID: 7298); thyroid hormone receptor (THRA, THRB; NCBI Gene IDs: 7606, 7608); thyroid stimulating hormone receptor (TSHR; NCBI Gene ID: 7253); TNF superfamily members (e.g., TNFSF4 (OX40L, CD252), TNFSF5 (CD40L), TNFSF7 (CD70), TNFSF8 (CD153, CD30L), TNFSF9 (4-1BB-L, CD137L), TNFSF10 (TRAIL, CD253, APO2L), TNFSF11 (CD254, RANKL2, TRANCE), TNFSF13 (APRIL, CD256, TRAIL2), TNFSF13b (BAFF, BLYS, CD257), TNFSF14 (CD258, LIGHT), TNFSF18 (GITRL); NCBI Gene IDs: 944, 959, 970, 7292, 8600, 8740, 8741, 8743, 8744, 8995); toll like receptors (e.g., TLR1 (CD281), TLR2 (CD282), TLR3 (CD283), TLR4 (CD284), TLR5, TLR6 (CD286), TLR7, TLR8 (CD288), TLR9 (CD289), TLR10 (CD290); NCBI Gene IDs: 7096, 7097, 7098, 7099, 10333, 51284, 51311, 54106, 81793); transferrin (TF; NCBI Gene ID: 7018); transferrin receptor (TFRC, CD71; NCBI Gene ID: 7037); transforming growth factors (e.g., TGFA, TGFB1; NCBI Gene ID: 7039, 7040); transforming growth factor receptors (e.g., TGFBR1, TGFBR2, TGFBR3; NCBI Gene ID: 7046, 7048, 7049); transforming protein E7 (E7; NCBI Gene ID: 1489079); transglutaminase 5 (TGM5; NCBI Gene ID: 9333); transient receptor potential cation channel subfamily V member 1 (TRPV1, VR1; NCBI Gene ID: 7442); transmembrane and immunoglobulin domain containing 2 (TMIGD2, CD28H, IGPR1; NCBI Gene ID: 126259); triggering receptors expressed on myeloid cells (e.g., TREM1 (CD354), TREM2; NCBI Gene ID: 54209, 54210); trophinin (TRO, MAGED3; NCBI Gene ID: 7216); trophoblast glycoprotein (TPBG; NCBI Gene ID: 7162); tryptophan 2,3-dioxygenase (TDO2; NCBI Gene ID: 6999); tryptophan hydroxylases (e.g., TPH1, TPH2; NCBI Gene ID: 7166, 121278); tumor associated calcium signal transducer 2 (TACSTD2, TROP2, EGP1; NCBI Gene ID: 4070); tumor necrosis factor (TNF; NCBI Gene ID: 7124); tumor necrosis factor (TNF) receptor superfamily members (e.g., TNFRSF1A (CD120a), TNFRSF1B (CD120b), TNFRSF4 (OX40), TNFRSF5 (CD40), TNFRSF6 (CD95, FAS receptor), TNFRSF7 (CD27), TNFRSF8 (CD30), TNFRSF9 (CD137, 4-1BB), TNFRSF10A (CD261), TNFRSF10B (TRAIL, DR5, CD262), TNFRSF10C, TNFRSF10D, TNFRSF11A, TNFRSF11B (OPG), TNFRSF12A, TNFRSF13B, TNFR13C (CD268, BAFFR), TNFRSF14 (CD270, LIGHTR), TNFRSF16, TNFRSF17 (CD269, BCMA), TNFRSF18 (GITR, CD357), TNFRSF19, TNFRSF21, TNFRSF25, NCBI Gene IDs: 355, 608, 939, 943, 958, 3604, 4804, 4982, 7132, 7133, 7293, 8718, 8764, 8784, 8792, 8793, 8794, 8795, 8797, 23495, 27242, 51330, 55504); tumor protein p53 (TP53; NCBI Gene ID: 7157); tumor suppressor 2, mitochondrial calcium regulator (TUSC2; NCBI Gene ID: 11334); TYRO3 protein tyrosine kinase (TYRO3; BYK; NCBI Gene ID: 7301); tyrosinase (TYR; NCBI Gene ID: 7299); tyrosine hydroxylase (TH; NCBI Gene ID: 7054); tyrosine kinase with immunoglobulin like and EGF like domains 1 (e.g., TIE1, TIE1; NCBI Gene ID: 7075); tyrosine-protein phosphatase non-receptor type 11 (PTPN11, SHP2; NCBI Gene ID: 5781); ubiquitin conjugating enzyme E2 I (UBE2I, UBC9; NCBI Gene ID: 7329); ubiquitin C-terminal hydrolase L5 (UCHL5; NCBI Gene ID: 51377); ubiquitin specific peptidase 7 (USP7; NCBI Gene ID: 7874); ubiquitin-like modifier activating enzyme 1 (UBA1; NCBI Gene ID: 7317); UL16 binding proteins (e.g., ULBP1, ULBP2, ULBP3; NCBI Gene ID: 79465, 80328, 80328); valosin-containing protein (VCP, CDC48; NCBI Gene ID: 7415); vascular cell adhesion molecule 1 (VCAM1, CD106; NCBI Gene ID: 7412); vascular endothelial growth factors (e.g., VEGFA, VEGFB; NCBI Gene ID: 7422, 7423); vimentin (VIM; NCBI Gene ID: 7431); vitamin D receptor (VDR; NCBI Gene ID: 7421); V-set domain containing T cell activation inhibitor 1 (VTCN1, B7-H4; NCBI Gene ID: 79679); V-set immunoregulatory receptor (VSIR, VISTA, B7-H5; NCBI Gene ID: 64115); WEE1 G2 checkpoint kinase (WEE1; NCBI Gene ID: 7465); WRN RecQ like helicase (WRN; RECQ3; NCBI Gene ID: 7486); WT1 transcription factor (WT1; NCBI Gene ID: 7490); WW domain containing transcription regulator 1 (WWTR1; TAZ; NCBI Gene ID: 25937); X—C motif chemokine ligand 1 (XCL1, ATAC; NCBI Gene ID: 6375); X—C motif chemokine receptor 1 (XCR1, GPR5, CCXCR1; NCBI Gene ID: 2829); Yes1 associated transcriptional regulator (YAP1; NCBI Gene ID: 10413); or zeta chain associated protein kinase 70 (ZAP70; NCBI Gene ID: 7535).

In some embodiments, the one or more additional therapeutic agents include, e.g., an agent targeting 5'-nucleotidase ecto (NT5E or CD73; NCBI Gene ID: 4907); adenosine A2A receptor (ADORA2A; NCBI Gene ID: 135); adenosine AzB receptor (ADORA2B; NCBI Gene ID: 136); C—C motif chemokine receptor 8 (CCR8, CDw198; NCBI Gene ID: 1237); cytokine inducible SH2 containing protein (CISH; NCBI Gene ID: 1154); diacylglycerol kinase alpha (DGKA, DAGK, DAGK1 or DGK-alpha; NCBI Gene ID: 1606); fms like tyrosine kinase 3 (FLT3, CD135; NCBI Gene ID: 2322); integrin associated protein (IAP, CD47; NCBI Gene ID: 961); interleukine-2 (IL2; NCBI Gene ID:3558); interleukine 2 receptor (IL2RA, IL2RB, IL2RG; NCBI Gene IDs: 3559, 3560, 3561); Kirsten rat sarcoma virus (KRAS; NCBI Gene ID: 3845; including mutations, such as KRAS G12C or G12D); mitogen-activated protein kinase kinase kinase kinase 1 (MAP4K1) (also called Hematopoietic Progenitor Kinase 1 (HPK1), NCBI Gene ID: 11184); myeloid cell leukemia sequence 1 apoptosis regulator (MCL1; NCBI Gene ID: 4170); phosphatidylinositol-4,5-bisphosphate 3-kinase, catalytic subunit delta (PIK3CD; NCBI Gene ID: 5293); programmed death-ligand 1 (PD-L1, CD274; NCBI Gene ID 29126); programmed cell death protein 1 (PD-1, CD279; NCBI Gene ID: 5133); proto-oncogen c-KIT (KIT, CD117; NCBI Gene ID: 3815); signal-regulatory protein alpha (SIRPA, CD172A; NCBI Gene ID: 140885); TCDD inducible poly(ADP-ribose) polymerase (TIPARP, PARP7; NCBI Gene ID: 25976); T cell immunoreceptor with Ig and ITIM domains (TIGIT; NCBI Gene ID: 201633); triggering receptor expressed on myeloid cells 1 (TREM1; NCBI Gene ID: 54210); triggering receptor expressed on myeloid cells 2 (TREM2; NCBI Gene ID: 54209); tumor-associated calcium signal transducer 2 (TACSTD2, TROP2, EGP1; NCBI Gene ID: 4070); tumor necrosis factor receptor superfamily, member 4 (TNFRSF4, CD134, OX40; NCBI Gene ID:7293); tumor necrosis factor receptor superfamily, member 9 (TNFRSF9, 4-1BB, CD137; NCBI Gene ID: 3604); tumor necrosis factor receptor superfamily, member 18 (TNFRSF18, CD357, GITR; NCBI Gene ID: 8784); WRN RecQ like helicase (WRN; NCBI Gene ID: 7486); or zinc finger protein Helios (IKZF2; NCBI Gene ID: 22807).

Illustrative Mechanisms of Action

Immune Checkpoint Modulators

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of cancer cells within the tumor microenvironment. Activation or stimulation of stimulatory immune check points can augment the effect of immune checkpoint inhibitors in cancer therapeutics. In some embodiments, the immune checkpoint proteins or receptors regulate T cell responses (e.g., reviewed in Xu, et al., *J Exp Clin Cancer Res.* (2018) 37:110). In some embodiments, the immune checkpoint proteins or receptors regulate NK cell responses (e.g., reviewed in Davis, et al., *Semin Immunol.* (2017) 31:64-75 and Chiossone, et al., *Nat Rev Immunol.* (2018) 18(11):671-688). Inhibition of regulatory T-cells (Treg) or Treg depletion can alleviate their suppression of antitumor immune responses and have anticancer effects (e.g., reviewed in Plitas and Rudensky, *Annu. Rev. Cancer Biol.* (2020) 4:459-77; Tanaka and Sakaguchi, *Eur. J. Immunol.* (2019) 49:1140-1146).

Examples of immune checkpoint proteins or receptors that can be combined with a compound provided herein, or pharmaceutically acceptable salt thereof, include CD27 (NCBI Gene ID: 939), CD70 (NCBI Gene ID: 970); CD40 (NCBI Gene ID: 958), CD40LG (NCBI Gene ID: 959); CD47 (NCBI Gene ID: 961), SIRPA (NCBI Gene ID: 140885); CD48 (SLAMF2; NCBI Gene ID: 962), transmembrane and immunoglobulin domain containing 2 (TMIGD2, CD28H; NCBI Gene ID: 126259), CD84 (LY9B, SLAMF5; NCBI Gene ID: 8832), CD96 (NCBI Gene ID: 10225), CD160 (NCBI Gene ID: 11126), MS4A1 (CD20; NCBI Gene ID: 931), CD244 (SLAMF4; NCBI Gene ID: 51744); CD276 (B7H3; NCBI Gene ID: 80381); V-set domain containing T cell activation inhibitor 1 (VTCN1, B7H4); V-set immunoregulatory receptor (VSIR, B7H5, VISTA; NCBI Gene ID: 64115); immunoglobulin superfamily member 11 (IGSF11, VSIG3; NCBI Gene ID: 152404); natural killer cell cytotoxicity receptor 3 ligand 1 (NCR3LG1, B7H6; NCBI Gene ID: 374383); HERV-H LTR-associating 2 (HHLA2, B7H7; NCBI Gene ID: 11148); inducible T cell co-stimulator (ICOS, CD278; NCBI Gene ID: 29851); inducible T cell co-stimulator ligand (ICOSLG, B7H2; NCBI Gene ID: 23308); TNF receptor superfamily member 4 (TNFRSF4, OX40; NCBI Gene ID: 7293); TNF superfamily member 4 (TNFSF4, OX40L; NCBI Gene ID: 7292); TNFRSF8 (CD30; NCBI Gene ID: 943), TNFSF8

(CD30L; NCBI Gene ID: 944); TNFRSF10A (CD261, DR4, TRAILR1; NCBI Gene ID: 8797), TNFRSF9 (CD137; NCBI Gene ID: 3604), TNFSF9 (CD137L; NCBI Gene ID: 8744); TNFRSF10B (CD262, DR5, TRAILR2; NCBI Gene ID: 8795), TNFRSF10 (TRAIL; NCBI Gene ID: 8743); TNFRSF14 (HVEM, CD270; NCBI Gene ID: 8764), TNFSF14 (HVEML; NCBI Gene ID: 8740); CD272 (B and T lymphocyte associated (BTLA); NCBI Gene ID: 151888); TNFRSF17 (BCMA, CD269; NCBI Gene ID: 608), TNFSF13B (BAFF; NCBI Gene ID: 10673); TNFRSF18 (GITR; NCBI Gene ID: 8784), TNFSF18 (GITRL; NCBI Gene ID: 8995); MHC class I polypeptide-related sequence A (MICA; NCBI Gene ID: 100507436); MHC class I polypeptide-related sequence B (MICB; NCBI Gene ID: 4277); CD274 (CD274, PDL1, PD-L1; NCBI Gene ID: 29126); programmed cell death 1 (PDCD1, PD1, PD-1; NCBI Gene ID: 5133); cytotoxic T-lymphocyte associated protein 4 (CTLA4, CD152; NCBI Gene ID: 1493); CD80 (B7-1; NCBI Gene ID: 941), CD28 (NCBI Gene ID: 940); nectin cell adhesion molecule 2 (NECTIN2, CD112; NCBI Gene ID: 5819); CD226 (DNAM-1; NCBI Gene ID: 10666); Poliovirus receptor (PVR) cell adhesion molecule (PVR, CD155; NCBI Gene ID: 5817); PVR related immunoglobulin domain containing (PVRIG, CD112R; NCBI Gene ID: 79037); T cell immunoreceptor with Ig and ITIM domains (TIGIT; NCBI Gene ID: 201633); T cell immunoglobulin and mucin domain containing 4 (TIMD4; TIM4; NCBI Gene ID: 91937); hepatitis A virus cellular receptor 2 (HAVCR2, TIMD3, TIM3; NCBI Gene ID: 84868); galectin 9 (LGALS9; NCBI Gene ID: 3965); lymphocyte activating 3 (LAG3, CD223; NCBI Gene ID: 3902); signaling lymphocytic activation molecule family member 1 (SLAMF1, SLAM, CD150; NCBI Gene ID: 6504); lymphocyte antigen 9 (LY9, CD229, SLAMF3; NCBI Gene ID: 4063); SLAM family member 6 (SLAMF6, CD352; NCBI Gene ID: 114836); SLAM family member 7 (SLAMF7, CD319; NCBI Gene ID: 57823); UL16 binding protein 1 (ULBP1; NCBI Gene ID: 80329); UL16 binding protein 2 (ULBP2; NCBI Gene ID: 80328); UL16 binding protein 3 (ULBP3; NCBI Gene ID: 79465); retinoic acid early transcript 1E (RAET1E; ULBP4; NCBI Gene ID: 135250); retinoic acid early transcript 1G (RAET1G; ULBP5; NCBI Gene ID: 353091); retinoic acid early transcript IL (RAET1L; ULBP6; NCBI Gene ID: 154064); killer cell immunoglobulin like receptor, three Ig domains and long cytoplasmic tail 1 (KIR, CD158E1; NCBI Gene ID: 3811, e.g., lirilumab (IPH-2102, IPH-4102)); killer cell lectin like receptor C1 (KLRC1, NKG2A, CD159A; NCBI Gene ID: 3821); killer cell lectin like receptor K1 (KLRK1, NKG2D, CD314; NCBI Gene ID: 22914); killer cell lectin like receptor C2 (KLRC2, CD159c, NKG2C; NCBI Gene ID: 3822); killer cell lectin like receptor C3 (KLRC3, NKG2E; NCBI Gene ID: 3823); killer cell lectin like receptor C4 (KLRC4, NKG2F; NCBI Gene ID: 8302); killer cell immunoglobulin like receptor, two Ig domains and long cytoplasmic tail 1 (KIR2DL1; NCBI Gene ID: 3802); killer cell immunoglobulin like receptor, two Ig domains and long cytoplasmic tail 2 (KIR2DL2; NCBI Gene ID: 3803); killer cell immunoglobulin like receptor, two Ig domains and long cytoplasmic tail 3 (KIR2DL3; NCBI Gene ID: 3804); killer cell immunoglobulin like receptor, three Ig domains and long cytoplasmic tail 1 (KIR3DL1); killer cell lectin like receptor D1 (KLRD1; NCBI Gene ID: 3824); killer cell lectin like receptor G1 (KLRG1; CLEC15A, MAFA, 2F1; NCBI Gene ID: 10219); sialic acid binding Ig like lectin 7 (SIGLEC7; NCBI Gene ID: 27036); and sialic acid binding Ig like lectin 9 (SIGLEC9; NCBI Gene ID: 27180).

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with one or more blockers or inhibitors of one or more T-cell inhibitory immune checkpoint proteins or receptors. Illustrative T-cell inhibitory immune checkpoint proteins or receptors include CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the compound or pharmaceutically acceptable salt thereof provided herein is administered with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., *J Exp Clin Cancer Res.* (2018) 37:110.

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with one or more blockers or inhibitors of one or more NK-cell inhibitory immune checkpoint proteins or receptors. Illustrative NK-cell inhibitory immune checkpoint proteins or receptors include killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); killer cell lectin like receptor D1 (KLRD1, CD94), killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In some embodiments the compound or pharmaceutically acceptable salt thereof provided herein is administered with one or more agonist or activators of one or more NK-cell stimulatory immune checkpoint proteins or receptors. Illustrative NK-cell stimulatory immune checkpoint proteins or receptors include CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immunol.* (2017) 31:64-75; Fang, et al., *Semin Immunol.* (2017) 31:37-54; and Chiossone, et al., *Nat Rev Immunol.* (2018) 18(11):671-688.

In some embodiments the one or more immune checkpoint inhibitors comprise a proteinaceous (e.g., antibody or fragment thereof, or antibody mimetic) inhibitor of PD-L1 (CD274), PD-1 (PDCD1), CTLA4, or TIGIT. In some embodiments the one or more immune checkpoint inhibitors comprise a small organic molecule inhibitor of PD-L1 (CD274), PD-1 (PDCD1), CTLA4, or TIGIT. In some embodiments the one or more immune checkpoint inhibitors comprise a proteinaceous (e.g., antibody or fragment thereof, or antibody mimetic) inhibitor of LAG3.

Examples of inhibitors of CTLA4 that can be co-administered include ipilimumab, tremelimumab, BMS-986218, AGEN1181, zalifrelimab (AGEN1884), BMS-986249, MK-1308, REGN-4659, ADU-1604, CS-1002 (ipilimumab biosimilar), BCD-145, APL-509, JS-007, BA-3071, ONC-392, AGEN-2041, HBM-4003, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include pembrolizumab, nivolumab, cemiplimab, pidilizumab, AMP-224, MEDI0680 (AMP-514), spartalizumab, atezolizumab, avelumab, durvalumab, BMS-936559, cosibelimab (CK-301), sasanlimab (PF-06801591), tislelizumab (BGB-A317), GLS-010 (WBP-3055), AK-103 (HX-008), AK-105, CS-1003, HLX-10, retifanlimab (MGA-012), BI-754091, balstilimab (AGEN-2034), AMG-404, toripalimab (JS-001), cetrelimab (JNJ-63723283), genolimzumab (CBT-501), LZM-009, prolgolimab (BCD-100), lodapolimab (LY-3300054), SHR-1201, camrelizumab (SHR-1210), Sym-021, budigalimab (ABBV-181), PD1-PIK, BAT-1306, avelumab (MSB0010718C), CX-072, CBT-502, dostarlimab (TSR-042), MSB-2311, JTX-4014, BGB-A333, SHR-1316, CS-1001 (WBP-3155, envafolimab (KN-035), sintilimab (IBI-308), HLX-20, KL-A167, STI-A1014, STI-A1015 (IMC-001), BCD-135, FAZ-053, TQB-2450, MDX1105-01, GS-4224, GS-4416, INCB086550, MAX10181, zimberelimab (AB122), spartalizumab (PDR-001), and compounds disclosed in WO2018195321, WO2020014643, WO2019160882, or WO2018195321, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1), RO-7247669 (PD-1/LAG-3), MGD-019 (PD-1/CTLA4), KN-046 (PD-1/CTLA4), MEDI-5752 (CTLA4/PD-1), RO-7121661 (PD-1/TIM-3), RG7769 (PD-1/TIM-3), TAK-252 (PD-1/OX40L), XmAb-20717 (PD-1/CTLA4), AK-104 (CTLA4/PD-1), FS-118 (LAG-3/PD-L1), FPT-155 (CTLA4/PD-L1/CD28), GEN-1046 (PD-L1/4-1BB), bintrafusp alpha (M7824; PD-L1/TGFβ-EC domain), CA-170 (PD-L1/VISTA), CDX-527 (CD27/PD-L1), LY-3415244 (TIM3/PDL1), and INBRX-105 (4-1BB/PDL1). In some embodiments the PD-L1 inhibitor is a small molecule inhibitor, such as CA-170, GS-4224, GS-4416 and lazertinib (GNS-1480; PD-L1/EGFR).

Examples of inhibitors of TIGIT that can be co-administered include tiragolumab (RG-6058), vibostolimab, domvanalimab (AB154), AB308, BMS-986207, AGEN-1307, COM-902, or etigilimab.

Examples of inhibitors of LAG3 that can be co-administered include leramilimab (LAG525).

Inhibition of regulatory T-cell (Treg) activity or Treg depletion can alleviate their suppression of antitumor immune responses and have anticancer effects. See, e.g., Plitas and Rudensky, *Annu. Rev. Cancer Biol.* (2020) 4:459-77; Tanaka and Sakaguchi, *Eur. J. Immunol.* (2019) 49:1140-1146. In some embodiments, a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, provided herein is administered with one or more inhibitors of Treg activity or a Treg depleting agent. Treg inhibition or depletion can augment the effect of immune checkpoint inhibitors in cancer therapeutics.

In some embodiments compound or pharmaceutically acceptable salt thereof provided herein is administered with one or more Treg inhibitors. In some embodiments the Treg inhibitor can suppress the migration of Tregs into the tumor microenvironment. In some embodiments Treg inhibitor can reduce the immunosuppressive function of Tregs. In some embodiments, the Treg inhibitor can modulate the cellular phenotype and induce production of proinflammatory cytokines. Exemplary Treg inhibitors include, without limitation, CCR4 (NCBI Gene ID: 1233) antagonists and degraders of Ikaros zinc-finger proteins (e.g., Ikaros (IKZF1; NCBI Gene ID: 10320), Helios (IKZF2; NCBI Gene ID: 22807), Aiolos (IKZF3; NCBI Gene ID: 22806), and Eos (IKZF4; NCBI Gene ID: 64375).

Examples of Helios degraders that can be co-administered include without limitation I-57 (Novartis) and compounds disclosed in WO2019038717, WO2020012334, WO20200117759, and WO2021101919.

In some embodiments a compound or pharmaceutically acceptable salt thereof provided herein is administered with one or more Treg depleting agents. In some embodiments the Treg depleting agent is an antibody. In some embodiments the Treg depleting antibody has antibody-dependent cytotoxic (ADCC) activity. In some embodiments, the Treg depleting antibody is Fc-engineered to possess an enhanced ADCC activity. In some embodiments the Treg depleting antibody is an antibody-drug conjugate (ADC). Illustrative targets for Treg depleting agents include without limitation CD25 (IL2RA; NCBI Gene ID: 3559), CTLA4 (CD152; NCBI Gene ID: 1493); GITR (TNFRSF18; NCBI Gene ID: 8784); 4-1BB (CD137; NCBI Gene ID: 3604), OX-40 (CD134; NCBI Gene ID: 7293), LAG3 (CD223; NCBI Gene ID: 3902), TIGIT (NCBI Gene ID: 201633), CCR4 (NCBI Gene ID: 1233), and CCR8 (NCBI Gene ID: 1237).

In some embodiments the Treg inhibitor or Treg depleting agent that can be co-administered comprises an antibody or antigen-binding fragment thereof that selectively binds to a cell surface receptor selected from the group consisting of C—C motif chemokine receptor 4 (CCR4), C—C motif chemokine receptor 7 (CCR7), C—C motif chemokine receptor 8 (CCR8), C—X—C motif chemokine receptor 4 (CXCR4; CD184), TNFRSF4 (OX40), TNFRSF18 (GITR, CD357), TNFRSF9 (4-1BB, CD137), cytotoxic T-lymphocyte associated protein 4 (CTLA4, CD152), programmed cell death 1 (PDCD1, PD-1), Sialyl Lewis× (CD15s), CD27, ectonucleoside triphosphate diphosphohydrolase 1 (EN- TPD1; CD39), protein tyrosine phosphatase receptor type C (PTPRC; CD45), neural cell adhesion molecule 1 (NCAM1; CD56), selectin L (SELL; CD62L), integrin subunit alpha E (ITGAE; CD103), interleukin 7 receptor (IL7R; CD127), CD40 ligand (CD40LG; CD154), folate receptor alpha (FOLR1), folate receptor beta (FOLR2), leucine rich repeat containing 32 (LRRC32; GARP), IKAROS family zinc finger 2 (IKZF2; HELIOS), inducible T cell costimulatory (ICOS; CD278), lymphocyte activating 3 (LAG3; CD223), transforming growth factor beta 1 (TGFB1), hepatitis A virus cellular receptor 2 (HAVCR2; CD366; TIM3), T cell immunoreceptor with Ig and ITIM domains (TIGIT), TNF receptor superfamily member 1B (CD120b; TNFR2), IL2RA (CD25) or a combination thereof.

Examples of Treg depleting anti-CCR8 antibodies that can be administered include without limitation JTX-1811 (GS-1811) (Jounce Therapeutics, Gilead Sciences), BMS-986340 (Bristol Meyers Squibb), S-531011 (Shionogi), FPA157 (Five Prime Therapeutics), SRF-114 (Surface Oncology), HBM1022 (Harbor BioMed), IO-1 (Oncurious), and antibodies disclosed in WO2021163064, WO2020138489, and WO2021152186.

Examples of Treg depleting anti-CCR4 antibodies that can be administered include mogamulizumab.

Inhibiting, depleting, or reprogramming of non-stimulatory myeloid cells in the tumor microenvironment can enhance anti-cancer immune responses (see, e.g., Binnewies et al., *Nat. Med.* (2018) 24(5): 541-550; WO2016049641). Illustrative targets for depleting or reprogramming non-stimulatory myeloid cells include triggering receptors expressed on myeloid cells, TREM-1 (CD354, NCBI Gene ID: 54210) and TREM-2 (NCBI Gene ID: 54209). In some embodiments a compound or pharmaceutically acceptable salt thereof provided herein is administered with one or more myeloid cell depleting or reprogramming agents, such as an anti-TREM-1 antibody (e.g., PY159; antibodies disclosed in WO2019032624) or an anti-TREM-2 antibody (e.g., PY314; antibodies disclosed in WO2019118513).

Cluster of Differentiation Agonists or Activators

In some embodiments, a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with agents targeting a cluster of differentiation (CD) marker. Exemplary CD marker targeting agents that can be co-administered include without limitation A6, AD-IL24, neratinib, tucatinib (ONT 380), mobocertinib (TAK-788), tesevatinib, trastuzumab (HERCEPTIN®), trastuzumab biosimimar (HLX-02), margetuximab, BAT-8001, pertuzumab (Perjeta), pegfilgrastim, RG6264, zanidatamab (ZW25), cavatak, AIC-100, tagraxofusp (SL-401), HLA-A2402/HLA-A0201 restricted epitope peptide vaccine, dasatinib, imatinib, nilotinib, sorafenib, lenvatinib mesylate, ofranergene obadenovec, cabozantinib malate, AL-8326, ZLJ-33, KBP-7018, sunitinib malate, pazopanib derivatives, AGX-73, rebastinib, NMS-088, lucitanib hydrochloride, midostaurin, cediranib, dovitinib, sitravatinib, tivozanib, masitinib, regorafenib, olverembatinib dimesylate (HQP-1351), cabozantinib, ponatinib, and famitinib L-malate, CX-2029 (ABBV-2029), SCB-313, CA-170, COM-701, CDX-301, GS-3583, asunercept (APG-101), APO-010, and compounds disclosed in WO2016196388, WO2016033570, WO2015157386, WO199203459, WO199221766, WO2004080462, WO2005020921, WO2006009755, WO2007078034, WO2007092403, WO2007127317, WO2008005877, WO2012154480, WO2014100620, WO2014039714, WO2015134536, WO2017167182, WO2018112136, WO2018112140, WO2019155067, WO2020076105, PCT/US2019/063091, WO19173692, WO2016179517, WO2017096179, WO2017096182, WO2017096281, WO2018089628, WO2017096179, WO2018089628, WO2018195321, WO2020014643, WO2019160882, WO2018195321, WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170, WO2020068752, Cancer Discov. 2019 Jan. 9(1):8; and Gariepy J., et al. 106th Annu Meet Am Assoc Immunologists (AAI) (May 9-13, San Diego, 2019, Abst 71.5).

In some embodiments the CD marker targeting agents that can be co-administered include small molecule inhibitors, such as PBF-1662, BLZ-945, pemigatinib (INCB-054828), rogaratinib (BAY-1163877), AZD4547, roblitinib (FGF-401), quizartinib dihydrochloride, SX-682, AZD-5069, PLX-9486, avapritinib (BLU-285), ripretinib (DCC-2618), imatinib mesylate, JSP-191, BLU-263, CD117-ADC, AZD3229, telatinib, vorolanib, GO-203-2C, AB-680, PSB-12379, PSB-12441, PSB-12425, CB-708, HM-30181A, motixafortide (BL-8040), LY2510924, burixafor (TG-0054), X4P-002, mavorixafor (X4P-001-IO), plerixafor, CTX-5861, and REGN-5678 (PSMA/CD28).

In some embodiments the CD marker targeting agent that can be co-administered include small molecule agonists, such as interleukin 2 receptor subunit gamma, eltrombopag, rintatolimod, poly-ICLC (NSC-301463), Riboxxon, Apoxxim, RIBOXXIM®, MCT-465, MCT-475, G100, PEPA-10, eftozanermin alfa (ABBV-621), E-6887, motolimod, resiquimod, selgantolimod (GS-9688), VTX-1463, NKTR-262, AST-008, CMP-001, cobitolimod, tilsotolimod, litenimod, MGN-1601, BB-006, IMO-8400, IMO-9200, agatolimod, DIMS-9054, DV-1079, lefitolimod (MGN-1703), CYT-003, and PUL-042.

In some embodiments the CD marker targeting agent that can be co-administered include antibodies, such as tafasitamab (MOR208; MorphoSys AG), Inebilizumab (MEDI-551), obinutuzumab, IGN-002, rituximab biosimilar (PF-05280586), varlilumab (CDX-1127), AFM-13 (CD16/CD30), AMG330, otlertuzumab (TRU-016), isatuximab, felzartamab (MOR-202), TAK-079, TAK573, daratumumab (DARZALEX®), TTX-030, selicrelumab (RG7876), APX-005M, ABBV-428, ABBV-927, mitazalimab (JNJ-64457107), lenziluma, alemtuzuma, emactuzumab, AMG-820, FPA-008 (cabiralizumab), PRS-343 (CD-137/Her2), AFM-13 (CD16/CD30), belantamab mafodotin (GSK-2857916), AFM26 (BCMA/CD16A), simlukafusp alfa (RG7461), urelumab, utomilumab (PF-05082566), AGEN2373, ADG-106, BT-7480, PRS-343 (CD-137/HER2), FAP-4-IBBL (4-1BB/FAP), ramucirumab, CDX-0158, CDX-0159 and FSI-174, relatlimab (ONO-4482), LAG-525, MK-4280, fianlimab (REGN-3767), INCAGN2385, encelimab (TSR-033), atipotuzumab, BrevaRex (Mab-AR-20.5), MEDI-9447 (oleclumab), CPX-006, IPH-53, BMS-986179, NZV-930, CPI-006, PAT-SC1, lirilumab (IPH-2102), lacutamab (IPH-4102), monalizumab, BAY-1834942, NEO-201 (CEACAM 5/6), Iodine (131I) apamistamab (131I-BC8 (lomab-B)), MEDI0562 (tavolixizumab), GSK-3174998, INCAGN1949, BMS-986178, GBR-8383, ABBV-368, denosumab, BION-1301, MK-4166, INCAGN-1876, TRX-518, BMS-986156, MK-1248, GWN-323, CTB-006, INBRX-109, GEN-1029, pepinemab (VX-15), vopratelimab (JTX-2011), GSK3359609, cobolimab (TSR-022), MBG-453, INCAGN-2390, and compounds disclosed in WO 2017096179, WO2017096276, WO2017096189, and WO2018089628.

In some embodiments the CD marker targeting agent that can be co-administered include cell therapies, such as CD19-ARTEMIS, TBI-1501, CTL-119 huCART-19 T cells, 1 iso-cell, lisocabtagene maraleucel (JCAR-017), axicabtagene ciloleucel (KTE-C19, Yescarta®), axicabtagene ciloleucel (KTE-X19), U.S. Pat. Nos. 7,741,465, 6,319,494, UCART-19, tabelecleucel (EBV-CTL), T tisagenlecleucel-T (CTL019), CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, IM19 CAR-T, TC-110, anti-CD19 CAR T-cell therapy (B-cell acute lymphoblastic leukemia, Universiti Kebangsaan Malaysia), anti-CD19 CAR T-cell therapy (acute lymphoblastic leukemia/Non-Hodgkin's lymphoma, University Hospital Heidelberg), anti-CD19 CAR T-cell therapy (silenced IL-6 expression, cancer, Shanghai Unicar-Therapy Bio-medicine Technology), MB-CART2019.1 (CD19/CD20), GC-197 (CD19/CD7), CLIC-1901, ET-019003, anti-CD19-STAR-T cells, AVA-001, BCMA-CD19 cCAR (CD19/APRIL), ICG-134, ICG-132 (CD19/CD20), CTA-101, WZTL-002, dual anti-CD19/anti-CD20 CAR T-cells (chronic lymphocytic leukemia/B-cell lymphomas), HY-001, ET-019002, YTB-323, GC-012 (CD19/APRIL), GC-022 (CD19/CD22), CD19CAR-CD28-CD3zeta-EGFRt-expressing Tn/mem, UCAR-011, ICTCAR-014, GC-007F, PTG-01, CC-97540, GC-007G, TC-310, GC-197, tisagenlecleucel-T, CART-19, tisagenlecleucel (CTL-019)), anti-CD20 CAR T-cell therapy (non-Hodgkin's lymphoma), MB-CART2019.1 (CD19/CD20), WZTL-002 dual anti-CD19/anti-CD20 CAR-T cells, ICG-132 (CD19/CD20), ACTR707 ATTCK-20, PBCAR-20A, LB-1905, CIK-CAR.CD33, CD33CART, dual anti-BCMA/anti-CD38 CAR T-cell therapy, CART-ddBCMA, MB-102, IM-23, JEZ-567, UCART-123, PD-1 knockout T cell therapy (esophageal cancer/NSCLC), ICTCAR-052, Tn MUC-1 CAR-T, ICTCAR-053, PD-1 knockout T cell therapy (esophageal cancer/NSCLC), AUTO-2, anti-BCMA CAR T-cell therapy, Descartes-011, anti-BCMA/anti-CD38 CAR T-cell therapy, CART-ddBCMA, BCMA-CS1 cCAR, CYAD-01 (NKG2D LIGAND MODULATOR), KD-045, PD-L1 t-haNK, BCMA-CS1 cCAR, MEDI5083, anti-CD276 CART, and therapies disclosed in WO2012079000 or WO2017049166.

Cluster of Differentiation 47 (CD47) Inhibitors

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an inhibitor of CD47 (IAP, MER6, OA3; NCBI Gene ID: 961). Examples of CD47 inhibitors include anti-CD47 mAbs (Vx-1004), anti-human CD47 mAbs (CNTO-7108), CC-90002, CC-90002-ST-001, humanized anti-CD47 antibody or a CD47-blocking agent, NI-1701, NI-1801, RCT-1938, ALX148, SG-404, SRF-231, and TTI-621. Additional exemplary anti-CD47 antibodies include CC-90002, magrolimab (Hu5F9-G4), AO-176 (Vx-1004), letaplimab (IBI-188) (letaplimab), lemzoparlimab (TJC-4), SHR-1603, HLX-24, LQ-001, IMC-002, ZL-1201, IMM-01, B6H12, GenSci-059, TAY-018, PT-240, 1F8-GMCSF, SY-102, KD-015, ALX-148, AK-117, TTI-621, TTI-622, or compounds disclosed in WO199727873, WO199940940, WO2002092784, WO2005044857, WO2009046541, WO2010070047, WO2011143624, WO2012170250, WO2013109752, WO2013119714, WO2014087248, WO2015191861, WO2016022971, WO2016023040, WO2016024021, WO2016081423, WO2016109415, WO2016141328, WO2016188449, WO2017027422, WO2017049251, WO2017053423, WO2017121771, WO2017194634, WO2017196793, WO2017215585, WO2018075857, WO2018075960, WO2018089508, WO2018095428, WO2018137705, WO2018233575, WO2019027903, WO2019034895, WO2019042119, WO2019042285, WO2019042470, WO2019086573, WO2019108733, WO2019138367, WO2019144895, WO2019157843, WO2019179366, WO2019184912, WO2019185717, WO2019201236, WO2019238012, WO2019241732, WO2020019135, WO2020036977, WO2020043188, and WO2020009725. In some embodiments, the CD47 inhibitor is RRx-001, DSP-107, VT-1021, IMM-02, SGN-CD47M, or SIRPa-Fc-CD40L (SL-172154). In some embodiments the CD47 inhibitor is magrolimab.

In some embodiments, the CD47 inhibitor is a bispecific antibodies targeting CD47, such as IBI-322 (CD47/PD-L1), IMM-0306 (CD47/CD20), TJ-LIC4 (CD47/PD-L1), HX-009 (CD47/PD-1), PMC-122 (CD47/PD-L1), PT-217, (CD47/DLL3), IMM-26011 (CD47/FLT3), IMM-0207 (CD47/VEGF), IMM-2902 (CD47/HER2), BH29xx (CD47/PD-L1), IMM-03 (CD47/CD20), IMM-2502 (CD47/PD-L1), HMBD-004B (CD47/BCMA), HMBD-004A (CD47/CD33), TG-1801 (NI-1701), or NI-1801.

SIRPα Targeting Agents

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with a SIRPα targeting agent (NCBI Gene ID: 140885; UniProt P78324). Examples of SIRPα targeting agents that can be co-administered include SIRPα inhibitors, such as AL-008, RRx-001, and CTX-5861, and anti-SIRPα antibodies, such as FSI-189 (GS-0189), ES-004, BI-765063, ADU1805, CC-95251, Q-1801 (SIRPα/PD-L1). Additional SIRPα-targeting agents of use are described, for example, in WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170 and WO2020068752.

FLT3R Agonists

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with a FLT3R agonist. In some embodiments, the compound provided herein, or pharmaceutically acceptable salt thereof, is administered with a FLT3 ligand. In some embodiments, the compound provided herein, or pharmaceutically acceptable salt thereof, is administered with a FLT3L-Fc fusion protein, e.g., as described in WO2020263830. In some embodiments the compound provided herein, or pharmaceutically acceptable salt thereof, is administered with GS-3583 or CDX-301. In some embodiments the compound provided herein, or pharmaceutically acceptable salt thereof, is administered with GS-3583.

TNF Receptor Superfamily (TNFRSF) Member Agonists or Activators

In some embodiments, a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include MEDI6469, MEDI6383, tavolixizumab (MEDI0562), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Example anti-TNFRSF5 (CD40) antibodies that can be co-administered include RG7876, SEA-CD40, APX-005M, and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include urelumab, utomilumab (PF-05082566), AGEN-2373, and ADG-106.

In some embodiments the anti-TNFRSF17 (BCMA) antibody GSK-2857916 is co-administered.

Example anti-TNFRSF18 (GITR) antibodies that can be co-administered include MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Bi-specific antibodies targeting TNFRSF family members that can be co-administered include PRS-343 (CD-137/HER2), AFM26 (BCMA/CD16A), AFM-13 (CD16/CD30), odronextamab (REGN-1979; CD20/CD3), AMG-420 (BCMA/CD3), INHIBRX-105 (4-1BB/PDL1), FAP-4-IBBL (4-1BB/FAP), plamotamab (XmAb-13676; CD3/CD20), RG-7828 (CD20/CD3), CC-93269 (CD3/BCMA), REGN-5458 (CD3/BCMA), and IMM-0306 (CD47/CD20).

TGFβ Antagonists

In some embodiments, a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with a TGFβ antagonist. In some embodiments, the TGFβ antagonist is a TGFβ-specific antibody. TGFβ-specific antibodies can be prepared and characterized using methods known to those of skill in the art, such as those described in PCT International Application Publication No. WO 2018/129329 and in U.S. Pat. No. 9,518,112. In some embodiments, the TGFβ antagonist binds to a TGFβ latency-associated peptide (LAP), e.g., TGFβ 1-LAP. TGFβ 1-LAP-specific antibodies can be prepared and characterized using methods known to those of skill in the art, such as those described in U.S. Pat. No. 8,198,412 or 10,017,567. In some embodiments, the TGFβ antagonist binds to TGFβ (e.g., TGFβ 1) in a context independent manner (e.g., independent of the presentation of TGFβ in a specific tissue or organ). In some embodiments, the TGFβ antagonist binds to TGFβ (e.g., TGFβ 1) in a context-dependent manner. In some embodiments, the TGFβ antagonist blocks activation of latent TGFβ (e.g., latent TGFβ 1) that is localized in extracellular matrix, e.g., in connective tissue of the liver. In some embodiments, the TGFβ antagonist blocks activation of latent TGFβ (e.g., latent TGFβ 1) that is localized in the thymus, a lymph node, or in a tumor microenvironment (e.g., in a patient having liver cancer). In some embodiments, the TGFβ antagonist blocks activation of latent TGFβ (e.g., latent TGFβ 1) by Latent TGFβ Binding Protein (LTBP). In some embodiments, the TGFβ antagonist blocks activation of latent TGFβ (e.g., latent TGFβ 1) by Glycoprotein-A Repetitions Predominant protein (GARP), as described, e.g., in U.S. Pat. No. 10,000,572. In some embodiments, the TGFβ antagonist is ARGX-115. In some embodiments, the TGFβ antagonist is SK-181. In some embodiments, the TGFβ antagonist is an anti-latency-associated peptide (LAP) antibody that specifically binds to a LAP-TGFβ complex. In some embodiments, the anti-LAP antibody specifically binds to LAP-TGFβ complexes in extracellular matrix (ECM), e.g., of connective tissue in the liver. In some embodiments, the anti-LAP antibody specifically binds to LAP-TGFβ complexes on the surfaces of certain immunosuppressive cell types, such as regulatory T cells (Tregs), tumor-associated macrophages, or myeloid-derived suppressor cells, e.g., in a tumor microenvironment. In some embodiments, the anti-LAP antibody is a TLS-01 antibody. In some embodiments, the anti-LAP antibody specifically binds to LAP-TGFβ complexes in any context. In some embodiments, the anti-LAP antibody is a TLS-02 antibody. In some embodiments, the TGFβ antagonist comprises a TGFβ receptor. In some embodiments, the TGFβ antagonist is a TGFβ receptor-Fc fusion protein. In some embodiments, the TGFβ antagonist is an antibody comprising a TGFβ receptor. TGFβ antagonists comprising a TGFβ receptor that can be useful in connection with the compositions and methods provided herein have been described, e.g., in PCT International Publication Nos. WO 2019/113123 A1 and WO 2019/113464 A1.

Bi-Specific T-Cell Engagers

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with a bi-specific T-cell engager (e.g., not having an Fc) or an anti-CD3 bi-specific antibody (e.g., having an Fc). Illustrative anti-CD3 bi-specific antibodies or BiTEs that can be co-administered include duvortuxizumab (JNJ-64052781; CD19/CD3), AMG-211 (CEA/CD3), AMG-160 (PSMA/CD3), RG7802 (CEA/CD3), ERY-974 (CD3/GPC3), PF-06671008 (Cadherins/CD3), APVO436 (CD123/CD3), flotetuzumab (CD123/CD3), odronextamab (REGN-1979; CD20/CD3), MCLA-117 (CD3/CLEC12A), JNJ-0819 (heme/CD3), JNJ-7564 (CD3/heme), AMG-757 (DLL3-CD3), AMG-330 (CD33/CD3), AMG-420 (BCMA/CD3), AMG-427 (FLT3/CD3), AMG-562 (CD19/CD3), AMG-596 (EGFRvIII/CD3), AMG-673 (CD33/CD3), AMG-701 (BCMA/CD3), AMG-757 (DLL3/CD3), AMG-211 (CEA/CD3), blinatumomab (CD19/CD3), huGD2-BsAb (CD3/GD2), ERY974 (GPC3/CD3), GEMoab (CD3/PSCA), RG6026 (CD20/CD3), RG6194 (HER2/CD3), PF-06863135 (BCMA/CD3), SAR440234 (CD3/CDw123), JNJ-9383 (MGD-015), AMG-424 (CD38/CD3), tidutamab (XmAb-18087 (SSTR2/CD3)), JNJ-63709178 (CD123/CD3), MGD-007 (CD3/gpA33), MGD-009 (CD3/B7H3), IMCgp100 (CD3/gp100), XmAb-14045 (CD123/CD3), XmAb-13676 (CD3/CD20), tidutamab (XmAb-18087; SSTR2/CD3), catumaxomab (CD3/Ep-CAM), REGN-4018 (MUC16/CD3), mosunetuzumab (RG-7828; CD20/CD3), CC-93269 (CD3/BCMA), REGN-5458 (CD3/BCMA), GRB-1302 (CD3/Erbb2), GRB-1342 (CD38/CD3), GEM-333 (CD3/CD33). As appropriate, the anti-CD3 binding bi-specific molecules may or may not have an Fc. Illustrative bi-specific T-cell engagers that can be co-administered target CD3 and a tumor-associated antigen as described herein, including, e.g., CD19 (e.g., blinatumomab); CD33 (e.g., AMG330); CEA (e.g., MEDI-565); receptor tyrosine kinase-like orphan receptor 1 (ROR1) (Gohil, et al., *Oncoimmunology*. (2017) May 17; 6(7): e1326437); PD-L1 (Horn, et al., *Oncotarget*. 2017 Aug. 3; 8(35):57964-57980); and EGFRvIII (Yang, et al., *Cancer Lett*. 2017 Sep. 10; 403:224-230).

Bi- and Tri-Specific Natural Killer (NK)-Cell Engagers

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). Illustrative anti-CD16 bi-specific antibodies, BiKEs or TriKEs that can be co-administered include AFM26 (BCMA/CD16A) and AFM-13 (CD16/CD30). As appropriate, the anti-CD16 binding bi-specific molecules may or may not have an Fc. Illustrative bi-specific NK-cell engagers that can be co-administered target CD16 and one or more tumor-associated antigens as described herein, including, e.g., CD19, CD20, CD22, CD30, CD33, CD123, EGFR, EpCAM, ganglioside GD2, HER2/neu, HLA Class II and FOLR1. BiKEs and TriKEs are described, e.g., in Felices, et al., *Methods Mol Biol*. (2016) 1441:333-346; Fang, et al., *Semin Immunol*. (2017) 31:37-54.

MCL1 Apoptosis Regulator, BCL2 Family Member (MCL1) Inhibitors

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an inhibitor of MCL1 apoptosis regulator, BCL2 family member (MCL1, TM; EAT; MCL1L; MCL1S; Mcl-1; BCL2L3; MCL1-ES; bcl2-L-3; mcl1/EAT; NCBI Gene ID: 4170). Examples of MCL1 inhibitors include tapotoclax (AMG-176), AMG-397, S-64315, AZD-5991, 483-LM, A-1210477, UMI-77, JKY-5-037, PRT-1419, GS-9716, and those described in WO2018183418, WO2016033486, and WO2017147410.

SHP2 Inhibitors

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an inhibitor of protein tyrosine phosphatase non-receptor type 11 (PTPN11; BPTP3, CFC, JMML, METCDS, NS1, PTP-1D, PTP2C, SH-PTP2, SH-PTP3, SHP2; NCBI Gene ID: 5781). Examples of SHP2 inhibitors include TNO155 (SHP-099), RMC-4550, JAB-3068, RMC-4630, and those described in WO2018172984 and WO2017211303.

Hematopoietic Progenitor Kinase 1 (HPK1) Inhibitors and Degraders

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an inhibitor of mitogen-activated protein kinase kinase kinase kinase 1 (MAP4K1, HPK1; NCBI Gene ID: 11184). Examples of Hematopoietic Progenitor Kinase 1 (HPK1) inhibitors include without limitation, those described in WO2020092621, WO2018183956, WO2018183964, WO2018167147, WO2018049152, WO2020092528, WO2016205942, WO2016090300, WO2018049214, WO2018049200, WO2018049191, WO2018102366, WO2018049152, and WO2016090300.

Apoptosis Signal-Regulating Kinase (ASK) Inhibitors

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an ASK inhibitor, e.g., mitogen-activated protein kinase kinase kinase 5 (MAP3K5; ASK1, MAPKKK5, MEKK5; NCBI Gene ID: 4217). Examples of ASK1 inhibitors include those described in WO2011008709 (Gilead Sciences) and WO 2013112741 (Gilead Sciences).

Bruton Tyrosine Kinase (BTK) Inhibitors

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an inhibitor of Bruton tyrosine kinase (BTK, AGMX1, AT, ATK, BPK, IGHD3, IMDI, PSCTK1, XLA; NCBI Gene ID: 695). Examples of BTK inhibitors include (S)-6-amino-9-(1-(but-2-ynoyl)pyrrolidin-3-yl)-7-(4-phenoxyphenyl)-7H-purin-8(9H)-one, acalabrutinib (ACP-196), zanubrutinib (BGB-3111), CB988, HM71224, ibrutinib, M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, PCI-32765, and TAS-5315.

Cyclin-Dependent Kinase ((DK) Inhibitors

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an inhibitor of cyclin dependent kinase 1 (CDK1, CDC2; CDC28A; P34CDC2; NCBI Gene ID: 983); cyclin dependent kinase 2 (CDK2, CDKN2; p33(CDK2); NCBI Gene ID: 1017); cyclin dependent kinase 3 (CDK3, NCBI Gene ID: 1018); cyclin dependent kinase 4 (CDK4, CMM3; PSK-J3; NCBI Gene ID: 1019); cyclin dependent kinase 6 (CDK6, MCPH12; PLSTIRE; NCBI Gene ID: 1021); cyclin dependent kinase 7 (CDK7, CAK; CAK1; HCAK; MO15; STK1; CDKN7; p39MO15; NCBI Gene ID: 1022), or cyclin dependent kinase 9 (CDK9, TAK; C-2k; CTK1; CDC2L4; PITALRE; NCBI Gene ID: 1025). Inhibitors of CDK 1, 2, 3, 4, 6, 7 and/or 9, include abemaciclib, alvocidib (HMR-1275, flavopiridol), AT-7519, dinaciclib, ibrance, FLX-925, LEE001, palbociclib, samuraciclib, ribociclib, rigosertib, selinexor, UCN-01, SY1365, CT-7001, SY-1365, G1T38, milciclib, trilaciclib, simurosertib hydrate (TAK931), and TG-02.

Discoidin Domain Receptor (DDR) Inhibitors

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is combined with an inhibitor of discoidin domain receptor tyrosine kinase 1 (DDR1, CAK, CD167, DDR, EDDR1, HGK2, MCK10, NEP, NTRK4, PTK3, PTK3A, RTK6, TRKE; NCBI Gene ID: 780); and/or discoidin domain receptor tyrosine kinase 2 (DDR2, MIG20a, NTRKR3, TKT, TYRO10, WRCN; NCBI Gene ID: 4921). Examples of DDR inhibitors include dasatinib and those disclosed in WO2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO2013/034933 (Imperial Innovations).

Targeted E3 Ligase Ligand Conjugates

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with a targeted E3 ligase ligand conjugate. Such conjugates have a target protein binding moiety and an E3 ligase binding moiety (e.g., an inhibitor of apoptosis protein (IAP) (e.g., XIAP, c-IAP1, c-IAP2, NIL-IAP, Bruce, and surviving) E3 ubiquitin ligase binding moiety, Von Hippel-Lindau E3 ubiquitin ligase (VHL) binding moiety, a cereblon E3 ubiquitin ligase binding moiety, mouse double minute 2 homolog (MDM2) E3 ubiquitin ligase binding moiety), and can be used to promote or increase the degradation of targeted proteins, e.g., via the ubiquitin pathway. In some embodiments the targeted E3 ligase ligand conjugates comprise a targeting or binding moiety that targets or binds a protein described herein, and an E3 ligase ligand or binding moiety. In some embodiments the targeted E3 ligase ligand conjugates comprise a targeting or binding moiety that targets or binds a protein selected from Cbl proto-oncogene B (CBLB; Cbl-b, Nbla00127, RNF56; NCBI Gene ID: 868) and hypoxia inducible factor 1 subunit alpha (HIF1A; NCBI Gene ID: 3091). In some embodiments the targeted E3 ligase ligand conjugates comprise a kinase inhibitor (e.g., a small molecule kinase inhibitor, e.g., of BTK and an E3 ligase ligand or binding moiety. See, e.g., WO2018098280. In some embodiments the targeted E3 ligase ligand conjugates comprise a binding moiety targeting or binding to Interleukin-1 (IL-1) Receptor-Associated Kinase-4 (IRAK-4); Rapidly Accelerated Fibrosarcoma (RAF, such as c-RAF, A-RAF and/or B-RAF), c-Met/p38, or a BRD protein; and an E3 ligase ligand or binding moiety. See, e.g., WO2019099926, WO2018226542, WO2018119448, WO2018223909, WO2019079701. Additional targeted E3 ligase ligand conjugates that can be co-administered are described, e.g., in WO2018237026, WO2019084026, WO2019084030, WO2019067733, WO2019043217, WO2019043208, and WO2018144649.

Histone Deacetylase (HDAC) Inhibitors

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an inhibitor of a histone deacetylase, e.g., histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, and entinostat.

Indoleamine-pyrrole-2,3-dioxygenase (IDO1) Inhibitors

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an inhibitor of indoleamine 2,3-dioxygenase 1 (IDO1; NCBI Gene ID: 3620). Examples of IDO1 inhibitors include BLV-0801, epacadostat, linrodostat (F-001287, BMS-986205), GBV-1012, GBV-1028, GDC-0919, indoximod, NKTR-218, NLG-919-based vaccine, PF-06840003, pyranonaphthoquinone derivatives (SN-35837), resminostat, SBLK-200802, and shIDO-ST, EOS-200271, KHK-2455, and LY-3381916.

Janus Kinase (JAK) Inhibitors

In some embodiments, a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an inhibitor of Janus kinase 1 (JAK1, JAK1A, JAK1B, JTK3; NCBI Gene ID: 3716); Janus kinase 2 (JAK2, JTK10, THCYT3; NCBI Gene ID: 3717); and/or Janus kinase 3 (JAK3, JAK-3, JAK3_HUMAN, JAKL, L-JAK, LJAK; NCBI Gene ID: 3718). Examples of JAK inhibitors include AT9283, AZD1480, baricitinib, BMS-911543, fedratinib, filgotinib (GLPG0634), gandotinib (LY2784544), INCB039110 (itacitinib), lestaurtinib, momelotinib (CYT0387), ilginatinib maleate (NS-018), pacritinib (SB1518), peficitinib (ASP015K), ruxolitinib, tofacitinib (formerly tasocitinib), INCB052793, and XL019.

Lysyl Oxidase-Like Protein (LOXL) Inhibitors

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an inhibitor of a LOXL protein, e.g., LOXL1 (NCBI Gene ID: 4016), LOXL2 (NCBI Gene ID: 4017), LOXL3 (NCBI Gene ID: 84695), LOXL4 (NCBI Gene ID: 84171), and/or LOX (NCBI Gene ID: 4015). Examples of LOXL2 inhibitors include the antibodies described in WO 2009017833 (Arresto Biosciences), WO 2009035791 (Arresto Biosciences), and WO 2011097513 (Gilead Biologics).

Matrix Metalloprotease (MMP) Inhibitors

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13), (Ia), (Ib), or (Ic) provided herein, or pharmaceutically acceptable salt thereof, is administered with an inhibitor of a matrix metallopeptidase (MMP), e.g., an inhibitor of MMP1 (NCBI Gene ID: 4312), MMP2 (NCBI Gene ID: 4313), MMP3 (NCBI Gene ID: 4314), MMP7 (NCBI Gene ID: 4316), MMP8 (NCBI Gene ID: 4317), MMP9 (NCBI Gene ID: 4318); MMP10 (NCBI Gene ID: 4319); MMP11 (NCBI Gene ID: 4320); MMP12 (NCBI Gene ID: 4321), MMP13 (NCBI Gene ID: 4322), MMP14 (NCBI Gene ID: 4323), MMP15 (NCBI Gene ID: 4324), MMP16 (NCBI Gene ID: 4325), MMP17 (NCBI Gene ID: 4326), MMP19 (NCBI Gene ID: 4327), MMP20 (NCBI Gene ID: 9313), MMP21 (NCBI Gene ID: 118856), MMP24 (NCBI Gene ID: 10893), MMP25 (NCBI Gene ID: 64386), MMP26 (NCBI Gene ID: 56547), MMP27 (NCBI Gene ID: 64066) and/or MMP28 (NCBI Gene ID: 79148). Examples of MMP9 inhibitors include marimastat (BB-2516), cipemastat (Ro 32-3555), GS-5745 (andecaliximab), and those described in WO 2012027721 (Gilead Biologics).

RAS and RAS Pathway Inhibitors

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an inhibitor of KRAS proto-oncogene, GTPase (KRAS; a.k.a., NS; NS3; CFC2; RALD; K-Ras; KRAS1; KRAS2; RASK2; KI-RAS; C—K-RAS; K-RAS2A; K-RAS2B; K-RAS4A; K-RAS4B; c-Ki-ras2; NCBI Gene ID: 3845); NRAS proto-oncogene, GTPase (NRAS; a.k.a., NS6; CMNS; NCMS; ALPS4; N-ras; NRAS1; NCBI Gene ID: 4893) or HRAS proto-oncogene, GTPase (HRAS; a.k.a., CTLO; KRAS; HAMSV; HRAS1; KRAS2; RASH1; RASK2; Ki-Ras; p21ras; C—H-RAS; c-K-ras; H-RASIDX; c-Ki-ras; C-BAS/HAS; C-HA-RAS1; NCBI Gene ID: 3265). The Ras inhibitors can inhibit Ras at either the polynucleotide (e.g., transcriptional inhibitor) or polypeptide (e.g., GTPase enzyme inhibitor) level. In some embodiments, the inhibitors target one or more proteins in the Ras pathway, e.g., inhibit one or more of EGFR, Ras, Raf (A-Raf, B-Raf, C-Raf), MEK (MEK1, MEK2), ERK, PI3K, AKT and mTOR. Illustrative K-Ras inhibitors that can be co-administered include sotorasib (AMG-510), COTI-219, ARS-3248, WDB-178, BI-3406, BI-1701963, SML-8-73-1 (G12C), adagrasib (MRTX-849), ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 and KRpep-2d. Illustrative KRAS mRNA inhibitors include anti-KRAS U1 adaptor, AZD-4785, siG12D-LODER™, and siG12D exosomes. Illustrative MEK inhibitors that can be co-administered include binimetinib, cobimetinib, PD-0325901, pimasertib, RG-7304, selumetinib, trametinib, and those described below and herein. Illustrative Raf dimer inhibitors that can be co-administered include BGB-283, HM-95573, LXH-254, LY-3009120, RG7304 and TAK-580. Illustrative ERK inhibitors that can be co-administered include LTT-462, LY-3214996, MK-8353, ravoxertinib and ulixertinib. Illustrative Ras GTPase inhibitors that can be co-administered include rigosertib. Illustrative PI3K inhibitors that can be co-administered include idelalisib (Zydelig®), alpelisib, buparlisib, pictilisib, inavolisib (RG6114), ASN-003. Illustrative AKT inhibitors that can be co-administered include capivasertib and GSK2141795. Illustrative PI3K/mTOR inhibitors that can be co-administered include dactolisib, omipalisib, voxtalisib, gedatolisib, GSK2141795, GSK-2126458, inavolisib (RG6114), sapanisertib, ME-344, sirolimus (oral nano-amorphous formulation, cancer), racemetyrosine (TYME-88 (mTOR/cytochrome P450 3A4)), temsirolimus (TORISEL®, CCI-779), CC-115, onatasertib (CC-223), SF-1126, and PQR-309 (bimiralisib). In some embodiments, Ras-driven cancers (e.g., NSCLC) having CDKN2A mutations can be inhibited by co-administration of the MEK inhibitor selumetinib and the CDK4/6 inhibitor palbociclib. See, e.g., Zhou, et al., *Cancer Lett.* 2017 Nov. 1; 408:130-137. Also, K-RAS and mutant N-RAS can be reduced by the irreversible ERBB1/2/4 inhibitor neratinib. See, e.g., Booth, et al., *Cancer Biol Ther.* 2018 Feb. 1; 19(2): 132-137.

Mitogen-Activated Protein Kinase (MEK) Inhibitors

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an inhibitor of mitogen-activated protein kinase kinase 7 (MAP2K7, JNKK2, MAPKK7, MEK, MEK 7, MKK7, PRKMK7, SAPKK-4, SAPKK4; NCBI Gene ID: 5609). Examples of MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, and refametinib.

Phosphatidylinositol 3-kinase (PI3K) Inhibitors

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an inhibitor of a phosphatidylinositol-4,5-bisphosphate 3-kinase catalytic subunit, e.g., phosphatidylinositol-4,5-bisphosphate 3-kinase catalytic subunit alpha (PIK3CA, CLAPO, CLOVE, CWS5, MCAP, MCM, MCMTC, PI3K, PI3K-alpha, p110-alpha; NCBI Gene ID: 5290); phosphatidylinositol-4,5-bisphosphate 3-kinase catalytic subunit beta (PIK3CB, P110BETA, PI3K, PI3KBETA, PIK3C1; NCBI Gene ID: 5291); phosphatidylinositol-4,5-bisphosphate 3-kinase catalytic subunit gamma (PIK3CG, PI3CG, PI3K, PI3Kgamma, PIK3, p110gamma, p120-PI3K; Gene ID: 5494); and/or phosphatidylinositol-4,5-bisphosphate 3-kinase catalytic subunit delta (PIK3CD, APDS, IMD14, P110DELTA, PI3K, p110D, NCBI Gene ID: 5293). In some embodiments the PI3K inhibitor is a pan-PI3K inhibitor. Examples of PI3K inhibitors include ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TG100115, TGR-1202 (umbralisib), TGX221, WX-037, X-339, X-414, XL147 (SAR245408), XL499, XL756, wortmannin, ZSTK474, and the compounds described in WO2005113556 (ICOS), WO 2013/052699 (Gilead Calistoga), WO2013116562 (Gilead Calistoga), WO2014100765 (Gilead Calistoga), WO2014100767 (Gilead Calistoga), and WO2014201409 (Gilead Sciences).

Spleen Tyrosine Kinase (SYK) Inhibitors

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an inhibitor of spleen associated tyrosine kinase (SYK, p72-Syk, NCBI Gene ID: 6850). Examples of SYK inhibitors include 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), gusacitinib (ASN-002), and those described in U.S. Pat. No. 8,450,321 (Gilead Connecticut) and US20150175616.

Toll-Like Receptor (TLR) Agonists

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include DS-0509, GS-9620 (vesatolimod), vesatolimod analogs, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, BDB-001, DSP-0509, and the compounds disclosed in US20100143301 (Gilead Sciences), US20110098248 (Gilead Sciences), and US20090047249 (Gilead Sciences), US20140045849 (Janssen), US20140073642 (Janssen), WO2014056953 (Janssen), WO2014076221 (Janssen), WO2014128189 (Janssen), US20140350031 (Janssen), WO2014023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262. Example TLR8 agonists that can be co-administered include E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include AST-008, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, leftolimod (MGN-1703), CYT-003, CYT-003-QbG10 and PUL-042. Examples of TLR3 agonist include rintatolimod, poly-ICLC, RIBOXXON®, Apoxxim, RIBOXXIM®, IPH-33, MCT-465, MCT-475, and ND-1.1.

Tyrosine-Kinase Inhibitors (TKIs)

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with a tyrosine kinase inhibitor (TKI). TKIs may target epidermal growth factor receptors (EGFRs) and receptors for fibroblast growth factor (FGF), platelet-derived growth factor (PDGF), and vascular endothelial growth factor (VEGF). Examples of TKIs include without limitation afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, osimertinib (AZD-9291), ponatinib, poziotinib, quizartinib, radotinib, rociletinib, sulfatinib (HMPL-012), sunitinib, famitinib L-malate, (MAC-4), tivoanib, TH-4000, and MEDI-575 (anti-PDGFR antibody). Exemplary EGFR targeting agents include neratinib, tucatinib (ONT-380), tesevatinib, mobocertinib (TAK-788), DZD-9008, varlitinib, abivertinib (ACEA-0010), EGF816 (nazartinib), olmutinib (BI-1482694), osimertinib (AZD-9291), AMG-596 (EGFRvIII/CD3), lifirafenib (BGB-283), vectibix, lazertinib (LECLAZAR), and compounds disclosed in Booth, et al., Cancer Biol Ther. 2018 Feb. 1; 19(2):132-137. Antibodies targeting EGFR include without limitation modotuximab, cetuximab sarotalocan (RM-1929), seribantumab, necitumumab, depatuxizumab mafodotin (ABT-414), tomuzotuximab, depatuxizumab (ABT-806), and cetuximab.

Chemotherapeutic Agents

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with a chemotherapeutic agent or anti-neoplastic agent.

As used herein, the term "chemotherapeutic agent" or "chemotherapeutic" (or "chemotherapy" in the case of treatment with a chemotherapeutic agent) is meant to encompass any non-proteinaceous (e.g., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, e.g., bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as cladribine, pentostatin, fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; sabizabulin (Veru-111); platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-trichlorotriemylamine; urethane; vindesine; dacarbazine; mannomustine; mitobronitol; mitolactol; pipobroman; gacytosine; arabinoside (“Ara-C”); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFOX (folinic acid, 5-fluorouracil, oxaliplatin); FOLFIRI (folinic acid, 5-fluorouracil, irinotecan); FOLFOXIRI (folinic acid, 5-fluorouracil, oxaliplatin, irinotecan), FOLFIRINOX (folinic acid, 5-fluorouracil, irinotecan, oxaliplatin), and pharmaceutically acceptable salts, acids, or derivatives of any of the above. Such agents can be conjugated onto an antibody or any targeting agent described herein to create an antibody-drug conjugate (ADC) or targeted drug conjugate.

Anti-Hormonal Agents

Also included in the definition of “chemotherapeutic agent” are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204, enobosarm (GTX-024), darolutamide, and IONIS-AR-2.5Rx (antisense).

An example progesterone receptor antagonist includes onapristone. Additional progesterone targeting agents include TRI-CYCLEN LO (norethindrone+ethinyl estradiol), norgestimate+ethinylestradiol (Tri-Cyclen) and levonorgestrel.

Anti-Angiogenic Agents

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an anti-angiogenic agent. Anti-angiogenic agents that can be co-administered include retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inbibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cis-hydroxyproline, d,I-3,4-dehydroproline, thiaproline, $\alpha,\alpha'$-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or “CCA”, thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2. Examples for anti-VEGFA antibodies that can be co-administered include bevacizumab, vanucizumab, faricimab, dilpacimab (ABT-165; DLL4/VEGF), or navicixizumab (OMP-305B83; DLL4/VEGF).

Anti-Fibrotic Agents

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an anti-fibrotic agent. Anti-fibrotic agents that can be co-administered include the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 20040248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio) butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Anti-Inflammatory Agents

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an anti-inflammatory agent. Example anti-inflammatory agents include without limitation inhibitors of one or more of arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CASA (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240), soluble epoxide hydrolase 2 (EPHX2, SEH; NCBI Gene ID: 2053) and/or mitogen-activated protein kinase kinase kinase 8 (MAP3K8, TPL2; NCBI Gene ID: 1326). In some embodiments, the inhibitor is a dual inhibitor, e.g., a dual inhibitor of COX-2/COX-1, COX-2/SEH, COX-2/CA, COX-2/5-LOX.

Examples of inhibitors of prostaglandin-endoperoxide synthase 1 (PTGS1, COX-1; NCBI Gene ID: 5742) that can be co-administered include mofezolac, GLY-230, and TRK-700.

Examples of inhibitors of prostaglandin-endoperoxide synthase 2 (PTGS2, COX-2; NCBI Gene ID: 5743) that can be co-administered include diclofenac, meloxicam, parecoxib, etoricoxib, AP-101, celecoxib, AXS-06, diclofenac potassium, DRGT-46, AAT-076, meisuoshuli, lumiracoxib, meloxicam, valdecoxib, zaltoprofen, nimesulide, anitrazafen, apricoxib, cimicoxib, deracoxib, flumizole, firocoxib, mavacoxib, NS-398, pamicogrel, parecoxib, robenacoxib, rofecoxib, rutecarpine, tilmacoxib, and zaltoprofen. Examples of dual COX1/COX2 inhibitors that can be co-administered include HP-5000, lornoxicam, ketorolac tromethamine, bromfenac sodium, ATB-346, HP-5000. Examples of dual COX-2/carbonic anhydrase (CA) inhibitors that can be co-administered include polmacoxib and imrecoxib.

Examples of inhibitors of secreted phospholipase A2, prostaglandin E synthase (PTGES, PGES; Gene ID: 9536) that can be co-administered include LY3023703, GRC 27864, and compounds described in WO2015158204, WO2013024898, WO2006063466, WO2007059610, WO2007124589, WO2010100249, WO2010034796, WO2010034797, WO2012022793, WO2012076673, WO2012076672, WO2010034798, WO2010034799, WO2012022792, WO2009103778, WO2011048004, WO2012087771, WO2012161965, WO2013118071, WO2013072825, WO2014167444, WO2009138376, WO2011023812, WO2012110860, WO2013153535, WO2009130242, WO2009146696, WO2013186692, WO2015059618, WO2016069376, WO2016069374, WO2009117985, WO2009064250, WO2009064251, WO2009082347, WO2009117987, and WO2008071173. Metformin has further been found to repress the COX2/PGE2/STAT3 axis, and can be co-administered. See, e.g., Tong, et al., *Cancer Lett*. (2017) 389:23-32; and Liu, et al., *Oncotarget*. (2016) 7(19):28235-46.

Examples of inhibitors of carbonic anhydrase (e.g., one or more of CA1 (NCBI Gene ID: 759), CA2 (NCBI Gene ID: 760), CA3 (NCBI Gene ID: 761), CA4 (NCBI Gene ID: 762), CASA (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)) that can be co-administered include acetazolamide, methazolamide, dorzolamide, zonisamide, brinzolamide and dichlorphenamide. A dual COX-2/CA1/CA2 inhibitor that can be co-administered includes CG100649.

Examples of inhibitors of arachidonate 5-lipoxygenase (ALOX5, 5-LOX; NCBI Gene ID: 240) that can be co-administered include meclofenamate sodium, zileuton.

Examples of inhibitors of soluble epoxide hydrolase 2 (EPHX2, SEH; NCBI Gene ID: 2053) that can be co-administered include compounds described in WO2015148954. Dual inhibitors of COX-2/SEH that can be co-administered include compounds described in WO2012082647. Dual inhibitors of SEH and fatty acid amide hydrolase (FAAH; NCBI Gene ID: 2166) that can be co-administered include compounds described in WO2017160861.

Examples of inhibitors of mitogen-activated protein kinase kinase kinase 8 (MAP3K8, tumor progression loci-2, TPL2; NCBI Gene ID: 1326) that can be co-administered include GS-4875, GS-5290, BHM-078 and those described in WO2006124944, WO2006124692, WO2014064215, WO2018005435, Teli, et al., *J Enzyme Inhib Med Chem*. (2012) 27(4):558-70; Gangwall, et al., *Curr Top Med Chem*.

(2013) 13(9): 1015-35; Wu, et al., *Bioorg Med Chem Lett.* (2009) 19(13):3485-8; Kaila, et al., *Bioorg Med Chem.* (2007) 15(19):6425-42; and Hu, et al., *Bioorg Med Chem Lett.* (2011) 21(16):4758-61.

Tumor Oxygenation Agents

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an agent that promotes or increases tumor oxygenation or reoxygenation, or prevents or reduces tumor hypoxia. Illustrative agents that can be co-administered include, e.g., Hypoxia inducible factor-1 alpha (HIF-1$\alpha$) inhibitors, such as PT-2977, PT-2385; VEGF inhibitors, such as bevasizumab, IMC-3C5, GNR-011, tanibirumab, LYN-00101, ABT-165; and/or an oxygen carrier protein (e.g., a heme nitric oxide and/or oxygen binding protein (HNOX)), such as OMX-302 and HNOX proteins described in WO2007137767, WO2007139791, WO2014107171, and WO2016149562.

Immunotherapeutic Agents

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with an immunotherapeutic agent. In some embodiments the immunotherapeutic agent is an antibody. Example immunotherapeutic agents that can be co-administered include abagovomab, AB308, ABP-980, adecatumumab, afutuzumab, alemtuzumab, altumomab, amatuximab, anatumomab, arcitumomab, atezolizumab, bavituximab, bectumomab, bevacizumab, bivatuzumab, blinatumomab, brentuximab, camidanlumab, cantuzumab, catumaxomab, CC49, cetuximab, citatuzumab, cixutumumab, clivatuzumab, conatumumab, dacetuzumab, dalotuzumab, daratumumab, detumomab, dinutuximab, domvanalimab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ubilituximab, veltuzumab, vorsetuzumab, votumumab, zalutumumab, zimberelimab, and 3F8. Rituximab can be used for treating indolent B-cell cancers, including marginal-zone lymphoma, WM, CLL, and small lymphocytic lymphoma. A combination of rituximab and chemotherapy agents is especially effective.

The exemplified therapeutic antibodies can be further labeled or combined with a radioisotope particle such as indium-111, yttrium-90 (90Y-clivatuzumab), or iodine-131.

In some embodiments, the immunotherapeutic agent that can be co-administered is an antibody-drug conjugate (ADC). Illustrative ADCs that can be co-administered include without limitation drug-conjugated antibodies, fragments thereof, or antibody mimetics targeting the proteins or antigens listed above and herein. Example ADCs that can be co-administered include gemtuzumab, brentuximab, belantamab (e.g., belantamab mafodotin), camidanlumab (e.g., camidanlumab tesirine), trastuzumab (e.g., trastuzumab deruxtecan; trasuzumab emtansine), inotuzumab, glembatumumab, anetumab, mirvetuximab (e.g., mirvetuximab soravtansine), depatuxizumab, vadastuximab, labetuzumab, ladiratuzumab (e.g., ladiratuzumab vedotin), loncastuximab (e.g., loncastuximab tesirine), sacituzumab (e.g., sacituzumab govitecan), datopotamab (e.g., datopotamab deruxtecan; DS-1062; Dato-DXd), patritumab (e.g., patritumab deruxtecan), lifastuzumab, indusatumab, polatuzumab (e.g., polatuzumab vedotin), pinatuzumab, coltuximab, upifitamab (e.g., upifitamab rilsodotin), indatuximab, milatuzumab, rovalpituzumab (e.g., rovalpituzumab tesirine), enfortumab (e.g., enfortumab vedotin), tisotumab (e.g., tisotumab vedotin), tusamitamab (e.g., tusamitamab ravtansine), disitamab (e.g., disitamab vedotin), telisotuzumab vedotin (ABBV-399), AGS-16C3F, ASG-22ME, AGS67E, AMG172, AMG575, BAY1129980, BAY1187982, BAY94-9343, GSK2857916, Humax-TF-ADC, IMGN289, IMGN151, IMGN529, IMGN632, IMGN853, IMGC936, LOP628, PCA062, MDX-1203 (BMS936561), MEDI-547, PF-06263507, PF-06647020, PF-06647263, PF-06664178, RG7450, RG7458, RG7598, SAR566658, SGN-CD19A, SGN-CD33A, SGN-CD70A, SGN-LIV1A, SYD985, DS-7300, XMT-1660, IMMU-130, and IMMU-140. ADCs that can be co-administered are described, e.g., in Lambert, et al., *Adv Ther* (2017) 34:1015-1035 and in de Goeij, *Current Opinion in Immunology* (2016) 40:14-23.

Illustrative therapeutic agents (e.g., anticancer or antineoplastic agents) that can be conjugated to the drug-conjugated antibodies, fragments thereof, or antibody mimetics include without limitation monomethyl auristatin E (MMAE), monomethyl auristatin F (MMAF), a calicheamicin, ansamitocin, maytansine or an analog thereof (e.g., mertansine/emtansine (DM1), ravtansine/soravtansine (DM4)), an anthracyline (e.g., doxorubicin, daunorubicin, epirubicin, idarubicin), pyrrolobenzodiazepine (PBD) DNA cross-linking agent SC-DR002 (D6.5), duocarmycin, a microtubule inhibitors (MTI) (e.g., a taxane, a vinca alkaloid, an epothilone), a pyrrolobenzodiazepine (PBD) or dimer thereof, a duocarmycin (A, B1, B2, C1, C2, D, SA, CC-1065), and other anticancer or anti-neoplastic agents described herein. In some embodiments, the therapeutic agent conjugated to the drug-conjugated antibody is a topoisomerase I inhibitor (e.g., a camptothecin analog, such as irinotecan or its active metabolite SN38). In some embodiments, the therapeutic agents (e.g., anticancer or antineoplastic agents) that can be conjugated to the drug-conjugated antibodies, fragments thereof, or antibody mimetics include an immune checkpoint inhibitor. In some embodiments the conjugated immune checkpoint inhibitor is a conjugated small molecule inhibitor of CD274 (PDL1, PD-L1), programmed cell death 1 (PDCD1, PD1, PD-1) or CTLA4. In some embodiments the conjugated small molecule inhibitor of CD274 or PDCD1 is selected from the group consisting of GS-4224, GS-4416, INCB086550 and MAX10181. In some embodiments the conjugated small molecule inhibitor of CTLA4 comprises BPI-002.

In some embodiments the ADCs that can be co-administered include an antibody targeting tumor-associated calcium signal transducer 2 (TROP-2; TACSTD2; EGP-1; NCBI Gene ID: 4070). Illustrative anti-TROP-2 antibodies include without limitation TROP2-XPAT (Amunix), BAT-8003 (Bio-Thera Solutions), TROP-2-IR700 (Chiome Bioscience), datopotamab deruxtecan (Daiichi Sankyo, AstraZeneca), GQ-1003 (Genequantum Healthcare, Samsung BioLogics), DAC-002 (Hangzhou DAC Biotech, Shanghai Junshi Biosciences), sacituzumab govitecan (Gilead Sciences), E1-3s (Immunomedics/Gilead, IBC Pharmaceuticals), TROP2-TRACTr (Janux Therapeutics), LIV-2008 (LivTech/Chiome, Yakult Honsha, Shanghai Henlius BioTech), LIV-2008b (LivTech/Chiome), anti-TROP-2a (Oncoxx), anti-TROP-2b (Oncoxx), OXG-64 (Oncoxx), OXS-55 (Oncoxx), humanized anti-Trop2-SN38 antibody conjugate (Shanghai Escugen Biotechnology, TOT Biopharma), anti-Trop2 antibody-CLB-SN-38 conjugate (Shanghai Fudan-Zhangjiang Bio-Pharmaceutical), SKB-264 (Sichuan Kelun Pharmaceutical/Klus Pharma), TROP2-Ab8 (Abmart), Trop2-IgG (Nanjing Medical University (NMU)), 90Y-DTPA-AF650 (Peking University First Hospital), hRS7-CM (SynAffix), 89Zr-DFO-AF650 (University of Wisconsin-Madison), anti-Trop2 antibody (Mediterranea Theranostic, LegoChem Biosciences), KD-065 (Nanjing KAEDI Biotech), and those described in WO2020016662 (Abmart), WO2020249063 (Bio-Thera Solutions), US20190048095 (Bio-Thera Solutions), WO2013077458 (LivTech/Chiome), EP20110783675 (Chiome), WO2015098099 (Daiichi Sankyo), WO2017002776 (Daiichi Sankyo), WO2020130125 (Daiichi Sankyo), WO2020240467 (Daiichi Sankyo), US2021093730 (Daiichi Sankyo), U.S. Pat. No. 9,850,312 (Daiichi Sankyo), CN112321715 (Biosion), US2006193865 (Immunomedics/Gilead), WO2011068845 (Immunomedics/Gilead), US2016296633 (Immunomedics/Gilead), US2017021017 (Immunomedics/Gilead), US2017209594 (Immunomedics/Gilead), US2017274093 (Immunomedics/Gilead), US2018110772 (Immunomedics/Gilead), US2018185351 (Immunomedics/Gilead), US2018271992 (Immunomedics/Gilead), WO2018217227 (Immunomedics/Gilead), US2019248917 (Immunomedics/Gilead), CN111534585 (Immunomedics/Gilead), US2021093730 (Immunomedics/Gilead), US2021069343 (Immunomedics/Gilead), U.S. Pat. No. 8,435,539 (Immunomedics/Gilead), U.S. Pat. No. 8,435,529 (Immunomedics/Gilead), U.S. Pat. No. 9,492,566 (Immunomedics/Gilead), WO2003074566 (Gilead), WO2020257648 (Gilead), US2013039861 (Gilead), WO2014163684 (Gilead), U.S. Pat. No. 9,427,464 (LivTech/Chiome), U.S. Ser. No. 10/501,555 (Abruzzo Theranostic/Oncoxx), WO2018036428 (Sichuan Kelun Pharma), WO2013068946 (Pfizer), WO2007095749 (Roche), and WO2020094670 (SynAffix). In some embodiments, the anti-Trop-2 antibody is selected from hRS7, Trop-2-XPAT, and BAT-8003. In some embodiments, the anti-Trop-2 antibody is hRS7. In some embodiments, hRS7 is as disclosed in U.S. Pat. Nos. 7,238,785; 7,517,964 and 8,084,583, which are incorporated herein by reference. In some embodiments, the antibody-drug conjugate comprises an anti-Trop-2 antibody and an anticancer agent linked by a linker. In some embodiments, the linker includes the linkers disclosed in U.S. Pat. No. 7,999,083. In some embodiments, the linker is CL2A. In some embodiments, the drug moiety of antibody-drug conjugate is a chemotherapeutic agent. In some embodiments, the chemotherapeutic agent is selected from doxorubcin (DOX), epirubicin, morpholinodoxorubicin (morpholino-DOX), cyanomorpholino-doxorubicin (cyanomorpholinoDOX), 2-pyrrolino-doxorubicin (2-PDOX), CPT, 10-hydroxy camptothecin, SN-38, topotecan, lurtotecan, 9-aminocamptothecin, 9-nitrocamptothecin, taxanes, geldanamycin, ansamycins, and epothilones. In some embodiments, the chemotherapeutic moiety is SN-38. In some embodiments the antibody and/or fusion protein provided herein is administered with sacituzumab govitecan.

In some embodiments the ADCs that can be co-administered include an antibody targeting carcinoembryonic antigen-related cell adhesion molecule 5 (CEACAM5; CD66a; NCBI Gene ID: 634). In some embodiments the CEACAM5 antibody is hMN-14 (e.g., as described in WO1996011013). In some embodiments the CEACAM5-ADC is as described in WO2010093395 (anti-CEACAM-5-CL2A-SN38). In some embodiments the antibody and/or fusion protein provided herein is administered with the CEACAM5-ADC IMMU-130.

In some embodiments the ADCs that can be co-administered include an antibody targeting MHC class II cell surface receptor encoded by the human leukocyte antigen complex (HLA-DR). In some embodiments the HLA-DR antibody is hL243 (e.g., as described in WO2006094192). In some embodiments the HLA-DR-ADC is as described in WO2010093395 (anti-HLA-DR-CL2A-SN38). In some embodiments the antibody and/or fusion protein provided herein is administered with the HLA-DR-ADC IMMU-140.

Cancer Gene Therapy and Cell Therapy

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with a cancer gene therapy and cell therapy. Cancer gene therapies and cell therapies include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer.

Cellular Therapies

In some embodiments a compound of Formula (I), (Ia), (Ia-1), (Ia-2), (Ia-3), (Ib), (Ib-1), (Ib-2), (Ib-3), (Ib-4), (Ib-5), (Ib-6), (Ib-7), (Ib-8), (Ib-9), (Ib-10), (Ib-11), (Ib-12), or (Ib-13) provided herein, or pharmaceutically acceptable salt thereof, is administered with one or more cellular therapies. Illustrative cellular therapies include without limitation co-administration of one or more of a population of natural killer (NK) cells, NK-T cells, T cells, cytokine-induced killer (CIK) cells, macrophage (MAC) cells, tumor infiltrating lymphocytes (TILs) and/or dendritic cells (DCs). In some embodiments, the cellular therapy entails a T cell therapy, e.g., co-administering a population of alpha/beta TCR T cells, gamma/delta TCR T cells, regulatory T (Treg) cells and/or TRuC™ T cells. In some embodiments, the cellular therapy entails a NK cell therapy, e.g., co-administering NK-92 cells. As appropriate, a cellular therapy can entail the co-administration of cells that are autologous, syngeneic or allogeneic to the subject.

In some embodiments the cellular therapy entails co-administering cells comprising chimeric antigen receptors (CARs). In such therapies, a population of immune effector cells engineered to express a CAR, wherein the CAR comprises a tumor antigen-binding domain. In T cell therapies, the T cell receptors (TCRs) are engineered to target tumor derived peptides presented on the surface of tumor cells.

With respect to the structure of a CAR, in some embodiments, the CAR comprises an antigen binding domain, a transmembrane domain, and an intracellular signaling domain. In some embodiments, the intracellular domain comprises a primary signaling domain, a costimulatory domain, or both of a primary signaling domain and a costimulatory domain. In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon R1b), CD79a, CD79b, Fcgamma RIIa, DAP10, and DAP12.

In some embodiments, the costimulatory domain comprises a functional domain of one or more proteins selected from the group consisting of CD27, CD28, 4-1BB(CD137), OX40, CD30, CD40, PD-1, ICOS, CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRFI), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, ITGAE, CD103, ITGAL, CD1A (NCBI Gene ID: 909), CD1B (NCBI Gene ID: 910), CD1C (NCBI Gene ID: 911), CD1D (NCBI Gene ID: 912), CDIE (NCBI Gene ID: 913), ITGAM, ITGAX, ITGB1, CD29, ITGB2 (CD18, LFA-1), ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, ICOS (CD278), 4-1BB(CD137), GITR, CD40, BAFFR, HVEM (LIGHTR), SLAMF7, NKp80 (KLRF1), CD160, CD19, IL2R beta, IL2R gamma, IL7R, ITGA1, VLA1, CD49a, ITGA4, IA4, CD49D, ITGA6, VLA-6, CD49f, ITGAD, CD1A, CD1B, CD1C, CD1D, CDIE, ITGAE, CD103, ITGAL, ITGAM, ITGAX, ITGB1, CD29, ITGB2 (LFA-1, CD18), ITGB7, TNFR2, DNAM1 (CD226), SLAMF4 (CD244, 2B4), CD84, CD96 (TACTILE), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C.

In some embodiments, the TCR or CAR antigen binding domain or the immunotherapeutic agent described herein (e.g., monospecific or multi-specific antibody or antigen-binding fragment thereof or antibody mimetic) binds a tumor-associated antigen (TAA). In some embodiments, the tumor-associated antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvlll); ganglioside G2 (GD2); ganglioside GD3 (αNeuSAc(2-8)αNeuSAc(2-3)βDGaip(1-4)bDGIcp(1-1) Cer); ganglioside GM3 (αNeuSAc(2-3)βDGalp(1-4) βDGIcp(1-1)Cer); TNF receptor superfamily member 17 (TNFRSF17, BCMA); Tn antigen ((Tn Ag) or (GaINAcu-Ser/Thr)); prostate-specific membrane antigen (PSMA); receptor tyrosine kinase-like orphan receptor 1 (ROR1); tumor-associated glycoprotein 72 (TAG72); CD38; CD44v6; Carcinoembryonic antigen (CEA); epithelial cell adhesion molecule (EPCAM); B7H3 (CD276); KIT (CD117); interleukin-13 receptor subunit alpha-2 (IL-13Ra2 or CD213A2); mesothelin; interleukin 11 receptor alpha (IL-11Ra); prostate stem cell antigen (PSCA); protease serine 21 (Testisin or PRSS21); vascular endothelial growth factor receptor 2 (VEGFR2); Lewis(Y)antigen; CD24; platelet-derived growth factor receptor beta (PDGFR-beta); stage-specific embryonic antigen-4 (SSEA-4); CD20; delta like 3 (DLL3); folate receptor alpha; receptor tyrosine-protein kinase, ERBB2 (Her2/neu); mucin 1, cell surface associated (MUC1); epidermal growth factor receptor (EGFR); neural cell adhesion molecule (NCAM); prostase; prostatic acid phosphatase (PAP); elongation factor 2 mutated (ELF2M); ephrin B2; fibroblast activation protein alpha (FAP); insulin-like growth factor 1 receptor (IGF-I receptor), carbonic anhydrase IX (CAIX); proteasome (Prosome, Macropain) subunit, beta type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); fucosyl GM1; sialyl Lewis adhesion molecule (sLe); transglutaminase 5 (TGS5); high molecular weight-melanoma associated antigen (HMWMAA); o-acetyl-GD2 ganglioside (OAcGD2); folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); chromosome X open reading frame 61 (CXORF61); CD97; CD179a; anaplastic lymphoma kinase (ALK); polysialic acid; placenta-specific 1 (PLAC1); hexasaccharide portion of globoH glycoceramide (GloboH); mammary gland differentiation antigen (NY-BR-1); uroplakin 2 (UPK2); hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); olfactory receptor 51E2 (ORS IE2); TCR Gamma Alternate Reading Frame Protein (TARP); Wilms tumor protein (WT1); cancer/testis antigen 1 (NY-ESO-1); cancer/testis antigen 2 (LAGE-la); melanoma associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); rat sarcoma (Ras) mutant; human telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); androgen receptor; cyclin B1; v-myc avian myelocytomatosis viral oncogene neuroblastoma derived homolog (MYCN); ras homolog family member C (RhoC); tyrosinase-related protein 2 (TRP-2); cytochrome P450 1B1(CYP IBI); CCCTC- Binding Factor (Zinc Finger Protein)-Like (BORIS or Brother of the Regulator of Imprinted Sites), squamous cell carcinoma antigen recognized by T-cells 3 (SART3); paired box protein Pax-5 (PAX5); proacrosin binding protein sp32 (OY-TES I); lymphocyte-specific protein tyrosine kinase (LCK); A kinase anchor protein 4 (AKAP-4); synovial sarcoma, X breakpoint 2 (SSX2); receptor for advanced glycation endproducts (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; leukocyte-associated immunoglobulin-like receptor 1 (LAIRI); Fc fragment of IgA receptor (FCAR or CD89); leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1). In some embodiments, the target is an epitope of the tumor associated antigen presented in an MHC.

In some embodiments, the tumor antigen is selected from CD150, 5T4, ActRIIA, B7, TNF receptor superfamily member 17 (TNFRSF17, BCMA), CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRVIII, EGP-2, EGP-4, EPHa2, ErbB2, ErbB3, ErbB4, FBP, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-IR, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acetylcholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microglobulin, Fc Receptor-like 5 (FcRL5).

In some embodiments, the antigen binding domain binds to an epitope of a target or tumor associated antigen (TAA) presented in a major histocompatibility complex (MHC) molecule. In some embodiments, the TAA is a cancer testis antigen. In some embodiments, the cancer testis antigen is selected from the group consisting of acrosin binding protein (ACRBP; CT23, OY-TES-1, SP32; NCBI Gene ID: 84519), alpha fetoprotein (AFP; AFPD, FETA, HPAFP; NCBI Gene ID: 174); A-kinase anchoring protein 4 (AKAP4; AKAP 82, AKAP-4, AKAP82, CT99, FSC1, HI, PRKA4, hAKAP82, p82; NCBI Gene ID: 8852), ATPase family AAA domain containing 2 (ATAD2; ANCCA, CT137, PRO2000; NCBI Gene ID: 29028), kinetochore scaffold 1 (KNL1; AF15Q14, CASC5, CT29, D40, MCPH4, PPP1R55, Spc7, hKNL-1, hSpc105; NCBI Gene ID: 57082), centrosomal protein 55 (CEP55; C10orf3, CT111, MARCH, URCC6; NCBI Gene ID: 55165), cancer/testis antigen 1A (CTAG1A; ESO1; CT6.1; LAGE-2; LAGE2A; NY-ESO-1; NCBI Gene ID: 246100), cancer/testis antigen 1B (CTAG1B; CT6.1, CTAG, CTAG1, ESO1, LAGE-2, LAGE2B, NY-ESO-1; NCBI Gene ID: 1485), cancer/testis antigen 2 (CTAG2; CAMEL, CT2, CT6.2, CT6.2a, CT6.2b, ESO2, LAGE-1, LAGE2B; NCBI Gene ID: 30848), CCCTC-binding factor like (CTCFL; BORIS, CT27, CTCF-T, HMGB1L1, dJ579F20.2; NCBI Gene ID: 140690), catenin alpha 2 (CTNNA2; CAP-R, CAPR, CDCBM9, CT114, CTNR; NCBI Gene ID: 1496), cancer/testis antigen 83 (CT83; CXorf61, KK-LC-1, KKLC1; NCBI Gene ID: 203413), cyclin A1 (CCNA1; CT146; NCBI Gene ID: 8900), DEAD-box helicase 43 (DDX43; CT13, HAGE; NCBI Gene ID: 55510), developmental pluripotency associated 2 (DPPA2; CT100, ECAT15-2, PESCRG1; NCBI Gene ID: 151871), fetal and adult testis expressed 1 (FATE1; CT43, FATE; NCBI Gene ID: 89885), FMR 1 neighbor (FMR1NB; CT37, NY-SAR-35, NYSAR35; NCBI Gene ID: 158521), HORMA domain containing 1 (HORMAD1; CT46, NOHMA; NCBI Gene ID: 84072), insulin like growth factor 2 mRNA binding protein 3 (IGF2BP3; CT98, IMP-3, IMP3, KOC, KOC1, VICKZ3; NCBI Gene ID: 10643), leucine zipper protein 4 (LUZP4; CT-28, CT-8, CT28, HOM-TES-85; NCBI Gene ID: 51213), lymphocyte antigen 6 family member K (LY6K; CT97, HSJ001348, URLC10, ly-6K; NCBI Gene ID: 54742), maelstrom spermatogenic transposon silencer (MAEL; CT128, SPATA35; NCBI Gene ID: 84944), MAGE family member A1 (MAGEA1; CT1.1, MAGE1; NCBI Gene ID: 4100); MAGE family member A3 (MAGEA3; CT1.3, HIP8, HYPD, MAGE3, MAGEA6; NCBI Gene ID: 4102); MAGE family member A4 (MAGEA4; CT1.4, MAGE-41, MAGE-X2, MAGE4, MAGE4A, MAGE4B; NCBI Gene ID: 4103); MAGE family member A11 (MAGEA11; CT1.11, MAGE-11, MAGE11, MAGEA-11; NCBI Gene ID: 4110); MAGE family member C1 (MAGEC1; CT7, CT7.1; NCBI Gene ID: 9947); MAGE family member C2 (MAGEC2; CT10, HCA587, MAGEE1; NCBI Gene ID: 51438); MAGE family member D1 (MAGED1; DLXIN-1, NRAGE; NCBI Gene ID: 9500); MAGE family member D2 (MAGED2; 11B6, BARTS5, BCG-1, BCG1, HCA10, MAGE-D2; NCBI Gene ID: 10916), kinesin family member 20B (KIF20B; CT90, KRMP1, MPHOSPH1, MPP-1, MPP1; NCBI Gene ID: 9585), NUF2 component of NDC80 kinetochore complex (NUF2; CDCA1, CT106, NUF2R; NCBI Gene ID: 83540), nuclear RNA export factor 2 (NXF2; CT39, TAPL-2, TCP11X2; NCBI Gene ID: 56001), PAS domain containing repressor 1 (PASD1; CT63, CT64, OXTES1; NCBI Gene ID: 139135), PDZ binding kinase (PBK; CT84, HEL164, Nori-3, SPK, TOPK; NCBI Gene ID: 55872), piwi like RNA-mediated gene silencing 2 (PIWIL2; CT80, HILI, PIWIL1L, mili; NCBI Gene ID: 55124), preferentially expressed antigen in melanoma (PRAME; CT130, MAPE, OIP-4, OIP4; NCBI Gene ID: 23532), sperm associated antigen 9 (SPAG9; CT89, HLC-6, HLC4, HLC6, JIP-4, JIP4, JLP, PHET, PIG6; NCBI Gene ID: 9043), sperm protein associated with the nucleus, X-linked, family member A1 (SPANXA1; CT11.1, CT11.3, NAP-X, SPAN-X, SPAN-Xa, SPAN-Xb, SPANX, SPANX-A; NCBI Gene ID: 30014), SPANX family member A2 (SPANXA2; CT11.1, CT11.3, SPANX, SPANX-A, SPANX-C, SPANXA, SPANXC; NCBI Gene ID: 728712), SPANX family member C (SPANXC; CT11.3, CTp11, SPANX-C, SPANX-E, SPANXE; NCBI Gene ID: 64663), SPANX family member D (SPANXD; CT11.3, CT11.4, SPANX-C, SPANX-D, SPANX-E, SPANXC, SPANXE, dJ171K16.1; NCBI Gene ID: 64648), SSX family member 1 (SSX1; CT5.1, SSRC; NCBI Gene ID: 6756), SSX family member 2 (SSX2; CT5.2, CT5.2A, HD21, HOM-MEL-40, SSX; NCBI Gene ID: 6757), synaptonemal complex protein 3 (SYCP3; COR1, RPRGL4, SCP3, SPGF4; NCBI Gene ID: 50511), testis expressed 14, intercellular bridge forming factor (TEX14; CT113, SPGF23; NCBI Gene ID: 56155), transcription factor Dp family member 3 (TFDP3; CT30, DP4, HCA661; NCBI Gene ID: 51270), serine protease 50 (PRSS50; CT20, TSP50; NCBI Gene ID: 29122), TTK protein kinase (TTK; CT96, ESK, MPH1, MPS1, MPSIL1, PYT; NCBI Gene ID: 7272) and zinc finger protein 165 (ZNF165; CT53, LD65, ZSCAN7; NCBI Gene ID: 7718). T cell receptors (TCRs) and TCR-like antibodies that bind to an epitope of a cancer testis antigen presented in a major histocompatibility complex (MHC) molecule are known in the art and can be used in the herein described heterodimers. Cancer testis antigens associated with neoplasia are summarized, e.g., in Gibbs, et al., *Trends Cancer* 2018 October; 4(10):701-712 and the CT database website at cta.lncc.br/index.php. Illustrative TCRs and TCR-like antibodies that bind to an epitope of NY-ESO-1 presented in an MHC are described, e.g., in Stewart-Jones, et al., *Proc Natl Acad Sci USA*. 2009 Apr. 7; 106(14):5784-8; WO2005113595, WO2006031221, WO2010106431, WO2016177339, WO2016210365, WO2017044661, WO2017076308, WO2017109496, WO2018132739, WO2019084538, WO2019162043, WO2020086158 and WO2020086647. Illustrative TCRs and TCR-like antibodies that bind to an epitope of PRAME presented in an MHC are described, e.g., in WO2011062634, WO2016142783, WO2016191246, WO2018172533, WO2018234319 and WO2019109821. Illustrative TCRs and TCR-like antibodies that bind to an epitope of a MAGE variant presented in an MHC are described, e.g., in WO2007032255, WO2012054825, WO2013039889, WO2013041865, WO2014118236, WO2016055785, WO2017174822, WO2017174823, WO2017174824, WO2017175006, WO2018097951, WO2018170338, WO2018225732 and WO2019204683. Illustrative TCRs and TCR-like antibodies that bind to an epitope of alpha fetoprotein (AFP) presented in an MHC are described, e.g., in WO2015011450. Illustrative TCRs and TCR-like antibodies that bind to an epitope of SSX2 presented in an MHC are described, e.g., in WO2020063488. Illustrative TCRs and TCR-like antibodies that bind to an epitope of KK-LC-1 (CT83) presented in an MHC are described, e.g., in WO2017189254.

Examples of cell therapies include: Algenpantucel-L, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, CryoStim, AlloStim, lentiviral transduced huCART-meso cells, CART-22 cells, EGFRt/19-28z/4-1BBL CAR T cells, autologous 4H11-28z/fIL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, and CSG-005.

In some embodiments the one or more additional co-administered therapeutic agents can be categorized by their mechanism of action, e.g., into the following groups:

- agents targeting adenosine deaminase, such as pentostatin or cladribine;
- agents targeting ATM, such as AZD1390;
- agents targeting MET, such as savolitinib, capmatinib, tepotinib, ABT-700, AG213, JNJ-38877618 (OMO-1), merestinib, HQP-8361, BMS-817378, or TAS-115;
- agents targeting mitogen-activated protein kinase, such as antroquinonol, binimetinib, cobimetinib, selumetinib, trametinib, uprosertib, mirdametinib (PD-0325901), pimasertib, refametinib, or compounds disclosed in WO2011008709, WO2013112741, WO2006124944, WO2006124692, WO2014064215, WO2018005435, Zhou, et al., Cancer Lett. 2017 Nov. 1, 408:130-137, Teli, et al., J Enzyme Inhib Med Chem. (2012) 27(4):558-70; Gangwall, et al., Curr Top Med Chem. (2013) 13(9):1015-35; Wu, et al., Bioorg Med Chem Lett. (2009) 19(13):3485-8; Kaila, et al., Bioorg Med Chem. (2007) 15(19):6425-42, or Hu, et al., Bioorg Med Chem Lett. (2011) 21(16):4758-61;
- agents targeting thymidine kinase, such as aglatimagene besadenovec (ProstAtak, PancAtak, GliAtak, GMCI, or AdV-tk);
- agents targeting targeting an interleukin pathway, such as pegilodecakin (AM-0010) (pegylated IL10), CA-4948 (IRAK4 inhibitor);
- agents targeting cytochrome P450 family members, such as letrozole, anastrozole, aminoglutethimide, megestrol acetate (MEGACE®), exemestane, formestane, fadrozole, vorozole (RIVISOR®), letrozole (FEMARA®), or anastrozole (ARIMIDEX®);
- agents targeting CD73, such as a CD73 inhibitor (e.g., quemliclustat (AB680)) or an anti-CD73 antibody (e.g., oleclumab);
- agents targeting DKK3, such as MTG-201;
- agents targeting EEF1A2, such as plitidepsin;
- agents targeting EIF4A1, such as rohinitib;
- agents targeting endoglin, such as TRC105 (carotuximab);
- agents targeting exportin-1, such as eltanexor;
- agents targeting fatty acid amide hydrolase, such as compounds disclosed in WO2017160861;
- agents targeting heat shock protein 90 beta family member 1, such as anlotinib;
- agents targeting lactotransferrin, such as ruxotemitide (LTX-315);
- agents targeting lysyl oxidase, such as compounds disclosed in U.S. Pat. Nos. 4,965,288, 4,997,854, 4,943,593, 5,021,456, 5,059,714, 5,120,764, 5,182,297, 5,252,608, or US20040248871;
- agents targeting MAGE family members, such as KITE-718, MAGE-A10C796T, or MAGE-A10 TCR;
- agents targeting MDM2, such as ALRN-6924, CMG-097, milademetan monotosylate monohydrate (DS-3032b), or AMG-232;
- agents targeting MDM4, such as ALRN-6924;
- agents targeting melan-A, such as MART-1 F5 TCR engineered PBMCs;
- agents targeting mesothelin, such as CSG-MESO or TC-210;
- agents targeting METAP2, such as M8891 or APL-1202;
- agents targeting NLRP3, such as BMS-986299;
- agents targeting oxoglutarate dehydrogenase, such as devimistat (CPI-613);

agents targeting placenta growth factor, such as aflibercept;

agents targeting SLC10A3, such as compounds disclosed in WO2015148954, WO2012082647, or WO2017160861;

agents targeting transforming growth factor alpha (TGFα), such as compounds disclosed in WO2019103203;

agents targeting tumor protein p53, such as kevetrin (stimulator);

agents targeting vascular endothelial growth factor A, such as aflibercept;

agents targeting vascular endothelial growth factor receptor, such as fruquintinib or MP0250;

agents targeting VISTA, such as CA-170, or HMBD-002;

agents targeting WEE1, such as adavosertib (AZD-1775);

small molecule inhibitors targeting ABL1, such as imatinib, rebastinib, asciminib, or ponatinib (ICLUSIG®);

small molecule antagonists targeting adenosine receptor, such as CPI-444, AZD-4635, preladenant, etrumadenant (AB928), or PBF-509;

small molecule inhibitors targeting arachidonate 5-lipoxygenase, such as meclofenamate sodium or zileuton;

small molecule inhibitors targeting ATR serine/threonine kinase, such as BAY-937, ceralasertib (AZD6738), AZD6783, VX-803, or VX-970 (berzosertib);

small molecule inhibitors targeting AXL receptor tyrosine kinase, such as bemcentinib (BGB-324), SLC-0211, or gilteritinib (Axl/Flt3);

small molecule inhibitors targeting Bruton's tyrosine kinase (BTK), such as (S)-6-amino-9-(1-(but-2-ynoyl) pyrrolidin-3-yl)-7-(4-phenoxyphenyl)-7H-purin-8 (9H)-one, acalabrutinib (ACP-196), zanubrutinib (BGB-3111), CB988, poseltinib (HM71224), ibrutinib (Imbruvica), M-2951 (evobrutinib), tirabrutinib (ONO-4059), rilzabrutinib (PRN-1008), spebrutinib (CC-292), vecabrutinib, ARQ-531 (MK-1026), SHR-1459, DTRMWXHS-12, or TAS-5315;

small molecule inhibitors targeting neurotrophic receptor tyrosine kinase such as larotrectinib, entrectinib, or selitrectinib (LOXO-195);

small molecule inhibitors targeting ROS proto-oncogene 1, receptor tyrosine kinase, such as entrectinib, repotrectinib (TPX-0005), or lorlatinib;

small molecule inhibitors targeting SRC proto-oncogene, non-receptor tyrosine kinase, such as VAL-201, tirbanibulin (KX2-391), or ilginatinib maleate (NS-018);

small molecule inhibitors targeting B-cell lymphoma 2, such as navitoclax (ABT-263), venetoclax (ABT-199, RG-7601), or AT-101 (gossypol);

small molecule inhibitors targeting bromodomain and external domain (BET) bromodomain containing protein, such as ABBV-744, INCB-054329, INCB057643, AZD-5153, ABT-767, BMS-986158, CC-90010, NHWD-870, ODM-207, ZBC246, ZEN3694, CC-95775 (FT-1101), mivebresib, BI-894999, PLX-2853, PLX-51107, CPI-0610, or GS-5829;

small molecule inhibitors targeting carbohydrate sulfotransferase 15, such as STNM-01;

small molecule inhibitors targeting carbonic anhydrase, such as polmacoxib, acetazolamide, or methazolamide;

small molecule inhibitors targeting catenin beta 1, such as CWP-291, or PRI-724;

small molecule antagonists targeting a C—C motif chemokine receptor, such as CCX-872, BMS-813160 (CCR2/CCR5) or MK-7690 (vicriviroc);

small molecule antagonists targeting a C—X—C motif chemokine receptor (e.g., CXCR4), blixafortide;

small molecule inhibitors targeting cereblon, such as avadomide (CC-122), CC-92480, CC-90009, or iberdomide;

small molecule inhibitors targeting checkpoint kinase 1, such as SRA737;

small molecule inhibitors targeting a complement component, such as Imprime PGG (Biothera Pharmaceuticals);

small molecule inhibitor targeting a C—X—C motif chemokine ligand (e.g., CXCL12), such as olaptesed pegol (NOX-A12);

small molecule inhibitors targeting cytochrome P450 family, such as ODM-209, LAE-201, seviteronel (VT-464), CFG920, abiraterone, or abiraterone acetate;

small molecule inhibitors targeting DEAD-box helicase 5, such as supinoxin (RX-5902);

small molecule inhibitors targeting DGKα, e.g., such as described in WO2021130638;

small molecule inhibitors targeting diablo IAP-binding mitochondrial protein, such as BI-891065;

small molecule inhibitors targeting dihydrofolate reductase, such as pralatrexate or pemetrexed disodium;

small molecule inhibitors targeting DNA dependent protein kinase, such as MSC2490484A (nedisertib), VX-984, AsiDNA (DT-01), LXS-196, or sotrastaurin;

small molecule inhibitors targeting MARCKS, such as BIO-11006;

small molecule inhibitors targeting RIPK1, such as GSK-3145094;

small molecule inhibitors targeting Rho associated coiled-coil containing protein kinase, such as AT13148 or KD025;

small molecule inhibitors targeting DNA topoisomerase, such as irinotecan, firtecan pegol, or amrubicin;

small molecule inhibitors targeting dopamine receptor D2, such as ONC-201;

small molecule inhibitors targeting DOT1 like histone lysine methyltransferase, such as pinometostat (EPZ-5676);

small molecule inhibitors targeting EZH2, such as tazemetostat, CPI-1205, or PF-06821497;

small molecule inhibitors targeting fatty acid synthase, such as TVB-2640 (Sagimet Biosciences);

small molecule inhibitors targeting fibroblast growth factor receptor 2 (FGFR2), such as bemarituzumab (FPA144);

small molecule inhibitors targeting focal adhesion kinase (FAK, PTK2), such as VS-4718, defactinib, or GSK2256098;

small molecule inhibitors targeting folate receptor 1, such as pralatrexate;

small molecule inhibitors targeting FOXM1, such as thiostrepton;

small molecule inhibitors targeting galectin 3, such as belapectin (GR-MD-02);

small molecule antagonists targeting glucocorticoid receptor, such as relacorilant (CORT-125134);

small molecule inhibitors targeting glutaminase include without limitation CB-839 (telaglenastat), or bis-2-(5-phenylacetamido-1,3,4-thiadiazol-2-yl)ethyl sulfide (BPTES);

small molecule inhibitors targeting GNRHR, such as elagolix, relugolix, or degarelix;

small molecule inhibitors targeting EPAS1, such as belzutifan (PT-2977 (Merck & Co.));

small molecule inhibitors targeting isocitrate dehydrogenase (NADP(+)), such as limitation ivosidenib (AG-120), vorasidenib (AG-881) (IDH1 and IDH2), IDH-305, or enasidenib (AG-221);

small molecule inhibitors targeting lysine demethylase 1A, such as CC-90011;

small molecule inhibitors targeting MAPK interacting serine/threonine kinase, such as tomivosertib (eFT-508);

small molecule inhibitors targeting notch receptor, such as AL-101 (BMS-906024);

small molecule inhibitors targeting polo like kinase 1 (PLK1), such as volasertib or onvansertib;

small molecule inhibitors targeting poly(ADP-ribose) polymerase (PARP), such as olaparib (MK7339), rucaparib, veliparib, talazoparib, ABT-767, pamiparib (BGB-290), fluazolepali (SHR-3162), niraparib (JNJ-64091742), stenoparib (2X-121 (e-7499)), simmiparib, IMP-4297, SC-10914, IDX-1197, HWH-340, CEP 9722, CEP-8983, E7016, 3-aminobenzamide, or CK-102;

small molecule inhibitors targeting polycomb protein EED, such as MAK683;

small molecule inhibitors targeting porcupine O-acyltransferase, such as WNT-974;

small molecule inhibitors targeting prostaglandin-endoperoxide synthase, such as HP-5000, lornoxicam, ketorolac tromethamine, bromfenac sodium, otenaproxesul (ATB-346), mofezolac, GLY-230, TRK-700, diclofenac, meloxicam, parecoxib, etoricoxib, celecoxib, AXS-06, diclofenac potassium, reformulated celecoxib (DRGT-46), AAT-076, meisuoshuli, lumiracoxib, meloxicam, valdecoxib, zaltoprofen, nimesulide, anitrazafen, apricoxib, cimicoxib, deracoxib, flumizole, firocoxib, mavacoxib, pamicogrel, parecoxib, robenacoxib, rofecoxib, rutecarpine, tilmacoxib, zaltoprofen, or imrecoxib;

small molecule inhibitors targeting protein arginine N methyltransferase, such as MS203, PF-06939999, GSK3368715, or GSK3326595;

small molecule inhibitors targeting PTPN11, such as TNO155 (SHP-099), RMC-4550, JAB-3068, RMC-4630 (SAR442720), or compounds disclosed in WO2018172984 or WO2017211303;

small molecule antagonist targeting retinoic acid receptor, such as tamibarotene (SY-1425);

small molecule inhibitors targeting ribosomal protein S6 kinase B1, such as MSC2363318A;

small molecule inhibitors targeting S100 calcium binding protein A9, such as tasquinimod;

small molecule inhibitors targeting selectin E, such as uproleselan sodium (GMI-1271);

small molecule inhibitors targeting SF3B1, such as H3B-8800;

small molecule inhibitors targeting Sirtuin-3, such as YC8-02;

small molecule inhibitors targeting SMO, such as sonidegib (Odomzo®, formerly LDE-225), vismodegib (GDC-0449), glasdegib (PF-04449913), itraconazole, or patidegib, taladegib;

small molecule antagonists targeting somatostatin receptor, such as OPS-201;

small molecule inhibitors targeting sphingosine kinase 2, such as opaganib (Yeliva®, ABC294640);

small molecule inhibitors targeting STAT3, such as napabucasin (BBI-608);

small molecule inhibitors targeting tankyrase, such as G007-LK or stenoparib (2X-121 (e-7499));

small molecule inhibitors targeting TFGBR1, such as galunisertib, PF-06952229;

small molecule inhibitors targeting thymidylate synthase, such as idetrexed (ONX-0801);

small molecule inhibitors targeting tumor protein p53, such as CMG-097;

small molecule inhibitors targeting valosin-containing protein, such as CB-5083;

small molecule inhibitors targeting WT1, such as ombipepimut-S (DSP-7888);

small molecule agonists targeting adenosine receptor, such as namodenoson (CF102);

small molecule agonist(s) targeting asparaginase, such as crisantaspase (Erwinase®), GRASPA (ERY-001, ERY-ASP), calaspargase pegol, or pegaspargase;

small molecule agonists targeting CCAAT enhancer binding protein alpha, such as MTL-501;

small molecule agonists targeting cytochrome P450 family, such as mitotane;

small molecule agonists targeting DExD/H-box helicase 58, such as RGT-100;

small molecule agonists targeting GNRHR, such as leuprorelin acetate, leuprorelin acetate sustained release depot (ATRIGEL), triptorelin pamoate, or goserelin acetate;

small molecule agonists targeting GRB2, such as prexigebersen (BP1001);

small molecule agonists targeting NFE2L2, such as omaveloxolone (RTA-408);

small molecule agonists targeting NOD2, such as mifamurtide (liposomal);

small molecule agonists targeting RAR-related orphan receptor gamma, such as cintirorgon (LYC-55716);

small molecule agonists targeting retinoic acid receptor (RAR), such as tretinoin;

small molecule agonists targeting STING1, such as ADU-S100 (MIW-815), SB-11285, MK-1454, SR-8291, AdVCA0848, GSK-532, SYN-STING, MSA-1, SR-8291, cyclic-GAMP (cGAMP), or cyclic-di-AMP;

small molecule agonists targeting thyroid hormone receptor beta, such as levothyroxine sodium;

small molecule agonists targeting tumor necrosis factor, such as tasonermin;

antisense agents targeting baculoviral IAP repeat containing 5, such as EZN-3042;

antisense agents targeting GRB2, such as prexigebersen;

antisense agents targeting heat shock protein 27, such as apatorsen;

antisense agents targeting STAT3, such as danvatirsen (IONIS-STAT3-2.5Rx);

gene therapies targeting a C—C motif chemokine receptor, such as SB-728-T;

gene therapies targeting an interleukin, such as EGENE-001, tavokinogene telseplasmid, nogapendekin alfa (ALT-803), NKTR-255, NIZ-985 (hetIL-15), SAR441000, or MDNA-55;

antibodies targeting claudin 18, such as claudiximab;

antibodies targeting clusterin, such as AB-16B5;

antibodies targeting a complement component, such as ravulizumab (ALXN-1210);

antibodies targeting a C—X—C motif chemokine ligand, such as BMS-986253 (HuMax-Inflam);

- antibodies targeting delta like canonical Notch ligand 4 (DLL4), such as demcizumab, navicixizumab (DLL4/VEGF);
- antibodies targeting EPH receptor A3, such as fibatuzumab (KB-004);
- antibodies targeting epithelial cell adhesion molecule, such as oportuzumab monatox (VB4-845);
- antibodies targeting fibroblast growth factor, such as GAL-F2, B-701 (vofatamab);
- antibodies targeting hepatocyte growth factor, such as MP-0250;
- antibodies targeting an interleukin, such as canakinumab (ACZ885), gevokizumab (VPM087), CJM-112, guselkumab, talacotuzumab (JNJ-56022473), siltuximab, or tocilizumab;
- antibodies targeting LRRC15, such as ABBV-085 or cusatuzumab (ARGX-110);
- antibodies targeting mesothelin, such as BMS-986148, SEL-403, or anti-MSLN-MMAE;
- antibodies targeting myostatin, such as landogrozumab;
- antibodies targeting notch receptor, such as tarextumab;
- antibodies targeting TGFB1 (TGFβ1), such as SAR439459, ABBV-151, NIS793, SRK-181, XOMA089, or compounds disclosed in WO2019103203;
- vaccines targeting fms related receptor tyrosine kinase, such as HLA-A2402/HLA-A0201 restricted epitope peptide vaccine;
- vaccines targeting heat shock protein 27, such as PSV-AML (PhosphoSyn Vax);
- vaccines targeting PD-L1, such as IO-120+IO-103 (PD-L1/PD-L2 vaccines) or IO-103;
- vaccines targeting tumor protein p53, such as MVA-p53;
- vaccines targeting WT1, such as WT-1 analog peptide vaccine (WT1-CTL);
- cell therapies targeting baculoviral IAP repeat containing 5, such as tumor lysate/MUC1/survivin PepTivator-loaded dendritic cell vaccine;
- cell therapies targeting carbonic anhydrase, such as DC-Ad-GMCAIX;
- cell therapies targeting C—C motif chemokine receptor, such as CCR5-SBC-728-HSPC;
- cell therapies targeting folate hydrolase 1, such as CIK-CAR.PSMA or CART-PSMA-TGFβRDN;
- cell therapies targeting GSTP1, such as CPG3-CAR (GLYCAR);
- cell therapies targeting HLA-A, such as FH-MCVA2TCR or NeoTCR-P1;
- cell therapies targeting an interleukin, such as CST-101;
- cell therapies targeting KRAS, such as anti-KRAS G12D mTCR PBL;
- cell therapies targeting MET, such as anti-cMet RNA CAR T;
- cell therapies targeting MUC16, such as JCAR-020;
- cell therapies targeting PD-1, such as PD-1 knockout T cell therapy (esophageal cancer/NSCLC);
- cell therapies targeting PRAME, such as BPX-701;
- cell therapies targeting transforming protein E7, such as KITE-439;
- cell therapies targeting WT1, such as WT1-CTL, ASP-7517, or JTCR-016.

Exemplified Combination Therapies

Lymphoma or Leukemia Combination Therapy

Some chemotherapy agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541, bortezomib (VELCADE®), bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17 AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R MCP (rituximab and MCP), R-roscovitine (seliciclib, CYC202), sargramostim, sildenafil citrate, simvastatin, sirolimus, styryl sulphones, tacrolimus, tanespimycin, temsirolimus (CCI-779), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy

Treatment of non-Hodgkin's lymphomas (NHL), especially those of B cell origin, includes using monoclonal antibodies, standard chemotherapy approaches (e.g., CHOP (cyclophosphamide, doxorubicin, vincristine, and prednisone), CVP (cyclophosphamide, vincristine, and prednisone), FCM (fludarabine, cyclophosphamide, and mitoxantrone), MCP (Mitoxantrone, Chlorambucil, Prednisolone), all optionally including rituximab (R) and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP (rituximab, cyclophosphamide, doxorubicin, vincristine, and prednisone), R-FCM, R-CVP, and R MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

Therapeutic treatments for mantle cell lymphoma (MCL) include combination chemotherapies such as CHOP, hyperCVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

An alternative approach to treating MCL is immunotherapy. One immunotherapy uses monoclonal antibodies like rituximab. Another uses cancer vaccines, such as GTOP-99, which are based on the genetic makeup of an individual patient's tumor.

A modified approach to treat MCL is radioimmunotherapy, wherein a monoclonal antibody is combined with a radioisotope particle, such as iodine-131 tositumomab (BEXXAR®) and yttrium-90 ibritumomab tiuxetan (ZEVALIN®). In another example, BEXXAR® is used in sequential treatment with CHOP.

Other approaches to treating MCL include autologous stem cell transplantation coupled with high-dose chemotherapy, administering proteasome inhibitors such as bortezomib (VELCADE® or PS-341), or administering antiangiogenesis agents such as thalidomide, especially in combination with rituximab.

Another treatment approach is administering drugs that lead to the degradation of Bcl-2 protein and increase cancer cell sensitivity to chemotherapy, such as oblimersen, in combination with other chemotherapeutic agents.

A further treatment approach includes administering mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents.

Other recent therapies for MCL have been disclosed. Such examples include flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CCI-779), everolimus (RAD001), BMS-345541, curcumin, SAHA, thalidomide, lenalidomide (REVLIMID®, CC-5013), and geldanamycin (17 AAG).

Waldenstrom's Macroglobulinemia Combination Therapy

Therapeutic agents used to treat Waldenstrom's Macroglobulinemia (WM) include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ibrutinib, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, ulocuplumab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-Cell Lymphoma (DLBCL) Combination Therapy

Therapeutic agents used to treat diffuse large B-cell lymphoma (DLBCL) include cyclophosphamide, doxorubicin, vincristine, prednisone, anti-CD20 monoclonal antibodies, etoposide, bleomycin, many of the agents listed for WM, and any combination thereof, such as ICE and RICE. In some embodiments therapeutic agents used to treat DLBCL include rituximab (Rituxan®), cyclophosphamide, doxorubicin hydrochloride (hydroxydaunorubicin), vincristine sulfate (Oncovin®), prednisone, bendamustine, ifosfamide, carboplatin, etoposide, ibrutinib, polatuzumab vedotin piiq, bendamustine, copanlisib, lenalidomide (Revlimid®), dexamethasone, cytarabine, cisplatin, Yescarta®, Kymriah®, Polivy® (polatuzumab vedotin), BR (bendamustine (Treanda®), gemcitabine, oxiplatin, oxaliplatin, tafasitamab, polatuzumab, cyclophosphamide, or combinations thereof.

In some embodiments therapeutic agents used to treat DLBCL include R-CHOP (rituximab+cyclophosphamide+doxorubicin hydrochloride (hydroxydaunorubicin)+vincristine sulfate (Oncovin®), +prednisone), rituximab+bendamustine, R-ICE (Rituximab+Ifosfamide+Carboplatin+Etoposide), rituximab+lenalomide, R-DHAP (rituximab+dexamethasone+high-dose cytarabine (Ara C)+cisplatin), Polivy® (polatuzumab vedotin)+BR (bendamustine (Treanda®) and rituximab (Rituxan®), R-GemOx (Gemcitabine+oxaliplatin+rituximab), Tafa-Len (tafasitamab+lenalidomide), Tafasitamab+Revlimid®, polatuzumab+bendamustine, Gemcitabine+oxaliplatin, R-EPOCH (rituximab+etoposide phosphate+prednisone+vincristine sulfate (Oncovin®)+cyclophosphamide+doxorubicin hydrochloride (hydroxydaunorubicin)), or CHOP (cyclophosphamide+doxorubicin hydrochloride (hydroxydaunorubicin)+vincristine sulfate (Oncovin®)+prednisone). In some embodiments therapeutic agents used to treat DLBCL include tafasitamab, glofitamab, epcoritamab, Lonca-T (loncastuximab tesirine), Debio-1562, polatuzumab, Yescarta, JCAR017, ADCT-402, brentuximab vedotin, MT-3724, odronextamab, Auto-03, Allo-501A, or TAK-007.

Chronic Lymphocytic Leukemia Combination Therapy

Therapeutic agents used to treat chronic lymphocytic leukemia (CLL) include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

High Risk Myelodysplastic Syndrome (HR MDS) Combination Therapy

Therapeutic agents used to treat HR MDS include azacitidine (Vidaza®), decitabine (Dacogen®), lenalidomide (Revlimid®), cytarabine, idarubicin, daunorubicin, and combinations thereof. In some embodiments, combinations include cytarabine+daunorubicin and cytarabine+idarubicin. In some embodiments therapeutic agents used to treat HR MDS include pevonedistat, venetoclax, sabatolimab, guadecitabine, rigosertib, ivosidenib, enasidenib, selinexor, BGB324, DSP-7888, or SNS-301.

Low Risk Myelodysplastic Syndrome (LR MDS) Combination Therapy

Therapeutic agents used to treat LR MDS include lenalidomide, azacytidine, and combinations thereof. In some embodiments therapeutic agents used to treat LR MDS include roxadustat, luspatercept, imetelstat, LB-100, or rigosertib.

Acute Myeloid Leukemia (AML) Combination Therapy

Therapeutic agents used to treat AML include cytarabine, idarubicin, daunorubicin, midostaurin (Rydapt®), venetoclax, azacitidine, ivasidenib, gilteritinib, enasidenib, low-dose cytarabine (LoDAC), mitoxantrone, fludarabine, granulocyte-colony stimulating factor, idarubicin, gilteritinib (Xospata®), enasidenib (Idhifa®), ivosidenib (Tibsovo®), decitabine (Dacogen®), mitoxantrone, etoposide, Gemtuzumab ozogamicin (Mylotarg®), glasdegib (Daurismo®), and combinations thereof. In some embodiments therapeutic agents used to treat AML include FLAG-Ida (fludarabine, cytarabine (Ara-C), granulocyte-colony stimulating factor (G-CSF) and idarubicin), cytarabine+idarubicin, cytarabine+daunorubicin+midostaurin, venetoclax+azacitidine, cytarabine+daunorubicin, or MEC (mitoxantrone, etoposide, and cytarabine). In some embodiments, therapeutic agents used to treat AML include pevonedistat, venetoclax, sabatolimab, eprenetapopt, or lemzoparlimab.

Multiple Myeloma (MM) Combination Therapy

Therapeutic agents used to treat MM include lenalidomide, bortezomib, dexamethasone, daratumumab (Darzalex®), pomalidomide, Cyclophosphamide, Carfilzomib (Kyprolis®), Elotuzumab (Empliciti), and combinations thereof. In some embodiments therapeutic agents used to treat MM include RVS (lenalidomide+bortezomib+dexamethasone), RevDex (lenalidomide plus dexamethasone), CYBORD (Cyclophosphamide+Bortezomib+Dexamethasone), Vel/Dex (bortezomib plus dexamethasone), or PomDex (Pomalidomide+low-dose dexamethasone). In some embodiments therapeutic agents used to treat MM include JCARH125, TAK-573, belantamab-m, ide-cel (CAR-T).

Breast Cancer Combination Therapy

Therapeutic agents used to treat breast cancer include albumin-bound paclitaxel, anastrozole, atezolizumab, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, letrozole, methotrexate, mitoxantrone, paclitaxel, pegylated liposomal doxorubicin, pertuzumab, tamoxifen, toremifene, trastuzumab, vinorelbine, and any combinations thereof. In some embodiments therapeutic agents used to treat breast cancer (e.g., HR4+/−/HER2+/−) include trastuzumab (Herceptin®), pertuzumab (Perjeta®), docetaxel, carboplatin, palbociclib (Ibrance®), letrozole, trastuzumab emtansine (Kadcyla®), fulvestrant (Faslodex®), olaparib (Lynparza®), eribulin, tucatinib, capecitabine, lapatinib, everolimus (Afinitor®), exemestane, eribulin mesylate (Halaven®), and combinations thereof. In some embodiments therapeutic agents used to treat breast cancer include trastuzumab+pertuzumab+docetaxel, trastuzumab+pertuzumab+docetaxel+carboplatin, palbociclib+letrozole, tucatinib+capecitabine, lapatinib+capecitabine, palbociclib+fulvestrant, or everolimus+exemestane. In some embodiments therapeutic agents used to treat breast cancer include trastuzumab deruxtecan (Enhertu®), datopotamab deruxtecan (DS-1062), enfortumab vedotin (Padcev®), balixafortide, elacestrant, or a combination thereof. In some embodiments therapeutic agents used to treat breast cancer include balixafortide+eribulin.

Triple Negative Breast Cancer (TNBC) Combination Therapy

Therapeutic agents used to treat TNBC include atezolizumab, cyclophosphamide, docetaxel, doxorubicin, epirubicin, fluorouracil, paclitaxel, and combinations thereof. In some embodiments therapeutic agents used to treat TNBC include olaparib (Lynparza®), atezolizumab (Tecentriq®), paclitaxel (Abraxane®), eribulin, bevacizumab (Avastin®), carboplatin, gemcitabine, eribulin mesylate (Halaven®), sacituzumab govitecan (Trodelvy®), pembrolizumab (Keytruda®), cisplatin, doxorubicin, epirubicin, or a combination thereof. In some embodiments therapeutic agents to treat TNBC include atezolizumab+paclitaxel, bevacizumab+paclitaxel, carboplatin+paclitaxel, carboplatin+gemcitabine, or paclitaxel+gemcitabine. In some embodiments therapeutic agents used to treat TNBC include eryaspase, capivasertib, alpelisib, rucaparib+nivolumab, atezolumab+paclitaxel+gemcitabine+capecitabine+carboplatin, ipatasertib+paclitaxel, ladiratuzumab vedotin+pembrolimab, durvalumab+DS-8201a, trilaciclib+gemcitabine+carboplatin. In some embodiments therapeutic agents used to treat TNBC include trastuzumab deruxtecan (Enhertu®), datopotamab deruxtecan (DS-1062), enfortumab vedotin (Padcev®), balixafortide, adagloxad simolenin, nelipepimut-s (NeuVax®), nivolumab (Opdivo®), rucaparib, toripalimab (Tuoyi®), camrelizumab, capivasertib, durvalumab (Imfinzi), and combinations thereof. In some embodiments therapeutic agents use to treat TNBC include nivolumab+rucaparib, bevacizumab (Avastin®)+chemotherapy, toripalimab+paclitaxel, toripalimab+albumin-bound paclitaxel, camrelizumab+chemotherapy, pembrolizumab+chemotherapy, balixafortide+eribulin, durvalumab+trastuzumab deruxtecan, durvalumab+paclitaxel, or capivasertib+paclitaxel.

Bladder Cancer Combination Therapy

Therapeutic agents used to treat bladder cancer include datopotamab deruxtecan (DS-1062), trastuzumab deruxtecan (Enhertu®), erdafitinib, eganelisib, lenvatinib, bempegaldesleukin (NKTR-214), or a combination thereof. In some embodiments therapeutic agents used to treat bladder cancer include eganelisib+nivolumab, pembrolizumab (Keytruda®)+enfortumab vedotin (Padcev®), nivolumab+ipilimumab, duravalumab+tremelimumab, lenvatinib+pembrolizumab, enfortumab vedotin (Padcev®)+pembrolizumab, and bempegaldesleukin+nivolumab.

Colorectal Cancer (CRC) Combination Therapy

Therapeutic agents used to treat CRC include bevacizumab, capecitabine, cetuximab, fluorouracil, irinotecan, leucovorin, oxaliplatin, panitumumab, ziv-aflibercept, and any combinations thereof. In some embodiments therapeutic agents used to treat CRC include bevacizumab (Avastin®), leucovorin, 5-FU, oxaliplatin (FOLFOX), pembrolizumab (Keytruda®), FOLFIRI, regorafenib (Stivarga®), aflibercept (Zaltrap®), cetuximab (Erbitux®), Lonsurf (Orcantas®), XELOX, FOLFOXIRI, or a combination thereof. In some embodiments therapeutic agents used to treat CRC include bevacizumab+leucovorin+5-FU+oxaliplatin (FOLFOX), bevacizumab+FOLFIRI, bevacizumab+FOLFOX, aflibercept+FOLFIRI, cetuximab+FOLFIRI, bevacizumab+XELOX, and bevacizumab+FOLFOXIRI. In some embodiments therapeutic agents used to treat CRC include binimetinib+encorafenib+cetuximab, trametinib+dabrafenib+panitumumab, trastuzumab+pertuzumab, napabucasin+FOLFIRI+bevacizumab, nivolumab+ipilimumab.

Esophageal and Esophagogastric Junction Cancer Combination Therapy

Therapeutic agents used to treat esophageal and esophagogastric junction cancer include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof. In some embodiments therapeutic agents used to treat gastroesophageal junction cancer (GEJ) include herceptin, cisplatin, 5-FU, ramicurimab, or paclitaxel. In some embodiments therapeutic agents used to treat GEJ cancer include ALX-148, AO-176, or IBI-188.

Gastric Cancer Combination Therapy

Therapeutic agents used to treat gastric cancer include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head and Neck Cancer Combination Therapy

Therapeutic agents used to treat head & neck cancer include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Therapeutic agents used to treat head and neck squamous cell carcinoma (HNSCC) include pembrolizumab, carboplatin, 5-FU, docetaxel, cetuximab (Erbitux®), cisplatin, nivolumab (Opdivo®), and combinations thereof. In some embodiments therapeutic agents used to treat HNSCC include pembrolizumab+carboplatin+5-FU, cetuximab+cisplatin+5-FU, cetuximab+carboplatin+5-FU, cisplatin+5-FU, and carboplatin+5-FU. In some embodiments therapeutic agents used to treat HNSCC include durvalumab, durvalumab+tremelimumab, nivolumab+ipilimumab, rovaluecel, pembrolizumab, pembrolizumab+epacadostat, GSK3359609+pembrolizumab, lenvatinib+pembrolizumab, retifanlimab, retifanlimab+enobituzumab, ADU-S100+pembrolizumab, epacadostat+nivolumab+ipilimumab/lirilumab.

Non-Small Cell Lung Cancer Combination Therapy

Therapeutic agents used to treat non-small cell lung cancer (NSCLC) include afatinib, albumin-bound paclitaxel, alectinib, atezolizumab, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof. In some embodiments therapeutic agents used to treat NSCLC include alectinib (Alecensa®), dabrafenib (Tafinlar®), trametinib (Mekinist®), osimertinib (Tagrisso), entrectinib (Tarceva®), crizotinib (Xalkori®), pembrolizumab (Keytruda®), carboplatin, pemetrexed (Alimta®), nab-paclitaxel (Abraxane®), ramucirumab (Cyramza®), docetaxel, bevacizumab (Avastin®), brigatinib, gemcitabine, cisplatin, afatinib (Gilotrif®), nivolumab (Opdivo®), gefitinib (Iressa®), and combinations thereof. In some embodiments therapeutic agents used to treat NSCLC include dabrafenib+trametinib, pembrolizumab+carboplatin+pemetrexed, pembrolizumab+carboplatin+nab-paclitaxel, ramucirumab+docetaxel, bevacizumab+carboplatin+pemetrexed, pembrolizumab+pemetrexed+carboplatin, cisplatin+pemetrexed, bevacizumab+carboplatin+nab-paclitaxel, cisplatin+gemcitabine, nivolumab+docetaxel, carboplatin+pemetrexed, carboplatin+nab-paclitaxel, or pemetrexed+cisplatin+carboplatin. In some embodiments therapeutic agents used to NSCLC include datopotamab deruxtecan (DS-1062), trastuzumab deruxtecan (Enhertu®), enfortumab vedotin (Padcev®), durvalumab, canakinumab, cemiplimab, nogapendekin alfa, avelumab, tiragolumab, domvanalimab, vibostolimab, ociperlimab, or a combination thereof. In some embodiments therapeutic agents used to treat NSCLC include datopotamab deruxtecan+pembrolizumab, datopotamab deruxtecan+durvalumab, durvalumab+tremelimumab, pembrolizumab+lenvatinib+pemetrexed, pembrolizumab+olaparib, nogapendekin alfa (N-803)+pembrolizumab, tiragolumab+atezolizumab, vibostolimab+pembrolizumab, or ociperlimab+tislelizumab.

Small Cell Lung Cancer Combination Therapy

Therapeutic agents used to treat small cell lung cancer (SCLC) include atezolizumab, bendamustime, carboplatin, cisplatin, cyclophosphamide, docetaxel, doxorubicin, etoposide, gemcitabine, ipillimumab, irinotecan, nivolumab, paclitaxel, temozolomide, topotecan, vincristine, vinorelbine, and any combinations thereof. In some embodiments therapeutic agents used to treat SCLC include atezolizumab, carboplatin, cisplatin, etoposide, paclitaxel, topotecan, nivolumab, durvalumab, trilaciclib, or combinations thereof. In some embodiments therapeutic agents used to treat SCLC include atezolizumab+carboplatin+etoposide, atezolizumab+carboplatin, atezolizumab+etoposide, or carboplatin+paclitaxel.

Ovarian Cancer Combination Therapy

Therapeutic agents used to treat ovarian cancer include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcitabine, ifosfamide, irinotecan, letrozole, leuprolide acetate, liposomal doxorubicin, megestrol acetate, melphalan, olaparib, oxaliplatin, paclitaxel, pazopanib, pemetrexed, tamoxifen, topotecan, vinorelbine, and any combinations thereof.

Pancreatic Cancer Combination Therapies

Therapeutic agents used to treat pancreatic cancer include 5-FU, leucovorin, oxaliplatin, irinotecan, gemcitabine, nab-paclitaxel (Abraxane®), FOLFIRINOX, and combinations thereof. In some embodiments therapeutic agents used to treat pancreatic cancer include 5-FU+leucovorin+oxaliplatin+irinotecan, 5-FU+nanoliposomal irinotecan, leucovorin+nanoliposomal irinotecan, and gemcitabine+nab-paclitaxel.

Prostate Cancer Combination Therapies

Therapeutic agents used to treat prostate cancer include enzalutamide (Xtandi®), leuprolide, trifluridine, tipiracil (Lonsurf), cabazitaxel, prednisone, abiraterone (Zytiga®), docetaxel, mitoxantrone, bicalutamide, LHRH, flutamide, ADT, sabizabulin (Veru-111), and combinations thereof. In some embodiments therapeutic agents used to treat prostate cancer include enzalutamide+leuprolide, trifluridine+tipiracil (Lonsurf), cabazitaxel+prednisone, abiraterone+prednisone, docetaxel+prednisone, mitoxantrone+prednisone, bicalutamide+LHRH, flutamide+LHRH, leuprolide+flutamide, and abiraterone+prednisone+ADT.

Additional Exemplified Combination Therapies

In some embodiments the antibody and/or fusion protein provided herein is administered with one or more therapeutic agents selected from a PI3K inhibitor, a Trop-2 binding agent, CD47 antagonist, a SIRPα antagonist, a FLT3R agonist, a PD-1 antagonist, a PD-L1 antagonist, an MCL1 inhibitor, a CCR8 binding agent, an HPK1 antagonist, a DGKα inhibitor, a CISH inhibitor, a PARP-7 inhibitor, a Cbl-b inhibitor, a KRAS inhibitor (e.g., a KRAS G12C or G12D inhibitor), a KRAS degrader, a beta-catenin degrader, a helios degrader, a CD73 inhibitor, an adenosine receptor antagonist, a TIGIT antagonist, a TREM1 binding agent, a TREM2 binding agent, a CD137 agonist, a GITR binding agent, an OX40 binding agent, and a CAR-T cell therapy.

In some embodiments the antibody and/or fusion protein provided herein is administered with one or more therapeutic agents selected from a PI3K8 inhibitor (e.g., idealisib), an anti-Trop-2 antibody drug conjugate (e.g., sacituzumab govitecan, datopotamab deruxtecan (DS-1062)), an anti-CD47 antibody or a CD47-blocking agent (e.g., magrolimab, DSP-107, AO-176, ALX-148, letaplimab (IBI-188), lemzoparlimab, TTI-621, TTI-622), an anti-SIRPα antibody (e.g., GS-0189), a FLT3L-Fc fusion protein (e.g., GS-3583), an anti-PD-1 antibody (pembrolizumab, nivolumab, zimberelimab), a small molecule PD-L1 inhibitor (e.g., GS-4224), an anti-PD-L1 antibody (e.g., atezolizumab, avelumab), a small molecule MCL1 inhibitor (e.g., GS-9716), a small molecule HPK1 inhibitor (e.g., GS-6451), a HPK1 degrader (PROTAC; e.g., ARV-766), a small molecule DGKα inhibitor, a small molecule CD73 inhibitor (e.g., quemliclustat (AB680)), an anti-CD73 antibody (e.g., oleclumab), a dual A2a/A2b adenosine receptor antagonist (e.g., etrumadenant (AB928)), an anti-TIGIT antibody (e.g., tiragolumab, vibostolimab, domvanalimab, AB308), an anti-TREM1 antibody (e.g., PY159), an anti-TREM2 antibody (e.g., PY314), a CD137 agonist (e.g., AGEN-2373), a GITR/OX40 binding agent (e.g., AGEN-1223) and a CAR-T cell therapy (e.g., axicabtagene ciloleucel, brexucabtagene autoleucel, tisagenlecleucel).

In some embodiments the antibody and/or fusion protein provided herein is administered with one or more therapeutic agents selected from idealisib, sacituzumab govitecan, magrolimab, GS-0189, GS-3583, zimberelimab, GS-4224, GS-9716, GS-6451, quemliclustat (AB680), etrumadenant (AB928), domvanalimab, AB308, PY159, PY314, AGEN-1223, AGEN-2373, axicabtagene ciloleucel and brexucabtagene autoleucel.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that these examples are exemplary and not exhaustive. Many changes can be made in the specific embodiments which are disclosed and still obtain a like or similar result without departing from the spirit and scope of the disclosure.

Compounds disclosed herein can be prepared according to the procedures of the following Schemes and Examples, using appropriate materials and are further exemplified by the following specific examples. Moreover, by utilizing the procedures described herein, in conjunction with ordinary skills in the art, additional compounds of the present disclosure claimed herein can be readily prepared. The examples further illustrate details for the preparation of the compounds of the present disclosure. Those skilled in the art will readily understand that known variations of the conditions and processes of the following preparative procedures can be used to prepare these compounds. For synthesizing compounds which are embodiments described in the present disclosure, inspection of the structure of the compound to be synthesized will provide the identity of each substituent group. In some cases, the identity of the final product can render apparent the identity of the necessary starting materials by a process of inspection, given the examples herein. Compounds can be isolated in the form of their pharmaceutically acceptable salts, such as those described above. Compounds described herein are typically stable and isolatable at room temperature and pressure.

An illustration of the preparation of compounds disclosed herein is shown below. Unless otherwise indicated, variables have the same meaning as described above. The examples presented below are intended to illustrate particular embodiments of the disclosure. Suitable starting materials, building blocks and reagents employed in the synthesis as described below are commercially available from AbovChem, Acros Organics, Astatech, Combi Blocks, Oakwood Chemical, or Sigma-Aldrich, for example, or can be routinely prepared by procedures described in the literature, for example in "March's Advanced Organic Chemistry: Reactions, Mechanisms, and Structure", 5th Edition; John Wiley & Sons or T. Eicher, S. Hauptmann "The Chemistry of Heterocycles; Structures, Reactions, Synthesis and Application", 2nd edition, Wiley-VCH 2003; Fieser et al. "Fiesers' Reagents for organic Synthesis" John Wiley & Sons 2000.

Synthesis of Intermediates A

General Procedure I-A for the Synthesis of Intermediates Aa

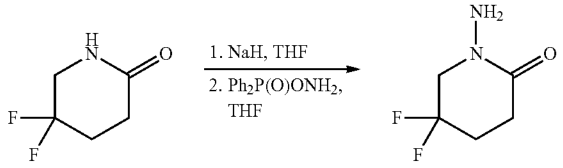

Aa-1

1-amino-5,5-difluoropiperidin-2-one (Aa-1). To a solution of 5,5-difluoropiperidin-2-one (2 g, 14.8 mmol, 1 eq) in THF (70 ml) was added NaH (1.1 g, 29.6 mmol, 60% purity, 2 eq) at 0 °C. The mixture was stirred at 0 °C for 30 min. O-diphenylphosphorylhydroxylamine (8.6 g, 37.0 mmol, 2.5 eq) in THF (30 mL) was added to the mixture at 0 °C. The mixture was stirred at 25 °C for 12 hr under $N_2$. LC-MS showed the desired compound was detected. The reaction mixture was filtered and concentrated under reduced pressure to give a residue. The residue was purified by flash silica gel chromatography (20 g Flash Silica Column, Eluent of 5~80% Ethyl acetate/Petroleum ether gradient @ 60 mL/min). The crude product was triturated with MTBE (20 mL) at 25 °C for 2 hr to give desired product.

MS (ESI): m/z=151.2 $[M+H]^+$: $^1H$ NMR (400 MHz, DMSO-$d_6$) δ 4.94 (s, 2H), 3.78 (t, J=12.9 Hz, 2H), 2.47-2.38 (m, 2H), 2.36-2.24 (m, 2H).

Aa-2

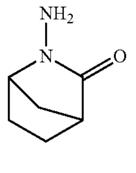

2-amino-2-azabicyclo[2.2.1]heptan-3-one (Aa-2). Prepared using general procedure I-A starting with 2-azabicyclo [2.2.1]heptan-3-one. ES/MS: m/z=127.3 $[M+H]^+$.

Aa-3

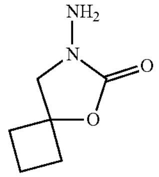

7-amino-5-oxa-7-azaspiro[3.4]octan-6-one (Aa-3). Prepared using general procedure I-A starting with 5-oxa-7-azaspiro[3.4]octan-6-one. ES/MS: m/z=143.3 $[M+H]^+$.

Aa-4

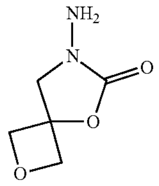

7-amino-2,5-dioxa-7-azaspiro[3.4]octan-6-one (Aa-4). Prepared using general procedure I-A starting with 2,5-dioxa-7-azaspiro[3.4]octan-6-one[1]. 5-(Trifluoromethyl)oxazolidin-2-one was prepared from 3-(aminomethyl)oxetan-3-ol using CDI in THF at 50 °C. $^1H$ NMR (400 MHz, methanol-$d_4$) δ 4.90 (s, 2H), 4.85 (d, J=8.5 Hz, 2H), 4.75 (d, J=8.0 Hz, 2H), 3.95 (s, 2H).

Aa-5

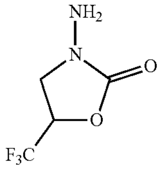

3-amino-5-(trifluoromethyl)oxazolidin-2-one (Aa-5). Prepared using general procedure I-A starting with 5-(trifluoromethyl)oxazolidin-2-one. 5-(trifluoromethyl)oxazolidin-2-one was prepared from 3-amino-1,1,1-trifluoro-propan-2-ol using CDI in THF at 50 °C. ES/MS: m/z=170.0 $[M+H]^+$.

Aa-6

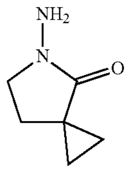

5-amino-5-azaspiro[2.4]heptan-4-one (Aa-6). Prepared using general procedure I-A starting with 5-azaspiro[2.4] heptan-4-one. $^1H$ NMR (400 MHz, DMSO-$d_6$) δ 4.59 (m, 1H), 3.48-3.39 (m, 2H), 2.04-1.96 (m, 2H), 0.84-0.77 (m, 2H), 0.73-0.64 (m, 2H).

Aa-7

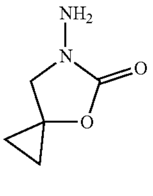

6-amino-4-oxa-6-azaspiro[2.4]heptan-5-one (Aa-7). Prepared using general procedure I-A starting with 4-oxa-6-azaspiro[2.4]heptan-5-one. $^1H$ NMR (400 MHz, DMSO-$d_6$) δ 4.64 (s, 2H), 3.64 (s, 2H), 1.04-0.96 (m, 2H), 0.79-0.71 (m, 2H).

Aa-8

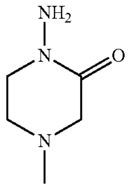

1-amino-4-methylpiperazin-2-one (Aa-8). Prepared using general procedure I-A starting with 4-methylpiperazin-2-one $^1$H NMR (400 MHz, DMSO-$d_6$) δ 5.06-4.74 (m, 2H), 3.34 (t, J=5.5 Hz, 2H), 3.17 (s, 1H), 2.95 (s, 1H), 2.60 (t, J=5.6 Hz, 2H), 2.21 (s, 3H).

Aa-9

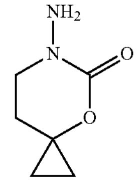

6-amino-4-oxa-6-azaspiro[2.5]octan-5-one (Aa-9). Prepared using general procedure I-A starting with 4-oxa-6-azaspiro[2.5]octan-5-one (Prepared from 1-(2-aminoethyl) cyclopropan-1-ol using CDI in THF at 50 °C). $^1$H NMR (400 MHz, DMSO-$d_6$) δ 4.77 (br s, 2H), 3.47 (t, J=6.3 Hz, 2H), 1.83 (q, J=6.4 Hz, 2H), 0.81 (s, 2H), 0.69-0.65 (m, 2H).

Aa-10

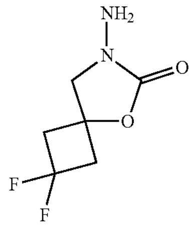

2,2-difluoro-5-oxa-7-azaspiro[3.4]octan-6-one (Aa-10). Prepared using general procedure I-A starting with 7-amino-2,2-difluoro-5-oxa-7-azaspiro[3.4]octan-6-one (Prepared from 1-(aminomethyl)-3,3-difluoro-cyclobutanol using CDI in THF at 50 °C. $^1$H NMR (400 MHz, DMSO-$d_6$) δ 4.59 (s, 2H), 3.72 (s, 2H), 3.15-2.90 (m, 4H).

General Procedure II-A for the Synthesis of Intermediates Ab

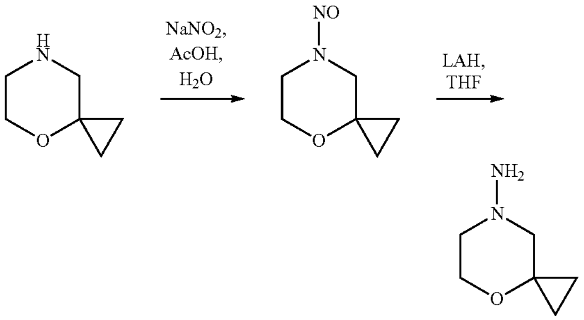

Ab-1

Step 1: 7-nitroso-4-oxa-7-azaspiro[2.5]octane

To a solution of 4-oxa-7-azaspiro[2.5]octane; hydrochloride (500 mg, 3.3 mmol, 1 eq) in $H_2O$ (10 mL) was added $NaNO_2$ (530.3 mg, 7.6 mmol, 2.3 eq) and AcOH (2 mL) at 0 °C. The mixture was stirred at 0 °C for 1 hr. TLC showed the formation of new spots. The reaction mixture was partitioned between $NaHCO_3$ 50 mL and DCM 50 mL. The water phase was separated, extracted with DCM (50 mL×3). The combined organic phase was washed with brine (50 mL×3), dried over $Na_2SO_4$, filtered and concentrated under reduced pressure to give desired product.

$^1$H NMR (400 MHz, DMSO-$d_6$) δ 4.23 (s, 1H), 4.03 (q, J=7.1 Hz, 1H), 3.85 (dt, J=1.2, 5.2 Hz, 2H), 3.76 (s, 1H), 3.62-3.57 (m, 1H), 0.80-0.69 (m, 3H), 0.53-0.52 (m, 1H).

Step 2: 4-oxa-7-azaspiro[2.5]octan-7-amine (Ab-1)

To a solution of LAH (2.5 M, 4.7 mL, 3 eq) in THF (20 mL) was added 7-nitroso-4-oxa-7-azaspiro[2.5]octane (560 mg, 3.9 mmol, 1 eq). The mixture was stirred at 0 °C for 2 hr. LC-MS showed the desired compound was detected. $Na_2SO_4 \cdot 10H_2O$ (4.4 g) was added to the mixture at 0 °C. The mixture was filtered with EtOAc (200 mL) and the filtrate was concentrated under reduced pressure to remove solvent to give title product. $^1$H NMR (400 MHz, DMSO-$d_6$) δ 3.58 (t, J=4.8 Hz, 2H), 3.46 (br s, 2H), 2.60-2.50 (m, 2H), 2.44 (s, 2H), 0.63-0.57 (m, 2H), 0.48-0.44 (m, 2H).

Ab-2

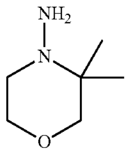

3,3-dimethylmorpholin-4-amine (Ab-2). Prepared using general procedure II-A starting with 3,3-dimethylmorpholine. $^1$H NMR (400 MHz, DMSO-$d_6$) δ 4.45-4.01 (m, 2H), 3.48-3.39 (m, 2H), 3.17 (s, 4H), 1.05 (t, J=7.0 Hz, 3H), 0.96-0.85 (m, 3H).

Ab-3

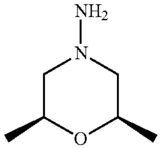

(2S,6R)-2,6-dimethylmorpholin-4-amine (Ab-3). Prepared using general procedure II-A starting with (2R,6S)-2,6-dimethylmorpholine. ES/MS: m/z=131.3 $[M+H]^+$. $^1$H NMR (400 MHz, DMSO-$d_6$) δ=3.51 (dqd, J=2.0, 6.3, 10.2 Hz, 2H), 2.87-2.80 (m, 2H), 1.69 (t, J=10.6 Hz, 2H), 1.03 (d, J=6.4 Hz, 6H).

Ab-4

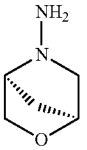

(1S,4S)-2-oxa-5-azabicyclo[2.2.1]heptan-5-amine (Ab-4). Prepared using general procedure II-A starting with (1S,4S)-2-oxa-5-azabicyclo[2.2.1]heptane. The product was used as a crude mixture.

Ab-5

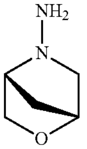

(1R,4R)-2-oxa-5-azabicyclo[2.2.1]heptan-5-amine (Ab-5). Prepared using general procedure II-A starting with (1R,4R)-2-oxa-5-azabicyclo[2.2.1]heptane. The product was used as a crude mixture.

Ab-6

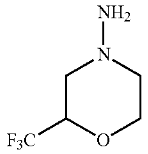

2-(trifluoromethyl)morpholin-4-amine (Ab-6). Prepared using general procedure II-A starting with 2-(trifluoromethyl)morpholine. $^1$H NMR (400 MHz, DMSO-$d_6$) δ 4.17-4.06 (m, 1H), 3.90 (dd, J=1.4, 11.4 Hz, 1H), 3.71 (br s, 2H), 3.59 (dt, J=2.3, 11.4 Hz, 1H), 3.00 (br d, J=10.5 Hz, 1H), 2.82 (br d, J=11.3 Hz, 1H), 2.29-2.13 (m, 2H).

General Procedure III-A for the Synthesis of Intermediates Ac

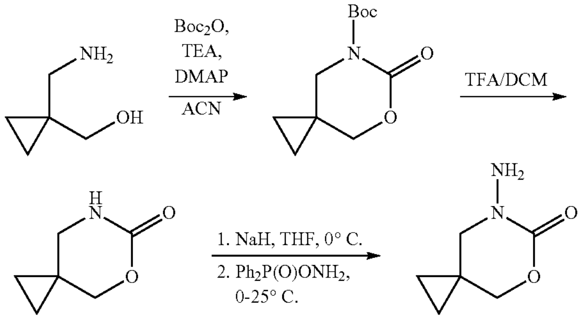

Ac-1

Step 1: tert-butyl 6-oxo-5-oxa-7-azaspiro[2.5]octane-7-carboxylate

To a solution of $Boc_2O$ (32.3 g, 148.3 mmol, 34.0 mL, 3 eq) in ACN (150 mL) was added triethylamine (15.0 g, 148.3 mmol, 20.6 mL, 3 eq) and DMAP (1.2 g, 9.8 mmol, 0.2 eq). [1-(aminomethyl)cyclopropyl]methanol (5 g, 49.4 mmol, 1 eq) in ACN (50 mL) was added to the mixture. The mixture was stirred at 25 °C for 12 hr. The reaction mixture was concentrated under reduced pressure to remove solvent. The residue was purified by flash silica gel chromatography (Ethyl acetate/Petroleum ether) to give desired product. $^1$H NMR (400 MHZ, DMSO-$d_6$) δ 4.05 (s, 2H), 3.48 (s, 2H), 1.44 (s, 9H), 0.70 (s, 4H).

Step 2: 5-oxa-7-azaspiro[2.5]octan-6-one

To a solution of tert-butyl 6-oxo-5-oxa-7-azaspiro[2.5]octane-7-carboxylate (4.4 g, 19.3 mmol, 1 eq) in DCM (40 mL) was added TFA (8 mL). The mixture was stirred at 25 °C for 12 hr. The reaction mixture was concentrated under reduced pressure to remove solvent. The residue was purified by flash silica gel chromatography (Ethyl acetate/Petroleum ether) to give desired product. $^1$H NMR (400 MHz, DMSO-$d_6$) δ 7.21 (br s, 1H), 3.93 (s, 2H), 3.01 (d, J=1.5 Hz, 2H), 0.67-0.57 (m, 4H).

Step 3: 7-amino-5-oxa-7-azaspiro[2.5]octan-6-one (Ac-1)

To a solution of 5-oxa-7-azaspiro[2.5]octan-6-one (2.4 g, 18.8 mmol, 1 eq) in THF (100 mL) was added NaH (1.5 g, 37.7 mmol, 60% purity, 2 eq) at 0 °C. The mixture was stirred at 0 °C for 0.5 hr. O-diphenylphosphorylhydroxylamine (11.0 g, 47.1 mmol, 2.5 eq) in THF (100 mL) was added to the mixture. The mixture was stirred at 25 °C for 12 hr. MeOH (1.5 mL) was added to the mixture. The mixture was filtered with EtOAc (1000 mL) and the filtrate was concentrated under reduced pressure to remove solvent to give the residue. The residue was purified by prep-HPLC ($H_2O$ (10 mM $NH_4HCO_3$)-ACN) to give desired product. ES/MS: m/z=142.1 $[M+H]^+$. $^1$H NMR (400 MHz, DMSO-$d_6$) δ 4.72 (s, 2H), 3.91 (s, 2H), 3.24 (s, 2H), 0.64 (d, J=3.6 Hz, 4H).

General Procedure IV-A for the Synthesis of Intermediates Ad-1 and Ad-2

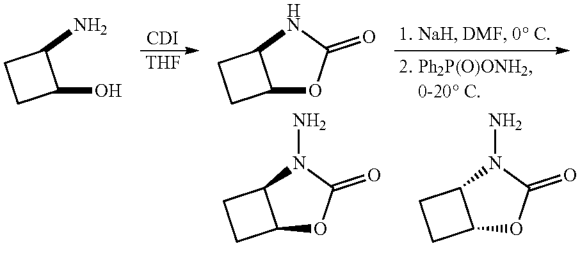

Ad-1 Ad-2 rac-(1R,5S)-2-oxa-4-azabicyclo[3.2.0]heptan-3-one

To a solution of 2-aminocyclobutanol (2 g, 22.9 mmol, 1 eq) in THF (30 mL) was added CDI (7.4 g, 45.9 mmol, 2 eq). The mixture was stirred at 50 °C for 12 hr. The reaction mixture was concentrated under reduced pressure to remove solvent. The residue was purified by flash silica gel chromatography (Ethyl acetate/Petroleum) to give rac-(1R,5S)-2-oxa-4-azabicyclo[3.2.0]heptan-3-one. ES/MS: m/z=113.1 $^1$H NMR (400 MHz, DMSO-$d_6$) δ 7.96 (br s, 1H), 5.01-4.92 (m, 1H), 4.20-4.11 (m, 1H), 2.45-2.38 (m, 1H), 2.25-2.16 (m, 2H), 1.92-1.84 (m, 1H).

(1S,5R)-4-amino-2-oxa-4-azabicyclo[3.2.0]heptan-3-one and (1R,5S)-4-amino-2-oxa-4-azabicyclo[3.2.0]heptan-3-one To a solution of rac-(1R,5S)-2-oxa-4-azabicyclo[3.2.0]heptan-3-one (1.5 g, 13.2 mmol, 1 eq) in THF (40 mL) was added NaH (1.0 g, 26.5 mmol, 60% purity, 2 eq) at 0 °C. The mixture was stirred at 0 °C for 0.5 hr. O-diphenylphosphorylhydroxylamine (7.7 g, 33.1 mmol, 2.5 eq) in THF (60 mL) was added to the mixture. The mixture was stirred at 25 °C for 12 hr. MeOH (1 mL) was added to the mixture at 0 °C. The mixture was filtered with EtOAc (1 L) and the filtrate was concentrated under reduced pressure to remove solvent to give product. The residue was purified by prep-HPLC (basic condition, column: Phenomenex Gemini-NX C18 75*30 mm*3 um; mobile phase: [$H_2O$ (10 mM $NH_4HCO_3$)-ACN]; gradient: 1%-25% B over 9.0 min). The residue was purified by prep-SFC(column: DAICEL CHIRALPAK AD (250 mm*30 mm, 10 um); mobile phase: [$CO_2$-MeOH(0.1% $NH_3H_2O$)]; B %:36%, isocratic elution mode) to give P1 (Rt=3.443 min) and P2 (Rt=3.856 min) both tentatively assigned as (1S,5R)-4-amino-2-oxa-4-azabicyclo[3.2.0]heptan-3-one (Ad-1) and (1R,5S)-4-amino-2-oxa-4-azabicyclo[3.2.0]heptan-3-one (Ad-2).

Ad-1

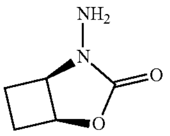

(1S,5R)-4-amino-2-oxa-4-azabicyclo[3.2.0]heptan-3-one (Ad-1). Prepared using general procedure I-A starting with (1S,5R)-2-oxa-4-azabicyclo[3.2.0]heptan-3-one. ES/MS: m/z=128.1 $^1$H NMR (400 MHz, methanol-$d_4$) δ 4.90 (s, 2H), 4.85 (d, J=8.5 Hz, 2H), 4.75 (d, J=8.0 Hz, 2H), 3.95 (s, 2H).

Ad-2

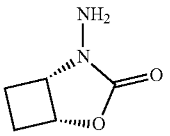

(1R,5S)-4-amino-2-oxa-4-azabicyclo[3.2.0]heptan-3-one (Ad-2). Prepared using general procedure I-A starting with (1R,5S)-2-oxa-4-azabicyclo[3.2.0]heptan-3-one. ES/MS: m/z=128.1 $^1$H NMR (400 MHz, methanol-$d_4$) δ 4.90 (s, 2H), 4.85 (d, J=8.5 Hz, 2H), 4.75 (d, J=8.0 Hz, 2H), 3.95 (s, 2H).

Synthesis of Intermediates B

General Procedure I-B for the Synthesis of Intermediates Ba

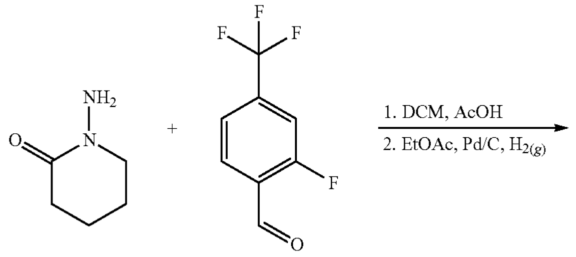

-continued

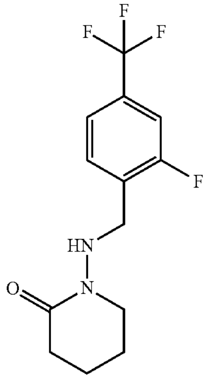

Ba-1

1-((2-fluoro-4-(trifluoromethyl)benzyl)amino)piperidin-2-one Ba-1

To a solution of 2-fluoro-4-(trifluoromethyl)benzaldehyde (192 mg, 1.0 mmol) and 1-aminopiperidin-2-one (114 mg, 1.0 mmol) in DCM (3 mL) was added acetic acid (0.035 mL, 0.74 mmol). The mixture was stirred at room temperature until full consumption of the starting aldehyde as judged by LCMS analysis. The crude mixture was then evaporated to dryness to give rise to (E)-1-((2-fluoro-4-(trifluoromethyl)benzylidene)amino)piperidin-2-one (ES/MS: m/z=289.1 $[M+H]^+$) which was used directly in the hydrogenation step without further purification.

The crude oil was dissolved in EtOAc (15 mL) and Pd/C (10% w/w, 192 mg) was added. The heterogenous mixture was then stirred vigorously at room temperature under an atmosphere of hydrogen (1 atm) until full conversion of the starting imine as determined by LCMS analysis. The crude mixture was then filtered over a pad of celite and evaporated to dryness to afford the desired product.

ES/MS: m/z=291.0 $[M+H]^+$; $^1$H NMR (400 MHz, DMSO-$d_6$) δ 7.69 (t, J=7.6 Hz, 1H), 7.63 (dd, J=10.0, 1.7 Hz, 1H), 7.56 (dd, J=7.6, 1.7 Hz, 1H), 4.02 (s, 2H), 3.27 (t, J=6.0 Hz, 2H), 2.21 (t, J=6.5 Hz, 2H), 1.79-1.58 (m, 4H).

Ba-2

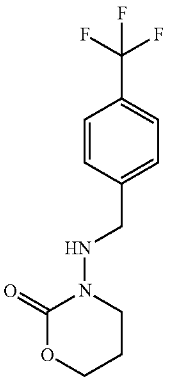

3-((4-(trifluoromethyl)benzyl)amino)-1,3-oxazinan-2-one (Ba-2). Prepared using general procedure I-B starting with 3-amino-1,3-oxazinan-2-one and 4-(trifluoromethyl)benzaldehyde. ES/MS: m/z=275.0 $[M+H]^+$.

Ba-3

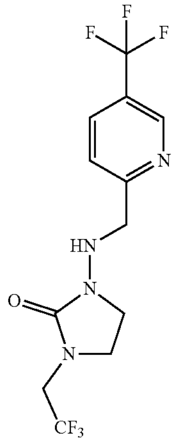

1-(2,2,2-trifluoroethyl)-3-(((5-(trifluoromethyl)pyridin-2 yl)methyl)amino)imidazolidin-2-one (Ba-3). Prepared using general procedure I-B starting with 1-amino-3-(2,2,2-trifluoroethyl)imidazolidin-2-one and 5-(trifluoromethyl)picolinaldehyde. ES/MS: m/z=343.1 [M+H]$^+$.

Ba-4

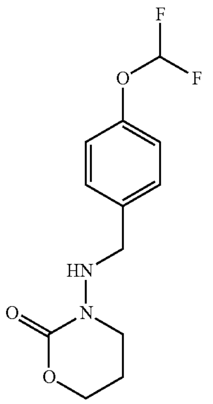

3-((4-(difluoromethoxy)benzyl)amino)-1,3-oxazinan-2-one (Ba-4). Prepared using general procedure I-B starting with 3-amino-1,3-oxazinan-2-one and 4-(difluoromethoxy) benzaldehyde. ES/MS: m/z=272.9 [M+H]$^+$.

Ba-5

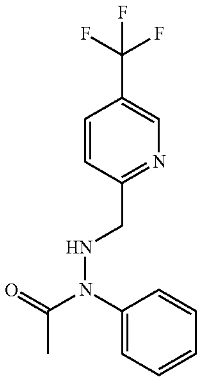

N-phenyl-N'-((5-(trifluoromethyl)pyridin-2-yl)methyl) acetohydrazide (Ba-5). Prepared using general procedure I-B starting with N-phenylacetohydrazide and 5-(trifluoromethyl)picolinaldehyde. ES/MS: m/z=400.0 [M+H]$^+$.

Ba-6

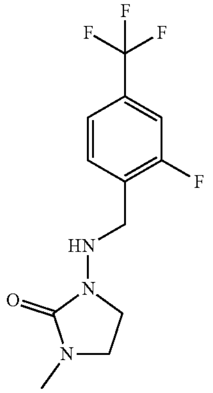

1-((2-fluoro-4-(trifluoromethyl)benzyl)amino)-3-methylimidazolidin-2-one (Ba-6). Prepared using general procedure I-B starting with 1-amino-3-methylimidazolidin-2-one and 2-fluoro-4-(trifluoromethyl)benzaldehyde. ES/MS: m/z=292.1 [M+H]$^+$.

Ba-7

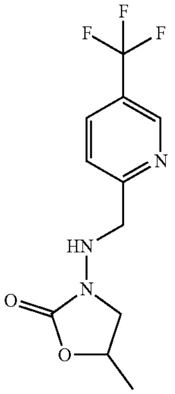

5-methyl-3-(((5-(trifluoromethyl)pyridin-2-yl)methyl) amino)oxazolidin-2-one (Ba-7). Prepared using general procedure I-B starting with 3-amino-5-methyloxazolidin-2-one and 5-(trifluoromethyl)picolinaldehyde. ES/MS: m/z=276.1 [M+H]$^+$.

Ba-8

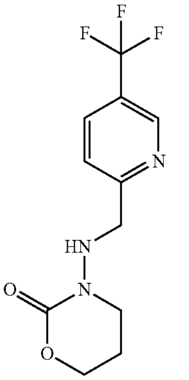

3-(((5-(trifluoromethyl)pyridin-2-yl)methyl)amino)-1,3-oxazinan-2-one (Ba-8). Prepared using general procedure I-B starting with 3-amino-1,3-oxazinan-2-one and 5-(trifluoromethyl)picolinaldehyde. ES/MS: m/z=276.0 $[M+H]^+$.

rel-(1R,4S)-2-(((5-(trifluoromethyl)pyridin-2-yl)methyl)amino)-2-azabicyclo[2.2.1]heptan-3-one (Ba-9) and rel-(1S,4R)-2-(((5-(trifluoromethyl)pyridin-2-yl)methyl)amino)-2-azabicyclo[2.2.1]heptan-3-one (Ba-10)

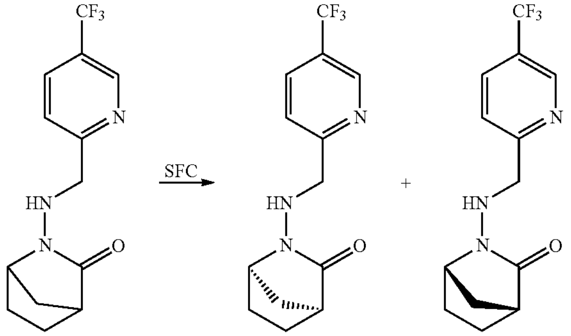

Ba-9 Ba-10

2-(((5-(trifluoromethyl)pyridin-2-yl)methyl)amino)-2-azabicyclo[2.2.1]heptan-3-one was prepared using general procedure I-B starting with 2-amino-2-azabicyclo[2.2.1]heptan-3-one (Aa-2) and 5-(trifluoromethyl)picolinaldehyde. The residue was separated by SFC (column: DAICEL CHIRALPAK AD (250 mm*30 mm, 10 um); mobile phase: [0.1% $NH_3H_2O$ EtOH]; B %: 17%-17%, 8 min) to give rel-(1R,4S)-2-(((5-(trifluoromethyl)pyridin-2-yl)methyl)amino)-2-azabicyclo[2.2.1]heptan-3-one (Ba-9) (Rt=2.108 min) and rel-(1S,4R)-2-(((5-(trifluoromethyl)pyridin-2-yl)methyl)amino)-2-azabicyclo[2.2.1]heptan-3-one (Ba-10) (Rt=2.435 min).

Ba-11

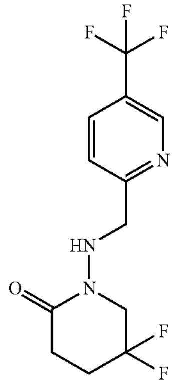

5,5-difluoro-1-(((5-(trifluoromethyl)pyridin-2-yl)methyl)amino)piperidin-2-one (Ba-11). Prepared using general procedure I-B starting with 1-amino-5,5-difluoropiperidin-2-one (Aa-1) and 5-(trifluoromethyl)picolinaldehyde. ES/MS: m/z=310.2 $[M+H]^+$.

Ba-12

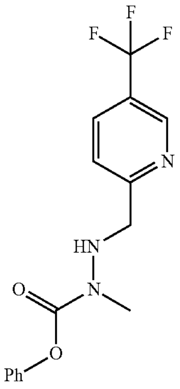

Phenyl 1-methyl-2-((5-(trifluoromethyl)pyridin-2-yl)methyl)hydrazine-1-carboxylate (Ba-12). Prepared using general procedure I-B starting with phenyl 1-methylhydrazine-1-carboxylate and 5-(trifluoromethyl)picolinaldehyde. ES/MS: m/z=326.0 $[M+H]^+$.

Ba-13

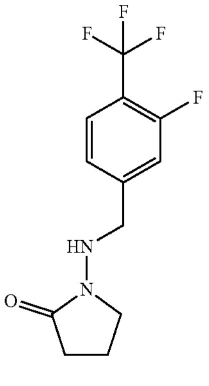

1-((3-fluoro-4-(trifluoromethyl)benzyl)amino)pyrrolidin-2-one (Ba-13). Prepared using general procedure I-B starting with 1-aminopyrrolidin-2-one and 3-fluoro-4-(trifluoromethyl)benzaldehyde. ES/MS: m/z=277.0 [M+H]$^+$.

Ba-14

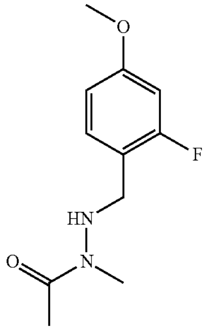

N'-(2-fluoro-4-methoxybenzyl)-N-methylacetohydrazide (Ba-14). Prepared using general procedure I-B starting with N-Methylacetohydrazide and 2-fluoro-4-methoxybenzaldehyde. ES/MS: m/z=227.0 [M+H]$^+$.

Ba-15

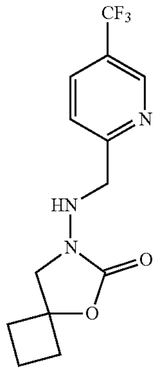

7-(((5-(trifluoromethyl)pyridin-2-yl)methyl)amino)-5-oxa-7-azaspiro[3.4]octan-6-one (Ba-15). Prepared using general procedure I-B starting with 7-amino-5-oxa-7-azaspiro[3.4]octan-6-one (Aa-3) and 2-methoxy-6-(trifluoromethyl)pyridine-3-carbaldehyde. ES/MS: m/z=302.2 [M+H]$^+$, $^1$H NMR (400 MHz, DMSO-$d_6$) δ 8.88 (s, 1H), 8.20 (dd, J=2.1, 8.3 Hz, 1H), 7.81 (d, J=8.3 Hz, 1H), 5.69 (t, J=4.4 Hz, 1H), 4.18 (d, J=4.3 Hz, 2H), 3.63 (s, 2H), 2.30-2.21 (m, 2H), 2.11-2.04 (m, 2H), 1.76-1.66 (m, 1H), 1.62-1.49 (m, 1H).

Ba-16

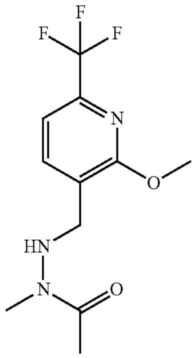

N'-[[2-methoxy-6-(trifluoromethyl)-3-pyridyl]methyl]-N-methyl acetohydrazide (Ba-16). Prepared using general procedure I-B starting with N-methylacetohydrazide and 2-methoxy-6-(trifluoromethyl)pyridine-3-carbaldehyde. ES/MS: m/z=278.2 [M+H]$^+$.

Ba-17

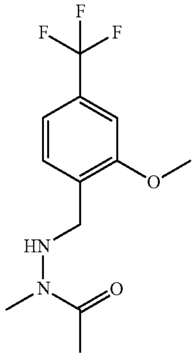

N'-[[2-methoxy-4-(trifluoromethyl)phenyl]methyl]-N-methyl-acetohydrazide (Ba-17). Prepared using general procedure I-B starting with N-methylacetohydrazide and 2-methoxy-4-(trifluoromethyl)benzaldehyde). ES/MS: m/z=277.2 [M+H]$^+$.

Ba-18

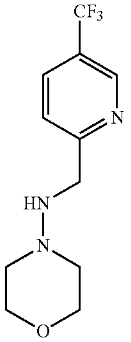

N-((5-(trifluoromethyl)pyridin-2-yl)methyl)morpholin-4-amine (Ba-18). Prepared following procedure I-B starting with morpholin-4-amine and 5-(trifluoromethyl)pyridine-2-carbaldehyde. ES/MS: m/z=261.2 [M+H]$^+$.

Ba-19

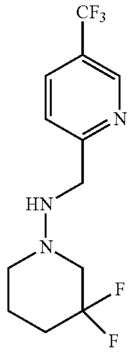

3,3-difluoro-N-((5-(trifluoromethyl)pyridin-2-yl)methyl) piperidin-1-amine (Ba-19). Prepared following procedure I-B using 3,3-difluoropiperidin-1-amine hydrochloride and 5-(trifluoromethyl)pyridine-2-carbaldehyde. ES/MS: m/z=296.2 $[M+H]^+$.

Ba-20

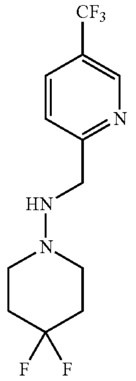

4,4-difluoro-N-[[5-(trifluoromethyl)-2-pyridyl]methyl] piperidin-1-amine (Ba-20). Prepared following procedure I-B using 4,4-difluoropiperidin-1-amine hydrochloride and 5-(trifluoromethyl)pyridine-2-carbaldehyde. ES/MS: m/z=296.2 $[M+H]^+$.

Ba-21

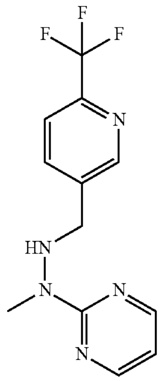

2-(1-methyl-2-((5-(trifluoromethyl)pyridin-2-yl)methyl) hydrazineyl)pyrimidine (Ba-21). Prepared using general procedure I-B starting with 2-(1-methylhydrazineyl)pyrimidine and 5-(trifluoromethyl)picolinaldehyde. ES/MS: m/z=284.1 $[M+H]^+$.

Ba-22

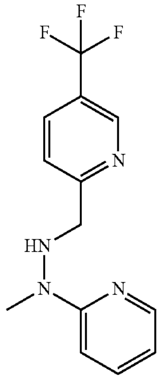

1-methyl-1-(2-pyridyl)-2-[[5-(trifluoromethyl)-2-pyridyl] methyl]hydrazine (Ba-22). Prepared using general procedure I-B starting with 2-(1-methylhydrazineyl)pyridine and 5-(trifluoromethyl)picolinaldehyde. ES/MS: m/z=283.1 $[M+H]^+$.

Ba-23

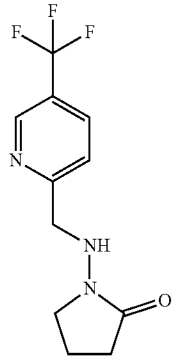

1-(((5-(trifluoromethyl)pyridin-2-yl)methyl)amino)pyrrolidin-2-one (Ba-23).

Prepared using general procedure I-B starting with 1-aminopyrrolidin-2-one and 5-(trifluoromethyl)picolinaldehyde. ES/MS: m/z=260.1 $[M+H]^+$.

Ba-24

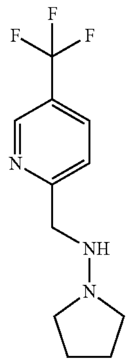

N-[[5-(trifluoromethyl)-2-pyridyl]methyl]pyrrolidin-1-amine (Ba-24). Prepared using general procedure I-B starting with pyrrolidin-1-amine and 5-(trifluoromethyl)picolinaldehyde. ES/MS: m/z=246.1 [M+H]$^+$.

Ba-25

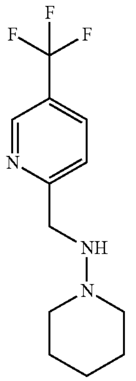

N-[[5-(trifluoromethyl)-2-pyridyl]methyl]piperidin-1-amine (Ba-25). Prepared using general procedure I-B starting with piperidin-1-amine and 5-(trifluoromethyl)picolinaldehyde. ES/MS: m/z=260.2 [M+H]$^+$.

Ba-26

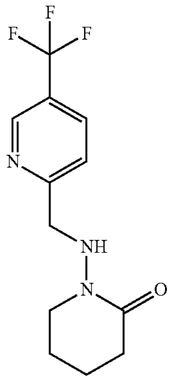

1-(((5-(trifluoromethyl)pyridin-2-yl)methyl)amino)piperidin-2-one (Ba-26). Prepared using general procedure I-B starting with 1-aminopiperidin-2-one and 5-(trifluoromethyl)picolinaldehyde. ES/MS: m/z=274.0 [M+H]$^+$.

Ba-27

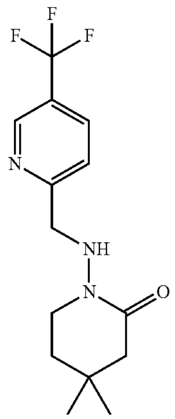

4,4-dimethyl-1-[[5-(trifluoromethyl)-2-pyridyl]methylamino]piperidin-2-one (Ba-27). Prepared using general procedure I-B starting with 1-amino-4,4-dimethyl-piperidin-2-one and 5-(trifluoromethyl)picolinaldehyde. ES/MS: m/z=302.2 [M+H]$^+$.

Ba-28

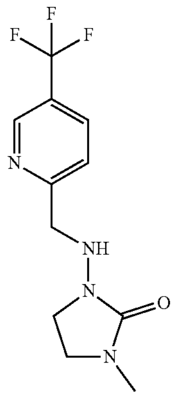

1-methyl-3-[[5-(trifluoromethyl)-2-pyridyl]methylamino]imidazolidin-2-one (Ba-28). Prepared using general procedure I-B starting with 1-amino-3-methyl-imidazolidin-2-one and 5-(trifluoromethyl)picolinaldehyde. ES/MS: m/z=275.1 [M+H]$^+$.

Ba-29

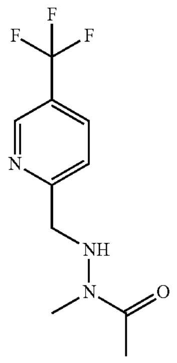

N-methyl-N'-((5-(trifluoromethyl)pyridin-2-yl)methyl)acetohydrazide (Ba-29). Prepared using general procedure I-B starting with N-methylacetohydrazide and 5-(trifluoromethyl)picolinaldehyde. ES/MS: m/z=248.1 [M+H]$^+$.

Ba-30

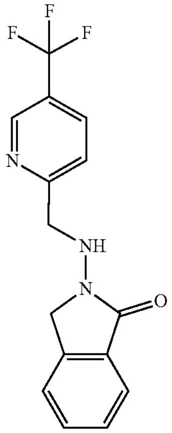

2-[[5-(trifluoromethyl)-2-pyridyl]methylamino]isoindolin-1-one (Ba-30). Prepared using general procedure I-B starting with 2-aminoisoindolin-1-one and 5-(trifluoromethyl)picolinaldehyde. ES/MS: m/z=308.1 [M+H]$^+$.

Ba-31

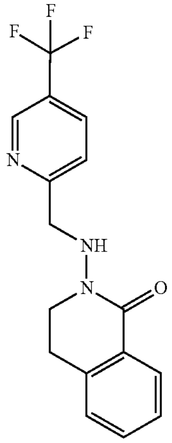

2-[[5-(trifluoromethyl)-2-pyridyl]methylamino]-3,4-dihydroisoquinolin-1-one (Ba-31). Prepared using general procedure I-B starting with 2-amino-3,4-dihydroisoquinolin-1-one and 5-(trifluoromethyl)picolinaldehyde. ES/MS: m/z=322.1 [M+H]$^+$.

Ba-32

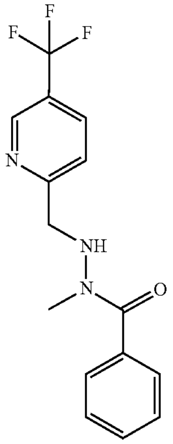

N-methyl-N'-[[5-(trifluoromethyl)-2-pyridyl]methyl]benzohydrazide (Ba-32). Prepared using general procedure I-B starting with N-methylbenzohydrazide and 5-(trifluoromethyl)picolinaldehyde. ES/MS: m/z=310.1 [M+H]$^+$.

Ba-33

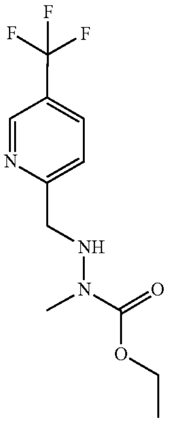

Ethyl N-methyl-N-[[5-(trifluoromethyl)-2-pyridyl]methylamino]carbamate (Ba-33). Prepared using general procedure I-B starting with ethyl N-amino-N-methyl-carbamate and 5-(trifluoromethyl)picolinaldehyde. ES/MS: m/z=278.1 [M+H]$^+$.

Ba-34

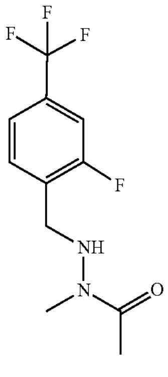

N'-(2-fluoro-4-(trifluoromethyl)benzyl)-N-methylacetohydrazide (Ba-34). Prepared using general procedure I-B starting with N-methylacetohydrazide and 2-fluoro-4-(trifluoromethyl)benzaldehyde. ES/MS: m/z=265.1 $[M+H]^+$.

Ba-35

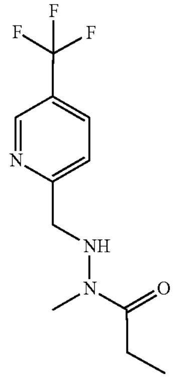

N-methyl-N'-[[5-(trifluoromethyl)-2-pyridyl]methyl]propanehydrazide (Ba-35). Prepared using general procedure I-B starting with N-methylpropanehydrazide and 5-(trifluoromethyl)picolinaldehyde. ES/MS: m/z=262.1 $[M+H]^+$.

Ba-36

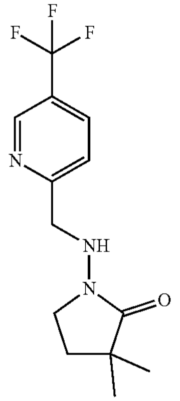

3,3-dimethyl-1-[[5-(trifluoromethyl)-2-pyridyl]methylamino]pyrrolidin-2-one (Ba-36). Prepared using general procedure I-B starting with 1-amino-3,3-dimethyl-pyrrolidin-2-one hydrochloride and 5-(trifluoromethyl)picolinaldehyde. ES/MS: m/z=288.1 $[M+H]^+$.

Ba-37

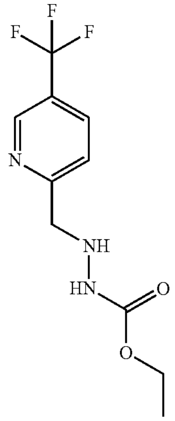

Ethyl N-[[5-(trifluoromethyl)-2-pyridyl]methylamino]carbamate (Ba-37). Prepared using general procedure I-B starting with ethyl N-aminocarbamate and 5-(trifluoromethyl)picolinaldehyde. ES/MS: m/z=264.1 $[M+H]^+$.

Ba-38

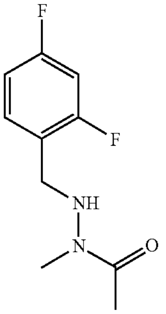

N'-[(2,4-difluorophenyl)methyl]-N-methyl-acetohydrazide (Ba-38). Prepared using general procedure I-B starting with N-methylacetohydrazide and 2,4-difluorobenzaldehyde. ES/MS: m/z=215.1 $[M+H]^+$.

Ba-39

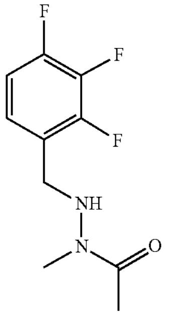

N-methyl-N'-[(2,3,4-trifluorophenyl)methyl]acetohydrazide (Ba-39). Prepared using general procedure I-B starting with N-methylacetohydrazide and 2,3,4-trifluorobenzaldehyde. ES/MS: m/z=233.1 $[M+H]^+$.

Ba-40

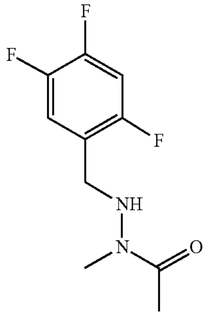

N-methyl-N'-[(2,4,5-trifluorophenyl)methyl]acetohydrazide (Ba-40). Prepared using general procedure I-B starting with N-methylacetohydrazide and 2,4,5-trifluorobenzaldehyde. ES/MS: m/z=233.1 $[M+H]^+$.

Ba-41

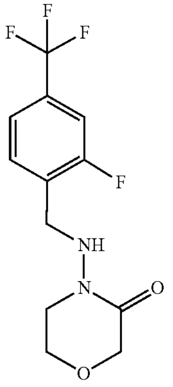

4-[[2-fluoro-4-(trifluoromethyl)phenyl]methylamino] morpholin-3-one (Ba-41). Prepared using general procedure I-B starting with 4-aminomorpholin-3-one and 2-fluoro-4-(trifluoromethyl)benzaldehyde. ES/MS: m/z=293.1 $[M+H]^+$.

Ba-42

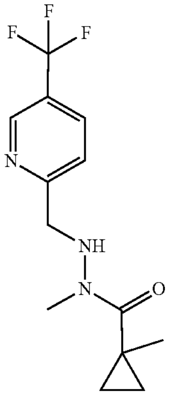

N,1-dimethyl-N'-[[5-(trifluoromethyl)-2-pyridyl]methyl] cyclopropanecarbohydrazide (Ba-42). Prepared using general procedure I-B starting with N,1-dimethylcyclopropanecarbohydrazide and 5-(trifluoromethyl)picolinaldehyde. ES/MS: m/z=288.1 $[M+H]^+$.

Ba-43

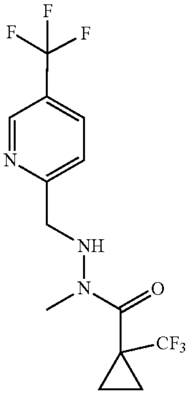

N-methyl-1-(trifluoromethyl)-N'-[[5-(trifluoromethyl)-2-pyridyl]methyl]cyclo propanecarbohydrazide (Ba-43). Prepared using general procedure I-B starting with N-methyl-1-(trifluoromethyl)cyclopropanecarbohydrazide and 5-(trifluoromethyl)picolinaldehyde. ES/MS: m/z=342.1 $[M+H]^+$.

Ba-44

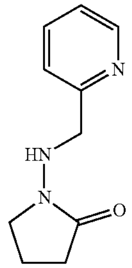

1-((pyridin-2-ylmethyl)amino)pyrrolidin-2-one (Ba-44). Prepared using general procedure I-B starting with 1-aminopyrrolidin-2-one and 2-pyridiylbenzaldehyde. ES/MS: m/z=192.1$[M+H]^+$.

Ba-45

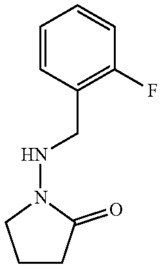

1-((2-fluorobenzyl)amino)pyrrolidin-2-one (Ba-45). Prepared using general procedure I-B starting with 1-aminopyrrolidin-2-one and 2-fluorobenzaldehyde. ES/MS: m/z=209.2 $[M+H]^+$.

Ba-46

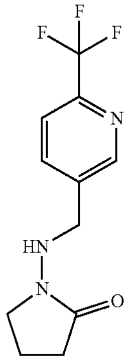

1-(((6-(trifluoromethyl)pyridin-3-yl)methyl)amino)pyrrolidin-2-one (Ba-46). Prepared using general procedure I-B starting with 1-aminopyrrolidin-2-one and 6-(trifluoromethyl)nicotinaldehyde. ES/MS: m/z=260.1 $[M+H]^+$.

Ba-47

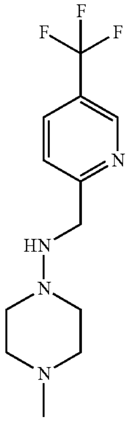

4-methyl-N-((5-(trifluoromethyl)pyridin-2-yl)methyl)piperazin-1-amine (Ba-47). Prepared using general procedure I-B starting with 4-methylpiperazin-1-amine and 5-(trifluoromethyl)picolinaldehyde. ES/MS: m/z=275.1 $[M+H]^+$.

Ba-48

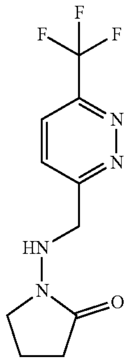

1-(((6-(trifluoromethyl)pyridazin-3-yl)methyl)amino)pyrrolidin-2-one (Ba-48). Prepared using general procedure I-B starting with 1-aminopyrrolidin-2-one and 6-(trifluoromethyl)pyridazine-3-carbaldehyde. ES/MS: m/z=261.2 $[M+H]^+$.

Ba-49

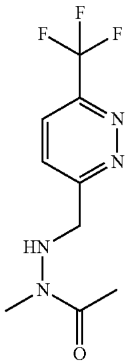

N-methyl-N'-((6-(trifluoromethyl)pyridazin-3-yl)methyl)acetohydrazide (Ba-49). Prepared using general procedure I-B starting with N-methylacetohydrazide and 6-(trifluoromethyl)pyridazine-3-carbaldehyde. ES/MS: m/z=249.1 $[M+H]^+$.

Ba-50

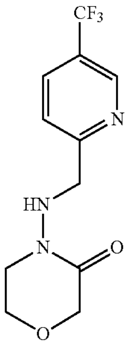

4-(((5-(trifluoromethyl)pyridin-2-yl)methyl)amino)morpholin-3-one (Ba-50). Prepared using general procedure I-B starting with 4-aminomorpholin-3-one and 5-(trifluoromethyl)pyridine-2-carbaldehyde. ES/MS: m/z=276.2 $[M+H]^+$.

Ba-51

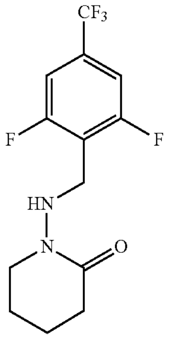

4-((2,6-difluoro-4-(trifluoromethyl)benzyl)amino)morpholin-3-one (Ba-51). Prepared using general procedure I-B starting with 1-aminopiperidin-2-one and 2,6-difluoro-4-(trifluoromethyl)benzaldehyde. ES/MS: m/z=309.0 $[M+H]^+$.

Ba-52

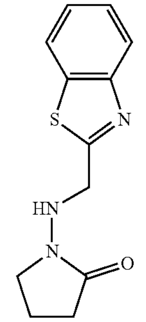

1-((benzo[d]thiazol-2-ylmethyl)amino)pyrrolidin-2-one (Ba-52). Prepared using general procedure I-B starting with 1-aminopiperidin-2-one and benzo[d]thiazole-2-carbaldehyde. ES/MS: m/z=248.2 [M+H]$^+$.

Ba-53

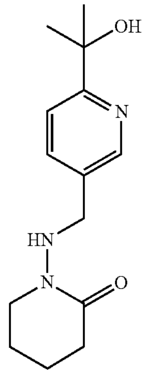

1-(((6-(2-hydroxypropan-2-yl)pyridin-3-yl)methyl) amino)piperidin-2-one (Ba-53). Prepared using general procedure I-B starting with 1-aminopiperidin-2-one and 6-(1-hydroxy-1-methyl-ethyl)pyridine-3-carbaldehyde. ES/MS: m/z=264.2 [M+H]$^+$.

Ba-54

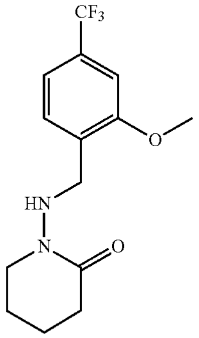

1-((2-methoxy-4-(trifluoromethyl)benzyl)amino)piperidin-2-one (Ba-54). Prepared using general procedure I-B starting with 1-aminopiperidin-2-one and 2-methoxy-4-(trifluoromethyl)benzaldehyde. ES/MS: m/z=303.2 [M+H]$^+$.

Ba-55

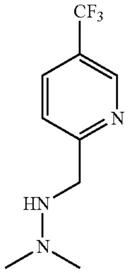

2-((2,2-dimethylhydrazineyl)methyl)-5-(trifluoromethyl) pyridine (Ba-55). Prepared using general procedure I-B starting with 1,1-dimethylhydrazine and 5-(trifluoromethyl) picolinaldehyde. ES/MS: m/z=220.2 [M+H]$^+$.

Ba-56

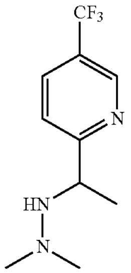

2-(1-(2,2-dimethylhydrazineyl)ethyl)-5-(trifluoromethyl) pyridine (Ba-56). Prepared using general procedure I-B starting with 1,1-dimethylhydrazine and 1-(5-(trifluoromethyl)pyridin-2-yl)ethan-1-one. ES/MS: m/z=234.2 [M+H]$^+$.

Ba-57

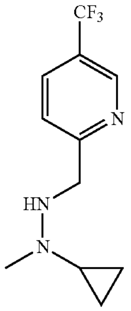

2-((2-cyclopropyl-2-methylhydrazineyl)methyl)-5-(trifluoromethyl)pyridine (Ba-57). Prepared using general procedure I-B starting with 1-cyclopropyl-1-methylhydrazine and 5-(trifluoromethyl)picolinaldehyde. ES/MS: m/z=245.9 [M+H]$^+$.

Ba-58

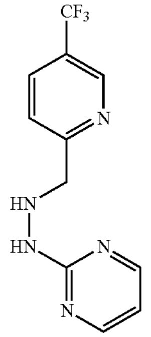

2-(2-((5-(trifluoromethyl)pyridin-2-yl)methyl)hydrazineyl)pyrimidine (Ba-58). Prepared using general procedure I-B starting with 2-hydrazineylpyrimidine and 4-(trifluoromethyl)benzaldehyde. ES/MS: m/z=270.0 [M+H]$^+$.

Ba-59

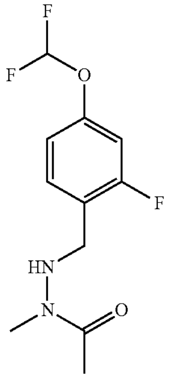

N'-(4-(difluoromethoxy)-2-fluorobenzyl)-N-methylacetohydrazide (Ba-59). Prepared using general procedure I-B starting with N-methylacetohydrazide and 4-(difluoromethoxy)-2-fluorobenzaldehyde. ES/MS: m/z=263.0 [M+H]$^+$.

Ba-60

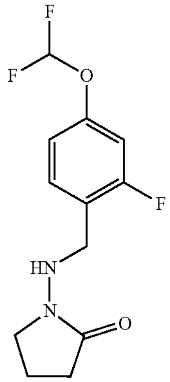

1-((4-(difluoromethoxy)-2-fluorobenzyl)amino)pyrrolidin-2-one (Ba-60). Prepared using general procedure I-B starting with 1-aminopyrrolidin-2-one and 4-(difluoromethoxy)-2-fluorobenzaldehyde. ES/MS: m/z=275.0 [M+H]$^+$.

Ba-61

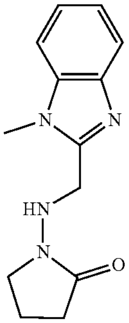

1-(((1-methyl-1H-benzo[d]imidazol-2-yl)methyl)amino)pyrrolidin-2-one (Ba-61). Prepared using general procedure I-B starting with 6-chloro-1-methyl-benzimidazole-2-carbaldehyde and 1-aminopyrrolidin-2-one. ES/MS: m/z=245.2 [M+H]$^+$.

Ba-63

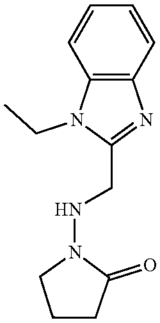

1-(((1-ethyl-1H-benzo[d]imidazol-2-yl)methyl)amino)pyrrolidin-2-one (Ba-63). Prepared using general procedure I-B starting with 1-ethylbenzimidazole-2-carbaldehyde and 1-aminopyrrolidin-2-one. ES/MS: m/z=257.3 [M+H]$^+$.

Ba-64

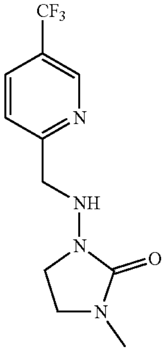

1-methyl-3-(((5-(trifluoromethyl)pyridin-2-yl)methyl)amino)imidazolidin-2-one (Ba-64). Prepared using general procedure I-B starting with 5-(trifluoromethyl)pyridine-2-carbaldehyde and 1-amino-3-methyl-imidazolidin-2-one. ES/MS: m/z=275.1 [M+H]$^+$.

Ba-65

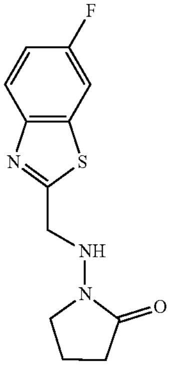

1-(((6-fluorobenzo[d]thiazol-2-yl)methyl)amino)pyrrolidin-2-one (Ba-65). Prepared using general procedure I-B starting with 6-fluoro-1,3-benzothiazole-2-carbaldehyde and 1-aminopyrrolidin-2-one. ES/MS: m/z=266 $[M+H]^+$.

Ba-66

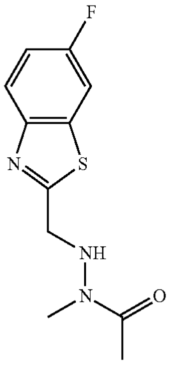

N'-[(6-fluoro-1,3-benzothiazol-2-yl)methyl]-N-methylacetohydrazide (Ba-66). Prepared using general procedure I-B starting with 6-fluoro-1,3-benzothiazole-2-carbaldehyde and N-methylacetohydrazide. ES/MS: m/z=254.1 $[M+H]^+$.

Ba-67

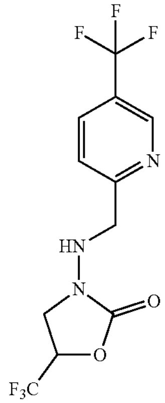

5-(trifluoromethyl)-3-(((5-(trifluoromethyl)pyridin-2-yl)methyl)amino)oxazolidin-2-one (Ba-67). Prepared using general procedure I-B starting with 3-amino-5-(trifluoromethyl)oxazolidin-2-one (Aa-5) and 5-(trifluoromethyl)picolinaldehyde. ES/MS: m/z=330.0 $[M+H]^+$. $^1H$ NMR (400 MHz, DMSO-$d_6$) δ 8.88 (s, 1H), 8.26-8.15 (m, 1H), 7.81 (d, J=8.3 Hz, 1H), 5.90 (t, J=4.1 Hz, 1H), 5.33-5.18 (m, 1H), 4.21 (br d, J=3.9 Hz, 2H), 3.90 (t, J=9.5 Hz, 1H), 3.68-3.58 (m, 1H).

Ba-68

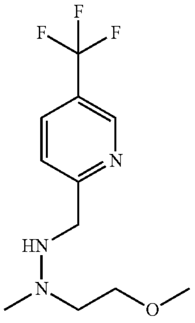

2-((2-(2-methoxyethyl)-2-methylhydrazineyl)methyl)-5-(trifluoromethyl)pyridine (Ba-68). Prepared using general procedure I-B starting with 1-(2-methoxyethyl)-1-methylhydrazine and 5-(trifluoromethyl)picolinaldehyde. ES/MS: m/z=264.1 $[M+H]^+$.

Ba-69

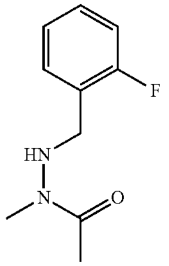

N'-(2-fluorobenzyl)-N-methylacetohydrazide (Ba-69). Prepared using general procedure I-B starting with N-methylacetohydrazide and 2-fluorobenzaldehyde. ES/MS: m/z=197.1 $[M+H]^+$.

Ba-70

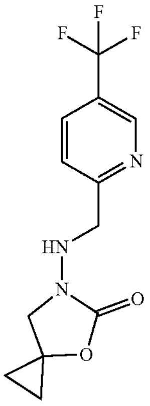

6-(((5-(trifluoromethyl)pyridin-2-yl)methyl)amino)-4-oxa-6-azaspiro[2.4]heptan-5-one (Ba-70). Prepared using general procedure I-B starting with 6-amino-4-oxa-6-azaspiro[2.4]heptan-5-one Aa-7 and 5-(trifluoromethyl)picolinaldehyde. ES/MS: m/z=288.1 $[M+H]^+$.

Ba-71

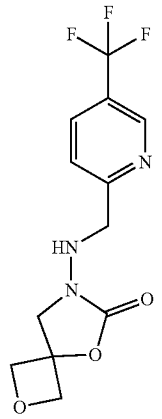

7-(((5-(trifluoromethyl)pyridin-2-yl)methyl)amino)-2,5-dioxa-7-azaspiro[3.4]octan-6-one (Ba-71). Prepared using general procedure I-B starting with 7-amino-2,5-dioxa-7-azaspiro[3.4]octan-6-one Aa-4 and 5-(trifluoromethyl)picolinaldehyde. ES/MS: m/z=304.1 $[M+H]^+$.

Ba-72

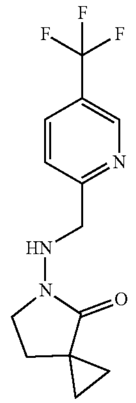

5-[[5-(trifluoromethyl)-2-pyridyl]methylamino]-5-azaspiro[2.4]heptan-4-one (Ba-72). Prepared using general procedure I-B starting with 5-amino-5-azaspiro[2.4]heptan-4-one (Aa-6) and 5-(trifluoromethyl)picolinaldehyde. ES/MS: m/z=286.2 $[M+H]^+$.

Ba-73

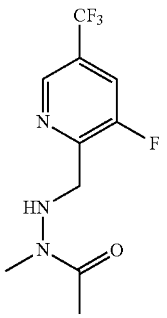

N'-((3-fluoro-5-(trifluoromethyl)pyridin-2-yl)methyl)-N-methylacetohydrazide (Ba-73). Prepared using general procedure I-B starting with 3-fluoro-5-(trifluoromethyl)picolinaldehyde and N-methylacetohydrazide. ES/MS: m/z=266.0 $[M+H]^+$.

Ba-74

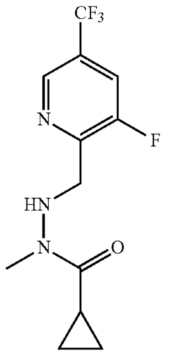

N'-((3-fluoro-5-(trifluoromethyl)pyridin-2-yl)methyl)-N-methylcyclopropanecarbohydrazide (Ba-74). Prepared using general procedure I-B starting with 3-fluoro-5-(trifluoromethyl)picolinaldehyde and N-methylcyclopropanecarbohydrazide. ES/MS: m/z=291.9 $[M+H]^+$.

Ba-75

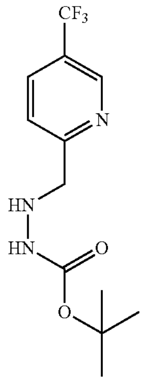

tert-butyl 2-((5-(trifluoromethyl)pyridin-2-yl)methyl)hydrazine-1-carboxylate (Ba-75). Prepared using general procedure I-B starting with 5-(trifluoromethyl)pyridine-2-carbaldehyde and tert-butyl N-aminocarbamate. ES/MS: m/z=291.7 $[M+H]^+$.

Ba-76

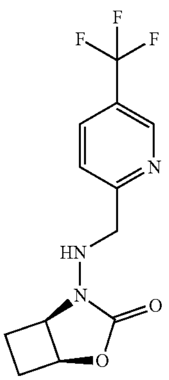

(1S,5R)-4-(((5-(trifluoromethyl)pyridin-2-yl)methyl)amino)-2-oxa-4-azabicyclo[3.2.0]heptan-3-one (Ba-76). Prepared using general procedure I-B starting with (1S,5R)-4-amino-2-oxa-4-azabicyclo[3.2.0]heptan-3-one Ad-1 and 5-(trifluoromethyl)picolinaldehyde. ES/MS: m/z=288.1 $[M+H]^+$. $^1H$ NMR (400 MHz, DMSO-$d_6$) δ 8.88 (s, 1H), 8.28-8.14 (m, 1H), 7.80 (d, J=8.3 Hz, 1H), 5.89 (t, J=4.4 Hz, 1H), 4.93-4.81 (m, 1H), 4.22 (t, J=3.9 Hz, 2H), 4.17-4.10 (m, 1H), 2.45-2.32 (m, 1H), 2.17-2.01 (m, 2H), 1.95-1.83 (m, 1H).

Ba-77

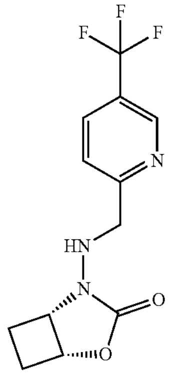

(1R,5S)-4-(((5-(trifluoromethyl)pyridin-2-yl)methyl)amino)-2-oxa-4-azabicyclo[3.2.0]heptan-3-one (Ba-77). Prepared using general procedure I-B starting with (1R,5S)-4-amino-2-oxa-4-azabicyclo[3.2.0]heptan-3-one Ad-2 and 5-(trifluoromethyl)picolinaldehyde. ES/MS: m/z=288.1 $[M+H]^+$. $^1H$ NMR (400 MHz, DMSO-$d_6$) δ 8.88 (s, 1H), 8.28-8.17 (m, 1H), 7.80 (d, J=8.3 Hz, 1H), 5.89 (t, J=4.4 Hz, 1H), 4.92-4.81 (m, 1H), 4.22 (t, J=3.9 Hz, 2H), 4.16-4.11 (m, 1H), 2.46-2.33 (m, 1H), 2.14-2.00 (m, 2H), 1.94-1.82 (m, 1H).

Ba-78

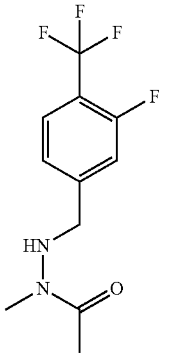

N'-(3-fluoro-4-(trifluoromethyl)benzyl)-N-methylacetohydrazide (Ba-78). Prepared using general procedure I-B starting with N-methylacetohydrazide and 3-fluoro-4-(trifluoromethyl)benzaldehyde. ES/MS: m/z=265.2 $[M+H]^+$.

Ba-79

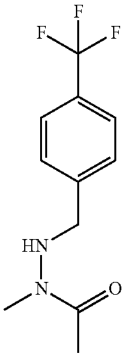

N-methyl-N'-(4-(trifluoromethyl)benzyl)acetohydrazide (Ba-79). Prepared using general procedure I-B starting with N-methylacetohydrazide and 4-(trifluoromethyl)benzaldehyde. ES/MS: m/z=247.2 $[M+H]^+$.

Ba-80

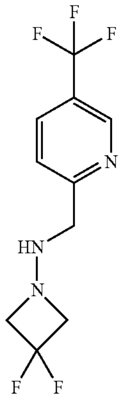

3,3-difluoro-N-((5-(trifluoromethyl)pyridin-2-yl)methyl)azetidin-1-amine (Ba-80). Prepared using general procedure I-B starting with 3,3-difluoroazetidin-1-amine; 2,2,2-trifluoroacetic acid and 5-(trifluoromethyl)picolinaldehyde. ES/MS: m/z=268.2 $[M+H]^+$.

Ba-81

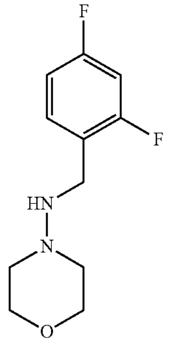

N-(2,4-difluorobenzyl)morpholin-4-amine (Ba-81). Prepared using general procedure I-B starting with 2,4-difluorobenzaldehyde and morpholin-4-amine. ES/MS: m/z=229.2 $[M+H]^+$.

Ba-82

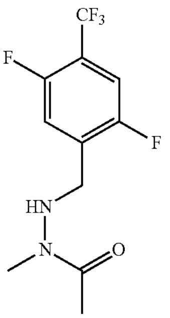

N'-(2,5-difluoro-4-(trifluoromethyl)benzyl)-N-methylacetohydrazide (Ba-82). Prepared using general procedure I-B starting with 2,5-difluoro-4-(trifluoromethyl)benzaldehyde and N-methylacetohydrazide. ES/MS: m/z=283.0 $[M+H]^+$.

Ba-83

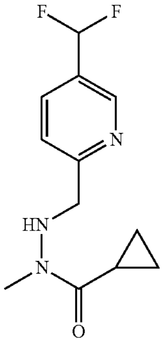

N'-((5-(difluoromethyl)pyridin-2-yl)methyl)-N-methylcyclopropanecarbohydrazide (Ba-83). Prepared using general procedure I-B starting with 5-(difluoromethyl)picolinaldehyde and N-methylcyclopropanecarbohydrazide. ES/MS: m/z=256.0 $[M+H]^+$.

Ba-84

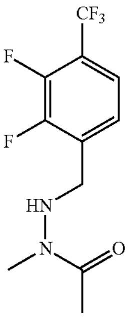

N'-(2,3-difluoro-4-(trifluoromethyl)benzyl)-N-methylacetohydrazide (Ba-84). Prepared using general procedure I-B starting with 2,3-difluoro-4-(trifluoromethyl)benzaldehyde and N-methylacetohydrazide. ES/MS: m/z=283.0 $[M+H]^+$.

Ba-85

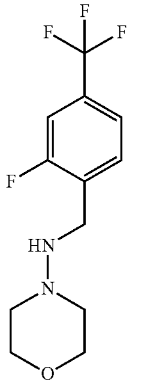

N-[[2-fluoro-4-(trifluoromethyl)benzyl]morpholin-4-amine (Ba-85). Prepared using general procedure I-B starting with morpholin-4-amine and 2-fluoro-4-(trifluoromethyl)benzaldehyde. ES/MS: m/z=279.2 $[M+H]^+$.

Ba-86

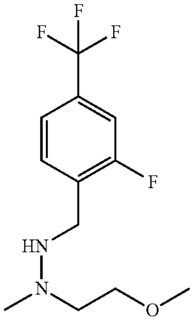

2-(2-fluoro-4-(trifluoromethyl)benzyl)-1-(2-methoxyethyl)-1-methylhydrazine (Ba-86). Prepared using general procedure I-B starting with 1-(2-methoxyethyl)-1-methylhydrazine and 2-fluoro-4-(trifluoromethyl)benzaldehyde. ES/MS: m/z=281.2 $[M+H]^+$.

Ba-87

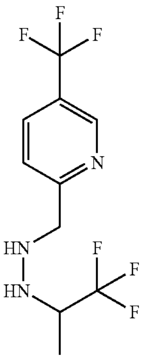

5-(trifluoromethyl)-2-((2-(1,1,1-trifluoropropan-2-yl)hydrazineyl)methyl)pyridine (Ba-87). Prepared using general procedure I-B starting with (1,1,1-trifluoropropan-2-yl)hydrazine and 5-(trifluoromethyl)nicotinaldehyde. ES/MS: m/z=288.2 $[M+H]^+$.

Ba-88

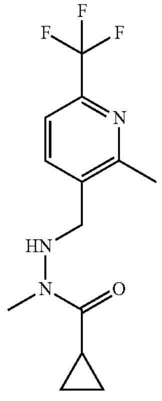

N-methyl-N'-[[2-methyl-6-(trifluoromethyl)-3-pyridyl]methyl]cyclopropanecarbohydrazide (Ba-88). Prepared using general procedure I-B starting with N-methylcyclopropanecarbohydrazide; 2,2,2-trifluoroacetic acid and 2-methyl-6-(trifluoromethyl)pyridine-3-carbaldehyde. ES/MS: m/z=288.1 $[M+H]^+$.

Ba-89

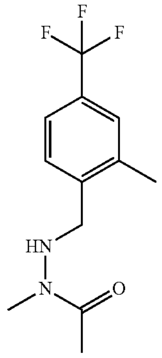

N-methyl-N'-[[2-methyl-4-(trifluoromethyl)phenyl]methyl]acetohydrazide (Ba-89). Prepared using general procedure I-B starting with 2-methyl-4-(trifluoromethyl)benzaldehyde and N-methylacetohydrazide. ES/MS: m/z=261.1 $[M+H]^+$.

Ba-90

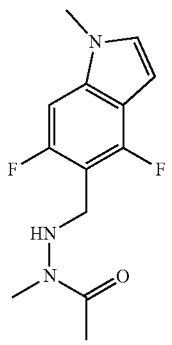

N'-[(4,6-difluoro-1-methyl-indol-5-yl)methyl]-N-methylacetohydrazide (Ba-90). Prepared using general procedure I-B starting with 4,6-difluoro-1-methyl-indole-5-carbaldehyde and N-methylacetohydrazide. ES/MS: m/z=268.1 $[M+H]^+$.

Ba-91

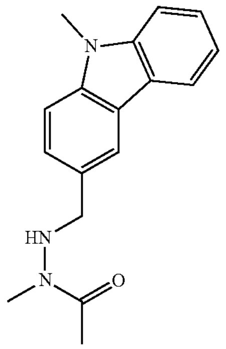

N-methyl-N'-[(9-methylcarbazol-3-yl)methyl]acetohydrazide (Ba-91). Prepared using general procedure I-B starting with 9-methylcarbazole-3-carbaldehyde and N-methylacetohydrazide. ES/MS: m/z=282.2 $[M+H]^+$.

Ba-92

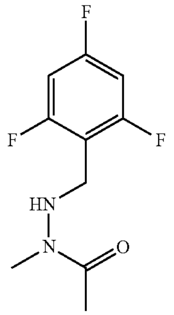

N-methyl-N'-[(2,4,6-trifluorophenyl)methyl]acetohydrazide (Ba-92). Prepared using general procedure I-B starting with 2,4,6-trifluorobenzaldehyde and N-methylacetohydrazide. ES/MS: m/z=233.1 $[M+H]^+$.

Ba-93

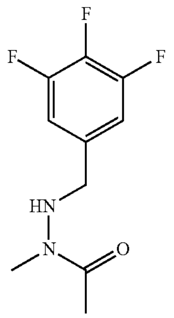

N-methyl-N'-[(3,4,5-trifluorophenyl)methyl]acetohydrazide (Ba-93). Prepared using general procedure I-B starting with 3,4,5-trifluorobenzaldehyde and N-methylacetohydrazide. ES/MS: m/z=233.1 $[M+H]^+$.

Ba-94

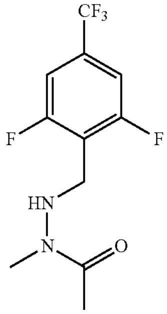

N'—[[2,6-difluoro-4-(trifluoromethyl)phenyl]methyl]-N-methyl-acetohydrazide (Ba-94). Prepared using general procedure I-B starting with 2,6-difluoro-4-(trifluoromethyl) benzaldehyde and N-methylacetohydrazide. ES/MS: m/z=283.2 $[M+H]^+$.

Ba-95

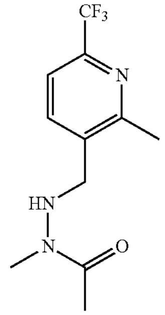

N-methyl-N'-[[2-methyl-6-(trifluoromethyl)-3-pyridyl] methyl]acetohydrazide (Ba-95). Prepared using general procedure I-B starting with 2-methyl-6-(trifluoromethyl)pyridine-3-carbaldehyde and N-methylacetohydrazide. ES/MS: m/z=262.2 $[M+H]^+$.

Ba-96

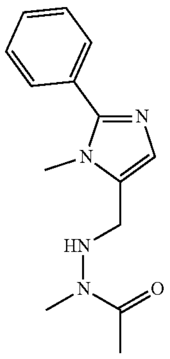

N-methyl-N'-((1-methyl-2-phenyl-1H-imidazol-5-yl) methyl)acetohydrazide (Ba-96). Prepared using general procedure I-B starting with 3-methyl-2-phenyl-imidazole-4-carbaldehyde and N-methylacetohydrazide. ES/MS: m/z=259.2 $[M+H]^+$.

Ba-97

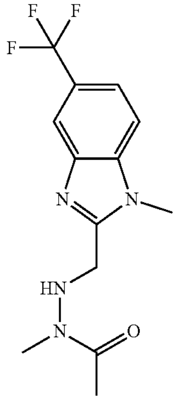

N-methyl-N'-((1-methyl-5-(trifluoromethyl)-1H-benzo [d]imidazol-2-yl)methyl)acetohydrazide (Ba-97). Prepared using general procedure I-B starting with 1-methyl-5-(trifluoromethyl)benzimidazole-2-carbaldehyde and N-methylacetohydrazide. ES/MS: m/z=301.1 $[M+H]^+$.

Ba-98

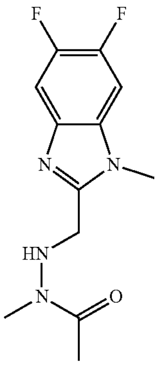

N'-((5,6-difluoro-1-methyl-1H-benzo[d]imidazol-2-yl) methyl)-N-methylacetohydrazide (Ba-98). Prepared using general procedure I-B starting with 5,6-difluoro-1-methylbenzimidazole-2-carbaldehyde and N-methylacetohydrazide. ES/MS: m/z=269.1

Ba-99

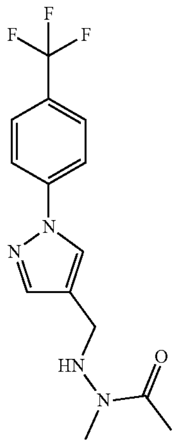

N-methyl-N'-((1-(4-(trifluoromethyl)phenyl)-1H-pyrazol-4-yl)methyl)acetohydrazide (Ba-99). Prepared using general procedure I-B starting with 1-[4-(trifluoromethyl)phenyl]pyrazole-4-carbaldehyde and N-methylacetohydrazide. ES/MS: m/z=313 [M+H]$^+$.

Ba-100

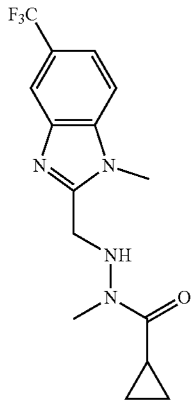

N-methyl-N'-((1-methyl-5-(trifluoromethyl)-1H-benzo[d]imidazol-2-yl)methyl)cyclopropanecarbohydrazide (Ba-100). Prepared using general procedure I-B starting with 1-methyl-5-(trifluoromethyl)benzimidazole-2-carbaldehyde and methylhydrazine. ES/MS: m/z=327.2 [M+H]$^+$.

General Procedure II-B for the Synthesis of Intermediate Bb

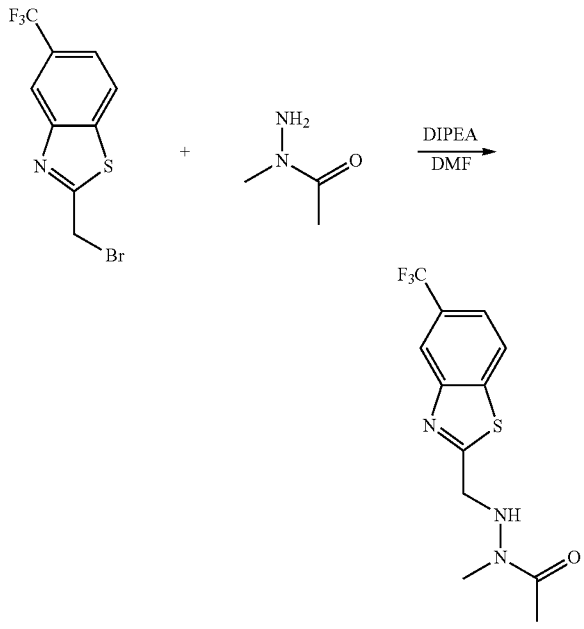

N-methyl-N'-((6-(trifluoromethyl)benzo[d]thiazol-2-yl)methyl)acetohydrazide (Bb-1). N-Methylacetohydrazide (54 mg, 0.6 mmol) was added to 2-(bromomethyl)-5-(trifluoromethyl)benzo[d]thiazole (150 mg, 0.5 mmol) and N,N-Diisopropylethylamine (164 mg, 1.27 mmol) in DMF (2.5 mL). The mixture was stirred overnight at 85 °C. The mixture was filtered through Celite and concentrated by rotary evaporation. The crude material was purified by chromatography (DCM/MeOH) to provide the titled compound. ES/MS: 303.9 [M+H]$^+$. 1H NMR (400 MHz, Methanol-$d_4$) δ 8.24 (dt, J=10.4, 4.1 Hz, 3H), 7.73 (dd, J=8.4, 1.8 Hz, 1H), 4.54 (s, 2H), 3.20 (s, 3H), 2.18 (s, 3H).

Bb-2

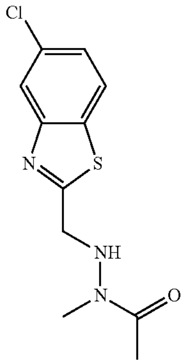

N'-[(5-chloro-1,3-benzothiazol-2-yl)methyl]-N-methyl-acetohydrazide (Bb-2). Prepared using general procedure II-B starting with 5-chloro-2-(chloromethyl)-1,3-benzothiazole and N-methylacetohydrazide. ES/MS: m/z=270 [M+H]$^+$.

Bb-3

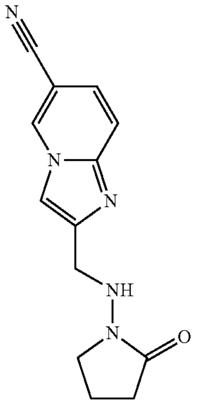

2-[[(2-oxopyrrolidin-1-yl)amino]methyl]imidazo[1,2-a]pyridine-6-carbonitrile (Bb-3). Prepared using general procedure II-B starting with 2-(chloromethyl)imidazo[1,2-a]pyridine-6-carbonitrile and 1-aminopyrrolidin-2-one. ES/MS: m/z=256.2[M+H]$^+$.

Bb-4

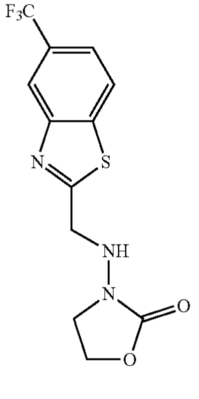

3-(((5-(trifluoromethyl)benzo[d]thiazol-2-yl)methyl)amino)oxazolidin-2-one (Bb-4). Prepared using general procedure II-B starting with 2-(bromomethyl)-5-(trifluoromethyl)-1,3-benzothiazole and 3-aminooxazolidin-2-one ES/MS: m/z=318.2[M+H]$^+$.

Bb-5

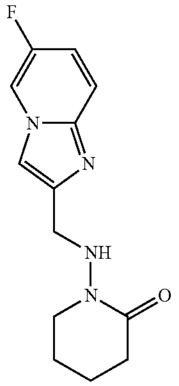

1-(((6-fluoroimidazo[1,2-a]pyridin-2-yl)methyl)amino)piperidin-2-one (Bb-5). Prepared using general procedure II-B starting with 2-(chloromethyl)-6-fluoro-imidazo[1,2-a]pyridine and 1-aminopiperidin-2-one ES/MS: m/z=263.2 [M+H]$^+$.

Bb-6

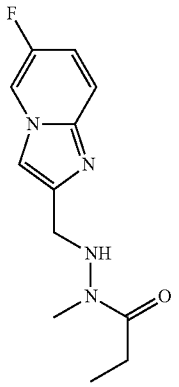

N'-[(6-fluoroimidazo[1,2-a]pyridin-2-yl)methyl]-N-methyl-propanehydrazide (Bb-6). Prepared using general procedure II-B starting with 2-(chloromethyl)-6-fluoro-imidazo[1,2-a]pyridine and N-methylpropanehydrazide. ES/MS: m/z=251.2 [M+H]$^+$.

Bb-7

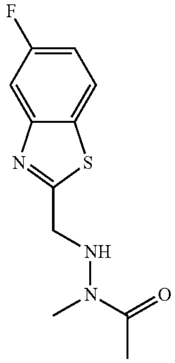

N'-[(5-fluoro-1,3-benzothiazol-2-yl)methyl]-N-methyl-acetohydrazide (Bb-7). Prepared using general procedure II-B starting with 2-(bromomethyl)-5-fluoro-1,3-benzothiazole and N-methylpropanehydrazide. ES/MS: m/z=253.9 [M+H]$^+$.

Bb-8

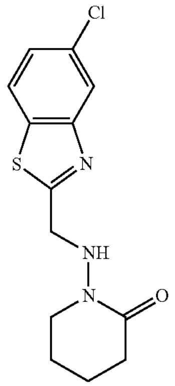

1-(((5-chlorobenzo[d]thiazol-2-yl)methyl)amino)piperidin-2-one (Bb-8). Prepared using general procedure II-B starting with 1-aminopiperidin-2-one and 5-chloro-2-(chloromethyl)-1,3-benzothiazole. ES/MS: m/z=296.0 [M+H]$^+$.

Bb-9

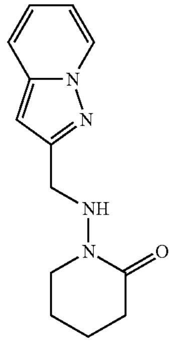

1-(pyrazolo[1,5-a]pyridin-2-ylmethylamino)piperidin-2-one (Bb-9). Prepared using general procedure II-B starting with 1-aminopiperidin-2-one and 2-(chloromethyl)pyrazolo[1,5-a]pyridine. ES/MS: m/z=245.2 [M+H]$^+$.

Bb-10

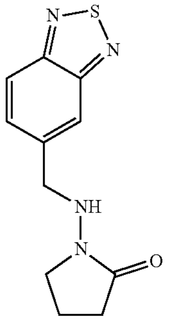

1-((benzo[c][1,2,5]thiadiazol-5-ylmethyl)amino)pyrrolidin-2-one (Bb-10). Prepared using general procedure II-B starting with 1-aminopyrrolidin-2-one and 5-(bromomethyl)-2,1,3-benzothiadiazole. ES/MS: m/z=248.9 $[M+H]^+$.

Bb-11

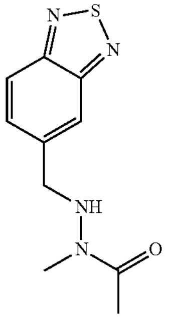

N'-(2,1,3-benzothiadiazol-5-ylmethyl)-N-methyl-acetohydrazide (Bb-11). Prepared using general procedure II-B starting with N-Methylacetohydrazide and 5-(bromomethyl)-2,1,3-benzothiadiazole. ES/MS: m/z=237.0 $[M+H]^+$.

Bb-12

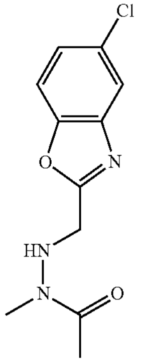

N'-((5-chlorobenzo[d]oxazol-2-yl)methyl)-N-methylacetohydrazide (Bb-12).

Prepared using general procedure II-B starting with N-methylacetohydrazide and 5-chloro-2-(chloromethyl)benzo[d]oxazole. ES/MS: m/z=254.9 $[M+H]^+$.

Bb-13

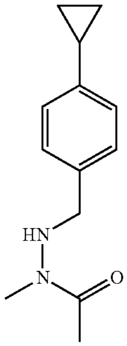

N'-(4-cyclopropylbenzyl)-N-methylacetohydrazide (Bb-13). Prepared using general procedure II-B starting with N-methylacetohydrazide and 1-(bromomethyl)-4-cyclopropylbenzene. ES/MS: m/z=219.0 $[M+H]^+$.

Bb-14

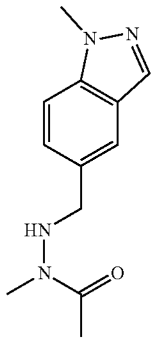

N-methyl-N'-((1-methyl-1H-indazol-5-yl)methyl)acetohydrazide (Bb-14). Prepared following the same procedure as II-B using 5-(bromomethyl)-1-methyl-1H-indazole hydrobromide and N-methylacetohydrazide. ES/MS: m/z=233.2 $[M+H]^+$.

Bb-15

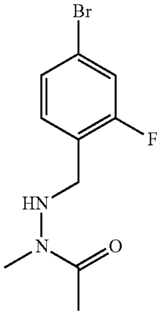

N'-(4-bromo-2-fluorobenzyl)-N-methylacetohydrazide (Bb-15). Prepared using general procedure II-B starting with N-methylacetohydrazide and 4-bromo-2-florobenzaldehyde. ES/MS: m/z=276.2 $[M+H]^+$.

Bb-16

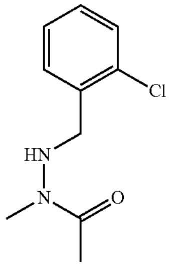

N'-(2-chlorobenzyl)-N-methylacetohydrazide (Bb-16). Prepared using general procedure II-B starting with N-methylacetohydrazide and 1-chloro-2-(chloromethyl) benzene. ES/MS: m/z=213.0 [M+H]$^+$.

Bb-17

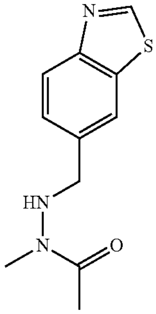

N'-(benzo[d]thiazol-6-ylmethyl)-N-methylacetohydrazide (Bb-17). Prepared using general procedure II-B starting with 6-(chloromethyl)-1,3-benzothiazole and N-methylacetohydrazide. ES/MS: m/z=236.2 [M+H]$^+$.

Bb-18

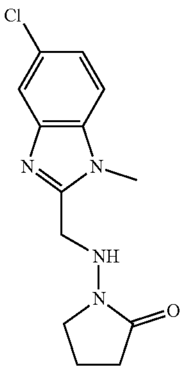

1-(((5-chloro-1-methyl-1H-benzo[d]imidazol-2-yl) methyl)amino)pyrrolidin-2-one (Bb-18). Prepared using general procedure II-B starting with 5-chloro-2-(chloromethyl)-1-methyl-1H-benzo[d]imidazole and 1-aminopyrrolidin-2-one. ES/MS: m/z=279.1[M+H]$^+$.

Bb-19

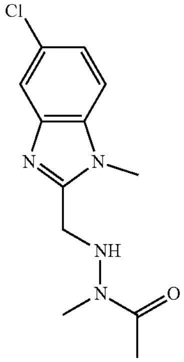

N'-[(5-chloro-1-methyl-benzimidazol-2-yl)methyl]-N-methyl-acetohydrazide (Bb-19). Prepared using general procedure II-B starting with 5-chloro-2-(chloromethyl)-1-methyl-1H-benzo[d]imidazole and N-methylacetohydrazide. ES/MS: m/z=267.2 [M+H]$^+$.

Bb-20

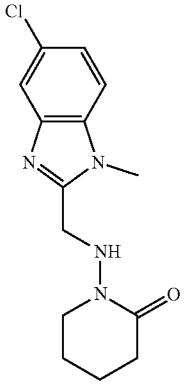

1-(((5-chloro-1-methyl-1H-benzo[d]imidazol-2-yl) methyl)amino)piperidin-2-one (Bb-20). Prepared using general procedure II-B starting with 5-chloro-2-(chloromethyl)-1-methyl-1H-benzo[d]imidazole and 1-aminopiperidin-2-one. ES/MS: m/z=293.2 [M+H]$^+$.

Bb-21

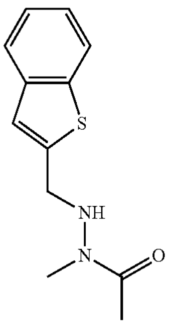

N'-(benzothiophen-2-ylmethyl)-N-methyl-acetohydrazide (Bb-21). Prepared using general procedure II-B starting with 2-(chloromethyl)benzothiophene and N-methylacetohydrazide. ES/MS: m/z=235.0 [M+H]$^+$.

Bb-22

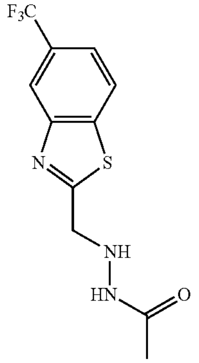

N'-[[5-(trifluoromethyl)-1,3-benzothiazol-2-yl]methyl] acetohydrazide (Bb-22). Prepared using general procedure II-B starting with 2-(chloromethyl)-5-(trifluoromethyl)-1,3-benzothiazole and acetohydrazide. ES/MS: m/z=290.0 $[M+H]^+$.

Bb-23

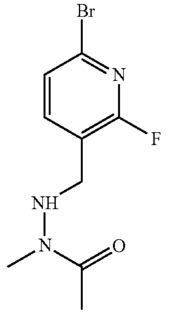

N'-((6-bromo-2-fluoropyridin-3-yl)methyl)-N-methylacetohydrazide (Bb-23).

Prepared using general procedure II-B starting with 6-bromo-3-(bromomethyl)-2-fluoropyridine and N-methylacetohydrazide. ES/MS: m/z=277.0 $[M+H]^+$.

Bb-24

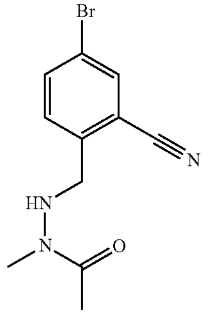

N'-(4-bromo-2-cyanobenzyl)-N-methylacetohydrazide (Bb-24). Prepared using general procedure II-B starting with 5-bromo-2-(bromomethyl)benzonitrile and N-methylacetohydrazide. ES/MS: m/z=284.0 $[M+H]^+$.

Bb-25

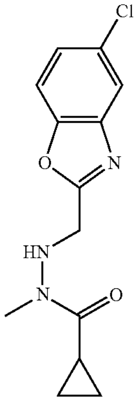

N'-((5-chlorobenzo[d]oxazol-2-yl)methyl)-N-methylcyclopropanecarbohydrazide (Bb-25). Prepared using general procedure II-B starting with 5-chloro-2-(chloromethyl) benzo[d]oxazole and N-methylcyclopropanecarbohydrazide. ES/MS: m/z=281.8 $[M+H]^+$.

Bb-26

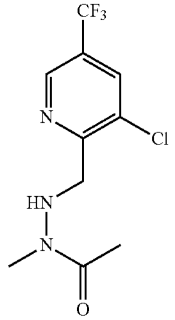

N'-((3-chloro-5-(trifluoromethyl)pyridin-2-yl)methyl)-N-methylacetohydrazide (Bb-26). Prepared using general procedure II-B starting with 3-chloro-2-(chloromethyl)-5-(trifluoromethyl)pyridine and N-methylacetohydrazide. ES/MS: m/z=283.8 $[M+H]^+$.

Bb-27

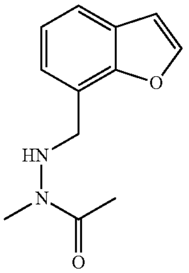

N'-(benzofuran-7-ylmethyl)-N-methylacetohydrazide (Bb-27). Prepared using general procedure II-B starting with N-methylacetohydrazide and 7-(chloromethyl)benzofuran. ES/MS: m/z=219.0 $[M+H]^+$.

Bb-28

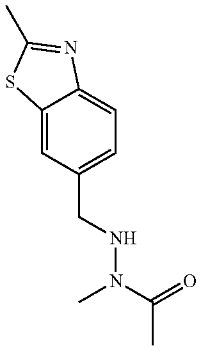

N-methyl-N'-((2-methylbenzo[d]thiazol-6-yl)methyl)acetohydrazide (Bb-28).

Prepared using general procedure II-B starting with 6-(chloromethyl)-2-methyl-1,3-benzothiazole and N-methylacetohydrazide. ES/MS: m/z=250.2 [M+H]$^+$.

Bb-29

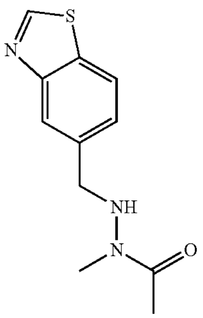

N'-(benzo[d]thiazol-5-ylmethyl)-N-methylacetohydrazide (Bb-29). Prepared using general procedure II-B starting with 5-(bromomethyl)-1,3-benzothiazole and N-methylacetohydrazide. ES/MS: m/z=236.2 [M+H]$^+$.

Bb-30

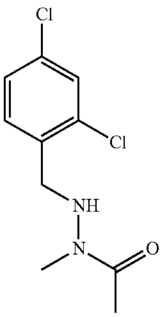

N'-(2,4-dichlorobenzyl)-N-methylacetohydrazide (Bb-30). Prepared using general procedure II-B starting with 1-(bromomethyl)-2,4-dichloro-benzene and N-methylacetohydrazide. ES/MS: m/z=247.2 [M+H]$^+$.

Bb-31

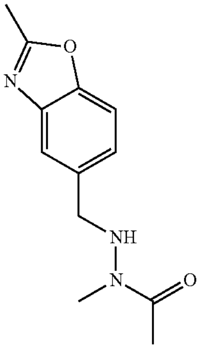

N-methyl-N'-((2-methylbenzo[d]oxazol-5-yl)methyl)acetohydrazide (Bb-31). Prepared using general procedure II-B starting with 5-(bromomethyl)-2-methyl-1,3-benzoxazole and N-methylacetohydrazide. ES/MS: m/z=234.2 [M+H]$^+$.

Bb-32

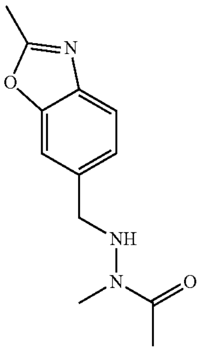

N-methyl-N'-((2-methylbenzo[d]oxazol-6-yl)methyl)acetohydrazide (Bb-32). Prepared using general procedure II-B starting with 6-(bromomethyl)-2-methyl-1,3-benzoxazole and N-methylacetohydrazide. ES/MS: m/z=234.2 [M+H]$^+$.

Bb-33

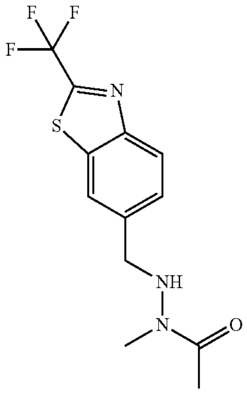

N-methyl-N'-((2-(trifluoromethyl)benzo[d]thiazol-6-yl)methyl)acetohydrazide (Bb-33). Prepared using general procedure II-B starting with 6-(bromomethyl)-2-(trifluoromethyl)-1,3-benzothiazole and N-methylacetohydrazide. ES/MS: m/z=304.2 [M+H]$^+$.

Bb-34

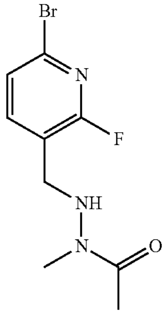

N'-((6-bromo-2-fluoropyridin-3-yl)methyl)-N-methylacetohydrazide (Bb-34). Prepared using general procedure II-B starting with 6-bromo-3-(bromomethyl)-2-fluoro-pyridine and N-methylacetohydrazide. ES/MS: m/z=277.0 $[M+H]^+$.

Bb-35

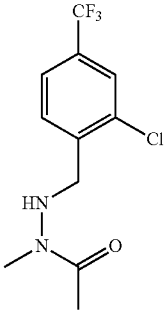

N'-(2-chloro-4-(trifluoromethyl)benzyl)-N-methylacetohydrazide (Bb-35). Prepared using general procedure II-B starting with 1-(bromomethyl)-2-chloro-4-(trifluoromethyl) benzene and N-methylacetohydrazide. ES/MS: m/z=281.2 $[M+H]^+$.

Bb-36

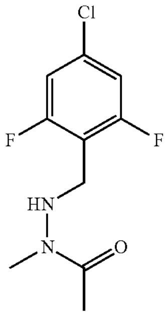

N'-(4-chloro-2,6-difluorobenzyl)-N-methylacetohydrazide (Bb-36). Prepared using general procedure II-B starting with 2-(bromomethyl)-5-chloro-1,3-difluorobenzene and N-methylacetohydrazide. ES/MS: m/z=249.2 $[M+H]^+$.

Bb-37

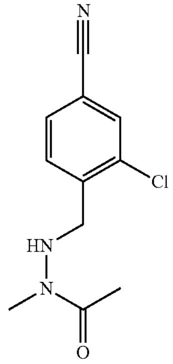

N'-(2-chloro-4-cyanobenzyl)-N-methylacetohydrazide (Bb-37). Prepared using general procedure II-B starting 4-(bromomethyl)-3-chlorobenzonitrile and N-methylacetohydrazide. ES/MS: m/z=238.1 $[M+H]^+$.

Bb-38

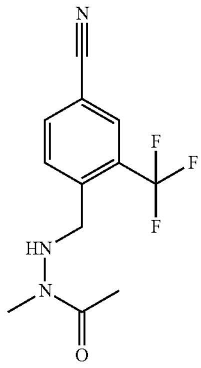

N'-(4-cyano-2-(trifluoromethyl)benzyl)-N-methylacetohydrazide (Bb-38). Prepared using general procedure II-B starting 4-(bromomethyl)-3-(trifluoromethyl)benzonitrile and N-methylacetohydrazide. ES/MS: m/z=272.2 $[M+H]^+$.

Bb-39

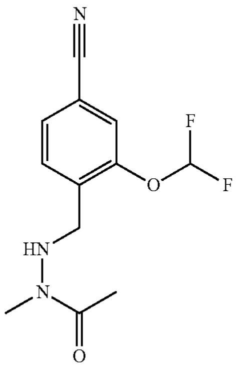

N'-(4-cyano-2-(difluoromethoxy)benzyl)-N-methylacetohydrazide (Bb-39). Prepared using general procedure II-B starting 4-(bromomethyl)-3-(difluoromethoxy)benzonitrile and N-methylacetohydrazide. ES/MS: m/z=270.1 $[M+H]^+$.

Bb-40

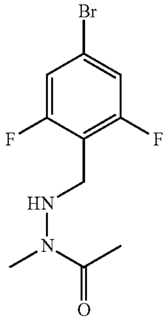

N'-(4-bromo-2,6-difluorobenzyl)-N-methylacetohydrazide (Bb-40). Prepared using general procedure II-B starting 5-bromo-2-(bromomethyl)-1,3-difluorobenzene and N-methylacetohydrazide. ES/MS: m/z=295.0 $[M+H]^+$.

Bb-41

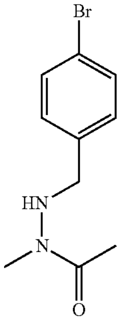

N'-(4-bromobenzyl)-N-methylacetohydrazide (Bb-41). Prepared using general procedure II-B starting 1-bromo-4-(bromomethyl)benzene and N-methylacetohydrazide. ES/MS: m/z=257.1 $[M+H]^+$.

Bb-42

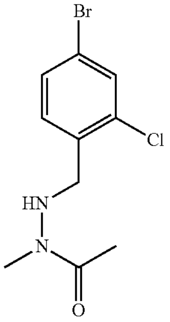

N'-(4-bromo-2-chlorobenzyl)-N-methylacetohydrazide (Bb-42). Prepared using general procedure II-B starting 4-bromo-1-(bromomethyl)-2-chlorobenzene and N-methylacetohydrazide. ES/MS: m/z=219.4 $[M+H]^+$.

Bb-43

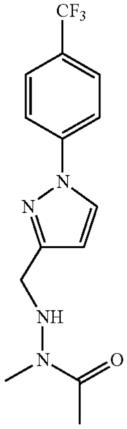

N-methyl-N'-((1-(4-(trifluoromethyl)phenyl)-1H-pyrazol-3-yl)methyl)acetohydrazide (Bb-43). Prepared using general procedure II-B starting with 3-(bromomethyl)-1-[4-(trifluoromethyl)phenyl]pyrazolel and N-methylacetohydrazide. ES/MS: m/z=313.2 $[M+H]^+$.

Bb-44

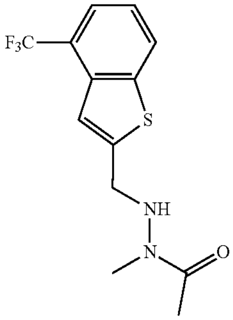

N-methyl-N'-((4-(trifluoromethyl)benzo[b]thiophen-2-yl)methyl)acetohydrazide (Bb-44). Prepared using general procedure II-B starting with 2-(bromomethyl)-4-(trifluoromethyl)benzothiophene and N-methylacetohydrazide. ES/MS: m/z=303.4 $[M+H]^+$.

Bb-45

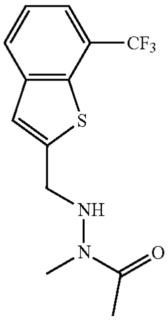

N-methyl-N'-((7-(trifluoromethyl)benzo[b]thiophen-2-yl)methyl)acetohydrazide (Bb-45). Prepared using general procedure II-B starting with 2-(bromomethyl)-7-(trifluoromethyl)benzothiophene and N-methylacetohydrazide. ES/MS: m/z=303.2 $[M+H]^+$.

Bb-46

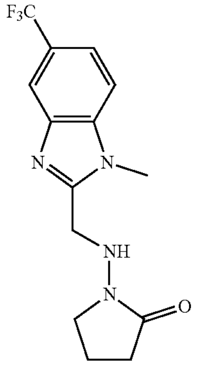

1-(((1-methyl-5-(trifluoromethyl)-1H-benzo[d]imidazol-2-yl)methyl)amino)pyrrolidin-2-one (Bb-46). Prepared using general procedure II-B starting with 2-(chloromethyl)-1-methyl-5-(trifluoromethyl)benzimidazole and 1-aminopyrrolidin-2-one. ES/MS: m/z=313.1 $[M+H]^+$.

Bb-47

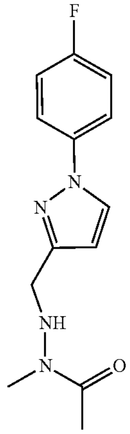

N'-((1-(4-fluorophenyl)-1H-pyrazol-3-yl)methyl)-N-methylacetohydrazide (Bb-47). Prepared using general procedure II-B starting with 3-(chloromethyl)-1-(4-fluorophenyl)pyrazole and N-methylacetohydrazide. ES/MS: m/z=263.1 $[M+H]^+$.

Bb-48

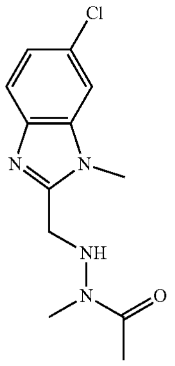

N'-((6-chloro-1-methyl-1H-benzo[d]imidazol-2-yl)methyl)-N-methylacetohydrazide (Bb-48). Prepared using general procedure II-B starting with 2-(bromomethyl)-6-chloro-1-methyl-benzimidazole and N-methylacetohydrazide. ES/MS: m/z=267.2 $[M+H]^+$.

Bb-49

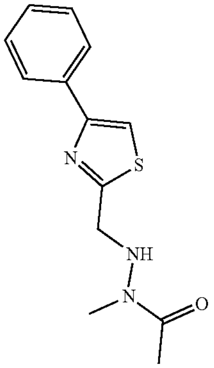

N-methyl-N'-((4-phenylthiazol-2-yl)methyl)acetohydrazide (Bb-49). Prepared using general procedure II-B starting with 2-(chloromethyl)-4-phenyl-thiazole and N-methylacetohydrazide. ES/MS: m/z=262.3 $[M+H]^+$.

Bb-50

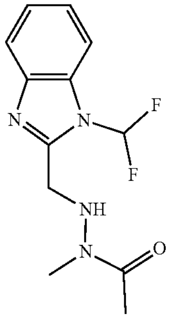

N'-((1-(difluoromethyl)-1H-benzo[d]imidazol-2-yl)methyl)-N-methylacetohydrazide (Bb-50). Prepared using general procedure II-B starting with 2 N'-((1-(difluoromethyl)-1H-benzo[d]imidazol-2-yl)methyl)-N-methylacetohydrazide and N-methylacetohydrazide. ES/MS: m/z=269.2 $[M+H]^+$.

Bb-51

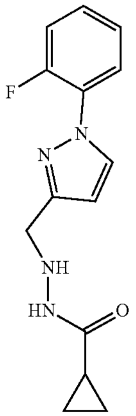

N'-((1-(2-fluorophenyl)-1H-pyrazol-3-yl)methyl)cyclopropanecarbohydrazide (Bb-51). Prepared using general procedure II-B starting with 3-(chloromethyl)-1-(2-fluorophenyl)pyrazole and cyclopropanecarbohydrazide. ES/MS: m/z=275.2 $[M+H]^+$.

Bb-52

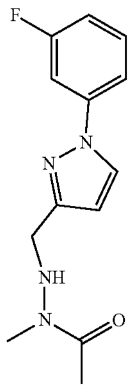

N'-((1-(3-fluorophenyl)-1H-pyrazol-3-yl)methyl)-N-methylacetohydrazide (Bb-52). Prepared using general procedure II-B starting with 3-(chloromethyl)-1-(3-fluorophenyl)pyrazole and N-methylacetohydrazide. ES/MS: m/z=263.1 $[M+H]^+$.

Bb-53

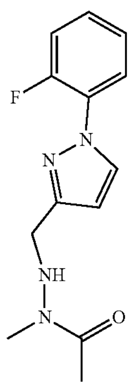

N'-((1-(2-fluorophenyl)-1H-pyrazol-3-yl)methyl)-N-methylacetohydrazide (Bb-53). Prepared using general procedure II-B starting with 3-(chloromethyl)-1-(2-fluorophenyl)pyrazole and N-methylacetohydrazide. ES/MS: m/z=263.2 $[M+H]^+$.

Bb-54

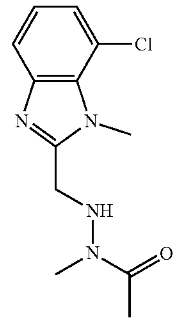

N'-((7-chloro-1-methyl-1H-benzo[d]imidazol-2-yl)methyl)-N-methylacetohydrazide (Bb-54). Prepared using general procedure II-B starting with 2-(bromomethyl)-7-chloro-1-methyl-benzimidazole and N-methylacetohydrazide. ES/MS: m/z=267.2 $[M+H]^+$.

Bb-55

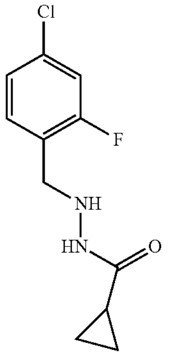

N'-(4-chloro-2-fluorobenzyl)cyclopropanecarbohydrazide (Bb-55). Prepared using general procedure II-B starting with 1-(bromomethyl)-4-chloro-2-fluoro-benzene and cyclopropanecarbohydrazide. ES/MS: m/z=243.1 $[M+H]^+$.

Bb-56

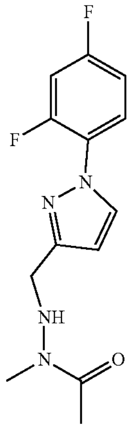

N'-((1-(2,4-difluorophenyl)-1H-pyrazol-3-yl)methyl)-N-methylacetohydrazide (Bb-56). Prepared using general procedure II-B starting with 3-(chloromethyl)-1-(2,4-difluorophenyl)pyrazole and N-methylacetohydrazide. ES/MS: m/z=281.1 $[M+H]^+$.

Bb-57

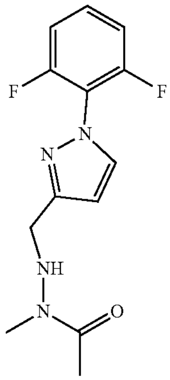

N'-((1-(2,6-difluorophenyl)-1H-pyrazol-3-yl)methyl)-N-methylacetohydrazide (Bb-57). Prepared using general procedure II-B starting with 3-(chloromethyl)-1-(2,6-difluorophenyl)pyrazole and N-methylacetohydrazide. ES/MS: m/z=281.1 $[M+H]^+$.

Bb-58

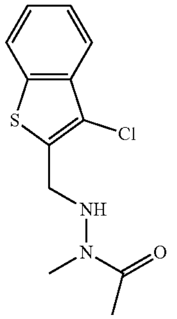

N'-((3-chlorobenzo[b]thiophen-2-yl)methyl)-N-methylacetohydrazide (Bb-58). Prepared using general procedure II-B starting with 3-chloro-2-(chloromethyl)benzothiophene and N-methylacetohydrazide. ES/MS: m/z=269.1 $[M+H]^+$.

Bb-59

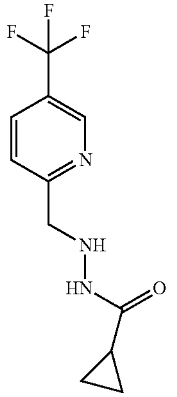

N'-((5-(trifluoromethyl)pyridin-2-yl)methyl)cyclopropanecarbohydrazide (Bb-59). Prepared using general procedure II-B starting with 2-(bromomethyl)-5-(trifluoromethyl)pyridine and cyclopropanecarbohydrazide. ES/MS: m/z=260.1 $[M+H]^+$.

Bb-60

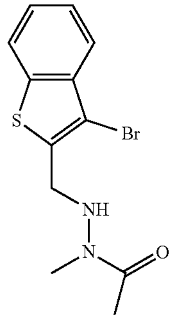

N'-((3-bromobenzo[b]thiophen-2-yl)methyl)-N-methylacetohydrazide (Bb-60). Prepared using general procedure II-B starting with 3-bromo-2-(bromomethyl)benzothiophene and N-methylacetohydrazide. ES/MS: m/z=314.9 $[M+H]^+$.

Bb-61

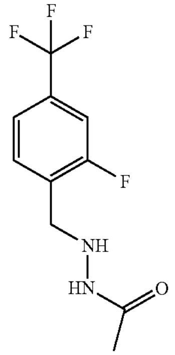

N'-(2-fluoro-4-(trifluoromethyl)benzyl)acetohydrazide (Bb-61). Prepared using general procedure II-B starting with 1-(bromomethyl)-2-fluoro-4-(trifluoromethyl)benzene and N-methylacetohydrazide. ES/MS: m/z=251.1 $[M+H]^+$.

Bb-62

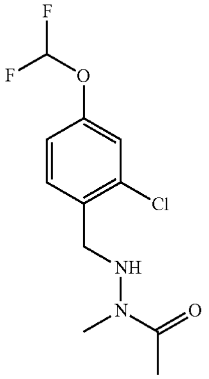

N'-(2-chloro-4-(difluoromethoxy)benzyl)-N-methylacetohydrazide (Bb-62). Prepared using general procedure II-B starting with 1-(bromomethyl)-2-chloro-4-(difluoromethoxy)benzene (prepared from the corresponding alcohol by reaction with $CBr_4$ and $PPh_3$) and N-methylacetohydrazide. ES/MS: m/z=278.9 $[M+H]^+$.

Bb-63

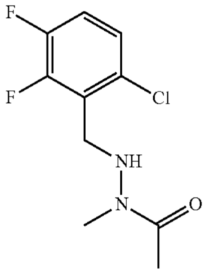

N'-(6-chloro-2,3-difluorobenzyl)-N-methylacetohydrazide (Bb-63). Prepared using general procedure II-B starting with 2-(bromomethyl)-1-chloro-3,4-difluoro-benzene and N-methylacetohydrazide. ES/MS: m/z=248.9 $[M+H]^+$.

Bb-64

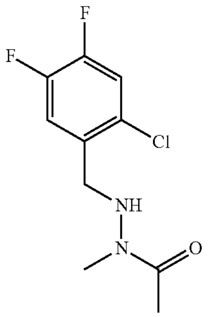

N'-(2-chloro-4,5-difluorobenzyl)-N-methylacetohydrazide (Bb-64). Prepared using general procedure II-B starting with 1-(bromomethyl)-2-chloro-4,5-difluoro-benzene and N-methylacetohydrazide. ES/MS: m/z=248.9 $[M+H]^+$.

Bb-65

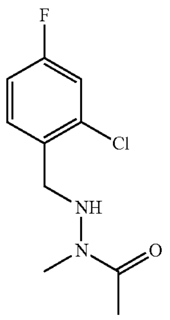

N'-(2-chloro-4-fluorobenzyl)-N-methylacetohydrazide (Bb-65). Prepared using general procedure II-B starting with 1-(bromomethyl)-2-chloro-4-fluoro-benzene and N-methylacetohydrazide. ES/MS: m/z=231.0 $[M+H]^+$.

Bb-66

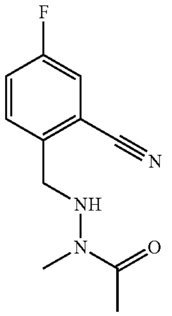

N'-(2-cyano-4-fluorobenzyl)-N-methylacetohydrazide (Bb-66). Prepared using general procedure II-B starting with 2-(bromomethyl)-5-fluoro-benzonitrile and N-methylacetohydrazide. ES/MS: m/z=222.0 $[M+H]^+$.

Bb-67

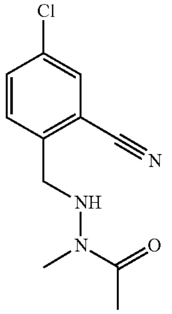

N'-(4-chloro-2-cyanobenzyl)-N-methylacetohydrazide (Bb-67). Prepared using general procedure II-B starting with 2-(bromomethyl)-5-chloro-benzonitrile and N-methylacetohydrazide. ES/MS: m/z=237.9 $[M+H]^+$.

General Procedure III-B for the Synthesis of Intermediates Bc

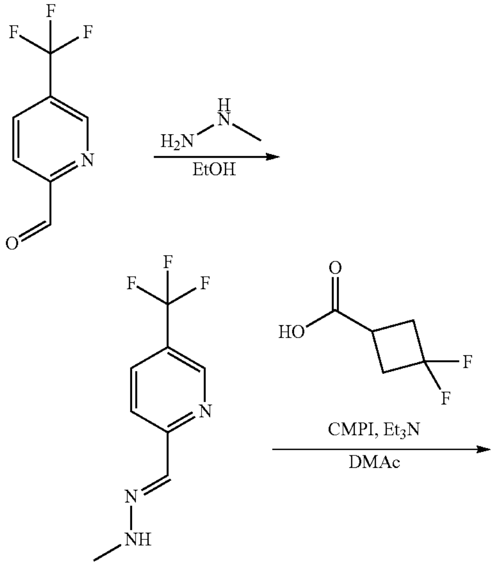

-continued

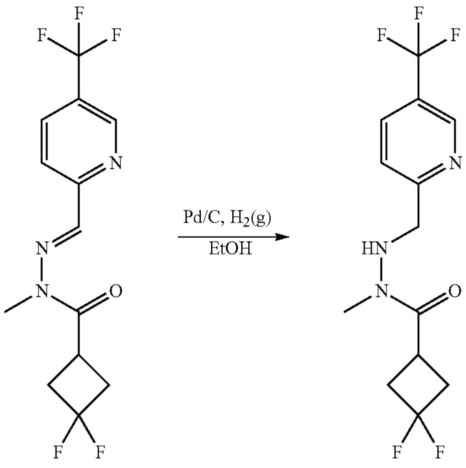

Bc-1

Step 1: (E)-2-((2-methylhydrazineylidene)methyl)-5-(trifluoromethyl)pyridine. 5-(trifluoromethyl)picolinaldehyde (1.50 g, 8.57 mmol) and methylhydrazide (0.41 g, 9.0 mmol) were dissolved in EtOH (30 mL). The mixture was left to stir at room temperature for 1 hour. The solution was reduced under pressure and purified by flash silica gel chromatography to yield the desired product. ES/MS: m/z=204.0 $[M+H]^+$.

Step 2: (E)-3,3-difluoro-N-methyl-N'-((5-(trifluoromethyl)pyridin-2-yl)methylene)cyclobutane-1-carbohydrazide. To a solution of (E)-2-((2-methylhydrazineylidene) methyl)-5-(trifluoromethyl)pyridine (150 mg g, 0.73 mmol) and 3,3-difluorocyclobutane-1-carboxylic acid (121 mg, 0.89 mmol) in DMAc (3 mL), DIPEA (0.286 g, 2.21 mmol) was added, followed by CMPI (226 mg, 0.886 mmol). The mixture was stirred at room temperature for 12 hours and upon completion by LCMS, dissolved in EtOAc. The mixture was washed with saturated $Na_2CO_3$ twice, 10% LiCl twice, and brine, then dried with $MgSO_4$. The organic layer was reduced under pressure and the resulting residue was purified by flash silica gel chromatography to yield the desired product. ES/MS: m/z=322.0 $[M+H]^+$.

Step 3: 3,3-difluoro-N-methyl-N'-((5-(trifluoromethyl) pyridin-2-yl)methyl)cyclobutane-1-carbohydrazide (Bc-1). (E)-3,3-difluoro-N-methyl-N'-((5-(trifluoromethyl)pyridin-2-yl)methylene)cyclobutane-1-carbohydrazide (176 mg, 0.54 mmol) was dissolved in EtOH (20 mL) and Pd/C (10% w/w, 88 mg) was added. The heterogeneous mixture was stirred vigorously at room temperature under hydrogen gas (1 atm). The reaction was stirred until LCMS showed full conversion of the imine. The mixture was filtered through a pad of celite and the organic solution was reduced under pressure and purified by flash silica gel chromatography to yield Bc-1.

ES/MS: m/z=324.0 [M+H]+; 1H NMR $^1$H NMR (400 MHz, Chloroform-d) δ 8.99-8.68 (m, 1H), 7.94 (ddd, J=13.2, 8.2, 2.3 Hz, 1H), 7.53 (d, J=8.1 Hz, 0.2H, minor rotamer), 7.43 (d, J=8.1 Hz, 1H), 4.17 (d, J=6.9 Hz, 2H), 3.53 (pd, J=8.8, 2.9 Hz, 1H), 3.14 (d, J=22.9 Hz, 3H), 2.93-2.69 (m, 3H), 2.68-2.51 (m, 2H).

Bc-2

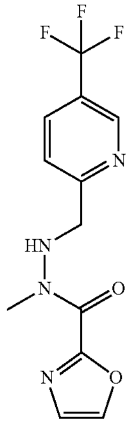

N-methyl-N'-((5-(trifluoromethyl)pyridin-2-yl)methyl) oxazole-2-carbohydrazide (Bc-2). Prepared following general procedure III-B using methylhydrazide, 5-(trifluoromethyl)picolinaldehyde and oxazole-2-carboxylic acid. ES/MS: m/z=301.2 [M+H].

Bc-3

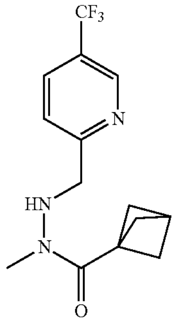

N-methyl-N'-((5-(trifluoromethyl)pyridin-2-yl)methyl) bicyclo[1.1.1]pentane-1-carbohydrazide (Bc-3). Prepared following general procedure III-B using methylhydrazide, 5-(trifluoromethyl)picolinaldehyde and bicyclo[1.1.1]pentane-1-carboxylic acid. ES/MS: m/z=300.2 $[M+H]^+$.

Bc-4

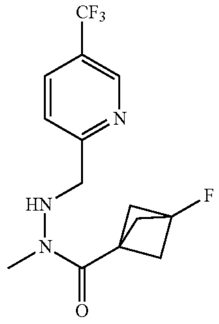

3-fluoro-N-methyl-N'-[[5-(trifluoromethyl)-2-pyridyl] methyl]bicyclo[1.1.1]pentane-1-carbohydrazide (Bc-4). Prepared following general procedure III-B using methylhydrazide, 5-(trifluoromethyl)picolinaldehyde and 3-fluorobicyclo[1.1.1]pentane-1-carboxylic acid. ES/MS: m/z=318.0 $[M+H]^+$.

Bc-5

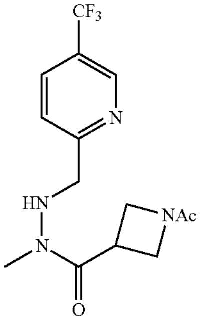

1-acetyl-N-methyl-N'-[[5-(trifluoromethyl)-2-pyridyl]methyl]azetidine-3-carbohydrazide (Bc-5). Prepared following general procedure III-B using methylhydrazide, 5-(trifluoromethyl)picolinaldehyde and 1-acetylazetidine-3-carboxylic acid. ES/MS: m/z=331.2

Bc-6

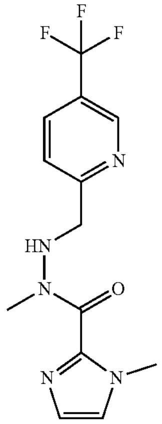

N,1-dimethyl-N'-((5-(trifluoromethyl)pyridin-2-yl)methyl)-1H-imidazole-2-carbohydrazide (Bc-6). Prepared following general procedure III-B using methylhydrazide, 5-(trifluoromethyl)picolinaldehyde and 1-methyl-1H-imidazole-2-carboxylic acid. ES/MS: m/z=314.2 $[M+H]^+$.

Bc-7

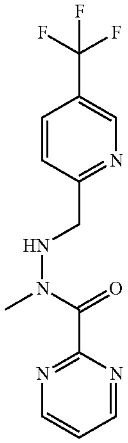

N-methyl-N'-((5-(trifluoromethyl)pyridin-2-yl)methyl)pyrimidine-2-carbohydrazide (Bc-7). Prepared following general procedure III-B using methylhydrazide, 5-(trifluoromethyl)picolinaldehyde and pyrimidine-2-carboxylic acid. ES/MS: m/z=314.2 $[M+H]^+$.

Bc-8

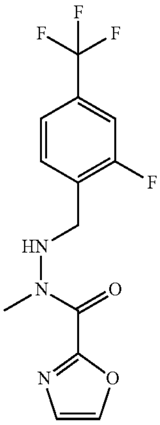

N'-(2-fluoro-4-(trifluoromethyl)benzyl)-N-methyloxazole-2-carbohydrazide (Bc-8). Prepared following general procedure III-B using methylhydrazide, 2-fluoro-4-(trifluoromethyl)benzaldehyde and oxazole-2-carboxylic acid. ES/MS: m/z=318.0 $[M+H]^+$.

Bc-9

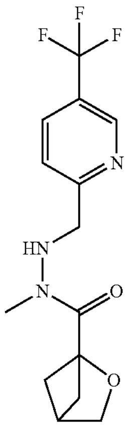

N-methyl-N'-[[5-(trifluoromethyl)-2-pyridyl]methyl]-2-oxabicyclo[2.1.1]hexane-1-carbohydrazide (Bc-9). Prepared using general procedure III-B using methylhydrazide, 5-(trifluoromethyl)picolinaldehyde and 2-oxabicyclo[2.1.1]hexane-1-carboxylic acid. ES/MS: m/z=316.2 $[M+H]^+$.

Bc-10

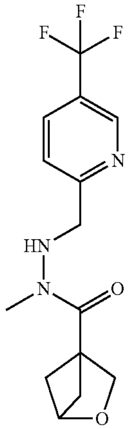

N-methyl-N'-[[5-(trifluoromethyl)-2-pyridyl]methyl]-2-oxabicyclo[2.1.1]hexane-4-carbohydrazide (Bc-10). Prepared using general procedure III-B using methylhydrazide, 5-(trifluoromethyl)picolinaldehyde and 2-oxabicyclo[2.1.1]hexane-4-carboxylic acid. ES/MS: m/z=316.2 [M+H]$^+$.

Bc-11

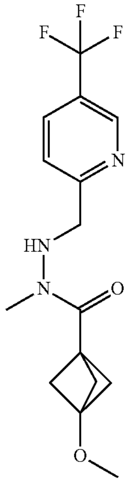

3-methoxy-N-methyl-N'-[[5-(trifluoromethyl)-2-pyridyl]methyl]bicyclo[1.1.1]pentane-1-carbohydrazide (Bc-11). Prepared using general procedure III-B using methylhydrazide, 5-(trifluoromethyl)picolinaldehyde and 3-methoxybicyclo[1.1.1]pentane-1-carboxylic acid. ES/MS: m/z=330.2 [M+H]$^+$.

Bc-12

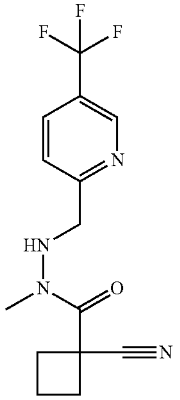

1-cyano-N-methyl-N'-[[5-(trifluoromethyl)-2-pyridyl]methyl]cyclobutanecarbohydrazide (Bc-12). Prepared using general procedure III-B using methylhydrazide, 5-(trifluoromethyl)picolinaldehyde and 1-cyanocyclobutanecarboxylic acid. ES/MS: m/z=313.2 [M+H]$^+$.

Bc-13

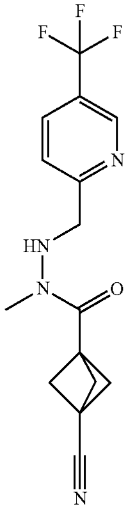

3-cyano-N-methyl-N'-[[5-(trifluoromethyl)-2-pyridyl]methyl]bicyclo[1.1.1]pentane-1-carbohydrazide (Bc-13). Prepared using general procedure III-B using methylhydrazide, 5-(trifluoromethyl)picolinaldehyde and 3-cyanobicyclo[1.1.1]pentane-1-carboxylic acid. ES/MS: m/z=325.2 [M+H]$^+$.

Bc-14

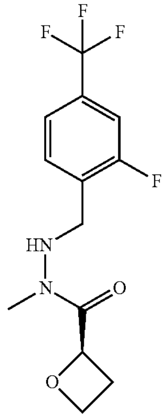

(2R)—N'-[[2-fluoro-4-(trifluoromethyl)phenyl]methyl]-N-methyl-oxetane-2-carbohydrazide (Bc-14). Prepared using general procedure III-B using methylhydrazide, 2-fluoro-4-(trifluoromethyl)benzaldehyde and (2R)-oxetane-2-carboxylic acid. ES/MS: m/z=307.2 [M+H]$^+$.

Bc-15

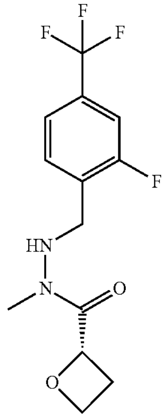

(2S)—N'-[[2-fluoro-4-(trifluoromethyl)phenyl]methyl]-N-methyl-oxetane-2-carbohydrazide (Bc-15). Prepared using general procedure III-B using methylhydrazide, 2-fluoro-4-(trifluoromethyl)benzaldehyde and (2S)-oxetane-2-carboxylic acid. ES/MS: m/z=307.2 [M+H]$^+$.

Bc-16

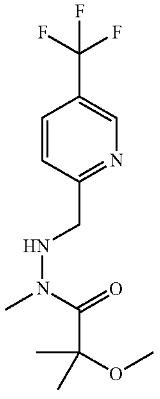

2-methoxy-N,2-dimethyl-N'-[[5-(trifluoromethyl)-2-pyridyl]methyl]propanehydrazide (Bc-16). Prepared using general procedure III-B using methylhydrazide, 5-(trifluoromethyl)picolinaldehyde and 2-methoxy-2-methyl-propanoic acid. ES/MS: m/z=306.2 [M+H]$^+$.

Bc-17

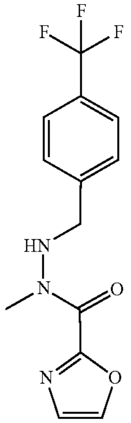

N-methyl-N'-(4-(trifluoromethyl)benzyl)oxazole-2-carbohydrazide (Bc-17). Prepared following general procedure III-B using methylhydrazide, 4-(trifluoromethyl)benzaldehyde and oxazole-2-carboxylic acid. ES/MS: m/z=300.2 [M+H]$^+$.

Bc-18

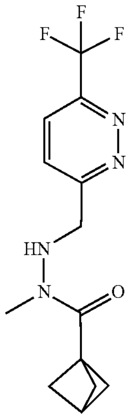

N-methyl-N'-((6-(trifluoromethyl)pyridazin-3-yl)methyl) bicyclo[1.1.1]pentane-1-carbohydrazide (Bc-18). Prepared following general procedure III-B using methylhydrazide, 6-(trifluoromethyl)pyridazine-3-carbaldehyde and bicyclo [1.1.1]pentane-1-carboxylic acid. ES/MS: m/z=301.2 [M+H]$^+$.

Bc-19

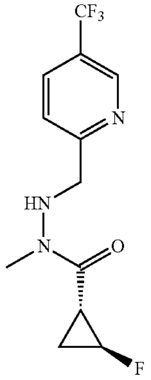

(1R,2S)-2-fluoro-N-methyl-N'-((5-(trifluoromethyl)pyridin-2-yl)methyl)cyclopropane-1-carbohydrazide (Bc-19). Prepared following general procedure III-B using methylhydrazide, 5-(trifluoromethyl)picolinaldehyde and (1R,2S)-2-fluorocyclopropane-1-carboxylic acid. ES/MS: m/z=292.0 [M+H]$^+$.

Bc-20

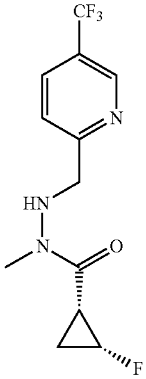

(1R,2R)-2-fluoro-N-methyl-N'-((5-(trifluoromethyl)pyridin-2-yl)methyl)cyclopropane-1-carbohydrazide (Bc-20). Prepared following general procedure III-B using methylhydrazide, 5-(trifluoromethyl)picolinaldehyde and (1R,2R)-2-fluorocyclopropane-1-carboxylic acid. ES/MS: m/z=292.0 [M+H]$^+$.

Bc-21

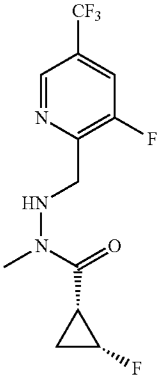

(1R,2R)-2-fluoro-N'-((3-fluoro-5-(trifluoromethyl)pyridin-2-yl)methyl)-N-methylcyclopropane-1-carbohydrazide (Bc-21). Prepared following general procedure III-B using methylhydrazide, 3-fluoro-5-(trifluoromethyl)picolinaldehyde and (1R,2R)-2-fluorocyclopropane-1-carboxylic acid. ES/MS: m/z=400.0 [M+H]$^+$.

Bc-22

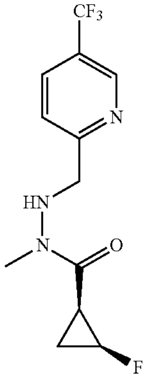

(1S,2S)-2-fluoro-N-methyl-N'-((5-(trifluoromethyl)pyridin-2-yl)methyl)cyclopropane-1-carbohydrazide (Bc-22). Prepared following general procedure III-B using methylhydrazide, 5-(trifluoromethyl)picolinaldehyde and (1S,2S)-2-fluorocyclopropane-1-carboxylic acid. ES/MS: m/z=292.0 $[M+H]^+$.

Bc-23

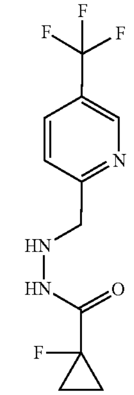

1-fluoro-N'-((5-(trifluoromethyl)pyridin-2-yl)methyl)cyclopropane-1-carbohydrazide (Bc-23). Prepared following general procedure III-B using hydrazine, 5-(trifluoromethyl) picolinaldehyde and 1-fluorocyclopropanecarboxylic acid. ES/MS: m/z=278.1 $[M+H]^+$.

Bc-24

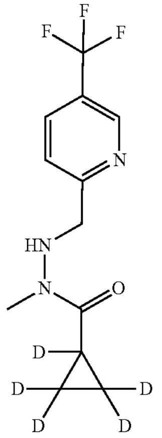

N-methyl-N'-((5-(trifluoromethyl)pyridin-2-yl)methyl) cyclopropane-1-carbohydrazide-d5 (Bc-24). Prepared following general procedure III-B using methylhydrazine, 5-(trifluoromethyl)picolinaldehyde and 1,2,2,3,3-pentadeuteriocyclopropanecarboxylic acid. ES/MS: m/z=279.1 $[M+H]^+$.

Bc-25

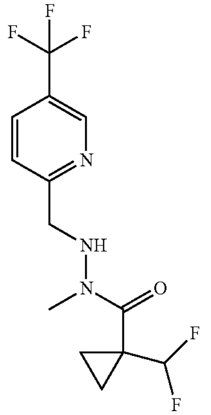

1-(difluoromethyl)-N-methyl-N'-((5-(trifluoromethyl) pyridin-2-yl)methyl)cyclopropane-1-carbohydrazide (Bc-25). Prepared using general procedure III-B using methylhydrazide, 5-(trifluoromethyl) picolinaldehyde, and 1-(difluoromethyl)cyclopropanecarboxylic acid. ES/MS: m/z=324.2 $[M+H]^+$.

Bc-26

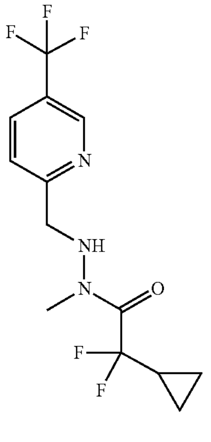

2-cyclopropyl-2,2-difluoro-N-methyl-N'-((5-(trifluoromethyl)pyridin-2-yl)methyl)acetohydrazide (Bc-26). Prepared using general procedure III-B using methylhydrazide, 5-(trifluoromethyl) picolinaldehyde, and 2-cyclopropyl-2,2-difluoro-acetic acid. ES/MS: m/z=324.2 $[M+H]^+$.

General Procedure IV-B for the Synthesis of Intermediate Bd

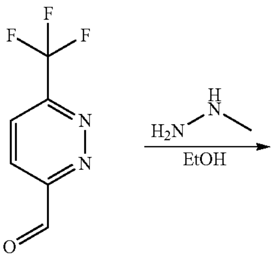

-continued

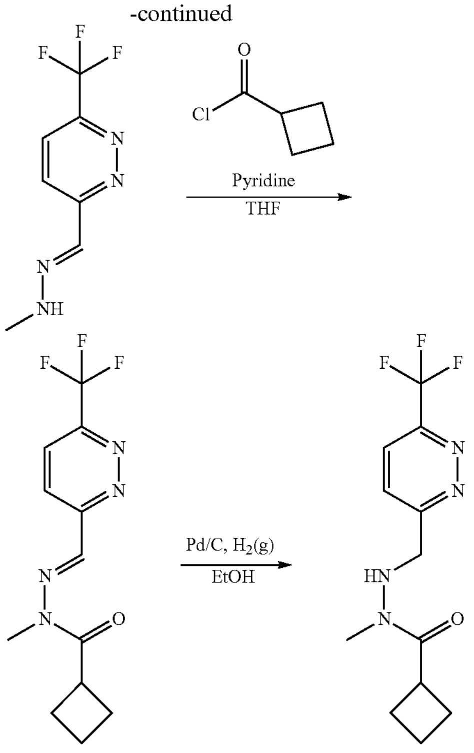

Bd-1

Step 1: (E)-3-((2-methylhydrazineylidene)methyl)-6-(trifluoromethyl)pyridazine. 6-(trifluoromethyl)pyridazine-3-carbaldehyde (500 mg, 2.84 mmol) and methylhydrazide (137 mg, 2.98 mmol) were dissolved in EtOH (10 mL). The mixture was left to stir at room temperature for 1 hour. The solution was reduced under pressure and purified by flash silica gel chromatography to yield the desired imine. ES/MS: m/z=205.2 $[M+H]^+$.

Step 2: (E)-N-methyl-N'-((6-(trifluoromethyl)pyridazin-3-yl)methylene)cyclobutanecarbohydrazide. To a solution of (E)-3-((2-methylhydrazineylidene)methyl)-6-(trifluoromethyl)pyridazine (150 mg, 0.73 mmol) and cyclobutanecarbonyl chloride (96 mg, 0.81 mmol) in THF (3 mL), pyridine (117 mg, 1.48 mmol) was added. The mixture was stirred at room temperature for 12 hours and upon completion by LCMS, dissolved in EtOAc and the organic layer was washed with water 2x and brine. The organic solvent was removed under pressure and the resulting residue was purified by flash silica gel chromatography desired product. ES/MS: m/z=287.2 $[M+H]^+$.

Step 3: N-methyl-N'-((6-(trifluoromethyl)pyridazin-3-yl)methyl)cyclobutanecarbohydrazide (Bd-1). (E)-N-methyl-N'-((6-(trifluoromethyl)pyridazin-3-yl)methylene)cyclobutanecarbohydrazide (97 mg, 0.34 mmol) was dissolved in EtOH (20 mL) and Pd/C (10% w/w, 55 mg) was added. The heterogeneous mixture was stirred vigorously at room temperature under hydrogen gas (1 atm). The reaction was left to stir until LCMS showed full conversion of the imine. The mixture was filtered through a pad of celite and the organic solvent was removed under pressure and purified by flash silica gel chromatography yield the desired product. ES/MS: m/z=289.2 $[M+H]^+$; $^1H$ NMR (400 MHZ, Methanol-$d_4$) δ 8.48-7.79 (m, 2H), 4.40 (d, J=13.8 Hz, 2H), 3.85-3.59 (m, 1H), 3.40-3.23 (m, 1H), 3.10 (s, 1H), 2.23-2.03 (m, 3H), 2.02-1.84 (m, 3H), 1.82-1.63 (m, 1H).

Bd-2

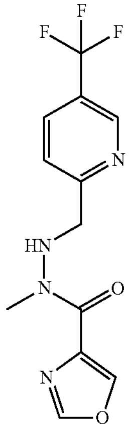

N-methyl-N'-((5-(trifluoromethyl)pyridin-2-yl)methyl)oxazole-4-carbohydrazide (Bd-2). Prepared following the same procedure as IV-B using 5-(trifluoromethyl)picolinaldehyde and oxazole-4-carbonyl chloride. ES/MS: m/z=301.2 $[M+H]^+$.

Bd-3

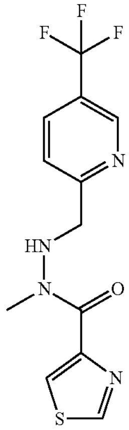

N-methyl-N'-((5-(trifluoromethyl)pyridin-2-yl)methyl)thiazole-4-carbohydrazide (Bd-3). Prepared following the same procedure as IV-B using 5-(trifluoromethyl)picolinaldehyde and thiazole-4-carbonyl chloride. ES/MS: m/z=317.2 $[M+H]^+$.

Bd-4

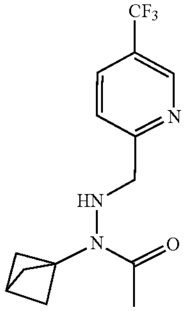

N-(1-bicyclo[1.1.1]pentanyl)-N'-[[5-(trifluoromethyl)-2-pyridyl]methyl]acetohydrazide (Bd-4). Prepared following procedure IV-B using bicyclo[1.1.1]pentan-1-ylhydrazine, 5-(trifluoromethyl)pyridine-2-carbaldehyde and acetyl chloride. ES/MS: m/z=300.2 [M+H]$^+$.

Bd-5

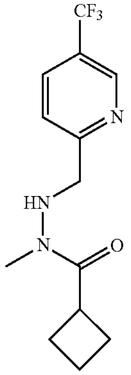

N-methyl-N'-[[5-(trifluoromethyl)-2-pyridyl]methyl]cyclobutanecarbohydrazide (Bd-5). Prepared following procedure IV-B using 5-(trifluoromethyl) picolinaldehyde and cyclobutanecarbonyl chloride. ES/MS: m/z=288.2 [M+H]$^+$.

Bd-6

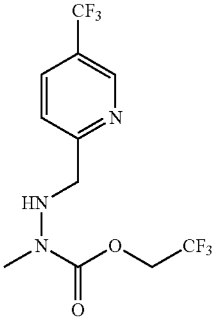

2,2,2-trifluoroethyl 1-methyl-2-((5-(trifluoromethyl)pyridin-2-yl)methyl)hydrazine-1-carboxylate (Bd-6). Prepared following the same procedure as IV-B using 5-(trifluoromethyl) picolinaldehyde and 2,2,2-trifluoroethyl carbonochloridate. ES/MS: m/z=332.2 [M+H]$^+$.

Bd-7

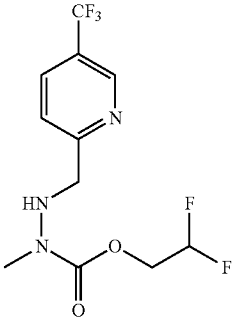

2,2-difluoroethyl 1-methyl-2-((5-(trifluoromethyl)pyridin-2-yl)methyl)hydrazine-1-carboxylate (Bd-7). Prepared following procedure IV-B using 5-(trifluoromethyl) picolinaldehyde and 2,2-difluoroethyl carbonochloridate. ES/MS: m/z=314.2 [M+H]$^+$.

Bd-8

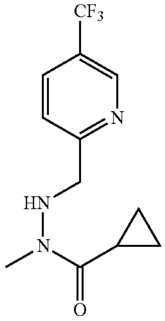

N-methyl-N'-[[5-(trifluoromethyl)-2-pyridyl]methyl]cyclopropanecarbo hydrazide (Bd-8). Prepared following the same procedure as IV-B using 5-(trifluoromethyl) picolinaldehyde and cyclopropanecarbonyl chloride. ES/MS: m/z=274.2 [M+H]$^+$.

Bd-9

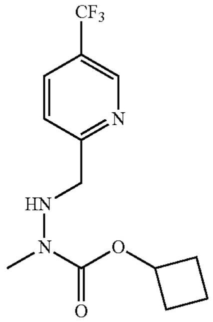

Cyclobutyl 1-methyl-2-((5-(trifluoromethyl)pyridin-2-yl)methyl)hydrazine-1-carboxylate (Bd-9). Prepared following procedure IV-B using 5-(trifluoromethyl) picolinaldehyde and cyclobutyl carbonochloridate. ES/MS: m/z=304.2 [M+H]$^+$.

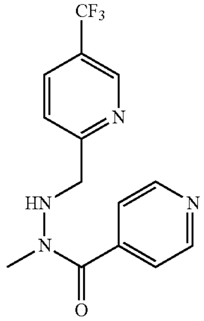 [SMILES: CN(NCc1ccc(C(F)(F)F)cn1)C(=O)c1ccncc1]

N-methyl-N'-((5-(trifluoromethyl)pyridin-2-yl)methyl) isonicotinohydrazide (Bd-10). Prepared following procedure IV-B using 5-(trifluoromethyl) picolinaldehyde and pyridine-4-carbonyl chloride hydrochloride. ES/MS: m/z=311.2 [M+H]$^+$.

Bd-11

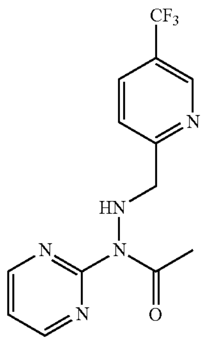

N-pyrimidin-2-yl-N'-[[5-(trifluoromethyl)-2-pyridyl] methyl]acetohydrazide (Bd-11). Prepared following procedure IV-B using 5-(trifluoromethyl) picolinaldehyde and pyrimidin-2-ylhydrazine and acetyl chloride. ES/MS: m/z=312.0 [M+H]$^+$.

Bd-12

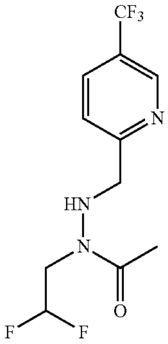

N-(2,2-difluoroethyl)-N'-[[5-(trifluoromethyl)-2-pyridyl] methyl]acetohydrazide (Bd-12). Prepared following procedure IV-B using 5-(trifluoromethyl) picolinaldehyde and 2,2-difluoroethylhydrazine hydrochloride and acetyl chloride. ES/MS: m/z=298.2 [M+H]$^+$.

Bd-13

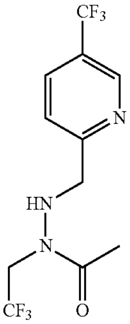

N-(2,2,2-trifluoroethyl)-N'-[[5-(trifluoromethyl)-2-pyridyl]methyl]acetohydrazide (Bd-13). Prepared following procedure as V-B using 5-(trifluoromethyl) picolinaldehyde and 2,2,2-trifluoroethylhydrazine and acetyl chloride. ES/MS: m/z=316.2 [M+H]$^+$.

Bd-14

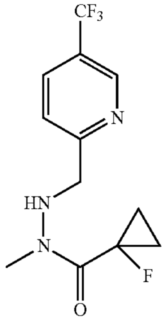

1-fluoro-N-methyl-N'-[[5-(trifluoromethyl)-2-pyridyl] methyl]cyclopropanecarbohydrazide (Bd-14). Prepared following procedure IV-B using 5-(trifluoromethyl) picolinaldehyde and 1-fluorocyclopropanecarbonyl chloride. ES/MS: m/z=292.2 [M+H]$^+$.

Bd-15

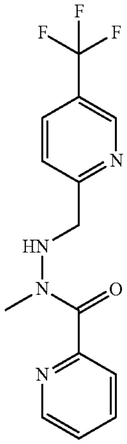

(E)-N-methyl-N'-((5-(trifluoromethyl)pyridin-2-yl)methylene)picolinohydrazide (Bd-15). Prepared following procedure IV-B using 5-(trifluoromethyl) picolinaldehyde and picolinoyl chloride. Triethylamine was used as a base and 1,2-DCE as the solvent in step 2. ES/MS: m/z=311.2 [M+H]$^+$.

Bd-16

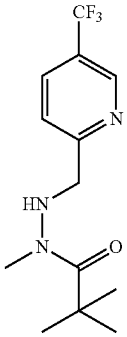

N-methyl-N'-((5-(trifluoromethyl)pyridin-2-yl)methyl) pivalohydrazide (Bd-16). Prepared using general procedure IV-B starting with methylhydrazine, 5-(trifluoromethyl)picolinaldehyde and pivaloyl chloride. ES/MS: m/z=290.0 $[M+H]^+$.

Bd-17

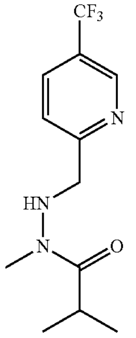

N-methyl-N'-((5-(trifluoromethyl)pyridin-2-yl)methyl) isobutyrohydrazide (Bd-17). Prepared using general procedure IV-B starting with methylhydrazine, 5-(trifluoromethyl)picolinaldehyde and isobutyryl chloride. ES/MS: m/z=276.0 $[M+H]^+$.

Bd-18

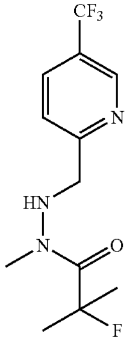

2-fluoro-N,2-dimethyl-N'-((5-(trifluoromethyl)pyridin-2-yl)methyl)propane hydrazide (Bd-18). Prepared using general procedure IV-B starting with methylhydrazine, 5-(trifluoromethyl)picolinaldehyde and 2-fluoro-2-methylpropanoyl chloride. ES/MS: m/z=294.0 $[M+H]^+$.

Bd-19

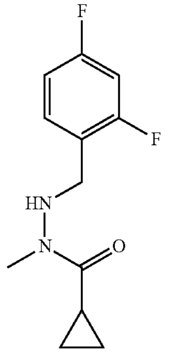

N'-(2,4-difluorobenzyl)-N-methylcyclopropanecarbohydrazide (Bd-19). Prepared using general procedure IV-B starting with methylhydrazine, 2,4-difluorobenzaldehyde and cyclopropanecarbonyl chloride. ES/MS: m/z=241.0 $[M+H]^+$.

Bd-20

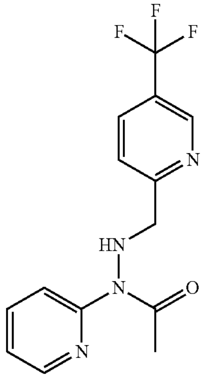

N-(2-pyridyl)-N'-[[5-(trifluoromethyl)-2-pyridyl]methyl] acetohydrazide (Bd-20). Prepared using general procedure IV-B starting with 2-pyridylhydrazine and acetyl chloride. ES/MS: m/z=311.1 $[M+H]^+$.

Bd-21

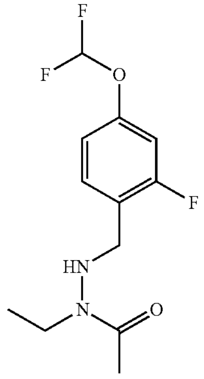

N'-(4-(difluoromethoxy)-2-fluorobenzyl)-N-ethylacetohydrazide (Bd-21). Prepared using general procedure IV-B starting with ethylhydrazine hydrochloride (triethylamine 1 equiv. was added in step 1), 4-(difluoromethoxy)-2-fluorobenzaldehyde and acetyl chloride. ES/MS: m/z=277.0 $[M+H]^+$.

Bd-22

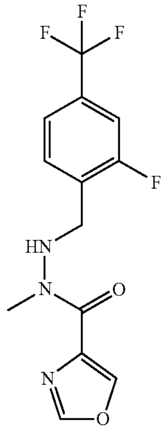

N'-(2-fluoro-4-(trifluoromethyl)benzyl)-N-methyloxazole-2-carbohydrazide (Bd-22). Prepared following the same procedure as IV-B using methylhydrazine, 2-fluoro-4-(trifluoromethyl)benzaldehyde and oxazole-4-carbonyl chloride. ES/MS: m/z=318.2 $[M+H]^+$.

Bd-23

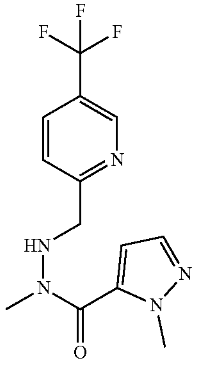

N,1-dimethyl-N'-((5-(trifluoromethyl)pyridin-2-yl)methyl)-1H-pyrazole-5-carbohydrazide (Bd-23). Prepared using general procedure IV-B starting with methylhydrazine, 5-(trifluoromethyl)picolinaldehyde and 1-methyl-1H-pyrazole-5-carbonyl chloride. ES/MS: m/z=312.1 $[M+H]^+$.

Bd-24

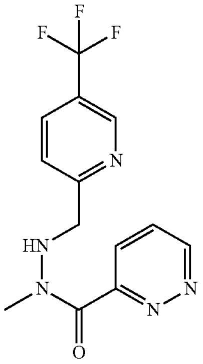

N-methyl-N'-((5-(trifluoromethyl)pyridin-2-yl)methyl)pyridazine-3-carbohydrazide (Bd-24). Prepared using general procedure IV-B starting with methylhydrazine, 5-(trifluoromethyl)picolinaldehyde and pyridazine-3-carbonyl chloride ES/MS: m/z=312.1 $[M+H]^+$.

Bd-25

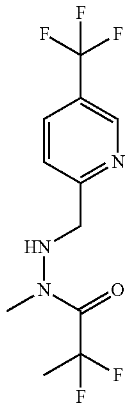

2,2-difluoro-N-methyl-N'-[[5-(trifluoromethyl)-2-pyridyl]methyl]propanehydrazide (Bd-25). Prepared using general procedure IV-B using methylhydrazine, 5-(trifluoromethyl)picolinaldehyde and 2,2-difluoropropanoyl chloride. ES/MS: m/z=298.2 $[M+H]^+$.

Bd-26

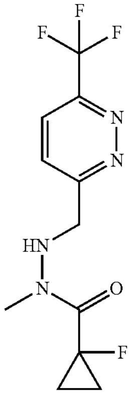

1-fluoro-N-methyl-N'-((6-(trifluoromethyl)pyridazin-3-yl)methyl)cyclopropane-1-carbohydrazide (Bd-26). Prepared using general procedure IV-B using methylhydrazine 6-(trifluoromethyl)pyridazine-3-carbaldehyde and 1-fluorocyclopropanecarbonyl chloride. ES/MS: m/z=293.2 $[M+H]^+$.

Bd-27

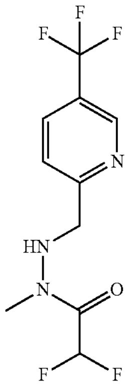

2,2-difluoro-N-methyl-N'-[[5-(trifluoromethyl)-2-pyridyl]methyl]acetohydrazide (Bd-27). Prepared using general procedure IV-B using methylhydrazine, 5-(trifluoromethyl)picolinaldehyde, and 2,2-difluoroacetyl chloride. ES/MS: m/z=284.2 [M+H]$^+$.

Bd-28

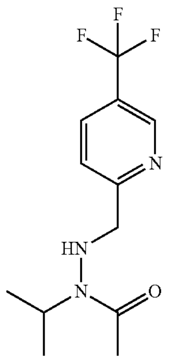

N-isopropyl-N'-[[5-(trifluoromethyl)-2-pyridyl]methyl]acetohydrazide (Bd-28). Prepared using general procedure IV-B starting with isopropyl hydrazine, acetyl chloride and 5-(trifluoromethyl)picolinaldehyde. ES/MS: m/z=276.1 [M+H]$^+$.

Bd-29

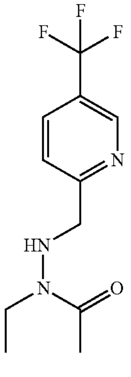

N-ethyl-N'-((5-(trifluoromethyl)pyridin-2-yl)methyl)acetohydrazide (Bd-29). Prepared using general procedure IV-B starting with ethylhydrazine; hydrochloride (triethylamine 1 equivalent was added in step 1), acetyl chloride and 5-(trifluoromethyl)picolinaldehyde. ES/MS: m/z=262.2 [M+H]$^+$.

Bd-30

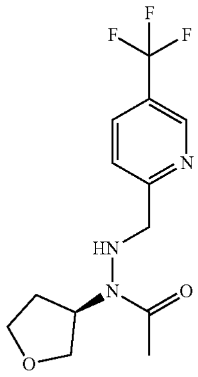

N-[(3R)-tetrahydrofuran-3-yl]-N'-[[5-(trifluoromethyl)-2-pyridyl]methyl]acetohydrazide (Bd-30). Prepared using general procedure IV-B starting with [(3R)-tetrahydrofuran-3-yl]hydrazine; hydrochloride (triethylamine 1 equivalent was added in step 1), acetyl chloride and 5-(trifluoromethyl)picolinaldehyde. ES/MS: m/z=304.2 [M+H]$^+$.

Bd-31

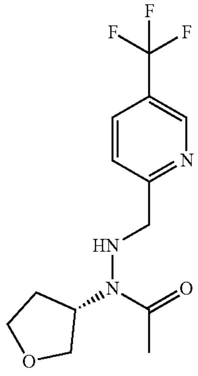

N-[(3S)-tetrahydrofuran-3-yl]-N'-[[5-(trifluoromethyl)-2-pyridyl]methyl]acetohydrazide (Bd-31). Prepared using general procedure IV-B starting with [(3S)-tetrahydrofuran-3-yl]hydrazine; hydrochloride (triethylamine 1 equivalent was added in step 1), acetyl chloride and 5-(trifluoromethyl)picolinaldehyde. ES/MS: m/z=304.2 [M+H]$^+$.

Bd-32

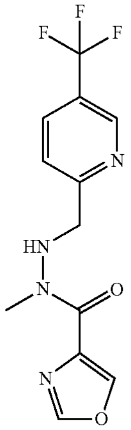

N-methyl-N'-(4-(trifluoromethyl)benzyl)oxazole-4-carbohydrazide (Bd-32). Prepared following the same procedure as IV-B using 4-(trifluoromethyl)benzaldehyde and oxazole-4-carbonyl chloride. ES/MS: m/z=300.2 $[M+H]^+$.

Bd-33

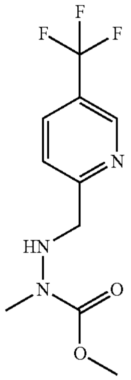

Methyl 1-methyl-2-((5-(trifluoromethyl)pyridin-2-yl)methyl)hydrazine-1-carboxylate (Bd-33). Prepared following the same procedure as IV-B using 5-(trifluoromethyl)picolinaldehyde and methyl carbonochloridate. ES/MS: m/z=262.2 $[M+H]^+$.

Bd-34

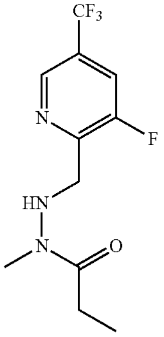

N'-((3-fluoro-5-(trifluoromethyl)pyridin-2-yl)methyl)-N-methylpropionohydrazide (Bd-34). Prepared following the same procedure as IV-B using 3-fluoro-5-(trifluoromethyl)pyridine-2-carbaldehyde and propionyl chloride. ES/MS: m/z=280.0 $[M+H]^+$.

Bd-35

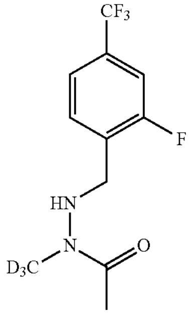

N'-(2-fluoro-4-(trifluoromethyl)benzyl)-N-(methyl-d3)acetohydrazide (Bd-35). Prepared using general procedure IV-B starting with 2-fluoro-4-(trifluoromethyl)benzaldehyde and trideuteriomethylhydrazine dihydrochloride. ES/MS: m/z=268.0 $[M+H]^+$.

Bd-36

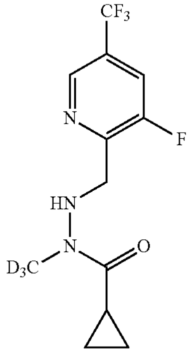

N'-((3-fluoro-5-(trifluoromethyl)pyridin-2-yl)methyl)-N-(methyl-d3)cyclopropanecarbohydrazide (Bd-36). Prepared using general procedure IV-B starting with 3-fluoro-5-(trifluoromethyl)picolinaldehyde and trideuteriomethylhydrazine dihydrochloride. ES/MS: m/z=295.0 $[M+H]^+$.

Bd-37

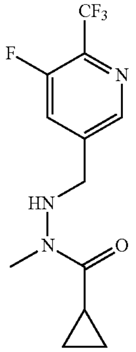

N'-((5-fluoro-6-(trifluoromethyl)pyridin-3-yl)methyl)-N-methylcyclopropanecarbohydrazide (Bd-37). Prepared using general procedure IV-B starting with 5-fluoro-6-(trifluoromethyl)pyridine-3-carbaldehyde and cyclopropanecarbonyl chloride. ES/MS: m/z=292.0 [M+H]+.

Bd-38

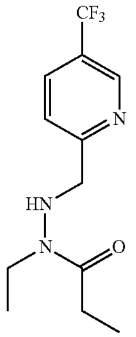

N-ethyl-N'-((5-(trifluoromethyl)pyridin-2-yl)methyl)propionohydrazide (Bd-38). Prepared using general procedure IV-B starting with ethylhydrazine, 5-(trifluoromethyl)picolinaldehyde and propanoyl chloride. ES/MS: m/z=276.2 [M+H]+.

Bd-39

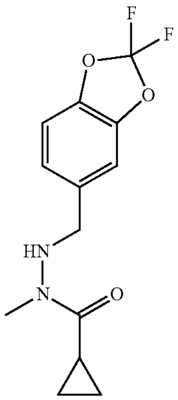

N'-((2,2-difluorobenzo[d][1,3]dioxol-5-yl)methyl)-N-methylcyclopropanecarbohydrazide (Bd-39). Prepared using general procedure IV-B starting with methylhydrazine, 2,2-difluoro-1,3-benzodioxole-5-carbaldehyde and cyclopropanecarbonyl chloride. ES/MS: m/z=285.2 [M+H]+.

Bd-40

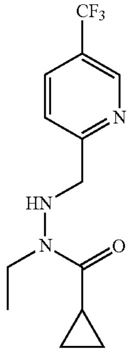

N-ethyl-N'-((5-(trifluoromethyl)pyridin-2-yl)methyl)cyclopropanecarbohydrazide (Bd-40). Prepared using general procedure IV-B starting with ethylhydrazine, 5-(trifluoromethyl)picolinaldehyde and cyclopropanecarbonyl chloride. ES/MS: m/z=288.2 [M+H]+.

Bd-41

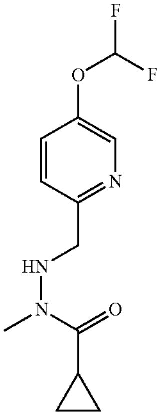

N'-((5-(difluoromethoxy)pyridin-2-yl)methyl)-N-methylcyclopropanecarbohydrazide (Bd-41). Prepared using general procedure IV-B starting with methylhydrazine, 5-(difluoromethoxy)pyridine-2-carbaldehyde and cyclopropanecarbonyl chloride. ES/MS: m/z=272.2 [M+H]+.

Bd-42

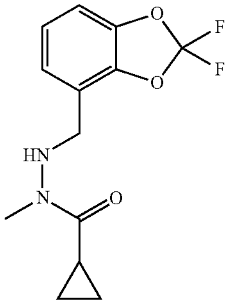

N'-((2,2-difluorobenzo[d][1,3]dioxol-4-yl)methyl)-N-methylcyclopropanecarbohydrazide (Bd-42). Prepared using general procedure IV-B starting with methylhydrazine, 2,2-difluoro-1,3-benzodioxole-4-carbaldehyde and cyclopropanecarbonyl chloride. ES/MS: m/z=285.2 [M+H]+.

Bd-43

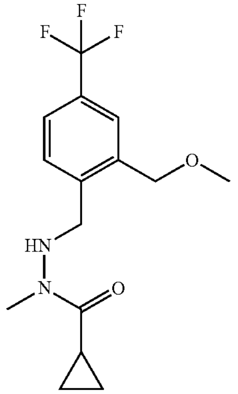

N'-(2-(methoxymethyl)-4-(trifluoromethyl)benzyl)-N-methylcyclopropanecarbohydrazide (Bd-43). Prepared using general procedure IV-B starting with methylhydrazine, 2-(methoxymethyl)-4-(trifluoromethyl)benzaldehyde and cyclopropanecarbonyl chloride. ES/MS: m/z=317.2 $[M+H]^+$.

Bd-44

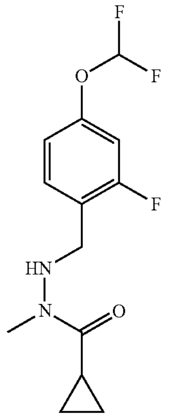

N'-(4-(difluoromethoxy)-2-fluorobenzyl)-N-methylcyclopropanecarbohydrazide (Bd-44). Prepared using general procedure IV-B starting with methylhydrazine, 4-(difluoromethoxy)-2-fluoro-benzaldehyde and cyclopropanecarbonyl chloride. ES/MS: m/z=289.2 $[M+H]^+$.

Bd-45

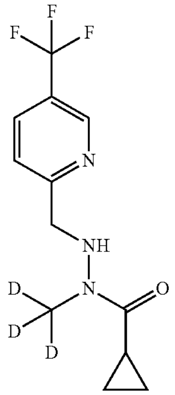

N-(methyl-d3)-N'-((5-(trifluoromethyl)pyridin-2-yl)methyl)cyclopropanecarbohydrazide (Bd-45). Prepared using general procedure IV-B using 5-(trifluoromethyl)picolinaldehyde, trideuteriomethylhydrazine dihydrochloride and cyclopropanecarbonyl chloride. ES/MS: m/z=277.2 $[M+H]^+$.

Bd-46

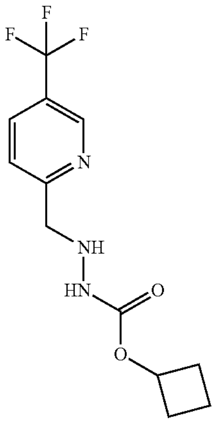

cyclobutyl 2-((5-(trifluoromethyl)pyridin-2-yl)methyl)hydrazine-1-carboxylate (Bd-46). Prepared using general procedure IV-B using 5-(trifluoromethyl) picolinaldehyde, hydrazine monohydrate and cyclobutyl carbonochloridate. ES/MS: m/z=290.2 $[M+H]^+$.

Bd-47

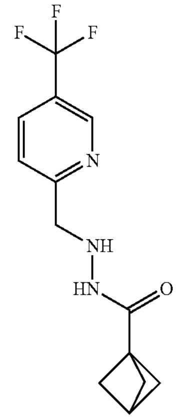

N'-((5-(trifluoromethyl)pyridin-2-yl)methyl)bicyclo[1.1.1]pentane-1-carbohydrazide (Bd-47). Prepared using general procedure IV-B using 5-(trifluoromethyl) picolinaldehyde, hydrazine monohydrate and bicyclo[1.1.1]pentane-1-carbonyl chloride. ES/MS: m/z=286.2 [M+H]$^+$.

Bd-48

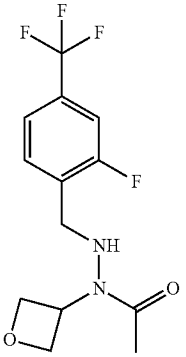

N'-(2-fluoro-4-(trifluoromethyl)benzyl)-N-(oxetan-3-yl)acetohydrazide (Bd-48). Prepared using general procedure IV-B using 2-fluoro-4-(trifluoromethyl)benzaldehyde, oxalic acid oxetan-3-ylhydrazine and acetyl chloride. ES/MS: m/z=307.2 [M+H]$^+$.

Bd-49

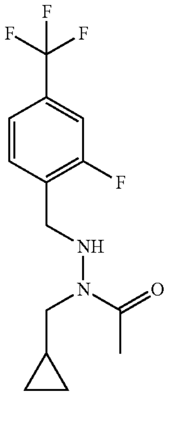

N-(cyclopropylmethyl)-N'-((5-(trifluoromethyl)pyridin-2-yl)methyl)acetohydrazide (Bd-49). Prepared using general procedure IV-B using 5-(trifluoromethyl) picolinaldehyde, cyclopropylmethylhydrazine dihydrochloride and, and acetyl chloride. ES/MS: m/z=288.2 [M+H]$^+$.

Bd-50

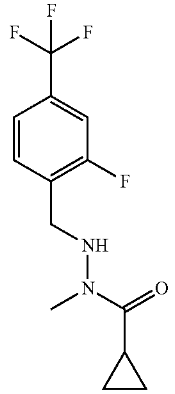

N'-(2-fluoro-4-(trifluoromethyl)benzyl)-N-methylcyclopropanecarbohydrazide (Bd-50). Prepared using general procedure IV-B using 2-fluoro-4-(trifluoromethyl)benzaldehyde, methylhydrazine and acetyl chloride. ES/MS: m/z=291.2 [M+H]$^+$.

Bd-51

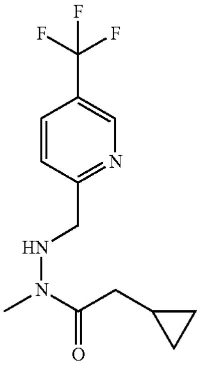

2-cyclopropyl-N-methyl-N'-((5-(trifluoromethyl)pyridin-2-yl)methyl)acetohydrazide (Bd-51). Prepared using general procedure IV-B starting with 2-cyclopropylacetyl chloride and 5-(trifluoromethyl)nicotinaldehyde. ES/MS: m/z=288.1 [M+H]$^+$.

Bd-52

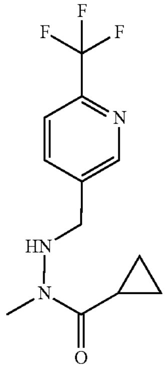

N-methyl-N'-((6-(trifluoromethyl)pyridin-3-yl)methyl) cyclopropanecarbohydrazide (Bd-52). Prepared using general procedure IV-B starting with cyclopropanecarbonyl chloride and 6-(trifluoromethyl)nicotinaldehyde. ES/MS: m/z=274.2 $[M+H]^+$.

General Procedure V-B for the Synthesis of Intermediates Be

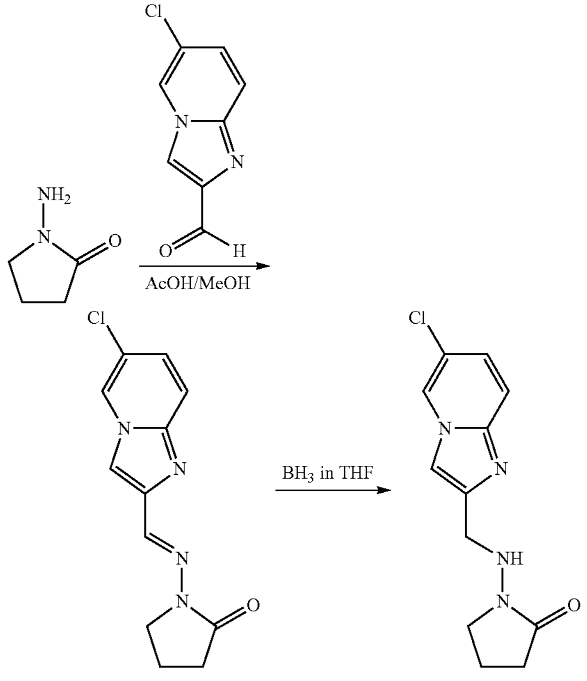

Be-1

Step 1: (E)-1-(((6-chloroimidazo[1,2-a]pyridin-2-yl) methylene)amino)pyrrolidin-2-one. To a solution of 1-aminopyrrolidin-2-one hydrochloride (90 mg, 0.51 mmol) and 6-chloro-1-methyl-benzimidazole-2-carbaldehyde (77 mg, 0.57 mmol) in MeOH was added AcOH (88 mg, 1.5 mmol). The mixture was stirred at 25 °C for 2h. The reaction mixture was concentrated under reduced pressure to remove the solvent to give a residue. The residue was used in the next step without further purification. ES/MS: m/z=263.1 $[M+H]^+$.

Step 2: 1-(((6-chloroimidazo[1,2-a]pyridin-2-yl)methyl) amino)pyrrolidin-2-one (Be-1). The crude residue was dissolved in THF and cooled to 0 °C. Then a solution of BH3 in THF (1 M, 1.5 mL) was added dropwise at 0 °C. The mixture was stirred at 0 °C for 1h. The reaction mixture was quenched by addition of MeOH and 1M HCl at 0 °C and stirred at rt for 1 h. The reaction mixture was concentrated under reduced pressure to remove the solvent. The crude mixture was purified by chromatography (DCM/MeOH) to provide the titled compound as a white solid (53 mg, 41%). ES/MS: m/z=265.1 $[M+H]^+$. $^1$H NMR (400 MHZ, Methanol-$d_4$) δ 8.98 (ddd, J=4.2, 2.0, 0.9 Hz, 1H), 8.22-8.06 (m, 1H), 8.06-7.83 (m, 2H), 4.32 (d, J=0.9 Hz, 2H), 3.64-3.44 (m, 2H), 2.47-2.22 (m, 2H), 2.03 (dq, J=8.9, 7.3 Hz, 2H).

Be-2

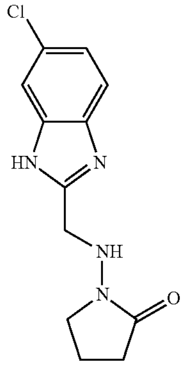

1-[(6-chloro-1H-benzimidazol-2-yl)methylamino]pyrrolidin-2-one (Be-2) Prepared using general procedure V-B starting with 6-chloro-1-methyl-benzimidazole-2-carbaldehyde and 1-aminopyrrolidin-2-one. ES/MS: m/z=265.1 $[M+H]^+$.

Be-3

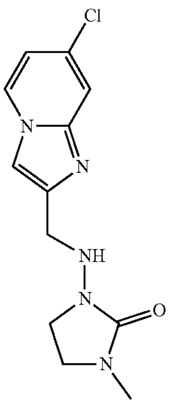

1-(((7-chloroimidazo[1,2-a]pyridin-2-yl)methyl)amino)-3-methylimidazolidin-2-one (Be-3). Prepared using general procedure V-B starting with 7-chloroimidazo[1,2-a]pyridine-2-carbaldehyde and 1-amino-3-methyl-imidazolidin-2-one. ES/MS: m/z=278.1 $[M+H]^+$.

General Procedure VI-B for the Synthesis of Intermediate Bf:

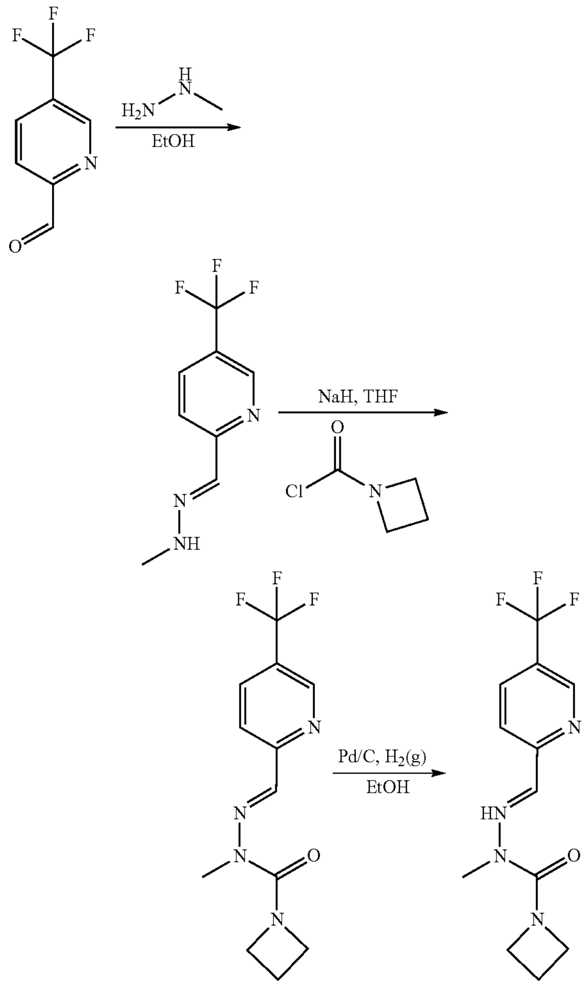

Bf-1

Step 1: (E)-2-((2-methylhydrazineylidene)methyl)-5-(trifluoromethyl)pyridine. 5-(trifluoromethyl)picolinaldehyde (1.50 g, 8.57 mmol) and methylhydrazide (0.41 g, 9.0 mmol) were dissolved in EtOH (30 mL). The mixture was left to stir at room temperature for 1 hour. The solution was reduced under pressure and purified by flash silica gel chromatography to yield the desired product as a white solid (1.54 g, 89%). ES/MS: m/z=204.0 $[M+H]^+$.

Step 2: (E)-N-methyl-N'-((5-(trifluoromethyl)pyridin-2-yl)methylene)azetidine-1-carbohydrazide. NaH (57 mg, 1.48 mmol) was slowly added to a solution of (E)-2-((2-methylhydrazineylidene)methyl)-5-(trifluoromethyl)pyridine (150 mg, 0.73 mmol) and azetidine-1-carbonyl chloride (97.1 mg, 0.812 mmol) in THF (3 mL) at 0 °C. The mixture was left to stir for 10 minutes at 0 °C, then warmed to room temperature. The mixture was stirred at room temperature and upon completion as judged by LCMS analysis; EtOAc and water were added and the organic layer was washed with water twice and brine. The organic solvent was removed under pressure and was used in the next step without further purification. ES/MS: 287.2 $[M+H]^+$.

Step 3: N-methyl-N'-((5-(trifluoromethyl)pyridin-2-yl)methyl)azetidine-1-carbohydrazide (E)-N-methyl-N'-((5-(trifluoromethyl)pyridin-2-yl)methylene)azetidine-1-carbohydrazide (Bf-1). (E)-N-methyl-N'-((5-(trifluoromethyl)pyridin-2-yl)methylene)azetidine-1-carbohydrazide (120 mg, 0.36 mmol) was dissolved in EtOH (20 mL) and Pd/C (10% w/w, 58 mg) was added. The heterogeneous mixture was stirred vigorously at room temperature under hydrogen gas (1 atm). The reaction was stirred until LCMS showed full conversion. The mixture was filtered through a pad of celite and the organic solution was reduced under pressure and purified by flash silica gel chromatography. The fractions were collected and reduced under pressure to yield the desired product (62 mg, 43%). ES/MS: 289.2 $[M+H]^+$. $^1$H NMR (400 MHz, $CDCl_3$) δ 8.95-8.78 (m, 1H), 8.03-7.84 (m, 2H), 7.66 (s, 1H), 4.25-3.78 (m, 4H), 3.42 (s, 2H), 3.04 (s, 1H), 2.41-2.07 (m, 3H).

Bf-2

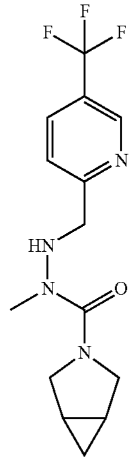

N-methyl-N'-((5-(trifluoromethyl)pyridin-2-yl)methyl)-3-azabicyclo[3.1.0]hexane-3-carbohydrazide (Bf-2). Prepared following procedure VI-B using methylhydrazide, 5-(trifluoromethyl)picolinaldehyde and 3-azabicyclo[3.1.0]hexane-3-carbonyl chloride in replacement of azetidine-1-carbonyl chloride. ES/MS: m/z=315.2 $[M+H]^+$.

Bf-3

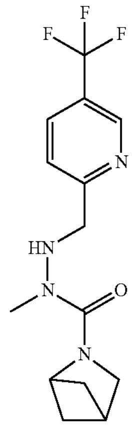

N-methyl-N'-((5-(trifluoromethyl)pyridin-2-yl)methyl)-3-azabicyclo[3.1.0]hexane-3-carbohydrazide (Bf-3). Prepared following procedure VI-B using methylhydrazide, 5-(trifluoromethyl)picolinaldehyde and 2-azabicyclo[2.1.1]

hexane-2-carbonyl chloride in replacement of azetidine-1-carbonyl chloride. ES/MS: m/z=315.2 $[M+H]^+$.

Bf-4

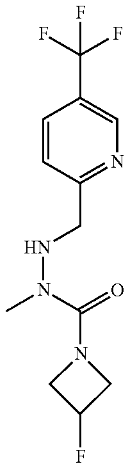

3-fluoro-N-methyl-N'-((5-(trifluoromethyl)pyridin-2-yl)methyl)azetidine-1-carbohydrazide (Bf-4). Prepared following procedure VI-B using methylhydrazide, 5-(trifluoromethyl)picolinaldehyde and 3-fluoroazetidine-1-carbonyl chloride. ES/MS: m/z=307.2 $[M+H]^+$.

Bf-5

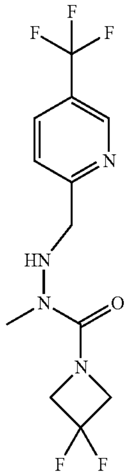

3,3-difluoro-N-methyl-N'-((5-(trifluoromethyl)pyridin-2-yl)methyl)azetidine-1-carbohydrazide (Bf-5). Prepared following procedure VI-B using methylhydrazide, 5-(trifluoromethyl)picolinaldehyde and 3,3-difluoroazetidine-1-carbonyl chloride. ES/MS: m/z=325.2 $[M+H]^+$.

General Procedure VII-B for the Synthesis of Intermediate Bg

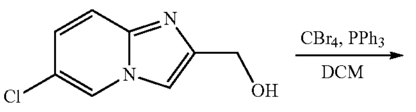

-continued

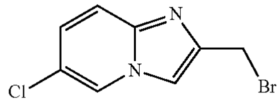

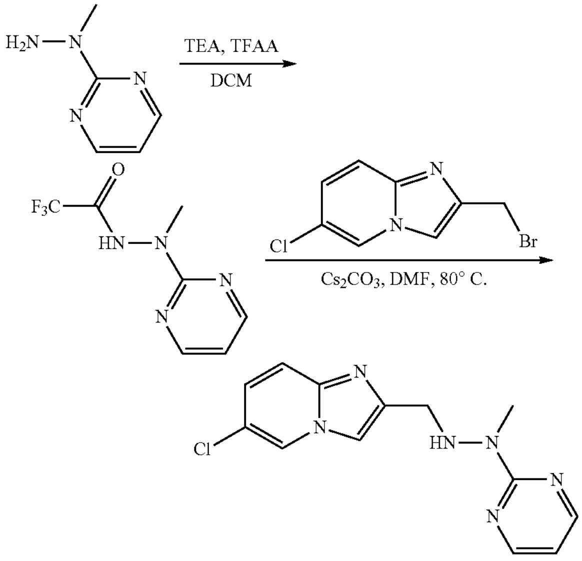

Bg-1

Step 1: 2-(bromomethyl)-6-chloroimidazo[1,2-a]pyridine. To a solution of (6-chloroimidazo[1,2-a]pyridin-2-yl)methanol (1 g, 5.4 mmol, 1 eq) in DCM (20 mL) was added $CBr_4$ (3.6 g, 10.9 mmol, 2 eq) and $PPh_3$ (2.8 g, 10.9 mmol, 2 eq) under $N_2$ atmosphere. The mixture was stirred at 25 °C for 12 hr. LC-MS showed desired compound was detected. The reaction mixture was concentrated under reduced pressure to give a residue. The residue was purified by flash silica gel chromatography (40 g Silica Flash Column, Eluent of 0~20% Ethyl acetate/Petroleum ether gradient @ 30 mL/min) to give 2-(bromomethyl)-6-chloroimidazo[1,2-a]pyridine. $^1H$ NMR (400 MHz, $CDCl_3$) δ 8.06 (s, 1H), 7.54 (s, 1H), 7.48 (d, J=9.5 Hz, 1H), 7.11 (dd, J=2.0, 9.5 Hz, 1H), 4.57 (s, 2H).

Step 2: 1-(difluoro-13-methyl)-N'-methyl-N'-(pyrimidin-2-yl)-12-fluoranecarbohydrazide. To a solution of 1-methyl-1-pyrimidin-2-yl-hydrazine (1 g, 8.0 mmol, 1 eq) in DCM (10 mL) was added TEA (2.4 g, 24.1 mmol, 3.3 mL, 3 eq) and cooled to 0 °C. Then TFAA (1.8 g, 8.8 mmol, 1.2 mL, 1.1 eq) was dropwise added to the solution at 0 °C. The mixture was stirred at 0 °C for 2 hr. LC-MS showed Reactant 1A was consumed completely and desired compound was detected. The mixture was diluted with $NH_4Cl$ (2 M, 22 ml) and extracted with dichloromethane (30 mL×3). The combined organic layers were dried over $Na_2SO_4$, filtered and concentrated under reduced pressure to give a residue. The residue was purified by flash silica gel chromatography (12 g Silica Flash Column, Eluent of 0~15% Ethyl acetate/Petroleum ether gradient @ 20 mL/min) to give 1-(difluoro-13-methyl)-N'-methyl-N'-(pyrimidin-2-yl)-12-fluoranecarbohydrazide. $^1H$ NMR (400 MHz, $CDCl_3$) δ 8.49 (d, J=4.9 Hz, 2H), 6.86 (t, J=5.0 Hz, 1H), 3.50 (s, 3H).

Step 3: 6-chloro-2-((2-methyl-2-(pyrimidin-2-yl)hydrazineyl)methyl)imidazo[1,2-a]pyridine (Bg-1). To a solution of 2,2,2-trifluoro-N'-methyl-N'-pyrimidin-2-yl-acetohydrazide (295.9 mg, 1.3 mmol, 1.1 eq) in DMF (10 mL) was added $Cs_2CO_3$ (1.5 g, 4.8 mmol, 4 eq.) and 2-(bromomethyl)-6-chloro-imidazo[1,2-a]pyridine (300 mg, 1.2 mmol, 1 eq.). The mixture was stirred at 80 °C for 12 hr. LC-MS showed reactant 1B was consumed completely and desired compound was detected. The reaction mixture was diluted with $H_2O$ (10 mL) and extracted with ethyl acetate (10 mL×3). The combined organic layers were washed with brine (10 mL×3), dried over $Na_2SO_4$, filtered and concentrated under reduced pressure to give a residue. The residue was purified by prep-HPLC (column: Waters Xbridge Prep OBD C18 150*40 mm*10 μm; mobile phase: [water ($NH_4HCO_3$)-ACN]; B %: 20%-40%, 8 min) to give 2-[(6-chloroimidazo[1,2-a]pyridin-2-yl)methyl]-1-methyl-1-pyrimidin-2-yl-hydrazine. MS (ESI): m/z=289.2 $[M+H]^+$. $^1H$ NMR (400 MHz, DMSO-$d_6$) δ 8.83-8.79 (m, 1H), 8.42 (d, J=4.6 Hz, 2H), 7.88 (s, 1H), 7.55 (d, J=9.5 Hz, 1H), 7.26 (dd, J=2.1, 9.6 Hz, 1H), 6.67 (t, J=4.7 Hz, 1H), 5.83 (t, J=6.0 Hz, 1H), 4.11 (d, J=5.9 Hz, 2H), 3.20 (s, 3H).

Bg-2

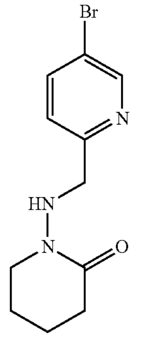

1-(((5-bromopyridin-2-yl)methyl)amino)piperidin-2-one (Bg-2). Prepared following general procedure VII-B starting with 1-aminopiperidin-2-one and 5-bromo-2-(bromomethyl)pyridine; hydrobromide salt. ES/MS: 285.2 $[M+H]^+$. $^1H$ NMR (400 MHZ, Methanol-$d_4$) δ 8.61 (dd, J=2.4, 0.7 Hz, 1H), 7.98 (dd, J=8.3, 2.4 Hz, 1H), 7.47 (d, J=8.3 Hz, 1H), 4.07 (s, 2H), 3.43 (t, J=6.0 Hz, 2H), 2.35 (t, J=6.5 Hz, 2H), 1.92-1.62 (m, 4H).

General Procedure VIII-B for the Synthesis of Intermediates Bh

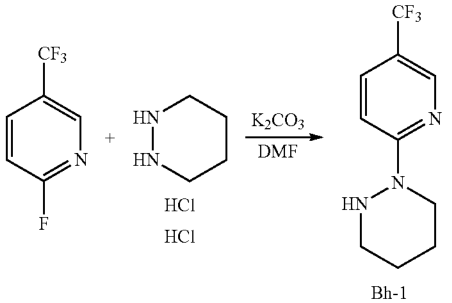

Bh-1

1-[5-(trifluoromethyl)-2-pyridyl]hexahydropyridazine (Bh-1). Hexahydropyridazine dihydrochloride (174 mg, 1.1 mmol) was added to 2-fluoro-5-(trifluoromethyl)pyridine (150 mg, 0.91 mmol) and potassium carbonate (377 mg, 2.7 mmol) in DMF (2.0 mL). The mixture was stirred overnight at 80 °C. The mixture was filtered through Celite. EtOAc and water were added, and the organic layer was washed with water twice and brine. The organic solvent was removed under pressure and was purified by flash silica gel chromatography to yield Bh-1. ES/MS: m/z=232.2 $[M+H]^+$.

Bh-2

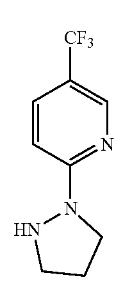

2-pyrazolidin-1-yl-5-(trifluoromethyl)pyridine (Bh-2). Prepared following the same procedure as VIII-B using 2-fluoro-5-(trifluoromethyl)pyridine and pyrazolidine dihydrochloride. ES/MS: m/z=218.2 $[M+H]^+$.

General Procedure IX-B for the Synthesis of Intermediates Bi

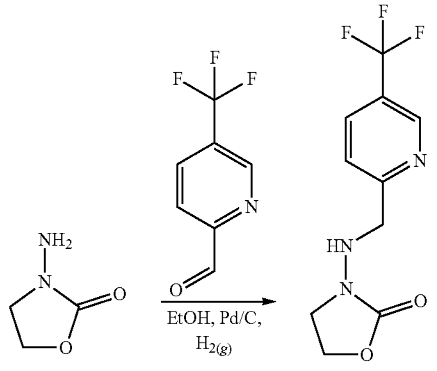

Bi-1

3-(((5-(trifluoromethyl)pyridin-2-yl)methyl)amino)oxazolidin-2-one (Bi-1). To a solution of 5-(trifluoromethyl) picolinaldehyde (0.450 g, 2.57 mmol) and 3-aminooxazolidin-2-one (0.250 g, 2.45 mmol) in EtOH (15 mL), was added Pd/C (10% w/w, 261 mg). The heterogenous mixture was then stirred vigorously at room temperature under an atmosphere of hydrogen (1 atm) until full conversion of the starting imine as determined by LCMS analysis. The crude mixture was then filtered over a pad of celite and evaporated to dryness to afford the desired product (279 mg, 44%). ES/MS: m/z=262.2 $[M+H]^+$. $^1H$ NMR (400 MHz, Methanol-$d_4$) δ 8.83 (dt, J=2.0, 0.9 Hz, 1H), 8.36-8.02 (m, 1H), 7.88-7.66 (m, 1H), 4.34-4.22 (m, 4H), 3.72-3.59 (m, 2H).

Bi-2

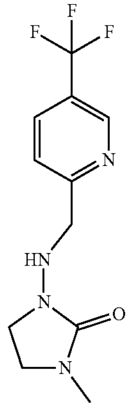

1-methyl-3-(((5-(trifluoromethyl)imidazol-2-yl)methyl) amino)imidazolidine-2-one (Bi-2). Prepared following procedure IX-B using 5-(trifluoromethyl)picolinaldehyde and 1-amino-3-methylimidazolidin-2-one. ES/MS: m/z=275.2 $[M+H]^+$.

Bi-3

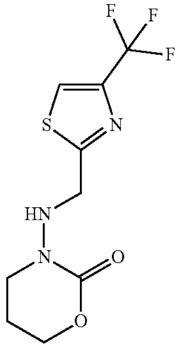

3-(((4-(trifluoromethyl)thiazol-2-yl)methyl)amino)-1,3-oxazinan-2-one (Bi-3). Prepared following procedure IX-B using 4-(trifluoromethyl)thiazole-2-carbaldehyde and 3-amino-1,3-oxazinan-2-one. ES/MS: m/z=282.0 $[M+H]^+$.

Bi-4

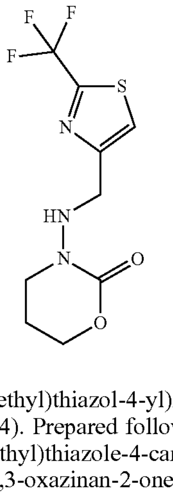

3-(((2-(trifluoromethyl)thiazol-4-yl)methyl)amino)-1,3-oxazinan-2-one (Bi-4). Prepared following procedure IX-B using 2-(trifluoromethyl)thiazole-4-carbaldehyde and intermediates 3-amino-1,3-oxazinan-2-one. ES/MS: m/z=282.0 $[M+H]^+$.

Bi-5

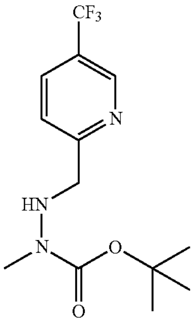

Tert-butyl N-methyl-N-[[5-(trifluoromethyl)-2-pyridyl] methylamino]carbamate (Bi-5). Prepared following procedure IX-B using tert-butyl N-amino-N-methyl-carbamate and 5-(trifluoromethyl)pyridine-2-carbaldehyde. ES/MS: m/z=306.2 $[M+H]^+$.

Bi-6

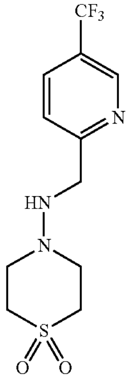

1,1-dioxo-N-[[5-(trifluoromethyl)-2-pyridyl]methyl]-1,4-thiazinan-4-amine (Bi-6). Prepared following procedure IX-B using 1,1-dioxo-1,4-thiazinan-4-amine and 5-(trifluoromethyl)pyridine-2-carbaldehyde. ES/MS: m/z=310.0 $[M+H]^+$.

Bi-7

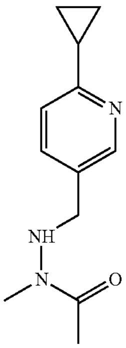

N'-((6-cyclopropylpyridin-3-yl)methyl)-N-methylacetohydrazide (Bi-7). Prepared following procedure IX-B using 6-cyclopropylnicotinaldehyde and N-methylacetohydrazide. ES/MS: m/z=220.2 $[M+H]^+$.

Bi-8

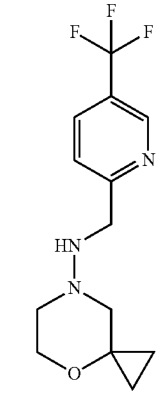

N-((5-(trifluoromethyl)pyridin-2-yl)methyl)-4-oxa-7-azaspiro[2.5]octan-7-amine (Bi-8). Prepared following procedure IX-B using 4-oxa-7-azaspiro[2.5]octan-7-amine Ab-1 and 5-(trifluoromethyl)pyridine-2-carbaldehyde. ES/MS: m/z=288.2 $[M+H]^+$.

Bi-9

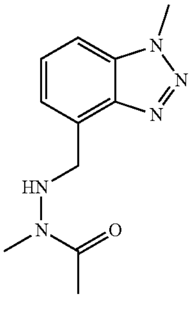

N-methyl-N'-((1-methyl-1H-benzo[d][1,2,3]triazol-4-yl)methyl)acetohydrazide (Bi-9). Prepared following procedure IX-B using N-methylacetohydrazide and 1-methylbenzotriazole-4-carbaldehyde. ES/MS: m/z=234.2 $[M+H]^+$.

Bi-10

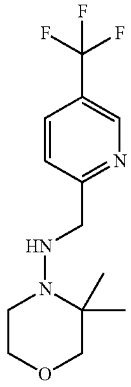

3,3-dimethyl-N-((5-(trifluoromethyl)pyridin-2-yl)methyl)morpholin-4-amine (Bi-10). Prepared following procedure IX-B using 3,3-dimethylmorpholin-4-amine Ab-2 and 5-(trifluoromethyl)pyridine-2-carbaldehyde. ES/MS: m/z=290.2 $[M+H]^+$.

Bi-11

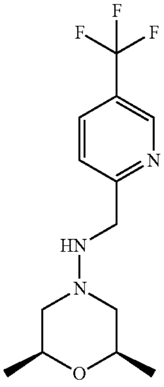

(2S,6R)-2,6-dimethyl-N-((5-(trifluoromethyl)pyridin-2-yl)methyl)morpholin-4-amine (Bi-11). Prepared following procedure IX-B using (2S,6R)-2,6-dimethylmorpholin-4-amine Ab-3 and 5-(trifluoromethyl)pyridine-2-carbaldehyde. ES/MS: m/z=290.2 $[M+H]^+$.

Bi-12

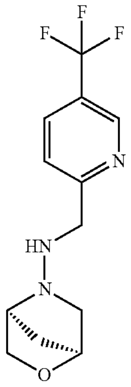

(1S,4S)—N-((5-(trifluoromethyl)pyridin-2-yl)methyl)-2-oxa-5-azabicyclo[2.2.1]heptan-5-amine (Bi-12). Prepared following procedure IX-B using (1S,4S)-2-oxa-5-azabicyclo[2.2.1]heptan-5-amine Ab-4 and 5-(trifluoromethyl)pyridine-2-carbaldehyde. ES/MS: m/z=274.2 $[M+H]^+$.

Bi-13

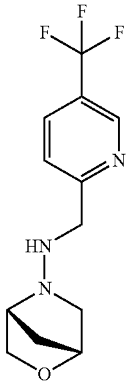

(1R,4R)—N-((5-(trifluoromethyl)pyridin-2-yl)methyl)-2-oxa-5-azabicyclo[2.2.1]heptan-5-amine (Bi-13). Prepared following procedure IX-B using (1R,4R)-2-oxa-5-azabicyclo[2.2.1]heptan-5-amine Ab-5 and 5-(trifluoromethyl)pyridine-2-carbaldehyde. ES/MS: m/z=274.2 [M+H]$^+$.

Bi-14

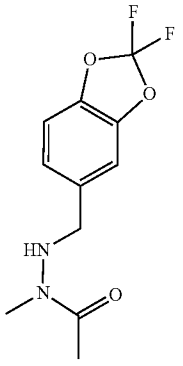

N'-((2,2-difluorobenzo[d][1,3]dioxol-5-yl)methyl)-N-methylacetohydrazide (Bi-14). Prepared following procedure IX-B using N-methylacetohydrazide and 2,2-difluoro-1,3-benzodioxole-5-carbaldehyde. ES/MS: m/z=259.2 [M+H]$^+$.

Bi-15

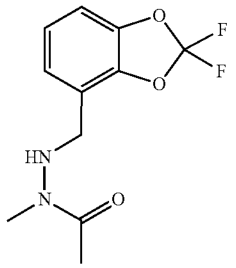

N'-((2,2-difluorobenzo[d][1,3]dioxol-4-yl)methyl)-N-methylacetohydrazide (Bi-15). Prepared following procedure IX-B using N-methylacetohydrazide and 2,2-difluoro-1,3-benzodioxole-4-carbaldehyde. ES/MS: m/z=259.2 [M+H]$^+$.

Bi-16

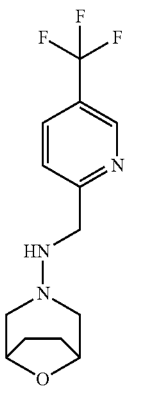

(1R,5S)—N-((5-(trifluoromethyl)pyridin-2-yl)methyl)-8-oxa-3-azabicyclo[3.2.1]octan-3-amine (Bi-16). Prepared following procedure IX-B using (1R,5S)-8-oxa-3-azabicyclo[3.2.1]octan-3-amine and 5-(trifluoromethyl)pyridine-2-carbaldehyde. ES/MS: m/z=288.1 [M+H]$^+$.

Bi-17

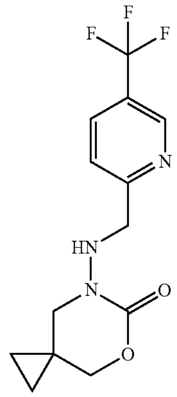

7-(((5-(trifluoromethyl)pyridin-2-yl)methyl)amino)-5-oxa-7-azaspiro[2.5]octan-6-one (Bi-17). Prepared following procedure IX-B using 7-amino-5-oxa-7-azaspiro[2.5]octan-6-one Ac-1 and 5-(trifluoromethyl)pyridine-2-carbaldehyde. ES/MS: m/z=302.2 [M+H]$^+$. $^1$H NMR (DMSO-$d_6$, 400 MHZ) § 8.90 (s, 1H), 8.18 (dd, 1H, J=2.3, 8.3 Hz), 7.70 (d, 1H, J=8.3 Hz), 5.92 (t, 1H, J=5.5 Hz), 4.17 (d, 2H, J=5.5 Hz), 3.90 (s, 2H), 3.20 (s, 2H), 0.6-0.6 (m, 2H), 0.5-0.6 (m, 2H).

Bi-18

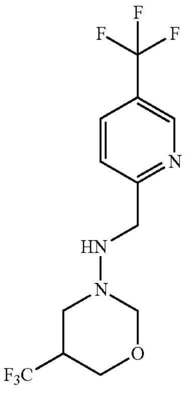

2-(trifluoromethyl)-N-((5-(trifluoromethyl)pyridin-2-yl)methyl)morpholin-4-amine (Bi-18). Prepared following procedure IX-B using 2-(trifluoromethyl)morpholin-4-amine Ab-6 and 5-(trifluoromethyl)pyridine-2-carbaldehyde. ES/MS: m/z=330.2 [M+H]$^+$.

Bi-19

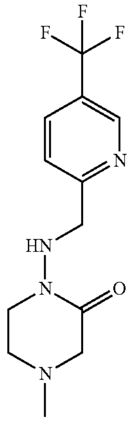

4-methyl-1-(((5-(trifluoromethyl)pyridin-2-yl)methyl)amino)piperazin-2-one (Bi-19). Prepared following procedure IX-B using 1-amino-4-methylpiperazin-2-one Aa-8 and 5-(trifluoromethyl)pyridine-2-carbaldehyde. ES/MS: m/z=289.1 $[M+H]^+$. $^1H$ NMR (400 MHZ, DMSO-$d_6$) § 8.89 (s, 1H), 8.18 (dd, J=2.3, 8.3 Hz, 1H), 7.72 (d, J=8.3 Hz, 1H), 6.29 (t, J=6.2 Hz, 1H), 4.13 (d, J=6.1 Hz, 2H), 3.32 (br s, 2H), 2.95 (s, 2H), 2.57 (t, J=5.5 Hz, 2H), 2.19 (s, 3H).

Bi-20

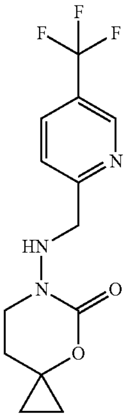

6-(((5-(trifluoromethyl)pyridin-2-yl)methyl)amino)-4-oxa-6-azaspiro[2.5]octan-5-one (Bi-20). Prepared following procedure IX-B using 6-amino-4-oxa-6-azaspiro[2.5]octan-5-one Aa-9 and 5-(trifluoromethyl)pyridine-2-carbaldehyde. ES/MS: m/z=302.1 $[M+H]^+$. $^1H$ NMR (400 MHz, DMSO-$d_6$) δ 8.90 (d, J=0.9 Hz, 1H), 8.20 (dd, J=2.1, 8.3 Hz, 1H), 7.73 (d, J=8.3 Hz, 1H), 5.97 (t, J=5.5 Hz, 1H), 4.18 (d, J=5.5 Hz, 2H), 3.39 (t, J=6.2 Hz, 2H), 1.92 (t, J=6.2 Hz, 2H), 0.91-0.80 (m, 2H), 0.67-0.57 (m, 2H).

Bi-21

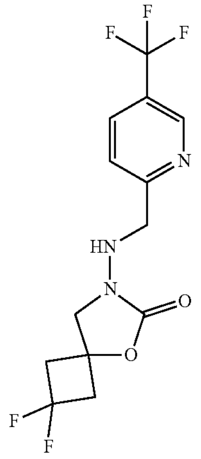

2,2-difluoro-7-(((5-(trifluoromethyl)pyridin-2-yl)methyl)amino)-5-oxa-7-azaspiro[3.4]octan-6-one (Bi-21). Prepared following procedure IX-B using 7-amino-2,2-difluoro-5-oxa-7-azaspiro[3.4]octan-6-one Aa-10 and 5-(trifluoromethyl)pyridine-2-carbaldehyde. ES/MS: m/z=338.1 $[M+H]^+$. $^1H$ NMR (400 MHz, DMSO-$d_6$) δ 8.88 (s, 1H), 8.27-8.15 (m, 1H), 7.80 (d, J=8.1 Hz, 1H), 5.74 (t, J=4.4 Hz, 1H), 4.18 (d, J=4.4 Hz, 2H), 3.75 (s, 2H), 3.03-2.93 (m, 4H) MS (ESI): m/z=338.1 $[M+H]^+$.

General Procedure X-B for the Synthesis of Intermediates Bj

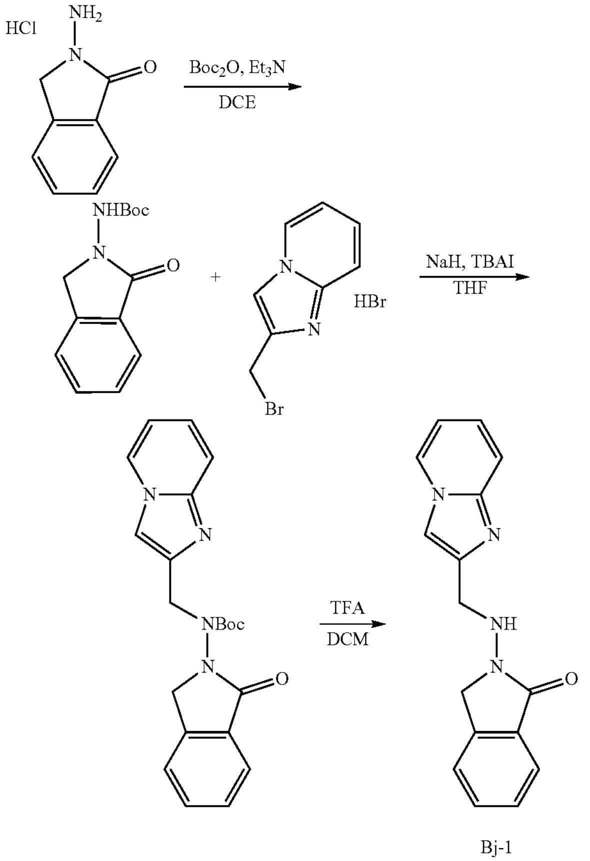

Bj-1

Step 1: tert-butyl N-(1-oxoisoindolin-2-yl)carbamate. A stirred solution of 2-aminoisoindolin-1-one hydrochloride (300 mg, 1.62 mmol) and $Boc_2O$ (532 mg, 2.44 mmol) in DCE (6 mL) was added $Et_3N$ (0.340 mL, 2.44 mmol). The mixture was heated to 50 °C overnight, allowed to cool to room temperature before directly being purified by column chromatography (EtOAc/hexanes) to afford the desired product. ES/MS: m/z=271.0 $[M+Na]^+$.

Step 2: tert-butyl N-(imidazo[1,2-a]pyridin-2-ylmethyl)-N-(1-oxoisoindolin-2-yl)carbamate. To a stirred suspension of tert-butyl N-(1-oxoisoindolin-2-yl)carbamate (70 mg, 0.282 mmol), 2-(bromomethyl)imidazo[1,2-a]pyridine hydrobromide (123 mg, 0.423 mmol), and TBAI (10 mg, 0.028 mmol) in dry THF (3 mL) under argon was added NaH (60% dispersion in mineral oil, 32.4 mg, 0.846 mmol). The mixture was heated to 50 °C for 10 minutes, at which point the reaction was deemed complete by LCMS. The reaction was allowed to cool to room temperature before directly being purified by column chromatography (MeOH/DCM) to afford the desired product. ES/MS: m/z=379.0 $[M+H]^+$.

Step 3: 2-(imidazo[1,2-a]pyridin-2-ylmethylamino)isoindolin-1-one (Bj-1). To a stirred solution of tert-butyl N-(imidazo[1,2-a]pyridin-2-ylmethyl)-N-(1-oxoisoindolin-2-yl) carbamate (93 mg, 0.246 mmol) in DCM (0.75 mL) at 0 °C was added TFA (0.75 mL) The mixture was allowed to warm to room temperature and stir for 15 minutes, then concentrated under reduced pressure and resuspended in EtOAc. The solution was washed with sat. aq. $NaHCO_3$, dried over $MgSO_4$, and concentrated to afford the desired product. ES/MS: m/z=279.0 $[M+H]^+$. $^1H$ NMR (400 MHz, Chloroform-d) δ 8.48 (dt, J=6.7, 1.1 Hz, 1H), 8.11 (s, 1H), 8.00 (d, J=9.1 Hz, 1H), 7.84 (ddd, J=9.1, 7.1, 1.1 Hz, 1H), 7.79-7.75 (m, 1H), 7.63 (td, J=7.5, 1.2 Hz, 1H), 7.54-7.44 (m, 2H), 7.37 (td, J=7.0, 1.1 Hz, 1H), 4.71 (s, 2H), 4.65 (s, 2H).

Bj-2

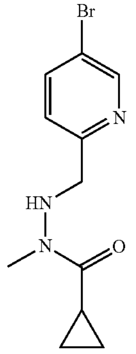

N'-((5-bromopyridin-2-yl)methyl)-N-methylcyclopropanecarbohydrazide (Bj-2). Prepared using general procedure X-B starting with tert-butyl N-[cyclopropanecarbonyl (methyl)amino]carbamate and 5-bromo-2-(bromomethyl) pyridine hydrobromide. ES/MS: m/z=284.2 $[M+H]^+$.

General Procedure XI-B for the Synthesis of Intermediates Bk

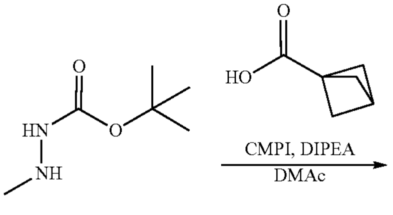

-continued

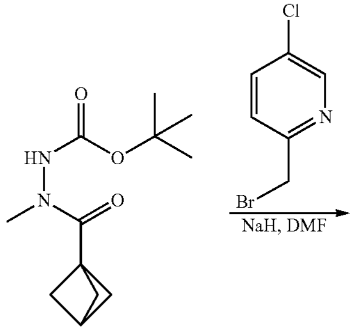

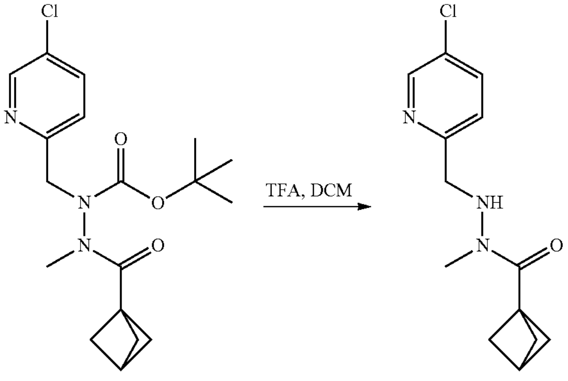

Bk-1

Step 1: tert-butyl 2-(bicyclo[1.1.1]pentane-1-carbonyl)-2-methylhydrazine-1-carboxylate. To a solution of tert-butyl 2-methylhydrazine-1-carboxylate (500 mg, 3.42 mmol) and bicyclo[1.1.1]pentane-1-carboxylic acid (460 mg, 4.10 mmol) in DMAc (12 mL), DIPEA (1.33 g, 10.3 mmol) was added, followed by CMPI (1.05 g, 4.10 mmol). The reaction was left to stir for 12 and upon completion by LCMS, dissolved in EtOAc. The $NaHCO_3$ twice, 10% LiCl twice, and brine, then dried with $MgSO_4$. The organic layer was reduced under pressure and the resulting residue was purified by flash silica gel chromatography to yield the desired product. ES/MS: m/z=241.0 $[M+H]^+$.

Step 2: tert-butyl 2-(bicyclo[1.1.1]pentane-1-carbonyl)-1-((5-chloropyridin-2-yl)methyl)-2-methylhydrazine-1-carboxylate. To a solution of tert-butyl 2-(bicyclo[1.1.1]pentane-1-carbonyl)-2-methylhydrazine-1-carboxylate (150 mg, 0.624 mmol) and 2-(bromomethyl)-5-chloropyridine (193 mg, 0.936 mmol) in DMF (2 mL), NaH (60% in mineral oil, 30 mg, 0.780 mmol) was slowly added at 0 C. The reaction was warmed to room temperature and left to stir for 12 hours and upon completion by LCMS, the reaction was quenched with 10% $NH_4Cl$. The mixture was dissolved in EtOAc and washed twice with $NaHCO_3$, once with brine, then dried with $MgSO_4$. The organic layer was reduced under pressure and the resulting residue was purified by flash silica gel chromatography to yield the desired product. ES/MS: m/z=366.2 $[M+H]^+$.

Step 3: N'-((5-chloropyridin-2-yl)methyl)-N-methylbicyclo[1.1.1]pentane-1-carbohydrazide (Bk-1). Tert-butyl 2-(bicyclo[1.1.1]pentane-1-carbonyl)-1-((5-chloropyridin-2-yl)methyl)-2-methylhydrazine-1-carboxylate (15.0 mg, 0.0410 mmol) was left to stir in 1:4 TFA/DCM (2 mL) at room temperature until LCMS showed full conversion. The mixture was reduced in vacuo, then dissolved in EtOAc. The mixture was washed twice with $NaHCO_3$, once with brine, and dried with $MgSO_4$. The organic layer was reduced under pressure and continued without any purification. ES/MS: m/z=266.2 $[M+H]^+$. $^1H$ NMR (400 MHz, Chloroform-d) δ 8.76-8.49 (m, 1H), 8.23-8.01 (m, 1H), 7.83-7.56 (m, 1H), 4.50 (s, 1H), 3.51 (s, 2H), 3.28 (s, 1H), 2.31 (s, 2H), 2.16 (s, 4H), 1.28 (s, 3H).

Bk-2

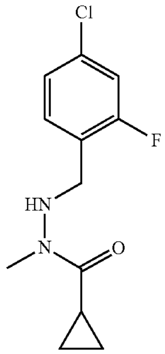

N'-(4-chloro-2-fluorobenzyl)-N-methylcyclopropanecarbohydrazide (Bk-2). Prepared using general procedure XI-B starting with tert-butyl 2-methylhydrazine-1-carboxylate, 1-(bromomethyl)-4-chloro-2-fluorobenzene and cyclopropanecarbonyl chloride. Step 1 was run with cyclopropaecarbonyl chloride and tert-butyl 2-methylhydrazine-1-carboxylate using conditions reported for step 2 in general procedure IV-B. ES/MS: m/z=257.2 $[M+H]^+$.

Bk-3

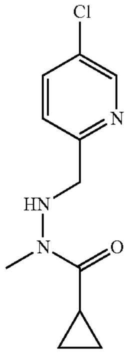

N'-((5-chloropyridin-2-yl)methyl)-N-methylcyclopropanecarbohydrazide. Prepared using general procedure XI-B starting with methylhydrazine, 2-(bromomethyl)-5-chloropyridine and cyclopropanecarbonyl chloride. ES/MS: m/z=240.0 $[M+H]^+$.

Bk-4

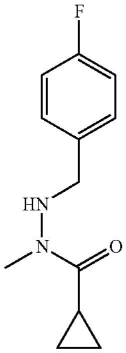

N'-(4-fluorobenzyl)-N-methylcyclopropanecarbohydrazide. Prepared using general procedure XI-B starting with methylhydrazine, 1-(bromomethyl)-4-fluorobenzene and cyclopropanecarbonyl chloride. ES/MS: m/z=223.2 $[M+H]^+$.

Bk-5

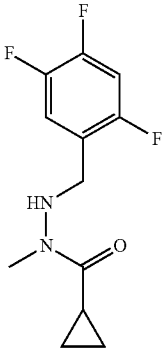

N-methyl-N'-(2,4,5-trifluorobenzyl)cyclopropanecarbohydrazide (Bk-5). Prepared using general procedure XI-B starting with tert-butyl N-(cyclopropanecarbonyl(methyl)amino)carbamate and 1-(bromomethyl)-2,4,5-trifluoro-benzene. ES/MS: m/z=259.2 $[M+H]^+$.

Bk-6

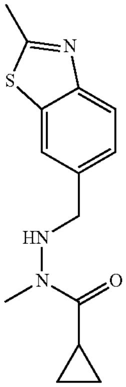

N-methyl-N'-((2-methylbenzo[d]thiazol-6-yl)methyl)cyclopropanecarbohydrazide (Bk-6). Prepared using general procedure XI-B starting with tert-butyl N-(cyclopropanecarbonyl(methyl)amino)carbamate and 6-(chloromethyl)-2-methyl-1,3-benzothiazole. ES/MS: m/z=276.0 $[M+H]^+$.

Bk-7

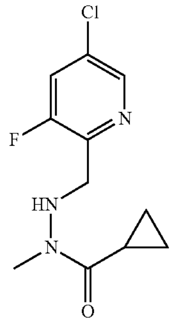

N'-((5-chloro-3-fluoropyridin-2-yl)methyl)-N-methylcyclopropanecarbohydrazide (Bk-7). Prepared using general procedure XI-B starting with tert-butyl N-[cyclopropanecarbonyl(methyl)amino]carbamate and 5-chloro-2-(chloromethyl)-3-fluoropyridine. ES/MS: m/z=258.2 [M+H]$^+$.

Bk-8

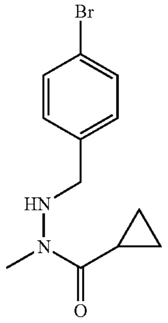

N'-(4-bromobenzyl)-N-methylcyclopropanecarbohydrazide (Bk-8). Prepared using general procedure XI-B starting 1-bromo-4-(bromomethyl)benzene and cyclopropanecarboxylic acid. ES/MS: m/z=285.0 [M+H]$^+$.

Bk-9

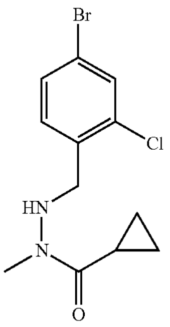

N'-(4-bromo-2-chlorobenzyl)-N-methylcyclopropanecarbohydrazide (Bk-9). Prepared using general procedure XI-B starting 4-bromo-1-(bromomethyl)-2-chlorobenzene and cyclopropanecarboxylic acid. ES/MS: m/z=319.1 [M+H]$^+$.

Bk-10

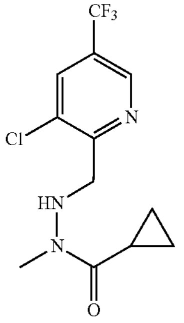

N'-((3-chloro-5-(trifluoromethyl)pyridin-2-yl)methyl)-N-methylcyclopropanecarbohydrazide (Bk-10). Prepared using general procedure XI-B starting 2-(bromomethyl)-3-chloro-5-(trifluoromethyl)pyridine and cyclopropanecarboxylic acid. ES/MS: m/z=307.9 [M+H]$^+$.

Bk-11

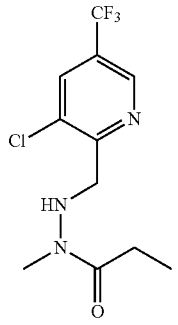

N'-((3-chloro-5-(trifluoromethyl)pyridin-2-yl)methyl)-N-methylpropionohydrazide (Bk-10). Prepared using general procedure XI-B starting 3-chloro-2-(chloromethyl)-5-(trifluoromethyl)pyridine and propanoyl chloride. ES/MS: m/z=296.0

General Procedure XII-B for the Synthesis of Intermediates Bl

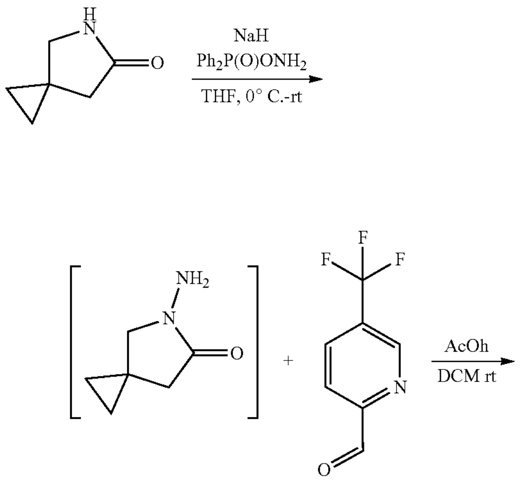

-continued

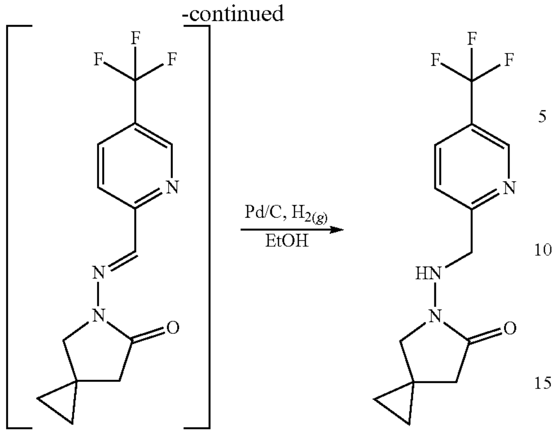

BI-1

Step 1: 5-amino-5-azaspiro[2.4]heptan-6-one. A solution at 0 °C containing 5-azaspiro[2.4]heptan-6-one (35.5 mg, 0.319 mmol) in THF (5.00 mL) was treated with sodium hydride (60.0%, 30.6 mg, 0.799 mmol) and allowed to stir at 0 °C for 1 hour. O-(diphenylphosphoryl)hydroxylamine (186 mg, 0.799 mmol) was then added and the mixture was allowed to warm to rt and stirred overnight.

Step 2: (E)-5-(((5-(trifluoromethyl)pyridin-2-yl)methylene)amino)-5-azaspiro[2.4]heptan-6-one. To the reaction mixture was added acetic acid (57.5 mg, 0.958 mmol) and 5-(trifluoromethyl)pyridine-2-carbaldehyde (67.1 mg, 0.383 mmol) then left to stir at rt for 30 min until confirming presence of imine by LCMS. The solvent was then removed in vacuo. ES/MS: m/z=284.2 $[M+H]^+$.

Step 3: 5-(((5-(trifluoromethyl)pyridin-2-yl)methyl)amino)-5-azaspiro[2.4]heptan-6-one (BI-1). To the crude imine mixture was added palladium on carbon (10%) (34.0 mg, 0.319 mmol) and EtOH (5.00 mL) and the vessel was evacuated then backfilled with hydrogen gas (1 atm) three times then left to stir at rt until LCMS showed full conversion of the imine. The mixture was filtered through a pad of celite and the organic solvent was removed under pressure and purified by flash silica gel chromatography yield the desired product. ES/MS: m/z=286.2 $[M+H]^+$.

BI-2

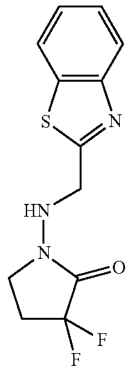

1-(1,3-benzothiazol-2-ylmethylamino)-3,3-difluoro-pyrrolidin-2-one (BI-2). Prepared using general procedure XII-B starting with 1-amino-3,3-difluoro-pyrrolidin-2-one and 1,3-benzothiazole-2-carbaldehyde. ES/MS: m/z=284.0 $[M+H]^+$.

BI-3

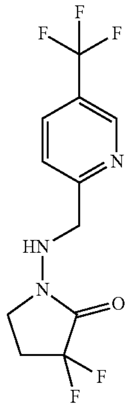

3,3-difluoro-1-(((5-(trifluoromethyl)pyridin-2-yl)methyl)amino)pyrrolidin-2-one (BI-3). Prepared using general procedure I-B starting with 1-amino-3,3-difluoropyrrolidin-2-one and 5-(trifluoromethyl)pyridine-2-carbaldehyde. ES/MS: m/z=296.0 $[M+H]^+$.

BI-4

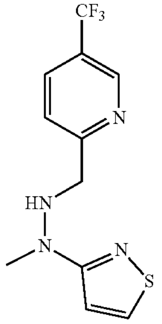

3-(1-methyl-2-((5-(trifluoromethyl)pyridin-2-yl)methyl)hydrazineyl)isothiazole (BI-4). Prepared using general procedure XII-B starting with tert-butyl 3-(1-methylhydrazineyl)isothiazole and 2-(bromomethyl)-5-(trifluoromethyl)pyridine. ES/MS: m/z=289.2 $[M+H]^+$.

BI-5

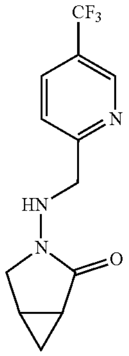

3-(((5-(trifluoromethyl)pyridin-2-yl)methyl)amino)-3-azabicyclo[3.1.0]hexan-2-one (BI-5). Prepared using general procedure XII-B starting with 5-(trifluoromethyl)pyridine-2-carbaldehyde and 3-azabicyclo[3.1.0]hexan-2-one. ES/MS: m/z=272.2 $[M+H]^+$.

Bl-6

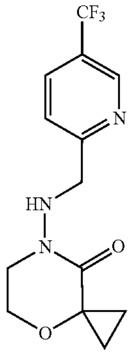

7-(((5-(trifluoromethyl)pyridin-2-yl)methyl)amino)-4-oxa-7-azaspiro[2.5]octan-8-one (Bl-6). Prepared using general procedure XII-B starting with 5-(trifluoromethyl)pyridine-2-carbaldehyde and 4-oxa-7-azaspiro[2.5]octan-8-one. ES/MS: m/z=272.2 $[M+H]^+$.

General Procedure XIII-B for the Synthesis of Intermediate Bm

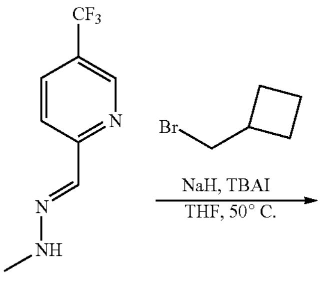

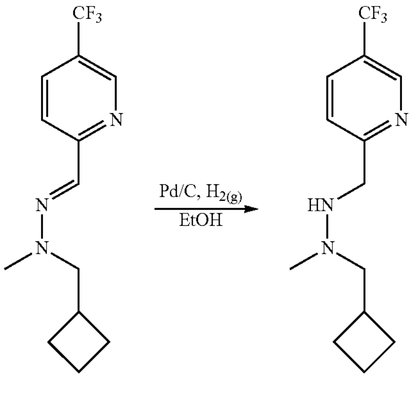

Bm-1

Step 1: 1-cyclobutyl-N-methyl-N-[(E)-[5-(trifluoromethyl)-2-pyridyl]methyleneamino]methanamine. To a stirred solution of N-[(E)-[5-(trifluoromethyl)-2-pyridyl]methyleneamino]methanamine (150 mg, 0.74 mmol), NaH (60% in mineral oil, 42 mg, 1.1 mmol), and TBAI (55 mg, 0.15 mmol) in dry THF (3 mL) under argon was added bromomethylcyclobutane (132 mg, 0.89 mmol). The mixture was heated to 50 °C for 2 hours, at which point the reaction was deemed complete by LCMS. The reaction was allowed to cool to room temperature before being diluted with ethyl acetate and transferred to a separatory funnel. The mixture was washed with brine, dried over anhydrous $MgSO_4$, and concentrated under reduced pressure. The crude residue was purified by column chromatography (EtOAc/Hexanes) to afford the desired product. ES/MS: m/z=272.0 $[M+H]^+$.

Step 2: 1-(cyclobutylmethyl)-1-methyl-2-[[5-(trifluoromethyl)-2-pyridyl]methyl]hydrazine (Bm-1). A suspension of 1-cyclobutyl-N-methyl-N-[(E)-[5-(trifluoromethyl)-2-pyridyl]methyleneamino]methanamine (150 mg, 0.55 mmol) and palladium on carbon (10% w/w, 147 mg, 0.14 mmol) in EtOH (2 mL) under an atmosphere of hydrogen gas was stirred for 20 minutes at which point the reaction was deemed complete by LCMS analysis. The reaction vessel a purged with argon and the mixture was filtered over celite to afford the desired product. ES/MS: m/z=274.0 $[M+H]^+$. $^1H$ NMR (400 MHz, Chloroform-d) 8.86 (dt, J=2.0, 0.9 Hz, 1H), 8.19 (dd, J=8.3, 2.4 Hz, 1H), 7.74 (d, J=8.3 Hz, 1H), 4.01 (d, J=3.3 Hz, 2H), 3.52 (d, J=7.4 Hz, 2H), 2.52-2.43 (m, 1H), 2.36 (s, 3H), 1.97-1.87 (m, 2H), 1.85-1.75 (m, 2H), 1.65-1.52 (m, 2H).

Bm-2

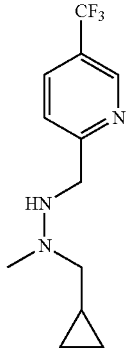

1-(cyclopropylmethyl)-1-methyl-2-[[5-(trifluoromethyl)-2-pyridyl]methyl]hydrazine (Bm-2). Prepared using general procedure XIII-B starting with N—[(E)-[5-(trifluoromethyl)-2-pyridyl]methyleneamino]methanamine and bromomethylcyclopropane. ES/MS: m/z=260.0 $[M+H]^+$.

Bm-3

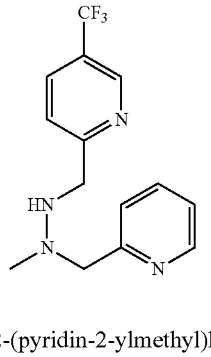

2-((2-methyl-2-(pyridin-2-ylmethyl)hydrazineyl)methyl)-5-(trifluoromethyl)pyridine (Bm-3). Prepared using general procedure XIII-B starting with N—[(E)-[5-(trifluoromethyl)-2-pyridyl]methyleneamino]methanamine and 2-(bromomethyl)pyridine hydrobromide. ES/MS: m/z=297.0 $[M+H]^+$.

Bm-4

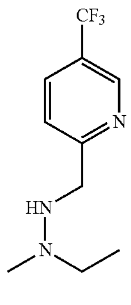

2-((2-ethyl-2-methylhydrazineyl)methyl)-5-(trifluoromethyl)pyridine (Bm-4).

Prepared using general procedure XIII-B starting with N-[(E)-[5-(trifluoromethyl)-2-pyridyl]methyleneamino]methanamine and iodoethane. ES/MS: m/z=234.0 $[M+H]^+$.

General Procedure XIV-B for the Synthesis of Intermediates Bn

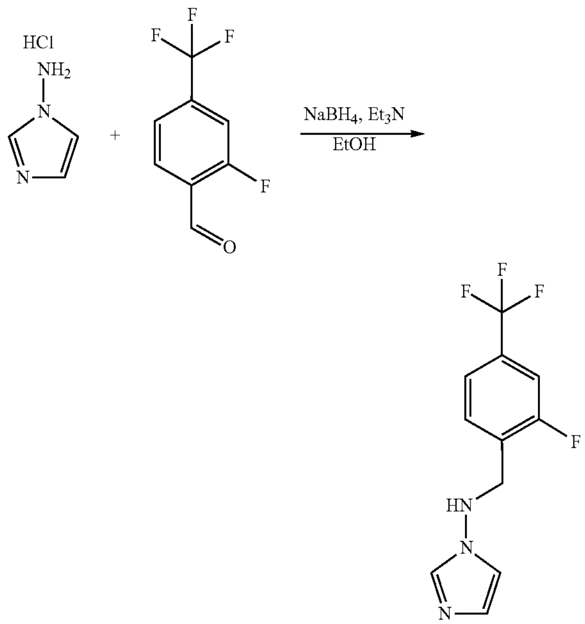

Bn-1

N-[[2-fluoro-4-(trifluoromethyl)phenyl]methyl]imidazol-1-amine (Bn-1). To a stirred solution of imidazol-1-amine HCl (96 mg, 0.80 mmol) and 2-fluoro-4-(trifluoromethyl)benzaldehyde (140 mg, 0.73 mmol) in EtOH (3.0 mL) at rt was added triethylamine (0.3 mL, 2.2 mmol). The mixture was stirred at rt for 1 h before addition of sodium borohydride (55 mg, 1.5 mmol). The mixture was stirred at room temperature and upon completion as judged by LCMS analysis; EtOAc and sat. aq. $NH_4Cl$ were added and the organic layer was washed with water twice and brine. The organic solvent was removed under pressure and purified by flash silica gel chromatography. The fractions were collected and reduced under pressure to yield the desired product. ES/MS: m/z=260.0 $[M+H]^+$.

Bn-2

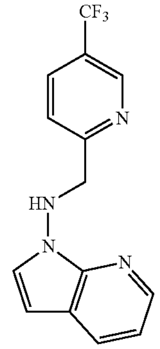

N-((5-(trifluoromethyl)pyridin-2-yl)methyl)-1H-pyrrolo[2,3-b]pyridin-1-amine (Bn-2). Prepared using general procedure XIV-B starting with pyrrolo[2,3-b]pyridin-1-amine and 5-(trifluoromethyl)pyridine-2-carbaldehyde. ES/MS: m/z=293.2 $[M+H]^+$.

Bn-3

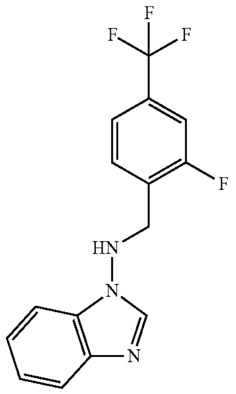

N-(2-fluoro-4-(trifluoromethyl)benzyl)-1H-benzo[d]imidazol-1-amine (Bn-3). Prepared using general procedure XIV-B starting with benzimidazol-1-amine and 2-fluoro-4-(trifluoromethyl)benzaldehyde. ES/MS: m/z=310.2 $[M+H]^+$.

General Procedure XV-B for the Synthesis of Intermediates Bo

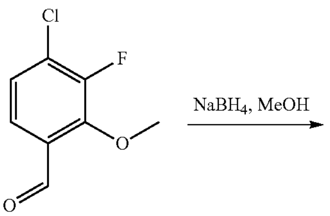

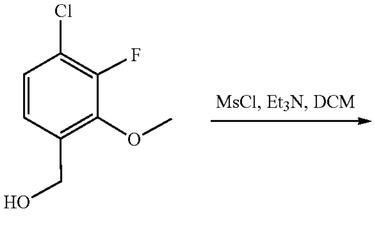

-continued

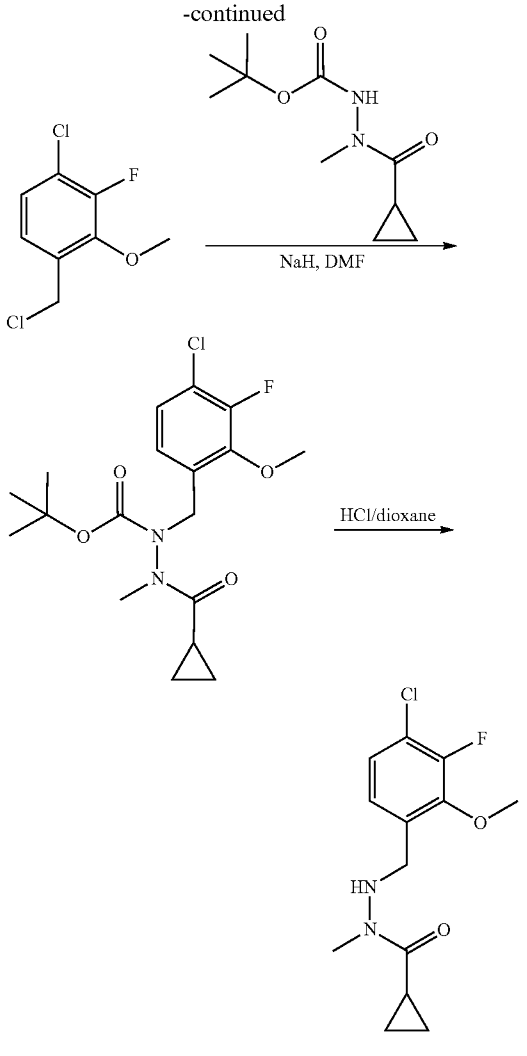

Bo-1

Step 1: (4-chloro-3-fluoro-2-methoxy-phenyl)methanol. To a suspension of 4-chloro-3-fluoro-2-methoxy-benzaldehyde (250 mg, 1.3 mmol) in MeOH (5 mL) at 0 deg, was added sodium borohydride (55 mg, 1.5 mmol). Gradually warmed to rt and stirred overnight. The reaction was quenched with sat'd $NH_4Cl$. Concentrated off MeOH. Extracted with EtOAc and dried over sodium sulfate to give desired product. ES/MS: m/z=173.2 $[M+H]^+$. $^1H$ NMR (400 MHz, Chloroform-d) δ 7.18-7.02 (m, 2H), 4.69 (d, J=3.8 Hz, 2H), 4.03 (d, J=2.4 Hz, 3H).

Step 2: 1-chloro-4-(chloromethyl)-2-fluoro-3-methoxy-benzene. To a solution of (4-chloro-3-fluoro-2-methoxy-phenyl)methanol (210 mg, 1.10 mmol) in DCM (5 mL) at 0 deg, was added triethylamine (0.184 mL, 1.32 mmol) followed by methanesulfonyl chloride (0.103 mL, 1.32 mmol). After 2.5h, the reaction was partitioned with EtOAc and brine. The organic extract was dried over sodium sulfate and concentrated to give desired product. $^1H$ NMR (400 MHZ, Chloroform-d) δ 7.14-7.11 (m, 2H), 5.25 (s, 2H), 4.05 (m, 3H).

Step 3: tert-butyl N-[(4-chloro-3-fluoro-2-methoxy-phenyl)methyl]-N-[cyclopropanecarbonyl(methyl)amino]carbamate. To a solution of tert-butyl N-[cyclopropanecarbonyl (methyl)amino]carbamate (210 mg, 0.980 mmol) in DMF (2 mL) at 0 deg, was added sodium hydride (60.0%, 45.1 mg, 1.18 mmol). After 15 min, added a solution of (4-chloro-3-fluoro-2-methoxy-phenyl)methyl methanesulfonate (303 mg, 0.00113 mol) in DMF (3 mL). Gradually warmed to rt and stirred overnight. The reaction was cooled to 0 deg, diluted with EtOAc, quenched with saturated $NH_4Cl$ solution. Added 5% LiCl, separated organic extract. Washed once more with 5% LiCl and brine. The organic extract was dried over sodium sulfate, concentrated, and purified by flash chromatography to give desired product. 1H NMR (400 MHz, Chloroform-d) δ 7.08 (d, J=3.0 Hz, 2H), 4.94-4.48 (m, 2H), 3.97 (d, J=2.5 Hz, 3H), 2.95 (s, 3H), 1.64-1.55 (m, 1H), 1.51 (s, 9H), 0.90 (d, J=5.4 Hz, 1H), 0.79 (s, 1H), 0.70 (dddd, J=9.8, 8.2, 6.6, 3.2 Hz, 1H), 0.60-0.34 (m, 1H).

Step 4: N'-[(4-chloro-3-fluoro-2-methoxy-phenyl)methyl]-N-methylcyclopropanecarbohydrazide (Bo-1). A solution of tert-butyl N-[(4-chloro-3-fluoro-2-methoxy-phenyl)methyl]-N-[cyclopropanecarbonyl(methyl)amino]carbamate (82.7 mg, 0.000214 mol) and hydrochloric acid (4M in dioxane) (4000 mmol/L, 0.534 mL, 0.00214 mol) in DCM (4 mL) was stirred at rt o/n. The reaction was concentrated to dryness to give title compound. ES/MS: m/z=287.0 $[M+H]^+$.

Bo-2

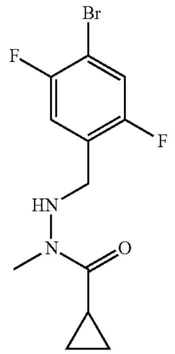

N'-(4-bromo-2,5-difluorobenzyl)-N-methylcyclopropanecarbohydrazide (Bo-2). Prepared using general procedure XV-B starting with starting with (4-bromo-2,5-difluorophenyl)methanol. ES/MS: m/z=319.0, 321 $[M+H]^+$.

Bo-3

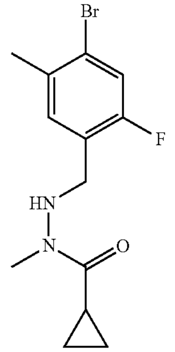

N'-(4-bromo-2-fluoro-5-methylbenzyl)-N-methylcyclopropanecarbohydrazide (Bo-3). Prepared using general procedure XV-B starting with starting with (4-bromo-2-fluoro-5-methyl-phenyl)methanol. ES/MS: m/z=315.0, 317.0 $[M+H]^+$.

Bo-4

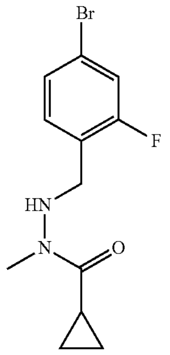

N'-(4-bromo-2-fluorobenzyl)-N-methylcyclopropanecarbohydrazide (Bo-4): Prepared using general procedure XV-B starting with methylhydrazine, (4-bromo-2-fluorophenyl)methanol, and cyclopropanecarbonyl chloride. ES/MS: m/z=302.0 [M+H]$^+$.

Bo-5

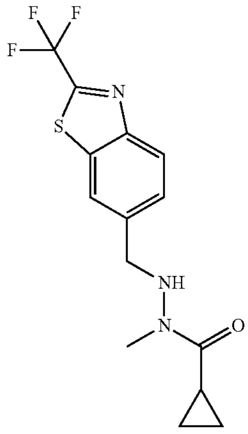

N-methyl-N'-((2-(trifluoromethyl)benzo[d]thiazol-6-yl)methyl)cyclopropanecarbohydrazide (Bo-5). Prepared using general procedure XV-B starting with [2-(trifluoromethyl)-1,3-benzothiazol-6-yl]methanol. ES/MS: m/z=330.0 [M+H]$^+$.

Bo-6

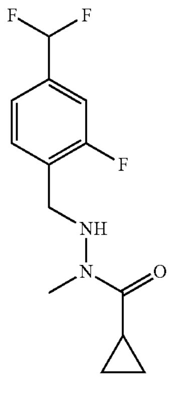

N'-(4-(difluoromethyl)-2-fluorobenzyl)-N-methylcyclopropanecarbohydrazide (Bo-6). Prepared using general procedure XV-B starting with [4-(difluoromethyl)-2-fluorophenyl]methanol. ES/MS: m/z=273.2 [M+H]$^+$.

Bo-7

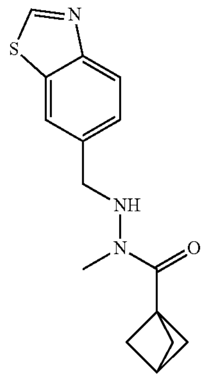

N'-(benzo[d]thiazol-6-ylmethyl)-N-methylbicyclo[1.1.1]pentane-1-carbohydrazide (Bo-7). Prepared using general procedure XV-B starting with 6-(chloromethyl)-1,3-benzothiazole and bicyclo[1.1.1]pentane-1-carbonyl chloride ES/MS: m/z=288.2 [M+H]$^+$.

Bo-8

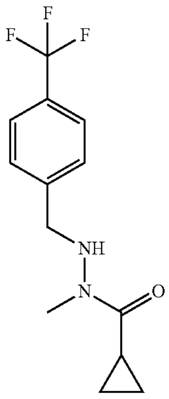

N-methyl-N'-(4-(trifluoromethyl)benzyl)cyclopropanecarbohydrazide (Bo-8). Prepared using general procedure XV-B starting with 1-(bromomethyl)-4-(trifluoromethyl)benzene. ES/MS: m/z=273.2 [M+H]$^+$.

General Procedure XVI-B for the Synthesis of Intermediates Bp

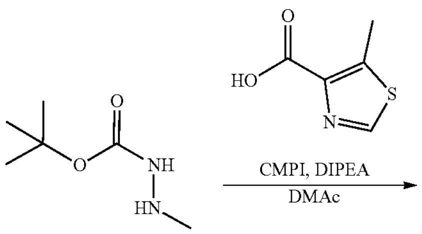

-continued

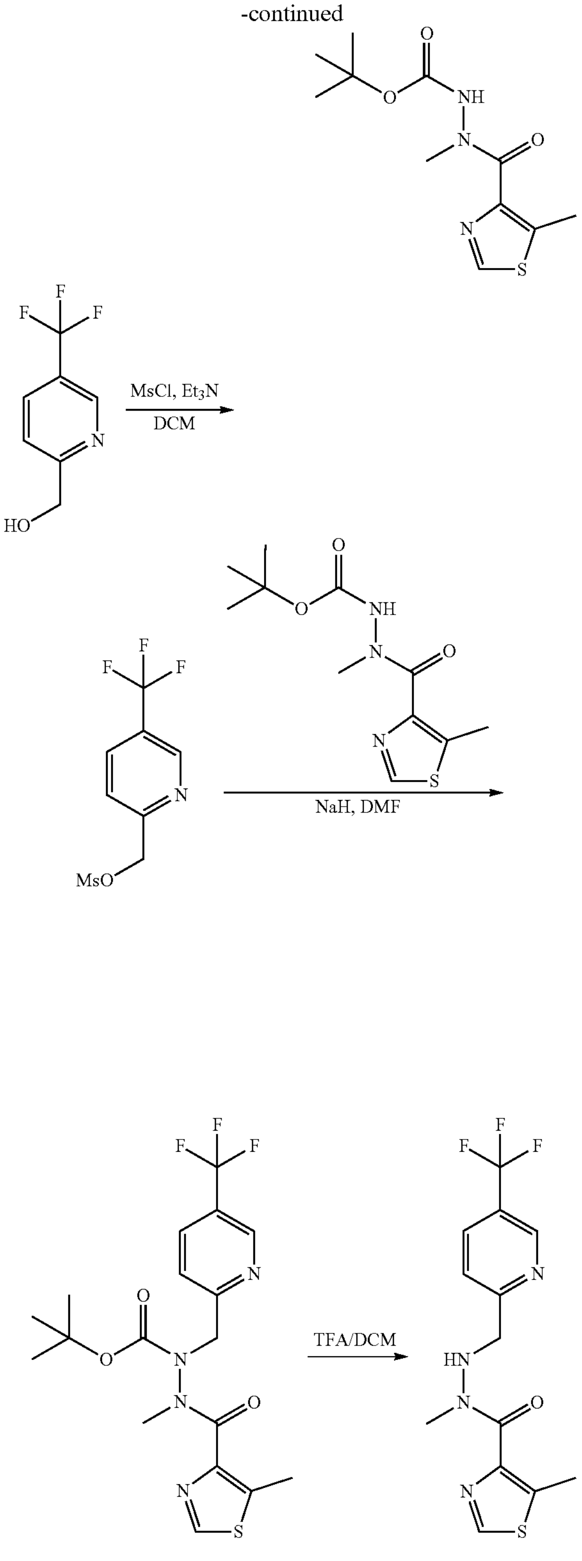

Bp-1 tert-butyl 2-methyl-2-(5-methylthiazole-4-carbonyl)hydrazine-1-carboxylate. To a suspension of tert-butyl N-(methylamino)carbamate (245 mg, 1.68 mmol) in DMAc (6 mL), was added DIPEA (0.365 mL, 2.10 mmol) and 5-methylthiazole-4-carboxylic acid (200 mg, 1.40 mmol), followed by CMPI (428 mg, 1.68 mmol). The reaction was stirred overnight, and then diluted with EtOAc and 10% aq. LiCl solution and transferred to a separatory funnel. The organic layer was separated, and the aqueous layer was washed with a further portion of EtOAc. The combined organic layers were dried over anhydrous $MgSO_4$ and concentrated under reduced pressure. The crude residue was purified by flash chromatography (EtOAc/hex) to afford the desired product. ES/MS: m/z=272.2 $[M+H]^+$.

Step 1: 2-((methylsulfonyl)methyl)-5-(trifluoromethyl)pyridine. To a solution (5-(trifluoromethyl)pyridin-2-yl)methanol (50.0 mg, 0.282 mmol) in DCM (5 mL) at 0 deg, was added triethylamine (0.0787 mL, 0.565 mmol) followed by methanesulfonyl chloride (0.0237 mL, 0.311 mmol). After 10 minutes, the reaction was partitioned with EtOAc and brine. The organic extract was dried over sodium sulfate and concentrated to give desired product. ES/MS: m/z=256.2 [M+H]

Step 2: tert-butyl 2-methyl-2-(5-methylthiazole-4-carbonyl)-1-((5-(trifluoromethyl)pyridin-2-yl)methyl)hydrazine-1-carboxylate. To a solution of tert-butyl 2-methyl-2-(5-methylthiazole-4-carbonyl)hydrazine-1-carboxylate (58.5 mg, 0.216 mmol) in DMF (2 mL) at 0 deg, was added sodium hydride (60.0%, 9.01 mg, 0.235 mmol). After 15 min, added a solution of 2-((methylsulfonyl)methyl)-5-(trifluoromethyl) (50.0 mg, 0.196 mmol) in DMF (3 mL). Gradually warmed to rt and stirred for 10 minutes. The reaction was cooled to 0 deg, diluted with EtOAc, quenched with saturated $NH_4Cl$ solution. Added 5% LiCl, separated organic extract. Washed once more with 5% LiCl and brine. The organic extract was dried over sodium sulfate, concentrated, and purified by flash chromatography to give desired product. ES/MS: m/z=431.0 [M+H].

Step 3: N,5-dimethyl-N'-((5-(trifluoromethyl)pyridin-2-yl)methyl)thiazole-4-carbohydrazide (Bp-1). Tert-butyl 2-methyl-2-(5-methylthiazole-4-carbonyl)-1-((5-(trifluoromethyl)pyridin-2-yl)methyl)hydrazine-1-carboxylate (27.0 mg, 0.0627 mmol) was left to stir in 1:4 TFA/DCM (2 mL) at room temperature until LCMS showed full conversion. The mixture was reduced in vacuo, then dissolved in EtOAc. The mixture was washed twice with $NaHCO_3$, once with brine, and dried with $MgSO_4$. The organic layer was reduced under pressure and continued without any purification. ES/MS: m/z=331.0.

Bp-2

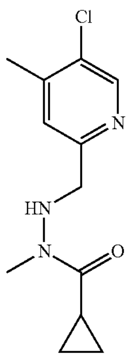

N'-((5-chloro-4-methylpyridin-2-yl)methyl)-N-methylcyclopropanecarbohydrazide (Bp-2). Prepared using general procedure XVI-B starting from step 2 with (5-chloro-4-methyl-2-pyridyl)methanol and tert-butyl 2-(cyclopropanecarbonyl)-2-methylhydrazine-1-carboxylate. ES/MS: m/z= $[M+H]^+$.

General Procedure XVII-B for the Synthesis of Intermediate Bq

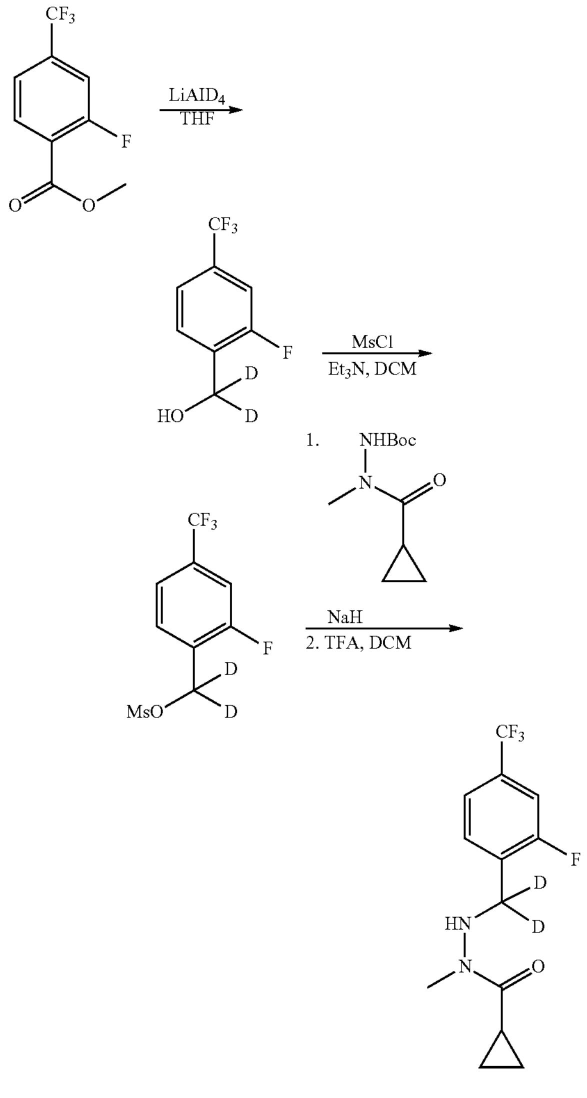

Bq-1

N'-((2-fluoro-4-(trifluoromethyl)phenyl)methyl-d2)-N-methylcyclopropanecarbohydrazide (Bq-1)

Step 1. A solution of methyl 2-fluoro-4-(trifluoromethyl) benzoate (1.62 g, 7.3 mmol) in THF (30 mL) was cooled to −78 °C and LiAlD4 powder (368 mg, 8.8 mmol) was added. The resulting mixture was warmed to room temperature at which point LCMS analysis showed full conversion of the starting material. Fieser work up was realized and the residue was purified by column chromatography over silica gel (Hexane/EtOAc 0-100%) to afford (2-fluoro-4-(trifluoromethyl)phenyl)methan-d2-ol. $^1$H NMR (400 MHz, Chloroform-d) δ 7.61 (t, J=7.6 Hz, 1H), 7.44 (dd, J=8.1, 1.6 Hz, 1H), 7.31 (dd, J=10.0, 1.6 Hz, 1H).

Step 2. (2-fluoro-4-(trifluoromethyl)phenyl)methan-d2-ol (1.1 g, 5.6 mmol) was dissolved in DCM (15 mL) and the solution was cooled to 0 °C and triethylamine (1.6 mL, 11.2 mmol) was added followed by the dropwise addition of methanesulfonyl chloride (642 mg, 5.6 mmol). The resulting solution was stirred for 30 minutes and then quenched with $NaHCO_{3(sat.)}$. After work up the combined organics were dried over magnesium sulfate, filtered and then evaporated to dryness to afford (2-fluoro-4-(trifluoromethyl)phenyl) methyl-d2 methanesulfonate, which was used without further purification.

Step 3. NaH (60% dispersion in mineral oil, 46 mg, 1.2 mmol) was added to a solution of tert-butyl 2-(cyclopropanecarbonyl)-2-methylhydrazine-1-carboxylate (214 mg, 1 mmol) in DMF (2 mL) at 0 °C. The mixture was stirred for 30 minutes before a solution of (2-fluoro-4-(trifluoromethyl) phenyl)methyl-d2 methanesulfonate (274 mg, 1 mmol) in THF (1 mL) was added. The reaction was stirred for 20 minutes at which point the reaction was deemed complete by LCMS. The reaction was quenched with $NH_4Cl_{(sat.)}$ and after usual work up the residue was purified by flash column chromatography (Hexane/EtOAc 0-100%) to afford tert-butyl 2-(cyclopropanecarbonyl)-1-((2-fluoro-4-(trifluoromethyl)phenyl)methyl-d2)-2-methylhydrazine-1-carboxylate ES/MS: m/z=393.6 $[M+H]^+$. 1-((2-fluoro-4-(trifluoromethyl)phenyl)methyl-d2)-2-methylhydrazine-1-carboxylate (380 mg, 0.97 mmol) was dissolved in DCM (2 mL) and TFA (1 mL) was added. Upon completion of the reaction as judged by LCMS analysis, the volatiles were evaporated and the residue was taken in DCM and extracted with $NaHCO_3$ (sat.) 3 times. The organic layer was dried over sodium sulfate and evaporated to dryness to afford N'-((2-fluoro-4-(trifluoromethyl)phenyl)methyl-d2)-N-methylcyclopropanecarbohydrazide. ES/MS: m/z=293.1 $[M+H]^+$.

Bq-2

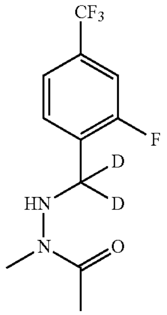

N'-((2-fluoro-4-(trifluoromethyl)phenyl)methyl-d2)-N-methylacetohydrazide (Bq-2). Prepared using general procedure XVII-B starting with methyl 2-fluoro-4-(trifluoromethyl)benzoate and tert-butyl 2-acetyl-2-methylhydrazine-1-carboxylate. ES/MS: m/z=267.0 $[M+H]^+$.

Bq-3

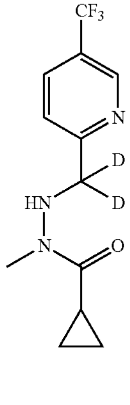

N-methyl-N'-((5-(trifluoromethyl)pyridin-2-yl)methyl-d2)cyclopropanecarbohydrazide (Bq-3). Prepared using general procedure XVII-B starting with methyl 5-(trifluoromethyl)picolinate and tert-butyl 2-(cyclopropanecarbonyl)-2-methylhydrazine-1-carboxylate. ES/MS: m/z=276.0 $[M+H]^+$.

General Procedure XVIII-B for the Synthesis of Intermediates Br

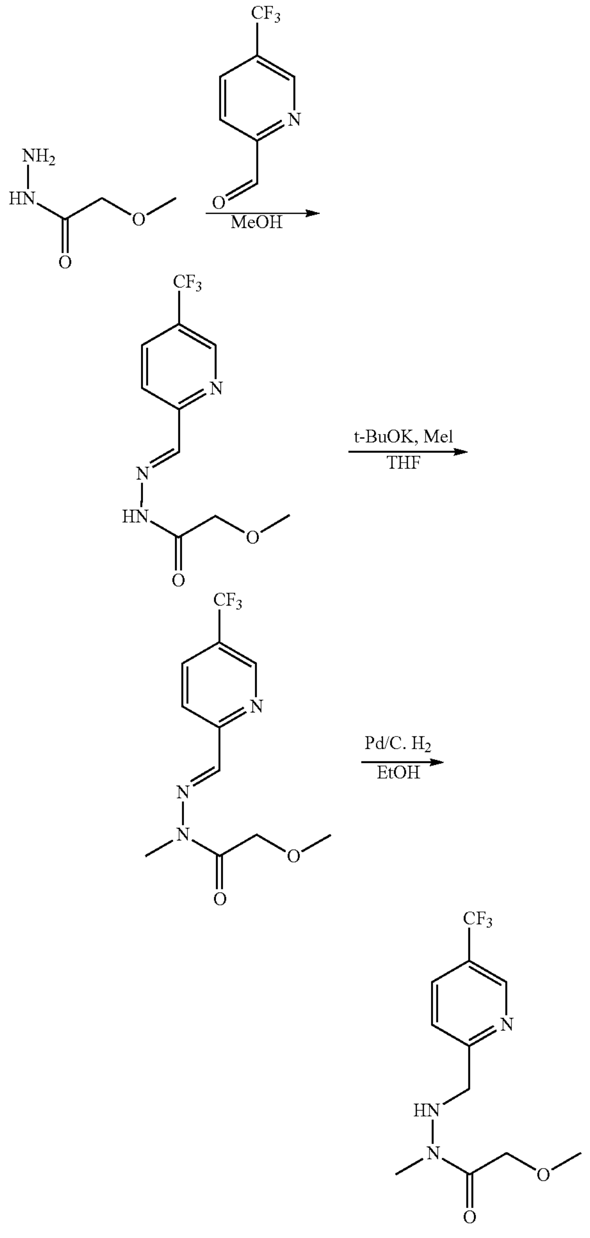

Br-1

2-methoxy-N'-((5-(trifluoromethyl)pyridin-2-yl) methylene)acetohydrazide

To a solution of 2-methoxyacetohydrazide (0.4 g, 4.3 mmol, 1 eq) in MeOH (10 mL) was added 5-(trifluoromethyl)pyridine-2-carbaldehyde (756.9 mg, 4.3 mmol, 1 eq). The mixture was stirred at 25 °C for 5 hr. The reaction mixture was concentrated under reduced pressure to give a residue to give crude product which was used into the next step without further purification. $^1$H NMR (400 MHz, METHANOL-d4) δ 8.90-8.84 (m, 1H), 8.40-8.35 (m, 2H), 8.14 (d, J=2.1 Hz, 1H), 4.12 (s, 2H), 3.48 (s, 3H).

methoxy-N-methyl-N'-((5-(trifluoromethyl)pyridin-2-yl)methylene)acetohydrazide

To a solution of 2-methoxy-N-[(E)-[5-(trifluoromethyl)-2-pyridyl]methyleneamino]acetamide (0.9 g, 3.5 mmol, 1 eq) in THF (30 mL) was added t-BuOK (479.4 mg, 4.2 mmol, 1.2 eq) and MeI (555.9 mg, 3.9 mmol, 243.8 μL, 1.1 eq). The mixture was stirred at 25 °C for 12 hr. The reaction mixture was diluted with $H_2O$ (50 mL) and extracted with ethyl acetate (50 mL×3). The combined organic layers were dried over $Na_2SO_4$, filtered and concentrated under reduced pressure to give a residue. The residue was purified by flash silica gel chromatography (Ethyl acetate/Petroleum ether) to give desired product. $^1$H NMR (400 MHz, DMSO-$d_6$) δ 9.00 (s, 1H), 8.26 (dd, J=1.9, 8.5 Hz, 1H), 8.12 (d, J=8.4 Hz, 1H), 7.93 (s, 1H), 4.63 (s, 2H), 3.36 (s, 3H), 3.35 (s, 3H).

2-methoxy-N-methyl-N'-((5-(trifluoromethyl)pyridin-2-yl)methyl)acetohydrazide (Br-1). To a bottle of Pd/C (0.4 g, 10% purity) in EtOH (7 mL) was added 2-methoxy-N-methyl-N—[(E)-[5-(trifluoromethyl)-2-pyridyl]methyleneamino]acetamide (625 mg, 2.2 mmol, 1 eq) in EtOH (7 mL) under $H_2$ at 15 psi. The mixture was stirred at 25 °C for 16 hr. The reaction mixture was filtered, washed with 200 mL MeOH and concentrated under reduced pressure to give a residue. The residue was purified by prep-HPLC (column: Waters Xbridge BEH C18 100*30 mm*10 um; mobile phase: [water($NH_3H_2O$+$NH_4HCO_3$)-ACN]; B %: 15%-45%, 8 min) to give desired product. ES/MS: m/z=277.9 $[M+H]^+$. $^1$H NMR (400 MHz, DMSO-$d_6$) δ 8.93 (s, 1H), 8.23 (dd, J=2.1, 8.1 Hz, 1H), 7.69 (d, J=8.3 Hz, 1H), 5.44 (t, J=5.1 Hz, 1H), 4.11 (d, J=5.1 Hz, 2H), 4.03 (s, 2H), 3.11 (s, 3H), 3.01 (s, 3H).

General Procedure XIX-B for the Synthesis of Intermediates Bs

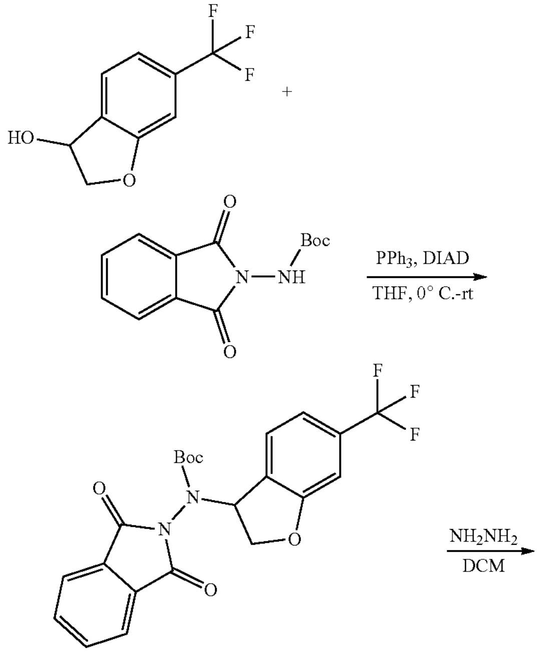

-continued

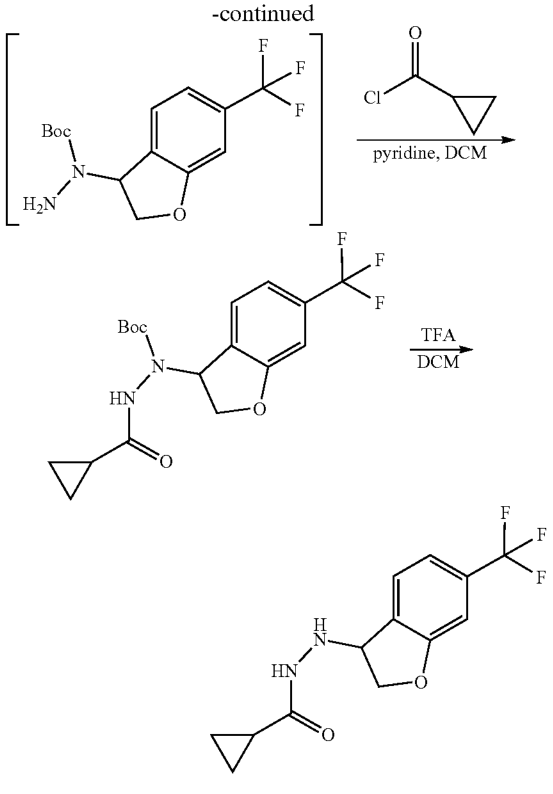

Bs-1

Step 1: tert-butyl (1,3-dioxoisoindolin-2-yl)(6-(trifluoromethyl)-2,3-dihydrobenzofuran-3-yl)carbamate. A solution at 0 °C containing 6-(trifluoromethyl)-2,3-dihydrobenzofuran-3-ol (40 mg, 0.20 mmol) and tert-butyl N-(1,3-dioxoisoindolin-2-yl)carbamate (57 mg, 0.22 mmol) in THF (5.00 mL) was treated with triphenylphosphine (77 mg, 0.29 mmol) and DIAD (59 mg, 0.29 mmol) and allowed to stir at 0 °C. The mixture was warmed to rt and stirred for 1 h before concentrating in vacuo. The crude reside was purified by flash silica gel chromatography yield the desired product (40 mg, 46%). ES/MS: m/z=471.0 $[M+Na]^+$.

Step 2: tert-butyl 2-(cyclopropanecarbonyl)-1-(6-(trifluoromethyl)-2,3-dihydrobenzofuran-3-yl)hydrazine-1-carboxylate. tert-butyl (1,3-dioxoisoindolin-2-yl)(6-(trifluoromethyl)-2,3-dihydrobenzofuran-3-yl)carbamate (36 mg, 0.08 mmol) in DCM (3 mL) was added hydrazine hydrate (8 mg, 0.16 mmol) at rt. The solution was stirred for 12 h before concentrating in vacuo. The crude residue was re-dissolved in DCM (3 mL), followed by addition of pyridine (13 mg, 0.16 mmol) and cyclopropanecarbonyl chloride (13 mg, 0.12 mmol) at rt. The mixture was stirred for 5 h before concentrating in vacuo. The crude reside was purified by flash silica gel chromatography yield the desired product (31 mg, 99%). ES/MS: m/z=387.2 $[M+H]^+$.

Step 3: N'-(6-(trifluoromethyl)-2,3-dihydrobenzofuran-3-yl)cyclopropanecarbohydrazide (Bs-1). tert-butyl 2-(cyclopropanecarbonyl)-1-(6-(trifluoromethyl)-2,3-dihydrobenzofuran-3-yl)hydrazine-1-carboxylate (31 mg, 0.08 mmol) in DCM (2 mL) was added TFA (0.5 mL) at rt. The mixture was stirred for 2 h before concentrating in vacuo. The residue was re-dissolved in EtOAc (5 mL), washed with saturated sodium bicarbonate (5 mL), dried over $MgSO_4$, and filtered. The organic solvent was removed under reduced pressure to yield the desired product without further purification (23 mg, 99%). ES/MS: m/z=309.2 $[M+H]^+$.

Bs-2

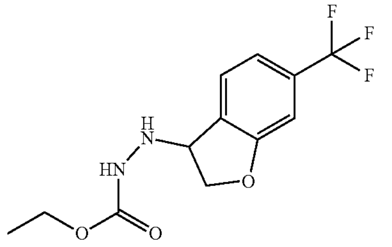

ethyl 2-(6-(trifluoromethyl)-2,3-dihydrobenzofuran-3-yl)hydrazine-1-carboxylate (Bs-2). Prepared using general procedure XIX-B using ethyl carbonochloridate. ES/MS: m/z=313.0 [M+Na]+.

General Procedure XX-B for the Synthesis of Intermediates Bt

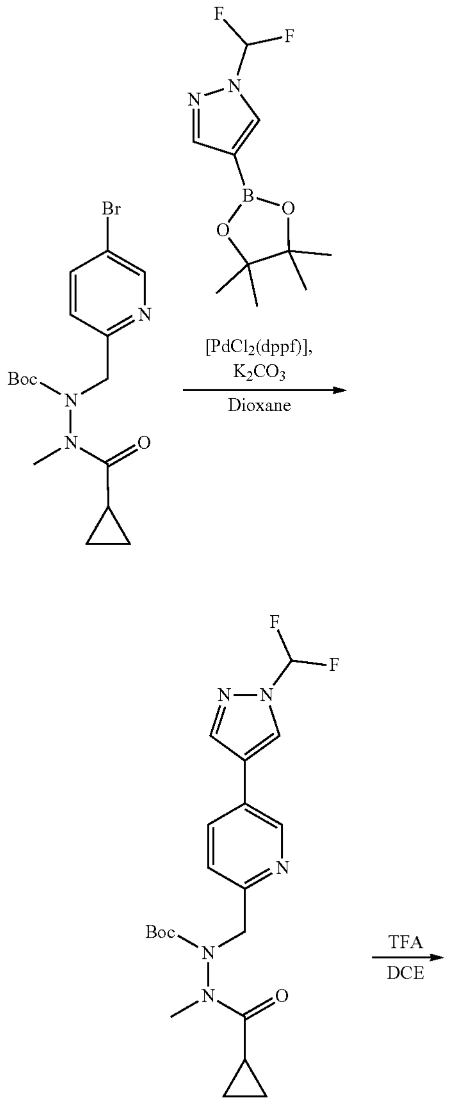

-continued

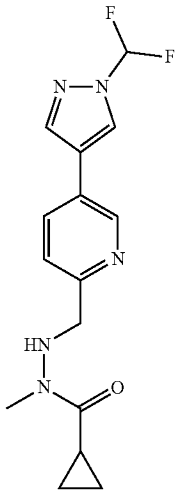

Bt-1

N'-((5-(1-(difluoromethyl)-1H-pyrazol-4-yl)pyridin-2-yl) methyl)-N-methylcyclopropanecarbohydrazide (Bt-1). To a solution of tert-butyl 1-((5-bromopyridin-2-yl)methyl)-2-(cyclopropanecarbonyl)-2-methylhydrazine-1-carboxylate (100 mg, 0.260 mmol) and 1-(difluoromethyl)-4-(4,4,5,5-tetramethyl-1,3,2-dioxaborolan-2-yl)-1H-pyrazole (69.9 mg, 0.286 mmol), and $PdCl_2$(dppf) (30.1 mg, 0.0406 mmol) in dioxane (2 mL), was added $K_2CO_3$ (180 mg, 1.30 mmol). The mixture was bubbled through argon for 1 minute and left to stir at 90 °C for 6 hours. The mixture was filtered through a pad of celite and anhydrous $MgSO_4$. The solution was reduced under pressure, dissolved in DCE (3 mL) and treated with TFA (1 mL) before stirring for 1 h at 70 °C. The solution was diluted with ethyl acetate then reduced under pressure and purified by column chromatography (MeOH/EtOAc). ES/MS: m/z=322.2 $[M+H]^+$.

Bt-2

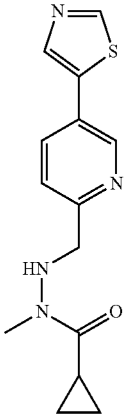

N-methyl-N'-((5-(thiazol-5-yl)pyridin-2-yl)methyl)cyclopropanecarbohydrazide (Bt-2). Prepared using general procedure XX-B starting with tert-butyl 1-((5-bromopyridin-2-yl)methyl)-2-(cyclopropanecarbonyl)-2-methylhydrazine-1-carboxylate and 5-(4,4,5,5-tetramethyl-1,3,2-dioxaborolan-2-yl)thiazole. ES/MS: m/z=247.2 $[M+H]^+$.

Bt-3

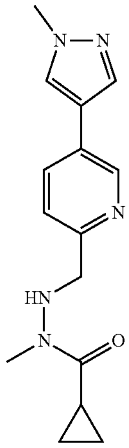

N-methyl-N'-((5-(1-methyl-1H-pyrazol-4-yl)pyridin-2-yl)methyl)cyclopropanecarbohydrazide (Bt-3). Prepared using general procedure XX-B starting with tert-butyl 1-((5-bromopyridin-2-yl)methyl)-2-(cyclopropanecarbonyl)-2-methylhydrazine-1-carboxylate and 1-methyl-4-(4,4,5,5-tetramethyl-1,3,2-dioxaborolan-2-yl)-1H-pyrazole. ES/MS: m/z=286.2 $[M+H]^+$.

Bt-4

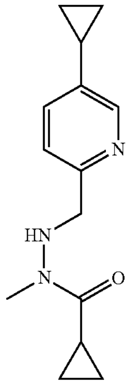

N'-((5-cyclopropylpyridin-2-yl)methyl)-N-methylcyclopropanecarbohydrazide (Bt-4). Prepared using general procedure XX-B starting with tert-butyl 1-((5-bromopyridin-2-yl)methyl)-2-(cyclopropanecarbonyl)-2-methylhydrazine-1-carboxylate and cyclopropylboronic acid (5 equiv). ES/MS: m/z=286.2 $[M+H]^+$.

Bt-5

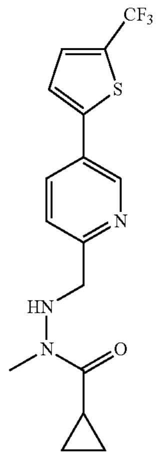

N-methyl-N'-((5-(5-(trifluoromethyl)thiophen-2-yl)pyridin-2-yl)methyl)cyclopropanecarbohydrazide (Bt-5). Prepared using general procedure XX-B starting with tert-butyl 1-((5-bromopyridin-2-yl)methyl)-2-(cyclopropanecarbonyl)-2-methylhydrazine-1-carboxylate and (5-(trifluoromethyl)thiophen-2-yl)boronic acid. ES/MS: m/z=356.2 [M+H]+.

Bt-6

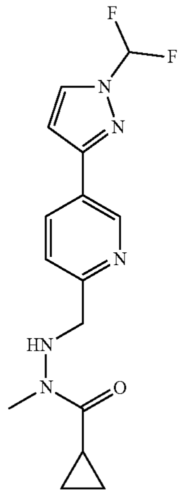

N'-((5-(1-(difluoromethyl)-1H-pyrazol-3-yl)pyridin-2-yl)methyl)-N-methylcyclopropanecarbohydrazide (Bt-6). Prepared using general procedure XX-B starting with tert-butyl 1-((5-bromopyridin-2-yl)methyl)-2-(cyclopropanecarbonyl)-2-methylhydrazine-1-carboxylate and 1-(difluoromethyl)-3-(4,4,5,5-tetramethyl-1,3,2-dioxaborolan-2-yl)-1H-pyrazole. ES/MS: m/z=322.2 [M+H]+.

General Procedure XXI-B for the Synthesis of Intermediates Bu

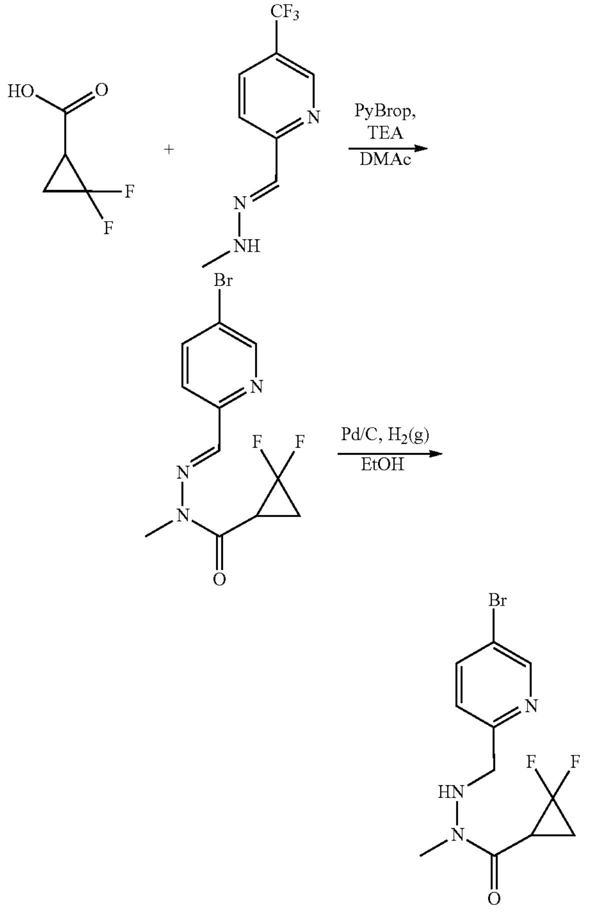

Bu-1

(E)-N'-((5-bromopyridin-2-yl)methylene)-2,2-difluoro-N-methylcyclopropane-1-carbohydrazide (Bu-1)

To a stirred suspension of (E)-2-((2-methylhydrazineylidene)methyl)-5-(trifluoromethyl)pyridine (200 mg, 0.98 mmol), 2,2-difluorocyclopropane-1-carboxylic acid (240 mg, 2.0 mmol), and Triethylamine (0.34 mL, 2.5 mmol) in DMAc (8 mL) was added Bromo-tris-pyrrolidino-phosphonium hexafluorophosphate (PyBroP) (1147 mg, 2.5 mmol). The mixture was stirred overnight at room temperature. The reaction was diluted with EtOAc and washed with 5% aqueous LiCl solution three times. The organic layer was dried over magnesium sulfate and evaporated under reduced pressure. The crude residue was dissolved in EtOH (10 mL), and Pd/C (10% w/w, 105 mg) was added. The heterogeneous mixture was stirred vigorously at room temperature under hydrogen gas (1 atm). The reaction was stirred until LCMS showed full conversion of the imine. The mixture was filtered through a pad of celite and the organic solution was reduced under pressure and purified by flash silica gel chromatography (MeOH/EtOAc) to afford the desired product (304 mg, 47%). ES/MS: m/z=310.2 [M+H]+.

General Procedure XXII-B for the Synthesis of Intermediates Bv

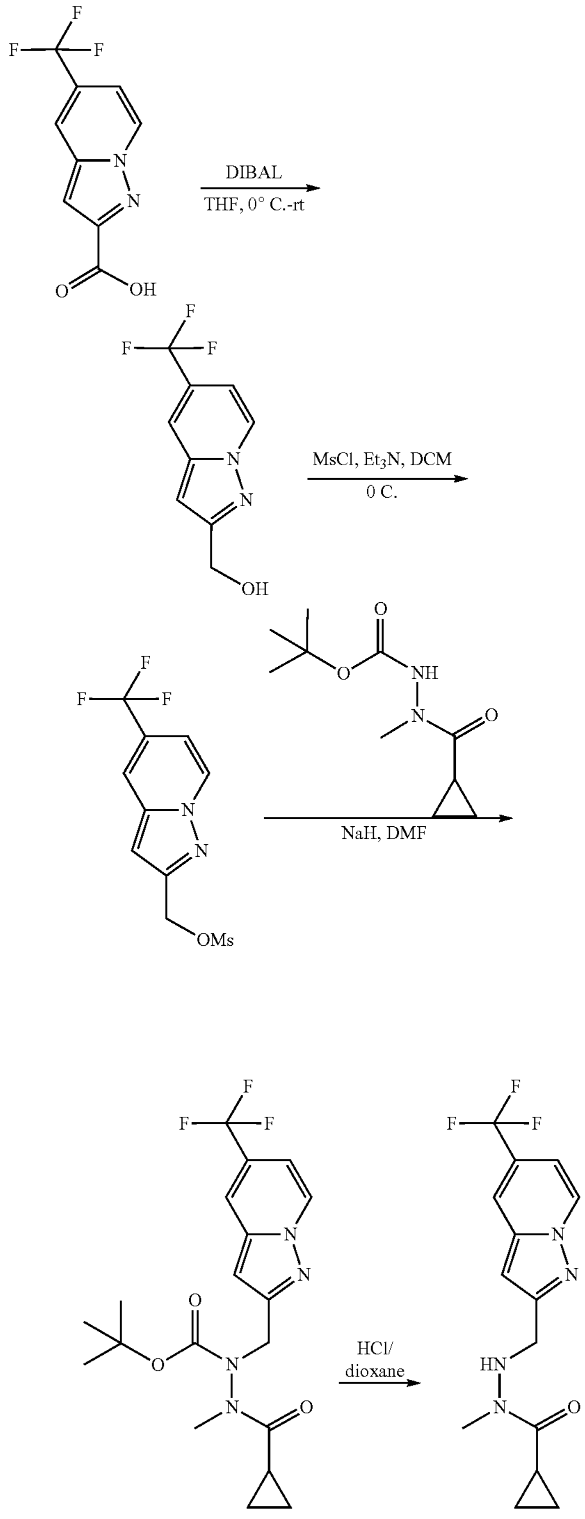

Bv-1

Step 1: (5-(trifluoromethyl)pyrazolo[1,5-a]pyridin-2-yl) methanol. To a suspension of 5-(trifluoromethyl)pyrazolo[1,5-a]pyridine-2-carboxylic acid (300 mg, 1.3 mmol) in THF (5 mL) at 0 deg, was added diisobutylaluminum hydride (1.0 M in THF) (1.63 mL, 3.3 mmol). Gradually warmed to rt and for an hour. The reaction was slowly quenched with sat'd $NH_4Cl$. Concentrated off THF. Extracted with EtOAc and dried over sodium sulfate to give desired product. ES/MS: m/z=217.0 $[M+H]^+$.

Step 2: (5-(trifluoromethyl)pyrazolo[1,5-a]pyridin-2-yl) methyl methanesulfonate. To a solution of (5-(trifluoromethyl)pyrazolo[1,5-a]pyridin-2-yl)methanol (282 mg, 1.30 mmol) in DCM (5 mL) at 0 deg, was added triethylamine (0.218 mL, 1.57 mmol) followed by methanesulfonyl chloride (0.122 mL, 1.57 mmol). After 10 min, the reaction was partitioned with EtOAc and brine. The organic extract was dried over sodium sulfate and concentrated to give desired product. ES/MS: m/z=295.0 $[M+H]^+$.

Step 3: tert-butyl 2-(cyclopropanecarbonyl)-2-methyl-1-((5-(trifluoromethyl)pyrazolo[1,5-a]pyridin-2-yl)methyl) hydrazine-1-carboxylate. To a solution of tert-butyl N-[cyclopropanecarbonyl(methyl)amino]carbamate (135 mg, 0.63 mmol) in DMF (2 mL) at 0 deg, was added sodium hydride (60.0%, 17.4 mg, 0.0.77 mmol). After 15 min, added a solution of (5-(trifluoromethyl)pyrazolo[1,5-a]pyridin-2-yl)methyl methanesulfonate (135 mg, 0.63 mmol) in DMF (3 mL) and stirred for 10 min. The reaction was diluted with EtOAc, quenched with saturated $NH_4Cl$ solution. Added 5% LiCl, separated organic extract. Washed once more with 5% LiCl and brine. The organic extract was dried over sodium sulfate, concentrated, and purified by flash chromatography to give desired product. ES/MS: m/z=413.0 $[M+H]^+$.

Step 4: N-methyl-N'-((5-(trifluoromethyl)pyrazolo[1,5-a]pyridin-2-yl)methyl)cyclopropanecarbohydrazide (Bv-1). A solution tert-butyl 2-(cyclopropanecarbonyl)-2-methyl-1-((5-(trifluoromethyl)pyrazolo[1,5-a]pyridin-2-yl)methyl) hydrazine-1-carboxylate. (260 mg, 0.63 mmol) and hydrochloric acid (4M in dioxane) (4000 mmol/L, 0.63 mL, 2.5 mmol) in DCM (4 mL) was stirred at rt o/n. The reaction was concentrated to dryness to give title compound. ES/MS: m/z=313.3 $[M+H]^+$.

Bv-2

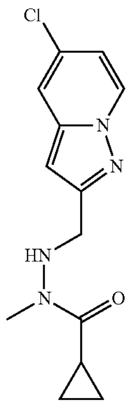

N'-((5-chloropyrazolo[1,5-a]pyridin-2-yl)methyl)-N-methylcyclopropanecarbohydrazide (Bv-2). Prepared using general procedure XXII-B starting with starting with methyl 5-chloropyrazolo[1,5-a]pyridine-2-carboxylate. ES/MS: m/z=279.3

Bv-3

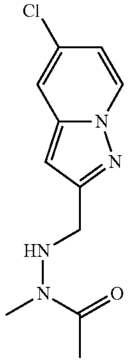

N'-((5-chloropyrazolo[1,5-a]pyridin-2-yl)methyl)-N-methylacetohydrazide (Bv-3). Prepared using general procedure XXII-B starting with starting with methyl 5-chloropyrazolo[1,5-a]pyridine-2-carboxylate and tert-butyl 2-acetyl-2-methylhydrazine-1-carboxylate. ES/MS: m/z=253.1 $[M+H]^+$.

Bv-4

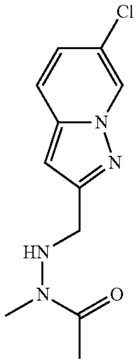

N'-((6-chloropyrazolo[1,5-a]pyridin-2-yl)methyl)-N-methylacetohydrazide (Bv-4). Prepared using general procedure XXII-B starting with starting with methyl 6-chloropyrazolo[1,5-a]pyridine-2-carboxylate and tert-butyl 2-acetyl-2-methylhydrazine-1-carboxylate. ES/MS: m/z=253.1 $[M+H]^+$.

Bv-5

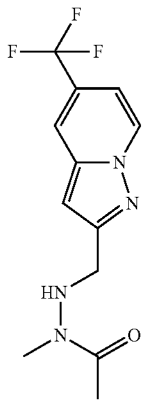

N-methyl-N'-((5-(trifluoromethyl)pyrazolo[1,5-a]pyridin-2-yl)methyl)acetohydrazide (Bv-5). Prepared using general procedure XXII-B starting with starting with 5-(trifluoromethyl)pyrazolo[1,5-a]pyridine-2-carboxylic acid and tert-butyl 2-acetyl-2-methylhydrazine-1-carboxylate. ES/MS: m/z=287.2 $[M+H]^+$.

General Procedure XXIII-B for the Synthesis of Intermediates Bw

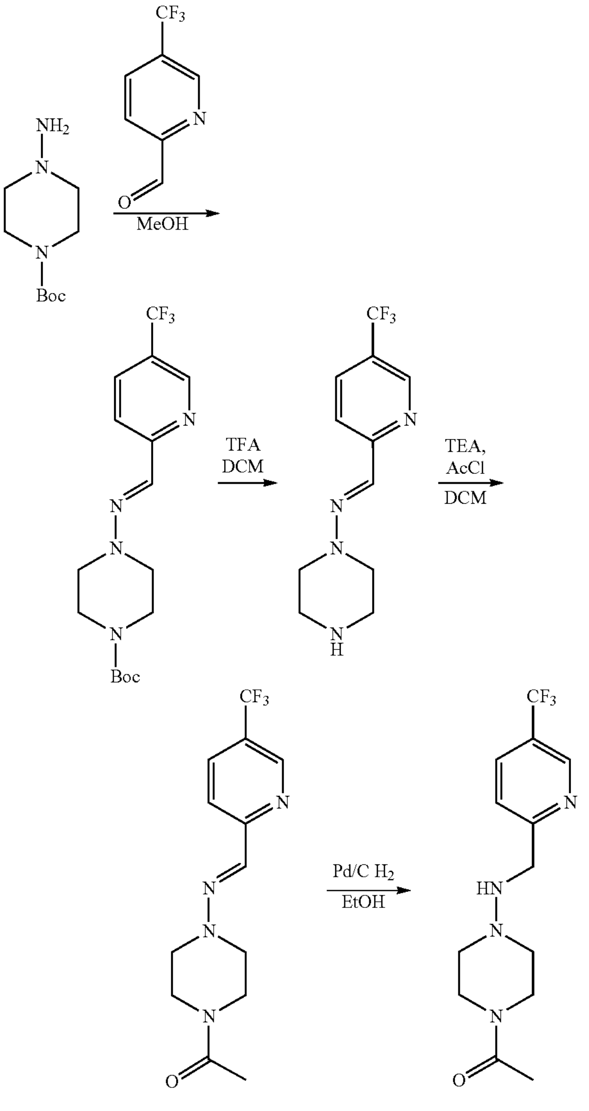

Bw-1

Step 1: (E)-tert-butyl 4-(((5-(trifluoromethyl)pyridin-2-yl)methylene)amino)piperazine-1-carboxylate To a solution of tert-butyl 4-aminopiperazine-1-carboxylate (1.1 g, 5.4 mmol, 1 eq) in MeOH (8 mL) was added 5-(trifluoromethyl)pyridine-2-carbaldehyde (765.6 mg, 4.3 mmol, 0.8 eq). The mixture was stirred at 25 °C for 4 hr. The reaction mixture concentrated under reduced pressure to give desired product, which was used into the next step without further purification. $^1H$ NMR (DMSO-$d_6$, 400

MHZ) δ 8.85 (d, 1H, J=1.0 Hz), 8.09 (dd, 1H, J=2.2, 8.5 Hz), 7.9-7.9 (m, 1H), 7.62 (s, 1H), 3.5-3.6 (m, 4H), 3.3-3.3 (m, 4H), 1.41 (s, 9H).

Step 2: (E)-N-((5-(trifluoromethyl)pyridin-2-yl) methylene)piperazin-1-amine

To a solution of (E)-tert-butyl 4-(((5-(trifluoromethyl) pyridin-2-yl)methylene)amino)piperazine-1-carboxylate (1.9 g, 5.4 mmol, 1 eq) in DCM (20 mL) was added TFA (3.0 g, 26.9 mmol, 2 mL, 4.9 eq). The mixture was stirred at 25 °C for 1 hr. LC-MS showed Reactant 4 remained and desired compound was detected. The mixture was stirred at 25 °C for 12 hr, after which additional TFA (1.5 g, 13.4 mmol, 1 mL, 2.4 eq) was added to the solution. The mixture was stirred at 25 °C for 5 hr. The reaction mixture concentrated under reduced pressure to give a residue. The residue was purified by flash silica gel chromatography (dichloromethane/methanol) to give desired product. ES/MS: m/z=259.3 $[M+H]^+$. $^1H$ NMR (DMSO-$d_6$, 400 MHz) δ 9.30 (br s, 1H), 8.89 (br d, 1H, J=0.9 Hz), 8.14 (dd, 1H, J=2.1, 8.4 Hz), 7.94 (d, 1H, J=8.6 Hz), 7.7-7.8 (m, 1H), 3.4-3.6 (m, 4H), 3.3-3.4 (m, 4H).

Step 3: (E)-1-(4-(((5-(trifluoromethyl)pyridin-2-yl) methylene)amino)piperazin-1-yl)ethanone To a solution of (E)-N-((5-(trifluoromethyl)pyridin-2-yl) methylene)piperazin-1-amine (1 g, 3.8 mmol, 1 eq) in DCM (10 mL) was added TEA (431.0 mg, 4.2 mmol, 592.8 μL, 1.1 eq) adjust pH 6-7. Then acetyl chloride (334.3 mg, 4.2 mmol, 302.8 μL, 1.1 eq) was added to the solution at 0 °C. The mixture was stirred at 25 °C for 1 hr. The reaction mixture concentrated under reduced pressure to give a residue. The reaction mixture was quenched by addition $NaHCO_3$20 mL, and then diluted with $H_2O$ 10 mL and extracted with Dichloromethane 45 mL (15 mL×3). The combined organic layers were washed with solvent 90 mL (30 mL×3), dried over $Na_2SO_4$, filtered and concentrated under reduced pressure to give a residue. The residue was purified by flash silica gel chromatography (Ethyl acetate/Petroleum ether) to give desired product. ES/MS: m/z=301.2 $[M+H]^+$. $^1H$ NMR (DMSO-$d_6$, 400 MHz) δ 8.86 (s, 1H), 8.1-8.2 (m, 1H), 7.92 (d, 1H, J=8.4 Hz), 7.63 (s, 1H), 3.63 (br d, 4H, J=4.8 Hz), 3.3-3.4 (m, 2H), 3.2-3.3 (m, 2H), 2.05 (s, 3H).

Step 4: 1-(4-(((5-(trifluoromethyl)pyridin-2-yl) methyl)amino)piperazin-1-yl)ethan-1-one (Bw-1)

(E)-1-(4-(((5-(trifluoromethyl)pyridin-2-yl)methylene) amino)piperazin-1-yl)ethenone (75 mg, 0.25 mmol) was dissolved in EtOH (3 mL) and Pd/C (10% w/w, 40 mg, 0.37 mmol) was added. The heterogeneous mixture was stirred vigorously at room temperature under hydrogen gas (1 atm) for 15 hr. The reaction was stirred until LCMS showed full conversion of the imine. The mixture was filtered through a pad of celite and the organic solution was reduced under pressure and purified by flash chromatography to give desired product. ES/MS: m/z=303.2 $[M+H]^+$.

General Procedure C-1 for the Synthesis of Intermediates Ca

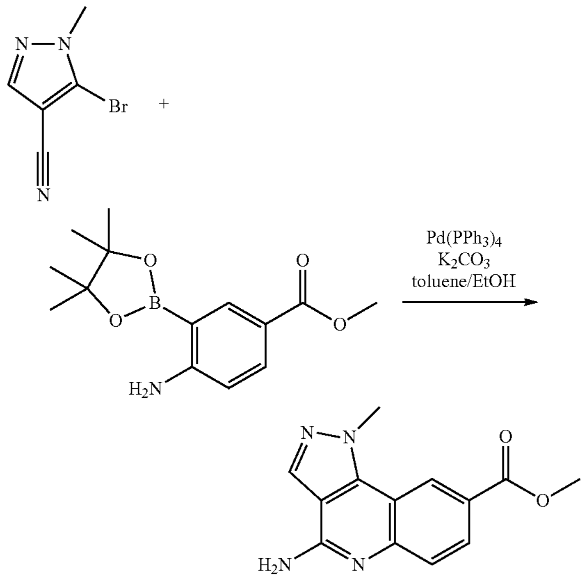

Ca-1

Methyl 4-amino-1-methyl-1H-pyrazolo[4,3-c]quinoline-8-carboxylate (Ca-1). A suspension of methyl 4-amino-3-(4,4,5,5-tetramethyl-1,3,2-dioxaborolan-2-yl)benzoate (1095 mg, 3.95 mmol) 5-bromo-1-methyl-pyrazole-4-carbonitrile (736 mg, 3.96 mmol), tetrakis(triphenylphosphine) palladium(O) (457 mg, 0.395 mmol), and potassium carbonate (1092 mg, 7.90 mmol) in toluene (10 mL) and EtOH (2 mL) was degassed with argon for 5 min, then heated at 100 deg for overnight. The reaction was diluted with EtOAc and washed with saturated $NH_4Cl$. The resulting solid was filtered and air-dried to give desired product. ES/MS: m z 257.2 $[M+H]^+$. $^1H$ NMR (400 MHz, DMSO-$d_6$) δ 8.82 (d, J=2.0 Hz, 1H), 8.29 (s, 1H), 8.03 (dd, J=8.7, 2.0 Hz, 1H), 7.62 (d, J=8.7 Hz, 1H), 7.38 (s, 2H), 4.43 (s, 3H), 3.90 (s, 3H).

General Procedure C-2 for the Synthesis of Intermediates Cb

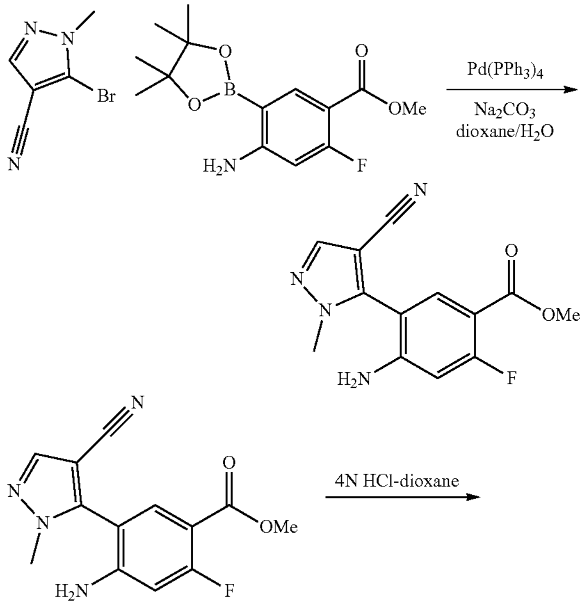

-continued

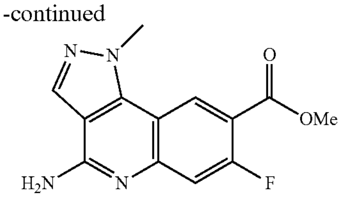

Cb-1

Step 1. Methyl 4-amino-1-methyl-1H-pyrazolo[4,3-c]quinoline-8-carboxylate. A suspension of methyl 4-amino-2-fluoro-5-(4,4,5,5-tetramethyl-1,3,2-dioxaborolan-2-yl)benzoate (40.0 g, 136 mmol), 5-bromo-1-methyl-pyrazole-4-carbonitrile (30.3 g, 163 mmol), sodium carbonate (28.7 g, 271 mmol), and tetrakis(triphenylphosphine)palladium(O) (15.7 g, 13.7 mmol) in dioxane (240 mL) and water (40 mL), was degassed with nitrogen. The reaction was heated at 100 deg for 12 hr. The reaction was partitioned with EtOAc (200 mL) and water (200 mL). The organic layer was washed with brine (200 mL), dried over sodium sulfate, concentrated, and carried onto the next step.

Step 2. Methyl 4-amino-7-fluoro-1-methyl-1H-pyrazolo[4,3-c]quinoline-8-carboxylate (Cb-1). A solution of crude material (20.0 g, 73 mmol) and 4.0M HCl in dioxane (50 mL, 200 mmol) was heated at 90 deg for 1 hr. The reaction was filtered, and the resulting filtrate was concentrated. The crude reaction mixture was triturated with petroleum ether/EtOAc (1:1, 30 mL) at rt for 1 hr to give desired product. $^1$H NMR (400 MHz, DMSO-$d_6$) δ 14.7-13.8 (m, 1H) 10.1 (br s, 1H) 8.92 (br s, 1H) 8.78-8.68 (m, 2H) 7.74 (d, J=11.6 Hz, 1H) 4.45 (s, 3H) 3.93 (s, 3H).

General Procedure C-3 for the Synthesis of Intermediates Cc

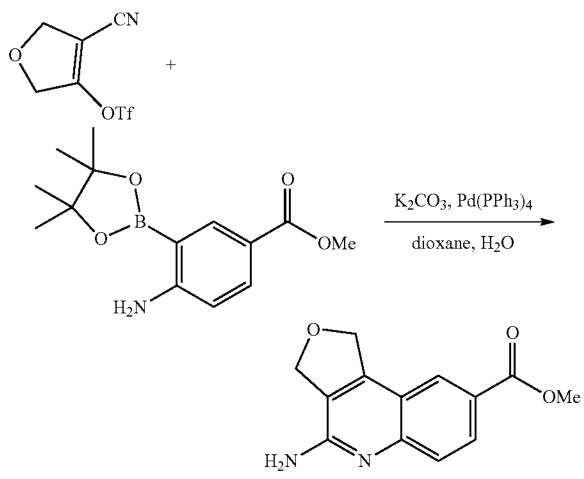

Cc-1

Methyl 4-amino-1,3-dihydrofuro[3,4-c]quinoline-8-carboxylate (Cc-1). $K_2CO_3$ (3.58 g, 25.9 mmol) and tetrakis(triphenylphosphine)palladium(O) (831 mg, 0.72 mmol) were successively added to a degassed solution of 4-cyano-2,5-dihydrofuran-3-yl trifluoromethanesulfonate (2.19 g, 8.99 mmol) and methyl 4-amino-3-(4,4,5,5-tetramethyl-1,3,2-dioxaborolan-2-yl)benzoate (4.00 g, 7.19 mmol) in dioxane/water (10:1, 22 mL). tetrakis(triphenylphosphine) palladium(O) (125 mg, 0.108 mmol). The resulting mixture was stirred under argon at 80 °C for 16 hours. Dioxane was evaporated under reduced pressure and the crude product was triturated with $H_2O$ (5.00 mL) and DCM (4.00 mL) at 25 °C for 1 hr then filtered and to give the desired product. $^1$H NMR (400 MHz, DMSO-$d_6$): δ 7.07-7.00 (m, 1H), 6.97-6.88 (m, 1H), 6.58-6.42 (m, 1H), 5.94-5.79 (m, 1H), 4.39-4.25 (m, 2H), 4.02-3.83 (m, 2H), 3.07-2.55 (m, 1H), 2.80 (s, 3H).

General Procedure C-4 for the Synthesis of Intermediates Cd

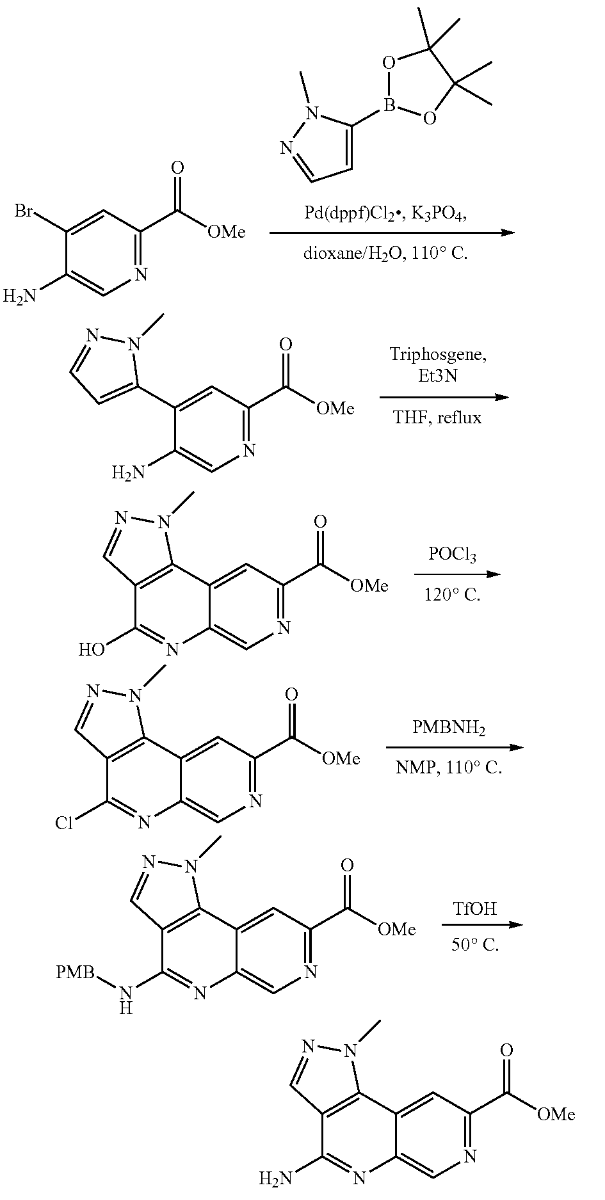

Cd-1

Step 1: Methyl 5-amino-4-(1-methyl-1H-pyrazol-5-yl)picolinate. To a stirred solution of methyl 5-amino-4-bromopicolinate 1-methyl-5-(4,4,5,5-tetramethyl-1,3,2-dioxaborolan-2-yl)-1H-pyrazole in dioxane-water (4:1) was added $K_3PO_4$ under argon purging. Then added $PdCl_2$(dppf) and reaction mixture was purged with argon for 10 min. Reaction mixture was heated to 110 °C for 5 h. Reaction progress was monitored by LCMS and TLC. Reaction mixture was cooled to RT, filtered through celite pad, washed with 100 mL EtOAc. Filtrate was distilled under vacuum, to get crude.

The obtained crude was purified by column chromatography using 2% MeOH in DCM to afford methyl 5-amino-4-(1-methyl-1H-pyrazol-5-yl)picolinate. ES/MS: m/z=233.1 $[M+H]^+$.

Step 2: Methyl 4-hydroxy-1-methyl-1H-pyrazolo[4,3-c][1,7]naphthyridine-8-carboxylate. Methyl 5-amino-4-(1-methyl-1H-pyrazol-5-yl)picolinate was dissolved in THF, added Triphosgene under argon followed by trimethylamine Reaction mixture was heated to 80 °C for 24 h. Progress of the reaction was monitored by LCMS/TLC. Reaction mixture was cooled to room temperature, poured in to crush ice, stirred for 10 min. added 10% MeOH-DCM (5 vol) and filtered through celite pad. Filtrate taken and separated the organic layer. Organic layer was dried over $Na_2SO_4$, concentrated to get methyl 4-hydroxy-1-methyl-1H-pyrazolo[4,3-c][1,7]naphthyridine-8-carboxylate (Crude with 35% purity by LCMS) as Brown solid. The obtained crude was used to next step without further purification.

Step 3: Methyl 4-chloro-1-methyl-1H-pyrazolo[4,3-c][1,7]naphthyridine-8-carboxylate. Methyl 4-hydroxy-1-methyl-1H-pyrazolo[4,3-c][1,7]naphthyridine-8-carboxylate and $POCl_3$ were heated to reflux for 3 h. Reaction progress was monitored by LCMS/TLC. After completion of the reaction cooled to RT, concentrated the reaction mixture under vacuum to get crude. The obtained crude was diluted with DCM (100 mL) and loaded on 100-200 silicagel. Column was eluted with 2% MeOH-DCM to afford methyl 4-chloro-1-methyl-1H-pyrazolo[4,3-c][1,7]naphthyridine-8-carboxylate as a Pale yellow solid. ES/MS: m/z=277.1 $[M+H]^+$.

Step 4: Methyl 4-((4-methoxybenzyl)amino)-1-methyl-1H-pyrazolo[4,3-c][1,7]naphthyridine-8-carboxylate. To a stirred solution of methyl 4-chloro-1-methyl-1H-pyrazolo[4,3-c][1,7]naphthyridine-8-carboxylate in NMP added PMBNH2. The reaction mixture was heated to 110 °C for 12 h. Reaction mixture was cooled to RT, quenched with ice cooled water. Reaction mixture was extracted with EtOAc (3×50 mL). Taken the organic layer and dried over $Na_2SO_4$. Concentrated the organic layer to get crude. purified by column chromatography by using 1% MeOH in DCM to afford methyl 4-((4-methoxybenzyl)amino)-1-methyl-1H-pyrazolo[4,3-c][1,7]naphthyridine-8-carboxylate as a yellow solid. ES/MS: m/z=378.1 $[M+H]^+$.

Step 5: Methyl 4-amino-1-methyl-1H-pyrazolo[4,3-c][1,7]naphthyridine-8-carboxylate (Cd-1). To a stirred solution of methyl 4-((4-methoxybenzyl)amino)-1-methyl-1H-pyrazolo[4,3-c][1,7]naphthyridine-8-carboxylate in DCM added triflic acid drop wise at RT. Reaction mixture was heated to 50 °C for 12 h. Reaction progress was monitored by LCMS/TLC. Reaction mixture was cooled to rt, distilled out DCM, poured in ice cooled water and ph was adjusted to 8 with sat $NaHCO_3$ solution. Stirred for 5 min. Filtered the reaction mixture to afford pure methyl 4-amino-1-methyl-1H-pyrazolo[4,3-c][1,7]naphthyridine-8-carboxylate. ES/MS: m/z=378.1 $[M+H]^+$.

General Procedure D-1 for the Synthesis of Intermediates Da

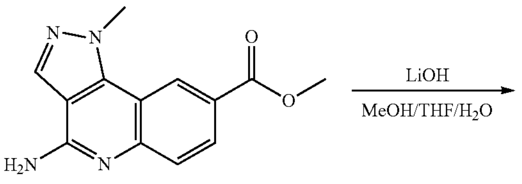

Ca-1

-continued

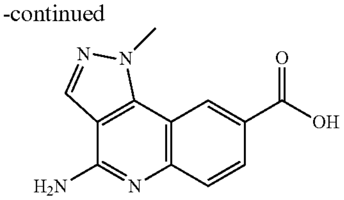

Da-1

4-amino-1-methyl-1H-pyrazolo[4,3-c]quinoline-8-carboxylic acid (Da-1). A suspension of methyl 4-amino-1-methyl-pyrazolo[4,3-c]quinoline-8-carboxylate (885 mg, 3.45 mmol) and Lithium hydroxide, monohydrate (435 mg, 10.4 mmol) in MeOH (5 mL), THF (5 mL), and water (5 mL) was stirred at 50 deg until starting material was consumed. The reaction was concentrated to dryness, diluted with water (2 mL), $CH_3CN$ (5 mL), and 1N HCl (8 mL) to pH 5. The resulting suspension was filtered and air-dried to give desired product. ES/MS: m z 243.2 $[M+H]^+$. $^1H$ NMR (400 MHz, DMSO-$d_6$) δ 8.81 (d, J=1.9 Hz, 1H), 8.29 (s, 1H), 8.02 (dd, J=8.7, 1.9 Hz, 1H), 7.60 (d, J=8.7 Hz, 1H), 7.35 (s, 2H), 4.42 (s, 3H).

Da-2

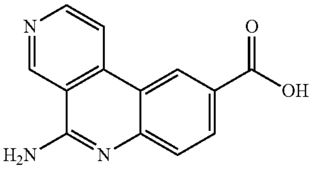

5-aminobenzo[c][2,7]naphthyridine-9-carboxylic acid (Da-2). Prepared using general procedures C-1 and D-1 starting with 4-bromonicotinonitrile. ES/MS: m z 240.1

Da-3

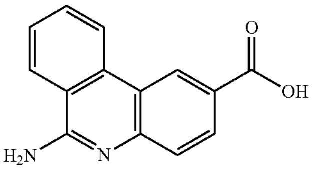

6-aminophenanthridine-2-carboxylic acid (Da-3). Prepared using general procedures C-1 and D-1 starting with 2-bromobenzonitrile. ES/MS: m/z 239.2 $[M+H]^+$.

Da-4

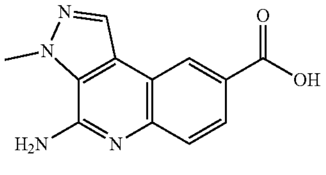

4-amino-3-methyl-3H-pyrazolo[3,4-c]quinoline-8-carboxylic acid (Da-4). Prepared using general procedures C-1 and D-1 starting with 4-bromo-1-methyl-1H-pyrazole-5-carbonitrile. ES/MS: m/z 257.1 $[M+H]^+$.

Da-5

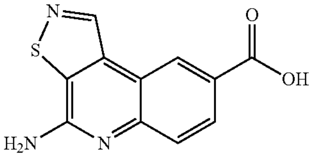

4-aminoisothiazolo[5,4-c]quinoline-8-carboxylic acid (Da-5). Prepared using general procedures C-1 and D-1 starting with 4-bromoisothiazole-5-carbonitrile. ES/MS: m/z 246.0 $[M+H]^+$.

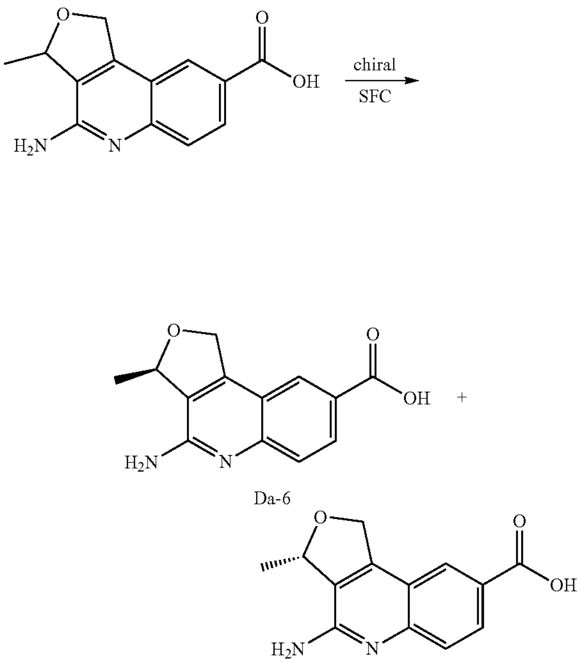

Da-6

(R)-4-amino-3-methyl-1,3-dihydrofuro[3,4-c]quinoline-8-carboxylic acid (Da-6). 4-amino-3-methyl-1,3-dihydrofuro[3,4-c]quinoline-8-carboxylic acid was prepared using general procedures C-3 and D-1. Chiral SFC (column: DAICEL CHIRALPAK IC (250 mm×50 mm, 10 um) mobile phase: [0.1% $NH_3$·$H_2O$ MeOH]; B %: 50%-50%, 9 min) afforded Da-6 (second peak). ES/MS: m/z 245.1 $[M+H]^+$. $^1H$ NMR (DMSO-$d_6$ 400 MHz): δ 12.8 (s, 1H), 8.09-7.97 (m, 2H), 7.58-7.56 (d, J=8.0 Hz, 2H), 5.44-5.30 (s, 3H), 1.42-1.41 (d, J=4.0 Hz, 3H).

Da-7

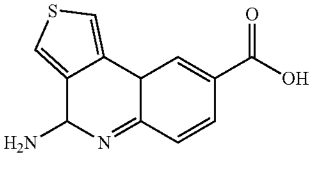

4-amino-4,9a-dihydrothieno[3,4-c]quinoline-8-carboxylic acid (Da-7). Prepared using general procedures C-1 and D-1 starting with 4-bromothiophene-3-carbonitrile. ES/MS: m/z 245.1 $[M+H]^+$.

4-amino-2-(2-trimethylsilylethoxymethyl)pyrazolo [4,3-c]quinoline-8-carboxylic acid (Da-8)

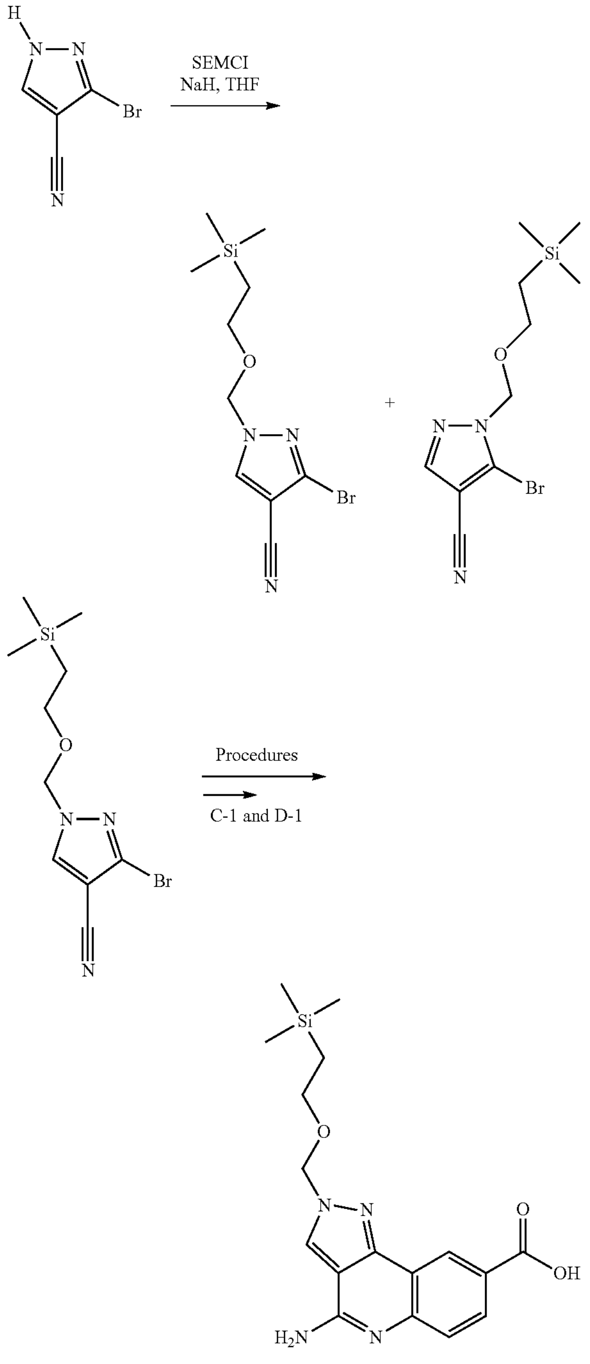

Da-8

Step 1. 3-bromo-1-(2-trimethylsilylethoxymethyl)pyrazole-4-carbonitrile and 5-bromo-1-(2-trimethylsilylethoxymethyl)pyrazole-4-carbonitrile. To a solution of 3-bromo-1H-pyrazole-4-carbonitrile (1000 mg, 5.81 mmol) in THF (15 ml) at 0 deg, was added sodium hydride (60.0%, 446 mg, 11.6 mmol). The gray slurry was stirred for 30 min, then added 2-(Trimethylsilyl)ethoxymethyl Chloride (1.29 ml, 7.27 mmol). Gradually warmed to rt and stirred overnight. The reaction was diluted with EtOAc and water. The organic extract was washed with brine. The aqueous layer was extracted with EtOAc. The organic extracts were combined and dried over sodium sulfate. Purification by flash chromatography gave a 1:1 mix of regio-isomeric products. $^1H$ NMR (400 MHz, Chloroform-d) δ 7.95 (s, 1H), 7.87 (s, 1H), 5.54 (s, 2H), 5.43 (s, 2H), 3.84-3.48 (m, 4H), 1.01-0.91 (m, 4H), 0.03 (s, 9H), 0.01 (s, 9H).

Step 2. 4-amino-2-(2-trimethylsilylethoxymethyl)pyrazolo[4,3-c]quinoline-8-carboxylic acid (Da-8). Prepared general procedures C-1 and D-1 starting with a 1:1 mixture of 3-bromo-1-(2-trimethylsilylethoxymethyl)pyrazole-4-carbonitrile and 5-bromo-1-(2-trimethylsilylethoxymethyl) pyrazole-4-carbonitrile. ES/MS: m/z 359.0 $[M+H]^+$. $^1H$ NMR (400 MHz, DMSO-$d_6$) δ 12.81 (s, 1H), 8.85 (d, J=1.9 Hz, 1H), 8.41 (s, 1H), 8.05 (s, 1H), 7.64 (s, 1H), 7.43 (s, 2H), 6.00 (s, 2H), 3.63 (t, J=8.0 Hz, 2H), 0.87 (dd, J=8.5, 7.4 Hz, 2H), −0.12 (s, 9H).

Da-9

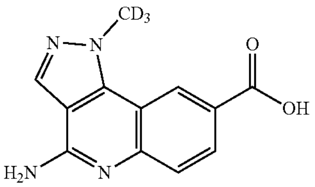

4-amino-1-(methyl-d3)-1H-pyrazolo[4,3-c]quinoline-8-carboxylic acid (Da-9). Prepared using general procedures C-2 and D-1 starting with 5-bromo-1-(methyl-d3)-1H-pyrazole-4-carbonitrile. 5-bromo-1-(methyl-d3)-1H-pyrazole-4-carbonitrile was obtained by alkylation of commercial 5-bromo-1H-pyrazole-4-carbonitrile using NaH in DMF and $CD_3I$. ES/MS: m/z=246.1 $[M+H]^+$.

Da-10

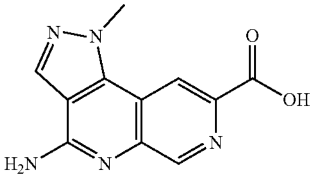

4-Amino-1-methyl-1H-pyrazolo[4,3-c][1,7]naphthyridine-8-carboxylic acid (Da-10). Prepared using general procedure D-1 (MeCN/$H_2O$ used as solvent) starting with Cd-1. ES/MS: m/z=244.2 $[M+H]^+$.

General Procedure D-2 for the Synthesis of Intermediates Db

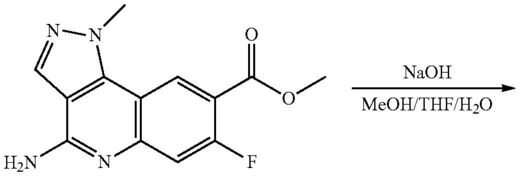

Cb-1

-continued

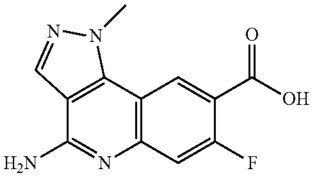

Db-1

4-amino-7-fluoro-1-methyl-1H-pyrazolo[4,3-c]quinoline-8-carboxylic acid (Db-1). NaOH (10.9 g, 273 mmol) was added to a solution of methyl 4-amino-7-fluoro-1-methyl-1H-pyrazolo[4,3-c]quinoline-8-carboxylate (15.0 g, 54.7 mmol) in $H_2O$ (75.0 mL), MeOH (150 mL) and THF (150 mL). The reaction was heated at 60 deg for 2 hr. The reaction mixture was concentrated under reduced pressure and neutralized to pH 6 with HCl. The resulting mixture was filtered and dried to give desired product. ES/MS: m/z 259.0/260.0 $[M+H]^+$. $^1H$ NMR (400 MHz, DMSO-$d_6$) δ 9.90 (br s, 1H) 9.23 (br s, 1H) 8.78 (d, J=7.2 Hz, 1H) 8.62 (s, 1H) 7.60 (d, J=11.2 Hz, 1H) 4.46 (s, 3H).

Db-2

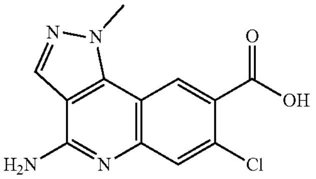

4-amino-7-chloro-1-methyl-1H-pyrazolo[4,3-c]quinoline-8-carboxylic acid (Db-2). Prepared following general procedure C-2 and D-2 starting with 5-bromo-1-methyl-pyrazole-4-carbonitrile and methyl 4-amino-2-chloro-5-(4,4,5,5-tetramethyl-1,3,2-dioxaborolan-2-yl)benzoate. ES/MS: m/z 277.0 $[M+H]^+$. $^1H$ NMR (400 MHz, DMSO-$d_6$) δ 9.95 (br s, 1H), 9.35 (br s, 1H), 8.77-8.55 (m, 2H), 7.82 (s, 1H), 4.44 (s, 3H).

Db-3

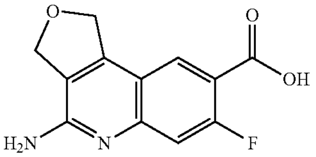

4-amino-7-fluoro-1,3-dihydrofuro[3,4-c]quinoline-8-carboxylic acid (Db-3). Prepared using general procedures C-3 and D-2 starting with 4-cyano-2,5-dihydrofuran-3-yl trifluoromethanesulfonate and methyl 4-amino-2-fluoro-5-(4,4,5,5-tetramethyl-1,3,2-dioxaborolan-2-yl)benzoate. $^1H$ NMR (400 MHz, DMSO-$d_6$) δ 9.18 (br s, 2H), 8.23 (d, J=7.6 Hz, 1H), 7.56 (d, J=11.4 Hz, 1H), 5.47 (t, J=3.6 Hz, 2H), 5.07 (t, J=3.4 Hz, 2H). ES/MS: m/z 249.9 $[M+H]^+$.

Db-4

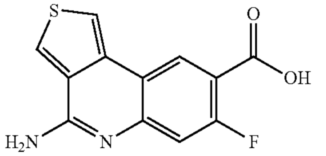

4-amino-7-fluorothieno[3,4-c]quinoline-8-carboxylic acid (Db-4). Prepared using general procedures C-2 and D-2 starting with methyl 4-amino-2-fluoro-5-(4,4,5,5-tetramethyl-1,3,2-dioxaborolan-2-yl)benzoate and 4-bromothiophene-3-carbonitrile. ES/MS: m/z 262.9 $[M+H]^+$. $^1$H NMR (400 MHz, DMSO-$d_6$) δ 10.1 (br s, 1H), 9.74 (br s, 1H), 9.21 (d, J=2.8 Hz, 1H), 8.82 (d, J=3.0 Hz, 1H), 8.70 (d, J=7.4 Hz, 1H), 7.36 (d, J=11.4 Hz, 1H).

Db-5

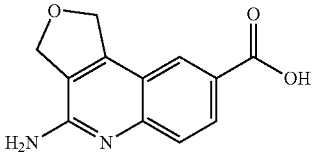

4-amino-1,3-dihydrofuro[3,4-c]quinoline-8-carboxylic acid (Db-5). Prepared using general procedures D-2 starting with Cc-1. ES/MS: m/z 231.2 $[M+H]^+$. $^1$H NMR (400 MHZ, DMSO-$d_6$) δ 13.0-12.7 (m, 1H), 8.06 (d, J=1.8 Hz, 1H), 7.96 (dd, J=8.8, 1.8 Hz, 1H), 7.54 (d, J=8.8 Hz, 1H), 6.89-6.79 (m, 2H), 5.36 (t, J=3.4 Hz, 2H), 5.00 (t, J=3.4 Hz, 2H).

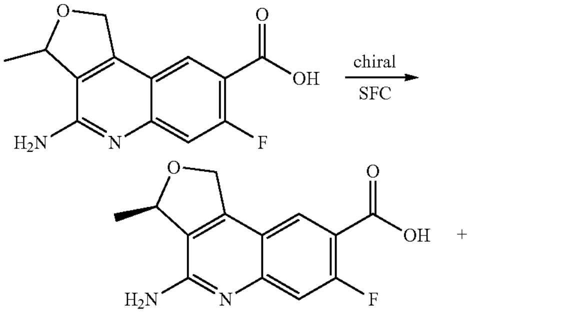

Db-6

(R)-4-amino-7-fluoro-3-methyl-1,3-dihydrofuro[3,4-c]quinoline-8-carboxylic acid (Db-6). 4-amino-7-fluoro-3-methyl-1,3-dihydrofuro[3,4-c]quinoline-8-carboxylic acid was prepared using general procedures C-3 and D-2. Chiral SFC (column: DAICEL CHIRALPAK IC (250 mm×50 mm, 10 um) mobile phase: [0.1% $NH_3 \cdot H_2O$ MEOH]; B %: 50%-50%, 9 min) afforded Db-6 (second peak). ES/MS: m/z 263.0 $[M+H]^+$. $^1$H NMR (DMSO 400 MHZ): δ 8.05-8.03 (d, J=8.0 Hz, 1H), 7.26-7.23 (d, J=13.2 Hz, 1H), 6.97 (s, 2H), 5.27-5.41 (m, 3H), 1.40-1.39 (d, J=5.2 Hz, 3H).

General procedure E-1 for the coupling of hydrazides with acids

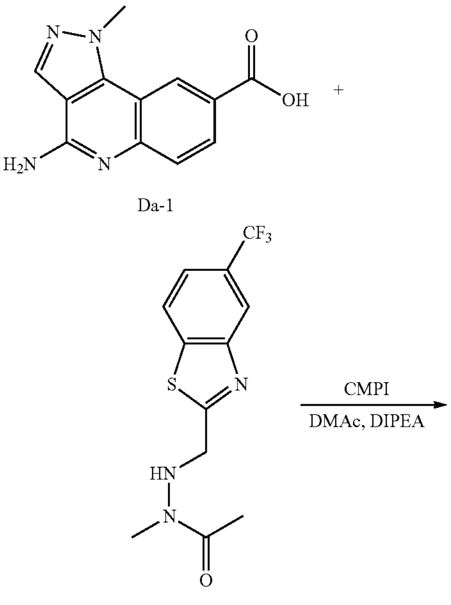

Da-1

Bb-1

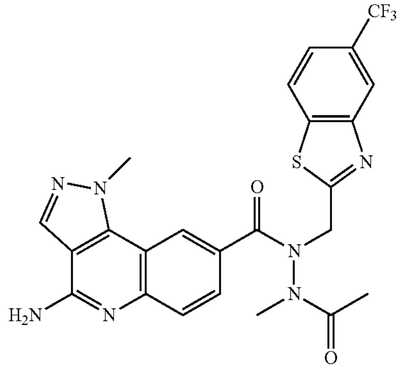

Example 1

Example 1: N'-acetyl-4-amino-N',1-dimethyl-N-((5-(trifluoromethyl)benzo[d]thiazol-2-yl)methyl)-3a,9b-dihydro-1H-pyrazolo[4,3-c]quinoline-8-carbohydrazide. 4-amino-1-methyl-1H-pyrazolo[4,3-c]quinoline-8-carboxylic acid Da-1 (30 mg, 0.12 mmol), N-methyl-N'-((5-(trifluoromethyl)benzo[d]thiazol-2-yl)methyl)acetohydrazide Bb-1 (44 mg, 0.14 mmol) and 2-chloro-1-methyl-pyridin-1-ium iodide (44 mg, 0.17 mmol) were dissolved in DMAc (1.5 mL) and DIPEA (44 μL, 0.25 mmol) was added. The resulting mixture was stirred at 30 °C overnight and then diluted with EtOAc and 10% aq. LiCl solution and transferred to a separatory funnel. The organic layer was separated, and the aqueous layer was washed with a further portion of EtOAc. The combined organic layers were dried over anhydrous $MgSO_4$ and concentrated under reduced pressure. The crude residue was purified by preparative HPLC. ES/MS: m/z=528.2 $[M+H]^+$. $^1$H NMR (400 MHz, Methanol-d4) δ 8.55-8.45 (m, 2H), 8.33-8.19 (m, 2H), 7.91 (d, J=10.7 Hz, 1H), 7.88-7.72 (m, 2H), 5.41 (dd, J=23.1, 16.1 Hz, 1H), 5.22 (d, J=15.9 Hz, 1H), 4.51 (d, J=8.0 Hz, 3H), 3.80-3.61 (m, 2H), 3.42 (s, 3H), 3.26 (s, 1H).

Example 2

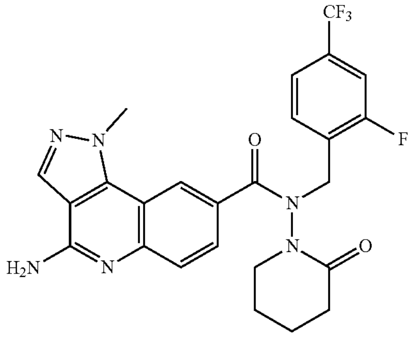

Example 2: 4-amino-N-(2-fluoro-4-(trifluoromethyl)benzyl)-1-methyl-N-(2-oxopiperidin-1-yl)-1H-pyrazolo[4,3-c] quinoline-8-carboxamide. Prepared following general procedure E-1 starting with intermediates Da-1 and Ba-1. ES/MS: m/z=515.3 $[M+H]^+$. 1H NMR (400 MHz, DMSO-$d_6$) δ 13.56 (brs, 1H), 9.65 (brs, 1H), 8.86 (brs, 1H), 8.62 (s, 1H), 8.35 (s, 1H), 7.93 (t, J=7.7 Hz, 1H), 7.81 (s, 2H), 7.71 (d, J=10.0 Hz, 1H), 7.62 (dd, J=8.0, 1.7 Hz, 1H), 5.10 (d, J=15.2 Hz, 1H), 4.81 (d, J=15.2 Hz, 1H), 4.43 (s, 3H), 3.61-3.41 (m, 1H), 3.40-3.29 (m, 1H), 2.30-2.13 (m, 1H), 2.01-1.84 (m, 1H), 1.73-1.44 (m, 2H), 1.40-1.16 (m, 2H).

Example 3

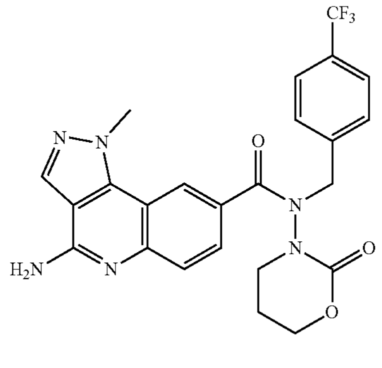

Example 3: 4-amino-1-methyl-N-(2-oxo-1,3-oxazinan-3-yl)-N-(4-(trifluoromethyl)benzyl)-1H-pyrazolo[4,3-c]quinoline-8-carboxamide. Prepared following general procedure E-1 starting with intermediates Da-1 and Ba-2. ES/MS: m/z=499.3 $[M+H]^+$. $^1$H NMR (400 MHz, DMSO-$d_6$) δ 13.66 (brs, 1H), 9.67 (brs, 1H), 8.96 (brs, 1H), 8.62 (s, 1H), 8.40 (s, 1H), 7.88 (dd, J=8.6, 1.7 Hz, 1H), 7.83 (d, J=8.6 Hz, 1H), 7.81-7.72 (m, 4H), 5.21 (d, J=15.3 Hz, 1H), 4.77 (d, J=15.3 Hz, 1H), 4.43 (s, 3H), 4.07 (t, J=9.9 Hz, 1H), 3.86-3.72 (m, 1H), 3.37-3.21 (m, 1H), 1.90-1.76 (m, 1H), 1.55-1.41 (m, 1H).

Example 4

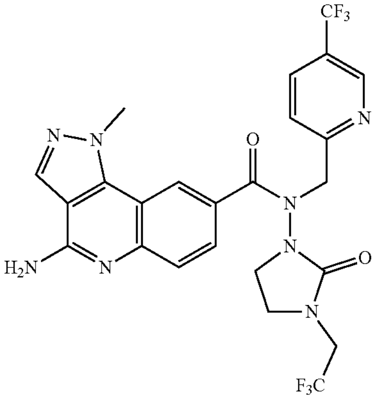

Example 4: 4-amino-1-methyl-N-(2-oxo-3-(2,2,2-trifluoroethyl)imidazolidin-1-yl)-N-((5-(trifluoromethyl)pyridin-2-yl)methyl)-1H-pyrazolo [4,3-c]quinoline-8-carboxamide. Prepared following general procedure E-1 starting with intermediates Da-1 and Ba-3. ES/MS: m/z=567.2 $[M+H]^+$. $^1$H NMR (400 MHz, DMSO-$d_6$) δ 13.45 (brs, 1H), 9.66 (brs, 1H), 8.94 (s, 1H), 8.77 (brs, 1H), 8.61 (d, J=3.7 Hz, 1H), 8.51 (d, J=1.8 Hz, 1H), 8.25 (dd, J=8.4, 2.4 Hz, 1H), 7.92 (d, J=8.5 Hz, 2H), 7.82 (d, J=8.5 Hz, 1H), 5.14 (d, J=15.9 Hz, 1H), 4.92 (d, J=15.9 Hz, 1H), 4.38 (s, 3H), 4.04-3.78 (m, 3H), 3.46-3.09 (m, 3H).

Example 5

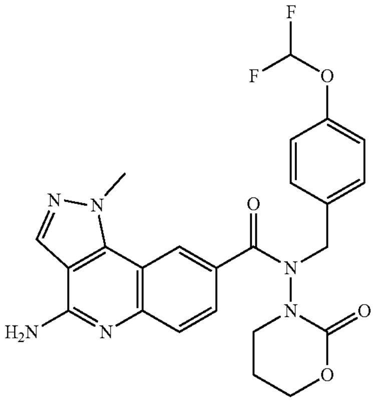

Example 5: 4-amino-N-(4-(difluoromethoxy)benzyl)-1-methyl-N-(2-oxo-1,3-oxazinan-3-yl)-1H-pyrazolo[4,3-c] quinoline-8-carboxamide. Prepared following general procedure E-1 starting with intermediates Da-1 and Ba-4. ES/MS: m/z=497.2 $[M+H]^+$. 1H NMR (400 MHz, DMSO-$d_6$) δ 13.50 (brs, 1H), 9.63 (brs, 1H), 8.80 (brs, 1H), 8.62 (s, 1H), 8.39 (s, 1H), 7.89-7.79 (m, 2H), 7.59 (d, J=8.1 Hz, 2H), 7.26 (t, J=74.1 Hz, 1H), 7.19 (d, J=8.4 Hz, 2H), 5.15 (d, J=14.8 Hz, 1H), 4.61 (d, J=14.8 Hz, 1H), 4.43 (s, 3H), 4.10-3.97 (m, 1H), 3.84-3.72 (m, 1H), 3.27-3.12 (m, 1H), 1.80-1.66 (m, 1H), 1.53-1.33 (m, 1H).

Example 6

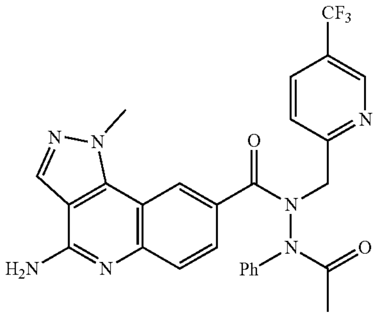

Example 6: N'-acetyl-4-amino-1-methyl-N'-phenyl-N-((5-(trifluoromethyl)pyridin-2-yl)methyl)-1H-pyrazolo[4,3-c]quinoline-8-carbohydrazide. Prepared following general procedure E-1 starting with intermediates Da-1 and Ba-5. ES/MS: m/z=534.2 $[M+H]^+$. $^1H$ NMR (400 MHz, DMSO-$d_6$) δ 13.70 (brs, 1H), 9.71 (brs, 1H), 8.99 (s, 1H), 8.89 (s, 1H), 8.69 (s, 0.3H minor rotamer), 8.63 (s, 1H), 8.43 (s, 0.7H major rotamer), 8.21 (s, 0.3H minor rotamer), 8.14 (s, 0.7H major rotamer), 8.00-7.57 (m, 2H), 7.46-7.19 (m, 4H), 7.02 (brs, 1H), 5.45-4.77 (m, 2H), 4.49 (s, 0.9H minor rotamer), 4.31 (s, 2.1H major rotamer), 2.20 (s, 0.9H minor rotamer), 1.99-1.69 (m, 2.1H major rotamer).

Example 7

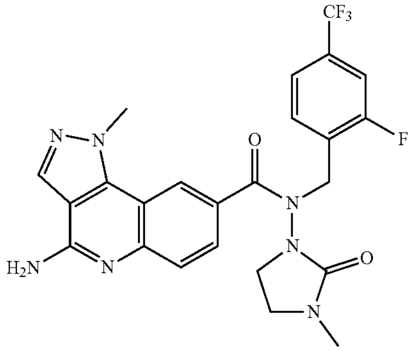

Example 7: 4-amino-N-(2-fluoro-4-(trifluoromethyl)benzyl)-1-methyl-N-(3-methyl-2-oxoimidazolidin-1-yl)-1H-pyrazolo[4,3-c]quinoline-8-carboxamide. Prepared following general procedure E-1 starting with intermediates Da-1 and Ba-6. ES/MS: m/z=516.2 $[M+H]^+$. $^1H$ NMR (400 MHz, DMSO-$d_6$) δ 13.57 (brs, 1H), 9.64 (brs, 1H), 8.87 (brs, 1H), 8.61 (s, 1H), 8.51 (brs, 1H), 7.99 (brs, 1H), 7.93 (dd, J=8.6, 1.7 Hz, 1H), 7.81 (d, J=8.6 Hz, 1H), 7.69 (dd, J=10.2, 1.7 Hz, 1H), 7.61 (dd, J=8.1, 1.7 Hz, 1H), 4.93 (d, J=15.9 Hz, 1H), 4.85 (d, J=15.9 Hz, 1H), 4.40 (s, 3H), 3.60-3.40 (m, 2H), 3.32-3.21 (m, 1H), 3.19-3.01 (m, 1H), 2.62 (s, 3H).

Examples 8 and 9: 4-amino-1-methyl-N-(5-methyl-2-oxo-oxazolidin-3-yl)-N-[[5-(trifluoromethyl)-2-pyridyl]methyl]pyrazolo[4,3-c]quinoline-8-carboxamide. Prepared following general procedure E-1 starting with intermediates Da-1 and Ba-7. The resulting isomers were separated by chiral SFC (SFC AD-H column with MeOH-diethylamine cosolvent) to give two distinct stereoisomers which were arbitrarily assigned.

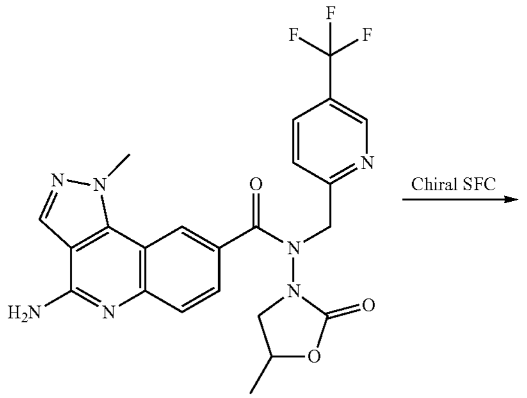

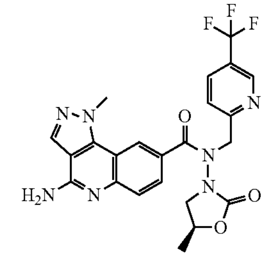

Example 8

+

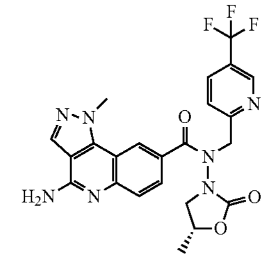

Example 9

Example 8: 4-amino-1-methyl-N-[(5S)-5-methyl-2-oxo-oxazolidin-3-yl]-N-[[5-(trifluoromethyl)-2-pyridyl]methyl]pyrazolo[4,3-c]quinoline-8-carboxamide (ES/MS: 500.0 $(M+H^+)$. $^1H$ NMR (400 MHz, DMSO-$d_6$) δ 13.35 (s, 1H), 9.69 (s, 1H), 8.99 (s, 1H), 8.63 (s, 1H), 8.49 (s, 1H), 8.28 (dd, J=8.3, 2.4 Hz, 1H), 8.08-7.69 (m, 3H), 5.21 (d, J=16.7 Hz, 1H), 5.05 (t, J=15.5 Hz, 1H), 4.60 (s, 1H), 4.43 (s, 3H), 3.94 (s, 0.5H, rotamer), 3.70 (s, 0.5H, rotamer), 1.43-1.16 (m, 3H).

Example 9: 4-amino-1-methyl-N-[(5R)-5-methyl-2-oxo-oxazolidin-3-yl]-N-[[5-(trifluoromethyl)-2-pyridyl]methyl]pyrazolo[4,3-c]quinoline-8-carboxamide. ES/MS: 500.0 $(M+H^+)$. $^1H$ NMR (400 MHz, DMSO-$d_6$) δ 13.35 (s, 1H), 9.69 (s, 1H), 8.99 (s, 1H), 8.63 (s, 1H), 8.49 (s, 1H), 8.28 (dd, J=8.3, 2.4 Hz, 1H), 8.08-7.69 (m, 3H), 5.21 (d, J=16.7 Hz, 1H), 5.05 (t, J=15.5 Hz, 1H), 4.60 (s, 1H), 4.43 (s, 3H), 3.94 (s, 0.5H, rotamer), 3.70 (s, 0.5H, rotamer), 1.43-1.16 (m, 3H).

Example 10

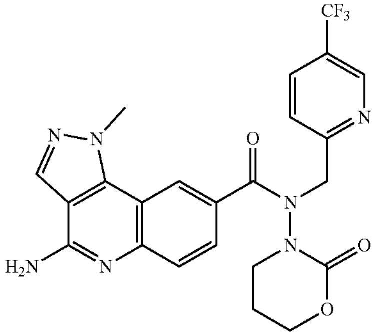

Example 10: 4-amino-1-methyl-N-(2-oxo-1,3-oxazinan-3-yl)-N-((5-(trifluoromethyl)pyridin-2-yl)methyl)-1H-pyrazolo[4,3-c]quinoline-8-carboxamide. Prepared following general procedure E-1 starting with intermediates Da-1 and Ba-8. ES/MS: m/z=500.3 $[M+H]^+$. $^1H$ NMR (400 MHz, DMSO-$d_6$) δ 13.64 (brs, 1H), 9.69 (brs, 1H), 8.98 (s, 1H), 8.94 (brs, 1H), 8.63 (s, 1H), 8.48 (s, 1H), 8.27 (dd, J=8.3, 2.3 Hz, 1H), 8.01-7.74 (m, 3H), 5.20 (d, J=16.5 Hz, 1H), 5.11-4.95 (m, 1H), 4.68-4.52 (m, 1H), 4.42 (s, 3H), 3.55-3.39 (m, 1H), 3.25-3.03 (m, 1H), 1.26 (d, J=6.1 Hz, 1H), 1.00-0.57 (m, 1H).

Example 11

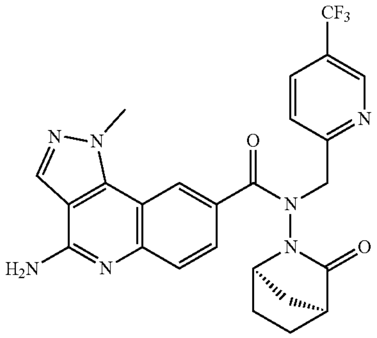

Example 11: 4-amino-1-methyl-N-[(1R,4S)-3-oxo-2-azabicyclo[2.2.1]heptan-2-yl]-N-[[5-(trifluoromethyl)-2-pyridyl]methyl]pyrazolo[4,3-c]quinoline-8-carboxamide. Prepared following general procedure E-1 starting with intermediates Da-1 and Ba-9. ES/MS: m/z=510.2 $[M+H]^+$. $^1H$ NMR (400 MHz, MeOD) δ 8.92 (s, 0.6H, major rotamer), 8.86-8.81 (m, 0.4H, minor rotamer), 8.60 (s, 0.4H, minor rotamer), 8.50 (s, 0.6H, major rotamer), 8.18 (dd, J=8.3, 2.3 Hz, 0.6H, major rotamer), 8.13 (dd, J=8.2, 2.4 Hz, 0.4H, minor rotamer), 7.98-7.79 (m, 4H), 5.45-4.95 (m, J=16.6 Hz, 1H), 4.53 (s, 1.8H, major rotamer), 4.24 (d, J=2.8 Hz, 1H), 4.15 (s, 1.2H, minor rotamer), 3.90 (q, J=1.7 Hz, 1H), 2.81-2.56 (m, 1H), 2.01-1.85 (m, 1H), 1.83-1.61 (m, 2H), 1.61-1.40 (m, 1H), 1.39-1.02 (m, 2H).

Example 12

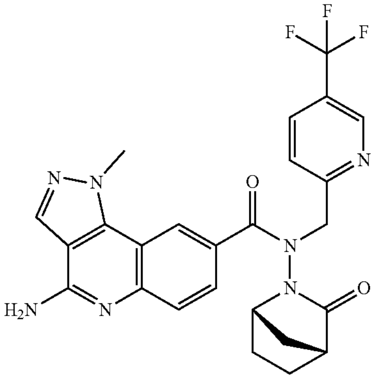

Example 12: 4-amino-1-methyl-N-[(1S,4R)-3-oxo-2-azabicyclo[2.2.1]heptan-2-yl]-N-[[6-(trifluoromethyl)-3-pyridyl]methyl]pyrazolo[4,3-c]quinoline-8-carboxamide. Prepared following general procedure E-1 starting with intermediates Da-1 and Ba-10. ES/MS: m/z=510.0 $[M+H]^+$. $^1H$ NMR (400 MHz, DMSO-$d_6$) δ 13.70 (s, 1H), 9.69 (s, 1H), 8.98 (s, 2H), 8.77-8.48 (m, 1H), 8.44 (s, 1H), 8.27 (d, J=8.2 Hz, 1H), 7.88 (dtd, J=16.7, 8.5, 4.5 Hz, 3H), 5.18 (d, J=16.9 Hz, 1H), 4.77 (d, J=16.7 Hz, 1H), 4.46 (s, 3H), 4.10 (s, 2H), 1.78 (d, J=10.5 Hz, 1H), 1.60 (d, J=14.0 Hz, 2H), 1.44 (d, J=12.1 Hz, 1H), 1.32-1.06 (m, 1H), 0.96 (s, 1H).

Example 13

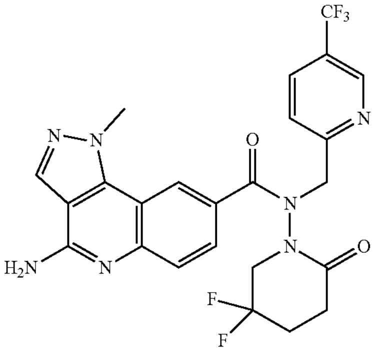

Example 13: 4-amino-N-(5,5-difluoro-2-oxo-1-piperidyl)-1-methyl-N-[[5-(trifluoromethyl)-2-pyridyl]methyl]pyrazolo[4,3-c]quinoline-8-carboxamide. Prepared following general procedure E-1 starting with intermediates Da-1 and Ba-11. ES/MS: m/z=534.0 $[M+H]^+$. $^1H$ NMR (400 MHz, MeOD) δ 8.94 (s, 1H), 8.64-8.38 (m, 2H), 8.17 (d, J=8.2 Hz, 1H), 8.01-7.63 (m, 3H), 5.31 (d, J=15.8 Hz, 1H), 4.94 (d, J=15.8 Hz, 1H), 4.51 (s, 3H), 4.44-4.19 (m, 1H), 4.16-3.92 (m, 1H), 2.63-2.42 (m, 1H), 2.40-2.21 (m, 1H), 2.21-1.90 (m, 2H).

Example 14

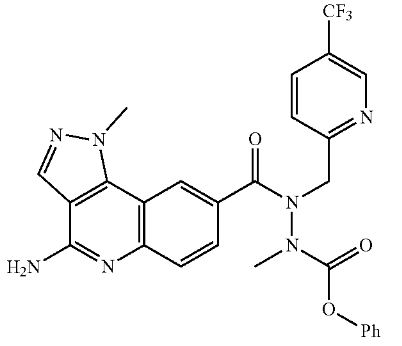

Example 14: Phenyl 2-(4-amino-1-methyl-1H-pyrazolo[4,3-c]quinoline-8-carbonyl)-1-methyl-2-((5-(trifluoromethyl)pyridin-2-yl)methyl)hydrazine-1-carboxylate. Prepared following general procedure E-1 starting with intermediates Da-1 and Ba-12. ES/MS: m/z=550.3 [M+H]$^+$. $^1$H NMR (400 MHz, DMSO-$d_6$) δ 13.63 (brs, 1H), 9.68 (brs, 1H), 9.03 (s, 1H), 8.91 (brs, 1H), 8.64 (s, 1H), 8.47 (s, 1H), 8.28 (dd, J=8.3, 2.4 Hz, 1H), 8.11-7.76 (m, 3H), 7.42-7.23 (m, 3H), 7.08-6.51 (m, 2H), 5.43-4.95 (m, 2H), 4.36 (s, 3H), 3.27 (s, 3H).

Example 15

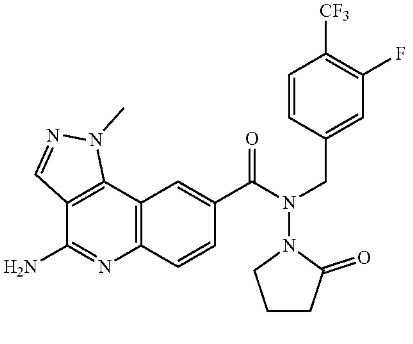

Example 15: 4-amino-N-(3-fluoro-4-(trifluoromethyl)benzyl)-1-methyl-N-(2-oxopyrrolidin-1-yl)-1H-pyrazolo[4,3-c]quinoline-8-carboxamide. Prepared following general procedure E-1 starting with intermediates Da-1 and Ba-13. ES/MS: m/z=535.2 [M+H]$^+$. $^1$H NMR (400 MHz, DMSO-$d_6$) δ 9.60 (brs, 1H), 9.13 (brs, 1H), 8.60 (s, 1H), 8.32 (s, 1H), 7.89 (s, 1H), 7.88-7.80 (m, 1H), 7.70 (d, J=11.8 Hz, 1H), 7.61 (d, J=8.1 Hz, 1H), 5.22 (d, J=15.9 Hz, 1H), 4.82 (d, J=15.9 Hz, 1H), 4.42 (s, 3H), 3.12 (brs, 2H), 2.22-2.06 (m, 1H), 1.91-1.72 (m, 2H), 1.52-1.37 (m, 1H).

Example 16

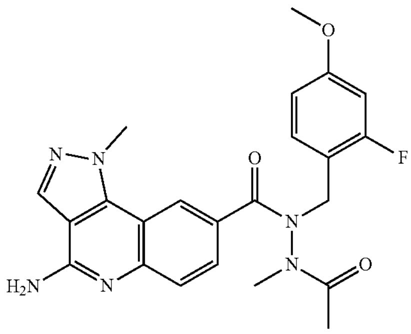

Example 16: N'-acetyl-4-amino-N-(2-fluoro-4-methoxybenzyl)-N',1-dimethyl-1H-pyrazolo[4,3-c]quinoline-8-carbohydrazide. Prepared following general procedure E-1 starting with intermediates Da-1 and Ba-14. ES/MS: m/z=451.2 [M+H]$^+$. $^1$H NMR (400 MHZ, DMSO-$d_6$) δ 13.62 (brs, 1H), 9.66 (brs, 1H), 8.92 (brs, 1H), 8.63 (s, 0.4H minor rotamer), 8.62 (s, 0.6H major rotamer), 8.43 (s, 0.6H major rotamer), 8.31 (s, 0.4H minor rotamer), 7.95-7.82 (m, 1H), 7.79 (s, 1H), 7.46 (t, J=8.7 Hz, 1H), 7.41 (brs, 1H), 6.97-6.76 (m, 2H), 5.01 (d, J=14.2 Hz, 1H), 4.75 (d, J=14.2 Hz, 1H), 4.53 (d, J=14.2 Hz, 0.6H major rotamer), 4.49-4.42 (m, 2H+0.4H minor rotamer), 3.77 (s, 3H), 2.98 (s, 1.2H minor rotamer), 2.97 (s, 1.8H major rotamer).

Example 17

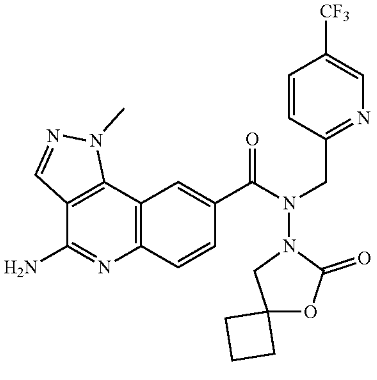

Example 17: 4-amino-1-methyl-N-(6-oxo-5-oxa-7-azaspiro[3.4]octan-7-yl)-N-[[5-(trifluoromethyl)-2-pyridyl]methyl]pyrazolo[4,3-c]quinoline-8-carboxamide. Prepared following general procedure E-1 starting with intermediates Da-1 and Ba-15. ES/MS: m/z=526.0 [M+H]$^+$. $^1$H NMR (400 MHz, MeOD) δ 8.94 (s, 1H), 8.62 (s, 1H), 8.49 (s, 1H), 8.18 (dd, J=8.4, 2.4 Hz, 1H), 7.98 (dd, J=8.5, 1.7 Hz, 1H), 7.91-7.77 (m, 2H), 5.25 (d, J=16.0 Hz, 1H), 5.06 (d, J=15.8 Hz, 1H), 4.49 (s, 3H), 3.99-3.68 (m, 2H), 2.42 (d, J=10.4 Hz, 1H), 2.28-1.91 (m, 2H), 1.91-1.46 (m, 3H).

Example 18

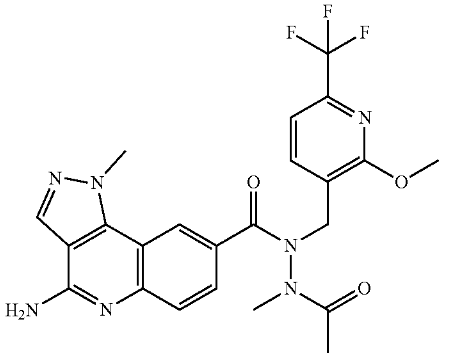

Example 18: N'-acetyl-4-amino-N-[[2-methoxy-6-(trifluoromethyl)-3-pyridyl]methyl]-N', 1-dimethyl-pyrazolo[4,3-c]quinoline-8-carbohydrazide. Prepared following general procedure E-1 starting with intermediates Da-1 and Ba-16. ES/MS: m/z=502.0 $[M+H]^+$. $^1H$ NMR (400 MHz, DMSO-$d_6$) δ 13.36 (s, 1H), 9.66 (s, 1H), 8.63 (d, J=2.3 Hz, 1H), 8.45 (d, J=1.7 Hz, 1H), 8.37 (d, J=1.5 Hz, 1H), 8.17 (d, J=7.5 Hz, 1H), 7.82 (d, J=2.8 Hz, 1H), 7.68-7.36 (m, 1H), 4.95 (d, J=15.3 Hz, 1.4H, major rotamer), 4.65 (d, J=15.7 Hz, 0.7H, minor rotamer), 4.48 (d, J=8.2 Hz, 3H), 3.96 (d, J=23.2 Hz, 3H), 3.21 (s, 2H, major rotamer), 2.97 (s, 1H, minor rotamer), 1.79 (s, 3H).

Example 19

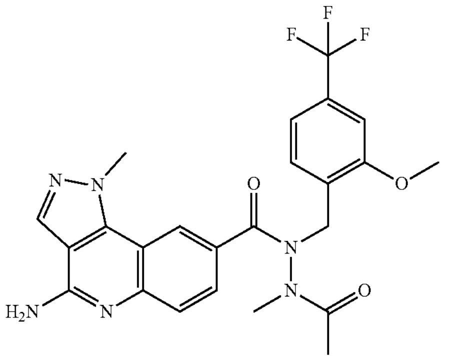

Example 19: N'-acetyl-4-amino-N-[[2-methoxy-4-(trifluoromethyl)phenyl]methyl]-N',1-dimethyl-pyrazolo[4,3-c]quinoline-8-carbohydrazide. Prepared following general procedure E-1 starting with intermediates Da-1 and Ba-17. ES/MS: m/z=501.0 $[M+H]^+$. $^1H$ NMR (400 MHz, DMSO-$d_6$) δ 13.59 (s, 1H), 9.66 (s, 1H), 8.89 (s, 1H), 8.63 (d, J=3.7 Hz, 1H), 8.44 (d, J=1.7 Hz, 1H), 8.35 (d, J=1.5 Hz, 1H), 7.81 (t, J=6.3 Hz, 1H), 7.73 (d, J=7.8 Hz, 1H), 7.41-7.28 (m, 2H), 5.08 (d, J=15.3 Hz, 1H), 4.94 (s, 2H), 4.56 (d, J=15.2 Hz, 1H), 4.47 (d, J=11.1 Hz, 3H), 3.95 (s, 1H), 3.07 (s, 1H), 2.92 (s, 2H), 1.74 (d, J=29.0 Hz, 3H).

Example 20

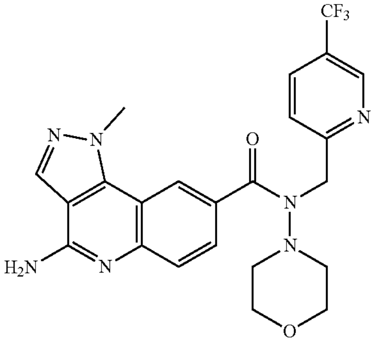

Example 20: 4-amino-1-methyl-N-morpholino-N-((5-(trifluoromethyl)pyridin-2-yl)methyl)-1H-pyrazolo[4,3-c]quinoline-8-carboxamide. Prepared following general procedure E-1 starting with intermediates Da-1 and Ba-18. ES/MS: m/z=486.0 $[M+H]^+$. $^1H$ NMR (400 MHz, MeOD) δ 8.89 (s, 1H), 8.61 (s, 1H), 8.50 (s, 1H), 8.18-8.12 (m, 1H), 8.09 (dd, J=8.6, 1.7 Hz, 1H), 7.82 (d, J=8.6 Hz, 1H), 7.78 (d, J=8.3 Hz, 1H), 5.08 (s, 2H), 4.54 (s, 3H), 3.76 (d, J=11.3 Hz, 2H), 3.38-3.31 (m, 2H), 3.04 (d, J=11.2 Hz, 2H), 2.95 (d, J=10.9 Hz, 2H).

Example 21

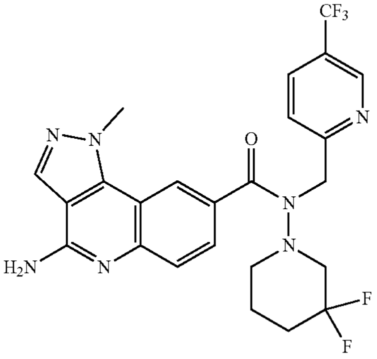

Example 21: 4-amino-N-(3,3-difluoro-1-piperidyl)-1-methyl-N-[[5-(trifluoromethyl)-2-pyridyl]methyl]pyrazolo[4,3-c]quinoline-8-carboxamide. Prepared following general procedure E-1 starting with intermediates Da-1 and Ba-19. ES/MS: m/z=520.0 $[M+H]^+$. $^1H$ NMR (400 MHz, MeOD) δ 8.91 (s, 1H), 8.61 (s, 1H), 8.50 (s, 1H), 8.15 (dd, J=8.4, 2.4 Hz, 1H), 8.06 (dd, J=8.7, 1.7 Hz, 1H), 7.78 (d, J=8.6 Hz, 2H), 5.06 (s, 2H), 4.55 (s, 3H), 3.56-3.41 (m, 1H), 3.24-3.05 (m, 2H), 2.87 (t, J=11.5 Hz, 1H), 2.06-1.85 (m, 1H), 1.81-1.53 (m, 2H), 1.48-1.26 (m, 1H).

Example 22

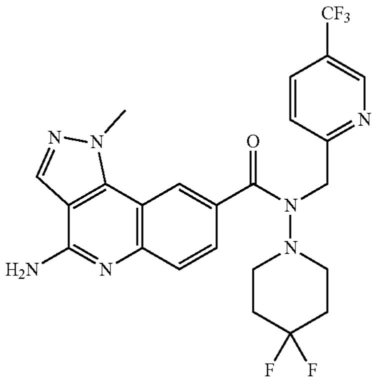

Example 22: 4-amino-N-(4,4-difluoro-1-piperidyl)-1-methyl-N-[[5-(trifluoromethyl)-2-pyridyl]methyl]pyrazolo[4,3-c]quinoline-8-carboxamide. Prepared following general procedure E-1 starting with intermediates Da-1 and Ba-20. ES/MS: m/z=520.0 $[M+H]^+$. $^1H$ NMR (400 MHz, MeOD) δ 8.90 (s, 1H), 8.60 (s, 1H), 8.51 (s, 1H), 8.15 (dd, J=8.5, 2.4 Hz, 1H), 8.08 (dd, J=8.6, 1.7 Hz, 1H), 7.83 (d, J=8.6 Hz, 1H), 7.78 (d, J=8.3 Hz, 1H), 5.06 (s, 2H), 4.55 (s, 3H), 3.23-3.13 (m, 2H), 3.12-3.01 (m, 2H), 2.05-1.91 (m, 2H), 1.88-1.61 (m, 2H).

Example 23

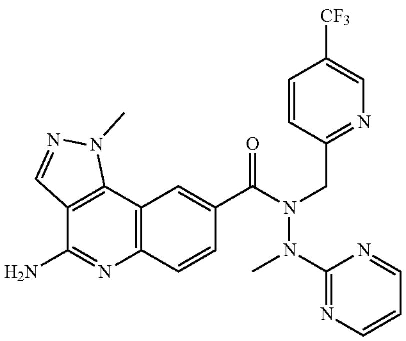

Example 23: 4-amino-N', 1-dimethyl-N'-(pyrimidin-2-yl)-N-((5-(trifluoromethyl)pyridin-2-yl)methyl)-1H-pyrazolo[4,3-c]quinoline-8-carbohydrazide. Prepared following general procedure E-1 starting with intermediates Da-1 and Ba-21. ES/MS: m/z=508.2 $[M+H]^+$. $^1H$ NMR (400 MHz, Methanol-d4) δ 8.82 (s, 1H), 8.53 (s, 1H), 8.50-8.36 (m, 3H), 8.16 (d, J=8.3 Hz, 1H), 7.93 (dd, J=20.5, 8.4 Hz, 2H), 7.71 (d, J=8.6 Hz, 1H), 6.83 (t, J=4.8 Hz, 1H), 5.48 (d, J=15.4 Hz, 1H), 4.81 (s, 1H), 4.33 (s, 3H), 3.35 (s, 3H).

Example 24

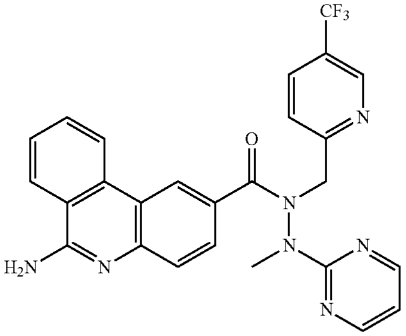

Example 24: 6-amino-N'-methyl-N'-(pyrimidin-2-yl)-N-((5-(trifluoromethyl)pyridin-2-yl)methyl)phenanthridine-2-carbohydrazide. Prepared following general procedure E-1 starting with intermediates Da-3 and Ba-21. ES/MS: m/z=504.2 $[M+H]^+$. $^1H$ NMR (400 MHz, Methanol-d4) δ 8.83 (s, 1H), 8.73 (s, 1H), 8.59 (d, J=8.3 Hz, 1H), 8.53 (d, J=8.3 Hz, 1H), 8.40 (d, J=4.8 Hz, 2H), 8.21-8.08 (m, 2H), 7.98-7.83 (m, 3H), 7.61 (d, J=8.5 Hz, 1H), 6.78 (t, J=4.8 Hz, 1H), 5.50 (d, J=15.4 Hz, 1H), 4.83 (d, J=15.5 Hz, 1H), 3.36 (s, 3H).

Example 25

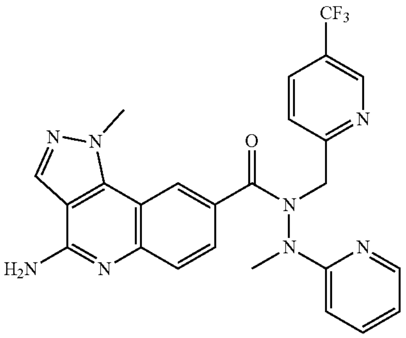

Example 25: 4-amino-N', 1-dimethyl-N'-(2-pyridyl)-N-[[5-(trifluoromethyl)-2-pyridyl]methyl]pyrazolo[4,3-c]quinoline-8-carbohydrazide. Prepared following general procedure E-1 starting with intermediates Da-1 and Ba-22. ES/MS: m/z=507.2 $[M+H]^+$. 1H NMR (400 MHz, Methanol-d4) δ 8.92 (d, J=13.2 Hz, 1H), 8.53 (d, J=7.1 Hz, 1H), 8.45 (s, 1H), 8.34 (ddd, J=5.7, 1.8, 0.8 Hz, 1H), 8.20-8.11 (m, 1H), 7.98 (d, J=8.7 Hz, 1H), 7.86 (d, J=7.4 Hz, 1H), 7.76 (s, 2H), 6.98 (s, 2H), 5.41 (d, J=15.7 Hz, 1H), 4.16 (s, 3H), 3.78 (d, J=0.7 Hz, 3H).

Example 26

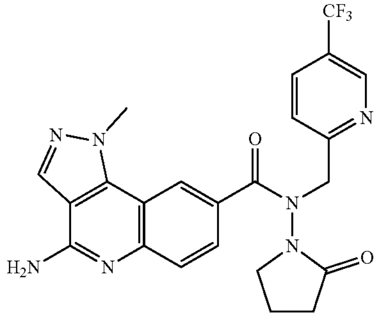

Example 26: 4-amino-1-methyl-N-(2-oxopyrrolidin-1-yl)-N-[[5-(trifluoromethyl)-2-pyridyl]methyl]pyrazolo[4,3-c]quinoline-8-carboxamide. Prepared following general procedure E-1 starting with intermediates Da-1 and Ba-23. ES/MS: m/z=484.2 $[M+H]^+$. $^1H$ NMR (400 MHz, Methanol-d4) δ 8.91 (s, 1H), 8.61 (s, 1H), 8.50 (s, 1H), 8.23-8.11 (m, 1H), 8.03-7.86 (m, 2H), 7.83 (d, J=8.6 Hz, 1H), 5.21 (d, J=15.7 Hz, 1H), 5.05 (d, J=15.6 Hz, 1H), 4.51 (s, 3H), 3.81-3.62 (m, 1H), 3.55-3.41 (m, 1H), 2.38-2.22 (m, 1H), 2.17-1.87 (m, 2H), 1.74 (s, 1H).

Example 27

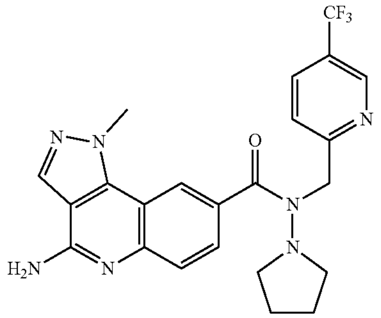

Example 27: 4-amino-1-methyl-N-pyrrolidin-1-yl-N-[[5-(trifluoromethyl)-2-pyridyl]methyl]pyrazolo[4,3-c]quinoline-8-carboxamide. Prepared following general procedure E-1 starting with intermediates Da-1 and Ba-24. ES/MS: m/z=470.2 $[M+H]^+$. $^1H$ NMR (400 MHz, Methanol-d4) δ 8.89 (s, 1H), 8.71 (d, J=1.7 Hz, 1H), 8.50 (s, 1H), 8.12 (ddd, J=15.9, 8.5, 2.0 Hz, 2H), 7.77 (dd, J=13.2, 8.5 Hz, 2H), 5.02 (s, 2H), 4.56 (s, 3H), 3.02 (s, 4H), 1.74 (s, 4H).

Example 28

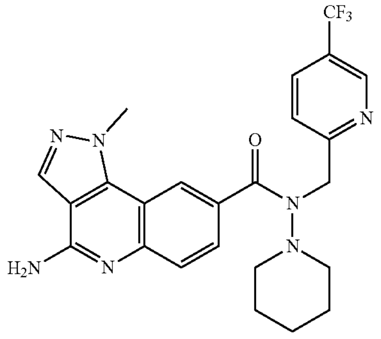

Example 28: 4-amino-1-methyl-N-(1-piperidyl)-N-[[5-(trifluoromethyl)-2-pyridyl]methyl]pyrazolo[4,3-c]quinoline-8-carboxamide. Prepared following general procedure E-1 starting with intermediates Da-1 and Ba-25. ES/MS: m/z=484.2 $[M+H]^+$. 1H NMR (400 MHz, Methanol-d4) δ 8.88 (s, 1H), 8.63 (s, 1H), 8.51 (s, 1H), 8.14 (dd, J=8.3, 2.4 Hz, 1H), 8.09 (dd, J=8.7, 1.7 Hz, 1H), 7.79 (t, J=9.3 Hz, 2H), 5.06 (s, 2H), 4.56 (s, 3H), 3.06 (d, J=10.3 Hz, 2H), 2.80 (t, J=11.2 Hz, 2H), 1.60 (dd, J=33.8, 13.0 Hz, 3H), 1.35 (dd, J=13.4, 9.9 Hz, 2H), 1.13 (t, J=13.1 Hz, 1H).

Example 29

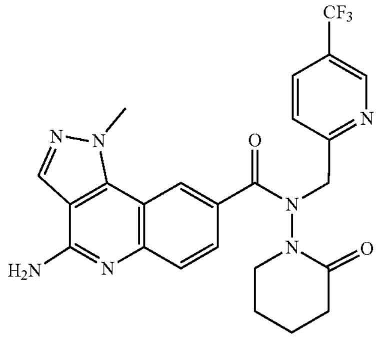

Example 29: 4-amino-1-methyl-N-(2-oxo-1-piperidyl)-N-[[5-(trifluoromethyl)-2-pyridyl]methyl]pyrazolo[4,3-c]quinoline-8-carboxamide. Prepared following general procedure E-1 starting with intermediates Da-1 and Ba-26. ES/MS: m/z=498.3 $[M+H]^+$. $^1H$ NMR (400 MHz, Methanol-d4) δ 8.97-8.85 (m, 1H), 8.50 (d, J=5.2 Hz, 2H), 8.24-8.12 (m, 1H), 8.02-7.87 (m, 2H), 7.83 (d, J=8.5 Hz, 1H), 5.41-5.22 (m, 1H), 4.94-4.9 (m, 1H), 4.51 (s, 3H), 3.79 (d, J=15.3 Hz, 1H), 3.58-3.40 (m, 1H), 2.34 (d, J=18.1 Hz, 1H), 2.04-1.89 (m, 1H), 1.80 (s, 1H), 1.65 (s, 1H), 1.48 (s, 2H).

Example 30

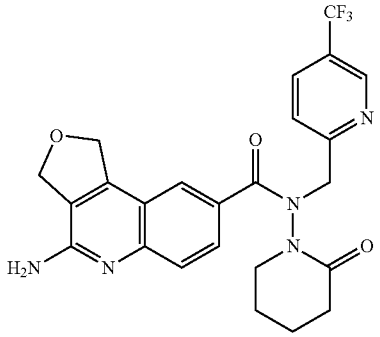

Example 30: 4-amino-N-(2-oxo-1-piperidyl)-N-[[5-(trifluoromethyl)-2-pyridyl]methyl]-1,3-dihydrofuro[3,4-c]quinoline-8-carboxamide. Prepared following general procedure E-1 starting with intermediates Db-5 and Ba-26. ES/MS: m/z=486.2 $[M+H]^+$. 1H NMR (400 MHz, Methanol-d4) δ 8.88 (s, 1H), 8.16 (d, J=8.4 Hz, 1H), 7.97-7.83 (m, 3H), 7.80 (d, J=8.6 Hz, 1H), 5.53 (t, J=3.7 Hz, 2H), 5.31 (d, J=15.5 Hz, 1H), 5.21 (t, J=3.8 Hz, 2H), 3.78 (d, J=10.3 Hz, 1H), 3.66-3.50 (m, 1H), 2.31 (d, J=18.4 Hz, 1H), 2.01-1.77 (m, 3H), 1.66 (s, 1H), 1.48 (s, 2H).

Example 31

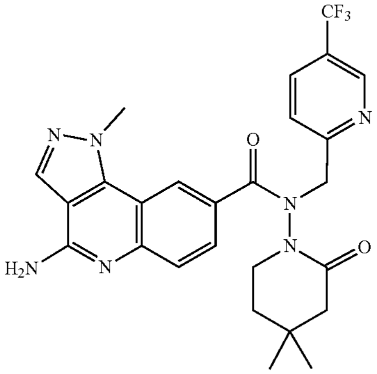

Example 31: 4-amino-N-(4,4-dimethyl-2-oxo-1-piperidyl)-1-methyl-N-[[5-(trifluoromethyl)-2-pyridyl]methyl] pyrazolo[4,3-c]quinoline-8-carboxamide. Prepared following general procedure E-1 starting with intermediates Da-1 and Ba-27. ES/MS: m/z=526.3 $[M+H]^+$. $^1H$ NMR (400 MHz, Methanol-d4) δ 8.90 (s, 1H), 8.54 (s, 1H), 8.50 (s, 1H), 8.18 (d, J=8.2 Hz, 1H), 7.91 (d, J=14.9 Hz, 2H), 7.82 (d, J=8.5 Hz, 1H), 5.26 (d, J=15.6 Hz, 1H), 4.97 (d, J=14.4 Hz, 1H), 4.53 (s, 3H), 3.60 (d, J=11.3 Hz, 1H), 3.23-3.06 (m, 1H), 2.36 (d, J=18.1 Hz, 1H), 2.13 (s, 1H), 1.60 (dt, J=15.2, 7.8 Hz, 1H), 1.31 (s, 1H), 0.93 (s, 3H), 0.42 (s, 3H).

Example 32

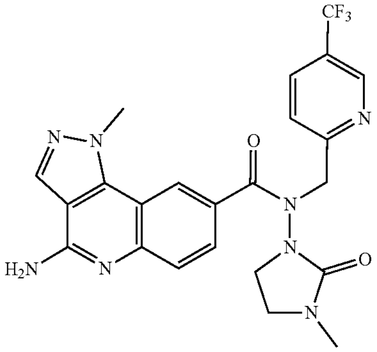

Example 32: 4-amino-1-methyl-N-(3-methyl-2-oxo-imidazolidin-1-yl)-N-[[5-(trifluoromethyl)-2-pyridyl]methyl] pyrazolo[4,3-c]quinoline-8-carboxamide. Prepared following general procedure E-1 starting with intermediates Da-1 and Ba-28. ES/MS: m/z=499.2 $[M+H]^+$. $^1H$ NMR (400 MHz, Methanol-d4) δ 8.91 (s, 1H), 8.71 (s, 1H), 8.50 (s, 1H), 8.17 (dd, J=8.3, 2.4 Hz, 1H), 8.00 (t, J=9.4 Hz, 1H), 7.94-7.85 (m, 1H), 7.81 (d, J=8.6 Hz, 1H), 5.28 (d, J=16.3 Hz, 1H), 4.84 (s, 1H), 4.60 (d, J=10.2 Hz, 1H), 4.50 (s, 3H), 3.90-3.41 (m, 2H), 3.39 (d, J=10.3 Hz, 1H), 2.76 (s, 3H).

Example 33

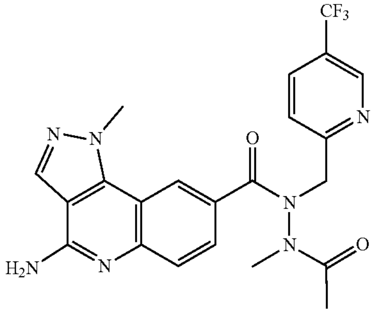

Example 33: N'-acetyl-4-amino-N', 1-dimethyl-N-[[5-(trifluoromethyl)-2-pyridyl]methyl]pyrazolo[4,3-c]quinoline-8-carbohydrazide. Prepared following general procedure E-1 starting with intermediates Da-1 and Ba-29. ES/MS: m/z=472.2 $[M+H]^+$. 1H NMR (400 MHz, Methanol-d4) δ 9.00 (s, 1H), 8.90 (s, 1H), 8.53 (s, 1H), 8.49 (d, J=4.1 Hz, 2H), 8.22-8.12 (m, 1H), 7.84 (dd, J=24.4, 8.7 Hz, 3H), 5.17 (dd, J=75.2, 15.2 Hz, 1H), 4.53 (d, J=16.8 Hz, 3H), 3.30-3.12 (m, 3H), 2.08-1.82 (m, 3H).

Example 34

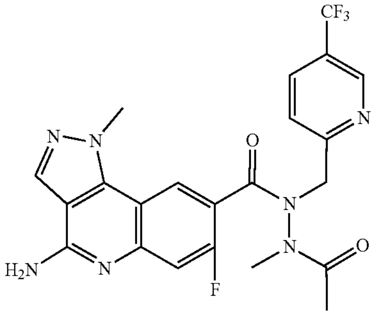

Example 34: N'-acetyl-4-amino-7-fluoro-N', 1-dimethyl-N-[[5-(trifluoromethyl)-2-pyridyl]methyl]pyrazolo[4,3-c] quinoline-8-carbohydrazide. Prepared following general procedure E-1 starting with intermediates Db-1 and Ba-29. ES/MS: m/z=490.2 $[M+H]^+$. 1H NMR (400 MHz, Methanol-d4) δ 9.02 (s, 1H), 8.90 (s, 1H), 8.49 (d, J=5.2 Hz, 1H), 8.42 (d, J=6.5 Hz, 1H), 8.10 (d, J=8.2 Hz, 1H), 8.19 (d, J=8.4 Hz, 1H), 7.87 (d, J=8.2 Hz, 1H), 7.60 (d, J=10.2 Hz, 1H), 5.30 (d, J=15.4 Hz, 1H), 4.92 (d, J=15.6 Hz, 1H), 4.51 (d, J=20.5 Hz, 4H), 1.85 (s, 3H).

Example 35

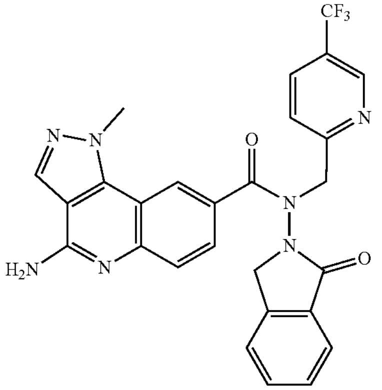

Example 35: 4-amino-1-methyl-N-(1-oxoisoindolin-2-yl)-N-[[5-(trifluoromethyl)-2-pyridyl]methyl]pyrazolo[4,3-c]quinoline-8-carboxamide. Prepared following general procedure E-1 starting with intermediates Da-1 and Ba-30. ES/MS: m/z=532.2 $[M+H]^+$. 1H NMR (400 MHz, Methanol-d4) δ 8.85 (s, 1H), 8.67 (s, 1H), 8.44 (s, 1H), 8.18 (dd, J=8.2, 2.3 Hz, 1H), 7.95 (d, J=12.7 Hz, 2H), 7.92 (brs, 1H), 7.79-7.69 (m, 2H), 7.67-7.56 (m, 1H), 7.55-7.42 (m, 2H), 5.38 (d, J=15.7 Hz, 1H), 5.20 (d, J=15.5 Hz, 1H), 4.50 (s, 4H).

Example 36

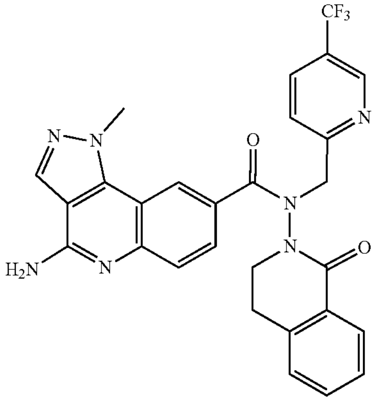

Example 36: 4-amino-1-methyl-N-(1-oxo-3,4-dihydroisoquinolin-2-yl)-N-[[5-(trifluoromethyl)-2-pyridyl]methyl]pyrazolo[4,3-c]quinoline-8-carboxamide. Prepared following general procedure E-1 starting with intermediates Da-1 and Ba-31. ES/MS: m/z=546.3 $[M+H]^+$. $^1$H NMR (400 MHz, Methanol-d4) δ 8.86 (s, 1H), 8.61 (s, 1H), 8.44 (s, 1H), 8.18 (d, J=8.2 Hz, 1H), 7.97 (d, J=21.7 Hz, 2H), 7.91-7.73 (m, 2H), 7.47 (d, J=21.6 Hz, 1H), 7.32 (s, 1H), 7.16 (s, 1H), 5.44 (d, J=15.5 Hz, 1H), 5.02 (d, J=15.5 Hz, 1H), 4.48 (s, 3H), 4.04 (s, 1H), 3.79 (t, J=7.0 Hz, 1H), 2.89 (dd, J=16.0, 5.3 Hz, 1H), 2.67 (s, 1H).

Example 37

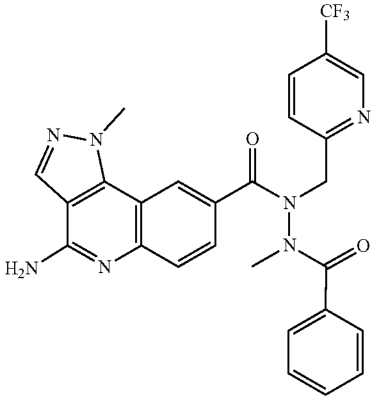

Example 37: 4-amino-N'-benzoyl-N', 1-dimethyl-N-[[5-(trifluoromethyl)-2-pyridyl]methyl]pyrazolo[4,3-c]quinoline-8-carbohydrazide. Prepared following general procedure E-1 starting with intermediates Da-1 and Ba-32. ES/MS: m/z=534.2 $[M+H]^+$. $^1$H NMR (400 MHz, Methanol-d4) δ 8.93 (s, 1H), 8.49 (s, 2H), 8.20 (s, 1H), 8.00 (s, 2H), 7.87 (d, J=8.4 Hz, 1H), 7.44 (s, 3H), 7.00 (s, 2H), 5.36 (s, 1H), 5.12 (s, 1H), 4.44 (d, J=33.1 Hz, 6H).

Example 38

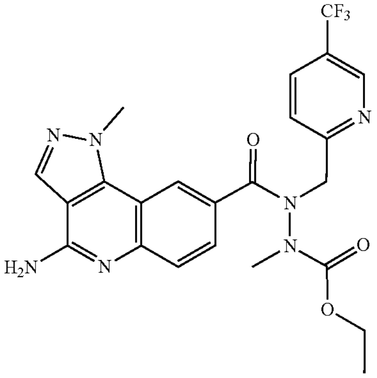

Example 38: ethyl N-[(4-amino-1-methyl-pyrazolo[4,3-c]quinoline-8-carbonyl)-[[5-(trifluoromethyl)-2-pyridyl]methyl]amino]-N-methyl-carbamate. Prepared following general procedure E-1 starting with intermediates Da-1 and Ba-33. ES/MS: m/z=502.2 $[M+H]^+$. $^1$H NMR (400 MHz, Methanol-d4) δ 8.97-8.85 (m, 1H), 8.50 (d, J=5.2 Hz, 2H), 8.24-8.12 (m, 1H), 8.02-7.87 (m, 2H), 7.83 (d, J=8.5 Hz, 1H), 5.41-5.22 (m, 1H), 4.94-4.9 (m, 1H), 4.51 (s, 3H), 3.79 (d, J=15.3 Hz, 1H), 3.58-3.40 (m, 1H), 2.34 (d, J=18.1 Hz, 1H), 2.04-1.89 (m, 1H), 1.80 (s, 1H), 1.65 (s, 1H), 1.48 (s, 2H).

Example 39

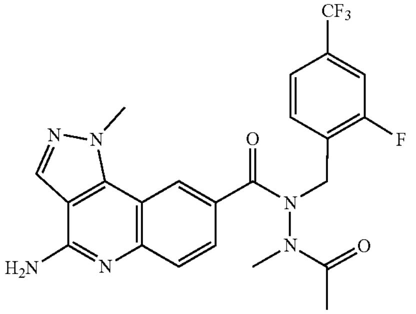

Example 39: N'-acetyl-4-amino-N-[[2-fluoro-4-(trifluoromethyl)phenyl]methyl]-N',1-dimethyl-pyrazolo[4,3-c]quinoline-8-carbohydrazide. Prepared following general procedure E-1 starting with intermediates Da-1 and Ba-34. ES/MS: m/z=489.2 $[M+H]^+$. $^1H$ NMR (400 MHz, Methanol-d4) δ 8.62-8.43 (m, 2H), 8.02-7.77 (m, 3H), 7.69-7.43 (m, 2H), 5.16 (d, J=15.8 Hz, 1H), 4.91-4.83 (m, 2H), 4.53 (s, 3H), 3.18 (s, 3H), 1.85 (s, 2H).

Example 40

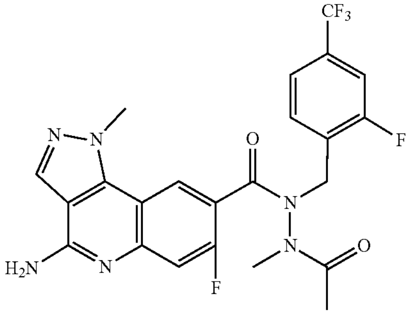

Example 40: N'-acetyl-4-amino-7-fluoro-N-[[2-fluoro-4-(trifluoromethyl)phenyl]methyl]-N',1-dimethyl-pyrazolo[4,3-c]quinoline-8-carbohydrazide. Prepared following general procedure E-1 starting with intermediates Db-1 and Ba-34. ES/MS: m/z=507.2 $[M+H]^+$. $^1H$ NMR (400 MHz, Methanol-d4) δ 8.62-8.43 (m, 2H), 8.02-7.77 (m, 3H), 7.69-7.43 (m, 2H), 5.16 (d, J=15.8 Hz, 1H), 4.91 (s, 1H), 4.53 (d, J=12.9 Hz, 3H), 3.18 (d, J=40.6 Hz, 3H), 1.85 (s, 2H).

Example 41

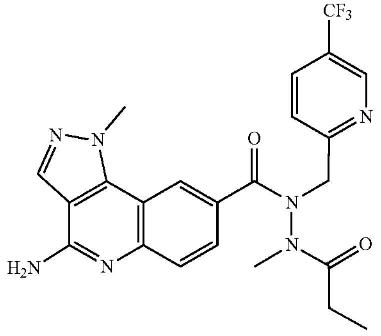

Example 41: 4-amino-N', 1-dimethyl-N'-propanoyl-N-[[5-(trifluoromethyl)-2-pyridyl]methyl]pyrazolo[4,3-c]quinoline-8-carbohydrazide. Prepared following general procedure E-1 starting with intermediates Da-1 and Ba-35. ES/MS: m/z=486.3 $[M+H]^+$. 1H NMR (400 MHz, Methanol-d4) δ 9.03 (s, 1H), 8.87 (s, 1H), 8.50 (d, J=5.2 Hz, 2H), 8.25-7.75 (m, 4H), 5.26 (d, J=15.3 Hz, 1H), 4.56 (d, J=16.2 Hz, 3H), 3.26-3.10 (m, 3H), 2.54-2.10 (m, 2H), 0.80 (s, 3H).

Example 42

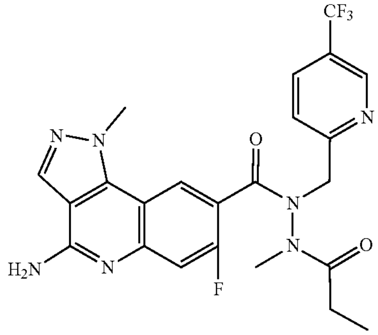

Example 42: 4-amino-7-fluoro-N', 1-dimethyl-N'-propanoyl-N-[[5-(trifluoromethyl)-2-pyridyl]methyl]pyrazolo[4,3-c]quinoline-8-carbohydrazide. Prepared following general procedure E-1 starting with intermediates Db-1 and Ba-35. ES/MS: m/z=504.2 $[M+H]^+$. $^1H$ NMR (400 MHz, Methanol-d4) δ 8.89 (s, 1H), 8.79-8.68 (m, 1H), 8.48 (d, J=4.4 Hz, 1H), 8.41 (d, J=6.5 Hz, 1H), 8.28-8.14 (m, 1H), 7.87 (d, J=8.2 Hz, 1H), 7.70-7.47 (m, 1H), 5.29 (d, J=15.3 Hz, 1H), 4.52 (d, J=17.8 Hz, 3H), 3.31 (s, 3H), 2.35-1.88 (m, 2H), 0.76 (t, J=7.4 Hz, 3H).

Example 43

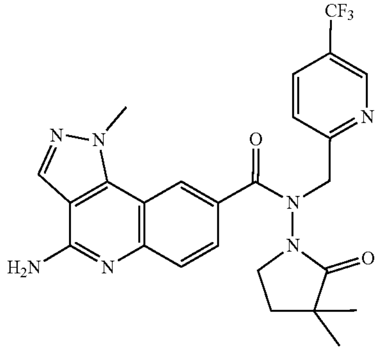

Example 43: 4-amino-N-(3,3-dimethyl-2-oxo-pyrrolidin-1-yl)-1-methyl-N-[[5-(trifluoromethyl)-2-pyridyl]methyl]pyrazolo[4,3-c]quinoline-8-carboxamide. Prepared following general procedure E-1 starting with intermediates Da-1 and Ba-36. ES/MS: m/z=512.2 $[M+H]^+$. $^1H$ NMR (400 MHz, Methanol-d4) δ 8.90 (s, 1H), 8.59 (s, 1H), 8.50 (s, 1H), 8.18 (dd, J=8.3, 2.3 Hz, 1H), 7.91 (s, 2H), 7.83 (d, J=8.6 Hz, 1H), 5.12 (s, 2H), 4.53 (s, 3H), 3.65 (s, 1H), 1.82 (ddd, J=13.2, 8.1, 5.6 Hz, 1H), 1.55 (s, 1H), 0.98 (s, 3H), 0.55 (s, 3H).

Example 44

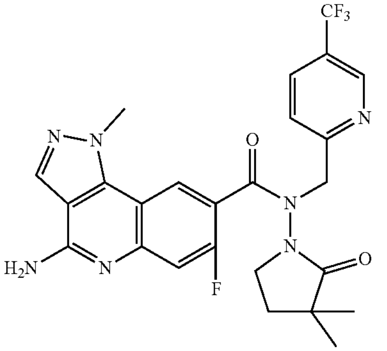

Example 44: 4-amino-N-(3,3-dimethyl-2-oxo-pyrrolidin-1-yl)-7-fluoro-1-methyl-N-[[5-(trifluoromethyl)-2-pyridyl] methyl]pyrazolo[4,3-c]quinoline-8-carboxamide. Prepared following general procedure E-1 starting with intermediates Db-1 and Ba-36. ES/MS: m/z=530.3 $[M+H]^+$. $^1H$ NMR (400 MHz, Methanol-d4) δ 8.89 (t, J=1.4 Hz, 1H), 8.48 (s, 1H), 8.27-8.14 (m, 1H), 7.91 (d, J=8.2 Hz, 1H), 7.62 (d, J=10.2 Hz, 2H), 5.14 (t, J=13.1 Hz, 2H), 4.51 (s, 3H), 3.73 (s, 1H), 3.35 (d, J=2.5 Hz, 1H), 1.84 (dd, J=12.7, 7.5 Hz, 1H), 1.64-1.41 (m, 1H), 0.95 (s, 3H), 0.41 (s, 3H).

Example 45

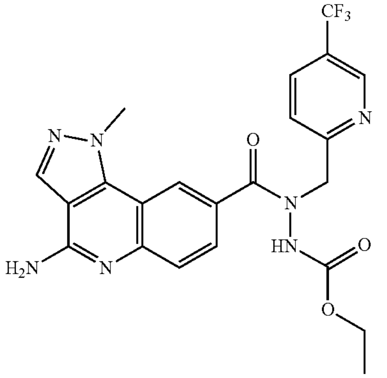

Example 45: ethyl N-[(4-amino-1-methyl-pyrazolo[4,3-c] quinoline-8-carbonyl)-[[5-(trifluoromethyl)-2-pyridyl] methyl]amino]carbamate. Prepared following general procedure E-1 starting with intermediates Da-1 and Ba-37. ES/MS: m/z=488.3 $[M+H]^+$. $^1H$ NMR (400 MHz, Methanol-d4) δ 8.92 (d, J=1.9 Hz, 1H), 8.65 (s, 1H), 8.50 (s, 1H), 8.19 (dd, J=8.3, 2.3 Hz, 1H), 7.98 (d, J=8.4 Hz, 1H), 7.80 (dd, J=8.4, 5.0 Hz, 2H), 5.46 (brs, 2H), 4.54 (s, 3H), 4.01 (s, 2H), 1.07 (s, 3H).

Example 46

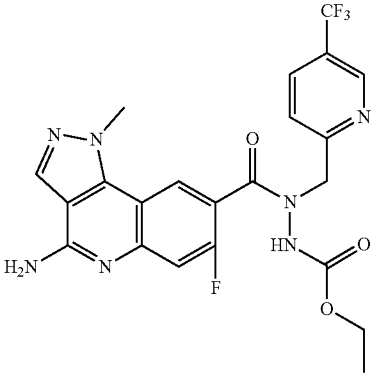

Example 46: ethyl N-[(4-amino-7-fluoro-1-methyl-pyrazolo[4,3-c]quinoline-8-carbonyl)-[[5-(trifluoromethyl)-2-pyridyl]methyl]amino]carbamate. Prepared following general procedure E-1 starting with intermediates Db-1 and Ba-37. ES/MS: m/z=506.2 $[M+H]^+$. $^1H$ NMR (400 MHz, Methanol-d4) δ 8.91 (s, 1H), 8.54 (d, J=6.4 Hz, 1H), 8.49 (s, 1H), 8.20 (d, J=8.1 Hz, 1H), 7.79 (d, J=8.2 Hz, 1H), 7.58 (d, J=10.1 Hz, 1H), 5.51 (s, 1H), 4.53 (s, 3H), 4.30-4.08 (m, 1H), 3.97 (s, 2H), 1.02 (s, 3H).

Example 47

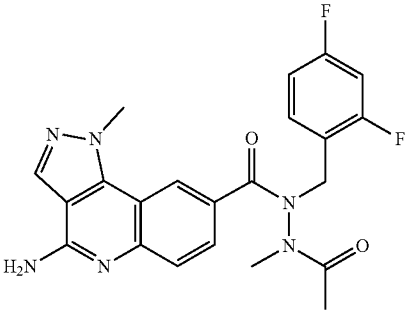

Example 47: N'-acetyl-4-amino-N-[(2,4-difluorophenyl) methyl]-N',1-dimethyl-pyrazolo[4,3-c]quinoline-8-carbohydrazide. Prepared following general procedure E-1 starting with intermediates Da-1 and Ba-38. ES/MS: m/z=439.2 $[M+H]^+$. $^1H$ NMR (400 MHZ, Methanol-d4) δ 8.63-8.41 (m, 2H), 8.02-7.75 (m, 2H), 7.64 (s, 1H), 7.06 (dt, J=20.6, 8.6 Hz, 2H), 5.10 (s, 2H), 4.54 (d, J=12.5 Hz, 3H), 3.13 (d, J=14.7 Hz, 3H), 1.81 (s, 2H), 1.31 (s, 1H).

Example 48

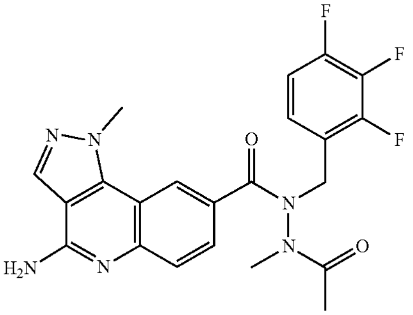

Example 48: N'-acetyl-4-amino-N',1-dimethyl-N-[(2,3,4-trifluorophenyl)methyl]pyrazolo[4,3-c]quinoline-8-carbohydrazide. Prepared following general procedure E-1 starting with intermediates Da-1 and Ba-39. ES/MS: m/z=457.2 $[M+H]^+$. $^1$H NMR (400 MHz, Methanol-d4) δ 8.64-8.42 (m, 2H), 8.03-7.74 (m, 2H), 7.44 (s, 1H), 7.30-7.06 (m, 1H), 5.02 (t, J=17.1 Hz, 1H), 4.95-4.89 (m, 1H), 4.54 (d, J=12.3 Hz, 3H), 3.17 (d, J=39.4 Hz, 3H), 1.85 (s, 3H).

Example 49

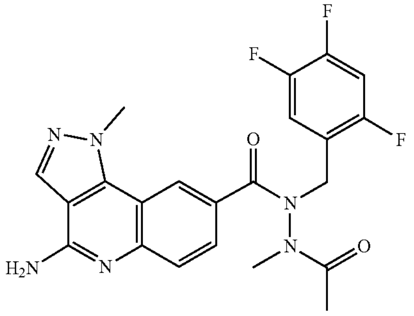

Example 49: N'-acetyl-4-amino-N',1-dimethyl-N-[(2,4,5-trifluorophenyl)methyl]pyrazolo[4,3-c]quinoline-8-carbohydrazide. Prepared following general procedure E-1 starting with intermediates Da-1 and Ba-40. ES/MS: m/z=457.2 $[M+H]^+$. $^1$H NMR (400 MHz, Methanol-d4) δ 8.62-8.40 (m, 2H), 8.02-7.75 (m, 2H), 7.63 (s, 1H), 7.22 (dtd, J=16.5, 10.0, 6.6 Hz, 1H), 5.00 (d, J=14.8 Hz, 1H), 4.54 (d, J=10.4 Hz, 3H), 3.24 (s, 2H), 3.12 (s, 1H), 1.85 (s, 3H).

Example 50

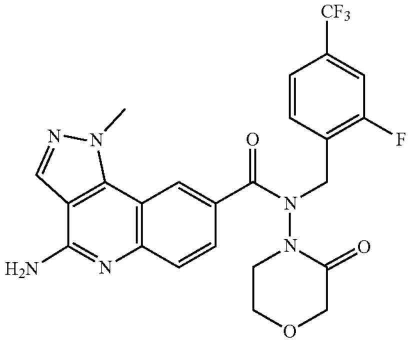

Example 50: 4-amino-N-[[2-fluoro-4-(trifluoromethyl)phenyl]methyl]-1-methyl-N-(3-oxomorpholin-4-yl)pyrazolo[4,3-c]quinoline-8-carboxamide. Prepared following general procedure E-1 starting with intermediates Da-1 and Ba-41. ES/MS: m/z=517.2 $[M+H]^+$. 1H NMR (400 MHz, Methanol-d4) δ 8.53 (s, 1H), 8.50 (s, 1H), 7.92 (d, J=8.5 Hz, 1H), 7.83 (d, J=8.5 Hz, 1H), 7.70 (t, J=7.6 Hz, 1H), 7.58 (d, J=8.0 Hz, 1H), 7.51-7.42 (m, 1H), 5.17 (d, J=15.1 Hz, 1H), 5.04 (d, J=15.0 Hz, 1H), 4.51 (s, 3H), 4.19 (s, 1H), 4.12 (s, 1H), 3.96-3.87 (m, 1H), 3.81 (d, J=9.6 Hz, 1H), 3.55 (s, 1H), 3.52-3.45 (m, 1H).

Example 51

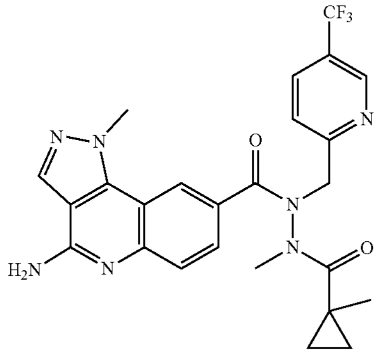

Example 51: 4-amino-N',1-dimethyl-N'-(1-methylcyclopropanecarbonyl)-N-[[5-(trifluoromethyl)-2-pyridyl]methyl]pyrazolo[4,3-c]quinoline-8-carbohydrazide. Prepared following general procedure E-1 starting with intermediates Da-1 and Ba-42. ES/MS: m/z=512.3 $[M+H]^+$. $^1$NMR (400 MHz, Methanol-d4) δ 8.95-8.74 (m, 1H), 8.50 (d, J=1.6 Hz, 1H), 8.22-8.08 (m, 2H), 7.97-7.68 (m, 3H), 5.16 (d, J=15.2 Hz, 1H), 4.99 (d, J=17.3 Hz, 1H), 4.55 (s, 3H), 3.58-3.40 (m, 3H), 0.78 (s, 3H), 0.75-0.61 (m, 1H), 0.51 (s, 1H), 0.38 (s, 2H).

Example 52

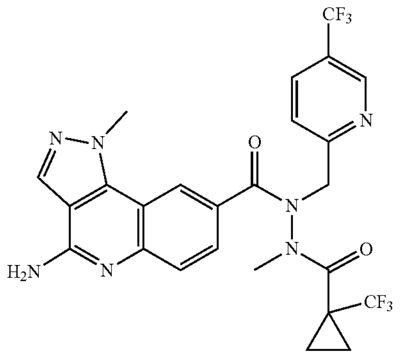

Example 52: 4-amino-N', 1-dimethyl-N'-[1-(trifluoromethyl)cyclopropanecarbonyl]-N-[[5-(trifluoromethyl)-2-pyridyl]methyl]pyrazolo[4,3-c]quinoline-8-carbohydrazide. Prepared following general procedure E-1 starting with intermediates Da-1 and Ba-43. ES/MS: m/z=566.0 $[M+H]^+$. 1H NMR (400 MHz, Methanol-d4) δ 8.86 (s, 1H), 8.50 (s, 2H), 8.18 (d, J=7.7 Hz, 1H), 7.95-7.73 (m, 3H), 5.26-4.99 (m, 2H), 4.54 (s, 3H), 3.51 (d, J=3.9 Hz, 3H), 1.41-1.05 (m, 4H).

Example 53

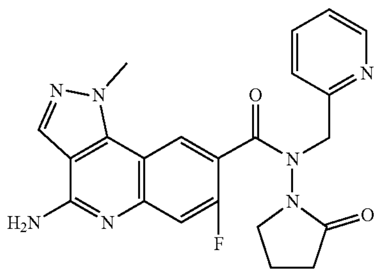

Example 53: 4-amino-7-fluoro-1-methyl-N-(2-oxopyrrolidin-1-yl)-N-(pyridin-2-ylmethyl)-1H-pyrazolo[4,3-c]quinoline-8-carboxamide. Prepared following general procedure E-1 starting with intermediates Db-1 and Ba-44. ES/MS: m/z=434.3 $[M+H]^+$. $^1H$ NMR (400 MHz, DMSO) δ 9.72 (s, 1H), 8.93 (s, 1H), 8.60 (d, J=5.1 Hz, 2H), 8.35 (d, J=6.5 Hz, 1H), 7.88 (d, J=8.2 Hz, 1H), 7.64 (dd, J=16.4, 9.1 Hz, 2H), 7.38 (dd, J=7.5, 4.9 Hz, 1H), 5.19 (d, J=15.2 Hz, 1H), 4.79 (d, J=15.2 Hz, 1H), 4.41 (s, 3H), 3.17 (s, 1H), 2.23-2.00 (m, 1H), 1.95-1.62 (m, 3H), 1.63-1.33 (m, 1H).

Example 54

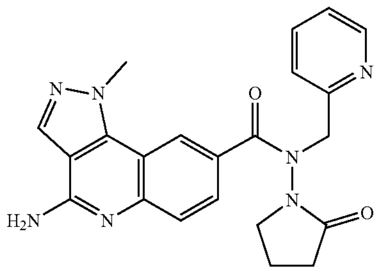

Example 54: 4-amino-1-methyl-N-(2-oxopyrrolidin-1-yl)-N-(pyridin-2-ylmethyl)-1H-pyrazolo[4,3-c]quinoline-8-carboxamide. Prepared following general procedure E-1 starting with intermediates Da-1 and Ba-44. ES/MS: m/z=416.3 $[M+H]^+$. $^1H$ NMR (400 MHZ, MeOD) δ 8.74 (d, J=5.3 Hz, 1H), 8.62 (s, 1H), 8.50 (s, 1H), 8.33-8.15 (m, 1H), 8.16-7.90 (m, 2H), 7.84 (d, J=8.6 Hz, 1H), 7.71 (s, 1H), 5.16 (s, 2H), 4.52 (s, 3H), 3.75-3.53 (m, 1H), 3.49-3.30 (m, 1H), 2.32 (dp, J=17.2, 8.4, 8.0 Hz, 1H), 2.24-1.92 (m, 2H).

Example 55

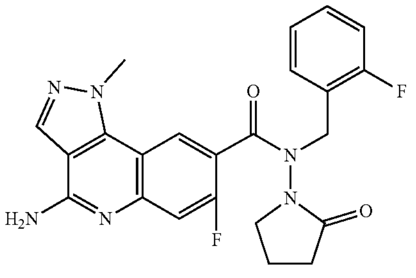

Example 55: 4-amino-7-fluoro-N-(2-fluorobenzyl)-1-methyl-N-(2-oxopyrrolidin-1-yl)-1H-pyrazolo[4,3-c]quinoline-8-carboxamide. Prepared following general procedure E-1 starting with intermediates Db-1 and Ba-45. ES/MS: m/z=451.2 $[M+H]^+$. $^1H$ NMR (400 MHZ, DMSO) δ 8.59 (s, 1H), 8.31 (d, J=6.6 Hz, 1H), 7.72-7.54 (m, 2H), 7.54-7.36 (m, 1H), 7.36-7.17 (m, 2H), 5.10 (d, J=15.0 Hz, 1H), 4.81 (d, J=14.7 Hz, 1H), 4.39 (s, 3H), 3.75 (t, J=7.2 Hz, 1H), 3.11 (s, 1H), 2.23-1.98 (m, 2H), 1.96-1.62 (m, 1H), 1.47 (s, 1H).

Example 56

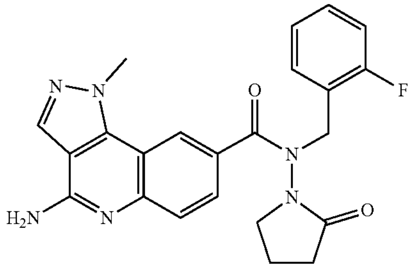

Example 56: 4-amino-N-(2-fluorobenzyl)-1-methyl-N-(2-oxopyrrolidin-1-yl)-1H-pyrazolo[4,3-c]quinoline-8-carboxamide. Prepared following general procedure E-1 starting with intermediates Da-1 and Ba-45. ES/MS: m/z=433.2 $[M+H]^+$. $^1H$ NMR (400 MHz, DMSO) § 13.50 (s, 1H), 9.64 (s, 1H), 8.80 (s, 1H), 8.62 (s, 1H), 8.38 (d, J=1.6 Hz, 1H), 7.92-7.70 (m, 2H), 7.65 (td, J=7.8, 2.0 Hz, 1H), 7.41 (tdd, J=7.5, 5.4, 1.8 Hz, 1H), 5.01 (d, J=14.9 Hz, 1H), 4.83 (d, J=14.9 Hz, 1H), 4.42 (s, 3H), 3.34 (q, J=8.1 Hz, 1H), 3.18 (s, 2H), 2.11 (dt, J=17.0, 8.7 Hz, 1H), 1.84 (s, 1H), 1.83-1.64 (m, 1H), 1.52 (s, 1H).

Example 57

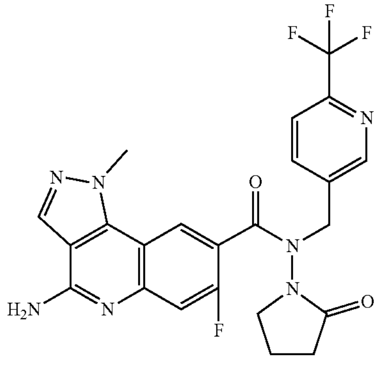

Example 57: 4-amino-7-fluoro-1-methyl-N-(2-oxopyrrolidin-1-yl)-N-((6-(trifluoromethyl)pyridin-3-yl)methyl)-1H-pyrazolo[4,3-c]quinoline-8-carboxamide. Prepared following general procedure E-1 starting with intermediates Db-1 and Ba-46. ES/MS: m/z=502.2 $[M+H]^+$. $^1H$ NMR (400 MHz, DMSO) δ 8.90 (s, 1H), 8.55 (s, 1H), 8.35 (d, J=6.7 Hz, 1H), 8.22 (d, J=7.7 Hz, 1H), 7.96 (d, J=8.0 Hz, 1H), 7.54 (s, 1H), 6.44 (s, 1H), 5.04 (s, 3H), 4.40 (s, 4H), 3.61 (s, 2H), 2.20-2.04 (m, 1H), 1.85 (s, 2H), 1.52 (dd, J=14.9, 6.8 Hz, 1H).

Example 58

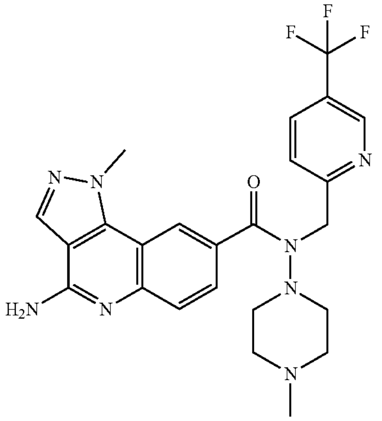

Example 58: 4-amino-1-methyl-N-(4-methylpiperazin-1-yl)-N-((5-(trifluoromethyl)pyridin-2-yl)methyl)-1H-pyrazolo[4,3-c]quinoline-8-carboxamide. Prepared following general procedure E-1 starting with intermediates Da-1 and Ba-47. ES/MS: m/z=499.1 $[M+H]^+$. $^1H$ NMR (400 MHz, DMSO) δ 13.79 (s, 1H), 9.58 (d, J=53.4 Hz, 2H), 8.98 (s, 1H), 8.64 (s, 1H), 8.46 (s, 1H), 8.39-8.20 (m, 1H), 7.98 (d, J=8.6 Hz, 1H), 7.81 (d, J=8.6 Hz, 1H), 7.78 (s, 1H), 4.95 (s, 2H), 4.46 (d, J=11.7 Hz, 3H), 3.39 (d, J=11.8 Hz, 1H), 3.20 (d, J=10.8 Hz, 1H), 3.08 (s, 1H), 2.80 (s, 1H), 2.74 (d, J=38.1 Hz, 5H).

Example 59

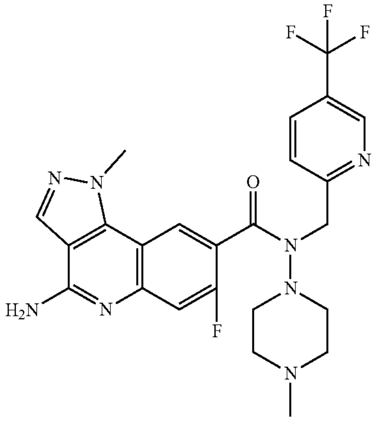

Example 59: 4-amino-7-fluoro-1-methyl-N-(4-methylpiperazin-1-yl)-N-((5-(trifluoromethyl)pyridin-2-yl)methyl)-1H-pyrazolo[4,3-c]quinoline-8-carboxamide. Prepared following general procedure E-1 starting with intermediates Db-1 and Ba-47. ES/MS: m/z=517.2 $[M+H]^+$. $^1H$ NMR (400 MHz, DMSO) δ 13.91 (s, 1H), 9.56 (s, 1H), 8.99 (s, 1H), 8.60 (s, 1H), 8.40 (d, J=6.4 Hz, 1H), 8.34-8.18 (m, 1H), 7.74 (d, J=8.1 Hz, 1H), 7.59 (d, J=10.2 Hz, 1H), 4.99 (s, 2H), 4.46 (s, 2H), 3.05 (d, J=20.5 Hz, 4H), 2.62 (d, J=11.2 Hz, 5H), 2.47-2.42 (m, 2H).

Example 60

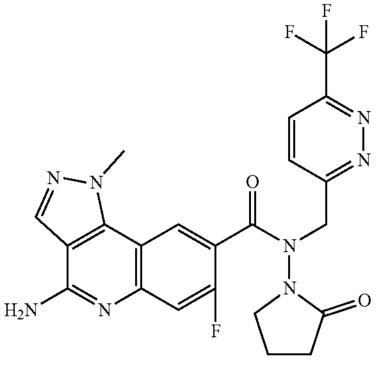

Example 60: 4-amino-7-fluoro-1-methyl-N-(2-oxopyrrolidin-1-yl)-N-((6-(trifluoromethyl)pyridazin-3-yl)methyl)-1H-pyrazolo[4,3-c]quinoline-8-carboxamide. Prepared following general procedure E-1 starting with intermediates Db-1 and Ba-48. ES/MS: m/z=503.2 $[M+H]^+$. $^1H$ NMR (400 MHz, DMSO) δ 8.94 (s, 1H), 8.60 (s, 1H), 8.49-8.32 (m, 2H), 8.28 (d, J=9.0 Hz, 1H), 7.65 (d, J=10.5 Hz, 1H), 5.34 (s, 2H), 4.41 (s, 3H), 3.28 (s, 2H), 2.23-2.05 (m, 1H), 1.90 (d, J=15.3 Hz, 2H), 1.55 (s, 1H).

Example 61

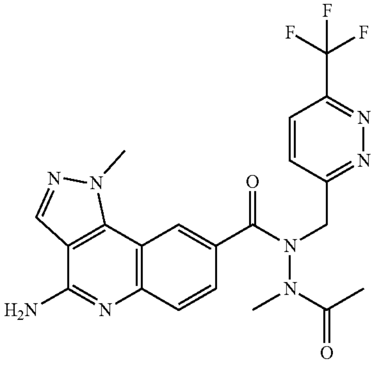

Example 61: N'-acetyl-4-amino-N',1-dimethyl-N-((6-(trifluoromethyl)pyridazin-3-yl)methyl)-1H-pyrazolo[4,3-c]quinoline-8-carbohydrazide. Prepared following general procedure E-1 starting with intermediates Da-1 and Ba-49. ES/MS: m/z=473.2 $[M+H]^+$. 1H NMR (400 MHz, DMSO) δ 13.55 (s, 1H), 9.67 (s, 1H), 8.94 (s, 1H), 8.63 (s, 1H), 8.45-8.22 (m, 2H), 7.91-7.75 (m, 2H), 5.33-5.08 (m, 2H), 4.46 (d, J=3.7 Hz, 3H), 3.11 (s, 1H, minor rotamer), 2.55 (s, 2H, major rotamer), 1.99 (s, 1H, minor rotamer), 1.82 (s, 2H, major rotamer).

Example 62

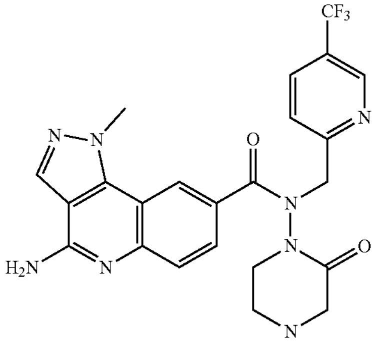

Example 62: 4-amino-1-methyl-N-(3-oxomorpholin-4-yl)-N-[[5-(trifluoromethyl)-2-pyridyl]methyl]pyrazolo[4,3-c]quinoline-8-carboxamide. Prepared following general procedure E-1 starting with intermediates Da-1 and Ba-50. ES/MS: m/z=500.0 $[M+H]^+$. $^1H$ NMR (400 MHz, DMSO-$d_6$) δ 13.42 (s, 1H), 9.68 (s, 1H), 8.98 (s, 1H), 8.63 (s, 1H), 8.40 (s, 1H), 8.27 (dd, J=8.3, 2.4 Hz, 1H), 7.92 (s, 1H), 7.85 (s, 2H), 5.26 (d, J=15.9 Hz, 1H), 4.92 (d, J=15.9 Hz, 1H), 4.43 (s, 3H), 4.08 (d, J=16.6 Hz, 1H), 3.82-3.75 (m, 2H), 2.68 (dt, J=3.4, 1.6 Hz, 2H), 2.33 (dt, J=3.7, 1.8 Hz, 2H), 2.52 (s, 6H).

Example 63

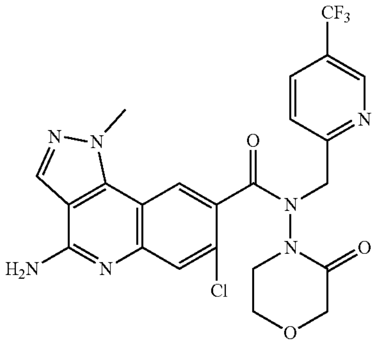

Example 63: 4-amino-7-chloro-1-methyl-N-(3-oxomorpholin-4-yl)-N-[[5-(trifluoromethyl)-2-pyridyl]methyl]pyrazolo[4,3-c]quinoline-8-carboxamide. Prepared following general procedure E-1 starting with intermediates Db-2 and Ba-50. ES/MS: m/z=534.0 $[M+H]^+$. $^1H$ NMR (400 MHz, DMSO-$d_6$) δ 8.98 (d, J=2.3 Hz, 1H), 8.61 (s, 1H), 8.36-8.26 (m, 2H), 7.95-7.81 (m, 2H), 5.15 (dd, J=197.5, 16.0 Hz, 2H), 4.38 (s, 3H), 4.08 (d, J=16.8 Hz, 1H), 3.88 (d, J=16.8 Hz, 1H), 3.76 (ddt, J=10.8, 7.6, 4.5 Hz, 2H), 2.51 (ddt, J=136.9, 3.6, 1.8 Hz, 1H).

Example 64

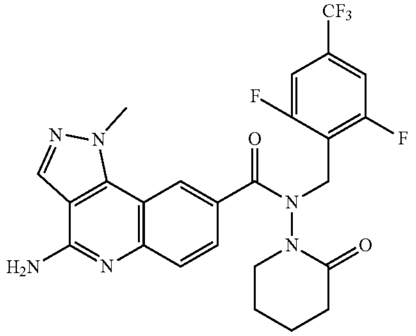

Example 64: 4-amino-N-[[2,6-difluoro-4-(trifluoromethyl)phenyl]methyl]-1-methyl-N-(2-oxo-1-piperidyl)pyrazolo[4,3-c]quinoline-8-carboxamide. Prepared following general procedure E-1 starting with intermediates Da-1 and Ba-51. ES/MS: m/z=533.0 $[M+H]^+$. $^1H$ NMR (400 MHz, DMSO-$d_6$) δ 8.62 (s, 1H), 8.30 (s, 1H), 7.79 (d, J=9.9 Hz, 2H), 7.69 (d, J=7.0 Hz, 2H), 5.10-4.91 (m, 2H), 4.41 (s, 3H), 3.27 (s, 1H), 2.51 (ddt, J=137.2, 3.5, 1.6 Hz, 1H), 2.15 (d, J=17.7 Hz, 1H), 1.92 (s, 1H), 1.59 (s, 1H), 1.44 (s, 1H), 1.24 (s, 2H).

Example 65

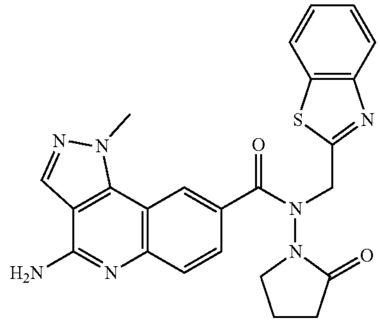

Example 65: 4-amino-N-(1,3-benzothiazol-2-ylmethyl)-1-methyl-N-(2-oxopyrrolidin-1-yl)pyrazolo[4,3-c]quinoline-8-carboxamide. Prepared following general procedure E-1 starting with intermediates Da-1 and Ba-52. ES/MS: m/z=472.0 $[M+H]^+$. $^1H$ NMR (400 MHz, DMSO-$d_6$) δ 8.62 (s, 1H), 8.44 (s, 1H), 8.14 (d, J=7.9 Hz, 1H), 8.02 (d, J=8.0 Hz, 1H), 7.86 (d, J=7.3 Hz, 2H), 7.57-7.52 (m, 1H), 7.50-7.46 (m, 1H), 5.41 (d, J=16.0 Hz, 1H), 5.18 (d, J=16.0 Hz, 1H), 4.43 (s, 4H), 3.66 (s, 1H), 2.68 (p, J=1.8 Hz, 2H), 2.33 (p, J=1.9 Hz, 2H), 1.20 (d, J=34.9 Hz, 1H).

Example 66

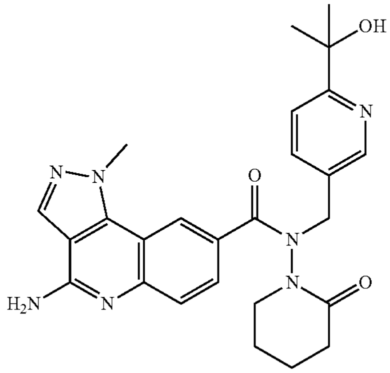

Example 66: 4-amino-N-[[6-(1-hydroxy-1-methyl-ethyl)-3-pyridyl]methyl]-1-methyl-N-(2-oxo-1-piperidyl)pyrazolo [4,3-c]quinoline-8-carboxamide. Prepared following general procedure E-1 starting with intermediates Da-1 and Ba-53. ES/MS: m/z=488.2 $[M+H]^+$. $^1H$ NMR (400 MHz, DMSO-$d_6$) δ 13.34 (s, 1H), 9.63 (s, 1H), 8.64 (d, J=7.9 Hz, 2H), 8.35 (s, 1H), 8.00 (s, 1H), 7.81 (s, 2H), 7.73 (d, J=8.3 Hz, 1H), 5.11 (d, J=14.8 Hz, 1H), 4.63 (d, J=15.0 Hz, 1H), 4.44 (s, 3H), 2.68 (dt, J=3.5, 1.9 Hz, 2H), 2.33 (dt, J=3.7, 1.9 Hz, 2H), 2.22 (d, J=16.8 Hz, 1H), 1.46 (s, 6H), 1.30 (s, 3H).

Example 67

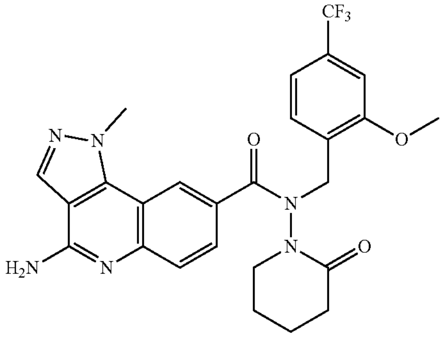

Example 67: 4-amino-N-[[2-methoxy-4-(trifluoromethyl) phenyl]methyl]-1-methyl-N-(2-oxo-1-piperidyl)pyrazolo[4,3-c]quinoline-8-carboxamide. Prepared following general procedure E-1 starting with intermediates Da-1 and Ba-54. ES/MS: m/z=527.2 $[M+H]^+$. 1H NMR (400 MHz, DMSO-$d_6$) δ 8.63 (s, 1H), 8.34 (s, 1H), 7.82 (s, 2H), 7.75 (d, J=7.8 Hz, 1H), 7.38-7.29 (m, 2H), 6.54 (s, 2H), 5.13 (d, J=15.5 Hz, 1H), 4.61 (d, J=15.4 Hz, 1H), 4.44 (dd, J=872.3, 278.4 Hz, 3H), 3.95 (s, 3H), 2.23 (d, J=18.4 Hz, 2H), 2.01-1.81 (m, 2H), 1.50 (d, J=44.7 Hz, 2H), 1.27 (d, J=25.7 Hz, 2H).

Example 68

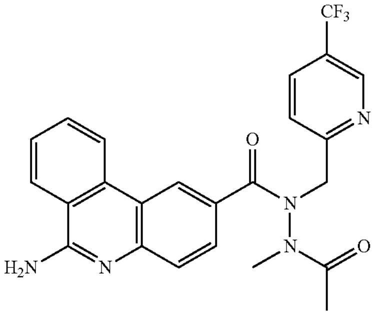

Example 68: N'-acetyl-6-amino-N'-methyl-N-[[5-(trifluoromethyl)-2-pyridyl]methyl]phenanthridine-2-carbohydrazide. Prepared following general procedure E-1 starting with intermediates Da-3 and Ba-29. ES/MS: m/z=468.0 $[M+H]^+$. $^1H$ NMR (400 MHZ, DMSO-$d_6$) δ 9.06 (s, 2H), 8.83 (dd, J=11.7, 8.4 Hz, 1H), 8.68 (d, J=8.2 Hz, 2H), 8.26 (d, J=8.4 Hz, 1H), 8.15 (d, J=6.9 Hz, 1H), 7.85 (dt, J=66.1, 8.1 Hz, 3H), 5.30-4.66 (m, 2H), 3.16 (d, J=74.9 Hz, 3H), 1.84 (d, J=74.1 Hz, 3H).

Example 69

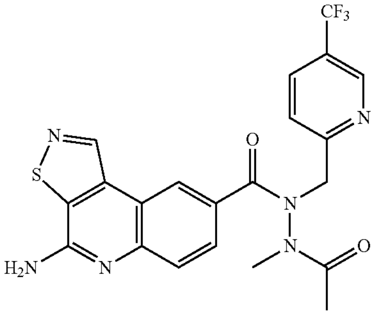

Example 69: N'-acetyl-4-amino-N'-methyl-N-[[5-(trifluoromethyl)-2-pyridyl]methyl]isothiazolo[5,4-c]quinoline-8-carbohydrazide. Prepared following general procedure E-1 starting with intermediates Da-5 and Ba-29. ES/MS: m/z=475.0 $[M+H]^+$. 1H NMR (400 MHz, DMSO-$d_6$) δ 9.89 (d, J=18.8 Hz, 1H), 9.00-8.91 (m, 2H), 8.31-8.12 (m, 2H), 7.77 (d, J=7.9 Hz, 1H), 7.71 (d, J=8.1 Hz, 1H), 5.35-4.61 (m, 2H), 3.28 (s, 1H), 3.06 (s, 1H), 3.00 (s, 1H), 1.96 (d, J=10.4 Hz, 3H), 1.87 (s, 2H), 1.75 (s, 2H).

Example 70

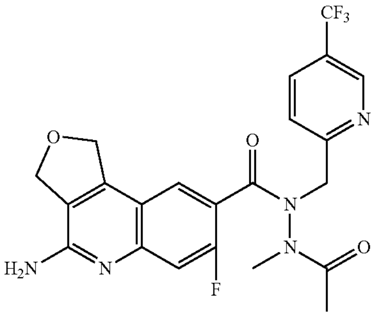

Example 70: N'-acetyl-4-amino-7-fluoro-N'-methyl-N-[[5-(trifluoromethyl)-2-pyridyl]methyl]-1,3-dihydrofuro[3, 4-c]quinoline-8-carbohydrazide. Prepared following general procedure E-1 starting with intermediates Db-3 and Ba-29. ES/MS: m/z=478.0 $[M+H]^+$. $^1H$ NMR (400 MHz, DMSO-$d_6$) δ 9.05-8.87 (m, 2H), 8.55 (s, 2H), 8.22 (dd, J=8.2, 2.4 Hz, 1H), 7.71 (d, J=8.3 Hz, 1H), 7.50 (dd, J=31.0, 9.5 Hz, 1H), 5.51-5.29 (m, 1H), 5.06 (d, J=4.4 Hz, 1H), 5.26-4.68 (m, 2H), 4.13 (s, 2H), 3.00 (s, 3H), 1.87 (s, 3H).

Example 71

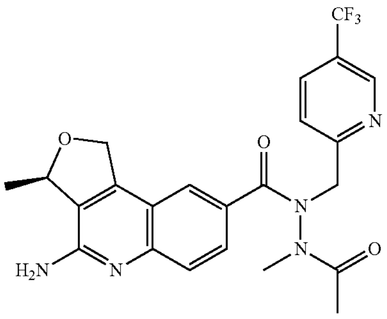

Example 71: (3R)—N'-acetyl-4-amino-N',3-dimethyl-N-[[5-(trifluoromethyl)-2-pyridyl]methyl]-1,3-dihydrofuro[3,4-c]quinoline-8-carbohydrazide. Prepared following general procedure E-1 starting with intermediates Db-6 and Ba-29. ES/MS: m/z=474.0 $[M+H]^+$. $^1H$ NMR (400 MHz, DMSO-$d_6$) δ 9.16-8.90 (m, 1H), 8.65 (s, 2H), 8.24 (dt, J=8.2, 4.8 Hz, 1H), 7.87-7.76 (m, 3H), 5.58-5.37 (m, 3H), 5.30-4.61 (m, 2H), 3.24 (d, J=2.4 Hz, 1H), 3.01 (d, J=6.0 Hz, 2H), 1.89-1.75 (m, 3H), 1.45 (dd, J=6.1, 3.3 Hz, 3H).

Example 72

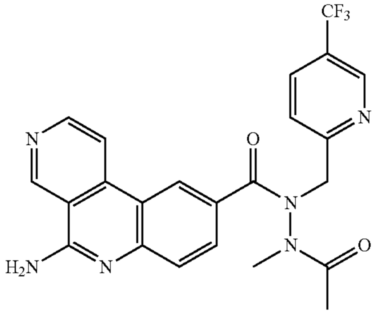

Example 72: N'-acetyl-5-amino-N'-methyl-N-((5-(trifluoromethyl)pyridin-2-yl)methyl)benzo[c][2,7]naphthyridine-9-carbohydrazide. Prepared following general procedure E-1 starting with intermediates Da-2 and Ba-29. ES/MS: m/z=469.0 $[M+H]^+$. 1H NMR (400 MHz, DMSO-$d_6$) δ 9.85 (s, 1H), 9.03 (d, J=44.5 Hz, 3H), 8.70 (s, 2H), 8.25 (d, J=8.8 Hz, 1H), 7.94-7.67 (m, 4H), 5.32-4.64 (m, 2H), 3.09-2.98 (m, 3H), 1.90 (d, J=22.5 Hz, 3H).

Example 73

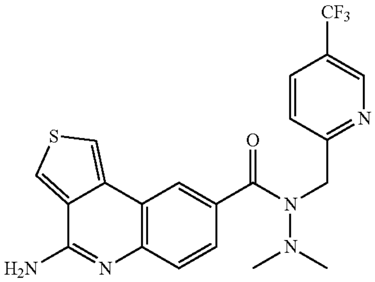

Example 73: 4-amino-N',N'-dimethyl-N-((5-(trifluoromethyl)pyridin-2-yl)methyl)thieno[3,4-c]quinoline-8-carbohydrazide. Prepared following general procedure E-1 starting with intermediates Da-7 and Ba-55. ES/MS: m/z=446.0 $[M+H]^+$. $^1H$ NMR (400 MHz, DMSO-$d_6$) δ 13.13 (brs, 1H), 9.84 (s, 1H), 9.21 (d, J=2.9 Hz, 1H), 8.96 (brs, 2H), 8.83 (d, J=3.0 Hz, 1H), 8.44 (d, J=1.8 Hz, 1H), 8.20 (dd, J=8.3, 2.4 Hz, 1H), 7.76 (dd, J=8.5, 1.8 Hz, 1H), 7.73 (d, J=8.3 Hz, 1H), 7.60 (d, J=8.5 Hz, 1H), 4.90 (s, 2H). 2.52 (s, 6H).

Example 74

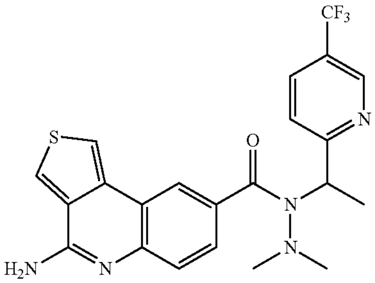

Example 74: 4-amino-N',N'-dimethyl-N-(1-(5-(trifluoromethyl)pyridin-2-yl)ethyl)thieno[3,4-c]quinoline-8-carbohydrazide. Prepared following general procedure E-1 starting with intermediates Da-7 and Ba-56. ES/MS: m/z=460.0 $[M+H]^+$. $^1H$ NMR (400 MHZ, DMSO-$d_6$) δ 13.15 (brs, 1H), 9.82 (brs, 1H), 9.20 (d, J=3.0 Hz, 1H), 8.97 (brs, 2H), 8.85 (d, J=3.0 Hz, 1H), 8.34 (brs, 1H), 8.18 (dd, J=8.5, 2.4 Hz, 1H), 7.77 (d, J=8.4 Hz, 1H), 7.66 (s, 1H), 7.58 (d, J=8.4 Hz, 1H), 5.03 (q, J=7.0 Hz, 1H), 2.66 (s, 3H), 2.59 (s, 3H), 1.91 (brs, 3H).

Example 75

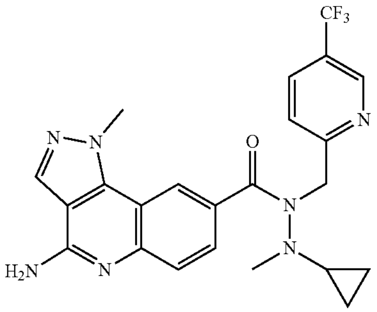

Example 75: 4-amino-N'-cyclopropyl-N',1-dimethyl-N-((5-(trifluoromethyl)pyridin-2-yl)methyl)-1H-pyrazolo[4,3-c]quinoline-8-carbohydrazide. Prepared following general procedure E-1 starting with intermediates Da-1 and Ba-57. ES/MS: m/z=470.2 [M+H]$^+$. $^1$H NMR (400 MHz, DMSO-$d_6$) δ 13.35 (brs, 1H), 9.62 (brs, 1H), 8.96 (s, 1H), 8.70 (brs, 1H), 8.63 (s, 1H), 8.54 (d, J=1.8 Hz, 1H), 8.21 (dd, J=8.3, 2.4 Hz, 1H), 7.97 (dd, J=8.7, 1.8 Hz, 1H), 7.84-7.72 (m, 2H), 5.13-4.99 (m, 2H), 4.48 (s, 3H), 2.84 (s, 3H), 2.43-2.33 (m, 1H), 0.57-0.41 (m, 1H), 0.31--0.03 (m, 3H).

Example 76

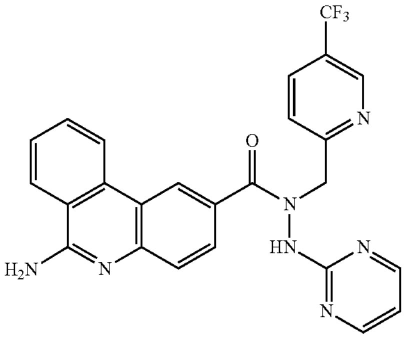

Example 76: 6-amino-N'-(pyrimidin-2-yl)-N-((5-(trifluoromethyl)pyridin-2-yl)methyl)phenanthridine-2-carbohydrazide. Prepared following general procedure E-1 starting with intermediates Da-3 and Ba-58. ES/MS: m/z=490.0 [M+H]$^+$. $^1$H NMR (400 MHZ, DMSO-$d_6$) δ 13.61 (brs, 1H), 10.02 (s, 1H), 9.66 (brs, 1H), 9.06 (brs, 1H), 8.95 (s, 1H), 8.84 (d, J=1.7 Hz, 1H), 8.73 (d, J=8.3 Hz, 1H), 8.64 (d, J=8.2 Hz, 1H), 8.34 (brs, 2H), 8.29 (dd, J=8.3, 2.4 Hz, 1H), 8.12 (dd, J=7.7, 7.7 Hz, 1H), 7.93-7.83 (m, 3H), 7.64 (d, J=8.5 Hz, 1H), 6.76 (t, J=4.8 Hz, 1H), 5.63 (d, J=15.7 Hz, 1H), 4.56 (d, J=15.6 Hz, 1H).

Example 77

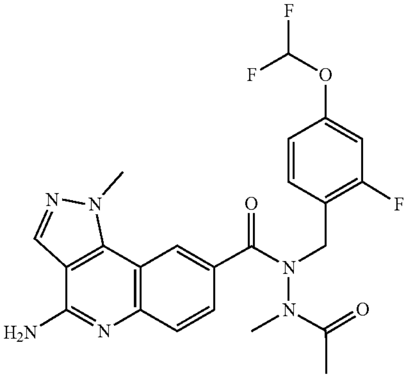

Example 77: N'-acetyl-4-amino-N-(4-(difluoromethoxy)-2-fluorobenzyl)-N',1-dimethyl-1H-pyrazolo[4,3-c]quinoline-8-carbohydrazide. Prepared following general procedure E-1 starting with intermediates Da-1 and Ba-59. ES/MS: m/z=487.2 [M+H]$^+$. 1H NMR (400 MHz, DMSO-$d_6$) δ 13.58 (brs, 1H), 9.66 (brs, 1H), 8.88 (brs, 1H), 8.63 (s, 0.5H rotamer), 8.62 (s, 0.5H rotamer), 8.44 (s, 0.5H rotamer), 8.33 (s, 0.5H rotamer), 7.98-7.80 (m, 1H), 7.80 (s, 1H), 7.67 (t, J=8.6 Hz, 0.5H rotamer), 7.60 (brs, 0.5H rotamer), 7.51 (d, J=3.8 Hz, 0.5H rotamer), 7.32 (d, J=4.0 Hz, 0.5H rotamer), 7.24-7.12 (m, 1H), 7.11-7.02 (m, 1H), 5.16-4.94 (m, 1H), 4.85 (d, J=14.5 Hz, 0.5H rotamer), 4.63 (d, J=14.5 Hz, 0.5H rotamer), 4.47 (s, 1.5H rotamer), 4.44 (s, 1.5H rotamer), 3.08 (s, 1.5H rotamer), 2.99 (s, 1.5H rotamer), 1.75 (s, 1.5H rotamer), 1.67 (s, 1.5H rotamer).

Example 78

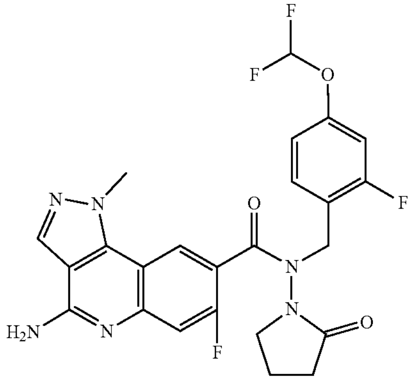

Example 78: 4-amino-N-(4-(difluoromethoxy)-2-fluorobenzyl)-7-fluoro-1-methyl-N-(2-oxopyrrolidin-1-yl)-1H-pyrazolo[4,3-c]quinoline-8-carboxamide. Prepared following general procedure E-1 starting with intermediates Db-1 and Ba-60. ES/MS: m/z=517.2 [M+H]$^+$. $^1$H NMR (400 MHz, DMSO-$d_6$) δ 13.65 (brs, 1H), 9.49 (brs, 1H), 9.01 (brs, 1H), 8.57 (s, 1H), 8.30 (d, J=6.7 Hz, 1H), 7.65 (d, J=8.5 Hz, 0.8H minor rotamer), 7.61 (d, J=10.2 Hz, 1.2H major rotamer), 7.33 (t, J=73.5 Hz, 1H), 7.21-7.14 (m, 1H), 7.07 (dd, J=8.4, 2.4 Hz, 1H), 4.98 (d, J=15.0 Hz, 1H), 4.84 (d, J=15.0 Hz, 1H), 4.38 (s, 3H), 3.22-3.05 (s, 1H), 2.14-1.97 (m, 1H), 1.91-1.74 (m, 2H), 1.57-1.40 (m, 1H).

Example 79

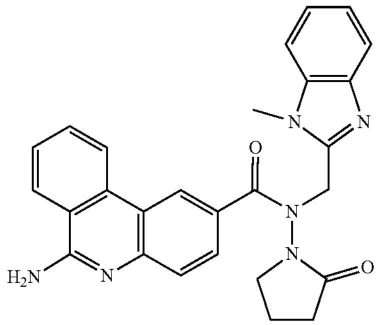

Example 79: 6-Amino-N-[(1-methylbenzimidazol-2-yl) methyl]-N-(2-oxopyrrolidin-1-yl) phenanthridine-2-carboxamide. Prepared following general procedure E-1 starting with intermediates Da-3 and Ba-61. ES/MS: m/z=465.1 [M+H]$^+$. $^1$H NMR (400 MHz, Methanol-d4) δ 8.87-8.77 (m, 1H), 8.77-8.68 (m, 1H), 8.58 (dd, J=8.3, 1.2 Hz, 1H), 8.25-8.07 (m, 1H), 8.02-7.72 (m, 5H), 7.72-7.38 (m, 2H), 5.78 (d, J=16.3 Hz, 1H), 5.34-5.12 (m, 2H), 4.20 (d, J=1.7 Hz, 3H), 3.88 (q, J=8.6 Hz, 1H), 3.58-3.41 (m, 1H), 3.23 (d, J=7.3 Hz, 1H), 2.35-2.20 (m, 1H), 2.14-1.81 (m, 1H).

Example 80

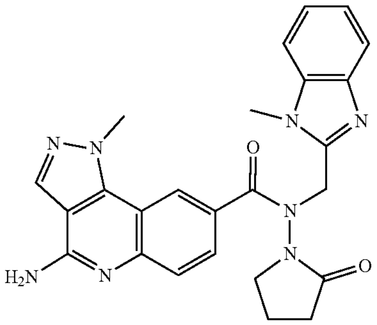

Example 80: 4-Amino-1-methyl-N-[(1-methylbenzimidazol-2-yl)methyl]-N-(2-oxopyrrolidin-1-yl)pyrazolo[4,3-c]quinoline-8-carboxamide. Prepared following general procedure E-1 starting with intermediates Da-1 and Ba-61. ES/MS: m/z=469.2 $[M+H]^+$. 1H NMR (400 MHz, Methanol-d4) δ 8.59 (d, J=1.7 Hz, 1H), 8.50 (s, 1H), 8.02-7.80 (m, 4H), 7.74-7.49 (m, 2H), 5.83 (d, J=16.3 Hz, 1H), 5.21 (d, J=16.3 Hz, 1H), 4.49 (s, 3H), 4.21 (s, 3H), 3.89 (q, J=8.0 Hz, 1H), 3.39 (dd, J=8.8, 4.0 Hz, 2H), 3.01 (d, J=55.2 Hz, 1H), 2.49-1.51 (m, 3H).

Example 81

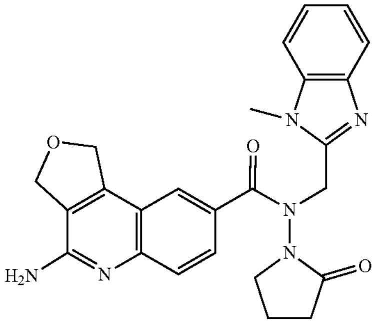

Example 81: 4-Amino-N-[(1-methylbenzimidazol-2-yl)methyl]-N-(2-oxopyrrolidin-1-yl)-1,3-dihydrofuro[3,4-c]quinoline-8-carboxamide. Prepared following general procedure E-1 starting with intermediates Db-5 and Ba-61. ES/MS: m/z=457.2 $[M+H]^+$. $^1$H NMR (400 MHz, Methanol-d4) δ 7.97 (d, J=6.3 Hz, 2H), 7.89-7.69 (m, 3H), 7.50 (dt, J=19.6, 7.3 Hz, 2H), 5.62 (d, J=15.9 Hz, 1H), 5.51 (q, J=3.9 Hz, 2H), 5.27-5.07 (m, 3H), 4.10 (s, 3H), 3.81 (d, J=8.2 Hz, 1H), 3.58-3.38 (m, 1H), 3.15 (p, J=1.7 Hz, 1H), 2.15 (dt, J=17.0, 7.9 Hz, 1H), 2.09-1.83 (m, 2H), 1.69 (s, 1H).

Example 83

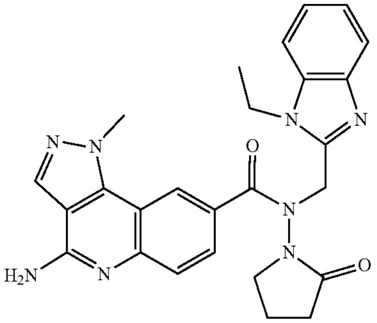

Example 83: 4-Amino-N-[(1-ethylbenzimidazol-2-yl)methyl]-1-methyl-N-(2-oxopyrrolidin-1-yl)pyrazolo[4,3-c]quinoline-8-carboxamide. Prepared following general procedure E-1 starting with intermediates Da-1 and Ba-63. ES/MS: m/z=483.2 $[M+H]^+$. $^1$H NMR (400 MHz, Methanol-d4) δ 8.58 (d, J=1.7 Hz, 1H), 8.52 (s, 1H), 7.98 (ddd, J=10.5, 8.6, 1.8 Hz, 2H), 7.94-7.80 (m, 2H), 7.70 (tt, J=7.5, 5.9 Hz, 2H), 5.86 (d, J=16.5 Hz, 1H), 5.23 (d, J=16.5 Hz, 1H), 4.49 (s, 3H), 3.41 (td, J=8.9, 3.9 Hz, 1H), 3.33 (p, J=1.6 Hz, 2H), 3.08 (s, 1H), 2.94 (s, 1H), 2.16-2.04 (m, 4H), 1.68 (t, J=7.3 Hz, 3H).

Example 84

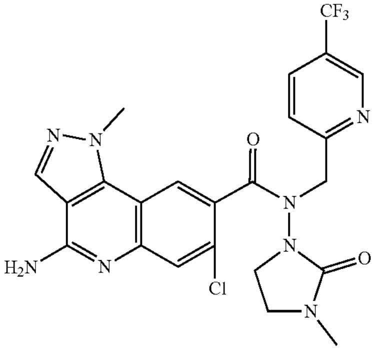

Example 84: 4-Amino-7-chloro-1-methyl-N-(3-methyl-2-oxo-imidazolidin-1-yl)-N-[[5-(trifluoromethyl)-2-pyridyl]methyl]pyrazolo[4,3-c]quinoline-8-carboxamide. Prepared following general procedure E-1 starting with intermediates Db-2 and Ba-64. ES/MS: m/z=533.4 $[M+H]^+$. $^1$H NMR (400 MHz, Methanol-d4) δ 8.98-8.82 (m, 1H), 8.50 (d, J=15.2 Hz, 2H), 8.20 (dd, J=8.4, 2.3 Hz, 1H), 8.01-7.72 (m, 2H), 5.41 (d, J=16.0 Hz, 1H), 4.82 (d, J=16.0 Hz, 1H), 4.50 (s, 3H), 3.84-3.63 (m, 1H), 3.50 (td, J=8.6, 2.7 Hz, 1H), 3.37 (s, 1H), 3.15-2.83 (m, 2H), 2.66 (s, 3H).

Example 85

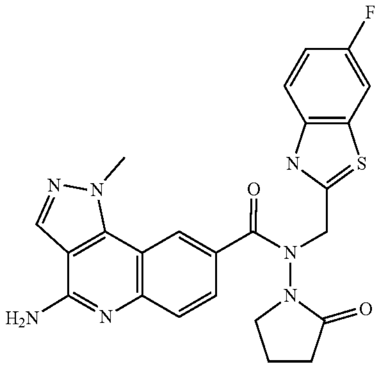

Example 85: 4-Amino-N-[(6-fluoro-1,3-benzothiazol-2-yl)methyl]-1-methyl-N-(2-oxopyrrolidin-1-yl)pyrazolo[4,3-c]quinoline-8-carboxamide. Prepared following general procedure E-1 starting with intermediates Da-1 and Ba-65. ES/MS: m/z=490.2 $[M+H]^+$. 1H NMR (400 MHz, Methanol-d4) δ 8.73-8.57 (m, 1H), 8.49 (s, 1H), 8.10-8.00 (m, 1H), 8.00-7.89 (m, 1H), 7.89-7.78 (m, 2H), 7.34 (td, J=9.0, 2.6 Hz, 1H), 5.39 (d, J=15.8 Hz, 1H), 5.24 (d, J=15.8 Hz, 1H), 4.50 (s, 3H), 3.76 (t, J=7.9 Hz, 1H), 3.45 (s, 1H), 3.01 (d, J=55.1 Hz, 1H), 2.44-1.92 (m, 4H).

Example 86

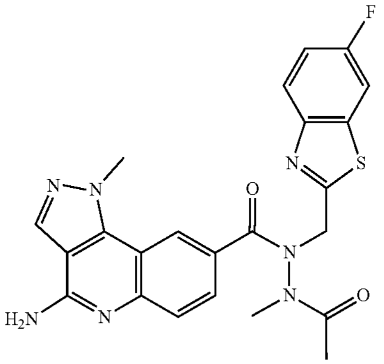

Example 86: N'-Acetyl-4-amino-N-[(6-fluoro-1,3-benzothiazol-2-yl)methyl]-N', 1-dimethyl-pyrazolo[4,3-c]quinoline-8-carbohydrazide. Prepared following general procedure E-1 starting with intermediates Da-1 and Ba-66. ES/MS: m/z=478.2$[M+H]^+$. $^1$H NMR (400 MHz, Methanol-d4) δ 8.55 (s, 1H), 8.50 (d, J=2.7 Hz, 1H), 8.17-7.97 (m, 2H), 7.97-7.73 (m, 2H), 7.35 (ddd, J=11.8, 7.2, 2.7 Hz, 1H), 5.37 (dd, J=27.9, 15.9 Hz, 1H), 5.13 (d, J=15.8 Hz, 1H), 4.52 (s, 3H), 3.39 (s, 3H), 3.31-3.13 (m, 1H), 2.21-1.66 (m, 3H).

Example 87

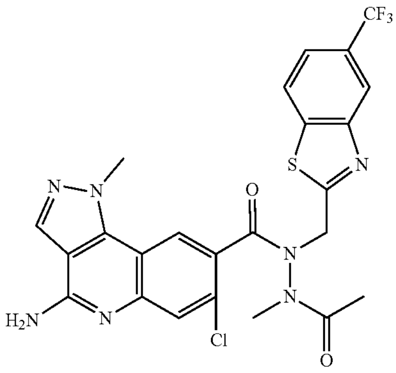

Example 87: N'-Acetyl-4-amino-7-chloro-N',1-dimethyl-N-[[5-(trifluoromethyl)-1,3-benzothiazol-2-yl]methyl]pyrazolo[4,3-c]quinoline-8-carbohydrazide. Prepared following general procedure E-1 starting with intermediates Db-2 and Bb-1. ES/MS: m/z=562.2 $[M+H]^+$. $^1$H NMR (400 MHz, Methanol-d4) δ 8.48 (s, 1H), 8.38 (d, J=11.9 Hz, 1H), 8.33-8.18 (m, 2H), 7.93 (d, J=18.5 Hz, 1H), 7.77 (dd, J=8.6, 1.7 Hz, 1H), 5.61 (d, J=15.8 Hz, 1H), 5.28-5.02 (m, 1H), 4.46 (s, 3H), 3.30 (m, 3H), 2.24 (d, J=54.5 Hz, 1H), 1.89 (s, 3H).

Example 88

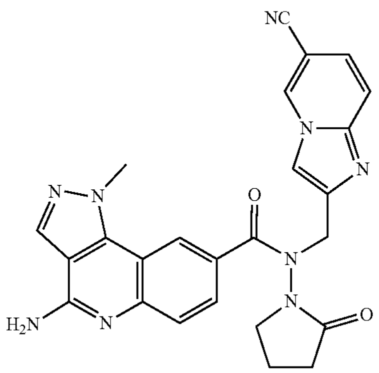

Example 88: 4-Amino-N-[(6-cyanoimidazo[1,2-a]pyridin-2-yl)methyl]-1-methyl-N-(2-oxopyrrolidin-1-yl)pyrazolo[4,3-c]quinoline-8-carboxamide. Prepared following general procedure E-1 starting with intermediates Da-1 and Bb-3. ES/MS: m/z=480.2. $[M+H]^+$. $^1$H NMR (400 MHz, Methanol-d4) δ 9.26 (s, 1H), 8.59 (s, 1H), 8.49 (s, 1H), 8.28 (s, 1H), 8.05-7.65 (m, 4H), 5.15 (s, 2H), 4.50 (s, 3H), 3.66 (s, 1H), 3.34 (s, 2H), 2.30 (q, J=8.7 Hz, 1H), 2.06 (s, 3H).

Example 89

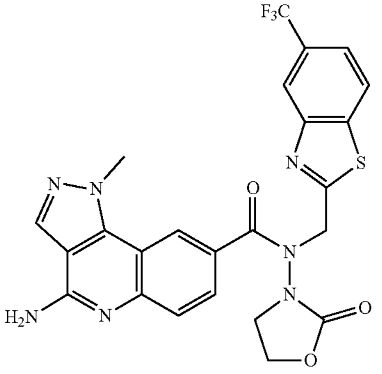

Example 89: 4-Amino-1-methyl-N-(2-oxooxazolidin-3-yl)-N-[[5-(trifluoromethyl)-1,3-benzothiazol-2-yl]methyl] pyrazolo[4,3-c]quinoline-8-carboxamide. Prepared following general procedure E-1 starting with intermediates Da-1 and Bb-4. ES/MS: m/z=542.1 $[M+H]^+$. $^1$H NMR (400 MHz, Methanol-d4) δ 8.59 (d, J=1.9 Hz, 1H), 8.33 (d, J=1.6 Hz, 1H), 8.31-8.19 (m, 2H), 7.84 (dd, J=8.6, 1.9 Hz, 1H), 7.81-7.66 (m, 2H), 5.62-5.25 (m, 2H), 4.92 (t, J=2.5 Hz, 1H), 4.38 (s, 3H), 4.00 (d, J=16.3 Hz, 1H), 3.75-3.64 (m, 3H).

Example 90

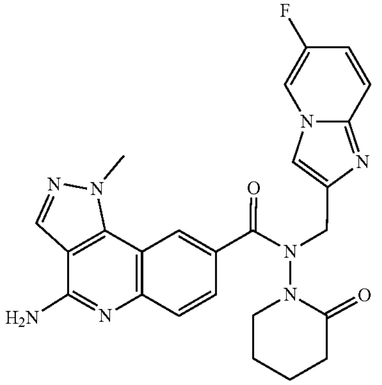

Example 90: 4-Amino-N-[(6-fluoroimidazo[1,2-a]pyridin-2-yl)methyl]-1-methyl-N-(2-oxo-1-piperidyl)pyrazolo [4,3-c]quinoline-8-carboxamide. Prepared following general procedure E-1 starting with intermediates Da-1 and Bb-5. ES/MS: m/z=487.2 $[M+H]^+$. 1H NMR (400 MHz, Methanol-d4) δ 8.95 (s, 1H), 8.50 (d, J=6.2 Hz, 2H), 8.38 (s, 1H), 8.01 (td, J=12.3, 11.0, 6.3 Hz, 2H), 7.93-7.66 (m, 2H), 5.27 (d, J=15.8 Hz, 1H), 5.13 (d, J=15.8 Hz, 1H), 4.50 (s, 3H), 3.86 (d, J=8.3 Hz, 1H), 3.66-3.49 (m, 1H), 3.37-3.33 (m, 1H), 3.01 (d, J=55.4 Hz, 1H), 2.37 (dt, J=18.1, 5.4 Hz, 1H), 2.20-1.84 (m, 2H), 1.84-1.30 (m, 2H).

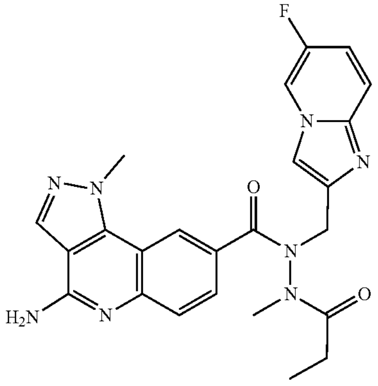 [SMILES: CCC(=O)N(C)N(Cc1cn2cc(F)ccc2n1)C(=O)c1ccc2nc(N)c3cnn(C)c3c2c1]

Example 91: 4-Amino-N-[(6-fluoroimidazo[1,2-a]pyridin-2-yl)methyl]-N',1-dimethyl-N'-propanoyl-pyrazolo[4,3-c]quinoline-8-carbohydrazide. Prepared following general procedure E-1 starting with intermediates Da-1 and Bb-6. ES/MS: m/z=475.1 $[M+H]^+$. $^1$H NMR (400 MHz, Methanol-d4) δ 8.91 (s, 1H), 8.50 (d, J=4.3 Hz, 2H), 8.44-8.25 (m, 1H), 8.09-7.48 (m, 4H), 5.32-5.02 (m, 2H), 4.52 (s, 3H), 3.43-3.33 (m, 1H), 3.08 (s, 1H), 2.94 (s, 1H), 2.37-2.19 (m, 1H), 2.10 (s, 2H), 1.39 (dd, J=6.7, 3.5 Hz, 1H), 0.81 (dt, J=24.0, 7.4 Hz, 3H).

Example 92

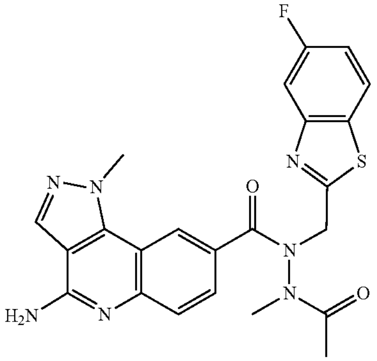

Example 92: N'-Acetyl-4-amino-N-[(5-fluoro-1,3-benzothiazol-2-yl)methyl]-N',1-dimethyl-pyrazolo[4,3-c]quinoline-8-carbohydrazide. Prepared following general procedure E-1 starting with intermediates Da-1 and Bb-7. ES/MS: m/z=478.2$[M+H]^+$. $^1$H NMR (400 MHz, Methanol-d4) δ 8.57-8.39 (m, 2H), 8.03 (dd, J=9.0, 5.0 Hz, 1H), 7.85 (dd, J=24.6, 8.8 Hz, 2H), 7.72 (dd, J=9.5, 2.5 Hz, 1H), 7.42-7.02 (m, 1H), 5.38 (dd, J=34.8, 15.9 Hz, 1H), 5.13 (d, J=15.9 Hz, 1H), 4.51 (s, 3H), 3.39 (s, 3H), 3.24 (s, 1H), 1.97 (d, J=68.2 Hz, 3H).

Example 93

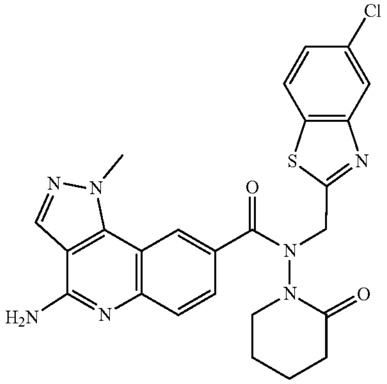

Example 93: 4-amino-N-[(5-chloro-1,3-benzothiazol-2-yl)methyl]-1-methyl-N-(2-oxo-1-piperidyl)pyrazolo[4,3-c]quinoline-8-carboxamide. Prepared following general procedure E-1 starting with intermediates Da-1 and Bb-8. ES/MS: m/z=520.0 $[M+H]^+$. 1H NMR (400 MHz, Methanol-d4) δ 8.55 (s, 1H), 8.50 (s, 1H), 8.10-7.97 (m, 2H), 7.92 (s, 1H), 7.83 (d, J=8.6 Hz, 1H), 7.50 (dd, J=8.7, 2.0 Hz, 1H), 5.49 (d, J=15.9 Hz, 1H), 5.17 (d, J=15.8 Hz, 1H), 4.52 (s, 3H), 3.83 (s, 1H), 3.62 (d, J=33.2 Hz, 1H), 2.35 (d, J=18.2 Hz, 1H), 1.98 (d, J=17.1 Hz, 1H), 1.87 (s, 1H), 1.72 (s, 1H), 1.51 (s, 2H).

Example 94

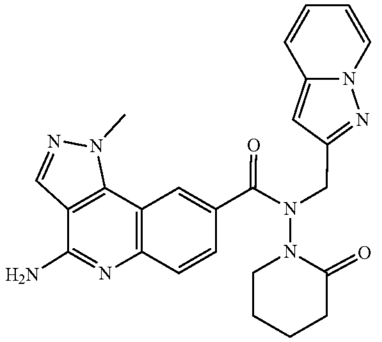

Example 94: 4-amino-1-methyl-N-(2-oxo-1-piperidyl)-N-(pyrazolo[1,5-a]pyridin-2-ylmethyl)pyrazolo[4,3-c]quinoline-8-carboxamide. Prepared following general procedure E-1 starting with intermediates Da-1 and Bb-9. ES/MS: m/z=469.3 $[M+H]^+$. $^1H$ NMR (400 MHz, Methanol-d4) δ 8.54 (d, J=8.1 Hz, 2H), 8.49 (s, 1H), 7.95-7.76 (m, 2H), 7.65 (dt, J=8.9, 1.2 Hz, 1H), 7.26 (dd, J=8.9, 7.1 Hz, 1H), 6.92 (t, J=6.8 Hz, 1H), 6.76 (s, 1H), 5.59-5.41 (m, 1H), 4.79 (d, J=14.8 Hz, 1H), 4.48 (d, J=31.8 Hz, 3H), 3.37 (s, 2H), 2.67-2.27 (m, 1H), 2.14-1.93 (m, 1H), 1.93-1.71 (m, 1H), 1.60 (s, 2H), 1.36 (d, J=49.7 Hz, 1H).

Example 95

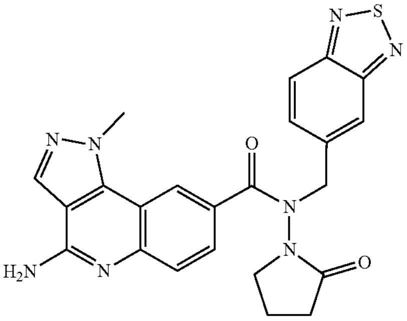

Example 95: 4-amino-N-(2,1,3-benzothiadiazol-5-ylmethyl)-1-methyl-N-(2-oxopyrrolidin-1-yl)pyrazolo[4,3-c]quinoline-8-carboxamide. Prepared following general procedure E-1 starting with intermediates Da-1 and Bb-10. ES/MS: m/z=472.9 $[M+H]^+$. 1H NMR (400 MHz, DMSO-$d_6$) δ 8.60 (s, 1H), 8.44 (d, J=1.8 Hz, 1H), 8.26 (s, 1H), 8.12 (d, J=9.1 Hz, 1H), 7.94-7.86 (m, 2H), 7.81 (d, J=8.6 Hz, 1H), 6.53 (s, 2H), 5.15 (d, J=15.4 Hz, 1H), 5.00 (d, J=15.4 Hz, 1H), 4.42 (s, 3H), 3.55 (q, J=7.9 Hz, 2H), 2.13 (dt, J=15.4, 7.5 Hz, 1H), 1.92 (s, 1H), 1.81 (dd, J=8.6, 4.3 Hz, 1H), 1.55 (s, 1H).

Example 96

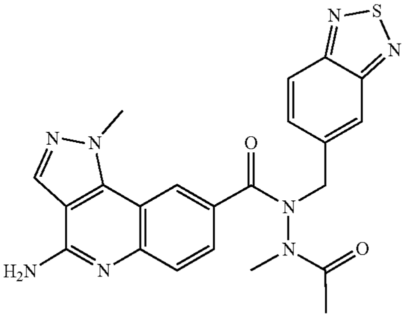

Example 96: N'-acetyl-4-amino-N-(2,1,3-benzothiadiazol-5-ylmethyl)-N',1-dimethyl-pyrazolo[4,3-c]quinoline-8-carbohydrazide. Prepared following general procedure E-1 starting with intermediates Da-1 and Bb-11. ES/MS: m/z=460.9 $[M+H]^+$. $^1H$ NMR (400 MHz, DMSO-$d_6$) δ 8.63 (s, 1H), 8.50 (d, J=1.8 Hz, 0.4H, minor rotamer), 8.41 (d, J=1.7 Hz, 0.6H, major rotamer), 8.25-8.07 (m, 2H), 8.01-7.78 (m, 3H), 6.53 (s, 2H), 5.32-5.12 (m, 1.2H, major rotamer), 4.80 (d, J=15.3 Hz, 0.8H, minor rotamer), 4.47 (s, 2H), 3.18 (s, 1.8H, major rotamer), 3.05 (s, 1.2H, minor rotamer), 1.77 (d, J=9.3 Hz, 3H).

Example 97

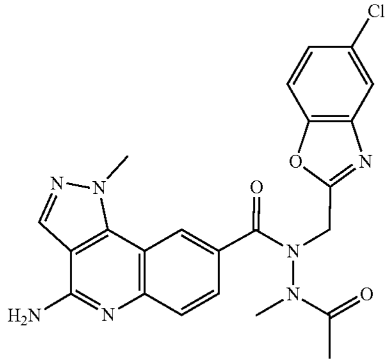

Example 97: N'-acetyl-4-amino-N-((5-chlorobenzo[d]oxazol-2-yl)methyl)-N',1-dimethyl-1H-pyrazolo[4,3-c]quinoline-8-carbohydrazide. Prepared following general procedure E-1 starting with intermediates Da-1 and Bb-12. ES/MS: m/z=478.2 $[M+H]^+$. 1H NMR (400 MHz, DMSO-$d_6$) δ 8.49 (brs, 0.6H major rotamer), 8.33 (s, 0.4H minor rotamer), 8.27 (s, 0.6H major rotamer), 8.26 (s, 0.4H minor rotamer), 7.94 (d, J=2.1 Hz, 0.6H major rotamer), 7.91 (s, 0.4H minor rotamer), 7.83 (d, J=8.7 Hz, 1H), 7.74 (brs, 0.6H major rotamer), 7.72 (s, 0.4H minor rotamer), 7.62 (d, J=8.7 Hz, 1H), 7.59 (s, 1H), 7.53-7.47 (m, 1H), 7.29 (s, 1.2H major rotamer), 7.22 (s, 0.8H minor rotamer), 5.39-5.17 (m, 1H+0.6H major rotamer), 4.97 (d, J=16.3 Hz, 0.4H minor rotamer), 4.38 (s, 1.8H major rotamer), 4.35 (s, 1.2H minor rotamer), 3.30 (s, 1.2H minor rotamer), 3.15 (s, 1.8H major rotamer), 2.06 (s, 1.8H major rotamer), 1.89 (s, 1.2H minor rotamer).

Example 98

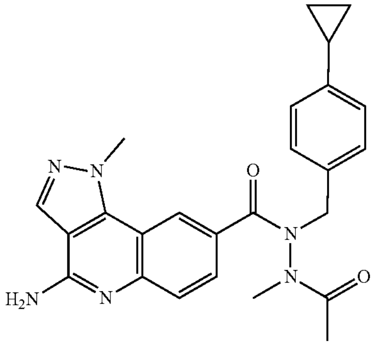

Example 98: N'-acetyl-4-amino-N-(4-cyclopropylbenzyl)-N',1-dimethyl-1H-pyrazolo[4,3-c]quinoline-8-carbohydrazide. Prepared following general procedure E-1 starting with intermediates Da-1 and Bb-13. ES/MS: m/z=517.2 $[M+H]^+$. $^1$H NMR (400 MHZ, DMSO-$d_6$) δ 13.60 (brs, 1H), 9.65 (brs, 1H), 8.89 (brs, 1H), 8.63 (s, 0.4H minor rotamer), 8.62 (s, 0.6H major rotamer), 8.43 (d, J=1.7 Hz, 0.6H major rotamer), 8.33 (s, 0.4H minor rotamer), 7.97-7.73 (m, 2H), 7.41-7.20 (m, 2H), 7.15-7.03 (m, 2H), 5.13 (d, J=14.4 Hz, 0.4H minor rotamer), 4.97 (brs, 0.4H minor rotamer), 4.76 (d, J=14.4 Hz, 0.6H major rotamer), 4.46 (s, 1.8H major rotamer), 4.44 (s, 1.2H minor rotamer), 4.35 (d, J=14.4 Hz, 0.6H major rotamer), 2.99 (s, 1.8H major rotamer), 2.93 (s, 1.2H minor rotamer), 1.98-1.87 (m, 1H), 1.76 (brs, 1.2H minor rotamer), 1.57 (brs, 1.8H major rotamer), 1.00-0.89 (m, 2H), 0.74-0.58 (m, 2H).

Example 99

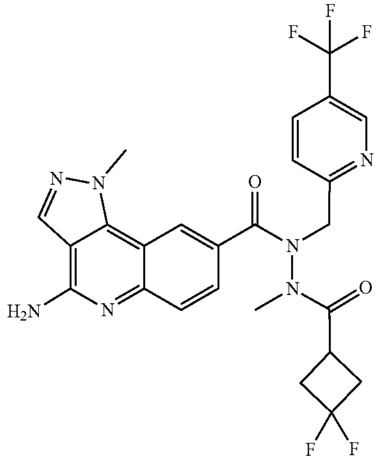

Example 99: 4-amino-N'-(3,3-difluorocyclobutane-1-carbonyl)-N',1-dimethyl-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bc-1. ES/MS: m/z=548.0. $^1$H NMR (400 MHz, Methanol-d4) δ 8.98 (d, J=73.6 Hz, 1H), 8.51 (d, J=6.1 Hz, 2H), 8.18 (d, J=8.5 Hz, 1H), 7.81 (d, J=8.5 Hz, 3H), 5.42-4.98 (m, 2H), 4.56 (d, J=21.9 Hz, 3H), 3.26 (s, 3H), 2.99 (s, 1H), 2.68 (s, 4H).

Example 100

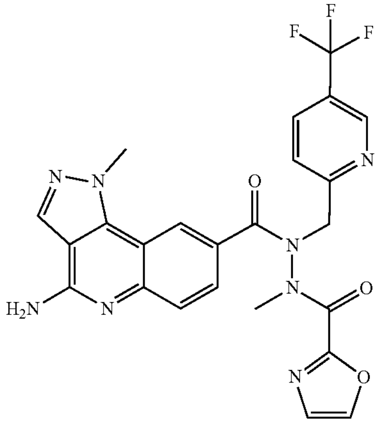

Example 100: N'-(4-amino-1-methyl-1H-pyrazolo[4,3-c]quinoline-8-carbonyl)-N-methyl-N'-((5-(trifluoromethyl)pyridin-2-yl)methyl)oxazole-2-carbohydrazide. Prepared following general procedure E-1 starting with intermediates Da-1 and Bc-2. ES/MS: m/z=525.0. $^1$H NMR (400 MHz, Methanol-d4) δ 9.00-8.72 (m, 2H), 8.48 (s, 2H), 8.23-7.90 (m, 3H), 7.78 (d, J=24.2 Hz, 1H), 7.47 (s, 1H), 5.51-4.92 (m, 3H), 4.62-4.29 (m, 3H), 3.87-3.37 (m, 2H).

Example 101

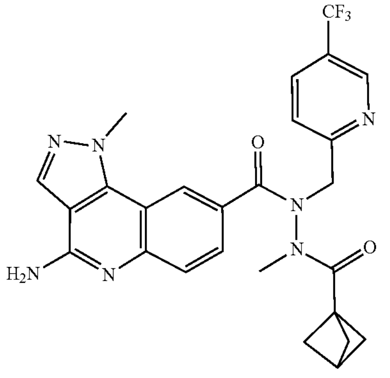

Example 101: 4-amino-N'-(bicyclo[1.1.1]pentane-1-carbonyl)-N',1-dimethyl-N-[[5-(trifluoromethyl)-2-pyridyl]methyl]pyrazolo[4,3-c]quinoline-8-carbohydrazide. Prepared following general procedure E-1 starting with intermediates Da-1 and Bc-3. ES/MS: m/z=524.2 $[M+H]^+$. $^1H$ NMR (400 MHz, MeOD) δ 9.10 (s, 0.11H, minor rotamer), 8.98-8.82 (m, 1H), 8.64 (s, 0.11H, minor rotamer), 8.50 (s, 2H), 8.23 (dd, J=8.6, 1.8 Hz, 0.11H, minor rotamer), 8.17 (dd, J=8.2, 2.4 Hz, 1H), 8.07-7.75 (m, 3H), 7.58 (d, J=8.1 Hz, 0.11H, minor rotamer), 5.42 (d, J=16.4 Hz, 0.11H, minor rotamer), 5.22 (d, J=15.3 Hz, 1H), 5.00 (d, J=16.4 Hz, 0.11H, minor rotamer), 4.95-4.88 (m, 1H), 4.53 (s, 3H), 3.37 (s, 3H), 3.28 (s, 0.33H, minor rotamer), 3.05 (s, 1H), 2.68 (s, 0.11H, minor rotamer), 2.35-2.12 (m, 2H), 1.86 (d, J=15.6 Hz, 4H).

Example 102

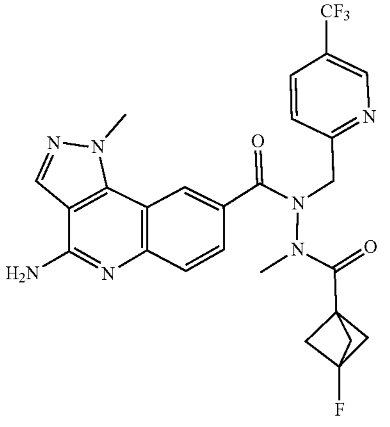

Example 102: 4-amino-N'-(3-fluorobicyclo[1.1.1]pentane-1-carbonyl)-N',1-dimethyl-N-[[5-(trifluoromethyl)-2-pyridyl]methyl]pyrazolo[4,3-c]quinoline-8-carbohydrazide. Prepared following general procedure E-1 starting with intermediates Da-1 and Bc-4. ES/MS: m/z=542.2 $[M+H]^+$. $^1H$ NMR (400 MHz, MeOD) δ 9.17-8.83 (m, 1H), 8.51 (s, 2H), 8.25 (dd, J=8.7, 1.8 Hz, 0.2H, minor rotamer), 8.21-8.13 (m, 1H), 7.95-7.73 (m, 3H), 7.59 (d, J=8.1 Hz, 0.2H, minor rotamer), 5.41 (d, J=16.3 Hz, 0.2H, minor rotamer), 5.23 (d, J=15.3 Hz, 1H), 5.04-4.89 (m, 1H), 4.54 (s, 3H), 3.35 (s, 3H), 3.09 (s, 0.6H, minor rotamer), 2.56-2.33 (m, 2H), 2.17-2.07 (m, 4H).

Example 103

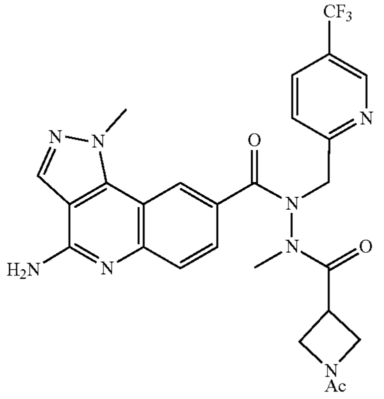

Example 103: N'-(1-acetylazetidine-3-carbonyl)-4-amino-N',1-dimethyl-N-[[5-(trifluoromethyl)-2-pyridyl]methyl]pyrazolo[4,3-c]quinoline-8-carbohydrazide. Prepared following general procedure E-1 starting with intermediates Da-1 and Bc-5. ES/MS: m/z=555.0 $[M+H]^+$. $^1H$ NMR (400 MHz, MeOD) δ 8.90 (s, 1H), 8.66-8.34 (m, 2H), 8.19 (d, J=8.3 Hz, 1H), 8.05-7.71 (m, 3H), 5.39-5.10 (m, 1H), 4.67-4.46 (m, 4H), 4.40-3.63 (m, 3H), 3.42 (s, 1H), 3.22-3.11 (m, 3H), 2.28 (s, 1H), 1.83 (s, 1H), 1.59 (s, 2H).

Example 104

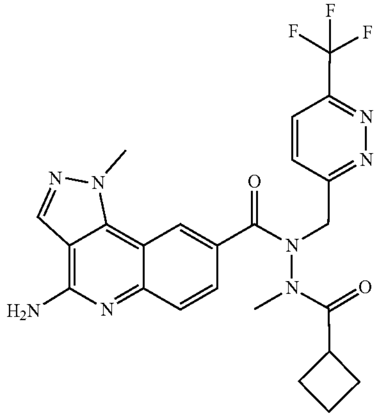

Example 104: 4-amino-N'-(cyclobutanecarbonyl)-N',1-dimethyl-N-((6-(trifluoromethyl)pyridazin-3-yl)methyl)-1H-pyrazolo[4,3-c]quinoline-8-carbohydrazide. Prepared following general procedure E-1 starting with intermediates Da-1 and Bd-1. ES/MS: m/z=514.0. 1H NMR (400 MHz, Methanol-d4) δ 8.50 (s, 2H), 8.18 (d, J=8.7 Hz, 2H), 7.80 (d, J=8.5 Hz, 2H), 5.24 (s, 2H), 4.55 (s, 6H), 3.10 (s, 3H), 2.07 (d, J=11.7 Hz, 3H), 1.52 (s, 1H).

Example 105

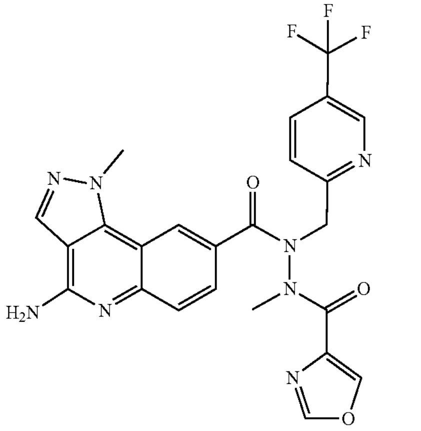

Example 105: N'-(4-amino-1-methyl-1H-pyrazolo[4,3-c] quinoline-8-carbonyl)-N-methyl-N'-((5-(trifluoromethyl) pyridin-2-yl)methyl)oxazole-4-carbohydrazide. Prepared following general procedure E-1 starting with intermediates Da-1 and Bd-2. ES/MS: m/z=525.0. 1H NMR (400 MHz, Methanol-d4) δ 8.98 (s, 0.4H, rotamer), 8.87 (d, J=9.9 Hz, 2H), 8.52 (s, 0.3H, rotamer), 8.48 (s, 2H), 8.43 (s, 0.4H, rotamer), 8.35 (s, 1H), 8.12 (d, J=8.2 Hz, 2H), 8.06 (d, J=8.2 Hz, 0.3H, rotamer), 7.84 (d, J=8.6 Hz, 0.3H, rotamer), 7.79 (d, J=8.9 Hz, 2H), 5.45 (dd, J=51.9, 16.3 Hz, 2H), 4.55 (d, J=12.9 Hz, 3H), 3.68 (s, 2H), 3.23 (s, 1H).

Example 106

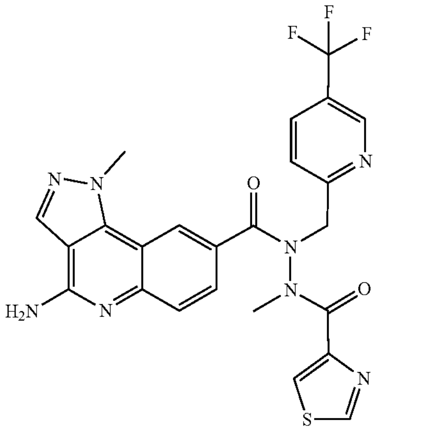

Example 106: N'-(4-amino-1-methyl-1H-pyrazolo[4,3-c] quinoline-8-carbonyl)-N-methyl-N'-((5-(trifluoromethyl) pyridin-2-yl)methyl)thiazole-4-carbohydrazide. Prepared following general procedure E-1 starting with intermediates Da-1 and Bd-3. ES/MS: m/z=541.0. $^1$H NMR (400 MHz, Methanol-d4) δ 9.11 (s, 1H), 8.96-8.82 (m, 2H), 8.69-8.44 (m, 2H), 8.24-7.88 (m, 3H), 7.86-7.64 (m, 2H), 4.54 (brs, 1H), 4.27 (brs, 1H), 3.78-3.44 (m, 2H), 2.68 (s, 3H).

Example 107

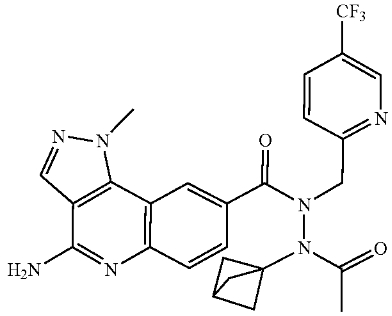

Example 107: N'-acetyl-4-amino-N'-(1-bicyclo[1.1.1] pentanyl)-1-methyl-N-[[5-(trifluoromethyl)-2-pyridyl] methyl]pyrazolo[4,3-c]quinoline-8-carbohydrazide. Prepared following general procedure E-1 starting with intermediates Da-1 and Bd-4. ES/MS: m/z=524.0 [M+H]$^+$. $^1$H NMR (400 MHz, DMSO) δ 9.70 (s, 1H), 9.13 (d, J=6.8 Hz, 0.3H, minor rotamer), 8.96 (s, 1H), 8.90-8.75 (m, 1H), 8.65 (d, J=7.5 Hz, 1H), 8.38 (s, 1H), 8.34-8.22 (m, 1H), 8.13-7.98 (m, 1H), 7.95-7.81 (m, 2H), 7.64 (dd, J=8.1, 3.9 Hz, 0.3H, minor rotamer), 5.11-4.89 (m, 2H), 4.74-4.35 (m, 3H), 2.40-2.29 (m, 1H), 2.07-1.96 (m, 3H), 1.89-1.64 (m, 6H).

Example 108

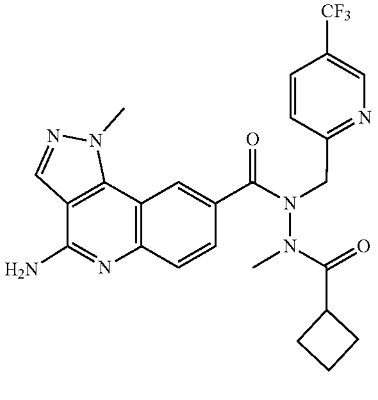

Example 108: 4-amino-N'-(cyclobutanecarbonyl)-N',1-dimethyl-N-[[5-(trifluoromethyl)-2-pyridyl]methyl]pyrazolo[4,3-c]quinoline-8-carbohydrazide. Prepared following general procedure E-1 starting with intermediates Da-1 and Bd-5. ES/MS: m/z=512.2 [M+H]$^+$. $^1$H NMR (400 MHz, DMSO) δ 9.69 (s, 1H), 9.25-8.85 (m, 2H), 8.63 (s, 1H), 8.37 (s, 1H), 8.26 (dd, J=8.3, 2.4 Hz, 1H), 7.93 (d, J=8.2 Hz, 1H), 7.88-7.77 (m, 2H), 5.20 (d, J=15.6 Hz, 1H), 4.78 (d, J=15.7 Hz, 1H), 4.47 (s, 3H), 3.52-2.91 (m, 4H), 2.18-1.55 (m, 5H), 1.50-1.13 (m, 1H).

Example 109

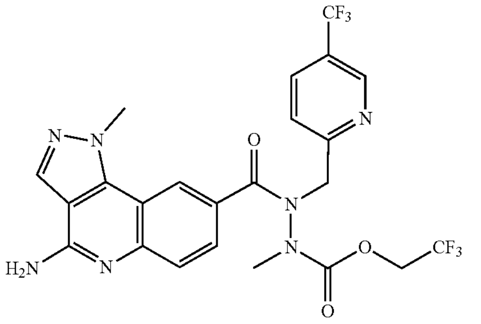

Example 109: 2,2,2-trifluoroethyl N-[(4-amino-1-methyl-pyrazolo[4,3-c]quinoline-8-carbonyl)-[[5-(trifluoromethyl)-2-pyridyl]methyl]amino]-N-methyl-carbamate. Prepared following general procedure E-1 starting with intermediates Da-1 and Bd-6. ES/MS: m/z=556.0 $[M+H]^+$. $^1H$ NMR (400 MHz, MeOD) δ 8.92 (s, 1H), 8.71-8.52 (m, 1H), 8.50 (s, 1H), 8.18 (dd, J=8.3, 2.3 Hz, 1H), 8.11-7.56 (m, 3H), 5.24 (d, J=15.5 Hz, 1H), 5.01 (d, J=15.7 Hz, 1H), 4.72-4.28 (m, 5H), 3.19 (s, 3H).

Example 110

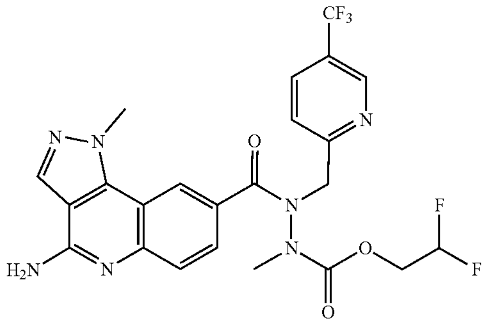

Example 110: 2,2-difluoroethyl N-[(4-amino-1-methyl-pyrazolo[4,3-c]quinoline-8-carbonyl)-[[5-(trifluoromethyl)-2-pyridyl]methyl]amino]-N-methyl-carbamate. Prepared following general procedure E-1 starting with intermediates Da-1 and Bd-7. ES/MS: m/z=538.0 $[M+H]^+$. $^1H$ NMR (400 MHz, MeOD) δ 8.92 (s, 1H), 8.69-8.52 (m, 1H), 8.50 (s, 1H), 8.18 (dd, J=8.5, 2.3 Hz, 1H), 8.03-7.46 (m, 3H), 6.30-5.61 (m, 1H), 5.25 (d, J=15.5 Hz, 1H), 4.99 (d, J=15.6 Hz, 1H), 4.52 (s, 3H), 4.44-3.88 (m, 2H), 3.17 (s, 3H).

Example 111

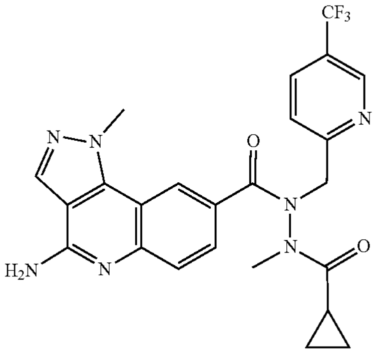

Example 111: 4-amino-N'-(cyclopropanecarbonyl)-N',1-dimethyl-N-[[5-(trifluoromethyl)-2-pyridyl]methyl]pyrazolo[4,3-c]quinoline-8-carbohydrazide. Prepared following general procedure E-1 starting with intermediates Da-1 and Bd-8. ES/MS: m/z=498.0 $[M+H]^+$. $^1H$ NMR (400 MHz, MeOD) δ 9.19-8.80 (m, 1H), 8.74-8.39 (m, 2H), 8.18 (t, J=9.1 Hz, 1H), 8.10-7.42 (m, 3H), 5.27-5.24 (m, 2H), 4.64-4.43 (m, 3H), 3.48 (s, 1H, minor rotamer), 3.19 (s, 3H), 2.02 (p, J=7.1 Hz, 1H), 1.63 (s, 0.4H, minor rotamer), 1.09-0.30 (m, 4H).

Example 112

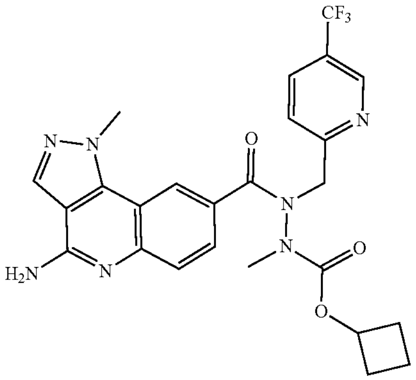

Example 112: cyclobutyl N-[(4-amino-1-methyl-pyrazolo[4,3-c]quinoline-8-carbonyl)-[[5-(trifluoromethyl)-2-pyridyl]methyl]amino]-N-methyl-carbamate. Prepared following general procedure E-1 starting with intermediates Da-1 and Bd-9. ES/MS: m/z=528.2 $[M+H]^+$. $^1H$ NMR (400 MHz, MeOD) δ 9.14-8.80 (m, 1H), 8.70-8.43 (m, 2H), 8.19 (d, J=8.2 Hz, 1H), 7.82 (d, J=8.6 Hz, 3H), 5.29-4.94 (m, 2H), 4.79-4.42 (m, 4H), 3.15 (s, 3H), 2.55-1.38 (m, 6H).

Example 113

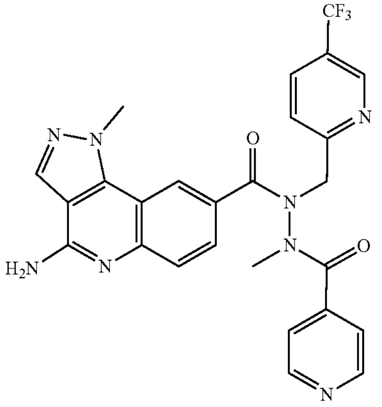

Example 113: 4-amino-N',1-dimethyl-N'-(pyridine-4-carbonyl)-N-[[5-(trifluoromethyl)-2-pyridyl]methyl]pyrazolo[4,3-c]quinoline-8-carbohydrazide. Prepared following general procedure E-1 starting with intermediates Da-1 and Bd-10. ES/MS: m/z=535.2 $[M+H]^+$. $^1H$ NMR (400 MHz, MeOD) δ 9.05-8.77 (m, 1H), 8.71-8.43 (m, 4H), 8.28-8.17 (m, 1H), 8.13-7.83 (m, 2H), 7.73 (s, 2H), 7.31 (s, 1H), 7.00 (s, 0.3H, minor rotamer), 5.34 (d, J=15.5 Hz, 0.3H, minor rotamer), 5.13-4.95 (m, 1H), 4.57-4.35 (m, 4H), 3.39 (s, 3H).

Example 114

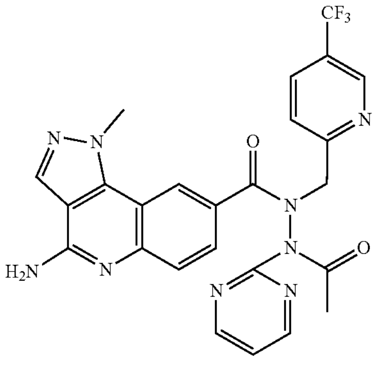

Example 114: N'-acetyl-4-amino-1-methyl-N'-pyrimidin-2-yl-N-[[5-(trifluoromethyl)-2-pyridyl]methyl]pyrazolo[4,3-c]quinoline-8-carbohydrazide. Prepared following general procedure E-1 starting with intermediates Da-1 and Bd-11. ES/MS: m/z=536.0 $[M+H]^+$. $^1H$ NMR (400 MHz, MeOD) δ 8.80-8.62 (m, 3H), 8.59 (d, J=1.8 Hz, 1H), 8.46 (s, 1H), 8.12 (d, J=8.2 Hz, 1H), 8.02 (d, J=8.3 Hz, 1H), 7.85 (dd, J=8.6, 1.7 Hz, 1H), 7.67 (d, J=8.6 Hz, 1H), 7.26 (t, J=4.9 Hz, 1H), 5.34-5.04 (m, 2H), 4.39 (s, 3H), 2.28 (s, 3H).

Example 115

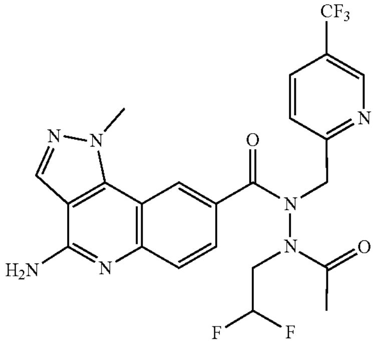

Example 115: N'-acetyl-4-amino-N'-(2,2-difluoroethyl)-1-methyl-N-[[5-(trifluoromethyl)-2-pyridyl]methyl]pyrazolo[4,3-c]quinoline-8-carbohydrazide. Prepared following general procedure E-1 starting with intermediates Da-1 and Bd-12. ES/MS: m/z=522.0 $[M+H]^+$. $^1H$ NMR (400 MHz, MeOD) δ 9.16-8.64 (m, 2H), 8.50 (s, 1H), 8.31-7.99 (m, 2H), 7.90-7.77 (m, 1H), 7.53 (s, 1H), 6.42-5.83 (m, 1H), 5.18 (s, 2H), 4.54 (s, 3H), 4.38-3.89 (m, 2H), 2.25-2.00 (m, 3H).

Example 116

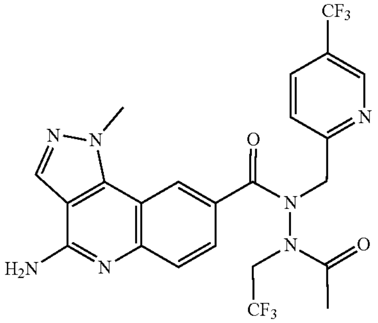

Example 116: N'-acetyl-4-amino-1-methyl-N'-(2,2,2-trifluoroethyl)-N-[[5-(trifluoromethyl)-2-pyridyl]methyl]pyrazolo[4,3-c]quinoline-8-carbohydrazide. Prepared following general procedure E-1 starting with intermediates Da-1 and Bd-13. ES/MS: m/z=540.2 $[M+H]^+$. $^1H$ NMR (400 MHz, MeOD) δ 9.08 (s, 1H), 8.80 (s, 1H), 8.50 (s, 1H), 8.35-7.96 (m, 2H), 7.98-7.72 (m, 1H), 7.48 (s, 1H), 5.41-5.12 (m, 2H), 4.71-4.23 (m, 5H), 2.42-2.02 (m, 3H).

Example 117

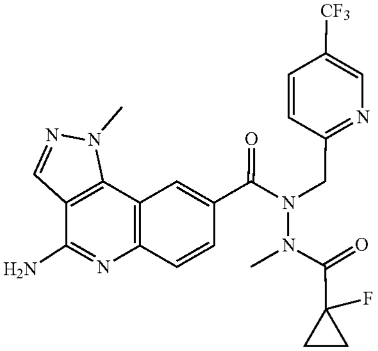

Example 117: 4-amino-N'-(1-fluorocyclopropanecarbonyl)-N',1-dimethyl-N-[[5-(trifluoromethyl)-2-pyridyl]methyl]pyrazolo[4,3-c]quinoline-8-carbohydrazide. Prepared following general procedure E-1 starting with intermediates Da-1 and Bd-14. ES/MS: m/z=516.0 $[M+H]^+$. $^1H$ NMR (400 MHz, MeOD) δ 9.12-8.80 (m, 1H), 8.70-8.44 (m, 2H), 8.18 (d, J=8.2 Hz, 1H), 8.09-7.75 (m, 3H), 7.51-7.40 (m, 0.3H, minor rotamer), 5.57-5.19 (m, 1H), 5.10-4.89 (m, 1H), 4.53 (s, 3H), 3.65-3.40 (m, 3H), 3.16 (d, J=7.2 Hz, 1H, minor rotamer), 1.57-0.67 (m, 4H).

Example 118

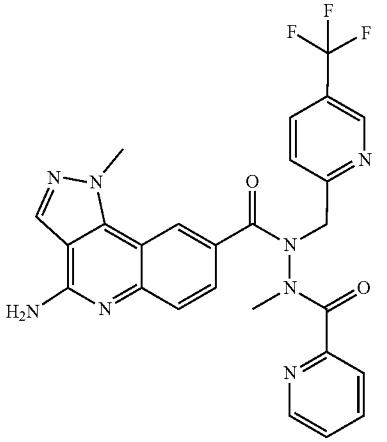

Example 118: 4-amino-N',1-dimethyl-N'-picolinoyl-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bd-15. ES/MS: m/z=535.0. $^1H$ NMR (400 MHz, Methanol-d4) δ 9.00-8.78 (m, 1H), 8.67 (s, 1H), 8.49 (d, J=4.8 Hz, 1H), 8.42-8.16 (m, 1H), 8.03 (s, 2H), 7.83 (d, J=8.6 Hz, 2H), 7.55 (s, 2H), 7.43 (s, 1H), 5.59-4.98 (m, 2H), 4.53 (s, 3H), 3.55-3.34 (m, 3H).

Example 119

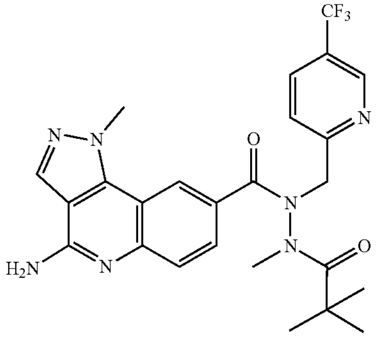

Example 119: 4-amino-N',1-dimethyl-N'-pivaloyl-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bd-16. ES/MS: m/z=514.3 $[M+H]^+$. 1H NMR (400 MHz, Methanol-d4) δ 9.03 (s, 0.2H minor rotamer), 8.89 (s, 0.8H major rotamer), 8.50 (s, 2H), 8.22-8.12 (m, 1H), 8.13 (brs, 1H), 7.93-7.85 (m, 1.6H major rotamer), 7.80 (d, J=8.6 Hz, 1H), 7.55 (s, 0.4H minor rotamer), 5.27 (d, J=15.1 Hz, 1H), 4.86 (d, J=15.1 Hz, 1H), 4.55 (s, 3H), 3.51 (s, 3H), 1.35 (s, 2H minor rotamer), 0.89 (s, 7H major rotamer).

Example 120

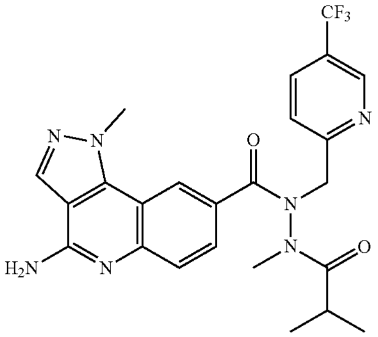

Example 120: 4-amino-N'-isobutyryl-N',1-dimethyl-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bd-17. ES/MS: m/z=500.3 $[M+H]^+$. $^1H$ NMR (400 MHz, Methanol-d4) δ 8.76-8.55 (m, 1H), 8.52 (d, J=2.7 Hz, 1H), 8.17-7.69 (m, 4H), 7.48 (dd, J=8.6, 2.0 Hz, 1H), 6.99-6.76 (m, 1H), 5.42-5.19 (m, 2H), 5.14-5.00 (m, 1H), 4.55 (s, 3H), 3.46 (s, 1.8H major rotamer), 3.36-3.33 (m, 1H), 3.31 (s, 1.2H minor rotamer), 2.26 (s, 1.8H major rotamer), 2.19 (s, 1.2H minor rotamer), 1.98 (s, 1.2H minor rotamer), 1.90 (s, 1.8H major rotamer).

Example 121

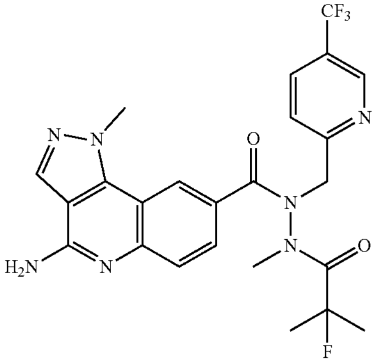

Example 121: 4-amino-N'-(2-fluoro-2-methylpropanoyl)-N',1-dimethyl-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bd-18. ES/MS: m/z=518.2 $[M+H]^+$. $^1H$ NMR (400 MHz, Methanol-d4) δ 8.99 (s, 0.2H minor rotamer), 8.88 (s, 0.8H major rotamer), 8.66 (s, 0.2H minor rotamer), 8.51 (s, 0.8H major rotamer), 8.48 (s, 1H), 8.16 (d, J=8.5 Hz, 1H), 8.04-7.73 (m, 3H), 5.37 (d, J=16.9 Hz, 0.2H minor rotamer), 5.23 (d, J=15.3 Hz, 1H), 4.95 (d, J=16.5 Hz, 0.8H major rotamer), 4.53 (s, 3H), 3.53 (s, 3H), 1.67 (dd, J=22.1, 7.3 Hz, 2H), 1.39 (d, J=21.7 Hz, 3H), 0.93 (d, J=21.6 Hz, 3H).

Example 122

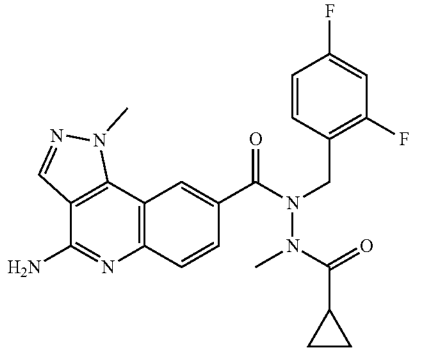

Example 122: 4-amino-N'-(cyclopropanecarbonyl)-N-(2,4-difluorobenzyl)-N',1-dimethyl-1H-pyrazolo[4,3-c]quinoline-8-carbohydrazide. Prepared following general procedure E-1 starting with intermediates Da-1 and Bd-19. ES/MS: m/z=465.2 $[M+H]^+$. 1H NMR (400 MHz, DMSO-$d_6$) δ 13.43 (brs, 1H), 9.64 (brs, 1H), 8.83 (brs, 1H), 8.62 (s, 1H), 8.47 (s, 0.75H major rotamer), 8.31 (s, 0.25H minor rotamer), 7.98-7.73 (m, 2H), 7.69-7.53 (m, 1H), 7.38-7.23 (m, 1H), 7.20-7.07 (m, 1H), 5.29 (brs, 0.75H major rotamer), 4.96 (d, J=14.5 Hz, 0.25H minor rotamer), 4.78 (d, J=14.5 Hz, 0.75H major rotamer), 4.68 (d, J=14.5 Hz, 0.25H minor rotamer), 4.46 (s, 2.25H major rotamer), 4.43 (s, 0.75H minor rotamer), 3.18 (s, 0.75H minor rotamer), 3.03 (s, 2.25H major rotamer), 1.76-1.46 (m, 1H), 0.74-0.62 (m, 0.75H major rotamer), 0.62-0.54 (m, 0.25H minor rotamer), 0.51-0.42 (m, 0.5H minor rotamer), 0.40-0.21 (m, 1.5H major rotamer).

Example 123

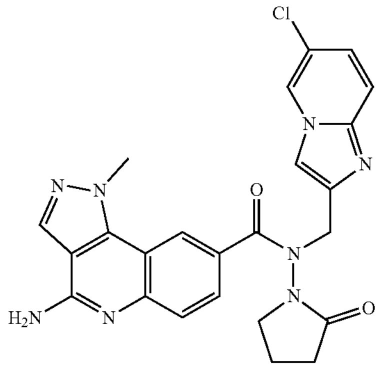

Example 123: 4-Amino-N-[(6-chloroimidazo[1,2-a]pyridin-2-yl)methyl]-1-methyl-N-(2-oxopyrrolidin-1-yl)pyrazolo[4,3-c]quinoline-8-carboxamide. Prepared following general procedure E-1 starting with intermediates Da-1 and Be-1. ES/MS: m/z=489.1 $[M+H]^+$. $^1$H NMR (400 MHz, Methanol-d4) δ 8.86 (s, 1H), 8.60 (s, 1H), 8.50 (s, 1H), 8.21 (s, 1H), 7.94 (d, J=8.7 Hz, 1H), 7.89-7.61 (m, 3H), 5.38-4.98 (m, 2H), 4.51 (s, 3H), 3.34 (m, 3H), 2.30 (d, J=8.4 Hz, 2H), 2.12-1.87 (m, 2H).

Example 124

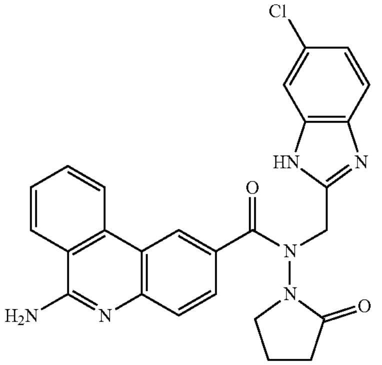

Example 124: 6-amino-N-((6-chloro-1H-benzo[d]imidazol-2-yl)methyl)-N-(2-oxopyrrolidin-1-yl)phenanthridine-2-carboxamide. Prepared following general procedure E-1 starting with intermediates Da-3 and Be-2. ES/MS: m/z=485.2 $[M+H]^+$. $^1$H NMR (400 MHZ, Methanol-d4) δ 9.00 (d, J=1.7 Hz, 1H), 8.77 (d, J=8.3 Hz, 1H), 8.58 (dd, J=8.3, 1.2 Hz, 1H), 8.27-8.06 (m, 1H), 8.02-7.85 (m, 2H), 7.72 (dd, J=11.0, 8.6 Hz, 2H), 7.63-7.40 (m, 2H), 7.20-7.12 (m, 1H), 5.22 (s, 2H), 4.09 (s, 3H), 3.98 (s, 2H), 2.16 (s, 2H).

Example 125

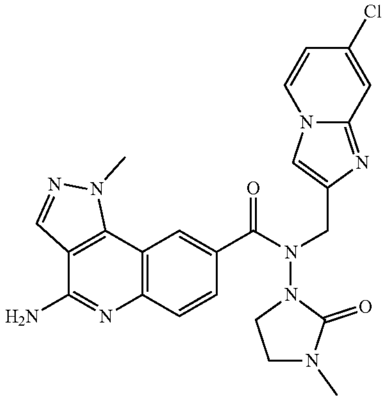

Example 125: 4-Amino-N-[(7-chloroimidazo[1,2-a]pyridin-2-yl)methyl]-1-methyl-N-(3-methyl-2-oxo-imidazolidin-1-yl)pyrazolo[4,3-c]quinoline-8-carboxamide. Prepared following general procedure E-1 starting with intermediates Da-1 and Be-3. ES/MS: m/z=504.1 $[M+H]^+$. $^1$H NMR (400 MHz, Methanol-d4) δ 8.67 (s, 2H), 8.49 (s, 1H), 8.25 (s, 1H), 8.11-7.90 (m, 2H), 7.83 (d, J=8.6 Hz, 1H), 7.37 (s, 1H), 5.11 (s, 2H), 4.49 (s, 3H), 3.69 (s, 1H), 3.40 (s, 2H), 3.39-3.35 (m, 2H), 2.75 (s, 3H).

Example 126

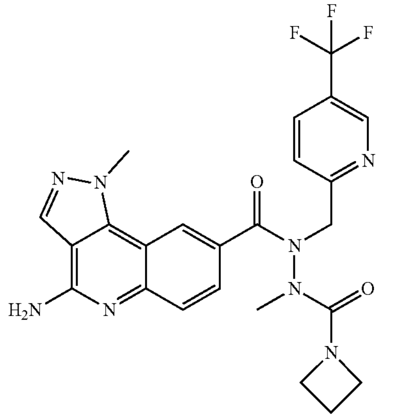

Example 126: 4-amino-N'-(azetidine-1-carbonyl)-N',1-dimethyl-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bf-1. ES/MS: m/z=513.0 $[M+H]^+$. $^1H$ NMR (400 MHz, Methanol-d4) δ 8.92 (s, 1H), 8.63 (s, 1H), 8.50 (s, 1H), 8.27-8.10 (m, 1H), 7.99 (d, J=8.7 Hz, 1H), 7.85 (d, J=8.7 Hz, 2H), 5.44 (d, J=15.6 Hz, 1H), 4.85 (d, J=19.4 Hz, 1H, overlapping with solvent peak), 4.54 (s, 3H), 4.01 (q, J=7.9 Hz, 2H), 3.88 (q, J=7.9 Hz, 2H), 3.08 (s, 3H), 2.45-1.89 (m, 2H).

Example 127

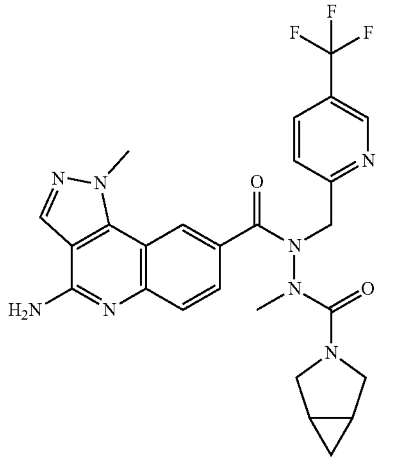

Example 127: 4-amino-N'-(3-azabicyclo[3.1.0]hexane-3-carbonyl)-N',1-dimethyl-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bf-2. ES/MS: m/z=539.0 $[M+H]^+$. $^1H$ NMR (400 MHz, Methanol-d4) δ 8.83 (s, 1H), 8.45 (d, J=9.7 Hz, 2H), 8.09 (d, J=8.5 Hz, 1H), 7.87 (d, J=8.6 Hz, 1H), 7.77 (d, J=8.6 Hz, 2H), 5.43 (d, J=16.2 Hz, 1H), 4.70 (d, J=16.2 Hz, 1H), 4.49 (s, 3H), 3.68 (d, J=10.9 Hz, 1H), 3.18 (s, 3H), 3.12-2.89 (m, 2H), 2.75-2.53 (m, 1H), 1.47-0.99 (m, 2H), 0.21--0.02 (m, 1H), −0.97 (d, J=5.2 Hz, 1H).

Example 128

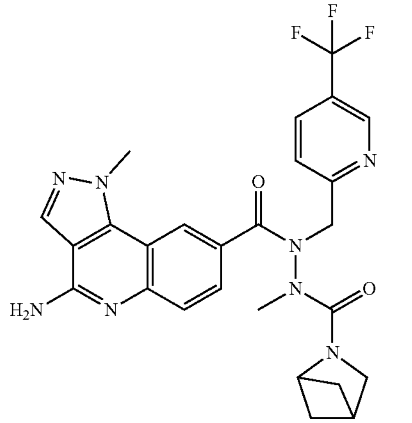

Example 128: 4-amino-N'-(2-azabicyclo[2.1.1]hexane-2-carbonyl)-N',1-dimethyl-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bf-3. ES/MS: m/z=539.0 $[M+H]^+$. $^1H$ NMR (400 MHz, Methanol-d4) δ 8.90 (s, 1H), 8.60 (s, 1H), 8.50 (s, 1H), 8.17 (d, J=8.3 Hz, 1H), 7.96 (d, J=8.6 Hz, 1H), 7.89 (d, J=8.2 Hz, 1H), 7.81 (d, J=8.6 Hz, 1H), 5.44 (d, J=15.7 Hz, 1H), 4.90 (s, 1H, overlapped with solvent), 4.55 (s, 3H), 4.07 (d, J=7.0 Hz, 1H), 3.31-3.11 (m, 4H, overlapped with solvent), 2.67 (d, J=9.7 Hz, 2H), 2.05-1.55 (m, 2H), 0.96 (dt, J=125.3, 9.2 Hz, 2H).

Example 129

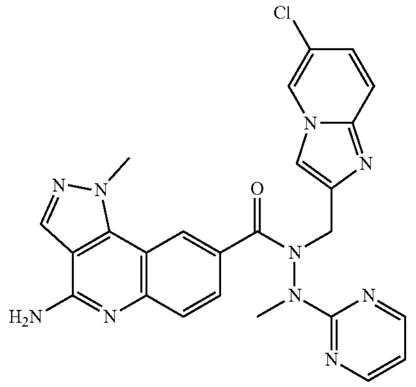

Example 129: 4-amino-N-[(6-chloroimidazo[1,2-a]pyridin-2-yl)methyl]-N',1-dimethyl-N'-pyrimidin-2-yl-pyrazolo[4,3-c]quinoline-8-carbohydrazide. Prepared following general procedure E-1 starting with intermediates Da-1 and Bg-1. ES/MS: m/z=514.0 $[M+H]^+$. $^1H$ NMR (400 MHz, MeOD) δ 8.87 (s, 1H), 8.54-8.49 (m, 1H), 8.48-8.41 (m, 3H), 8.19 (s, 1H), 7.95 (dd, J=8.7, 1.7 Hz, 1H), 7.87-7.77 (m, 2H), 7.72 (d, J=8.6 Hz, 1H), 6.84 (t, J=4.9 Hz, 1H), 5.40 (d, J=15.6 Hz, 1H), 4.99 (d, J=15.6 Hz, 1H), 4.31 (s, 3H), 3.34 (s, 3H).

Example 130: 4-amino-1-methyl-N-((5-(1-methyl-1H-pyrazol-4-yl)pyridin-2-yl)methyl)-N-(2-oxopiperidin-1-yl)-1H-pyrazolo[4,3-c]quinoline-8-carboxamide

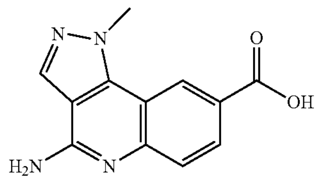

+

Da-1

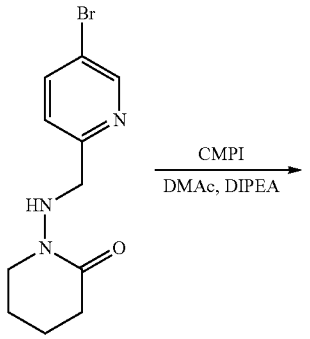

Bg-2

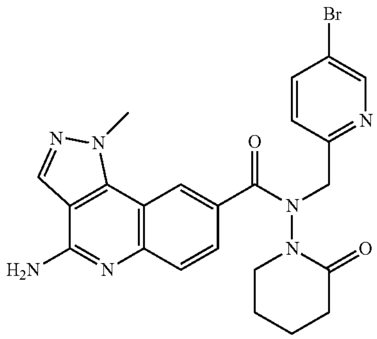

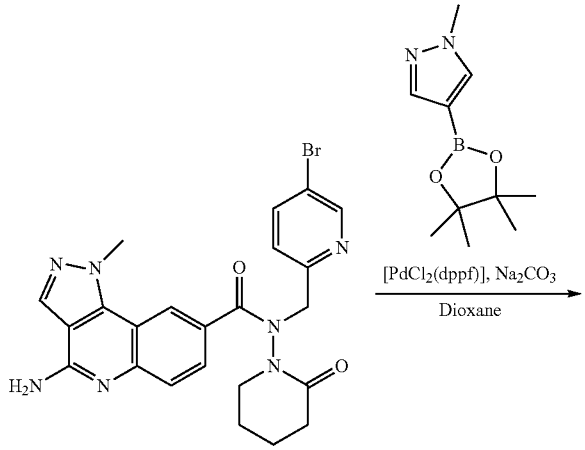

-continued

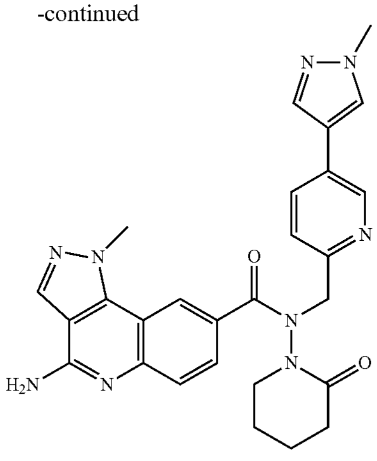

Example 130

Step 1: 4-amino-N-((5-bromopyridin-2-yl)methyl)-1-methyl-N-(2-oxopiperidin-1-yl)-1H-pyrazolo[4,3-c]quinoline-8-carboxamide Prepared following general procedure E-1 starting with intermediates Da-1 and Bg-2. ES/MS: m/z=509.0 $[M+H]^+$.

Step 2: Example 130: 4-amino-1-methyl-N-((5-(1-methyl-1H-pyrazol-4-yl)pyridin-2-yl)methyl)-N-(2-oxopiperidin-1-yl)-1H-pyrazolo[4,3-c]quinoline-8-carboxamide. To a solution of 4-amino-1-methyl-1H-pyrazolo[4,3-c]quinoline-8-carboxylic acid (15.3 mg, 0.0301 mmol) and 1-methyl-4-(3,3,4,4-tetramethyl-1,3,2,5-bromadioxolan-1-yl)-1H-pyrazole (7.0 mg, 0.0251 mmol), and $PdCl_2$(dppf) (2.8 mg, 0.00376 mmol) in dioxane (2 mL), was added 2M $Na_2CO_3$ (0.013, 0.125 mmol). The mixture was bubbled through argon for 1 minute and left to stir at 90 C for 6 hours. The mixture was filtered through a pad of celite and anhydrous $MgSO_4$. The solution was reduced under pressure and the crude was purified by preparative HPLC. ES/MS: m/z=510.2. 1H NMR (400 MHz, Methanol-d4) δ 8.86 (s, 1H), 8.50 (s, 2H), 8.17 (s, 2H), 7.94 (d, J=31.2 Hz, 2H), 7.82 (d, J=8.5 Hz, 2H), 4.54 (s, 3H), 3.98 (s, 3H), 3.73-3.43 (m, 2H), 2.68 (s, 2H), 2.38 (d, J=17.3 Hz, 1H), 1.99 (d, J=25.6 Hz, 1H), 1.69 (d, J=44.2 Hz, 2H), 1.53-1.13 (m, 2H).

Example 131

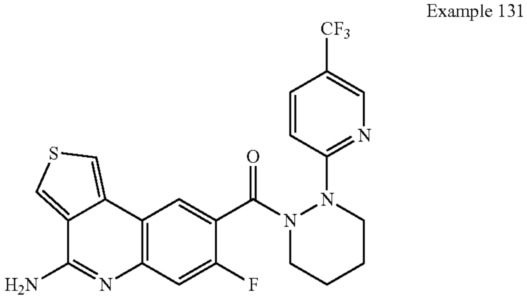 [SMILES: Nc1nc2cc(F)c(C(=O)N3CCCCN3c3ccc(C(F)(F)F)cn3)cc2c2cscc12]

Example 131: (4-amino-7-fluoro-thieno[3,4-c]quinolin-8-yl)-[2-[5-(trifluoromethyl)-2-pyridyl]hexahydropyridazin-1-yl]methanone. Prepared following general procedure E-1 starting with intermediates Db-4 and Bh-1. ES/MS: m/z=476.0 $[M+H]^+$. $^1H$ NMR (400 MHz, DMSO) δ 9.90 (s, 1H), 9.26-9.03 (m, 2H), 8.67 (d, J=3.0 Hz, 1H), 8.59-8.48 (m, 2H), 8.02 (dd, J=9.0, 2.5 Hz, 1H), 7.34 (d, J=10.5 Hz, 1H), 7.18 (d, J=8.9 Hz, 1H), 4.69-4.42 (m, 2H), 3.30 (t, J=12.8 Hz, 1H), 3.04-2.92 (m, 1H), 1.92 (q, J=12.7 Hz, 1H), 1.82-1.74 (m, 1H), 1.71-1.46 (m, 2H).

Example 132

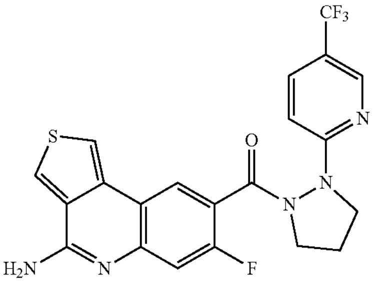

Example 132: (4-amino-7-fluoro-thieno[3,4-c]quinolin-8-yl)-[2-[5-(trifluoromethyl)-2-pyridyl]pyrazolidin-1-yl] methanone. Prepared following general procedure E-1 starting with intermediates Db-4 and Bh-2. ES/MS: m/z=462.0 $[M+H]^+$. $^1H$ NMR (400 MHz, DMSO) δ 9.91 (s, 1H), 9.36-9.01 (m, 2H), 8.88-8.46 (m, 3H), 7.99 (s, 1H), 7.71-6.79 (m, 2H), 4.63-4.11 (m, 2H), 3.42-3.04 (m, 1H), 2.35-1.83 (m, 3H).

Example 133

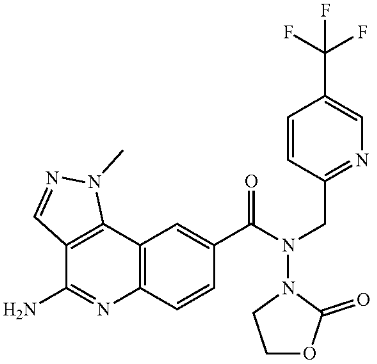

Example 133: 4-amino-1-methyl-N-(2-oxooxazolidin-3-yl)-N-((5-(trifluoromethyl)pyridin-2-yl)methyl)-1H-pyrazolo[4,3-c]quinoline-8-carboxamide. Prepared following general procedure E-1 starting with intermediates Da-1 and Bi-1. ES/MS: m/z=486.0 $[M+H]^+$. $^1H$ NMR (400 MHz, Methanol-d4) δ 8.94 (s, 1H), 8.68 (s, 1H), 8.50 (s, 1H), 8.19 (dd, J=8.3, 2.4 Hz, 1H), 8.01 (d, J=8.8 Hz, 1H), 7.84 (d, J=8.6 Hz, 2H), 5.51 (s, 2H), 5.26 (d, J=16.2 Hz, 1H), 5.08 (d, J=15.9 Hz, 1H), 4.49 (s, 3H), 4.28 (d, J=56.3 Hz, 2H), 3.99-3.57 (m, 2H).

Example 134

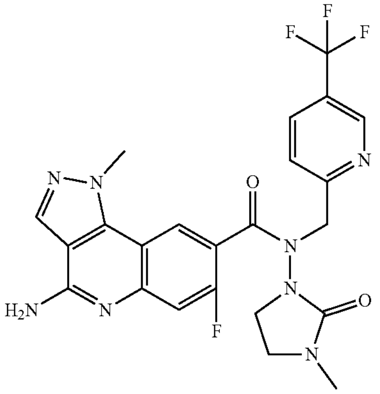

Example 134: 4-amino-7-fluoro-1-methyl-N-(3-methyl-2-oxoimidazolidin-1-yl)-N-((5-(trifluoromethyl)pyridin-2-yl)methyl)-1H-pyrazolo[4,3-c]quinoline-8-carboxamide. Prepared following general procedure E-1 starting with intermediates Db-1 and Bi-2. ES/MS: m/z=517.0 $[M+H]^+$. $^1H$ NMR (400 MHz, Methanol-d4) δ 8.95-8.86 (m, 1H), 8.64-8.54 (m, 1H), 8.48 (s, 1H), 8.16 (dd, J=20.6, 8.8 Hz, 2H), 7.92-7.75 (m, 2H), 7.58 (d, J=10.2 Hz, 1H), 4.50 (s, 3H), 3.79-3.38 (m, 4H), 2.83-2.75 (m, 2H), 2.67 (d, J=3.3 Hz, 3H).

Example 135

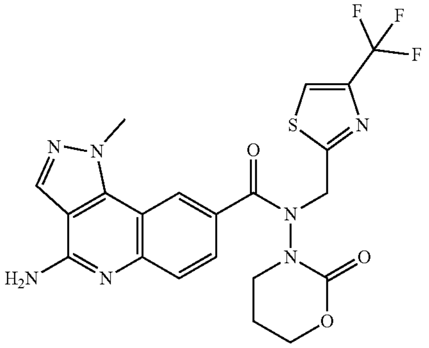

Example 135: 4-amino-1-methyl-N-(2-oxo-1,3-oxazinan-3-yl)-N-((4-(trifluoromethyl)thiazol-2-yl)methyl)-1H-pyrazolo[4,3-c]quinoline-8-carboxamide. Prepared following general procedure E-1 starting with intermediates Da-1 and Bi-3. ES/MS: m/z=506.0 $[M+H]^+$. $^1H$ NMR (400 MHz, Methanol-d4) δ 8.58 (s, 1H), 8.50 (s, 1H), 8.28 (d, J=1.0 Hz, 1H), 7.95 (d, J=8.7 Hz, 1H), 7.85 (d, J=8.6 Hz, 1H), 5.30 (d, J=6.3 Hz, 3H), 4.51 (s, 3H), 4.26 (t, J=9.6 Hz, 1H), 3.94 (d, J=43.7 Hz, 2H), 2.68 (s, 1H), 1.87 (d, J=70.3 Hz, 3H).

Example 136

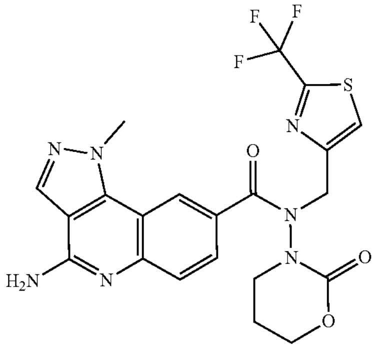

Example 136: 4-amino-1-methyl-N-(2-oxo-1,3-oxazinan-3-yl)-N-((2-(trifluoromethyl)thiazol-4-yl)methyl)-1H-pyrazolo[4,3-c]quinoline-8-carboxamide. Prepared following general procedure E-1 starting with intermediates Da-1 and Bi-4. ES/MS: m/z=506.0 $[M+H]^+$. $^1H$ NMR (400 MHz, Methanol-d4) δ 8.50 (s, 2H), 8.16-7.78 (m, 3H), 5.32-4.94 (m, 2H), 4.52 (s, 4H), 4.30-3.66 (m, 2H), 1.98 (s, 3H).

Example 137

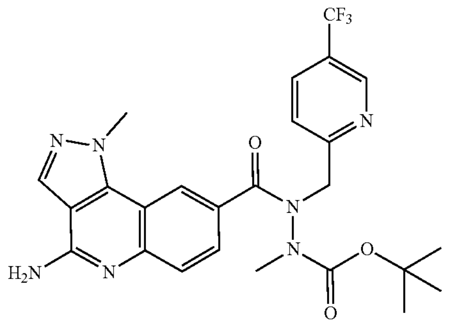

Example 137: tert-butyl N-[(4-amino-1-methyl-pyrazolo[4,3-c]quinoline-8-carbonyl)-[[5-(trifluoromethyl)-2-pyridyl]methyl]amino]-N-methyl-carbamate. Prepared following general procedure E-1 starting with intermediates Da-1 and Bi-5. ES/MS: m/z=530.0 $[M+H]^+$. $^1H$ NMR (400 MHz, DMSO) δ 9.67 (s, 1H), 9.14-8.81 (m, 2H), 8.63 (s, 1H), 8.44 (s, 1H), 8.28 (s, 1H), 8.09-7.65 (m, 3H), 5.27-4.73 (m, 2H), 4.48 (s, 3H), 3.26-2.92 (m, 3H), 1.50-0.66 (m, 9H).

Example 138

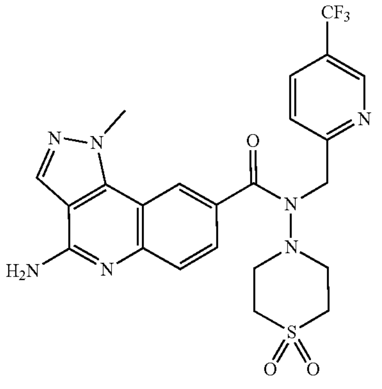

Example 138: 4-amino-N-(1,1-dioxo-1,4-thiazinan-4-yl)-1-methyl-N-[[5-(trifluoromethyl)-2-pyridyl]methyl]pyrazolo[4,3-c]quinoline-8-carboxamide. Prepared following general procedure E-1 starting with intermediates Da-1 and Bi-6. ES/MS: m/z=534.0 $[M+H]^+$. $^1H$ NMR (400 MHz, MeOD) δ 8.92 (s, 1H), 8.65-8.41 (m, 2H), 8.16 (dd, J=8.4, 2.3 Hz, 1H), 8.07 (dd, J=8.7, 1.7 Hz, 1H), 7.84 (d, J=8.6 Hz, 1H), 7.78 (s, 1H), 5.10 (s, 2H), 4.54 (s, 3H), 3.52 (d, J=13.9 Hz, 4H), 3.02 (s, 4H).

Example 139

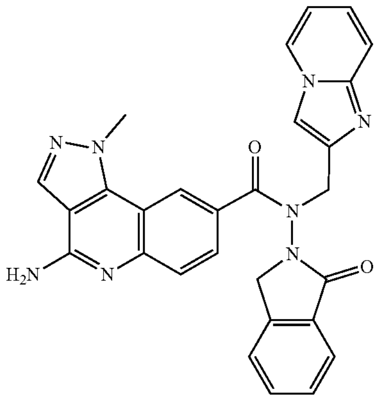

Example 139: 4-amino-N-(imidazo[1,2-a]pyridin-2-ylmethyl)-1-methyl-N-(1-oxoisoindolin-2-yl)pyrazolo[4,3-c]quinoline-8-carboxamide. Prepared following general procedure E-1 starting with intermediates Da-1 and Bj-1. ES/MS: m/z=503.0 $[M+H]^+$. 1H NMR (400 MHz, DMSO-$d_6$) δ 13.54 (s, 1H), 9.61 (s, 1H), 8.95-8.69 (m, 2H), 8.57 (s, 2H), 8.51 (s, 1H), 8.29 (s, 1H), 7.94 (s, 1H), 7.84-7.58 (m, 4H), 7.53-7.37 (m, 2H), 7.28 (s, 1H), 5.31 (d, J=15.4 Hz, 1H), 5.19 (s, 1H), 4.93-4.70 (m, 1H), 4.41 (s, 4H).

Example 140

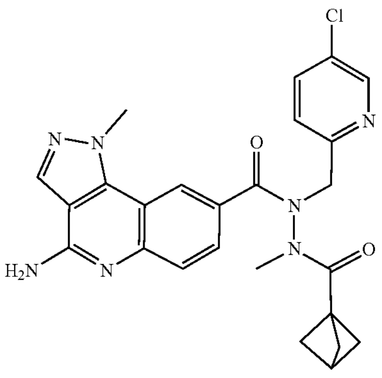

Example 140: 4-amino-N'-(bicyclo[1.1.1]pentane-1-carbonyl)-N-((5-chloropyridin-2-yl)methyl)-N',1-dimethyl-1H-pyrazolo[4,3-c]quinoline-8-carbohydrazide. Prepared following general procedure E-1 starting with intermediates Da-1 and Bk-1. ES/MS: m/z=490.0 $[M+H]^+$. $^1H$ NMR (400 MHz, Methanol-d4) δ 8.61 (d, J=28.9 Hz, 1H), 8.51 (d, J=4.8 Hz, 2H), 7.94-7.71 (m, 3H), 7.64 (d, J=32.2 Hz, 1H), 5.21 (dd, J=55.8, 15.4 Hz, 1H), 4.55 (s, 3H), 3.15 (q, J=1.7 Hz, 1H), 3.01 (s, 1H), 2.68 (s, 1H), 2.32 (s, 1H), 2.22-2.02 (m, 3H), 1.85 (d, J=16.7 Hz, 4H).

Example 141

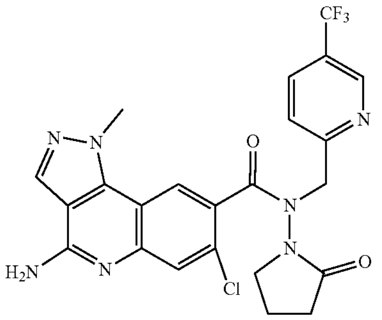

Example 141: 4-amino-7-chloro-1-methyl-N-(2-oxopyrrolidin-1-yl)-N-[[5-(trifluoromethyl)-2-pyridyl]methyl]pyrazolo[4,3-c]quinoline-8-carboxamide. Prepared following general procedure E-1 starting with intermediates Db-2 and Ba-23. ES/MS: m/z=517.9 $[M+H]^+$. $^1H$ NMR (400 MHz, DMSO-$d_6$) δ 9.77 (s, 1H), 9.16 (s, 1H), 9.01 (s, 1H), 8.65 (s, 1H), 8.41-8.30 (m, 2H), 7.95 (d, J=12.7 Hz, 2H), 5.33 (d, J=16.1 Hz, 1H), 4.95 (d, J=16.0 Hz, 1H), 4.46 (s, 3H), 3.59 (q, J=8.1 Hz, 1H), 3.22 (s, 1H), 2.17 (dt, J=16.9, 8.8 Hz, 1H), 1.96-1.80 (m, 2H), 1.48 (q, J=11.1, 9.6 Hz, 1H).

Example 142

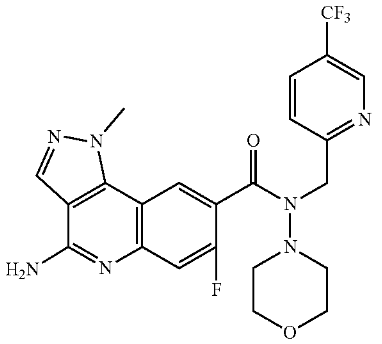

Example 142: 4-amino-7-fluoro-1-methyl-N-morpholino-N-((5-(trifluoromethyl)pyridin-2-yl)methyl)-1H-pyrazolo[4,3-c]quinoline-8-carboxamide. Prepared following general procedure E-1 starting with intermediates Db-1 and Ba-18. ES/MS: m/z=504.2 $[M+H]^+$. $^1H$ NMR (400 MHz, DMSO) δ 9.67 (s, 1H), 9.10-8.82 (m, 2H), 8.61 (s, 1H), 8.40 (d, J=6.5 Hz, 1H), 8.28 (dd, J=8.4, 2.5 Hz, 1H), 7.70 (d, J=8.3 Hz, 1H), 7.63 (d, J=10.4 Hz, 1H), 5.03 (s, 2H), 4.46 (s, 3H), 3.65 (d, J=11.0 Hz, 2H), 2.99 (t, J=10.9 Hz, 2H), 2.91-2.81 (m, 2H), 2.78 (d, J=10.2 Hz, 2H).

Example 143

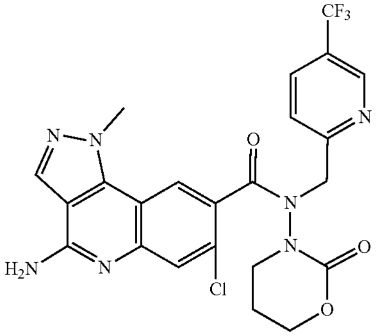

Example 143: 4-amino-7-chloro-1-methyl-N-(2-oxo-1,3-oxazinan-3-yl)-N-[[5-(trifluoromethyl)-2-pyridyl]methyl]pyrazolo[4,3-c]quinoline-8-carboxamide. Prepared following general procedure E-1 starting with intermediates Db-2 and Ba-8. ES/MS: m/z=534.2 $[M+H]^+$. $^1H$ NMR (400 MHz, MeOD) δ 8.95-8.87 (m, 1H), 8.86-8.82 (m, 0.4H, minor rotamer), 8.63 (s, 0.2H, minor rotamer), 8.49 (d, J=1.8 Hz, 2H), 8.21 (dd, J=8.3, 2.4 Hz, 1H), 8.15-8.06 (m, 0.4H, minor rotamer), 7.98-7.86 (m, 2H), 7.77 (d, J=8.2 Hz, 0.2H, minor rotamer), 7.58 (d, J=8.2 Hz, 0.2H, minor rotamer), 5.43 (d, J=15.5 Hz, 1H), 4.99 (d, J=15.5 Hz, 1H), 4.63-4.40 (m, 4H), 4.25-4.13 (m, 1H), 3.91-3.76 (m, 2H), 3.53-3.44 (m, 1H), 2.24 (s, 0.2H, minor rotamer), 2.11-2.02 (m, 1H), 2.02-1.91 (m, 1H), 1.69-1.51 (m, 1H).

Example 144

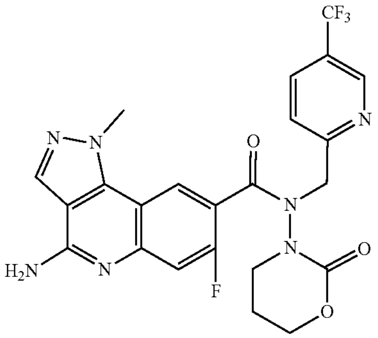

Example 144: 4-amino-7-fluoro-1-methyl-N-(2-oxo-1,3-oxazinan-3-yl)-N-[[5-(trifluoromethyl)-2-pyridyl]methyl]pyrazolo[4,3-c]quinoline-8-carboxamide. Prepared following general procedure E-1 starting with intermediates Db-1 and Ba-8. ES/MS: m/z=518.0 $[M+H]^+$. $^1H$ NMR (400 MHz, MeOD) δ 8.98-8.88 (m, 1H), 8.87-8.82 (m, 0.3H, minor rotamer), 8.53-8.47 (m, 2H), 8.20 (d, J=8.2 Hz, 1H), 8.14 (dd, J=8.1, 2.4 Hz, 0.3H, minor rotamer), 7.87 (d, J=8.2 Hz, 1H), 7.77 (d, J=8.2 Hz, 0.3H, minor rotamer), 7.65 (d, J=10.2 Hz, 1H), 5.36 (d, J=15.5 Hz, 1H), 5.04 (d, J=15.5 Hz, 1H), 4.47 (s, 3H), 4.27 (s, 1H, minor rotamer), 4.24-4.18 (m, 1H), 3.98-3.85 (m, 2H), 3.58-3.40 (m, 2H), 2.11-1.95 (m, 2H), 1.72 (dt, J=14.1, 4.5 Hz, 1H).

Example 145

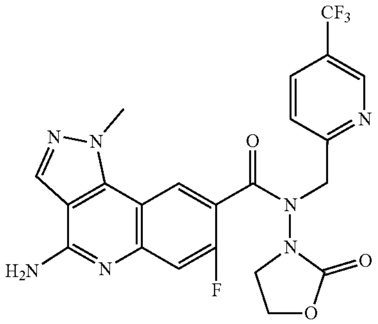

Example 145: 4-amino-7-fluoro-1-methyl-N-(2-oxooxazolidin-3-yl)-N-[[5-(trifluoromethyl)-2-pyridyl]methyl] pyrazolo[4,3-c]quinoline-8-carboxamide. Prepared following general procedure E-1 starting with intermediates Db-1 and Bi-1. ES/MS: m/z=504.2 [M+H]$^+$. $^1$H NMR (400 MHz, MeOD) δ 8.91 (s, 1H), 8.56 (s, 1H), 8.48 (s, 1H), 8.18 (d, J=8.2 Hz, 1H), 7.83 (d, J=13.9 Hz, 1H), 7.62 (d, J=10.2 Hz, 1H), 5.41-5.19 (m, 1H), 5.18-4.99 (m, 1H), 4.48 (s, 3H), 4.38 (s, 1H), 4.08 (s, 2H), 3.66 (s, 1H).

Example 146

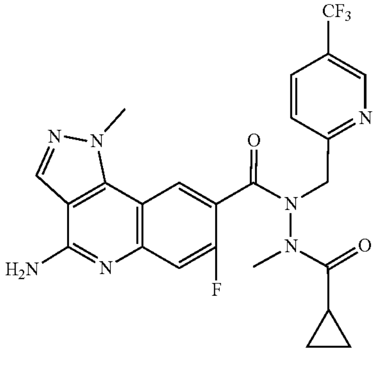

Example 146: 4-amino-N'-(cyclopropanecarbonyl)-7-fluoro-N',1-dimethyl-N-[[5-(trifluoromethyl)-2-pyridyl] methyl]pyrazolo[4,3-c]quinoline-8-carbohydrazide. Prepared following general procedure E-1 starting with intermediates Db-1 and Bd-8. ES/MS: m/z=516.0 [M+H]$^+$. $^1$H NMR (400 MHz, MeOD) δ 9.08-8.70 (m, 1H), 8.55 (d, J=6.3 Hz, 0.4H, minor rotamer), 8.49 (d, J=3.4 Hz, 1H), 8.39 (d, J=6.5 Hz, 1H), 8.27-8.05 (m, 1H), 7.86 (d, J=8.2 Hz, 1H), 7.76-7.46 (m, 1H), 5.37-5.22 (m, 1H), 5.16-4.91 (m, 1H), 4.64-4.42 (m, 3H), 3.48 (s, 1H, minor rotamer), 3.16 (s, 3H), 2.14-1.92 (m, 1H), 1.62 (s, 0.4H, minor rotamer), 1.08-0.22 (m, 4H).

Example 147

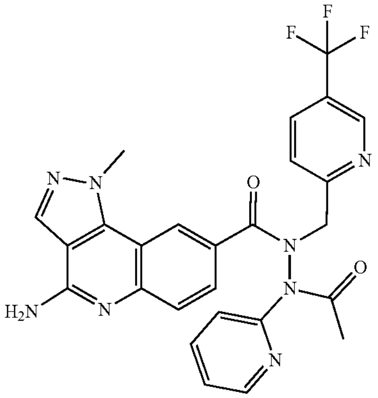

Example 147: N'-acetyl-4-amino-1-methyl-N'-(2-pyridyl)-N-[[5-(trifluoromethyl)-2-pyridyl]methyl]pyrazolo [4,3-c]quinoline-8-carbohydrazide. Prepared following general procedure E-1 starting with intermediates Da-1 and Bd-20. ES/MS: m/z=535.0 [M+H]$^+$. $^1$H NMR (400 MHz, DMSO-$d_6$) δ 13.30 (s, 1H), 9.63 (s, 1H), 8.85 (s, 1H), 8.57 (d, J=15.6 Hz, 2H), 8.46-8.39 (m, 1H), 8.21-8.12 (m, 1H), 8.09 (s, 1H), 7.86 (d, J=30.3 Hz, 1H), 7.78 (dd, J=11.7, 8.1 Hz, 3H), 7.54 (d, J=8.3 Hz, 1H), 7.29 (dd, J=7.4, 4.9 Hz, 1H), 5.13 (s, 2H), 4.53 (s, 1H), 4.17 (s, 3H), 2.11 (s, 3H).

Example 148

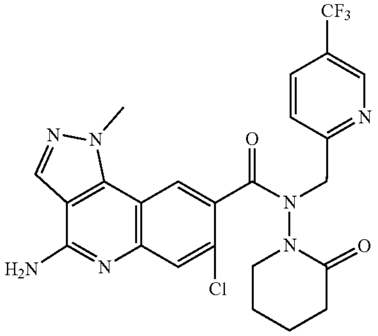

Example 148: 4-amino-7-chloro-1-methyl-N-(2-oxopiperidin-1-yl)-N-((5-(trifluoromethyl)pyridin-2-yl)methyl)-1H-pyrazolo[4,3-c]quinoline-8-carboxamide. Prepared following general procedure E-1 starting with intermediates Db-2 and Ba-26. ES/MS: m/z=532.2 [M+H]$^+$. $^1$H NMR (400 MHz, DMSO) δ 13.42 (brs, 1H), 8.98 (d, J=2.3 Hz, 1H), 8.59 (s, 1H), 8.43-8.20 (m, 2H), 7.88 (d, J=11.6 Hz, 2H), 6.51 (s, 2H), 5.38 (d, J=16.3 Hz, 1H), 4.79 (d, J=16.0 Hz, 1H), 4.39 (s, 3H), 2.45-2.38 (m, 1H), 2.26 (d, J=16.6 Hz, 1H), 1.93 (d, J=15.3 Hz, 1H), 1.70-1.43 (m, 2H), 1.20 (d, J=35.9 Hz, 3H).

Example 149

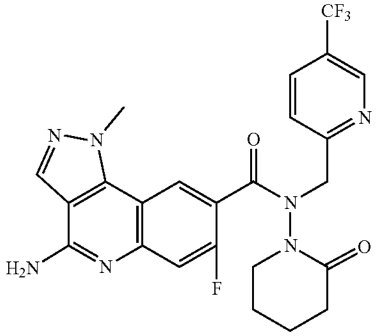

Example 149: 4-amino-7-fluoro-1-methyl-N-(2-oxopiperidin-1-yl)-N-((5-(trifluoromethyl)pyridin-2-yl)methyl)-1H-pyrazolo[4,3-c]quinoline-8-carboxamide. Prepared following general procedure E-1 starting with intermediates Db-1 and Ba-26. ES/MS: m/z=516.3 $[M+H]^+$. $^1H$ NMR (400 MHz, DMSO) δ 9.72 (brs, 1H), 9.07 (brs, 0.1H), 9.01-8.87 (m, 1H), 8.61 (s, 1H), 8.29 (dd, J=7.6, 2.6 Hz, 2H), 7.85 (d, J=8.3 Hz, 1H), 7.65 (d, J=10.4 Hz, 1H), 5.32 (d, J=16.0 Hz, 1H), 4.83 (d, J=16.0 Hz, 1H), 4.40 (s, 3H), 3.68-3.51 (m, 1H), 3.41-3.27 (m, 1H), 2.22 (dt, J=17.4, 5.4 Hz, 1H), 1.92 (ddd, J=16.7, 9.3, 6.0 Hz, 1H), 1.78-1.61 (m, 1H), 1.51 (s, 1H), 1.36-1.17 (m, 2H).

Example 150

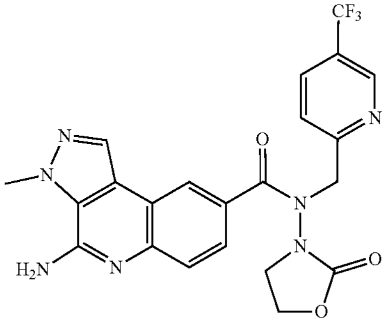

Example 150: 4-amino-3-methyl-N-(2-oxooxazolidin-3-yl)-N-((5-(trifluoromethyl)pyridin-2-yl)methyl)-3H-pyrazolo[3,4-c]quinoline-8-carboxamide. Prepared following general procedure E-1 starting with intermediates Da-4 and Bi-1. ES/MS: m/z=486.2 $[M+H]^+$. $^1H$ NMR (400 MHz, DMSO-$d_6$) δ 8.99 (s, 1H), 8.74 (brs, 2H), 8.43 (s, 1H), 8.27 (dd, J=8.3, 2.4 Hz, 1H), 7.85 (d, J=8.3 Hz, 1H), 7.80-7.69 (m, 2H), 5.34-5.08 (m, 1H), 4.95 (d, J=15.8 Hz, 1H), 4.41 (s, 3H), 4.30-3.60 (m, 4H).

Example 151

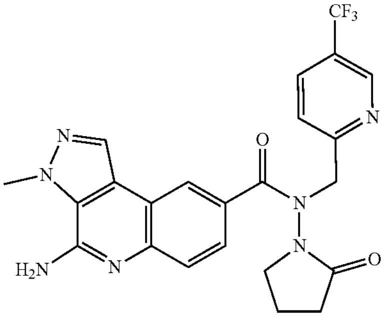

Example 151: 4-amino-3-methyl-N-(2-oxopyrrolidin-1-yl)-N-((5-(trifluoromethyl)pyridin-2-yl)methyl)-3H-pyrazolo[3,4-c]quinoline-8-carboxamide. Prepared following general procedure E-1 starting with intermediates Da-4 and Ba-23. ES/MS: m/z=484.22 $[M+H]^+$. $^1H$ NMR (400 MHz, DMSO-$d_6$) δ 9.02 (brs, 1H), 8.97 (s, 1H), 8.78 (s, 1H), 8.39 (s, 1H), 8.26 (dd, J=8.3, 2.4 Hz, 1H), 7.87 (d, J=8.3 Hz, 1H), 7.79-7.65 (m, 2H), 5.20 (d, J=15.9 Hz, 1H), 4.86 (d, J=15.9 Hz, 1H), 4.42 (s, 3H), 3.55-3.34 (m, 3H), 2.28-2.06 (m, 1H), 1.95-1.72 (m, 2H), 1.65-1.44 (m, 1H).

Example 152

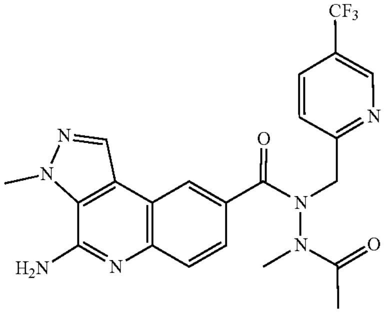

Example 152: N'-acetyl-4-amino-N',3-dimethyl-N-((5-(trifluoromethyl)pyridin-2-yl)methyl)-3H-pyrazolo[3,4-c]quinoline-8-carbohydrazide. Prepared following general procedure E-1 starting with intermediates Da-4 and Ba-29. ES/MS: m/z=472.2 $[M+H]^+$. $^1H$ NMR (400 MHz, Methanol-d4) δ 9.04 (brs, 1H), 8.89 (s, 1H), 8.63 (s, 0.6H major rotamer), 8.61 (s, 0.4H minor rotamer), 8.36 (s, 1H), 8.24-8.07 (m, 2H), 7.89 (d, J=8.2 Hz, 1H), 7.82 (d, J=8.4 Hz, 1H), 7.80-7.68 (m, 2H), 5.31 (d, J=15.5 Hz, 1H), 5.02 (d, J=15.5 Hz, 1H), 4.51 (s, 1.2H minor rotamer), 4.50 (s, 1.8H major rotamer), 3.18 (s, 1.8H major rotamer), 3.08 (s, 1.2H minor rotamer), 2.05 (s, 1.8H major rotamer), 1.81 (s, 1.2H minor rotamer).

Example 153

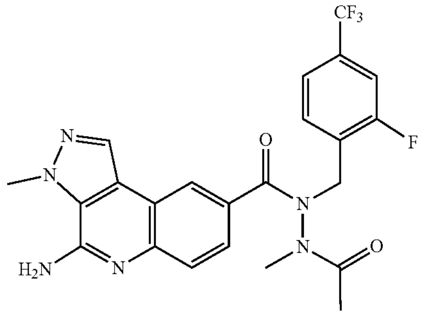

Example 153: N'-acetyl-4-amino-N-(2-fluoro-4-(trifluoromethyl)benzyl)-N',3-dimethyl-3H-pyrazolo[3,4-c]quinoline-8-carbohydrazide. Prepared following general procedure E-1 starting with intermediates Da-4 and Ba-34. ES/MS: m/z=489.2 [M+H]$^+$. 1H NMR (400 MHz, Methanol-d4) δ 8.63 (s, 0.35H minor rotamer), 8.59 (s, 0.65H major rotamer), 8.46 (brs, 0.35H minor rotamer), 8.33 (s, 0.65H major rotamer), 7.94-7.65 (m, 3H), 7.62-7.47 (m, 2H), 5.21 (d, J=14.9 Hz, 1H), 5.09 (brs, 1H), 4.83 (s, 0.65H major rotamer), 4.79 (s, 0.35H minor rotamer), 4.50 (s, 1.05H minor rotamer), 4.49 (s, 1.95H major rotamer), 3.20 (s, 1.95H major rotamer), 3.09 (s, 1.05H minor rotamer), 1.81 (s, 1.05H minor rotamer), 1.76 (s, 1.95H major rotamer).

Example 154

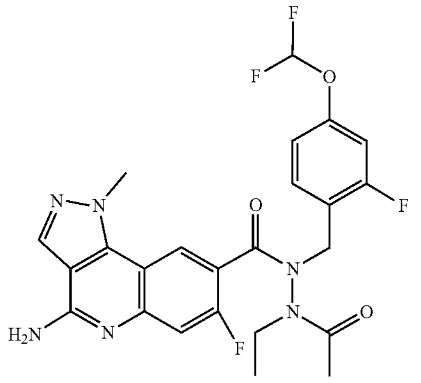

Example 154: N'-acetyl-4-amino-N-(4-(difluoromethoxy)-2-fluorobenzyl)-N'-ethyl-7-fluoro-1-methyl-1H-pyrazolo[4,3-c]quinoline-8-carbohydrazide. Prepared following general procedure E-1 starting with intermediates Db-1 and Bd-21. ES/MS: m/z=519.2 [M+H]$^+$. $^1$H NMR (400 MHz, DMSO-$d_6$) δ 13.67 (s, 1H), 9.67 (s, 1H), 8.98 (brs, 1H), 8.62 (s, 0.4H minor rotamer), 8.59 (s, 0.6H major rotamer), 8.45 (brs, 0.6H major rotamer), 8.36-8.21 (m, 0.4H minor rotamer), 7.77-7.57 (m, 2H), 7.54-7.28 (m, 1H), 7.26-6.97 (m, 2H), 5.08 (d, J=15.1 Hz, 0.6H major rotamer), 4.90-4.57 (m, 1H), 4.50 (s, 1.2H minor rotamer), 4.43 (d, J=15.1 Hz, 0.4H minor rotamer), 4.36 (s, 1.8H major rotamer), 3.43-3.27 (m, 2H), 1.90 (s, 1.2H minor rotamer), 1.68 (s, 1.8H major rotamer), 1.08 (t, J=7.1 Hz, 1.2H minor rotamer), 0.81 (t, J=7.1 Hz, 1.8H major rotamer).

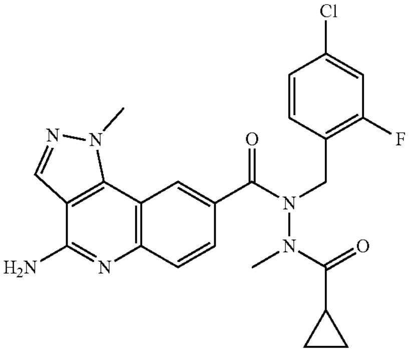 [SMILES: CN(C(=O)C1CC1)N(Cc1ccc(Cl)cc1F)C(=O)c1ccc2nc(N)c3cnn(C)c3c2c1]

Example 155: 4-amino-N-(4-chloro-2-fluorobenzyl)-N'-(cyclopropanecarbonyl)-N',1-dimethyl-1H-pyrazolo[4,3-c]quinoline-8-carbohydrazide. Prepared following general procedure E-1 starting with intermediates Da-1 and Bk-2. ES/MS: m/z=481.2 [M+H]$^+$. 1H NMR (400 MHz, DMSO-$d_6$) δ 13.56 (brs, 1H), 9.66 (brs, 1H), 8.89 (brs, 1H), 8.63 (s, 1H), 8.48 (s, 0.7H major rotamer), 8.32 (s, 0.3H minor rotamer), 7.98-7.73 (m, 2H), 7.70-7.54 (m, 1H), 7.54-7.43 (m, 1H), 7.40-7.30 (m, 1H), 5.28 (brs, 0.7H major rotamer), 4.96 (d, J=14.7 Hz, 0.3H minor rotamer), 4.81 (d, J=14.7 Hz, 0.7H major rotamer), 4.69 (d, J=14.7 Hz, 0.3H minor rotamer), 4.47 (s, 2.1H major rotamer), 4.44 (s, 0.9H minor rotamer), 3.22 (s, 0.9H minor rotamer), 3.04 (s, 2.1H major rotamer), 1.74-1.45 (m, 1H), 0.75-0.65 (m, 0.7H major rotamer), 0.58 (brs, 0.3H minor rotamer), 0.48 (brs, 0.3H minor rotamer), 0.42-0.25 (m, 2H+0.7H major rotamer).

Example 156

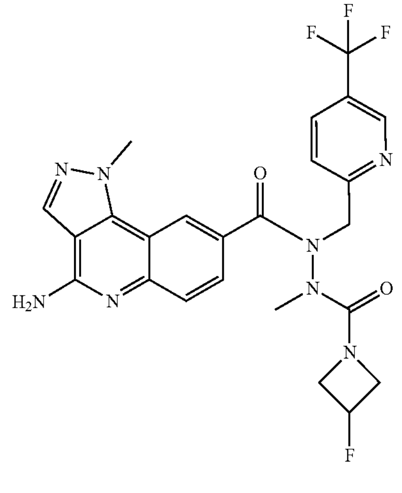

Example 156: 4-amino-N'-(3-fluoroazetidine-1-carbonyl)-N',1-dimethyl-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bf-4. ES/MS: m/z=531.0 [M+H]$^+$. $^1$H NMR (400 MHz, Methanol-d4) δ 8.92 (s, 1H), 8.61 (s, 1H), 8.50 (s, 1H), 8.18 (d, J=8.3 Hz, 1H), 7.97 (d, J=8.6 Hz, 1H), 7.85 (t, J=10.1 Hz, 2H), 5.47-5.16 (m, 2H), 4.54 (s, 3H), 4.34-3.94 (m, 3H), 3.71 (dd, J=25.3, 10.4 Hz, 1H), 3.11 (s, 3H), 2.68 (s, 1H).

Example 157

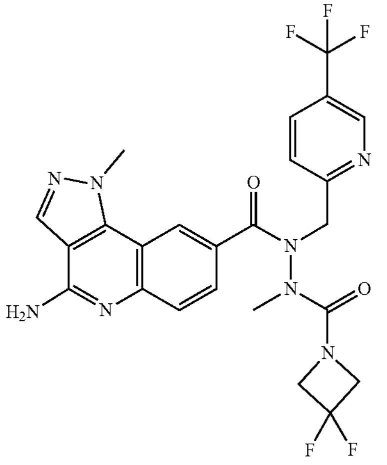

Example 157: 4-amino-N'-(3,3-difluoroazetidine-1-carbonyl)-N',1-dimethyl-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bf-5. ES/MS: m/z=549.0 $[M+H]^+$. $^1H$ NMR (400 MHz, Methanol-d4) δ 8.91 (s, 1H), 8.59 (s, 1H), 8.51 (s, 1H), 8.18 (d, J=8.2 Hz, 1H), 8.03-7.76 (m, 3H), 5.32 (d, J=15.7 Hz, 1H), 4.99 (d, J=15.7 Hz, 1H), 4.54 (s, 3H), 4.30 (d, J=12.1 Hz, 2H), 4.06 (d, J=12.7 Hz, 2H), 3.16 (d, J=2.6 Hz, 4H), 2.68 (s, 1H).

Example 158

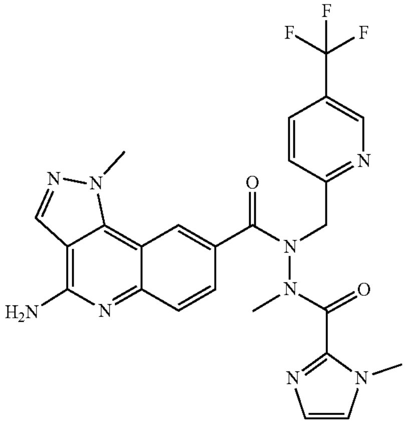

Example 158: 4-amino-N',1-dimethyl-N'-(1-methyl-1H-imidazole-2-carbonyl)-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bc-6. ES/MS: m/z=538.0 $[M+H]^+$. $^1H$ NMR (400 MHz, Methanol-d4) δ 8.88 (dd, J=45.2, 25.1 Hz, 2H), 8.48 (s, 2H), 8.18 (s, 1H), 7.78 (s, 2H), 7.15 (d, J=21.3 Hz, 2H), 5.32 (d, J=40.7 Hz, 2H), 4.49 (s, 3H), 3.65 (d, J=30.8 Hz, 6H), 2.68 (s, 2H).

Example 159

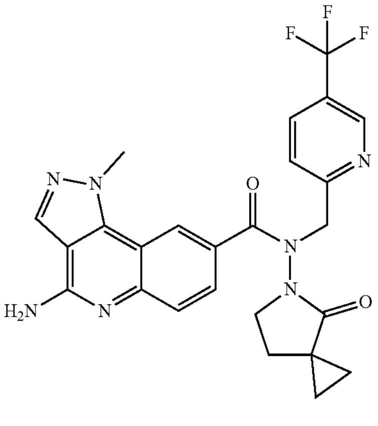

Example 159: 4-amino-1-methyl-N-(4-oxo-5-azaspiro[2.4]heptan-5-yl)-N-((5-(trifluoromethyl)pyridin-2-yl)methyl)-1H-pyrazolo[4,3-c]quinoline-8-carboxamide. Prepared following general procedure E-1 starting with intermediates Da-1 and Ba-72. ES/MS: m/z=510.0 $[M+H]^+$. $^1H$ NMR (400 MHz, Methanol-d4) δ 8.91 (s, 1H), 8.62 (s, 1H), 8.50 (s, 1H), 8.22-8.12 (m, 1H), 8.03-7.77 (m, 3H), 5.30-5.00 (m, 2H), 4.51 (s, 3H), 3.93-3.39 (m, 2H), 1.97 (q, J=28.7, 26.2 Hz, 2H), 1.04-0.37 (m, 4H).

Example 160

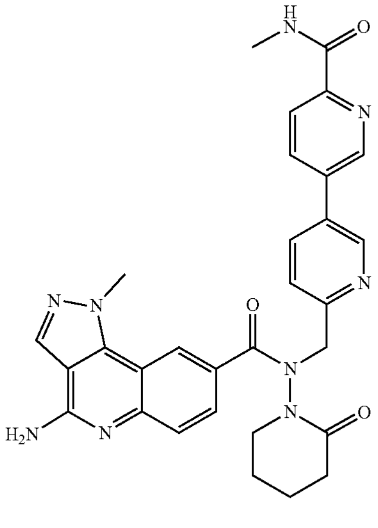

Example 160: 4-amino-1-methyl-N-((6'-(methylcarbamoyl)-[3,3'-bipyridin]-6-yl)methyl)-N-(2-oxopiperidin-1-yl)-1H-pyrazolo[4,3-c]quinoline-8-carboxamide. Prepared following the procedure reported for example 130 starting with intermediates Da-1, Bg-2, and N-methyl-5-(4,4,5,5-tetramethyl-1,3,2-dioxaborolan-2-yl)picolinamide. ES/MS: m/z=564.2 $[M+H]^+$. $^1H$ NMR (400 MHz, Methanol-d4) δ 9.07-8.89 (m, 2H), 8.50 (s, 2H), 8.36-8.18 (m, 3H), 7.91 (s, 2H), 7.82 (s, 1H), 5.36 (d, J=15.2 Hz, 1H), 4.54 (s, 3H), 3.78-3.42 (m, 2H), 3.02 (s, 3H), 2.68 (s, 1H), 2.36 (d, J=18.3 Hz, 1H), 2.11-1.90 (m, 1H), 1.55 (dd, J=133.2, 52.6 Hz, 4H).

Example 161

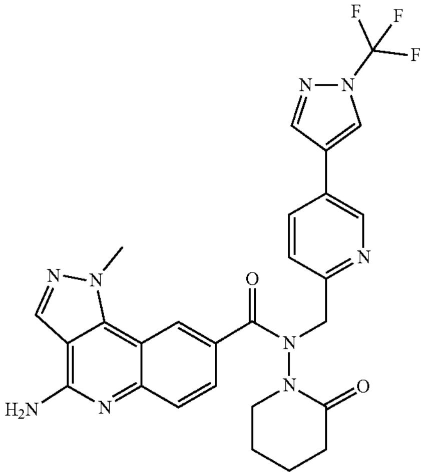

Example 161: 4-amino-1-methyl-N-(2-oxopiperidin-1-yl)-N-((5-(1-(trifluoromethyl)-1H-pyrazol-4-yl)pyridin-2-yl)methyl)-1H-pyrazolo[4,3-c]quinoline-8-carboxamide. Prepared following the procedure reported for example 130 starting with intermediates Da-1, Bg-2, and 4-(4,4,5,5-tetramethyl-1,3,2-dioxaborolan-2-yl)-1-(trifluoromethyl)-1H-pyrazole. ES/MS: m/z=564.0 $[M+H]^+$. $^1$H NMR (400 MHz, Methanol-d4) δ 8.98 (s, 1H), 8.83 (s, 1H), 8.50 (s, 2H), 8.44-8.21 (m, 2H), 8.03 (s, 1H), 7.86 (dd, J=21.3, 9.6 Hz, 2H), 5.29 (d, J=15.2 Hz, 1H), 4.96 (s, 1H), 4.54 (s, 3H), 3.78-3.40 (m, 2H), 2.37 (d, J=18.2 Hz, 1H), 2.12-1.15 (m, 5H).

Example 162

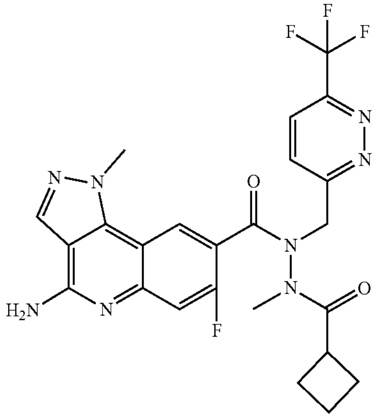

Example 162: 4-amino-N'-(cyclobutanecarbonyl)-7-fluoro-N',1-dimethyl-N-((6-(trifluoromethyl)pyridazin-3-yl)methyl)-1H-pyrazolo[4,3-c]quinoline-8-carbohydrazide. Prepared following general procedure E-1 starting with intermediates Db-1 and Bd-1. ES/MS: m/z=531.0 $[M+H]^+$. $^1$H NMR (400 MHz, Methanol-d4) δ 8.61 (d, J=28.9 Hz, 1H), 8.51 (d, J=4.8 Hz, 2H), 7.94-7.71 (m, 3H), 7.64 (d, J=32.2 Hz, 1H), 5.21 (dd, J=55.8, 15.4 Hz, 1H), 4.55 (s, 3H), 3.15 (q, J=1.7 Hz, 1H), 3.01 (s, 1H), 2.68 (s, 1H), 2.32 (s, 1H), 2.22-2.02 (m, 3H), 1.85 (d, J=16.7 Hz, 4H).

Example 163

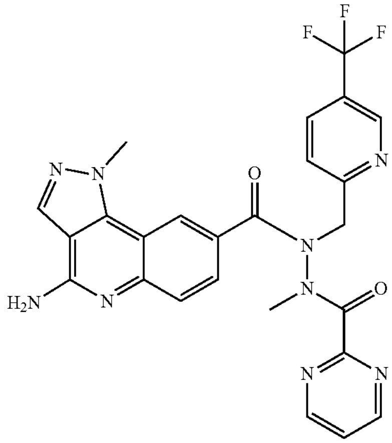

Example 163: 4-amino-N',1-dimethyl-N'-(pyrimidine-2-carbonyl)-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bc-7. ES/MS: m/z=536.0 $[M+H]^+$. $^1$H NMR (400 MHz, Methanol-d4) δ 9.00-8.88 (m, 2H), 8.83 (s, 1H), 8.72 (s, 1H), 8.51 (s, 1H), 8.20 (dd, J=8.3, 2.4 Hz, 1H), 8.06 (t, J=11.2 Hz, 1H), 7.84 (d, J=8.6 Hz, 1H), 7.64 (t, J=5.0 Hz, 1H), 7.53 (d, J=8.2 Hz, 1H), 5.54-4.94 (m, 3H), 4.57 (s, 2H), 3.18 (s, 2H), 2.68 (s, 1H).

Example 164

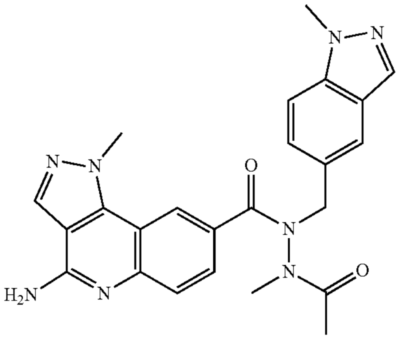

Example 164: N'-acetyl-4-amino-N',1-dimethyl-N-((1-methyl-1H-indazol-5-yl)methyl)-1H-pyrazolo[4,3-c]quinoline-8-carbohydrazide. Prepared following general procedure E-1 starting with intermediates Da-1 and Bb-14. ES/MS: m/z=457.2 $[M+H]^+$. $^1$H NMR (400 MHz, Methanol-d4) δ 8.57-8.47 (m, 2H), 8.09-7.73 (m, 4H), 7.63 (d, J=11.4 Hz, 2H), 5.15 (dd, J=103.2, 38.5 Hz, 2H), 4.52 (d, J=6.4 Hz, 3H), 4.09 (s, 3H), 3.18-2.97 (m, 3H), 1.72 (d, J=55.0 Hz, 3H).

Example 165

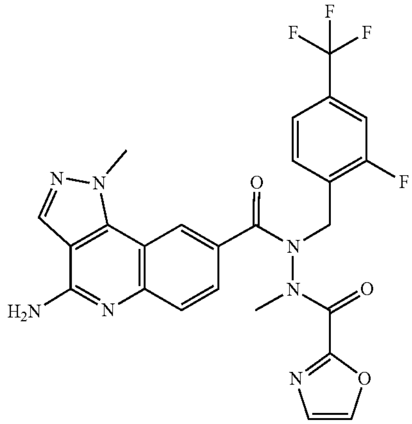

Example 165: N'-(4-amino-1-methyl-1H-pyrazolo[4,3-c]quinoline-8-carbonyl)-N'-(2-fluoro-4-(trifluoromethyl)benzyl)-N-methyloxazole-2-carbohydrazide. Prepared following general procedure E-1 starting with intermediates Da-1 and Bc-8. ES/MS: m/z=542.0. $[M+H]^+$. $^1H$ NMR (400 MHz, Methanol-d4) δ 8.60 (d, J=18.0 Hz, 1H), 8.48 (s, 1H), 8.11-7.89 (m, 3H), 7.86-7.62 (m, 1H), 7.61-7.21 (m, 3H), 5.38-4.98 (m, 2H), 4.53 (s, 1H), 4.33 (s, 1H), 3.68 (s, 1H), 3.28 (s, 2H), 2.68 (s, 1H).

Example 166

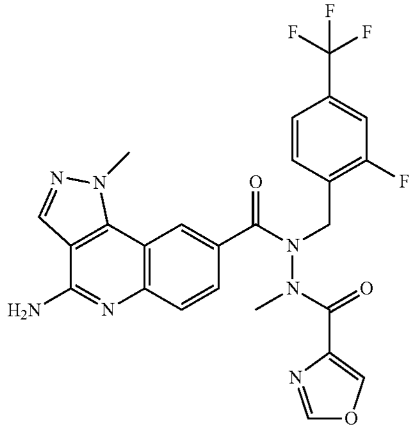

Example 166: N'-(4-amino-1-methyl-1H-pyrazolo[4,3-c]quinoline-8-carbonyl)-N'-(2-fluoro-4-(trifluoromethyl)benzyl)-N-methyloxazole-4-carbohydrazide. Prepared following general procedure E-1 starting with intermediates Da-1 and Bd-22. ES/MS: m/z=542.0 $[M+H]^+$. $^1H$ NMR (400 MHz, Methanol-d4) δ 8.60 (d, J=18.0 Hz, 1H), 8.48 (s, 1H), 8.11-7.89 (m, 3H), 7.86-7.62 (m, 1H), 7.61-7.21 (m, 3H), 5.38-4.98 (m, 2H), 4.53 (s, 1H), 4.33 (s, 1H), 3.68 (s, 1H), 3.28 (s, 2H), 2.68 (s, 1H).

Example 167

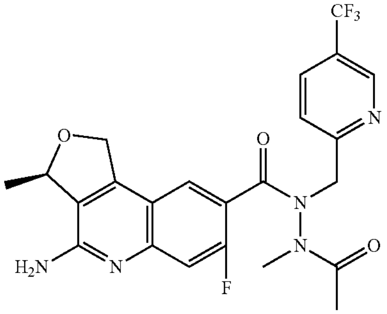

Example 167: (3R)—N'-acetyl-4-amino-7-fluoro-N',3-dimethyl-N-[[5-(trifluoromethyl)-2-pyridyl]methyl]-1,3-dihydrofuro[3,4-c]quinoline-8-carbohydrazide. Prepared following general procedure E-1 starting with intermediates Db-6 and Ba-29. ES/MS: m/z=492.2 $[M+H]^+$. $^1H$ NMR (400 MHz, DMSO-$d_6$) δ 9.03 (s, 1H), 8.96 (s, 1H), 8.29 (s, 1H), 8.15 (s, 1H), 7.80 (s, 1H), 7.52 (s, 1H), 5.48 (s, 1H), 5.44-5.34 (m, 1H), 4.99 (d, J=13.4 Hz, 1H), 4.71 (brs, 1H), 2.99 (d, J=7.9 Hz, 3H), 1.94 (d, J=12.2 Hz, 3H), 1.43 (s, 3H).

Example 168

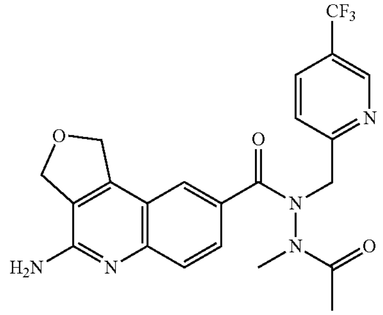

Example 168: N'-acetyl-4-amino-N'-methyl-N-[[5-(trifluoromethyl)-2-pyridyl]methyl]-1,3-dihydrofuro[3,4-c]quinoline-8-carbohydrazide. Prepared following general procedure E-1 starting with intermediates Db-5 and Ba-29. ES/MS: m/z=460.0 $[M+H]^+$. $^1H$ NMR (400 MHz, DMSO-$d_6$) δ 8.98-8.92 (m, 1H), 8.24 (dd, J=8.4, 2.4 Hz, 1H), 7.85 (d, J=8.2 Hz, 1H), 7.80 (d, J=9.4 Hz, 2H), 5.45 (s, 2H), 5.25-5.18 (m, 1H), 5.09 (t, J=3.5 Hz, 2H), 5.01-4.95 (m, 1H), 4.68 (d, J=7.7 Hz, 0.53H, minor rotamer), 3.12 (d, J=85.5 Hz, 3H), 1.82 (d, J=46.1 Hz, 3H).

Example 169

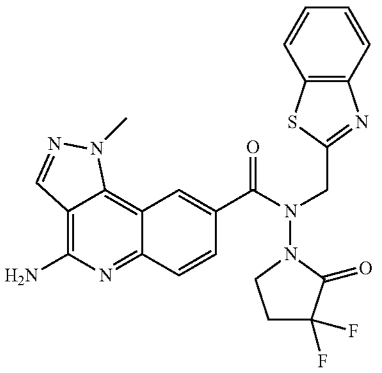

Example 169: 4-amino-N-(1,3-benzothiazol-2-ylmethyl)-N-(3,3-difluoro-2-oxo-pyrrolidin-1-yl)-1-methyl-pyrazolo[4,3-c]quinoline-8-carboxamide. Prepared following general procedure E-1 starting with intermediates Da-1 and BI-2. ES/MS: m/z=508.0 $[M+H]^+$. $^1H$ NMR (400 MHz, DMSO-$d_6$) δ 8.42 (s, 1H), 8.20-7.96 (m, 2H), 7.83 (s, 2H), 7.61-7.44 (m, 2H), 6.53 (s, 4H), 5.41 (s, 2H), 4.40 (s, 3H), 1.24 (s, 2H).

Example 170

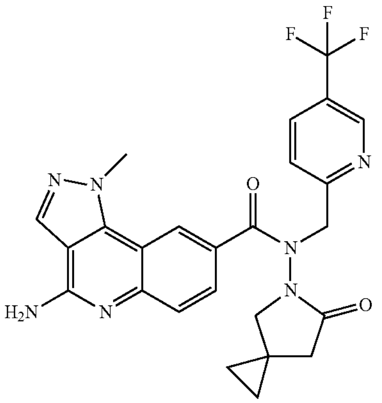

Example 170: 4-amino-1-methyl-N-(6-oxo-5-azaspiro[2.4]heptan-5-yl)-N-((5-(trifluoromethyl)pyridin-2-yl)methyl)-1H-pyrazolo[4,3-c]quinoline-8-carboxamide. Prepared following general procedure E-1 starting with intermediates Da-1 and BI-1. ES/MS: m/z=510.0 $[M+H]^+$. $^1H$ NMR (400 MHz, DMSO-$d_6$) δ 8.97 (s, 1H), 8.64 (s, 1H), 8.45 (s, 1H), 8.27 (d, J=8.8 Hz, 1H), 7.87 (dt, J=15.9, 8.3 Hz, 3H), 5.22 (d, J=16.0 Hz, 2H), 4.96 (d, J=16.0 Hz, 2H), 4.43 (s, 3H), 2.35 (d, J=12.5 Hz, 1H), 1.92 (s, 1H), 0.47 (s, 4H).

Example 171

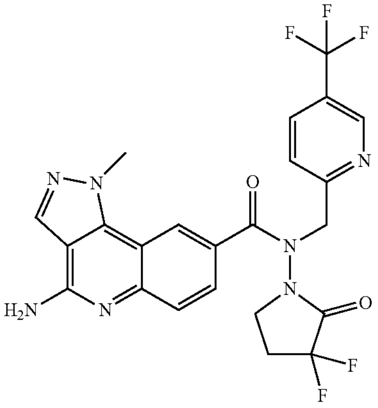

Example 171: 4-amino-N-(3,3-difluoro-2-oxo-pyrrolidin-1-yl)-1-methyl-N-[[5-(trifluoromethyl)-2-pyridyl]methyl]pyrazolo[4,3-c]quinoline-8-carboxamide. Prepared following general procedure E-1 starting with intermediates Da-1 and BI-3. ES/MS: m/z=520.0 $[M+H]^+$. $^1H$ NMR (400 MHz, DMSO-$d_6$) δ 8.98 (d, J=2.2 Hz, 1H), 8.63 (s, 1H), 8.43 (s, 1H), 8.29 (dd, J=8.3, 2.4 Hz, 1H), 7.96-7.82 (m, 3H), 5.17 (d, J=4.9 Hz, 2H), 4.42 (s, 3H), 3.84 (s, 2H), 3.45 (s, 2H).

Example 172

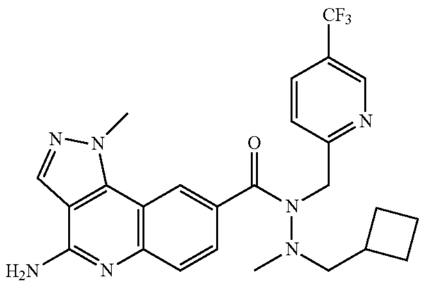

Example 172: 4-amino-N'-(cyclobutylmethyl)-N',1-dimethyl-N-[[5-(trifluoromethyl)-2-pyridyl]methyl]pyrazolo[4,3-c]quinoline-8-carbohydrazide. Prepared following general procedure E-1 starting with intermediates Da-1 and Bm-1. ES/MS: m/z=498.0 $[M+H]^+$. $^1H$ NMR (400 MHz, DMSO-$d_6$) δ 13.49 (s, 1H), 9.66 (s, 1H), 8.98 (s, 1H), 8.79 (s, 1H), 8.67 (s, 2H), 8.22 (dd, J=8.4, 2.4 Hz, 1H), 8.05 (dd, J=8.6, 1.8 Hz, 1H), 7.81 (dd, J=17.9, 8.5 Hz, 2H), 4.98 (d, J=16.4 Hz, 1H), 4.85 (d, J=16.4 Hz, 1H), 4.53 (s, 3H), 2.88 (dd, J=12.4, 7.0 Hz, 1H), 2.74 (s, 3H), 2.72-2.65 (m, 1H), 2.14 (p, J=7.7 Hz, 1H), 1.83-1.73 (m, 1H), 1.70-1.59 (m, 2H), 1.54-1.44 (m, 1H), 1.32 (ddq, J=27.4, 18.0, 8.7 Hz, 2H).

Example 173

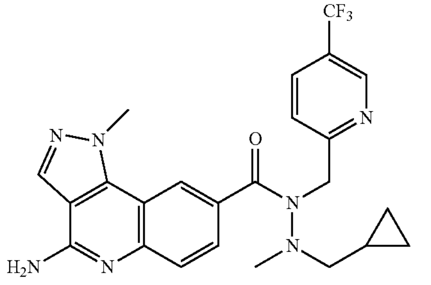

Example 173: 4-amino-N'-(cyclopropylmethyl)-N',1-dimethyl-N-[[5-(trifluoromethyl)-2-pyridyl]methyl]pyrazolo[4,3-c]quinoline-8-carbohydrazide. Prepared following general procedure E-1 starting with intermediates Da-1 and Bm-2. ES/MS: m/z=483.9 $[M+H]^+$. $^1H$ NMR (400 MHz, DMSO-$d_6$) δ 13.39 (s, 1H), 9.65 (s, 1H), 8.99 (s, 1H), 8.67 (s, 2H), 8.23 (dd, J=8.4, 2.4 Hz, 1H), 8.07 (dd, J=8.6, 1.8 Hz, 1H), 7.81 (dd, J=13.1, 8.5 Hz, 2H), 5.02 (d, J=16.5 Hz, 1H), 4.78 (d, J=16.4 Hz, 1H), 4.52 (s, 3H), 2.74 (s, 3H), 2.73-2.65 (m, 1H), 2.63-2.55 (m, 1H), 0.50-0.43 (m, 1H), 0.42-0.34 (m, 1H), 0.31-0.20 (m, 1H), 0.09--0.01 (m, 1H), −0.04--0.16 (m, 1H).

Example 174

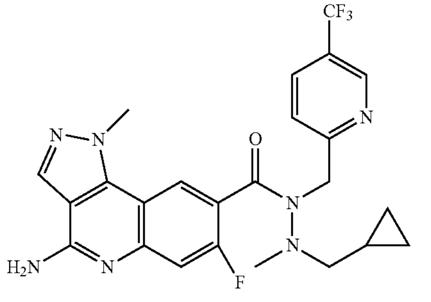

Example 174: 4-amino-N'-(cyclopropylmethyl)-7-fluoro-N',1-dimethyl-N-[[5-(trifluoromethyl)-2-pyridyl]methyl]pyrazolo[4,3-c]quinoline-8-carbohydrazide. Prepared following general procedure E-1 starting with intermediates Db-1 and Bm-2. ES/MS: m/z=501.9 $[M+H]^+$. $^1H$ NMR (400 MHz, DMSO-$d_6$) δ 13.51 (s, 1H), 9.69 (s, 1H), 9.01 (d, J=2.3 Hz, 1H), 8.90 (s, 1H), 8.65 (s, 1H), 8.41 (d, J=6.6 Hz, 1H), 8.30 (dd, J=8.3, 2.4 Hz, 1H), 7.70 (dd, J=33.0, 9.4 Hz, 2H), 5.02 (d, J=16.6 Hz, 1H), 4.87 (d, J=16.7 Hz, 1H), 4.47 (s, 3H), 2.75-2.65 (m, 1H), 2.61 (s, 3H), 2.51-2.46 (m, 1H), 0.58-0.47 (m, 1H), 0.34 (qd, J=10.1, 9.6, 6.0 Hz, 2H), 0.05 (d, J=4.9 Hz, 2H).

Example 175

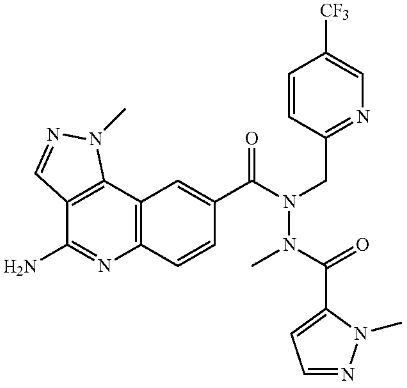

Example 175: 4-amino-N',1-dimethyl-N'-(1-methyl-1H-pyrazole-5-carbonyl)-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bd-23. ES/MS: m/z=538.5 $[M+H]^+$. $^1H$ NMR (400 MHz, DMSO) δ 9.67 (d, J=3.3 Hz, 0.1H), 8.95 (d, J=38.8 Hz, 1H), 8.62 (s, 1H), 8.50-8.14 (m, 1H), 8.05-7.66 (m, 2H), 7.67-7.28 (m, 1H), 6.60 (s, 1H), 6.23 (s, 0.2H), 5.25 (s, 0.4H), 5.06 (d, J=16.1 Hz, 1H), 4.42 (d, J=11.0 Hz, 3H), 3.65 (s, 1H), 3.42 (s, 1H), 3.25 (s, 1H).

Example 176: N'-acetyl-4-amino-N-(2-fluoro-4-(3-methyl-3-(methylsulfonyl)but-1-yn-1-yl)benzyl)-N',1-dimethyl-1H-pyrazolo[4,3-c]quinoline-8-carbohydrazide

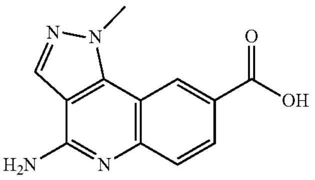

Da-1

+

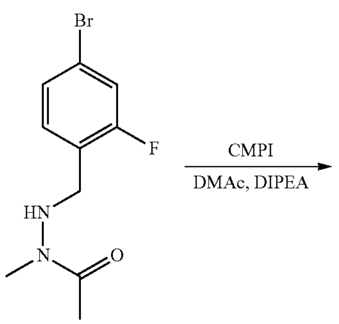

Bb-15

-continued

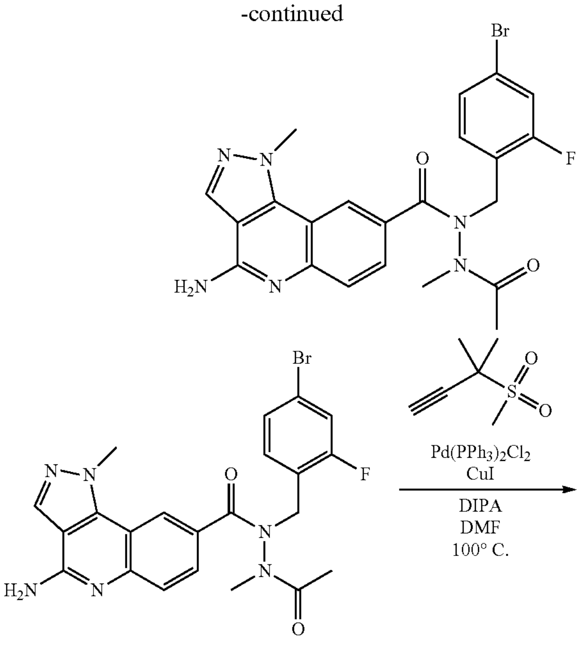

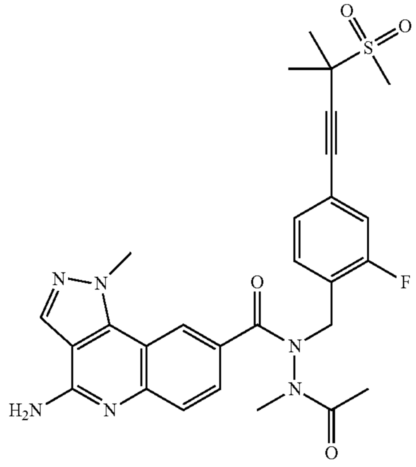

Example 176

Step 1. N'-acetyl-4-amino-N-(4-bromo-2-fluorobenzyl)-N',1-dimethyl-1H-pyrazolo[4,3-c]quinoline-8-carbohydrazide was prepared following general procedure E-1 starting with intermediates Da-1 and Bb-15. ES/MS: m/z=499.2 $[M+H]^+$.

Step 2. To a solution of N'-acetyl-4-amino-N-(4-bromo-2-fluorobenzyl)-N',1-dimethyl-1H-pyrazolo[4,3-c]quinoline-8-carbohydrazide (35.0 mg, 0.07 mmol, 1 equiv) in DMF (0.5 M) was added $Pd(PPh_3)_2Cl_2$ (25.0 mg, 0.035 mmol, 0.5 equiv), CuI (6.7 mg, 0.035 mmol, 0.5 equiv), 3-methyl-3-methylsulfonyl-but-1-yne (51.2 mg, 0.35 mmol, 5 equiv) and diisopropylamine (0.20 mL, 1.4 mmol, 20 equiv). The reaction mixture was then degassed with argon for 5 min. The reaction mixture was then heated at 100 C for 1 h. LCMS analysis confirms full conversion to product. Reaction mixture was diluted with EtOAc, washed with water and 5% aq LiCl, dried over $MgSO_4$, filtered, and concentrated under reduced pressure to give a residue. The residue was purified by column chromatography (4 g Silica Flash Column, Eluent 0-10% MeOH/EtOAc @ 13 mL/min). Final purification by reverse phase HPLC. ES/MS: m/z=565.1 $[M+H]^+$. $^1H$ NMR (400 MHz, Methanol-d4) δ 8.51 (d, J=7.8 Hz, 2H), 7.99-7.71 (m, 2H), 7.63 (s, 1H), 7.40-7.24 (m, 2H), 5.12 (s, 1H), 4.54 (d, J=12.6 Hz, 3H), 3.16 (s, 2H), 3.14 (d, J=1.8 Hz, 3H), 3.11 (s, 1H), 1.83 (s, 2H), 1.74 (d, J=1.3 Hz, 6H), 1.31 (s, 1H).

Example 177

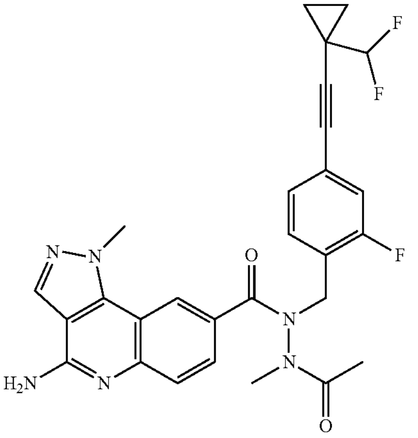

Example 177: N'-acetyl-4-amino-N-(4-((1-(difluoromethyl)cyclopropyl)ethynyl)-2-fluorobenzyl)-N',1-dimethyl-1H-pyrazolo[4,3-c]quinoline-8-carbohydrazide. Prepared in following the procedure described for example 176 starting with intermediates Da-1 and Bb-15 and 1-(difluoromethyl)-1-ethynylcyclopropane. ES/MS: m/z=535.2 $[M+H]^+$. $^1H$ NMR (400 MHz, Methanol-$d_4$) δ 8.58-8.46 (m, 2H), 7.98-7.79 (m, 2H), 7.56 (s, 1H), 7.32-7.24 (m, 1H), 7.20 (d, J=11.3 Hz, 1H), 5.69 (t, J=56.5 Hz, 1H), 4.54 (d, J=12.6 Hz, 3H), 3.12 (d, J=10.7 Hz, 3H), 2.68 (s, 1H), 1.82 (s, 3H), 1.31 (s, 1H), 1.26-1.22 (m, 2H), 1.19 (q, J=2.4 Hz, 2H).

Example 178

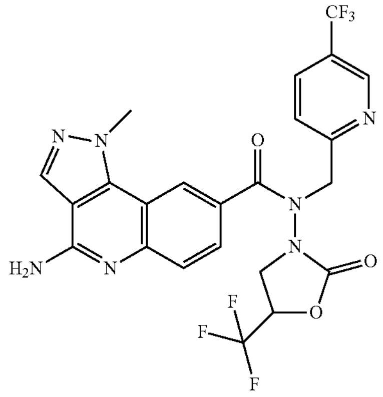

Example 178: 4-amino-1-methyl-N-(2-oxo-5-(trifluoromethyl)oxazolidin-3-yl)-N-((5-(trifluoromethyl)pyridin-2-yl)methyl)-1H-pyrazolo[4,3-c]quinoline-8-carboxamide. Prepared in following general procedure E-1 starting with intermediates Da-1 and Ba-67. ES/MS: m/z=554.2 $[M+H]^+$. $^1H$ NMR (400 MHz, DMSO-$d_6$) δ 9.00 (s, 1H), 8.62 (s, 1H), 8.45 (s, 1H), 8.29 (d, J=8.4 Hz, 1H), 7.87 (d, J=19.1 Hz, 3H), 6.53 (brs, 4H), 5.19 (d, J=33.0 Hz, 1H), 4.39 (s, 3H).

Example 179

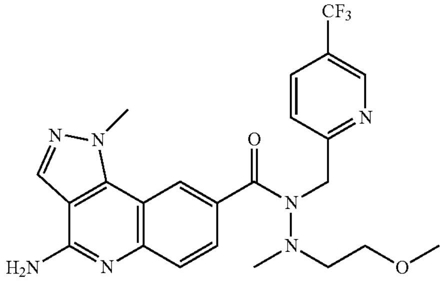

Example 179: 4-amino-N'-(2-methoxyethyl)-N',1-dimethyl-N-((5-(trifluoromethyl)pyridin-2-yl)methyl)-1H-pyrazolo[4,3-c]quinoline-8-carbohydrazide. Prepared following general procedure E-1 starting with intermediates Da-1 and Ba-68. ES/MS: m/z=488.2 $[M+H]^+$. $^1$H NMR (400 MHz, DMSO) δ 13.28 (s, 1H), 8.95 (d, J=2.4 Hz, 1H), 8.71 (s, 1H), 8.63 (s, 1H), 8.20 (d, J=9.0 Hz, 1H), 8.04 (d, J=8.4 Hz, 1H), 7.77 (dd, J=16.7, 8.6 Hz, 2H), 6.53 (s, 2H), 5.10-4.77 (m, 2H), 4.49 (s, 3H), 3.17 (d, J=5.5 Hz, 2H), 3.13-3.04 (m, 1H), 2.95 (s, 3H), 2.79 (d, J=13.5 Hz, 1H), 2.71 (s, 3H).

Example 180

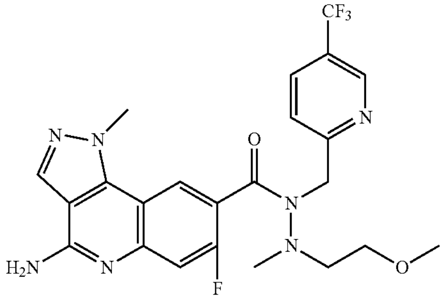

Example 180: 4-amino-7-fluoro-N'-(2-methoxyethyl)-N',1-dimethyl-N-((5-(trifluoromethyl)pyridin-2-yl)methyl)-1H-pyrazolo[4,3-c]quinoline-8-carbohydrazide. Prepared following general procedure E-1 starting with intermediates Db-1 and Ba-68. ES/MS: m/z=506.3 $[M+H]^+$. $^1$H NMR (400 MHz, DMSO) δ 9.05-8.88 (m, 1H), 8.62 (s, 1H), 8.39 (d, J=6.5 Hz, 1H), 8.27 (dd, J=8.3, 2.4 Hz, 1H), 7.72 (d, J=8.3 Hz, 1H), 7.61 (d, J=10.4 Hz, 1H), 5.08-4.84 (m, 2H), 4.46 (s, 3H), 3.22-3.12 (m, 2H), 3.05 (dt, J=11.7, 5.6 Hz, 1H), 2.97 (s, 3H), 2.74 (dt, J=13.0, 5.5 Hz, 1H), 2.57 (s, 3H).

Example 181

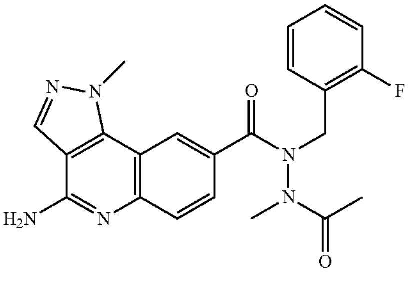

Example 181: N'-acetyl-4-amino-N-(2-fluorobenzyl)-N',1-dimethyl-1H-pyrazolo[4,3-c]quinoline-8-carbohydrazide. Prepared following general procedure E-1 starting with intermediates Da-1 and Ba-69. ES/MS: m/z=421.2 $[M+H]^+$. $^1$H NMR (400 MHZ, MeOD) δ 8.70-8.44 (m, 2H), 8.06-7.77 (m, 2H), 7.77-7.35 (m, 1H), 7.35-7.06 (m, 2H), 5.23 (s, 1H), 4.97 (d, J=15.7 Hz, 1H), 4.75 (d, J=14.5 Hz, 1H), 4.54 (d, J=13.8 Hz, 3H), 3.09 (d, J=11.5 Hz, 3H), 1.80 (d, J=20.2 Hz, 3H).

Example 182

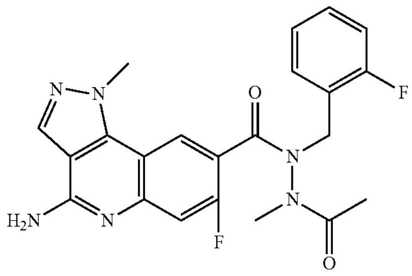

Example 182: N'-acetyl-4-amino-7-fluoro-N-(2-fluorobenzyl)-N',1-dimethyl-1H-pyrazolo[4,3-c]quinoline-8-carbohydrazide. Prepared following general procedure E-1 starting with intermediates Db-2 and Ba-69. ES/MS: m/z=439.2 $[M+H]^+$. $^1$H NMR (400 MHZ, MeOD) δ 8.70-8.20 (m, 3H), 7.60 (p, J=8.2, 7.4 Hz, 2H), 7.53-6.91 (m, 4H), 5.30 (d, J=14.6 Hz, 1H), 4.74 (d, J=14.4 Hz, 1H), 4.47 (s, 3H), 3.05 (s, 3H), 1.80 (s, 3H).

Example 183

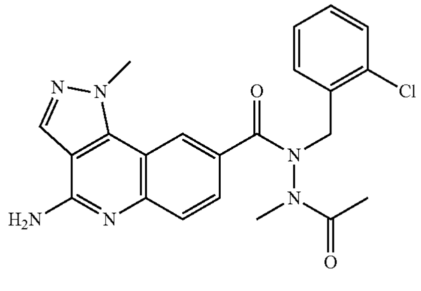

Example 183: N'-acetyl-4-amino-N-(2-chlorobenzyl)-N',1-dimethyl-1H-pyrazolo[4,3-c]quinoline-8-carbohydrazide. Prepared following general procedure E-1 starting with intermediates Da-1 and Bb-16. ES/MS: m/z=437.1 $[M+H]^+$. $^1$H NMR (400 MHZ, DMSO) δ 13.33 (s, 1H), 8.63 (s, 1H), 8.40 (d, J=36.8 Hz, 1H), 8.04-7.75 (m, 2H), 7.75-7.23 (m, 5H), 6.53 (s, 1H), 5.36-4.91 (m, 2H), 4.47 (d, J=12.2 Hz, 3H), 2.94 (d, J=28.0 Hz, 2H), 1.73 (d, J=33.0 Hz, 3H).

Example 184

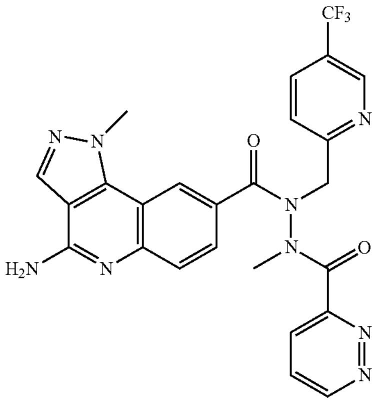

Example 184: 14-amino-N',1-dimethyl-N'-(pyridazine-3-carbonyl)-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bd-24. ES/MS: m/z=538.1 $[M+H]^+$. $^1$H NMR (400 MHz, MeOD) δ 8.97-8.76 (m, 2H), 8.47 (s, 1H), 8.32-7.75 (m, 5H), 7.62 (d, J=8.8 Hz, 1H), 4.47 (s, 3H), 4.23-4.05 (m, 2H), 3.46 (s, 3H), 2.67 (d, J=6.0 Hz, 3H).

Example 185

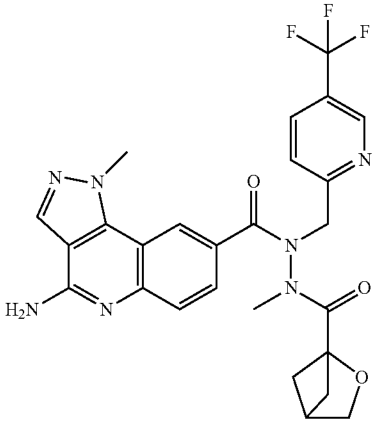

Example 185: 4-amino-N',1-dimethyl-N'-(2-oxabicyclo[2.1.1]hexane-1-carbonyl)-N-[[5-(trifluoromethyl)-2-pyridyl]methyl]pyrazolo[4,3-c]quinoline-8-carbohydrazide. Prepared following general procedure E-1 starting with intermediates Da-1 and Bc-9. ES/MS: m/z=540.0 $[M+H]^+$. $^1$H NMR (400 MHz, MeOD) δ 9.04 (s, 0.1H, minor rotamer), 8.92 (d, J=14.2 Hz, 1H), 8.77 (d, J=7.7 Hz, 0.2H, minor rotamer), 8.50 (s, 2H), 8.21-8.14 (m, 1H), 8.06 (dt, J=17.1, 8.8 Hz, 0.3H, minor rotamer), 7.99-7.70 (m, 3H), 7.48 (d, J=8.2 Hz, 0.1H, minor rotamer), 5.43 (d, J=16.6 Hz, 0.1H, minor rotamer), 5.29 (d, J=15.5 Hz, 1H), 5.12 (d, J=16.7 Hz, 0.1H, minor rotamer), 4.94 (d, J=15.6 Hz, 1H), 4.53 (d, J=6.4 Hz, 3H), 3.78-3.53 (m, 2H), 3.39 (s, 3H), 3.20 (s, 0.2H, minor rotamer), 3.07 (s, 0.3H, minor rotamer), 2.80 (s, 1H), 2.39-1.26 (m, 4H).

Example 186

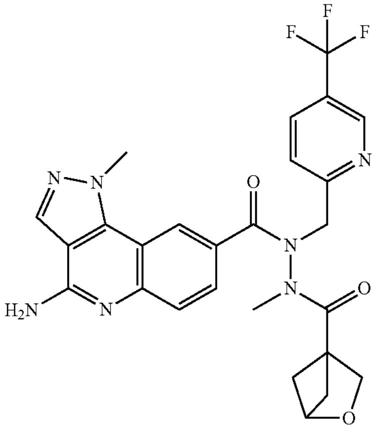

Example 186: 4-amino-N',1-dimethyl-N'-(2-oxabicyclo[2.1.1]hexane-4-carbonyl)-N-[[5-(trifluoromethyl)-2-pyridyl]methyl]pyrazolo[4,3-c]quinoline-8-carbohydrazide. Prepared following general procedure E-1 starting with intermediates Da-1 and Bc-10. ES/MS: m/z=540.0 $[M+H]^+$. $^1$H NMR (400 MHz, MeOD) δ 9.05 (s, 0.1H, minor rotamer), 8.91 (s, 1H), 8.73 (s, 0.1H, minor rotamer), 8.63-8.41 (m, 2H), 8.26-8.14 (m, 1H), 8.01-7.71 (m, 3H), 5.43 (d, J=16.9 Hz, 0.1H, minor rotamer), 5.23 (d, J=15.3 Hz, 1H), 5.09-4.93 (m, 1H), 4.60-4.44 (m, 4H), 4.31 (s, 1H), 3.21 (s, 1H), 1.92-1.45 (m, 4H), one signal (s, 3H) overlaps with MeOH solvent peak.

Example 187

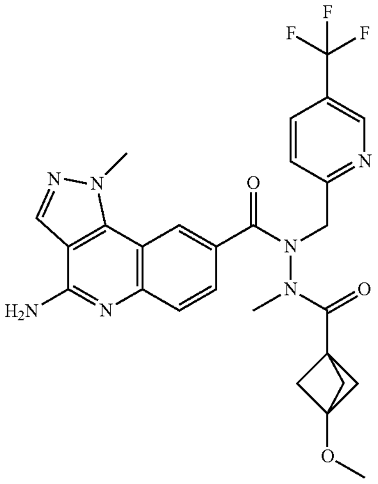

Example 187: 4-amino-N'-(3-methoxybicyclo[1.1.1]pentane-1-carbonyl)-N',1-dimethyl-N-[[5-(trifluoromethyl)-2-pyridyl]methyl]pyrazolo[4,3-c]quinoline-8-carbohydrazide. Prepared following general procedure E-1 starting with intermediates Da-1 and Bc-11. ES/MS: m/z=554.0 $[M+H]^+$. $^1$H NMR (400 MHz, MeOD) δ 9.10 (s, 0.1H, minor rotamer), 8.90 (s, 1H), 8.65 (s, 0.1H, minor rotamer), 8.50 (s, 2H), 8.29-8.02 (m, 1H), 7.99-7.72 (m, 3H), 7.58 (d, J=8.2 Hz, 0.1H, minor rotamer), 5.41 (d, J=16.4 Hz, 0.1H, minor rotamer), 5.24 (d, J=15.3 Hz, 1H), 5.03-4.93 (m, 1H), 4.53 (s, 3H), 3.35 (s, 3H), 3.18 (s, 3H), 2.32-2.14 (m, 2H), 2.10-1.73 (m, 4H).

Example 188

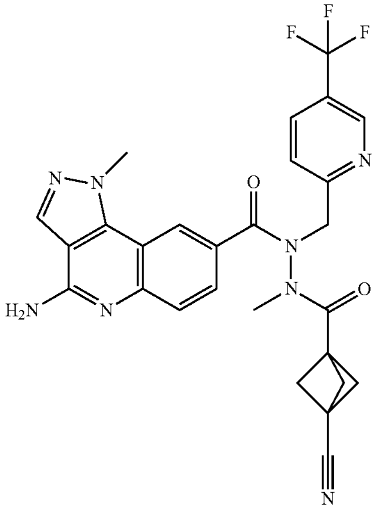

Example 188: 4-amino-N'-(3-cyanobicyclo[1.1.1]pentane-1-carbonyl)-N',1-dimethyl-N-[[5-(trifluoromethyl)-2-pyridyl]methyl]pyrazolo[4,3-c]quinoline-8-carbohydrazide. Prepared following general procedure E-1 starting with intermediates Da-1 and Bc-13. ES/MS: m/z=549.0 $[M+H]^+$. $^1$H NMR (400 MHz, MeOD) δ 9.14-8.83 (m, 1H), 8.72-8.40 (m, 2H), 8.28 (dd, J=8.7, 1.8 Hz, 0.2H, minor rotamer), 8.17 (d, J=8.1 Hz, 1H), 8.06 (d, J=8.8 Hz, 0.1H, minor rotamer), 7.96-7.73 (m, 3H), 7.59 (d, J=8.2 Hz, 0.2H, minor rotamer), 5.41 (d, J=16.4 Hz, 0.2H, minor rotamer), 5.22 (d, J=15.5 Hz, 1H), 5.03 (d, J=16.4 Hz, 0.2H, minor rotamer), 4.91 (d, J=15.1 Hz, 1H), 4.59-4.46 (m, 3H), 3.37 (s, 3H), 3.06 (s, 0.3H, minor rotamer), 2.64-2.52 (m, 2H), 2.47-2.17 (m, 4H).

Example 189

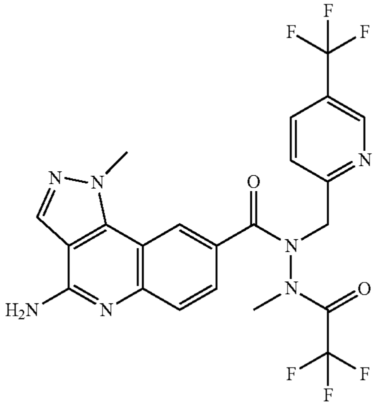

Example 189: 4-amino-N'-(2,2-difluoropropanoyl)-N',1-dimethyl-N-[[5-(trifluoromethyl)-2-pyridyl]methyl]pyrazolo[4,3-c]quinoline-8-carbohydrazide. Prepared following general procedure E-1 starting with intermediates Da-1 and Bd-25. ES/MS: m/z=522.0 $[M+H]^+$. $^1$H NMR (400 MHz, MeOD) δ 9.05-8.82 (m, 1H), 8.63-8.39 (m, 2H), 8.18 (d, J=8.2 Hz, 1H), 8.07-7.64 (m, 3H), 7.35 (s, 0.2H, minor rotamer), 5.48 (d, J=17.7 Hz, 0.2H, minor rotamer), 5.28 (d, J=15.5 Hz, 1H), 5.00 (d, J=17.3 Hz, 1H), 4.52 (s, 3H), 3.48 (s, 3H), 3.23 (s, 0.6H, minor rotamer), 2.03-1.31 (m, 3H).

Example 190

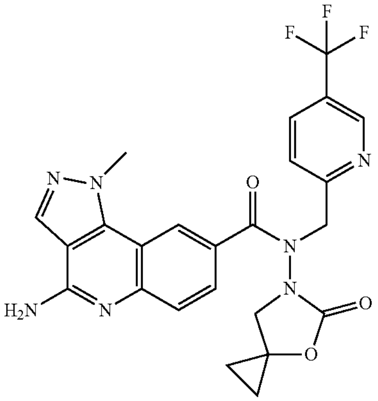

Example 190: 4-amino-1-methyl-N-(5-oxo-4-oxa-6-azaspiro[2.4]heptan-6-yl)-N-[[5-(trifluoromethyl)-2-pyridyl]methyl]pyrazolo[4,3-c]quinoline-8-carboxamide. Prepared following general procedure E-1 starting with intermediates Da-1 and Ba-70. ES/MS: m/z=512.0 $[M+H]^+$. $^1$H NMR (400 MHz, MeOD) δ 8.94 (s, 1H), 8.69 (s, 1H), 8.50 (s, 1H), 8.19 (dd, J=8.3, 2.4 Hz, 1H), 8.02 (dd, J=8.4, 1.7 Hz, 1H), 7.85 (dd, J=8.4, 3.7 Hz, 2H), 5.30 (d, J=16.1 Hz, 1H), 5.12 (d, J=15.8 Hz, 1H), 4.48 (s, 3H), 4.20-3.56 (m, 2H), 1.09 (s, 1H), 0.92 (s, 1H), 0.76 (s, 1H), 0.60 (s, 1H).

Example 191

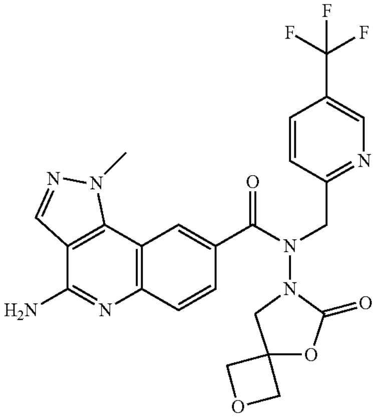

Example 191: 4-amino-1-methyl-N-(6-oxo-2,5-dioxa-7-azaspiro[3.4]octan-7-yl)-N-[[5-(trifluoromethyl)-2-pyridyl]methyl]pyrazolo[4,3-c]quinoline-8-carboxamide. Prepared following general procedure E-1 starting with intermediates Da-1 and Ba-71. ES/MS: m/z=528.0 $[M+H]^+$. $^1$H NMR (400 MHz, MeOD) δ 8.96 (s, 1H), 8.63 (s, 1H), 8.50 (s, 1H), 8.18 (dd, J=8.2, 2.4 Hz, 1H), 7.97 (s, 1H), 7.86-7.77 (m, 2H), 5.24 (d, J=16.0 Hz, 1H), 5.10 (s, 1H), 4.80 (s, 1H), 4.68 (d, J=7.8 Hz, 1H), 4.62-4.33 (m, 4H), 4.18 (s, 1H), 4.00 (s, 1H), one signal (1H) overlaps MeOH solvent peak.

Example 192

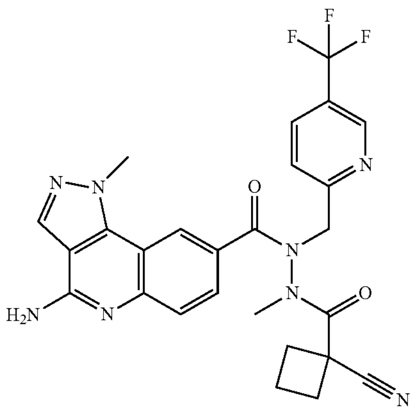

Example 192: 4-amino-N'-(1-cyanocyclobutanecarbonyl)-N',1-dimethyl-N-[[5-(trifluoromethyl)-2-pyridyl] methyl]pyrazolo[4,3-c]quinoline-8-carbohydrazide. Prepared following general procedure E-1 starting with intermediates Da-1 and Bc-12. ES/MS: m/z=537.0 $[M+H]^+$. $^1$H NMR (400 MHz, MeOD) δ 8.92 (s, 1H), 8.73 (s, 0.3H, minor rotamer), 8.49 (s, 2H), 8.19 (d, J=8.2 Hz, 1H), 8.07 (d, J=8.6 Hz, 0.3H, minor rotamer), 7.97-7.69 (m, 3H), 7.35 (d, J=8.2 Hz, 0.3H, minor rotamer), 5.80-5.68 (m, 0.3H, minor rotamer), 5.22 (d, J=15.2 Hz, 1H), 5.10 (d, J=16.5 Hz, 1H), 4.62 (s, 1H, minor rotamer), 4.54 (s, 3H), 3.34 (s, 3H), 3.20 (s, 1H, minor rotamer), 2.67-2.50 (m, 2H), 2.46-2.34 (m, 1H), 2.31-2.19 (m, 1H), 2.13-2.03 (m, 1H), 1.85-1.65 (m, 1H).

Example 193

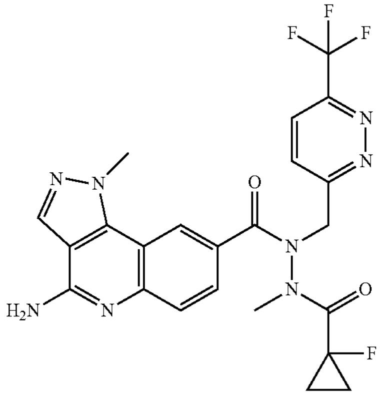

Example 193: 4-amino-N'-(1-fluorocyclopropanecarbonyl)-N',1-dimethyl-N-[[6-(trifluoromethyl)pyridazin-3-yl] methyl]pyrazolo[4,3-c]quinoline-8-carbohydrazide. Prepared following general procedure E-1 starting with intermediates Da-1 and Bd-26. ES/MS: m/z=517.2 $[M+H]^+$. $^1$H NMR (400 MHz, MeOD) δ 8.85 (s, 0.2H, minor rotamer), 8.69-8.45 (m, 2H), 8.40-8.07 (m, 2H), 8.05-7.89 (m, 1H), 7.82 (d, J=8.8 Hz, 1H), 5.68-5.15 (m, 2H), 4.54 (s, 3H), 3.81-3.36 (m, 3H), 1.61-0.64 (m, 4H).

Example 194

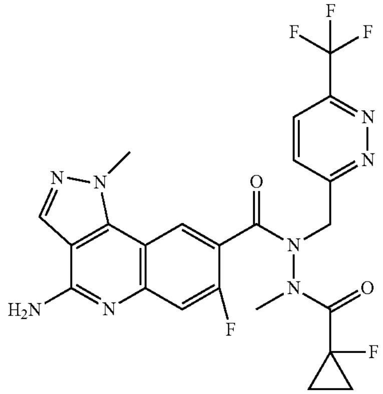

Example 194: 4-amino-7-fluoro-N'-(1-fluorocyclopropanecarbonyl)-N', 1-dimethyl-N-[[6-(trifluoromethyl) pyridazin-3-yl]methyl]pyrazolo[4,3-c]quinoline-8-carbohydrazide. Prepared following general procedure E-1 starting with intermediates Db-1 and Bd-26. ES/MS: m/z=535.0 $[M+H]^+$. $^1$H NMR (400 MHz, MeOD) δ 8.79 (d, J=6.3 Hz, 0.2H, minor rotamer), 8.49 (s, 1H), 8.42 (s, 1H), 8.30-8.13 (m, 2H), 8.10 (d, J=8.6 Hz, 0.2H, minor rotamer), 7.90 (d, J=8.7 Hz, 0.2H, minor rotamer), 7.62 (d, J=10.2 Hz, 1H), 5.55-5.38 (m, 1H), 5.31 (d, J=17.2 Hz, 1H), 4.55 (s, 1H, minor rotamer), 4.47 (s, 2H, major rotamer), 3.55 (s, 2H, major rotamer), 3.20 (s, 1H, minor rotamer), 1.51-0.69 (m, 4H).

Example 195

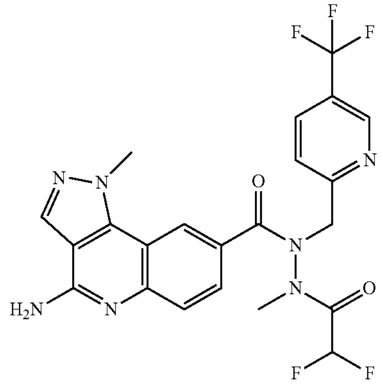

Example 195: 4-amino-N'-(2,2-difluoroacetyl)-N',1-dimethyl-N-[[5-(trifluoromethyl)-2-pyridyl]methyl]pyrazolo[4,3-c]quinoline-8-carbohydrazide. Prepared following general procedure E-1 starting with intermediates Da-1 and Bd-27. ES/MS: m/z=508.2 $[M+H]^+$. $^1$H NMR (400 MHz, MeOD) Rotamer A: δ 9.04 (s, 1H), 8.74 (s, 1H), 8.50 (s, 2H), 8.18 (dd, J=8.1, 2.3 Hz, 1H), 7.84 (dd, J=8.6, 6.1 Hz, 2H), 6.98-6.57 (m, 1H), 5.30 (d, J=15.7 Hz, 1H), 5.16 (d, J=16.8 Hz, 1H), 4.52 (s, 3H), 3.27 (s, 3H). Rotamer B: 8.93 (s, 1H), 8.53 (d, J=11.2 Hz, 1H), 8.11 (t, J=7.5 Hz, 2H), 8.00-7.88 (m, 2H), 7.55 (s, 1H), 6.53-6.09 (m, 1H), 5.28 (d, J=16.9 Hz, 1H), 4.95 (d, J=15.7 Hz, 1H), 4.54 (s, 3H), 3.39 (s, 3H).

Example 196

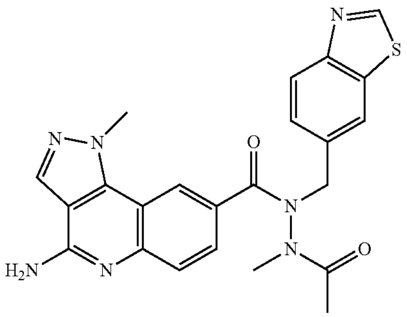

Example 196: N'-acetyl-4-amino-N-(1,3-benzothiazol-6-ylmethyl)-N',1-dimethyl-pyrazolo[4,3-c]quinoline-8-carbohydrazide. Prepared following general procedure E-1 starting with intermediates Da-1 and Bb-17. ES/MS: m/z=460.0 $[M+H]^+$. $^1$H NMR (400 MHz, MeOD) δ 9.41-9.21 (m, 1H), 8.59-8.45 (m, 2H), 8.26 (s, 1H), 8.19-8.07 (m, 1H), 8.05-7.58 (m, 3H), 5.52-5.03 (m, 1H), 4.81 (d, J=14.7 Hz, 1H), 4.52 (s, 3H), 3.21-2.99 (m, 3H), 2.01-1.59 (m, 3H).

Example 197

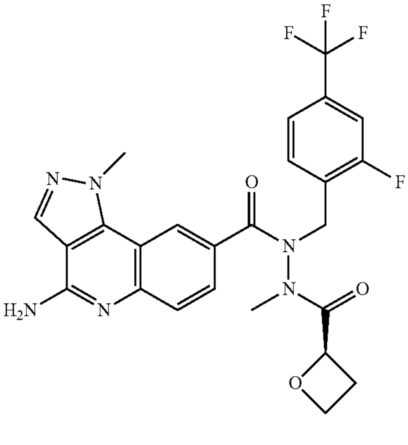

Example 197: 4-amino-N-[[2-fluoro-4-(trifluoromethyl)phenyl]methyl]-N',1-dimethyl-N'-[(2R)-oxetane-2-carbonyl]pyrazolo[4,3-c]quinoline-8-carbohydrazide. Prepared following general procedure E-1 starting with intermediates Da-1 and Bc-14. ES/MS: m/z=531.0 $[M+H]^+$. $^1$H NMR (400 MHz, MeOD) δ 8.63-8.44 (m, 1H), 8.34 (d, J=5.5 Hz, 1H), 7.97-7.86 (m, 1H), 7.85-7.67 (m, 2H), 7.65-7.48 (m, 2H), 5.34-4.93 (m, 3H), 4.74-4.31 (m, 4H), 4.25-3.99 (m, 1H), 3.05 (d, J=11.6 Hz, 3H), 2.92-2.45 (m, 2H).

Example 198

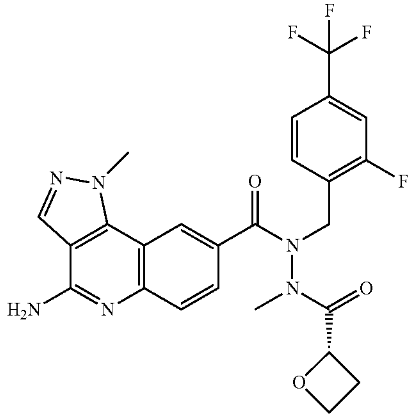

Example 198: 4-amino-N-[[2-fluoro-4-(trifluoromethyl)phenyl]methyl]-N',1-dimethyl-N'-[(2S)-oxetane-2-carbonyl]pyrazolo[4,3-c]quinoline-8-carbohydrazide. Prepared following general procedure E-1 starting with intermediates Da-1 and Bc-15. ES/MS: m/z=531.0 $[M+H]^+$. $^1$H NMR (400 MHz, MeOD) δ 8.63-8.43 (m, 1H), 8.34 (d, J=5.5 Hz, 1H), 7.98-7.86 (m, 1H), 7.85-7.67 (m, 2H), 7.65-7.48 (m, 2H), 5.34-4.93 (m, 3H), 4.74-4.31 (m, 4H), 4.25-3.99 (m, 1H), 3.05 (d, J=11.6 Hz, 3H), 2.93-2.45 (m, 2H).

Example 199

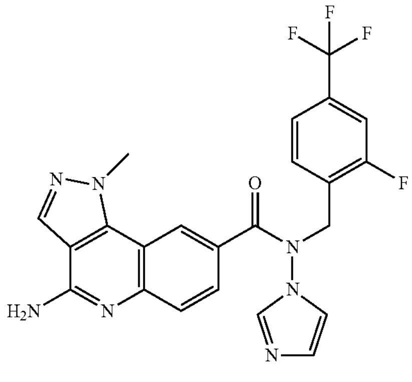

Example 199: 4-amino-N-[[2-fluoro-4-(trifluoromethyl)phenyl]methyl]-N-imidazol-1-yl-1-methyl-pyrazolo[4,3-c]quinoline-8-carboxamide. Prepared following general procedure E-1 starting with intermediates Da-1 and Bn-1. ES/MS: m/z=484.0 $[M+H]^+$. $^1$H NMR (400 MHz, MeOD) δ 8.50-8.44 (m, 2H), 7.98 (s, 1H), 7.88 (dd, J=8.7, 1.8 Hz, 1H), 7.78-7.66 (m, 2H), 7.55 (t, J=9.0 Hz, 2H), 7.44 (d, J=1.5 Hz, 1H), 6.97 (s, 1H), 5.38 (s, 2H), 4.49 (s, 3H).

Example 200

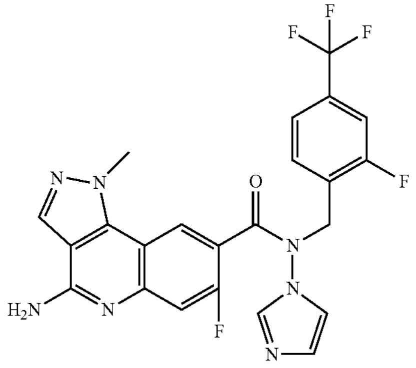

Example 200: 4-amino-7-fluoro-N-[[2-fluoro-4-(trifluoromethyl)phenyl]methyl]-N-imidazol-1-yl-1-methyl-pyrazolo[4,3-c]quinoline-8-carboxamide. Prepared following general procedure E-1 starting with intermediates Db-1 and Bn-1. ES/MS: m/z=501.0 $[M+H]^+$. $^1H$ NMR (400 MHz, MeOD) δ 8.53 (d, J=6.5 Hz, 1H), 8.47 (s, 1H), 8.02 (s, 1H), 7.65 (t, J=7.6 Hz, 1H), 7.59-7.47 (m, 3H), 7.37 (s, 1H), 6.93 (s, 1H), 5.39 (s, 2H), 4.51 (s, 3H).

Example 201

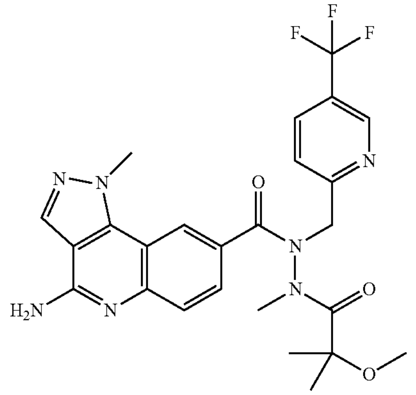

Example 201: 4-amino-N'-(2-methoxy-2-methyl-propanoyl)-N',1-dimethyl-N-[[5-(trifluoromethyl)-2-pyridyl]methyl]pyrazolo[4,3-c]quinoline-8-carbohydrazide. Prepared following general procedure E-1 starting with intermediates Da-1 and Bc-16. ES/MS: m/z=530.2 $[M+H]^+$. $^1H$ NMR (400 MHz, MeOD) δ 8.89 (s, 1H), 8.59-8.44 (m, 2H), 8.18 (d, J=8.3 Hz, 1H), 7.92 (s, 2H), 7.81 (d, J=8.6 Hz, 1H), 5.29 (d, J=15.3 Hz, 1H), 4.95-4.87 (m, 1H), 4.56 (s, 3H), 3.63 (s, 2.4H, major rotamer), 3.47 (s, 0.6H, minor rotamer), 2.79 (s, 3H), 1.54-1.35 (m, 1H, minor rotamer), 1.24 (s, 2.5H, major rotamer), 0.82 (s, 2.5H, major rotamer).

Example 202: 4-amino-N-(2-oxo-1-piperidyl)-N-[[5-(trifluoromethyl)-2-pyridyl]methyl]-1H-pyrazolo[4,3-c]quinoline-8-carboxamide

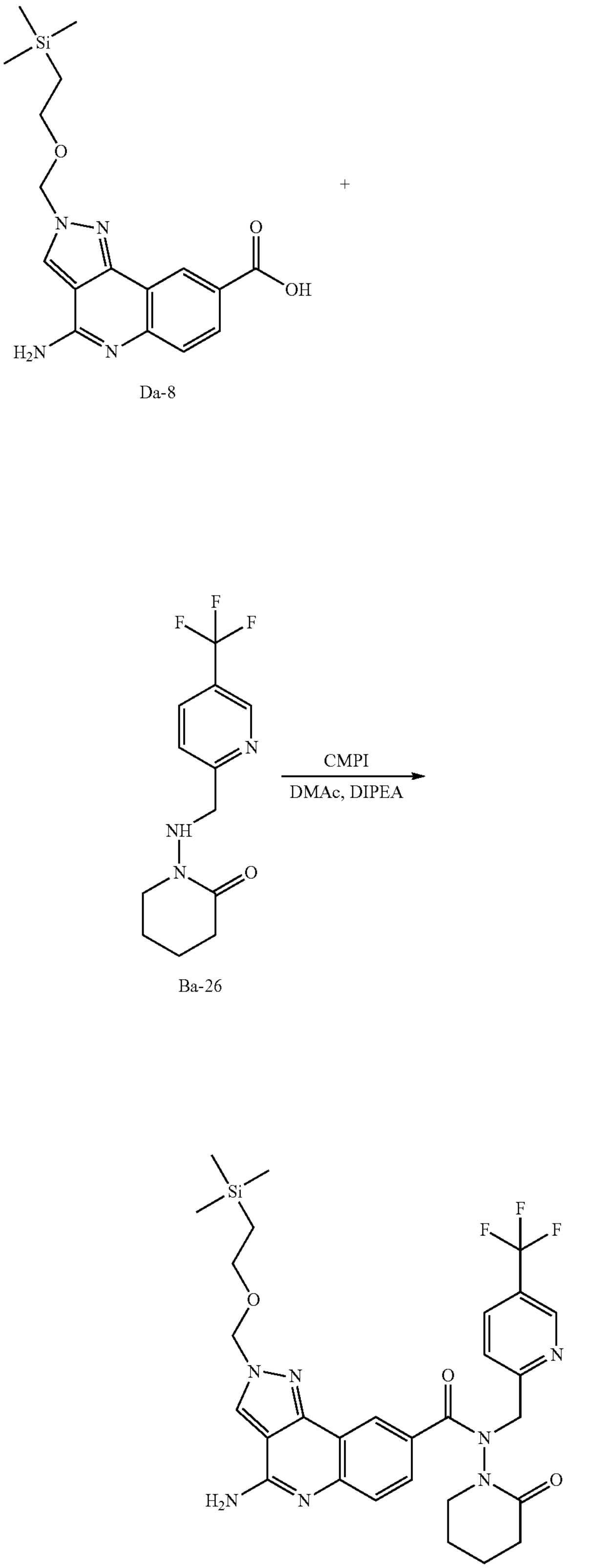

-continued

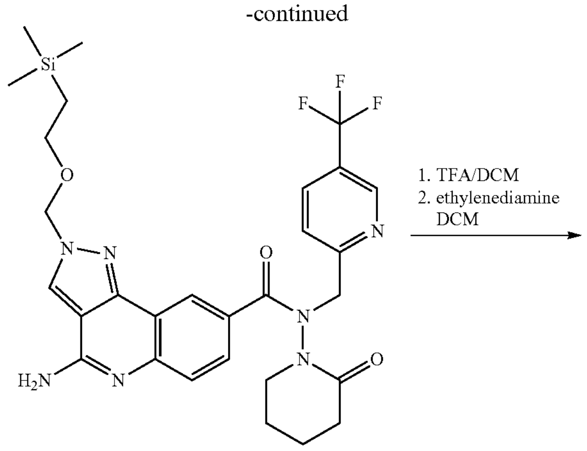

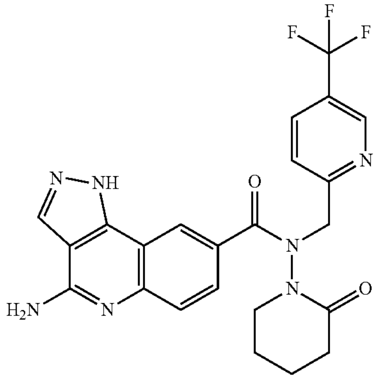

Example 202

Step 1: 4-amino-N-(2-oxo-1-piperidyl)-N-[[5-(trifluoromethyl)-2-pyridyl]methyl]-2-(2-trimethylsilylethoxymethyl)pyrazolo[4,3-c]quinoline-8-carboxamide. Prepared following general procedure E-1 starting with intermediates Da-8 and Ba-26. ES/MS: m/z=614.0 $[M+H]^+$.

Step 2: 4-amino-N-(2-oxo-1-piperidyl)-N-[[5-(trifluoromethyl)-2-pyridyl]methyl]-1H-pyrazolo[4,3-c]quinoline-8-carboxamide (Example 202). To a solution of 4-amino-N-(2-oxo-1-piperidyl)-N-[[5-(trifluoromethyl)-2-pyridyl]methyl]-2-(2-trimethylsilylethoxymethyl)pyrazolo[4,3-c]quinoline-8-carboxamide (24 mg, 0.039 mmol) in DCM (3 mL) was added TFA (0.053 mL, 0.70 mmol). The reaction was stirred overnight. Added more TFA (0.1 mL) and stirred at rt for 4 hr. The reaction was concentrated to dryness, taken up in MeOH and DCM and re-concentrated to dryness and used directly in the next step. To a solution of the crude residue from the previous step in DCM (5 mL), was added ethylenediamine (0.093 mL, 1.4 mmol). Stirred at rt for 2 hr, then concentrated to dryness. The crude reaction mixture was purified by preparative HPLC. ES/MS: m/z=484.0 $[M+H]^+$. $^1H$ NMR (400 MHz, DMSO-$d_6$) δ 14.88 (s, 1H), 13.32 (s, 1H), 9.71 (s, 1H), 8.97 (d, J=2.2 Hz, 1H), 8.67 (s, 1H), 8.41 (s, 1H), 8.26 (d, J=8.2 Hz, 1H), 7.86 (s, 1H), 7.77 (s, 3H), 5.32 (d, J=16.0 Hz, 1H), 4.72 (d, J=15.9 Hz, 1H), 3.68 (s, 2H), 2.25-2.09 (m, 1H), 2.04-1.62 (m, 1H), 1.58 (d, J=12.5 Hz, 1H), 1.50-1.29 (m, 3H), 1.24 (s, 0.3H, minor rotamer).

Example 203

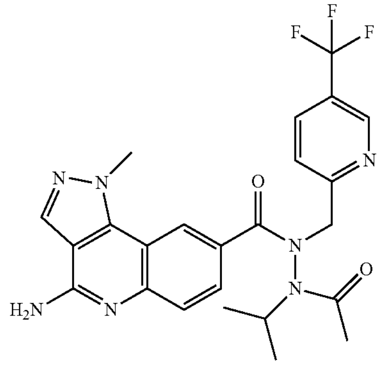

Example 203: N'-acetyl-4-amino-N'-isopropyl-1-methyl-N-[[5-(trifluoromethyl)-2-pyridyl]methyl]pyrazolo[4,3-c]quinoline-8-carbohydrazide. Prepared following general procedure E-1 starting with intermediates Da-1 and Bd-28. ES/MS: m/z=500.0 $[M+H]^+$. 1H NMR (400 MHz, DMSO-$d_6$) δ 13.35 (s, 1H), 9.68 (s, 1H), 9.12 (s, 0.5H, rotamer), 8.98 (d, J=25.9 Hz, 0.5H, rotamer), 8.68 (s, 1H), 8.63 (s, 1H), 8.40 (s, 0.4H, minor rotamer), 8.23 (s, 0.7H, major rotamer), 8.00 (s, 0.6H, major rotamer), 7.85 (d, J=8.3 Hz, 2H), 7.57 (s, 0.5H, minor rotamer), 5.09 (s, 1H), 4.57-4.32 (m, 3H), 4.42 (s, 1H), 4.17 (s, 1H), 2.19 (d, J=4.0 Hz, 1H), 1.95 (s, 1H), 1.25 (d, J=4.9 Hz, 2H), 1.13 (s, 2H), 0.84 (d, J=18.8 Hz, 1H).

Example 204

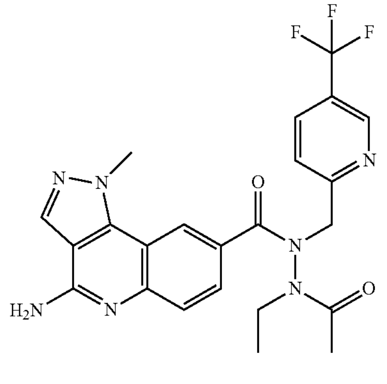

Example 204: N'-acetyl-4-amino-N'-ethyl-1-methyl-N-[[5-(trifluoromethyl)-2-pyridyl]methyl]pyrazolo[4,3-c]quinoline-8-carbohydrazide. Prepared following general procedure E-1 starting with intermediates Da-1 and Bd-29. ES/MS: m/z=486.2 $[M+H]^+$. 1H NMR (400 MHz, DMSO-$d_6$) δ 13.43 (s, 1H), 9.67 (s, 1H), 9.11 (s, 0.3H, minor rotamer), 8.96 (s, 0.6H, major rotamer), 8.71 (s, 1H), 8.63 (s, 1H), 8.39 (s, 0.6H, major rotamer), 8.25 (d, J=8.0 Hz, 1H), 8.03 (s, 0.3H, minor rotamer), 7.96 (d, J=8.3 Hz, 0.6H, major rotamer), 7.91-7.70 (m, 2H), 7.61 (s, 0.4H, minor rotamer), 5.24 (d, J=16.3 Hz, 0.4H, minor rotamer), 5.03 (d, J=16.8 Hz, 1H), 4.76 (d, J=16.5 Hz, 0.6H, major rotamer), 4.46 (d, J=13.3 Hz, 3H), 3.59 (m, 2H), 1.95 (m, 3H), 0.93 (d, J=9.7 Hz, 3H).

Example 205

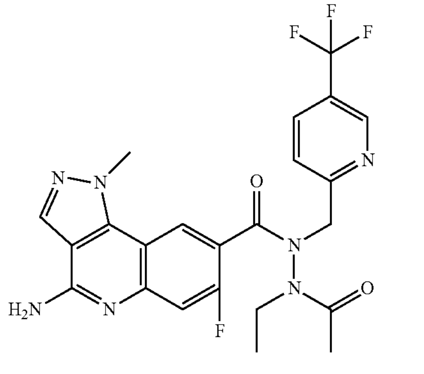

Example 205: N'-acetyl-4-amino-N'-ethyl-7-fluoro-1-methyl-N-[[5-(trifluoromethyl)-2-pyridyl]methyl]pyrazolo[4,3-c]quinoline-8-carbohydrazide. Prepared following general procedure E-1 starting with intermediates Db-1 and Bd-29. ES/MS: m/z=504.0 $[M+H]^+$. $^1H$ NMR (400 MHz, DMSO-$d_6$) δ 9.06 (d, J=2.1 Hz, 0.4H, rotamer), 8.97 (s, 0.4H, rotamer), 8.57 (s, 1H), 8.50 (d, J=6.5 Hz, 0.4H, rotamer), 8.29 (d, J=8.1 Hz, 1H), 8.17 (d, J=8.2 Hz, 0.4H, rotamer), 7.84 (d, J=8.3 Hz, 0.5H, rotamer), 7.63 (d, J=10.5 Hz, 1H), 7.52 (d, J=8.2 Hz, 0.4H, rotamer), 5.30 (d, J=16.2 Hz, 0.4H, rotamer), 5.18-4.93 (m, 1H), 4.75 (d, J=16.1 Hz, 0.4H, rotamer), 4.44 (d, J=7.0 Hz, 2H), 4.39 (s, 1H), 3.57 (s, 3H), 1.97 (d, J=18.2 Hz, 2H), 0.92 (t, J=6.9 Hz, 3H).

Example 206

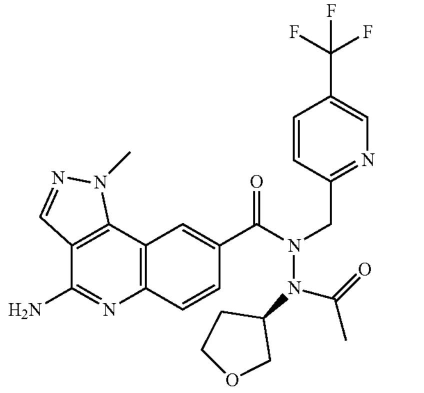

Example 206: N'-acetyl-4-amino-1-methyl-N'-[(3R)-tetrahydrofuran-3-yl]-N-[[5-(trifluoromethyl)-2-pyridyl]methyl]pyrazolo[4,3-c]quinoline-8-carbohydrazide. Prepared following general procedure E-1 starting with intermediates Da-1 and Bd-30. ES/MS: m/z=528.0 $[M+H]^+$. $^1H$ NMR (400 MHz, DMSO-$d_6$) δ 13.33 (s, 1H), 9.69 (brs, 1H), 9.12 (s, 0.4H, rotamer), 8.79 (s, 0.4H, rotamer), 8.63 (s, 1H), 8.37 (s, 0.4H, rotamer), 8.26 (d, J=8.5 Hz, 1H), 8.06 (s, 0.4H, rotamer), 7.86 (s, 2H), 7.59 (s, 0.5H, rotamer), 5.12 (d, J=15.5 Hz, 1H), 4.49 (d, J=35.3 Hz, 4H), 4.33 (s, 1H), 3.89-3.55 (m, 4H), 2.17 (d, J=16.8 Hz, 1H), 1.97 (d, J=31.7 Hz, 3H), 1.76 (s, 0.1H, rotamer).

Example 207

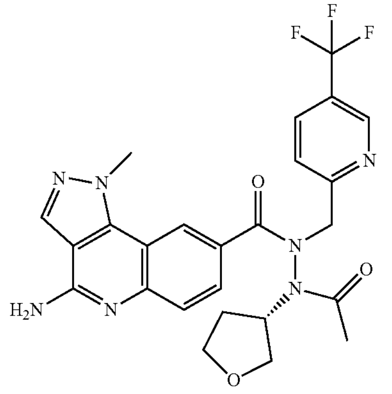

Example 207: N'-acetyl-4-amino-1-methyl-N'-[(3S)-tetrahydrofuran-3-yl]-N-[[5-(trifluoromethyl)-2-pyridyl]methyl]pyrazolo[4,3-c]quinoline-8-carbohydrazide. Prepared following general procedure E-1 starting with intermediates Da-1 and Bd-31. ES/MS: m/z=528.0 $[M+H]^+$. $^1H$ NMR (400 MHz, DMSO-$d_6$) δ 13.44 (s, 1H), 9.69 (s, 1H), 9.12 (s, 0.6H, rotamer), 8.99 (s, 1H), 8.79 (s, 0.5H, rotamer), 8.64 (s, 1H), 8.37 (s, 0.3H, rotamer), 8.26 (d, J=8.3 Hz, 1H), 8.07 (s, 0.4H, rotamer), 7.88 (d, J=10.5 Hz, 2H), 7.60 (d, J=8.7 Hz, 0.5H, rotamer), 5.09 (t, J=17.2 Hz, 2H), 4.49 (d, J=38.5 Hz, 3H), 4.33 (s, 1H), 3.79 (d, J=10.1 Hz, 1H), 2.17 (d, J=17.2 Hz, 1H), 2.05-1.83 (m, 3H), 1.76 (s, 0.1H, rotamer).

Example 208

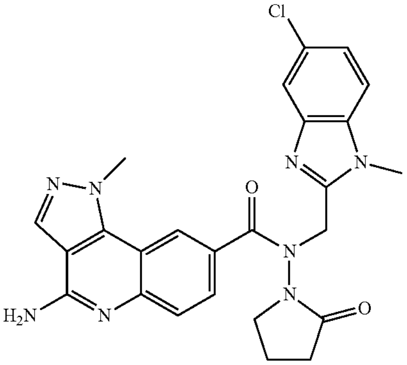

Example 208: 4-Amino-N-[(5-chloro-1-methyl-benzimidazol-2-yl)methyl]-1-methyl-N-(2-oxopyrrolidin-1-yl)pyrazolo[4,3-c]quinoline-8-carboxamide Prepared following general procedure E-1 starting with intermediates Da-1 and Bb-18. ES/MS: m/z=503.4 $[M+H]^+$. $^1H$ NMR (400 MHz, Methanol-d4) δ 8.58 (d, J=1.7 Hz, 1H), 8.49 (s, 1H), 7.94 (dd, J=8.6, 1.8 Hz, 1H), 7.84 (d, J=8.6 Hz, 1H), 7.81-7.67 (m, 2H), 7.48 (dd, J=8.8, 1.9 Hz, 1H), 5.66 (d, J=15.9 Hz, 1H), 5.14 (d, J=15.9 Hz, 1H), 4.49 (s, 3H), 4.10 (s, 3H), 3.83 (q, J=8.1 Hz, 1H), 3.35 (s, 1H), 3.01 (d, J=55.2 Hz, 1H), 2.35-1.36 (m, 4H).

Example 209

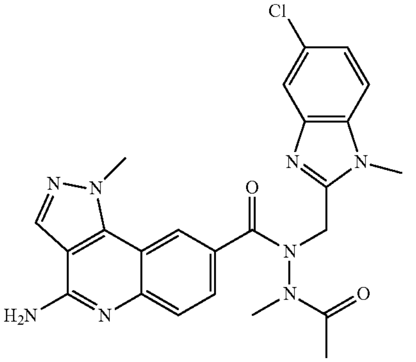

Example 209: N'-Acetyl-4-amino-N-[(5-chloro-1-methyl-benzimidazol-2-yl)methyl]-N',1-dimethyl-pyrazolo[4,3-c]quinoline-8-carbohydrazide. Prepared using general procedure E-1 starting with intermediates Da-1 and Bb-19. ES/MS: m/z=491.2 $[M+H]^+$. $^1$H NMR (400 MHz, Methanol-d4) δ 8.52 (d, J=19.9 Hz, 2H), 7.92 (d, J=8.6 Hz, 1H), 7.81 (d, J=8.6 Hz, 1H), 7.77-7.58 (m, 2H), 7.53-7.33 (m, 1H), 5.19 (d, J=15.7 Hz, 1H), 4.98 (m, 1H), 4.53 (d, J=10.0 Hz, 4H), 4.16-3.99 (m, 3H), 3.77-3.63 (m, 3H), 1.78 (s, 3H).

Example 210

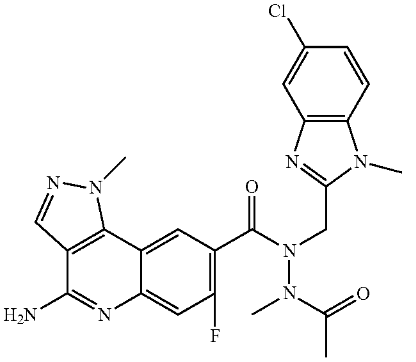

Example 210: N'-acetyl-4-amino-N-[(5-chloro-1-methyl-benzimidazol-2-yl)methyl]-7-fluoro-N',1-dimethyl-pyrazolo[4,3-c]quinoline-8-carbohydrazide. Prepared using general procedure E-1 starting with intermediates Db-1 and Bb-19. ES/MS: m/z=509.1 $[M+H]^+$. $^1$H NMR (400 MHz, Methanol-d4) δ 8.47 (s, 1H), 8.41 (d, J=6.5 Hz, 1H), 7.78-7.66 (m, 2H), 7.62 (d, J=10.2 Hz, 1H), 7.46 (dd, J=8.8, 1.9 Hz, 1H), 5.53 (d, J=15.6 Hz, 1H), 5.19 (d, J=15.6 Hz, 1H), 4.46 (s, 3H), 4.10 (s, 3H), 3.33-3.24 (m, 4H), 1.75 (s, 3H).

Example 211

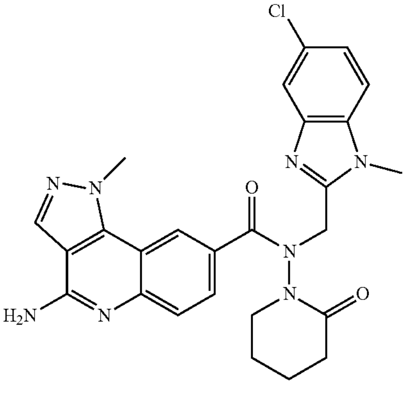

Example 211: 4-amino-N-((5-chloro-1-methyl-1H-benzo[d]imidazol-2-yl)methyl)-1-methyl-N-(2-oxopiperidin-1-yl)-1H-pyrazolo[4,3-c]quinoline-8-carboxamide. Prepared using general procedure E-1 starting with intermediates Da-1 and Bb-20. ES/MS: m/z=517.22 $[M+H]^+$. $^1$H NMR (400 MHz, Methanol-d4) δ 8.51 (d, J=15.2 Hz, 2H), 7.92 (d, J=8.7 Hz, 1H), 7.84 (d, J=8.5 Hz, 1H), 7.80-7.62 (m, 2H), 7.48 (dd, J=8.8, 1.9 Hz, 1H), 5.65-5.42 (m, 1H), 5.26 (d, J=15.9 Hz, 1H), 4.50 (s, 3H), 4.22-4.00 (m, 3H), 3.88-3.64 (m, 2H), 3.64-3.45 (m, 1H), 2.43-2.10 (m, 1H), 2.10-1.77 (m, 2H), 1.65 (s, 1H), 1.38 (d, J=58.4 Hz, 2H).

Example 212

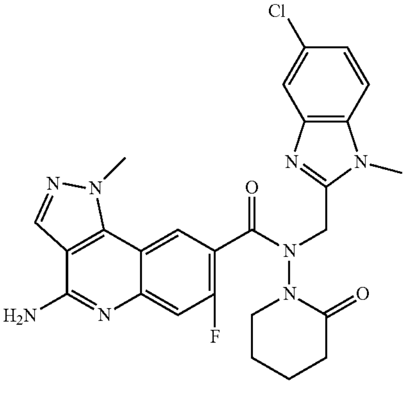

Example 212: 4-Amino-N-[(5-chloro-1-methyl-benzimidazol-2-yl)methyl]-7-fluoro-1-methyl-N-(2-oxo-1-piperidyl)pyrazolo[4,3-c]quinoline-8-carboxamide. Prepared using general procedure E-1 starting with intermediates Db-1 and Bb-20. ES/MS: m/z=535.2 $[M+H]^+$. $^1$H NMR (400 MHz, Methanol-d4) δ 8.47 (s, 1H), 8.41 (d, J=6.5 Hz, 1H), 7.88-7.74 (m, 2H), 7.66 (d, J=10.3 Hz, 1H), 7.53 (dd, J=8.8, 1.9 Hz, 1H), 5.62 (d, J=15.9 Hz, 1H), 5.29 (d, J=15.8 Hz, 1H), 4.44 (s, 3H), 4.14 (s, 3H), 3.68 (m, 2H), 3.58-3.44 (m, 2H), 2.20 (dt, J=17.8, 5.4 Hz, 1H), 2.08-1.76 (m, 2H), 1.45 (s, 2H).

Example 213

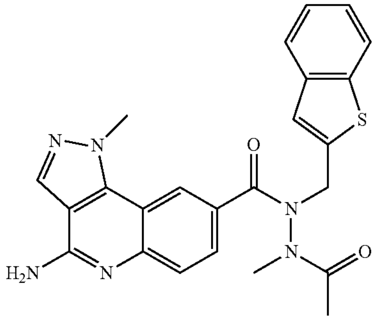

Example 213: N'-Acetyl-4-amino-N-(benzothiophen-2-ylmethyl)-N',1-dimethyl-pyrazolo[4,3-c]quinoline-8-carbohydrazide. Prepared using general procedure E-1 starting with intermediates Da-1 and Bb-21. ES/MS: m/z=459.2 $[M+H]^+$. $^1H$ NMR (400 MHZ, Methanol-d4) δ 8.56 (d, J=1.7 Hz, 1H), 8.55-8.36 (m, 2H), 8.00 (d, J=8.6 Hz, 1H), 7.95-7.67 (m, 4H), 7.46 (s, 1H), 7.37 (td, J=5.6, 2.8 Hz, 2H), 5.25 (s, 1H), 4.52 (s, 3H), 3.27-3.05 (m, 3H), 1.97-1.82 (m, 3H).

Example 214

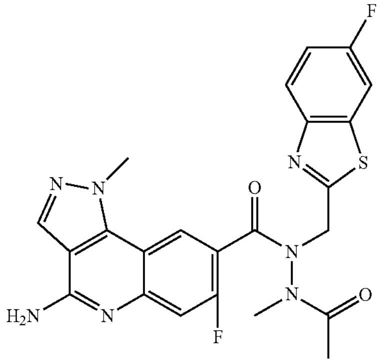

Example 214: N'-acetyl-4-amino-7-fluoro-N-[(6-fluoro-1,3-benzothiazol-2-yl)methyl]-N',1-dimethyl-pyrazolo[4,3-c]quinoline-8-carbohydrazide. Prepared using general procedure E-1 starting with intermediates Db-1 and Ba-66. ES/MS: m/z=496.2 $[M+H]^+$. $^1H$ NMR (400 MHz, Methanol-d4) δ 8.54-8.36 (m, 2H), 8.01 (dd, J=9.0, 4.8 Hz, 1H), 7.83 (dd, J=8.4, 2.6 Hz, 1H), 7.59 (d, J=10.3 Hz, 1H), 7.34 (td, J=8.7, 2.4 Hz, 1H), 5.46 (d, J=15.7 Hz, 1H), 5.14 (d, J=15.7 Hz, 1H), 4.48 (s, 3H), 3.79-3.70 (m, 1H), 3.46 (s, 3H), 1.86 (s, 3H).

Example 215

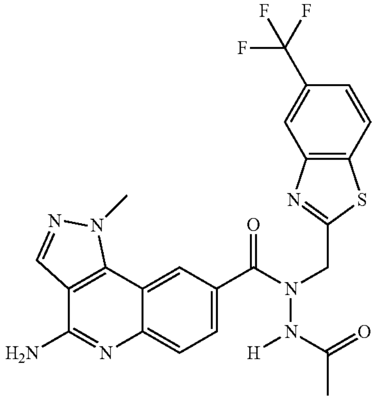

Example 215: N'-acetyl-4-amino-1-methyl-N-[[5-(trifluoromethyl)-1,3-benzothiazol-2-yl]methyl]pyrazolo[4,3-c]quinoline-8-carbohydrazide. Prepared using general procedure E-1 starting with intermediates Da-1 and Bb-22. ES/MS: m/z=514.6 $[M+H]^+$. $^1H$ NMR (400 MHz, DMSO-$d_6$) δ 10.91 (s, 1H), 8.61 (d, J=4.0 Hz, 2H), 8.47-8.37 (m, 4H), 7.99-7.75 (m, 4H), 5.55 (s, 2H), 4.47 (s, 3H), 1.67 (s, 3H).

Example 216

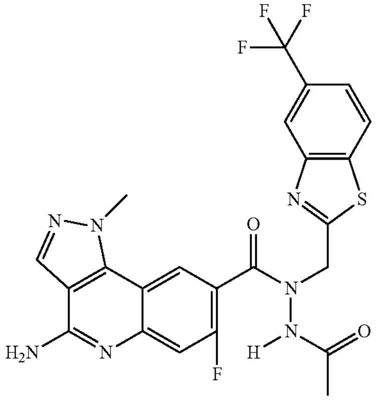

Example 216: N'-acetyl-4-amino-7-fluoro-1-methyl-N-[[5-(trifluoromethyl)-1,3-benzothiazol-2-yl]methyl]pyrazolo[4,3-c]quinoline-8-carbohydrazide. Prepared using general procedure E-1 starting with intermediates Db-1 and Bb-22. ES/MS: m/z=532.1 $[M+H]^+$. $^1H$ NMR (400 MHz, Methanol-d4) δ 8.47 (d, J=7.9 Hz, 2H), 8.36-8.24 (m, 2H), 7.76 (dd, J=8.5, 1.7 Hz, 1H), 7.60 (d, J=10.2 Hz, 1H), 4.91 (t, J=2.6 Hz, 2H), 4.50 (s, 3H), 3.77-3.64 (m, 2H), 3.34 (d, J=1.7 Hz, 1H), 1.70 (s, 3H).

Example 217: N'-acetyl-4-amino-N-(2-fluoro-4-(2-(trifluoromethyl)thiazol-5-yl)benzyl)-N',1-dimethyl-1H-pyrazolo[4,3-c]quinoline-8-carbohydrazide

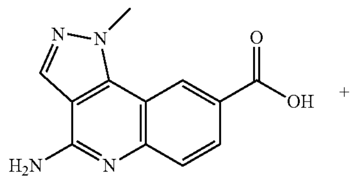

Da-1

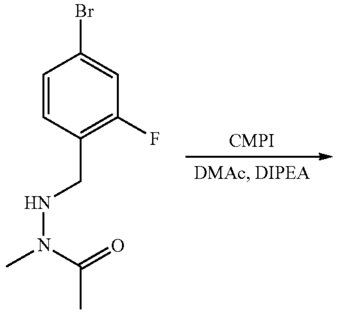

Bb-15

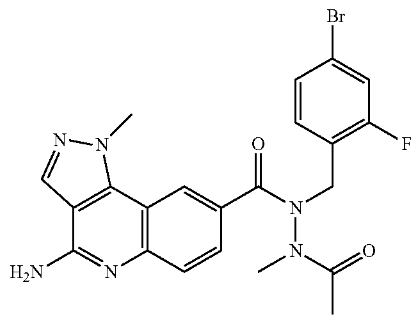

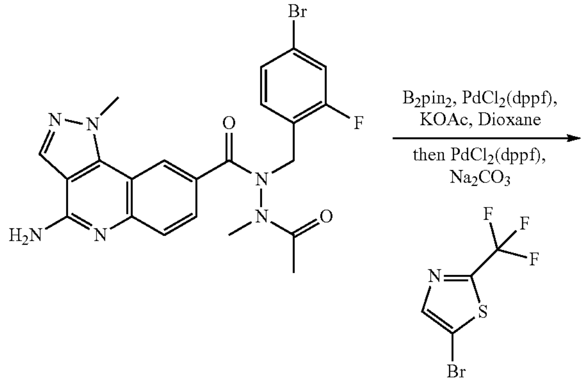

-continued

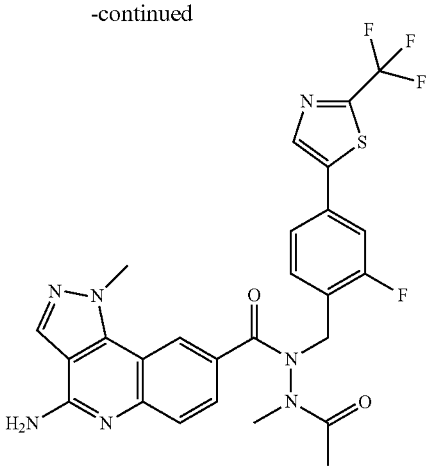

Example 217

Step 1: N'-acetyl-4-amino-N-(4-bromo-2-fluorobenzyl)-N',1-dimethyl-1H-pyrazolo[4,3-c]quinoline-8-carbohydrazide Prepared following general procedure E-1 starting with intermediates Da-1 and Bb-15. ES/MS: m/z=500.0 [M+H]$^+$.

Step 2: N'-acetyl-4-amino-N-(2-fluoro-4-(2-(trifluoromethyl)thiazol-5-yl)benzyl)-N',1-dimethyl-1H-pyrazolo[4,3-c]quinoline-8-carbohydrazide. To a solution of N'-acetyl-4-amino-N-(4-bromo-2-fluorobenzyl)-N',1-dimethyl-1H-pyrazolo[4,3-c]quinoline-8-carbohydrazide (22.0 mg, 0.0441 mmol), $PdCl_2$(dppf) (4.9 mg, 0.00661 mmol), bis (pinacolato)diboron (13.4 mg, 0.0529 mmol) in dioxane (2 mL), was added potassium propionate (14.8 mg, 0.132 mmol). The mixture was bubbled through argon for 1 minute and left to stir at 110 C for 1 hour. After, 5-bromo-2-(trifluoromethyl)thiazole (12.3 mg, 0.0529 mmol), 2M $Na_2CO_3$ (11.7 mg, 0.110 mmol), and $PdCl_2$(dppf) (1.6 mg, 0.00220 mmol) was added to the mixture and bubbled through argon for 1 minute. The reaction was left to stir at 90 C for 6 hours. The mixture was filtered through a pad of celite and anhydrous $MgSO_4$ and the solution was reduced under pressure and the crude was purified by preparative HPLC. ES/MS: m/z=572.0 [M+H]$^+$. $^1$H NMR (400 MHz, Methanol-d4) δ 8.69-8.45 (m, 2H), 8.39 (dd, J=6.3, 1.2 Hz, 1H), 8.10-7.41 (m, 5H), 5.11 (d, J=25.9 Hz, 1H), 4.85 (s, 1H), 4.54 (d, J=13.8 Hz, 3H), 3.18 (d, J=28.0 Hz, 3H), 1.91 (d, J=34.4 Hz, 3H).

Example 218

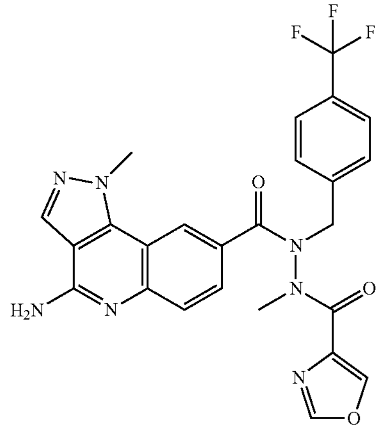

Example 218: N'-(4-amino-1-methyl-1H-pyrazolo[4,3-c]quinoline-8-carbonyl)-N-methyl-N'-(4-(trifluoromethyl)benzyl)oxazole-4-carbohydrazide. Prepared following general procedure E-1 starting with intermediates Da-1 and Bd-32. ES/MS: m/z=524.0 $[M+H]^+$. 1H NMR (400 MHz, Methanol-d4) δ 8.53 (d, J=44.5 Hz, 2H), 8.42-8.05 (m, 2H), 7.98 (d, J=8.6 Hz, 1H), 7.88-7.42 (m, 5H), 5.48-4.98 (m, 2H), 4.41 (d, J=86.0 Hz, 3H), 3.51 (s, 1H), 3.10 (s, 2H).

Example 219

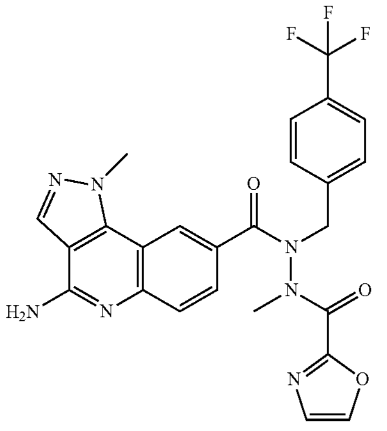

Example 219: N'-(4-amino-1-methyl-1H-pyrazolo[4,3-c]quinoline-8-carbonyl)-N-methyl-N'-(4-(trifluoromethyl)benzyl)oxazole-2-carbohydrazide. Prepared following general procedure E-1 starting with intermediates Da-1 and Bc-17. ES/MS: m/z=524.0 $[M+H]^+$. 1H NMR (400 MHz, Methanol-d4) δ 8.65-8.55 (m, 1H), 8.48 (d, J=5.3 Hz, 1H), 8.14-7.93 (m, 2H), 7.85-7.76 (m, 1H), 7.71 (d, J=8.1 Hz, 1H), 7.66-7.22 (m, 4H), 5.15 (s, 2H), 4.43 (d, J=71.3 Hz, 3H), 3.61 (s, 1H), 3.27 (s, 2H).

Example 220

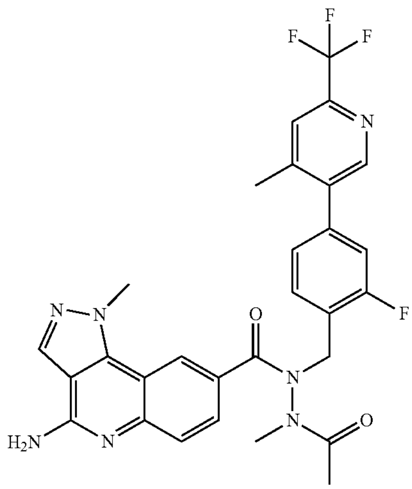

Example 220: N'-acetyl-4-amino-N-(2-fluoro-4-(4-methyl-6-(trifluoromethyl)pyridin-3-yl)benzyl)-N',1-dimethyl-1H-pyrazolo[4,3-c]quinoline-8-carbohydrazide. Prepared following the procedure reported for example 217 starting with intermediates Da-1, Bb-15, and 5-bromo-4-methyl-2-(trifluoromethyl)pyridine. ES/MS: m/z=580.0 $[M+H]^+$. 1H NMR (400 MHz, Methanol-d4) δ 8.70-8.37 (m, 3H), 8.08-7.61 (m, 4H), 7.32 (td, J=11.4, 10.8, 4.2 Hz, 2H), 5.07 (d, J=118.7 Hz, 2H), 4.56 (d, J=12.1 Hz, 3H), 3.24-3.12 (m, 3H), 2.43 (d, J=9.9 Hz, 3H), 1.91 (d, J=37.6 Hz, 3H).

Example 221

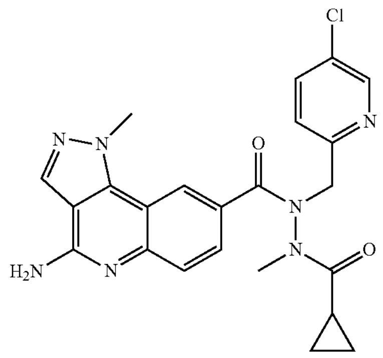

Example 221: 4-amino-N-((5-chloropyridin-2-yl)methyl)-N'-(cyclopropanecarbonyl)-N',1-dimethyl-1H-pyrazolo[4,3-c]quinoline-8-carbohydrazide. Prepared following general procedure E-1 starting with intermediates Da-1 and Bk-3. ES/MS: m/z=464.3 $[M+H]^+$. 1H NMR (400 MHz, Methanol-d4) δ 8.77-8.37 (m, 3H), 8.03-7.34 (m, 4H), 5.17 (s, 2H), 4.58-4.51 (m, 4H), 3.15 (p, J=1.7 Hz, 2H), 2.68 (s, 3H), 1.96 (s, 1H), 0.72 (d, J=56.3 Hz, 3H).

Example 222

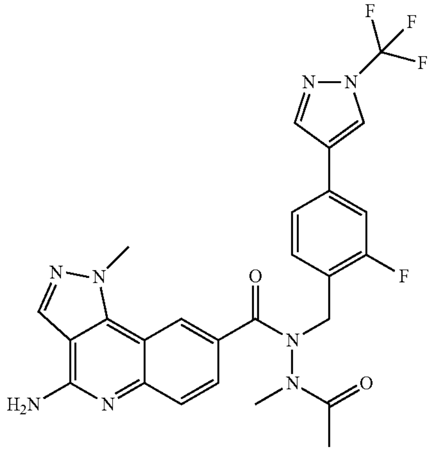

Example 222: N'-acetyl-4-amino-N-(2-fluoro-4-(1-(trifluoromethyl)-1H-pyrazol-4-yl)benzyl)-N',1-dimethyl-1H-pyrazolo[4,3-c]quinoline-8-carbohydrazide. Prepared following the procedure reported for example 130 starting with intermediates Da-1, Bb-15, and 4-(4,4,5,5-tetramethyl-1,3,2-dioxaborolan-2-yl)-1-(trifluoromethyl)-1H-pyrazole. ES/MS: m/z=555.0 $[M+H]^+$. $^1$H NMR (400 MHz, Methanol-d4) δ 8.98 (s, 1H), 8.83 (s, 1H), 8.50 (s, 2H), 8.44-8.21 (m, 2H), 8.03 (s, 1H), 7.86 (dd, J=21.3, 9.6 Hz, 2H), 5.29 (d, J=15.2 Hz, 1H), 4.96 (s, 1H), 4.54 (s, 3H), 3.78-3.40 (m, 2H), 2.37 (d, J=18.2 Hz, 1H), 2.12-1.15 (m, 5H).

Example 223

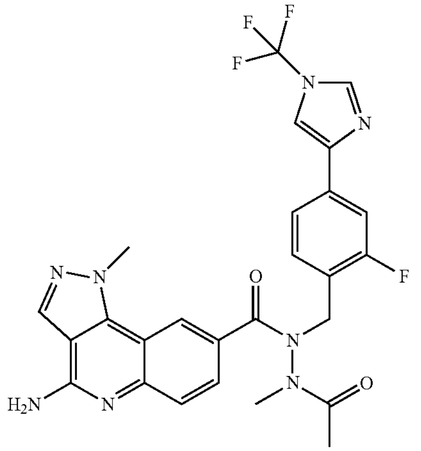

Example 223: N'-acetyl-4-amino-N-(2-fluoro-4-(1-(trifluoromethyl)-1H-imidazol-4-yl)benzyl)-N',1-dimethyl-1H-pyrazolo[4,3-c]quinoline-8-carbohydrazide. Prepared following the procedure reported for example 217 starting with intermediates Da-1, Bb-15, and 4-bromo-1-(trifluoromethyl)-1H-imidazole. ES/MS: m/z=555.0 $[M+H]^+$. 1H NMR (400 MHz, Methanol-d4) δ 8.67-8.45 (m, 2H), 8.38 (d, J=1.1 Hz, 1H), 8.07-7.60 (m, 3H), 7.48-7.29 (m, 2H), 7.26 (d, J=3.7 Hz, 1H), 5.33-4.99 (m, 1H), 4.85 (s, 1H), 4.55 (d, J=12.1 Hz, 3H), 3.18 (d, J=19.7 Hz, 3H), 1.89 (d, J=54.4 Hz, 3H).

Example 224

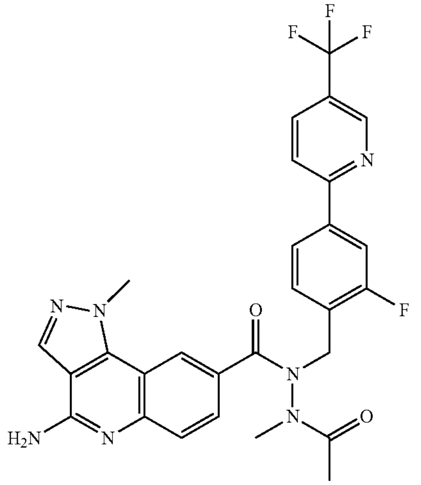

Example 224: N'-acetyl-4-amino-N-(2-fluoro-4-(5-(trifluoromethyl)pyridin-2-yl)benzyl)-N',1-dimethyl-1H-pyrazolo[4,3-c]quinoline-8-carbohydrazide. Prepared following the procedure reported for example 130 starting with intermediates Da-1, Bb-15, and (5-(trifluoromethyl)pyridin-2-yl) boronic acid. ES/MS: m/z=566.0 $[M+H]^+$. 1H NMR (400 MHZ, Methanol-d4) δ 8.99 (s, 1H), 8.64-8.38 (m, 2H), 8.34-8.10 (m, 3H), 8.09-7.63 (m, 6H), 4.53 (s, 3H), 3.50 (p, J=1.6 Hz, 2H), 3.15 (dt, J=3.3, 1.5 Hz, 3H), 1.86 (s, 3H).

Example 225

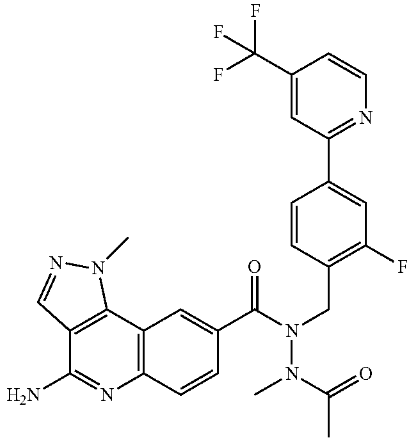

Example 225: N'-acetyl-4-amino-N-(2-fluoro-4-(4-(trifluoromethyl)pyridin-2-yl)benzyl)-N',1-dimethyl-1H-pyrazolo[4,3-c]quinoline-8-carbohydrazide. Prepared following the procedure reported for example 130 starting with intermediates Da-1, Bb-15, and (4-(trifluoromethyl)pyridin-2-yl) boronic acid. ES/MS: m/z=566.0 $[M+H]^+$. 1H NMR (400 MHZ, Methanol-d4) δ 8.92 (d, J=5.1 Hz, 1H), 8.67-8.40 (m, 2H), 8.21 (s, 1H), 8.12-7.61 (m, 6H), 5.16 (d, J=52.0 Hz, 2H), 4.55 (d, J=13.7 Hz, 3H), 3.24-3.10 (m, 3H), 2.04-1.71 (m, 3H).

Example 226

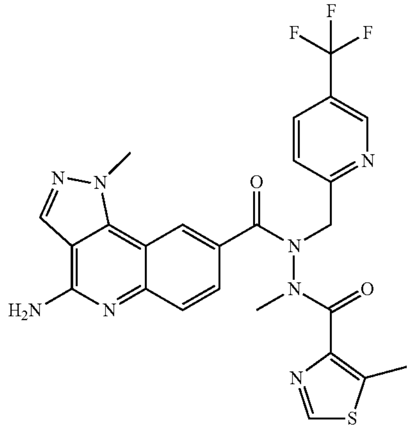

Example 226: N'-(4-amino-1-methyl-1H-pyrazolo[4,3-c]quinoline-8-carbonyl)-N,5-dimethyl-N'-((5-(trifluoromethyl)pyridin-2-yl)methyl)thiazole-4-carbohydrazide. Prepared following general procedure E-1 starting with intermediates Da-1 and Bp-1. ES/MS: m/z=555.0 $[M+H]^+$. 1H NMR (400 MHz, Methanol-d4) δ 9.04-8.75 (m, 2H), 8.49 (s, 2H), 8.25-7.93 (m, 2H), 7.71 (dd, J=81.4, 8.5 Hz, 2H), 5.53-4.92 (m, 2H), 4.44 (d, J=74.9 Hz, 3H), 3.34 (s, 3H, overlapping with solvent peak), 2.51 (s, 1H, minor rotamer), 2.31 (s, 2H, major rotamer).

Example 227

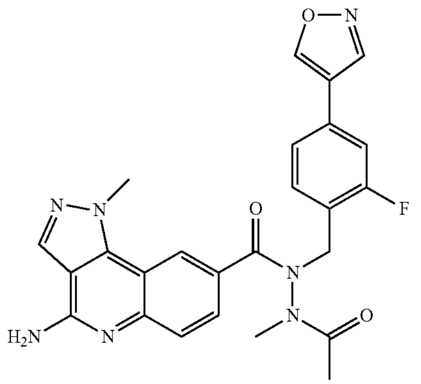

Example 227: N'-acetyl-4-amino-N-(2-fluoro-4-(isoxazol-4-yl)benzyl)-N',1-dimethyl-1H-pyrazolo[4,3-c]quinoline-8-carbohydrazide: Prepared following the procedure reported for Example 130 starting with intermediates Da-1, Bb-15, and isoxazol-4-ylboronic acid. ES/MS: m/z=488.2 $[M+H]^+$. 1H NMR (400 MHz, Methanol-d4) δ 9.19 (d, J=5.1 Hz, 1H), 9.05 (s, 1H), 8.91 (d, J=1.4 Hz, 1H), 8.77 (s, 1H), 8.62-8.43 (m, 2H), 8.06-7.75 (m, 2H), 7.75-7.29 (m, 3H), 5.35-4.96 (m, 2H), 4.54 (d, J=13.8 Hz, 3H), 3.15 (d, J=10.9 Hz, 3H), 1.89 (d, J=48.8 Hz, 3H).

Example 228

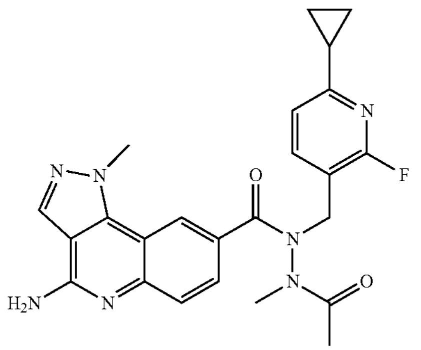

Example 228: N'-acetyl-4-amino-N-((6-cyclopropyl-2-fluoropyridin-3-yl)methyl)-N',1-dimethyl-1H-pyrazolo[4,3-c]quinoline-8-carbohydrazide. Prepared following the procedure reported for example 130 starting with intermediates Da-1, Bb-23, 2-cyclopropyl-4,4,5,5-tetramethyl-1,3,2-dioxaborolane. ES/MS: m/z=462.2 $[M+H]^+$. 1H NMR (400 MHZ, Methanol-d4) δ 8.60-8.41 (m, 2H), 8.04-7.72 (m, 3H), 7.30-7.16 (m, 1H), 4.97 (d, J=16.4 Hz, 2H), 4.52 (s, 3H), 3.23 (s, 3H), 2.17-2.02 (m, 1H), 1.96 (s, 1H), 1.84 (s, 3H), 1.13-0.89 (m, 4H).

Example 229

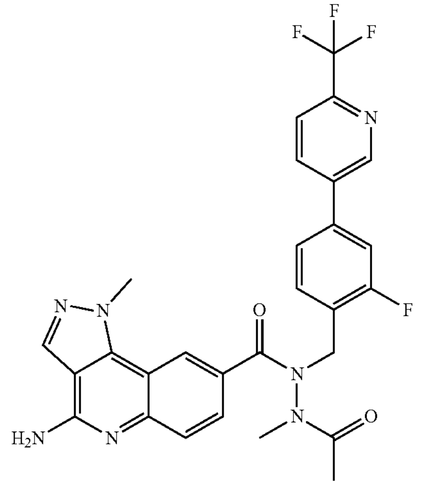

Example 229: N'-acetyl-4-amino-N-(2-fluoro-4-(6-(trifluoromethyl)pyridin-3-yl)benzyl)-N',1-dimethyl-1H-pyrazolo[4,3-c]quinoline-8-carbohydrazide: Prepared following the procedure reported for example 130 starting with intermediates Da-1, Bb-15, and 5-(4,4,5,5-tetramethyl-1,3,2-dioxaborolan-2-yl)-2-(trifluoromethyl)pyridine. ES/MS: m/z=566.0 $[M+H]^+$. 1H NMR (400 MHz, Methanol-d4) δ 9.04 (d, J=2.2 Hz, 1H), 8.64-8.46 (m, 2H), 8.34 (dd, J=8.2, 2.3 Hz, 1H), 8.22 (d, J=2.8 Hz, 1H), 7.75-7.56 (m, 3H), 7.35 (ddd, J=8.6, 2.8, 0.7 Hz, 2H), 5.15 (d, J=38.8 Hz, 2H), 4.55 (d, J=13.9 Hz, 3H), 3.18 (d, J=21.8 Hz, 3H), 1.87 (s, 3H).

Example 230

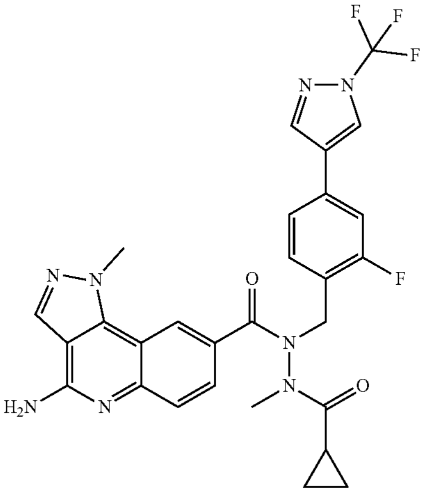

Example 230: 4-amino-N'-(cyclopropanecarbonyl)-N-(2-fluoro-4-(1-(trifluoromethyl)-1H-pyrazol-4-yl)benzyl)-N', 1-dimethyl-1H-pyrazolo[4,3-c]quinoline-8-carbohydrazide: Prepared following the procedure reported for example 130 starting with intermediates Da-1, Bo-4, and 4-(4,4,5,5-tetramethyl-1,3,2-dioxaborolan-2-yl)-1-(trifluoromethyl)-1H-pyrazole. ES/MS: m/z=581.0 $[M+H]^+$. 1H NMR (400 MHz, Methanol-d4) δ 8.71 (d, J=5.3 Hz, 1H), 8.59 (d, J=1.7 Hz, 1H), 8.50 (d, J=4.0 Hz, 1H), 8.29 (s, 1H), 7.91 (dd, J=59.7, 9.5 Hz, 2H), 7.76-7.39 (m, 3H), 5.20 (d, J=135.5 Hz, 2H), 4.53 (d, J=8.5 Hz, 3H), 3.28 (s, 1H, minor rotamer), 3.19-3.05 (m, 2H, major rotamer), 1.96 (s, 1H), 0.97-0.22 (m, 4H).

Example 231

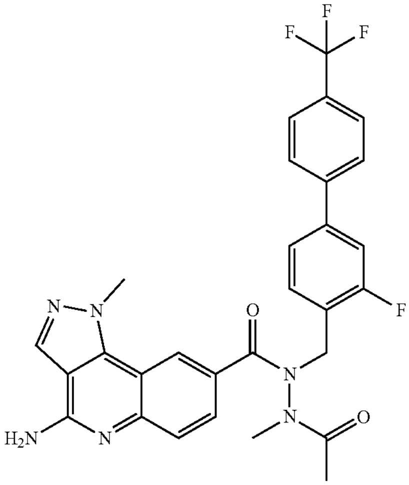

Example 231: N'-acetyl-4-amino-N-((3-fluoro-4'-(trifluoromethyl)-[1,1'-biphenyl]-4-yl)methyl)-N',1-dimethyl-1H-pyrazolo[4,3-c]quinoline-8-carbohydrazide. Prepared following the procedure reported for example 130 starting with intermediates Da-1, Bb-15, and [4-(trifluoromethyl)phenyl] boronic acid. ES/MS: m/z=565.0 $[M+H]^+$. $^1H$ NMR (400 MHZ, Methanol-d4) δ 8.69-8.41 (m, 2H), 8.10-7.70 (m, 6H), 7.70-7.49 (m, 3H), 5.15 (d, J=54.5 Hz, 1H), 4.83 (s, 1H), 4.55 (d, J=13.8 Hz, 3H), 3.17 (d, J=13.0 Hz, 3H), 1.91 (d, J=38.6 Hz, 3H).

Example 232

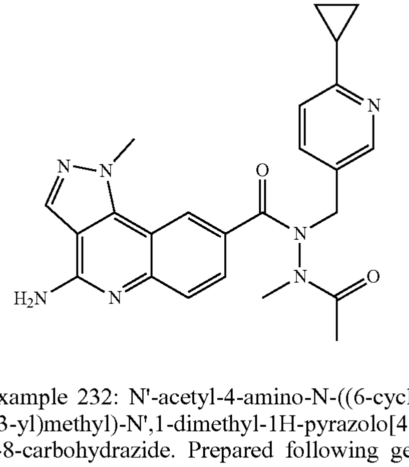

Example 232: N'-acetyl-4-amino-N-((6-cyclopropylpyridin-3-yl)methyl)-N',1-dimethyl-1H-pyrazolo[4,3-c]quinoline-8-carbohydrazide. Prepared following general procedure E-1 starting with intermediates Da-1 and Bi-7. ES/MS: m/z=555.0 $[M+H]^+$. 1H NMR (400 MHz, Methanol-d4) δ 8.74 (s, 1H), 8.50 (d, J=1.8 Hz, 3H), 8.00-7.75 (m, 2H), 7.61-7.38 (m, 1H), 5.07 (d, J=15.0 Hz, 1H), 4.90 (s, 1H), 4.53 (d, J=6.7 Hz, 3H), 3.15 (q, J=1.7 Hz, 1H), 2.68 (s, 2H), 2.34-2.19 (m, 1H), 1.88 (s, 3H), 1.47-0.95 (m, 4H).

Example 233

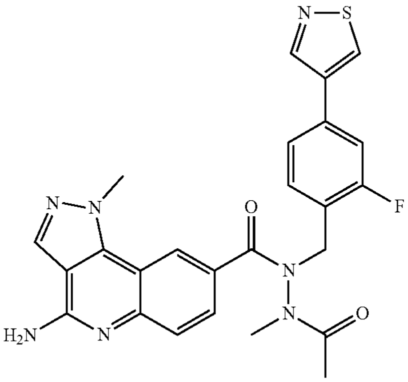

Example 233: N'-acetyl-4-amino-N-(2-fluoro-4-(isothiazol-4-yl)benzyl)-N',1-dimethyl-1H-pyrazolo[4,3-c]quinoline-8-carbohydrazide. Prepared following the procedure reported for example 217 starting with intermediates Da-1, Bb-15, and 4-bromoisothiazole. ES/MS: m/z=504.0 $[M+H]^+$. 1H NMR (400 MHz, Methanol-d4) δ 9.23 (d, J=7.5 Hz, 1H), 8.94 (s, 1H), 8.63-8.39 (m, 2H), 7.95-7.51 (m, 5H), 5.11 (d, J=55.8 Hz, 1H), 4.55 (d, J=13.8 Hz, 3H), 3.18-3.08 (m, 4H), 2.68 (s, 1H), 1.90 (d, J=43.5 Hz, 4H).

Example 234

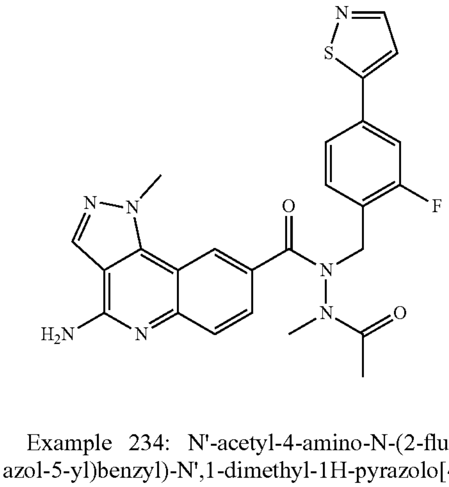

Example 234: N'-acetyl-4-amino-N-(2-fluoro-4-(isothiazol-5-yl)benzyl)-N',1-dimethyl-1H-pyrazolo[4,3-c]quinoline-8-carbohydrazide: Prepared following the procedure reported for example 217 starting with intermediates Da-1, Bb-15, and 5-bromoisothiazole. ES/MS: m/z=504.0 $[M+H]^+$. 1H NMR (400 MHz, Methanol-d4) δ 8.62-8.44 (m, 3H), 7.93 (d, J=37.2 Hz, 1H), 7.83-7.67 (m, 2H), 7.69-7.51 (m, 2H), 5.16 (s, 2H), 4.55 (d, J=13.1 Hz, 3H), 3.24-3.10 (m, 4H), 2.68 (s, 1H), 1.86 (s, 3H).

Example 235

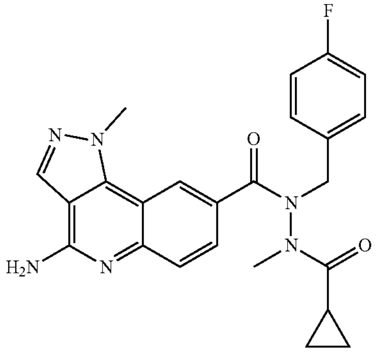

Example 235: 4-amino-N'-(cyclopropanecarbonyl)-N-(4-fluorobenzyl)-N',1-dimethyl-1H-pyrazolo[4,3-c]quinoline-8-carbohydrazide. Prepared following general procedure E-1 starting with intermediates Da-1 and Bk-4. ES/MS: m/z=447.2 $[M+H]^+$. 1H NMR (400 MHz, Methanol-d4) δ 8.62-8.41 (m, 2H), 7.90 (dd, J=59.5, 9.5 Hz, 2H), 7.55 (s, 2H), 7.15 (td, J=8.7, 7.3 Hz, 2H), 5.36-4.92 (m, 2H), 4.53 (d, J=5.8 Hz, 3H), 3.21-3.00 (m, 3H), 1.96 (s, 1H), 0.95-0.27 (m, 4H).

Example 236

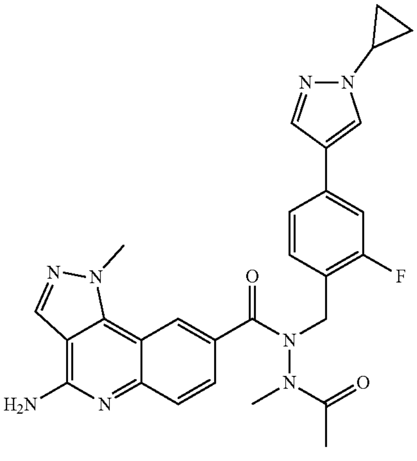

Example 236: N'-acetyl-4-amino-N-(4-(1-cyclopropyl-1H-pyrazol-4-yl)-2-fluorobenzyl)-N',1-dimethyl-1H-pyrazolo[4,3-c]quinoline-8-carbohydrazide. Prepared following the procedure reported for example 130 starting with intermediates Da-1, Bb-15, and 1-cyclopropyl-4-(4,4,5,5-tetramethyl-1,3,2-dioxaborolan-2-yl)-1H-pyrazole. ES/MS: m/z=527.2 $[M+H]^+$. 1H NMR (400 MHz, Methanol-d4) δ 8.64-8.42 (m, 2H), 8.14 (d, J=3.8 Hz, 1H), 8.02-7.74 (m, 3H), 7.67-7.28 (m, 3H), 5.17 (s, 2H), 4.54 (d, J=13.7 Hz, 3H), 3.71 (tt, J=7.3, 3.8 Hz, 1H), 3.18-3.02 (m, 3H), 1.82 (s, 3H), 1.27-1.03 (m, 5H).

Example 237

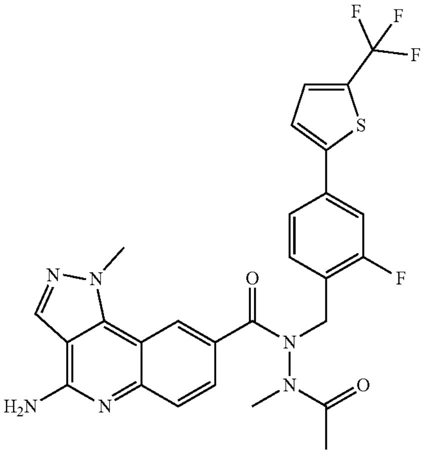

Example 237: N'-acetyl-4-amino-N-(2-fluoro-4-(5-(trifluoromethyl)thiophen-2-yl)benzyl)-N',1-dimethyl-1H-pyrazolo[4,3-c]quinoline-8-carbohydrazide. Prepared following the procedure reported for example 130 starting with intermediates Da-1, Bb-15, and (5-(trifluoromethyl)thiophen-2-yl)boronic acid. ES/MS: m/z=571.0 $[M+H]^+$. 1H NMR (400 MHz, Methanol-d4) δ 8.70-8.41 (m, 2H), 8.22-7.78 (m, 2H), 7.77-7.42 (m, 5H), 5.10 (d, J=39.9 Hz, 1H), 4.82 (s, 1H), 4.54 (d, J=13.5 Hz, 3H), 3.17 (d, J=19.3 Hz, 3H), 1.91 (d, J=39.8 Hz, 3H).

Example 238

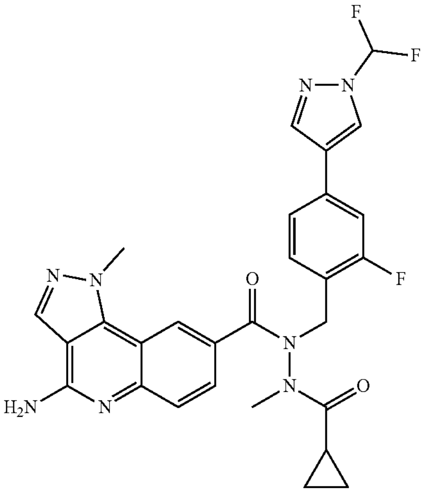

Example 238: 4-amino-N'-(cyclopropanecarbonyl)-N-(4-(1-(difluoromethyl)-1H-pyrazol-4-yl)-2-fluorobenzyl)-N',1-dimethyl-1H-pyrazolo[4,3-c]quinoline-8-carbohydrazide. Prepared following the procedure reported for example 130 starting with intermediates Da-1, Bo-4, and 1-(difluoromethyl)-4-(4,4,5,5-tetramethyl-1,3,2-dioxaborolan-2-yl)-1H-pyrazole. ES/MS: m/z=563.0 $[M+H]^+$. 1H NMR (400 MHz, Methanol-d4) δ 8.65-8.43 (m, 3H), 8.16 (s, 1H), 7.91 (dd, J=58.8, 9.7 Hz, 2H), 7.64 (s, 1H), 7.57-7.50 (m, 2H), 5.28 (d, J=67.9 Hz, 2H), 4.53 (d, J=8.6 Hz, 3H), 3.27 (s, 1H), 3.11 (s, 2H), 1.96 (s, 1H), 1.81 (d, J=10.8 Hz, 1H), 0.92-0.29 (m, 4H).

Example 239

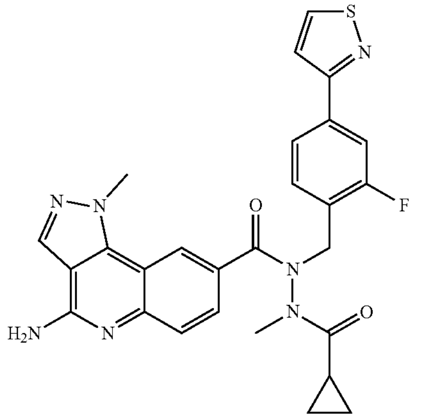

Example 239: 4-amino-N'-(cyclopropanecarbonyl)-N-(2-fluoro-4-(isothiazol-3-yl)benzyl)-N',1-dimethyl-1H-pyrazolo[4,3-c]quinoline-8-carbohydrazide. Prepared following the procedure reported for example 217 starting with intermediates Da-1, Bo-4, and 3-bromoisothiazole. ES/MS: m/z=530.0 $[M+H]^+$. 1H NMR (400 MHz, Methanol-d4) δ 8.71-8.40 (m, 3H), 8.07-7.65 (m, 3H), 7.59 (dd, J=16.5, 9.4 Hz, 3H), 5.52-5.00 (m, 2H), 4.53 (d, J=8.4 Hz, 3H), 3.14 (d, J=7.3 Hz, 2H), 1.95 (s, 1H), 1.70 (d, J=91.6 Hz, 1H), 0.94-0.22 (m, 4H).

Example 240

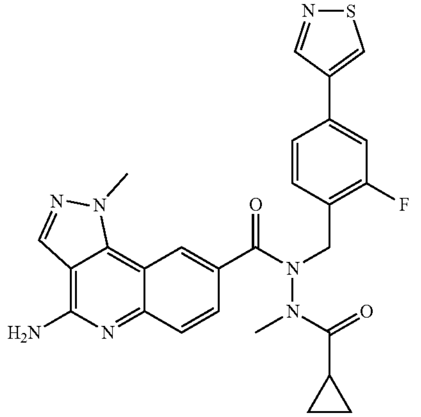

Example 240: 4-amino-N'-(cyclopropanecarbonyl)-N-(2-fluoro-4-(isothiazol-4-yl)benzyl)-N',1-dimethyl-1H-pyrazolo[4,3-c]quinoline-8-carbohydrazide. Prepared following the procedure reported for example 217 starting with intermediates Da-1, Bo-4, and 4-bromoisothiazole. ES/MS: m/z=530.0 $[M+H]^+$. 1H NMR (400 MHz, Methanol-d4) δ 9.23 (d, J=4.7 Hz, 1H), 8.95 (s, 1H), 8.66-8.34 (m, 2H), 8.07-7.35 (m, 5H), 5.53-4.96 (m, 2H), 4.54 (d, J=8.5 Hz, 3H), 3.19-3.08 (m, 2H), 2.68 (s, 1H), 1.96 (s, 1H), 0.92-0.30 (m, 4H).

Example 241

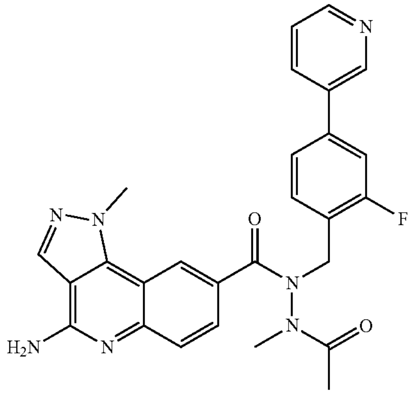

Example 241: N'-acetyl-4-amino-N-(2-fluoro-4-(pyridin-3-yl)benzyl)-N',1-dimethyl-1H-pyrazolo[4,3-c]quinoline-8-carbohydrazide. Prepared following the procedure reported for example 130 starting with intermediates Da-1, Bb-15, and 3-(4,4,5,5-tetramethyl-1,3,2-dioxaborolan-2-yl)pyridine. ES/MS: m/z=498.0 $[M+H]^+$. 1H NMR (400 MHz, Methanol-d4) δ 9.18-8.99 (m, 1H), 8.78 (dddd, J=24.0, 5.3, 3.7, 1.5 Hz, 1H), 8.67-8.33 (m, 3H), 8.15-7.70 (m, 4H), 7.71-7.52 (m, 2H), 5.05 (d, J=96.9 Hz, 1H), 4.55 (d, J=14.3 Hz, 3H), 3.19 (d, J=29.6 Hz, 3H), 1.91 (d, J=38.3 Hz, 3H), 1.24 (d, J=18.4 Hz, 1H).

Example 242

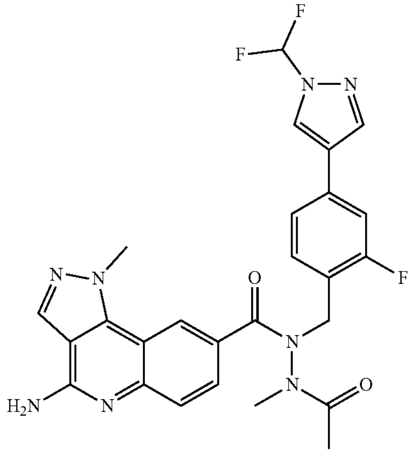

Example 242: N'-acetyl-4-amino-N-(4-(1-(difluoromethyl)-1H-pyrazol-4-yl)-2-fluorobenzyl)-N',1-dimethyl-1H-pyrazolo[4,3-c]quinoline-8-carbohydrazide. Prepared following the procedure reported for example 130 starting with intermediates Da-1, Bb-15, 1-(difluoromethyl)-4-(4,4,5,5-tetramethyl-1,3,2-dioxaborolan-2-yl)-1H-pyrazole. ES/MS: m/z=537.0 $[M+H]^+$. 1H NMR (400 MHz, Methanol-d4) δ 8.65-8.45 (m, 3H), 8.20-8.12 (m, 1H), 8.04-7.73 (m, 2H), 7.63-7.33 (m, 3H), 5.30-4.91 (m, 1H), 4.79 (d, J=14.6 Hz, 2H, overlapping with solvent peak), 4.54 (d, J=14.0 Hz, 3H), 3.14 (t, J=1.8 Hz, 3H), 1.89 (d, J=48.5 Hz, 3H).

Example 243

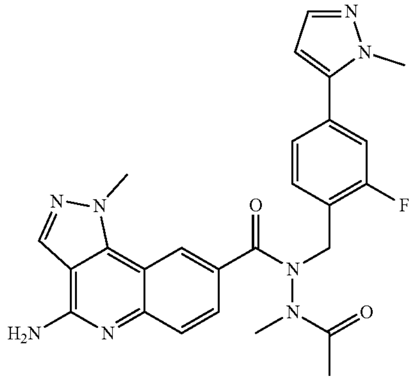

Example 243: N'-acetyl-4-amino-N-(2-fluoro-4-(1-methyl-1H-pyrazol-5-yl)benzyl)-N',1-dimethyl-1H-pyrazolo[4,3-c]quinoline-8-carbohydrazide. Prepared following the procedure reported for example 130 starting with intermediates Da-1, Bb-15, 1-methyl-5-(4,4,5,5-tetramethyl-1,3,2-dioxaborolan-2-yl)-1H-pyrazole. ES/MS: m/z=501.2 $[M+H]^+$. 1H NMR (400 MHz, Methanol-d4) δ 8.66-8.40 (m, 2H), 8.06-7.66 (m, 3H), 7.66-7.09 (m, 3H), 6.57-6.39 (m, 1H), 5.18 (s, 2H, overlapping with solvent peak), 4.53 (d, J=3.6 Hz, 3H), 3.92 (d, J=5.7 Hz, 3H), 3.18 (d, J=24.1 Hz, 3H), 1.86 (s, 3H).

Example 244

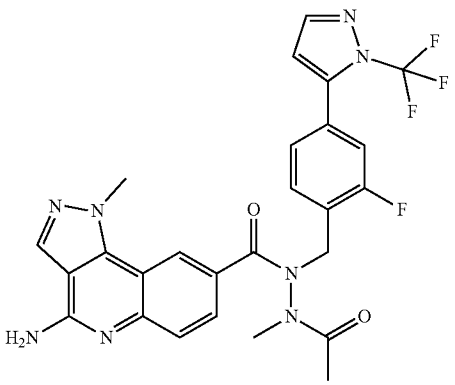

Example 244: N'-acetyl-4-amino-N-(2-fluoro-4-(1-(trifluoromethyl)-1H-pyrazol-5-yl)benzyl)-N',1-dimethyl-1H-pyrazolo[4,3-c]quinoline-8-carbohydrazide. Prepared following the procedure reported for example 130 starting with intermediates Da-1, Bb-15, 5-(4,4,5,5-tetramethyl-1,3,2-dioxaborolan-2-yl)-1-(trifluoromethyl)-1H-pyrazole. ES/MS: m/z=555.0 $[M+H]^+$. 1H NMR (400 MHz, Methanol-d4) δ 8.66-8.33 (m, 2H), 8.03-7.63 (m, 3H), 7.36 (td, J=14.0, 13.0, 8.1 Hz, 3H), 6.70-6.59 (m, 1H), 5.26-4.89 (m, 2H), 4.56 (s, 0.75H, minor rotamer), 4.53 (s, 2.25H, major rotamer), 3.20 (s, 2.25H, major rotamer), 3.15 (s, 0.75H, minor rotamer), 1.82 (s, 3H).

Example 245

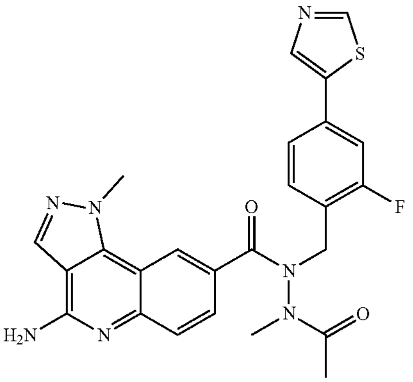

Example 245: N'-acetyl-4-amino-N-(2-fluoro-4-(thiazol-5-yl)benzyl)-N',1-dimethyl-1H-pyrazolo[4,3-c]quinoline-8-carbohydrazide. Prepared following the procedure reported for example 217 starting with intermediates Da-1, Bb-15, and 5-bromothiazole. ES/MS: m/z=504.0 $[M+H]^+$. 1H NMR (400 MHz, Methanol-d4) δ 9.04 (d, J=3.1 Hz, 2H), 8.64-8.42 (m, 2H), 8.28 (d, J=5.8 Hz, 1H), 8.15 (s, 1H), 8.06-7.77 (m, 2H), 7.77-7.45 (m, 3H), 5.10 (d, J=43.9 Hz, 2H), 4.54 (d, J=13.7 Hz, 3H), 3.17 (d, J=17.6 Hz, 3H), 1.85 (s, 3H).

Example 246

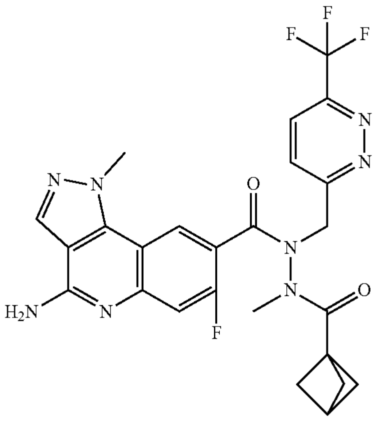

Example 246: 4-amino-N'-(bicyclo[1.1.1]pentane-1-carbonyl)-7-fluoro-N', 1-dimethyl-N-((6-(trifluoromethyl)pyridazin-3-yl)methyl)-1H-pyrazolo[4,3-c]quinoline-8-carbohydrazide. Prepared following general procedure E-1 starting with intermediates Db-1 and Bc-18. ES/MS: m/z=543.0 $[M+H]^+$. 1H NMR (400 MHz, Methanol-d4) δ 8.49 (s, 1H), 8.38 (d, J=6.5 Hz, 1H), 8.28-8.11 (m, 2H), 7.60 (d, J=10.2 Hz, 1H), 5.52-5.12 (m, 2H), 4.49 (s, 3H), 3.58-3.43 (m, 3H), 2.32-1.93 (m, 2H), 1.90-1.66 (m, 5H).

Example 247

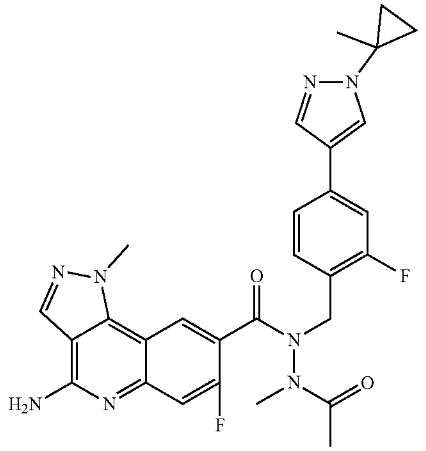

Example 247: N'-acetyl-4-amino-N-(2-fluoro-4-(1-(1-methylcyclopropyl)-1H-pyrazol-4-yl)benzyl)-N',1-dimethyl-1H-pyrazolo[4,3-c]quinoline-8-carbohydrazide. Prepared following the procedure reported for example 217 starting with intermediates Da-1, Bb-15, and 4-bromo-1-(1-methylcyclopropyl)-1H-pyrazole. ES/MS: m/z=541.0 $[M+H]^+$. 1H NMR (400 MHz, Methanol-d4) δ 8.63-8.44 (m, 2H), 8.24-8.05 (m, 1H), 8.04-7.74 (m, 3H), 7.73-7.30 (m, 4H), 5.07 (d, J=81.9 Hz, 2H), 4.54 (d, J=13.7 Hz, 3H), 3.21-2.95 (m, 3H), 1.89 (d, J=53.5 Hz, 3H), 1.65 (d, J=1.4 Hz, 3H), 1.30 (q, J=6.7, 5.8 Hz, 2H), 1.10-0.95 (m, 2H).

Example 248

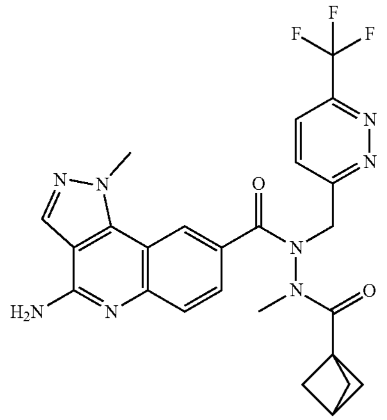

Example 248: 4-amino-N'-(bicyclo[1.1.1]pentane-1-carbonyl)-N',1-dimethyl-N-((6-(trifluoromethyl)pyridazin-3-yl)methyl)-1H-pyrazolo[4,3-c]quinoline-8-carbohydrazide. Prepared following general procedure E-1 starting with intermediates Da-1 and Bc-18. ES/MS: m/z=525.0 $[M+H]^+$. 1H NMR (400 MHz, Methanol-d4) δ 8.51 (d, J=2.1 Hz, 2H), 8.32-8.11 (m, 2H), 7.96-7.75 (m, 2H), 5.50-5.11 (m, 2H), 4.61 (s, 0.2H, minor rotamer), 4.54 (s, 2.8H, major rotamer), 3.50 (s, 3H), 2.39-2.06 (m, 1.6H, major rotamer), 1.96 (s, 0.4H, minor rotamer), 1.94-1.71 (m, 5H).

Example 249

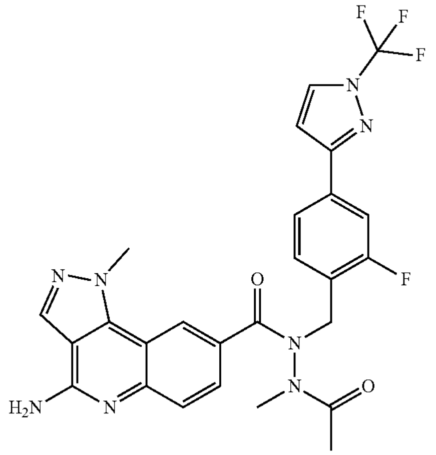

Example 249: N'-acetyl-4-amino-N-(2-fluoro-4-(1-(trifluoromethyl)-1H-pyrazol-3-yl)benzyl)-N',1-dimethyl-1H-pyrazolo[4,3-c]quinoline-8-carbohydrazide. Prepared following the procedure reported for example 130 starting with intermediates Da-1, Bb-15 3-(4,4,5,5-tetramethyl-1,3,2-dioxaborolan-2-yl)-1-(trifluoromethyl)-1H-pyrazole. ES/MS: m/z=555.0 $[M+H]^+$. 1H NMR (400 MHz, Methanol-d4) δ 8.63-8.41 (m, 2H), 8.26 (t, J=2.2 Hz, 1H), 8.06-7.49 (m, 5H), 7.03 (d, J=2.6 Hz, 1H), 5.40-4.93 (m, 2H), 4.54 (d, J=14.1 Hz, 3H), 3.15 (d, J=6.5 Hz, 3H), 1.85 (s, 3H).

Example 250

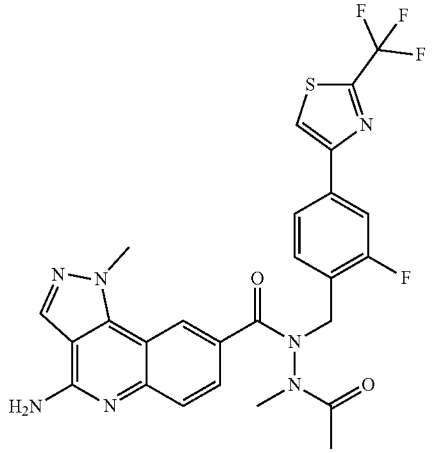

Example 250: N'-acetyl-4-amino-N-(2-fluoro-4-(2-(trifluoromethyl)thiazol-4-yl)benzyl)-N',1-dimethyl-1H-pyrazolo[4,3-c]quinoline-8-carbohydrazide. Prepared following the procedure reported for example 217 starting with intermediates Da-1, Bb-15, and 4-bromo-2-(trifluoromethyl)thiazole. ES/MS: m/z=572.0 $[M+H]^+$. 1H NMR (400 MHZ, Methanol-d4) δ 8.66-8.45 (m, 2H), 8.36 (d, J=9.0 Hz, 1H), 8.10-7.54 (m, 5H), 5.37-4.96 (m, 1H), 4.82 (s, 1H), 4.54 (d, J=13.9 Hz, 3H), 3.16 (d, J=8.8 Hz, 3H), 1.90 (d, J=42.3 Hz, 3H).

Example 251

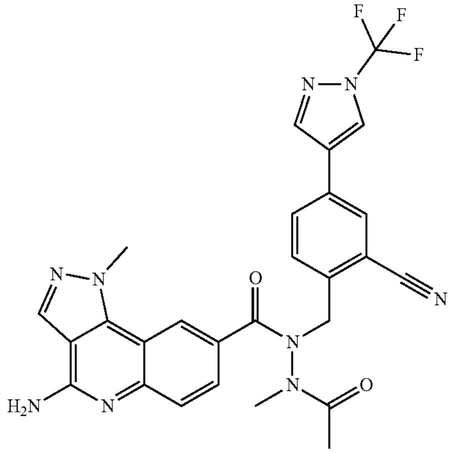

Example 251: N'-acetyl-4-amino-N-(2-cyano-4-(1-(trifluoromethyl)-1H-pyrazol-4-yl)benzyl)-N',1-dimethyl-1H-pyrazolo[4,3-c]quinoline-8-carbohydrazide. Prepared following the procedure reported for example 130 starting with intermediates Da-1, Bb-24, 4-(4,4,5,5-tetramethyl-1,3,2-dioxaborolan-2-yl)-1-(trifluoromethyl)-1H-pyrazole. ES/MS: m/z=562.0 $[M+H]^+$. 1H NMR (400 MHz, Methanol-d4) δ 8.79 (d, J=5.5 Hz, 1H), 8.66-8.46 (m, 2H), 8.34 (s, 1H), 8.22-8.12 (m, 1H), 8.12-7.99 (m, 1H), 7.99-7.72 (m, 3H), 5.11 (dd, J=81.0, 14.5 Hz, 2H), 4.54 (d, J=13.3 Hz, 3H), 3.16 (d, J=52.4 Hz, 3H), 1.88 (s, 3H).

Example 252

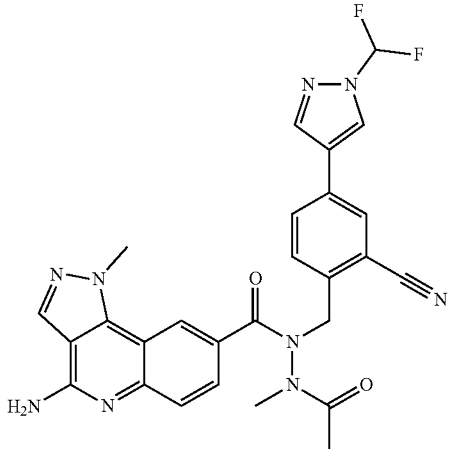

Example 252: N'-acetyl-4-amino-N-(2-cyano-4-(1-(difluoromethyl)-1H-pyrazol-4-yl)benzyl)-N',1-dimethyl-1H-pyrazolo[4,3-c]quinoline-8-carbohydrazide. Prepared following the procedure reported for example 130 starting with intermediates Da-1, Bb-24, 1-(difluoromethyl)-4-(4,4,5,5-tetramethyl-1,3,2-dioxaborolan-2-yl)-1H-pyrazole. ES/MS: m/z=544.0 $[M+H]^+$. 1H NMR (400 MHz, Methanol-d4) δ 8.69-8.58 (m, 1H), 8.58-8.47 (m, 2H), 8.21 (s, 1H), 8.13 (dd, J=17.9, 1.9 Hz, 1H), 8.08-7.95 (m, 1H), 7.95-7.69 (m, 3H), 7.47 (d, J=59.7 Hz, 1H), 5.36-4.92 (m, 2H), 4.54 (d, J=13.3 Hz, 3H), 3.21 (s, 2H), 3.09 (s, 1H), 1.88 (s, 3H).

Example 253

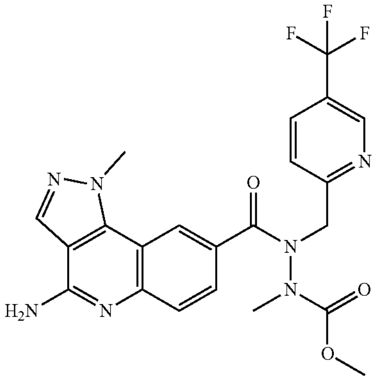

Example 253: methyl 2-(4-amino-1-methyl-1H-pyrazolo[4,3-c]quinoline-8-carbonyl)-1-methyl-2-((5-(trifluoromethyl)pyridin-2-yl)methyl)hydrazine-1-carboxylate. Prepared following general procedure E-1 starting with intermediates Da-1 and Bd-33. ES/MS: m/z=488.0 $[M+H]^+$. 1H NMR (400 MHz, Methanol-d4) δ 8.92 (s, 2H), 8.50 (s, 2H), 8.19 (d, J=8.2 Hz, 2H), 7.82 (d, J=8.5 Hz, 1H), 4.53 (s, 5H), 3.59 (s, 2H), 3.14 (d, J=8.0 Hz, 4H).

Example 254

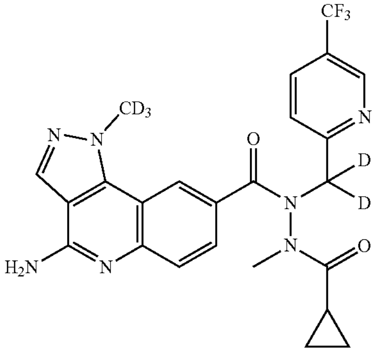

Example 254: 4-amino-N'-(cyclopropanecarbonyl)-N'-methyl-1-(methyl-d3)-N-((5-(trifluoromethyl)pyridin-2-yl)methyl-d2)-1H-pyrazolo[4,3-c]quinoline-8-carbohydrazide. Prepared following general procedure E-1 starting with intermediates Da-9 and Bq-3. $^1H$ NMR (400 MHz, DMSO-$d_6$) δ 13.58 (brs, 1H), 9.68 (brs, 1H), 9.18-8.79 (m, 2H), 8.63 (s, 1H), 8.55-8.20 (m, 2H), 8.04-7.74 (m, 3H), 3.35 (s, 1H minor rotamer), 3.10 (s, 2H major rotamer), 1.87 (brs, 0.67H major rotamer), 1.65 (brs, 0.33H minor rotamer), 0.75-0.57 (m, 1.2H minor rotamer), 0.54-0.18 (m, 2.8H major rotamer). ES/MS: m/z=503.3 $[M+H]^+$.

Example 255

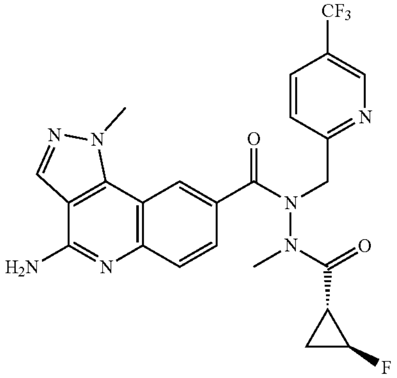

Example 255: 4-amino-N'-((1R,2S)-2-fluorocyclopropane-1-carbonyl)-N',1-dimethyl-N-((5-(trifluoromethyl) pyridin-2-yl)methyl)-1H-pyrazolo[4,3-c]quinoline-8-carbohydrazide. Prepared following general procedure E-1 starting with intermediates Da-1 and Bc-19. $^1H$ NMR (400 MHz, DMSO-$d_6$) δ 13.76 (brs, 1H), 9.70 (brs, 1H), 9.05 (brs, 1H), 8.99 (s, 1H), 8.64 (s, 1H), 8.48-8.15 (m, 1H), 8.18-7.56 (m, 2H), 5.54-4.77 (m, 2H), 4.64-4.30 (m, 4H), 3.42 (s, 1H minor rotamer), 3.13 (s, 2H major rotamer), 2.47-2.26 (m, 1H), 1.54-0.63 (m, 3H). ES/MS: m/z=516.2 $[M+H]^+$.

Example 256

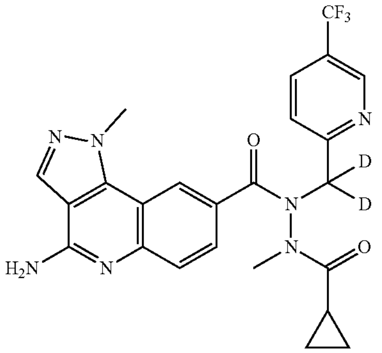

Example 256: 4-amino-N'-(cyclopropanecarbonyl)-N',1-dimethyl-N-((5-(trifluoromethyl)pyridin-2-yl)methyl-d2)-1H-pyrazolo[4,3-c]quinoline-8-carbohydrazide. Prepared following general procedure E-1 starting with intermediates Da-1 and Bq-3. $^1H$ NMR (400 MHz, DMSO-$d_6$) δ 13.68 (brs, 1H), 9.68 (s, 1H), 9.15-8.76 (m, 2H), 8.63 (s, 1H), 8.52-8.16 (m, 2H), 8.10-7.58 (m, 3H), 4.48 (s, 3H), 3.35 (s, 1H minor rotamer), 3.10 (s, 2H major rotamer), 1.86 (brs, 0.67H major rotamer), 1.65 (brs, 0.33H minor rotamer), 0.86-0.55 (m, 1.2H minor rotamer), 0.41 (s, 2.8H major rotamer). ES/MS: m/z=500.3 $[M+H]^+$.

Example 257

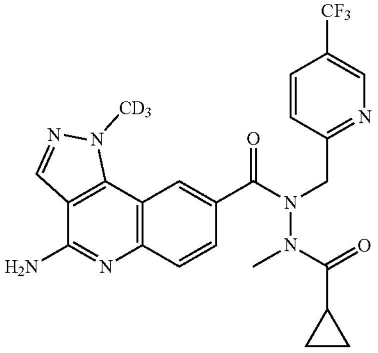

Example 257: 4-amino-N'-(cyclopropanecarbonyl)-N'-methyl-1-(methyl-d3)-N-((5-(trifluoromethyl)pyridin-2-yl) methyl)-1H-pyrazolo[4,3-c]quinoline-8-carbohydrazide. Prepared following general procedure E-1 starting with intermediates Da-9 and Bd-8. $^1H$ NMR (400 MHz, DMSO-$d_6$) δ 13.64 (brs, 1H), 9.68 (brs, 1H), 9.24-8.79 (m, 2H), 8.63 (s, 1H), 8.52-8.20 (m, 2H), 8.11-7.63 (m, 3H), 5.40-4.65 (m, 2H), 3.35 (s, 1H minor rotamer), 3.10 (s, 2H major rotamer), 1.87 (s, 0.67H major rotamer), 1.65 (s, 0.33H minor rotamer), 0.92-0.54 (m, 1.2H minor rotamer), 0.54-0.09 (m, 2.8H major rotamer). ES/MS: m/z=501.2 $[M+H]^+$.

Example 258

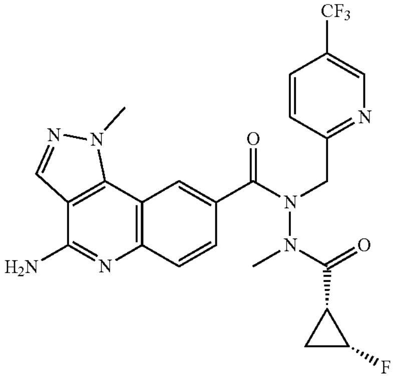

Example 258: 4-amino-N'-((1R,2R)-2-fluorocyclopropane-1-carbonyl)-N',1-dimethyl-N-((5-(trifluoromethyl) pyridin-2-yl)methyl)-1H-pyrazolo[4,3-c]quinoline-8-carbohydrazide. Prepared following general procedure E-1 starting with intermediates Da-1 and Bc-20. $^1H$ NMR (400 MHz, DMSO-$d_6$) δ 13.39 (brs, 1H), 9.65 (brs, 1H), 9.10-8.66 (m, 1H), 8.66-8.56 (m, 1H), 8.54-8.13 (m, 2H), 8.05-7.65 (m, 3H), 5.34-4.62 (m, 2H), 4.55-4.41 (m, 2H), 4.39 (s, 1H), 3.28 (s, 2H major rotamer), 3.24 (s, 1H minor rotamer), 3.07 (s, 1H), 2.31-1.89 (m, 1H), 1.49-0.66 (m, 2H). ES/MS: m/z=516.2 $[M+H]^+$.

Example 259

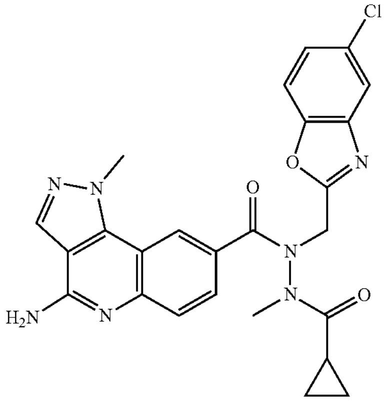

Example 259: 4-amino-N-((5-chlorobenzo[d]oxazol-2-yl)methyl)-N'-(cyclopropanecarbonyl)-N',1-dimethyl-1H-pyrazolo[4,3-c]quinoline-8-carbohydrazide. Prepared following general procedure E-1 starting with intermediates Da-1 and Bb-25, and purified by reverse phase chromatography using CAN 0.5% TFA and water 0.5% TFA as the mobile phase. $^1$H NMR (400 MHz, DMSO-$d_6$) δ 8.50 (brs, 1H), 8.27 (s, 0.8H major rotamer), 8.26 (s, 0.2H minor rotamer), 7.93 (d, J=2.1 Hz, 0.8H major rotamer), 7.91-7.88 (m, 0.2H minor rotamer), 7.82 (d, J=8.8 Hz, 1H), 7.73 (brs, 1H), 7.65-7.54 (m, 1H), 7.53-7.44 (m, 1H), 7.27 (s, 1.6H major rotamer), 7.20 (s, 0.4H minor rotamer), 5.39 (d, J=16.3 Hz, 0.8H major rotamer), 5.31-5.13 (m, 1H), 4.98 (d, J=16.0 Hz, 0.2H minor rotamer), 4.39 (s, 2.4H major rotamer), 4.35 (s, 0.6H minor rotamer), 3.43 (s, 0.6H minor rotamer), 3.16 (s, 2.4H major rotamer), 2.16-2.05 (m, 1H), 1.04-0.22 (m, 4H). ES/MS: m/z=504.2 $[M+H]^+$.

Example 260

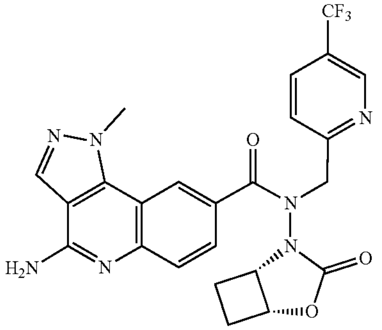

Example 260: 4-amino-1-methyl-N-((1R,5S)-3-oxo-2-oxa-4-azabicyclo[3.2.0]heptan-4-yl)-N-((5-(trifluoromethyl)pyridin-2-yl)methyl)-1H-pyrazolo[4,3-c]quinoline-8-carboxamide. Prepared following general procedure E-1 starting with intermediates Da-1 and Ba-77. $^1$H NMR (400 MHz, DMSO-$d_6$) δ 9.68 (brs, 1H), 9.15-8.75 (m, 2H), 8.68-8.54 (m, 2H), 8.37-8.09 (m, 2H), 8.03-7.74 (m, 3H), 5.46-5.04 (m, 1H), 5.03-4.78 (m, 1H), 4.43 (s, 3H), 4.28-4.09 (m, 2H), 2.45-2.24 (m, 1H), 2.24-1.78 (m, 3H). ES/MS: m/z=512.2 $[M+H]^+$.

Example 261

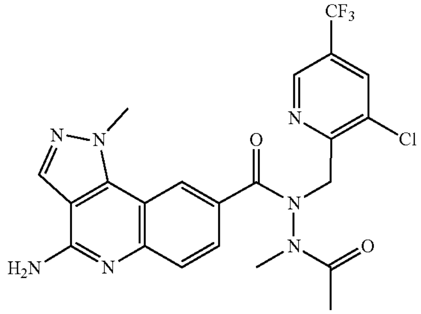

Example 261: N'-acetyl-4-amino-N-((3-chloro-5-(trifluoromethyl)pyridin-2-yl)methyl)-N',1-dimethyl-1H-pyrazolo[4,3-c]quinoline-8-carbohydrazide. Prepared following general procedure E-1 starting with intermediates Da-1 and Bb-26. $^1$H NMR (400 MHz, DMSO-$d_6$) δ 13.63 (brs, 1H), 9.65 (brs, 1H), 8.98 (brs, 1H), 8.62 (s, 1H), 8.57-8.27 (m, 2H), 8.06-7.73 (m, 2H), 5.58-5.25 (m, 1H), 5.12 (d, J=16.9 Hz, 0.6H major rotamer), 4.84 (d, J=16.0 Hz, 0.4H minor rotamer), 4.45 (s, 1.8H major rotamer), 4.43 (s, 1.2H minor rotamer), 3.16 (s, 1H), 3.07 (s, 2H), 2.07 (s, 1.8H major rotamer), 1.81 (s, 1.2H minor rotamer). ES/MS: m/z=506.2 $[M+H]^+$.

Example 262

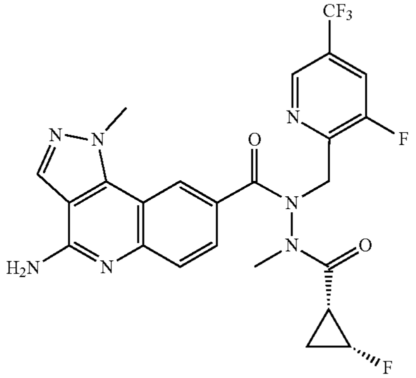

Example 262: 4-amino-N-((3-fluoro-5-(trifluoromethyl)pyridin-2-yl)methyl)-N'-((1R,2R)-2-fluorocyclopropane-1-carbonyl)-N',1-dimethyl-1H-pyrazolo[4,3-c]quinoline-8-carbohydrazide. Prepared following general procedure E-1 starting with intermediates Da-1 and Bc-21. $^1$H NMR (400 MHz, DMSO-$d_6$) § 13.63 (s, 1H), 9.67 (s, 1H), 9.13-8.69 (m, 1H), 8.66-8.57 (m, 1H), 8.56-8.21 (m, 2H), 8.16-7.71 (m, 2H), 5.38-4.50 (m, 3H), 4.49-4.31 (m, 3H), 3.46-3.06 (m, 3H), 2.36-1.80 (m, 1H), 1.59-0.85 (m, 3H). ES/MS: m/z=534.2 $[M+H]^+$.

Example 263

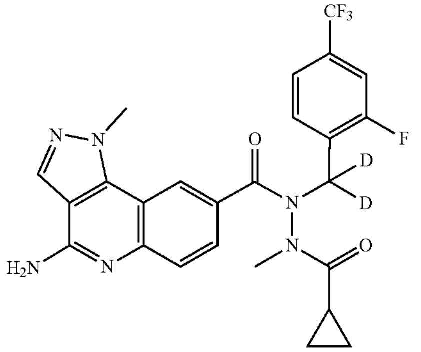

Example 263: 4-amino-N'-(cyclopropanecarbonyl)-N-((2-fluoro-4-(trifluoromethyl)phenyl)methyl-d2)-N',1-dimethyl-1H-pyrazolo[4,3-c]quinoline-8-carbohydrazide. Prepared following general procedure E-1 starting with intermediates Da-1 and Bq-1 $^1$H NMR (400 MHz, DMSO-$d_6$) δ 13.66 (brs, 1H), 9.67 (brs, 1H), 8.98 (brs, 1H), 8.62 (s, 1H), 8.48 (s, 0.7H major rotamer), 8.33 (s, 0.3H minor rotamer), 8.04-7.55 (m, 5H), 4.46 (s, 2.1H major rotamer), 4.44 (s, 0.9H minor rotamer), 3.28 (s, 0.9H minor rotamer), 3.08 (s, 2.1H major rotamer), 1.70-1.53 (m, 1H), 0.80-0.37 (m, 2H), 0.38-0.14 (m, 2H). ES/MS: m/z=517.2 [M+H]$^+$.

Example 264

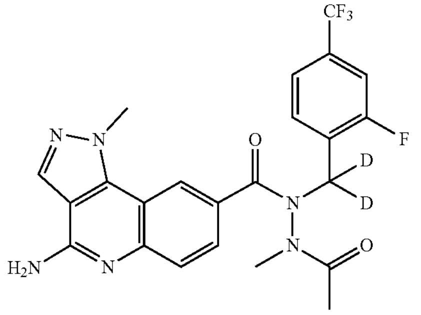

Example 264: N'-acetyl-4-amino-N-((2-fluoro-4-(trifluoromethyl)phenyl)methyl-d2)—N',1-dimethyl-1H-pyrazolo[4,3-c]quinoline-8-carbohydrazide. Prepared following general procedure E-1 starting with intermediates Da-1 and Bq-2. $^1$H NMR (400 MHz, DMSO-$d_6$) δ 13.58 (brs, 1H), 9.65 (brs, 1H), 8.87 (brs, 1H), 8.63 (s, 0.35H minor rotamer), 8.62 (s, 0.65H major rotamer), 8.45 (d, J=1.8 Hz, 0.35H minor rotamer), 8.35 (s, 0.65H major rotamer), 7.98-7.58 (m, 5H), 4.47 (s, 1.05H minor rotamer), 4.44 (s, 1.95H major rotamer), 3.16 (s, 1.95H major rotamer), 3.01 (s, 1.05H minor rotamer), 1.78 (s, 1.95H major rotamer), 1.73 (s, 1.05H minor rotamer). ES/MS: m/z=491.2 [M+H]$^+$.

Example 265

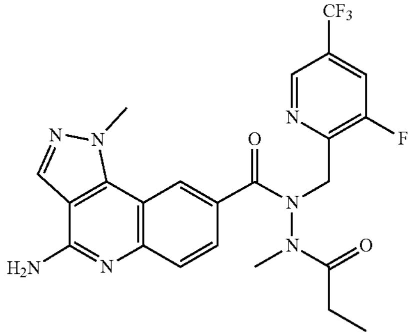

Example 265: 4-amino-N-((3-fluoro-5-(trifluoromethyl)pyridin-2-yl)methyl)-N',1-dimethyl-N'-propionyl-1H-pyrazolo[4,3-c]quinoline-8-carbohydrazide. Prepared following general procedure E-1 starting with intermediates Da-1 and Bd-34. $^1$H NMR (400 MHz, DMSO-$d_6$) δ 13.70 (brs, 1H), 9.68 (brs, 1H), 8.96 (brs, 2H), 8.63 (s, 0.5H rotamer), 8.61 (s, 0.5H rotamer), 8.60-8.26 (m, 1H), 8.11-7.72 (m, 2H), 5.47-4.90 (m, 2H), 4.46 (s, 1.5H rotamer), 4.42 (s, 1.5H rotamer), 3.19 (s, 1.5H rotamer), 3.14 (brs, 1.5H rotamer), 2.44-1.94 (m, 2H), 0.92-0.76 (m, 1.5H rotamer), 0.75-0.60 (m, 1.5H rotamer). ES/MS: m/z=506.2 [M+H]$^+$.

Example 266

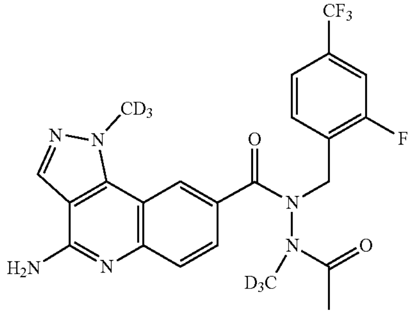

Example 266: N'-acetyl-4-amino-N-(2-fluoro-4-(trifluoromethyl)benzyl)-N',1-bis(methyl-d3)-1H-pyrazolo[4,3-c]quinoline-8-carbohydrazide. Prepared following general procedure E-1 starting with intermediates Da-9 and Bd-35. $^1$H NMR (400 MHz, DMSO-$d_6$) δ 13.56 (brs, 1H), 9.65 (brs, 1H), 8.86 (brs, 1H), 8.63 (s, 0.35H minor rotamer), 8.62 (s, 0.65H major rotamer), 8.45 (d, J=1.8 Hz, 0.35H minor rotamer), 8.34 (s, 0.65H major rotamer), 7.95-7.59 (m, 5H), 5.05 (d, J=15.1 Hz, 1.3H major rotamer), 4.76 (d, J=15.2 Hz, 0.7H minor rotamer), 1.77 (s, 1.95H major rotamer), 1.73 (s, 1.05H minor rotamer). ES/MS: m/z=495.3 [M+H]$^+$.

Example 267

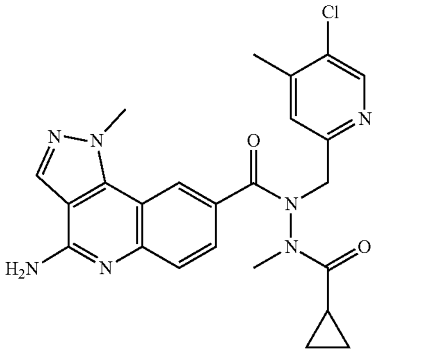

Example 267: 4-amino-N-((5-chloro-4-methylpyridin-2-yl)methyl)-N'-(cyclopropanecarbonyl)-N',1-dimethyl-1H-pyrazolo[4,3-c]quinoline-8-carbohydrazide. Prepared following general procedure E-1 starting with intermediates Da-1 and Bp-2. $^1$H NMR (400 MHz, DMSO-$d_6$) δ 13.55 (brs, 1H), 9.67 (brs, 1H), 8.87 (brs, 1H), 8.63 (s, 1H), 8.58-7.75 (m, 3H), 7.69-7.36 (m, 1H), 5.29-4.82 (m, 2H), 4.69-4.36 (m, 3H), 3.27 (s, 1H minor rotamer), 3.05 (s, 2H major rotamer), 2.38 (s, 3H), 2.05-1.57 (m, 1H), 0.76-0.56 (m, 2H), 0.54-0.26 (m, 2H). ES/MS: m/z=478.3 [M+H]$^+$.

Example 268

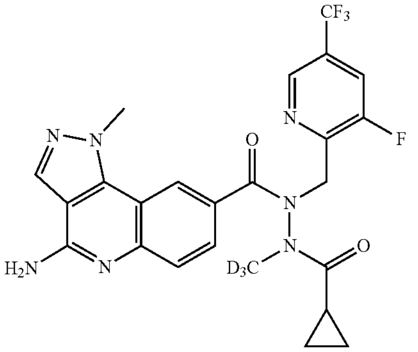

Example 268: 4-amino-N'-(cyclopropanecarbonyl)-N-((3-fluoro-5-(trifluoromethyl)pyridin-2-yl)methyl)-1-methyl-N'-(methyl-d3)-1H-pyrazolo[4,3-c]quinoline-8-carbohydrazide. Prepared following general procedure E-1 starting with intermediates Da-1 and Bd-36. $^1$H NMR (400 MHz, DMSO-$d_6$) δ 13.57 (brs, 1H), 9.66 (brs, 1H), 8.91 (brs, 1H), 8.86 (s, 1H), 8.62 (s, 1H), 8.52-8.25 (m, 2H), 8.11-7.71 (m, 2H), 5.47-4.86 (m, 2H), 4.47 (s, 2.4H major rotamer), 4.42 (s, 0.6H minor rotamer), 2.04-1.92 (m, 0.8H major rotamer), 1.70-1.52 (m, 0.2H minor rotamer), 0.80-0.59 (m, 1H), 0.58-0.24 (m, 3H). ES/MS: m/z=519.3 [M+H]$^+$.

Example 269

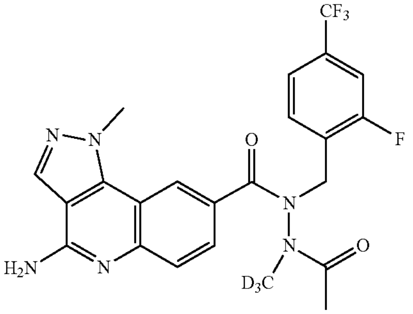

Example 269: N'-acetyl-4-amino-N-(2-fluoro-4-(trifluoromethyl)benzyl)-1-methyl-N'-(methyl-d3)-1H-pyrazolo[4,3-c]quinoline-8-carbohydrazide. Prepared following general procedure E-1 starting with intermediates Da-1 and Bd-35. $^1$H NMR (400 MHz, DMSO-$d_6$) δ 13.57 (brs, 1H), 9.66 (brs, 1H), 8.88 (brs, 1H), 8.63 (s, 0.35H minor rotamer), 8.62 (s, 0.65H major rotamer), 8.45 (d, J=1.8 Hz, 0.35H minor rotamer), 8.35 (s, 0.65H major rotamer), 7.97-7.56 (m, 5H), 5.05 (d, J=15.2 Hz, 1H), 4.76 (d, J=15.2 Hz, 1H), 4.47 (s, 1.05H minor rotamer), 4.44 (s, 1.95H major rotamer), 1.77 (s, 1.95H major rotamer), 1.73 (s, 1.05H minor rotamer). ES/MS: m/z=492.2 [M+H]$^+$.

Example 270

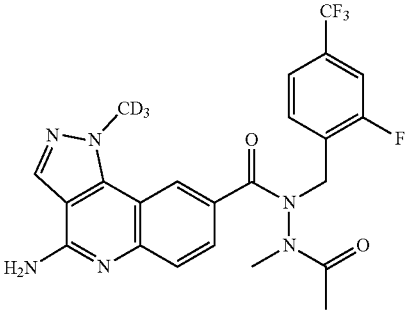

Example 270: N'-acetyl-4-amino-N-(2-fluoro-4-(trifluoromethyl)benzyl)-N'-methyl-1-(methyl-d3)-1H-pyrazolo[4,3-c]quinoline-8-carbohydrazide. Prepared following general procedure E-1 starting with intermediates Da-9 and Ba-34. $^1$H NMR (400 MHz, DMSO-$d_6$) δ 13.45 (brs, 1H), 9.65 (brs, 1H), 8.75 (brs, 1H), 8.63 (s, 0.35H minor rotamer), 8.62 (s, 0.65H major rotamer), 8.45 (d, J=1.8 Hz, 0.35H minor rotamer), 8.35 (s, 0.65H major rotamer), 7.95-7.58 (m, 4H), 5.05 (d, J=15.1 Hz, 1H), 4.76 (d, J=15.1 Hz, 1H), 3.17 (s, 1.95H major rotamer), 3.01 (s, 1.05H minor rotamer), 1.78 (s, 1.95H major rotamer), 1.73 (s, 1.05H minor rotamer). ES/MS: m/z=492.3 [M+H]$^+$.

Example 271

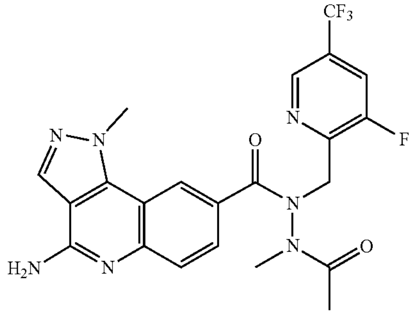

Example 271: N'-acetyl-4-amino-N-((3-fluoro-5-(trifluoromethyl)pyridin-2-yl)methyl)-N',1-dimethyl-1H-pyrazolo[4,3-c]quinoline-8-carbohydrazide. Prepared following general procedure E-1 starting with intermediates Da-1 and Ba-73. $^1$H NMR (400 MHz, DMSO-$d_6$) δ 13.71 (brs, 1H), 9.66 (brs, 1H), 8.94 (brs, 2H), 8.87 (s, 1H), 8.62 (s, 0.5H $1^{st}$ rotamer), 8.62 (s, 0.5H $2^{nd}$ rotamer), 8.48-8.27 (m, 1.5H), 7.91-7.77 (m, 1.5H), 5.53-5.16 (m, 1H), 5.09 (d, J=16.2 Hz, 0.5H $1^{st}$ rotamer), 4.90 (d, J=15.4 Hz, 0.5H $2^{nd}$ rotamer), 4.46 (s, 1.5H $1^{st}$ rotamer), 4.42 (s, 1.5H $2^{nd}$ rotamer), 3.21 (s, 1.5H $1^{st}$ rotamer), 3.09 (s, 1.5H $2^{nd}$ rotamer), 2.00 (s, 1.5H $1^{st}$ rotamer), 1.79 (s, 1.5H $2^{nd}$ rotamer). ES/MS: m/z=490.2 $[M+H]^+$.

Example 272

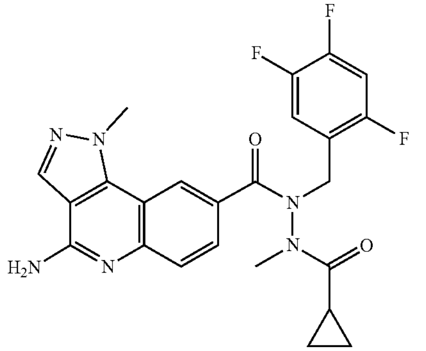

Example 272: 4-amino-N'-(cyclopropanecarbonyl)-N',1-dimethyl-N-(2,4,5-trifluorobenzyl)-1H-pyrazolo[4,3-c]quinoline-8-carbohydrazide. Prepared following general procedure E-1 starting with intermediates Da-1 and Bk-5. $^1$H NMR (400 MHz, DMSO-$d_6$) δ 13.66 (brs, 1H), 9.59 (brs, 1H), 8.86 (brs, 1H), 8.61 (s, 1H), 8.48 (d, J=1.8 Hz, 0.65H major rotamer), 8.33 (s, 0.35H minor rotamer), 7.99-7.51 (m, 4H), 5.26 (brs, 0.65H major rotamer), 4.87 (d, J=14.8 Hz, 0.35H minor rotamer), 4.80-4.68 (m, 1H), 4.46 (s, 1.95H major rotamer), 4.44 (s, 1.05H minor rotamer), 3.27 (s, 1.05H minor rotamer), 3.06 (s, 1.95H major rotamer), 1.74-1.55 (m, 1H), 0.82-0.47 (m, 2H), 0.45-0.18 (m, 2H). ES/MS: m/z=483.2 $[M+H]^+$.

Example 273

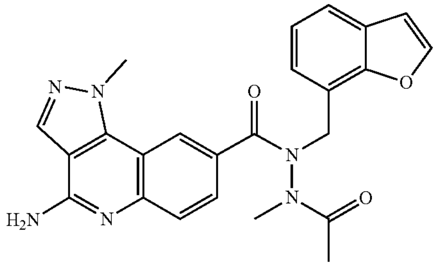

Example 273: N'-acetyl-4-amino-N-(benzofuran-7-ylmethyl)-N',1-dimethyl-1H-pyrazolo[4,3-c]quinoline-8-carbohydrazide Prepared following general procedure E-1 starting with intermediates Da-1 and Bb-27. $^1$H NMR (400 MHz, DMSO-$d_6$) δ 13.66 (brs, 1H), 9.66 (brs, 1H), 8.95 (brs, 1H), 8.63 (s, 0.6H major rotamer), 8.61 (s, 0.4H minor rotamer), 8.46 (s, 0.6H major rotamer), 8.34 (s, 0.4H minor rotamer), 8.11-7.76 (m, 3H), 7.71-7.62 (m, 1H), 7.45 (d, J=7.3 Hz, 0.4H minor rotamer), 7.32-7.23 (m, 1H), 7.00 (s, 0.6H major rotamer), 5.52-5.35 (m, 0.4H minor rotamer), 5.29 (brs, 0.6H major rotamer), 5.13 (d, J=14.1 Hz, 0.6H major rotamer), 4.78 (d, J=14.8 Hz, 0.4H minor rotamer), 4.46 (s, 1.8H major rotamer), 4.43 (s, 1.2H minor rotamer), 2.93 (s, 1.8H major rotamer), 2.90 (s, 1.2H minor rotamer), 1.74 (s, 1.2H minor rotamer), 1.53 (brs, 1.8H major rotamer). ES/MS: m/z=443.2 $[M+H]^+$.

Example 274

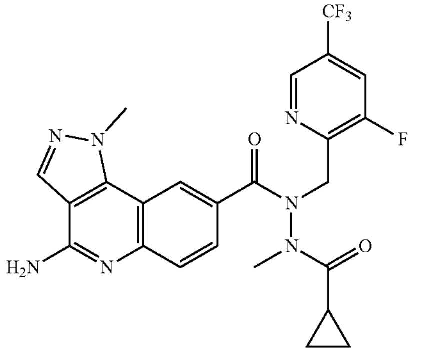

Example 274: 4-amino-N'-(cyclopropanecarbonyl)-N-((3-fluoro-5-(trifluoromethyl)pyridin-2-yl)methyl)-N',1-dimethyl-1H-pyrazolo[4,3-c]quinoline-8-carbohydrazide. Prepared following general procedure E-1 starting with intermediates Da-1 and Ba-74. $^1$H NMR (400 MHz, DMSO-$d_6$) δ 13.63 (brs, 1H), 9.66 (brs, 1H), 8.91 (brs, 1H), 8.86 (brs, 1H), 8.62 (s, 0.7H major rotamer), 8.61-8.21 (m, 1H+0.3H minor rotamer), 8.09-7.70 (m, 2H), 5.37 (brs, 0.7H major rotamer), 5.28-5.08 (m, 1H), 4.99 (d, J=14.9 Hz, 0.3H minor rotamer), 4.47 (s, 2.1H major rotamer), 4.42 (s, 0.9H minor rotamer), 3.35 (s, 0.9H minor rotamer), 3.12 (s, 2.1H major rotamer), 1.97-1.89 (m, 0.7H major rotamer), 1.62 (brs, 0.3H minor rotamer), 0.83-0.63 (m, 1H), 0.58-0.27 (m, 3H). ES/MS: m/z=443.2 $[M+H]^+$.

Example 275

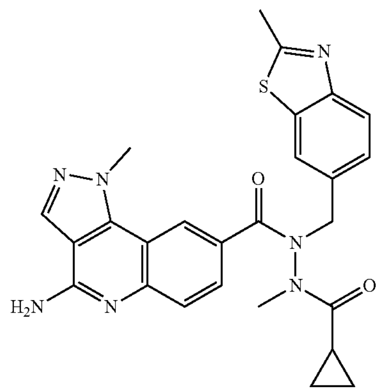

Example 275: 4-amino-N'-(cyclopropanecarbonyl)-N',1-dimethyl-N-((2-methylbenzo[d]thiazol-6-yl)methyl)-1H-pyrazolo[4,3-c]quinoline-8-carbohydrazide. Prepared following general procedure E-1 starting with intermediates Da-1 and Bk-6. $^1$H NMR (400 MHz, DMSO-$d_6$) δ 13.54 (brs, 1H), 9.65 (brs, 1H), 8.87 (brs, 1H), 8.62 (s, 1H), 8.48 (d, J=1.7 Hz, 0.7H major rotamer), 8.34 (s, 0.3H minor rotamer), 8.13 (brs, 0.7H major rotamer), 8.00-7.86 (m, 1H+0.3H minor rotamer), 7.86-7.75 (m, 1H), 7.64-7.53 (m, 1H), 5.39-5.15 (m, 1H), 4.93 (d, J=14.4 Hz, 0.7H major rotamer), 4.60 (d, J=14.6 Hz, 0.3H minor rotamer), 4.45 (s, 3H), 3.12 (s, 0.9H minor rotamer), 3.04 (s, 2.1H major rotamer), 2.80 (s, 3H), 1.70-1.47 (m, 1H), 0.70-0.38 (m, 2H), 0.32--0.03 (m, 2H). ES/MS: m/z=500.2 [M+H]$^+$.

Example 276

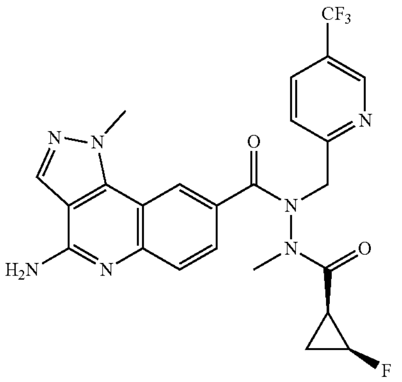

Example 276: 4-amino-N'-((1S,2S)-2-fluorocyclopropane-1-carbonyl)-N',1-dimethyl-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bc-22. $^1$H NMR (400 MHz, DMSO-$d_6$) δ 13.61 (brs, 1H), 9.67 (brs, 1H), 9.11-8.77 (m, 2H), 8.63 (s, 0.7H major rotamer), 8.61 (s, 0.3H minor rotamer), 8.48-8.15 (m, 2H), 7.99-7.68 (m, 2H), 5.31-4.55 (m, 2H), 4.49 (s, 2.1H major rotamer), 4.39 (s, 0.9H minor rotamer), 3.37 (s, 0.9H minor rotamer), 3.28 (s, 2.1H major rotamer), 3.16-3.03 (m, 1H), 2.26-1.88 (m, 1H), 1.67-1.28 (m, 1H), 1.19-0.79 (m, 1H). ES/MS: m/z=516.2 [M+H]$^+$.

Example 277

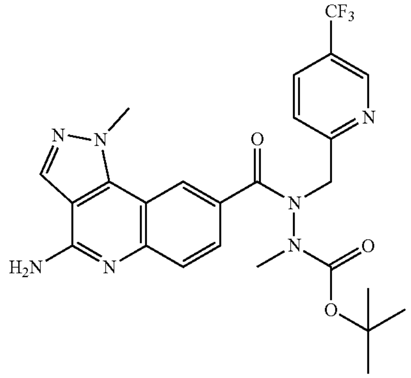

Example 277: tert-butyl 2-(4-amino-1-methyl-1H-pyrazolo[4,3-c]quinoline-8-carbonyl)-2-((5-(trifluoromethyl)pyridin-2-yl)methyl)hydrazine-1-carboxylate. Prepared following general procedure E-1 starting with intermediates Da-1 and Ba-75. $^1$H NMR (400 MHZ, DMSO-$d_6$) δ 13.41 (brs, 1H), 9.91 (brs, 1H), 9.62 (brs, 1H), 8.97 (s, 1H), 8.75 (brs, 1H), 8.63 (s, 1H), 8.47 (s, 1H), 8.29 (d, J=7.6 Hz, 1H), 7.90 (d, J=8.4 Hz, 1H), 7.84 (s, 1H), 7.81 (s, 1H), 5.25-4.58 (m, 2H), 4.49 (s, 3H), 1.14 (s, 7H major rotamer), 1.07 (s, 2H minor rotamer). ES/MS: m/z=516.0 [M+H]$^+$.

Example 278

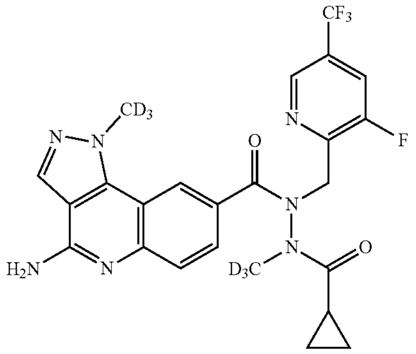

Example 278: 4-amino-N'-(cyclopropanecarbonyl)-N-((3-fluoro-5-(trifluoromethyl)pyridin-2-yl)methyl)-N',1-bis(methyl-d3)-1H-pyrazolo[4,3-c]quinoline-8-carbohydrazide. Prepared following general procedure E-1 starting with intermediates Da-9 and Bd-36. $^1$H NMR (400 MHz, DMSO-$d_6$) δ 13.37 (brs, 1H), 9.65 (brs, 1H), 8.98-8.83 (m, 1H), 8.69 (brs, 1H), 8.62 (s, 1H), 8.54-8.22 (m, 2H), 8.00-7.70 (m, 2H), 5.45-4.88 (m, 2H), 2.03-1.90 (m, 1H), 0.78-0.64 (m, 1H), 0.55-0.28 (m, 3H). ES/MS: m/z=522.2 [M+H]$^+$.

Example 279

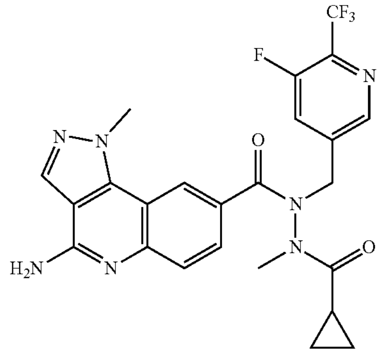

Example 279: 4-amino-N'-(cyclopropanecarbonyl)-N-((5-fluoro-6-(trifluoromethyl)pyridin-3-yl)methyl)-N',1-dimethyl-1H-pyrazolo[4,3-c]quinoline-8-carbohydrazide. Prepared following general procedure E-1 starting with intermediates Da-1 and Bd-37 $^{1}$H NMR (400 MHz, DMSO-$d_6$) δ 13.57 (brs, 1H), 9.66 (brs, 1H), 8.89 (brs, 1H), 8.76 (s, 1H), 8.63 (s, 1H), 8.51 (s, 0.6H major rotamer), 8.38 (s, 0.4H minor rotamer), 8.25 (d, J=11.1 Hz, 1H), 7.96 (d, J=8.6 Hz, 1H), 7.86-7.75 (m, 1H), 5.30 (brs, 0.6H major rotamer), 5.11-4.83 (m, 1H+0.3H minor rotamer), 4.46 (s, 3H), 3.42 (s, 1.2H minor rotamer), 3.15 (s, 1.8H major rotamer), 1.68 (brs, 1H), 0.88-0.16 (m, 4H). ES/MS: m/z=522.2 $[M+H]^+$.

Example 280

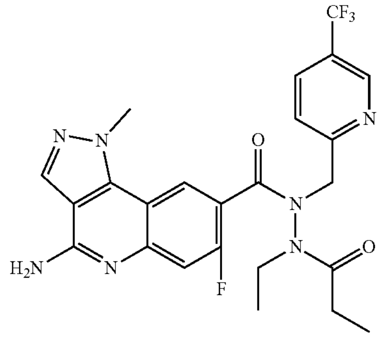

Example 280: 4-amino-N'-ethyl-7-fluoro-1-methyl-N'-propionyl-N-((5-(trifluoromethyl)pyridin-2-yl)methyl)-1H-pyrazolo[4,3-c]quinoline-8-carbohydrazide. Prepared using general procedure E-1 starting with intermediates Db-1 and Bd-38. ES/MS: m/z=518.0 $[M+H]^+$. $^{1}$H NMR (400 MHz, DMSO-$d_6$) δ 9.06 (d, J=2.2 Hz, 0.5H, rotamer), 8.97 (s, 0.5H, rotamer), 8.58 (d, J=4.0 Hz, 1H), 8.52 (d, J=6.6 Hz, 0.4H, rotamer), 8.36-8.23 (m, 1H), 8.18 (d, J=8.5 Hz, 0.4H, rotamer), 7.86 (d, J=8.3 Hz, 0.5H, rotamer), 7.65 (d, J=10.7 Hz, 1H), 7.52 (d, J=8.1 Hz, 0.5H, rotamer), 5.29 (d, J=16.2 Hz, 0.5H, rotamer), 5.18-4.91 (m, 1H), 4.76 (d, J=16.6 Hz, 0.5H, rotamer), 4.43 (d, J=18.0 Hz, 3H), 3.57 (dd, J=14.6, 7.2 Hz, 2H), 2.39-2.15 (m, 1H), 2.10 (q, J=6.8, 4.7 Hz, 0.4H, rotamer), 1.00-0.81 (m, 4H, rotamer), 0.79 (t, J=7.3 Hz, 2H, rotamer).

Example 281

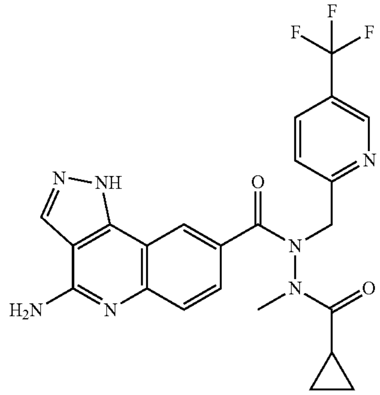

Example 281: 4-amino-N'-(cyclopropanecarbonyl)-N'-methyl-N-((5-(trifluoromethyl)pyridin-2-yl)methyl)-1H-pyrazolo[4,3-c]quinoline-8-carbohydrazide. Prepared following procedure reported for example 202 starting with intermediates Da-8 and Bd-8. ES/MS: m/z=614.0 $[M+H]^+$. ES/MS: m/z=484.0 $[M+H]^+$. $^{1}$H NMR (400 MHZ, Methanol-d4) δ 8.94 (d, J=25.9 Hz, 1H), 8.61 (d, J=61.1 Hz, 1H), 8.39 (s, 0.3H, minor rotamer), 8.18 (s, 1H), 7.80 (dt, J=40.9, 9.1 Hz, 2.6H, major rotamer), 5.36-5.13 (m, 2H), 3.48 (s, 1H, minor rotamer), 3.19 (s, 2H, major rotamer), 1.60 (s, 1H), 0.94-0.38 (m, 4H).

Example 282

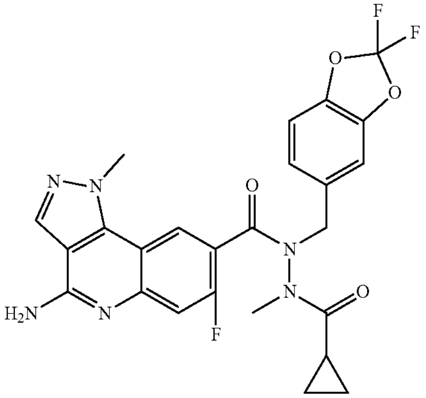

Example 282: 4-amino-N'-(cyclopropanecarbonyl)-N-((2,2-difluorobenzo[d][1,3]dioxol-5-yl)methyl)-7-fluoro-N',1-dimethyl-1H-pyrazolo[4,3-c]quinoline-8-carbohydrazide. Prepared using general procedure E-1 starting with intermediates Db-1 and Bd-39. ES/MS: m/z=527.0 $[M+H]^+$. $^{1}$H NMR (400 MHz, MeOD) δ 8.54 (d, J=6.5 Hz, 0.5H, rotamer), 8.49 (d, J=2.4 Hz, 1H), 8.37 (d, J=6.5 Hz, 0.5H, rotamer), 7.59 (dd, J=10.3, 4.8 Hz, 1H), 7.43 (d, J=21.1 Hz, 1H), 7.34 (t, J=9.4 Hz, 0.5H, rotamer), 7.29 (d, J=5.2 Hz, 0.5H, rotamer), 7.24 (t, J=7.5 Hz, 0.5H, rotamer), 5.31 (d, J=14.5 Hz, 0.5H, rotamer), 5.13 (d, J=14.6 Hz, 0.5H, rotamer), 4.96 (d, J=14.5 Hz, 0.5H, rotamer), 4.76 (d, J=14.6 Hz, 0.5H, rotamer), 4.48 (d, J=9.9 Hz, 3H), 3.29 (s, 1H), 3.09 (s, 2H, major rotamer), 1.66 (d, J=73.6 Hz, 1H), 0.87-0.18 (m, 4H).

Example 283

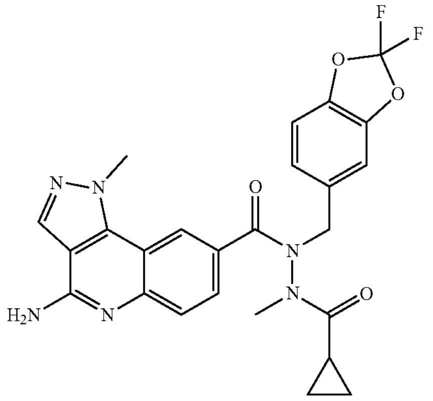

Example 283: 4-amino-N'-(cyclopropanecarbonyl)-N-((2, 2-difluorobenzo[d][1,3]dioxol-5-yl)methyl)-N',1-dimethyl-1H-pyrazolo[4,3-c]quinoline-8-carbohydrazide. Prepared using general procedure E-1 starting with intermediates Da-1 and Bd-39. ES/MS: m/z=509.0 $[M+H]^+$. $^1$H NMR (400 MHz, MeOD) δ 8.60 (d, J=1.7 Hz, 1H), 8.50 (d, J=2.6 Hz, 1H), 7.98 (d, J=8.7 Hz, 0.6H), major rotamer, 7.86 (s, 0.3H, minor rotamer), 7.80 (t, J=8.8 Hz, 1H), 7.45 (s, 1H), 7.32 (t, J=10.9 Hz, 1H), 7.24 (dd, J=14.2, 8.2 Hz, 1H), 5.28 (s, 0.5H, major rotamer), 5.08 (d, J=14.6 Hz, 0.4H, minor rotamer), 4.94 (s, 0.5H, major rotamer), 4.74 (d, J=14.5 Hz, 0.4H, minor rotamer), 4.53 (d, J=4.3 Hz, 3H), 3.30 (s, 1H, minor rotamer), 3.12 (s, 2H, major rotamer), 1.72 (s, 1H), 0.93-0.65 (m, 1H), 0.65-0.29 (m, 4H).

Example 284

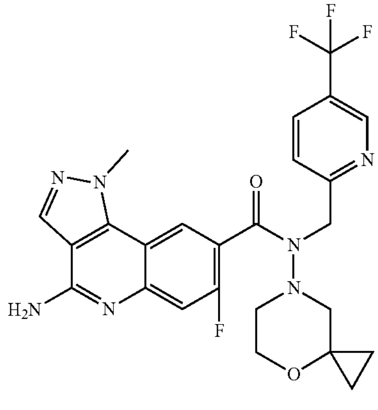

Example 284: 4-amino-7-fluoro-1-methyl-N-(4-oxa-7-azaspiro[2.5]octan-7-yl)-N-((5-(trifluoromethyl)pyridin-2-yl)methyl)-1H-pyrazolo[4,3-c]quinoline-8-carboxamide. Prepared using general procedure E-1 starting with intermediates Db-1 and Bi-8. ES/MS: m/z=530.0 $[M+H]^+$. $^1$H NMR (400 MHz, Methanol-d4) δ 8.91 (dt, J=2.0, 0.9 Hz, 1H), 8.50 (s, 1H), 8.48 (d, J=6.4 Hz, 1H), 8.26-8.08 (m, 1H), 7.76 (d, J=8.3 Hz, 1H), 7.60 (d, J=10.1 Hz, 1H), 5.11 (s, 2H), 4.52 (s, 3H), 3.65 (d, J=11.0 Hz, 1H), 3.46-3.34 (m, 2H), 3.05 (td, J=11.0, 3.3 Hz, 1H), 2.95 (d, J=10.6 Hz, 1H), 2.35 (d, J=10.6 Hz, 1H), 0.68 (dt, J=10.7, 6.4 Hz, 1H), 0.46 (dt, J=10.1, 6.3 Hz, 1H), 0.33 (t, J=6.3 Hz, 1H), −0.10 (s, 1H).

Example 285

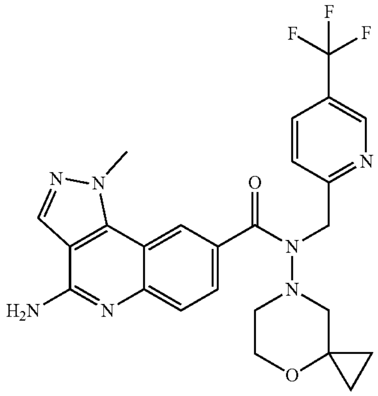

Example 285: 4-amino-1-methyl-N-(4-oxa-7-azaspiro[2.5]octan-7-yl)-N-((5-(trifluoromethyl)pyridin-2-yl)methyl)-1H-pyrazolo[4,3-c]quinoline-8-carboxamide. Prepared using general procedure E-1 starting with intermediates Da-1 and Bi-8. ES/MS: m/z=512.2 $[M+H]^+$. $^1$H NMR (400 MHz, Methanol-d4) δ 8.90 (s, 1H), 8.60 (s, 1H), 8.51 (s, 1H), 8.14 (ddd, J=8.7, 4.3, 2.0 Hz, 2H), 7.81 (d, J=8.6 Hz, 1H), 7.77 (d, J=8.5 Hz, 1H), 5.09 (s, 2H), 4.54 (s, 3H), 3.71 (d, J=11.1 Hz, 1H), 3.59-3.41 (m, 2H), 3.20-2.90 (m, 2H), 2.41 (d, J=10.7 Hz, 1H), 0.71 (dt, J=11.5, 6.4 Hz, 1H), 0.45 (d, J=31.7 Hz, 2H), 0.06 (s, 1H).

Example 286

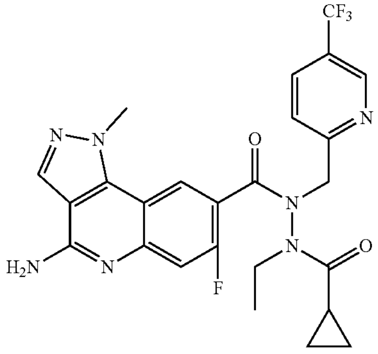

Example 286: 4-amino-N'-(cyclopropanecarbonyl)-N'-ethyl-7-fluoro-1-methyl-N-((5-(trifluoromethyl)pyridin-2-yl)methyl)-1H-pyrazolo[4,3-c]quinoline-8-carbohydrazide. Prepared using general procedure E-1 starting with intermediates Db-1 and Bd-40. ES/MS: m/z=530.0 $[M+H]^+$. $^1$H NMR (400 MHz, DMSO-$d_6$) δ 9.68 (s, 1H), 9.15-8.90 (m, 1H), 8.86 (s, 0.7H rotamer), 8.61 (s, 1H), 8.47 (s, 0.3H rotamer), 8.36-8.09 (m, 1H), 7.84 (d, J=8.2 Hz, 0.6H rotamer), 7.68 (dd, J=10.5, 6.7 Hz, 1H), 7.60 (d, J=8.0 Hz, 0.4H rotamer), 5.33 (t, J=21.6 Hz, 0.6H), 5.17 (d, J=16.1 Hz, 0.4H rotamer), 5.05 (s, 0.6H rotamer), 4.77 (s, 0.4H rotamer), 4.57-4.37 (m, 3H), 3.76 (s, 2H), 1.90 (d, J=14.4 Hz, 0.5H rotamer), 1.69 (s, 0.5H rotamer), 1.01 (s, 2H), 0.89 (s, 0.8H rotamer), 0.84-0.61 (m, 1.2H rotamer), 0.51 (d, J=40.0 Hz, 3H).

Example 287

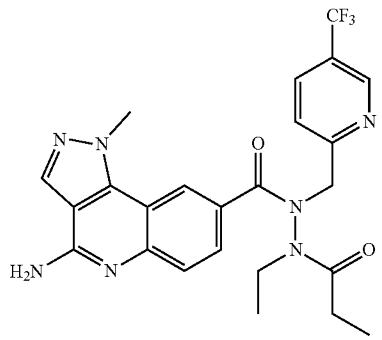

Example 287: 4-amino-N'-ethyl-1-methyl-N'-propionyl-N-((5-(trifluoromethyl)pyridin-2-yl)methyl)-1H-pyrazolo[4,3-c]quinoline-8-carbohydrazide. Prepared using general procedure E-1 starting with intermediates Da-1 and Bd38. ES/MS: m/z=500.0 [M+H]$^+$. $^1$H NMR (400 MHz, DMSO-$d_6$) δ 8.22 (s, 1H), 8.08 (s, 1H), 7.70 (s, 1H), 7.35 (s, 1H), 7.19-6.92 (m, 2.6H, major rotamer), 6.75 (s, 0.4H, minor rotamer), 4.54 (d, J=15.8 Hz, 0.5H, minor rotamer), 4.35 (s, 1.5H, major rotamer), 3.73 (s, 3H), 2.89 (s, 2H), 1.60 (d, J=63.8 Hz, 1.3H, major rotamer), 1.35 (s, 0.7H, minor rotamer), 0.24 (d, J=34.6 Hz, 4H, major rotamer), 0.09 (s, 2H, minor rotamer).

Example 288

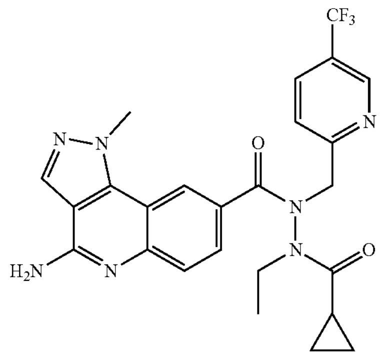

Example 288: 4-amino-N'-(cyclopropanecarbonyl)-N'-ethyl-1-methyl-N-((5-(trifluoromethyl)pyridin-2-yl)methyl)-1H-pyrazolo[4,3-c]quinoline-8-carbohydrazide. Prepared using general procedure E-1 starting with intermediates Da-1 and Bd-40. ES/MS: m/z=512.2 [M+H]$^+$. $^1$H NMR (400 MHz, DMSO-$d_6$) δ 8.09 (s, 1H), 7.79 (s, 1H), 7.70 (s, 1H), 7.36 (s, 2H), 7.04 (d, J=15.0 Hz, 1H), 6.81 (s, 1H), 4.81-4.46 (m, 1H), 4.37 (s, 1H), 3.72 (s, 3H), 3.27-2.65 (m, 2H), 1.60-1.03 (m, 0.6H, major rotamer), 0.88 (s, 0.4H, minor rotamer), 0.10 (dd, J=129.9, 68.2 Hz, 7H).

Example 289

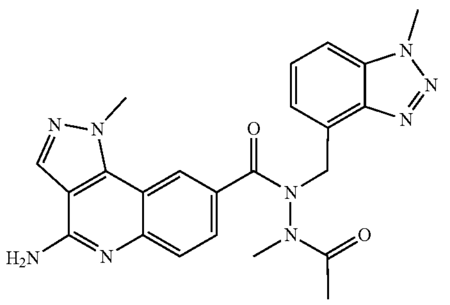

Example 289: N'-acetyl-4-amino-N',1-dimethyl-N-((1-methyl-1H-benzo[d][1,2,3]triazol-4-yl)methyl)-1H-pyrazolo[4,3-c]quinoline-8-carbohydrazide. Prepared using general procedure E-1 starting with intermediates Da-1 and Bi-9. ES/MS: m/z=458.2 [M+H]$^+$. $^1$H NMR (400 MHz, Methanol-d4) δ 8.92 (s, 0.5H, minor rotamer), 8.51 (d, J=10.9 Hz, 1.5H, major rotamer), 8.14 (s, 0.3H, minor rotamer), 7.89 (d, J=8.6 Hz, 0.7H, major rotamer), 7.83 (d, J=8.4 Hz, 0.3H, minor rotamer), 7.79 (d, J=9.2 Hz, 0.7H, major rotamer), 7.60 (t, J=7.7 Hz, 2.5H, major rotamer), 7.51 (s, 0.5H, minor rotamer), 5.64 (s, 1H), 5.42 (s, 0.5H, rotamer), 5.15 (s, 0.5H, rotamer), 4.65 (s, 1H, minor rotamer), 4.55 (s, 2H, major rotamer), 4.38 (s, 1H, minor rotamer), 4.37 (s, 2H, major rotamer), 3.07 (s, 2H, major rotamer), 3.02 (s, 1H, minor rotamer), 1.75 (s, 3H).

Example 290

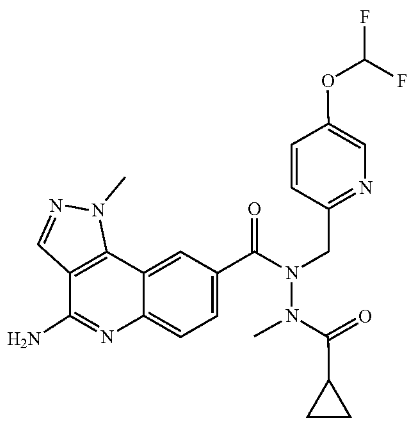

Example 290: 4-amino-N'-(cyclopropanecarbonyl)-N-((5-(difluoromethoxy)pyridin-2-yl)methyl)-7-fluoro-N',1-dimethyl-1H-pyrazolo[4,3-c]quinoline-8-carbohydrazide. Prepared using general procedure E-1 starting with intermediates Db-1 and Bd-41. ES/MS: m/z=514.0 [M+H]$^+$. $^1$H NMR (400 MHz, Methanol-d4) δ 8.88 (d, J=6.4 Hz, 0.3H, minor rotamer), 8.55 (s, 0.7H, major rotamer), 8.49 (d, J=4.1 Hz, 2H), 8.45 (s, 0.6H, major rotamer), 8.38 (d, J=6.5 Hz, 0.4H, minor rotamer), 7.71 (d, J=6.5 Hz, 2H), 7.65-7.54 (m, 0.7H, major rotamer), 7.44 (d, J=8.7 Hz, 0.3H, minor rotamer), 7.20-6.69 (m, 1H), 5.39-5.09 (m, 1.2H, major rotamer), 4.99 (d, J=14.2 Hz, 0.8H, minor rotamer), 4.72-4.36 (m, 3H), 3.39 (s, 1.3H, minor rotamer), 3.11 (s, 1.7H, major rotamer), 0.85 (dd, J=69.3, 34.0 Hz, 3H), 0.58 (d, J=30.1 Hz, 1.5H, major rotamer), 0.32 (s, 0.5H, minor rotamer).

Example 291

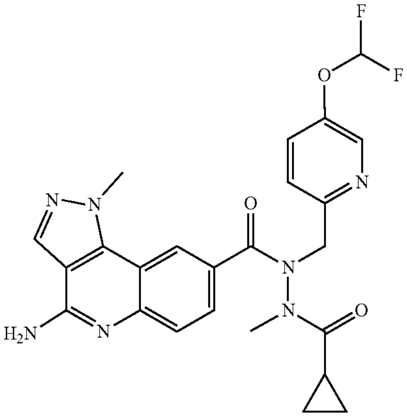

Example 291: 4-amino-N'-(cyclopropanecarbonyl)-N-((5-(difluoromethoxy)pyridin-2-yl)methyl)-N',1-dimethyl-1H-pyrazolo[4,3-c]quinoline-8-carbohydrazide. Prepared using general procedure E-1 starting with intermediates Da-1 and Bd-41. ES/MS: m/z=496.0 [M+H]$^+$. $^1$H NMR (400 MHz, DMSO-$d_6$) δ 13.45 (s, 1H), 9.65 (s, 1H), 8.79 (s, 1H), 8.63 (s, 1H), 8.50 (d, J=16.0 Hz, 2H), 8.05-7.60 (m, 2H), 7.60-6.92 (m, 1H), 5.28-4.79 (m, 2H), 4.47 (s, 3H), 3.28 (s, 1H, minor rotamer), 3.07 (s, 2H, major rotamer), 0.86-0.57 (m, 1.4H, minor rotamer), 0.57-0.12 (m, 2.6H, major rotamer).

Example 292

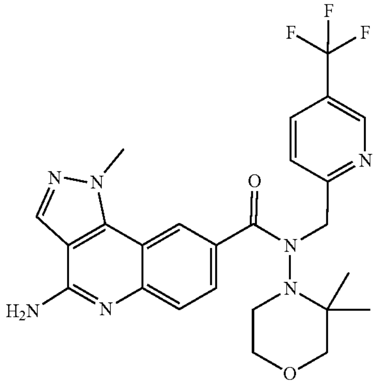

Example 292: 4-amino-N-(3,3-dimethylmorpholino)-1-methyl-N-((5-(trifluoromethyl)pyridin-2-yl)methyl)-1H-pyrazolo[4,3-c]quinoline-8-carboxamide. Prepared using general procedure E-1 starting with intermediates Da-1 and Bi-10. ES/MS: m/z=514.0 [M+H]$^+$. $^1$H NMR (400 MHz, Methanol-d4) δ 8.87 (s, 1H), 8.57 (d, J=1.7 Hz, 1H), 8.51 (s, 1H), 8.10 (d, J=8.6 Hz, 2H), 7.80 (d, J=8.7 Hz, 1H), 7.72 (d, J=8.3 Hz, 1H), 5.23 (d, J=16.2 Hz, 1H), 4.93 (d, J=16.3 Hz, 1H), 4.52 (s, 3H), 4.00 (d, J=8.9 Hz, 1H), 3.85-3.57 (m, 2H), 3.40 (d, J=11.0 Hz, 2H), 2.92 (d, J=10.9 Hz, 1H), 1.32 (d, J=10.3 Hz, 6H).

Example 293

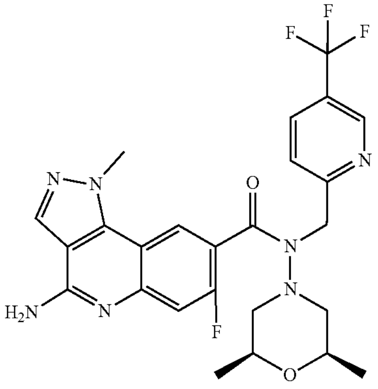

Example 293: 4-amino-N-((2S,6R)-2,6-dimethylmorpholino)-7-fluoro-1-methyl-N-((5-(trifluoromethyl)pyridin-2-yl)methyl)-1H-pyrazolo[4,3-c]quinoline-8-carboxamide. Prepared using general procedure E-1 starting with intermediates Db-1 and Bi-11 ES/MS: m/z=532.0 [M+H]$^+$. $^1$H NMR (400 MHz, Methanol-d4) δ 9.04-8.89 (m, 1H), 8.50 (s, 1H), 8.49 (d, J=6.3 Hz, 1H), 8.24-8.06 (m, 1H), 7.76 (d, J=8.3 Hz, 1H), 7.57 (d, J=10.1 Hz, 1H), 5.06 (s, 2H), 4.53 (s, 3H), 3.32 (m, 2H), 2.92 (d, J=10.2 Hz, 2H), 2.51 (t, J=10.2 Hz, 2H), 1.04 (d, J=6.3 Hz, 6H).

Example 294

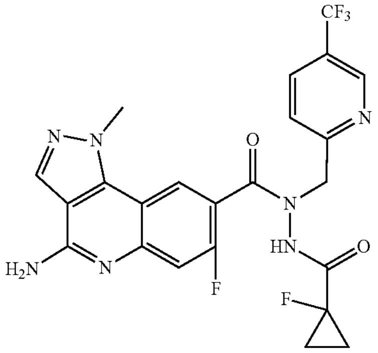

Example 294: 4-amino-7-fluoro-N'-(1-fluorocyclopropane-1-carbonyl)-1-methyl-N-((5-(trifluoromethyl)pyridin-2-yl)methyl)-1H-pyrazolo[4,3-c]quinoline-8-carbohydrazide. Prepared using general procedure E-1 starting with intermediates Db-1 and Bc-23. ES/MS: m/z=530.0 [M+H]$^+$. $^1$H NMR (400 MHz, Methanol-d4) δ 8.90 (d, J=2.2 Hz, 1H), 8.50 (s, 1H), 8.49 (s, 1H), 8.41-8.09 (m, 1H), 7.88 (d, J=8.3 Hz, 1H), 7.59 (d, J=10.1 Hz, 1H), 5.06 (s, 2H), 4.50 (s, 3H), 1.12 (t, J=80.4 Hz, 4H).

Example 295

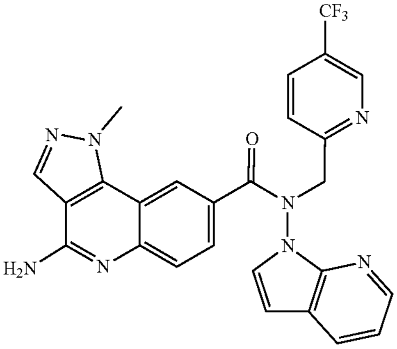

Example 295: 4-amino-1-methyl-N-(1H-pyrrolo[2,3-b]pyridin-1-yl)-N-((5-(trifluoromethyl)pyridin-2-yl)methyl)-1H-pyrazolo[4,3-c]quinoline-8-carboxamide. Prepared using general procedure E-1 starting with intermediates Da-1 and Bn-2. ES/MS: m/z=517.0 $[M+H]^+$. $^1H$ NMR (400 MHz, MeOD) δ 8.86 (s, 1H), 8.40 (s, 1H), 8.32 (dd, J=4.8, 1.5 Hz, 1H), 8.11 (dd, J=8.3, 2.3 Hz, 1H), 7.92 (t, J=8.7 Hz, 2H), 7.75 (d, J=7.9 Hz, 1H), 7.59 (d, J=8.7 Hz, 1H), 7.51 (d, J=3.8 Hz, 1H), 7.19 (dd, J=7.8, 4.8 Hz, 1H), 6.38 (d, J=3.9 Hz, 1H), 5.81 (d, J=15.6 Hz, 1H), 5.11 (d, J=15.6 Hz, 1H), 4.18 (s, 3H).

Example 296

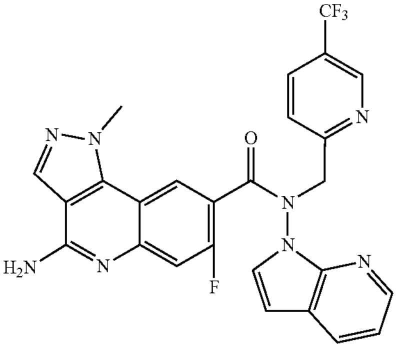

Example 296: 4-amino-7-fluoro-1-methyl-N-(1H-pyrrolo[2,3-b]pyridin-1-yl)-N-((5-(trifluoromethyl)pyridin-2-yl)methyl)-1H-pyrazolo[4,3-c]quinoline-8-carboxamide. Prepared using general procedure E-1 starting with intermediates Db-1 and Bn-2. ES/MS: m/z=535.0 $[M+H]^+$. $^1H$ NMR (400 MHz, Methanol-d4) δ 8.86 (s, 1H), 8.38 (s, 2H), 8.32 (dd, J=4.8, 1.5 Hz, 1H), 8.13 (d, J=8.2 Hz, 1H), 7.82 (d, J=7.8 Hz, 1H), 7.76 (d, J=8.1 Hz, 1H), 7.48 (dd, J=4.0, 1.6 Hz, 1H), 7.37 (d, J=9.9 Hz, 1H), 7.14 (t, J=6.5 Hz, 1H), 6.33 (s, 1H), 5.83 (d, J=15.5 Hz, 1H), 5.10 (d, J=15.5 Hz, 1H), 4.29 (s, 3H).

Example 297

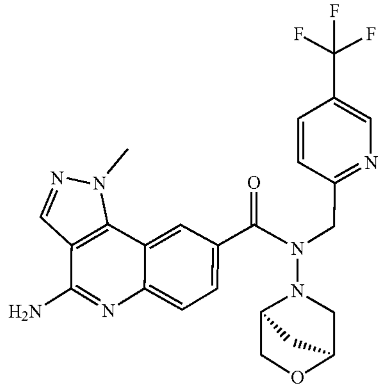

Example 297: 4-amino-N-((1S,4S)-2-oxa-5-azabicyclo[2.2.1]heptan-5-yl)-1-methyl-N-((5-(trifluoromethyl)pyridin-2-yl)methyl)-1H-pyrazolo[4,3-c]quinoline-8-carboxamide. Prepared using general procedure E-1 starting with intermediates Da-1 and Bi-12. ES/MS: m/z=498.0 $[M+H]^+$. $^1H$ NMR (400 MHz, Methanol-d4) δ 8.91 (s, 1H), 8.66 (d, J=1.6 Hz, 1H), 8.51 (s, 1H), 8.16 (dd, J=8.3, 2.4 Hz, 1H), 8.07 (dd, J=8.6, 1.7 Hz, 1H), 7.79 (dd, J=8.8, 6.8 Hz, 2H), 5.21 (d, J=16.5 Hz, 1H), 5.03 (d, J=16.7 Hz, 1H), 4.57 (s, 3H), 4.51 (s, 1H), 3.93 (s, 1H), 3.50 (p, J=1.7 Hz, 1H), 3.26 (d, J=11.0 Hz, 3H), 1.68 (d, J=9.5 Hz, 1H), 1.31 (s, 1H).

Example 298

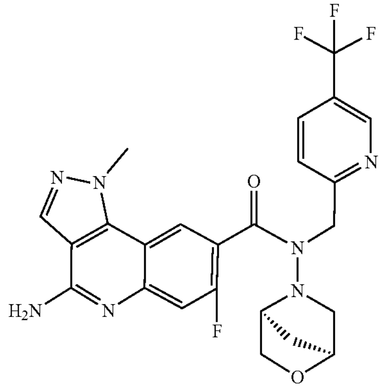

Example 298: 4-amino-N-((1S,4S)-2-oxa-5-azabicyclo[2.2.1]heptan-5-yl)-7-fluoro-1-methyl-N-((5-(trifluoromethyl)pyridin-2-yl)methyl)-1H-pyrazolo[4,3-c]quinoline-8-carboxamide. Prepared using general procedure E-1 starting with intermediates Db-1 and Bi-12. ES/MS: m/z=516.0 $[M+H]^+$. $^1H$ NMR (400 MHz, Methanol-d4) δ 8.93 (s, 1H), 8.50 (s, 1H), 8.49 (d, J=6.4 Hz, 1H), 8.19 (dd, J=8.2, 2.3 Hz, 1H), 7.78 (d, J=8.3 Hz, 1H), 7.57 (d, J=10.0 Hz, 1H), 5.27 (d, J=16.8 Hz, 1H), 5.00 (d, J=18.3 Hz, 1H), 4.54 (s, 3H), 4.44 (s, 1H), 3.87 (s, 1H), 3.46 (s, 1H), 3.18 (d, J=10.8 Hz, 1H), 3.10 (d, J=11.0 Hz, 1H), 1.64 (d, J=10.7 Hz, 1H), 1.31 (s, 1H).

Example 299

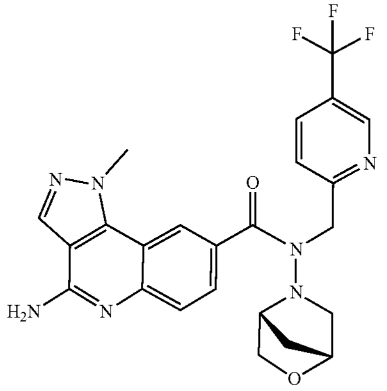

Example 299: 4-amino-N-((1R,4R)-2-oxa-5-azabicyclo[2.2.1]heptan-5-yl)-1-methyl-N-((5-(trifluoromethyl)pyridin-2-yl)methyl)-1H-pyrazolo[4,3-c]quinoline-8-carboxamide. Prepared using general procedure E-1 starting with intermediates Da-1 and Bi-13. ES/MS: m/z=498.0 $[M+H]^+$. $^1$H NMR (400 MHz, Methanol-d4) δ 8.91 (s, 1H), 8.66 (d, J=1.6 Hz, 1H), 8.51 (s, 1H), 8.16 (dd, J=8.2, 2.4 Hz, 1H), 8.07 (dd, J=8.6, 1.7 Hz, 1H), 7.79 (d, J=8.7 Hz, 1H), 7.78 (d, J=8.5 Hz, 1H), 5.21 (d, J=16.5 Hz, 1H), 5.03 (d, J=16.7 Hz, 1H), 4.57 (s, 3H), 4.51 (s, 1H), 3.93 (s, 1H), 3.50 (p, J=1.6 Hz, 1H), 3.25 (t, J=10.8 Hz, 2H), 1.68 (d, J=10.2 Hz, 1H), 1.31 (s, 1H).

Example 300

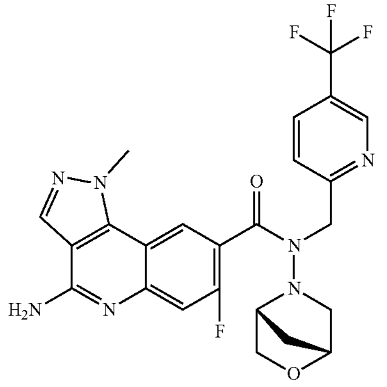

Example 300: 4-amino-N-((1R,4R)-2-oxa-5-azabicyclo[2.2.1]heptan-5-yl)-7-fluoro-1-methyl-N-((5-(trifluoromethyl)pyridin-2-yl)methyl)-1H-pyrazolo[4,3-c]quinoline-8-carboxamide. Prepared using general procedure E-1 starting with intermediates Db-1 and Bi-13. ES/MS: m/z=516.0 $[M+H]^+$. $^1$H NMR (400 MHz, Methanol-d4) δ 8.91 (s, 1H), 8.66 (d, J=1.6 Hz, 1H), 8.51 (s, 1H), 8.16 (dd, J=8.3, 2.4 Hz, 1H), 8.07 (dd, J=8.6, 1.7 Hz, 1H), 7.79 (dd, J=8.8, 6.8 Hz, 2H), 5.21 (d, J=16.5 Hz, 1H), 5.03 (d, J=16.7 Hz, 1H), 4.57 (s, 3H), 4.51 (s, 1H), 3.93 (s, 1H), 3.50 (p, J=1.7 Hz, 1H), 3.26 (d, J=11.0 Hz, 3H), 1.68 (d, J=9.5 Hz, 1H), 1.31 (s, 1H).

Example 301

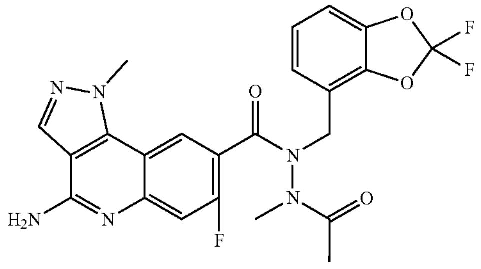

Example 301: N'-acetyl-4-amino-N-((2,2-difluorobenzo[d][1,3]dioxol-4-yl)methyl)-7-fluoro-N',1-dimethyl-1H-pyrazolo[4,3-c]quinoline-8-carbohydrazide. Prepared using general procedure E-1 starting with intermediates Db-1 and Bi-15. ES/MS: m/z=501.0 $[M+H]^+$. $^1$H NMR (400 MHz, MeOD) δ 8.62 (s, 0.3H, minor rotamer), 8.47 (s, 0.7H, major rotamer), 8.39 (d, J=6.5 Hz, 1H), 7.70 (s, 0.3H, minor rotamer), 7.58 (d, J=10.2 Hz, 1H), 7.41-7.32 (m, 0.7H, major rotamer), 7.32-7.03 (m, 2H), 5.18 (d, J=14.8 Hz, 1H), 4.61-4.49 (m, 1H), 4.47 (s, 3H), 3.19 (s, 3H), 1.86 (s, 1H, minor rotamer), 1.80 (s, 2H, major rotamer).

Example 302

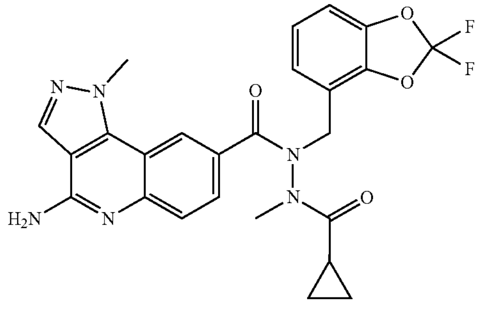

Example 302: 4-amino-N'-(cyclopropanecarbonyl)-N-((2,2-difluorobenzo[d][1,3]dioxol-4-yl)methyl)-N',1-dimethyl-1H-pyrazolo[4,3-c]quinoline-8-carbohydrazide. Prepared using general procedure E-1 starting with intermediates Da-1 and Bd-42. ES/MS: m/z=509.0 $[M+H]^+$. $^1$H NMR (400 MHz, MeOD) δ 8.59 (d, J=1.8 Hz, 0.6H, major rotamer), 8.50 (d, J=3.7 Hz, 1H), 8.47 (s, 0.4H, minor rotamer), 7.97 (d, J=8.7 Hz, 0.6H, minor rotamer), 7.83 (d, J=10.4 Hz, 1.4H, major rotamer), 7.39 (s, 1H), 7.29-7.23 (m, 1H), 7.23-7.20 (m, 1H), 5.38 (s, 0.6H, major rotamer), 5.13 (d, J=14.6 Hz, 0.4H, minor rotamer), 5.00 (d, J=14.7 Hz, 1H), 4.53 (d, J=7.8 Hz, 3H), 3.15 (s, 3H), 1.73 (s, 0.6H, major rotamer), 1.58 (s, 0.4H, minor rotamer), 0.97-0.28 (m, 4H).

Example 303

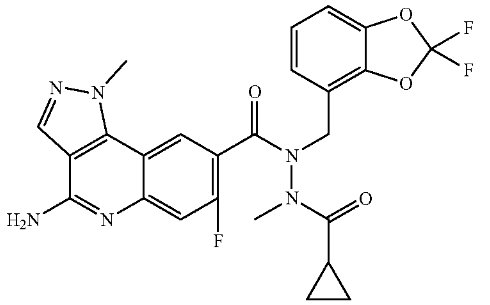

Example 303: 4-amino-N'-(cyclopropanecarbonyl)-N-((2,2-difluorobenzo[d][1,3]dioxol-4-yl)methyl)-7-fluoro-N',1-dimethyl-1H-pyrazolo[4,3-c]quinoline-8-carbohydrazide. Prepared using general procedure E-1 starting with intermediates Db-1 and Bd-42. ES/MS: m/z=527.0 $[M+H]^+$. $^1$H NMR (400 MHz, MeOD) δ 8.64 (s, 0.2H, minor rotamer), 8.53 (d, J=6.0 Hz, 0.8H, major rotamer), 8.49 (d, J=3.7 Hz, 0.7H, major rotamer), 8.35 (d, J=6.5 Hz, 0.3H, minor rotamer), 7.73 (d, J=9.9 Hz, 0.2H, minor rotamer), 7.60 (dd, J=10.2, 5.3 Hz, 0.8H, major rotamer), 7.45-7.30 (m, 1H), 7.30-7.20 (m, 1.8H, major rotamer), 7.14 (d, J=7.6 Hz, 0.2H, minor rotamer), 5.44 (d, J=14.7 Hz, 0.4H, minor rotamer), 5.18 (d, J=14.8 Hz, 0.6H, major rotamer), 5.02 (d, J=14.8 Hz, 0.6H, major rotamer), 4.90 (d, J=2.2 Hz, 0.4H, minor rotamer), 4.54 (d, J=14.9 Hz, 1H, minor rotamer), 4.48 (d, J=16.9 Hz, 2H, major rotamer), 3.25 (s, 1H, minor rotamer), 3.12 (s, 2H, major rotamer), 1.75 (s, 0.6H, major rotamer), 1.67-1.47 (m, 0.4H, minor rotamer), 1.06-0.22 (m, 4H).

Example 304

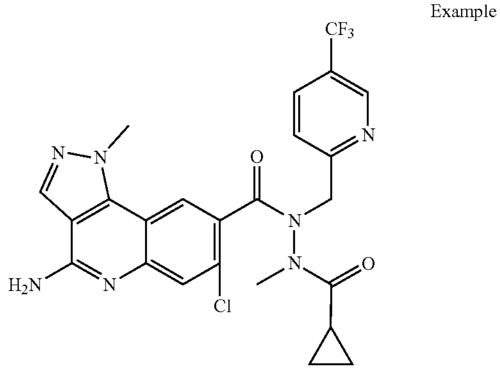

Example 304: 4-amino-7-chloro-N'-(cyclopropanecarbonyl)-N',1-dimethyl-N-((5-(trifluoromethyl)pyridin-2-yl)methyl)-1H-pyrazolo[4,3-c]quinoline-8-carbohydrazide. Prepared using general procedure E-1 starting with intermediates Db-2 and Bd-8. ES/MS: m/z=532.0 $[M+H]^+$. $^1$H NMR (400 MHz, Methanol-d4) δ 9.01 (s, 0.6H, major rotamer), 8.95 (s, 0.4H, minor rotamer), 8.91 (s, 0.6H, major rotamer), 8.73 (s, 0.4H, minor rotamer), 8.67 (s, 0.2H, minor rotamer), 8.50 (s, 1H), 8.34 (s, 0.8H, major rotamer), 8.20 (d, J=8.9 Hz, 0.8H, major rotamer), 8.10 (d, J=13.2 Hz, 0.2H, minor rotamer), 7.95 (s, 0.4H, minor rotamer), 7.89 (d, J=7.9 Hz, 1.6H, major rotamer), 7.56 (s, 1H), 5.42 (d, J=16.9 Hz, 0.6H, major rotamer), 5.37 (d, J=15.3 Hz, 1H), 5.26 (s, 0.4H, minor rotamer), 4.54 (d, J=14.1 Hz, 1H, minor rotamer), 4.46 (s, 2H, major rotamer), 3.40 (s, 2H), 3.21-3.12 (m, 1H), 2.20 (s, 0.8H, major rotamer), 1.59 (s, 0.2H, minor rotamer), 0.82 (s, 3H), 0.56 (s, 0.5H, minor rotamer), 0.44 (s, 0.5H, minor rotamer).

Example 305

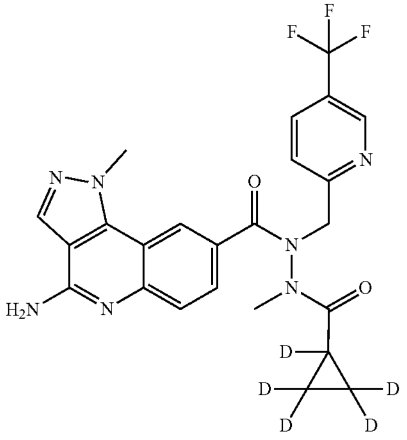

Example 305: 4-amino-N'-(cyclopropane-1-carbonyl-d5)-N',1-dimethyl-N-((5-(trifluoromethyl)pyridin-2-yl)methyl)-1H-pyrazolo[4,3-c]quinoline-8-carbohydrazide. Prepared using general procedure E-1 starting with intermediates Da-1 and Bc-24. ES/MS: m/z=503.1 $[M+H]^+$. $^1$H NMR (400 MHz, Methanol-d4) δ 8.93 (d, J=24.8 Hz, 1.6H, major rotamer), 8.63 (s, 0.4H, minor rotamer), 8.51 (d, J=3.8 Hz, 1H), 8.18 (t, J=9.3 Hz, 1H), 8.00 (s, 0.5H, minor rotamer), 7.94-7.71 (m, 2.5H, major rotamer), 5.25 (d, J=14.2 Hz, 1.3H, major rotamer), 4.9 (s, 0.7H, minor rotamer), 4.55 (d, J=12.2 Hz, 3H), 3.48 (s, 1H, minor rotamer), 3.19 (s, 2H, major rotamer).

Example 306

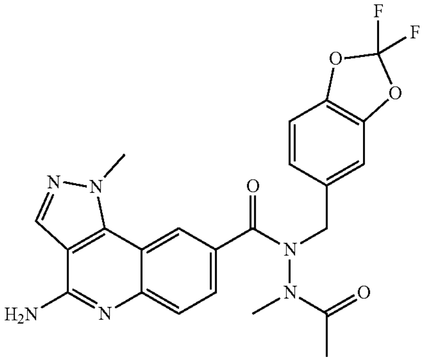

Example 306: N'-acetyl-4-amino-N-((2,2-difluorobenzo[d][1,3]dioxol-5-yl)methyl)-N',1-dimethyl-1H-pyrazolo[4,3-c]quinoline-8-carbohydrazide. Prepared using general procedure E-1 starting with intermediates Da-1 and Bi-14. ES/MS: m/z=509.0 $[M+H]^+$. $^1$H NMR (400 MHz, MeOD) δ 8.60 (d, J=1.7 Hz, 1H), 8.50 (d, J=2.6 Hz, 1H), 7.98 (d, J=8.7 Hz, 0.6H), major rotamer, 7.86 (s, 0.3H, minor rotamer), 7.80 (t, J=8.8 Hz, 1H), 7.45 (s, 1H), 7.32 (t, J=10.9 Hz, 1H), 7.24 (dd, J=14.2, 8.2 Hz, 1H), 5.28 (s, 0.5H, major rotamer), 5.08 (d, J=14.6 Hz, 0.4H, minor rotamer), 4.94 (s, 0.5H, major rotamer), 4.74 (d, J=14.5 Hz, 0.4H, minor rotamer), 4.53 (d, J=4.3 Hz, 3H), 3.30 (s, 1H, minor rotamer), 3.12 (s, 2H, major rotamer), 1.72 (s, 1H), 0.93-0.65 (m, 1H), 0.65-0.29 (m, 4H).

Example 307

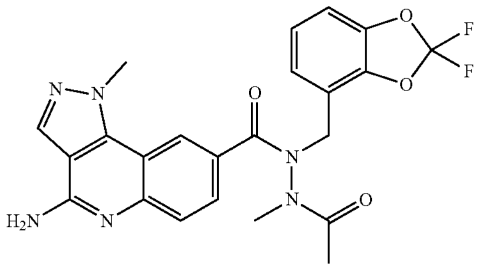

Example 307: N'-acetyl-4-amino-N-((2,2-difluorobenzo[d][1,3]dioxol-4-yl)methyl)-N',1-dimethyl-1H-pyrazolo[4,3-c]quinoline-8-carbohydrazide. Prepared using general procedure E-1 starting with intermediates Da-1 and Bi-15. ES/MS: m/z=483.0 $[M+H]^+$. $^1H$ NMR (400 MHz, Methanol-d4) δ 8.57 (d, J=1.8 Hz, 0.3H, minor rotamer), 8.50 (d, J=8.1 Hz, 1.7H, major rotamer), 7.97 (d, J=8.6 Hz, 0.3H, minor rotamer), 7.86 (s, 0.7H, major rotamer), 7.81 (d, J=8.5 Hz, 1H), 7.38 (s, 1H), 7.27 (d, J=2.2 Hz, 0.4H, minor rotamer), 7.25-7.17 (m, 1.6H, major rotamer), 5.12 (d, J=16.7 Hz, 2H), 4.54 (s, 1H, minor rotamer), 4.52 (s, 2H, major rotamer), 3.21 (s, 2H, major rotamer), 3.15 (s, 1H, minor rotamer), 1.83 (s, 3H).

Example 308

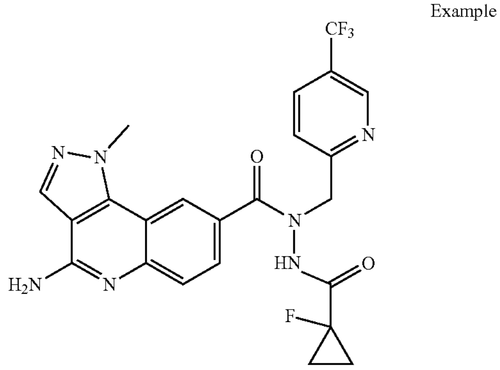

Example 308: 4-amino-N'-(1-fluorocyclopropane-1-carbonyl)-1-methyl-N-((5-(trifluoromethyl)pyridin-2-yl)methyl)-1H-pyrazolo[4,3-c]quinoline-8-carbohydrazide. Prepared using general procedure E-1 starting with intermediates Da-1 and Bc-23. ES/MS: m/z=502.0 $[M+H]^+$. $^1H$ NMR (400 MHz, Methanol-d4) δ 8.92 (d, J=2.2 Hz, 1H), 8.64 (s, 1H), 8.51 (s, 1H), 8.19 (dd, J=8.3, 2.4 Hz, 1H), 7.99 (dd, J=8.5, 1.8 Hz, 1H), 7.88 (d, J=8.2 Hz, 1H), 7.80 (d, J=8.6 Hz, 1H), 5.11 (s, 2H), 4.54 (s, 3H), 1.24 (d, J=52.7 Hz, 4H).

Example 309

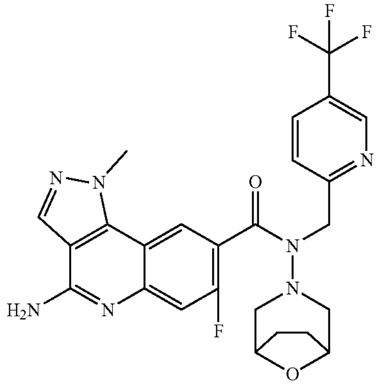

Example 309: 4-amino-N-((1R,5S)-8-oxa-3-azabicyclo[3.2.1]octan-3-yl)-7-fluoro-1-methyl-N-((5-(trifluoromethyl)pyridin-2-yl)methyl)-1H-pyrazolo[4,3-c]quinoline-8-carboxamide. Prepared using general procedure E-1 starting with intermediates Db-1 and Bi-16. ES/MS: m/z=530.0 $[M+H]^+$. $^1H$ NMR (400 MHz, Methanol-d4) δ 8.90 (d, J=2.2 Hz, 1H), 8.53-8.49 (m, 2H), 8.17 (dd, J=8.2, 2.4 Hz, 1H), 7.74 (d, J=8.3 Hz, 1H), 7.65 (d, J=9.9 Hz, 1H), 5.13 (s, 2H), 4.54 (s, 3H), 4.20 (s, 2H), 3.07 (d, J=10.1 Hz, 2H), 2.93 (s, 1H), 2.68 (s, 1H), 1.57 (s, 3H), 0.62 (s, 1H).

Example 310

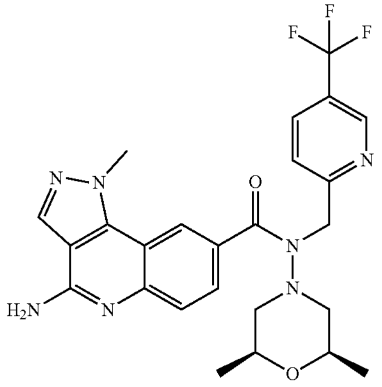

Example 310: 4-amino-N-((2S,6R)-2,6-dimethylmorpholino)-1-methyl-N-((5-(trifluoromethyl)pyridin-2-yl)methyl)-1H-pyrazolo[4,3-c]quinoline-8-carboxamide. Prepared using general procedure E-1 starting with intermediates Da-1 and Bi-11. ES/MS: m/z=514.1 $[M+H]^+$. $^1H$ NMR (400 MHz, Methanol-d4) δ 8.90 (s, 1H), 8.61 (s, 1H), 8.51 (s, 1H), 8.19-8.11 (m, 1H), 8.09 (dd, J=8.6, 1.7 Hz, 1H), 7.78 (t, J=8.0 Hz, 2H), 5.04 (s, 2H), 4.55 (s, 3H), 3.44 (d, J=8.3 Hz, 3H), 3.00 (d, J=9.9 Hz, 2H), 2.59 (t, J=10.3 Hz, 2H), 1.09 (d, J=6.3 Hz, 6H).

Example 311

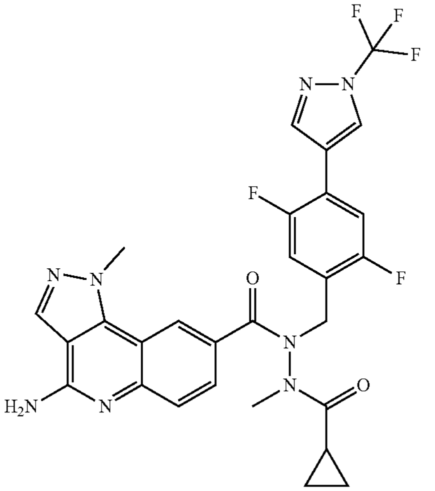

Example 311: 4-amino-N'-(cyclopropanecarbonyl)-N-(2,5-difluoro-4-(1-(trifluoromethyl)-1H-pyrazol-4-yl)benzyl)-N',1-dimethyl-1H-pyrazolo[4,3-c]quinoline-8-carbohydrazide. Prepared following the procedure reported for example 130 starting with intermediates Da-1, Bo-2, and 4-(4,4,5,5-tetramethyl-1,3,2-dioxaborolan-2-yl)-1-(trifluoromethyl)-1H-pyrazole. ES/MS: m/z=599.0 $[M+H]^+$. $^1$H NMR (400 MHz, Methanol-d4) δ 8.68 (s, 0.5H, rotamer), 8.66 (s, 0.5H, rotamer), 8.61 (d, J=1.7 Hz, 0.5H, rotamer), 8.51 (d, J=3.8 Hz, 1H), 8.32 (s, 0.5H, rotamer), 7.99 (d, J=8.7 Hz, 0.6H major rotamer), 7.87 (s, 0.4H, minor rotamer), 7.81 (t, J=9.5 Hz, 1H), 7.68 (dd, J=10.3, 6.1 Hz, 0.6H, major rotamer), 7.63 (dd, J=10.5, 6.1 Hz, 0.4H, minor rotamer), 7.56 (s, 1H), 5.33 (s, 1H), 5.00 (d, J=14.9 Hz, 1H), 4.54 (d, J=6.5 Hz, 3H), 3.39 (s, 1H, minor rotamer), 3.15 (q, J=1.7 Hz, 2H, major rotamer), 1.83 (s, 0.5H, rotamer), 1.58 (2, 0.5H, rotamer) 0.92-0.31 (m, 4H).

Example 312

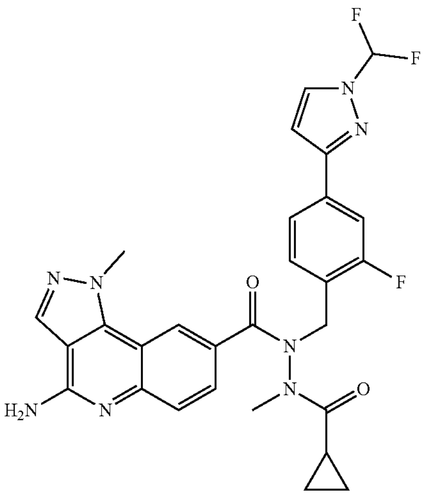

Example 312: 4-amino-N'-(cyclopropanecarbonyl)-N-(4-(1-(difluoromethyl)-1H-pyrazol-3-yl)-2-fluorobenzyl)-N',1-dimethyl-1H-pyrazolo[4,3-c]quinoline-8-carbohydrazide. Prepared following the procedure reported for example 130 starting with intermediates Da-1, Bo-4 and 1-(difluoromethyl)-3-(4,4,5,5-tetramethyl-1,3,2-dioxaborolan-2-yl)-1H-pyrazole. ES/MS: m/z=563.0 $[M+H]^+$. $^1$H NMR (400 MHz, Methanol-d4)) δ 8.60 (s, 1H), 8.50 (d, J=4.1 Hz, 1H), 8.13 (dd, J=2.8, 1.5 Hz, 1H), 7.99 (d, J=8.6 Hz, 1H), 7.88-7.65 (m, 2H), 7.71-7.33 (m, 1H), 6.97 (d, J=2.8 Hz, 1H), 5.39 (s, 0.8H, major rotamer), 5.21 (s, 0.2H, minor rotamer), 5.03 (d, J=14.4 Hz, 1H), 4.54 (d, J=8.4 Hz, 3H), 3.28 (s, 1H, minor rotamer), 3.16-3.06 (m, 2H, major rotamer), 1.83 (s, 1H), 0.61 (t, J=52.6 Hz, 4H).

Example 313

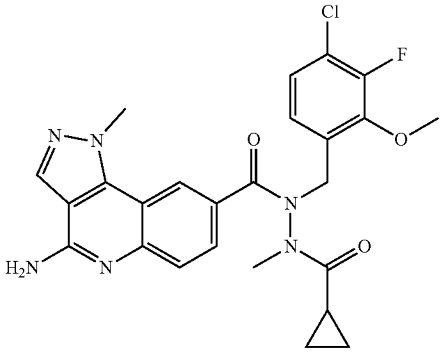

Example 313: 4-amino-N-(4-chloro-3-fluoro-2-methoxybenzyl)-N'-(cyclopropanecarbonyl)-N',1-dimethyl-1H-pyrazolo[4,3-c]quinoline-8-carbohydrazide. Prepared using general procedure E-1 starting with intermediates Da-1 and Bo-1. ES/MS: m/z=511.0 $[M+H]^+$. $^1$H NMR (400 MHz, Methanol-d4) δ 8.57 (s, 0.6H, major rotamer), 8.50 (d, J=3.9 Hz, 1H), 8.46 (s, 0.3H, minor rotamer), 7.96 (s, 0.7H, minor rotamer), 7.83 (s, 1.3H, major rotamer), 7.36 (s, 1H), 7.24 (q, J=7.7 Hz, 1H), 5.29 (s, 0.7H, major rotamer), 5.11 (d, J=14.1 Hz, 0.3H, minor rotamer), 4.97 (d, J=14.3 Hz, 0.7H, major rotamer), 4.78 (d, J=14.3 Hz, 0.3H, minor rotamer), 4.53 (d, J=9.4 Hz, 3H), 4.04 (d, J=17.7 Hz, 3H), 3.25 (s, 1H, minor rotamer), 3.07 (s, 2H, major rotamer), 1.77 (dt, J=7.9, 4.6 Hz, 0.6H, major rotamer), 1.57 (s, 0.4H, minor rotamer), 0.92-0.35 (m, 4H).

Example 314

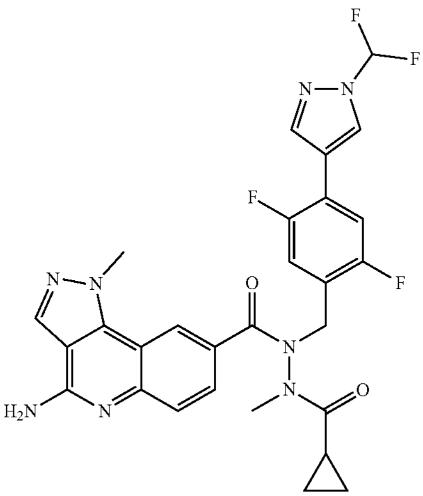

Example 314: 4-amino-N'-(cyclopropanecarbonyl)-N-(4-(1-(difluoromethyl)-1H-pyrazol-4-yl)-2,5-difluorobenzyl)-N',1-dimethyl-1H-pyrazolo[4,3-c]quinoline-8-carbohydrazide. Prepared following the procedure reported for example 130 starting with intermediates Da-1, Bo-2, and 4-(4,4,5,5-tetramethyl-1,3,2-dioxaborolan-2-yl)-1-(difluoromethyl)-1H-pyrazole. ES/MS: m/z=581.0 $[M+H]^+$. $^1H$ NMR (400 MHz, Methanol-d4) δ 8.61 (d, J=1.8 Hz, 0.5H, rotamer), 8.58-8.52 (m, 0.5H, rotamer), 8.53 (d, J=1.7 Hz, 0.6H, minor rotamer), 8.50 (d, J=4.0 Hz, 1.4H, major rotamer), 8.20 (d, J=3.6 Hz, 1H), 7.99 (d, J=8.6 Hz, 0.6H, minor rotamer), 7.84 (dt, J=19.4, 9.2 Hz, 1.4H, major rotamer), 7.65 (dd, J=10.3, 6.1 Hz, 0.6H, major rotamer), 7.60 (dd, J=10.4, 6.1 Hz, 0.4H, minor rotamer), 7.57 (t, J=59.6 Hz, 1H), 7.53 (s, 1H), 5.33 (s, 0.7H, major rotamer), 5.07 (d, J=14.5 Hz, 0.3H), 4.99 (d, J=14.6 Hz, 1H), 4.54 (d, J=6.7 Hz, 3H), 3.38 (s, 1H, minor rotamer), 3.15 (s, 2H, major rotamer), 1.83 (d, J=5.2 Hz, 1H), 0.98-0.36 (m, 4H).

Example 315

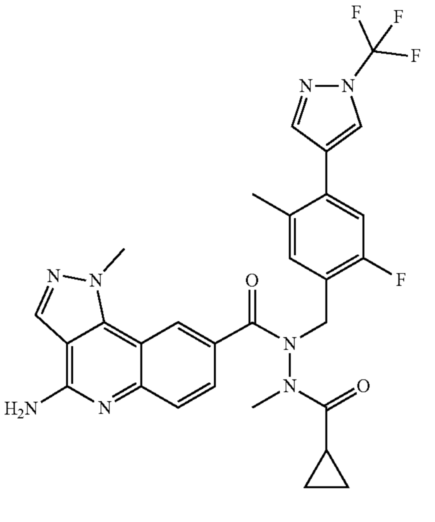

Example 315: 4-amino-N'-(cyclopropanecarbonyl)-N-(2-fluoro-5-methyl-4-(1-(trifluoromethyl)-1H-pyrazol-4-yl)benzyl)-N',1-dimethyl-1H-pyrazolo[4,3-c]quinoline-8-carbohydrazide. Prepared following the procedure reported for example 130 starting with intermediates Da-1, Bo-3, and 4-(4,4,5,5-tetramethyl-1,3,2-dioxaborolan-2-yl)-1-(trifluoromethyl)-1H-pyrazole. ES/MS: m/z=595.0 $[M+H]^+$. $^1H$ NMR (400 MHz, Methanol-d4) δ 8.60 (d, J=1.8 Hz, 1H), 8.51 (s, 0.6H, major rotamer), 8.50 (s, 0.4H, minor rotamer), 8.45 (s, 0.6H, major rotamer), 8.44 (s, 0.4H, minor rotamer), 8.14-8.02 (m, 1H), 7.99 (d, J=8.7 Hz, 1H), 7.83 (d, J=9.7 Hz, 1H), 7.52 (s, 1H), 7.28 (t, J=10.4 Hz, 1H), 5.36 (s, 0.7H, major rotamer), 5.17 (s, 0.3H, minor rotamer), 4.98 (d, J=14.4 Hz, 0.7H, major rotamer), 4.78 (d, J=14.1 Hz, 0.3H, minor rotamer), 4.54 (d, J=8.9 Hz, 3H), 3.28 (s, 1H, minor rotamer), 3.12 (s, 2H, major rotamer), 2.42 (s, 3H), 1.84 (s, 0.7H, major rotamer), 1.58 (s, 0.3H, minor rotamer), 0.90-0.38 (m, 4H).

Example 316

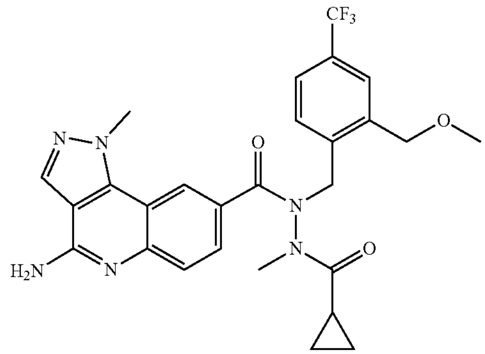

Example 316: 4-amino-N'-(cyclopropanecarbonyl)-N-(2-(methoxymethyl)-4-(trifluoromethyl)benzyl)-N',1-dimethyl-1H-pyrazolo[4,3-c]quinoline-8-carbohydrazide. Prepared using general procedure E-1 starting with intermediates Da-1 and Bd-43. ES/MS: m/z=541.0 $[M+H]^+$. $^1H$ NMR (400 MHz, Methanol-d4) δ 8.58 (s, 0.5H, minor rotamer), 8.50 (d, J=2.3 Hz, 1H), 8.48 (s, 0.5H, major rotamer), 7.97 (d, J=8.7 Hz, 0.7H, major rotamer), 7.87 (s, 0.3H, minor rotamer), 7.79 (t, J=10.6 Hz, 2H), 7.70 (d, J=1.3 Hz, 2H), 5.43 (dd, J=27.4, 14.8 Hz, 1H), 5.14 (d, J=14.7 Hz, 1H), 4.71 (s, 3H), 4.53 (d, J=6.2 Hz, 3H), 3.50 (dt, J=3.4, 1.7 Hz, 0.4H, minor rotamer), 3.16-3.05 (m, 1.6H, major rotamer), 2.99 (s, 3H), 1.82 (dd, J=8.1, 4.0 Hz, 1H), 0.91-0.26 (m, 4H).

Example 317

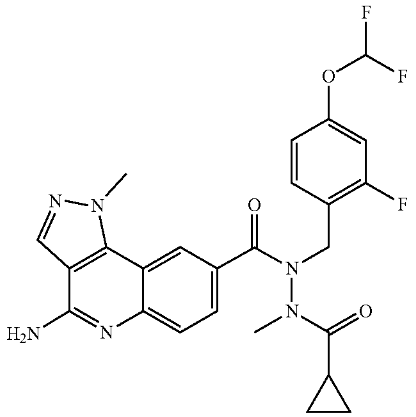

Example 317: 4-amino-N'-(cyclopropanecarbonyl)-N-(4-(difluoromethoxy)-2-fluorobenzyl)-N',1-dimethyl-1H-pyrazolo[4,3-c]quinoline-8-carbohydrazide. Prepared using general procedure E-1 starting with intermediates Da-1 and Bd-44. ES/MS: m/z=513.0 $[M+H]^+$. $^1H$ NMR (400 MHz, Methanol-d4) δ 8.59 (s, 0.6H, major rotamer), 8.50 (d, J=3.6 Hz, 1H), 8.48 (s, 0.4H, major rotamer), 7.97 (d, J=8.6 Hz, 1H), 7.82 (d, J=9.6 Hz, 1H), 7.66 (s, 1H), 7.05 (dd, J=17.7, 9.3 Hz, 2H), 6.94 (td, J=73.3, 6.6 Hz, 1H), 5.36 (s, 0.7H, major rotamer), 5.11 (d, J=14.4 Hz, 0.3H, minor rotamer), 4.95 (d, J=14.5 Hz, 0.7H, major rotamer), 4.84 (s, 0.3H, minor rotamer), 4.53 (d, J=7.6 Hz, 3H), 3.29 (s, 1H, minor rotamer), 3.11 (s, 2H, major rotamer), 1.76 (s, 1H), 1.57 (s, 1H), 0.93-0.29 (m, 3H).

Example 318

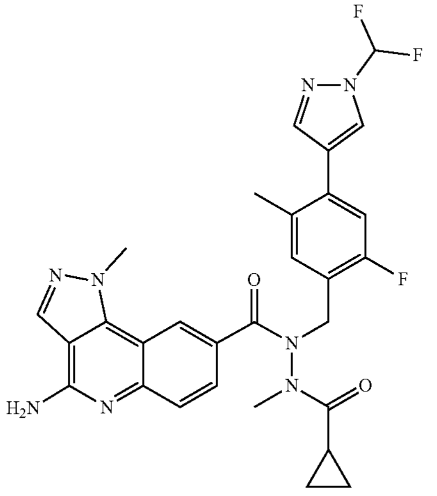

Example 318: 4-amino-N'-(cyclopropanecarbonyl)-N-(4-(1-(difluoromethyl)-1H-pyrazol-4-yl)-2-fluoro-5-methylbenzyl)-N',1-dimethyl-1H-pyrazolo[4,3-c]quinoline-8-carbohydrazide. Prepared following the procedure reported for example 130 starting with intermediates Da-1, Bo-3, and 4-(4,4,5,5-tetramethyl-1,3,2-dioxaborolan-2-yl)-1-(difluoromethyl)-1H-pyrazole. ES/MS: m/z=577.0 $[M+H]^+$. $^1$H NMR (400 MHz, Methanol-d4) δ 8.60 (d, J=1.7 Hz, 1H), 8.51 (s, 0.6H, major rotamer), 8.50 (s, 0.4H, minor rotamer), 8.32 (d, J=0.7 Hz, 0.6H, major rotamer), 8.30 (s, 0.4H, minor rotamer), 7.97 (s, 2H), 7.82 (d, J=9.5 Hz, 1H), 7.55 (t, J=59.6 Hz, 1H), 7.50 (s, 1H), 7.26 (dd, J=10.8, 9.2 Hz, 1H), 5.36 (s, 0.5H, minor rotamer), 5.16 (s, 0.5H, minor rotamer), 4.97 (d, J=14.5 Hz, 1H), 4.54 (d, J=8.9 Hz, 3H), 3.27 (s, 1H, minor rotamer), 3.21-3.03 (m, 2H, major rotamer), 2.42 (s, 3H), 1.83 (s, 0.7H, major rotamer), 1.57 (s, 0.3H, minor rotamer), 1.01-0.37 (m, 4H).

Example 319

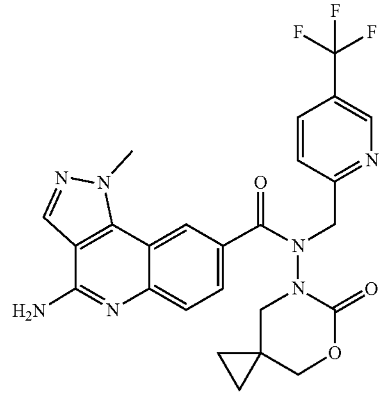

Example 319: 4-amino-1-methyl-N-(6-oxo-5-oxa-7-azaspiro[2.5]octan-7-yl)-N-((5-(trifluoromethyl)pyridin-2-yl)methyl)-1H-pyrazolo[4,3-c]quinoline-8-carboxamide. Prepared using general procedure E-1 starting with intermediates Da-1 and Bi-17. ES/MS: m/z=526.0 $[M+H]^+$. $^1$H NMR (400 MHz, Methanol-d4) δ 8.92 (s, 1H), 8.64 (s, 1H), 8.51 (s, 1H), 8.22-8.15 (m, 1H), 8.08-7.68 (m, 3H), 5.33 (d, J=15.8 Hz, 1H), 5.02 (d, J=15.5 Hz, 1H), 4.52 (s, 3H), 4.25 (s, 1H), 3.95 (s, 1H), 3.67-3.42 (m, 1H), 3.08-2.86 (m, 1H), 0.97-0.18 (m, 3H), −0.19 (s, 1H).

Example 320

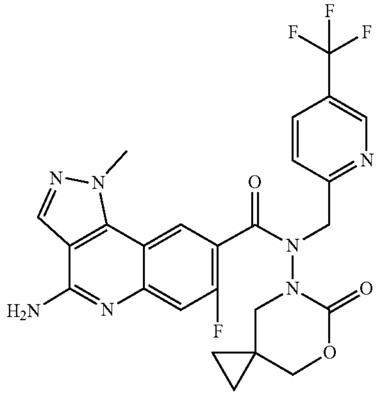

Example 320: 4-amino-7-fluoro-1-methyl-N-(6-oxo-5-oxa-7-azaspiro[2.5]octan-7-yl)-N-((5-(trifluoromethyl)pyridin-2-yl)methyl)-1H-pyrazolo[4,3-c]quinoline-8-carboxamide. Prepared using general procedure E-1 starting with intermediates Db-1 and Bi-17. ES/MS: m/z=544.0 $[M+H]^+$. $^1$H NMR (400 MHz, MeOD) δ 8.91 (d, J=2.2 Hz, 1H), 8.54 (d, J=6.5 Hz, 1H), 8.49 (s, 1H), 8.19 (d, J=8.2 Hz, 1H), 7.86 (d, J=8.2 Hz, 1H), 7.66 (d, J=10.2 Hz, 1H), 5.36 (d, J=15.5 Hz, 1H), 5.04 (d, J=15.5 Hz, 1H), 4.48 (s, 3H), 4.25 (d, J=11.2 Hz, 1H), 4.02 (d, J=11.0 Hz, 1H), 3.54 (d, J=11.1 Hz, 1H), 3.09 (d, J=11.0 Hz, 1H), 0.96-0.59 (m, 2H), 0.42 (dd, J=9.9, 5.1 Hz, 1H), 0.12 (dd, J=9.9, 5.2 Hz, 1H).

Example 321

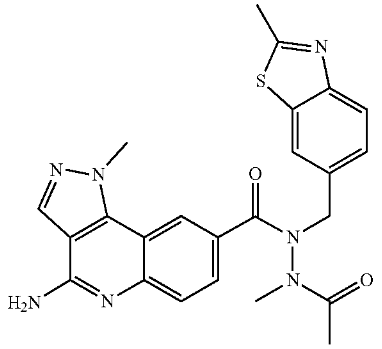

Example 321: N'-acetyl-4-amino-N',1-dimethyl-N-((2-methylbenzo[d]thiazol-6-yl)methyl)-1H-pyrazolo[4,3-c]quinoline-8-carbohydrazide. Prepared using general procedure E-1 starting with intermediates Da-1 and Bb-28. ES/MS: m/z=474.2 $[M+H]^+$. $^1$H NMR (400 MHz, MeOD) δ 8.61-8.40 (m, 2H), 8.20-7.95 (m, 1H), 7.95-7.75 (m, 3H), 7.65 (s, 1H), 5.42-4.99 (m, 1H), 4.77 (d, J=14.6 Hz, 1H), 4.52 (s, 3H), 3.21-2.99 (m, 3H), 2.85 (s, 3H), 1.93-1.57 (m, 3H).

Example 322

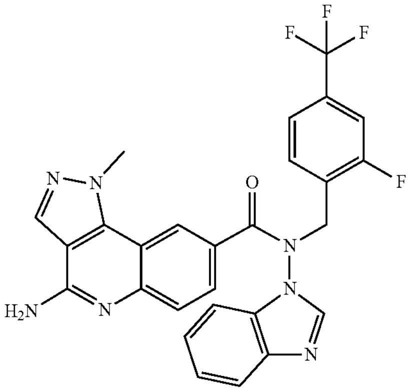

Example 322: 4-amino-N-(1H-benzo[d]imidazol-1-yl)-N-(2-fluoro-4-(trifluoromethyl)benzyl)-1-methyl-1H-pyrazolo[4,3-c]quinoline-8-carboxamide. Prepared using general procedure E-1 starting with intermediates Da-1 and Bn-3. ES/MS: m/z=534.0 $[M+H]^+$. $^1$H NMR (400 MHz, MeOD) δ 8.39 (s, 1H), 8.23 (d, J=1.8 Hz, 1H), 8.19 (s, 1H), 7.91 (dd, J=8.7, 1.8 Hz, 1H), 7.69 (t, J=7.6 Hz, 1H), 7.63-7.54 (m, 3H), 7.52-7.46 (m, 1H), 7.44-7.28 (m, 3H), 5.60 (d, J=14.6 Hz, 1H), 5.38 (d, J=14.5 Hz, 1H), 4.04 (s, 3H).

Example 323

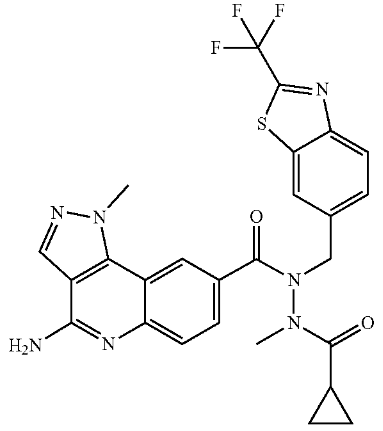

Example 323: 4-amino-N'-(cyclopropanecarbonyl)-N',1-dimethyl-N-((2-(trifluoromethyl)benzo[d]thiazol-6-yl)methyl)-1H-pyrazolo[4,3-c]quinoline-8-carbohydrazide. Prepared using general procedure E-1 starting with intermediates Da-1 and Bo-5. ES/MS: m/z=554.0 $[M+H]^+$. $^1$H NMR (400 MHz, MeOD) δ 8.64-8.45 (m, 2H), 8.36 (s, 1H), 8.24 (dd, J=11.9, 8.5 Hz, 1H), 8.05-7.74 (m, 3H), 5.57-5.22 (m, 1H), 5.14 (d, J=14.5 Hz, 0.7H, major rotamer), 4.97-4.85 (m, 0.3H, minor rotamer), 4.54 (s, 3H), 3.34-3.24 (m, 1H, minor rotamer), 3.13 (s, 2H, major rotamer), 1.79-1.44 (m, 1H), 0.92-0.15 (m, 4H).

Example 324

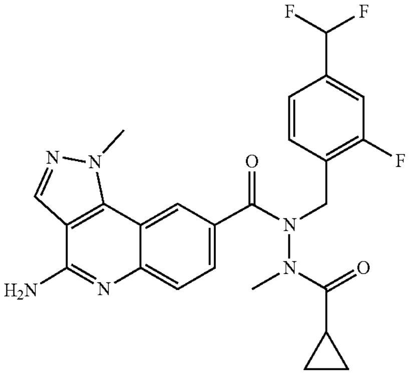

Example 324: 4-amino-N'-(cyclopropanecarbonyl)-N-(4-(difluoromethyl)-2-fluorobenzyl)-N',1-dimethyl-1H-pyrazolo[4,3-c]quinoline-8-carbohydrazide. Prepared using general procedure E-1 starting with intermediates Da-1 and Bo-6. ES/MS: m/z=497.0 $[M+H]^+$. $^1$H NMR (400 MHz, MeOD) δ 8.68-8.42 (m, 2H), 8.03-7.69 (m, 3H), 7.51-7.30 (m, 2H), 7.03-6.62 (m, 1H), 5.41 (s, 0.6H, major rotamer), 5.16 (s, 0.4H, minor rotamer), 5.02 (d, J=14.5 Hz, 1H), 4.60-4.39 (m, 3H), 3.33-3.29 (m, 1.2H, minor rotamer), 3.21-3.02 (m, 1.8H, major rotamer), 1.83-1.43 (m, 1H), 1.06-0.24 (m, 4H).

Example 325

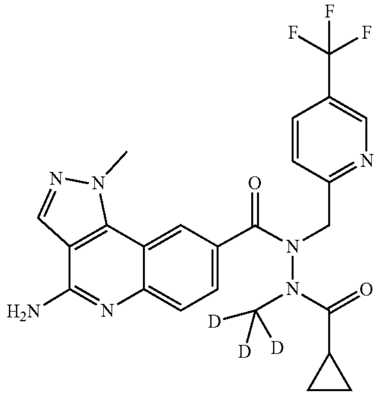

Example 325: 4-amino-N'-(cyclopropanecarbonyl)-1-methyl-N'-(methyl-d3)-N-((5-(trifluoromethyl)pyridin-2-yl)methyl)-1H-pyrazolo[4,3-c]quinoline-8-carbohydrazide. Prepared using general procedure E-1 starting with intermediates Da-1 and Bd-45. ES/MS: m/z=501.2 $[M+H]^+$. $^1$H NMR (400 MHz, MeOD) δ 9.15-8.79 (m, 1H), 8.75-8.43 (m, 2H), 8.18 (t, J=9.2 Hz, 1H), 8.08-7.56 (m, 3H), 5.25 (d, J=14.2 Hz, 1.6H), 4.90 (d, J=5.4 Hz, 0.4H, minor rotamer), 4.64-4.42 (m, 3H), 2.11-1.96 (m, 0.6H, major rotamer), 1.62 (s, 0.4H, minor rotamer), 1.03-0.28 (m, 4H).

Example 326

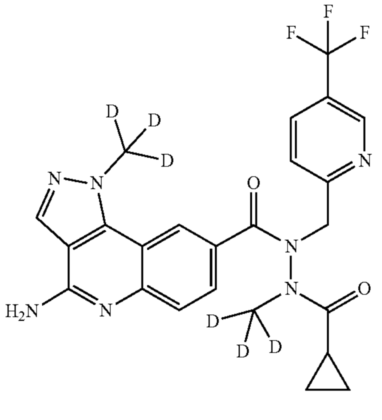

Example 326: 4-amino-N'-(cyclopropanecarbonyl)-N',1-bis(methyl-d3)-N-((5-(trifluoromethyl)pyridin-2-yl)methyl)-1H-pyrazolo[4,3-c]quinoline-8-carbohydrazide. Prepared using general procedure E-1 starting with intermediates Da-9 and Bd-45. ES/MS: m/z=504.2 $[M+H]^+$. $^1$H NMR (400 MHz, MeOD) δ 9.19-8.79 (m, 1H), 8.51 (d, J=3.9 Hz, 2H), 8.18 (t, J=9.3 Hz, 1H), 8.10-7.29 (m, 3H), 5.25 (d, J=14.3 Hz, 1.5H), 4.90 (d, J=1.2 Hz, 0.5H, minor rotamer), 2.07-2.00 (m, 0.7H, major rotamer), 1.62 (s, 0.3H, minor rotamer), 1.20-0.28 (m, 4H).

Example 327

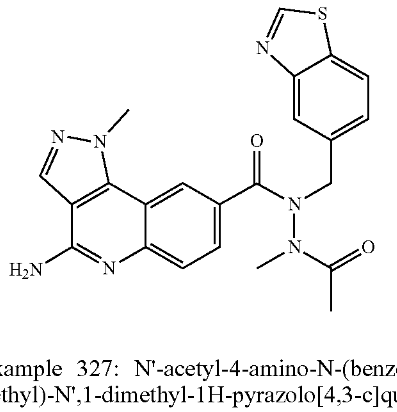

Example 327: N'-acetyl-4-amino-N-(benzo[d]thiazol-5-ylmethyl)-N',1-dimethyl-1H-pyrazolo[4,3-c]quinoline-8-carbohydrazide. Prepared using general procedure E-1 starting with intermediates Da-1 and Bb-29. ES/MS: m/z=460.0 $[M+H]^+$. $^1$H NMR (400 MHz, MeOD) δ 9.31 (d, J=5.0 Hz, 1H), 8.66-8.42 (m, 2H), 8.36-8.08 (m, 2H), 8.04-7.76 (m, 2H), 7.69 (s, 1H), 5.53-5.00 (m, 1H), 4.83 (d, J=14.6 Hz, 1H), 4.52 (s, 3H), 3.23-2.93 (m, 3H), 2.11-1.61 (m, 3H).

Example 328

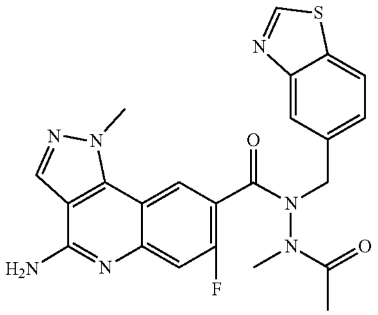

Example 328: N'-acetyl-4-amino-N-(benzo[d]thiazol-5-ylmethyl)-7-fluoro-N',1-dimethyl-1H-pyrazolo[4,3-c]quinoline-8-carbohydrazide. Prepared using general procedure E-1 starting with intermediates Db-1 and Bb-29. ES/MS: m/z=478.0 $[M+H]^+$. $^1$H NMR (400 MHz, MeOD) δ 9.39-9.18 (m, 1H), 8.56-8.38 (m, 2H), 8.32-8.00 (m, 2H), 7.93-7.43 (m, 2H), 5.57-5.21 (m, 1H), 4.81 (d, J=14.7 Hz, 1H), 4.49 (s, 3H), 3.23-2.92 (m, 3H), 2.00-1.72 (m, 3H).

Example 329

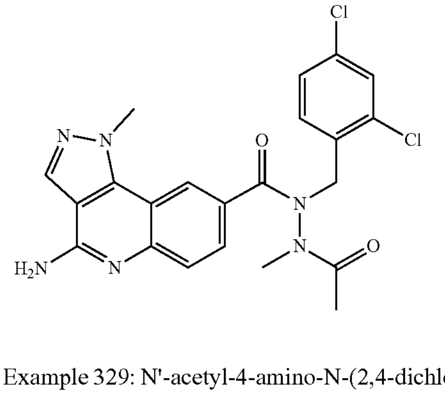

Example 329: N'-acetyl-4-amino-N-(2,4-dichlorobenzyl)-N',1-dimethyl-1H-pyrazolo[4,3-c]quinoline-8-carbohydrazide. Prepared using general procedure E-1 starting with intermediates Da-1 and Bb-30. ES/MS: m/z=471.0 $[M+H]^+$. $^1$H NMR (400 MHz, MeOD) δ 8.62-8.41 (m, 2H), 8.05-7.77 (m, 2H), 7.67 (s, 1H), 7.61-7.54 (m, 1H), 7.52-7.39 (m, 1H), 5.42-5.04 (m, 1H), 4.82 (d, J=14.7 Hz, 1H), 4.57-4.52 (m, 3H), 3.08-3.01 (m, 3H), 2.07-1.62 (m, 3H).

Example 330

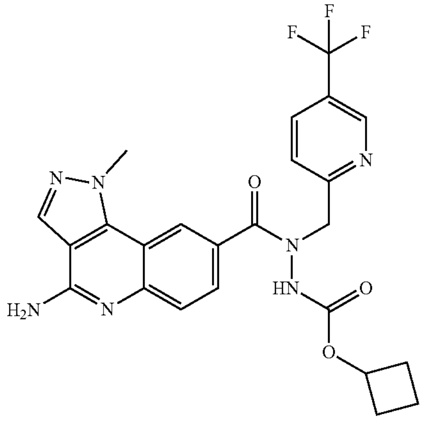

Example 330: cyclobutyl 2-(4-amino-1-methyl-1H-pyrazolo[4,3-c]quinoline-8-carbonyl)-2-((5-(trifluoromethyl) pyridin-2-yl)methyl)hydrazine-1-carboxylate. Prepared using general procedure E-1 starting with intermediates Da-1 and Bd-46. ES/MS: m/z=514.0 $[M+H]^+$. $^1$H NMR (400 MHz, MeOD) δ 8.92 (s, 1H), 8.64 (s, 1H), 8.50 (s, 1H), 8.19 (d, J=8.2 Hz, 1H), 7.97 (d, J=8.7 Hz, 1H), 7.80 (t, J=7.5 Hz, 2H), 5.43 (s, 1H), 4.80-4.76 (m, 2H), 4.54 (s, 3H), 2.49-1.19 (m, 6H).

Example 331

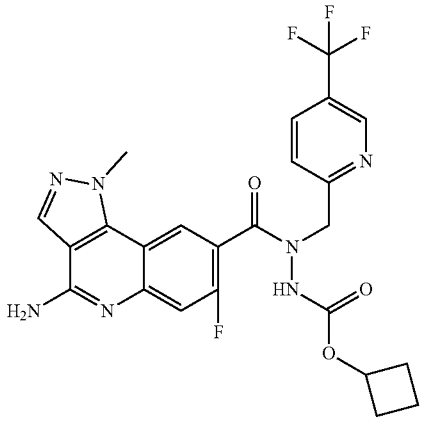

Example 331: cyclobutyl 2-(4-amino-7-fluoro-1-methyl-1H-pyrazolo[4,3-c]quinoline-8-carbonyl)-2-((5-(trifluoromethyl)pyridin-2-yl)methyl)hydrazine-1-carboxylate. Prepared using general procedure E-1 starting with intermediates Db-1 and Bd-46. ES/MS: m/z=532.0 $[M+H]^+$. $^1$H NMR (400 MHz, MeOD) δ 8.91 (s, 1H), 8.52 (d, J=6.4 Hz, 1H), 8.49 (s, 1H), 8.20 (d, J=8.3 Hz, 1H), 7.78 (d, J=8.3 Hz, 1H), 7.58 (d, J=10.1 Hz, 1H), 5.47 (s, 1H), 4.98-4.77 (m, 1H), 4.71 (s, 1H), 4.52 (s, 3H), 2.34-1.34 (m, 6H).

Example 332

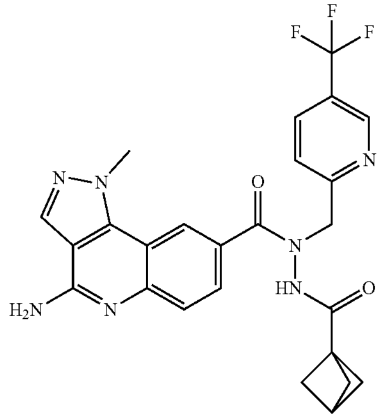

Example 332: 4-amino-N'-(bicyclo[1.1.1]pentane-1-carbonyl)-1-methyl-N-((5-(trifluoromethyl)pyridin-2-yl) methyl)-1H-pyrazolo[4,3-c]quinoline-8-carbohydrazide. Prepared using general procedure E-1 starting with intermediates Da-1 and Bd-47. ES/MS: m/z=510.0 $[M+H]^+$. $^1$H NMR (400 MHz, MeOD) δ 8.91 (d, J=2.2 Hz, 1H), 8.57 (s, 1H), 8.50 (s, 1H), 8.19 (dd, J=8.2, 2.3 Hz, 1H), 7.92 (d, J=8.6 Hz, 1H), 7.85 (d, J=8.3 Hz, 1H), 7.79 (d, J=8.6 Hz, 1H), 5.29 (s, 1H), 5.01-4.72 (m, 1H), 4.54 (s, 3H), 2.31 (s, 1H), 1.79 (s, 6H).

Example 333

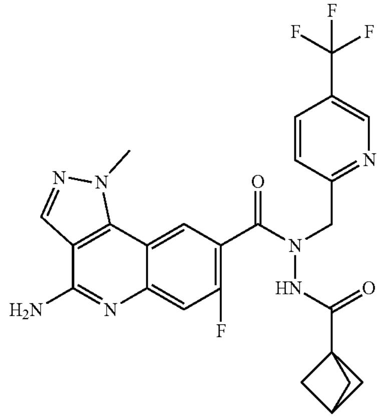

Example 333: 4-amino-N'-(bicyclo[1.1.1]pentane-1-carbonyl)-7-fluoro-1-methyl-N-((5-(trifluoromethyl)pyridin-2-yl)methyl)-1H-pyrazolo[4,3-c]quinoline-8-carbohydrazide. Prepared using general procedure E-1 starting with intermediates Db-1 and Bd-47. ES/MS: m/z=528.0 $[M+H]^+$. $^1$H NMR (400 MHz, MeOD) δ 8.92-8.86 (m, 1H), 8.49 (s, 1H), 8.46 (d, J=6.4 Hz, 1H), 8.23-8.16 (m, 1H), 7.85 (d, J=8.2 Hz, 1H), 7.59 (d, J=10.1 Hz, 1H), 5.31 (s, 1H), 4.88 (s, 1H), 4.52 (s, 3H), 2.27 (s, 1H), 1.73 (s, 6H).

Example 334

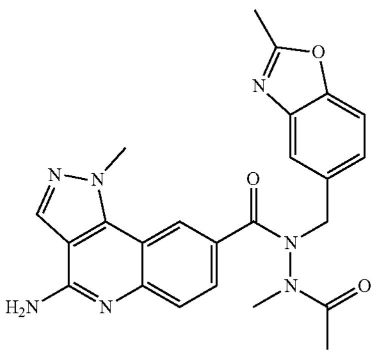

Example 334: N'-acetyl-4-amino-N',1-dimethyl-N-((2-methylbenzo[d]oxazol-5-yl)methyl)-1H-pyrazolo[4,3-c] quinoline-8-carbohydrazide. Prepared using general procedure E-1 starting with intermediates Da-1 and Bb-31. ES/MS: m/z=458.0 $[M+H]^+$. $^1H$ NMR (400 MHz, MeOD) δ 8.57-8.40 (m, 1H), 8.26 (d, J=6.0 Hz, 1H), 7.86-7.65 (m, 3H), 7.61 (t, J=8.0 Hz, 1H), 7.56-7.47 (m, 1H), 5.26-5.00 (m, 1H), 4.71 (d, J=14.5 Hz, 1H), 4.52-4.21 (m, 3H), 3.19-2.76 (m, 3H), 2.66 (d, J=1.3 Hz, 3H), 2.03-1.61 (m, 3H).

Example 335

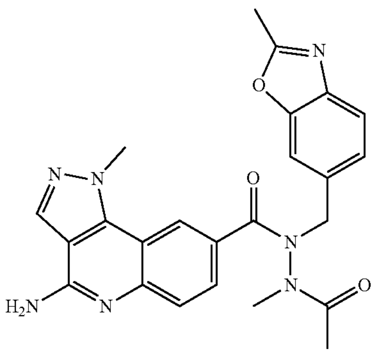

Example 335: N'-acetyl-4-amino-N',1-dimethyl-N-((2-methylbenzo[d]oxazol-6-yl)methyl)-1H-pyrazolo[4,3-c] quinoline-8-carbohydrazide. Prepared using general procedure E-1 starting with intermediates Da-1 and Bb-32. ES/MS: m/z=458.0 $[M+H]^+$. $^1H$ NMR (400 MHz, MeOD) δ 8.52-8.43 (m, 1H), 8.25 (d, J=5.6 Hz, 1H), 7.85-7.58 (m, 4H), 7.50 (s, 1H), 5.26-5.02 (m, 1H), 4.73 (d, J=14.7 Hz, 1H), 4.62-4.33 (m, 3H), 3.18-2.94 (m, 3H), 2.66 (d, J=1.6 Hz, 3H), 1.99-1.53 (m, 3H).

Example 336

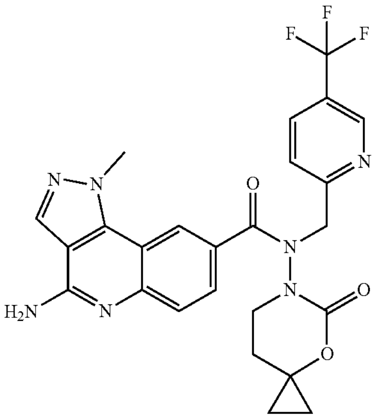

Example 336: 4-amino-1-methyl-N-(5-oxo-4-oxa-6-azaspiro[2.5]octan-6-yl)-N-((5-(trifluoromethyl)pyridin-2-yl)methyl)-1H-pyrazolo[4,3-c]quinoline-8-carboxamide. Prepared using general procedure E-1 starting with intermediates Da-1 and Bi-20. ES/MS: m/z=526.0 $[M+H]^+$. $^1H$ NMR (400 MHz, MeOD) δ 8.94 (s, 1H), 8.51 (s, 2H), 8.19 (dd, J=8.2, 2.4 Hz, 1H), 8.09-7.68 (m, 3H), 5.33 (d, J=15.5 Hz, 1H), 5.03 (d, J=15.4 Hz, 1H), 4.51 (s, 3H), 3.91 (s, 1H), 3.68-3.43 (m, 1H), 2.09-1.92 (m, 1H), 1.70 (s, 1H), 1.04-0.22 (m, 4H).

Example 337

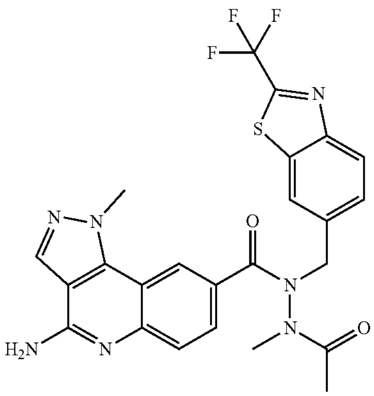

Example 337: N'-acetyl-4-amino-N',1-dimethyl-N-((2-(trifluoromethyl)benzo[d]thiazol-6-yl)methyl)-1H-pyrazolo [4,3-c]quinoline-8-carbohydrazide. Prepared using general procedure E-1 starting with intermediates Da-1 and Bb-33. ES/MS: m/z=528.0 $[M+H]^+$. $^1H$ NMR (400 MHz, MeOD) § 8.60-8.47 (m, 2H), 8.36 (s, 1H), 8.24 (dd, J=12.3, 8.5 Hz, 1H), 8.07-7.84 (m, 2H), 7.81 (d, J=8.6 Hz, 1H), 5.48-5.12 (m, 1H), 4.90 (s, 1H), 4.65-4.35 (m, 3H), 3.25-3.08 (m, 3H), 2.00-1.70 (m, 3H).

Example 338

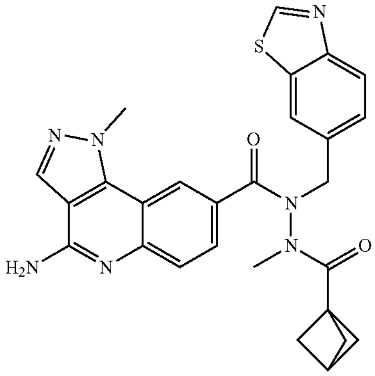

Example 338: 4-amino-N-(benzo[d]thiazol-6-ylmethyl)-N'-(bicyclo[1.1.1]pentane-1-carbonyl)-N',1-dimethyl-1H-pyrazolo[4,3-c]quinoline-8-carbohydrazideide. Prepared using general procedure E-1 starting with intermediates Da-1 and Bo-7. ES/MS: m/z=512.0 $[M+H]^+$. $^1H$ NMR (400 MHz, MeOD) δ 9.30 (s, 1H), 8.55-8.45 (m, 2H), 8.22 (s, 1H), 8.11 (d, J=8.4 Hz, 1H), 7.87 (s, 1H), 7.80 (d, J=8.3 Hz, 1H), 7.72 (s, 1H), 5.30 (d, J=14.5 Hz, 1H), 4.64-4.38 (m, 4H), 3.09 (s, 3H), 2.29 (s, 1H), 1.91-1.64 (m, 6H).

Example 339

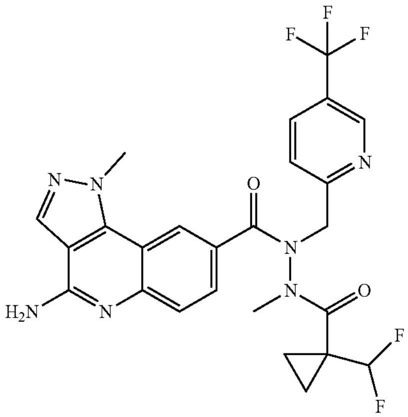

Example 339: 4-amino-N'-(1-(difluoromethyl)cyclopropane-1-carbonyl)-N',1-dimethyl-N-((5-(trifluoromethyl)pyridin-2-yl)methyl)-1H-pyrazolo[4,3-c]quinoline-8-carbohydrazide. Prepared using general procedure E-1 starting with intermediates Da-1 and Bc-25. ES/MS: m/z=548.0 $[M+H]^+$. $^1H$ NMR (400 MHz, MeOD) δ 8.86 (s, 1H), 8.59-8.42 (m, 2H), 8.17 (d, J=8.3 Hz, 1H), 7.94-7.84 (m, 2H), 7.80 (d, J=8.5 Hz, 1H), 5.49-4.95 (m, 3H), 4.54 (s, 3H), 3.49 (s, 3H), 1.46-0.52 (m, 4H).

Example 340

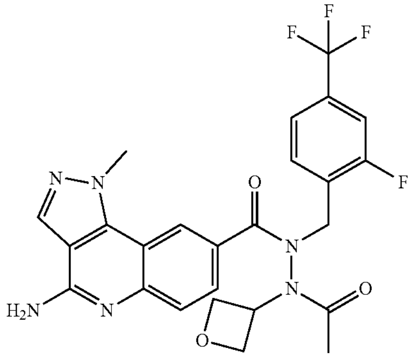

Example 340: N'-acetyl-4-amino-N-(2-fluoro-4-(trifluoromethyl)benzyl)-1-methyl-N'-(oxetan-3-yl)-1H-pyrazolo[4,3-c]quinoline-8-carbohydrazide. Prepared using general procedure E-1 starting with intermediates Da-1 and Bd-48. ES/MS: m/z=531.0 $[M+H]^+$. 1H NMR (400 MHz, MeOD) δ 8.53 (d, J=17.3 Hz, 1H), 8.39 (s, 1H), 8.03-7.70 (m, 3H), 7.64-7.48 (m, 2H), 5.23 (d, J=14.6 Hz, 1H), 5.02 (d, J=14.1 Hz, 1H), 4.69-4.29 (m, 8H), 2.13 (s, 3H).

Example 341

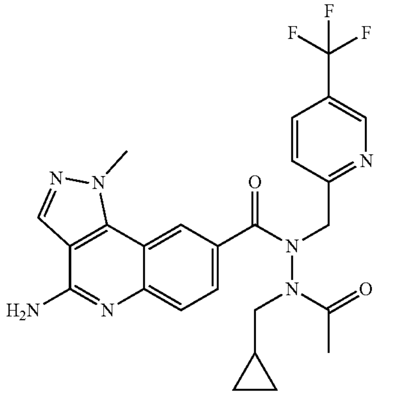

Example 341: N'-acetyl-4-amino-N'-(cyclopropylmethyl)-1-methyl-N-((5-(trifluoromethyl)pyridin-2-yl)methyl)-1H-pyrazolo[4,3-c]quinoline-8-carbohydrazide. Prepared using general procedure E-1 starting with intermediates Da-1 and Bd-49. ES/MS: m/z=512.2 $[M+H]^+$. $^1H$ NMR (400 MHz, MeOD) δ 9.15-8.83 (m, 1H), 8.58 (s, 0.6H, minor rotamer), 8.50 (s, 1H), 8.30-7.72 (m, 4H), 7.58 (s, 0.3H, minor rotamer), 5.26-5.01 (m, 2H), 4.67-4.40 (m, 3H), 3.85-3.55 (m, 1H), 3.45 (dd, J=15.1, 7.0 Hz, 1H), 2.27 (s, 1H, minor rotamer), 2.03 (d, J=16.9 Hz, 2H), 0.92 (s, 1H), 0.61--0.07 (m, 4H).

Example 342

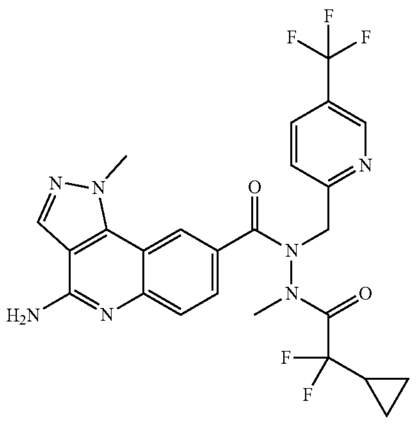

Example 342: 4-amino-N'-(2-cyclopropyl-2,2-difluoroacetyl)-N',1-dimethyl-N-((5-(trifluoromethyl)pyridin-2-yl)methyl)-1H-pyrazolo[4,3-c]quinoline-8-carbohydrazide. Prepared using general procedure E-1 starting with intermediates Da-1 and Bc-26. ES/MS: m/z=548.0 $[M+H]^+$. $^1H$ NMR (400 MHz, MeOD) δ 9.02-8.83 (m, 1H), 8.68-8.39 (m, 2H), 8.18 (d, J=8.3 Hz, 1H), 8.02-7.65 (m, 3H), 5.24 (d, J=15.4 Hz, 1H), 5.03 (s, 1H), 4.54 (s, 3H), 3.56-3.40 (m, 3H), 3.26-3.09 (m, 1H), 1.83-0.17 (m, 4H).

Example 343

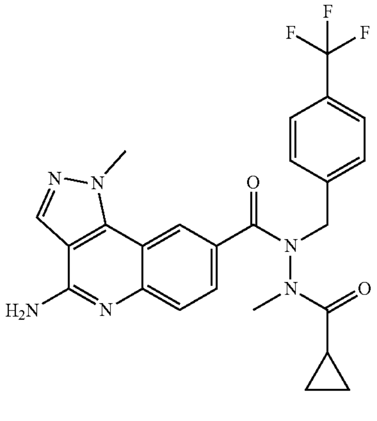

Example 343: 4-amino-N'-(cyclopropanecarbonyl)-N',1-dimethyl-N-(4-(trifluoromethyl)benzyl)-1H-pyrazolo[4,3-c]quinoline-8-carbohydrazide. Prepared using general procedure E-1 starting with intermediates Da-1 and Bo-8. ES/MS: m/z=497.2 $[M+H]^+$. $^1H$ NMR (400 MHz, MeOD) δ 8.59 (d, J=1.8 Hz, 0.7H, minor rotamer), 8.50 (d, J=2.6 Hz, 1.3H), 8.04-7.62 (m, 6H), 5.50-5.14 (m, 1H), 5.03 (d, J=14.5 Hz, 0.6H), 4.74 (d, J=14.7 Hz, 0.4H, minor rotamer), 4.53 (s, 3H), 3.28 (s, 1H, minor rotamer), 3.12 (s, 2H), 1.71 (s, 0.6H), 1.57 (s, 0.4H, minor rotamer), 0.93-0.20 (m, 4H).

Example 344

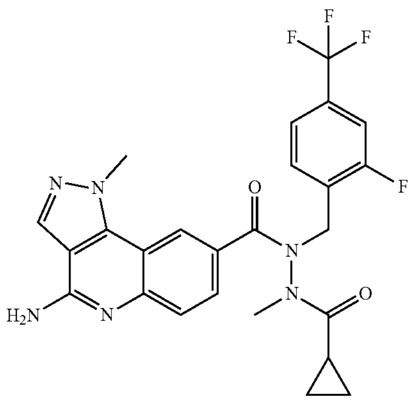

Example 344: 4-amino-N'-(cyclopropanecarbonyl)-N-(2-fluoro-4-(trifluoromethyl)benzyl)-N',1-dimethyl-1H-pyrazolo[4,3-c]quinoline-8-carbohydrazide. Prepared using general procedure E-1 starting with intermediates Da-1 and Bd-50. ES/MS: m/z=515.0 $[M+H]^+$. $^1H$ NMR (400 MHz, MeOD) δ 8.60 (s, 0.5H), 8.55-8.46 (m, 1.5H), 7.98 (d, J=8.7 Hz, 0.5H), 7.87 (s, 2.5H), 7.70-7.45 (m, 2H), 5.43 (s, 0.5H), 5.14 (d, J=14.1 Hz, 0.5H), 5.05 (d, J=14.6 Hz, 0.5H), 4.95 (s, 0.5H), 4.54 (s, 1.5H), 4.53 (s, 1.5H), 3.37 (s, 1.5H), 3.14 (s, 1.5H), 1.80-1.66 (m, 0.5H), 1.59 (s, 0.5H), 0.97-0.24 (m, 4H). Note: 1:1 rotamer with multiple overlapping signals.

Example 345

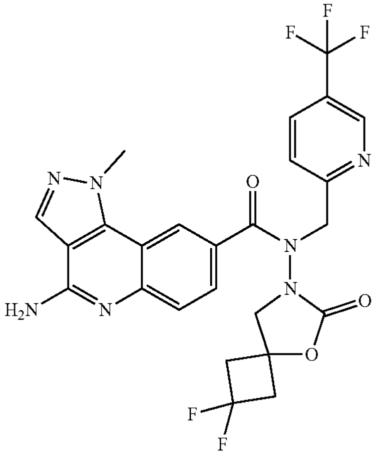

Example 345: 4-amino-N-(2,2-difluoro-6-oxo-5-oxa-7-azaspiro[3.4]octan-7-yl)-1-methyl-N-((5-(trifluoromethyl)pyridin-2-yl)methyl)-1H-pyrazolo[4,3-c]quinoline-8-carboxamide. Prepared using general procedure E-1 starting with intermediates Da-1 and Bi-21. ES/MS: m/z=562.2 $[M+H]^+$. $^1H$ NMR (400 MHz, MeOD) δ 8.95 (s, 1H), 8.65 (s, 1H), 8.50 (s, 1H), 8.19 (dd, J=8.5, 2.2 Hz, 1H), 8.00 (d, J=8.6 Hz, 1H), 7.87-7.78 (m, 2H), 5.25 (d, J=16.2 Hz, 1H), 5.09 (d, J=15.6 Hz, 1H), 4.48 (s, 3H), 4.07 (s, 1H), 3.87 (s, 1H), 3.14-2.43 (m, 4H).

Exmple 346

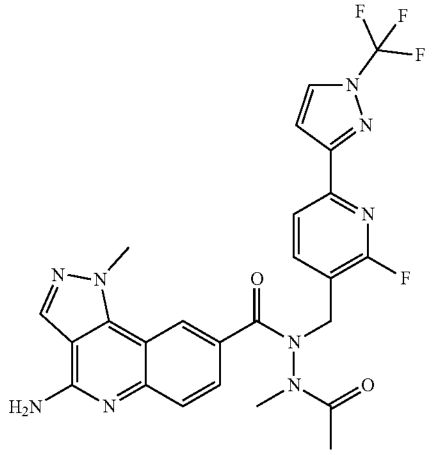

Example 346: N'-acetyl-4-amino-N-((2-fluoro-6-(1-(trifluoromethyl)-1H-pyrazol-3-yl)pyridin-3-yl)methyl)-N',1-dimethyl-1H-pyrazolo[4,3-c]quinoline-8-carbohydrazide. Prepared following the procedure reported for example 130 starting with intermediates Da-1, Bb-34, and 3-(4,4,5,5-tetramethyl-1,3,2-dioxaborolan-2-yl)-1-(trifluoromethyl) pyrazole. ES/MS: m/z=556.0 $[M+H]^+$. $^1H$ NMR (400 MHz, MeOD) δ 8.65-8.40 (m, 2H), 8.36-8.12 (m, 2H), 8.10-7.96 (m, 1H), 7.90 (d, J=8.9 Hz, 1H), 7.80 (d, J=8.6 Hz, 1H), 7.14 (d, J=2.8 Hz, 1H), 5.19-4.90 (m, 2H), 4.65-4.40 (m, 3H), 3.32 (s, 3H), 2.06-1.75 (m, 3H).

Exmple 347

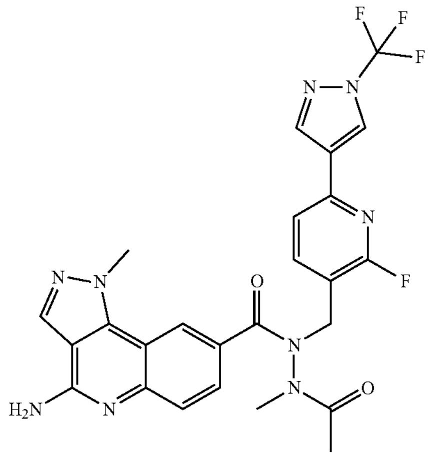

Example 347: N'-acetyl-4-amino-N-((2-fluoro-6-(1-(trifluoromethyl)-1H-pyrazol-4-yl)pyridin-3-yl)methyl)-N',1-dimethyl-1H-pyrazolo[4,3-c]quinoline-8-carbohydrazide. Prepared following the procedure reported for example 130 starting with intermediates Da-1, Bb-34, and 4-(4,4,5,5-tetramethyl-1,3,2-dioxaborolan-2-yl)-1-(trifluoromethyl) pyrazole. ES/MS: m/z=556.0 $[M+H]^+$. $^1H$ NMR (400 MHz, MeOD) δ 8.82 (d, J=7.6 Hz, 1H), 8.61-8.34 (m, 3H), 8.30-8.02 (m, 1H), 7.93-7.69 (m, 3H), 5.19-4.89 (m, 2H), 4.58-4.50 (m, 3H), 3.32 (s, 2H, major rotamer), 3.19-3.14 (m, 1H, minor rotamer), 2.03-1.74 (m, 3H).

Exmple 348

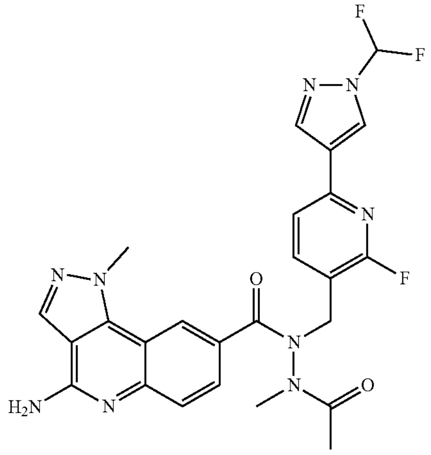

Example 348: N'-acetyl-4-amino-N-((6-(1-(difluoromethyl)-1H-pyrazol-4-yl)-2-fluoropyridin-3-yl)methyl)-N',1-dimethyl-1H-pyrazolo[4,3-c]quinoline-8-carbohydrazide. Prepared following the procedure reported for example 130 starting with intermediates Da-1, Bb-34, and 1-(difluoromethyl)-4-(4,4,5,5-tetramethyl-1,3,2-dioxaborolan-2-yl)pyrazole. ES/MS: m/z=538.0 $[M+H]^+$. $^1H$ NMR (400 MHz, MeOD) δ 8.66 (d, J=6.3 Hz, 1H), 8.60-8.47 (m, 2H), 8.34-8.03 (m, 2H), 7.99-7.75 (m, 2H), 7.74-7.36 (m, 2H), 5.08-4.91 (m, 2H), 4.58-4.50 (m, 3H), 3.31 (s, 2H, major rotamer), 3.16 (s, 1H, minor rotamer), 2.01-1.67 (m, 3H).

Example 349

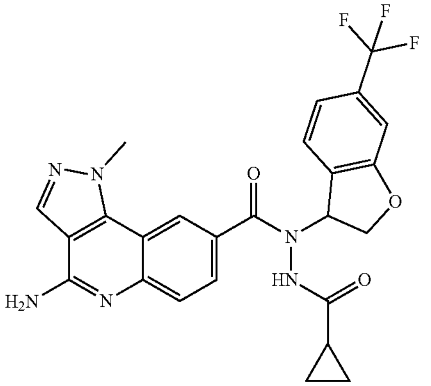

Example 349: 4-amino-N'-(cyclopropanecarbonyl)-1-methyl-N-(6-(trifluoromethyl)-2,3-dihydrobenzofuran-3-yl)-1H-pyrazolo[4,3-c]quinoline-8-carbohydrazide. Prepared using general procedure E-1 starting with intermediates Da-1 and Bs-1. ES/MS: m/z=511.0 $[M+H]^+$. $^1H$ NMR (400 MHz, MeOD) δ 8.58 (s, 1H), 8.50 (s, 1H), 7.92 (d, J=8.7 Hz, 1H), 7.84-7.54 (m, 2H), 7.44-7.07 (m, 2H), 6.34 (s, 1H), 5.00-4.87 (m, 2H), 4.55 (s, 3H), 1.15 (s, 1H), 0.82-0.19 (m, 4H).

Example 350

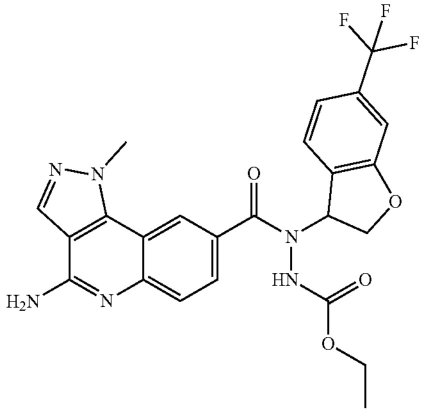

Example 350: ethyl 2-(4-amino-1-methyl-1H-pyrazolo[4,3-c]quinoline-8-carbonyl)-2-(6-(trifluoromethyl)-2,3-dihydrobenzofuran-3-yl)hydrazine-1-carboxylate. Prepared using general procedure E-1 starting with intermediates Da-1 and Bs-2. ES/MS: m/z=515.0 $[M+H]^+$. $^1H$ NMR (400 MHz, MeOD) δ 8.62 (s, 1H), 8.50 (s, 1H), 7.95 (d, J=8.6 Hz, 1H), 7.78 (d, J=8.7 Hz, 1H), 7.67 (d, J=7.8 Hz, 1H), 7.32 (s, 1H), 7.13 (s, 1H), 6.32 (s, 1H), 4.97 (s, 1H), 4.56 (s, 3H), 4.06-3.86 (m, 1H), 3.86-3.56 (m, 2H), 1.01-0.68 (m, 3H).

Example 351

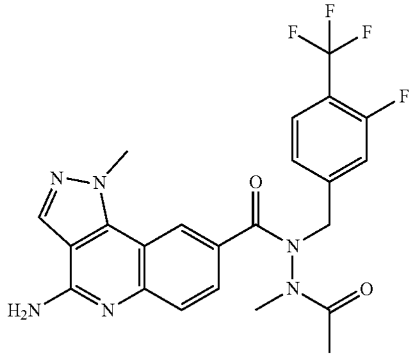

Example 351: N'-acetyl-4-amino-N-(3-fluoro-4-(trifluoromethyl)benzyl)-N',1-dimethyl-1H-pyrazolo[4,3-c]quinoline-8-carbohydrazide. Prepared following general procedure E-1 starting with intermediates Da-1 and Ba-78. ES/MS: m/z=489.0 $[M+H]^+$. $^1H$ NMR (400 MHz, DMSO-$d_6$) δ 13.66 (s, 1H), 9.66 (s, 1H), 8.95 (s, 1H), 8.63 (d, J=1.3 Hz, 1H), 8.43 (dd, J=35.1, 1.8 Hz, 1H), 8.00-7.76 (m, 3H), 7.64 (dd, J=49.8, 9.9 Hz, 2H), 5.10 (d, J=15.4 Hz, 1H), 4.67 (d, J=15.5 Hz, 1H), 4.47 (d, J=2.6 Hz, 3H), 3.20 (s, 2H), 3.03 (s, 1H), 1.81 (s, 3H).

Example 352

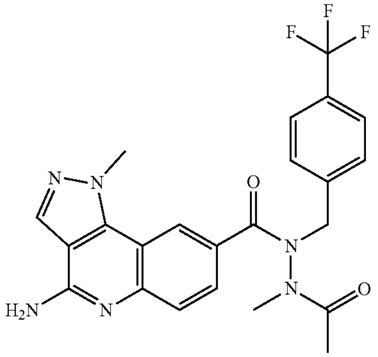

Example 352: N'-acetyl-4-amino-N',1-dimethyl-N-(4-(trifluoromethyl)benzyl)-1H-pyrazolo[4,3-c]quinoline-8-carbohydrazide. Prepared following general procedure E-1 starting with intermediates Da-1 and Ba-79. ES/MS: m/z=489.0 $[M+H]^+$. $^1H$ NMR (400 MHz, DMSO-d6) δ 13.77 (s, 1H), 9.73 (s, 1H), 8.87 (s, 1H), 8.66 (d, J=2.0 Hz, 1H), 8.49-8.32 (m, 1H), 7.97-7.85 (m, 1H), 7.83 (d, J=1.7 Hz, 1H), 7.78 (d, J=7.8 Hz, 1H), 7.75 (s, 2H), 5.15 (d, J=15.1 Hz, 1H), 5.04 (s, 1H), 4.62 (d, J=15.2 Hz, 1H), 4.46 (d, J=4.6 Hz, 3H), 3.06 (d, J=40.2 Hz, 3H), 1.75 (d, J=34.2 Hz, 3H).

Exmple 353

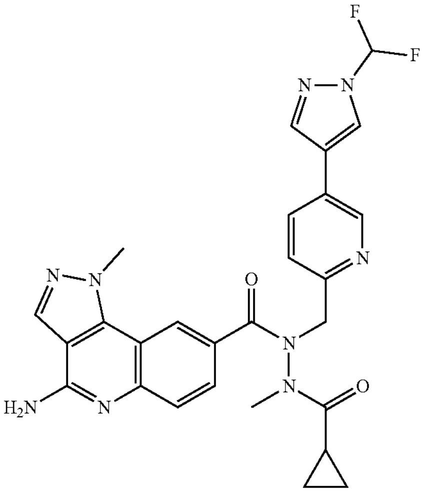

Example 353: 4-amino-N'-(cyclopropanecarbonyl)-N-((5-(1-(difluoromethyl)-1H-pyrazol-4-yl)pyridin-2-yl)methyl)-N',1-dimethyl-1H-pyrazolo[4,3-c]quinoline-8-carbohydrazide. Prepared following general procedure E-1 starting with intermediates Da-1 and Bt-1. ES/MS: m/z=546.0 $[M+H]^+$. $^1H$ NMR (400 MHz, DMSO-$d_6$) δ 13.50 (s, 1H), 8.99 (s, 3H), 8.91 (s, 1H), 8.64 (s, 1H), 8.42 (s, 1H), 8.15 (dd, J=8.0, 2.2 Hz, 2H), 7.89 (t, J=59.3 Hz, 1H), 5.17 (d, J=13.6 Hz, 1H), 5.01 (s, 2H), 4.62 (d, J=15.2 Hz, 2H), 4.46 (s, 1H), 3.27 (s, 1H), 3.07 (s, 3H), 1.98-1.80 (m, 1H), 0.68 (d, J=8.0 Hz, 2H), 0.41 (s, 3H).

Exmple 354

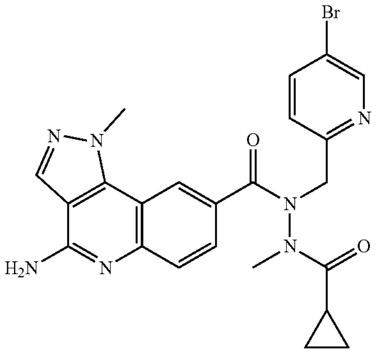

Example 354: 4-amino-N-((5-bromopyridin-2-yl)methyl)-N'-(cyclopropanecarbonyl)-N',1-dimethyl-1H-pyrazolo[4,3-c]quinoline-8-carbohydrazide. Prepared following general procedure E-1 starting with intermediates Da-1 and Bj-2. ES/MS: m/z=508.0 $[M+H]^+$. $^1$H NMR (400 MHz, Methanol-d4) δ 8.83-8.57 (m, 2H), 8.51 (d, J=4.3 Hz, 1H), 8.05 (t, J=7.5 Hz, 1H), 7.83 (d, J=19.7 Hz, 2H), 7.62 (s, 1H), 5.15 (s, 1H), 4.53 (s, 3H), 3.41 (s, 1H), 3.20-3.10 (m, 2H), 1.96 (s, 1H), 0.85-0.72 (m, 2H), 0.70-0.52 (m, 3H).

Exmple 355

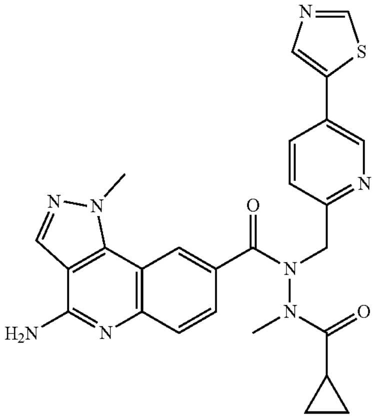

Example 355: 4-amino-N'-(cyclopropanecarbonyl)-N',1-dimethyl-N-((5-(thiazol-5-yl)pyridin-2-yl)methyl)-1H-pyrazolo[4,3-c]quinoline-8-carbohydrazide. Prepared following general procedure E-1 starting with intermediates Da-1 and Bt-2. ES/MS: m/z=513.0 $[M+H]^+$. $^1$H NMR (400 MHz, DMSO-$d_6$) δ 13.53 (s, 1H), 9.20 (d, J=3.7 Hz, 1H), 9.03-8.76 (m, 4H), 8.63 (s, 1H), 8.48 (d, J=4.5 Hz, 1H), 8.15 (d, J=7.6 Hz, 1H), 7.83 (d, J=11.9 Hz, 1H), 5.17 (d, J=15.7 Hz, 1H), 5.04 (s, 1H), 4.49 (d, J=17.9 Hz, 3H), 3.09 (s, 3H), 1.24 (s, 1H), 0.69 (s, 1H), 0.45 (d, J=12.0 Hz, 2H), 0.32 (s, 1H).

Exmple 356

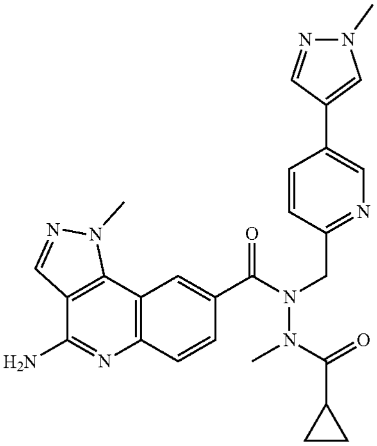

Example 356: 4-amino-N'-(cyclopropanecarbonyl)-N',1-dimethyl-N-((5-(1-methyl-1H-pyrazol-4-yl)pyridin-2-yl)methyl)-1H-pyrazolo[4,3-c]quinoline-8-carbohydrazide. Prepared following general procedure E-1 starting with intermediates Da-1 and Bt-3. ES/MS: m/z=510.0 $[M+H]^+$. $^1$H NMR (400 MHz, DMSO-$d_6$) δ 13.48 (s, 1H), 8.84 (s, 3H), 8.63 (d, J=1.8 Hz, 1H), 8.29 (s, 1H), 7.99 (d, J=9.4 Hz, 2H), 7.81 (s, 1H), 7.48 (d, J=70.7 Hz, 1H), 5.15 (d, J=13.7 Hz, 1H), 4.96 (s, 1H), 4.51 (d, J=39.6 Hz, 3H), 3.15 (d, J=72.5 Hz, 3H), 1.89 (d, J=18.5 Hz, 1H), 0.71-0.27 (m, 4H).

Exmple 357

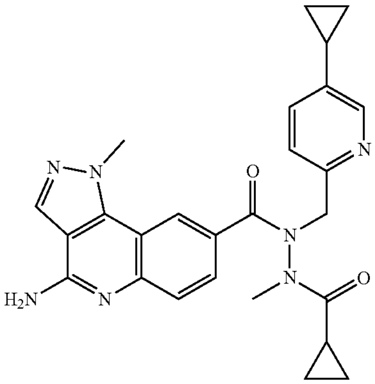

Example 357: 4-amino-N'-(cyclopropanecarbonyl)-N-((5-cyclopropylpyridin-2-yl)methyl)-N',1-dimethyl-1H-pyrazolo[4,3-c]quinoline-8-carbohydrazide. Prepared following general procedure E-1 starting with intermediates Da-1 and Bt-4. ES/MS: m/z=470.2 $[M+H]^+$. $^1$H NMR (400 MHz, DMSO-$d_6$) δ 13.61 (s, 1H), 9.68 (s, 1H), 8.94 (s, 1H), 8.64 (d, J=4.5 Hz, 1H), 8.46 (s, 2H), 7.85 (d, J=32.1 Hz, 2H), 7.51 (d, J=39.7 Hz, 2H), 5.14 (s, 1H), 4.92 (s, 2H), 4.51 (d, J=37.0 Hz, 4H), 3.25-2.97 (m, 3H), 2.00 (d, J=8.8 Hz, 1H), 1.03 (dt, J=9.3, 3.3 Hz, 2H), 0.76 (d, J=5.4 Hz, 2H), 0.38 (s, 3H).

Exmple 358

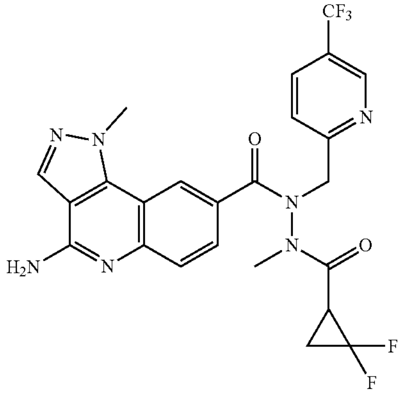

Example 358: 4-amino-N'-(2,2-difluorocyclopropane-1-carbonyl)-N',1-dimethyl-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bu-1. ES/MS: m/z=534.0 [M+H]$^+$. $^1$H NMR (400 MHz, DMSO-$d_6$) δ 13.67 (s, 1H), 9.71 (s, 1H), 9.07 (s, 1H), 9.03-8.93 (m, 2H), 8.64 (d, J=1.6 Hz, 1H), 8.31-8.22 (m, 1H), 7.91 (s, 1H), 7.85 (d, J=8.6 Hz, 1H), 5.22 (d, J=16.9 Hz, 1H), 5.08-4.73 (m, 1H), 4.44 (d, J=6.6 Hz, 1H), 3.58 (s, 3H), 3.13 (d, J=23.1 Hz, 1H), 1.79 (d, J=26.3 Hz, 2H).

Example 359

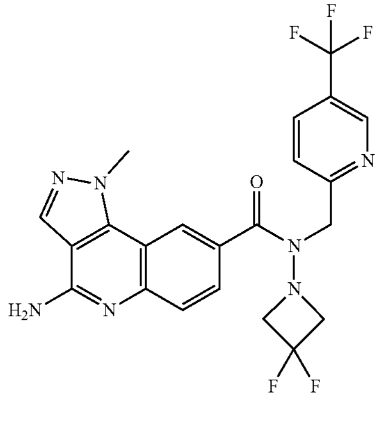

Example 359: 4-amino-N-(3,3-difluoroazetidin-1-yl)-1-methyl-N-((5-(trifluoromethyl)pyridin-2-yl)methyl)-1H-pyrazolo[4,3-c]quinoline-8-carboxamide. Prepared following general procedure E-1 starting with intermediates Da-1 and Ba-80. ES/MS: m/z=492.0 [M+H]$^+$. $^1$H NMR (400 MHz, DMSO-$d_6$) δ 13.94 (s, 1H), 9.66 (s, 1H), 9.21 (s, 1H), 8.97 (s, 1H), 8.63 (s, 1H), 8.59 (s, 1H), 8.23 (dd, J=8.3, 2.4 Hz, 1H), 7.99 (d, J=8.6 Hz, 1H), 7.79 (d, J=8.7 Hz, 1H), 7.73 (d, J=8.3 Hz, 1H), 5.06 (s, 2H), 4.46 (d, J=11.1 Hz, 3H), 4.23 (t, J=12.1 Hz, 4H).

Example 360

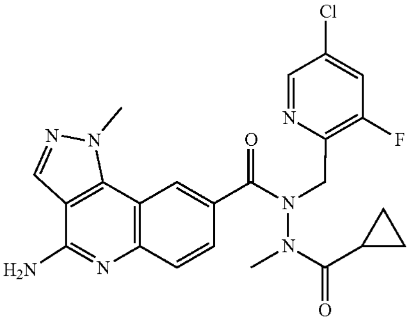

Example 360: 4-amino-N-((5-chloro-3-fluoropyridin-2-yl)methyl)-N'-(cyclopropanecarbonyl)-N',1-dimethyl-1H-pyrazolo[4,3-c]quinoline-8-carbohydrazide. Prepared following general procedure E-1 starting with intermediates Da-1 and Bk-7. ES/MS: m/z=482.0 [M+H]$^+$. $^1$H NMR (400 MHz, Methanol-$d_4$) δ 8.51 (d, J=5.2 Hz, 3H), 7.90 (dd, J=9.4, 2.0 Hz, 1H), 7.85 (dd, J=9.2, 2.1 Hz, 1H), 7.82-7.76 (m, 1H), 5.24 (s, 3H), 4.58 (d, J=5.1 Hz, 2H), 4.53 (s, 1H), 3.43 (s, 1H), 3.18 (s, 2H), 0.82 (s, 2H), 0.67 (s, 2H).

Example 361

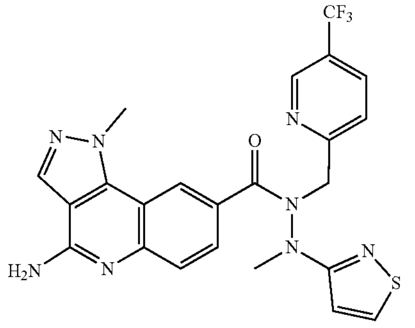

Example 361: 4-amino-N-((5-chloro-3-fluoropyridin-2-yl)methyl)-N'-(cyclopropanecarbonyl)-N',1-dimethyl-1H-pyrazolo[4,3-c]quinoline-8-carbohydrazide. Prepared following general procedure E-1 starting with intermediates Da-1 and BI-4. ES/MS: m/z=513.0 [M+H]$^+$. $^1$H NMR (400 MHz, Methanol-$d_4$) δ 8.91 (s, 1H), 8.67 (s, 1H), 8.47 (s, 1H), 8.17-8.12 (m, 1H), 8.06 (d, J=8.6 Hz, 1H), 7.80 (d, J=8.6 Hz, 1H), 7.31 (d, J=3.6 Hz, 1H), 6.98 (d, J=3.6 Hz, 1H), 5.45 (d, J=16.2 Hz, 1H), 4.94 (d, J=17.1 Hz, 2H), 4.31 (s, 3H), 3.30 (s, 3H).

Example 362

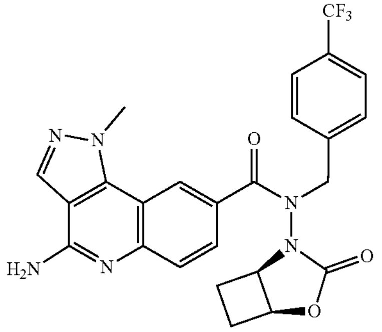

Example 362: 4-amino-1-methyl-N-((1S,5R)-3-oxo-2-oxa-4-azabicyclo[3.2.0]heptan-4-yl)-N-((5-(trifluoromethyl)pyridin-2-yl)methyl)-1H-pyrazolo[4,3-c]quinoline-8-carboxamide. Prepared following general procedure E-1 starting with intermediates Da-1 and Ba-76. ES/MS: m/z=512.0 $[M+H]^+$. $^1H$ NMR (400 MHz, Methanol-$d_4$) δ 8.94 (d, J=37.3 Hz, 1H), 8.76 (s, 1H), 8.50 (s, 1H), 8.18 (s, 1H), 8.04 (d, J=8.7 Hz, 1H), 7.86 (s, 2H), 5.24-5.10 (m, 1H), 5.46-4.94 (m, 2H), 4.51 (s, 4H), 2.46-1.99 (m, 2H), 1.52 (s, 2H).

Example 363

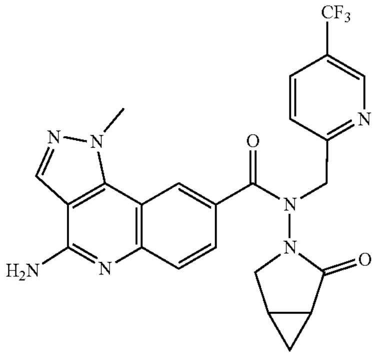

Example 363: 4-amino-N-((5-chloro-3-fluoropyridin-2-yl)methyl)-N'-(cyclopropanecarbonyl)-N',1-dimethyl-1H-pyrazolo[4,3-c]quinoline-8-carbohydrazide. Prepared following general procedure E-1 starting with intermediates Da-1 and BI-5. ES/MS: m/z=513.0 $[M+H]^+$. $^1H$ NMR (400 MHz, Methanol-$d_4$) δ 8.91 (s, 1H), 8.67 (s, 1H), 8.47 (s, 1H), 8.17-8.12 (m, 1H), 8.06 (d, J=8.6 Hz, 1H), 7.80 (d, J=8.6 Hz, 1H), 7.31 (d, J=3.6 Hz, 1H), 6.98 (d, J=3.6 Hz, 1H), 5.45 (d, J=16.2 Hz, 1H), 4.94 (d, J=17.1 Hz, 2H), 4.31 (s, 3H), 3.30 (s, 3H).

Example 364

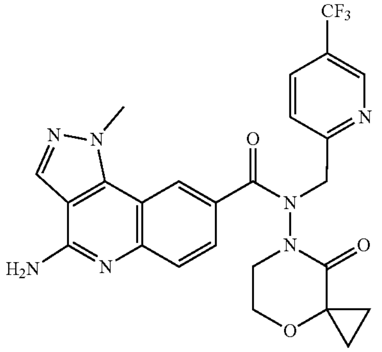

Example 364: 4-amino-1-methyl-N-(8-oxo-4-oxa-7-azaspiro[2.5]octan-7-yl)-N-((5-(trifluoromethyl)pyridin-2-yl)methyl)-1H-pyrazolo[4,3-c]quinoline-8-carboxamide. Prepared following general procedure E-1 starting with intermediates Da-1 and BI-6. ES/MS: m/z=513.0 $[M+H]^+$. $^1H$ NMR (400 MHz, DMSO-$d_6$) δ 13.83 (s, 1H), 9.71 (s, 1H), 9.12 (s, 1H), 8.99 (s, 1H), 8.64 (s, 1H), 8.40 (d, J=5.5 Hz, 1H), 8.27 (dd, J=8.3, 2.4 Hz, 1H), 7.93 (d, J=8.4 Hz, 1H), 7.84 (s, 2H), 5.22 (d, J=15.7 Hz, 1H), 4.95 (d, J=15.6 Hz, 1H), 4.44 (s, 3H), 3.85-3.79 (m, 1H), 3.53 (d, J=61.1 Hz, 2H), 1.07 (td, J=9.1, 4.6 Hz, 1H), 0.93 (s, 1H), 0.70 (s, 2H).

Example 365

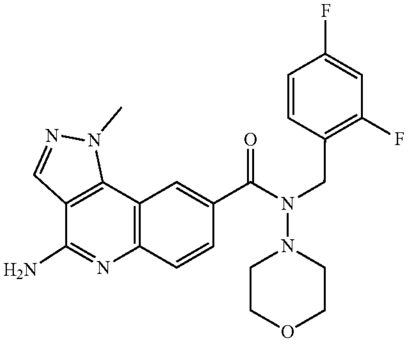

Example 365: 4-amino-N-(2,4-difluorobenzyl)-1-methyl-N-morpholino-1H-pyrazolo[4,3-c]quinoline-8-carboxamide. Prepared following general procedure E-1 starting with intermediates Da-1 and Ba-81. ES/MS: m/z=453.0 $[M+H]^+$. $^1H$ NMR (400 MHz, DMSO-$d_6$) δ 13.54 (s, 1H), 9.61 (s, 1H), 8.85 (s, 1H), 8.63 (s, 1H), 8.47 (d, J=1.7 Hz, 1H), 7.99 (dd, J=8.5, 1.7 Hz, 1H), 7.79 (d, J=8.6 Hz, 1H), 7.61 (td, J=8.7, 6.6 Hz, 1H), 7.29 (ddd, J=10.8, 9.3, 2.6 Hz, 1H), 7.10 (ddd, J=10.6, 8.0, 2.4 Hz, 1H), 4.79 (s, 2H), 4.46 (s, 3H), 3.67 (s, 2H), 3.11 (s, 2H), 2.87 (d, J=41.5 Hz, 4H).

Example 366

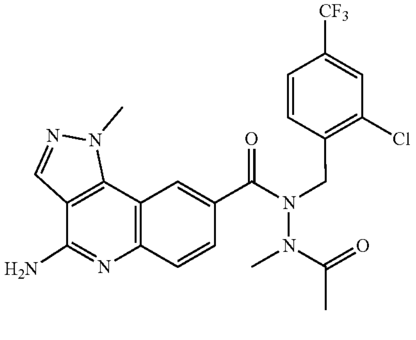

Example 366: N'-acetyl-4-amino-N-(2-chloro-4-(trifluoromethyl)benzyl)-N',1-dimethyl-1H-pyrazolo[4,3-c]quinoline-8-carbohydrazide. Prepared following general procedure E-1 starting with intermediates Da-1 and Bb-35. ES/MS: m/z=513.0 $[M+H]^+$. $^1H$ NMR (400 MHz, DMSO-$d_6$) δ 13.46 (s, 1H), 9.66 (s, 1H), 8.76 (s, 1H), 8.64 (d, J=1.3 Hz, 1H), 8.48-8.38 (m, 1H), 8.01-7.91 (m, 2H), 7.88-7.79 (m, 2H), 7.76 (dd, J=8.2, 1.9 Hz, 1H), 5.19 (d, J=16.4 Hz, 1H), 4.79 (s, 1H), 4.47 (d, J=7.6 Hz, 3H), 3.04 (d, J=70.3 Hz, 3H), 1.79 (d, J=11.5 Hz, 3H).

Example 367

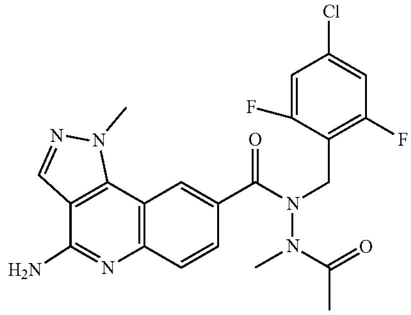

Example 367: N'-acetyl-4-amino-N-(4-chloro-2,6-difluorobenzyl)-N',1-dimethyl-1H-pyrazolo[4,3-c]quinoline-8-carbohydrazide. Prepared following general procedure E-1 starting with intermediates Da-1 and Bb-36. ES/MS: m/z=473.0 $[M+H]^+$. $^1H$ NMR (400 MHZ, DMSO-$d_6$) δ 13.94 (s, 1H), 9.70 (s, 1H), 9.22 (s, 1H), 8.63 (d, J=7.2 Hz, 1H), 8.37 (d, J=62.3 Hz, 1H), 7.88 (d, J=16.4 Hz, 1H), 7.78 (s, 1H), 7.49 (d, J=7.6 Hz, 1H), 7.42 (d, J=7.4 Hz, 1H), 5.01-4.74 (m, 2H), 4.46 (d, J=24.3 Hz, 3H), 3.03 (d, J=35.5 Hz, 3H), 1.72 (d, J=8.3 Hz, 3H).

Example 368

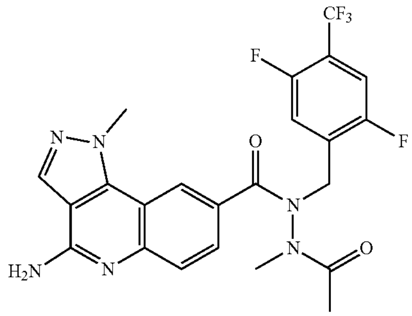

Example 368: N'-acetyl-4-amino-N-(2,5-difluoro-4-(trifluoromethyl)benzyl)-N', 1-dimethyl-1H-pyrazolo[4,3-c]quinoline-8-carbohydrazide. Prepared following general procedure E-1 starting with intermediates Da-1 and Ba-82. ES/MS: m/z=507.0 $[M+H]^+$. $^1H$ NMR (400 MHz, DMSO-$d_6$) δ 14.05 (s, 1H), 9.70 (s, 1H), 9.32 (s, 1H), 8.63 (d, J=2.9 Hz, 1H), 8.43 (dd, J=35.9, 1.8 Hz, 1H), 7.98-7.88 (m, 1H), 7.86 (dd, J=8.6, 1.7 Hz, 1H), 7.79 (dt, J=9.3, 3.4 Hz, 2H), 4.89 (dd, J=89.5, 15.6 Hz, 2H), 4.47 (d, J=7.2 Hz, 3H), 3.15 (d, J=81.3 Hz, 3H), 1.81 (d, J=3.3 Hz, 3H).

Example 369

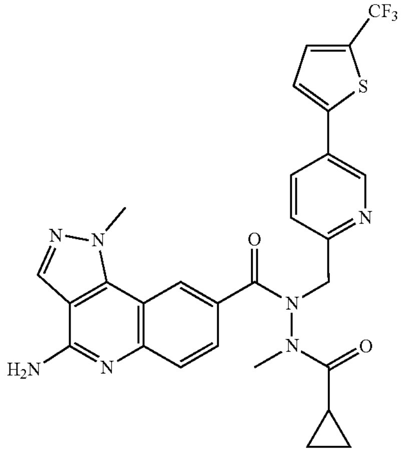

Example 369: 4-amino-N'-(cyclopropanecarbonyl)-N',1-dimethyl-N-((5-(5-(trifluoromethyl)thiophen-2-yl)pyridin-2-yl)methyl)-1H-pyrazolo[4,3-c]quinoline-8-carbohydrazide. Prepared following general procedure E-1 starting with intermediates Da-1 and Bt-5. ES/MS: m/z=580.0 $[M+H]^+$. $^1H$ NMR (400 MHz, DMSO-$d_6$) § 13.70 (s, 1H), 9.70 (s, 1H), 9.08-8.89 (m, 2H), 8.63 (s, 1H), 8.27-8.15 (m, 1H), 8.00-7.66 (m, 3H), 5.27-4.92 (m, 2H), 4.47 (s, 3H), 3.21 (d, J=89.0 Hz, 3H), 1.92 (d, J=31.3 Hz, 1H), 0.92-0.55 (m, 1H), 0.45 (d, J=10.9 Hz, 2H).

Example 370

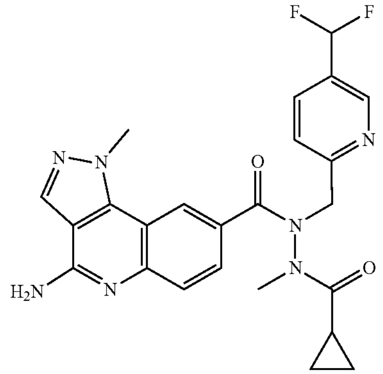

Example 370: 4-amino-N'-(cyclopropanecarbonyl)-N-((5-(difluoromethyl)pyridin-2-yl)methyl)-N',1-dimethyl-1H-pyrazolo[4,3-c]quinoline-8-carbohydrazide. Prepared following general procedure E-1 starting with intermediates Da-1 and Ba-83. ES/MS: m/z=480.0 $[M+H]^+$. $^1H$ NMR (400 MHz, DMSO-$d_6$) δ 13.56 (s, 1H), 8.96-8.76 (m, 2H), 8.63 (s, 1H), 8.12-8.02 (m, 1H), 7.86 (d, J=41.1 Hz, 3H), 7.38-7.00 (m, 1H), 5.28-4.94 (m, 2H), 4.47 (d, J=7.6 Hz, 3H), 3.32 (s, 1H), 3.07 (d, J=15.9 Hz, 3H), 1.90-1.76 (m, 1H), 0.78-0.66 (m, 1H), 0.52-0.32 (m, 2H).

Example 371

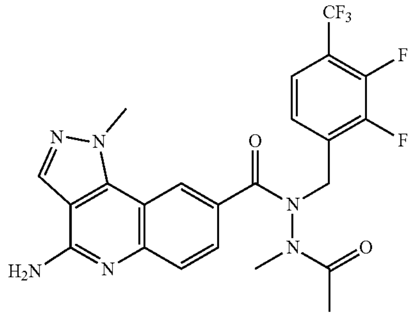

Example 371: N'-acetyl-4-amino-N-(2,3-difluoro-4-(trifluoromethyl)benzyl)-N',1-dimethyl-1H-pyrazolo[4,3-c]quinoline-8-carbohydrazide. Prepared following general procedure E-1 starting with intermediates Da-1 and Ba-84. ES/MS: m/z=507.0 $[M+H]^+$. 1H NMR (400 MHz, DMSO-$d_6$) δ 13.51 (s, 1H), 9.64 (s, 1H), 8.81 (s, 1H), 8.63 (d, J=1.9 Hz, 1H), 8.51-8.31 (m, 1H), 7.98-7.77 (m, 2H), 7.76-7.56 (m, 2H), 5.10 (s, 1H), 5.06-4.82 (m, 1H), 4.46 (d, J=9.3 Hz, 3H), 3.13 (d, J=72.4 Hz, 3H), 1.80 (s, 3H).

Example 372

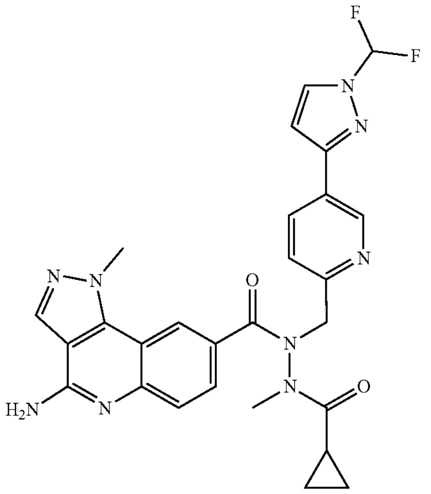

Example 372: 4-amino-N'-(cyclopropanecarbonyl)-N-((5-(1-(difluoromethyl)-1H-pyrazol-3-yl)pyridin-2-yl)methyl)-N',1-dimethyl-1H-pyrazolo[4,3-c]quinoline-8-carbohydrazide. Prepared following general procedure E-1 starting with intermediates Da-1 and Bt-6. ES/MS: m/z=513.0 $[M+H]^+$. $^1$H NMR (400 MHz, DMSO-$d_6$) δ 13.67 (s, 1H), 9.68 (s, 1H), 9.10 (d, J=9.5 Hz, 2H), 8.98 (s, 2H), 8.63 (s, 1H), 8.39 (d, J=2.7 Hz, 1H), 8.29 (dd, J=7.9, 2.3 Hz, 1H), 7.98 (d, J=59.1 Hz, 1H), 7.84-7.68 (m, 1H), 7.20 (s, 1H), 5.20 (d, J=13.6 Hz, 1H), 5.05 (s, 2H), 4.57 (d, J=86.7 Hz, 2H), 3.17 (d, J=79.1 Hz, 3H), 1.99-1.56 (m, 1H), 0.75-0.58 (m, 1H), 0.42 (s, 2H).

Example 373

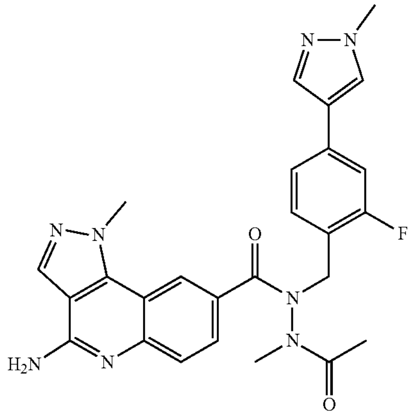

Example 373: N'-acetyl-4-amino-N-[[2-fluoro-4-(1-methylpyrazol-4-yl)phenyl]methyl]-N',1-dimethyl-pyrazolo[4,3-c]quinoline-8-carbohydrazide. Prepared following the procedure reported for example 130 starting with intermediates Da-1, and Bb-15, and 1-methyl-4-(4,4,5,5-tetramethyl-1,3,2-dioxaborolan-2-yl)-1H-pyrazole. ES/MS: m/z=501.4 $[M+H]^+$. $^1$H NMR (400 MHz, MeOD) δ 8.61-8.40 (m, 2H), 8.07-7.92 (m, 2H), 7.93-7.73 (m, 2H), 7.67-7.21 (m, 3H), 4.95 (d, J=15.6 Hz, 1H), 4.75 (d, J=14.5 Hz, 1H), 4.54 (d, J=14.1 Hz, 3H), 3.95 (d, J=1.8 Hz, 3H), 3.13 (d, J=5.6 Hz, 3H), 1.83 (s, 3H).

Example 374

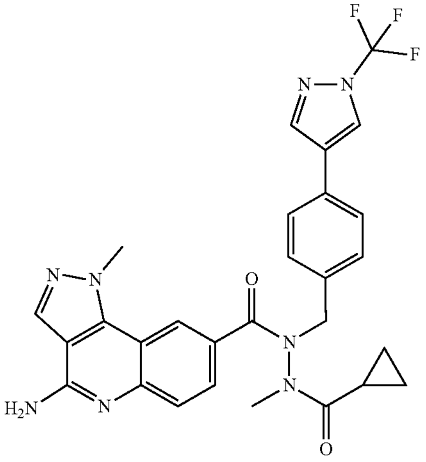

Example 374: 4-amino-N'-(cyclopropanecarbonyl)-N',1-dimethyl-N-[[4-[1-(trifluoromethyl)pyrazol-4-yl]phenyl]methyl]pyrazolo[4,3-c]quinoline-8-carbohydrazide. Prepared following the procedure reported for example 130 starting with intermediates Da-1, Bk-8 and 4-(4,4,5,5-tetramethyl-1,3,2-dioxaborolan-2-yl)-1-(trifluoromethyl)-1H-pyrazole. ES/MS: m/z=563.3 $[M+H]^+$. $^1$H NMR (400 MHz, MeOD) δ 8.69-8.55 (m, 2H), 8.50 (d, J=3.0 Hz, 1H), 8.26 (s, 1H), 8.05-7.77 (m, 2H), 7.73 (d, J=7.9 Hz, 2H), 7.58 (s, 2H), 5.25 (s, 1H), 4.99 (d, J=14.5 Hz, 1H), 4.62 (d, J=14.4 Hz, 0.4H minor rotamer), 4.54 (s, 2.2H major rotamer), 3.09 (s, 2.1H major rotamer), 2.68 (s, 0.8H minor rotamer), 1.78 (s, 1H), 0.96-0.34 (m, 4H).

Example 375

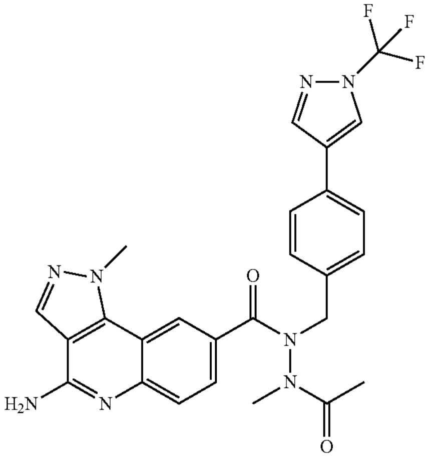

Example 375: N'-acetyl-4-amino-N',1-dimethyl-N-[[4-[1-(trifluoromethyl)pyrazol-4-yl]phenyl]methyl]pyrazolo[4,3-c]quinoline-8-carbohydrazide. Prepared following the procedure reported for example 130 starting with intermediates Da-1, Bb-41 and 4-(4,4,5,5-tetramethyl-1,3,2-dioxaborolan-2-yl)-1-(trifluoromethyl)-1H-pyrazole. ES/MS: m/z=537.2 $[M+H]^+$. $^1$H NMR (400 MHz, MeOD) δ 8.62 (d, J=4.7 Hz, 1H), 8.59-8.45 (m, 2H), 8.25 (s, 1H), 8.06-7.77 (m, 2H), 7.72 (dd, J=7.6, 5.5 Hz, 3H), 7.54 (dd, J=12.6, 6.1 Hz, 3H), 5.27 (s, 0.5H minor rotamer), 4.73-4.56 (m, 1.5H major rotamer), 4.53 (d, J=7.3 Hz, 3H), 3.15 (s, 1.3H major rotamer), 3.02 (s, 0.6H minor rotamer), 2.68 (s, 0.5H minor rotamer), 1.80 (d, J=27.8 Hz, 3H).

Example 376

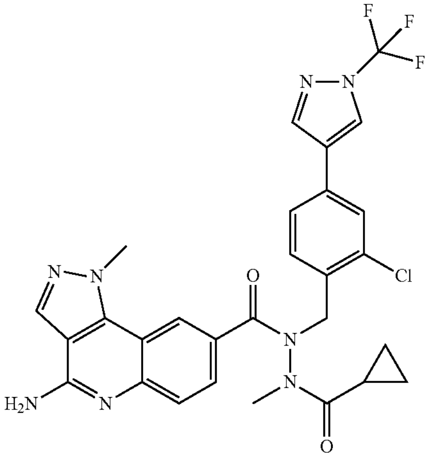

Example 376: 4-amino-N-[[2-chloro-4-[1-(trifluoromethyl)pyrazol-4-yl]phenyl]methyl]-N'-(cyclopropanecarbonyl)-N',1-dimethyl-pyrazolo[4,3-c]quinoline-8-carbohydrazide. Prepared following the procedure reported for example 130 starting with intermediates Da-1, Bk-9 and 4-(4,4,5,5-tetramethyl-1,3,2-dioxaborolan-2-yl)-1-(trifluoromethyl)-1H-pyrazole. ES/MS: m/z=597.2 $[M+H]^+$. $^1$H NMR (400 MHz, MeOD) δ 8.73 (d, J=3.2 Hz, 1H), 8.59 (s, 1H), 8.51 (d, J=3.0 Hz, 1H), 8.30 (s, 1H), 7.97 (s, 1H), 7.88-7.78 (m, 2H), 7.71 (d, J=5.5 Hz, 2H), 5.43 (s, 1H), 5.15 (d, J=14.3 Hz, 1H), 4.79 (d, J=14.3 Hz, 1H), 4.53 (d, J=7.9 Hz, 3H), 3.16 (s, 1.4H minor rotamer), 3.04 (s, 1.8H major rotamer), 1.94-1.82 (m, 1H), 1.00-0.40 (m, 4H).

Example 377

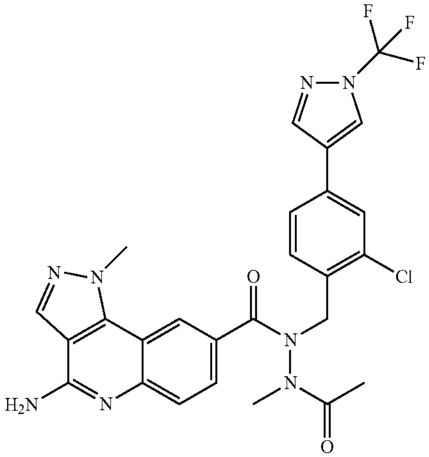

Example 377: N'-acetyl-4-amino-N-[[2-chloro-4-[1-(trifluoromethyl)pyrazol-4-yl]phenyl]methyl]-N',1-dimethyl-pyrazolo[4,3-c]quinoline-8-carbohydrazide. Prepared following the procedure reported for example 130 starting with intermediates Da-1, Bb-42 and 4-(4,4,5,5-tetramethyl-1,3,2-dioxaborolan-2-yl)-1-(trifluoromethyl)-1H-pyrazole. ES/MS: m/z=571.3 $[M+H]^+$. $^1$H NMR (400 MHz, MeOD) δ 8.72 (d, J=3.7 Hz, 1H), 8.63-8.36 (m, 2H), 8.29 (s, 1H), 8.04-7.75 (m, 3H), 7.71 (s, 2H), 4.82 (d, J=14.6 Hz, 1H 1H under solvent), 4.54 (d, J=12.8 Hz, 3H), 3.05 (d, J=6.1 Hz, 3H), 1.85 (s, 3H).

Example 378

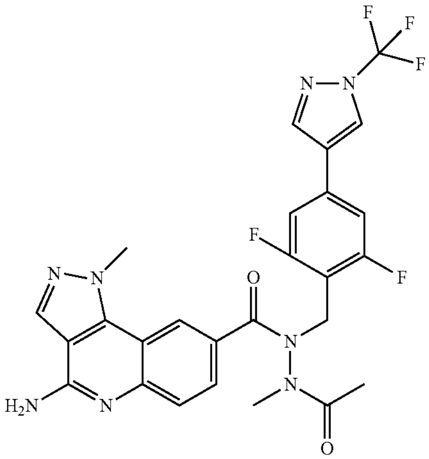

Example 378: N'-acetyl-4-amino-N-[[2,6-difluoro-4-[1-(trifluoromethyl)pyrazol-4-yl]phenyl]methyl]-N',1-dimethyl-pyrazolo[4,3-c]quinoline-8-carbohydrazide. Prepared following the procedure reported for example 130 starting with intermediates Da-1, Bb-40 and 4-(4,4,5,5-tetramethyl-1,3,2-dioxaborolan-2-yl)-1-(trifluoromethyl)-1H-pyrazole. ES/MS: m/z=573.2 $[M+H]^+$. $^1$H NMR (400 MHz, MeOD) δ 8.78 (d, J=4.7 Hz, 1H), 8.64-8.46 (m, 2H), 8.31 (s, 1H), 7.85 (d, J=24.8 Hz, 2H), 7.47 (dd, J=15.6, 8.7 Hz, 2H), 5.16-4.91 (m, 2H), 4.56 (d, J=18.1 Hz, 3H), 3.12 (s, 1.2H), 2.68 (s, 1H), 1.96 (s, 1.1H), 1.89 (s, 1.2H).

Example 379

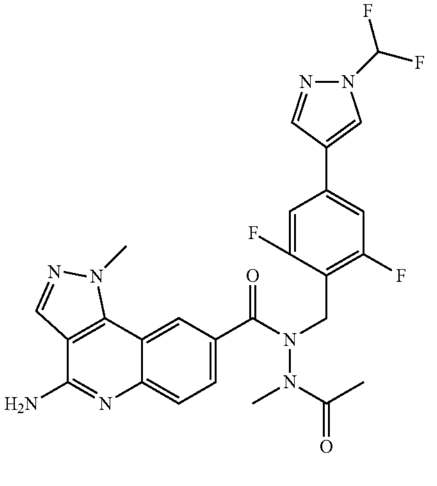

Example 379: N'-acetyl-4-amino-N-[[4-[1-(difluoromethyl)pyrazol-4-yl]-2,6-difluoro-phenyl]methyl]-N',1-dimethyl-pyrazolo[4,3-c]quinoline-8-carbohydrazide. Prepared following the procedure reported for example 130 starting with intermediates Da-1, Bb-40 and 1-(difluoromethyl)-4-(4,4,5,5-tetramethyl-1,3,2-dioxaborolan-2-yl)-1H-pyrazole. ES/MS: m/z=555.3 $[M+H]^+$. $^1$H NMR (400 MHz, MeOD) δ 8.60 (t, J=4.6 Hz, 1H), 8.51 (d, J=9.9 Hz, 1H), 8.18 (s, 1H), 8.04-7.74 (m, 2H), 7.57-7.25 (m, 3H), 5.33-4.92 (m, 3H), 4.55 (d, J=19.3 Hz, 3H), 3.23-3.06 (m, 4H), 1.92-1.82 (m, 3H).

Example 380

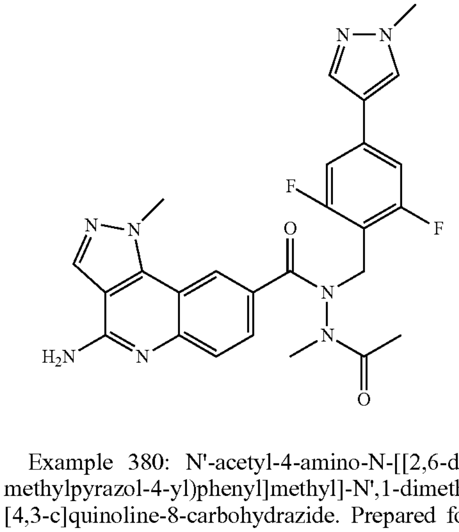

Example 380: N'-acetyl-4-amino-N-[[2,6-difluoro-4-(1-methylpyrazol-4-yl)phenyl]methyl]-N',1-dimethyl-pyrazolo[4,3-c]quinoline-8-carbohydrazide. Prepared following the procedure reported for example 130 starting with intermediates Da-1, Bb-40 and 1-methyl-4-(4,4,5,5-tetramethyl-1,3,2-dioxaborolan-2-yl)-1H-pyrazole. ES/MS: m/z=519.2 $[M+H]^+$. $^1$H NMR (400 MHz, MeOD) δ 8.62-8.39 (m, 2H), 8.09 (d, J=2.2 Hz, 1H), 7.87 (d, J=25.0 Hz, 3H), 7.30 (dd, J=11.7, 8.8 Hz, 2H), 4.55 (d, J=18.1 Hz, 3H), 3.95 (d, J=2.5 Hz, 3H), 3.13 (d, J=6.7 Hz, 3H), 1.86 (d, J=21.7 Hz, 3H).

Example 381

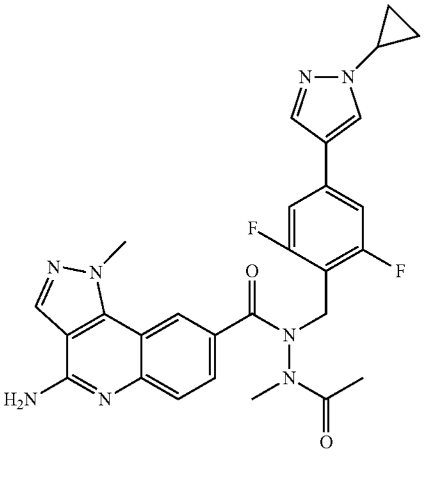

Example 381: N'-acetyl-4-amino-N-[[4-(1-cyclopropylpyrazol-4-yl)-2,6-difluoro-phenyl]methyl]-N',1-dimethyl-pyrazolo[4,3-c]quinoline-8-carbohydrazide. Prepared following the procedure reported for example 130 starting with intermediates Da-1, Bb-40 and 1-cyclopropyl-4-(4,4,5,5-tetramethyl-1,3,2-dioxaborolan-2-yl)-1H-pyrazole. ES/MS: m/z=545.3 $[M+H]^+$. $^1$H NMR (400 MHz, MeOD) δ 8.60-8.41 (m, 2H), 8.20 (d, J=3.2 Hz, 1H), 7.87 (d, J=28.7 Hz, 3H), 7.31 (dd, J=11.9, 8.8 Hz, 2H), 5.33-4.90 (m, 2H), 4.55 (d, J=18.1 Hz, 3H), 3.71 (tt, J=7.3, 3.6 Hz, 1H), 3.12 (d, J=6.4 Hz, 3H), 1.85 (d, J=19.8 Hz, 3H), 1.21-1.00 (m, 4H).

Example 382

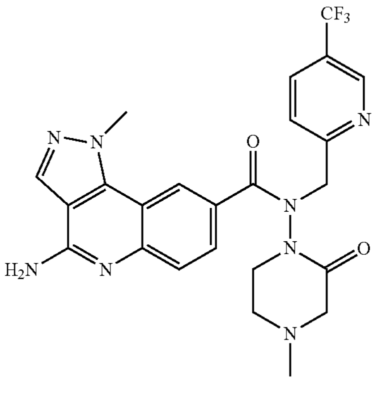

Example 382: 4-amino-1-methyl-N-(4-methyl-2-oxo-piperazin-1-yl)-N-[[5-(trifluoromethyl)-2-pyridyl]methyl]pyrazolo[4,3-c]quinoline-8-carboxamide. Prepared following general procedure E-1 starting with intermediates Da-1 and Bi-19. ES/MS: m/z=513.5 $[M+H]^+$. $^1$H NMR (400 MHz, Methanol-d4) δ 8.95 (s, 1H), 8.50 (s, 1H), 8.17 (d, J=8.3 Hz, 1H), 7.92 (s, 3H), 7.83 (d, J=8.4 Hz, 1H), 5.32 (d, J=16.1 Hz, 1H), 4.95 (d, J=16.1 Hz, 1H), 4.49 (s, 3H), 3.94 (s, 3H), 2.68 (s, 3H)

Example 383

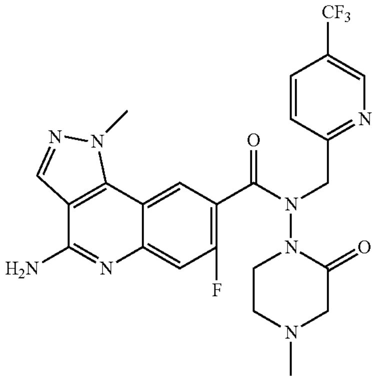

Example 383: 4-amino-7-fluoro-1-methyl-N-(4-methyl-2-oxo-piperazin-1-yl)-N-[[5-(trifluoromethyl)-2-pyridyl] methyl]pyrazolo[4,3-c]quinoline-8-carboxamide. Prepared following general procedure E-1 starting with intermediates Db-1 and Bi-19. ES/MS: m/z=531.2 $[M+H]^+$. $^1H$ NMR (400 MHz, Methanol-d4) δ 8.91 (s, 1H), 8.52-8.36 (m, 2H), 8.20 (d, J=8.3 Hz, 1H), 7.87 (d, J=8.2 Hz, 1H), 7.56 (dd, J=33.8, 10.3 Hz, 1H), 5.35 (d, J=15.3 Hz, 1H), 4.96 (d, J=15.1 Hz, 2H), 4.47 (s, 3H), 3.96 (s, 2H), 3.80-3.53 (m, 1H), 2.96-2.73 (m, 1H), 2.48-2.14 (m, 2H).

Example 384

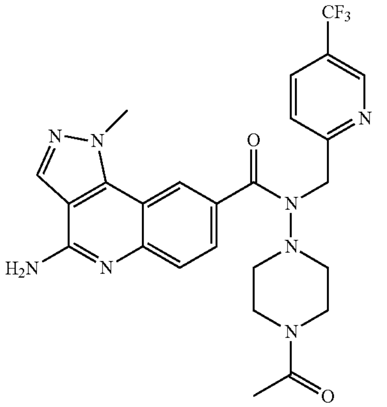

Example 384: N-(4-acetylpiperazin-1-yl)-4-amino-1-methyl-N-[[5-(trifluoromethyl)-2-pyridyl]methyl]pyrazolo [4,3-c]quinoline-8-carboxamide. Prepared following general procedure E-1 starting with intermediates Da-1 and Bw-1 ES/MS: m/z=527.2 $[M+H]^+$. $^1H$ NMR (400 MHz, Methanol-d4) δ 8.90 (s, 1H), 8.62 (s, 1H), 8.51 (s, 1H), 8.12 (ddd, J=20.0, 8.5, 2.0 Hz, 2H), 7.79 (dd, J=17.6, 8.5 Hz, 2H), 5.06 (s, 2H), 4.56 (s, 3H), 4.43 (d, J=13.2 Hz, 1H), 3.84 (d, J=12.0 Hz, 1H), 3.20-2.78 (m, 5H), 2.52 (d, J=12.3 Hz, 1H), 2.05 (s, 3H).

Example 385

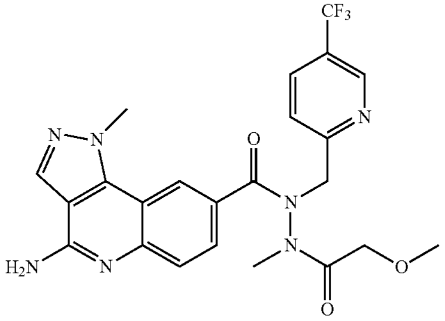

Example 385: 4-amino-N'-(2-methoxyacetyl)-N',1-dimethyl-N-[[5-(trifluoromethyl)-2-pyridyl]methyl]pyrazolo[4,3-c]quinoline-8-carbohydrazide. Prepared following general procedure E-1 starting with intermediates Da-1 and Br-1. ES/MS: m/z=502.2 $[M+H]^+$. $^1H$ NMR (400 MHz, Methanol-d4) δ 9.01 (d, J=32.5 Hz, 1H), 8.56 (d, J=23.3 Hz, 1H), 8.23 (d, J=46.6 Hz, 1H), 8.04-7.37 (m, 2H), 5.32-4.77 (m, 2H), 4.45 (d, J=16.5 Hz, 3H), 4.27-3.95 (m, 1H), 3.85 (s, 1H), 3.10 (dd, J=76.7, 34.7 Hz, 5H).

Example 386

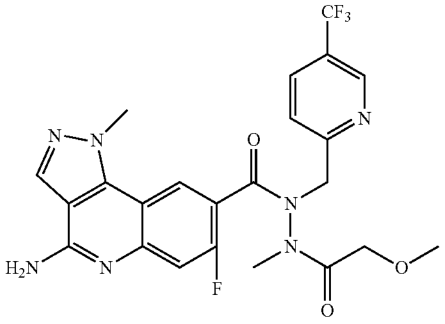

Example 386: 4-amino-7-fluoro-N'-(2-methoxyacetyl)-N',1-dimethyl-N-[[5-(trifluoromethyl)-2-pyridyl]methyl] pyrazolo[4,3-c]quinoline-8-carbohydrazide. Prepared following general procedure E-1 starting with intermediates Db-1 and Br-1. ES/MS: m/z=520.3 $[M+H]^+$. $^1H$ NMR (400 MHz, Methanol-d4) δ 9.03 (d, J=49.5 Hz, 1H), 8.63 (s, 2H), 8.48-8.17 (m, 2H), 8.10-7.54 (m, 2H), 6.93-6.24 (m, 1H), 5.32-4.69 (m, 2H), 4.48 (d, J=14.4 Hz, 3H), 4.17-3.98 (m, 1H), 3.88 (s, 1H), 3.18 (d, J=9.5 Hz, 3H), 3.03 (d, J=40.5 Hz, 3H).

Example 387

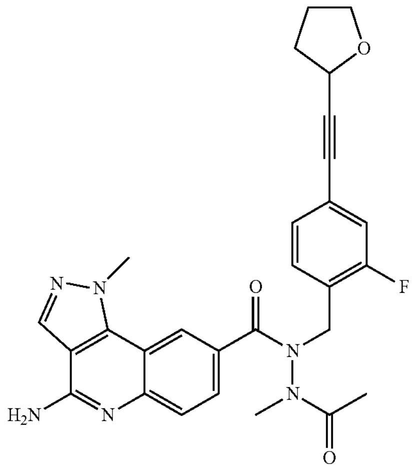

Example 387: N'-acetyl-4-amino-N-[[2-fluoro-4-(2-tetrahydrofuran-2-ylethynyl)phenyl]methyl]-N',1-dimethyl-pyrazolo[4,3-c]quinoline-8-carbohydrazide. Prepared in following the procedure described for example 176 starting with intermediates Da-1 and Bb-15 and 2-ethynyltetrahydrofuran. ES/MS: m/z=515.3 $[M+H]^+$. $^1H$ NMR (400 MHZ, DMSO-$d_6$) δ 13.44 (s, 1H), 8.61 (s, 1H), 8.44 (s, 1H), 8.34 (s, 1H), 7.84 (d, J=36.6 Hz, 2H), 7.73-7.43 (m, 1H), 7.44-7.17 (m, 2H), 6.53 (s, 3H), 5.02 (d, J=15.2 Hz, 1H), 4.89 (d, J=13.7 Hz, 0.3H minor rotamer), 4.80 (dd, J=7.2, 4.9 Hz, 1H), 4.66 (d, J=14.8 Hz, 1H), 4.46 (d, J=13.2 Hz, 3H), 3.85 (q, J=7.1 Hz, 1H), 3.75 (q, J=7.2 Hz, 1H), 3.09 (s, 1.7H major rotamer), 2.99 (s, 1.3H minor rotamer), 2.26-2.14 (m, 1H), 2.04-1.83 (m, 2H), 1.76 (s, 1.5H, minor rotamer), 1.69 (s, 2H, major rotamer).

Example 388

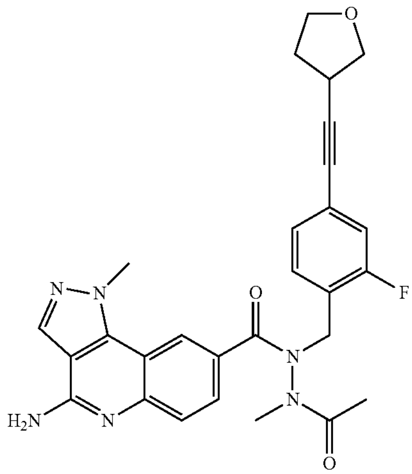

Example 388: N'-acetyl-4-amino-N-[[2-fluoro-4-(2-tetrahydrofuran-3-ylethynyl)phenyl]methyl]-N',1-dimethyl-pyrazolo[4,3-c]quinoline-8-carbohydrazide. Prepared in following the procedure described for example 176 starting with intermediates Da-1 and Bb-15 and 3-ethynyltetrahydrofuran. ES/MS: m/z=515.3 $[M+H]^+$. $^1H$ NMR (400 MHZ, DMSO-$d_6$) δ 13.43 (brs, 1H), 8.61 (s, 0.5H minor rotamer), 8.44 (s, 0.5H major rotamer), 8.33 (s, 1H), 7.82 (d, J=22.8 Hz, 2H), 7.69-7.39 (m, 1H), 7.39-6.99 (m, 2H), 6.53 (s, 4H), 5.02 (d, J=15.2 Hz, 0.7H major rotamer), 4.89 (s, 0.3H minor rotamer), 4.65 (d, J=14.9 Hz, 1H), 4.46 (d, J=13.4 Hz, 3H), 3.97 (td, J=7.7, 2.9 Hz, 1H), 3.92-3.70 (m, 2H), 3.61 (dd, J=8.1, 6.5 Hz, 1H), 3.07 (s, 1.8H major rotamer), 2.98 (s, 1.3H minor rotamer), 2.31-2.19 (m, 1H), 2.04-1.89 (m, 1H), 1.72 (d, J=31.7 Hz, 3H).

Example 389

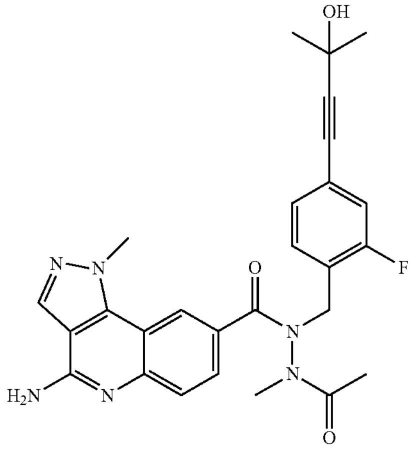

Example 389: N'-acetyl-4-amino-N-[[2-fluoro-4-(3-hydroxy-3-methyl-but-1-ynyl)phenyl]methyl]-N',1-dimethyl-pyrazolo[4,3-c]quinoline-8-carbohydrazide. Prepared in following the procedure described for example 176 starting with intermediates Da-1 and Bb-15 and 2-methylbut-3-yn-2-ol. ES/MS: m/z=503.2 $[M+H]^+$. $^1H$ NMR (400 MHz, DMSO-$d_6$) δ 13.34 (brs, 1H), 8.61 (s, 1H), 8.44 (s, 0.4H minor rotamer), 8.34 (s, 0.6H major rotamer), 8.04-7.69 (m, 2H), 7.69-7.43 (m, 1H), 7.27 (dd, J=18.9, 10.3 Hz, 2H), 6.53 (s, 2H), 5.51 (s, 1H), 5.02 (d, J=14.9 Hz, 0.6H major rotamer), 4.88 (d, J=13.5 Hz, 0.4H minor rotamer), 4.66 (d, J=14.8 Hz, 1H), 4.46 (d, J=13.6 Hz, 3H), 3.07 (s, 1.6H major rotamer), 2.98 (s, 1.4H minor rotamer), 1.72 (d, J=32.3 Hz, 3H), 1.47 (d, J=2.2 Hz, 6H).

Example 390

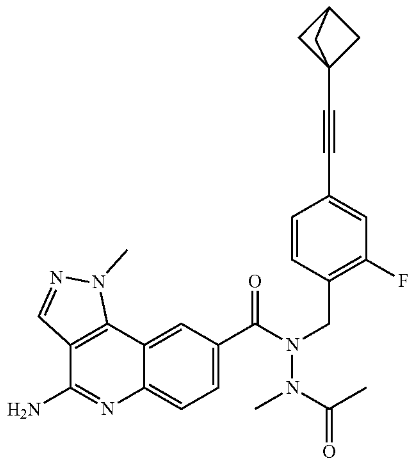

Example 390: N'-acetyl-4-amino-N-[[4-[2-(1-bicyclo[1.1.1]pentanyl)ethynyl]-2-fluoro-phenyl]methyl]-N',1-dimethyl-pyrazolo[4,3-c]quinoline-8-carbohydrazide. Prepared in following the procedure described for example 176 starting with intermediates Da-1 and Bb-15 and 1-ethynylbicyclo[1.1.1]pentane. ES/MS: m/z=511.3 $[M+H]^+$. $^1H$ NMR (400 MHZ, Methanol-$d_4$) δ 8.61-8.45 (m, 2H), 8.07-7.76 (m, 2H), 7.76-7.46 (m, 1H), 7.37-7.08 (m, 2H), 4.77 (d, J=14.4 Hz, 1H), 4.54 (d, J=12.3 Hz, 3H), 3.21-3.05 (m, 4H), 2.68 (s, 2H major rotamer), 2.35 (s, 0.9H minor rotamer), 2.18 (s, 6H), 1.96 (s, 1H).

Example 391

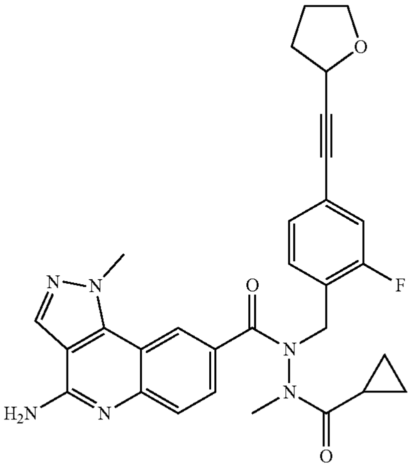

Example 391: 4-amino-N'-(cyclopropanecarbonyl)-N-(2-fluoro-4-((tetrahydrofuran-2-yl)ethynyl)benzyl)-N',1-dimethyl-1H-pyrazolo[4,3-c]quinoline-8-carbohydrazide. Prepared in following the procedure described for example 176 starting with intermediates Da-1 and Bo-4 and 2-ethynyltetrahydrofuran. ES/MS: m/z=541.4 $[M+H]^+$. $^1H$ NMR (400 MHZ, Methanol-d4) δ 8.66-8.37 (m, 2H), 8.02-7.70 (m, 2H), 7.59 (s, 1H), 7.36-7.13 (m, 2H), 4.85-4.75 (m, 1H), 4.53 (d, J=7.7 Hz, 3H), 3.98 (q, J=7.2 Hz, 1H), 3.86 (td, J=7.8, 5.6 Hz, 1H), 3.27 (s, 1,3H minor rotamer), 3.10 (s, 1.8H major rotamer), 2.36-2.19 (m, 1H), 2.20-1.95 (m, 3H), 0.86-0.34 (m, 4H).

Example 392

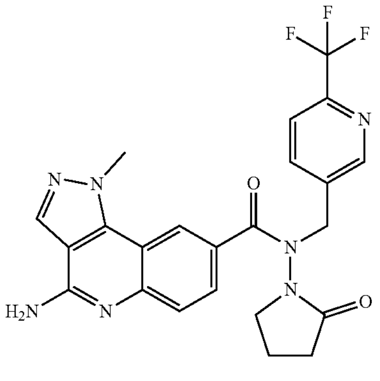

Example 392: 4-amino-1-methyl-N-(2-oxopyrrolidin-1-yl)-N-[[6-(trifluoromethyl)-3-pyridyl]methyl]pyrazolo[4,3-c]quinoline-8-carboxamide. Prepared following general procedure E-1 starting with intermediates Da-1 and Ba-46. ES/MS: m/z=484.2 $[M+H]^+$. $^1H$ NMR (400 MHz, DMSO-$d_6$) δ 13.43 (brs, 1H), 8.93 (d, J=2.0 Hz, 1H), 8.63 (s, 1H), 8.42 (d, J=1.8 Hz, 1H), 8.32-8.19 (m, 1H), 7.99-7.75 (m, 3H), 5.00 (d, J=2.2 Hz, 2H), 4.44 (s, 3H), 3.62 (q, J=8.0 Hz, 1H), 3.27 (s, 1H), 2.18 (dt, J=17.5, 8.9 Hz, 1H), 1.87 (d, J=12.3 Hz, 2H), 1.57 (dd, J=18.8, 5.3 Hz, 1H).

Example 393

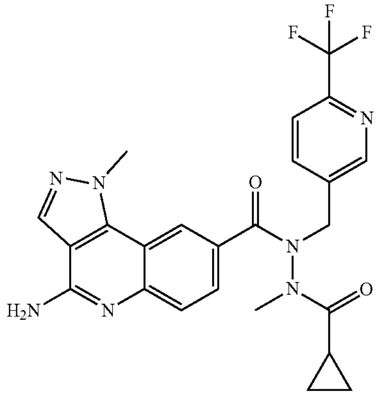

Example 393: 4-amino-N'-(cyclopropanecarbonyl)-N',1-dimethyl-N-[[6-(trifluoromethyl)-3-pyridyl]methyl]pyrazolo[4,3-c]quinoline-8-carbohydrazide. Prepared following general procedure E-1 starting with intermediates Da-1 and Bd-52. ES/MS: m/z=498.7 $[M+H]^+$. $^1H$ NMR (400 MHz, DMSO-$d_6$) δ 13.43 (brs, 1H), δ 9.68 (s, 1H), 8.90 (d, J=15.9 Hz, 1H), 8.59 (d, J=12.4 Hz, 2H), 8.24 (dt, J=20.5, 9.2 Hz, 1H), 7.98 (dd, J=18.2, 8.2 Hz, 1H), 7.65 (dd, J=10.8, 5.1 Hz, 1H), 5.42 (d, J=14.8 Hz, 1H), 5.22-4.82 (m, 1H), 4.41 (d, J=11.5 Hz, 3H), 3.33 (s, 1H), 3.21-2.97 (m, 2H), 1.63 (s, 1H), 0.81--0.02 (m, 4H).

Example 394

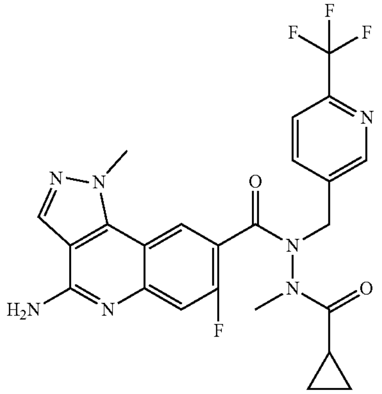

Example 394: 4-amino-N'-(cyclopropanecarbonyl)-N',1-dimethyl-N-[[6-(trifluoromethyl)-3-pyridyl]methyl]pyrazolo[4,3-c]quinoline-8-carbohydrazide. Prepared following general procedure E-1 starting with intermediates Db-1 and Bd-52. ES/MS: m/z=517.3 $[M+H]^+$. $^1H$ NMR (400 MHz, DMSO-$d_6$) δ 13.47 (s, 1H), 9.66 (s, 1H), 8.91 (s, 1H), 8.63 (s, 1H), 8.51 (d, J=1.8 Hz, 1H), 8.23 (d, J=8.1 Hz, 1H), 7.95 (dd, J=17.9, 8.1 Hz, 2H), 7.80 (s, 1H), 5.34 (s, 1H), 5.13-4.84 (m, 1H), 4.47 (s, 3H), 3.37 (s, 1H), 3.14 (s, 2H), 1.62 (s, 1H), 0.88-0.13 (m, 4H).

Example 395

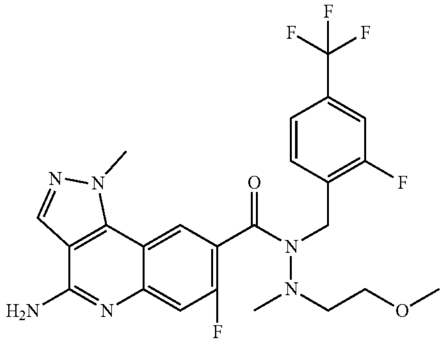

Example 395: 4-amino-7-fluoro-N-(2-fluoro-4-(trifluoromethyl)benzyl)-N'-(2-methoxyethyl)-N',1-dimethyl-1H-pyrazolo[4,3-c]quinoline-8-carbohydrazide. Prepared following general procedure E-1 starting with intermediates Db-1 and Ba-86. ES/MS: m/z=523.3 $[M+H]^+$. $^1H$ NMR (400 MHz, DMSO-$d_6$) δ 13.36 (s, 1H), 8.60 (s, 1H), 8.40 (d, J=6.6 Hz, 1H), 7.85-7.44 (m, 5H), 6.48 (d, J=66.0 Hz, 1H), 4.87 (q, J=16.6 Hz, 2H), 4.45 (s, 3H), 3.13 (t, J=5.6 Hz, 2H), 2.96 (s, 3H), 2.82-2.72 (m, 1H), 2.55 (s, 3H).

Example 396

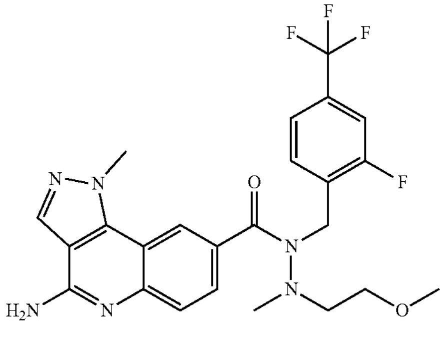

Example 396: 4-amino-N-[[2-fluoro-4-(trifluoromethyl)phenyl]methyl]-N'-(2-methoxyethyl)-N',1-dimethyl-pyrazolo[4,3-c]quinoline-8-carbohydrazide. Prepared following general procedure E-1 starting with intermediates Da-1 and Ba-86. ES/MS: m/z=505.3 $[M+H]^+$. $^1H$ NMR (400 MHz, DMSO-$d_6$) δ 13.36 (s, 1H), 8.66 (d, J=22.0 Hz, 2H), 8.04 (d, J=8.7 Hz, 1H), 7.89-7.64 (m, 3H), 7.68-7.48 (m, 2H), 6.53 (s, 1H), 4.89 (d, J=16.7 Hz, 1H), 4.74 (d, J=16.2 Hz, 1H), 4.63 (s, 1H), 4.50 (s, 3H), 3.14 (s, 1H), 2.95 (s, 3H), 2.81 (s, 1H), 2.70 (s, 3H).

Example 397

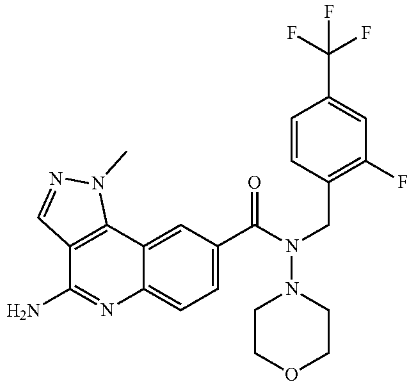

Example 397: 4-amino-N-[[2-fluoro-4-(trifluoromethyl)phenyl]methyl]-1-methyl-N-morpholino-pyrazolo[4,3-c]quinoline-8-carboxamide. Prepared following general procedure E-1 starting with intermediates Da-1 and Ba-85. ES/MS: m/z=503.4 $[M+H]^+$. $^1H$ NMR (400 MHz, DMSO-$d_6$) δ 13.36 (s, 1H), 8.61 (s, 1H), 8.42 (d, J=6.5 Hz, 1H), 7.85-7.58 (m, 4H), 4.94 (s, 2H), 4.46 (s, 3H), 3.65 (d, J=10.5 Hz, 2H), 2.92 (dt, J=36.1, 11.0 Hz, 4H), 2.75 (d, J=9.9 Hz, 2H).

Example 398

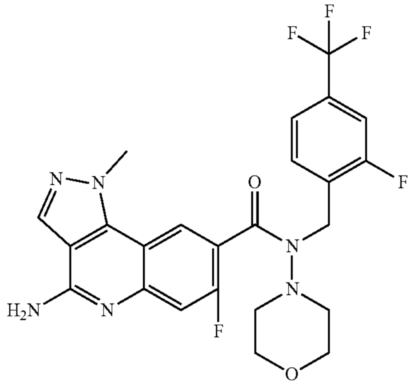

Example 398: 4-amino-7-fluoro-N-[[2-fluoro-4-(trifluoromethyl)phenyl]methyl]-1-methyl-N-morpholino-pyrazolo[4,3-c]quinoline-8-carboxamide. Prepared following general procedure E-1 starting with intermediates Db-1 and Ba-85. ES/MS: m/z=522.8 $[M+H]^+$. $^1H$ NMR (400 MHz, DMSO-$d_6$) δ 13.36 (s, 1H), 8.63 (s, 1H), 8.49 (s, 1H), 8.02 (d, J=8.5 Hz, 1H), 7.87-7.66 (m, 3H), 7.59 (d, J=7.9 Hz, 1H), 4.89 (s, 2H), 4.47 (s, 3H), 3.70 (s, 2H), 3.14 (s, 2H), 2.91 (d, J=33.7 Hz, 4H).

Example 399

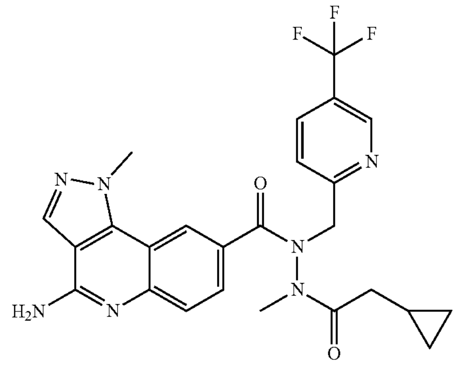

Example 399: 4-amino-N'-(2-cyclopropylacetyl)-N',1-dimethyl-N-[[5-(trifluoromethyl)-2-pyridyl]methyl]pyrazolo[4,3-c]quinoline-8-carbohydrazide. Prepared following general procedure E-1 starting with intermediates Da-1 and Bd-51. ES/MS: m/z=512.2 $[M+H]^+$. $^1H$ NMR (400 MHz, DMSO-$d_6$) δ 13.36 (s, 1H), 8.92 (s, 1H), 8.63 (s, 1H), 8.38 (s, 1H), 8.24 (d, J=8.5 Hz, 1H), 7.93 (d, J=8.0 Hz, 1H), 7.82 (d, J=6.3 Hz, 1H), 5.01 (d, J=15.3 Hz, 1H), 4.87 (d, J=15.4 Hz, 1H), 4.48 (s, 3H), 3.17 (d, J=9.4 Hz, 3H), 2.14-1.80 (m, 2H), 0.75--0.58 (m, 4H).

Example 400

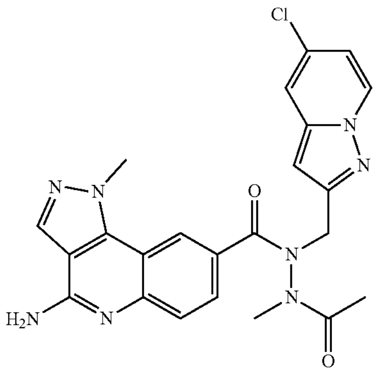

Example 400: N'-acetyl-4-amino-N-((5-chloropyrazolo[1,5-a]pyridin-2-yl)methyl)-N',1-dimethyl-1H-pyrazolo[4,3-c]quinoline-8-carbohydrazide. Prepared following general procedure E-1 starting with intermediates Da-1 and Bv-3. ES/MS: m/z=477.4 $[M+H]^+$. $^1H$ NMR (400 MHz, DMSO-$d_6$) δ 13.28 (brs, 1H), 8.73 (dd, J=10.6, 7.4 Hz, 1H), 8.62 (s, 1H), 7.98-7.70 (m, 2H), 7.08-6.87 (m, 1H), 6.68 (d, J=44.1 Hz, 1H), 6.52 (d, J=4.8 Hz, 1H), 5.44-5.20 (m, 1H), 5.04 (s, 1H), 4.67 (d, J=44.0 Hz, 1H), 4.47 (d, J=18.0 Hz, 3H), 3.06 (d, J=9.6 Hz, 3H), 1.78 (d, J=13.4 Hz, 3H).

Example 401

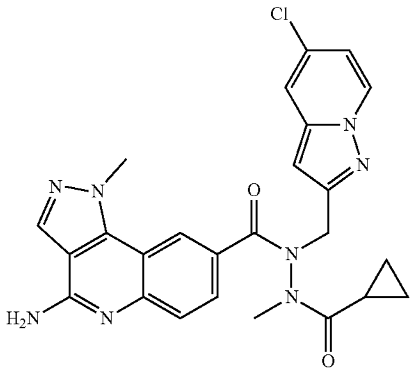

Example 401: 4-amino-N-((5-chloropyrazolo[1,5-a]pyridin-2-yl)methyl)-N'-(cyclopropanecarbonyl)-N',1-dimethyl-1H-pyrazolo[4,3-c]quinoline-8-carbohydrazide. Prepared following general procedure E-1 starting with intermediates Da-1 and Bv-2. ES/MS: m/z=503.2 $[M+H]^+$. $^1H$ NMR (400 MHz, MeOD-$d_4$) δ 8.76-8.39 (m, 2H), 7.94-7.57 (m, 3H), 7.05-6.62 (m, 2H), 5.23 (dd, J=111.3, 15.0 Hz, 2H), 4.54 (d, J=11.9 Hz, 3H), 3.26-3.03 (m, 2H major rotamer), 1.81 (s, 1H, minor rotamer), 0.51 (t, J=79.3 Hz, 4H).

Example 402

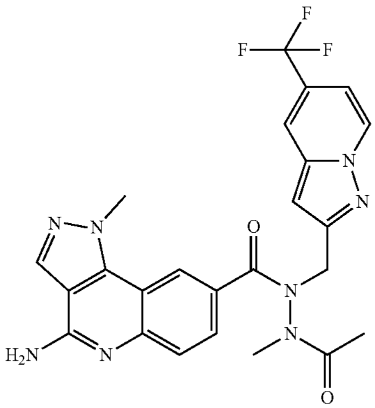

Example 402: N'-acetyl-4-amino-N',1-dimethyl-N-((5-(trifluoromethyl)pyrazolo[1,5-a]pyridin-2-yl)methyl)-1H-pyrazolo[4,3-c]quinoline-8-carbohydrazide. Prepared following general procedure E-1 starting with intermediates Da-1 and Bv-5. ES/MS: m/z=511.2 $[M+H]^+$. $^1H$ NMR (400 MHz, DMSO) δ 13.15 (brs, 0.2H), 8.91 (s, 1H), 8.62 (s, 1H), 8.35-8.16 (m, 1H), 8.11-7.71 (m, 2H), 7.27 (d, J=86.6 Hz, 1H), 7.09-6.85 (m, 1H), 5.32 (d, J=11.0 Hz, 1H), 5.23-5.03 (m, 1H), 4.47 (d, J=20.0 Hz, 3H), 3.07 (d, J=16.3 Hz, 3H), 1.78 (d, J=13.3 Hz, 3H).

Example 403

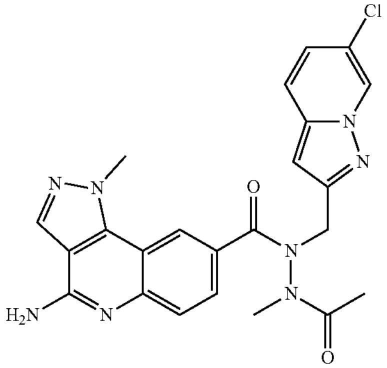

Example 403: N'-acetyl-4-amino-N-((6-chloropyrazolo[1,5-a]pyridin-2-yl)methyl)-N',1-dimethyl-1H-pyrazolo[4,3-c]quinoline-8-carbohydrazide. Prepared following general procedure E-1 starting with intermediates Da-1 and Bv-4. ES/MS: m/z=477.2 $[M+H]^+$. $^1H$ NMR (400 MHz, DMSO) δ 13.31 (s, 1H), 9.20-8.90 (m, 1H), 8.63 (d, J=3.6 Hz, 1H), 8.03-7.64 (m, 3H), 7.49-7.20 (m, 1H), 6.83 (s, 1H), 5.37-4.67 (m, 2H), 4.47 (d, J=14.3 Hz, 3H), 3.05 (s, 2H), 1.78 (d, J=13.7 Hz, 3H).

Example 404

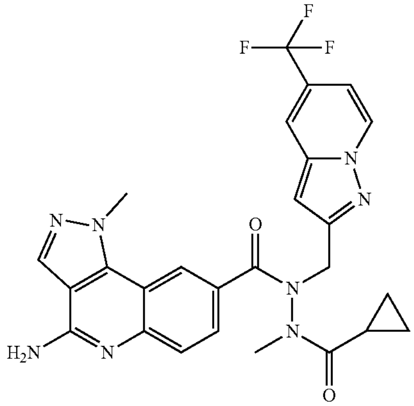

Example 404: 4-amino-N'-(cyclopropanecarbonyl)-N',1-dimethyl-N-((5-(trifluoromethyl)pyrazolo[1,5-a]pyridin-2-yl)methyl)-1H-pyrazolo[4,3-c]quinoline-8-carbohydrazide. Prepared following general procedure E-1 starting with intermediates Da-1 and Bv-1. ES/MS: m/z=537.2 $[M+H]^+$. $^1H$ NMR (400 MHz, MeOD) δ 8.92-8.44 (m, 3H), 7.99 (d, J=104.2 Hz, 3H), 7.19-6.88 (m, 2H), 5.28 (dd, J=91.6, 16.2 Hz, 2H), 4.54 (d, J=14.4 Hz, 3H), 3.16 (s, 2H, major rotamer), 1.91-1.39 (m, 1H, minor rotamer), 0.48 (dd, J=100.6, 66.0 Hz, 4H).

Example 405

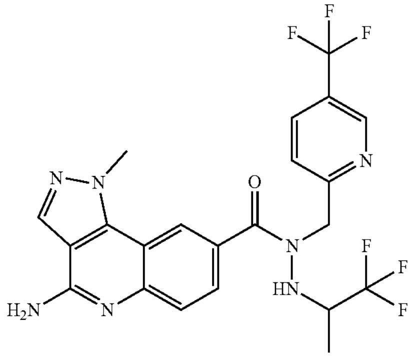

Example 405: 4-amino-1-methyl-N'-(2,2,2-trifluoro-1-methyl-ethyl)-N-[[5-(trifluoromethyl)-2-pyridyl]methyl]pyrazolo[4,3-c]quinoline-8-carbohydrazide. Prepared following general procedure E-1 starting with intermediates Da-1 and Ba-87. ES/MS: m/z=512.3 $[M+H]^+$. $^1H$ NMR (400 MHz, MeOD) δ 8.94 (s, 1H), 8.72 (d, J=63.5 Hz, 1H), 8.50 (s, 1H), 8.06 (d, J=51.6 Hz, 2H), 7.65 (d, J=105.1 Hz, 2H), 5.28 (s, 0.5H, minor rotamer), 5.04 (s, 1.5H major rotamer), 4.52 (s, 3H), 3.90 (s, 1H), 1.25 (d, J=102.8 Hz, 3H).

Example 406

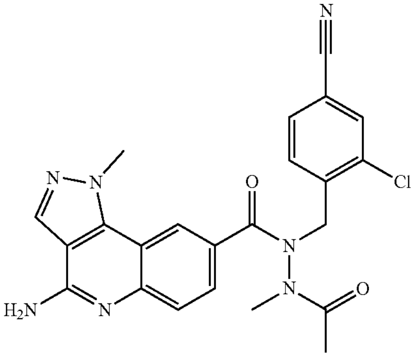

Example 406: N'-acetyl-4-amino-N-[(2-chloro-4-cyano-phenyl)methyl]-N',1-dimethyl-pyrazolo[4,3-c]quinoline-8-carbohydrazide. Prepared following general procedure E-1 starting with intermediates Da-1 and Bb-37. ES/MS: m/z=462.2 $[M+H]^+$. $^1H$ (400 MHZ, DMSO) δ 13.35 (brs, 0.2H), 8.63 (s, 1H), 8.43 (d, J=29.8 Hz, 1H), 8.10 (d, J=18.0 Hz, 1H), 8.02-7.77 (m, 4H), 5.13 (s, 1H), 4.77 (d, J=15.8 Hz, 1H), 4.47 (s, 3H), 3.15 (s, 2H), 3.03 (s, 1H), 1.79 (d, J=6.8 Hz, 4H).

Example 407

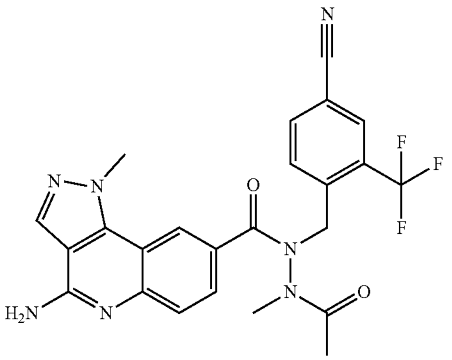

Example 407: N'-acetyl-4-amino-N-[[4-cyano-2-(trifluoromethyl)phenyl]methyl]-N',1-dimethyl-pyrazolo[4,3-c] quinoline-8-carbohydrazide. Prepared following general procedure E-1 starting with intermediates Da-1 and Bb-38. ES/MS: m/z=462.2 $[M+H]^+$. $^1H$ (400 MHz, MeOD) δ 8.52 (d, J=14.8 Hz, 2H), 8.19 (d, J=6.5 Hz, 2H), 8.08 (d, J=8.1 Hz, 1H), 7.94 (d, J=8.7 Hz, 1H), 7.82 (d, J=8.6 Hz, 1H), 5.40 (s, 1H), 4.94 (s, 1H), 4.54 (s, 3H), 3.13 (s, 3H), 1.87 (s, 3H).

Example 408

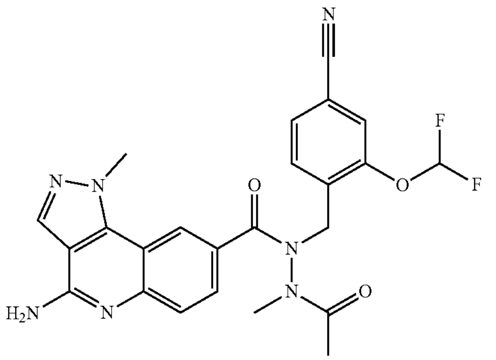

Example 408: N'-acetyl-4-amino-N-[[4-cyano-2-(difluoromethoxy)phenyl]methyl]-N',1-dimethyl-pyrazolo[4,3-c] quinoline-8-carbohydrazide. Prepared following general procedure E-1 starting with intermediates Da-1 and Bb-39. ES/MS: m/z=494.3 $[M+H]^+$. $^1H$ (400 MHz, MeOD) δ 8.51 (d, J=7.8 Hz, 2H), 7.84 (dd, J=31.6, 8.4 Hz, 3H), 7.74-7.56 (m, 2H), 5.09 (d, J=16.0 Hz, 1H), 4.97 (d, J=15.5 Hz, 1H), 4.53 (d, J=12.4 Hz, 3H), 3.59 (s, 0.3H), 3.21 (s, 2.1H major rotamer), 3.07 (s, 0.6H minor rotamer), 1.84 (d, J=18.3 Hz, 3H).

Example 409

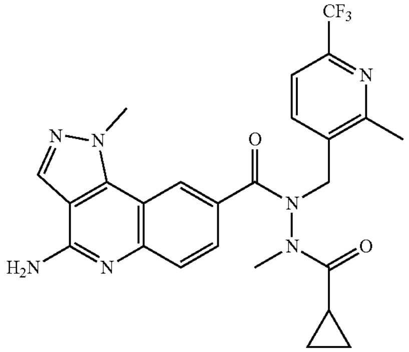

Example 409: 4-amino-N',1-dimethyl-N'-(pyrimidin-2-yl)-N-((5-(trifluoromethyl)pyridin-2-yl)methyl)-1H-pyrazolo[4,3-c]quinoline-8-carbohydrazide. Prepared following general procedure E-1 starting with intermediates Ba-88 and Da-1. ES/MS: m/z=512.3 $[M+H]^+$. $^1H$ NMR (400 MHz, Methanol-d4) δ 8.76-8.37 (m, 2H), 8.26-7.96 (m, 2H), 7.96-7.75 (m, 1H), 7.69 (t, J=8.6 Hz, 1H), 5.04 (dd, J=28.7, 12.8 Hz, 1H), 4.53 (d, J=7.7 Hz, 3H), 2.80 (d, J=15.6 Hz, 3H), 1.83-1.19 (m, 4H), 0.87-0.0 (m, 5H).

Example 410

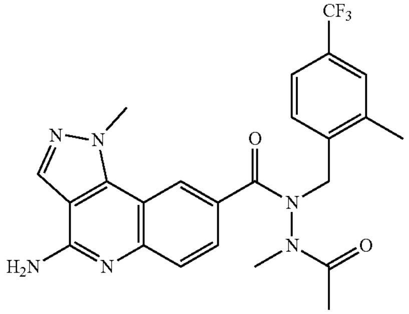

Example 410: N'-acetyl-4-amino-N',1-dimethyl-N-[[2-methyl-4-(trifluoromethyl)phenyl]methyl]pyrazolo[4,3-c] quinoline-8-carbohydrazide. Prepared following general procedure E-1 starting with intermediates Ba-89 and Da-1. ES/MS: m/z=485.3 $[M+H]^+$. $^1H$ NMR (400 MHz, Methanol-d4) δ 8.63-8.38 (m, 2H), 8.09-7.75 (m, 3H), 7.68-7.50 (m, 3H), 5.3-5.1 (m, 1H), 4.78 (d, J=14.8 Hz, 1H), 4.53 (d, J=8.3 Hz, 3H), 2.99 (s, 3H), 2.57 (s, 3H), 1.81 (d, J=9.8 Hz, 3H).

Example 411

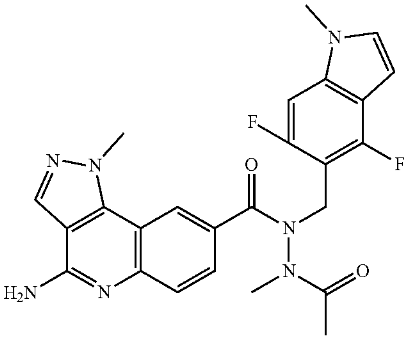

Example 411: N'-acetyl-4-amino-N-[(4,6-difluoro-1-methyl-indol-5-yl)methyl]-N',1-dimethyl-pyrazolo[4,3-c]quinoline-8-carbohydrazide. Prepared following general procedure E-1 starting with intermediates Ba-90 and Da-1. ES/MS: m/z=492.2 $[M+H]^+$. $^1H$ NMR (400 MHz, Methanol-d4) δ 8.60-8.34 (m, 2H), 7.89 (dd, J=35.9, 27.4 Hz, 2H), 7.21 (dd, J=4.4, 3.2 Hz, 1H), 7.11 (dd, J=10.2, 6.4 Hz, 1H), 6.50 (t, J=4.2 Hz, 1H), 5.41-4.98 (m, 2H), 4.52 (d, J=22.9 Hz, 3H), 3.78 (d, J=2.3 Hz, 3H), 3.00 (d, J=46.9 Hz, 3H), 1.87 (d, J=69.7 Hz, 3H).

Example 412

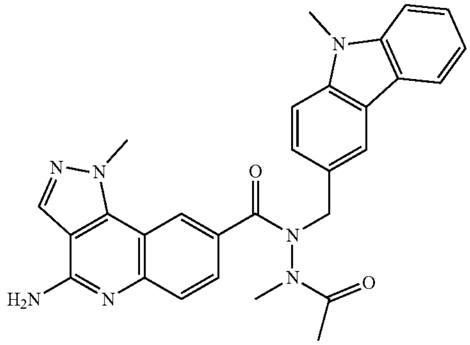

Example 412: N'-acetyl-4-amino-N',1-dimethyl-N-[(9-methylcarbazol-3-yl)methyl]pyrazolo[4,3-c]quinoline-8-carbohydrazide. Prepared following general procedure E-1 starting with intermediates Ba-91 and Da-1. ES/MS: M/Z=506.4 $[M+H]^+$. 1H NMR (400 MHz, METHANOL-D4) Δ 8.31 (DD, J=107.0, 35.3 HZ, 3H), 8.05-7.73 (M, 2H), 7.69-7.40 (M, 5H), 7.23 (D, J=7.3 HZ, 1H), 5.03 (D, J=14.3 HZ, 1H), 4.76 (D, J=14.3 HZ, 1H), 4.46 (D, J=42.6 HZ, 3H), 3.87 (D, J=18.0 HZ, 3H), 3.30-2.78 (M, 3H), 1.9-1.7 (M, 3H).

Example 413

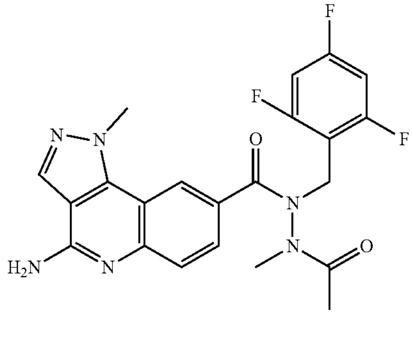

Example 413: N'-acetyl-4-amino-N',1-dimethyl-N-[(2,4,6-trifluorophenyl)methyl]pyrazolo[4,3-c]quinoline-8-carbohydrazide. Prepared following general procedure E-1 starting with intermediates Ba-92 and Da-1. ES/MS: m/z=457.3 $[M+H]^+$. $^1H$ NMR (400 MHz, Methanol-d4) δ 8.61-8.44 (m, 1H), 8.01-7.69 (m, 2H), 7.21-6.71 (m, 3H), 5.12-4.85 (m, 2H), 4.55 (d, J=16.7 Hz, 2H), 4.13-4.02 (m, 1H), 3.16 (s, 3H), 1.88 (d, J=5.9 Hz, 3H).

Example 414

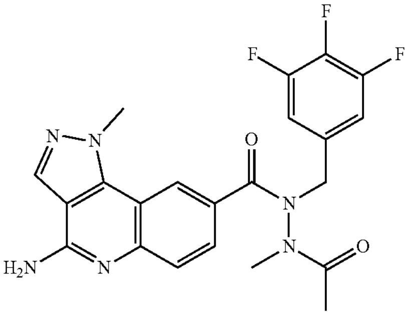

Example 414: N'-acetyl-4-amino-N',1-dimethyl-N-[(3,4,5-trifluorophenyl)methyl]pyrazolo[4,3-c]quinoline-8-carbohydrazide. Prepared following general procedure E-1 starting with intermediates Ba-93 and Da-1. ES/MS: m/z=457.2 $[M+H]^+$. 1H NMR (400 MHz, Methanol-d4) δ 8.55-8.43 (m, 2H), 8.04-7.75 (m, 2H), 7.37 (t, J=7.6 Hz, 2H), 5.10-4.94 (m, 1H), 4.71 (d, J=14.9 Hz, 1H), 4.54 (d, J=6.0 Hz, 3H), 3.18 (d, J=40.3 Hz, 3H), 1.91 (d, J=35.2 Hz, 3H).

Example 415

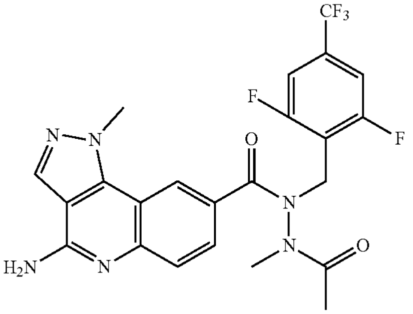

Example 415: N'-acetyl-4-amino-N-(2,6-difluoro-4-(trifluoromethyl)benzyl)-N',1-dimethyl-1H-pyrazolo[4,3-c]quinoline-8-carbohydrazide. Prepared following general procedure E-1 starting with intermediates Ba-94 and Da-1. ES/MS: m/z=507.3 $[M+H]^+$. 1H NMR (400 MHz, Methanol-d4) δ 8.64-8.39 (m, 2H), 8.01-7.74 (m, 2H), 7.50 (dd, J=28.0, 7.1 Hz, 2H), 5.31-4.98 (m, 2H), 4.54 (d, J=19.0 Hz, 3H), 3.22 (s, 2H), 3.11 (s, 1H), 1.95-1.71 (m, 3H).

Example 416

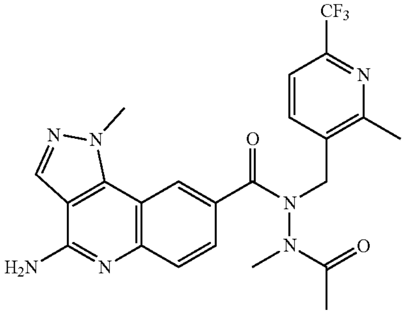

Example 416: N'-acetyl-4-amino-N',1-dimethyl-N-[[2-methyl-6-(trifluoromethyl)-3-pyridyl]methyl]pyrazolo[4,3-c]quinoline-8-carbohydrazide. Prepared following general procedure E-1 starting with intermediates Ba-95 and Da-1. ES/MS: m/z=486.3 $[M+H]^+$. 1H NMR (400 MHz, Methanol-d4) δ 8.51 (d, J=10.5 Hz, 2H), 8.12 (d, J=7.9 Hz, 1H), 7.95-7.57 (m, 3H), 5.24-4.94 (m, 2H), 4.54 (d, J=9.3 Hz, 3H), 3.17 (d, J=8.2 Hz, 3H), 2.76 (s, 3H), 1.84 (d, J=11.7 Hz, 3H).

Example 417

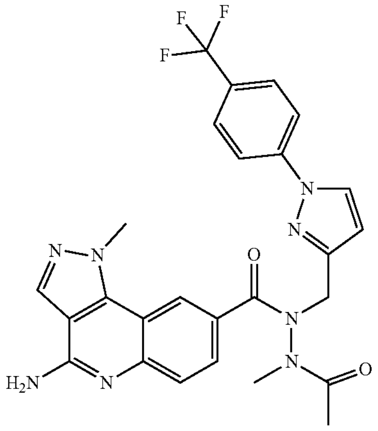

Example 417: N'-acetyl-4-amino-N',1-dimethyl-N-((1-(4-(trifluoromethyl)phenyl)-1H-pyrazol-3-yl)methyl)-1H-pyrazolo[4,3-c]quinoline-8-carbohydrazide. Prepared following general procedure E-1 starting with intermediates Da-1 and Bb-43. ES/MS: m/z=537.4 $[M+H]^+$. $^1H$ NMR (400 MHz, Methanol-d4) δ 8.63 (s, 1H), 8.47 (s, 1H), 8.40 (dd, J=7.3, 2.6 Hz, 1H), 7.99 (d, J=8.5 Hz, 2H), 7.81 (dd, J=8.8, 3.6 Hz, 4H), 6.70 (d, J=23.6 Hz, 1H), 5.51-4.95 (m, 2H), 4.77 (d, J=15.2 Hz, 1H), 4.46 (d, J=37.8 Hz, 3H), 3.23 (d, J=19.9 Hz, 3H), 2.10-1.68 (m, 3H).

Example 418

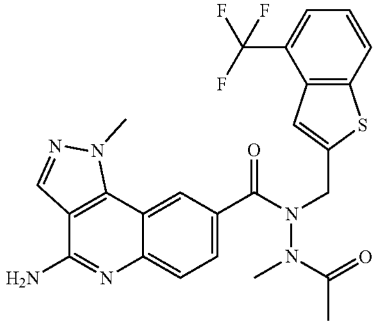

Example 418: N'-acetyl-4-amino-N',1-dimethyl-N-((4-(trifluoromethyl)benzo[b]thiophen-2-yl)methyl)-1H-pyrazolo[4,3-c]quinoline-8-carbohydrazide Prepared following general procedure E-1 starting with intermediates Da-1 and Bb-44. ES/MS: m/z=527.7 $[M+H]^+$. 1H NMR (400 MHz, Methanol-d4) δ 8.59-8.36 (m, 2H), 8.19 (t, J=8.2 Hz, 1H), 7.95-7.78 (m, 2H), 7.78-7.60 (m, 2H), 7.52 (q, J=7.5 Hz, 1H), 5.51-5.25 (m, 1H), 5.10-4.95 (m, 1H), 4.50 (d, J=5.2 Hz, 3H), 3.84-3.63 (m, 3H), 3.63-3.48 (m, 1H), 3.23 (d, J=26.2 Hz, 1H), 1.92 (d, J=23.0 Hz, 3H).

Example 419

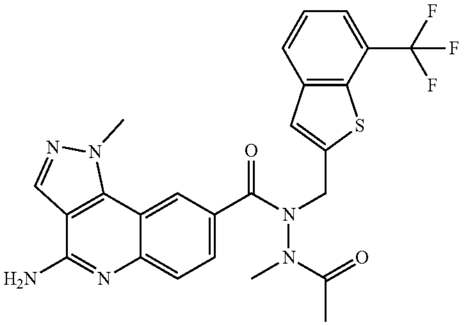

Example 419: N'-acetyl-4-amino-N',1-dimethyl-N-((7-(trifluoromethyl)benzo[b]thiophen-2-yl)methyl)-1H-pyrazolo[4,3-c]quinoline-8-carbohydrazide. Prepared following general procedure E-1 starting with intermediates Da-1 and Bb-45. ES/MS: m/z=527.4 [M+H]+. 1H NMR (400 MHz, DMSO-$d_6$) δ 8.61 (s, 1H), 8.36 (d, J=1.6 Hz, 1H), 8.18 (dd, J=13.6, 8.0 Hz, 1H), 7.91-7.68 (m, 4H), 7.61 (q, J=7.3 Hz, 1H), 5.45-5.12 (m, 2H), 5.02-4.84 (m, 1H), 4.45 (d, J=5.0 Hz, 3H), 3.70-3.53 (m, 2H), 3.22 (s, 1H), 3.08 (s, 1H), 1.84 (d, J=9.8 Hz, 3H).

Example 420

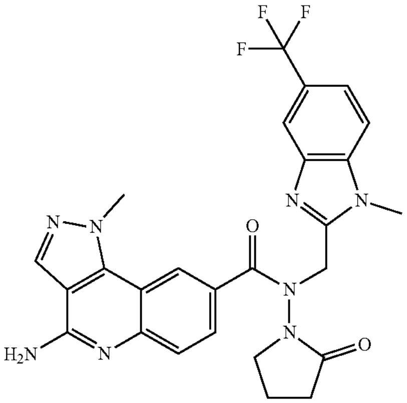

Example 420: 4-amino-1-methyl-N-((1-methyl-5-(trifluoromethyl)-1H-benzo[d]imidazol-2-yl)methyl)-N-(2-oxopyrrolidin-1-yl)-1H-pyrazolo[4,3-c]quinoline-8-carboxamide. Prepared following general procedure E-1 starting with intermediates Da-1 and Bb-46. ES/MS: m/z=537.4 [M+H]+. 1H NMR (400 MHz, Methanol-d4) δ 8.57 (d, J=1.7 Hz, 1H), 8.48 (s, 1H), 8.05-7.98 (m, 1H), 7.94 (dd, J=8.6, 1.7 Hz, 1H), 7.88-7.76 (m, 2H), 7.69 (dd, J=8.6, 1.6 Hz, 1H), 5.73-5.45 (m, 1H), 5.15 (d, J=15.7 Hz, 1H), 4.48 (s, 3H), 4.22-4.04 (m, 3H), 3.96-3.79 (m, 1H), 3.77-3.63 (m, 2H), 3.63-3.38 (m, 1H), 2.33-1.48 (m, 3H).

Example 421

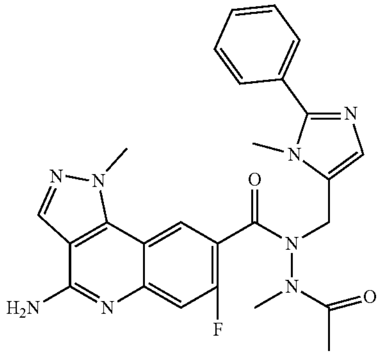

Example 421: N'-acetyl-4-amino-7-fluoro-N',1-dimethyl-N-((1-methyl-2-phenyl-1H-imidazol-5-yl)methyl)-1H-pyrazolo[4,3-c]quinoline-8-carbohydrazide. Prepared following general procedure E-1 starting with intermediates Db-1 and Ba-96. ES/MS: m/z=501.3 [M+H]+. 1H NMR (400 MHz, Methanol-d4) δ 8.48 (s, 1H), 8.41 (d, J=6.5 Hz, 1H), 7.87 (s, 1H), 7.77 (qd, J=7.1, 2.5 Hz, 5H), 7.65 (d, J=10.3 Hz, 1H), 5.64 (d, J=16.0 Hz, 1H), 4.90 (s, 1H), 4.48 (s, 3H), 4.04 (s, 3H), 3.39 (s, 3H), 1.81 (s, 3H).

Example 422

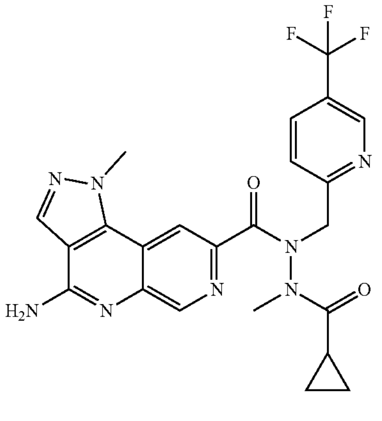

Example 422: 4-amino-N'-(cyclopropanecarbonyl)-N',1-dimethyl-N-((5-(trifluoromethyl)pyridin-2-yl)methyl)-1H-pyrazolo[4,3-c][1,7]naphthyridine-8-carbohydrazide. Prepared following general procedure E-1 starting with intermediates Da-10 and Bd-8. ES/MS: m/z=499.2 [M+H]+. 1H NMR (400 MHz, Methanol-d4) δ 9.02 (d, J=11.7 Hz, 1H), 8.90 (d, J=18.7 Hz, 1H), 8.74 (s, 1H), 8.64-8.49 (m, 2H), 8.18 (dd, J=16.6, 8.3 Hz, 1H), 7.87 (d, J=7.6 Hz, 1H), 5.48-5.19 (m, 2H), 4.57 (d, J=5.7 Hz, 3H), 3.72-3.43 (m, 2H), 3.25-3.10 (m, 3H), 0.94-0.33 (m, 4H).

Example 423

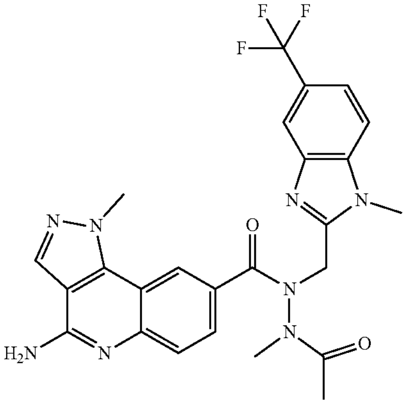

Example 423: N'-acetyl-4-amino-N',1-dimethyl-N-((1-methyl-5-(trifluoromethyl)-1H-benzo[d]imidazol-2-yl)methyl)-1H-pyrazolo[4,3-c]quinoline-8-carbohydrazide. Prepared following general procedure E-1 starting with intermediates Da-1 and Ba-97. ES/MS: m/z=525.5 [M+H]+. 1H NMR (400 MHz, Methanol-d4) δ 8.55 (s, 1H), 8.49 (s, 1H), 7.97 (s, 1H), 7.91 (d, J=8.8 Hz, 1H), 7.87-7.74 (m, 2H), 7.74-7.60 (m, 1H), 5.43 (d, J=15.7 Hz, 1H), 5.22 (d, J=15.6 Hz, 1H), 4.92 (t, J=2.6 Hz, 1H), 4.52 (s, 3H), 4.22-4.05 (m, 3H), 3.79-3.65 (m, 2H), 3.55 (dt, J=11.8, 2.8 Hz, 1H), 3.27 (s, 1H), 1.75 (s, 3H).

Example 424

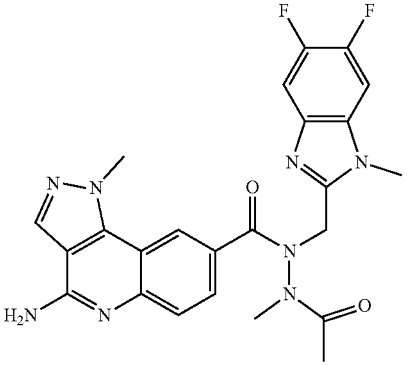

Example 424: N'-acetyl-4-amino-N-((5,6-difluoro-1-methyl-1H-benzo[d]imidazol-2-yl)methyl)-N',1-dimethyl-1H-pyrazolo[4,3-c]quinoline-8-carbohydrazide. Prepared following general procedure E-1 starting with intermediates Da-1 and Ba-98. ES/MS: m/z=493.2 [M+H]+. 1H NMR (400 MHz, Methanol-d4) δ 8.50 (d, J=10.8 Hz, 2H), 7.90 (d, J=8.8 Hz, 1H), 7.86-7.72 (m, 2H), 7.67 (dd, J=10.0, 7.0 Hz, 1H), 5.50 (d, J=15.9 Hz, 1H), 5.18 (d, J=15.9 Hz, 1H), 4.51 (d, J=12.2 Hz, 3H), 4.10 (s, 3H), 3.33 (p, J=1.6 Hz, 3H), 3.26-2.89 (m, 1H), 2.17-1.91 (m, 1H), 1.81 (s, 3H).

Example 425

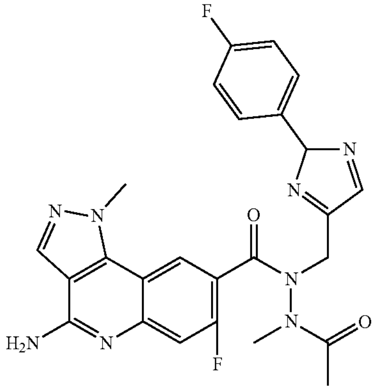

Example 425: N'-acetyl-4-amino-7-fluoro-N-((1-(4-fluorophenyl)-1H-pyrazol-3-yl)methyl)-N',1-dimethyl-1H-pyrazolo[4,3-c]quinoline-8-carbohydrazide. Prepared following general procedure E-1 starting with intermediates Db-1 and Bb-47. ES/MS: m/z=505.4 [M+H]+. 1H NMR (400 MHz, Methanol-d4) δ 8.60-8.37 (m, 1H), 8.28-8.10 (m, 1H), 7.80 (dd, J=8.7, 4.9 Hz, 1H), 7.75-7.45 (m, 2H), 7.23 (dt, J=23.9, 8.4 Hz, 3H), 6.76-6.51 (m, 1H), 5.29 (d, J=14.9 Hz, 1H), 4.76 (d, J=14.9 Hz, 1H), 4.48 (s, 2H), 4.30 (d, J=13.0 Hz, 2H), 3.21-3.03 (m, 2H), 2.28 (s, 1H), 2.10 (s, 1H), 1.89 (d, J=51.2 Hz, 3H).

Example 426

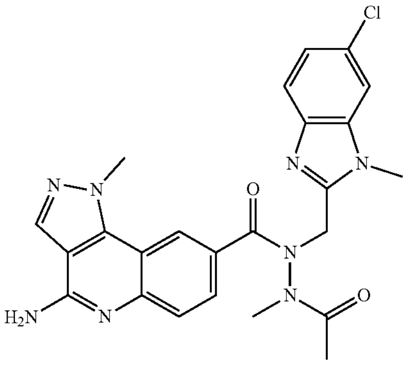

Example 426: N'-acetyl-4-amino-N-((6-chloro-1-methyl-1H-benzo[d]imidazol-2-yl)methyl)-N',1-dimethyl-1H-pyrazolo[4,3-c]quinoline-8-carbohydrazide. Prepared following general procedure E-1 starting with intermediates Da-1 and Bb-48. ES/MS: m/z=491.3 [M+H]+. 1H NMR (400 MHz, Methanol-d4) δ 8.51 (d, J=17.5 Hz, 2H), 7.92 (d, J=8.7 Hz, 1H), 7.83 (d, J=8.6 Hz, 2H), 7.78-7.61 (m, 1H), 7.45 (dd, J=8.8, 1.9 Hz, 1H), 5.20 (d, J=15.9 Hz, 2H), 4.52 (d, J=9.4 Hz, 3H), 4.09 (s, 3H), 3.36 (s, 3H), 1.81 (s, 3H).

Example 427

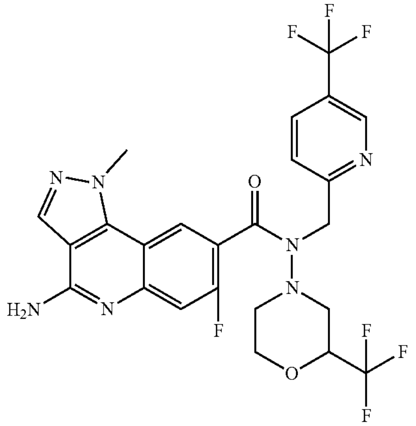

Example 427: 4-amino-7-fluoro-1-methyl-N-(2-(trifluoromethyl)morpholino)-N-((5-(trifluoromethyl)pyridin-2-yl)methyl)-1H-pyrazolo[4,3-c]quinoline-8-carboxamide. Prepared following general procedure E-1 starting with intermediates Db-1 and Bi-18. ES/MS: m/z=572.5 [M+H]+. 1H NMR (400 MHz, Methanol-d4) δ 8.98-8.84 (m, 1H), 8.56-8.42 (m, 2H), 8.17 (dd, J=8.3, 2.4 Hz, 1H), 7.77 (d, J=8.2 Hz, 1H), 7.61 (d, J=10.3 Hz, 1H), 5.23-5.03 (m, 2H), 4.99-4.90 (m, 1H), 4.52 (s, 2H), 4.18 (ddd, J=12.4, 9.1, 3.8 Hz, 1H), 3.95-3.85 (m, 1H), 3.81-3.63 (m, 3H), 3.55 (dt, J=11.8, 2.8 Hz, 1H), 3.23 (d, J=10.3 Hz, 1H), 3.08-2.88 (m, 2H).

Example 428

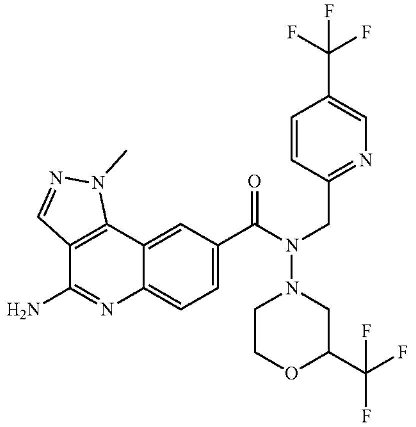

Example 428: 4-amino-1-methyl-N-(2-(trifluoromethyl)morpholino)-N-((5-(trifluoromethyl)pyridin-2-yl)methyl)-1H-pyrazolo[4,3-c]quinoline-8-carboxamide. Prepared following general procedure E-1 starting with intermediates Da-1 and Bi-18. ES/MS: m/z=554.5 [M+H]+. 1H NMR (400 MHz, Methanol-d4) δ 9.06-8.85 (m, 1H), 8.59 (s, 1H), 8.50 (s, 1H), 8.15 (dd, J=8.3, 2.4 Hz, 1H), 8.05 (dd, J=8.6, 1.7 Hz, 1H), 7.81 (dd, J=19.2, 8.4 Hz, 2H), 5.10 (d, J=10.5 Hz, 2H), 4.53 (s, 3H), 4.03-3.79 (m, 3H), 3.57-3.40 (m, 1H), 3.28 (d, J=10.6 Hz, 1H), 3.19-2.93 (m, 3H).

Example 429

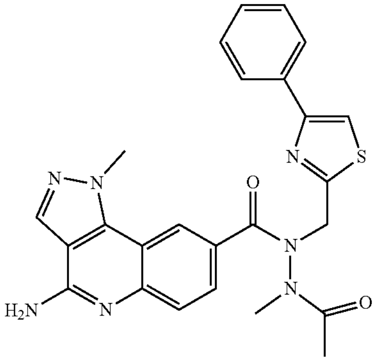

Example 429: N'-acetyl-4-amino-N',1-dimethyl-N-((4-phenylthiazol-2-yl)methyl)-1H-pyrazolo[4,3-c]quinoline-8-carbohydrazide. Prepared following general procedure E-1 starting with intermediates Da-1 and Bb-49. ES/MS: m/z=486.6 [M+H]+. 1H NMR (400 MHZ, Methanol-d4) δ 8.48 (d, J=41.1 Hz, 1H), 8.23 (d, J=11.5 Hz, 1H), 8.01-7.80 (m, 3H), 7.69 (dd, J=15.6, 8.6 Hz, 1H), 7.57-7.26 (m, 3H), 5.34 (d, J=33.0 Hz, 1H), 5.11-4.94 (m, 1H), 4.54-4.06 (m, 3H), 3.78-3.59 (m, 3H), 3.55 (dt, J=11.8, 2.8 Hz, 1H), 3.26 (s, 1H), 1.97 (d, J=56.6 Hz, 3H).

Example 430

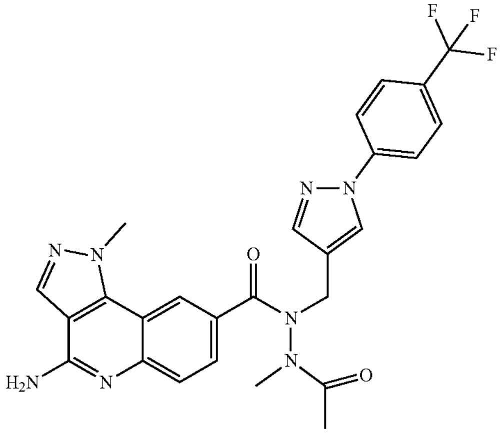

Example 430: N'-acetyl-4-amino-N',1-dimethyl-N-((1-(4-(trifluoromethyl)phenyl)-1H-pyrazol-4-yl)methyl)-1H-pyrazolo[4,3-c]quinoline-8-carbohydrazide. Prepared following general procedure E-1 starting with intermediates Da-1 and Ba-99. ES/MS: m/z=537.7 [M+H]+. 1H NMR (400 MHz, Methanol-d4) δ 8.59-8.37 (m, 3H), 7.97 (d, J=8.0 Hz, 3H), 7.91 (s, 1H), 7.80 (d, J=8.4 Hz, 3H), 4.98 (s, 1H), 4.74 (d, J=15.0 Hz, 1H), 4.51 (d, J=6.2 Hz, 3H), 3.23 (d, J=13.7 Hz, 3H), 2.03-1.77 (m, 3H).

Example 431

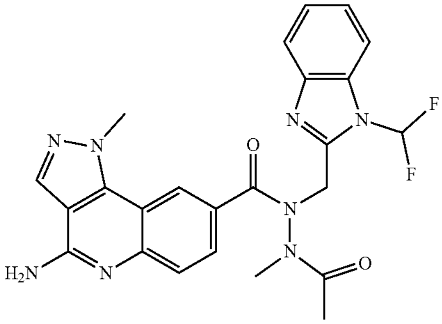

Example 431: N'-acetyl-4-amino-N-((1-(difluoromethyl)-1H-benzo[d]imidazol-2-yl)methyl)-N',1-dimethyl-1H-pyrazolo[4,3-c]quinoline-8-carbohydrazide. Prepared following general procedure E-1 starting with intermediates Da-1 and Bb-50. ES/MS: m/z=493.4 [M+H]+. 1H NMR (400 MHz, Methanol-d4) δ 8.46 (d, J=4.0 Hz, 2H), 7.96-7.61 (m, 4H), 7.50-7.23 (m, 2H), 5.31 (q, J=15.9 Hz, 2H), 4.48 (s, 3H), 3.44-3.30 (m, 4H), 3.22 (d, J=24.5 Hz, 1H), 1.79 (d, J=8.2 Hz, 3H).

Example 432

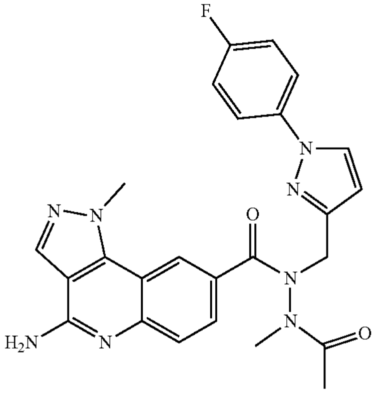

Example 432: N'-acetyl-4-amino-N-((1-(4-fluorophenyl)-1H-pyrazol-3-yl)methyl)-N',1-dimethyl-1H-pyrazolo[4,3-c]quinoline-8-carbohydrazide. Prepared following general procedure E-1 starting with intermediates Da-1 and Bb-47. ES/MS: m/z=487.5 [M+H]+. 1H NMR (400 MHz, Methanol-d4) δ 8.59 (s, 1H), 8.43 (s, 1H), 8.19 (dd, J=5.3, 2.4 Hz, 1H), 8.01-7.63 (m, 3H), 7.23 (td, J=8.6, 6.0 Hz, 2H), 6.62 (d, J=26.6 Hz, 1H), 4.70 (d, J=15.1 Hz, 1H), 4.58-4.25 (m, 3H), 3.67 (s, 3H), 3.19 (d, J=32.6 Hz, 3H), 2.06-1.66 (m, 3H).

Example 433

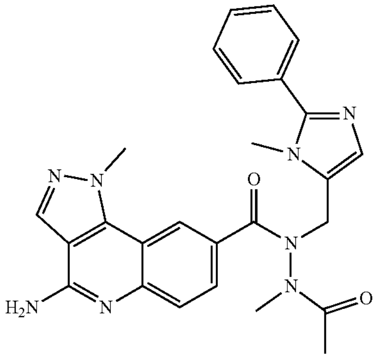

Example 433: N'-acetyl-4-amino-N',1-dimethyl-N-((1-methyl-2-phenyl-1H-imidazol-5-yl)methyl)-1H-pyrazolo[4,3-c]quinoline-8-carbohydrazide. Prepared following general procedure E-1 starting with intermediates Da-1 and Ba-96. ES/MS: m/z=483.3 [M+H]+. 1H NMR (400 MHz, Methanol-d4) δ 8.58-8.39 (m, 2H), 7.95-7.81 (m, 3H), 7.81-7.64 (m, 5H), 5.62 (d, J=15.9 Hz, 1H), 4.81 (s, 1H), 4.52 (s, 3H), 4.04 (s, 3H), 3.37 (s, 3H), 1.85 (s, 3H).

Example 434

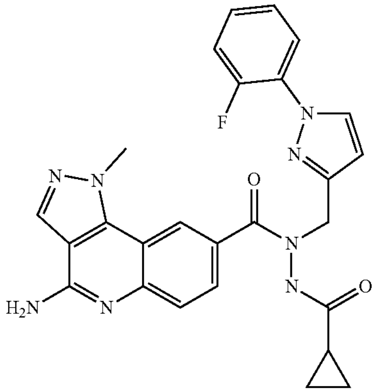

Example 434: 4-amino-N'-(cyclopropanecarbonyl)-N-((1-(2-fluorophenyl)-1H-pyrazol-3-yl)methyl)-1-methyl-1H-pyrazolo[4,3-c]quinoline-8-carbohydrazide. Prepared following general procedure E-1 starting with intermediates Da-1 and Bb-51. ES/MS: m/z=499.2 [M+H]+. 1H NMR (400 MHz, Methanol-d4) δ 8.58 (s, 1H), 8.49 (s, 1H), 8.12 (t, J=2.7 Hz, 1H), 8.03-7.65 (m, 3H), 7.53-7.20 (m, 3H), 6.68 (d, J=2.5 Hz, 1H), 5.40 (s, 2H), 4.51 (s, 3H), 2.00 (d, J=39.3 Hz, 2H), 0.75 (s, 4H).

Example 435

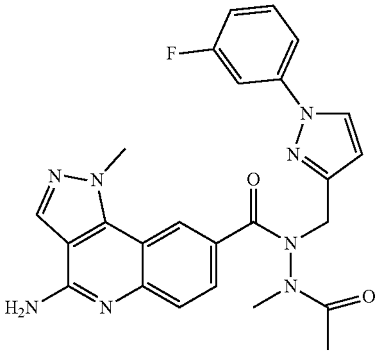

Example 435: N'-acetyl-4-amino-N-((1-(3-fluorophenyl)-1H-pyrazol-3-yl)methyl)-N',1-dimethyl-1H-pyrazolo[4,3-c]quinoline-8-carbohydrazide. Prepared following general procedure E-1 starting with intermediates Da-1 and Bb-52. ES/MS: m/z=487.4 [M+H]+. 1H NMR (400 MHz, Methanol-d4) δ 8.62 (s, 1H), 8.47 (s, 1H), 8.35-8.13 (m, 1H), 8.07-7.75 (m, 1H), 7.69-7.44 (m, 3H), 7.08 (td, J=9.8, 8.7, 2.7 Hz, 1H), 6.65 (d, J=25.3 Hz, 1H), 5.00 (s, 2H), 4.74 (d, J=15.2 Hz, 1H), 4.45 (d, J=37.6 Hz, 3H), 3.28-3.13 (m, 3H), 2.03 (d, J=18.0 Hz, 2H), 1.85 (s, 1H).

Example 436

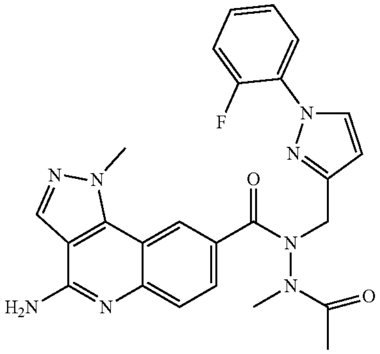

Example 436: N'-acetyl-4-amino-N-((1-(2-fluorophenyl)-1H-pyrazol-3-yl)methyl)-N',1-dimethyl-1H-pyrazolo[4,3-c]quinoline-8-carbohydrazide. Prepared following general procedure E-1 starting with intermediates Da-1 and Bb-53. ES/MS: m/z=487.4 [M+H]+. 1H NMR (400 MHz, Methanol-d4) δ 8.47 (s, 1H), 8.10 (q, J=2.4 Hz, 1H), 7.99-7.66 (m, 3H), 7.58-7.21 (m, 3H), 6.67 (d, J=28.3 Hz, 1H), 4.98 (s, 1H), 4.73 (d, J=15.1 Hz, 1H), 4.60-4.19 (m, 4H), 3.20 (d, J=30.8 Hz, 3H), 1.90 (d, J=41.9 Hz, 3H).

Example 437

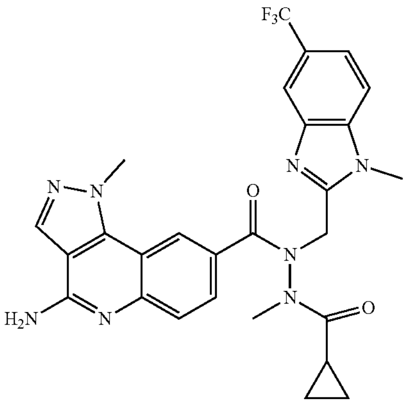

Example 437: 4-amino-N'-(cyclopropanecarbonyl)-N',1-dimethyl-N-((1-methyl-5-(trifluoromethyl)-1H-benzo[d]imidazol-2-yl)methyl)-1H-pyrazolo[4,3-c]quinoline-8-carbohydrazide. Prepared following general procedure E-1 starting with intermediates Da-1 and Ba-100. ES/MS: m/z=551.3 [M+H]+. 1H NMR (400 MHz, Methanol-d4) δ 8.81-8.37 (m, 2H), 8.01 (d, J=10.7 Hz, 2H), 7.98-7.81 (m, 2H), 7.81-7.56 (m, 1H), 5.58 (d, J=15.8 Hz, 1H), 5.25 (dd, J=68.5, 15.6 Hz, 1H), 4.53 (d, J=13.1 Hz, 3H), 4.13 (s, 3H), 3.54 (s, 2H), 3.23 (s, 1H), 1.77 (d, J=151.6 Hz, 1H), 0.89-0.11 (m, 4H).

Example 438

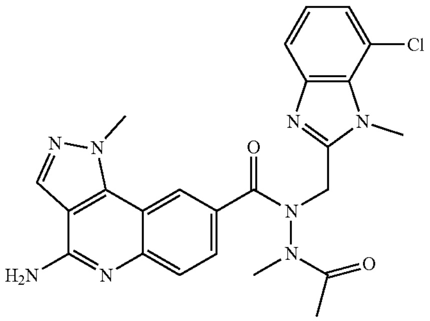

Example 438: N'-acetyl-4-amino-N-((7-chloro-1-methyl-1H-benzo[d]imidazol-2-yl)methyl)-N',1-dimethyl-1H-pyrazolo[4,3-c]quinoline-8-carbohydrazide. Prepared following general procedure E-1 starting with intermediates Da-1 and Bb-54. ES/MS: m/z=491.3 [M+H]+. 1H NMR (400 MHz, Methanol-d4) δ 8.52 (d, J=21.6 Hz, 2H), 7.92 (d, J=8.7 Hz, 1H), 7.83 (d, J=8.6 Hz, 1H), 7.67 (d, J=8.1 Hz, 1H), 7.43 (d, J=7.8 Hz, 1H), 7.40-7.18 (m, 1H), 5.49 (d, J=15.9 Hz, 1H), 5.20 (d, J=15.9 Hz, 1H), 4.51 (s, 3H), 4.38 (s, 3H), 3.25 (s, 1H), 2.00 (d, J=38.4 Hz, 1H), 1.79 (s, 3H).

Example 439

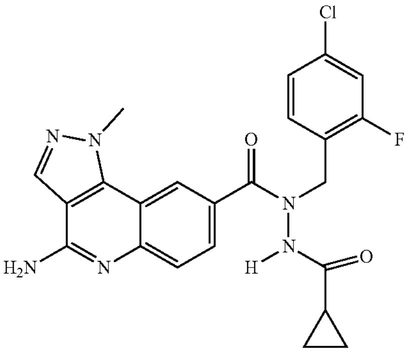

Example 439: 4-amino-N-(4-chloro-2-fluorobenzyl)-N'-(cyclopropanecarbonyl)-1-methyl-1H-pyrazolo[4,3-c]quinoline-8-carbohydrazide. Prepared following general procedure E-1 starting with intermediates Da-1 and Bb-55. ES/MS: m/z=467.4 [M+H]+. 1H NMR (400 MHz, DMSO-$d_6$) δ 13.60 (s, 1H), 10.71 (s, 1H), 8.61 (s, 1H), 8.37 (d, J=1.6 Hz, 1H), 7.92-7.66 (m, 2H), 7.68-7.45 (m, 2H), 7.37 (dd, J=8.2, 2.0 Hz, 1H), 5.05 (d, J=104.4 Hz, 1H), 4.44 (s, 3H), 1.45-1.08 (m, 1H), 0.34 (d, J=214.9 Hz, 5H).

Example 440

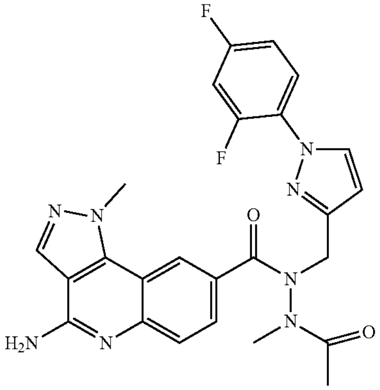

Example 440: N'-acetyl-4-amino-N-((1-(2,4-difluorophenyl)-1H-pyrazol-3-yl)methyl)-N',1-dimethyl-1H-pyrazolo[4,3-c]quinoline-8-carbohydrazide. Prepared following general procedure E-1 starting with intermediates Da-1 and Bb-56. ES/MS: m/z=505.3 [M+H]+. 1H NMR (400 MHz, Methanol-d4) δ 8.72 (s, 1H), 8.49 (d, J=1.7 Hz, 1H), 8.06 (dt, J=5.1, 2.4 Hz, 1H), 7.95-7.63 (m, 2H), 7.47-7.04 (m, 3H), 6.67 (d, J=24.5 Hz, 1H), 5.45-4.92 (m, 2H), 4.74 (d, J=15.1 Hz, 1H), 4.47 (d, J=35.1 Hz, 3H), 3.26-2.97 (m, 3H), 2.01-1.62 (m, 3H).

Example 441

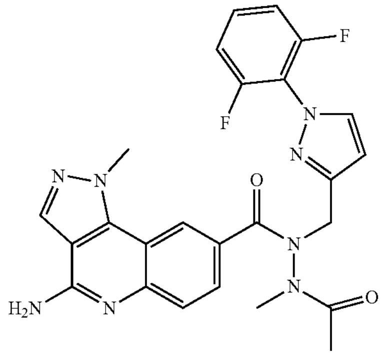

Example 441: N'-acetyl-4-amino-N-((1-(2,6-difluorophenyl)-1H-pyrazol-3-yl)methyl)-N',1-dimethyl-1H-pyrazolo[4,3-c]quinoline-8-carbohydrazide. Prepared following general procedure E-1 starting with intermediates Da-1 and Bb-57. ES/MS: m/z=505.4 [M+H]+. 1H NMR (400 MHz, Methanol-d4) δ 8.49 (d, J=1.3 Hz, 1H), 8.09 (s, 1H), 8.02-7.72 (m, 3H), 7.62 (p, J=7.4 Hz, 1H), 7.28 (q, J=9.2 Hz, 2H), 6.67 (s, 1H), 5.46-4.93 (m, 2H), 4.73 (d, J=15.1 Hz, 1H), 4.47 (d, J=38.2 Hz, 3H), 3.17 (d, J=38.9 Hz, 3H), 1.88 (d, J=28.7 Hz, 3H).

Example 442

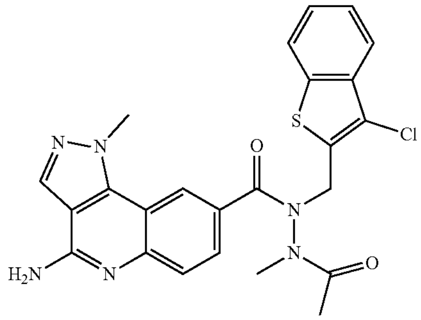

Example 442: N'-acetyl-4-amino-N-((3-chlorobenzo[b]thiophen-2-yl)methyl)-N',1-dimethyl-1H-pyrazolo[4,3-c]quinoline-8-carbohydrazide. Prepared following general procedure E-1 starting with intermediates Da-1 and Bb-58. ES/MS: m/z=493.3 [M+H]+. 1H NMR (400 MHz, Methanol-d4) δ 8.61-8.45 (m, 2H), 8.10-7.71 (m, 4H), 7.51 (tdt, J=10.2, 7.3, 3.5 Hz, 2H), 5.33 (s, 1H), 5.06 (d, J=15.4 Hz, 1H), 4.52 (d, J=7.1 Hz, 3H), 3.19 (d, J=5.7 Hz, 3H), 1.88 (s, 3H).

Example 443

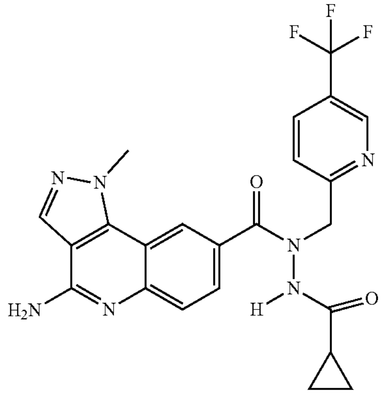

Example 443: 4-amino-N'-(cyclopropanecarbonyl)-1-methyl-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bb-59. ES/MS: m/z=484.5 [M+H]+. 1H NMR (400 MHz, Methanol-d4) δ 9.04-8.81 (m, 1H), 8.60 (s, 1H), 8.50 (s, 1H), 8.19 (dd, J=8.2, 2.3 Hz, 1H), 8.07-7.94 (m, 1H), 7.80 (dd, J=8.5, 3.3 Hz, 2H), 5.51 (s, 1H), 4.71 (s, 1H), 4.53 (s, 3H), 1.44 (d, J=61.9 Hz, 1H), 1.12-0.06 (m, 5H).

Example 444

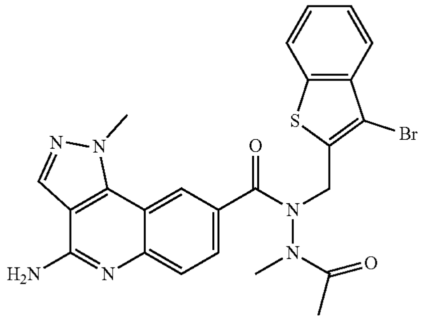

Example 444: N'-acetyl-4-amino-N-((3-bromobenzo[b]thiophen-2-yl)methyl)-N',1-dimethyl-1H-pyrazolo[4,3-c]quinoline-8-carbohydrazide. Prepared following general procedure E-1 starting with intermediates Da-1 and Bb-60. ES/MS: m/z=538.4 [M+H]+. 1H NMR (400 MHz, Methanol-d4) δ 8.67-8.47 (m, 2H), 8.10-7.88 (m, 1H), 7.82 (d, J=8.3 Hz, 3H), 7.50 (pd, J=7.2, 1.4 Hz, 2H), 5.59-5.30 (m, 2H), 5.06 (d, J=15.3 Hz, 1H), 4.52 (d, J=7.6 Hz, 3H), 3.17 (s, 3H), 1.92 (d, J=26.4 Hz, 3H).

Example 443

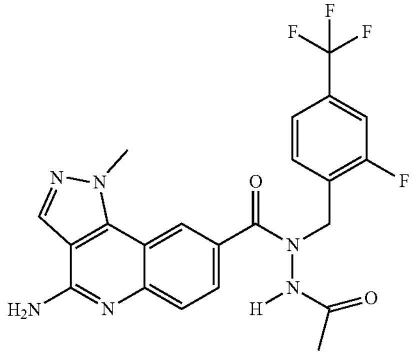

Example 445: N'-acetyl-4-amino-N-(2-fluoro-4-(trifluoromethyl)benzyl)-1-methyl-1H-pyrazolo[4,3-c]quinoline-8-carbohydrazide. Prepared following general procedure E-1 starting with intermediates Da-1 and Bb-61. ES/MS: m/z=475.5 [M+H]+. 1H NMR (400 MHZ, Methanol-d4) δ 8.62-8.42 (m, 2H), 7.96-7.73 (m, 3H), 7.57 (ddd, J=17.6, 8.9, 1.7 Hz, 2H), 4.52 (s, 3H), 3.33 (p, J=1.6 Hz, 4H), 1.69 (s, 3H).

Example 446

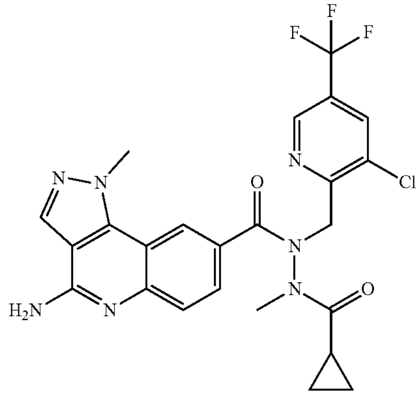

Example 446: 4-amino-N-((3-chloro-5-(trifluoromethyl)pyridin-2-yl)methyl)-N'-(cyclopropanecarbonyl)-N',1-dimethyl-1H-pyrazolo[4,3-c]quinoline-8-carbohydrazide. Prepared following general procedure E-1 starting with intermediates Da-1 and Bk-10. ES/MS: m/z=531.8 $[M+H]^+$. $^1$H NMR (400 MHz, DMSO-$d_6$) δ 13.52 (s, 1H), 9.68 (s, 1H), 9.04 (s, 1H), 8.80 (s, 1H), 8.66 (s, 1H), 8.63-8.47 (m, 2H), 7.99-7.74 (m, 2H), 5.38 (s, 2H), 4.50 (s, 3H), 3.13 (s, 3H), 2.18-2.02 (m, 1H), 0.88-0.42 (m, 4H).

Example 447

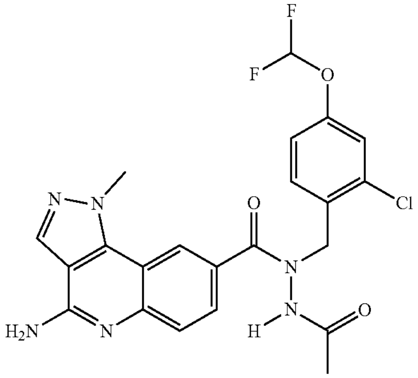

Example 447: N'-acetyl-4-amino-N-(2-chloro-4-(difluoromethoxy)benzyl)-N',1-dimethyl-1H-pyrazolo[4,3-c]quinoline-8-carbohydrazide. Prepared following general procedure E-1 starting with intermediates Da-1 and Bb-62. ES/MS: m/z=502.9 $[M+H]^+$. $^1$H NMR (400 MHz, DMSO-$d_6$) δ 13.70 (s, 1H), 9.72 (s, 1H), 8.99 (s, 1H), 8.66 (d, J=2.7 Hz, 1H), 8.48 (s, 0.33H, minor rotamer), 8.38 (s, 0.67H, major rotamer), 7.85 (q, J=9.1, 8.5 Hz, 1.33H, major rotamer), 7.78 (d, J=8.6 Hz, 0.67H, minor rotamer), 7.57 (d, J=4.3 Hz, 0.33H, minor rotamer), 7.43 (d, J=2.5 Hz, 1H), 7.39 (d, J=4.4 Hz, 0.67H, major rotamer), 7.30-7.17 (m, 1H), 5.19 (d, J=15.1 Hz, 1H), 5.00 (d, J=13.3 Hz, 1H), 4.66 (d, J=15.2 Hz, 1H), 4.50 (d, J=11.7 Hz, 3H), 3.06 (s, 2H, major rotamer), 2.95 (s, 1H, minor rotamer), 1.88-1.64 (m, 3H).

Example 448

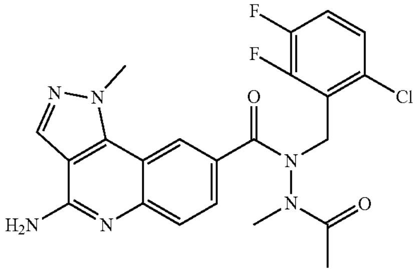

Example 448: N'-acetyl-4-amino-N-(6-chloro-2,3-difluorobenzyl)-N',1-dimethyl-1H-pyrazolo[4,3-c]quinoline-8-carbohydrazide. Prepared following general procedure E-1 starting with intermediates Da-1 and Bb-63. ES/MS: m/z=472.8 $[M+H]^+$. $^1$H NMR (400 MHZ, DMSO-$d_6$) δ 13.77 (s, 1H), 9.73 (s, 1H), 9.06 (s, 1H), 8.66 (d, J=7.1 Hz, 1H), 8.58-8.25 (m, 1H), 8.05-7.76 (m, 2H), 7.75-7.57 (m, 1H), 7.57-7.43 (m, 1H), 5.34-5.06 (m, 1H), 4.89 (d, J=14.2 Hz, 1H), 4.50 (d, J=30.0 Hz, 3H), 2.97 (s, 3H), 1.78 (d, J=10.1 Hz, 3H).

Example 449

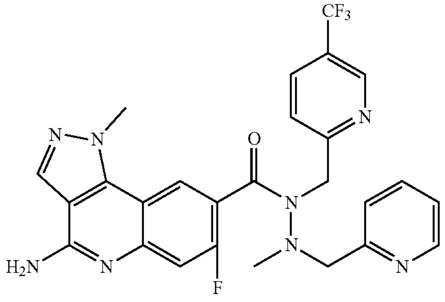

Example 449: 4-amino-7-fluoro-N',1-dimethyl-N'-(pyridin-2-ylmethyl)-N-((5-(trifluoromethyl)pyridin-2-yl)methyl)-1H-pyrazolo[4,3-c]quinoline-8-carbohydrazide. Prepared following general procedure E-1 starting with intermediates Db-1 and Bm-3. ES/MS: m/z=539.0 $[M+H]^+$. $^1H$ NMR (400 MHz, DMSO-$d_6$) δ 13.64 (s, 1H), 9.76 (s, 1H), 9.25-8.93 (m, 2H), 8.66 (s, 1H), 8.43-8.23 (m, 2H), 8.12 (d, J=6.5 Hz, 1H), 7.76 (d, J=8.3 Hz, 1H), 7.60 (d, J=10.3 Hz, 1H), 7.52 (td, J=7.7, 1.8 Hz, 1H), 7.20 (ddd, J=7.5, 4.9, 1.2 Hz, 1H), 6.76 (d, J=7.8 Hz, 1H), 5.14 (q, J=16.7 Hz, 2H), 4.38 (s, 3H), 4.27 (d, J=13.4 Hz, 1H), 3.94 (d, J=13.4 Hz, 1H), 2.67 (s, 3H).

Example 450

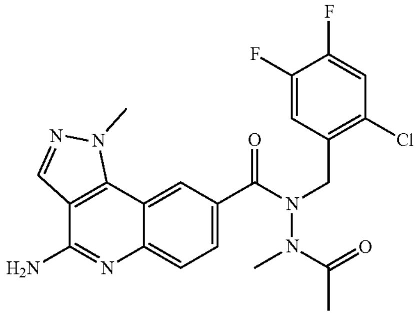

Example 450: N'-acetyl-4-amino-N-(2-chloro-4,5-difluorobenzyl)-N',1-dimethyl-1H-pyrazolo[4,3-c]quinoline-8-carbohydrazide. Prepared following general procedure E-1 starting with intermediates Da-1 and Bb-64. ES/MS: m/z=472.9 $[M+H]^+$. $^1H$ NMR (400 MHZ, DMSO-$d_6$) δ 13.36 (s, 1H), 9.67 (s, 1H), 8.65 (s, 2H), 8.49 (s, 0.33H, minor rotamer), 8.42 (d, J=1.4 Hz, 0.67H, major rotamer), 7.94-7.73 (m, 4H), 5.09 (d, J=16.2 Hz, 1H), 4.71 (d, J=15.4 Hz, 1H), 4.50 (d, J=7.0 Hz, 3H), 3.16 (s, 2H, major rotamer), 2.97 (s, 1H, minor rotamer), 1.82 (s, 3H).

Example 451

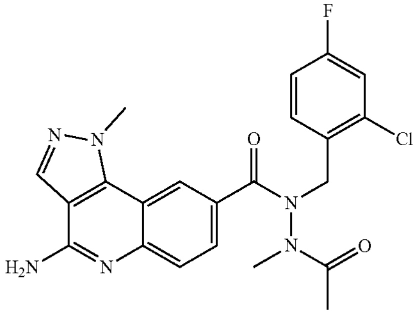

Example 451: N'-acetyl-4-amino-N-(2-chloro-4-fluorobenzyl)-N',1-dimethyl-1H-pyrazolo[4,3-c]quinoline-8-carbohydrazide. Prepared following general procedure E-1 starting with intermediates Da-1 and Bb-65. ES/MS: m/z=454.9 $[M+H]^+$. $^1H$ NMR (400 MHZ, DMSO-$d_6$) δ 13.61 (s, 1H), 9.67 (s, 1H), 8.90 (s, 1H), 8.66 (d, J=2.3 Hz, 1H), 8.48 (s, 0.4H, minor rotamer), 8.38 (s, 0.6H, major rotamer), 8.01-7.64 (m, 3H), 7.62-7.50 (m, 1H), 7.40-7.27 (m, 1H), 5.18 (d, J=15.2 Hz, 0.6H, major rotamer), 5.00 (d, J=14.2 Hz, 0.4H, minor rotamer), 4.68 (d, J=15.0 Hz, 1H), 4.51 (s, 1H, minor rotamer), 4.48 (s, 2H, major rotamer), 3.04 (s, 2H, major rotamer), 2.94 (s, 1H, minor rotamer), 1.77 (d, J=23.0 Hz, 3H).

Example 452

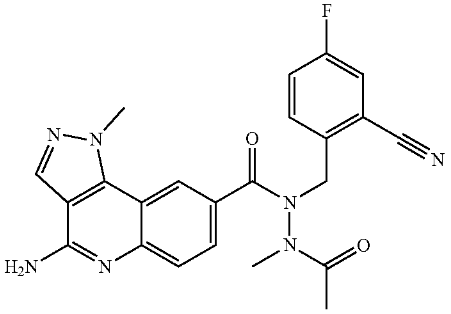

Example 452: N'-acetyl-4-amino-N-(2-cyano-4-fluorobenzyl)-N',1-dimethyl-1H-pyrazolo[4,3-c]quinoline-8-carbohydrazide. Prepared following general procedure E-1 starting with intermediates Da-1 and Bb-66. ES/MS: m/z=446.0 $[M+H]^+$. $^1H$ NMR (400 MHZ, DMSO-$d_6$) δ 13.44 (s, 1H), 9.66 (s, 1H), 8.75 (s, 1H), 8.66 (s, 1H), 8.50 (s, 0.33H, minor rotamer), 8.41 (s, 0.67H, major rotamer), 8.00-7.85 (m, 3H), 7.84 (s, 1H), 7.75-7.62 (m, 1H), 5.11 (d, J=15.1 Hz, 1H), 4.86 (d, J=15.2 Hz, 1H), 4.51 (s, 1H, minor rotamer), 4.49 (s, 2H, major rotamer), 3.19 (s, 2H, major rotamer), 3.01 (s, 1H, minor rotamer), 1.82 (s, 2H, major rotamer), 1.75 (s, 1H, minor rotamer).

Example 453

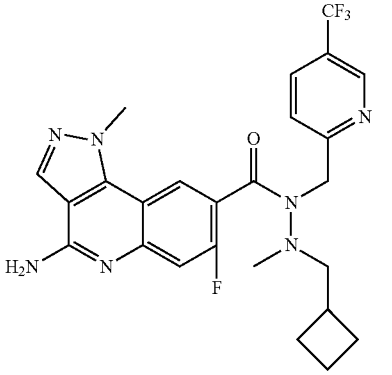

Example 453: 4-amino-N'-(cyclobutylmethyl)-7-fluoro-N',1-dimethyl-N-((5-(trifluoromethyl)pyridin-2-yl)methyl)-1H-pyrazolo[4,3-c]quinoline-8-carbohydrazide. Prepared following general procedure E-1 starting with intermediates Db-1 and Bm-1. ES/MS: m/z=515.9 $[M+H]^+$. $^1$H NMR (400 MHz, DMSO-$d_6$) δ 13.48 (s, 1H), 9.70 (s, 1H), 9.00 (s, 1H), 8.94 (s, 1H), 8.65 (s, 1H), 8.44 (d, J=6.6 Hz, 1H), 8.30 (dd, J=8.4, 2.4 Hz, 1H), 7.74 (d, J=8.3 Hz, 1H), 7.65 (d, J=10.4 Hz, 1H), 5.04-4.86 (m, 2H), 4.51 (s, 3H), 2.86 (dd, J=12.1, 8.0 Hz, 1H), 2.69 (dd, J=12.0, 6.6 Hz, 1H), 2.55 (s, 3H), 2.17 (p, J=7.6 Hz, 1H), 1.74-1.58 (m, 4H), 1.40-1.20 (m, 2H).

Example 454

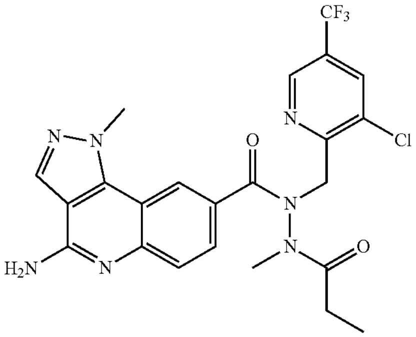

Example 454: 4-amino-N-((3-chloro-5-(trifluoromethyl)pyridin-2-yl)methyl)-N',1-dimethyl-N'-propionyl-1H-pyrazolo[4,3-c]quinoline-8-carbohydrazide. Prepared following general procedure E-1 starting with intermediates Da-1 and Bk-11. ES/MS: m z=519.9 $[M+H]^+$. $^1$H NMR (400 MHz, DMSO-$d_6$) δ 13.45 (s, 1H), 9.68 (s, 1H), 9.01 (s, 1H), 8.76 (s, 1H), 8.66 (s, 1H), 8.57 (s, 1.5H, major rotamer one), 8.34 (s, 0.5H, rotamer two), 7.86 (dd, J=15.0, 7.7 Hz, 2H), 5.44 (d, J=15.7 Hz, 1H), 5.15 (d, J=17.6 Hz, 0.5H, rotamer one), 4.92 (d, J=15.7 Hz, 0.5H, rotamer two), 4.48 (d, J=10.4 Hz, 3H), 3.18 (s, 3H), 2.44-2.27 (m, 1H), 2.29-1.96 (m, 1H), 0.92 (s, 1.5H, rotamer one), 0.75 (s, 1.5H, rotamer two).

Example 455

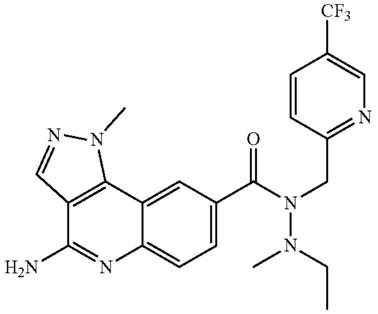

Example 455: 4-amino-N'-ethyl-N',1-dimethyl-N-((5-(trifluoromethyl)pyridin-2-yl)methyl)-1H-pyrazolo[4,3-c]quinoline-8-carbohydrazide. Prepared following general procedure E-1 starting with intermediates Da-1 and Bm-4. ES/MS: m/z=457.9 $[M+H]^+$. $^1$H NMR (400 MHz, DMSO-$d_6$) δ 13.41 (s, 1H), 9.66 (s, 1H), 8.99 (s, 1H), 8.86-8.53 (m, 3H), 8.23 (dd, J=8.4, 2.4 Hz, 1H), 8.02 (dd, J=8.6, 1.7 Hz, 1H), 7.82 (dd, J=12.4, 8.5 Hz, 2H), 4.98 (d, J=16.5 Hz, 1H), 4.85 (d, J=16.3 Hz, 1H), 4.52 (s, 3H), 2.99-2.84 (m, 1H), 2.75-2.60 (m, 4H), 0.80 (t, J=7.1 Hz, 3H).

Example 456

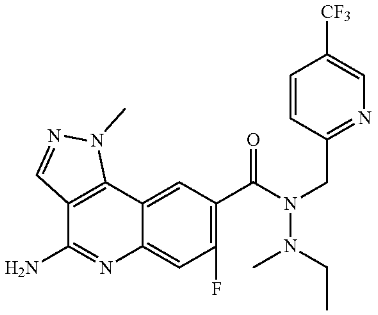

Example 456: 4-amino-N'-ethyl-7-fluoro-N',1-dimethyl-N-((5-(trifluoromethyl)pyridin-2-yl)methyl)-1H-pyrazolo[4,3-c]quinoline-8-carbohydrazide. Prepared following general procedure E-1 starting with intermediates Db-1 and Bm-4. ES/MS: m/z=475.9 $[M+H]^+$. $^1$H NMR (400 MHz, DMSO-$d_6$) δ 13.49 (s, 1H), 9.71 (s, 1H), 9.08-8.83 (m, 2H), 8.65 (s, 1H), 8.40 (d, J=6.5 Hz, 1H), 8.30 (dd, J=8.4, 2.4 Hz, 1H), 7.77 (d, J=8.3 Hz, 1H), 7.66 (d, J=10.4 Hz, 1H), 5.03-4.86 (m, 2H), 4.48 (s, 3H), 2.94-2.76 (m, 1H), 2.67-2.58 (m, 1H), 2.57 (s, 3H), 0.80 (t, J=7.1 Hz, 3H).

Example 457

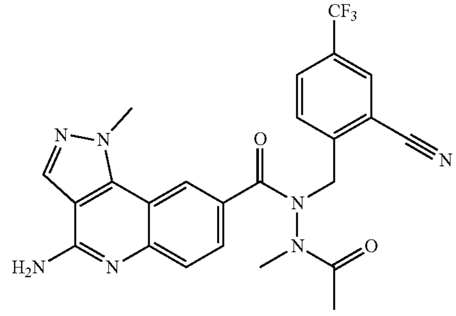

Example 457: N'-acetyl-4-amino-N-(4-chloro-2-cyano-benzyl)-N',1-dimethyl-1H-pyrazolo[4,3-c]quinoline-8-carbohydrazide. Prepared following general procedure E-1 starting with intermediates Da-1 and Bb-67. ES/MS: m/z=461.9 $[M+H]^+$. $^1H$ NMR (400 MHZ, DMSO-$d_6$) δ 13.77 (s, 1H), 9.70 (s, 1H), 9.06 (s, 1H), 8.69-8.64 (m, 1H), 8.50 (d, J=1.8 Hz, 0.25H, minor rotamer), 8.41 (d, J=1.5 Hz, 0.75H, major rotamer), 8.16 (s, 0.25H, minor rotamer), 8.10 (d, J=2.2 Hz, 0.75H, major rotamer), 7.97-7.79 (m, 4H), 5.10 (d, J=15.3 Hz, 1H), 4.87 (d, J=15.3 Hz, 1H), 4.55-4.45 (m, 3H), 3.21 (s, 2.25H, major rotamer), 3.02 (s, 0.75H, minor rotamer), 1.89-1.73 (m, 3H).

Cell Viability Assay

Cytotoxicity assay was performed using HCT116 WT (Horizon Discovery, Cat no. HD PAR-034) and HCT116 MTAP-deleted cell lines (Horizon Discovery, Cat no. HD R02-033) to demonstrate enhanced killing of MTAP-deleted cell in the presence of potent compounds. Control compounds were analyzed in parallel each time for quality control.

In Brief, on Day −1, a serial dilution of stock compounds in DMSO was performed using BioMek liquid handlers and dispensed using Echo acoustic dispenser into 384 well plates. Both tool compounds and sample compounds were spotted in the same plate for a dose response of PRMT5 inhibitors. Compound plates were stored as frozen until the cells were ready for seeding.

On Day 0, 100 HCT WT or HCT116 MTAP-deleted cells were seeded in compound-containing 384 well plates (50 μl per well) in RPMI 1640 media supplemented with 10% heat inactivated fetal bovine serum, Glutamax and penicillin streptomycin using EL460 liquid dispenser 5 μl cassette (BioTek, part no. 7170011). After equilibrating the plate in room temperature, the cells were incubated for 7 days inside the sealed incubator set at 37 °C with 90% humidity and 5% $CO_2$.

On Day 7, the viability of cells was measured using a CTG assay kit (CellTitre-Glo; Promega cat no. G7573). Shortly, 40 μl per well of luminescent cell viability assay reagent were dispensed using EL460 liquid dispenser 5 μl cassette. CTG luminescence signal was measured using an EnVision plate reader (PerkinElmer) in accordance with manufacturer's instruction. The $CC_{50}$ values for each compound after 7 days of treatment were calculated using 4 parameter non-linear logistical curve fit.

For the cell viability assay ie $CC_{50}$ shown in Table 3: A: $CC_{50}$≤100 nM; B: 100<CC50≤1 μM and C: CC50>1 μM.

Symmetric Di-Methyl Arginine Image-Based High Content Screen Assay (SDMA Assay)

Symmetric di-methyl arginine image-based high content screen assay assay (SDMA assay) was performed in HCT116 WT and HCT116 MTAP-deleted cell lines to measure Symmetric Di-methyl Arginine (SDMA) signal reduction after selective PRMT5 inhibition in the MTAP-deleted cells. Control compounds were analyzed in parallel each time for quality control.

Briefly, the same compound plates were generated as mentioned in the previous section of Cell viability assay on Day −1. On Day 0, 800 HCT WT or HCT116 MTAP-deleted cell were seeded in compound-containing 384 well plates (50 μl per well) in RPMI 1640 media supplemented with 10% heat inactivated fetal bovine serum, Glutamax and penicillin streptomycin using EL460 liquid dispenser 5 μl cassette (BioTek, part no. 7170011). After equilibrating the plate at room temperature, the cells were incubated for 3 days inside the sealed incubator set at 37 °C with 90% humidity and 5% $CO_2$.

On Day 3, the cells were fixed by adding 45 μl of 8% neutralized formalin solution to each well using EL460 liquid dispenser 5 μl cassette and the cells were incubated for 30 minutes at room temperature. The formalin solution was washed off with depleted phosphate buffered saline (dPBS), the 0.1% Triton X-100 solution in dPBS was used to permeabilize the cells for 15 minutes at room temperature. The triton solution was aspirated, 50 μl of Odyssey Blocking buffer+0.05% Tween20 was added and the plate was incubated at room temperature for 30 minutes.

The blocking solution was removed, a 20 μl of SDMA antibody (Cell Signaling Technology, Cat no. 13222) diluted 1:500 in Odyssey Blocking buffer+0.05% Tween20 was added and the plate was incubated at 4 °C overnight. Next day, the primary SDME antibody solution was washed from each well three times with 0.05% Tween20 in dPBS (PBST).

A 30 μl of the secondary antibody, a Goat anti-Rabbit Alexa Fluor Plus 488 (Invitrogen, Cat no. PIA32731) was diluted 1:500 in Odyssey Blocking buffer+0.05% Tween20 and the plate was incubated for 1.5 hours in dark at room temperature. The secondary antibody solution was removed, 30 μl of 5 mg/ml DAPI solution diluted 1:2000 in dPBS was added and the plate was incubated for 30 minutes in dark at room temperature. The DAPI solution was aspirated and the wells were washed six times with dPBS.

The SDMA signal and DAPI signal per cell were counted using a Cellomics CX7 LZR instrument reading under 488 and 405 nm laser, respectively. The SDMA signal was quantified by mean average intensity per cell from Alexa Fluor Plus 488 after the cell was defined with DAPI. The $EC_{50}$ values for each compound after 3 days of treatment were calculated using 4 parameter non-linear logistical curve fit.

For the SDMA assay ie $EC_{50}$ shown in Table 3: A: EC50≤1 nM, B: 1<EC50≤5 nM, C: EC50>5 nM.

Tables

Tables 1 and 1A provide some examples disclosed herein. The Examples listed in Tables 1 and 1A were prepared according to the procedures described herein and/or indicated in Table 2. Cell viability assay data SDMA assay data for some examples are provided in Table 3.

TABLE 1
| Compounds | | |
|---|---|---|
| Example | Structure | Name |
| 1 | 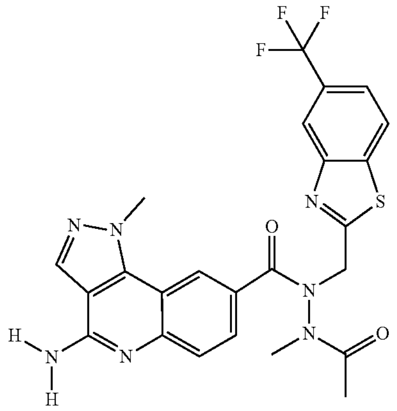 [SMILES: CC(=O)N(C)N(Cc1nc2cc(C(F)(F)F)ccc2s1)C(=O)c1ccc2nc(N)c3cnn(C)c3c2c1] | N'-acetyl-4-amino-N',1-dimethyl-N-((5-(trifluoromethyl)benzo[d]thiazol-2-yl)methyl)-1H-pyrazolo[4,3-c]quinoline-8-carbohydrazide |
| 2 | 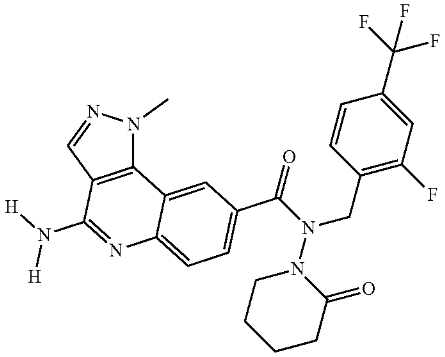 [SMILES: Cn1ncc2c(N)nc3ccc(C(=O)N(Cc4ccc(C(F)(F)F)cc4F)N4CCCCC4=O)cc3c21] | 4-amino-N-(2-fluoro-4-(trifluoromethyl)benzyl)-1-methyl-N-(2-oxopiperidin-1-yl)-1H-pyrazolo[4,3-c]quinoline-8-carboxamide |
| 3 | 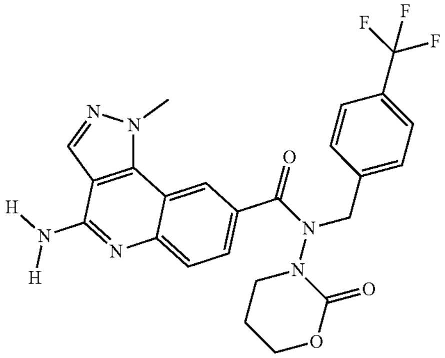 [SMILES: Cn1ncc2c(N)nc3ccc(C(=O)N(Cc4ccc(C(F)(F)F)cc4)N4CCCOC4=O)cc3c21] | 4-amino-1-methyl-N-(2-oxo-1,3-oxazinan-3-yl)-N-(4-(trifluoromethyl)benzyl)-1H-pyrazolo[4,3-c]quinoline-8-carboxamide |

TABLE 1-continued

| Compounds | | |
|---|---|---|
| Example | Structure | Name |
| 4 | 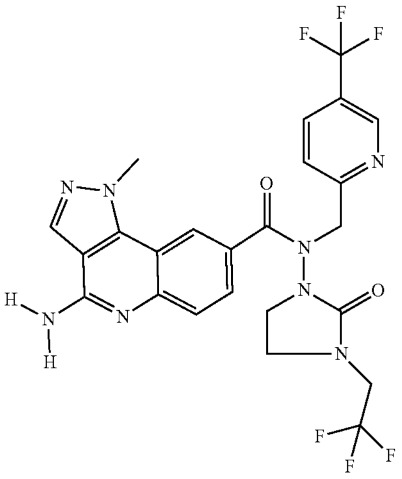 [SMILES: Cn1ncc2c(N)nc3ccc(C(=O)N(Cc4ccc(C(F)(F)F)cn4)N4CCN(CC(F)(F)F)C4=O)cc3c21] | 4-amino-1-methyl-N-(2-oxo-3-(2,2,2-trifluoroethyl)imidazolidin-1-yl)-N-((5-(trifluoromethyl)pyridin-2-yl)methyl)-1H-pyrazolo[4,3-c]quinoline-8-carboxamide |
| 5 | 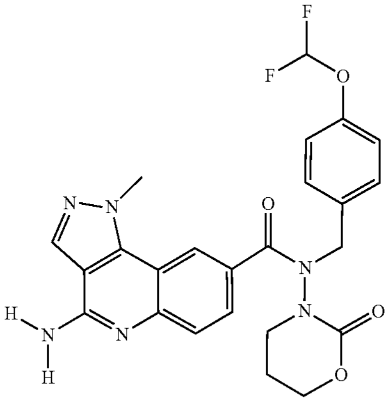 [SMILES: Cn1ncc2c(N)nc3ccc(C(=O)N(Cc4ccc(OC(F)F)cc4)N4CCCOC4=O)cc3c21] | 4-amino-N-(4-(difluoromethoxy)benzyl)-1-methyl-N-(2-oxo-1,3-oxazinan-3-yl)-1H-pyrazolo[4,3-c]quinoline-8-carboxamide |
| 6 | 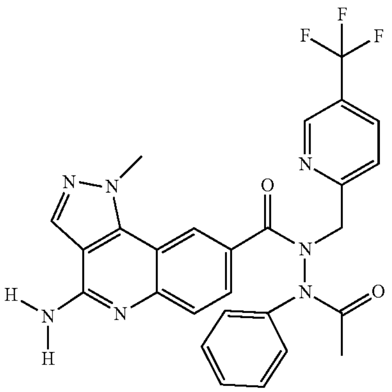 [SMILES: CC(=O)N(c1ccccc1)N(Cc1ccc(C(F)(F)F)cn1)C(=O)c1ccc2nc(N)c3cnn(C)c3c2c1] | N'-acetyl-4-amino-1-methyl-N'-phenyl-N-((5-(trifluoromethyl)pyridin-2-yl)methyl)-1H-pyrazolo[4,3-c]quinoline-8-carbohydrazide |

TABLE 1-continued

| Compounds | | |
|---|---|---|
| Example | Structure | Name |
| 7 | 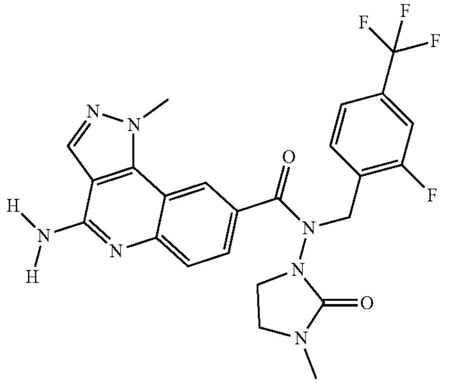 [SMILES: CN1CCN(N(Cc2ccc(C(F)(F)F)cc2F)C(=O)c2ccc3nc(N)c4cnn(C)c4c3c2)C1=O] | 4-amino-N-(2-fluoro-4-(trifluoromethyl)benzyl)-1-methyl-N-(3-methyl-2-oxoimidazolidin-1-yl)-1H-pyrazolo[4,3-c]quinoline-8-carboxamide |
| 8 | 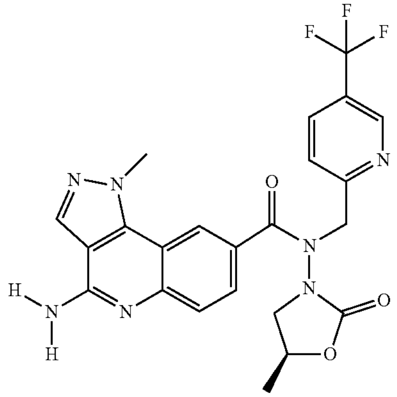 [SMILES: C[C@H]1CN(N(Cc2ccc(C(F)(F)F)cn2)C(=O)c2ccc3nc(N)c4cnn(C)c4c3c2)C(=O)O1] | (S)-4-amino-1-methyl-N-(5-methyl-2-oxooxazolidin-3-yl)-N-((5-(trifluoromethyl)pyridin-2-yl)methyl)-1H-pyrazolo[4,3-c]quinoline-8-carboxamide |
| 9 | 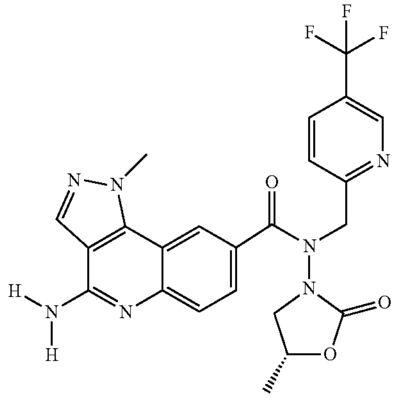 [SMILES: C[C@@H]1CN(N(Cc2ccc(C(F)(F)F)cn2)C(=O)c2ccc3nc(N)c4cnn(C)c4c3c2)C(=O)O1] | (R)-4-amino-1-methyl-N-(5-methyl-2-oxooxazolidin-3-yl)-N-((5-(trifluoromethyl)pyridin-2-yl)methyl)-1H-pyrazolo[4,3-c]quinoline-8-carboxamide |
| 10 | 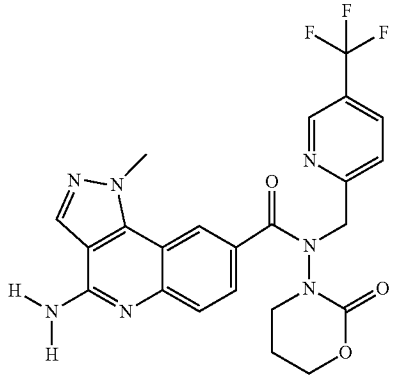 [SMILES: Cn1ncc2c(N)nc3ccc(C(=O)N(Cc4ccc(C(F)(F)F)cn4)N4CCCOC4=O)cc3c21] | 4-amino-1-methyl-N-(2-oxo-1,3-oxazinan-3-yl)-N-((5-(trifluoromethyl)pyridin-2-yl)methyl)-1H-pyrazolo[4,3-c]quinoline-8-carboxamide |

TABLE 1-continued

| Compounds | | |
|---|---|---|
| Example | Structure | Name |
| 11 | 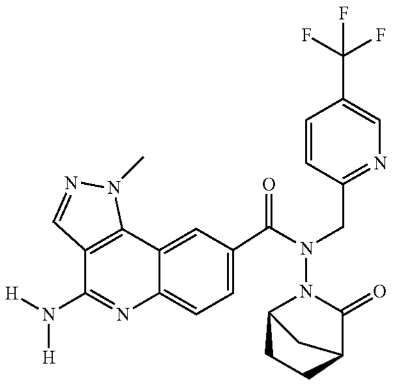 [SMILES: Cn1ncc2c(N)nc3ccc(C(=O)N(Cc4ccc(C(F)(F)F)cn4)N4C(=O)[C@H]5CC[C@@H]4C5)cc3c21] | 4-amino-1-methyl-N-((1R,4S)-3-oxo-2-azabicyclo[2.2.1]heptan-2-yl)-N-((5-(trifluoromethyl)pyridin-2-yl)methyl)-1H-pyrazolo[4,3-c]quinoline-8-carboxamide |
| 12 | 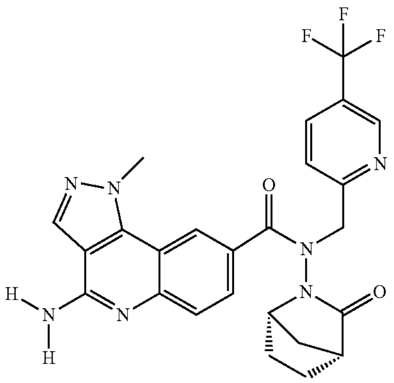 [SMILES: Cn1ncc2c(N)nc3ccc(C(=O)N(Cc4ccc(C(F)(F)F)cn4)N4C(=O)[C@@H]5CC[C@H]4C5)cc3c21] | 4-amino-1-methyl-N-((1S,4R)-3-oxo-2-azabicyclo[2.2.1]heptan-2-yl)-N-((5-(trifluoromethyl)pyridin-2-yl)methyl)-1H-pyrazolo[4,3-c]quinoline-8-carboxamide |
| 13 | 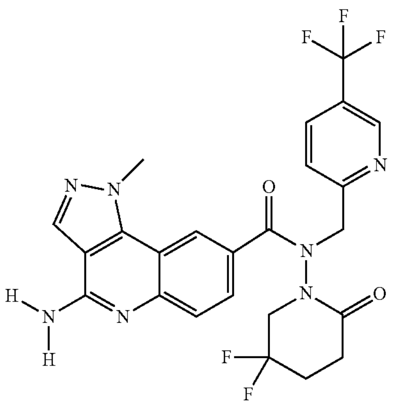 [SMILES: Cn1ncc2c(N)nc3ccc(C(=O)N(Cc4ccc(C(F)(F)F)cn4)N4CC(F)(F)CCC4=O)cc3c21] | 4-amino-N-(5,5-difluoro-2-oxopiperidin-1-yl)-1-methyl-N-((5-(trifluoromethyl)pyridin-2-yl)methyl)-1H-pyrazolo[4,3-c]quinoline-8-carboxamide |

TABLE 1-continued

| Compounds | | |
|---|---|---|
| Example | Structure | Name |
| 14 | 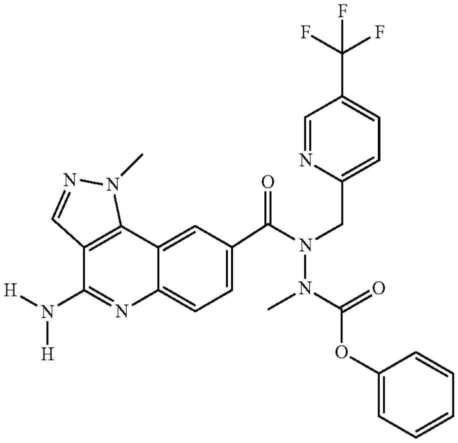 [SMILES: CN(C(=O)Oc1ccccc1)N(Cc1ccc(C(F)(F)F)cn1)C(=O)c1ccc2nc(N)c3cnn(C)c3c2c1] | phenyl 2-(4-amino-1-methyl-1H-pyrazolo[4,3-c]quinoline-8-carbonyl)-1-methyl-2-((5-(trifluoromethyl)pyridin-2-yl)methyl)hydrazine-1-carboxylate |
| 15 | 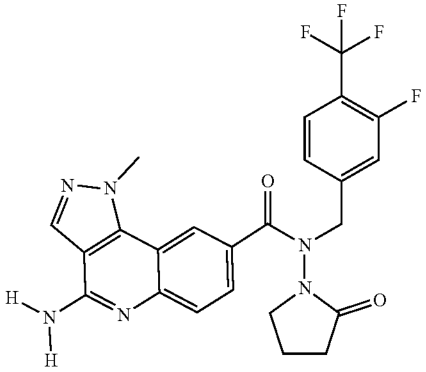 [SMILES: Cn1ncc2c(N)nc3ccc(C(=O)N(Cc4ccc(C(F)(F)F)c(F)c4)N4CCCC4=O)cc3c21] | 4-amino-N-(3-fluoro-4-(trifluoromethyl)benzyl)-1-methyl-N-(2-oxopyrrolidin-1-yl)-1H-pyrazolo[4,3-c]quinoline-8-carboxamide |
| 16 | 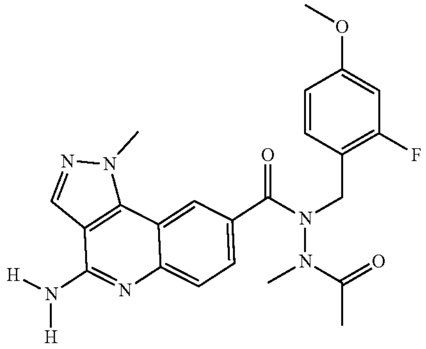 [SMILES: COc1ccc(CN(C(=O)c2ccc3nc(N)c4cnn(C)c4c3c2)N(C)C(C)=O)c(F)c1] | N'-acetyl-4-amino-N-(2-fluoro-4-methoxybenzyl)-N',1-dimethyl-1H-pyrazolo[4,3-c]quinoline-8-carbohydrazide |

TABLE 1-continued

| Compounds | | |
|---|---|---|
| Example | Structure | Name |
| 17 | 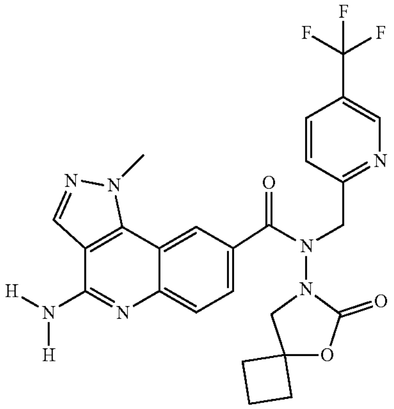 [SMILES: Cn1ncc2c(N)nc3ccc(C(=O)N(Cc4ccc(C(F)(F)F)cn4)N4CC5(CCC5)OC4=O)cc3c21] | 4-amino-1-methyl-N-(6-oxo-5-oxa-7-azaspiro[3.4]octan-7-yl)-N-((5-(trifluoromethyl)pyridin-2-yl)methyl)-1H-pyrazolo[4,3-c]quinoline-8-carboxamide |
| 18 | 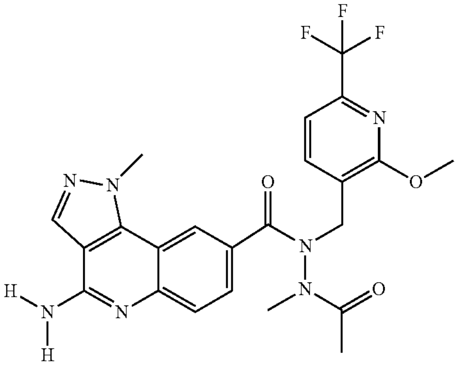 [SMILES: COc1nc(C(F)(F)F)ccc1CN(C(=O)c1ccc2nc(N)c3cnn(C)c3c2c1)N(C)C(C)=O] | N'-acetyl-4-amino-N-((2-methoxy-6-(trifluoromethyl)pyridin-3-yl)methyl)-N',1-dimethyl-1H-pyrazolo[4,3-c]quinoline-8-carbohydrazide |
| 19 | 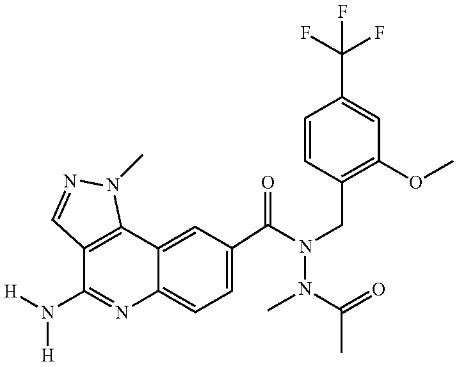 [SMILES: COc1cc(C(F)(F)F)ccc1CN(C(=O)c1ccc2nc(N)c3cnn(C)c3c2c1)N(C)C(C)=O] | N'-acetyl-4-amino-N-(2-methoxy-4-(trifluoromethyl)benzyl)-N',1-dimethyl-1H-pyrazolo[4,3-c]quinoline-8-carbohydrazide |
| 20 | 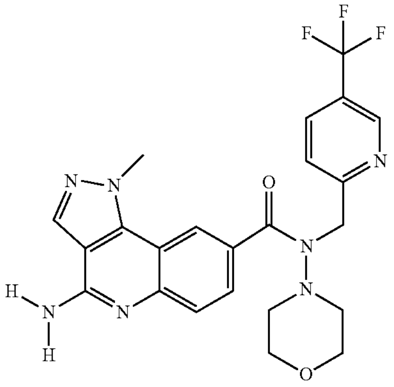 [SMILES: Cn1ncc2c(N)nc3ccc(C(=O)N(Cc4ccc(C(F)(F)F)cn4)N4CCOCC4)cc3c21] | 4-amino-1-methyl-N-morpholino-N-((5-(trifluoromethyl)pyridin-2-yl)methyl)-1H-pyrazolo[4,3-c]quinoline-8-carboxamide |

TABLE 1-continued

| Compounds | | |
|---|---|---|
| Example | Structure | Name |
| 21 | 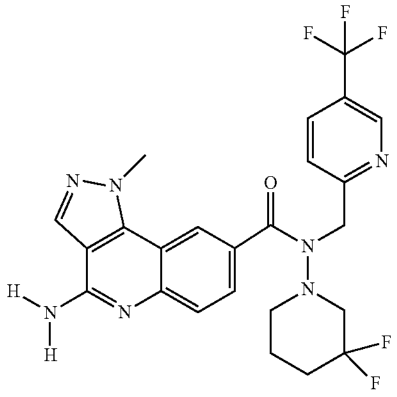 [SMILES: Cn1ncc2c(N)nc3ccc(C(=O)N(Cc4ccc(C(F)(F)F)cn4)N4CCCC(F)(F)C4)cc3c21] | 4-amino-N-(3,3-difluoropiperidin-1-yl)-1-methyl-N-((5-(trifluoromethyl)pyridin-2-yl)methyl)-1H-pyrazolo[4,3-c]quinoline-8-carboxamide |
| 22 | 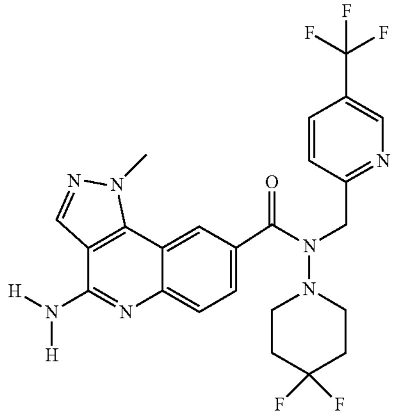 [SMILES: Cn1ncc2c(N)nc3ccc(C(=O)N(Cc4ccc(C(F)(F)F)cn4)N4CCC(F)(F)CC4)cc3c21] | 4-amino-N-(4,4-difluoropiperidin-1-yl)-1-methyl-N-((5-(trifluoromethyl)pyridin-2-yl)methyl)-1H-pyrazolo[4,3-c]quinoline-8-carboxamide |
| 23 | 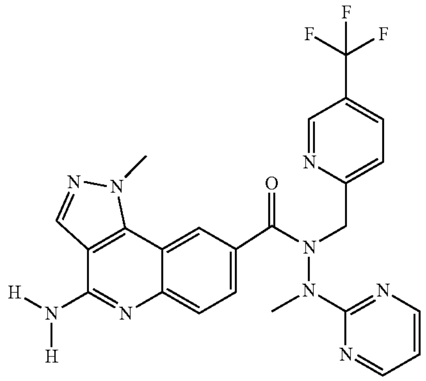 [SMILES: CN(c1ncccn1)N(Cc1ccc(C(F)(F)F)cn1)C(=O)c1ccc2nc(N)c3cnn(C)c3c2c1] | 4-amino-N',1-dimethyl-N'-(pyrimidin-2-yl)-N-((5-(trifluoromethyl)pyridin-2-yl)methyl)-1H-pyrazolo[4,3-c]quinoline-8-carbohydrazide |
| 24 | 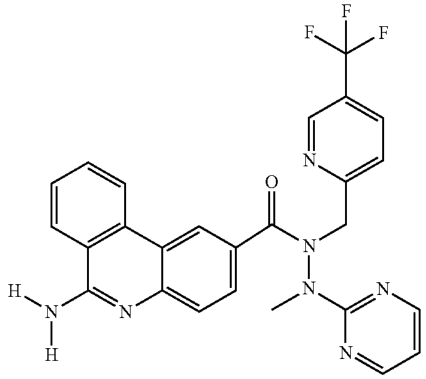 [SMILES: CN(c1ncccn1)N(Cc1ccc(C(F)(F)F)cn1)C(=O)c1ccc2nc(N)c3ccccc3c2c1] | 6-amino-N'-methyl-N'-(pyrimidin-2-yl)-N-((5-(trifluoromethyl)pyridin-2-yl)methyl)phenanthridine-2-carbohydrazide |

TABLE 1-continued

| Compounds | | |
|---|---|---|
| Example | Structure | Name |
| 25 | 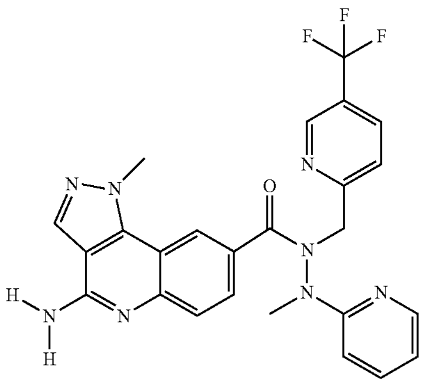 [SMILES: CN(c1ccccn1)N(Cc1ccc(C(F)(F)F)cn1)C(=O)c1ccc2nc(N)c3cnn(C)c3c2c1] | 4-amino-N',1-dimethyl-N'-(pyridin-2-yl)-N-((5-(trifluoromethyl)pyridin-2-yl)methyl)-1H-pyrazolo[4,3-c]quinoline-8-carbohydrazide |
| 26 | 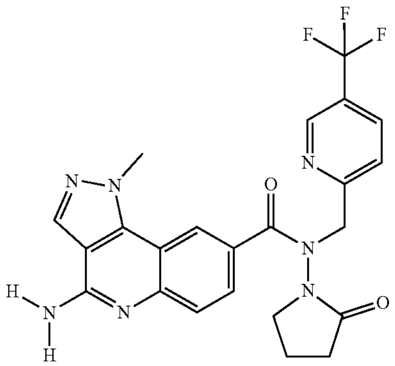 [SMILES: Cn1ncc2c(N)nc3ccc(C(=O)N(Cc4ccc(C(F)(F)F)cn4)N4CCCC4=O)cc3c21] | 4-amino-1-methyl-N-(2-oxopyrrolidin-1-yl)-N-((5-(trifluoromethyl)pyridin-2-yl)methyl)-1H-pyrazolo[4,3-c]quinoline-8-carboxamide |
| 27 | 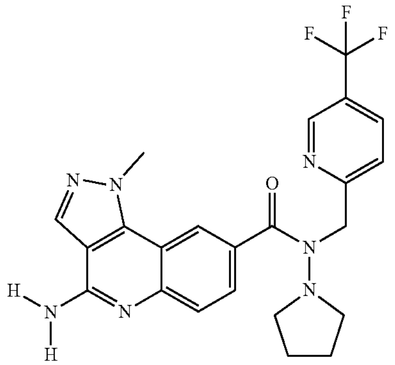 [SMILES: Cn1ncc2c(N)nc3ccc(C(=O)N(Cc4ccc(C(F)(F)F)cn4)N4CCCC4)cc3c21] | 4-amino-1-methyl-N-(pyrrolidin-1-yl)-N-((5-(trifluoromethyl)pyridin-2-yl)methyl)-1H-pyrazolo[4,3-c]quinoline-8-carboxamide |
| 28 | 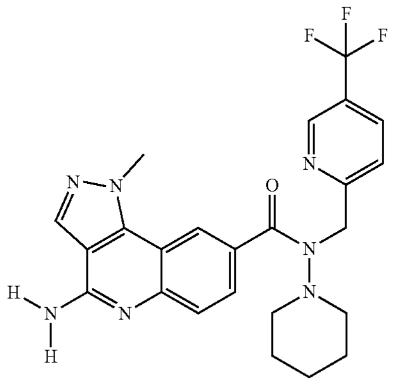 [SMILES: Cn1ncc2c(N)nc3ccc(C(=O)N(Cc4ccc(C(F)(F)F)cn4)N4CCCCC4)cc3c21] | 4-amino-1-methyl-N-(piperidin-1-yl)-N-((5-(trifluoromethyl)pyridin-2-yl)methyl)-1H-pyrazolo[4,3-c]quinoline-8-carboxamide |

TABLE 1-continued

| Compounds | | |
|---|---|---|
| Example | Structure | Name |
| 29 | 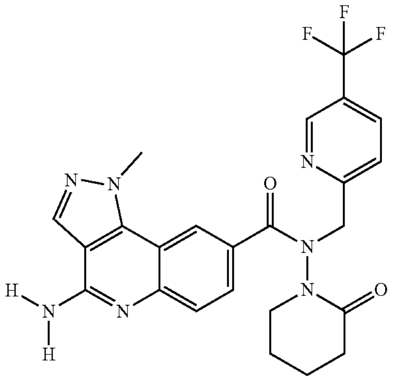 [SMILES: Cn1ncc2c(N)nc3ccc(C(=O)N(Cc4ccc(C(F)(F)F)cn4)N4CCCCC4=O)cc3c21] | 4-amino-1-methyl-N-(2-oxopiperidin-1-yl)-N-((5-(trifluoromethyl)pyridin-2-yl)methyl)-1H-pyrazolo[4,3-c]quinoline-8-carboxamide |
| 30 | 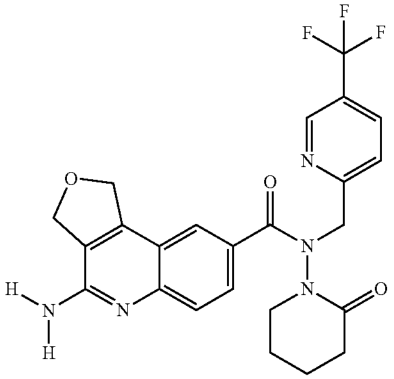 [SMILES: Nc1nc2ccc(C(=O)N(Cc3ccc(C(F)(F)F)cn3)N3CCCCC3=O)cc2c2c1COC2] | 4-amino-N-(2-oxopiperidin-1-yl)-N-((5-(trifluoromethyl)pyridin-2-yl)methyl)-1,3-dihydrofuro[3,4-c]quinoline-8-carboxamide |
| 31 | 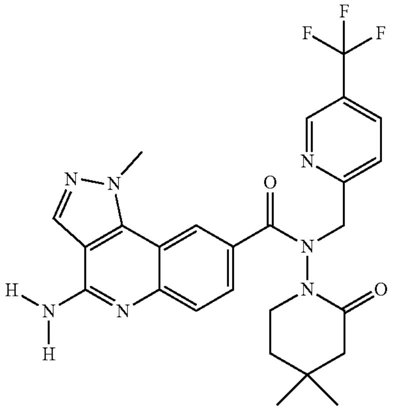 [SMILES: Cn1ncc2c(N)nc3ccc(C(=O)N(Cc4ccc(C(F)(F)F)cn4)N4CCC(C)(C)CC4=O)cc3c21] | 4-amino-N-(4,4-dimethyl-2-oxopiperidin-1-yl)-1-methyl-N-((5-(trifluoromethyl)pyridin-2-yl)methyl)-1H-pyrazolo[4,3-c]quinoline-8-carboxamide |
| 32 | 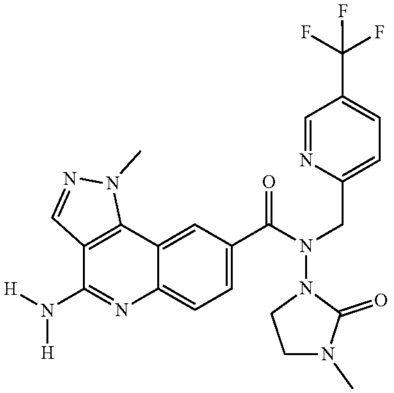 [SMILES: CN1CCN(N(Cc2ccc(C(F)(F)F)cn2)C(=O)c2ccc3nc(N)c4cnn(C)c4c3c2)C1=O] | 4-amino-1-methyl-N-(3-methyl-2-oxoimidazolidin-1-yl)-N-((5-(trifluoromethyl)pyridin-2-yl)methyl)-1H-pyrazolo[4,3-c]quinoline-8-carboxamide |

TABLE 1-continued

| Compounds | | |
|---|---|---|
| Example | Structure | Name |
| 33 | 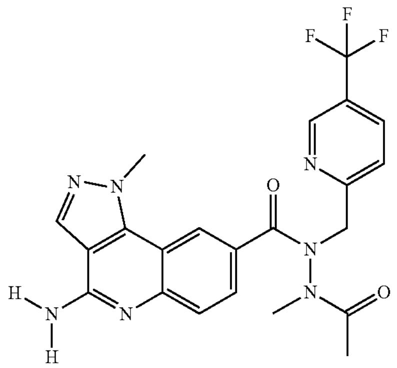 | N'-acetyl-4-amino-N',1-dimethyl-N-((5-(trifluoromethyl)pyridin-2-yl)methyl)-1H-pyrazolo[4,3-c]quinoline-8-carbohydrazide |
| 34 | 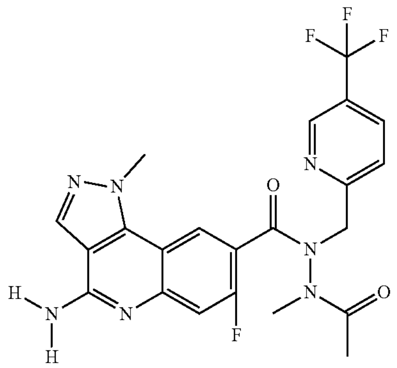 [SMILES: CC(=O)N(C)N(Cc1ccc(C(F)(F)F)cn1)C(=O)c1cc2c(cc1F)nc(N)c1cnn(C)c12] | N'-acetyl-4-amino-7-fluoro-N',1-dimethyl-N-((5-(trifluoromethyl)pyridin-2-yl)methyl)-1H-pyrazolo[4,3-c]quinoline-8-carbohydrazide |
| 35 | 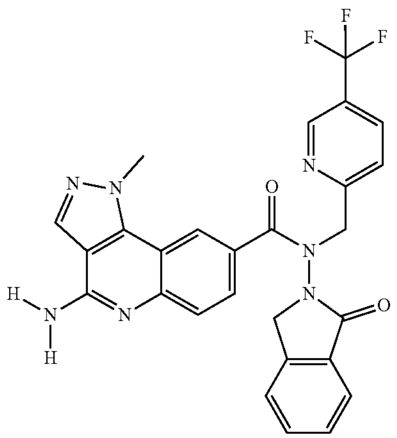 [SMILES: Cn1ncc2c(N)nc3ccc(C(=O)N(Cc4ccc(C(F)(F)F)cn4)N4Cc5ccccc5C4=O)cc3c21] | 4-amino-1-methyl-N-(1-oxoisoindolin-2-yl)-N-((5-(trifluoromethyl)pyridin-2-yl)methyl)-1H-pyrazolo[4,3-c]quinoline-8-carboxamide |

TABLE 1-continued

| Compounds | | |
|---|---|---|
| Example | Structure | Name |
| 36 | 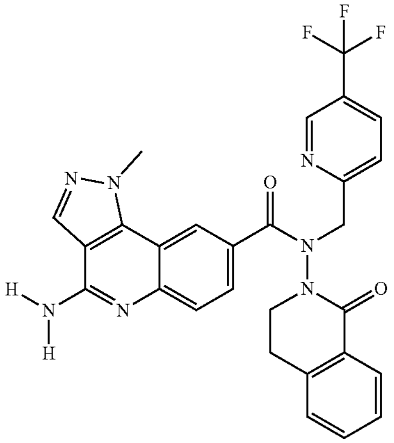 [SMILES: Cn1ncc2c(N)nc3ccc(C(=O)N(Cc4ccc(C(F)(F)F)cn4)N4CCc5ccccc5C4=O)cc3c21] | 4-amino-1-methyl-N-(1-oxo-3,4-dihydroisoquinolin-2(1H)-yl)-N-((5-(trifluoromethyl)pyridin-2-yl)methyl)-1H-pyrazolo[4,3-c]quinoline-8-carboxamide |
| 37 | 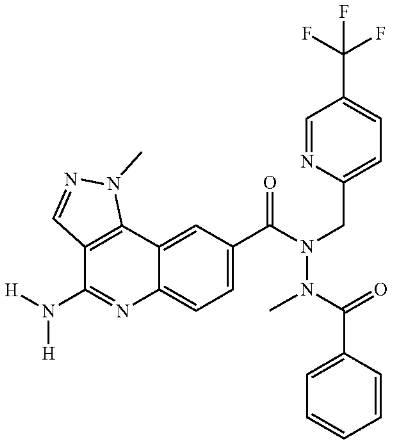 [SMILES: CN(C(=O)c1ccccc1)N(Cc1ccc(C(F)(F)F)cn1)C(=O)c1ccc2nc(N)c3cnn(C)c3c2c1] | 4-amino-N'-benzoyl-N',1-dimethyl-N-((5-(trifluoromethyl)pyridin-2-yl)methyl)-1H-pyrazolo[4,3-c]quinoline-8-carbohydrazide |
| 38 | 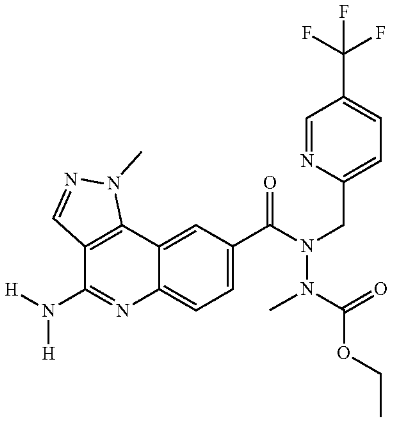 | ethyl 2-(4-amino-1-methyl-1H-pyrazolo[4,3-c]quinoline-8-carbonyl)-1-methyl-2-((5-(trifluoromethyl)pyridin-2-yl)methyl)hydrazine-1-carboxylate |

TABLE 1-continued

| Compounds | | |
|---|---|---|
| Example | Structure | Name |
| 39 | 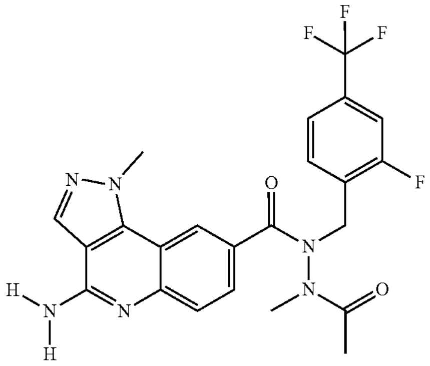 [SMILES: CC(=O)N(C)N(Cc1ccc(C(F)(F)F)cc1F)C(=O)c1ccc2nc(N)c3cnn(C)c3c2c1] | N'-acetyl-4-amino-N-(2-fluoro-4-(trifluoromethyl)benzyl)-N',1-dimethyl-1H-pyrazolo[4,3-c]quinoline-8-carbohydrazide |
| 40 | 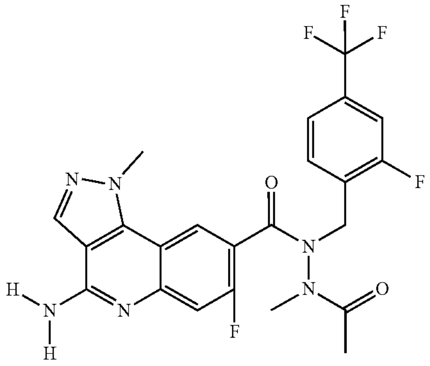 [SMILES: CC(=O)N(C)N(Cc1ccc(C(F)(F)F)cc1F)C(=O)c1cc2c(cc1F)nc(N)c1cnn(C)c12] | N'-acetyl-4-amino-7-fluoro-N-(2-fluoro-4-(trifluoromethyl)benzyl)-N',1-dimethyl-1H-pyrazolo[4,3-c]quinoline-8-carbohydrazide |
| 41 | 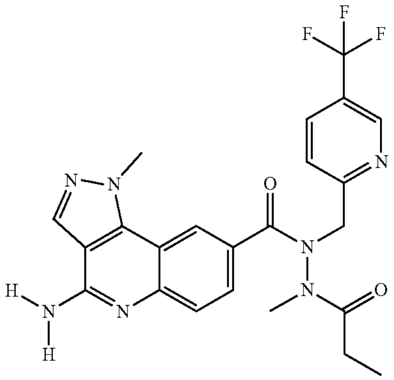 [SMILES: CCC(=O)N(C)N(Cc1ccc(C(F)(F)F)cn1)C(=O)c1ccc2nc(N)c3cnn(C)c3c2c1] | 4-amino-N',1-dimethyl-N'-propionyl-N-((5-(trifluoromethyl)pyridin-2-yl)methyl)-1H-pyrazolo[4,3-c]quinoline-8-carbohydrazide |
| 42 | 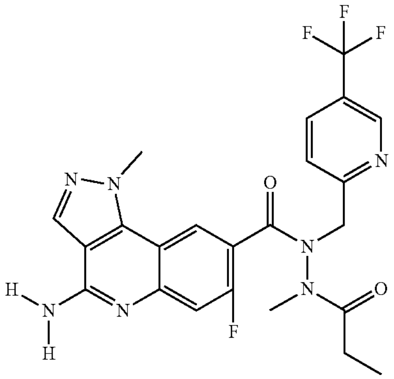 [SMILES: CCC(=O)N(C)N(Cc1ccc(C(F)(F)F)cn1)C(=O)c1cc2c(cc1F)nc(N)c1cnn(C)c12] | 4-amino-7-fluoro-N',1-dimethyl-N'-propionyl-N-((5-(trifluoromethyl)pyridin-2-yl)methyl)-1H-pyrazolo[4,3-c]quinoline-8-carbohydrazide |

TABLE 1-continued

| Compounds | | |
|---|---|---|
| Example | Structure | Name |
| 43 | 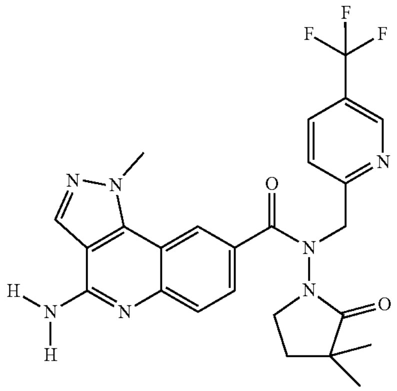 [SMILES: Cn1ncc2c(N)nc3ccc(C(=O)N(Cc4ccc(C(F)(F)F)cn4)N4CCC(C)(C)C4=O)cc3c21] | 4-amino-N-(3,3-dimethyl-2-oxopyrrolidin-1-yl)-1-methyl-N-((5-(trifluoromethyl)pyridin-2-yl)methyl)-1H-pyrazolo[4,3-c]quinoline-8-carboxamide |
| 44 | 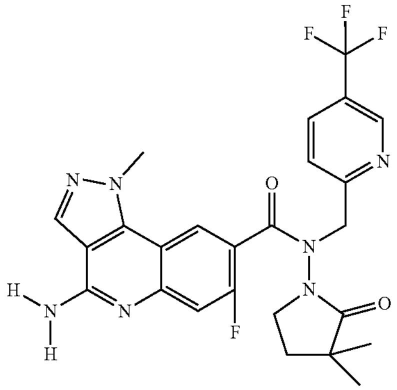 [SMILES: Cn1ncc2c(N)nc3cc(F)c(C(=O)N(Cc4ccc(C(F)(F)F)cn4)N4CCC(C)(C)C4=O)cc3c21] | 4-amino-N-(3,3-dimethyl-2-oxopyrrolidin-1-yl)-7-fluoro-1-methyl-N-((5-(trifluoromethyl)pyridin-2-yl)methyl)-1H-pyrazolo[4,3-c]quinoline-8-carboxamide |
| 45 | 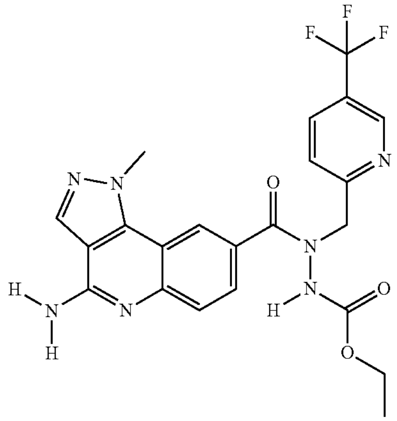 [SMILES: CCOC(=O)NN(Cc1ccc(C(F)(F)F)cn1)C(=O)c1ccc2nc(N)c3cnn(C)c3c2c1] | ethyl 2-(4-amino-1-methyl-1H-pyrazolo[4,3-c]quinoline-8-carbonyl)-2-((5-(trifluoromethyl)pyridin-2-yl)methyl)hydrazine-1-carboxylate |

TABLE 1-continued

| Compounds | | |
|---|---|---|
| Example | Structure | Name |
| 46 | 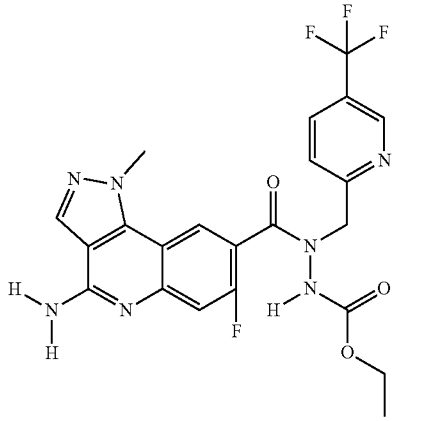 [SMILES: CCOC(=O)NN(Cc1ccc(C(F)(F)F)cn1)C(=O)c1cc2c(cc1F)nc(N)c1cnn(C)c12] | ethyl 2-(4-amino-7-fluoro-1-methyl-1H-pyrazolo[4,3-c]quinoline-8-carbonyl)-2-((5-(trifluoromethyl)pyridin-2-yl)methyl)hydrazine-1-carboxylate |
| 47 | 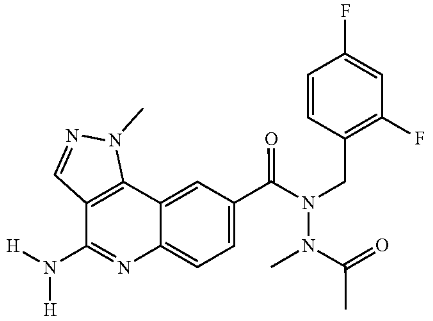 [SMILES: CC(=O)N(C)N(Cc1ccc(F)cc1F)C(=O)c1ccc2nc(N)c3cnn(C)c3c2c1] | N'-acetyl-4-amino-N-(2,4-difluorobenzyl)-N',1-dimethyl-1H-pyrazolo[4,3-c]quinoline-8-carbohydrazide |
| 48 | 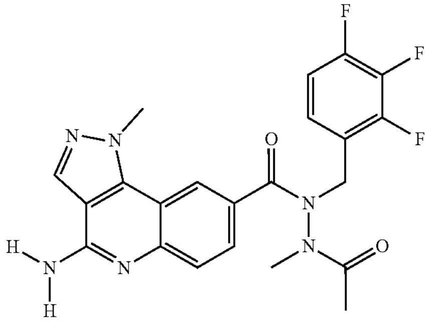 [SMILES: CC(=O)N(C)N(Cc1ccc(F)c(F)c1F)C(=O)c1ccc2nc(N)c3cnn(C)c3c2c1] | N'-acetyl-4-amino-N',1-dimethyl-N-(2,3,4-trifluorobenzyl)-1H-pyrazolo[4,3-c]quinoline-8-carbohydrazide |
| 49 | 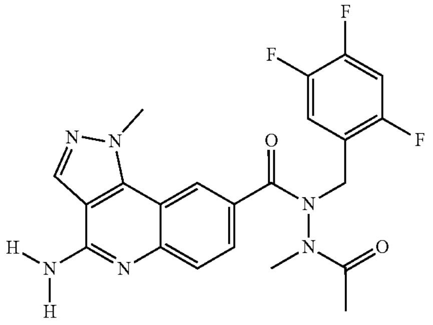 [SMILES: CC(=O)N(C)N(Cc1cc(F)c(F)cc1F)C(=O)c1ccc2nc(N)c3cnn(C)c3c2c1] | N'-acetyl-4-amino-N',1-dimethyl-N-(2,4,5-trifluorobenzyl)-1H-pyrazolo[4,3-c]quinoline-8-carbohydrazide |

TABLE 1-continued

| Compounds | | |
|---|---|---|
| Example | Structure | Name |
| 50 | 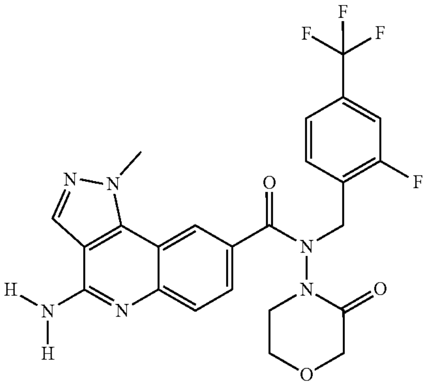 [SMILES: Cn1ncc2c(N)nc3ccc(C(=O)N(Cc4ccc(C(F)(F)F)cc4F)N4CCOCC4=O)cc3c21] | 4-amino-N-(2-fluoro-4-(trifluoromethyl)benzyl)-1-methyl-N-(3-oxomorpholino)-1H-pyrazolo[4,3-c]quinoline-8-carboxamide |
| 51 | 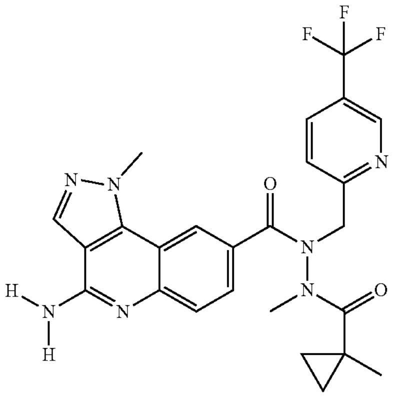 [SMILES: CN(C(=O)C1(C)CC1)N(Cc1ccc(C(F)(F)F)cn1)C(=O)c1ccc2nc(N)c3cnn(C)c3c2c1] | 4-amino-N',1-dimethyl-N'-(1-methylcyclopropane-1-carbonyl)-N-((5-(trifluoromethyl)pyridin-2-yl)methyl)-1H-pyrazolo[4,3-c]quinoline-8-carbohydrazide |
| 52 | 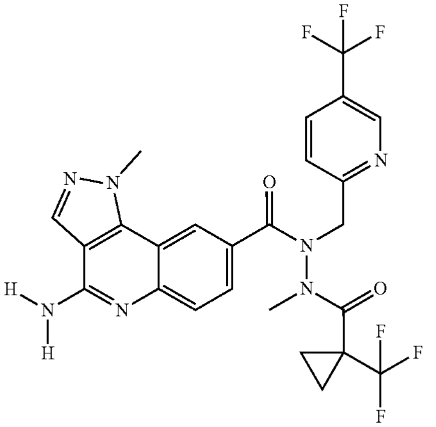 [SMILES: CN(C(=O)C1(C(F)(F)F)CC1)N(Cc1ccc(C(F)(F)F)cn1)C(=O)c1ccc2nc(N)c3cnn(C)c3c2c1] | 4-amino-N',1-dimethyl-N'-(1-(trifluoromethyl)cyclopropane-1-carbonyl)-N-((5-(trifluoromethyl)pyridin-2-yl)methyl)-1H-pyrazolo[4,3-c]quinoline-8-carbohydrazide |
| 53 | 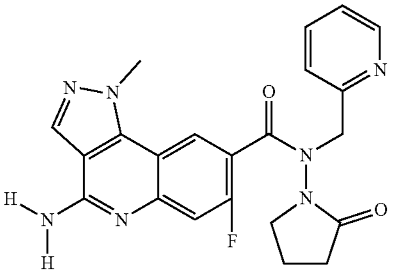 [SMILES: Cn1ncc2c(N)nc3cc(F)c(C(=O)N(Cc4ccccn4)N4CCCC4=O)cc3c21] | 4-amino-7-fluoro-1-methyl-N-(2-oxopyrrolidin-1-yl)-N-(pyridin-2-ylmethyl)-1H-pyrazolo[4,3-c]quinoline-8-carboxamide |

TABLE 1-continued

| Compounds | | |
|---|---|---|
| Example | Structure | Name |
| 54 | 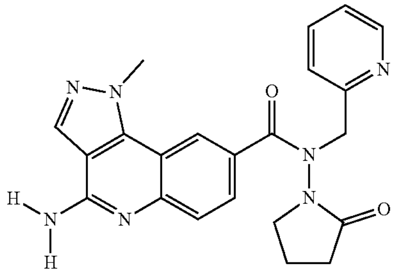 [SMILES: Cn1ncc2c(N)nc3ccc(C(=O)N(Cc4ccccn4)N4CCCC4=O)cc3c21] | 4-amino-1-methyl-N-(2-oxopyrrolidin-1-yl)-N-(pyridin-2-ylmethyl)-1H-pyrazolo[4,3-c]quinoline-8-carboxamide |
| 55 | 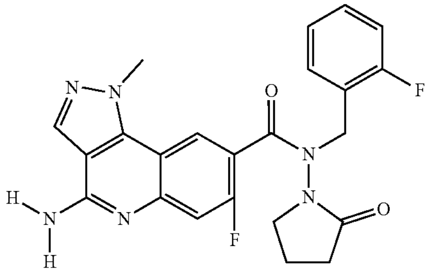 | 4-amino-7-fluoro-N-(2-fluorobenzyl)-1-methyl-N-(2-oxopyrrolidin-1-yl)-1H-pyrazolo[4,3-c]quinoline-8-carboxamide |
| 56 | 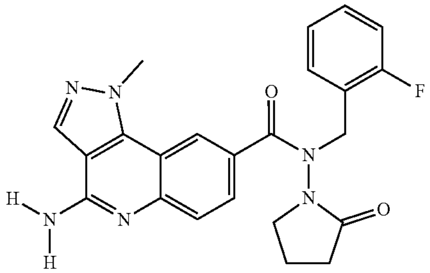 [SMILES: Cn1ncc2c(N)nc3ccc(C(=O)N(Cc4ccccc4F)N4CCCC4=O)cc3c21] | 4-amino-N-(2-fluorobenzyl)-1-methyl-N-(2-oxopyrrolidin-1-yl)-1H-pyrazolo[4,3-c]quinoline-8-carboxamide |
| 57 | 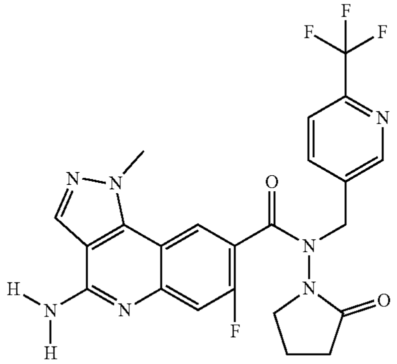 | 4-amino-7-fluoro-1-methyl-N-(2-oxopyrrolidin-1-yl)-N-((6-(trifluoromethyl)pyridin-3-yl)methyl)-1H-pyrazolo[4,3-c]quinoline-8-carboxamide |

TABLE 1-continued

| Compounds | | |
|---|---|---|
| Example | Structure | Name |
| 58 | 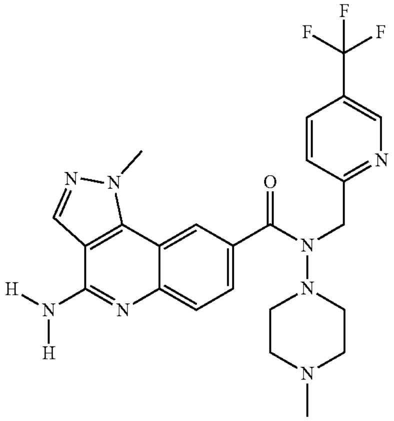 [SMILES: CN1CCN(N(Cc2ccc(C(F)(F)F)cn2)C(=O)c2ccc3nc(N)c4cnn(C)c4c3c2)CC1] | 4-amino-1-methyl-N-(4-methylpiperazin-1-yl)-N-((5-(trifluoromethyl)pyridin-2-yl)methyl)-1H-pyrazolo[4,3-c]quinoline-8-carboxamide |
| 59 | 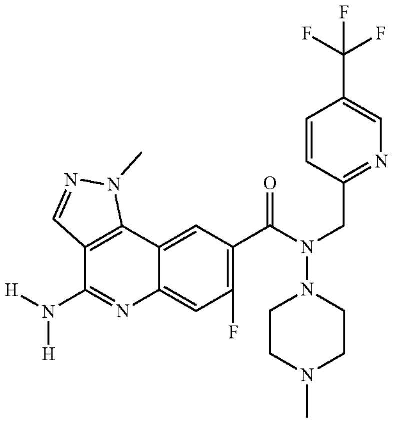 [SMILES: CN1CCN(N(Cc2ccc(C(F)(F)F)cn2)C(=O)c2cc3c(cc2F)nc(N)c2cnn(C)c23)CC1] | 4-amino-7-fluoro-1-methyl-N-(4-methylpiperazin-1-yl)-N-((5-(trifluoromethyl)pyridin-2-yl)methyl)-1H-pyrazolo[4,3-c]quinoline-8-carboxamide |
| 60 | 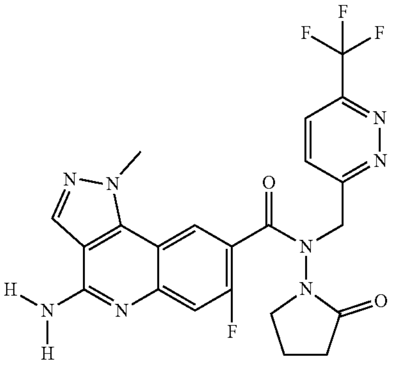 [SMILES: Cn1ncc2c(N)nc3cc(F)c(C(=O)N(Cc4ccc(C(F)(F)F)nn4)N4CCCC4=O)cc3c21] | 4-amino-7-fluoro-1-methyl-N-(2-oxopyrrolidin-1-yl)-N-((6-(trifluoromethyl)pyridazin-3-yl)methyl)-1H-pyrazolo[4,3-c]quinoline-8-carboxamide |

TABLE 1-continued

| Compounds | | |
|---|---|---|
| Example | Structure | Name |
| 61 | 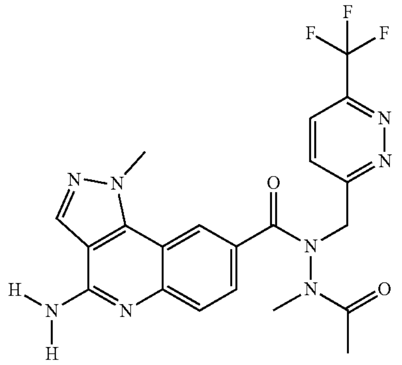 [SMILES: CC(=O)N(C)N(Cc1ccc(C(F)(F)F)nn1)C(=O)c1ccc2nc(N)c3cnn(C)c3c2c1] | N'-acetyl-4-amino-N',1-dimethyl-N-((6-(trifluoromethyl)pyridazin-3-yl)methyl)-1H-pyrazolo[4,3-c]quinoline-8-carbohydrazide |
| 62 | 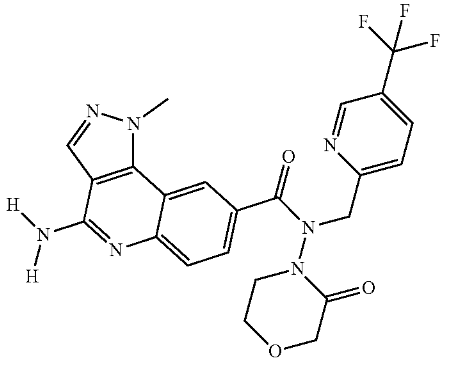 [SMILES: Cn1ncc2c(N)nc3ccc(C(=O)N(Cc4ccc(C(F)(F)F)cn4)N4CCOCC4=O)cc3c21] | 4-amino-1-methyl-N-(3-oxomorpholino)-N-((5-(trifluoromethyl)pyridin-2-yl)methyl)-1H-pyrazolo[4,3-c]quinoline-8-carboxamide |
| 63 | 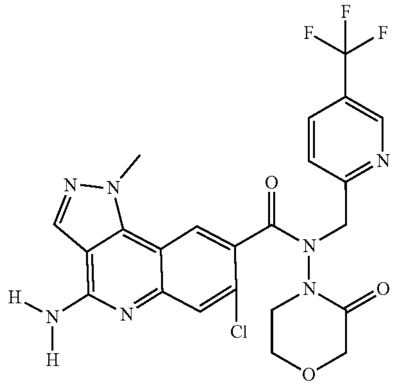 [SMILES: Cn1ncc2c(N)nc3cc(Cl)c(C(=O)N(Cc4ccc(C(F)(F)F)cn4)N4CCOCC4=O)cc3c21] | 4-amino-7-chloro-1-methyl-N-(3-oxomorpholino)-N-((5-(trifluoromethyl)pyridin-2-yl)methyl)-1H-pyrazolo[4,3-c]quinoline-8-carboxamide |
| 64 | 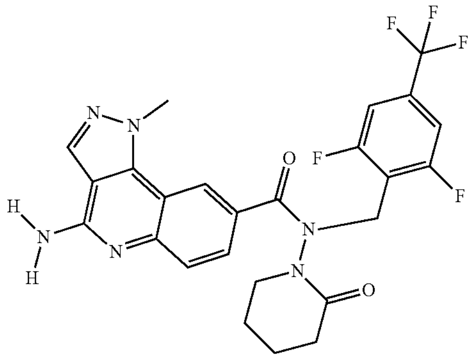 [SMILES: Cn1ncc2c(N)nc3ccc(C(=O)N(Cc4c(F)cc(C(F)(F)F)cc4F)N4CCCCC4=O)cc3c21] | 4-amino-N-(2,6-difluoro-4-(trifluoromethyl)benzyl)-1-methyl-N-(2-oxopiperidin-1-yl)-1H-pyrazolo[4,3-c]quinoline-8-carboxamide |

TABLE 1-continued

| Compounds | | |
|---|---|---|
| Example | Structure | Name |
| 65 | 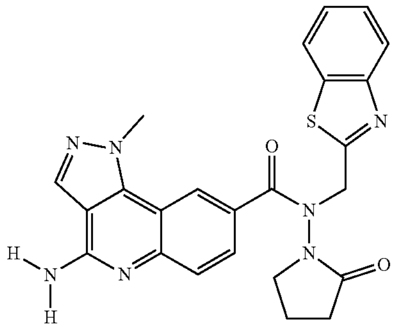 [SMILES: Cn1ncc2c(N)nc3ccc(C(=O)N(Cc4nc5ccccc5s4)N4CCCC4=O)cc3c21] | 4-amino-N-(benzo[d]thiazol-2-ylmethyl)-1-methyl-N-(2-oxopyrrolidin-1-yl)-1H-pyrazolo[4,3-c]quinoline-8-carboxamide |
| 66 | 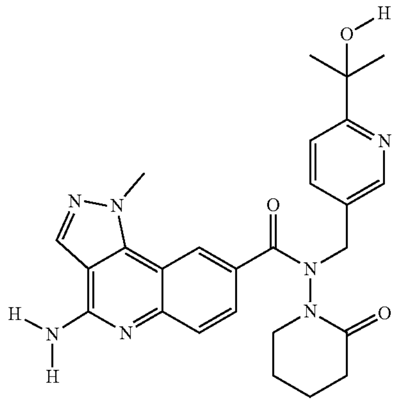 [SMILES: Cn1ncc2c(N)nc3ccc(C(=O)N(Cc4ccc(C(C)(C)O)nc4)N4CCCCC4=O)cc3c21] | 4-amino-N-((6-(2-hydroxypropan-2-yl)pyridin-3-yl)methyl)-1-methyl-N-(2-oxopiperidin-1-yl)-1H-pyrazolo[4,3-c]quinoline-8-carboxamide |
| 67 | 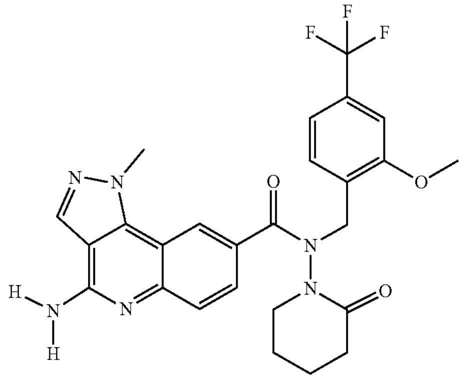 [SMILES: COc1cc(C(F)(F)F)ccc1CN(C(=O)c1ccc2nc(N)c3cnn(C)c3c2c1)N1CCCCC1=O] | 4-amino-N-(2-methoxy-4-(trifluoromethyl)benzyl)-1-methyl-N-(2-oxopiperidin-1-yl)-1H-pyrazolo[4,3-c]quinoline-8-carboxamide |
| 68 | 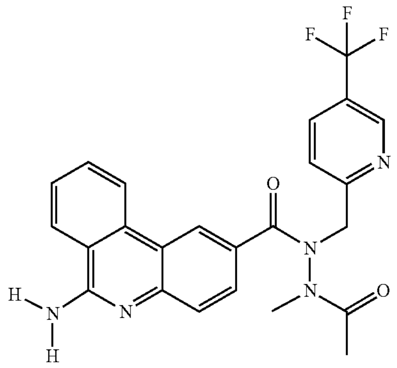 | N'-acetyl-6-amino-N'-methyl-N-((5-(trifluoromethyl)pyridin-2-yl)methyl)phenanthridine-2-carboxhydrazide |

TABLE 1-continued

| Compounds | | |
|---|---|---|
| Example | Structure | Name |
| 69 | 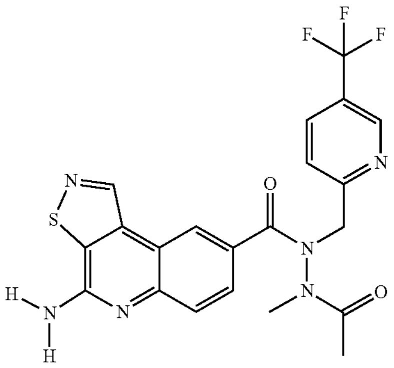 [SMILES: CC(=O)N(C)N(Cc1ccc(C(F)(F)F)cn1)C(=O)c1ccc2nc(N)c3sncc3c2c1] | N'-acetyl-4-amino-N'-methyl-N-((5-(trifluoromethyl)pyridin-2-yl)methyl)isothiazolo[5,4-c]quinoline-8-carbohydrazide |
| 70 | 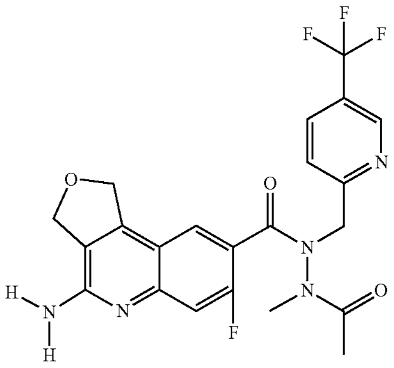 [SMILES: CC(=O)N(C)N(Cc1ccc(C(F)(F)F)cn1)C(=O)c1cc2c3c(c(N)nc2cc1F)COC3] | N'-acetyl-4-amino-7-fluoro-N'-methyl-N-((5-(trifluoromethyl)pyridin-2-yl)methyl)-1,3-dihydrofuro[3,4-c]quinoline-8-carbohydrazide |
| 71 | 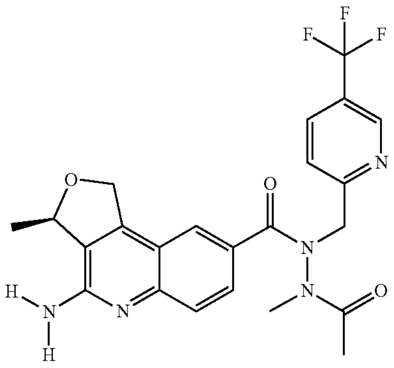 [SMILES: CC(=O)N(C)N(Cc1ccc(C(F)(F)F)cn1)C(=O)c1ccc2nc(N)c3c(c2c1)CO[C@@H]3C] | (R)-N'-acetyl-4-amino-N',3-dimethyl-N-((5-(trifluoromethyl)pyridin-2-yl)methyl)-1,3-dihydrofuro[3,4-c]quinoline-8-carbohydrazide |
| 72 | 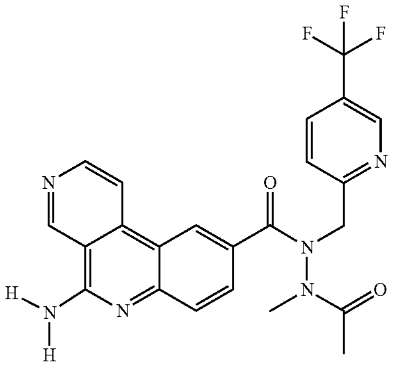 [SMILES: CC(=O)N(C)N(Cc1ccc(C(F)(F)F)cn1)C(=O)c1ccc2nc(N)c3cnccc3c2c1] | N'-acetyl-5-amino-N'-methyl-N-((5-(trifluoromethyl)pyridin-2-yl)methyl)benzo[c][2,7]naphthyridine-9-carbohydrazide |

TABLE 1-continued

| Compounds | | |
|---|---|---|
| Example | Structure | Name |
| 73 | 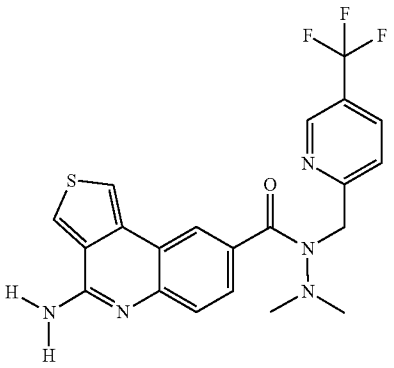 [SMILES: CN(C)N(Cc1ccc(C(F)(F)F)cn1)C(=O)c1ccc2nc(N)c3cscc3c2c1] | 4-amino-N',N'-dimethyl-N-((5-(trifluoromethyl)pyridin-2-yl)methyl)thieno[3,4-c]quinoline-8-carbohydrazide |
| 74 | 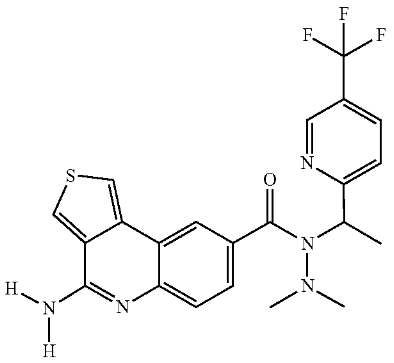 [SMILES: CC(c1ccc(C(F)(F)F)cn1)N(C(=O)c1ccc2nc(N)c3cscc3c2c1)N(C)C] | 4-amino-N',N'-dimethyl-N-(1-(5-(trifluoromethyl)pyridin-2-yl)ethyl)thieno[3,4-c]quinoline-8-carbohydrazide |
| 75 | 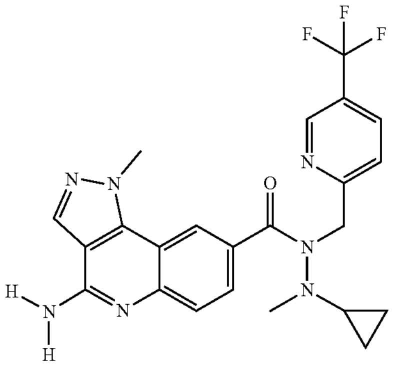 [SMILES: CN(C1CC1)N(Cc1ccc(C(F)(F)F)cn1)C(=O)c1ccc2nc(N)c3cnn(C)c3c2c1] | 4-amino-N'-cyclopropyl-N',1-dimethyl-N-((5-(trifluoromethyl)pyridin-2-yl)methyl)-1H-pyrazolo[4,3-c]quinoline-8-carbohydrazide |
| 76 | 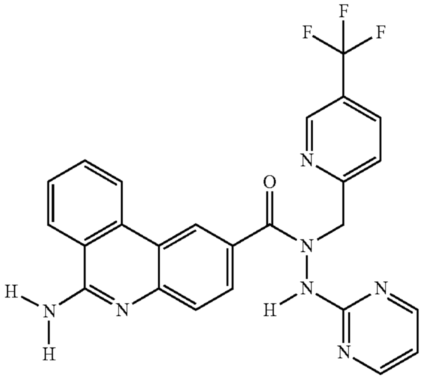 [SMILES: Nc1nc2ccc(C(=O)N(Cc3ccc(C(F)(F)F)cn3)Nc3ncccn3)cc2c2ccccc12] | 6-amino-N'-(pyrimidin-2-yl)-N-((5-(trifluoromethyl)pyridin-2-yl)methyl)phenanthridine-2-carbohydrazide |

TABLE 1-continued

| Compounds | | |
|---|---|---|
| Example | Structure | Name |
| 77 | 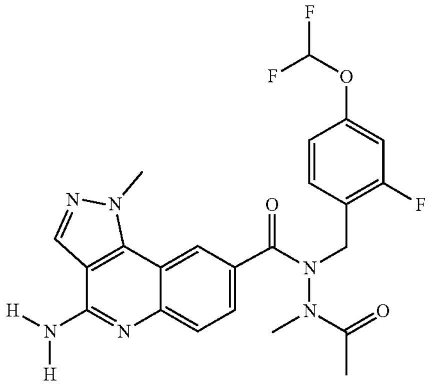 [SMILES: CC(=O)N(C)N(Cc1ccc(OC(F)F)cc1F)C(=O)c1ccc2nc(N)c3cnn(C)c3c2c1] | N'-acetyl-4-amino-N-(4-(difluoromethoxy)-2-fluorobenzyl)-N',1-dimethyl-1H-pyrazolo[4,3-c]quinoline-8-carbohydrazide |
| 78 | 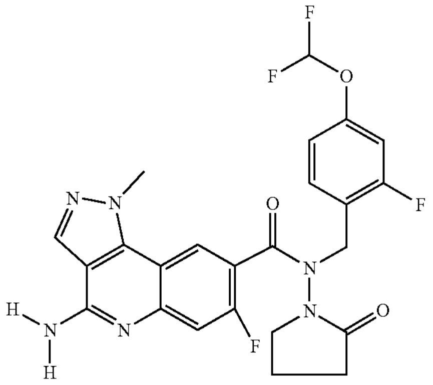 [SMILES: Cn1ncc2c(N)nc3cc(F)c(C(=O)N(Cc4ccc(OC(F)F)cc4F)N4CCCC4=O)cc3c21] | 4-amino-N-(4-(difluoromethoxy)-2-fluorobenzyl)-7-fluoro-1-methyl-N-(2-oxopyrrolidin-1-yl)-1H-pyrazolo[4,3-c]quinoline-8-carboxamide |
| 79 | 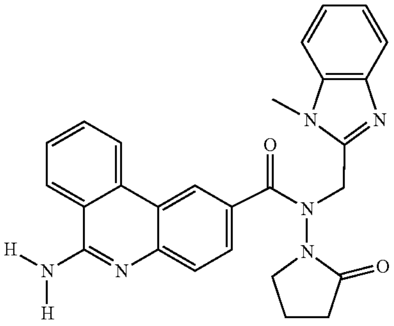 [SMILES: Cn1c(CN(C(=O)c2ccc3nc(N)c4ccccc4c3c2)N2CCCC2=O)nc2ccccc21] | 6-amino-N-((1-methyl-1H-benzo[d]imidazol-2-yl)methyl)-N-(2-oxopyrrolidin-1-yl)phenanthridine-2-carboxamide |
| 80 | 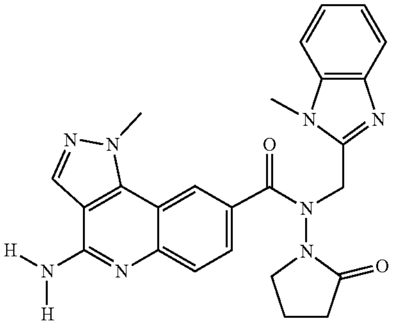 [SMILES: Cn1ncc2c(N)nc3ccc(C(=O)N(Cc4nc5ccccc5n4C)N4CCCC4=O)cc3c21] | 4-amino-1-methyl-N-((1-methyl-1H-benzo[d]imidazol-2-yl)methyl)-N-(2-oxopyrrolidin-1-yl)-1H-pyrazolo[4,3-c]quinoline-8-carboxamide |

TABLE 1-continued

| Compounds | | |
|---|---|---|
| Example | Structure | Name |
| 81 | 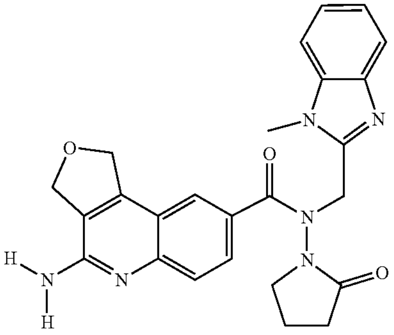 [SMILES: Cn1c(CN(C(=O)c2ccc3nc(N)c4c(c3c2)COC4)N2CCCC2=O)nc2ccccc21] | 4-amino-N-((1-methyl-1H-benzo[d]imidazol-2-yl)methyl)-N-(2-oxopyrrolidin-1-yl)-1,3-dihydrofuro[3,4-c]quinoline-8-carboxamide |
| 83 | 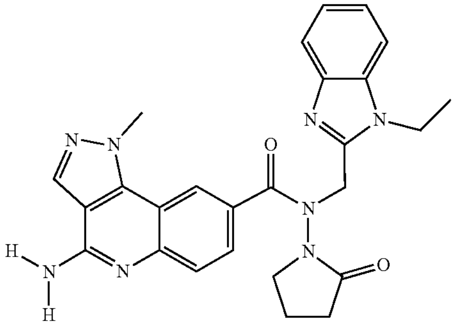 [SMILES: CCn1c(CN(C(=O)c2ccc3nc(N)c4cnn(C)c4c3c2)N2CCCC2=O)nc2ccccc21] | 4-amino-N-((1-ethyl-1H-benzo[d]imidazol-2-yl)methyl)-1-methyl-N-(2-oxopyrrolidin-1-yl)-1H-pyrazolo[4,3-c]quinoline-8-carboxamide |
| 84 | 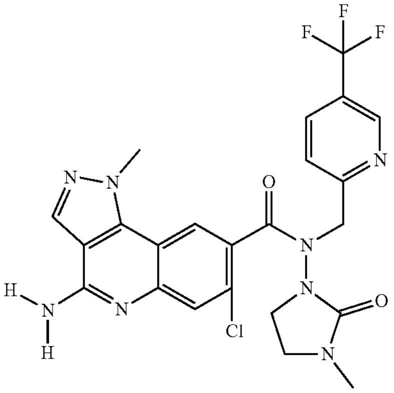 [SMILES: CN1CCN(N(Cc2ccc(C(F)(F)F)cn2)C(=O)c2cc3c(cc2Cl)nc(N)c2cnn(C)c23)C1=O] | 4-amino-7-chloro-1-methyl-N-(3-methyl-2-oxoimidazolidin-1-yl)-N-((5-(trifluoromethyl)pyridin-2-yl)methyl)-1H-pyrazolo[4,3-c]quinoline-8-carboxamide |
| 85 | 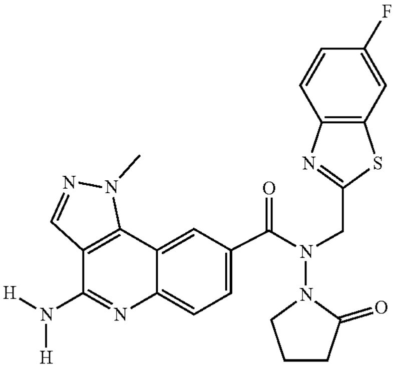 [SMILES: Cn1ncc2c(N)nc3ccc(C(=O)N(Cc4nc5ccc(F)cc5s4)N4CCCC4=O)cc3c21] | 4-amino-N-((6-fluorobenzo[d]thiazol-2-yl)methyl)-1-methyl-N-(2-oxopyrrolidin-1-yl)-1H-pyrazolo[4,3-c]quinoline-8-carboxamide |

TABLE 1-continued

| Compounds | | |
|---|---|---|
| Example | Structure | Name |
| 86 | 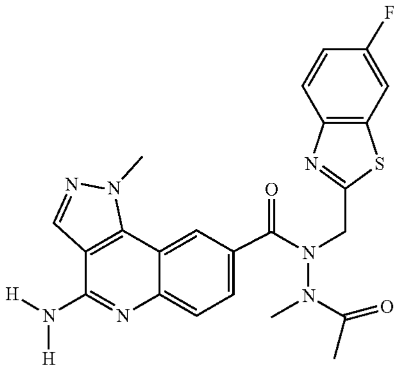 [SMILES: CC(=O)N(C)N(Cc1nc2ccc(F)cc2s1)C(=O)c1ccc2nc(N)c3cnn(C)c3c2c1] | N'-acetyl-4-amino-N-((6-fluorobenzo[d]thiazol-2-yl)methyl)-N',1-dimethyl-1H-pyrazolo[4,3-c]quinoline-8-carbohydrazide |
| 87 | 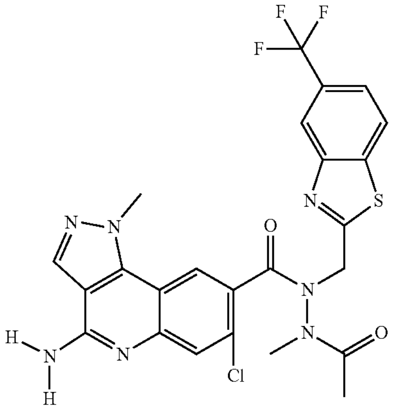 [SMILES: CC(=O)N(C)N(Cc1nc2cc(C(F)(F)F)ccc2s1)C(=O)c1cc2c(cc1Cl)nc(N)c1cnn(C)c12] | N'-acetyl-4-amino-7-chloro-N',1-dimethyl-N-((5-(trifluoromethyl)benzo[d]thiazol-2-yl)methyl)-1H-pyrazolo[4,3-c]quinoline-8-carbohydrazide |
| 88 | 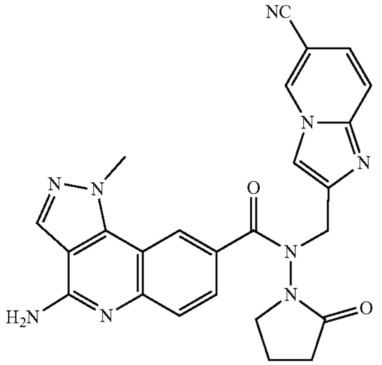 [SMILES: Cn1ncc2c(N)nc3ccc(C(=O)N(Cc4cn5cc(C#N)ccc5n4)N4CCCC4=O)cc3c21] | 4-Amino-N-[(6-cyanoimidazo[1,2-a]pyridin-2-yl)methyl]-1-methyl-N-(2-oxopyrrolidin-1-yl)pyrazolo[4,3-c]quinoline-8-carboxamide |
| 89 | 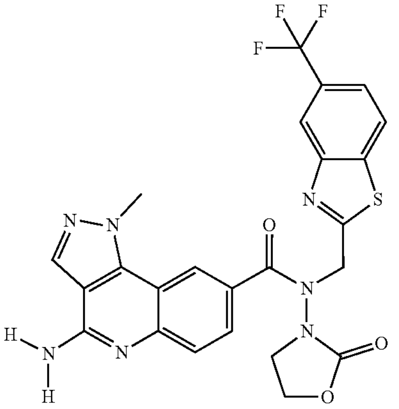 [SMILES: Cn1ncc2c(N)nc3ccc(C(=O)N(Cc4nc5cc(C(F)(F)F)ccc5s4)N4CCOC4=O)cc3c21] | 4-amino-1-methyl-N-(2-oxooxazolidin-3-yl)-N-((5-(trifluoromethyl)benzo[d]thiazol-2-yl)methyl)-1H-pyrazolo[4,3-c]quinoline-8-carboxamide |

TABLE 1-continued

| Compounds | | |
|---|---|---|
| Example | Structure | Name |
| 90 | 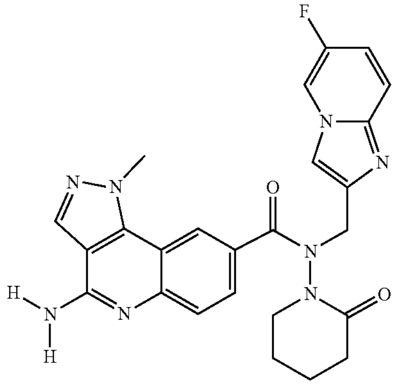 [SMILES: Cn1ncc2c(N)nc3ccc(C(=O)N(Cc4cn5cc(F)ccc5n4)N4CCCCC4=O)cc3c21] | 4-amino-N-((6-fluoroimidazo[1,2-a]pyridin-2-yl)methyl)-1-methyl-N-(2-oxopiperidin-1-yl)-1H-pyrazolo[4,3-c]quinoline-8-carboxamide |
| 91 | 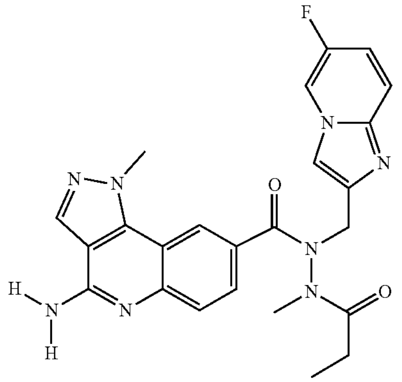 [SMILES: CCC(=O)N(C)N(Cc1cn2cc(F)ccc2n1)C(=O)c1ccc2nc(N)c3cnn(C)c3c2c1] | 4-amino-N-((6-fluoroimidazo[1,2-a]pyridin-2-yl)methyl)-N’,1-dimethyl-N’-propionyl-1H-pyrazolo[4,3-c]quinoline-8-carbohydrazide |
| 92 | 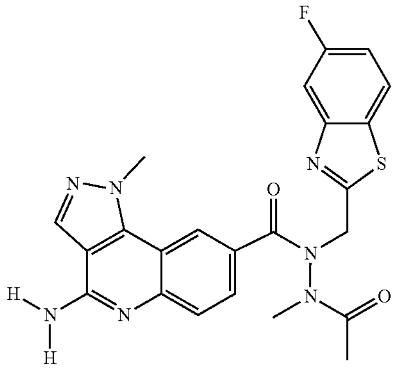 [SMILES: CC(=O)N(C)N(Cc1nc2cc(F)ccc2s1)C(=O)c1ccc2nc(N)c3cnn(C)c3c2c1] | N'-acetyl-4-amino-N-((5-fluorobenzo[d]thiazol-2-yl)methyl)-N',1-dimethyl-1H-pyrazolo[4,3-c]quinoline-8-carbohydrazide |
| 93 | 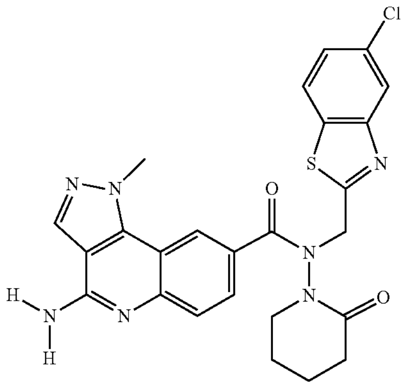 [SMILES: Cn1ncc2c(N)nc3ccc(C(=O)N(Cc4nc5cc(Cl)ccc5s4)N4CCCCC4=O)cc3c21] | 4-amino-N-((5-chlorobenzo[d]thiazol-2-yl)methyl)-1-methyl-N-(2-oxopiperidin-1-yl)-1H-pyrazolo[4,3-c]quinoline-8-carboxamide |

TABLE 1-continued

| Compounds | | |
|---|---|---|
| Example | Structure | Name |
| 94 | 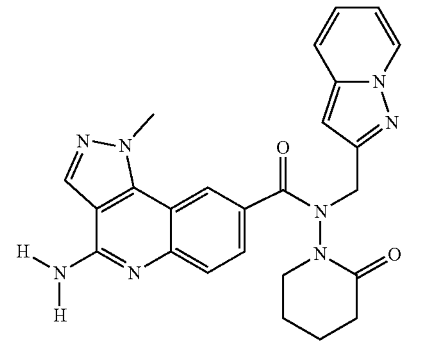 [SMILES: Cn1ncc2c(N)nc3ccc(C(=O)N(Cc4cc5ccccn5n4)N4CCCCC4=O)cc3c21] | 4-amino-1-methyl-N-(2-oxopiperidin-1-yl)-N-(pyrazolo[1,5-a]pyridin-2-ylmethyl)-1H-pyrazolo[4,3-c]quinoline-8-carboxamide |
| 95 | 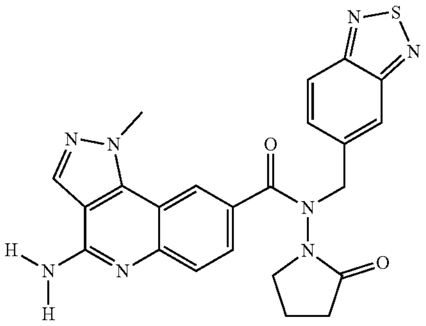 [SMILES: Cn1ncc2c(N)nc3ccc(C(=O)N(Cc4ccc5nsnc5c4)N4CCCC4=O)cc3c21] | 4-amino-N-(benzo[c][1,2,5]thiadiazol-5-ylmethyl)-1-methyl-N-(2-oxopyrrolidin-1-yl)-1H-pyrazolo[4,3-c]quinoline-8-carboxamide |
| 96 | 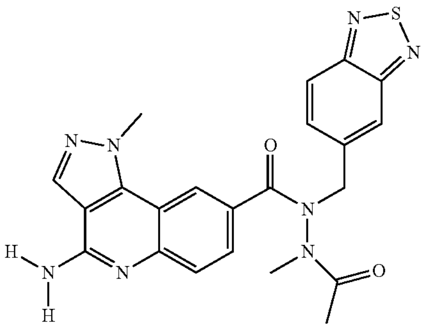 [SMILES: CC(=O)N(C)N(Cc1ccc2nsnc2c1)C(=O)c1ccc2nc(N)c3cnn(C)c3c2c1] | N'-acetyl-4-amino-N-(benzo[c][1,2,5]thiadiazol-5-ylmethyl)-N',1-dimethyl-1H-pyrazolo[4,3-c]quinoline-8-carbohydrazide |
| 97 | 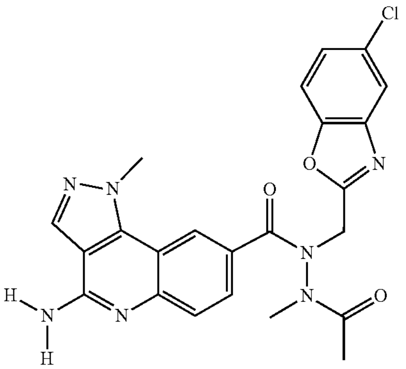 [SMILES: CC(=O)N(C)N(Cc1nc2cc(Cl)ccc2o1)C(=O)c1ccc2nc(N)c3cnn(C)c3c2c1] | N'-acetyl-4-amino-N-((5-chlorobenzo[d]oxazol-2-yl)methyl)-N',1-dimethyl-1H-pyrazolo[4,3-c]quinoline-8-carbohydrazide |

TABLE 1-continued

| Compounds | | |
|---|---|---|
| Example | Structure | Name |
| 98 | 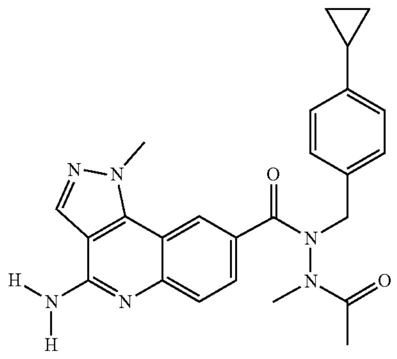 [SMILES: CC(=O)N(C)N(Cc1ccc(C2CC2)cc1)C(=O)c1ccc2nc(N)c3cnn(C)c3c2c1] | N'-acetyl-4-amino-N-(4-cyclopropylbenzyl)-N',1-dimethyl-1H-pyrazolo[4,3-c]quinoline-8-carbohydrazide |
| 99 | 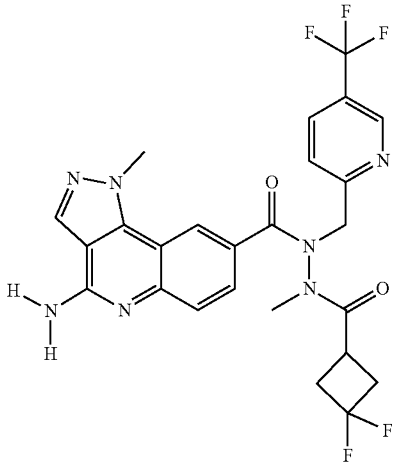 [SMILES: CN(C(=O)C1CC(F)(F)C1)N(Cc1ccc(C(F)(F)F)cn1)C(=O)c1ccc2nc(N)c3cnn(C)c3c2c1] | 4-amino-N'-(3,3-difluorocyclobutane-1-carbonyl)-N',1-dimethyl-N-((5-(trifluoromethyl)pyridin-2-yl)methyl)-1H-pyrazolo[4,3-c]quinoline-8-carbohydrazide |
| 100 | 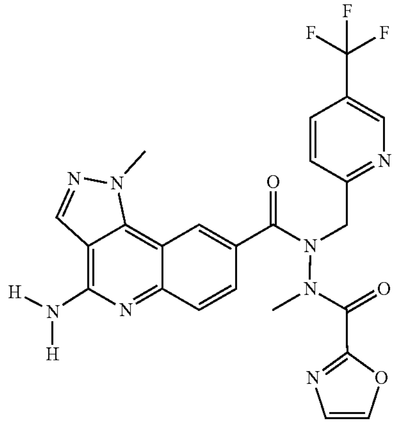 [SMILES: CN(C(=O)c1ncco1)N(Cc1ccc(C(F)(F)F)cn1)C(=O)c1ccc2nc(N)c3cnn(C)c3c2c1] | N'-(4-amino-1-methyl-1H-pyrazolo[4,3-c]quinoline-8-carbonyl)-N-methyl-N'-((5-(trifluoromethyl)pyridin-2-yl)methyl)oxazole-2-carbohydrazide |

TABLE 1-continued

| Compounds | | |
|---|---|---|
| Example | Structure | Name |
| 101 | 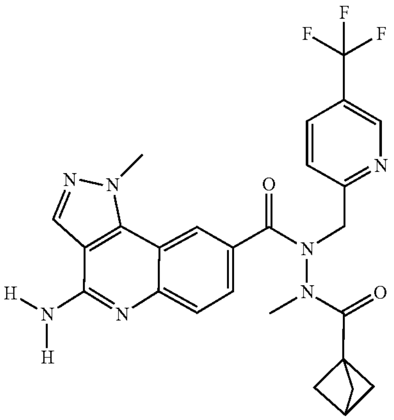 [SMILES: CN(C(=O)C12CC(C1)C2)N(Cc1ccc(C(F)(F)F)cn1)C(=O)c1ccc2nc(N)c3cnn(C)c3c2c1] | 4-amino-N'-(bicyclo[1.1.1]pentane-1-carbonyl)-N', 1-dimethyl-N-((5-(trifluoromethyl)pyridin-2-yl)methyl)-1H-pyrazolo[4,3-c]quinoline-8-carbohydrazide |
| 102 | 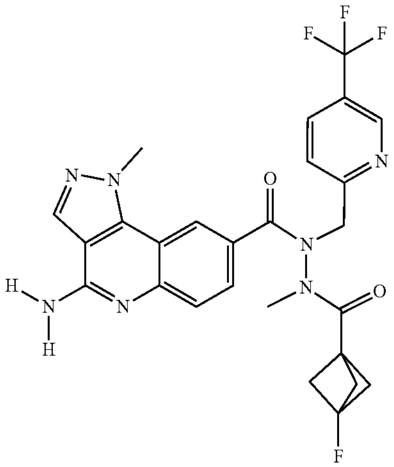 [SMILES: CN(C(=O)C12CC(F)(C1)C2)N(Cc1ccc(C(F)(F)F)cn1)C(=O)c1ccc2nc(N)c3cnn(C)c3c2c1] | 4-amino-N'-(3-fluorobicyclo[1.1.1]pentane-1-carbonyl)-N',1-dimethyl-N-((5-(trifluoromethyl)pyridin-2-yl)methyl)-1H-pyrazolo[4,3-c]quinoline-8-carbohydrazide |
| 103 | 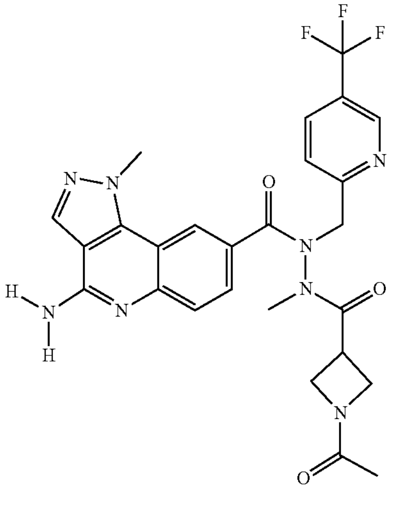 [SMILES: CC(=O)N1CC(C(=O)N(C)N(Cc2ccc(C(F)(F)F)cn2)C(=O)c2ccc3nc(N)c4cnn(C)c4c3c2)C1] | N'-(1-acetylazetidine-3-carbonyl)-4-amino-N',1-dimethyl-N-((5-(trifluoromethyl)pyridin-2-yl)methyl)-1H-pyrazolo[4,3-c]quinoline-8-carbohydrazide |

TABLE 1-continued

| Compounds | | |
|---|---|---|
| Example | Structure | Name |
| 104 | 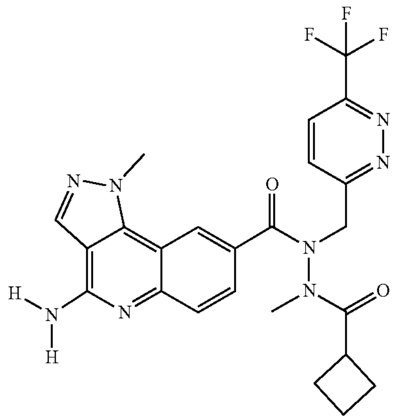 [SMILES: CN(C(=O)C1CCC1)N(Cc1ccc(C(F)(F)F)nn1)C(=O)c1ccc2nc(N)c3cnn(C)c3c2c1] | 4-amino-N'-(cyclobutanecarbonyl)-N',1-dimethyl-N-((6-(trifluoromethyl)pyridazin-3-yl)methyl)-1H-pyrazolo[4,3-c]quinoline-8-carbohydrazide |
| 105 | 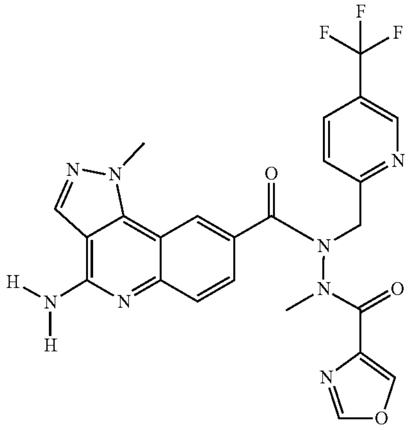 [SMILES: CN(C(=O)c1cocn1)N(Cc1ccc(C(F)(F)F)cn1)C(=O)c1ccc2nc(N)c3cnn(C)c3c2c1] | N'-(4-amino-1-methyl-1H-pyrazolo[4,3-c]quinoline-8-carbonyl)-N-methyl-N'-((5-(trifluoromethyl)pyridin-2-yl)methyl)oxazole-4-carbohydrazide |
| 106 | 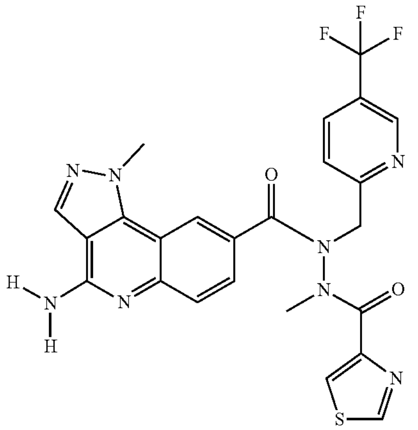 [SMILES: CN(C(=O)c1cscn1)N(Cc1ccc(C(F)(F)F)cn1)C(=O)c1ccc2nc(N)c3cnn(C)c3c2c1] | N'-(4-amino-1-methyl-1H-pyrazolo[4,3-c]quinoline-8-carbonyl)-N-methyl-N'-((5-(trifluoromethyl)pyridin-2-yl)methyl)thiazole-4-carbohydrazide |

TABLE 1-continued

| Compounds | | |
|---|---|---|
| Example | Structure | Name |
| 107 | 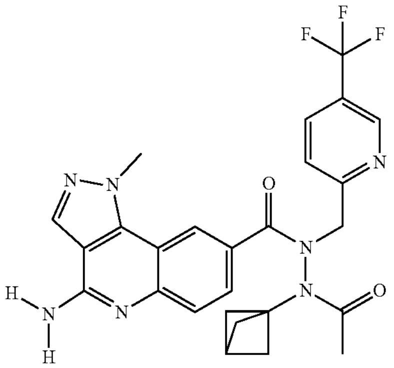 [SMILES: CC(=O)N(N(Cc1ccc(C(F)(F)F)cn1)C(=O)c1ccc2nc(N)c3cnn(C)c3c2c1)C12CC(C1)C2] | N'-acetyl-4-amino-N'-(bicyclo[1.1.1]pentan-1-yl)-1-methyl-N-((5-(trifluoromethyl)pyridin-2-yl)methyl)-1H-pyrazolo[4,3-c]quinoline-8-carbohydrazide |
| 108 | 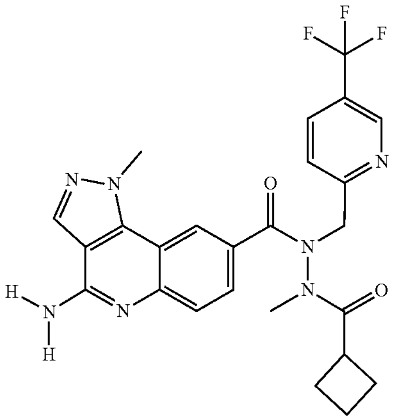 [SMILES: CN(C(=O)C1CCC1)N(Cc1ccc(C(F)(F)F)cn1)C(=O)c1ccc2nc(N)c3cnn(C)c3c2c1] | 4-amino-N'-(cyclobutanecarbonyl)-N',1-dimethyl-N-((5-(trifluoromethyl)pyridin-2-yl)methyl)-1H-pyrazolo[4,3-c]quinoline-8-carbohydrazide |
| 109 | 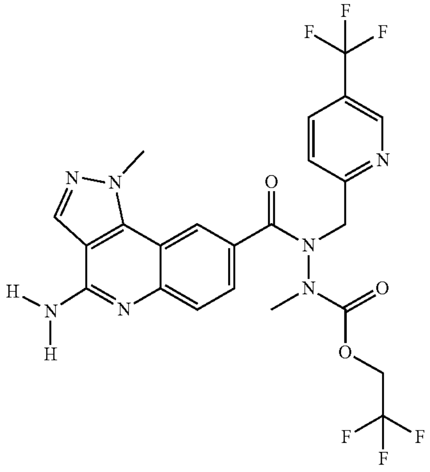 [SMILES: CN(C(=O)OCC(F)(F)F)N(Cc1ccc(C(F)(F)F)cn1)C(=O)c1ccc2nc(N)c3cnn(C)c3c2c1] | 2,2,2-trifluoroethyl 2-(4-amino-1-methyl-1H-pyrazolo[4,3-c]quinoline-8-carbonyl)-1-methyl-2-((5-(trifluoromethyl)pyridin-2-yl)methyl)hydrazine-1-carboxylate |

TABLE 1-continued

| Compounds | | |
|---|---|---|
| Example | Structure | Name |
| 110 | 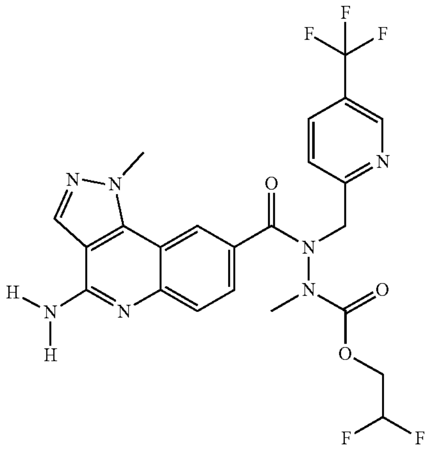 [SMILES: CN(C(=O)OCC(F)F)N(Cc1ccc(C(F)(F)F)cn1)C(=O)c1ccc2nc(N)c3cnn(C)c3c2c1] | 2,2-difluoroethyl 2-(4-amino-1-methyl-1H-pyrazolo[4,3-c]quinoline-8-carbonyl)-1-methyl-2-((5-(trifluoromethyl)pyridin-2-yl)methyl)hydrazine-1-carboxylate |
| 111 | 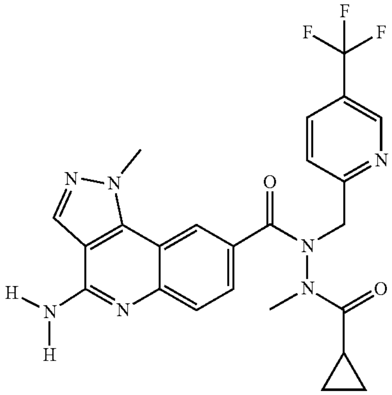 [SMILES: CN(C(=O)C1CC1)N(Cc1ccc(C(F)(F)F)cn1)C(=O)c1ccc2nc(N)c3cnn(C)c3c2c1] | 4-amino-N'-(cyclopropanecarbonyl)-N',1-dimethyl-N-((5-(trifluoromethyl)pyridin-2-yl)methyl)-1H-pyrazolo[4,3-c]quinoline-8-carbohydrazide |
| 112 | 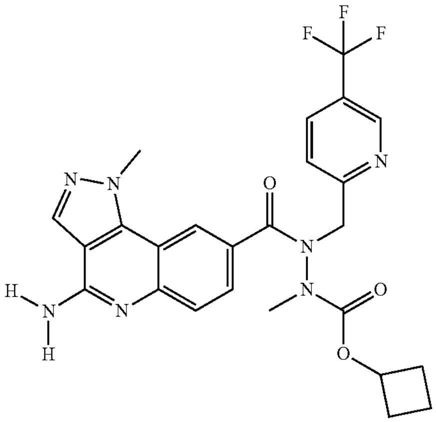 [SMILES: CN(C(=O)OC1CCC1)N(Cc1ccc(C(F)(F)F)cn1)C(=O)c1ccc2nc(N)c3cnn(C)c3c2c1] | cyclobutyl 2-(4-amino-1-methyl-1H-pyrazolo[4,3-c]quinoline-8-carbonyl)-1-methyl-2-((5-(trifluoromethyl)pyridin-2-yl)methyl)hydrazine-1-carboxylate |

TABLE 1-continued

| Compounds | | |
|---|---|---|
| Example | Structure | Name |
| 113 | 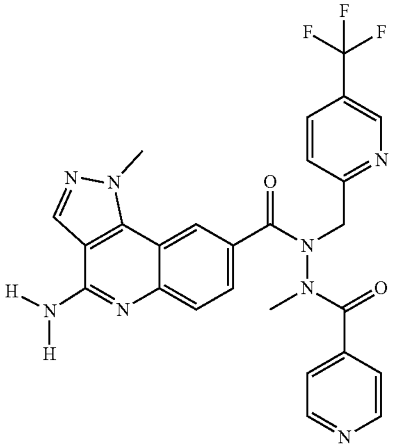 [SMILES: CN(C(=O)c1ccncc1)N(Cc1ccc(C(F)(F)F)cn1)C(=O)c1ccc2nc(N)c3cnn(C)c3c2c1] | 4-amino-N'-isonicotinoyl-N',1-dimethyl-N-((5-(trifluoromethyl)pyridin-2-yl)methyl)-1H-pyrazolo[4,3-c]quinoline-8-carbohydrazide |
| 114 | 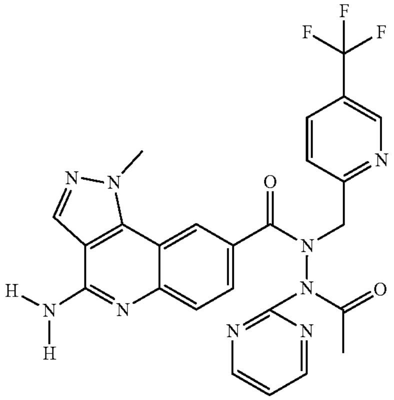 [SMILES: CC(=O)N(c1ncccn1)N(Cc1ccc(C(F)(F)F)cn1)C(=O)c1ccc2nc(N)c3cnn(C)c3c2c1] | N'-acetyl-4-amino-1-methyl-N'-(pyrimidin-2-yl)-N-((5-(trifluoromethyl)pyridin-2-yl)methyl)-1H-pyrazolo[4,3-c]quinoline-8-carbohydrazide |
| 115 | 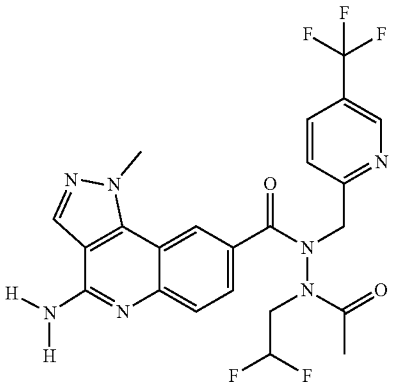 [SMILES: CC(=O)N(CC(F)F)N(Cc1ccc(C(F)(F)F)cn1)C(=O)c1ccc2nc(N)c3cnn(C)c3c2c1] | N'-acetyl-4-amino-N'-(2,2-difluoroethyl)-1-methyl-N-((5-(trifluoromethyl)pyridin-2-yl)methyl)-1H-pyrazolo[4,3-c]quinoline-8-carbohydrazide |

TABLE 1-continued

| Compounds | | |
|---|---|---|
| Example | Structure | Name |
| 116 | 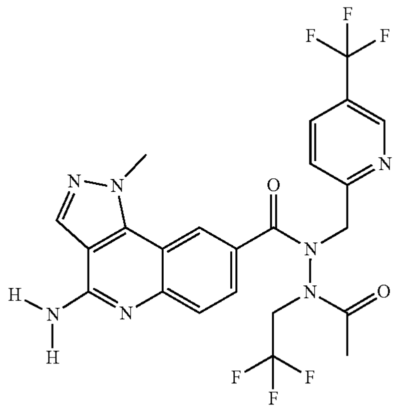 [SMILES: CC(=O)N(CC(F)(F)F)N(Cc1ccc(C(F)(F)F)cn1)C(=O)c1ccc2nc(N)c3cnn(C)c3c2c1] | N'-acetyl-4-amino-1-methyl-N'-(2,2,2-trifluoroethyl)-N-((5-(trifluoromethyl)pyridin-2-yl)methyl)-1H-pyrazolo[4,3-c]quinoline-8-carbohydrazide |
| 117 | 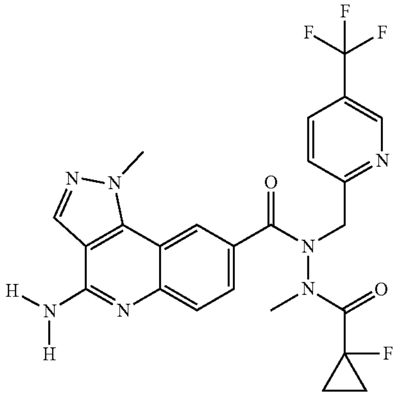 [SMILES: CN(C(=O)C1(F)CC1)N(Cc1ccc(C(F)(F)F)cn1)C(=O)c1ccc2nc(N)c3cnn(C)c3c2c1] | 4-amino-N'-(1-fluorocyclopropane-1-carbonyl)-N',1-dimethyl-N-((5-(trifluoromethyl)pyridin-2-yl)methyl)-1H-pyrazolo[4,3-c]quinoline-8-carbohydrazide |
| 118 | 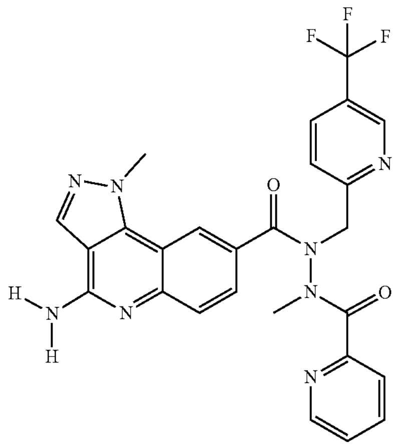 [SMILES: CN(C(=O)c1ccccn1)N(Cc1ccc(C(F)(F)F)cn1)C(=O)c1ccc2nc(N)c3cnn(C)c3c2c1] | 4-amino-N',1-dimethyl-N'-picolinoyl-N-((5-(trifluoromethyl)pyridin-2-yl)methyl)-1H-pyrazolo[4,3-c]quinoline-8-carbohydrazide |

TABLE 1-continued

| Compounds | | |
|---|---|---|
| Example | Structure | Name |
| 119 | 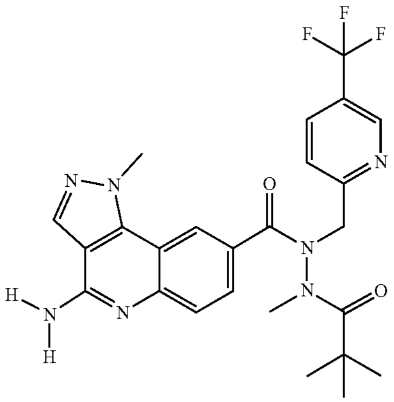 [SMILES: CN(C(=O)C(C)(C)C)N(Cc1ccc(C(F)(F)F)cn1)C(=O)c1ccc2nc(N)c3cnn(C)c3c2c1] | 4-amino-N',1-dimethyl-N'-pivaloyl-N-((5-(trifluoromethyl)pyridin-2-yl)methyl)-1H-pyrazolo[4,3-c]quinoline-8-carbohydrazide |
| 120 | 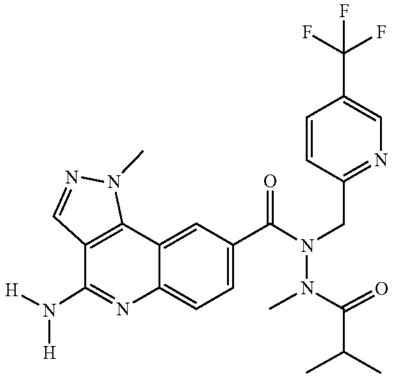 [SMILES: CC(C)C(=O)N(C)N(Cc1ccc(C(F)(F)F)cn1)C(=O)c1ccc2nc(N)c3cnn(C)c3c2c1] | 4-amino-N'-isobutyryl-N',1-dimethyl-N-((5-(trifluoromethyl)pyridin-2-yl)methyl)-1H-pyrazolo[4,3-c]quinoline-8-carbohydrazide |
| 121 | 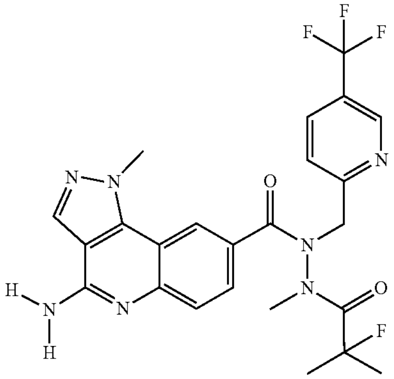 [SMILES: CN(C(=O)C(C)(C)F)N(Cc1ccc(C(F)(F)F)cn1)C(=O)c1ccc2nc(N)c3cnn(C)c3c2c1] | 4-amino-N'-(2-fluoro-2-methylpropanoyl)-N',1-dimethyl-N-((5-(trifluoromethyl)pyridin-2-yl)methyl)-1H-pyrazolo[4,3-c]quinoline-8-carbohydrazide |
| 122 | 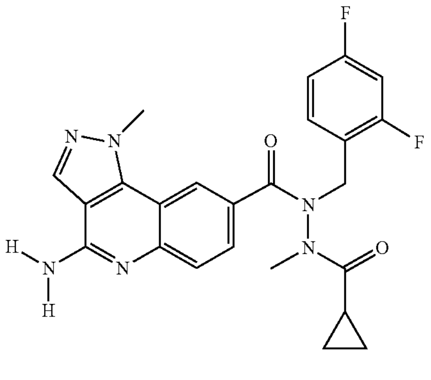 [SMILES: CN(C(=O)C1CC1)N(Cc1ccc(F)cc1F)C(=O)c1ccc2nc(N)c3cnn(C)c3c2c1] | 4-amino-N'-(cyclopropanecarbonyl)-N-(2,4-difluorobenzyl)-N',1-dimethyl-1H-pyrazolo[4,3-c]quinoline-8-carbohydrazide |

TABLE 1-continued

| Compounds | | |
|---|---|---|
| Example | Structure | Name |
| 123 | 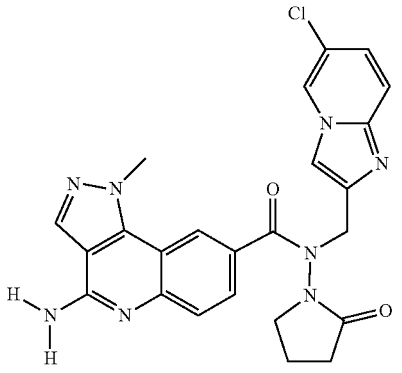 [SMILES: Cn1ncc2c(N)nc3ccc(C(=O)N(Cc4cn5cc(Cl)ccc5n4)N4CCCC4=O)cc3c21] | 4-amino-N-((6-chloroimidazo[1,2-a]pyridin-2-yl)methyl)-1-methyl-N-(2-oxopyrrolidin-1-yl)-1H-pyrazolo[4,3-c]quinoline-8-carboxamide |
| 124 | 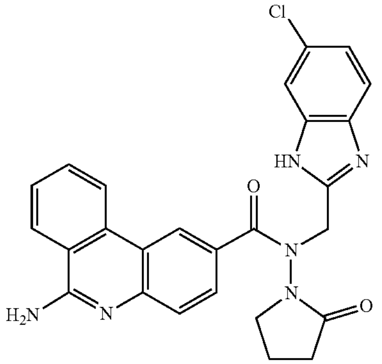 [SMILES: Nc1nc2ccc(C(=O)N(Cc3nc4ccc(Cl)cc4[nH]3)N3CCCC3=O)cc2c2ccccc12] | 6-amino-N-((6-chloro-1H-benzo[d]imidazol-2-yl)methyl)-N-(2-oxopyrrolidin-1-yl)phenanthridine-2-carboxamide |
| 125 | 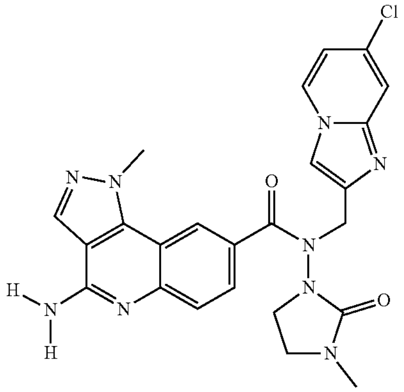 [SMILES: CN1CCN(N(Cc2cn3ccc(Cl)cc3n2)C(=O)c2ccc3nc(N)c4cnn(C)c4c3c2)C1=O] | 4-amino-N-((7-chloroimidazo[1,2-a]pyridin-2-yl)methyl)-1-methyl-N-(3-methyl-2-oxoimidazolidin-1-yl)-1H-pyrazolo[4,3-c]quinoline-8-carboxamide |
| 126 | 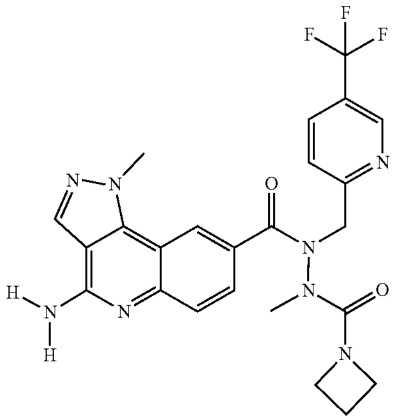 [SMILES: CN(C(=O)N1CCC1)N(Cc1ccc(C(F)(F)F)cn1)C(=O)c1ccc2nc(N)c3cnn(C)c3c2c1] | 4-amino-N'-(azetidine-1-carbonyl)-N',1-dimethyl-N-((5-(trifluoromethyl)pyridin-2-yl)methyl)-1H-pyrazolo[4,3-c]quinoline-8-carbohydrazide |

TABLE 1-continued

| Compounds | | |
|---|---|---|
| Example | Structure | Name |
| 127 | 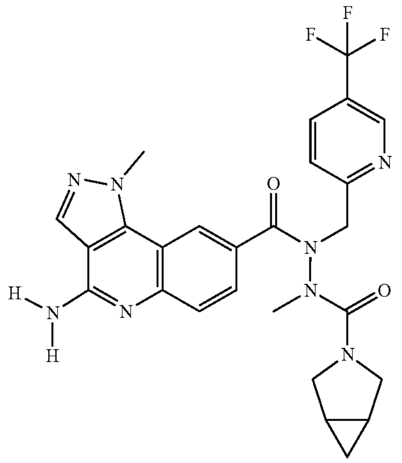 [SMILES: CN(C(=O)N1CC2CC2C1)N(Cc1ccc(C(F)(F)F)cn1)C(=O)c1ccc2nc(N)c3cnn(C)c3c2c1] | 4-amino-N'-(3-azabicyclo[3.1.0]hexane-3-carbonyl)-N',1-dimethyl-N-((5-(trifluoromethyl)pyridin-2-yl)methyl)-1H-pyrazolo[4,3-c]quinoline-8-carbohydrazide |
| 128 | 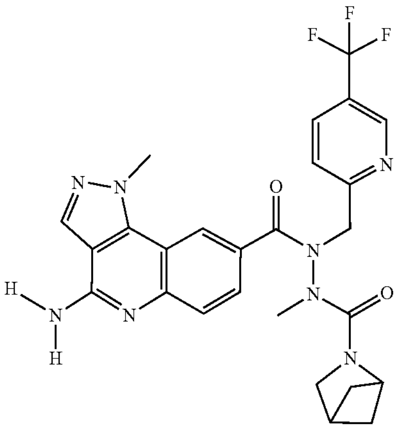 [SMILES: CN(C(=O)N1CC2CC1C2)N(Cc1ccc(C(F)(F)F)cn1)C(=O)c1ccc2nc(N)c3cnn(C)c3c2c1] | 4-amino-N'-(2-azabicyclo[2.1.1]hexane-2-carbonyl)-N',1-dimethyl-N-((5-(trifluoromethyl)pyridin-2-yl)methyl)-1H-pyrazolo[4,3-c]quinoline-8-carbohydrazide |
| 129 | 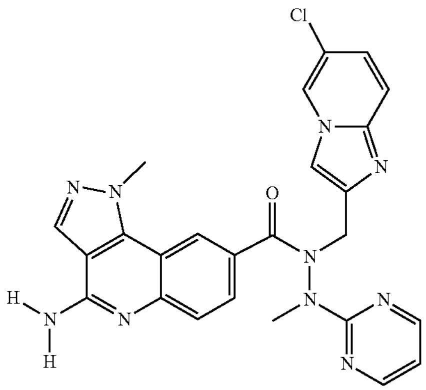 [SMILES: CN(c1ncccn1)N(Cc1cn2cc(Cl)ccc2n1)C(=O)c1ccc2nc(N)c3cnn(C)c3c2c1] | 4-amino-N-((6-chloroimidazo[1,2-a]pyridin-2-yl)methyl)-N',1-dimethyl-N'-(pyrimidin-2-yl)-1H-pyrazolo[4,3-c]quinoline-8-carbohydrazide |

TABLE 1-continued

| Compounds | | |
|---|---|---|
| Example | Structure | Name |
| 130 | 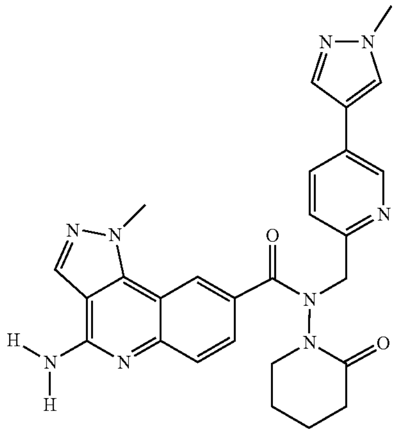 [SMILES: Cn1cc(-c2ccc(CN(C(=O)c3ccc4nc(N)c5cnn(C)c5c4c3)N3CCCCC3=O)nc2)cn1] | 4-amino-1-methyl-N-((5-(1-methyl-1H-pyrazol-4-yl)pyridin-2-yl)methyl)-N-(2-oxopiperidin-1-yl)-1H-pyrazolo[4,3-c]quinoline-8-carboxamide |
| 131 | 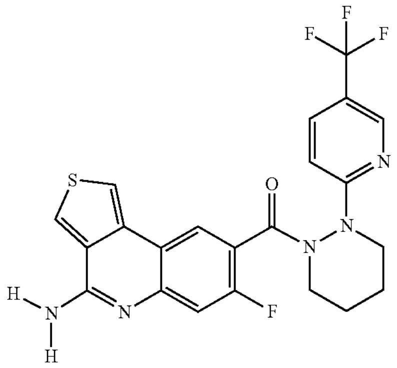 [SMILES: Nc1nc2cc(F)c(C(=O)N3CCCCN3c3ccc(C(F)(F)F)cn3)cc2c2cscc12] | (4-amino-7-fluorothieno[3,4-c]quinolin-8-yl)(2-(5-(trifluoromethyl)pyridin-2-yl)tetrahydropyridazin-1(2H)-yl)methanone |
| 132 | 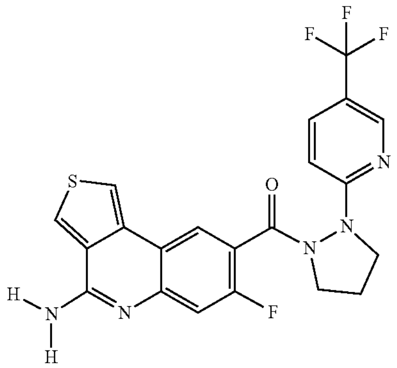 [SMILES: Nc1nc2cc(F)c(C(=O)N3CCCN3c3ccc(C(F)(F)F)cn3)cc2c2cscc12] | (4-amino-7-fluorothieno[3,4-c]quinolin-8-yl)(2-(5-(trifluoromethyl)pyridin-2-yl)pyrazolidin-1-yl)methanone |
| 133 | 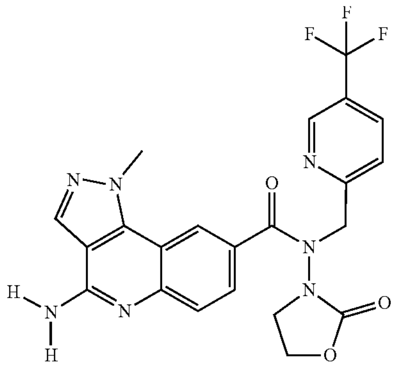 | 4-amino-1-methyl-N-(2-oxooxazolidin-3-yl)-N-((5-(trifluoromethyl)pyridin-2-yl)methyl)-1H-pyrazolo[4,3-c]quinoline-8-carboxamide |

TABLE 1-continued

| Compounds | | |
|---|---|---|
| Example | Structure | Name |
| 134 | 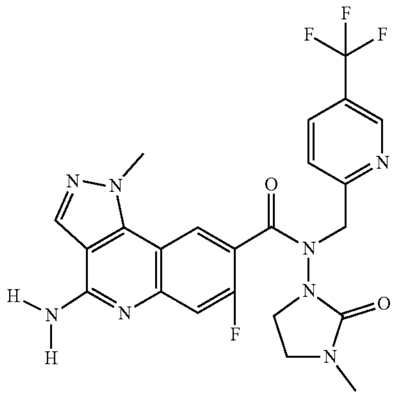 [SMILES: CN1CCN(N(Cc2ccc(C(F)(F)F)cn2)C(=O)c2cc3c(cc2F)nc(N)c2cnn(C)c23)C1=O] | 4-amino-7-fluoro-1-methyl-N-(3-methyl-2-oxoimidazolidin-1-yl)-N-((5-(trifluoromethyl)pyridin-2-yl)methyl)-1H-pyrazolo[4,3-c]quinoline-8-carboxamide |
| 135 | 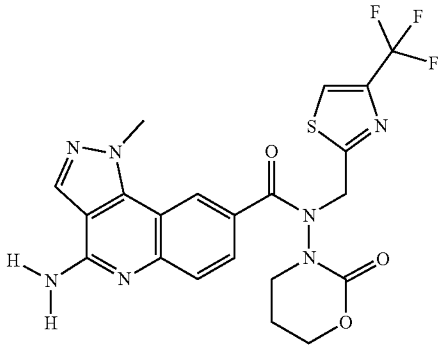 [SMILES: Cn1ncc2c(N)nc3ccc(C(=O)N(Cc4nc(C(F)(F)F)cs4)N4CCCOC4=O)cc3c21] | 4-amino-1-methyl-N-(2-oxo-1,3-oxazinan-3-yl)-N-((4-(trifluoromethyl)thiazol-2-yl)methyl)-1H-pyrazolo[4,3-c]quinoline-8-carboxamide |
| 136 | 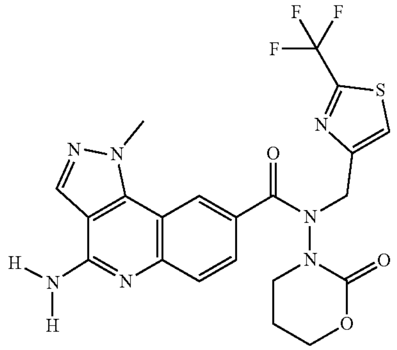 [SMILES: Cn1ncc2c(N)nc3ccc(C(=O)N(Cc4csc(C(F)(F)F)n4)N4CCCOC4=O)cc3c21] | 4-amino-1-methyl-N-(2-oxo-1,3-oxazinan-3-yl)-N-((2-(trifluoromethyl)thiazol-4-yl)methyl)-1H-pyrazolo[4,3-c]quinoline-8-carboxamide |
| 137 | 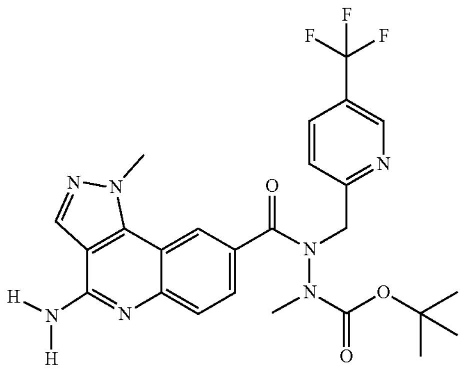 [SMILES: CN(C(=O)OC(C)(C)C)N(Cc1ccc(C(F)(F)F)cn1)C(=O)c1ccc2nc(N)c3cnn(C)c3c2c1] | tert-butyl 2-(4-amino-1-methyl-1H-pyrazolo[4,3-c]quinoline-8-carbonyl)-1-methyl-2-((5-(trifluoromethyl)pyridin-2-yl)methyl)hydrazine-1-carboxylate |

TABLE 1-continued

| Compounds | | |
|---|---|---|
| Example | Structure | Name |
| 138 | 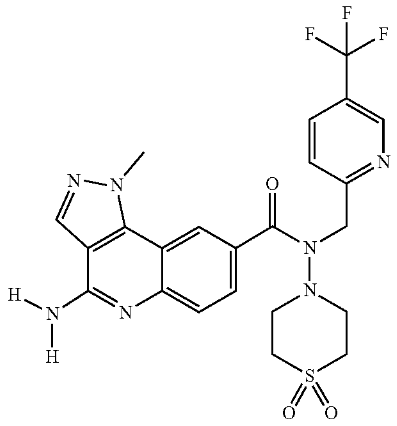 [SMILES: Cn1ncc2c(N)nc3ccc(C(=O)N(Cc4ccc(C(F)(F)F)cn4)N4CCS(=O)(=O)CC4)cc3c21] | 4-amino-N-(1,1-dioxidothiomorpholino)-1-methyl-N-((5-(trifluoromethyl)pyridin-2-yl)methyl)-1H-pyrazolo[4,3-c]quinoline-8-carboxamide |
| 139 | 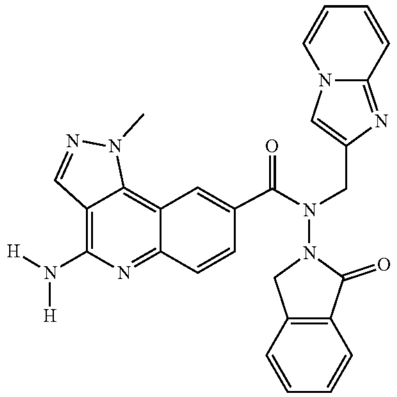 [SMILES: Cn1ncc2c(N)nc3ccc(C(=O)N(Cc4cn5ccccc5n4)N4Cc5ccccc5C4=O)cc3c21] | 4-amino-N-(imidazo[1,2-a]pyridin-2-ylmethyl)-1-methyl-N-(1-oxoisoindolin-2-yl)-1H-pyrazolo[4,3-c]quinoline-8-carboxamide |
| 140 | 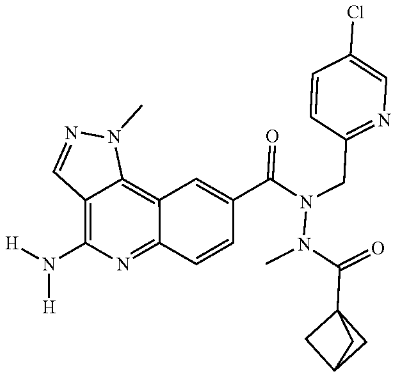 [SMILES: CN(C(=O)C12CC(C1)C2)N(Cc1ccc(Cl)cn1)C(=O)c1ccc2nc(N)c3cnn(C)c3c2c1] | 4-amino-N'-(bicyclo[1.1.1]pentane-1-carbonyl)-N-((5-chloropyridin-2-yl)methyl)-N',1-dimethyl-1H-pyrazolo[4,3-c]quinoline-8-carbohydrazide |
| 141 | 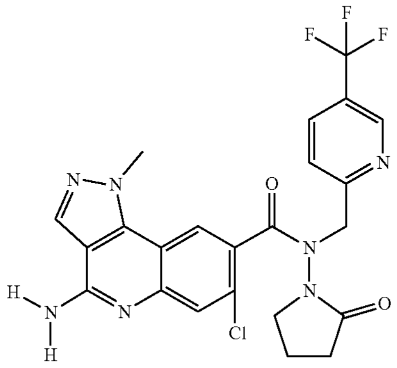 | 4-amino-7-chloro-1-methyl-N-(2-oxopyrrolidin-1-yl)-N-((5-(trifluoromethyl)pyridin-2-yl)methyl)-1H-pyrazolo[4,3-c]quinoline-8-carboxamide |

TABLE 1-continued

| Compounds | | |
|---|---|---|
| Example | Structure | Name |
| 142 | 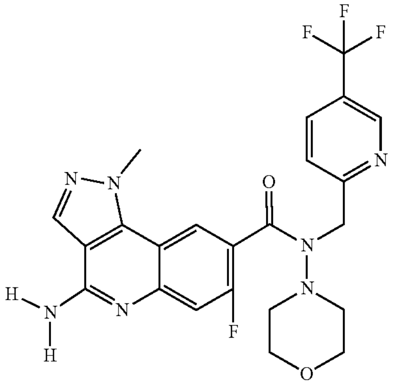 [SMILES: Cn1ncc2c(N)nc3cc(F)c(C(=O)N(Cc4ccc(C(F)(F)F)cn4)N4CCOCC4)cc3c21] | 4-amino-7-fluoro-1-methyl-N-morpholino-N-((5-(trifluoromethyl)pyridin-2-yl)methyl)-1H-pyrazolo[4,3-c]quinoline-8-carboxamide |
| 143 | 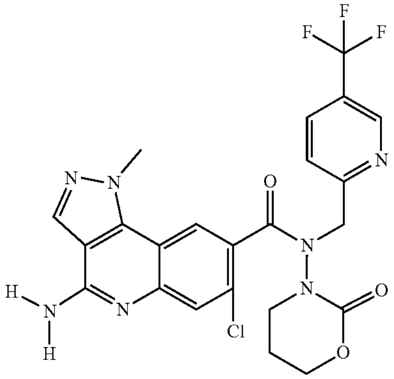 [SMILES: Cn1ncc2c(N)nc3cc(Cl)c(C(=O)N(Cc4ccc(C(F)(F)F)cn4)N4CCCOC4=O)cc3c21] | 4-amino-7-chloro-1-methyl-N-(2-oxo-1,3-oxazinan-3-yl)-N-((5-(trifluoromethyl)pyridin-2-yl)methyl)-1H-pyrazolo[4,3-c]quinoline-8-carboxamide |
| 144 | 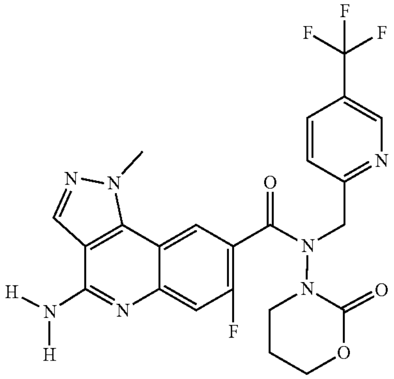 [SMILES: Cn1ncc2c(N)nc3cc(F)c(C(=O)N(Cc4ccc(C(F)(F)F)cn4)N4CCCOC4=O)cc3c21] | 4-amino-7-fluoro-1-methyl-N-(2-oxo-1,3-oxazinan-3-yl)-N-((5-(trifluoromethyl)pyridin-2-yl)methyl)-1H-pyrazolo[4,3-c]quinoline-8-carboxamide |
| 145 | 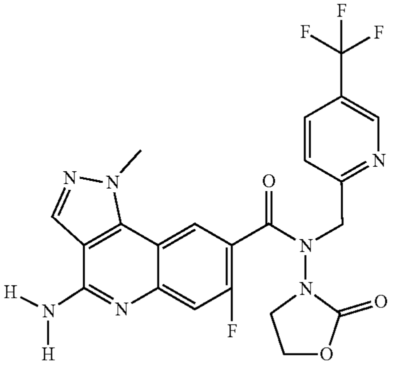 [SMILES: Cn1ncc2c(N)nc3cc(F)c(C(=O)N(Cc4ccc(C(F)(F)F)cn4)N4CCOC4=O)cc3c21] | 4-amino-7-fluoro-1-methyl-N-(2-oxooxazolidin-3-yl)-N-((5-(trifluoromethyl)pyridin-2-yl)methyl)-1H-pyrazolo[4,3-c]quinoline-8-carboxamide |

TABLE 1-continued

| Compounds | | |
|---|---|---|
| Example | Structure | Name |
| 146 | 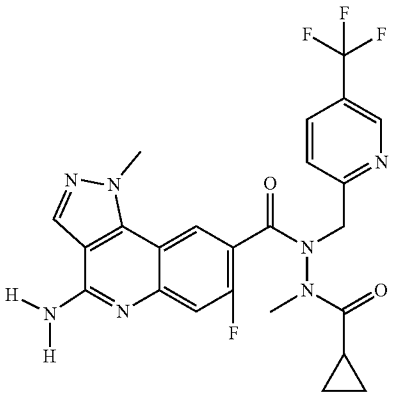 [SMILES: CN(C(=O)C1CC1)N(Cc1ccc(C(F)(F)F)cn1)C(=O)c1cc2c(cc1F)nc(N)c1cnn(C)c12] | 4-amino-N'-(cyclopropanecarbonyl)-7-fluoro-N',1-dimethyl-N-((5-(trifluoromethyl)pyridin-2-yl)methyl)-1H-pyrazolo[4,3-c]quinoline-8-carbohydrazide |
| 147 | 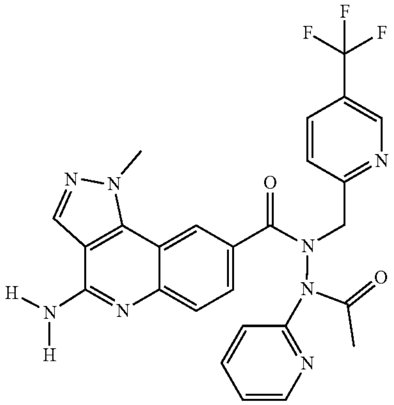 [SMILES: CC(=O)N(c1ccccn1)N(Cc1ccc(C(F)(F)F)cn1)C(=O)c1ccc2nc(N)c3cnn(C)c3c2c1] | N'-acetyl-4-amino-1-methyl-N'-(pyridin-2-yl)-N-((5-(trifluoromethyl)pyridin-2-yl)methyl)-1H-pyrazolo[4,3-c]quinoline-8-carbohydrazide |
| 148 | 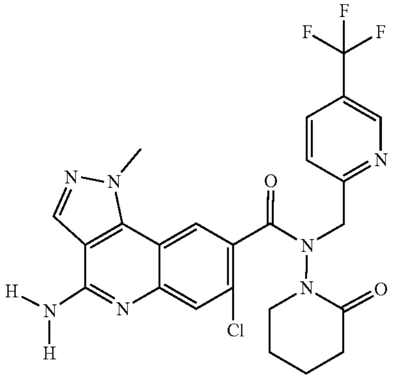 [SMILES: Cn1ncc2c(N)nc3cc(Cl)c(C(=O)N(Cc4ccc(C(F)(F)F)cn4)N4CCCCC4=O)cc3c21] | 4-amino-7-chloro-1-methyl-N-(2-oxopiperidin-1-yl)-N-((5-(trifluoromethyl)pyridin-2-yl)methyl)-1H-pyrazolo[4,3-c]quinoline-8-carboxamide |
| 149 | 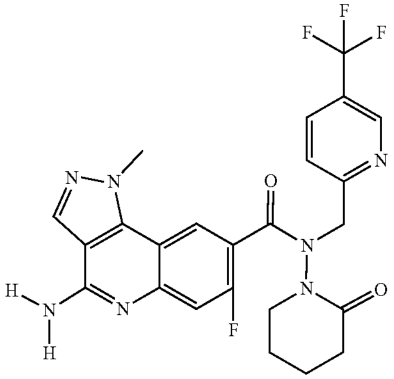 [SMILES: Cn1ncc2c(N)nc3cc(F)c(C(=O)N(Cc4ccc(C(F)(F)F)cn4)N4CCCCC4=O)cc3c21] | 4-amino-7-fluoro-1-methyl-N-(2-oxopiperidin-1-yl)-N-((5-(trifluoromethyl)pyridin-2-yl)methyl)-1H-pyrazolo[4,3-c]quinoline-8-carboxamide |

TABLE 1-continued

| Compounds | | |
|---|---|---|
| Example | Structure | Name |
| 150 | 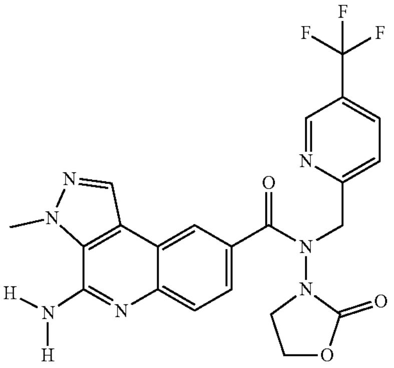 [SMILES: Cn1ncc2c3cc(C(=O)N(Cc4ccc(C(F)(F)F)cn4)N4CCOC4=O)ccc3nc(N)c21] | 4-amino-3-methyl-N-(2-oxooxazolidin-3-yl)-N-((5-(trifluoromethyl)pyridin-2-yl)methyl)-3H-pyrazolo[3,4-c]quinoline-8-carboxamide |
| 151 | 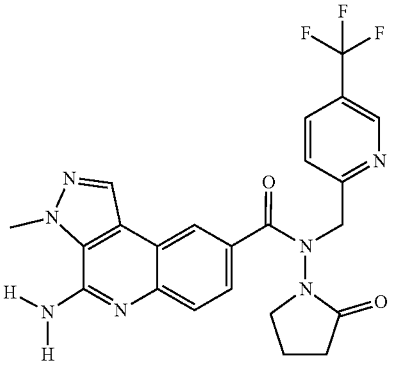 [SMILES: Cn1ncc2c3cc(C(=O)N(Cc4ccc(C(F)(F)F)cn4)N4CCCC4=O)ccc3nc(N)c21] | 4-amino-3-methyl-N-(2-oxopyrrolidin-1-yl)-N-((5-(trifluoromethyl)pyridin-2-yl)methyl)-3H-pyrazolo[3,4-c]quinoline-8-carboxamide |
| 152 | 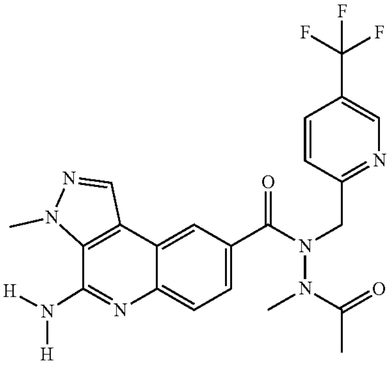 [SMILES: CC(=O)N(C)N(Cc1ccc(C(F)(F)F)cn1)C(=O)c1ccc2nc(N)c3c(cnn3C)c2c1] | N'-acetyl-4-amino-N',3-dimethyl-N-((5-(trifluoromethyl)pyridin-2-yl)methyl)-3H-pyrazolo[3,4-c]quinoline-8-carbohydrazide |
| 153 | 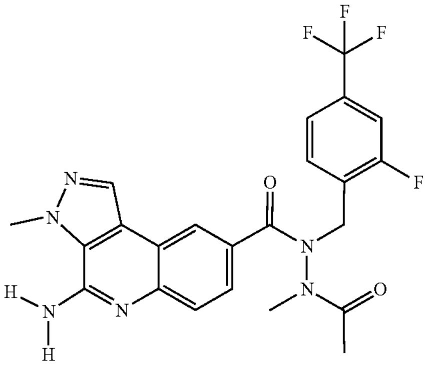 [SMILES: CC(=O)N(C)N(Cc1ccc(C(F)(F)F)cc1F)C(=O)c1ccc2nc(N)c3c(cnn3C)c2c1] | N'-acetyl-4-amino-N-(2-fluoro-4-(trifluoromethyl)benzyl)-N',3-dimethyl-3H-pyrazolo[3,4-c]quinoline-8-carbohydrazide |

TABLE 1-continued

| Compounds | | |
|---|---|---|
| Example | Structure | Name |
| 154 | 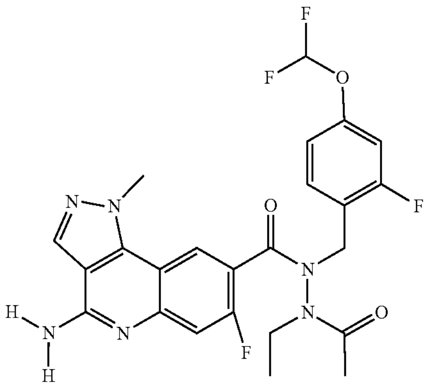 [SMILES: CCN(C(C)=O)N(Cc1ccc(OC(F)F)cc1F)C(=O)c1cc2c(cc1F)nc(N)c1cnn(C)c12] | N'-acetyl-4-amino-N-(4-(difluoromethoxy)-2-fluorobenzyl)-N'-ethyl-7-fluoro-1-methyl-1H-pyrazolo[4,3-c]quinoline-8-carbohydrazide |
| 155 | 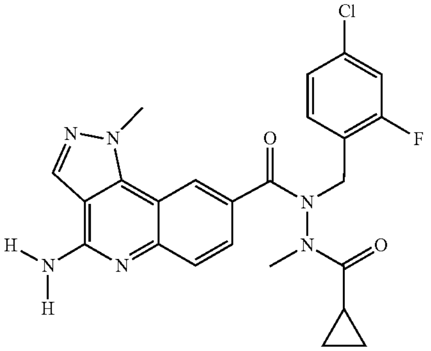 [SMILES: CN(C(=O)C1CC1)N(Cc1ccc(Cl)cc1F)C(=O)c1ccc2nc(N)c3cnn(C)c3c2c1] | 4-amino-N-(4-chloro-2-fluorobenzyl)-N'-(cyclopropanecarbonyl)-N',1-dimethyl-1H-pyrazolo[4,3-c]quinoline-8-carbohydrazide |
| 156 | 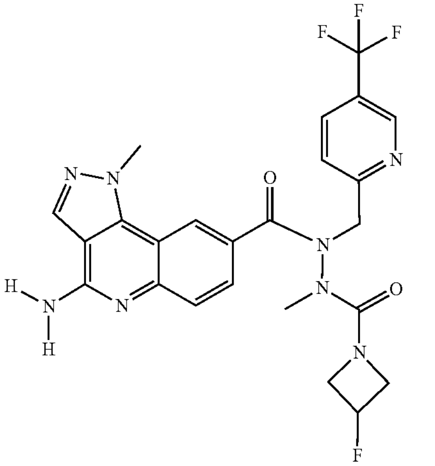 [SMILES: CN(C(=O)N1CC(F)C1)N(Cc1ccc(C(F)(F)F)cn1)C(=O)c1ccc2nc(N)c3cnn(C)c3c2c1] | 4-amino-N'-(3-fluoroazetidine-1-carbonyl)-N',1-dimethyl-N-((5-(trifluoromethyl)pyridin-2-yl)methyl)-1H-pyrazolo[4,3-c]quinoline-8-carbohydrazide |

TABLE 1-continued

| Compounds | | |
|---|---|---|
| Example | Structure | Name |
| 157 | 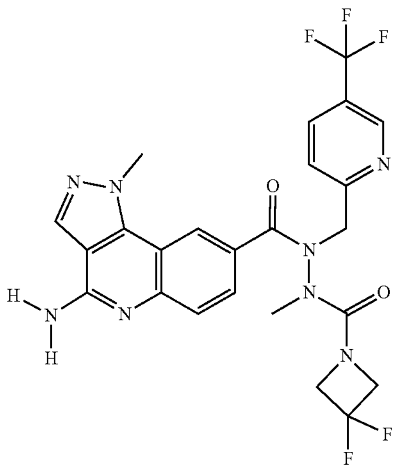 [SMILES: CN(C(=O)N1CC(F)(F)C1)N(Cc1ccc(C(F)(F)F)cn1)C(=O)c1ccc2nc(N)c3cnn(C)c3c2c1] | 4-amino-N'-(3,3-difluoroazetidine-1-carbonyl)-N',1-dimethyl-N-((5-(trifluoromethyl)pyridin-2-yl)methyl)-1H-pyrazolo[4,3-c]quinoline-8-carbohydrazide |
| 158 | 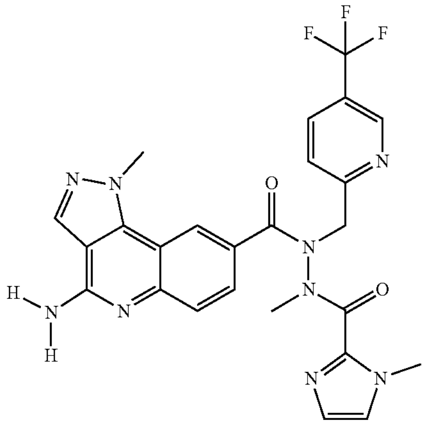 [SMILES: CN(C(=O)c1nccn1C)N(Cc1ccc(C(F)(F)F)cn1)C(=O)c1ccc2nc(N)c3cnn(C)c3c2c1] | 4-amino-N',1-dimethyl-N'-(1-methyl-1H-imidazole-2-carbonyl)-N-((5-(trifluoromethyl)pyridin-2-yl)methyl)-1H-pyrazolo[4,3-c]quinoline-8-carbohydrazide |
| 159 | 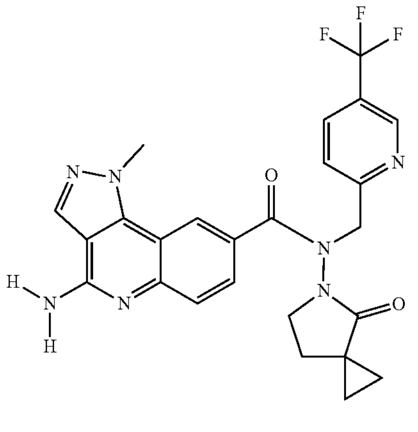 [SMILES: Cn1ncc2c(N)nc3ccc(C(=O)N(Cc4ccc(C(F)(F)F)cn4)N4CCC5(CC5)C4=O)cc3c21] | 4-amino-1-methyl-N-(4-oxo-5-azaspiro[2.4]heptan-5-yl)-N-((5-(trifluoromethyl)pyridin-2-yl)methyl)-1H-pyrazolo[4,3-c]quinoline-8-carboxamide |

TABLE 1-continued

| Compounds | | |
|---|---|---|
| Example | Structure | Name |
| 160 | 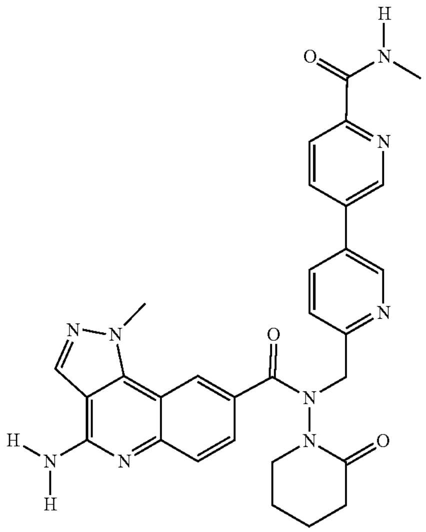 [SMILES: CNC(=O)c1ccc(-c2ccc(CN(C(=O)c3ccc4nc(N)c5cnn(C)c5c4c3)N3CCCCC3=O)nc2)cn1] | 4-amino-1-methyl-N-((6'-(methylcarbamoyl)-[3,3'-bipyridin]-6-yl)methyl)-N-(2-oxopiperidin-1-yl)-1H-pyrazolo[4,3-c]quinoline-8-carboxamide |
| 161 | 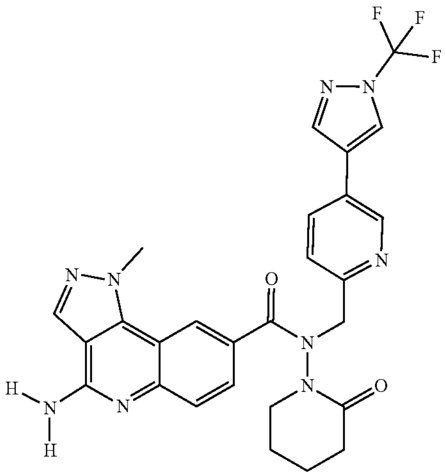 [SMILES: Cn1ncc2c(N)nc3ccc(C(=O)N(Cc4ccc(-c5cnn(C(F)(F)F)c5)cn4)N4CCCCC4=O)cc3c21] | 4-amino-1-methyl-N-(2-oxopiperidin-1-yl)-N-((5-(1-(trifluoromethyl)-1H-pyrazol-4-yl)pyridin-2-yl)methyl)-1H-pyrazolo[4,3-c]quinoline-8-carboxamide |
| 162 | 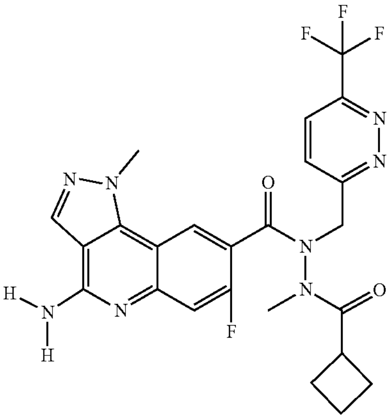 [SMILES: CN(C(=O)C1CCC1)N(Cc1ccc(C(F)(F)F)nn1)C(=O)c1cc2c(cc1F)nc(N)c1cnn(C)c12] | 4-amino-N'-(cyclobutanecarbonyl)-7-fluoro-N',1-dimethyl-N-((6-(trifluoromethyl)pyridazin-3-yl)methyl)-1H-pyrazolo[4,3-c]quinoline-8-carbohydrazide |

TABLE 1-continued

| Compounds | | |
|---|---|---|
| Example | Structure | Name |
| 163 | 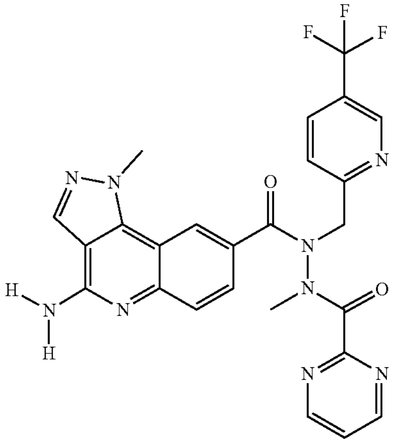 | 4-amino-N',1-dimethyl-N'-(pyrimidine-2-carbonyl)-N-((5-(trifluoromethyl)pyridin-2-yl)methyl)-1H-pyrazolo[4,3-c]quinoline-8-carbohydrazide |
| 164 | 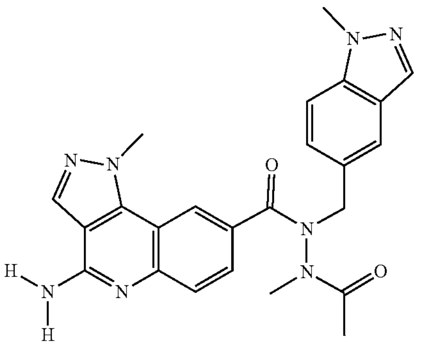 [SMILES: CC(=O)N(C)N(Cc1ccc2c(cnn2C)c1)C(=O)c1ccc2nc(N)c3cnn(C)c3c2c1] | N'-acetyl-4-amino-N',1-dimethyl-N-((1-methyl-1H-indazol-5-yl)methyl)-1H-pyrazolo[4,3-c]quinoline-8-carbohydrazide |
| 165 | 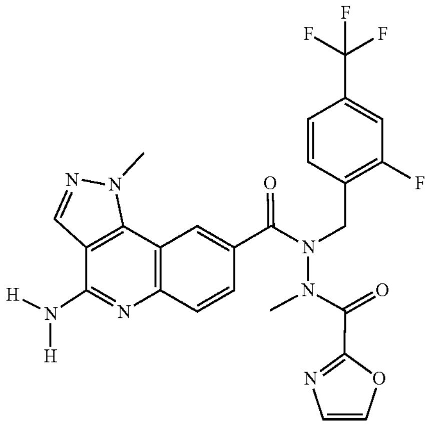 [SMILES: CN(C(=O)c1ncco1)N(Cc1ccc(C(F)(F)F)cc1F)C(=O)c1ccc2nc(N)c3cnn(C)c3c2c1] | N'-(4-amino-1-methyl-1H-pyrazolo[4,3-c]quinoline-8-carbonyl)-N'-(2-fluoro-4-(trifluoromethyl)benzyl)-N-methyloxazole-2-carbohydrazide |

TABLE 1-continued

| Compounds | | |
|---|---|---|
| Example | Structure | Name |
| 166 | 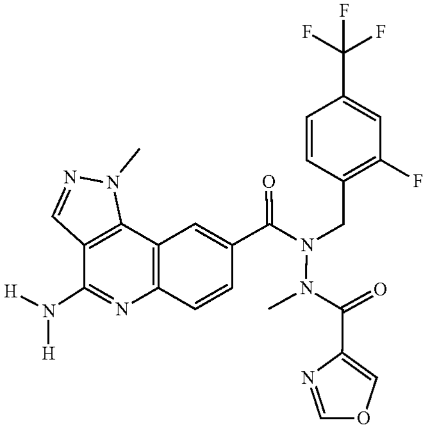 [SMILES: CN(C(=O)c1cocn1)N(Cc1ccc(C(F)(F)F)cc1F)C(=O)c1ccc2nc(N)c3cnn(C)c3c2c1] | N'-(4-amino-1-methyl-1H-pyrazolo[4,3-c]quinoline-8-carbonyl)-N'-(2-fluoro-4-(trifluoromethyl)benzyl)-N-methyloxazole-4-carbohydrazide |
| 167 | 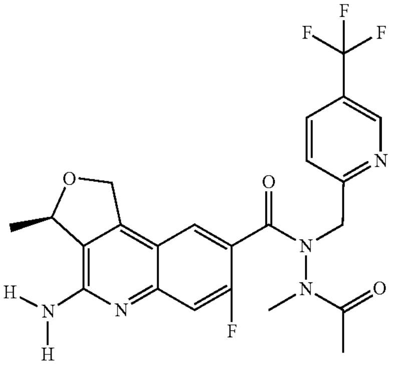 [SMILES: CC(=O)N(C)N(Cc1ccc(C(F)(F)F)cn1)C(=O)c1cc2c3c(c(N)nc2cc1F)[C@@H](C)OC3] | (R)-N'-acetyl-4-amino-7-fluoro-N',3-dimethyl-N-((5-(trifluoromethyl)pyridin-2-yl)methyl)-1,3-dihydrofuro[3,4-c]quinoline-8-carbohydrazide |
| 168 | 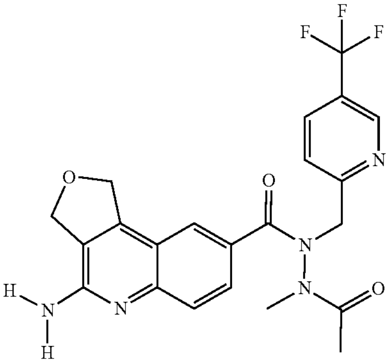 [SMILES: CC(=O)N(C)N(Cc1ccc(C(F)(F)F)cn1)C(=O)c1ccc2nc(N)c3c(c2c1)COC3] | N'-acetyl-4-amino-N'-methyl-N-((5-(trifluoromethyl)pyridin-2-yl)methyl)-1,3-dihydrofuro[3,4-c]quinoline-8-carbohydrazide |
| 169 | 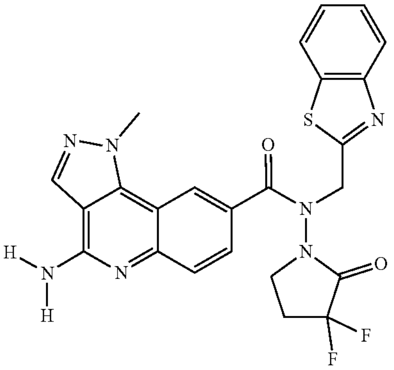 [SMILES: Cn1ncc2c(N)nc3ccc(C(=O)N(Cc4nc5ccccc5s4)N4CCC(F)(F)C4=O)cc3c21] | 4-amino-N-(benzo[d]thiazol-2-ylmethyl)-N-(3,3-difluoro-2-oxopyrrolidin-1-yl)-1-methyl-1H-pyrazolo[4,3-c]quinoline-8-carboxamide |

TABLE 1-continued

| Compounds | | |
|---|---|---|
| Example | Structure | Name |
| 170 | 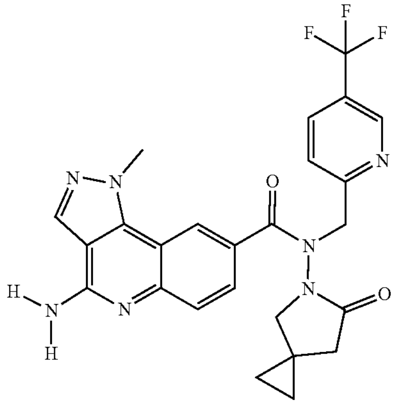 [SMILES: Cn1ncc2c(N)nc3ccc(C(=O)N(Cc4ccc(C(F)(F)F)cn4)N4CC5(CC5)CC4=O)cc3c21] | 4-amino-1-methyl-N-(6-oxo-5-azaspiro[2.4]heptan-5-yl)-N-((5-(trifluoromethyl)pyridin-2-yl)methyl)-1H-pyrazolo[4,3-c]quinoline-8-carboxamide |
| 171 | 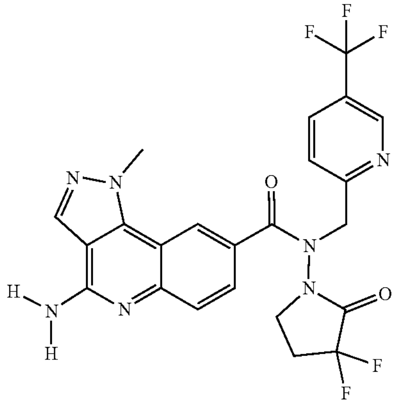 [SMILES: Cn1ncc2c(N)nc3ccc(C(=O)N(Cc4ccc(C(F)(F)F)cn4)N4CCC(F)(F)C4=O)cc3c21] | 4-amino-N-(3,3-difluoro-2-oxopyrrolidin-1-yl)-1-methyl-N-((5-(trifluoromethyl)pyridin-2-yl)methyl)-1H-pyrazolo[4,3-c]quinoline-8-carboxamide |
| 172 | 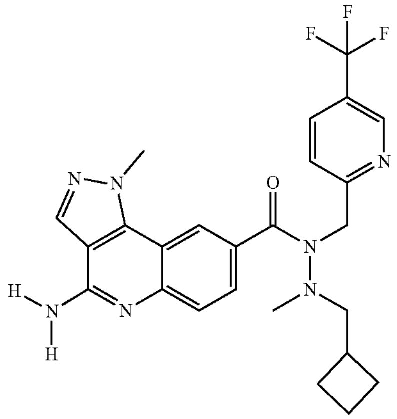 | 4-amino-N'-(cyclobutylmethyl)-N',1-dimethyl-N-((5-(trifluoromethyl)pyridin-2-yl)methyl)-1H-pyrazolo[4,3-c]quinoline-8-carbohydrazide |

TABLE 1-continued

| Example | Structure | Name |
|---|---|---|
| Compounds | | |
| 173 | 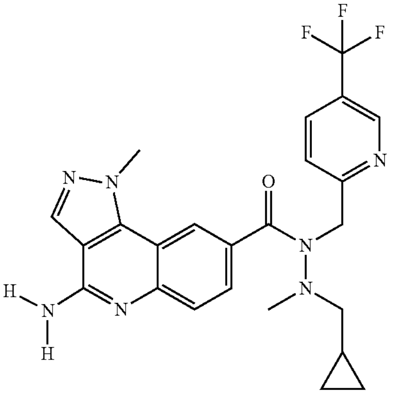 [SMILES: CN(CC1CC1)N(Cc1ccc(C(F)(F)F)cn1)C(=O)c1ccc2nc(N)c3cnn(C)c3c2c1] | 4-amino-N'-(cyclopropylmethyl)-N',1-dimethyl-N-((5-(trifluoromethyl)pyridin-2-yl)methyl)-1H-pyrazolo[4,3-c]quinoline-8-carbohydrazide |
| 174 | 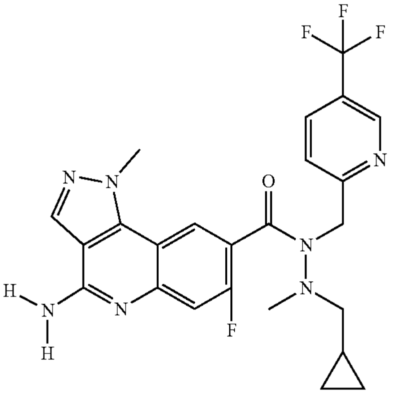 [SMILES: CN(CC1CC1)N(Cc1ccc(C(F)(F)F)cn1)C(=O)c1cc2c(cc1F)nc(N)c1cnn(C)c12] | 4-amino-N'-(cyclopropylmethyl)-7-fluoro-N',1-dimethyl-N-((5-(trifluoromethyl)pyridin-2-yl)methyl)-1H-pyrazolo[4,3-c]quinoline-8-carbohydrazide |
| 175 | 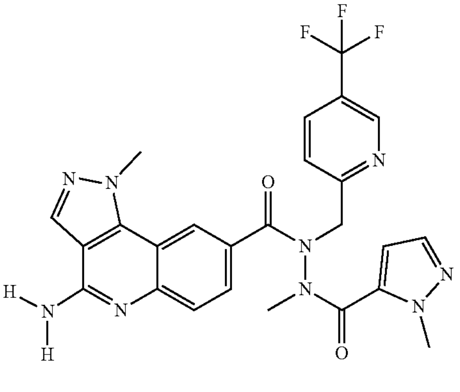 [SMILES: CN(C(=O)c1ccnn1C)N(Cc1ccc(C(F)(F)F)cn1)C(=O)c1ccc2nc(N)c3cnn(C)c3c2c1] | 4-amino-N',1-dimethyl-N'-(1-methyl-1H-pyrazole-5-carbonyl)-N-((5-(trifluoromethyl)pyridin-2-yl)methyl)-1H-pyrazolo[4,3-c]quinoline-8-carbohydrazide |

TABLE 1-continued

| Compounds | | |
|---|---|---|
| Example | Structure | Name |
| 176 | 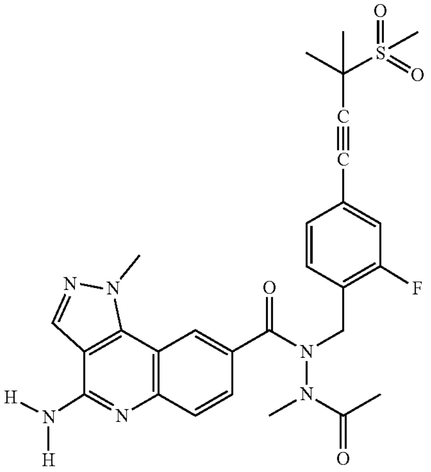 [SMILES: CC(=O)N(C)N(Cc1ccc(C#CC(C)(C)S(C)(=O)=O)cc1F)C(=O)c1ccc2nc(N)c3cnn(C)c3c2c1] | N'-acetyl-4-amino-N-(2-fluoro-4-(3-methyl-3-(methylsulfonyl)but-1-yn-1-yl)benzyl)-N',1-dimethyl-1H-pyrazolo[4,3-c]quinoline-8-carbohydrazide |
| 177 | 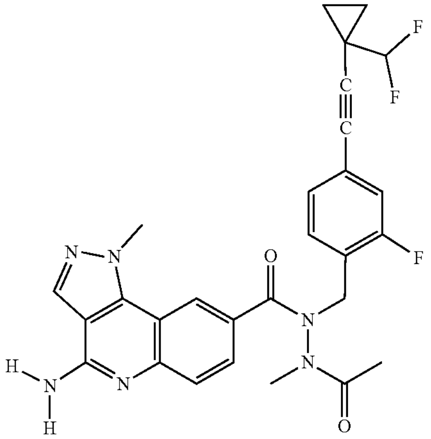 [SMILES: CC(=O)N(C)N(Cc1ccc(C#CC2(C(F)F)CC2)cc1F)C(=O)c1ccc2nc(N)c3cnn(C)c3c2c1] | N'-acetyl-4-amino-N-(4-((1-(difluoromethyl)cyclopropyl)ethynyl)-2-fluorobenzyl)-N',1-dimethyl-1H-pyrazolo[4,3-c]quinoline-8-carbohydrazide |
| 178 | 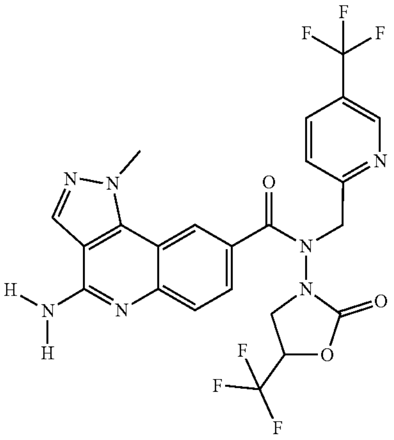 [SMILES: Cn1ncc2c(N)nc3ccc(C(=O)N(Cc4ccc(C(F)(F)F)cn4)N4CC(C(F)(F)F)OC4=O)cc3c21] | 4-amino-1-methyl-N-(2-oxo-5-(trifluoromethyl)oxazolidin-3-yl)-N-((5-(trifluoromethyl)pyridin-2-yl)methyl)-1H-pyrazolo[4,3-c]quinoline-8-carboxamide |

TABLE 1-continued

| Compounds | | |
|---|---|---|
| Example | Structure | Name |
| 179 | 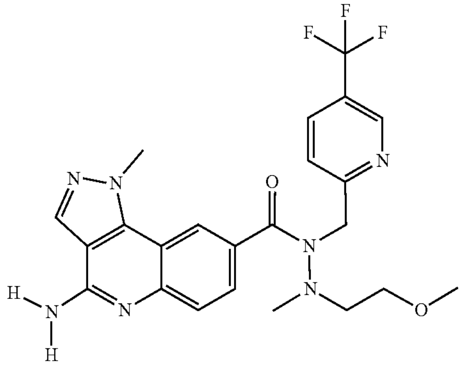 [SMILES: COCCN(C)N(Cc1ccc(C(F)(F)F)cn1)C(=O)c1ccc2nc(N)c3cnn(C)c3c2c1] | 4-amino-N'-(2-methoxyethyl)-N',1-dimethyl-N-((5-(trifluoromethyl)pyridin-2-yl)methyl)-1H-pyrazolo[4,3-c]quinoline-8-carbohydrazide |
| 180 | 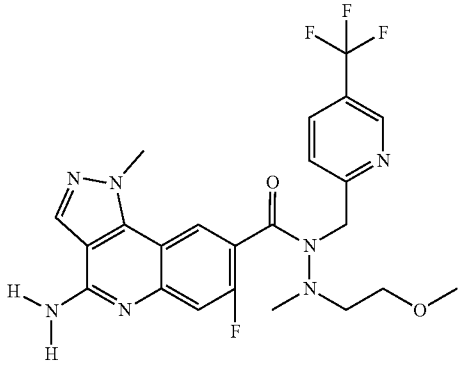 [SMILES: COCCN(C)N(Cc1ccc(C(F)(F)F)cn1)C(=O)c1cc2c(cc1F)nc(N)c1cnn(C)c12] | 4-amino-7-fluoro-N'-(2-methoxyethyl)-N',1-dimethyl-N-((5-(trifluoromethyl)pyridin-2-yl)methyl)-1H-pyrazolo[4,3-c]quinoline-8-carbohydrazide |
| 181 | 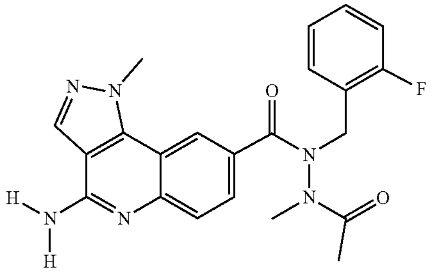 [SMILES: CC(=O)N(C)N(Cc1ccccc1F)C(=O)c1ccc2nc(N)c3cnn(C)c3c2c1] | N'-acetyl-4-amino-N-(2-fluorobenzyl)-N',1-dimethyl-1H-pyrazolo[4,3-c]quinoline-8-carbohydrazide |
| 182 | 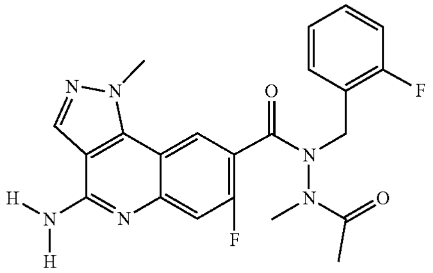 [SMILES: CC(=O)N(C)N(Cc1ccccc1F)C(=O)c1cc2c(cc1F)nc(N)c1cnn(C)c12] | N'-acetyl-4-amino-7-fluoro-N-(2-fluorobenzyl)-N',1-dimethyl-1H-pyrazolo[4,3-c]quinoline-8-carbohydrazide |
| 183 | 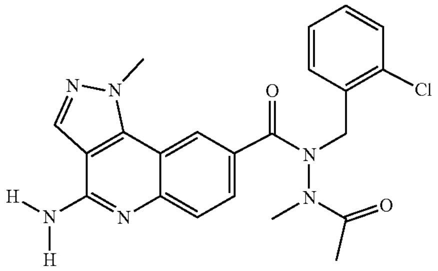 [SMILES: CC(=O)N(C)N(Cc1ccccc1Cl)C(=O)c1ccc2nc(N)c3cnn(C)c3c2c1] | N'-acetyl-4-amino-N-(2-chlorobenzyl)-N',1-dimethyl-1H-pyrazolo[4,3-c]quinoline-8-carbohydrazide |

TABLE 1-continued

| Compounds | | |
|---|---|---|
| Example | Structure | Name |
| 184 | 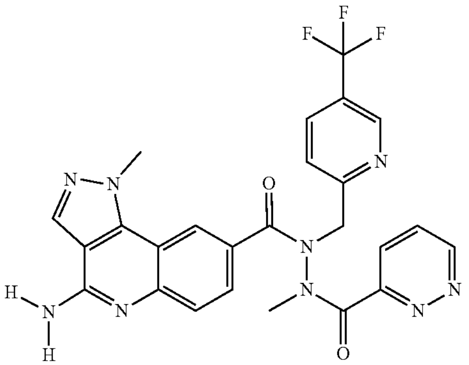 [SMILES: CN(C(=O)c1cccnn1)N(Cc1ccc(C(F)(F)F)cn1)C(=O)c1ccc2nc(N)c3cnn(C)c3c2c1] | 4-amino-N',1-dimethyl-N'-(pyridazine-3-carbonyl)-N-((5-(trifluoromethyl)pyridin-2-yl)methyl)-1H-pyrazolo[4,3-c]quinoline-8-carbohydrazide |
| 185 | 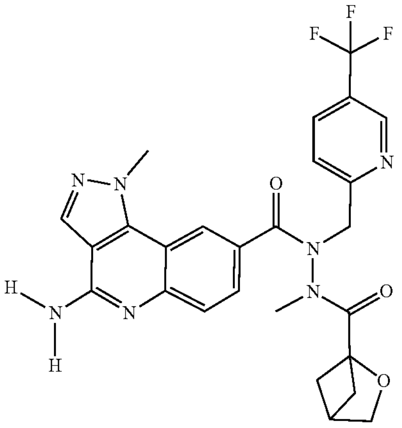 [SMILES: CN(C(=O)C12CC(CO1)C2)N(Cc1ccc(C(F)(F)F)cn1)C(=O)c1ccc2nc(N)c3cnn(C)c3c2c1] | 4-amino-N'-(2-oxabicyclo[2.1.1]hexane-1-carbonyl)-N',1-dimethyl-N-((5-(trifluoromethyl)pyridin-2-yl)methyl)-1H-pyrazolo[4,3-c]quinoline-8-carbohydrazide |
| 186 | 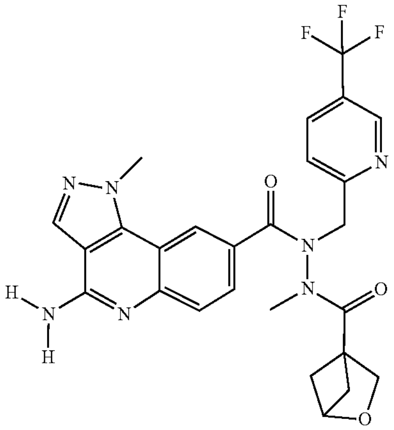 [SMILES: CN(C(=O)C12COC(C1)C2)N(Cc1ccc(C(F)(F)F)cn1)C(=O)c1ccc2nc(N)c3cnn(C)c3c2c1] | 4-amino-N'-(2-oxabicyclo[2.1.1]hexane-4-carbonyl)-N',1-dimethyl-N-((5-(trifluoromethyl)pyridin-2-yl)methyl)-1H-pyrazolo[4,3-c]quinoline-8-carbohydrazide |

TABLE 1-continued

| Compounds | | |
|---|---|---|
| Example | Structure | Name |
| 187 | 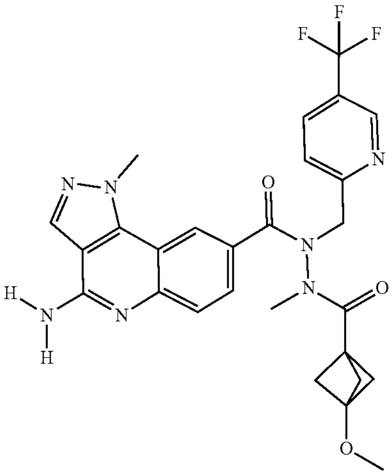 [SMILES: COC12CC(C(=O)N(C)N(Cc3ccc(C(F)(F)F)cn3)C(=O)c3ccc4nc(N)c5cnn(C)c5c4c3)(C1)C2] | 4-amino-N'-(3-methoxybicyclo[1.1.1]pentane-1-carbonyl)-N',1-dimethyl-N-((5-(trifluoromethyl)pyridin-2-yl)methyl)-1H-pyrazolo[4,3-c]quinoline-8-carbohydrazide |
| 188 | 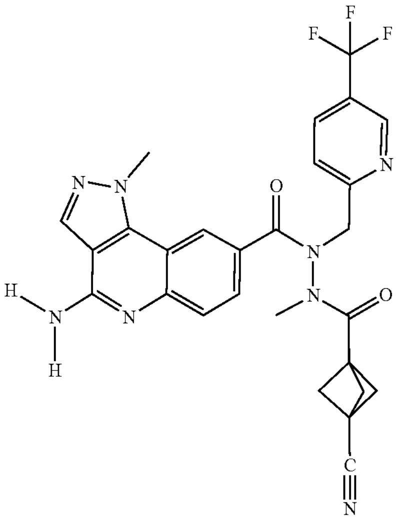 [SMILES: CN(C(=O)C12CC(C#N)(C1)C2)N(Cc1ccc(C(F)(F)F)cn1)C(=O)c1ccc2nc(N)c3cnn(C)c3c2c1] | 4-amino-N'-(3-cyanobicyclo[1.1.1]pentane-1-carbonyl)-N',1-dimethyl-N-((5-(trifluoromethyl)pyridin-2-yl)methyl)-1H-pyrazolo[4,3-c]quinoline-8-carbohydrazide |
| 189 | 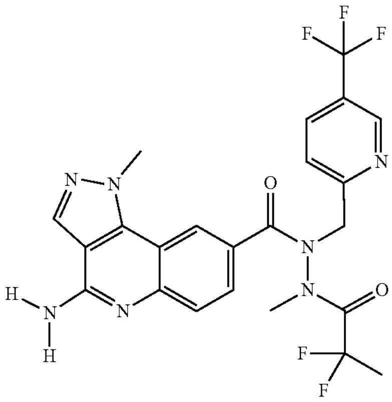 [SMILES: CN(C(=O)C(C)(F)F)N(Cc1ccc(C(F)(F)F)cn1)C(=O)c1ccc2nc(N)c3cnn(C)c3c2c1] | 4-amino-N'-(2,2-difluoropropanoyl)-N',1-dimethyl-N-((5-(trifluoromethyl)pyridin-2-yl)methyl)-1H-pyrazolo[4,3-c]quinoline-8-carbohydrazide |

TABLE 1-continued

| Compounds | | |
|---|---|---|
| Example | Structure | Name |
| 190 | 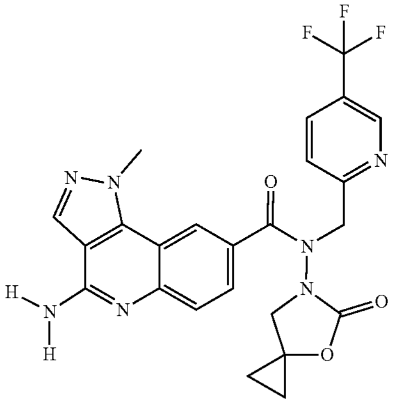 [SMILES: Cn1ncc2c(N)nc3ccc(C(=O)N(Cc4ccc(C(F)(F)F)cn4)N4CC5(CC5)OC4=O)cc3c21] | 4-amino-1-methyl-N-(5-oxo-4-oxa-6-azaspiro[2.4]heptan-6-yl)-N-((5-(trifluoromethyl)pyridin-2-yl)methyl)-1H-pyrazolo[4,3-c]quinoline-8-carboxamide |
| 191 | 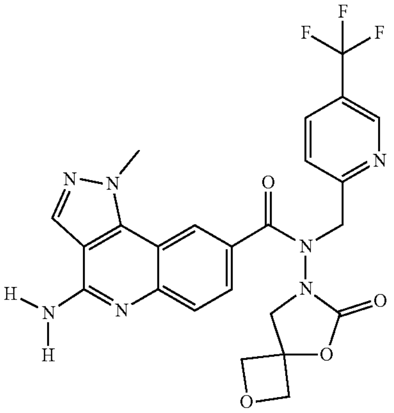 [SMILES: Cn1ncc2c(N)nc3ccc(C(=O)N(Cc4ccc(C(F)(F)F)cn4)N4CC5(COC5)OC4=O)cc3c21] | 4-amino-1-methyl-N-(6-oxo-2,5-dioxa-7-azaspiro[3.4]octan-7-yl)-N-((5-(trifluoromethyl)pyridin-2-yl)methyl)-1H-pyrazolo[4,3-c]quinoline-8-carboxamide |
| 192 | 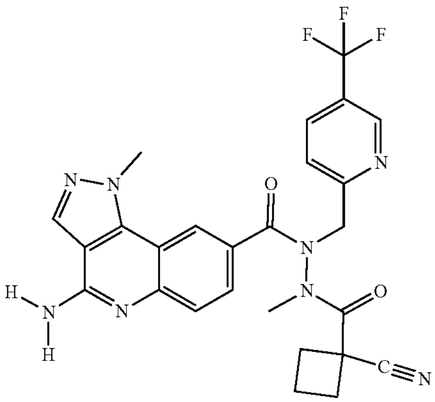 [SMILES: CN(C(=O)C1(C#N)CCC1)N(Cc1ccc(C(F)(F)F)cn1)C(=O)c1ccc2nc(N)c3cnn(C)c3c2c1] | 4-amino-N'-(1-cyanocyclobutane-1-carbonyl)-N',1-dimethyl-N-((5-(trifluoromethyl)pyridin-2-yl)methyl)-1H-pyrazolo[4,3-c]quinoline-8-carbohydrazide |

TABLE 1-continued

| Compounds | | |
|---|---|---|
| Example | Structure | Name |
| 193 | 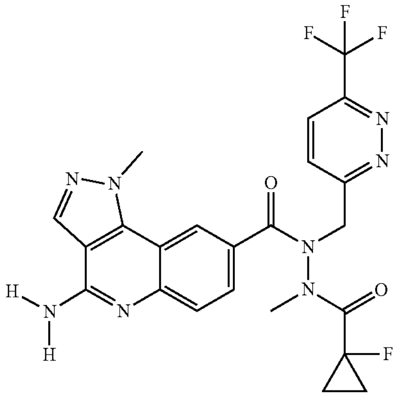 [SMILES: CN(C(=O)C1(F)CC1)N(Cc1ccc(C(F)(F)F)nn1)C(=O)c1ccc2nc(N)c3cnn(C)c3c2c1] | 4-amino-N'-(1-fluorocyclopropane-1-carbonyl)-N',1-dimethyl-N-((6-(trifluoromethyl)pyridazin-3-yl)methyl)-1H-pyrazolo[4,3-c]quinoline-8-carbohydrazide |
| 194 | 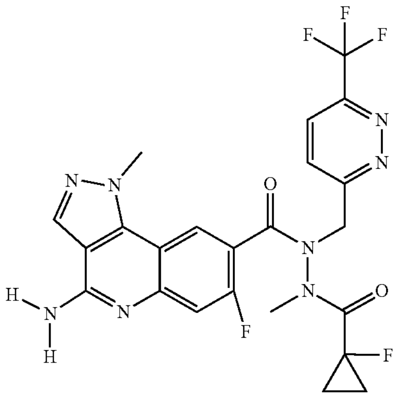 [SMILES: CN(C(=O)C1(F)CC1)N(Cc1ccc(C(F)(F)F)nn1)C(=O)c1cc2c(cc1F)nc(N)c1cnn(C)c12] | 4-amino-7-fluoro-N'-(1-fluorocyclopropane-1-carbonyl)-N',1-dimethyl-N-((6-(trifluoromethyl)pyridazin-3-yl)methyl)-1H-pyrazolo[4,3-c]quinoline-8-carbohydrazide |
| 195 | 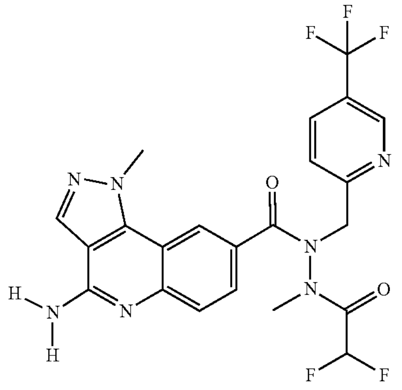 [SMILES: CN(C(=O)C(F)F)N(Cc1ccc(C(F)(F)F)cn1)C(=O)c1ccc2nc(N)c3cnn(C)c3c2c1] | 4-amino-N'-(2,2-difluoroacetyl)-N',1-dimethyl-N-((5-(trifluoromethyl)pyridin-2-yl)methyl)-1H-pyrazolo[4,3-c]quinoline-8-carbohydrazide |
| 196 | 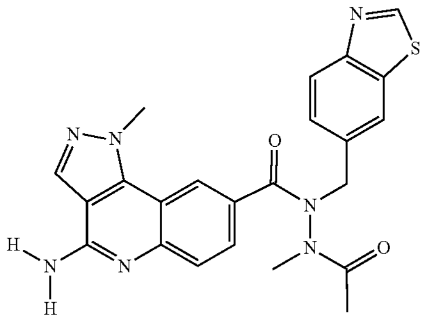 [SMILES: CC(=O)N(C)N(Cc1ccc2ncsc2c1)C(=O)c1ccc2nc(N)c3cnn(C)c3c2c1] | N'-acetyl-4-amino-N-(benzo[d]thiazol-6-ylmethyl)-N',1-dimethyl-1H-pyrazolo[4,3-c]quinoline-8-carbohydrazide |

TABLE 1-continued

| Compounds | | |
|---|---|---|
| Example | Structure | Name |
| 197 | 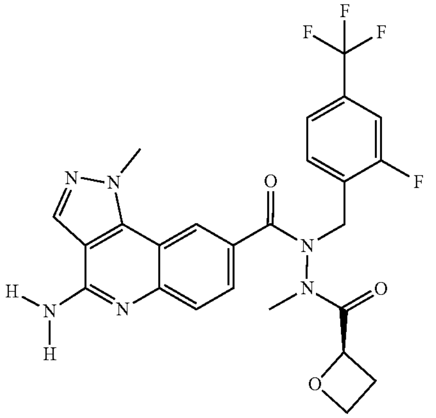 [SMILES: CN(C(=O)[C@H]1CCO1)N(Cc1ccc(C(F)(F)F)cc1F)C(=O)c1ccc2nc(N)c3cnn(C)c3c2c1] | (R)-4-amino-N-(2-fluoro-4-(trifluoromethyl)benzyl)-N',1-dimethyl-N'-(oxetane-2-carbonyl)-1H-pyrazolo[4,3-c]quinoline-8-carbohydrazide |
| 198 | 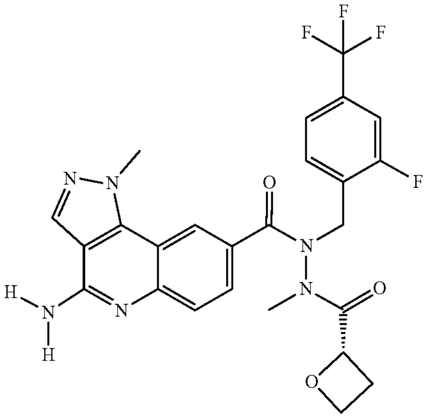 [SMILES: CN(C(=O)[C@@H]1CCO1)N(Cc1ccc(C(F)(F)F)cc1F)C(=O)c1ccc2nc(N)c3cnn(C)c3c2c1] | (S)-4-amino-N-(2-fluoro-4-(trifluoromethyl)benzyl)-N',1-dimethyl-N'-(oxetane-2-carbonyl)-1H-pyrazolo[4,3-c]quinoline-8-carbohydrazide |
| 199 | 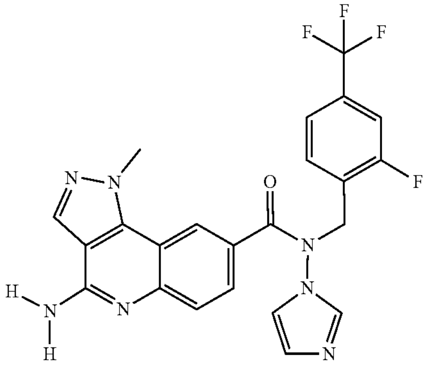 [SMILES: Cn1ncc2c(N)nc3ccc(C(=O)N(Cc4ccc(C(F)(F)F)cc4F)n4ccnc4)cc3c21] | 4-amino-N-(2-fluoro-4-(trifluoromethyl)benzyl)-N-(1H-imidazol-1-yl)-1-methyl-1H-pyrazolo[4,3-c]quinoline-8-carboxamide |

TABLE 1-continued

| Compounds | | |
|---|---|---|
| Example | Structure | Name |
| 200 | 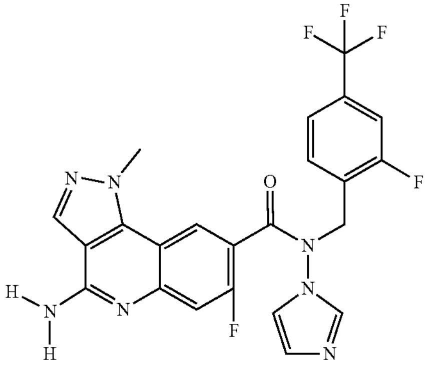 [SMILES: Cn1ncc2c(N)nc3cc(F)c(C(=O)N(Cc4ccc(C(F)(F)F)cc4F)n4ccnc4)cc3c21] | 4-amino-7-fluoro-N-(2-fluoro-4-(trifluoromethyl)benzyl)-N-(1H-imidazol-1-yl)-1-methyl-1H-pyrazolo[4,3-c]quinoline-8-carboxamide |
| 201 | 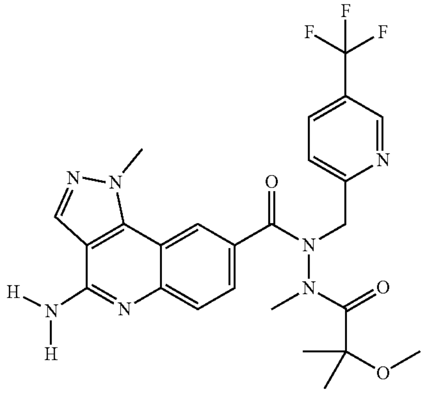 [SMILES: COC(C)(C)C(=O)N(C)N(Cc1ccc(C(F)(F)F)cn1)C(=O)c1ccc2nc(N)c3cnn(C)c3c2c1] | 4-amino-N'-(2-methoxy-2-methylpropanoyl)-N',1-dimethyl-N-((5-(trifluoromethyl)pyridin-2-yl)methyl)-1H-pyrazolo[4,3-c]quinoline-8-carbohydrazide |
| 202 | 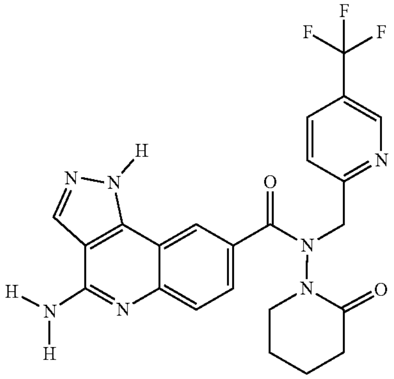 [SMILES: Nc1nc2ccc(C(=O)N(Cc3ccc(C(F)(F)F)cn3)N3CCCCC3=O)cc2c2[nH]ncc12] | 4-amino-N-(2-oxopiperidin-1-yl)-N-((5-(trifluoromethyl)pyridin-2-yl)methyl)-1H-pyrazolo[4,3-c]quinoline-8-carboxamide |
| 203 | 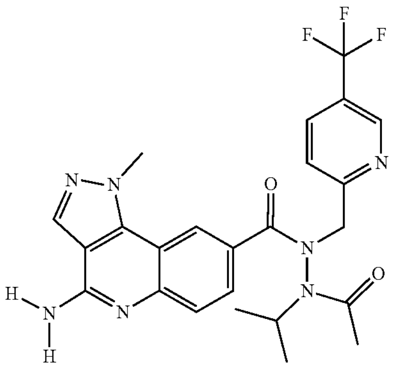 [SMILES: CC(=O)N(C(C)C)N(Cc1ccc(C(F)(F)F)cn1)C(=O)c1ccc2nc(N)c3cnn(C)c3c2c1] | N'-acetyl-4-amino-N'-isopropyl-1-methyl-N-((5-(trifluoromethyl)pyridin-2-yl)methyl)-1H-pyrazolo[4,3-c]quinoline-8-carbohydrazide |

TABLE 1-continued

| Compounds | | |
|---|---|---|
| Example | Structure | Name |
| 204 | 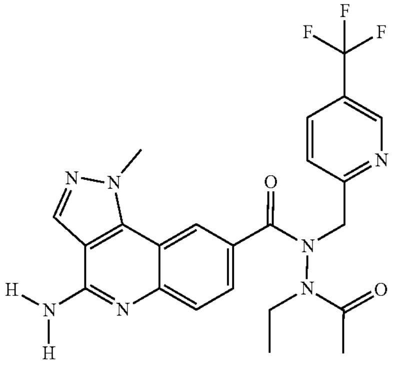 [SMILES: CCN(C(C)=O)N(Cc1ccc(C(F)(F)F)cn1)C(=O)c1ccc2nc(N)c3cnn(C)c3c2c1] | N'-acetyl-4-amino-N'-ethyl-1-methyl-N-((5-(trifluoromethyl)pyridin-2-yl)methyl)-1H-pyrazolo[4,3-c]quinoline-8-carbohydrazide |
| 205 | 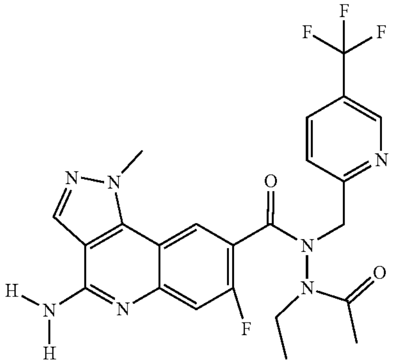 [SMILES: CCN(C(C)=O)N(Cc1ccc(C(F)(F)F)cn1)C(=O)c1cc2c(cc1F)nc(N)c1cnn(C)c12] | N'-acetyl-4-amino-N'-ethyl-7-fluoro-1-methyl-N-((5-(trifluoromethyl)pyridin-2-yl)methyl)-1H-pyrazolo[4,3-c]quinoline-8-carbohydrazide |
| 206 | 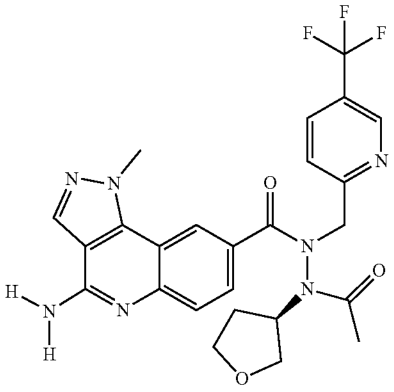 [SMILES: CC(=O)N([C@@H]1CCOC1)N(Cc1ccc(C(F)(F)F)cn1)C(=O)c1ccc2nc(N)c3cnn(C)c3c2c1] | (R)-N'-acetyl-4-amino-1-methyl-N'-(tetrahydrofuran-3-yl)-N-((5-(trifluoromethyl)pyridin-2-yl)methyl)-1H-pyrazolo[4,3-c]quinoline-8-carbohydrazide |
| 207 | 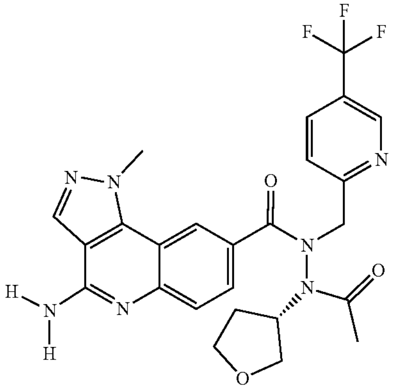 [SMILES: CC(=O)N([C@H]1CCOC1)N(Cc1ccc(C(F)(F)F)cn1)C(=O)c1ccc2nc(N)c3cnn(C)c3c2c1] | (S)-N'-acetyl-4-amino-1-methyl-N'-(tetrahydrofuran-3-yl)-N-((5-(trifluoromethyl)pyridin-2-yl)methyl)-1H-pyrazolo[4,3-c]quinoline-8-carbohydrazide |

TABLE 1-continued

| Compounds | | |
|---|---|---|
| Example | Structure | Name |
| 208 | 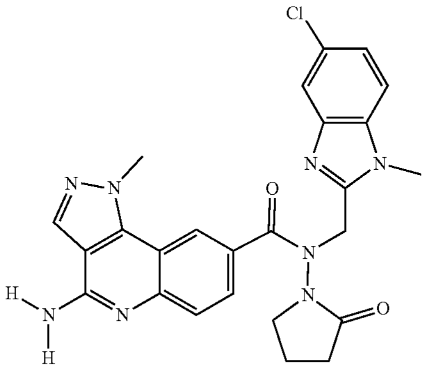 [SMILES: Cn1ncc2c(N)nc3ccc(C(=O)N(Cc4nc5cc(Cl)ccc5n4C)N4CCCC4=O)cc3c21] | 4-amino-N-((5-chloro-1-methyl-1H-benzo[d]imidazol-2-yl)methyl)-1-methyl-N-(2-oxopyrrolidin-1-yl)-1H-pyrazolo[4,3-c]quinoline-8-carboxamide |
| 209 | 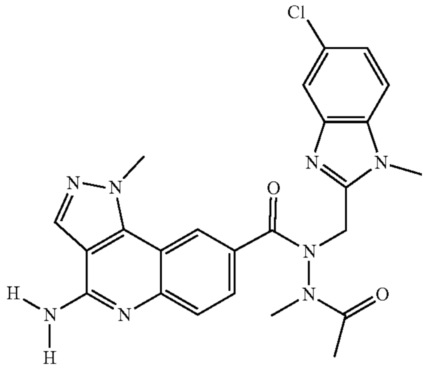 [SMILES: CC(=O)N(C)N(Cc1nc2cc(Cl)ccc2n1C)C(=O)c1ccc2nc(N)c3cnn(C)c3c2c1] | N'-acetyl-4-amino-N-((5-chloro-1-methyl-1H-benzo[d]imidazol-2-yl)methyl)-N',1-dimethyl-1H-pyrazolo[4,3-c]quinoline-8-carbohydrazide |
| 210 | 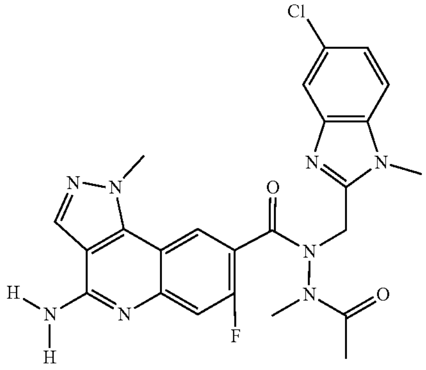 [SMILES: CC(=O)N(C)N(Cc1nc2cc(Cl)ccc2n1C)C(=O)c1cc2c(cc1F)nc(N)c1cnn(C)c12] | N'-acetyl-4-amino-N-((5-chloro-1-methyl-1H-benzo[d]imidazol-2-yl)methyl)-7-fluoro-N',1-dimethyl-1H-pyrazolo[4,3-c]quinoline-8-carbohydrazide |
| 211 | 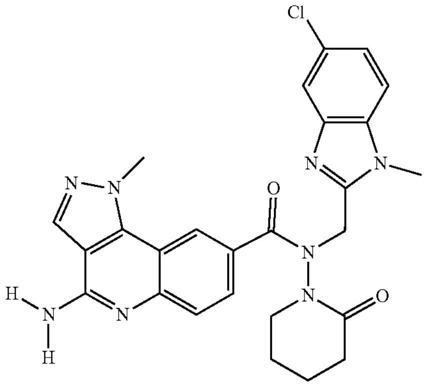 [SMILES: Cn1ncc2c(N)nc3ccc(C(=O)N(Cc4nc5cc(Cl)ccc5n4C)N4CCCCC4=O)cc3c21] | 4-amino-N-((5-chloro-1-methyl-1H-benzo[d]imidazol-2-yl)methyl)-1-methyl-N-(2-oxopiperidin-1-yl)-1H-pyrazolo[4,3-c]quinoline-8-carboxamide |

TABLE 1-continued

| Compounds | | |
|---|---|---|
| Example | Structure | Name |
| 212 | 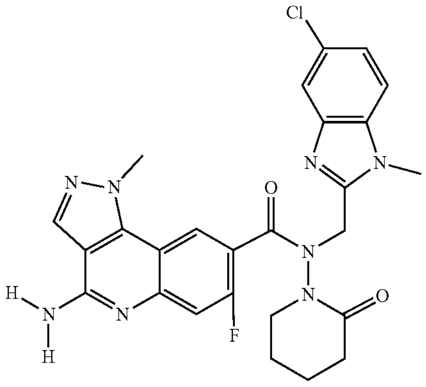 [SMILES: Cn1ncc2c(N)nc3cc(F)c(C(=O)N(Cc4nc5cc(Cl)ccc5n4C)N4CCCCC4=O)cc3c21] | 4-amino-N-((5-chloro-1-methyl-1H-benzo[d]imidazol-2-yl)methyl)-7-fluoro-1-methyl-N-(2-oxopiperidin-1-yl)-1H-pyrazolo[4,3-c]quinoline-8-carboxamide |
| 213 | 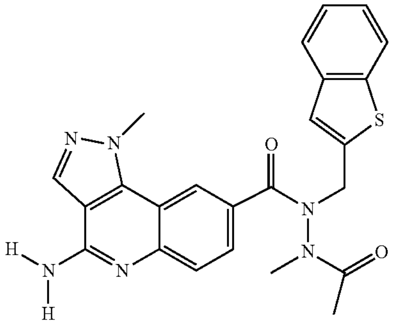 [SMILES: CC(=O)N(C)N(Cc1cc2ccccc2s1)C(=O)c1ccc2nc(N)c3cnn(C)c3c2c1] | N'-acetyl-4-amino-N-(benzo[b]thiophen-2-ylmethyl)-N',1-dimethyl-1H-pyrazolo[4,3-c]quinoline-8-carbohydrazide |
| 214 | 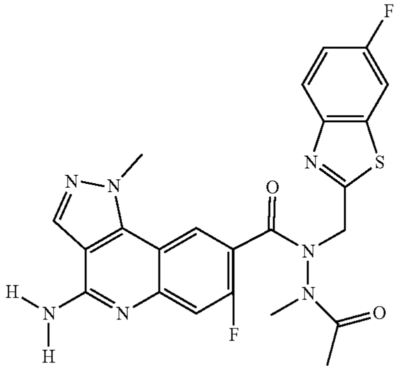 [SMILES: CC(=O)N(C)N(Cc1nc2ccc(F)cc2s1)C(=O)c1cc2c(cc1F)nc(N)c1cnn(C)c12] | N'-acetyl-4-amino-7-fluoro-N-((6-fluorobenzo[d]thiazol-2-yl)methyl)-N',1-dimethyl-1H-pyrazolo[4,3-c]quinoline-8-carbohydrazide |
| 215 | 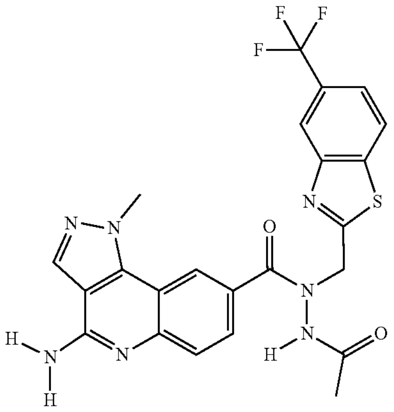 [SMILES: CC(=O)NN(Cc1nc2cc(C(F)(F)F)ccc2s1)C(=O)c1ccc2nc(N)c3cnn(C)c3c2c1] | N'-acetyl-4-amino-1-methyl-N-((5-(trifluoromethyl)benzo[d]thiazol-2-yl)methyl)-1H-pyrazolo[4,3-c]quinoline-8-carbohydrazide |

TABLE 1-continued

| Compounds | | |
|---|---|---|
| Example | Structure | Name |
| 216 | 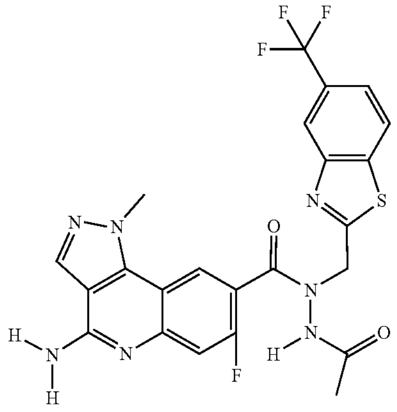 [SMILES: CC(=O)NN(Cc1nc2cc(C(F)(F)F)ccc2s1)C(=O)c1cc2c(cc1F)nc(N)c1cnn(C)c12] | N'-acetyl-4-amino-7-fluoro-1-methyl-N-((5-(trifluoromethyl)benzo[d]thiazol-2-yl)methyl)-1H-pyrazolo[4,3-c]quinoline-8-carbohydrazide |

TABLE 1A

| Some compounds | | |
|---|---|---|
| Example | Structure | Name |
| 217 | 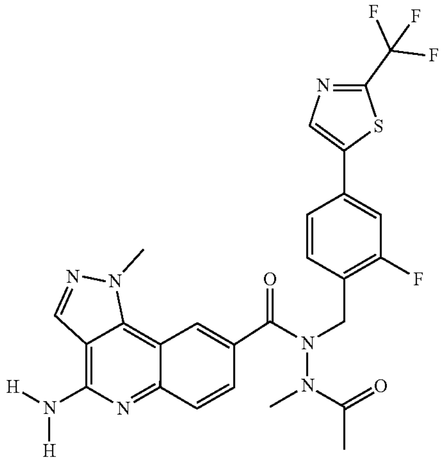 [SMILES: CC(=O)N(C)N(Cc1ccc(-c2cnc(C(F)(F)F)s2)cc1F)C(=O)c1ccc2nc(N)c3cnn(C)c3c2c1] | N'-acetyl-4-amino-N-(2-fluoro-4-(2-(trifluoromethyl)thiazol-5-yl)benzyl)-N',1-dimethyl-1H-pyrazolo[4,3-c]quinoline-8-carbohydrazide |
| 218 | 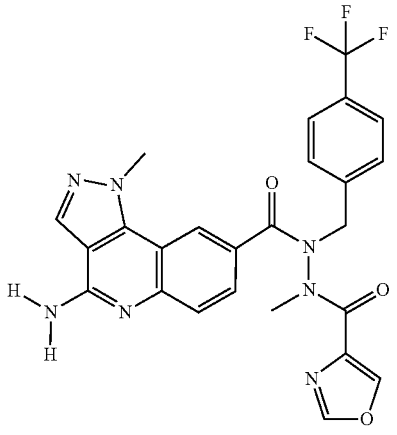 [SMILES: CN(C(=O)c1cocn1)N(Cc1ccc(C(F)(F)F)cc1)C(=O)c1ccc2nc(N)c3cnn(C)c3c2c1] | N'-(4-amino-1-methyl-1H-pyrazolo[4,3-c]quinoline-8-carbonyl)-N-methyl-N'-(4-(trifluoromethyl)benzyl)oxazole-4-carbohydrazide |

TABLE 1A-continued

| Example | Structure | Name |
|---|---|---|
| 219 | 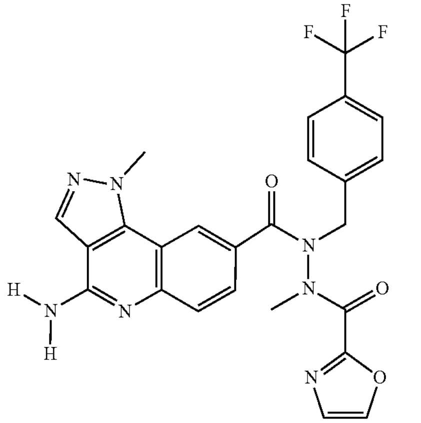 [SMILES: CN(C(=O)c1ncco1)N(Cc1ccc(C(F)(F)F)cc1)C(=O)c1ccc2nc(N)c3cnn(C)c3c2c1] | N'-(4-amino-1-methyl-1H-pyrazolo[4,3-c]quinoline-8-carbonyl)-N-methyl-N'-(4-(trifluoromethyl)benzyl)oxazole-2-carbohydrazide |
| 220 | 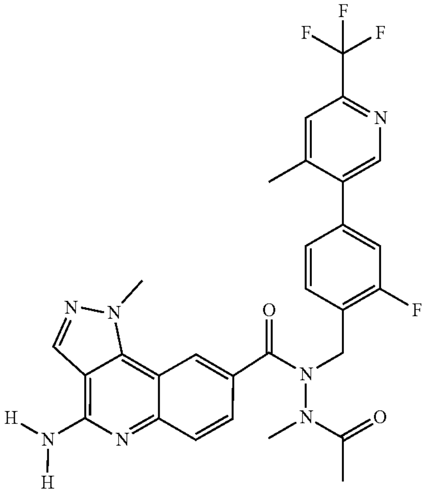 [SMILES: CC(=O)N(C)N(Cc1ccc(-c2cnc(C(F)(F)F)cc2C)cc1F)C(=O)c1ccc2nc(N)c3cnn(C)c3c2c1] | N'-acetyl-4-amino-N-(2-fluoro-4-(4-methyl-6-(trifluoromethyl)pyridin-3-yl)benzyl)-N',1-dimethyl-1H-pyrazolo[4,3-c]quinoline-8-carbohydrazide |
| 221 | 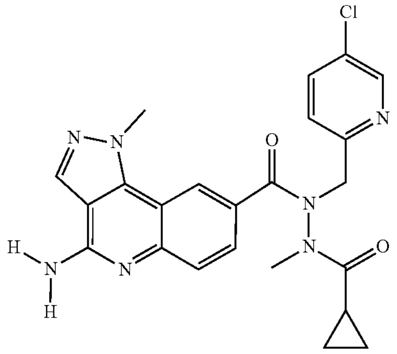 [SMILES: CN(C(=O)C1CC1)N(Cc1ccc(Cl)cn1)C(=O)c1ccc2nc(N)c3cnn(C)c3c2c1] | 4-amino-N-((5-chloropyridin-2-yl)methyl)-N'-(cyclopropanecarbonyl)-N',1-dimethyl-1H-pyrazolo[4,3-c]quinoline-8-carbohydrazide |

TABLE 1A-continued

| Some compounds | | |
|---|---|---|
| Example | Structure | Name |
| 222 | 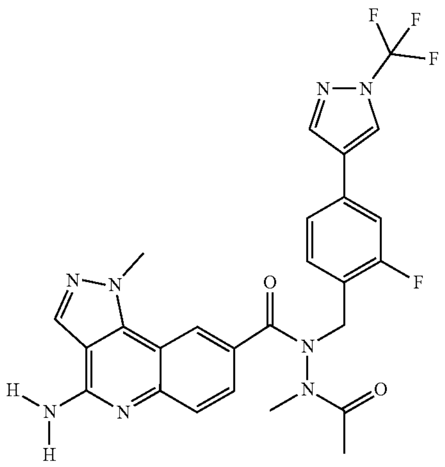 [SMILES: CC(=O)N(C)N(Cc1ccc(-c2cnn(C(F)(F)F)c2)cc1F)C(=O)c1ccc2nc(N)c3cnn(C)c3c2c1] | N'-acetyl-4-amino-N-(2-fluoro-4-(1-(trifluoromethyl)-1H-pyrazol-4-yl)benzyl)-N',1-dimethyl-1H-pyrazolo[4,3-c]quinoline-8-carbohydrazide |
| 223 | 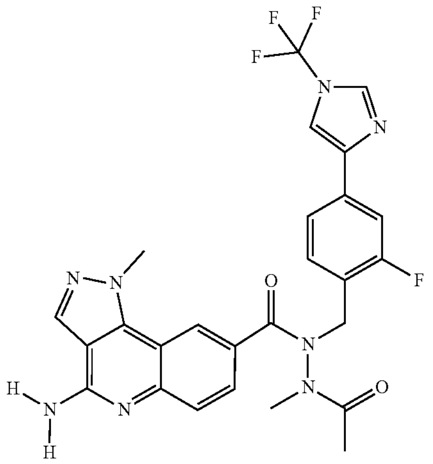 [SMILES: CC(=O)N(C)N(Cc1ccc(-c2cn(C(F)(F)F)cn2)cc1F)C(=O)c1ccc2nc(N)c3cnn(C)c3c2c1] | N'-acetyl-4-amino-N-(2-fluoro-4-(1-(trifluoromethyl)-1H-imidazol-4-yl)benzyl)-N',1-dimethyl-1H-pyrazolo[4,3-c]quinoline-8-carbohydrazide |
| 224 | 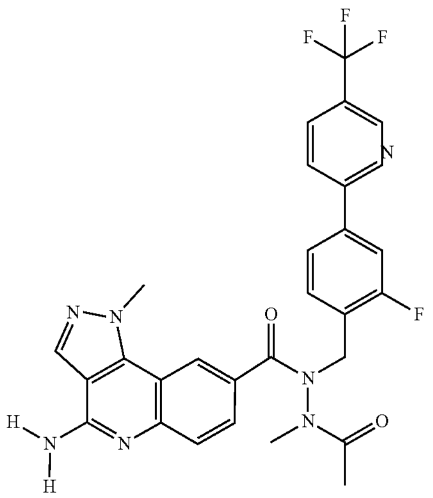 | N'-acetyl-4-amino-N-(2-fluoro-4-(5-(trifluoromethyl)pyridin-2-yl)benzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 225 | 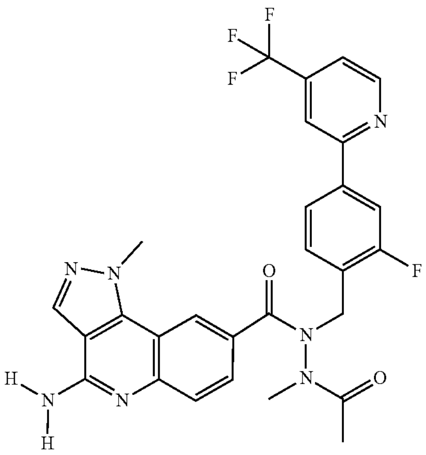 [SMILES: CC(=O)N(C)N(Cc1ccc(-c2cc(C(F)(F)F)ccn2)cc1F)C(=O)c1ccc2nc(N)c3cnn(C)c3c2c1] | N'-acetyl-4-amino-N-(2-fluoro-4-(4-(trifluoromethyl)pyridin-2-yl)benzyl)-N',1-dimethyl-1H-pyrazolo[4,3-c]quinoline-8-carbohydrazide |
| 226 | 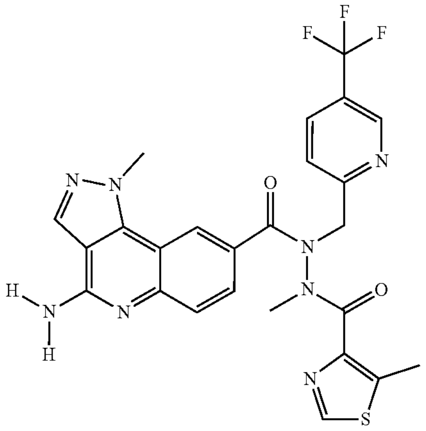 [SMILES: Cc1scnc1C(=O)N(C)N(Cc1ccc(C(F)(F)F)cn1)C(=O)c1ccc2nc(N)c3cnn(C)c3c2c1] | N'-(4-amino-1-methyl-1H-pyrazolo[4,3-c]quinoline-8-carbonyl)-N,5-dimethyl-N'-((5-(trifluoromethyl)pyridin-2-yl)methyl)thiazole-4-carbohydrazide |
| 227 | 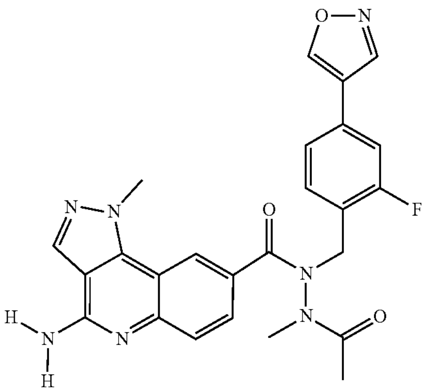 [SMILES: CC(=O)N(C)N(Cc1ccc(-c2cnoc2)cc1F)C(=O)c1ccc2nc(N)c3cnn(C)c3c2c1] | N'-acetyl-4-amino-N-(2-fluoro-4-(isoxazol-4-yl)benzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 228 | 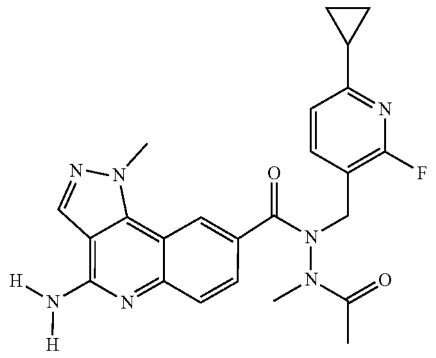 [SMILES: CC(=O)N(C)N(Cc1ccc(C2CC2)nc1F)C(=O)c1ccc2nc(N)c3cnn(C)c3c2c1] | N'-acetyl-4-amino-N-((6-cyclopropyl-2-fluoropyridin-3-yl)methyl)-N',1-dimethyl-1H-pyrazolo[4,3-c]quinoline-8-carbohydrazide |
| 229 | 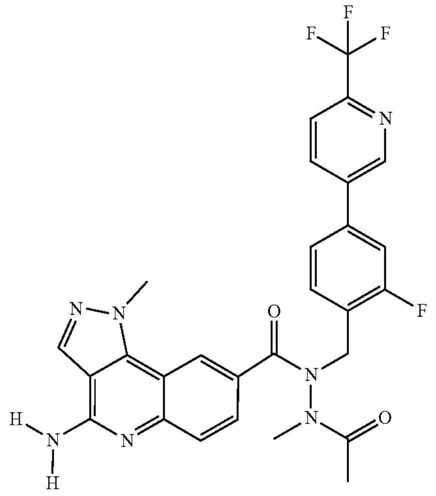 [SMILES: CC(=O)N(C)N(Cc1ccc(-c2ccc(C(F)(F)F)nc2)cc1F)C(=O)c1ccc2nc(N)c3cnn(C)c3c2c1] | N'-acetyl-4-amino-N-(2-fluoro-4-(6-(trifluoromethyl)pyridin-3-yl)benzyl)-N',1-dimethyl-1H-pyrazolo[4,3-c]quinoline-8-carbohydrazide |
| 230 | 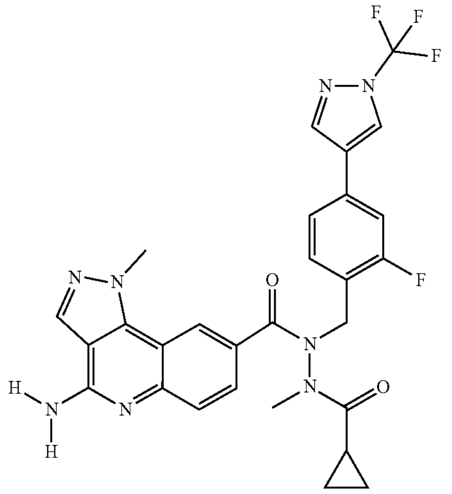 [SMILES: CN(C(=O)C1CC1)N(Cc1ccc(-c2cnn(C(F)(F)F)c2)cc1F)C(=O)c1ccc2nc(N)c3cnn(C)c3c2c1] | 4-amino-N'-(cyclopropanecarbonyl)-N-(2-fluoro-4-(1-(trifluoromethyl)-1H-pyrazol-4-yl)benzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 231 | 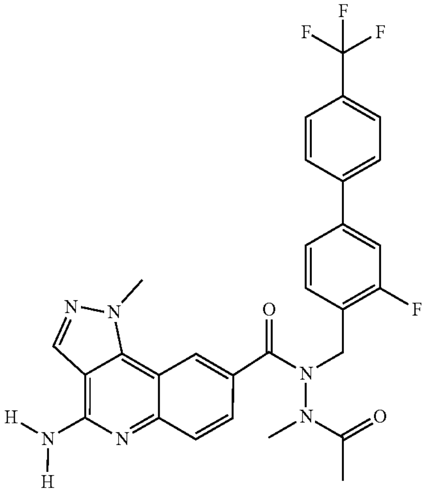 [SMILES: CC(=O)N(C)N(Cc1ccc(-c2ccc(C(F)(F)F)cc2)cc1F)C(=O)c1ccc2nc(N)c3cnn(C)c3c2c1] | N'-acetyl-4-amino-N-((3-fluoro-4'-(trifluoromethyl)-[1,1'-biphenyl]-4-yl)methyl)-N',1-dimethyl-1H-pyrazolo[4,3-c]quinoline-8-carbohydrazide |
| 232 | 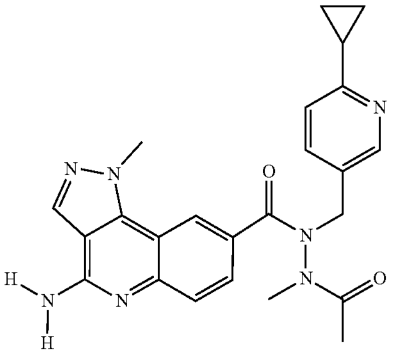 [SMILES: CC(=O)N(C)N(Cc1ccc(C2CC2)nc1)C(=O)c1ccc2nc(N)c3cnn(C)c3c2c1] | N'-acetyl-4-amino-N-((6-cyclopropylpyridin-3-yl)methyl)-N',1-dimethyl-1H-pyrazolo[4,3-c]quinoline-8-carbohydrazide |
| 233 | 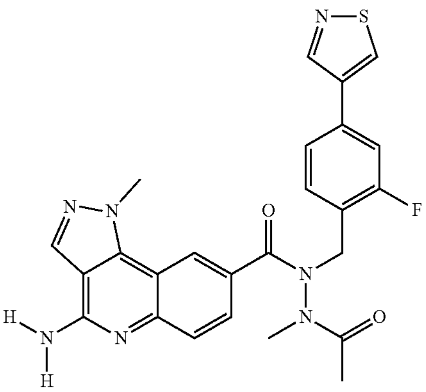 [SMILES: CC(=O)N(C)N(Cc1ccc(-c2cnsc2)cc1F)C(=O)c1ccc2nc(N)c3cnn(C)c3c2c1] | N'-acetyl-4-amino-N-(2-fluoro-4-(isothiazol-4-yl)benzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 234 | 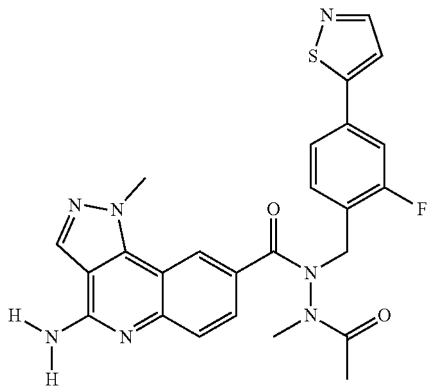 [SMILES: CC(=O)N(C)N(Cc1ccc(-c2ccns2)cc1F)C(=O)c1ccc2nc(N)c3cnn(C)c3c2c1] | N'-acetyl-4-amino-N-(2-fluoro-4-(isothiazol-5-yl)benzyl)-N',1-dimethyl-1H-pyrazolo[4,3-c]quinoline-8-carbohydrazide |
| 235 | 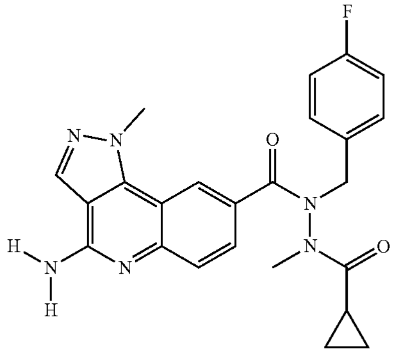 [SMILES: CN(C(=O)C1CC1)N(Cc1ccc(F)cc1)C(=O)c1ccc2nc(N)c3cnn(C)c3c2c1] | 4-amino-N'-(cyclopropanecarbonyl)-N-(4-fluorobenzyl)-N',1-dimethyl-1H-pyrazolo[4,3-c]quinoline-8-carbohydrazide |
| 236 | 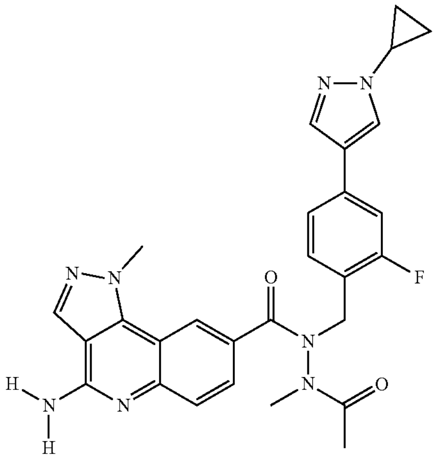 [SMILES: CC(=O)N(C)N(Cc1ccc(-c2cnn(C3CC3)c2)cc1F)C(=O)c1ccc2nc(N)c3cnn(C)c3c2c1] | N'-acetyl-4-amino-N-(4-(1-cyclopropyl-1H-pyrazol-4-yl)-2-fluorobenzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 237 | 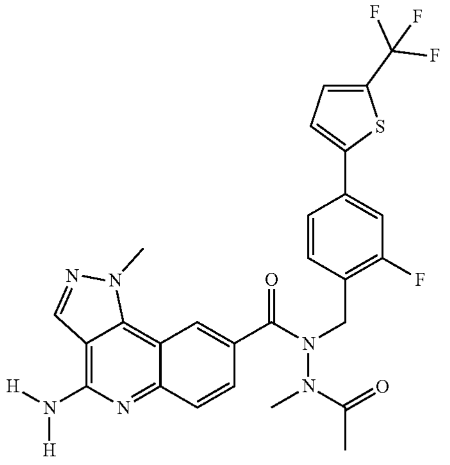 [SMILES: CC(=O)N(C)N(Cc1ccc(-c2ccc(C(F)(F)F)s2)cc1F)C(=O)c1ccc2nc(N)c3cnn(C)c3c2c1] | N'-acetyl-4-amino-N-(2-fluoro-4-(5-(trifluoromethyl)thiophen-2-yl)benzyl)-N',1-dimethyl-1H-pyrazolo[4,3-c]quinoline-8-carbohydrazide |
| 238 | 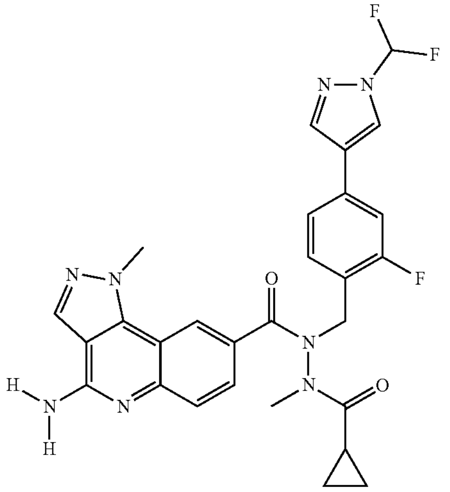 [SMILES: CN(C(=O)C1CC1)N(Cc1ccc(-c2cnn(C(F)F)c2)cc1F)C(=O)c1ccc2nc(N)c3cnn(C)c3c2c1] | 4-amino-N'-(cyclopropanecarbonyl)-N-(4-(1-(difluoromethyl)-1H-pyrazol-4-yl)-2-fluorobenzyl)-N',1-dimethyl-1H-pyrazolo[4,3-c]quinoline-8-carbohydrazide |
| 239 | 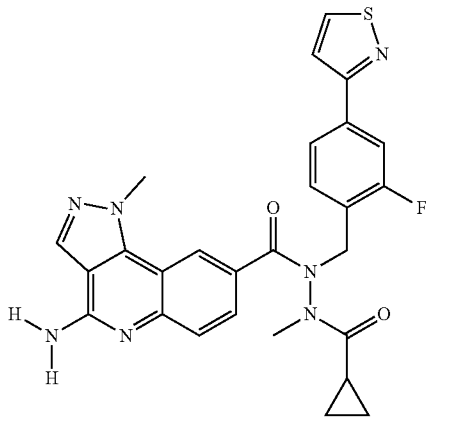 [SMILES: CN(C(=O)C1CC1)N(Cc1ccc(-c2ccsn2)cc1F)C(=O)c1ccc2nc(N)c3cnn(C)c3c2c1] | 4-amino-N'-(cyclopropanecarbonyl)-N-(2-fluoro-4-(isothiazol-3-yl)benzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 240 | 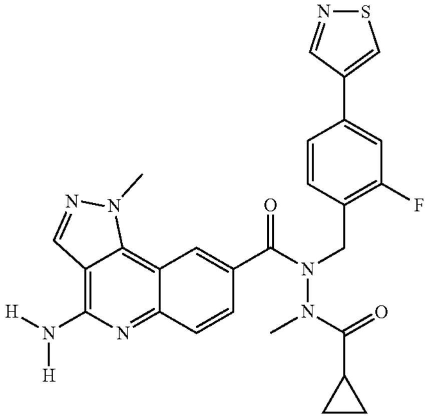 [SMILES: CN(C(=O)C1CC1)N(Cc1ccc(-c2cnsc2)cc1F)C(=O)c1ccc2nc(N)c3cnn(C)c3c2c1] | 4-amino-N'-(cyclopropanecarbonyl)-N-(2-fluoro-4-(isothiazol-4-yl)benzyl)-N',1-dimethyl-1H-pyrazolo[4,3-c]quinoline-8-carbohydrazide |
| 241 | 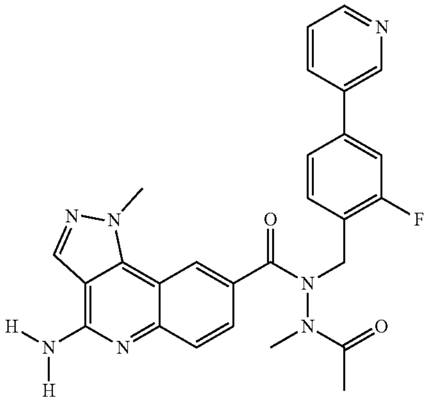 [SMILES: CC(=O)N(C)N(Cc1ccc(-c2cccnc2)cc1F)C(=O)c1ccc2nc(N)c3cnn(C)c3c2c1] | N'-acetyl-4-amino-N-(2-fluoro-4-(pyridin-3-yl)benzyl)-N',1-dimethyl-1H-pyrazolo[4,3-c]quinoline-8-carbohydrazide |
| 242 | 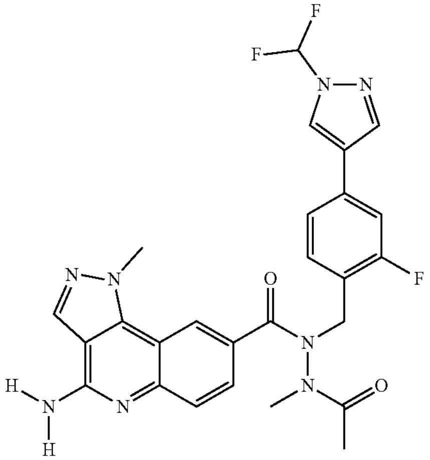 [SMILES: CC(=O)N(C)N(Cc1ccc(-c2cnn(C(F)F)c2)cc1F)C(=O)c1ccc2nc(N)c3cnn(C)c3c2c1] | N'-acetyl-4-amino-N-(4-(1-(difluoromethyl)-1H-pyrazol-4-yl)-2-fluorobenzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 243 | 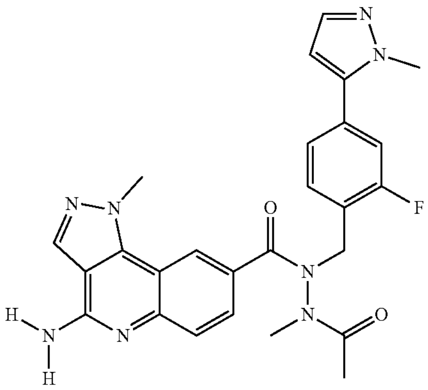 [SMILES: CC(=O)N(C)N(Cc1ccc(-c2ccnn2C)cc1F)C(=O)c1ccc2nc(N)c3cnn(C)c3c2c1] | N'-acetyl-4-amino-N-(2-fluoro-4-(1-methyl-1H-pyrazol-5-yl)benzyl)-N',1-dimethyl-1H-pyrazolo[4,3-c]quinoline-8-carbohydrazide |
| 244 | 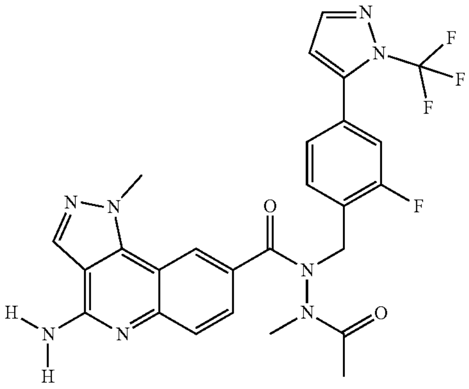 [SMILES: CC(=O)N(C)N(Cc1ccc(-c2ccnn2C(F)(F)F)cc1F)C(=O)c1ccc2nc(N)c3cnn(C)c3c2c1] | N'-acetyl-4-amino-N-(2-fluoro-4-(1-(trifluoromethyl)-1H-pyrazol-5-yl)benzyl)-N',1-dimethyl-1H-pyrazolo[4,3-c]quinoline-8-carbohydrazide |
| 245 | 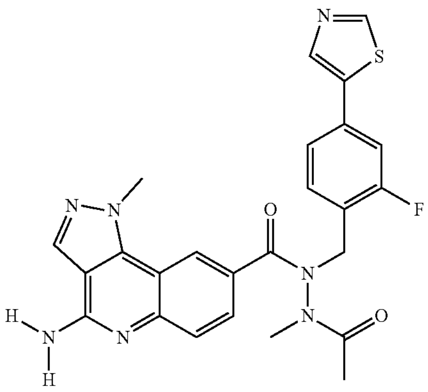 [SMILES: CC(=O)N(C)N(Cc1ccc(-c2cncs2)cc1F)C(=O)c1ccc2nc(N)c3cnn(C)c3c2c1] | N'-acetyl-4-amino-N-(2-fluoro-4-(thiazol-5-yl)benzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 246 | 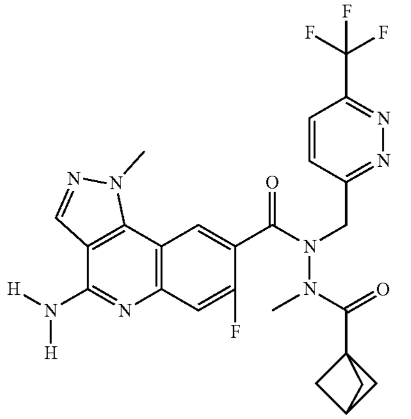 [SMILES: CN(C(=O)C12CC(C1)C2)N(Cc1ccc(C(F)(F)F)nn1)C(=O)c1cc2c(cc1F)nc(N)c1cnn(C)c12] | 4-amino-N'-(bicyclo[1.1.1]pentane-1-carbonyl)-7-fluoro-N',1-dimethyl-N-((6-(trifluoromethyl)pyridazin-3-yl)methyl)-1H-pyrazolo[4,3-c]quinoline-8-carbohydrazide |
| 247 | 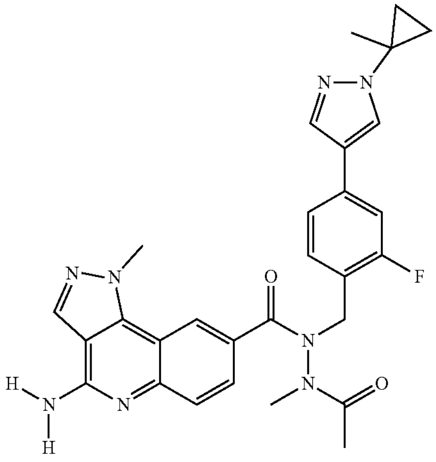 [SMILES: CC(=O)N(C)N(Cc1ccc(-c2cnn(C3(C)CC3)c2)cc1F)C(=O)c1ccc2nc(N)c3cnn(C)c3c2c1] | N'-acetyl-4-amino-N-(2-fluoro-4-(1-(1-methylcyclopropyl)-1H-pyrazol-4-yl)benzyl)-N',1-dimethyl-1H-pyrazolo[4,3-c]quinoline-8-carbohydrazide |
| 248 | 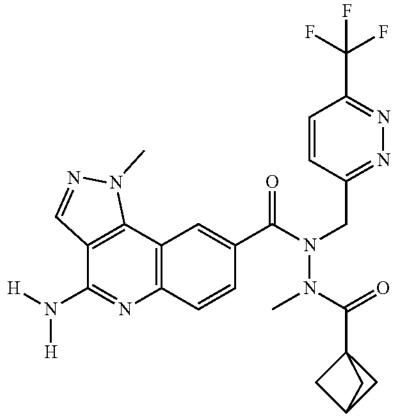 [SMILES: CN(C(=O)C12CC(C1)C2)N(Cc1ccc(C(F)(F)F)nn1)C(=O)c1ccc2nc(N)c3cnn(C)c3c2c1] | 4-amino-N'-(bicyclo[1.1.1]pentane-1-carbonyl)-N',1-dimethyl-N-((6-(trifluoromethyl)pyridazin-3-yl)methyl)-1H-pyrazolo[4,3-c]quinoline-8-carbohydrazide |

TABLE 1A-continued

| Some compounds | | |
|---|---|---|
| Example | Structure | Name |
| 249 | 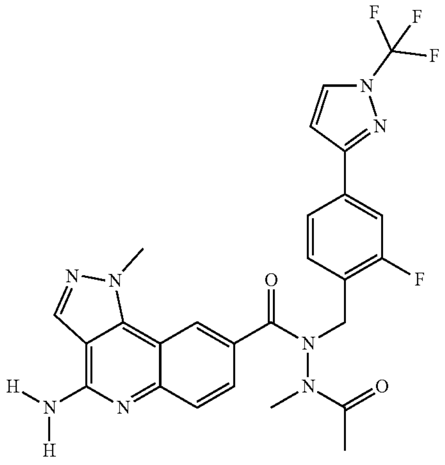 [SMILES: CC(=O)N(C)N(Cc1ccc(-c2ccn(C(F)(F)F)n2)cc1F)C(=O)c1ccc2nc(N)c3cnn(C)c3c2c1] | N'-acetyl-4-amino-N-(2-fluoro-4-(1-(trifluoromethyl)-1H-pyrazol-3-yl)benzyl)-N',1-dimethyl-1H-pyrazolo[4,3-c]quinoline-8-carbohydrazide |
| 250 | 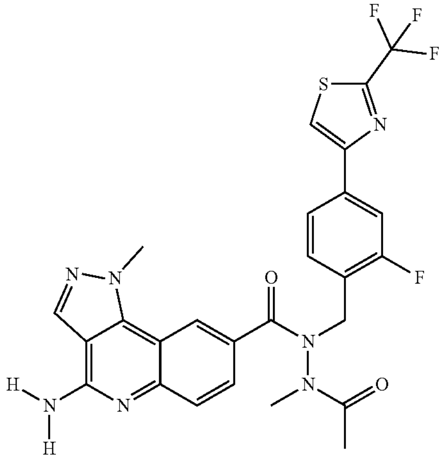 [SMILES: CC(=O)N(C)N(Cc1ccc(-c2csc(C(F)(F)F)n2)cc1F)C(=O)c1ccc2nc(N)c3cnn(C)c3c2c1] | N'-acetyl-4-amino-N-(2-fluoro-4-(2-(trifluoromethyl)thiazol-4-yl)benzyl)-N',1-dimethyl-1H-pyrazolo[4,3-c]quinoline-8-carbohydrazide |
| 251 | 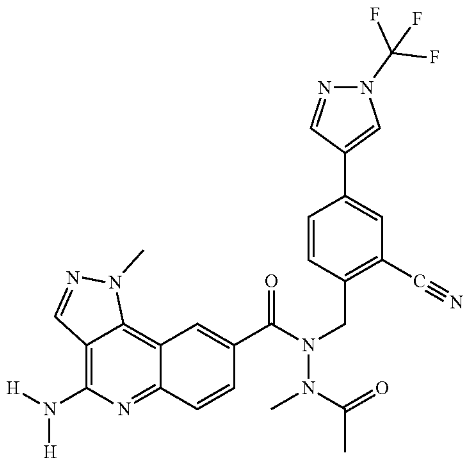 [SMILES: CC(=O)N(C)N(Cc1ccc(-c2cnn(C(F)(F)F)c2)cc1C#N)C(=O)c1ccc2nc(N)c3cnn(C)c3c2c1] | N'-acetyl-4-amino-N-(2-cyano-4-(1-(trifluoromethyl)-1H-pyrazol-4-yl)benzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 252 | 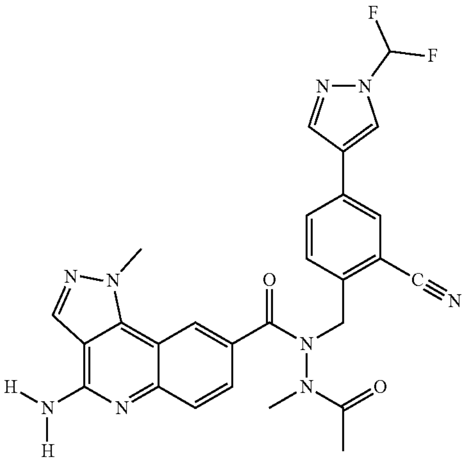 [SMILES: CC(=O)N(C)N(Cc1ccc(-c2cnn(C(F)F)c2)cc1C#N)C(=O)c1ccc2nc(N)c3cnn(C)c3c2c1] | N'-acetyl-4-amino-N-(2-cyano-4-(1-(difluoromethyl)-1H-pyrazol-4-yl)benzyl)-N',1-dimethyl-1H-pyrazolo[4,3-c]quinoline-8-carbohydrazide |
| 253 | 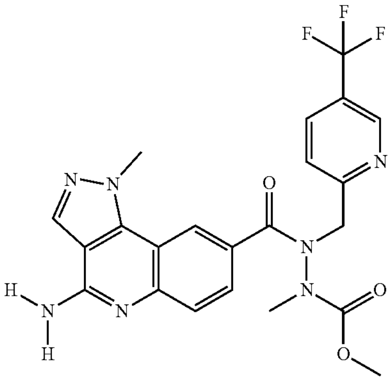 [SMILES: COC(=O)N(C)N(Cc1ccc(C(F)(F)F)cn1)C(=O)c1ccc2nc(N)c3cnn(C)c3c2c1] | methyl 2-(4-amino-1-methyl-1H-pyrazolo[4,3-c]quinoline-8-carbonyl)-1-methyl-2-((5-(trifluoromethyl)pyridin-2-yl)methyl)hydrazine-1-carboxylate |
| 254 | 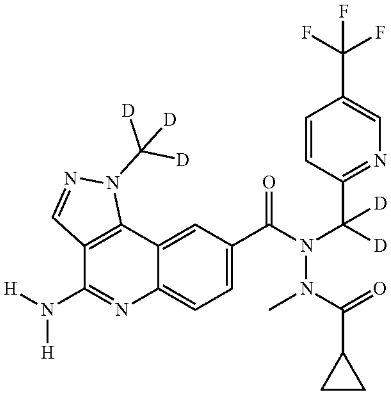 [SMILES: [2H]C([2H])(c1ccc(C(F)(F)F)cn1)N(C(=O)c1ccc2nc(N)c3cnn(C([2H])([2H])[2H])c3c2c1)N(C)C(=O)C1CC1] | 4-amino-N'-(cyclopropanecarbonyl)-N'-methyl-1-(methyl-d3)-N-((5-(trifluoromethyl)pyridin-2-yl)methyl-d2)-1H-pyrazolo[4,3-c]quinoline-8-carbohydrazide |

TABLE 1A-continued

| Some compounds | | |
|---|---|---|
| Example | Structure | Name |
| 255 | 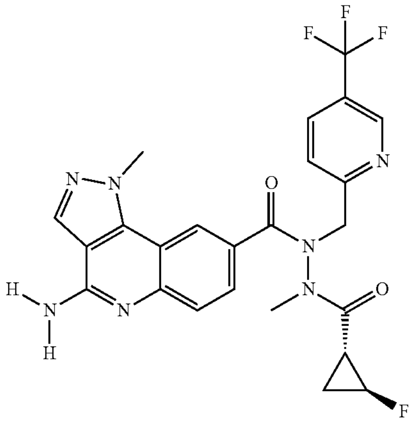 [SMILES: CN(C(=O)[C@H]1C[C@@H]1F)N(Cc1ccc(C(F)(F)F)cn1)C(=O)c1ccc2nc(N)c3cnn(C)c3c2c1] | 4-amino-N'-((1R,2S)-2-fluorocyclopropane-1-carbonyl)-N',1-dimethyl-N-((5-(trifluoromethyl)pyridin-2-yl)methyl)-1H-pyrazolo[4,3-c]quinoline-8-carbohydrazide |
| 256 | 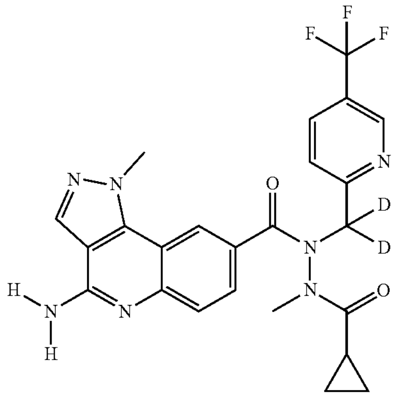 [SMILES: [2H]C([2H])(c1ccc(C(F)(F)F)cn1)N(C(=O)c1ccc2nc(N)c3cnn(C)c3c2c1)N(C)C(=O)C1CC1] | 4-amino-N'-(cyclopropanecarbonyl)-N',1-dimethyl-N-((5-(trifluoromethyl)pyridin-2-yl)methyl-d2)-1H-pyrazolo[4,3-c]quinoline-8-carbohydrazide |
| 257 | 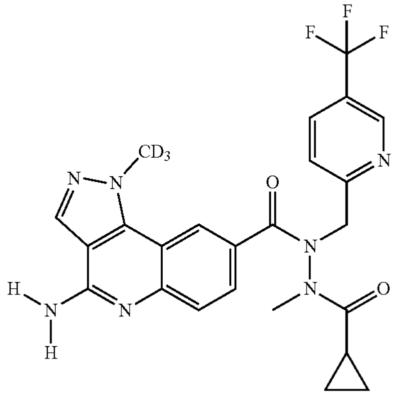 [SMILES: [2H]C([2H])([2H])n1ncc2c(N)nc3ccc(C(=O)N(Cc4ccc(C(F)(F)F)cn4)N(C)C(=O)C4CC4)cc3c21] | 4-amino-N'-(cyclopropanecarbonyl)-N'-methyl-1-(methyl-d3)-N-((5-(trifluoromethyl)pyridin-2-yl)methyl)-1H-pyrazolo[4,3-c]quinoline-8-carbohydrazide |

TABLE 1A-continued

| Some compounds | | |
|---|---|---|
| Example | Structure | Name |
| 258 | 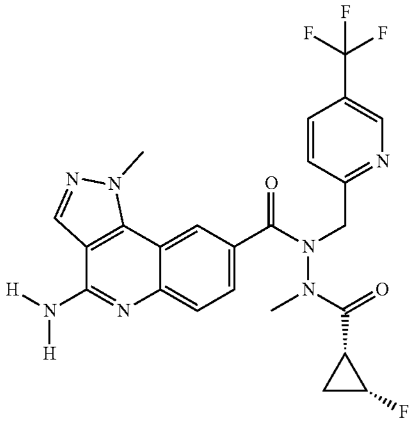 [SMILES: CN(C(=O)[C@H]1C[C@H]1F)N(Cc1ccc(C(F)(F)F)cn1)C(=O)c1ccc2nc(N)c3cnn(C)c3c2c1] | 4-amino-N'-((1R,2R)-2-fluorocyclopropane-1-carbonyl)-N',1-dimethyl-N-((5-(trifluoromethyl)pyridin-2-yl)methyl)-1H-pyrazolo[4,3-c]quinoline-8-carbohydrazide |
| 259 | 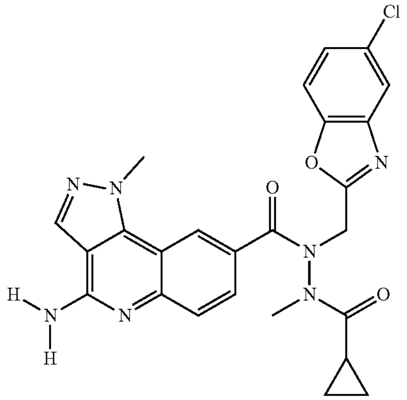 [SMILES: CN(C(=O)C1CC1)N(Cc1nc2cc(Cl)ccc2o1)C(=O)c1ccc2nc(N)c3cnn(C)c3c2c1] | 4-amino-N-((5-chlorobenzo[d]oxazol-2-yl)methyl)-N'-(cyclopropanecarbonyl)-N',1-dimethyl-1H-pyrazolo[4,3-c]quinoline-8-carbohydrazide |
| 260 | 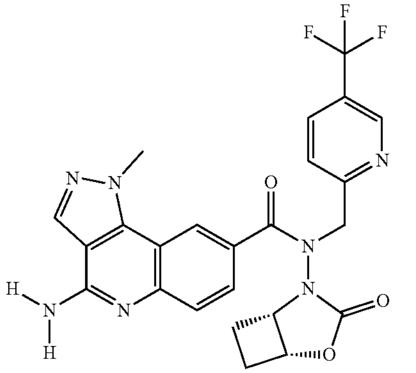 [SMILES: Cn1ncc2c(N)nc3ccc(C(=O)N(Cc4ccc(C(F)(F)F)cn4)N4C(=O)O[C@@H]5CC[C@@H]54)cc3c21] | 4-amino-1-methyl-N-((1R,5S)-3-oxo-2-oxa-4-azabicyclo[3.2.0]heptan-4-yl)-N-((5-(trifluoromethyl)pyridin-2-yl)methyl)-1H-pyrazolo[4,3-c]quinoline-8-carboxamide |
| 261 | 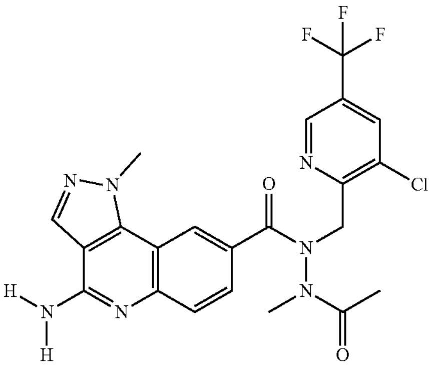 [SMILES: CC(=O)N(C)N(Cc1ncc(C(F)(F)F)cc1Cl)C(=O)c1ccc2nc(N)c3cnn(C)c3c2c1] | N'-acetyl-4-amino-N-((3-chloro-5-(trifluoromethyl)pyridin-2-yl)methyl)-N',1-dimethyl-1H-pyrazolo[4,3-c]quinoline-8-carbohydrazide |

TABLE 1A-continued

| Example | Structure | Name |
|---|---|---|
| Some compounds | | |
| 262 | 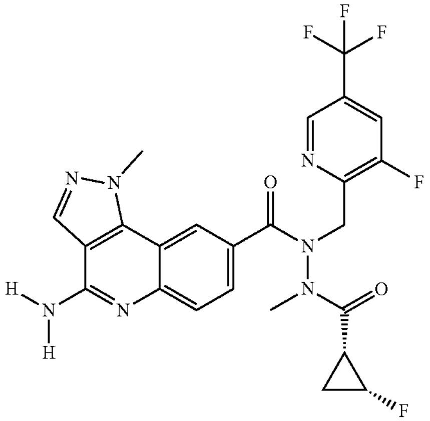 [SMILES: CN(C(=O)[C@H]1C[C@H]1F)N(Cc1ncc(C(F)(F)F)cc1F)C(=O)c1ccc2nc(N)c3cnn(C)c3c2c1] | 4-amino-N-((3-fluoro-5-(trifluoromethyl)pyridin-2-yl)methyl)-N'-((1R,2R)-2-fluorocyclopropane-1-carbonyl)-N',1-dimethyl-1H-pyrazolo[4,3-c]quinoline-8-carbohydrazide |
| 263 | 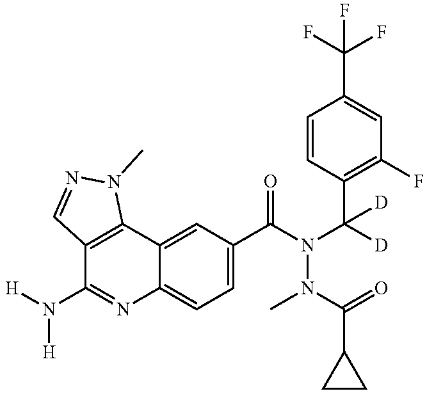 [SMILES: [2H]C([2H])(c1ccc(C(F)(F)F)cc1F)N(C(=O)c1ccc2nc(N)c3cnn(C)c3c2c1)N(C)C(=O)C1CC1] | 4-amino-N'-(cyclopropanecarbonyl)-N-((2-fluoro-4-(trifluoromethyl)phenyl)methyl-d2)-N',1-dimethyl-1H-pyrazolo[4,3-c]quinoline-8-carbohydrazide |
| 264 | 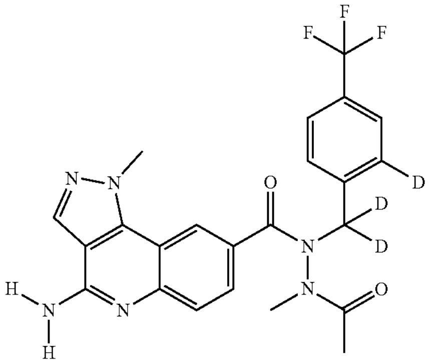 [SMILES: [2H]c1cc(C(F)(F)F)ccc1C([2H])([2H])N(C(=O)c1ccc2nc(N)c3cnn(C)c3c2c1)N(C)C(C)=O] | N'-acetyl-4-amino-N-((2-fluoro-4-(trifluoromethyl)phenyl)methyl-d2)-N',1-dimethyl-1H-pyrazolo[4,3-c]quinoline-8-carbohydrazide |
| 265 | 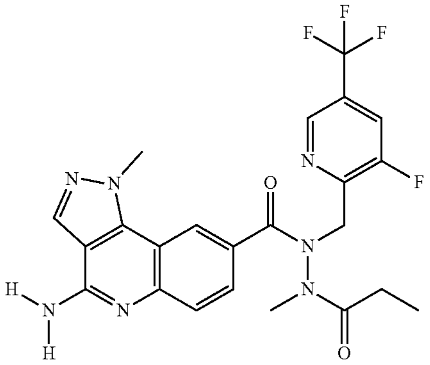 [SMILES: CCC(=O)N(C)N(Cc1ncc(C(F)(F)F)cc1F)C(=O)c1ccc2nc(N)c3cnn(C)c3c2c1] | 4-amino-N-((3-fluoro-5-(trifluoromethyl)pyridin-2-yl)methyl)-N',1-dimethyl-N'-propionyl-1H-pyrazolo[4,3-c]quinoline-8-carbohydrazide |

TABLE 1A-continued

| Some compounds | | |
|---|---|---|
| Example | Structure | Name |
| 266 | 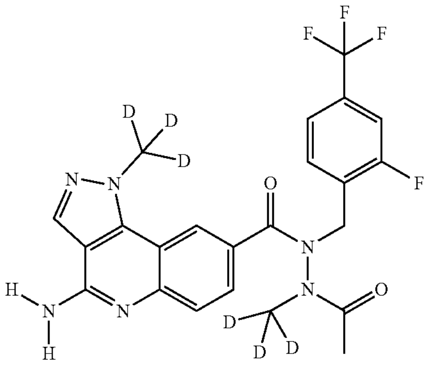 [SMILES: [2H]C([2H])([2H])N(C(C)=O)N(Cc1ccc(C(F)(F)F)cc1F)C(=O)c1ccc2nc(N)c3cnn(C([2H])([2H])[2H])c3c2c1] | 4-amino-N-((3-fluoro-5-(trifluoromethyl)pyridin-2-yl)methyl)-N',1-dimethyl-N'-propionyl-1H-pyrazolo[4,3-c]quinoline-8-carbohydrazide |
| 267 | 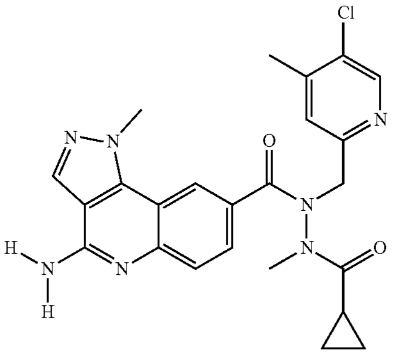 [SMILES: Cc1cc(CN(C(=O)c2ccc3nc(N)c4cnn(C)c4c3c2)N(C)C(=O)C2CC2)ncc1Cl] | 4-amino-N-((5-chloro-4-methylpyridin-2-yl)methyl)-N'-(cyclopropanecarbonyl)-N',1-dimethyl-1H-pyrazolo[4,3-c]quinoline-8-carbohydrazide |
| 268 | 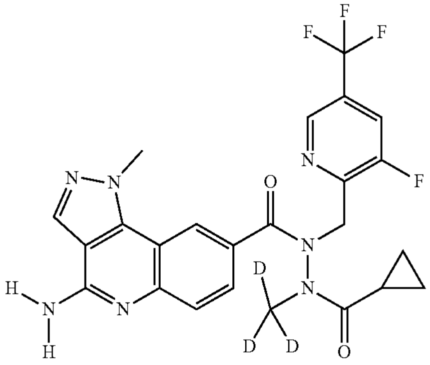 [SMILES: [2H]C([2H])([2H])N(C(=O)C1CC1)N(Cc1ncc(C(F)(F)F)cc1F)C(=O)c1ccc2nc(N)c3cnn(C)c3c2c1] | 4-amino-N'-(cyclopropanecarbonyl)-N-((3-fluoro-5-(trifluoromethyl)pyridin-2-yl)methyl)-1-methyl-N'-(methyl-d3)-1H-pyrazolo[4,3-c]quinoline-8-carbohydrazide |
| 269 | 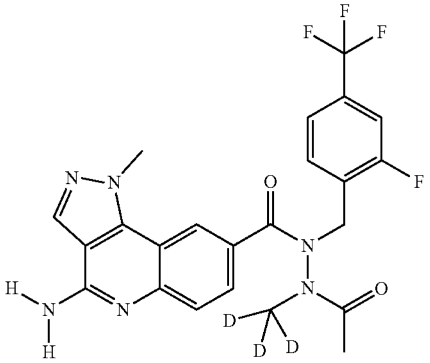 [SMILES: [2H]C([2H])([2H])N(C(C)=O)N(Cc1ccc(C(F)(F)F)cc1F)C(=O)c1ccc2nc(N)c3cnn(C)c3c2c1] | N'-acetyl-4-amino-N-(2-fluoro-4-(trifluoromethyl)benzyl)-1-methyl-N'-(methyl-d3)-1H-pyrazolo[4,3-c]quinoline-8-carbohydrazide |

TABLE 1A-continued

| Some compounds | | |
|---|---|---|
| Example | Structure | Name |
| 270 | 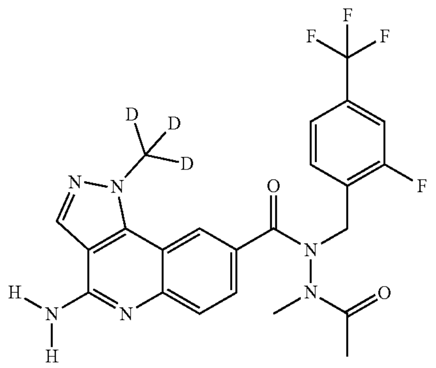 [SMILES: [2H]C([2H])([2H])n1ncc2c(N)nc3ccc(C(=O)N(Cc4ccc(C(F)(F)F)cc4F)N(C)C(C)=O)cc3c21] | N'-acetyl-4-amino-N-(2-fluoro-4-(trifluoromethyl)benzyl)-N'-methyl-1-(methyl-d3)-1H-pyrazolo[4,3-c]quinoline-8-carbohydrazide |
| 271 | 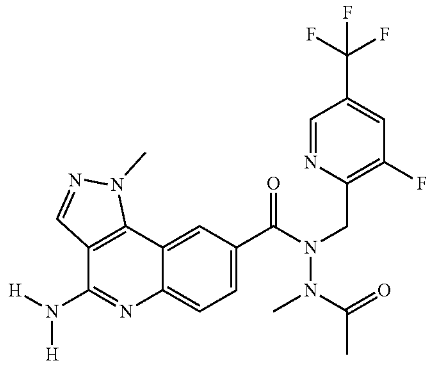 | N'-acetyl-4-amino-N-((3-fluoro-5-(trifluoromethyl)pyridin-2-yl)methyl)-N',1-dimethyl-1H-pyrazolo[4,3-c]quinoline-8-carbohydrazide |
| 272 | 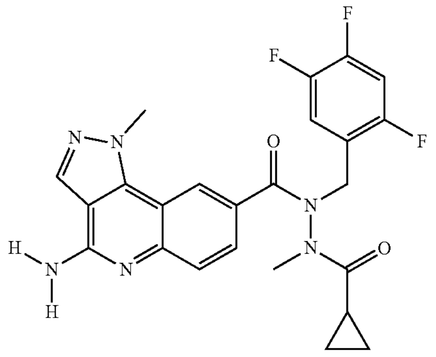 [SMILES: CN(C(=O)C1CC1)N(Cc1cc(F)c(F)cc1F)C(=O)c1ccc2nc(N)c3cnn(C)c3c2c1] | 4-amino-N'-(cyclopropanecarbonyl)-N',1-dimethyl-N-(2,4,5-trifluorobenzyl)-1H-pyrazolo[4,3-c]quinoline-8-carbohydrazide |
| 273 | 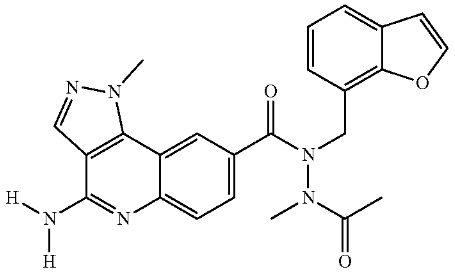 [SMILES: CC(=O)N(C)N(Cc1cccc2ccoc12)C(=O)c1ccc2nc(N)c3cnn(C)c3c2c1] | N'-acetyl-4-amino-N-(benzofuran-7-ylmethyl)-N',1-dimethyl-1H-pyrazolo[4,3-c]quinoline-8-carbohydrazide |

TABLE 1A-continued

| Example | Structure | Name |
|---|---|---|
| | Some compounds | |
| 274 | 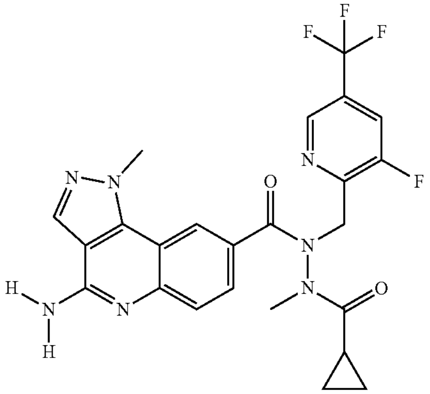 [SMILES: CN(C(=O)C1CC1)N(Cc1ncc(C(F)(F)F)cc1F)C(=O)c1ccc2nc(N)c3cnn(C)c3c2c1] | 4-amino-N'-(cyclopropanecarbonyl)-N-((3-fluoro-5-(trifluoromethyl)pyridin-2-yl)methyl)-N',1-dimethyl-1H-pyrazolo[4,3-c]quinoline-8-carbohydrazide |
| 275 | 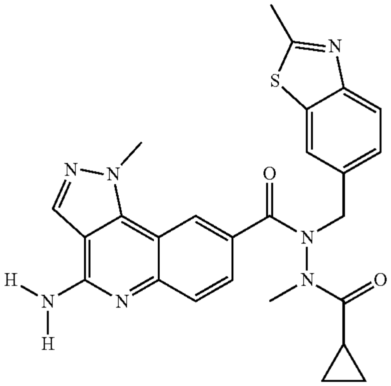 [SMILES: Cc1nc2ccc(CN(C(=O)c3ccc4nc(N)c5cnn(C)c5c4c3)N(C)C(=O)C3CC3)cc2s1] | 4-amino-N'-(cyclopropanecarbonyl)-N',1-dimethyl-N-((2-methylbenzo[d]thiazol-6-yl)methyl)-1H-pyrazolo[4,3-c]quinoline-8-carbohydrazide |
| 276 | 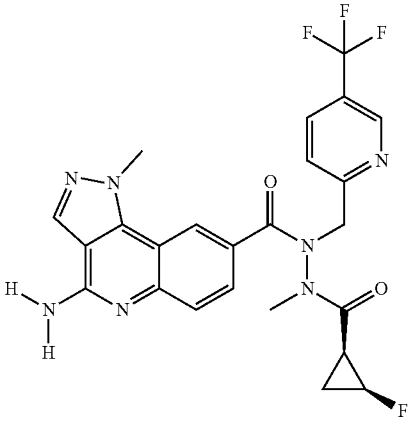 [SMILES: CN(C(=O)[C@@H]1C[C@@H]1F)N(Cc1ccc(C(F)(F)F)cn1)C(=O)c1ccc2nc(N)c3cnn(C)c3c2c1] | 4-amino-N'-((1S,2S)-2-fluorocyclopropane-1-carbonyl)-N',1-dimethyl-N-((5-(trifluoromethyl)pyridin-2-yl)methyl)-1H-pyrazolo[4,3-c]quinoline-8-carbohydrazide |
| 277 | 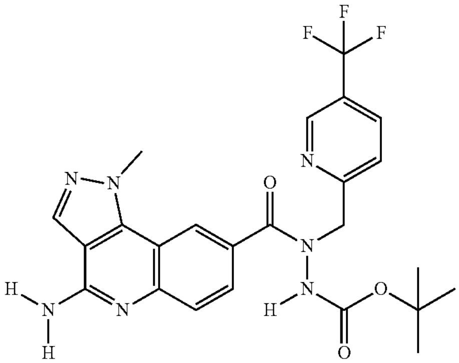 [SMILES: Cn1ncc2c(N)nc3ccc(C(=O)N(Cc4ccc(C(F)(F)F)cn4)NC(=O)OC(C)(C)C)cc3c21] | tert-butyl 2-(4-amino-1-methyl-1H-pyrazolo[4,3-c]quinoline-8-carbonyl)-2-((5-(trifluoromethyl)pyridin-2-yl)methyl)hydrazine-1-carboxylate |

TABLE 1A-continued

| Example | Structure | Name |
|---|---|---|
| | Some compounds | |
| 278 | 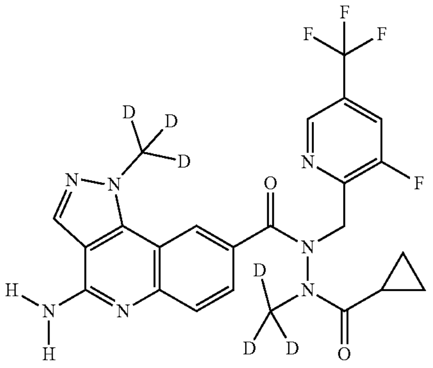 [SMILES: [2H]C([2H])([2H])N(C(=O)C1CC1)N(Cc1ncc(C(F)(F)F)cc1F)C(=O)c1ccc2nc(N)c3cnn(C([2H])([2H])[2H])c3c2c1] | 4-amino-N'-(cyclopropanecarbonyl)-N-((3-fluoro-5-(trifluoromethyl)pyridin-2-yl)methyl)-N',1-bis(methyl-d3)-1H-pyrazolo[4,3-c]quinoline-8-carbohydrazide |
| 279 | 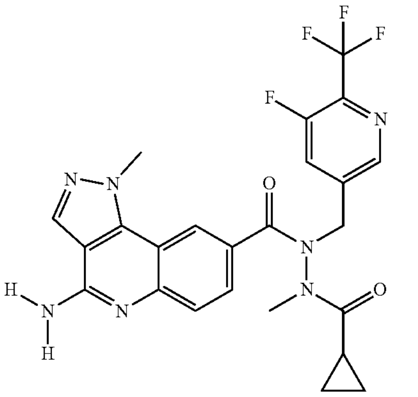 [SMILES: CN(C(=O)C1CC1)N(Cc1cnc(C(F)(F)F)c(F)c1)C(=O)c1ccc2nc(N)c3cnn(C)c3c2c1] | 4-amino-N'-(cyclopropanecarbonyl)-N-((5-fluoro-6-(trifluoromethyl)pyridin-3-yl)methyl)-N',1-dimethyl-1H-pyrazolo[4,3-c]quinoline-8-carbohydrazide |
| 280 | 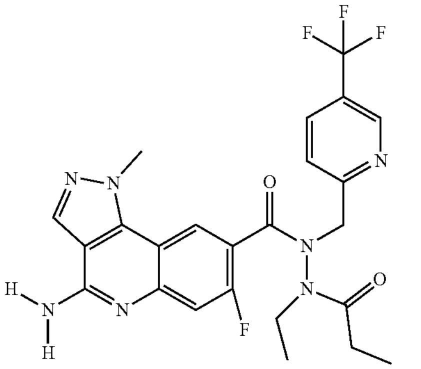 [SMILES: CCC(=O)N(CC)N(Cc1ccc(C(F)(F)F)cn1)C(=O)c1cc2c(cc1F)nc(N)c1cnn(C)c12] | 4-amino-N'-ethyl-7-fluoro-1-methyl-N'-propionyl-N-((5-(trifluoromethyl)pyridin-2-yl)methyl)-1H-pyrazolo[4,3-c]quinoline-8-carbohydrazide |
| 281 | 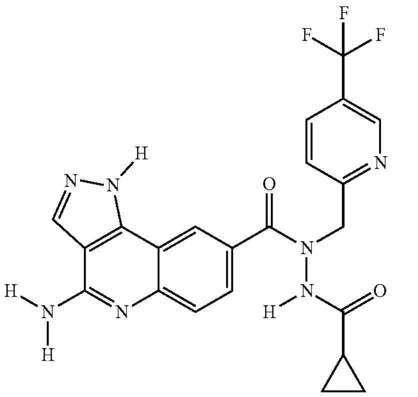 | 4-amino-N'-(cyclopropanecarbonyl)-N'-methyl-N-((5-(trifluoromethyl)pyridin-2-yl)methyl)-1H-pyrazolo[4,3-c]quinoline-8-carbohydrazide |

TABLE 1A-continued

| Some compounds | | |
|---|---|---|
| Example | Structure | Name |
| 282 | 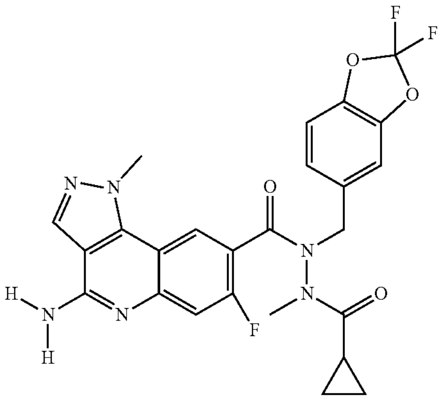 [SMILES: CN(C(=O)C1CC1)N(Cc1ccc2c(c1)OC(F)(F)O2)C(=O)c1cc2c(cc1F)nc(N)c1cnn(C)c12] | 4-amino-N'-(cyclopropanecarbonyl)-N-((2,2-difluorobenzo[d][1,3]dioxol-5-yl)methyl)-7-fluoro-N',1-dimethyl-1H-pyrazolo[4,3-c]quinoline-8-carbohydrazide |
| 283 | 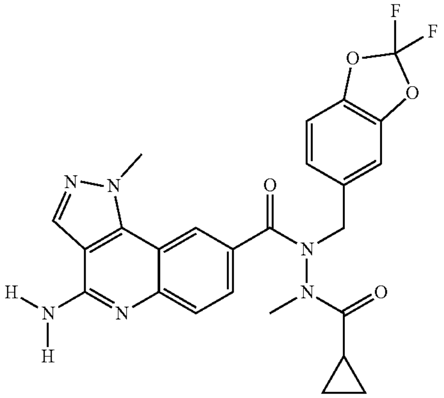 [SMILES: CN(C(=O)C1CC1)N(Cc1ccc2c(c1)OC(F)(F)O2)C(=O)c1ccc2nc(N)c3cnn(C)c3c2c1] | 4-amino-N'-(cyclopropanecarbonyl)-N-((2,2-difluorobenzo[d][1,3]dioxol-5-yl)methyl)-N',1-dimethyl-1H-pyrazolo[4,3-c]quinoline-8-carbohydrazide |
| 284 | 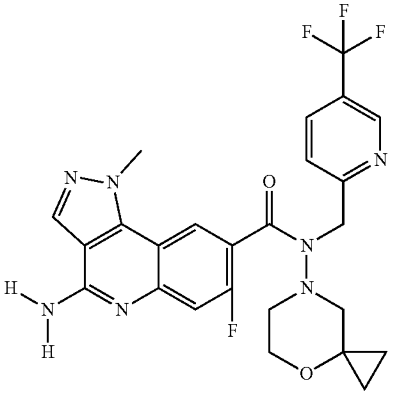 [SMILES: Cn1ncc2c(N)nc3cc(F)c(C(=O)N(Cc4ccc(C(F)(F)F)cn4)N4CCOC5(CC5)C4)cc3c21] | 4-amino-7-fluoro-1-methyl-N-(4-oxa-7-azaspiro[2.5]octan-7-yl)-N-((5-(trifluoromethyl)pyridin-2-yl)methyl)-1H-pyrazolo[4,3-c]quinoline-8-carboxamide |

TABLE 1A-continued

| Some compounds | | |
|---|---|---|
| Example | Structure | Name |
| 285 | 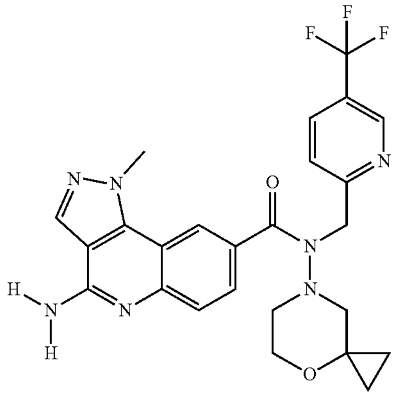 [SMILES: Cn1ncc2c(N)nc3ccc(C(=O)N(Cc4ccc(C(F)(F)F)cn4)N4CCOC5(CC5)C4)cc3c21] | 4-amino-1-methyl-N-(4-oxa-7-azaspiro[2.5]octan-7-yl)-N-((5-(trifluoromethyl)pyridin-2-yl)methyl)-1H-pyrazolo[4,3-c]quinoline-8-carboxamide |
| 286 | 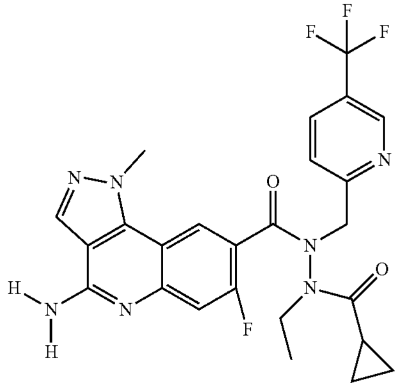 [SMILES: CCN(C(=O)C1CC1)N(Cc1ccc(C(F)(F)F)cn1)C(=O)c1cc2c(cc1F)nc(N)c1cnn(C)c12] | 4-amino-N'-(cyclopropanecarbonyl)-N'-ethyl-7-fluoro-1-methyl-N-((5-(trifluoromethyl)pyridin-2-yl)methyl)-1H-pyrazolo[4,3-c]quinoline-8-carbohydrazide |
| 287 | 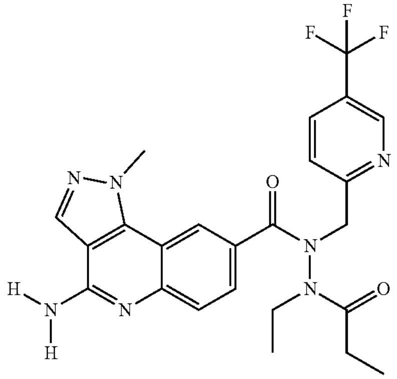 | 4-amino-N'-ethyl-1-methyl-N'-propionyl-N-((5-(trifluoromethyl)pyridin-2-yl)methyl)-1H-pyrazolo[4,3-c]quinoline-8-carbohydrazide |
| 288 | 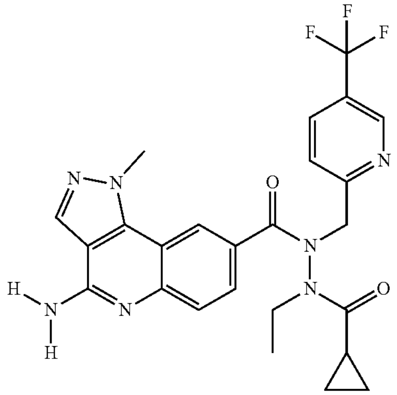 [SMILES: CCN(C(=O)C1CC1)N(Cc1ccc(C(F)(F)F)cn1)C(=O)c1ccc2nc(N)c3cnn(C)c3c2c1] | 4-amino-N'-(cyclopropanecarbonyl)-N'-ethyl-1-methyl-N-((5-(trifluoromethyl)pyridin-2-yl)methyl)-1H-pyrazolo[4,3-c]quinoline-8-carbohydrazide |

TABLE 1A-continued

| Some compounds | | |
|---|---|---|
| Example | Structure | Name |
| 289 | 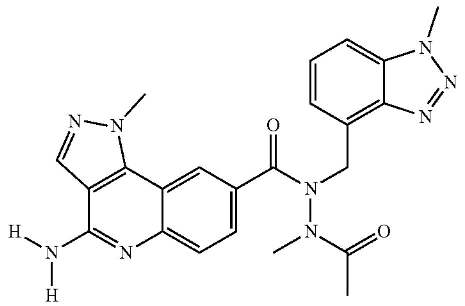 [SMILES: CC(=O)N(C)N(Cc1cccc2c1nnn2C)C(=O)c1ccc2nc(N)c3cnn(C)c3c2c1] | N'-acetyl-4-amino-N',1-dimethyl-N-((1-methyl-1H-benzo[d][1,2,3]triazol-4-yl)methyl)-1H-pyrazolo[4,3-c]quinoline-8-carbohydrazide |
| 290 | 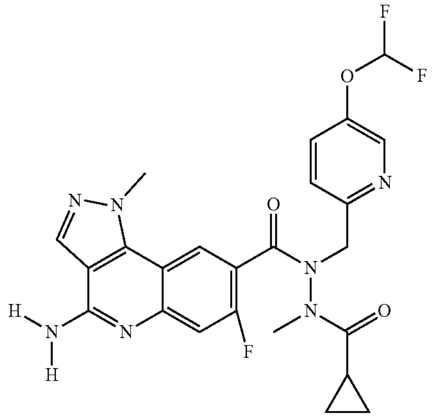 [SMILES: CN(C(=O)C1CC1)N(Cc1ccc(OC(F)F)cn1)C(=O)c1cc2c(cc1F)nc(N)c1cnn(C)c12] | 4-amino-N'-(cyclopropanecarbonyl)-N-((5-(difluoromethoxy)pyridin-2-yl)methyl)-7-fluoro-N',1-dimethyl-1H-pyrazolo[4,3-c]quinoline-8-carbohydrazide |
| 291 | 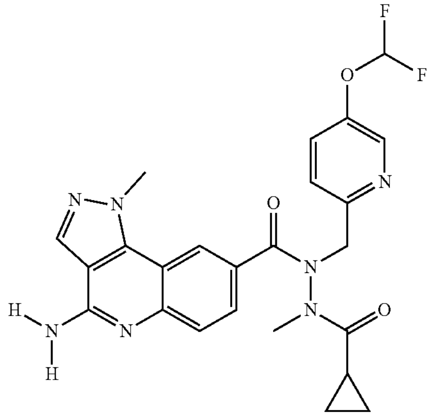 [SMILES: CN(C(=O)C1CC1)N(Cc1ccc(OC(F)F)cn1)C(=O)c1ccc2nc(N)c3cnn(C)c3c2c1] | 4-amino-N'-(cyclopropanecarbonyl)-N-((5-(difluoromethoxy)pyridin-2-yl)methyl)-N',1-dimethyl-1H-pyrazolo[4,3-c]quinoline-8-carbohydrazide |
| 292 | 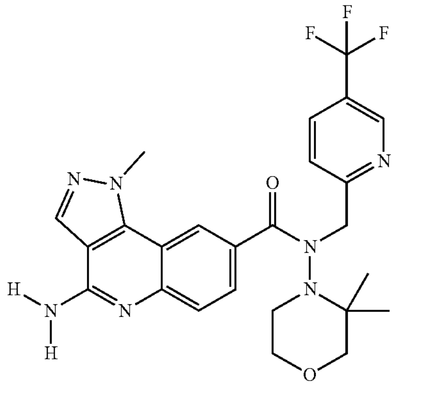 [SMILES: Cn1ncc2c(N)nc3ccc(C(=O)N(Cc4ccc(C(F)(F)F)cn4)N4CCOCC4(C)C)cc3c21] | 4-amino-N-(3,3-dimethylmorpholino)-1-methyl-N-((5-(trifluoromethyl)pyridin-2-yl)methyl)-1H-pyrazolo[4,3-c]quinoline-8-carboxamide |

TABLE 1A-continued

| Some compounds | | |
|---|---|---|
| Example | Structure | Name |
| 293 | 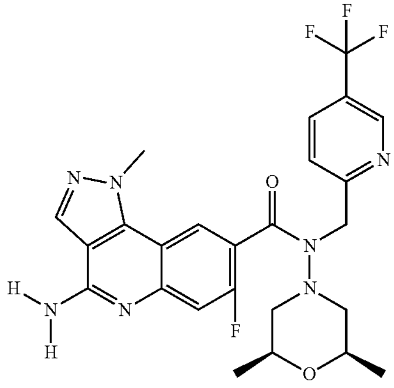 | 4-amino-N-((2S,6R)-2,6-dimethylmorpholino)-7-fluoro-1-methyl-N-((5-(trifluoromethyl)pyridin-2-yl)methyl)-1H-pyrazolo[4,3-c]quinoline-8-carboxamide |
| 294 | 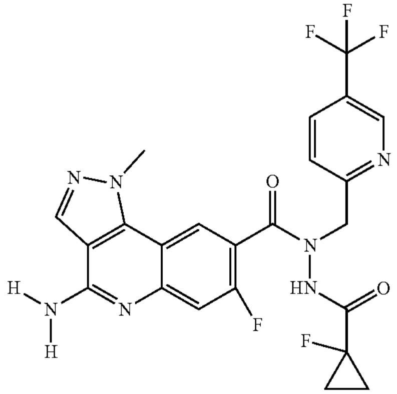 [SMILES: Cn1ncc2c(N)nc3cc(F)c(C(=O)N(Cc4ccc(C(F)(F)F)cn4)NC(=O)C4(F)CC4)cc3c21] | 4-amino-7-fluoro-N'-(1-fluorocyclopropane-1-carbonyl)-1-methyl-N-((5-(trifluoromethyl)pyridin-2-yl)methyl)-1H-pyrazolo[4,3-c]quinoline-8-carbohydrazide |
| 295 | 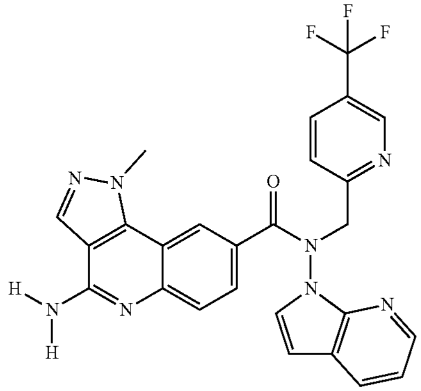 [SMILES: Cn1ncc2c(N)nc3ccc(C(=O)N(Cc4ccc(C(F)(F)F)cn4)n4ccc5cccnc54)cc3c21] | 4-amino-1-methyl-N-(1H-pyrrolo[2,3-b]pyridin-1-yl)-N-((5-(trifluoromethyl)pyridin-2-yl)methyl)-1H-pyrazolo[4,3-c]quinoline-8-carboxamide |
| 296 | 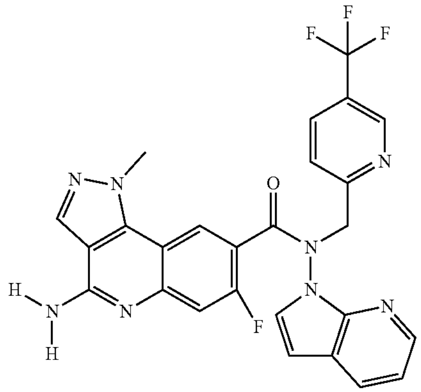 [SMILES: Cn1ncc2c(N)nc3cc(F)c(C(=O)N(Cc4ccc(C(F)(F)F)cn4)n4ccc5cccnc54)cc3c21] | 4-amino-7-fluoro-1-methyl-N-(1H-pyrrolo[2,3-b]pyridin-1-yl)-N-((5-(trifluoromethyl)pyridin-2-yl)methyl)-1H-pyrazolo[4,3-c]quinoline-8-carboxamide |

TABLE 1A-continued

| Example | Structure | Name |
|---|---|---|
| Some compounds | | |
| 297 | 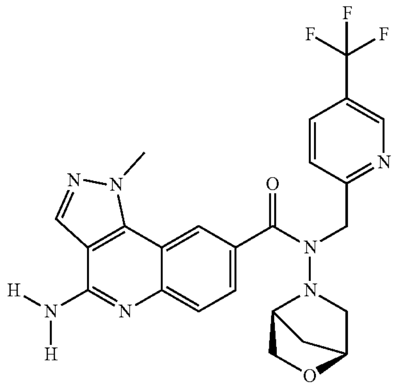 [SMILES: Cn1ncc2c(N)nc3ccc(C(=O)N(Cc4ccc(C(F)(F)F)cn4)N4C[C@@H]5C[C@H]4CO5)cc3c21] | 4-amino-N-((1S,4S)-2-oxa-5-azabicyclo[2.2.1]heptan-5-yl)-1-methyl-N-((5-(trifluoromethyl)pyridin-2-yl)methyl)-1H-pyrazolo[4,3-c]quinoline-8-carboxamide |
| 298 | 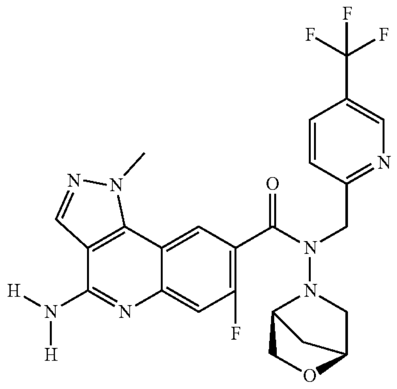 [SMILES: Cn1ncc2c(N)nc3cc(F)c(C(=O)N(Cc4ccc(C(F)(F)F)cn4)N4C[C@@H]5C[C@H]4CO5)cc3c21] | 4-amino-N-((1S,4S)-2-oxa-5-azabicyclo[2.2.1]heptan-5-yl)-7-fluoro-1-methyl-N-((5-(trifluoromethyl)pyridin-2-yl)methyl)-1H-pyrazolo[4,3-c]quinoline-8-carboxamide |
| 299 | 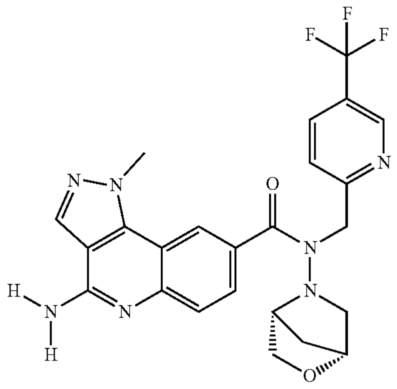 [SMILES: Cn1ncc2c(N)nc3ccc(C(=O)N(Cc4ccc(C(F)(F)F)cn4)N4C[C@H]5C[C@@H]4CO5)cc3c21] | 4-amino-N-((1R,4R)-2-oxa-5-azabicyclo[2.2.1]heptan-5-yl)-1-methyl-N-((5-(trifluoromethyl)pyridin-2-yl)methyl)-1H-pyrazolo[4,3-c]quinoline-8-carboxamide |
| 300 | 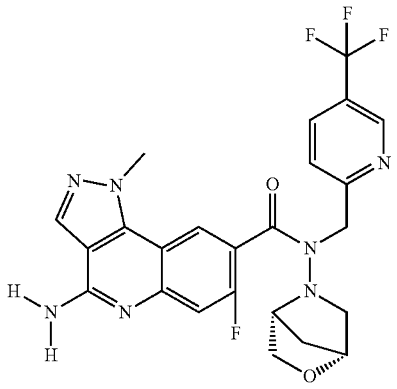 [SMILES: Cn1ncc2c(N)nc3cc(F)c(C(=O)N(Cc4ccc(C(F)(F)F)cn4)N4C[C@H]5C[C@@H]4CO5)cc3c21] | 4-amino-N-((1R,4R)-2-oxa-5-azabicyclo[2.2.1]heptan-5-yl)-7-fluoro-1-methyl-N-((5-(trifluoromethyl)pyridin-2-yl)methyl)-1H-pyrazolo[4,3-c]quinoline-8-carboxamide |

TABLE 1A-continued

| Some compounds | | |
|---|---|---|
| Example | Structure | Name |
| 301 | 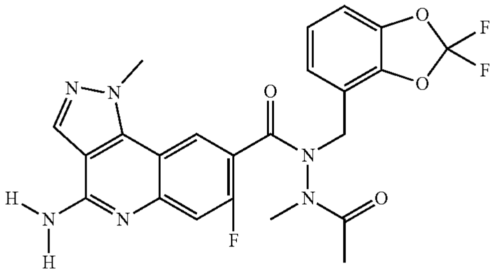 [SMILES: CC(=O)N(C)N(Cc1cccc2c1OC(F)(F)O2)C(=O)c1cc2c(cc1F)nc(N)c1cnn(C)c12] | N'-acetyl-4-amino-N-((2,2-difluorobenzo[d][1,3]dioxol-4-yl)methyl)-7-fluoro-N',1-dimethyl-1H-pyrazolo[4,3-c]quinoline-8-carbohydrazide |
| 302 | 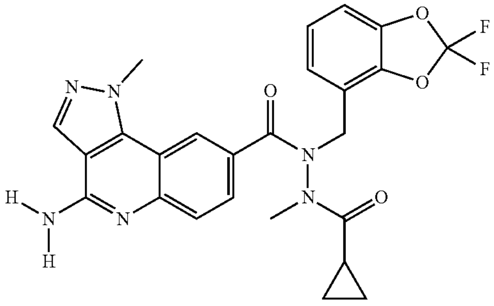 [SMILES: CN(C(=O)C1CC1)N(Cc1cccc2c1OC(F)(F)O2)C(=O)c1ccc2nc(N)c3cnn(C)c3c2c1] | 4-amino-N'-(cyclopropanecarbonyl)-N-((2,2-difluorobenzo[d][1,3]dioxol-4-yl)methyl)-N',1-dimethyl-1H-pyrazolo[4,3-c]quinoline-8-carbohydrazide |
| 303 | 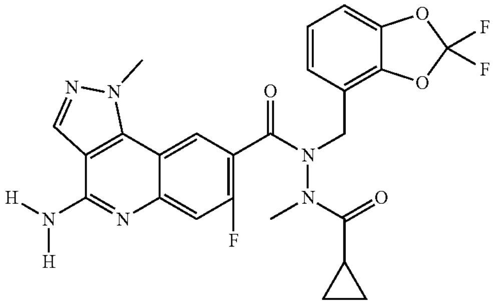 [SMILES: CN(C(=O)C1CC1)N(Cc1cccc2c1OC(F)(F)O2)C(=O)c1cc2c(cc1F)nc(N)c1cnn(C)c12] | 4-amino-N'-(cyclopropanecarbonyl)-N-((2,2-difluorobenzo[d][1,3]dioxol-4-yl)methyl)-7-fluoro-N',1-dimethyl-1H-pyrazolo[4,3-c]quinoline-8-carbohydrazide |
| 304 | 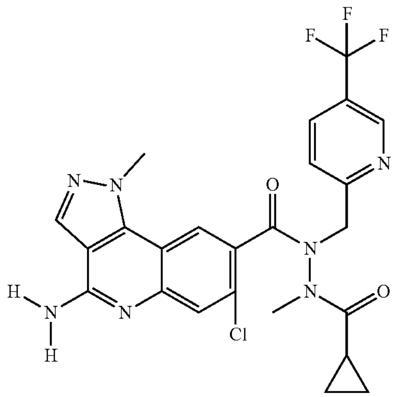 | 4-amino-7-chloro-N'-(cyclopropanecarbonyl)-N',1-dimethyl-N-((5-(trifluoromethyl)pyridin-2-yl)methyl)-1H-pyrazolo[4,3-c]quinoline-8-carbohydrazide |

TABLE 1A-continued

| Example | Structure | Name |
|---|---|---|
| 305 | 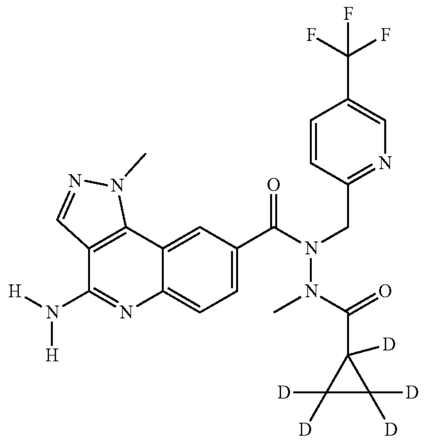 [SMILES: [2H]C1([2H])C([2H])([2H])C1([2H])C(=O)N(C)N(Cc1ccc(C(F)(F)F)cn1)C(=O)c1ccc2nc(N)c3cnn(C)c3c2c1] | 4-amino-N'-(cyclopropane-1-carbonyl-d5)-N',1-dimethyl-N-((5-(trifluoromethyl)pyridin-2-yl)methyl)-1H-pyrazolo[4,3-c]quinoline-8-carbohydrazide |
| 306 | 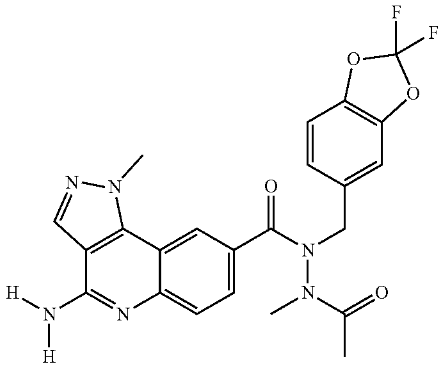 [SMILES: CC(=O)N(C)N(Cc1ccc2c(c1)OC(F)(F)O2)C(=O)c1ccc2nc(N)c3cnn(C)c3c2c1] | N'-acetyl-4-amino-N-((2,2-difluorobenzo[d][1,3]dioxol-5-yl)methyl)-N',1-dimethyl-1H-pyrazolo[4,3-c]quinoline-8-carbohydrazide |
| 307 | 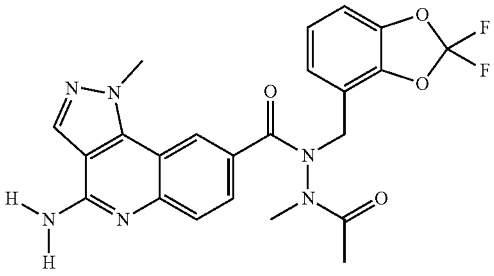 [SMILES: CC(=O)N(C)N(Cc1cccc2c1OC(F)(F)O2)C(=O)c1ccc2nc(N)c3cnn(C)c3c2c1] | N'-acetyl-4-amino-N-((2,2-difluorobenzo[d][1,3]dioxol-4-yl)methyl)-N',1-dimethyl-1H-pyrazolo[4,3-c]quinoline-8-carbohydrazide |
| 308 | 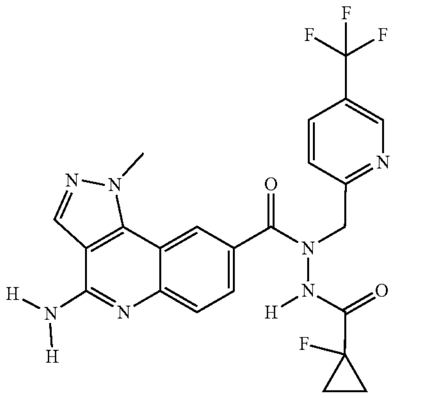 [SMILES: Cn1ncc2c(N)nc3ccc(C(=O)N(Cc4ccc(C(F)(F)F)cn4)NC(=O)C4(F)CC4)cc3c21] | 4-amino-N'-(1-fluorocyclopropane-1-carbonyl)-1-methyl-N-((5-(trifluoromethyl)pyridin-2-yl)methyl)-1H-pyrazolo[4,3-c]quinoline-8-carbohydrazide |

Some compounds

TABLE 1A-continued

| Some compounds | | |
|---|---|---|
| Example | Structure | Name |
| 309 | 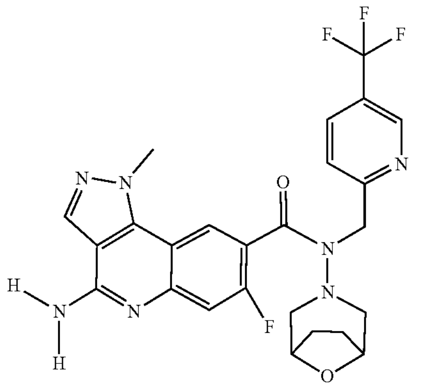 [SMILES: Cn1ncc2c(N)nc3cc(F)c(C(=O)N(Cc4ccc(C(F)(F)F)cn4)N4CC5CCC(C4)O5)cc3c21] | 4-amino-N-((1R,5S)-8-oxa-3-azabicyclo[3.2.1]octan-3-yl)-7-fluoro-1-methyl-N-((5-(trifluoromethyl)pyridin-2-yl)methyl)-1H-pyrazolo[4,3-c]quinoline-8-carboxamide |
| 310 | 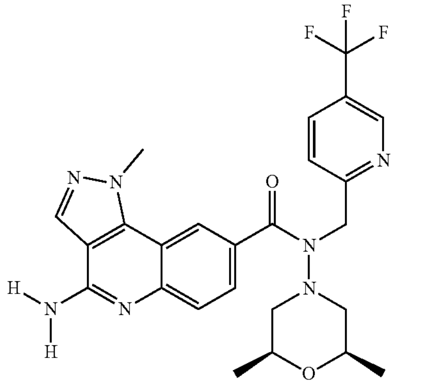 [SMILES: C[C@@H]1CN(N(Cc2ccc(C(F)(F)F)cn2)C(=O)c2ccc3nc(N)c4cnn(C)c4c3c2)C[C@H](C)O1] | 4-amino-N-((2S,6R)-2,6-dimethylmorpholino)-1-methyl-N-((5-(trifluoromethyl)pyridin-2-yl)methyl)-1H-pyrazolo[4,3-c]quinoline-8-carboxamide |
| 311 | 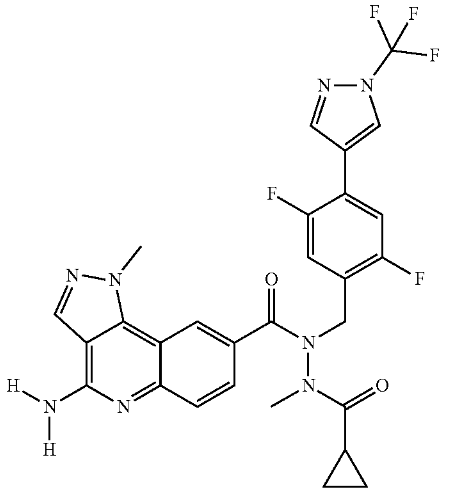 [SMILES: CN(C(=O)C1CC1)N(Cc1cc(F)c(-c2cnn(C(F)(F)F)c2)cc1F)C(=O)c1ccc2nc(N)c3cnn(C)c3c2c1] | 4-amino-N'-(cyclopropanecarbonyl)-N-(2,5-difluoro-4-(1-(trifluoromethyl)-1H-pyrazol-4-yl)benzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 312 | 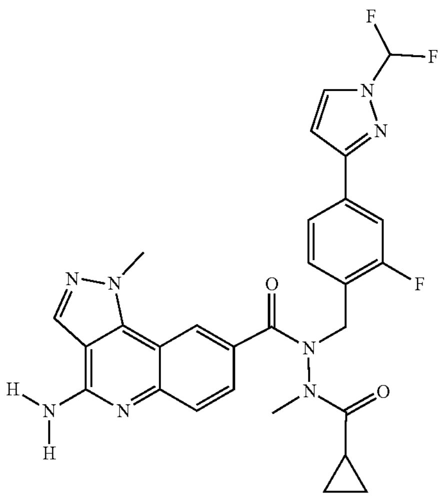 [SMILES: CN(C(=O)C1CC1)N(Cc1ccc(-c2ccn(C(F)F)n2)cc1F)C(=O)c1ccc2nc(N)c3cnn(C)c3c2c1] | 4-amino-N'-(cyclopropanecarbonyl)-N-(4-(1-(difluoromethyl)-1H-pyrazol-3-yl)-2-fluorobenzyl)-N',1-dimethyl-1H-pyrazolo[4,3-c]quinoline-8-carbohydrazide |
| 313 | 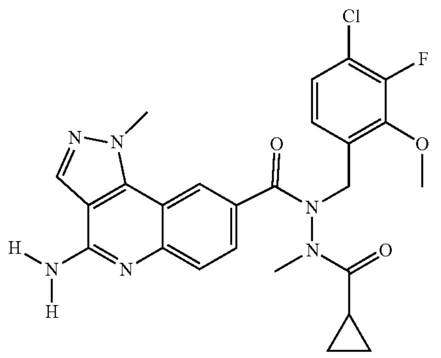 [SMILES: COc1c(CN(C(=O)c2ccc3nc(N)c4cnn(C)c4c3c2)N(C)C(=O)C2CC2)ccc(Cl)c1F] | 4-amino-N-(4-chloro-3-fluoro-2-methoxybenzyl)-N'-(cyclopropanecarbonyl)-N',1-dimethyl-1H-pyrazolo[4,3-c]quinoline-8-carbohydrazide |
| 314 | 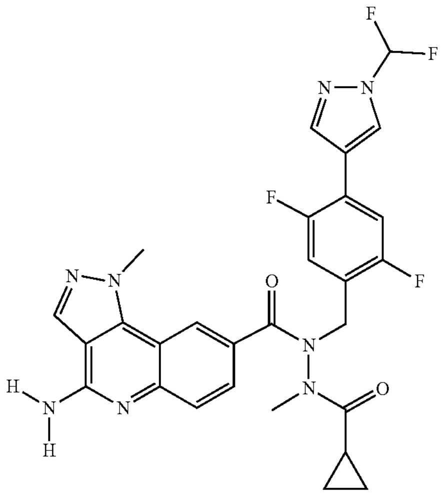 | 4-amino-N'-(cyclopropanecarbonyl)-N-(4-(1-(difluoromethyl)-1H-pyrazol-4-yl)-2,5-difluorobenzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 315 | 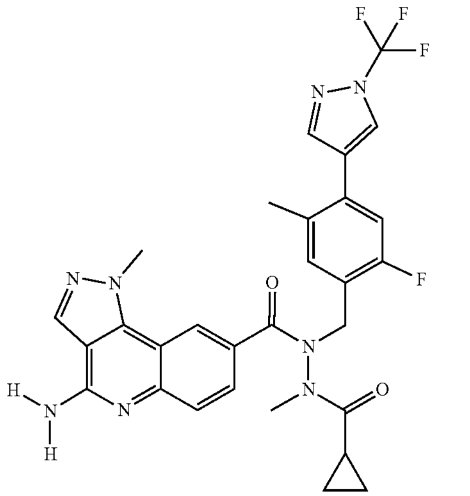 [SMILES: Cc1cc(CN(C(=O)c2ccc3nc(N)c4cnn(C)c4c3c2)N(C)C(=O)C2CC2)c(F)cc1-c1cnn(C(F)(F)F)c1] | 4-amino-N'-(cyclopropanecarbonyl)-N-(2-fluoro-5-methyl-4-(1-(trifluoromethyl)-1H-pyrazol-4-yl)benzyl)-N',1-dimethyl-1H-pyrazolo[4,3-c]quinoline-8-carbohydrazide |
| 316 | 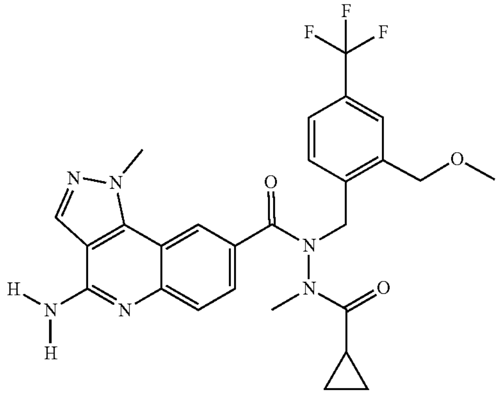 [SMILES: COCc1cc(C(F)(F)F)ccc1CN(C(=O)c1ccc2nc(N)c3cnn(C)c3c2c1)N(C)C(=O)C1CC1] | 4-amino-N'-(cyclopropanecarbonyl)-N-(2-(methoxymethyl)-4-(trifluoromethyl)benzyl)-N',1-dimethyl-1H-pyrazolo[4,3-c]quinoline-8-carbohydrazide |
| 317 | 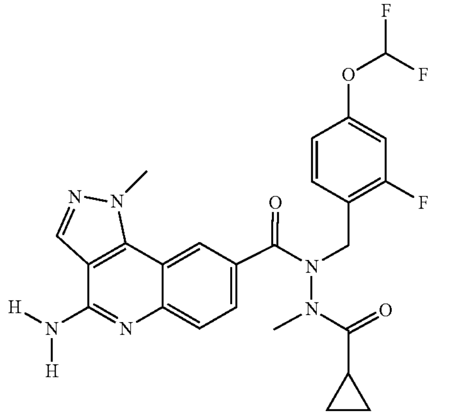 [SMILES: CN(C(=O)C1CC1)N(Cc1ccc(OC(F)F)cc1F)C(=O)c1ccc2nc(N)c3cnn(C)c3c2c1] | 4-amino-N'-(cyclopropanecarbonyl)-N-(4-(difluoromethoxy)-2-fluorobenzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 318 | 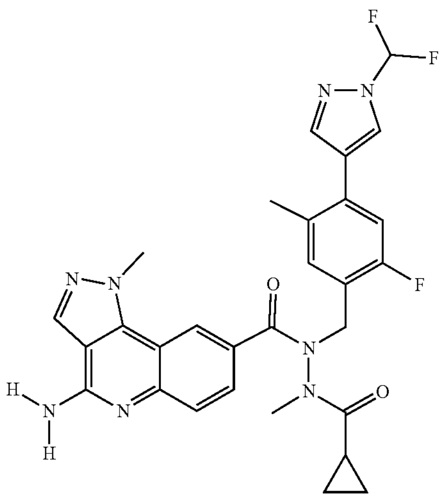 [SMILES: Cc1cc(CN(C(=O)c2ccc3nc(N)c4cnn(C)c4c3c2)N(C)C(=O)C2CC2)c(F)cc1-c1cnn(C(F)F)c1] | 4-amino-N'-(cyclopropanecarbonyl)-N-(4-(1-(difluoromethyl)-1H-pyrazol-4-yl)-2-fluoro-5-methylbenzyl)-N',1-dimethyl-1H-pyrazolo[4,3-c]quinoline-8-carbohydrazide |
| 319 | 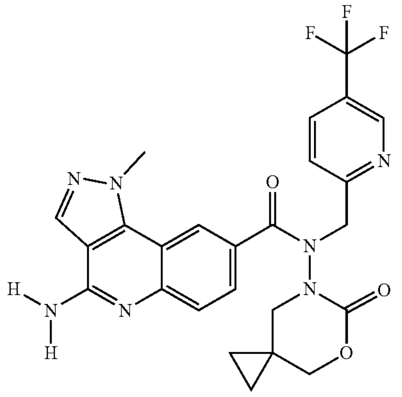 [SMILES: Cn1ncc2c(N)nc3ccc(C(=O)N(Cc4ccc(C(F)(F)F)cn4)N4CC5(CC5)COC4=O)cc3c21] | 4-amino-1-methyl-N-(6-oxo-5-oxa-7-azaspiro[2.5]octan-7-yl)-N-((5-(trifluoromethyl)pyridin-2-yl)methyl)-1H-pyrazolo[4,3-c]quinoline-8-carboxamide |
| 320 | 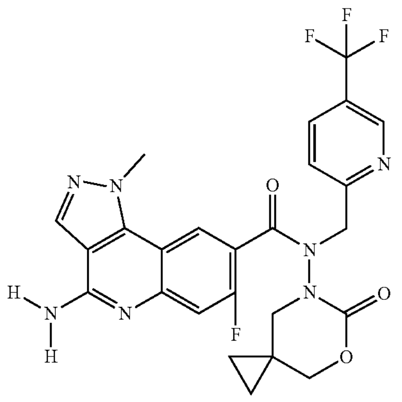 | 4-amino-7-fluoro-1-methyl-N-(6-oxo-5-oxa-7-azaspiro[2.5]octan-7-yl)-N-((5-(trifluoromethyl)pyridin-2-yl)methyl)-1H-pyrazolo[4,3-c]quinoline-8-carboxamide |

TABLE 1A-continued

| Some compounds | | |
|---|---|---|
| Example | Structure | Name |
| 321 | 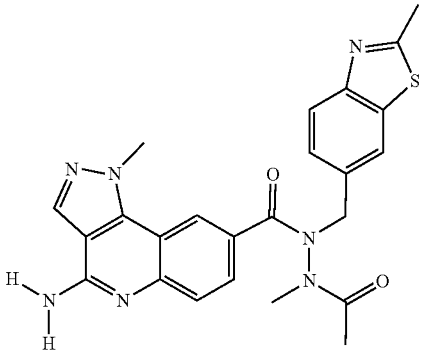 [SMILES: CC(=O)N(C)N(Cc1ccc2nc(C)sc2c1)C(=O)c1ccc2nc(N)c3cnn(C)c3c2c1] | N'-acetyl-4-amino-N',1-dimethyl-N-((2-methylbenzo[d]thiazol-6-yl)methyl)-1H-pyrazolo[4,3-c]quinoline-8-carbohydrazide |
| 322 | 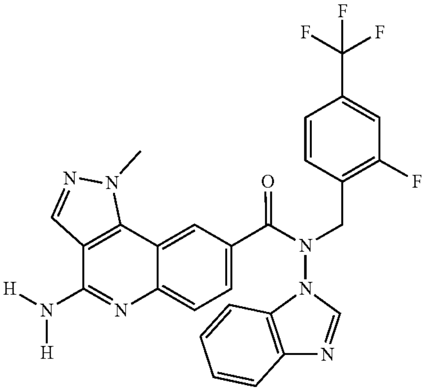 [SMILES: Cn1ncc2c(N)nc3ccc(C(=O)N(Cc4ccc(C(F)(F)F)cc4F)n4cnc5ccccc54)cc3c21] | 4-amino-N-(1H-benzo[d]imidazol-1-yl)-N-(2-fluoro-4-(trifluoromethyl)benzyl)-1-methyl-1H-pyrazolo[4,3-c]quinoline-8-carboxamide |
| 323 | 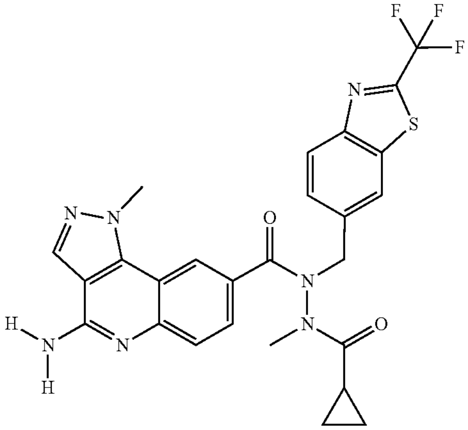 [SMILES: CN(C(=O)C1CC1)N(Cc1ccc2nc(C(F)(F)F)sc2c1)C(=O)c1ccc2nc(N)c3cnn(C)c3c2c1] | 4-amino-N'-(cyclopropanecarbonyl)-N',1-dimethyl-N-((2-(trifluoromethyl)benzo[d]thiazol-6-yl)methyl)-1H-pyrazolo[4,3-c]quinoline-8-carbohydrazide |
| 324 | 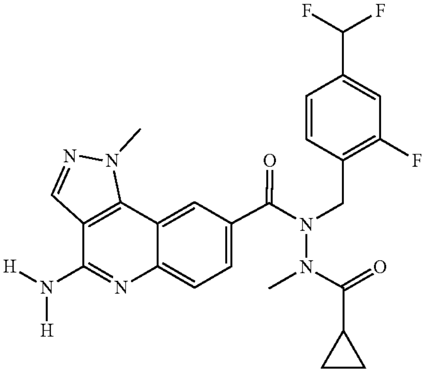 [SMILES: CN(C(=O)C1CC1)N(Cc1ccc(C(F)F)cc1F)C(=O)c1ccc2nc(N)c3cnn(C)c3c2c1] | 4-amino-N'-(cyclopropanecarbonyl)-N-(4-(difluoromethyl)-2-fluorobenzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 325 | 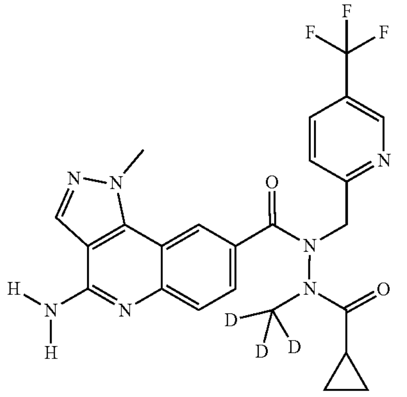 [SMILES: [2H]C([2H])([2H])N(C(=O)C1CC1)N(Cc1ccc(C(F)(F)F)cn1)C(=O)c1ccc2nc(N)c3cnn(C)c3c2c1] | 4-amino-N'-(cyclopropanecarbonyl)-1-methyl-N'-(methyl-d3)-N-((5-(trifluoromethyl)pyridin-2-yl)methyl)-1H-pyrazolo[4,3-c]quinoline-8-carbohydrazide |
| 326 | 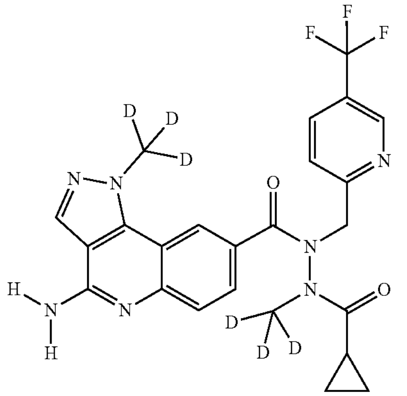 [SMILES: [2H]C([2H])([2H])N(C(=O)C1CC1)N(Cc1ccc(C(F)(F)F)cn1)C(=O)c1ccc2nc(N)c3cnn(C([2H])([2H])[2H])c3c2c1] | 4-amino-N'-(cyclopropanecarbonyl)-N',1-bis(methyl-d3)-N-((5-(trifluoromethyl)pyridin-2-yl)methyl)-1H-pyrazolo[4,3-c]quinoline-8-carbohydrazide |
| 327 | 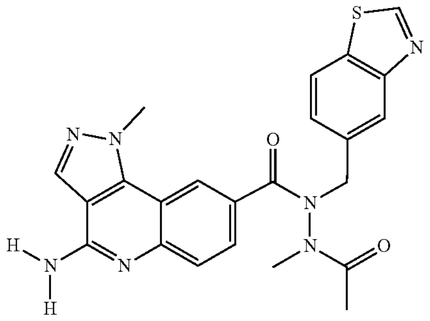 [SMILES: CC(=O)N(C)N(Cc1ccc2scnc2c1)C(=O)c1ccc2nc(N)c3cnn(C)c3c2c1] | N'-acetyl-4-amino-N-(benzo[d]thiazol-5-ylmethyl)-N',1-dimethyl-1H-pyrazolo[4,3-c]quinoline-8-carbohydrazide |
| 328 | 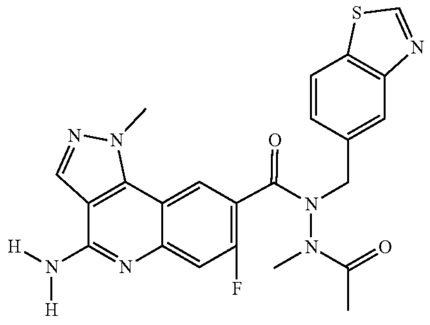 [SMILES: CC(=O)N(C)N(Cc1ccc2scnc2c1)C(=O)c1cc2c(cc1F)nc(N)c1cnn(C)c12] | N'-acetyl-4-amino-N-(benzo[d]thiazol-5-ylmethyl)-7-fluoro-N',1-dimethyl-1H-pyrazolo[4,3-c]quinoline-8-carbohydrazide |

TABLE 1A-continued

| Some compounds | | |
|---|---|---|
| Example | Structure | Name |
| 329 | 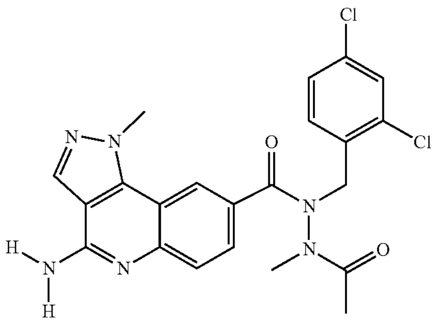 [SMILES: CC(=O)N(C)N(Cc1ccc(Cl)cc1Cl)C(=O)c1ccc2nc(N)c3cnn(C)c3c2c1] | N'-acetyl-4-amino-N-(2,4-dichlorobenzyl)-N',1-dimethyl-1H-pyrazolo[4,3-c]quinoline-8-carbohydrazide |
| 330 | 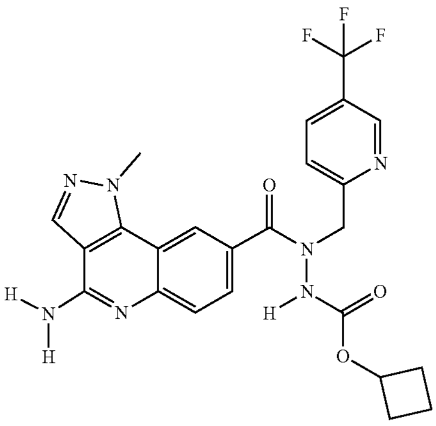 [SMILES: Cn1ncc2c(N)nc3ccc(C(=O)N(Cc4ccc(C(F)(F)F)cn4)NC(=O)OC4CCC4)cc3c21] | cyclobutyl 2-(4-amino-1-methyl-1H-pyrazolo[4,3-c]quinoline-8-carbonyl)-2-((5-(trifluoromethyl)pyridin-2-yl)methyl)hydrazine-1-carboxylate |
| 331 | 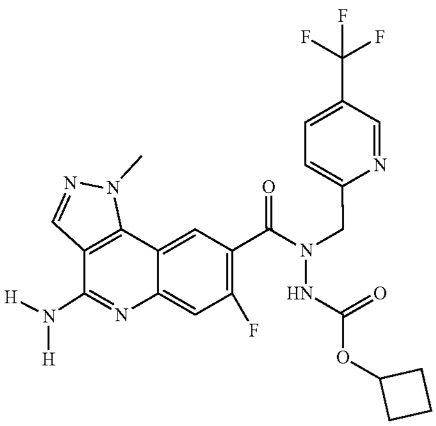 [SMILES: Cn1ncc2c(N)nc3cc(F)c(C(=O)N(Cc4ccc(C(F)(F)F)cn4)NC(=O)OC4CCC4)cc3c21] | cyclobutyl 2-(4-amino-7-fluoro-1-methyl-1H-pyrazolo[4,3-c]quinoline-8-carbonyl)-2-((5-(trifluoromethyl)pyridin-2-yl)methyl)hydrazine-1-carboxylate |

TABLE 1A-continued

| Example | Structure | Name |
|---|---|---|
| Some compounds | | |
| 332 | 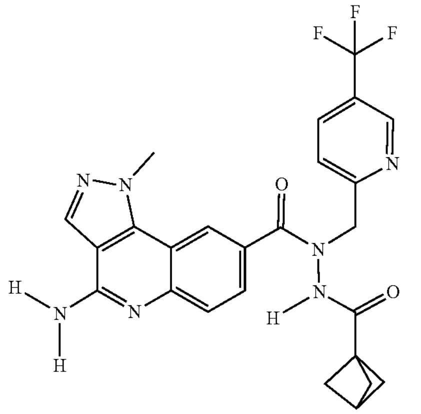 [SMILES: Cn1ncc2c(N)nc3ccc(C(=O)N(Cc4ccc(C(F)(F)F)cn4)NC(=O)C45CC(C4)C5)cc3c21] | 4-amino-N'-(bicyclo[1.1.1]pentane-1-carbonyl)-1-methyl-N-((5-(trifluoromethyl)pyridin-2-yl)methyl)-1H-pyrazolo[4,3-c]quinoline-8-carbohydrazide |
| 333 | 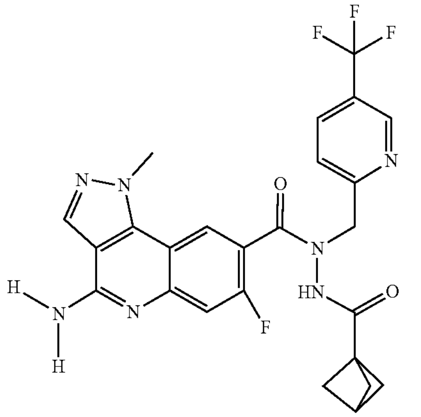 [SMILES: Cn1ncc2c(N)nc3cc(F)c(C(=O)N(Cc4ccc(C(F)(F)F)cn4)NC(=O)C45CC(C4)C5)cc3c21] | 4-amino-N'-(bicyclo[1.1.1]pentane-1-carbonyl)-7-fluoro-1-methyl-N-((5-(trifluoromethyl)pyridin-2-yl)methyl)-1H-pyrazolo[4,3-c]quinoline-8-carbohydrazide |
| 334 | 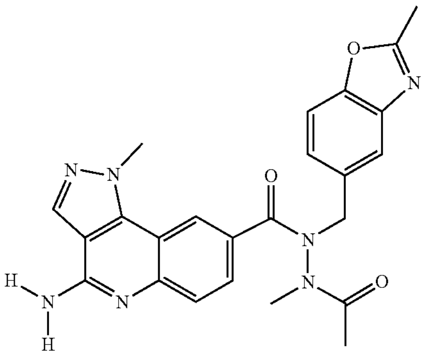 [SMILES: CC(=O)N(C)N(Cc1ccc2oc(C)nc2c1)C(=O)c1ccc2nc(N)c3cnn(C)c3c2c1] | N'-acetyl-4-amino-N',1-dimethyl-N-((2-methylbenzo[d]oxazol-5-yl)methyl)-1H-pyrazolo[4,3-c]quinoline-8-carbohydrazide |
| 335 | 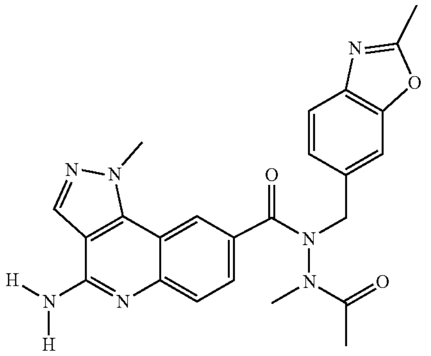 | N'-acetyl-4-amino-N',1-dimethyl-N-((2-methylbenzo[d]oxazol-6-yl)methyl)-1H-pyrazolo[4,3-c]quinoline-8-carbohydrazide |

TABLE 1A-continued

| Some compounds | | |
|---|---|---|
| Example | Structure | Name |
| 336 | 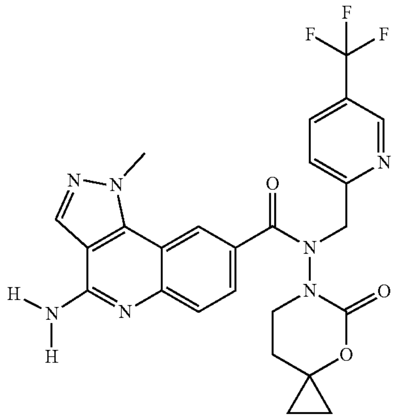 [SMILES: Cn1ncc2c(N)nc3ccc(C(=O)N(Cc4ccc(C(F)(F)F)cn4)N4CCC5(CC5)OC4=O)cc3c21] | 4-amino-1-methyl-N-(5-oxo-4-oxa-6-azaspiro[2.5]octan-6-yl)-N-((5-(trifluoromethyl)pyridin-2-yl)methyl)-1H-pyrazolo[4,3-c]quinoline-8-carboxamide |
| 337 | 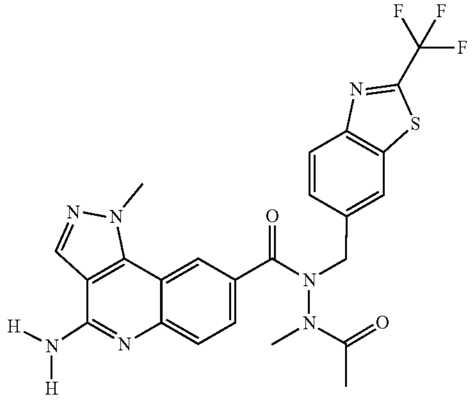 [SMILES: CC(=O)N(C)N(Cc1ccc2nc(C(F)(F)F)sc2c1)C(=O)c1ccc2nc(N)c3cnn(C)c3c2c1] | N'-acetyl-4-amino-N',1-dimethyl-N-((2-(trifluoromethyl)benzo[d]thiazol-6-yl)methyl)-1H-pyrazolo[4,3-c]quinoline-8-carbohydrazide |
| 338 | 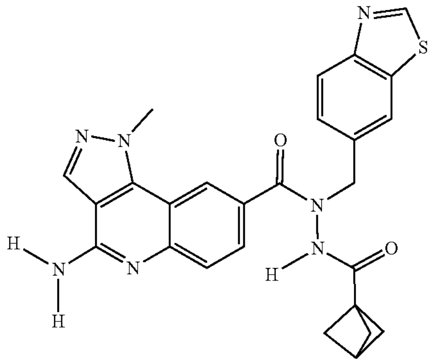 [SMILES: Cn1ncc2c(N)nc3ccc(C(=O)N(Cc4ccc5ncsc5c4)NC(=O)C45CC(C4)C5)cc3c21] | 4-amino-N-(benzo[d]thiazol-6-ylmethyl)-N'-(bicyclo[1.1.1]pentane-1-carbonyl)-N',1-dimethyl-1H-pyrazolo[4,3-c]quinoline-8-carbohydrazide |

TABLE 1A-continued

| Some compounds | | |
|---|---|---|
| Example | Structure | Name |
| 339 | 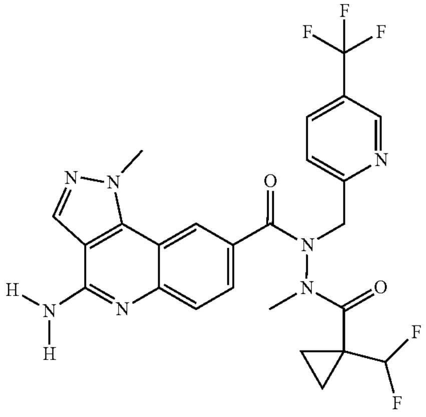 [SMILES: CN(C(=O)C1(C(F)F)CC1)N(Cc1ccc(C(F)(F)F)cn1)C(=O)c1ccc2nc(N)c3cnn(C)c3c2c1] | 4-amino-N'-(1-(difluoromethyl)cyclopropane-1-carbonyl)-N',1-dimethyl-N-((5-(trifluoromethyl)pyridin-2-yl)methyl)-1H-pyrazolo[4,3-c]quinoline-8-carbohydrazide |
| 340 | 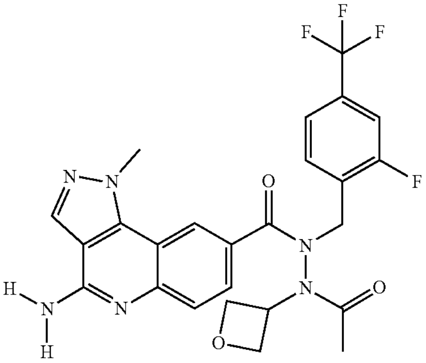 [SMILES: CC(=O)N(C1COC1)N(Cc1ccc(C(F)(F)F)cc1F)C(=O)c1ccc2nc(N)c3cnn(C)c3c2c1] | N'-acetyl-4-amino-N-(2-fluoro-4-(trifluoromethyl)benzyl)-1-methyl-N'-(oxetan-3-yl)-1H-pyrazolo[4,3-c]quinoline-8-carbohydrazide |
| 341 | 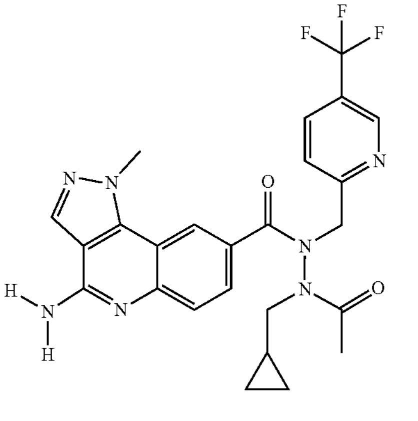 [SMILES: CC(=O)N(CC1CC1)N(Cc1ccc(C(F)(F)F)cn1)C(=O)c1ccc2nc(N)c3cnn(C)c3c2c1] | N'-acetyl-4-amino-N'-(cyclopropylmethyl)-1-methyl-N-((5-(trifluoromethyl)pyridin-2-yl)methyl)-1H-pyrazolo[4,3-c]quinoline-8-carbohydrazide |

TABLE 1A-continued

| Some compounds | | |
|---|---|---|
| Example | Structure | Name |
| 342 | 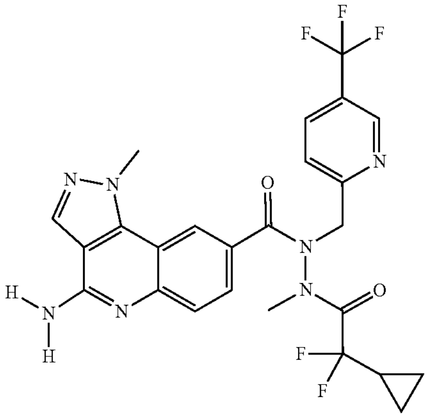 [SMILES: CN(C(=O)C(F)(F)C1CC1)N(Cc1ccc(C(F)(F)F)cn1)C(=O)c1ccc2nc(N)c3cnn(C)c3c2c1] | 4-amino-N'-(2-cyclopropyl-2,2-difluoroacetyl)-N',1-dimethyl-N-((5-(trifluoromethyl)pyridin-2-yl)methyl)-1H-pyrazolo[4,3-c]quinoline-8-carbohydrazide |
| 343 | 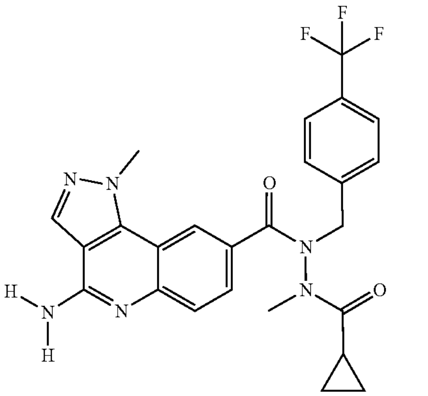 | 4-amino-N'-(cyclopropanecarbonyl)-N',1-dimethyl-N-(4-(trifluoromethyl)benzyl)-1H-pyrazolo[4,3-c]quinoline-8-carbohydrazide |
| 344 | 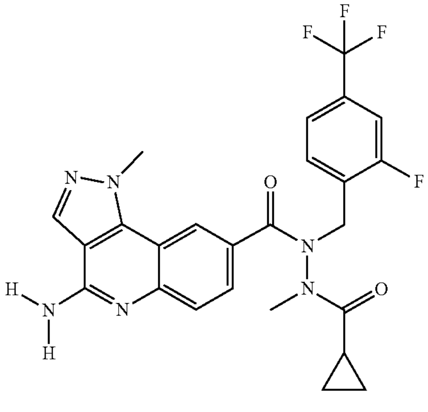 [SMILES: CN(C(=O)C1CC1)N(Cc1ccc(C(F)(F)F)cc1F)C(=O)c1ccc2nc(N)c3cnn(C)c3c2c1] | 4-amino-N'-(cyclopropanecarbonyl)-N-(2-fluoro-4-(trifluoromethyl)benzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 345 | 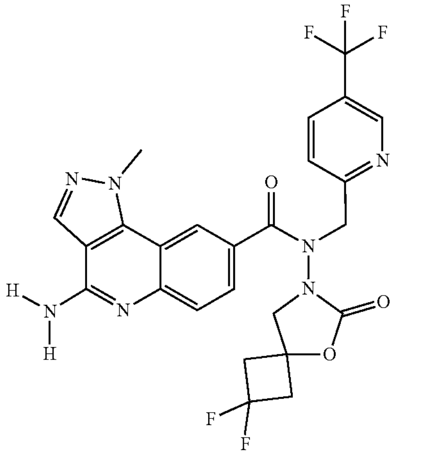 [SMILES: Cn1ncc2c(N)nc3ccc(C(=O)N(Cc4ccc(C(F)(F)F)cn4)N4CC5(CC(F)(F)C5)OC4=O)cc3c21] | 4-amino-N-(2,2-difluoro-6-oxo-5-oxa-7-azaspiro[3.4]octan-7-yl)-1-methyl-N-((5-(trifluoromethyl)pyridin-2-yl)methyl)-1H-pyrazolo[4,3-c]quinoline-8-carboxamide |
| 346 | 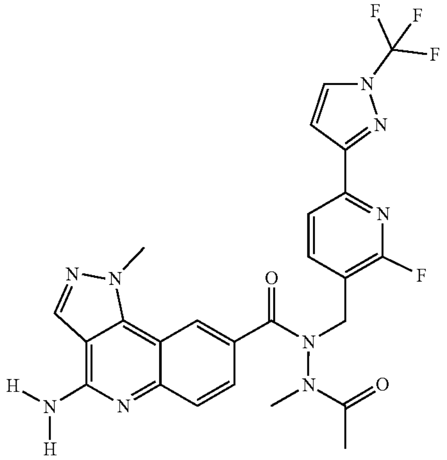 | N'-acetyl-4-amino-N-((2-fluoro-6-(1-(trifluoromethyl)-1H-pyrazol-3-yl)pyridin-3-yl)methyl)-N',1-dimethyl-1H-pyrazolo[4,3-c]quinoline-8-carbohydrazide |
| 347 | 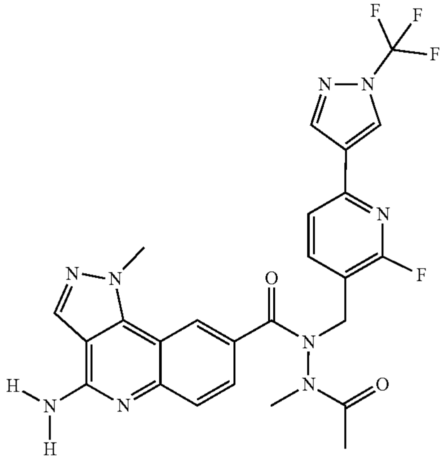 [SMILES: CC(=O)N(C)N(Cc1ccc(-c2cnn(C(F)(F)F)c2)nc1F)C(=O)c1ccc2nc(N)c3cnn(C)c3c2c1] | N'-acetyl-4-amino-N-((2-fluoro-6-(1-(trifluoromethyl)-1H-pyrazol-4-yl)pyridin-3-yl)methyl)-N',1-dimethyl-1H-pyrazolo[4,3-c]quinoline-8-carbohydrazide |

TABLE 1A-continued

| Some compounds | | |
|---|---|---|
| Example | Structure | Name |
| 348 | 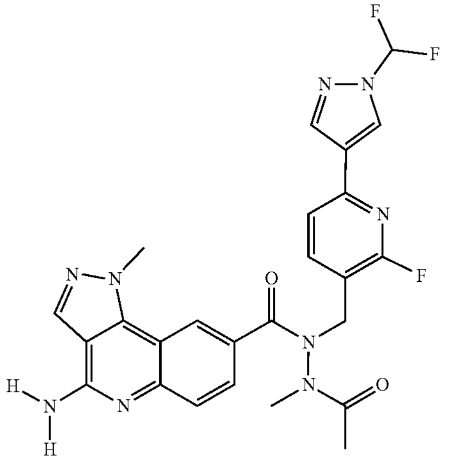 [SMILES: CC(=O)N(C)N(Cc1ccc(-c2cnn(C(F)F)c2)nc1F)C(=O)c1ccc2nc(N)c3cnn(C)c3c2c1] | N'-acetyl-4-amino-N-((6-(1-(difluoromethyl)-1H-pyrazol-4-yl)-2-fluoropyridin-3-yl)methyl)-N',1-dimethyl-1H-pyrazolo[4,3-c]quinoline-8-carbohydrazide |
| 349 | 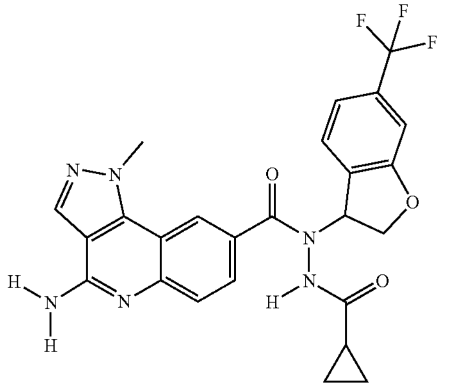 [SMILES: Cn1ncc2c(N)nc3ccc(C(=O)N(NC(=O)C4CC4)C4COc5cc(C(F)(F)F)ccc54)cc3c21] | 4-amino-N'-(cyclopropanecarbonyl)-1-methyl-N-(6-(trifluoromethyl)-2,3-dihydrobenzofuran-3-yl)-1H-pyrazolo[4,3-c]quinoline-8-carbohydrazide |
| 350 | 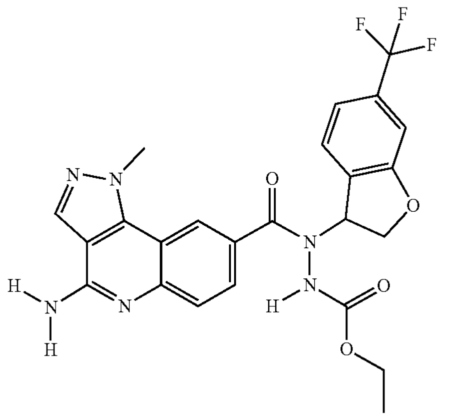 [SMILES: CCOC(=O)NN(C(=O)c1ccc2nc(N)c3cnn(C)c3c2c1)C1COc2cc(C(F)(F)F)ccc21] | ethyl 2-(4-amino-1-methyl-1H-pyrazolo[4,3-c]quinoline-8-carbonyl)-2-(6-(trifluoromethyl)-2,3-dihydrobenzofuran-3-yl)hydrazine-1-carboxylate |

TABLE 1A-continued

| Some compounds | | |
|---|---|---|
| Example | Structure | Name |
| 351 | 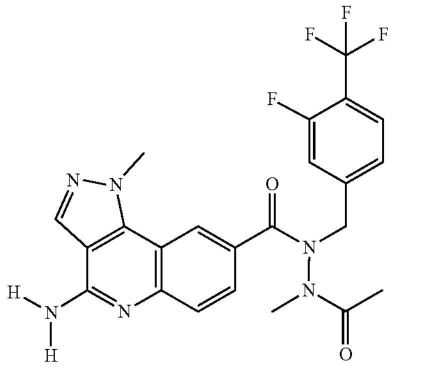 [SMILES: CC(=O)N(C)N(Cc1ccc(C(F)(F)F)c(F)c1)C(=O)c1ccc2nc(N)c3cnn(C)c3c2c1] | N'-acetyl-4-amino-N-(3-fluoro-4-(trifluoromethyl)benzyl)-N',1-dimethyl-1H-pyrazolo[4,3-c]quinoline-8-carbohydrazide |
| 352 | 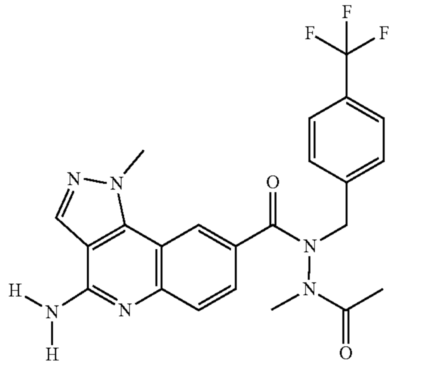 [SMILES: CC(=O)N(C)N(Cc1ccc(C(F)(F)F)cc1)C(=O)c1ccc2nc(N)c3cnn(C)c3c2c1] | N'-acetyl-4-amino-N',1-dimethyl-N-(4-(trifluoromethyl)benzyl)-1H-pyrazolo[4,3-c]quinoline-8-carbohydrazide |
| 353 | 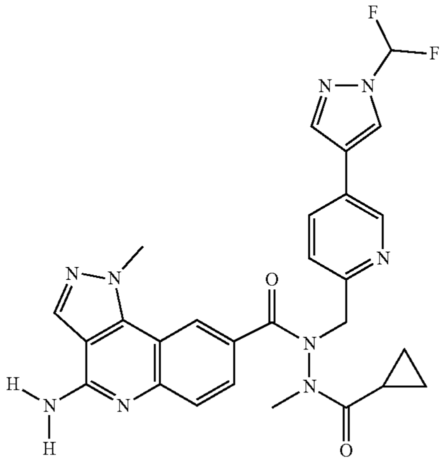 [SMILES: CN(C(=O)C1CC1)N(Cc1ccc(-c2cnn(C(F)F)c2)cn1)C(=O)c1ccc2nc(N)c3cnn(C)c3c2c1] | 4-amino-N'-(cyclopropanecarbonyl)-N-((5-(1-(difluoromethyl)-1H-pyrazol-4-yl)pyridin-2-yl)methyl)-N',1-dimethyl-1H-pyrazolo[4,3-c]quinoline-8-carbohydrazide |
| 354 | 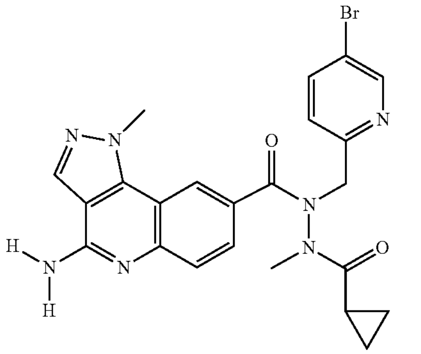 [SMILES: CN(C(=O)C1CC1)N(Cc1ccc(Br)cn1)C(=O)c1ccc2nc(N)c3cnn(C)c3c2c1] | 4-amino-N-((5-bromopyridin-2-yl)methyl)-N'-(cyclopropanecarbonyl)-N',1-dimethyl-1H-pyrazolo[4,3-c]quinoline-8-carbohydrazide |

TABLE 1A-continued

| Some compounds | | |
|---|---|---|
| Example | Structure | Name |
| 355 | 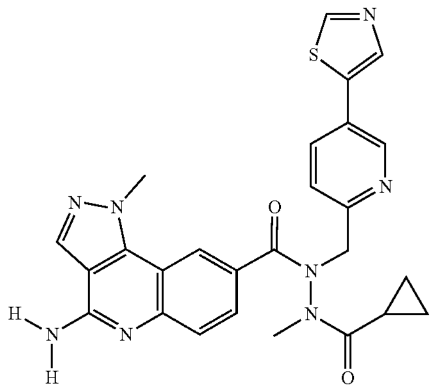 [SMILES: CN(C(=O)C1CC1)N(Cc1ccc(-c2cncs2)cn1)C(=O)c1ccc2nc(N)c3cnn(C)c3c2c1] | 4-amino-N'-(cyclopropanecarbonyl)-N',1-dimethyl-N-((5-(thiazol-5-yl)pyridin-2-yl)methyl)-1H-pyrazolo[4,3-c]quinoline-8-carbohydrazide |
| 356 | 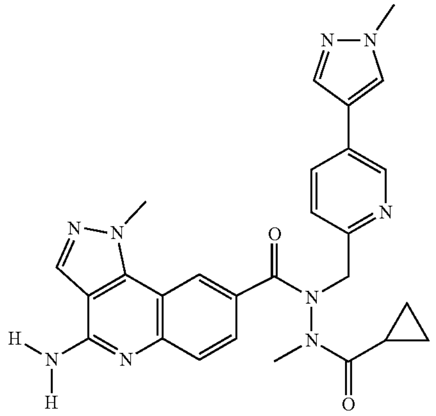 [SMILES: CN(C(=O)C1CC1)N(Cc1ccc(-c2cnn(C)c2)cn1)C(=O)c1ccc2nc(N)c3cnn(C)c3c2c1] | 4-amino-N'-(cyclopropanecarbonyl)-N',1-dimethyl-N-((5-(1-methyl-1H-pyrazol-4-yl)pyridin-2-yl)methyl)-1H-pyrazolo[4,3-c]quinoline-8-carbohydrazide |
| 357 | 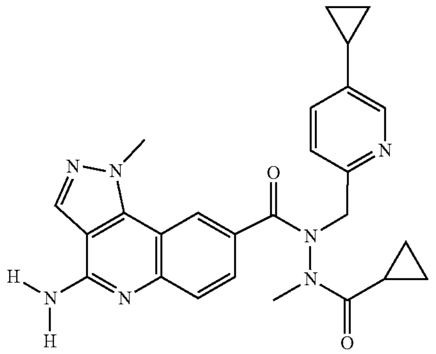 [SMILES: CN(C(=O)C1CC1)N(Cc1ccc(C2CC2)cn1)C(=O)c1ccc2nc(N)c3cnn(C)c3c2c1] | 4-amino-N'-(cyclopropanecarbonyl)-N-((5-cyclopropylpyridin-2-yl)methyl)-N',1-dimethyl-1H-pyrazolo[4,3-c]quinoline-8-carbohydrazide |
| 358 | 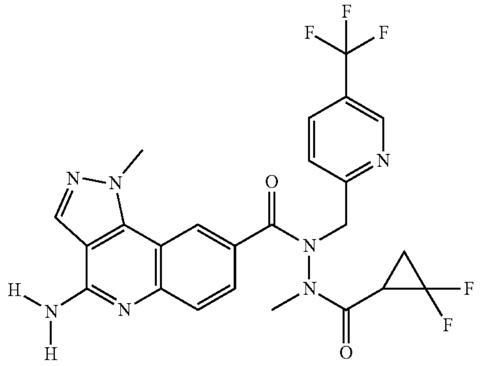 [SMILES: CN(C(=O)C1CC1(F)F)N(Cc1ccc(C(F)(F)F)cn1)C(=O)c1ccc2nc(N)c3cnn(C)c3c2c1] | 4-amino-N'-(2,2-difluorocyclopropane-1-carbonyl)-N',1-dimethyl-N-((5-(trifluoromethyl)pyridin-2-yl)methyl)-1H-pyrazolo[4,3-c]quinoline-8-carbohydrazide |

TABLE 1A-continued

| Some compounds | | |
|---|---|---|
| Example | Structure | Name |
| 359 | 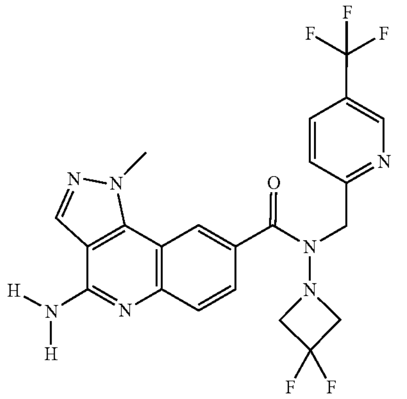 [SMILES: Cn1ncc2c(N)nc3ccc(C(=O)N(Cc4ccc(C(F)(F)F)cn4)N4CC(F)(F)C4)cc3c21] | 4-amino-N-(3,3-difluoroazetidin-1-yl)-1-methyl-N-((5-(trifluoromethyl)pyridin-2-yl)methyl)-1H-pyrazolo[4,3-c]quinoline-8-carboxamide |
| 360 | 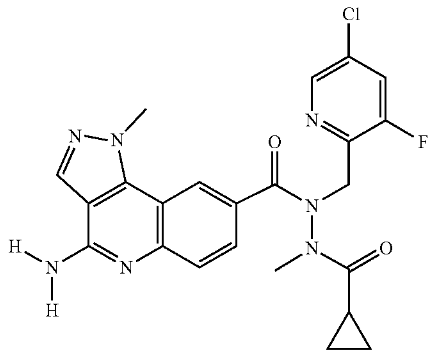 [SMILES: CN(C(=O)C1CC1)N(Cc1ncc(Cl)cc1F)C(=O)c1ccc2nc(N)c3cnn(C)c3c2c1] | 4-amino-N-((5-chloro-3-fluoropyridin-2-yl)methyl)-N'-(cyclopropanecarbonyl)-N',1-dimethyl-1H-pyrazolo[4,3-c]quinoline-8-carbohydrazide |
| 361 | 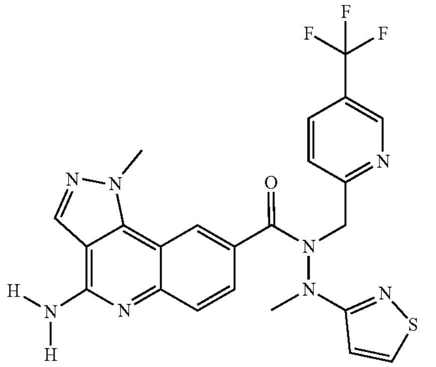 [SMILES: CN(c1ccsn1)N(Cc1ccc(C(F)(F)F)cn1)C(=O)c1ccc2nc(N)c3cnn(C)c3c2c1] | 4-amino-N'-(isothiazol-3-yl)-N',1-dimethyl-N-((5-(trifluoromethyl)pyridin-2-yl)methyl)-1H-pyrazolo[4,3-c]quinoline-8-carbohydrazide |
| 362 | 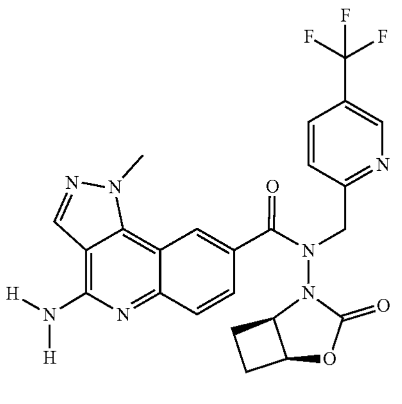 [SMILES: Cn1ncc2c(N)nc3ccc(C(=O)N(Cc4ccc(C(F)(F)F)cn4)N4C(=O)O[C@H]5CC[C@H]54)cc3c21] | 4-amino-1-methyl-N-((1S,5R)-3-oxo-2-oxa-4-azabicyclo[3.2.0]heptan-4-yl)-N-((5-(trifluoromethyl)pyridin-2-yl)methyl)-1H-pyrazolo[4,3-c]quinoline-8-carboxamide |

TABLE 1A-continued

| Some compounds | | |
|---|---|---|
| Example | Structure | Name |
| 363 | 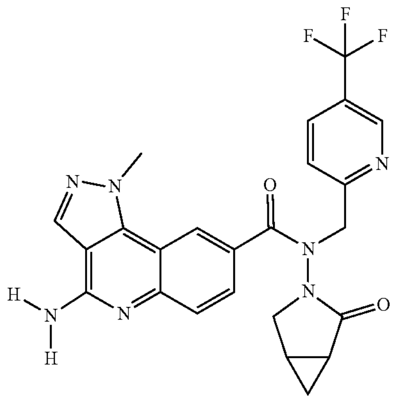 [SMILES: Cn1ncc2c(N)nc3ccc(C(=O)N(Cc4ccc(C(F)(F)F)cn4)N4CC5CC5C4=O)cc3c21] | 4-amino-1-methyl-N-(2-oxo-3-azabicyclo[3.1.0]hexan-3-yl)-N-((5-(trifluoromethyl)pyridin-2-yl)methyl)-1H-pyrazolo[4,3-c]quinoline-8-carboxamide |
| 364 | 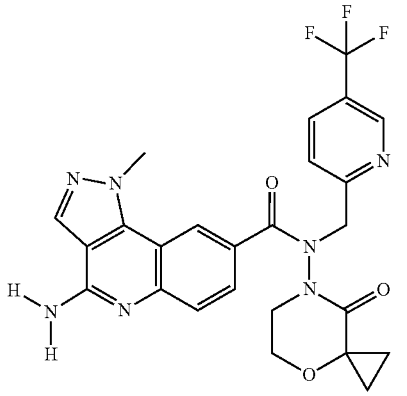 [SMILES: Cn1ncc2c(N)nc3ccc(C(=O)N(Cc4ccc(C(F)(F)F)cn4)N4CCOC5(CC5)C4=O)cc3c21] | 4-amino-1-methyl-N-(8-oxo-4-oxa-7-azaspiro[2.5]octan-7-yl)-N-((5-(trifluoromethyl)pyridin-2-yl)methyl)-1H-pyrazolo[4,3-c]quinoline-8-carboxamide |
| 365 | 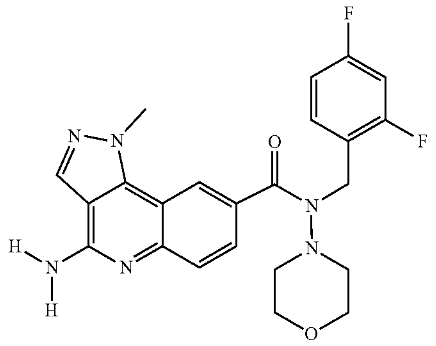 [SMILES: Cn1ncc2c(N)nc3ccc(C(=O)N(Cc4ccc(F)cc4F)N4CCOCC4)cc3c21] | 4-amino-N-(2,4-difluorobenzyl)-1-methyl-N-morpholino-1H-pyrazolo[4,3-c]quinoline-8-carboxamide |
| 366 | 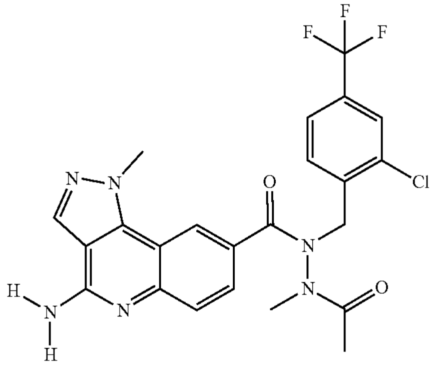 [SMILES: CC(=O)N(C)N(Cc1ccc(C(F)(F)F)cc1Cl)C(=O)c1ccc2nc(N)c3cnn(C)c3c2c1] | N'-acetyl-4-amino-N-(2-chloro-4-(trifluoromethyl)benzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 367 | 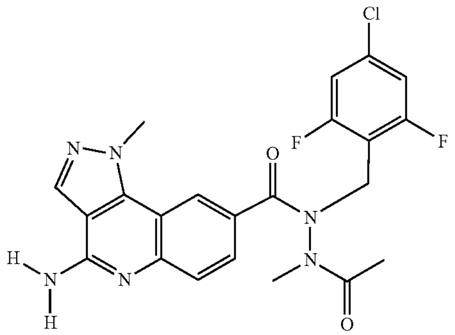 [SMILES: CC(=O)N(C)N(Cc1c(F)cc(Cl)cc1F)C(=O)c1ccc2nc(N)c3cnn(C)c3c2c1] | N'-acetyl-4-amino-N-(4-chloro-2,6-difluorobenzyl)-N',1-dimethyl-1H-pyrazolo[4,3-c]quinoline-8-carbohydrazide |
| 368 | 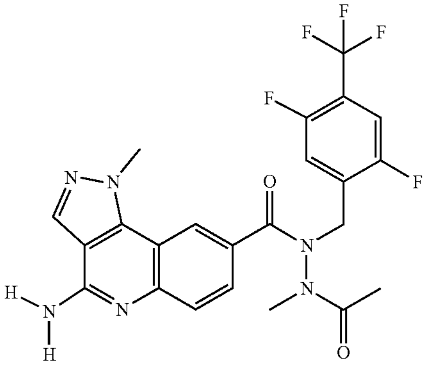 [SMILES: CC(=O)N(C)N(Cc1cc(F)c(C(F)(F)F)cc1F)C(=O)c1ccc2nc(N)c3cnn(C)c3c2c1] | N'-acetyl-4-amino-N-(2,5-difluoro-4-(trifluoromethyl)benzyl)-N',1-dimethyl-1H-pyrazolo[4,3-c]quinoline-8-carbohydrazide |
| 369 | 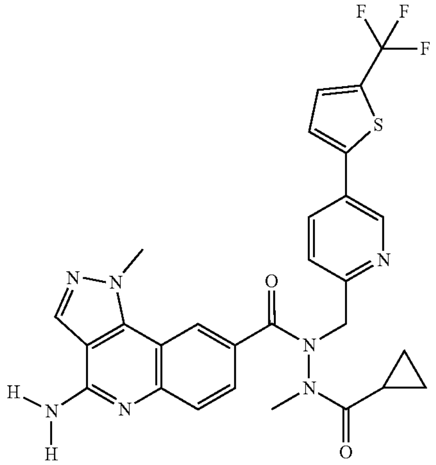 [SMILES: CN(C(=O)C1CC1)N(Cc1ccc(-c2ccc(C(F)(F)F)s2)cn1)C(=O)c1ccc2nc(N)c3cnn(C)c3c2c1] | 4-amino-N'-(cyclopropanecarbonyl)-N',1-dimethyl-N-((5-(5-(trifluoromethyl)thiophen-2-yl)pyridin-2-yl)methyl)-1H-pyrazolo[4,3-c]quinoline-8-carbohydrazide |
| 370 | 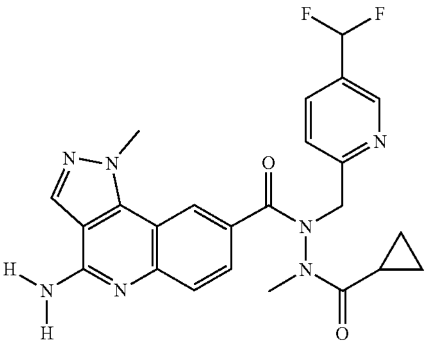 [SMILES: CN(C(=O)C1CC1)N(Cc1ccc(C(F)F)cn1)C(=O)c1ccc2nc(N)c3cnn(C)c3c2c1] | 4-amino-N'-(cyclopropanecarbonyl)-N-((5-(difluoromethyl)pyridin-2-yl)methyl)-N',1-dimethyl-1H-pyrazolo[4,3-c]quinoline-8-carbohydrazide |

TABLE 1A-continued

| Some compounds | | |
|---|---|---|
| Example | Structure | Name |
| 371 | 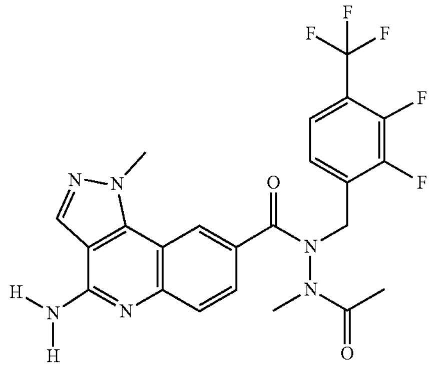 [SMILES: CC(=O)N(C)N(Cc1ccc(C(F)(F)F)c(F)c1F)C(=O)c1ccc2nc(N)c3cnn(C)c3c2c1] | N'-acetyl-4-amino-N-(2,3-difluoro-4-(trifluoromethyl)benzyl)-N',1-dimethyl-1H-pyrazolo[4,3-c]quinoline-8-carbohydrazide |
| 372 | 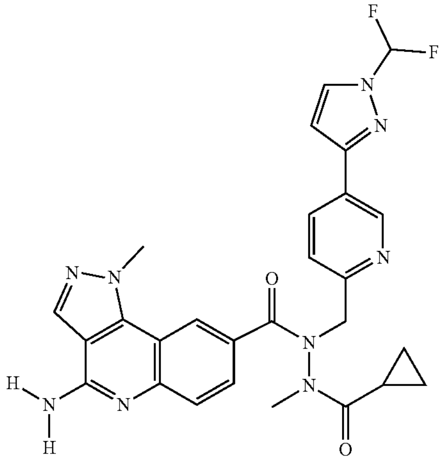 | 4-amino-N'-(cyclopropanecarbonyl)-N-((5-(1-(difluoromethyl)-1H-pyrazol-3-yl)pyridin-2-yl)methyl)-N',1-dimethyl-1H-pyrazolo[4,3-c]quinoline-8-carbohydrazide |
| 373 | 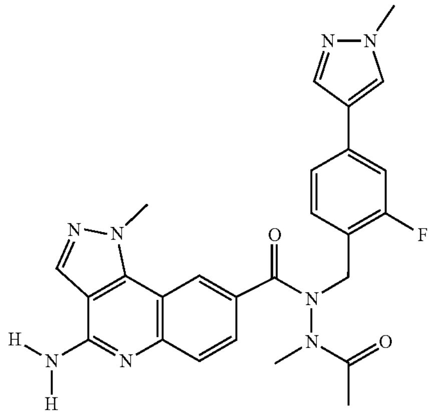 [SMILES: CC(=O)N(C)N(Cc1ccc(-c2cnn(C)c2)cc1F)C(=O)c1ccc2nc(N)c3cnn(C)c3c2c1] | N'-acetyl-4-amino-N-(2-fluoro-4-(1-methyl-1H-pyrazol-4-yl)benzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 374 | 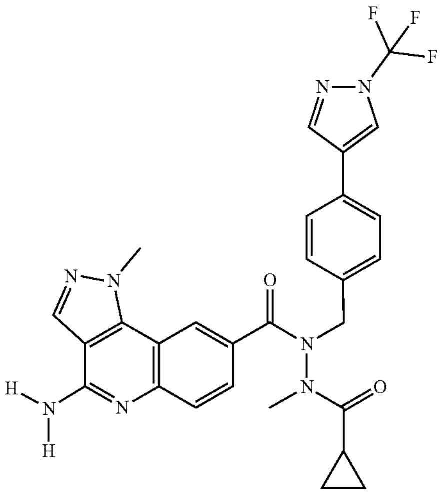 [SMILES: CN(C(=O)C1CC1)N(Cc1ccc(-c2cnn(C(F)(F)F)c2)cc1)C(=O)c1ccc2nc(N)c3cnn(C)c3c2c1] | 4-amino-N'-(cyclopropanecarbonyl)-N',1-dimethyl-N-(4-(1-(trifluoromethyl)-1H-pyrazol-4-yl)benzyl)-1H-pyrazolo[4,3-c]quinoline-8-carbohydrazide |
| 375 | 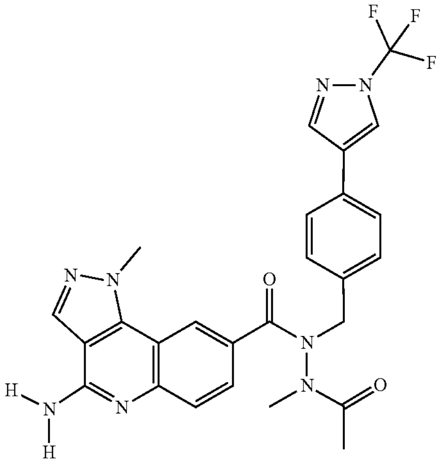 [SMILES: CC(=O)N(C)N(Cc1ccc(-c2cnn(C(F)(F)F)c2)cc1)C(=O)c1ccc2nc(N)c3cnn(C)c3c2c1] | N'-acetyl-4-amino-N',1-dimethyl-N-(4-(1-(trifluoromethyl)-1H-pyrazol-4-yl)benzyl)-1H-pyrazolo[4,3-c]quinoline-8-carbohydrazide |
| 376 | 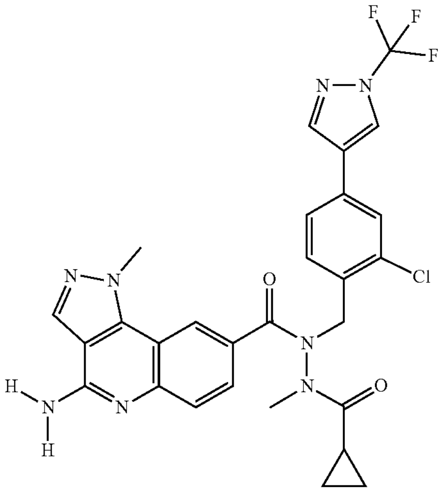 [SMILES: CN(C(=O)C1CC1)N(Cc1ccc(-c2cnn(C(F)(F)F)c2)cc1Cl)C(=O)c1ccc2nc(N)c3cnn(C)c3c2c1] | 4-amino-N-(2-chloro-4-(1-(trifluoromethyl)-1H-pyrazol-4-yl)benzyl)-N'-(cyclopropanecarbonyl)-N',1-dimethyl-1H-pyrazolo[4,3-c]quinoline-8-carbohydrazide |

TABLE 1A-continued

| Some compounds | | |
|---|---|---|
| Example | Structure | Name |
| 377 | 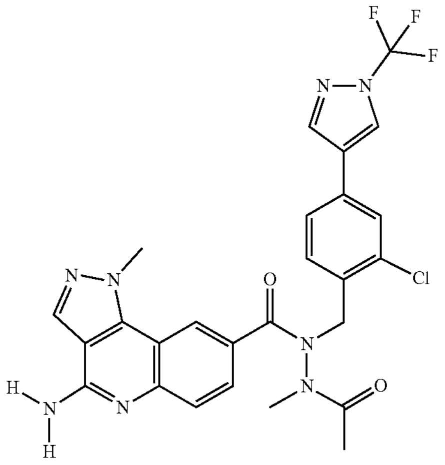 [SMILES: CC(=O)N(C)N(Cc1ccc(-c2cnn(C(F)(F)F)c2)cc1Cl)C(=O)c1ccc2nc(N)c3cnn(C)c3c2c1] | N'-acetyl-4-amino-N-(2-chloro-4-(1-(trifluoromethyl)-1H-pyrazol-4-yl)benzyl)-N',1-dimethyl-1H-pyrazolo[4,3-c]quinoline-8-carbohydrazide |
| 378 | 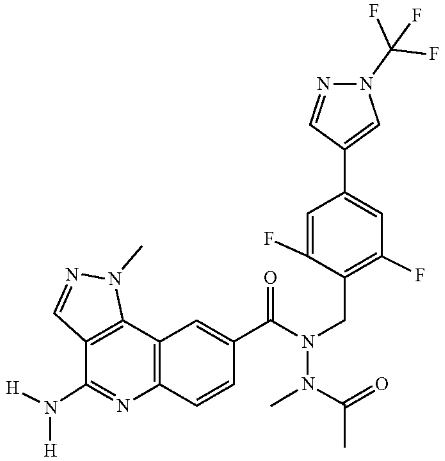 | N'-acetyl-4-amino-N-(2,6-difluoro-4-(1-(trifluoromethyl)-1H-pyrazol-4-yl)benzyl)-N',1-dimethyl-1H-pyrazolo[4,3-c]quinoline-8-carbohydrazide |
| 379 | 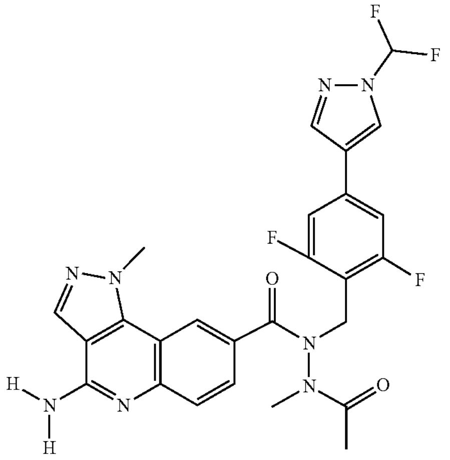 [SMILES: CC(=O)N(C)N(Cc1c(F)cc(-c2cnn(C(F)F)c2)cc1F)C(=O)c1ccc2nc(N)c3cnn(C)c3c2c1] | N'-acetyl-4-amino-N-(4-(1-(difluoromethyl)-1H-pyrazol-4-yl)-2,6-difluorobenzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 380 | 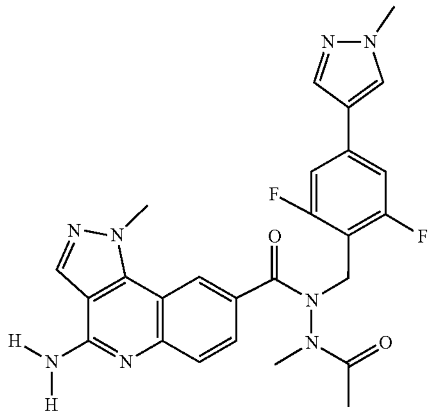 [SMILES: CC(=O)N(C)N(Cc1c(F)cc(-c2cnn(C)c2)cc1F)C(=O)c1ccc2nc(N)c3cnn(C)c3c2c1] | N'-acetyl-4-amino-N-(2,6-difluoro-4-(1-methyl-1H-pyrazol-4-yl)benzyl)-N',1-dimethyl-1H-pyrazolo[4,3-c]quinoline-8-carbohydrazide |
| 381 | 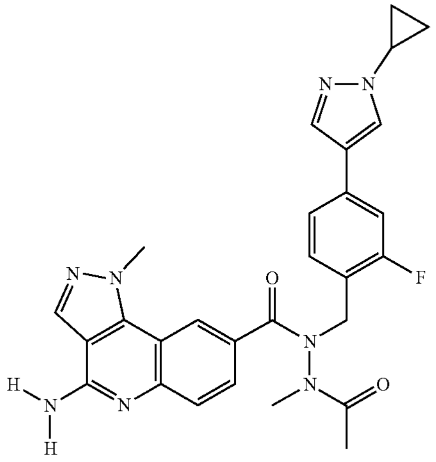 [SMILES: CC(=O)N(C)N(Cc1ccc(-c2cnn(C3CC3)c2)cc1F)C(=O)c1ccc2nc(N)c3cnn(C)c3c2c1] | N'-acetyl-4-amino-N-(4-(1-cyclopropyl-1H-pyrazol-4-yl)-2,6-difluorobenzyl)-N',1-dimethyl-1H-pyrazolo[4,3-c]quinoline-8-carbohydrazide |
| 382 | 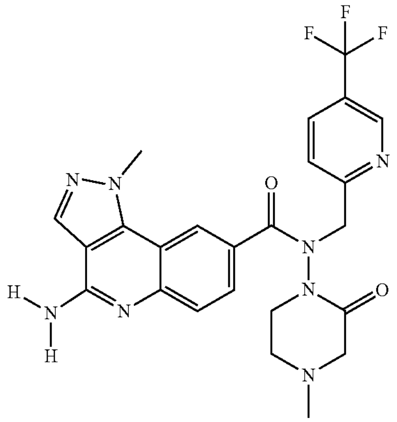 [SMILES: CN1CCN(N(Cc2ccc(C(F)(F)F)cn2)C(=O)c2ccc3nc(N)c4cnn(C)c4c3c2)C(=O)C1] | 4-amino-1-methyl-N-(4-methyl-2-oxopiperazin-1-yl)-N-((5-(trifluoromethyl)pyridin-2-yl)methyl)-1H-pyrazolo[4,3-c]quinoline-8-carboxamide |

TABLE 1A-continued

| Some compounds | | |
|---|---|---|
| Example | Structure | Name |
| 383 | 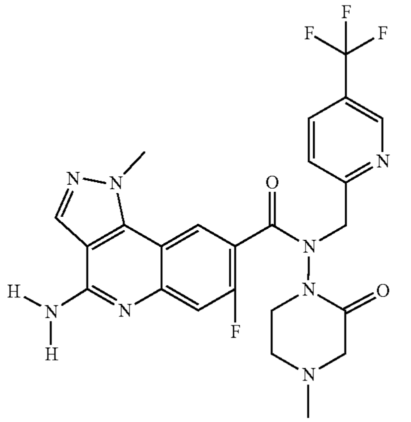 [SMILES: CN1CCN(N(Cc2ccc(C(F)(F)F)cn2)C(=O)c2cc3c(cc2F)nc(N)c2cnn(C)c23)C(=O)C1] | 4-amino-7-fluoro-1-methyl-N-(4-methyl-2-oxopiperazin-1-yl)-N-((5-(trifluoromethyl)pyridin-2-yl)methyl)-1H-pyrazolo[4,3-c]quinoline-8-carboxamide |
| 384 | 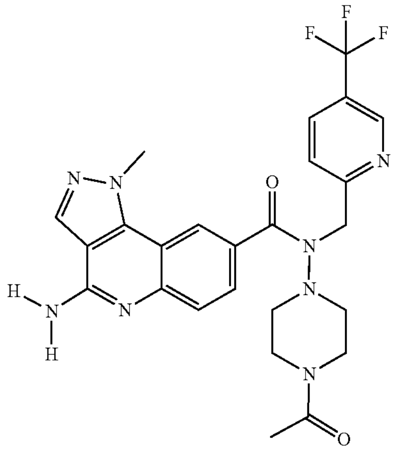 [SMILES: CC(=O)N1CCN(N(Cc2ccc(C(F)(F)F)cn2)C(=O)c2ccc3nc(N)c4cnn(C)c4c3c2)CC1] | N-(4-acetylpiperazin-1-yl)-4-amino-1-methyl-N-((5-(trifluoromethyl)pyridin-2-yl)methyl)-1H-pyrazolo[4,3-c]quinoline-8-carboxamide |
| 385 | 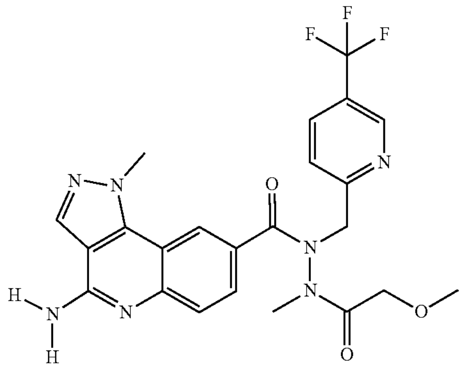 [SMILES: COCC(=O)N(C)N(Cc1ccc(C(F)(F)F)cn1)C(=O)c1ccc2nc(N)c3cnn(C)c3c2c1] | 4-amino-N'-(2-methoxyacetyl)-N',1-dimethyl-N-((5-(trifluoromethyl)pyridin-2-yl)methyl)-1H-pyrazolo[4,3-c]quinoline-8-carbohydrazide |

TABLE 1A-continued

| Some compounds | | |
|---|---|---|
| Example | Structure | Name |
| 386 | 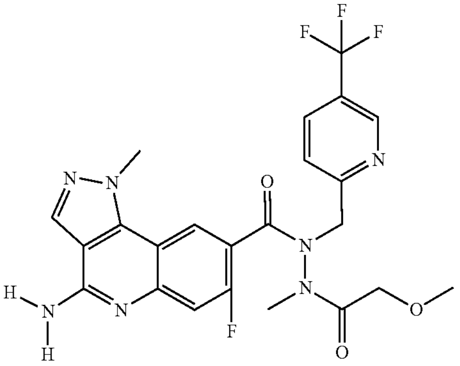 [SMILES: COCC(=O)N(C)N(Cc1ccc(C(F)(F)F)cn1)C(=O)c1cc2c(cc1F)nc(N)c1cnn(C)c12] | 4-amino-7-fluoro-N'-(2-methoxyacetyl)-N',1-dimethyl-N-((5-(trifluoromethyl)pyridin-2-yl)methyl)-1H-pyrazolo[4,3-c]quinoline-8-carbohydrazide |
| 387 | 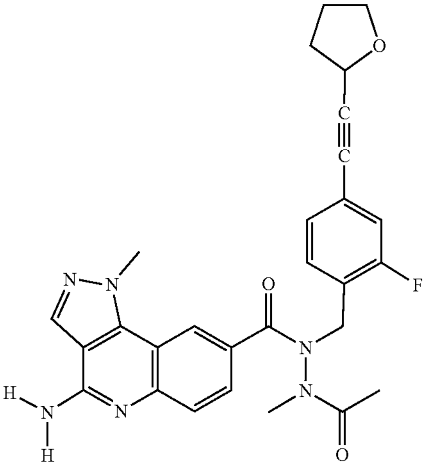 [SMILES: CC(=O)N(C)N(Cc1ccc(C#CC2CCCO2)cc1F)C(=O)c1ccc2nc(N)c3cnn(C)c3c2c1] | N'-acetyl-4-amino-N-(2-fluoro-4-((tetrahydrofuran-2-yl)ethynyl)benzyl)-N',1-dimethyl-1H-pyrazolo[4,3-c]quinoline-8-carbohydrazide |
| 388 | 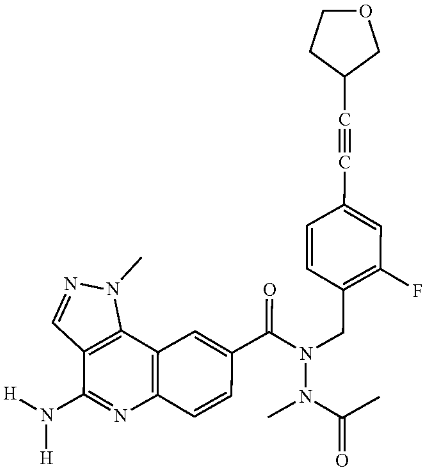 [SMILES: CC(=O)N(C)N(Cc1ccc(C#CC2CCOC2)cc1F)C(=O)c1ccc2nc(N)c3cnn(C)c3c2c1] | N'-acetyl-4-amino-N-(2-fluoro-4-((tetrahydrofuran-3-yl)ethynyl)benzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 389 | 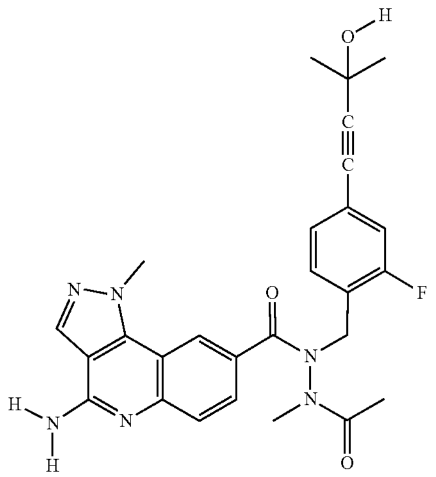 [SMILES: CC(=O)N(C)N(Cc1ccc(C#CC(C)(C)O)cc1F)C(=O)c1ccc2nc(N)c3cnn(C)c3c2c1] | N'-acetyl-4-amino-N-(2-fluoro-4-(3-hydroxy-3-methylbut-1-yn-1-yl)benzyl)-N',1-dimethyl-1H-pyrazolo[4,3-c]quinoline-8-carbohydrazide |
| 390 | 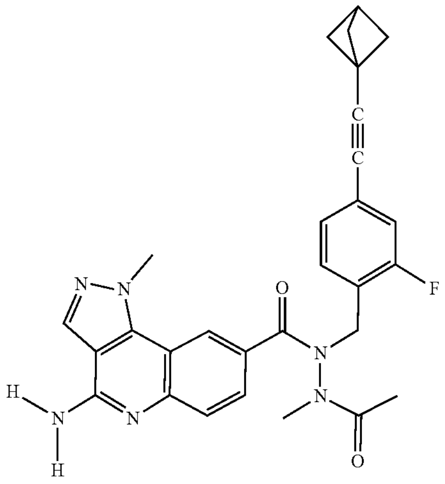 [SMILES: CC(=O)N(C)N(Cc1ccc(C#CC23CC(C2)C3)cc1F)C(=O)c1ccc2nc(N)c3cnn(C)c3c2c1] | N'-acetyl-4-amino-N-(4-(bicyclo[1.1.1]pentan-1-ylethynyl)-2-fluorobenzyl)-N',1-dimethyl-1H-pyrazolo[4,3-c]quinoline-8-carbohydrazide |
| 391 | 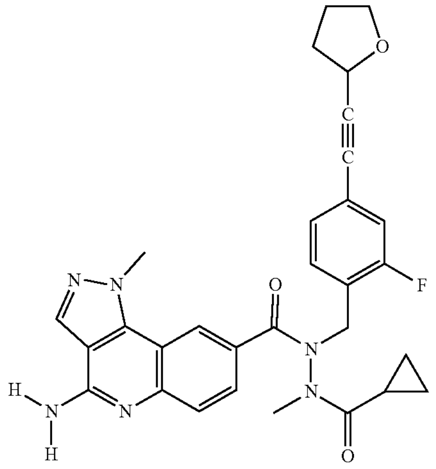 [SMILES: CN(C(=O)C1CC1)N(Cc1ccc(C#CC2CCCO2)cc1F)C(=O)c1ccc2nc(N)c3cnn(C)c3c2c1] | 4-amino-N'-(cyclopropanecarbonyl)-N-(2-fluoro-4-((tetrahydrofuran-2-yl)ethynyl)benzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 392 | 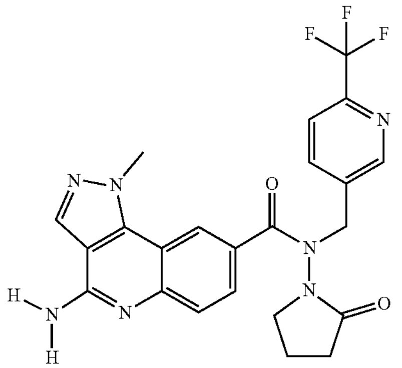 [SMILES: Cn1ncc2c(N)nc3ccc(C(=O)N(Cc4ccc(C(F)(F)F)nc4)N4CCCC4=O)cc3c21] | 4-amino-1-methyl-N-(2-oxopyrrolidin-1-yl)-N-((6-(trifluoromethyl)pyridin-3-yl)methyl)-1H-pyrazolo[4,3-c]quinoline-8-carboxamide |
| 393 | 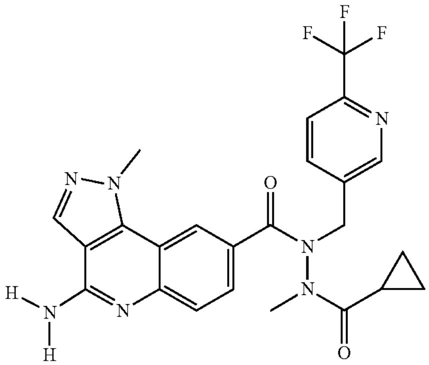 [SMILES: CN(C(=O)C1CC1)N(Cc1ccc(C(F)(F)F)nc1)C(=O)c1ccc2nc(N)c3cnn(C)c3c2c1] | 4-amino-N'-(cyclopropanecarbonyl)-N',1-dimethyl-N-((6-(trifluoromethyl)pyridin-3-yl)methyl)-1H-pyrazolo[4,3-c]quinoline-8-carbohydrazide |
| 394 | 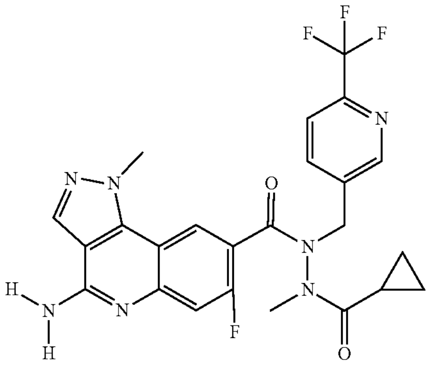 [SMILES: CN(C(=O)C1CC1)N(Cc1ccc(C(F)(F)F)nc1)C(=O)c1cc2c(cc1F)nc(N)c1cnn(C)c12] | 4-amino-N'-(cyclopropanecarbonyl)-7-fluoro-N',1-dimethyl-N-((6-(trifluoromethyl)pyridin-3-yl)methyl)-1H-pyrazolo[4,3-c]quinoline-8-carbohydrazide |
| 395 | 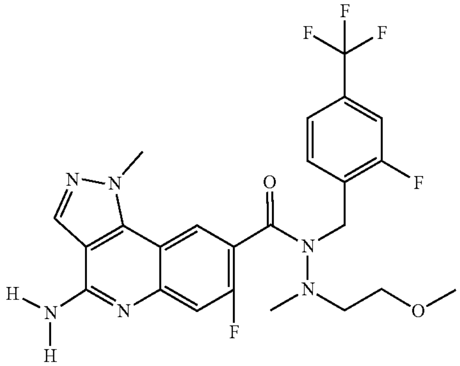 [SMILES: COCCN(C)N(Cc1ccc(C(F)(F)F)cc1F)C(=O)c1cc2c(cc1F)nc(N)c1cnn(C)c12] | 4-amino-7-fluoro-N-(2-fluoro-4-(trifluoromethyl)benzyl)-N'-(2-methoxyethyl)-N',1-dimethyl-1H-pyrazolo[4,3-c]quinoline-8-carbohydrazide |

TABLE 1A-continued

| Some compounds | | |
|---|---|---|
| Example | Structure | Name |
| 396 | 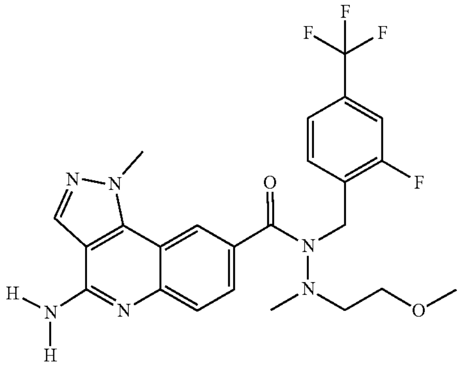 [SMILES: COCCN(C)N(Cc1ccc(C(F)(F)F)cc1F)C(=O)c1ccc2nc(N)c3cnn(C)c3c2c1] | 4-amino-N-(2-fluoro-4-(trifluoromethyl)benzyl)-N'-(2-methoxyethyl)-N',1-dimethyl-1H-pyrazolo[4,3-c]quinoline-8-carbohydrazide |
| 397 | 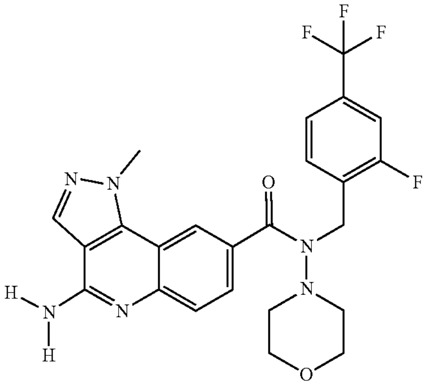 [SMILES: Cn1ncc2c(N)nc3ccc(C(=O)N(Cc4ccc(C(F)(F)F)cc4F)N4CCOCC4)cc3c21] | 4-amino-N-(2-fluoro-4-(trifluoromethyl)benzyl)-1-methyl-N-morpholino-1H-pyrazolo[4,3-c]quinoline-8-carboxamide |
| 398 | 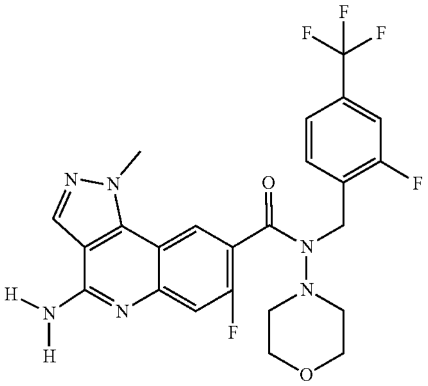 [SMILES: Cn1ncc2c(N)nc3cc(F)c(C(=O)N(Cc4ccc(C(F)(F)F)cc4F)N4CCOCC4)cc3c21] | 4-amino-7-fluoro-N-(2-fluoro-4-(trifluoromethyl)benzyl)-1-methyl-N-morpholino-1H-pyrazolo[4,3-c]quinoline-8-carboxamide |
| 399 | 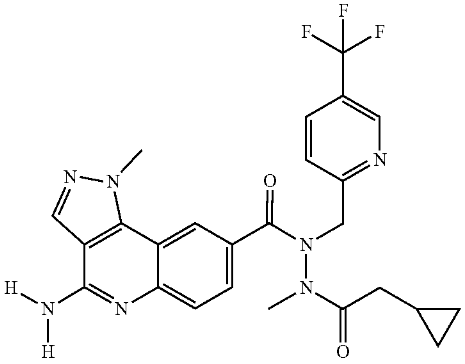 [SMILES: CN(C(=O)CC1CC1)N(Cc1ccc(C(F)(F)F)cn1)C(=O)c1ccc2nc(N)c3cnn(C)c3c2c1] | 4-amino-N'-(2-cyclopropylacetyl)-N',1-dimethyl-N-((5-(trifluoromethyl)pyridin-2-yl)methyl)-1H-pyrazolo[4,3-c]quinoline-8-carbohydrazide |

TABLE 1A-continued

| Some compounds | | |
|---|---|---|
| Example | Structure | Name |
| 400 | 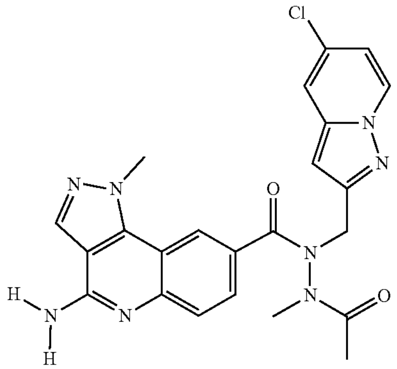 [SMILES: CC(=O)N(C)N(Cc1cc2cc(Cl)ccn2n1)C(=O)c1ccc2nc(N)c3cnn(C)c3c2c1] | N'-acetyl-4-amino-N-((5-chloropyrazolo[1,5-a]pyridin-2-yl)methyl)-N',1-dimethyl-1H-pyrazolo[4,3-c]quinoline-8-carbohydrazide |
| 401 | 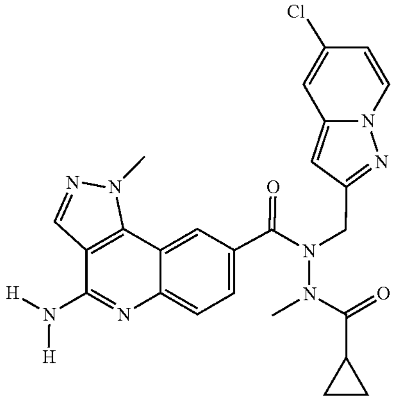 [SMILES: CN(C(=O)C1CC1)N(Cc1cc2cc(Cl)ccn2n1)C(=O)c1ccc2nc(N)c3cnn(C)c3c2c1] | 4-amino-N-((5-chloropyrazolo[1,5-alpyridin-2-yl)methyl)-N'-(cyclopropanecarbonyl)-N',1-dimethyl-1H-pyrazolo[4,3-c]quinoline-8-carbohydrazide |
| 402 | 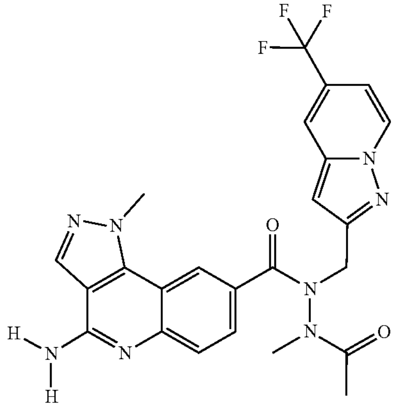 [SMILES: CC(=O)N(C)N(Cc1cc2cc(C(F)(F)F)ccn2n1)C(=O)c1ccc2nc(N)c3cnn(C)c3c2c1] | N'-acetyl-4-amino-N',1-dimethyl-N-((5-(trifluoromethyl)pyrazolo[1,5-a]pyridin-2-yl)methyl)-1H-pyrazolo[4,3-c]quinoline-8-carbohydrazide |
| 403 | 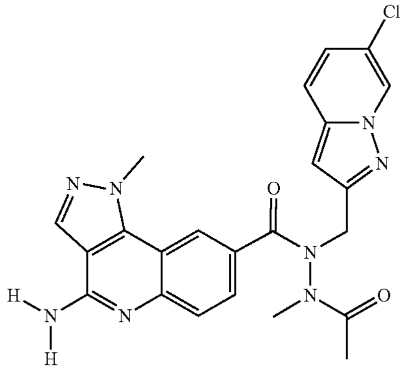 [SMILES: CC(=O)N(C)N(Cc1cc2ccc(Cl)cn2n1)C(=O)c1ccc2nc(N)c3cnn(C)c3c2c1] | N'-acetyl-4-amino-N-((6-chloropyrazolo[1,5-a]pyridin-2-yl)methyl)-N',1-dimethyl-1H-pyrazolo[4,3-c]quinoline-8-carbohydrazide |

TABLE 1A-continued

| Example | Structure | Name |
| --- | --- | --- |
| Some compounds | | |
| 404 | 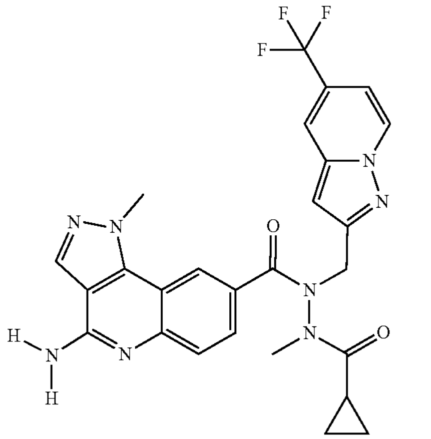 [SMILES: CN(C(=O)C1CC1)N(Cc1cc2cc(C(F)(F)F)ccn2n1)C(=O)c1ccc2nc(N)c3cnn(C)c3c2c1] | 4-amino-N'-(cyclopropanecarbonyl)-N',1-dimethyl-N-((5-(trifluoromethyl)pyrazolo[1,5-a]pyridin-2-yl)methyl)-1H-pyrazolo[4,3-c]quinoline-8-carbohydrazide |
| 405 | 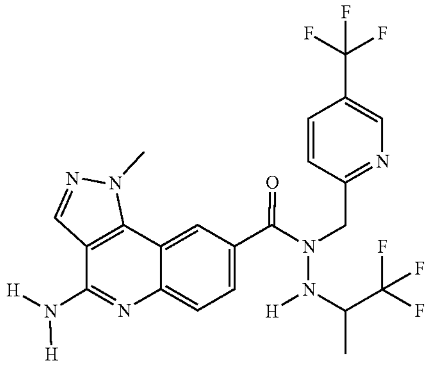 [SMILES: CC(NN(Cc1ccc(C(F)(F)F)cn1)C(=O)c1ccc2nc(N)c3cnn(C)c3c2c1)C(F)(F)F] | 4-amino-1-methyl-N-((5-(trifluoromethyl)pyridin-2-yl)methyl)-N'-(1,1,1-trifluoropropan-2-yl)-1H-pyrazolo[4,3-c]quinoline-8-carbohydrazide |
| 406 | 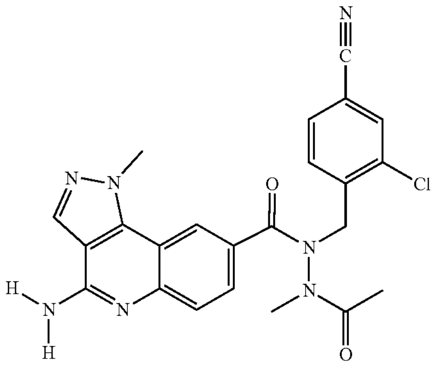 [SMILES: CC(=O)N(C)N(Cc1ccc(C#N)cc1Cl)C(=O)c1ccc2nc(N)c3cnn(C)c3c2c1] | N'-acetyl-4-amino-N-(2-chloro-4-cyanobenzyl)-N',1-dimethyl-1H-pyrazolo[4,3-c]quinoline-8-carbohydrazide |
| 407 | 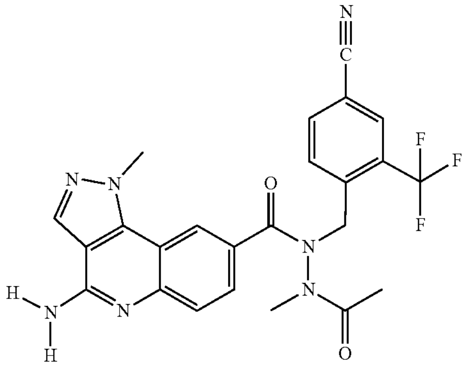 [SMILES: CC(=O)N(C)N(Cc1ccc(C#N)cc1C(F)(F)F)C(=O)c1ccc2nc(N)c3cnn(C)c3c2c1] | N'-acetyl-4-amino-N-(4-cyano-2-(trifluoromethyl)benzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 408 | 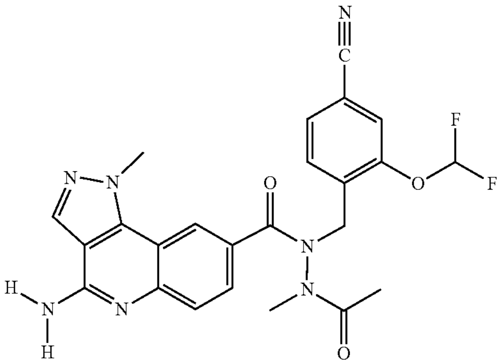 [SMILES: CC(=O)N(C)N(Cc1ccc(C#N)cc1OC(F)F)C(=O)c1ccc2nc(N)c3cnn(C)c3c2c1] | N'-acetyl-4-amino-N-(4-cyano-2-(difluoromethoxy)benzyl)-N',1-dimethyl-1H-pyrazolo[4,3-c]quinoline-8-carbohydrazide |
| 409 | 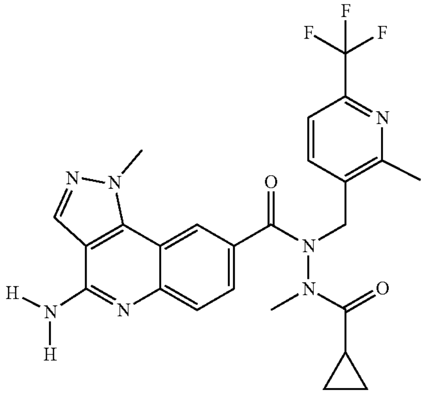 [SMILES: Cc1nc(C(F)(F)F)ccc1CN(C(=O)c1ccc2nc(N)c3cnn(C)c3c2c1)N(C)C(=O)C1CC1] | 4-amino-N'-(cyclopropanecarbonyl)-N',1-dimethyl-N-((2-methyl-6-(trifluoromethyl)pyridin-3-yl)methyl)-1H-pyrazolo[4,3-c]quinoline-8-carbohydrazide |
| 410 | 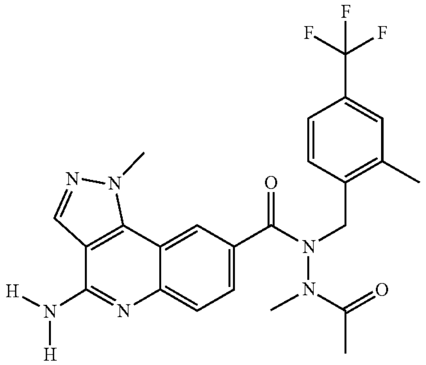 [SMILES: CC(=O)N(C)N(Cc1ccc(C(F)(F)F)cc1C)C(=O)c1ccc2nc(N)c3cnn(C)c3c2c1] | N'-acetyl-4-amino-N',1-dimethyl-N-(2-methyl-4-(trifluoromethyl)benzyl)-1H-pyrazolo[4,3-c]quinoline-8-carbohydrazide |
| 411 | 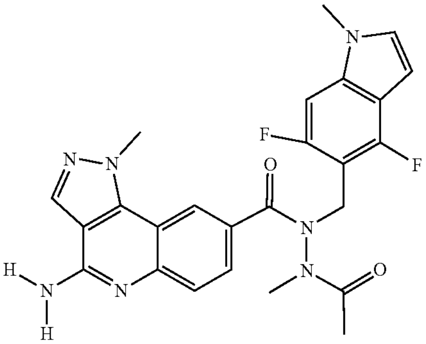 [SMILES: CC(=O)N(C)N(Cc1c(F)cc2c(ccn2C)c1F)C(=O)c1ccc2nc(N)c3cnn(C)c3c2c1] | N'-acetyl-4-amino-N-((4,6-difluoro-1-methyl-1H-indol-5-yl)methyl)-N',1-dimethyl-1H-pyrazolo[4,3-c]quinoline-8-carbohydrazide |

TABLE 1A-continued

| Some compounds | | |
|---|---|---|
| Example | Structure | Name |
| 412 | 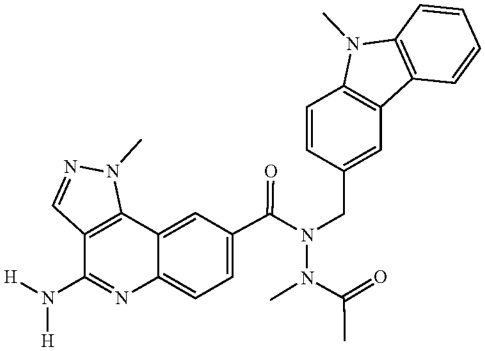 [SMILES: CC(=O)N(C)N(Cc1ccc2c(c1)c1ccccc1n2C)C(=O)c1ccc2nc(N)c3cnn(C)c3c2c1] | N'-acetyl-4-amino-N',1-dimethyl-N-((9-methyl-9H-carbazol-3-yl)methyl)-1H-pyrazolo[4,3-c]quinoline-8-carbohydrazide |
| 413 | 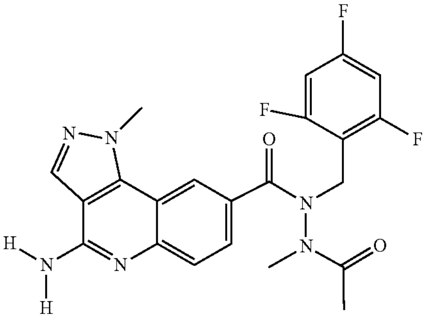 [SMILES: CC(=O)N(C)N(Cc1c(F)cc(F)cc1F)C(=O)c1ccc2nc(N)c3cnn(C)c3c2c1] | N'-acetyl-4-amino-N',1-dimethyl-N-(2,4,6-trifluorobenzyl)-1H-pyrazolo[4,3-c]quinoline-8-carbohydrazide |
| 414 | 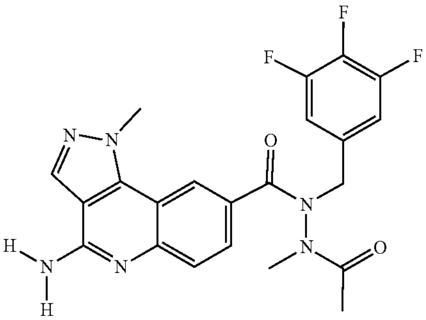 [SMILES: CC(=O)N(C)N(Cc1cc(F)c(F)c(F)c1)C(=O)c1ccc2nc(N)c3cnn(C)c3c2c1] | N'-acetyl-4-amino-N',1-dimethyl-N-(3,4,5-trifluorobenzyl)-1H-pyrazolo[4,3-c]quinoline-8-carbohydrazide |
| 415 | 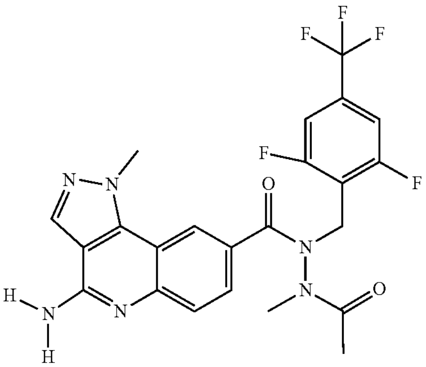 [SMILES: CC(=O)N(C)N(Cc1c(F)cc(C(F)(F)F)cc1F)C(=O)c1ccc2nc(N)c3cnn(C)c3c2c1] | N'-acetyl-4-amino-N-(2,6-difluoro-4-(trifluoromethyl)benzyl)-N',1-dimethyl-1H-pyrazolo[4,3-c]quinoline-8-carbohydrazide |

TABLE 1A-continued

| Some compounds | | |
|---|---|---|
| Example | Structure | Name |
| 416 | 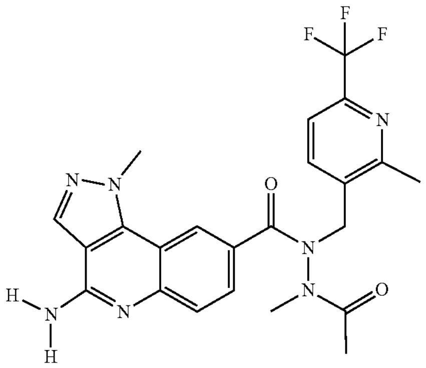 [SMILES: CC(=O)N(C)N(Cc1ccc(C(F)(F)F)nc1C)C(=O)c1ccc2nc(N)c3cnn(C)c3c2c1] | N'-acetyl-4-amino-N',1-dimethyl-N-((2-methyl-6-(trifluoromethyl)pyridin-3-yl)methyl)-1H-pyrazolo[4,3-c]quinoline-8-carbohydrazide |
| 417 | 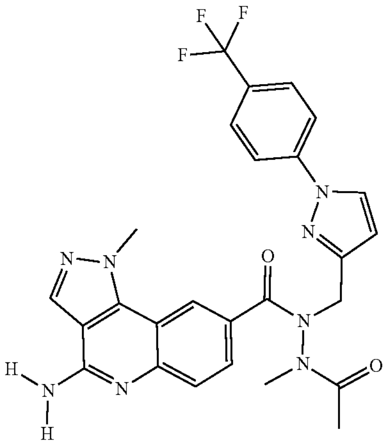 [SMILES: CC(=O)N(C)N(Cc1ccn(-c2ccc(C(F)(F)F)cc2)n1)C(=O)c1ccc2nc(N)c3cnn(C)c3c2c1] | N'-acetyl-4-amino-N',1-dimethyl-N-((1-(4-(trifluoromethyl)phenyl)-1H-pyrazol-3-yl)methyl)-1H-pyrazolo[4,3-c]quinoline-8-carbohydrazide |
| 418 | 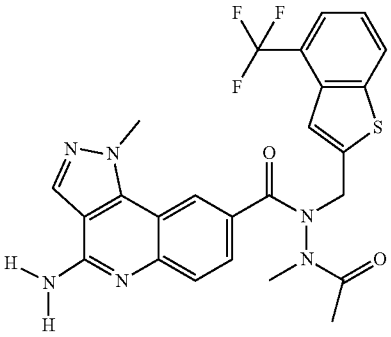 [SMILES: CC(=O)N(C)N(Cc1cc2c(C(F)(F)F)cccc2s1)C(=O)c1ccc2nc(N)c3cnn(C)c3c2c1] | N'-acetyl-4-amino-N',1-dimethyl-N-((4-(trifluoromethyl)benzo[b]thiophen-2-yl)methyl)-1H-pyrazolo[4,3-c]quinoline-8-carbohydrazide |
| 419 | 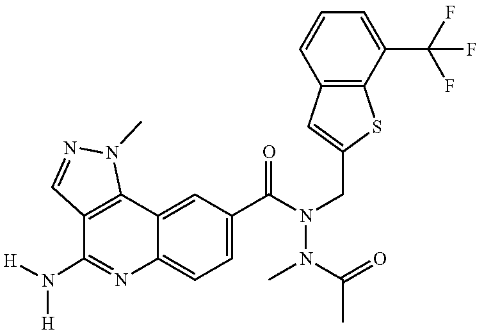 [SMILES: CC(=O)N(C)N(Cc1cc2cccc(C(F)(F)F)c2s1)C(=O)c1ccc2nc(N)c3cnn(C)c3c2c1] | N'-acetyl-4-amino-N',1-dimethyl-N-((7-(trifluoromethyl)benzo[b]thiophen-2-yl)methyl)-1H-pyrazolo[4,3-c]quinoline-8-carbohydrazide |

TABLE 1A-continued

| Some compounds | | |
|---|---|---|
| Example | Structure | Name |
| 420 | 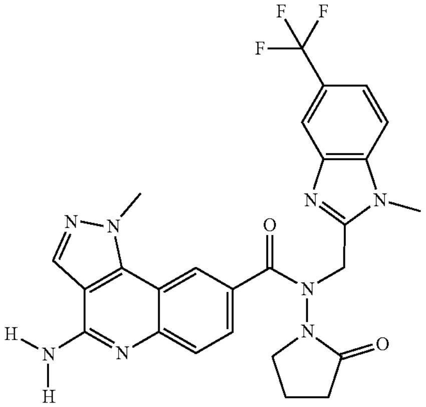 [SMILES: Cn1ncc2c(N)nc3ccc(C(=O)N(Cc4nc5cc(C(F)(F)F)ccc5n4C)N4CCCC4=O)cc3c21] | 4-amino-1-methyl-N-((1-methyl-5-(trifluoromethyl)-1H-benzo[d]imidazol-2-yl)methyl)-N-(2-oxopyrrolidin-1-yl)-1H-pyrazolo[4,3-c]quinoline-8-carboxamide |
| 421 | 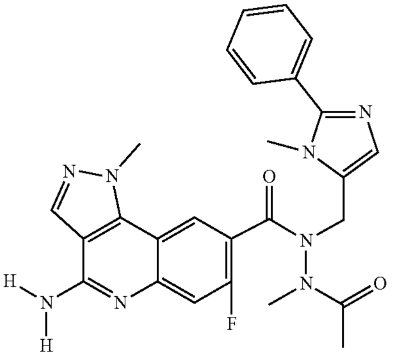 [SMILES: CC(=O)N(C)N(Cc1cnc(-c2ccccc2)n1C)C(=O)c1cc2c(cc1F)nc(N)c1cnn(C)c12] | N'-acetyl-4-amino-7-fluoro-N',1-dimethyl-N-((1-methyl-2-phenyl-1H-imidazol-5-yl)methyl)-1H-pyrazolo[4,3-c]quinoline-8-carbohydrazide |
| 422 | 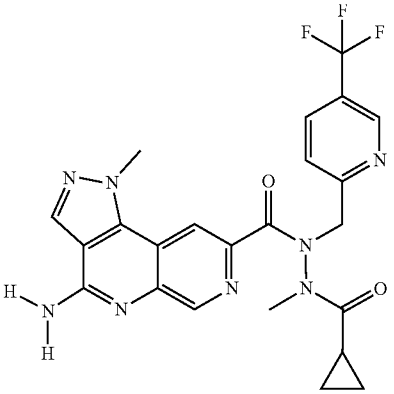 | 4-amino-N'-(cyclopropanecarbonyl)-N',1-dimethyl-N-((5-(trifluoromethyl)pyridin-2-yl)methyl)-1H-pyrazolo[4,3-c][1,7]naphthyridine-8-carbohydrazide |
| 423 | 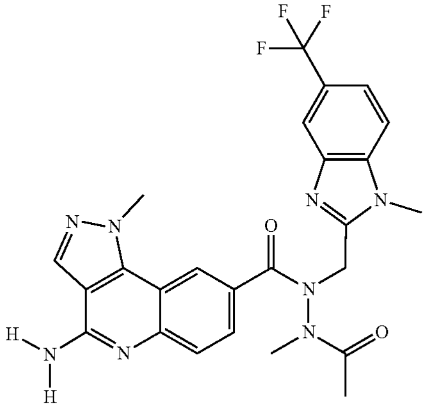 [SMILES: CC(=O)N(C)N(Cc1nc2cc(C(F)(F)F)ccc2n1C)C(=O)c1ccc2nc(N)c3cnn(C)c3c2c1] | N'-acetyl-4-amino-N',1-dimethyl-N-((1-methyl-5-(trifluoromethyl)-1H-benzo[d]imidazol-2-yl)methyl)-1H-pyrazolo[4,3-c]quinoline-8-carbohydrazide |

TABLE 1A-continued

| Some compounds | | |
|---|---|---|
| Example | Structure | Name |
| 424 | 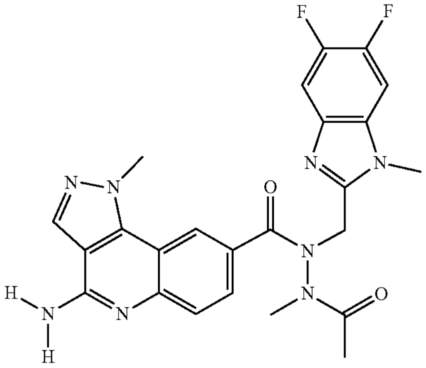 [SMILES: CC(=O)N(C)N(Cc1nc2cc(F)c(F)cc2n1C)C(=O)c1ccc2nc(N)c3cnn(C)c3c2c1] | N'-acetyl-4-amino-N-((5,6-difluoro-1-methyl-1H-benzo[d]imidazol-2-yl)methyl)-N',1-dimethyl-1H-pyrazolo[4,3-c]quinoline-8-carbohydrazide |
| 425 | 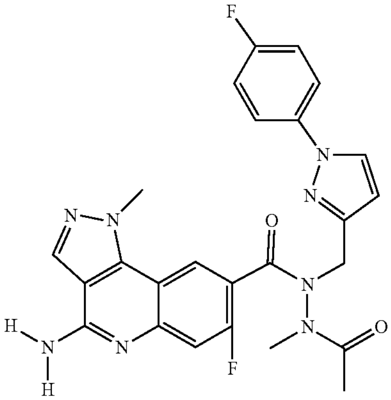 [SMILES: CC(=O)N(C)N(Cc1ccn(-c2ccc(F)cc2)n1)C(=O)c1cc2c(cc1F)nc(N)c1cnn(C)c12] | N'-acetyl-4-amino-7-fluoro-N-((1-(4-fluorophenyl)-1H-pyrazol-3-yl)methyl)-N',1-dimethyl-1H-pyrazolo[4,3-c]quinoline-8-carbohydrazide |
| 426 | 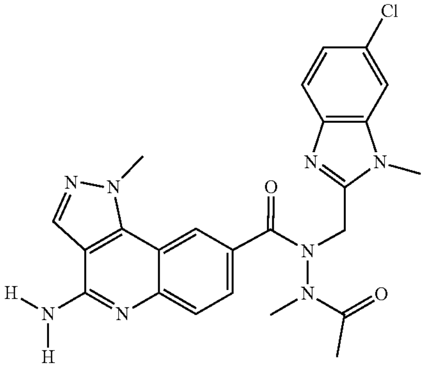 [SMILES: CC(=O)N(C)N(Cc1nc2ccc(Cl)cc2n1C)C(=O)c1ccc2nc(N)c3cnn(C)c3c2c1] | N'-acetyl-4-amino-N-((6-chloro-1-methyl-1H-benzo[d]imidazol-2-yl)methyl)-N',1-dimethyl-1H-pyrazolo[4,3-c]quinoline-8-carbohydrazide |

TABLE 1A-continued

| Some compounds | | |
|---|---|---|
| Example | Structure | Name |
| 427 | 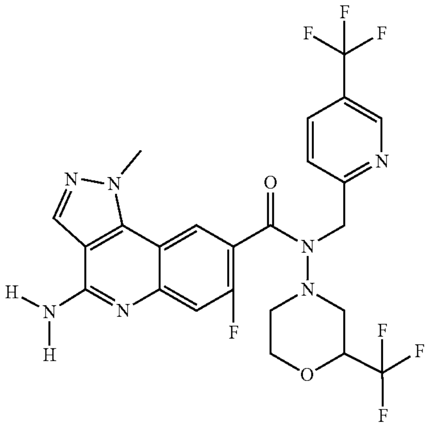 [SMILES: Cn1ncc2c(N)nc3cc(F)c(C(=O)N(Cc4ccc(C(F)(F)F)cn4)N4CCOC(C(F)(F)F)C4)cc3c21] | 4-amino-7-fluoro-1-methyl-N-(2-(trifluoromethyl)morpholino)-N-((5-(trifluoromethyl)pyridin-2-yl)methyl)-1H-pyrazolo[4,3-c]quinoline-8-carboxamide |
| 428 | 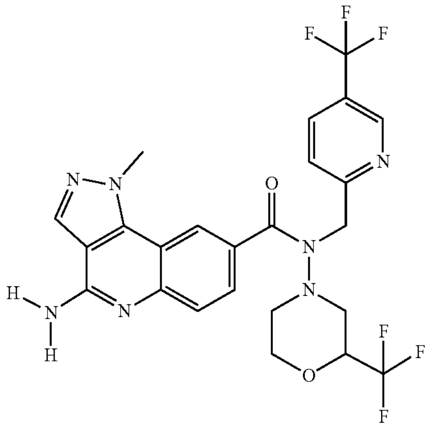 [SMILES: Cn1ncc2c(N)nc3ccc(C(=O)N(Cc4ccc(C(F)(F)F)cn4)N4CCOC(C(F)(F)F)C4)cc3c21] | 4-amino-1-methyl-N-(2-(trifluoromethyl)morpholino)-N-((5-(trifluoromethyl)pyridin-2-yl)methyl)-1H-pyrazolo[4,3-c]quinoline-8-carboxamide |
| 429 | 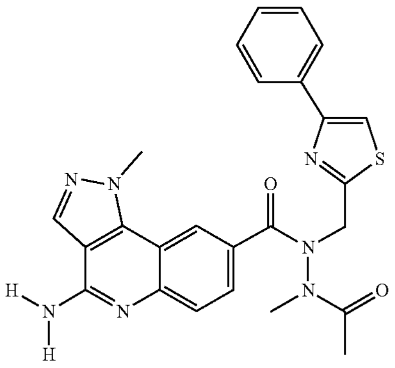 [SMILES: CC(=O)N(C)N(Cc1nc(-c2ccccc2)cs1)C(=O)c1ccc2nc(N)c3cnn(C)c3c2c1] | N'-acetyl-4-amino-N',1-dimethyl-N-((4-phenylthiazol-2-yl)methyl)-1H-pyrazolo[4,3-c]quinoline-8-carbohydrazide |

TABLE 1A-continued

| Some compounds | | |
|---|---|---|
| Example | Structure | Name |
| 430 | 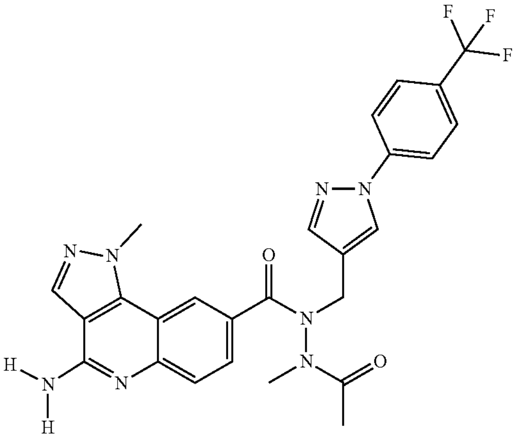 [SMILES: CC(=O)N(C)N(Cc1cnn(-c2ccc(C(F)(F)F)cc2)c1)C(=O)c1ccc2nc(N)c3cnn(C)c3c2c1] | N'-acetyl-4-amino-N',1-dimethyl-N-((1-(4-(trifluoromethyl)phenyl)-1H-pyrazol-4-yl)methyl)-1H-pyrazolo[4,3-c]quinoline-8-carbohydrazide |
| 431 | 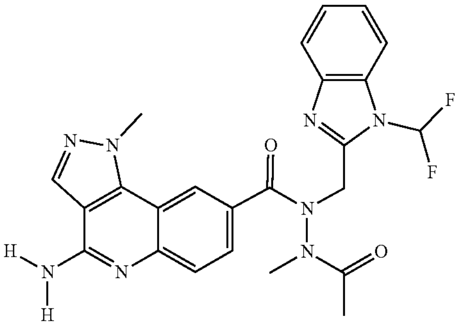 [SMILES: CC(=O)N(C)N(Cc1nc2ccccc2n1C(F)F)C(=O)c1ccc2nc(N)c3cnn(C)c3c2c1] | N'-acetyl-4-amino-N-((1-(difluoromethyl)-1H-benzo[d]imidazol-2-yl)methyl)-N',1-dimethyl-1H-pyrazolo[4,3-c]quinoline-8-carbohydrazide |
| 432 | 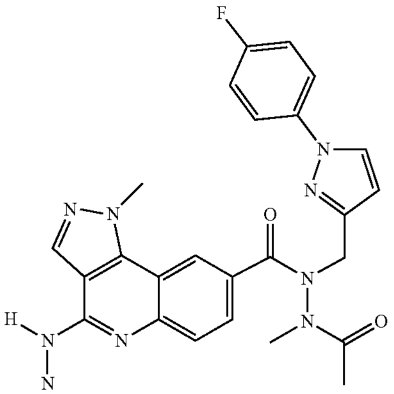 | N'-acetyl-4-amino-N-((1-(4-fluorophenyl)-1H-pyrazol-3-yl)methyl)-N',1-dimethyl-1H-pyrazolo[4,3-c]quinoline-8-carbohydrazide |
| 433 | 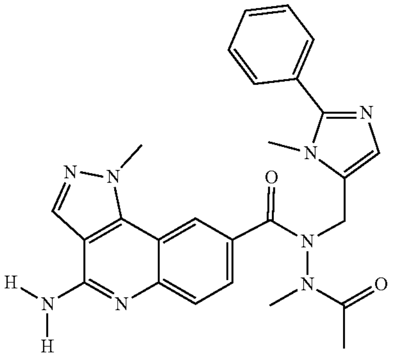 | N'-acetyl-4-amino-N',1-dimethyl-N-((1-methyl-2-phenyl-1H-imidazol-5-yl)methyl)-1H-pyrazolo[4,3-c]quinoline-8-carbohydrazide |

TABLE 1A-continued

| Some compounds | | |
|---|---|---|
| Example | Structure | Name |
| 434 | 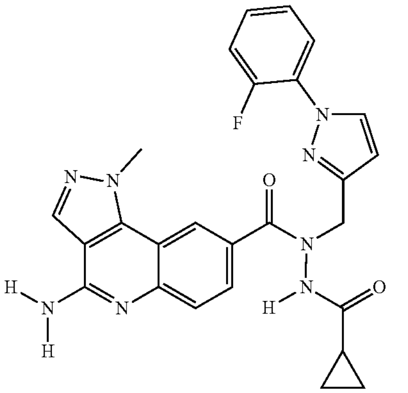 [SMILES: Cn1ncc2c(N)nc3ccc(C(=O)N(Cc4ccn(-c5ccccc5F)n4)NC(=O)C4CC4)cc3c21] | 4-amino-N'-(cyclopropanecarbonyl)-N-((1-(2-fluorophenyl)-1H-pyrazol-3-yl)methyl)-1-methyl-1H-pyrazolo[4,3-c]quinoline-8-carbohydrazide |
| 435 | 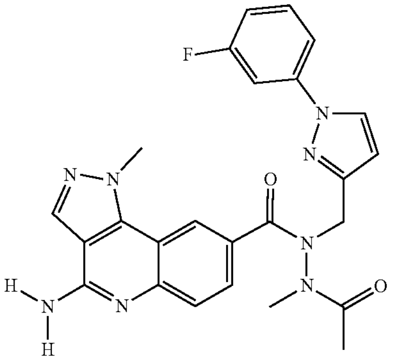 [SMILES: CC(=O)N(C)N(Cc1ccn(-c2cccc(F)c2)n1)C(=O)c1ccc2nc(N)c3cnn(C)c3c2c1] | N'-acetyl-4-amino-N-((1-(3-fluorophenyl)-1H-pyrazol-3-yl)methyl)-N',1-dimethyl-1H-pyrazolo[4,3-c]quinoline-8-carbohydrazide |
| 436 | 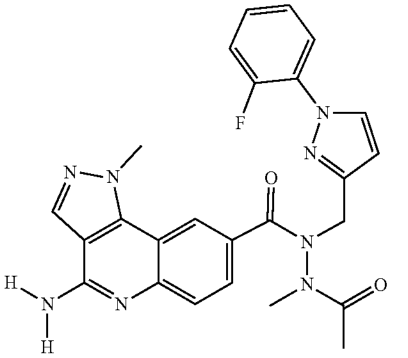 [SMILES: CC(=O)N(C)N(Cc1ccn(-c2ccccc2F)n1)C(=O)c1ccc2nc(N)c3cnn(C)c3c2c1] | N'-acetyl-4-amino-N-((1-(2-fluorophenyl)-1H-pyrazol-3-yl)methyl)-N',1-dimethyl-1H-pyrazolo[4,3-c]quinoline-8-carbohydrazide |
| 437 | 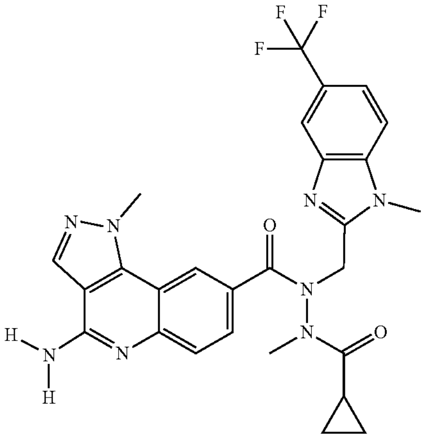 [SMILES: CN(C(=O)C1CC1)N(Cc1nc2cc(C(F)(F)F)ccc2n1C)C(=O)c1ccc2nc(N)c3cnn(C)c3c2c1] | 4-amino-N'-(cyclopropanecarbonyl)-N',1-dimethyl-N-((1-methyl-5-(trifluoromethyl)-1H-benzo[d]imidazol-2-yl)methyl)-1H-pyrazolo[4,3-c]quinoline-8-carbohydrazide |

TABLE 1A-continued

| Some compounds | | |
|---|---|---|
| Example | Structure | Name |
| 438 | 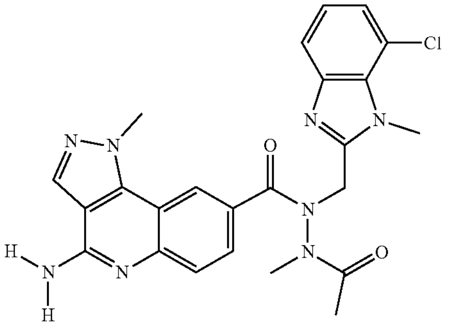 [SMILES: CC(=O)N(C)N(Cc1nc2cccc(Cl)c2n1C)C(=O)c1ccc2nc(N)c3cnn(C)c3c2c1] | N'-acetyl-4-amino-N-((7-chloro-1-methyl-1H-benzo[d]imidazol-2-yl)methyl)-N',1-dimethyl-1H-pyrazolo[4,3-c]quinoline-8-carbohydrazide |
| 439 | 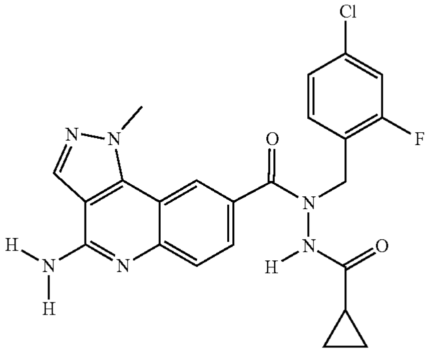 | 4-amino-N-(4-chloro-2-fluorobenzyl)-N'-(cyclopropanecarbonyl)-1-methyl-1H-pyrazolo[4,3-c]quinoline-8-carbohydrazide |
| 440 | 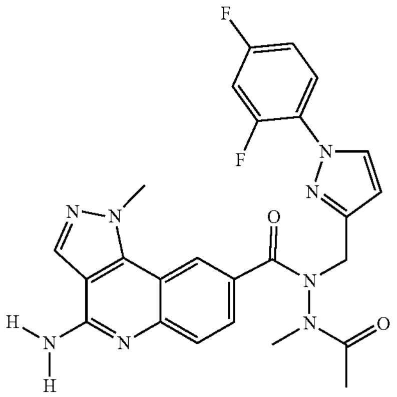 [SMILES: CC(=O)N(C)N(Cc1ccn(-c2ccc(F)cc2F)n1)C(=O)c1ccc2nc(N)c3cnn(C)c3c2c1] | N'-acetyl-4-amino-N-((1-(2,4-difluorophenyl)-1H-pyrazol-3-yl)methyl)-N',1-dimethyl-1H-pyrazolo[4,3-c]quinoline-8-carbohydrazide |
| 441 | 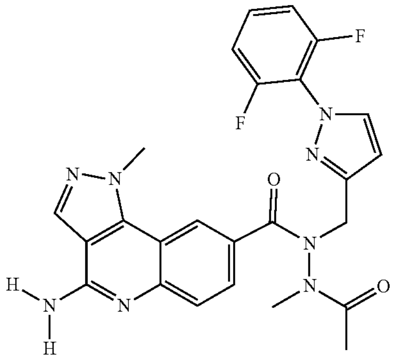 [SMILES: CC(=O)N(C)N(Cc1ccn(-c2c(F)cccc2F)n1)C(=O)c1ccc2nc(N)c3cnn(C)c3c2c1] | N'-acetyl-4-amino-N-((1-(2,6-difluorophenyl)-1H-pyrazol-3-yl)methyl)-N',1-dimethyl-1H-pyrazolo[4,3-c]quinoline-8-carbohydrazide |

TABLE 1A-continued

| Example | Structure | Name |
|---|---|---|
| Some compounds | | |
| 442 | 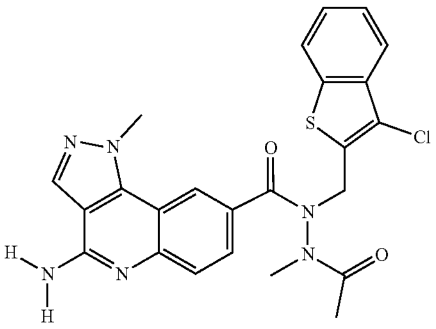 [SMILES: CC(=O)N(C)N(Cc1sc2ccccc2c1Cl)C(=O)c1ccc2nc(N)c3cnn(C)c3c2c1] | N'-acetyl-4-amino-N-((3-chlorobenzo[b]thiophen-2-yl)methyl)-N',1-dimethyl-1H-pyrazolo[4,3-c]quinoline-8-carbohydrazide |
| 443 | 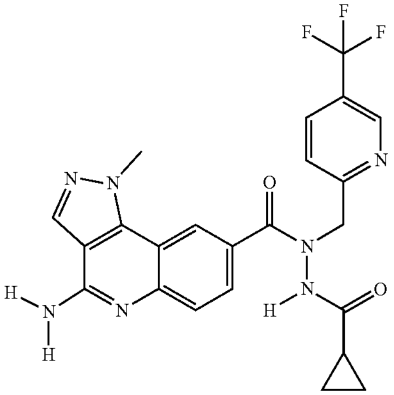 [SMILES: Cn1ncc2c(N)nc3ccc(C(=O)N(Cc4ccc(C(F)(F)F)cn4)NC(=O)C4CC4)cc3c21] | 4-amino-N'-(cyclopropanecarbonyl)-1-methyl-N-((5-(trifluoromethyl)pyridin-2-yl)methyl)-1H-pyrazolo[4,3-c]quinoline-8-carbohydrazide |
| 444 | 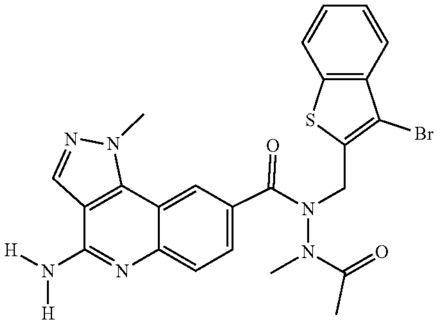 [SMILES: CC(=O)N(C)N(Cc1sc2ccccc2c1Br)C(=O)c1ccc2nc(N)c3cnn(C)c3c2c1] | N'-acetyl-4-amino-N-((3-bromobenzo[b]thiophen-2-yl)methyl)-N',1-dimethyl-1H-pyrazolo[4,3-c]quinoline-8-carbohydrazide |
| 445 | 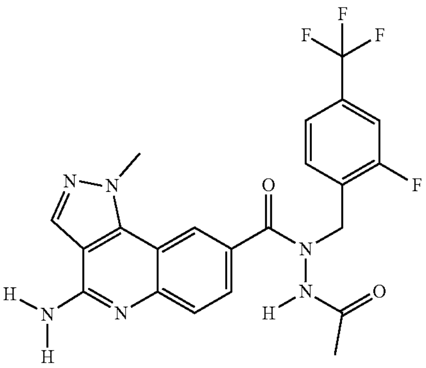 [SMILES: CC(=O)NN(Cc1ccc(C(F)(F)F)cc1F)C(=O)c1ccc2nc(N)c3cnn(C)c3c2c1] | N'-acetyl-4-amino-N-(2-fluoro-4-(trifluoromethyl)benzyl)-1-methyl-1H-pyrazolo[4,3-c]quinoline-8-carbohydrazide |

TABLE 1A-continued

| Some compounds | | |
|---|---|---|
| Example | Structure | Name |
| 446 | 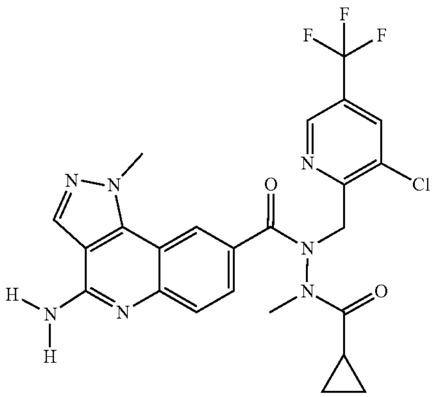 [SMILES: CN(C(=O)C1CC1)N(Cc1ncc(C(F)(F)F)cc1Cl)C(=O)c1ccc2nc(N)c3cnn(C)c3c2c1] | 4-amino-N-((3-chloro-5-(trifluoromethyl)pyridin-2-yl)methyl)-N'-(cyclopropanecarbonyl)-N',1-dimethyl-1H-pyrazolo[4,3-c]quinoline-8-carbohydrazide |
| 447 | 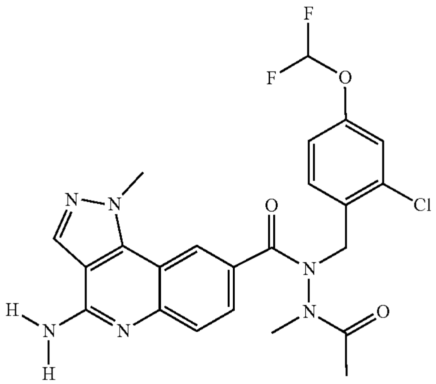 [SMILES: CC(=O)N(C)N(Cc1ccc(OC(F)F)cc1Cl)C(=O)c1ccc2nc(N)c3cnn(C)c3c2c1] | N'-acetyl-4-amino-N-(2-chloro-4-(difluoromethoxy)benzyl)-N',1-dimethyl-1H-pyrazolo[4,3-c]quinoline-8-carbohydrazide |
| 448 | 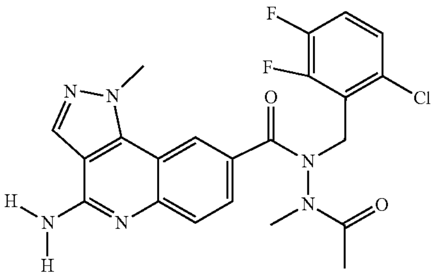 [SMILES: CC(=O)N(C)N(Cc1c(Cl)ccc(F)c1F)C(=O)c1ccc2nc(N)c3cnn(C)c3c2c1] | N'-acetyl-4-amino-N-(6-chloro-2,3-difluorobenzyl)-N',1-dimethyl-1H-pyrazolo[4,3-c]quinoline-8-carbohydrazide |
| 449 | 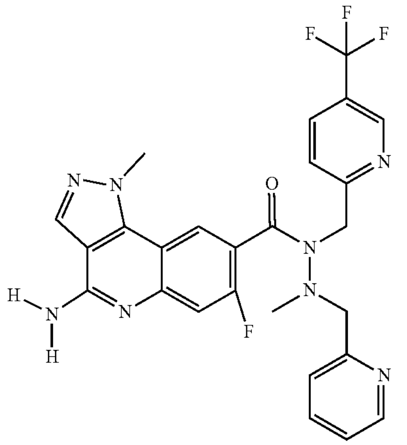 [SMILES: CN(Cc1ccccn1)N(Cc1ccc(C(F)(F)F)cn1)C(=O)c1cc2c(cc1F)nc(N)c1cnn(C)c12] | 4-amino-7-fluoro-N',1-dimethyl-N'-(pyridin-2-ylmethyl)-N-((5-(trifluoromethyl)pyridin-2-yl)methyl)-1H-pyrazolo[4,3-c]quinoline-8-carbohydrazide |

TABLE 1A-continued

| Some compounds | | |
|---|---|---|
| Example | Structure | Name |
| 450 | 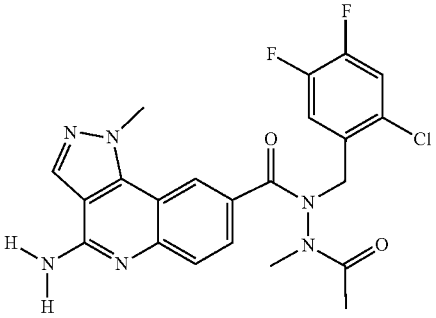 [SMILES: CC(=O)N(C)N(Cc1cc(F)c(F)cc1Cl)C(=O)c1ccc2nc(N)c3cnn(C)c3c2c1] | N'-acetyl-4-amino-N-(2-chloro-4,5-difluorobenzyl)-N',1-dimethyl-1H-pyrazolo[4,3-c]quinoline-8-carbohydrazide |
| 451 | 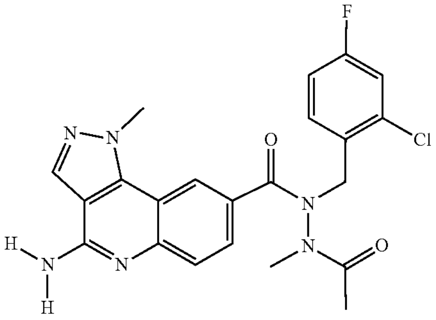 [SMILES: CC(=O)N(C)N(Cc1ccc(F)cc1Cl)C(=O)c1ccc2nc(N)c3cnn(C)c3c2c1] | N'-acetyl-4-amino-N-(2-chloro-4-fluorobenzyl)-N',1-dimethyl-1H-pyrazolo[4,3-c]quinoline-8-carbohydrazide |
| 452 | 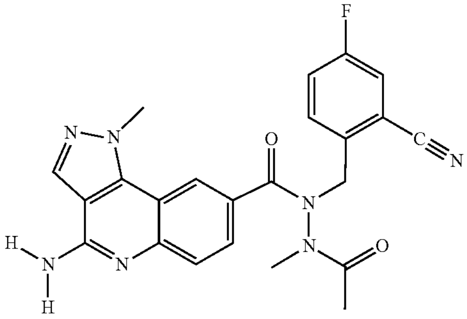 [SMILES: CC(=O)N(C)N(Cc1ccc(F)cc1C#N)C(=O)c1ccc2nc(N)c3cnn(C)c3c2c1] | N'-acetyl-4-amino-N-(2-cyano-4-fluorobenzyl)-N',1-dimethyl-1H-pyrazolo[4,3-c]quinoline-8-carbohydrazide |
| 453 | 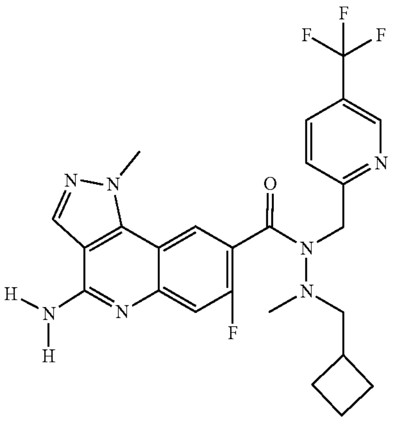 [SMILES: CN(CC1CCC1)N(Cc1ccc(C(F)(F)F)cn1)C(=O)c1cc2c(cc1F)nc(N)c1cnn(C)c12] | 4-amino-N'-(cyclobutylmethyl)-7-fluoro-N',1-dimethyl-N-((5-(trifluoromethyl)pyridin-2-yl)methyl)-1H-pyrazolo[4,3-c]quinoline-8-carbohydrazide |

TABLE 1A-continued

| Some compounds | | |
|---|---|---|
| Example | Structure | Name |
| 454 | 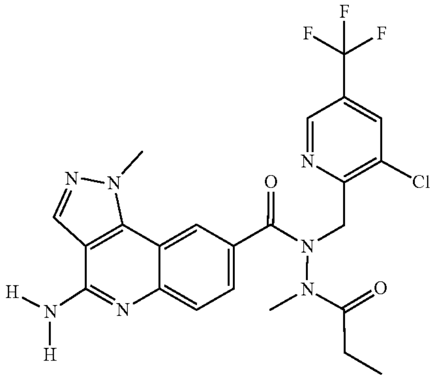 [SMILES: CCC(=O)N(C)N(Cc1ncc(C(F)(F)F)cc1Cl)C(=O)c1ccc2nc(N)c3cnn(C)c3c2c1] | 4-amino-N-((3-chloro-5-(trifluoromethyl)pyridin-2-yl)methyl)-N',1-dimethyl-N'-propionyl-1H-pyrazolo[4,3-c]quinoline-8-carbohydrazide |
| 455 | 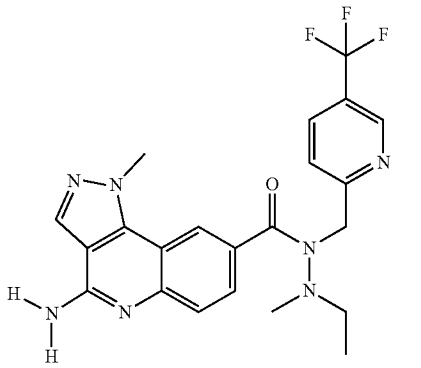 [SMILES: CCN(C)N(Cc1ccc(C(F)(F)F)cn1)C(=O)c1ccc2nc(N)c3cnn(C)c3c2c1] | 4-amino-N'-ethyl-N',1-dimethyl-N-((5-(trifluoromethyl)pyridin-2-yl)methyl)-1H-pyrazolo[4,3-c]quinoline-8-carbohydrazide |
| 456 | 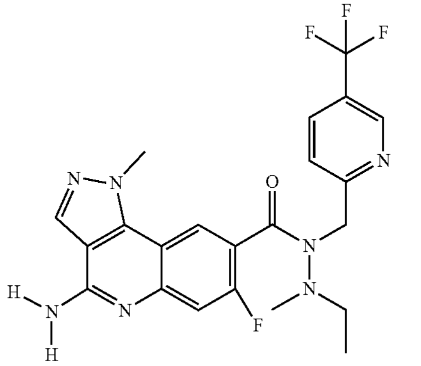 [SMILES: CCN(C)N(Cc1ccc(C(F)(F)F)cn1)C(=O)c1cc2c(cc1F)nc(N)c1cnn(C)c12] | 4-amino-N'-ethyl-7-fluoro-N',1-dimethyl-N-((5-(trifluoromethyl)pyridin-2-yl)methyl)-1H-pyrazolo[4,3-c]quinoline-8-carbohydrazide |
| 457 | 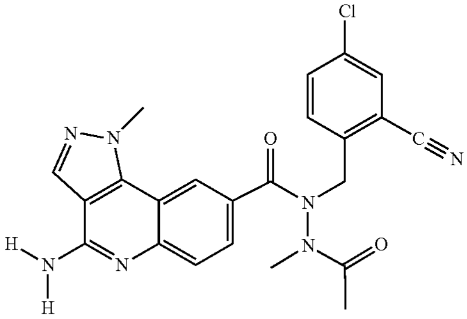 [SMILES: CC(=O)N(C)N(Cc1ccc(Cl)cc1C#N)C(=O)c1ccc2nc(N)c3cnn(C)c3c2c1] | N'-acetyl-4-amino-N-(4-chloro-2-cyanobenzyl)-N',1-dimethyl-1H-pyrazolo[4,3-c]quinoline-8-carbohydrazide |

TABLE 2

| Example | Coupling Procedure | Intermediate B | Intermediate D |
|---|---|---|---|
| Synthetic procedure for some examples disclosed herein | | | |
| 1 | E-1 | Bb-1 | Da-1 |
| 2 | E-1 | Ba-1 | Da-1 |
| 3 | E-1 | Ba-2 | Da-1 |
| 4 | E-1 | Ba-3 | Da-1 |
| 5 | E-1 | Ba-4 | Da-1 |
| 6 | E-1 | Ba-5 | Da-1 |
| 7 | E-1 | Ba6 | Da-1 |
| 8 | E-1 | Ba-7 | Da-1 |
| 9 | E-1 | Ba-7 | Da-1 |
| 10 | E-1 | Ba-8 | Da-1 |
| 11 | E-1 | Ba-9 | Da-1 |
| 12 | E-1 | Ba-10 | Da-1 |
| 13 | E-1 | Ba-11 | Da-1 |
| 14 | E-1 | Ba-12 | Da-1 |
| 15 | E-1 | Ba-13 | Da-1 |
| 16 | E-1 | Ba-14 | Da-1 |
| 17 | E-1 | Ba-15 | Da-1 |
| 18 | E-1 | Ba-16 | Da-1 |
| 19 | E-1 | Ba-17 | Da-1 |
| 20 | E-1 | Ba-18 | Da-1 |
| 21 | E-1 | Ba-19 | Da-1 |
| 22 | E-1 | Ba-20 | Da-1 |
| 23 | E-1 | Ba-21 | Da-1 |
| 24 | E-1 | Ba-21 | Da-3 |
| 25 | E-1 | Ba-22 | Da-1 |
| 26 | E-1 | Ba-23 | Da-1 |
| 27 | E-1 | Ba-24 | Da-1 |
| 28 | E-1 | Ba-25 | Da-1 |
| 29 | E-1 | Ba-26 | Da-1 |
| 30 | E-1 | Ba-26 | Db-5 |
| 31 | E-1 | Ba-27 | Da-1 |
| 32 | E-1 | Ba-28 | Da-1 |
| 33 | E-1 | Ba-29 | Da-1 |
| 34 | E-1 | Ba-29 | Db-1 |
| 35 | E-1 | Ba-30 | Da-1 |
| 36 | E-1 | Ba-31 | Da-1 |
| 37 | E-1 | Ba-32 | Da-1 |
| 38 | E-1 | Ba-33 | Da-1 |
| 39 | E-1 | Ba-34 | Da-1 |
| 40 | E-1 | Ba-34 | Db-1 |
| 41 | E-1 | Ba-35 | Da-1 |
| 42 | E-1 | Ba-35 | Db-1 |
| 43 | E-1 | Ba-36 | Da-1 |
| 44 | E-1 | Ba-36 | Db-1 |
| 45 | E-1 | Ba-37 | Da-1 |
| 46 | E-1 | Ba-37 | Db-1 |
| 47 | E-1 | Ba-38 | Da-1 |
| 48 | E-1 | Ba-39 | Da-1 |
| 49 | E-1 | Ba-40 | Da-1 |
| 50 | E-1 | Ba-41 | Da-1 |
| 51 | E-1 | Ba-42 | Da-1 |
| 52 | E-1 | Ba-43 | Da-1 |
| 53 | E-1 | Ba-44 | Db-1 |
| 54 | E-1 | Ba-44 | Da-1 |
| 55 | E-1 | Ba-45 | Db-1 |
| 56 | E-1 | Ba-45 | Da-1 |
| 57 | E-1 | Ba-46 | Db-1 |
| 58 | E-1 | Ba-47 | Da-1 |
| 59 | E-1 | Ba-47 | Db-1 |
| 60 | E-1 | Ba-48 | Db-1 |
| 61 | E-1 | Ba-49 | Da-1 |
| 62 | E-1 | Ba-50 | Da-1 |
| 63 | E-1 | Ba-50 | Db-2 |
| 64 | E-1 | Ba-51 | Da-1 |
| 65 | E-1 | Ba-52 | Da-1 |
| 66 | E-1 | Ba-53 | Da-1 |
| 67 | E-1 | Ba-54 | Da-1 |
| 68 | E-1 | Ba-29 | Da-3 |
| 69 | E-1 | Ba-29 | Da-5 |
| 70 | E-1 | Ba-29 | Db-3 |
| 71 | E-1 | Ba-29 | Db-6 |
| 72 | E-1 | Ba-29 | Da-2 |
| 73 | E-1 | Ba-55 | Da-7 |
| 74 | E-1 | Ba-56 | Da-7 |
| 75 | E-1 | Ba-57 | Da-1 |
| 76 | E-1 | Ba-58 | Da-3 |

TABLE 2-continued

| Example | Coupling Procedure | Intermediate B | Intermediate D |
|---|---|---|---|
| Synthetic procedure for some examples disclosed herein | | | |
| 77 | E-1 | Ba-59 | Da-1 |
| 78 | E-1 | Ba-60 | Db-1 |
| 79 | E-1 | Ba-61 | Da-3 |
| 80 | E-1 | Ba-61 | Da-1 |
| 81 | E-1 | Ba-61 | Db-5 |
| 83 | E-1 | Ba-63 | Da-1 |
| 84 | E-1 | Ba-64 | Db-2 |
| 85 | E-1 | Ba-65 | Da-1 |
| 86 | E-1 | Ba-66 | Da-1 |
| 87 | E-1 | Bb-1 | Db-2 |
| 88 | E-1 | Bb-3 | Da-1 |
| 89 | E-1 | Bb-4 | Da-1 |
| 90 | E-1 | Bb-5 | Da-1 |
| 91 | E-1 | Bb-6 | Da-1 |
| 92 | E-1 | Bb-7 | Da-1 |
| 93 | E-1 | Bb-8 | Da-1 |
| 94 | E-1 | Bb-9 | Da-1 |
| 95 | E-1 | Bb-10 | Da-1 |
| 96 | E-1 | Bb-11 | Da-1 |
| 97 | E-1 | Bb-12 | Da-1 |
| 98 | E-1 | Bb-13 | Da-1 |
| 99 | E-1 | Bc-1 | Da-1 |
| 100 | E-1 | Bc-2 | Da-1 |
| 101 | E-1 | Bc-3 | Da-1 |
| 102 | E-1 | Bc-4 | Da-1 |
| 103 | E-1 | Bc-5 | Da-1 |
| 104 | E-1 | Bd-1 | Da-1 |
| 105 | E-1 | Bd-2 | Da-1 |
| 106 | E-1 | Bd-3 | Da-1 |
| 107 | E-1 | Bd-4 | Da-1 |
| 108 | E-1 | Bd-5 | Da-1 |
| 109 | E-1 | Bd-6 | Da-1 |
| 110 | E-1 | Bd-7 | Da-1 |
| 111 | E-1 | Bd-8 | Da-1 |
| 112 | E-1 | Bd-9 | Da-1 |
| 113 | E-1 | Bd-10 | Da-1 |
| 114 | E-1 | Bd-11 | Da-1 |
| 115 | E-1 | Bd-12 | Da-1 |
| 116 | E-1 | Bd-13 | Da-1 |
| 117 | E-1 | Bd-14 | Da-1 |
| 118 | E-1 | Bd-15 | Da-1 |
| 119 | E-1 | Bd-16 | Da-1 |
| 120 | E-1 | Bd-17 | Da-1 |
| 121 | E-1 | Bd-18 | Da-1 |
| 122 | E-1 | Bd-19 | Da-1 |
| 123 | E-1 | Be-1 | Da-1 |
| 124 | E-1 | Be-2 | Da-3 |
| 125 | E-1 | Be-3 | Da-1 |
| 126 | E-1 | Bf-1 | Da-1 |
| 127 | E-1 | Bf-2 | Da-1 |
| 128 | E-1 | Bf-3 | Da-1 |
| 129 | E-1 | Bg-1 | Da-1 |
| 130 | E-1 | Bg-2 | Da-1 |
| 131 | E-1 | Bh-1 | Db-4 |
| 132 | E-1 | Bh-2 | Db-4 |
| 133 | E-1 | Bi-1 | Da-1 |
| 134 | E-1 | Bi-2 | Db-1 |
| 135 | E-1 | Bi-3 | Da-1 |
| 136 | E-1 | Bi-4 | Da-1 |
| 137 | E-1 | Bi-5 | Da-1 |
| 138 | E-1 | Bi-6 | Da-1 |
| 139 | E-1 | Bj-1 | Da-1 |
| 140 | E-1 | Bk-1 | Da-1 |
| 141 | E-1 | Ba-23 | Db-2 |
| 142 | E-1 | Ba-18 | Db-1 |
| 143 | E-1 | Ba-8 | Db-2 |
| 144 | E-1 | Ba-8 | Db-1 |
| 145 | E-1 | Bi-1 | Db-1 |
| 146 | E-1 | Bd-8 | Db-1 |
| 147 | E-1 | Bd-20 | Da-1 |
| 148 | E-1 | Ba-26 | Db-2 |
| 149 | E-1 | Ba-26 | Db-1 |
| 150 | E-1 | Bi-1 | Da-4 |
| 151 | E-1 | Ba-23 | Da-4 |
| 152 | E-1 | Ba-29 | Da-4 |
| 153 | E-1 | Ba-34 | Da-4 |

TABLE 2-continued

Synthetic procedure for some examples disclosed herein

| Example | Coupling Procedure | Intermediate B | Intermediate D |
|---|---|---|---|
| 154 | E-1 | Bd-21 | Db-1 |
| 155 | E-1 | Bk-2 | Da-1 |
| 156 | E-1 | Bf-4 | Da-1 |
| 157 | E-1 | Bf-5 | Da-1 |
| 158 | E-1 | Bc-6 | Da-1 |
| 159 | E-1 | Bj-7 | Da-1 |
| 160 | E-1 | Bg-2 | Da-1 |
| 161 | E-1 | Bg2 | Da-1 |
| 162 | E-1 | Bd-1 | Db-1 |
| 163 | E-1 | Bc-7 | Da-1 |
| 164 | E-1 | Bb-14 | Da-1 |
| 165 | E-1 | Bc-8 | Da-1 |
| 166 | E-1 | Bd-22 | Da-1 |
| 167 | E-1 | Ba-29 | Db-6 |
| 168 | E-1 | Ba-29 | Db-5 |
| 169 | E-1 | Bl-2 | Da-1 |
| 170 | E-1 | Bl-1 | Da-1 |
| 171 | E-1 | Bl-3 | Da-1 |
| 172 | E-1 | Bm-1 | Da-1 |
| 173 | E-1 | Bm-2 | Da-1 |
| 174 | E-1 | Bm-2 | Db-1 |
| 175 | E-1 | Bd-23 | Da-1 |
| 176 | E-1 + Sonogashira | Bb-15 | Da-1 |
| 177 | E-1 + Sonogashira | Bb-15 | Da-1 |
| 178 | E-1 | Ba-67 | Da-1 |
| 179 | E-1 | Ba-68 | Da-1 |
| 180 | E-1 | Ba-68 | Db-1 |
| 181 | E-1 | Ba-69 | Da-1 |
| 182 | E-1 | Ba-69 | Db-2 |
| 183 | E-1 | Bb-16 | Da-1 |
| 184 | E-1 | Bd-24 | Da-1 |
| 185 | E-1 | Bc-9 | Da-1 |
| 186 | E-1 | Bc-10 | Da-1 |
| 187 | E-1 | Bc-11 | Da-1 |
| 188 | E-1 | Bc-13 | Da-1 |
| 189 | E-1 | Bc-25 | Da-1 |
| 190 | E-1 | Ba-70 | Da-1 |
| 191 | E-1 | Ba-71 | Da-1 |
| 192 | E-1 | Bc-12 | Da-1 |
| 193 | E-1 | Bd-26 | Da-1 |
| 194 | E-1 | Bd-26 | Db-1 |
| 195 | E-1 | Bd-27 | Da-1 |
| 196 | E-1 | Bb-17 | Da-1 |
| 197 | E-1 | Bc-14 | Da-1 |
| 198 | E-1 | Bc-15 | Da-1 |
| 199 | E-1 | Bn-1 | Da-1 |
| 200 | E-1 | Bn-1 | Db-1 |
| 201 | E-1 | Bc-16 | Da-1 |
| 202 | E-1 + SEM deprotection | Ba-26 | Da-8 |
| 203 | E-1 | Bd-28 | Da-1 |
| 204 | E-1 | Bd-29 | Da-1 |
| 205 | E-1 | Bd-29 | Db-1 |
| 206 | E-1 | Bd-30 | Da-1 |
| 207 | E-1 | Bd-31 | Da-1 |
| 208 | E-1 | Bb-18 | Da-1 |
| 209 | E-1 | Bb-19 | Da-1 |
| 210 | E-1 | Bb-19 | Db-1 |
| 211 | E-1 | Bb-20 | Da-1 |
| 212 | E-1 | Bb-20 | Db-1 |
| 213 | E-1 | Bb-21 | Da-1 |
| 214 | E-1 | Ba-66 | Db-1 |
| 215 | E-1 | Bb-22 | Da-1 |
| 216 | E-1 | Bb-22 | Db-1 |
| 217 | E-1 + Suzuki | Bb-15 | Da-1 |
| 218 | E-1 | Bd-32 | Da-1 |
| 219 | E-1 | Bc-17 | Da-1 |
| 220 | Example 217 | Bb-15 | Da-1 |
| 221 | E-1 | Bk-3 | Da-1 |
| 222 | Example 130 | Bb-15 | Da-1 |
| 223 | Example 217 | Bb-15 | Da-1 |
| 224 | Example 130 | Bb-15 | Da-1 |
| 225 | Example 130 | Bb-15 | Da-1 |
| 226 | E-1 | Bp-1 | Da-1 |
| 227 | Example 130 | Bb-15 | Da-1 |
| 228 | Example 130 | Bb-23 | Da-1 |
| 229 | Example 130 | Bb-15 | Da-1 |

TABLE 2-continued

Synthetic procedure for some examples disclosed herein

| Example | Coupling Procedure | Intermediate B | Intermediate D |
|---|---|---|---|
| 230 | Example 130 | Bo-4 | Da-1 |
| 231 | Example 130 | Bb-15 | Da-1 |
| 232 | E-1 | Bi-7 | Da-1 |
| 233 | Example 217 | Bb-15 | Da-1 |
| 234 | Example 217 | Bb-15 | Da-1 |
| 235 | E-1 | Bk-4 | Da-1 |
| 236 | Example 130 | Bb-15 | Da-1 |
| 237 | Example 130 | Bb-15 | Da-1 |
| 238 | Example 130 | Bo-4 | Da-1 |
| 239 | Example 217 | Bo-4 | Da-1 |
| 240 | Example 217 | Bo-4 | Da-1 |
| 241 | Example 130 | Bb-15 | Da-1 |
| 242 | Example 130 | Bb-15 | Da-1 |
| 243 | Example 130 | Bb-15 | Da-1 |
| 244 | Example 130 | Bb-15 | Da-1 |
| 245 | Example 217 | Bb-15 | Da-1 |
| 246 | E-1 | Bc-18 | Db-1 |
| 247 | Example 217 | Bb-15 | Da-1 |
| 248 | E-1 | Bc-18 | Da-1 |
| 249 | Example 130 | Bb-15 | Da-1 |
| 250 | Example 217 | Bb-16 | Da-1 |
| 251 | Example 130 | Bb-24 | Da-1 |
| 252 | Example 130 | Bb-24 | Da-1 |
| 253 | E-1 | Bd-33 | Da-1 |
| 254 | E-1 | Bq-3 | Da-9 |
| 255 | E-1 | Bc-19 | Da-1 |
| 256 | E-1 | Bq-3 | Da-1 |
| 257 | E-1 | Bd-8 | Da-9 |
| 258 | E-1 | Bc-20 | Da-1 |
| 259 | E-1 | Bb-25 | Da-1 |
| 260 | E-1 | Ba-77 | Da-1 |
| 261 | E-1 | Bb-26 | Da-1 |
| 262 | E-1 | Bc-21 | Da-1 |
| 263 | E-1 | Bq-1 | Da-1 |
| 264 | E-1 | Bq-2 | Da-1 |
| 265 | E-1 | Bd-34 | Da-1 |
| 266 | E-1 | Bd-35 | Da-9 |
| 267 | E-1 | Bp-2 | Da-1 |
| 268 | E-1 | Bd-36 | Da-1 |
| 269 | E-1 | Bd-35 | Da-1 |
| 270 | E-1 | Ba-34 | Da-9 |
| 271 | E-1 | Ba-73 | Da-1 |
| 272 | E-1 | Bk-5 | Da-1 |
| 273 | E-1 | Bb-27 | Da-1 |
| 274 | E-1 | Ba-74 | Da-1 |
| 275 | E-1 | Bk-6 | Da-1 |
| 276 | E-1 | Bc-22 | Da-1 |
| 277 | E-1 | Ba-75 | Da-1 |
| 278 | E-1 | Bd-36 | Da-9 |
| 279 | E-1 | Bd-37 | Da-1 |
| 280 | E-1 | Bd-38 | Db-1 |
| 281 | E-1 + SEM deprotection | Bd-8 | Da-8 |
| 282 | E-1 | Bd-39 | Db-1 |
| 283 | E-1 | Bd-39 | Da-1 |
| 284 | E-1 | Bi-8 | Db-1 |
| 285 | E-1 | Bi-8 | Da-1 |
| 286 | E-1 | Bd-40 | Db-1 |
| 287 | E-1 | Bd-38 | Da-1 |
| 288 | E-1 | Bd-40 | Da-1 |
| 289 | E-1 | Bi-9 | Da-1 |
| 290 | E-1 | Bd-41 | Db-1 |
| 291 | E-1 | Bd-41 | Da-1 |
| 292 | E-1 | Bi-10 | Da-1 |
| 293 | E-1 | Bi-11 | Db-1 |
| 294 | E-1 | Bc-23 | Db-1 |
| 295 | E-1 | Bn-2 | Da-1 |
| 296 | E-1 | Bn-2 | Db-1 |
| 297 | E-1 | Bi-12 | Da-1 |
| 298 | E-1 | Bi-12 | Db-1 |
| 299 | E-1 | Bi-13 | Da-1 |
| 300 | E-1 | Bi-13 | Db-1 |
| 301 | E-1 | Bi-15 | Db-1 |
| 302 | E-1 | Bd-42 | Da-1 |
| 303 | E-1 | Bd-42 | Db-1 |
| 304 | E-1 | Bd-8 | Db-2 |
| 305 | E-1 | Bc-24 | Da-1 |

TABLE 2-continued

Synthetic procedure for some examples disclosed herein

| Example | Coupling Procedure | Intermediate B | Intermediate D |
|---|---|---|---|
| 306 | E-1 | Bi-14 | Da-1 |
| 307 | E-1 | Bi-15 | Da-1 |
| 308 | E-1 | Bc-23 | Da-1 |
| 309 | E-1 | Bi-16 | Db-1 |
| 310 | E-1 | Bi-11 | Da-1 |
| 311 | Example 130 | Bo-2 | Da-1 |
| 312 | Example 130 | Bo-4 | Da-1 |
| 313 | E-1 | Bo-1 | Da-1 |
| 314 | Example 130 | Bo-2 | Da-1 |
| 315 | Example 130 | Bo-3 | Da-1 |
| 316 | E-1 | Bd-43 | Da-1 |
| 317 | E-1 | Bd-44 | Da-1 |
| 318 | ex 130 | Bo-3 | Da-1 |
| 319 | E-1 | Bi-17 | Da-1 |
| 320 | E-1 | Bi-17 | Db-b |
| 321 | E-1 | Bb-28 | Da-1 |
| 322 | E-1 | Bn-3 | Da-1 |
| 323 | E-1 | Bo-5 | Da-1 |
| 324 | E-1 | Bo-6 | Da-1 |
| 325 | E-1 | Bd-45 | Da-1 |
| 326 | E-1 | Bd-45 | Da-9 |
| 327 | E-1 | Bb-29 | Da-1 |
| 328 | E-1 | Bb-29 | Db-1 |
| 329 | E-1 | Bb-30 | Da-1 |
| 330 | E-1 | Bd-46 | Da-1 |
| 331 | E-1 | Bd-46 | Db-1 |
| 332 | E-1 | Bd-47 | Da-1 |
| 333 | E-1 | Bd-47 | Db-1 |
| 334 | E-1 | Bb-31 | Da-1 |
| 335 | E-1 | Bb-32 | Da-1 |
| 336 | E-1 | Bi-20 | Da-1 |
| 337 | E-1 | Bb-33 | Da-1 |
| 338 | E-1 | Bo-7 | Da-1 |
| 339 | E-1 | Bc-25 | Da-1 |
| 340 | E-1 | Bd-48 | Da-1 |
| 341 | E-1 | Bd-49 | Da-1 |
| 342 | E-1 | Bc-26 | Da-1 |
| 343 | E-1 | Bo-8 | Da-1 |
| 344 | E-1 | Bd-50 | Da-1 |
| 345 | E-1 | Bi-21 | Da-1 |
| 346 | Example 130 | Bb-34 | Da-1 |
| 347 | Example 130 | Bb-34 | Da-1 |
| 348 | Example 130 | Bb-34 | Da-1 |
| 349 | E-1 | Bs-1 | Da-1 |
| 350 | E-1 | Bs-1 | Da-1 |
| 351 | E-1 | Ba-78 | Da-1 |
| 352 | E-1 | Ba-79 | Da-1 |
| 353 | E-1 | Bt-1 | Da-1 |
| 354 | E-1 | Bj-2 | Da-1 |
| 355 | E-1 | Bt-2 | Da-1 |
| 356 | E-1 | Bt-3 | Da-1 |
| 357 | E-1 | Bt-4 | Da-1 |
| 358 | E-1 | Bu-1 | Da-1 |
| 359 | E-1 | Ba-80 | Da-1 |
| 360 | E-1 | Bk-7 | Da-1 |
| 361 | E-1 | Bl-4 | Da-1 |
| 362 | E-1 | Ba-76 | Da-1 |
| 363 | E-1 | Bl-5 | Da-1 |
| 364 | E-1 | Bl-6 | Da-1 |
| 365 | E-1 | Ba-81 | Da-1 |
| 366 | E-1 | Bb-35 | Da-1 |
| 367 | E-1 | Bb-36 | Da-1 |
| 368 | E-1 | Ba-82 | Da-1 |
| 369 | E-1 | Bt-5 | Da-1 |
| 370 | E-1 | Ba-83 | Da-1 |
| 371 | E-1 | Ba-84 | Da-1 |
| 372 | E-1 | Bt-6 | Da-1 |
| 373 | Example 130 | Bb-15 | Da-1 |
| 374 | Example 130 | Bk-8 | Da-1 |
| 375 | Example 130 | Bb-41 | Da-1 |
| 376 | Example 130 | Bk-9 | Da-1 |
| 377 | Example 130 | Bb-42 | Da-1 |
| 378 | Example 130 | Bb-40 | Da-1 |
| 379 | Example 130 | Bb-40 | Da-1 |
| 380 | Example 130 | Bb-40 | Da-1 |
| 381 | Example 130 | Bb-40 | Da-1 |

TABLE 2-continued

Synthetic procedure for some examples disclosed herein

| Example | Coupling Procedure | Intermediate B | Intermediate D |
|---|---|---|---|
| 382 | E-1 | Bi-19 | Da-1 |
| 383 | E-1 | Bi-19 | Db-1 |
| 384 | E-1 | Bw-1 | Da-1 |
| 385 | E-1 | Br-1 | Da-1 |
| 386 | E-1 | Br-1 | Db-1 |
| 387 | Example 176 | Bb-15 | Da-1 |
| 388 | Example 176 | Bb-15 | Da-1 |
| 389 | Example 176 | Bb-15 | Da-1 |
| 390 | Example 176 | Bb-15 | Da-1 |
| 391 | Example 176 | Bo-4 | Da-1 |
| 392 | E-1 | Ba-46 | Da-1 |
| 393 | E-1 | Bd-52 | Da-1 |
| 394 | E-1 | Bd-52 | Db-1 |
| 395 | E-1 | Ba-86 | Da-1 |
| 396 | E-1 | Ba-86 | Db-1 |
| 397 | E-1 | Ba-85 | Da-1 |
| 398 | E-1 | Ba-85 | Db-1 |
| 399 | E-1 | Bd-51 | Da-1 |
| 400 | E-1 | Bv-3 | Da-1 |
| 401 | E-1 | Bv-2 | Da-1 |
| 402 | E-1 | Bv-5 | Da-1 |
| 403 | E-1 | Bv-4 | Da-1 |
| 404 | E-1 | Bv-1 | Da-1 |
| 405 | E-1 | Ba-87 | Da-1 |
| 406 | E-1 | Bb-37 | Da-1 |
| 407 | E-1 | Bb-38 | Da-1 |
| 408 | E-1 | Bb-39 | Da-1 |
| 409 | E-1 | Ba-88 | Da-1 |
| 410 | E-1 | Ba-89 | Da-1 |
| 411 | E-1 | Ba-90 | Da-1 |
| 412 | E-1 | Ba-91 | Da-1 |
| 413 | E-1 | Ba-92 | Da-1 |
| 414 | E-1 | Ba-93 | Da-1 |
| 415 | E-1 | Ba-94 | Da-1 |
| 416 | E-1 | Ba-95 | Da-1 |
| 417 | E-1 | Bb-43 | Da-1 |
| 418 | E-1 | Bb-44 | Da-1 |
| 419 | E-1 | Bb-45 | Da-1 |
| 420 | E-1 | Bb-46 | Da-1 |
| 421 | E-1 | Ba-96 | Da-1 |
| 422 | E-1 | Bd-8 | Da-10 |
| 423 | E-1 | Ba-97 | Da-1 |
| 424 | E-1 | Ba-98 | Da-1 |
| 425 | E-1 | Bb-47 | Db-1 |
| 426 | E-1 | Bb-48 | Da-1 |
| 427 | E-1 | Bi-18 | Db-1 |
| 428 | E-1 | Bi-18 | Da-1 |
| 429 | E-1 | Bb-49 | Da-1 |
| 430 | E-1 | Ba-99 | Da-1 |
| 431 | E-1 | Bb-50 | Da-1 |
| 432 | E-1 | Bb-47 | Da-1 |
| 433 | E-1 | Ba-96 | Da-1 |
| 434 | E-1 | Bb-51 | Da-1 |
| 435 | E-1 | Bb-52 | Da-1 |
| 436 | E-1 | Bb-53 | Da-1 |
| 437 | E-1 | Ba-100 | Da-1 |
| 438 | E-1 | Bb-54 | Da-1 |
| 439 | E-1 | Bb-55 | Da-1 |
| 440 | E-1 | Bb-56 | Da-1 |
| 441 | E-1 | Bb-57 | Da-1 |
| 442 | E-1 | Bb-58 | Da-1 |
| 443 | E-1 | Bb-59 | Da-1 |
| 444 | E-1 | Bb-60 | Da-1 |
| 445 | E-1 | Bb-61 | Da-1 |
| 446 | E-1 | Bk-10 | Da-1 |
| 447 | E-1 | Bb-62 | Da-1 |
| 448 | E-1 | Bb-63 | Da-1 |
| 449 | E-1 | Bm-3 | Db-1 |
| 450 | E-1 | Bb-64 | Da-1 |
| 451 | E-1 | Bb-65 | Da-1 |
| 452 | E-1 | Bb-66 | Da-1 |
| 453 | E-1 | Bm-1 | Db-1 |
| 454 | E-1 | Bk-11 | Da-1 |
| 455 | E-1 | Bm-4 | Da-1 |

TABLE 2-continued

| Synthetic procedure for some examples disclosed herein | | | |
|---|---|---|---|
| Example | Coupling Procedure | Intermediate B | Intermediate D |
| 456 | E-1 | Bm-4 | Db-1 |
| 457 | E-1 | Bb-67 | Da-1 |

TABLE 3

| Cell viability assay Data and SDMA assay Data | | | | |
|---|---|---|---|---|
| Example | $CC_{50}$ | $CC_{50}$ selectivity | $EC_{50}$ (SDMA assay) | $EC_{50}$ selectivity (SDMA assay) |
| 1 | A | 107 | A | 122 |
| 2 | A | 55 | A | 25 |
| 3 | A | 46 | A | 123 |
| 4 | A | 117 | B | 327 |
| 5 | A | 109 | A | 266 |
| 6 | A | 111 | A | 286 |
| 7 | A | 95 | A | 62 |
| 8 | A | 174 | A | 137 |
| 9 | A | 82 | A | 180 |
| 10 | A | 110 | A | 180 |
| 11 | A | 160 | A | 245 |
| 12 | B | 106 | B | 258 |
| 13 | A | 85 | A | 128 |
| 14 | A | 105 | B | 148 |
| 15 | A | 52 | B | 23 |
| 16 | A | 97 | A | 306 |
| 17 | A | 119 | A | 502 |
| 18 | A | 84 | A | 61 |
| 19 | A | 44 | A | 93 |
| 20 | A | 170 | A | 143 |
| 21 | A | 50 | A | 90 |
| 22 | A | 93 | B | 260 |
| 23 | A | 18 | A | 18 |
| 24 | A | 37 | A | 87 |
| 25 | A | 55 | B | 26 |
| 26 | A | 81 | B | 85 |
| 27 | A | 51 | A | 94 |
| 28 | A | 53 | A | 134 |
| 29 | A | 73 | A | 43 |
| 30 | A | 63 | A | 101 |
| 31 | A | 136 | B | 323 |
| 32 | A | 102 | A | 74 |
| 33 | A | 76 | A | 73 |
| 34 | A | 31 | B | 8 |
| 35 | A | 126 | A | 103 |
| 36 | A | 85 | A | 30 |
| 37 | B | 66 | B | 141 |
| 38 | A | 49 | A | 12 |
| 39 | A | 92 | A | 25 |
| 40 | A | 22 | A | 8 |
| 41 | A | 145 | A | 46 |
| 42 | A | 55 | A | 14 |
| 43 | A | 216 | B | 226 |
| 44 | A | 134 | B | 187 |
| 45 | A | 73 | A | 63 |
| 46 | A | 14 | A | 6 |
| 47 | A | 80 | A | 121 |
| 48 | A | 200 | B | 326 |
| 49 | A | 237 | A | 163 |
| 50 | A | 38 | A | 31 |
| 51 | A | 85 | B | 260 |
| 52 | B | 53 | B | 174 |
| 53 | B | 72 | B | 338 |
| 54 | B | 103 | C | 339 |
| 55 | A | 112 | A | 168 |
| 56 | A | 149 | A | 195 |
| 57 | A | 70 | B | 108 |
| 58 | B | 52 | B | 126 |
| 59 | A | 60 | A | 53 |
| 60 | A | 99 | B | 58 |
| 61 | B | 119 | B | 124 |
| 62 | A | 63 | A | 94 |
| 63 | A | 44 | B | 70 |

TABLE 3-continued

| Cell viability assay Data and SDMA assay Data | | | | |
|---|---|---|---|---|
| Example | $CC_{50}$ | $CC_{50}$ selectivity | $EC_{50}$ (SDMA assay) | $EC_{50}$ selectivity (SDMA assay) |
| 64 | A | 34 | A | 15 |
| 65 | A | 92 | A | 149 |
| 66 | B | 72 | C | 281 |
| 67 | A | 45 | A | 25 |
| 68 | B | 43 | B | 304 |
| 69 | B | 23 | B | 142 |
| 70 | A | 29 | B | 11 |
| 71 | A | 74 | B | 59 |
| 72 | B | 37 | B | 142 |
| 73 | B | 15 | C | 39 |
| 74 | B | 3 | C | >71 |
| 75 | A | 37 | A | 68 |
| 76 | B | 19 | B | 204 |
| 77 | A | 211 | A | 69 |
| 78 | A | 62 | A | 19 |
| 79 | B | 75 | B | 406 |
| 80 | A | 120 | A | 164 |
| 81 | A | 58 | B | 101 |
| 83 | B | 66 | B | 242 |
| 84 | A | 31 | B | 26 |
| 85 | A | 147 | A | 48 |
| 86 | A | 112 | A | 92 |
| 87 | B | 44 | B | 104 |
| 88 | B | 119 | C | 221 |
| 89 | A | 142 | A | 204 |
| 90 | A | 78 | B | 53 |
| 91 | A | 54 | B | 143 |
| 92 | A | 145 | A | 257 |
| 93 | A | 116 | A | 226 |
| 94 | A | 143 | A | 133 |
| 95 | A | 96 | A | 205 |
| 96 | A | 69 | B | 290 |
| 97 | A | 114 | B | 98 |
| 98 | A | 190 | A | 120 |
| 99 | A | 81 | B | 269 |
| 100 | A | 15 | A | 7 |
| 101 | A | 174 | B | 108 |
| 102 | A | 87 | B | 252 |
| 103 | C | <10 | C | <500 |
| 104 | A | 134 | B | 173 |
| 105 | A | 20 | A | 15 |
| 106 | A | 32 | A | 16 |
| 107 | A | 98 | A | 163 |
| 108 | A | 82 | A | 70 |
| 109 | A | 27 | A | 12 |
| 110 | A | 8 | A | 11 |
| 111 | A | 162 | A | 129 |
| 112 | A | 131 | A | 46 |
| 113 | B | 88 | B | 404 |
| 114 | A | 44 | A | 32 |
| 115 | B | 61 | B | 382 |
| 116 | B | 47 | B | 189 |
| 117 | A | 52 | A | 34 |
| 118 | A | 73 | A | 96 |
| 119 | A | 105 | A | 156 |
| 120 | A | 98 | A | 542 |
| 121 | A | 101 | A | 106 |
| 122 | A | 204 | A | 261 |
| 123 | A | 110 | A | 39 |
| 124 | B | 12 | | |
| 125 | A | 105 | B | 60 |
| 126 | A | 40 | A | 45 |
| 127 | A | 90 | B | 228 |
| 128 | A | 54 | A | 131 |
| 129 | A | 53 | A | 11 |
| 130 | A | 102 | B | 34 |
| 131 | C | 4 | C | 279 |
| 132 | C | 1 | C | 3193 |
| 133 | A | 97 | A | 92 |
| 134 | A | 33 | B | 18 |
| 135 | B | 105 | B | 495 |
| 136 | B | 87 | B | 724 |
| 137 | A | 62 | B | 159 |
| 138 | C | 14 | C | 174 |
| 139 | A | 154 | C | 20 |

TABLE 3-continued

Cell viability assay Data and SDMA assay Data

| Example | $CC_{50}$ | $CC_{50}$ selectivity | $EC_{50}$ (SDMA assay) | $EC_{50}$ selectivity (SDMA assay) |
|---|---|---|---|---|
| 140 | A | 160 | A | 456 |
| 141 | A | 35 | B | 58 |
| 142 | A | 26 | A | 32 |
| 143 | A | 126 | B | 67 |
| 144 | A | 66 | B | 43 |
| 145 | A | 57 | A | 45 |
| 146 | A | 26 | A | 16 |
| 147 | A | 39 | A | 16 |
| 148 | A | 42 | B | 66 |
| 149 | A | 39 | B | 18 |
| 150 | A | 79 | B | 138 |
| 151 | A | 59 | A | 525 |
| 152 | B | 63 | B | 128 |
| 153 | A | 79 | B | 54 |
| 154 | A | 85 | A | 45 |
| 155 | A | 149 | A | 94 |
| 156 | A | 48 | A | 34 |
| 157 | A | 62 | A | 54 |
| 158 | A | 19 | A | 4 |
| 159 | A | 76 | A | 69 |
| 160 | A | 47 | B | 10 |
| 161 | A | 84 | B | 51 |
| 162 | A | 120 | A | 127 |
| 163 | A | 82 | B | 145 |
| 164 | A | 73 | B | 163 |
| 165 | A | 17 | A | 11 |
| 166 | A | 21 | A | 21 |
| 167 | A | 19 | A | 10 |
| 168 | A | 37 | A | 97 |
| 169 | A | 24 | B | 14 |
| 170 | A | 169 | A | 146 |
| 171 | A | 159 | A | 571 |
| 172 | A | 80 | B | 153 |
| 173 | A | 100 | A | 117 |
| 174 | A | 18 | A | 24 |
| 175 | A | 50 | B | 19 |
| 176 | B | 48 | B | 35 |
| 177 | A | 40 | B | 36 |
| 178 | B | 98 | C | 138 |
| 179 | A | 162 | A | 318 |
| 180 | A | 60 | A | 50 |
| 181 | B | 152 | B | 441 |
| 182 | A | 91 | A | 209 |
| 183 | A | 156 | B | 300 |
| 184 | C | >43 | C | 195 |
| 185 | A | 73 | A | 33 |
| 186 | B | 81 | B | 66 |
| 187 | A | 71 | B | 50 |
| 188 | B | 60 | C | 62 |
| 189 | A | 30 | A | 13 |
| 190 | A | 81 | A | 144 |
| 191 | B | 72 | C | 103 |
| 192 | B | 108 | B | 185 |
| 193 | A | 110 | A | 202 |
| 194 | A | 92 | A | 68 |
| 195 | A | 120 | A | 146 |
| 196 | A | 190 | B | 137 |
| 197 | A | 53 | A | 61 |
| 198 | A | 59 | A | 57 |
| 199 | A | 47 | A | 26 |
| 200 | A | 8 | A | 6 |
| 201 | A | 112 | B | 423 |
| 202 | A | 23 | B | 10 |
| 203 | B | 66 | B | 159 |
| 204 | A | 145 | B | 150 |
| 205 | A | 51 | A | 44 |
| 206 | B | 55 | C | 220 |
| 207 | B | 69 | B | 364 |
| 208 | A | 85 | A | 91 |
| 209 | A | 129 | A | 228 |
| 210 | A | 82 | B | 59 |
| 211 | A | 148 | A | 142 |
| 212 | A | 111 | B | 80 |
| 213 | A | 165 | A | 209 |
| 214 | A | 64 | A | 74 |

TABLE 3-continued

Cell viability assay Data and SDMA assay Data

| Example | $CC_{50}$ | $CC_{50}$ selectivity | $EC_{50}$ (SDMA assay) | $EC_{50}$ selectivity (SDMA assay) |
|---|---|---|---|---|
| 215 | A | 69 | A | 90 |
| 216 | A | 67 | A | 54 |
| 217 | A | 116 | | |
| 218 | A | 24 | A | 6 |
| 219 | A | 18 | A | 9 |
| 220 | A | 141 | B | 15 |
| 221 | A | 190 | B | 218 |
| 222 | A | 226 | A | 123 |
| 223 | A | 92 | B | 139 |
| 224 | A | 66 | | |
| 225 | A | 105 | | |
| 226 | A | 59 | B | 86 |
| 227 | A | 67 | | |
| 228 | A | 103 | B | 205 |
| 229 | A | 130 | B | 43 |
| 230 | A | 102 | A | 228 |
| 231 | A | 86 | B | 18 |
| 232 | A | 159 | B | 298 |
| 233 | A | 153 | A | 89 |
| 234 | A | 99 | A | 39 |
| 235 | A | 214 | B | 259 |
| 236 | A | 162 | A | 203 |
| 237 | A | 43 | | |
| 238 | A | 236 | A | 77 |
| 239 | A | 85 | | |
| 240 | A | 114 | A | 95 |
| 241 | A | 93 | | |
| 242 | A | 213 | A | 77 |
| 243 | A | 118 | A | 171 |
| 244 | A | 80 | A | 109 |
| 245 | A | 70 | | |
| 246 | B | 51 | B | 288 |
| 247 | A | 148 | | |
| 248 | B | 175 | B | 536 |
| 249 | A | 117 | A | 193 |
| 250 | A | 113 | A | 153 |
| 251 | A | 203 | | |
| 252 | A | 107 | | |
| 253 | A | 88 | A | 28 |
| 254 | A | 120 | A | 266 |
| 255 | A | 56 | A | 51 |
| 256 | A | 198 | A | 130 |
| 257 | A | 156 | A | 213 |
| 258 | A | 142 | B | 221 |
| 259 | A | 216 | B | 182 |
| 260 | A | 270 | B | 211 |
| 261 | A | 140 | B | 257 |
| 262 | A | 92 | B | 169 |
| 263 | A | 100 | A | 46 |
| 264 | A | 80 | A | 281 |
| 265 | A | 106 | A | 209 |
| 266 | A | 85 | A | 63 |
| 267 | A | 188 | B | 223 |
| 268 | A | 99 | | |
| 269 | A | 88 | | |
| 270 | A | 90 | A | 129 |
| 271 | A | 69 | A | 86 |
| 272 | A | 158 | A | 466 |
| 273 | A | 155 | | |
| 274 | A | 148 | A | 243 |
| 275 | A | 207 | A | 129 |
| 276 | A | 124 | B | 166 |
| 277 | A | 107 | B | 229 |
| 278 | A | 162 | A | 121 |
| 279 | B | 145 | B | 494 |
| 280 | A | 36 | B | 31 |
| 281 | A | 30 | B | 70 |
| 282 | A | 22 | | |
| 283 | A | 124 | A | 80 |
| 284 | A | 106 | | |
| 285 | B | 109 | | |
| 286 | A | 43 | A | 16 |
| 287 | A | 127 | B | 174 |
| 288 | A | 136 | A | 267 |
| 289 | B | 143 | B | 155 |

TABLE 3-continued

| Cell viability assay Data and SDMA assay Data | | | | |
|---|---|---|---|---|
| Example | $CC_{50}$ | $CC_{50}$ selectivity | $EC_{50}$ (SDMA assay) | $EC_{50}$ selectivity (SDMA assay) |
| 290 | A | 40 | | |
| 291 | A | 80 | | |
| 292 | B | 33 | B | 80 |
| 293 | A | 11 | A | 9 |
| 294 | A | 86 | A | 97 |
| 295 | A | 30 | A | 18 |
| 296 | A | 6 | A | 27 |
| 297 | B | 96 | B | 151 |
| 298 | A | 23 | A | 23 |
| 299 | A | 98 | A | 144 |
| 300 | A | 16 | A | 24 |
| 301 | A | 81 | A | 106 |
| 302 | A | 162 | B | 248 |
| 303 | A | 138 | A | 58 |
| 304 | A | 40 | B | 15 |
| 305 | A | 145 | A | 75 |
| 306 | A | 121 | A | 96 |
| 307 | A | 145 | A | 359 |
| 308 | A | 111 | A | 122 |
| 309 | A | 88 | B | 52 |
| 310 | A | 184 | A | 132 |
| 311 | A | 134 | B | 58 |
| 312 | A | 108 | | |
| 313 | A | 195 | | |
| 314 | A | 126 | | |
| 315 | A | 150 | A | 160 |
| 316 | A | 106 | | |
| 317 | A | 263 | | |
| 318 | A | 178 | A | 130 |
| 319 | A | 149 | | |
| 320 | A | 88 | | |
| 321 | A | 128 | A | 85 |
| 322 | A | 51 | A | 34 |
| 323 | A | 96 | B | 44 |
| 324 | A | 147 | A | 111 |
| 325 | A | 133 | A | 103 |
| 326 | A | 141 | A | 114 |
| 327 | A | 115 | B | 549 |
| 328 | A | 66 | B | 143 |
| 329 | A | 127 | A | 134 |
| 330 | A | 79 | A | 225 |
| 331 | A | 34 | A | 37 |
| 332 | A | 110 | A | 308 |
| 333 | A | 54 | A | 317 |
| 334 | B | 86 | B | 178 |
| 335 | A | 66 | B | 272 |
| 336 | A | 93 | B | 94 |
| 337 | A | 101 | B | 67 |
| 338 | A | 223 | A | 373 |
| 339 | B | 74 | B | 280 |
| 340 | A | 131 | A | 50 |
| 341 | A | 158 | B | 188 |
| 342 | A | 31 | B | 30 |
| 343 | A | 135 | A | 96 |
| 344 | A | 123 | A | 48 |
| 345 | B | 90 | B | 152 |
| 346 | A | 166 | | |
| 347 | A | 172 | | |
| 348 | A | 92 | | |
| 349 | A | 61 | A | 13 |
| 350 | A | 101 | A | 42 |
| 351 | A | 100 | B | 33 |
| 352 | A | 90 | | |
| 353 | A | 140 | | |
| 354 | A | 129 | | |
| 355 | A | 81 | | |
| 356 | B | 92 | | |
| 357 | A | 93 | | |
| 358 | A | 57 | | |
| 359 | A | 128 | A | 320 |
| 360 | A | 143 | B | 446 |
| 361 | A | 43 | A | 34 |
| 362 | A | 98 | B | 468 |
| 363 | A | 37 | A | 30 |
| 364 | A | 173 | B | 77 |

TABLE 3-continued

| Cell viability assay Data and SDMA assay Data | | | | |
|---|---|---|---|---|
| Example | $CC_{50}$ | $CC_{50}$ selectivity | $EC_{50}$ (SDMA assay) | $EC_{50}$ selectivity (SDMA assay) |
| 365 | B | 162 | B | 233 |
| 366 | A | 90 | A | 21 |
| 367 | A | 103 | | |
| 368 | A | 117 | | |
| 369 | A | 81 | | |
| 370 | A | 104 | | |
| 371 | A | 114 | | |
| 372 | A | 125 | | |
| 373 | A | 119 | | |
| 374 | A | 88 | B | 125 |
| 375 | A | 179 | B | 141 |
| 376 | A | 130 | B | 164 |
| 377 | A | 144 | | |
| 378 | A | 241 | | |
| 379 | A | 131 | | |
| 380 | A | 110 | | |
| 381 | A | 262 | | |
| 382 | A | 184 | B | 167 |
| 383 | A | 99 | B | 168 |
| 384 | B | 74 | B | 283 |
| 385 | A | 139 | B | 52 |
| 386 | A | 51 | B | 20 |
| 387 | A | 100 | B | 44 |
| 388 | A | 93 | A | 40 |
| 389 | A | 85 | B | 31 |
| 390 | A | 59 | B | 27 |
| 391 | A | 113 | B | 64 |
| 392 | A | 136 | B | 285 |
| 393 | A | 212 | B | 380 |
| 394 | A | 47 | A | 116 |
| 395 | A | 54 | B | 33 |
| 396 | A | 138 | B | 135 |
| 397 | A | 102 | B | 78 |
| 398 | A | 39 | B | 31 |
| 399 | A | 200 | B | 358 |
| 400 | A | 97 | A | 278 |
| 401 | A | 157 | | |
| 402 | A | 173 | A | 311 |
| 403 | A | 123 | A | 476 |
| 404 | A | 181 | | |
| 405 | A | 43 | A | 154 |
| 406 | A | 142 | A | 212 |
| 407 | B | 84 | | |
| 408 | A | 181 | | |
| 409 | A | 162 | | |
| 410 | A | 87 | | |
| 411 | A | 115 | | |
| 412 | B | 65 | | |
| 413 | A | 168 | A | 497 |
| 414 | B | 79 | | |
| 415 | A | 88 | A | 26 |
| 416 | A | 114 | B | 133 |
| 417 | A | 84 | | |
| 418 | A | 106 | B | 114 |
| 419 | A | 147 | B | 118 |
| 420 | A | 148 | A | 87 |
| 421 | A | 64 | B | 73 |
| 422 | B | 92 | | |
| 423 | A | 95 | B | 149 |
| 424 | A | 65 | | |
| 425 | A | 79 | | |
| 426 | A | 88 | | |
| 427 | A | 59 | | |
| 428 | B | 63 | | |
| 429 | A | 146 | | |
| 430 | B | 108 | | |
| 431 | B | 184 | | |
| 432 | A | 146 | B | 297 |
| 433 | A | 109 | | |
| 434 | A | 94 | | |
| 435 | A | 140 | | |
| 436 | A | 162 | | |
| 437 | A | 84 | B | 256 |
| 438 | A | 124 | A | 141 |
| 439 | A | 78 | A | 51 |

TABLE 3-continued

| Cell viability assay Data and SDMA assay Data | | | | |
|---|---|---|---|---|
| Example | $CC_{50}$ | $CC_{50}$ selectivity | $EC_{50}$ (SDMA assay) | $EC_{50}$ selectivity (SDMA assay) |
| 440 | A | 167 | | |
| 441 | A | 151 | | |
| 442 | A | 60 | A | 163 |
| 443 | A | 68 | A | 400 |
| 444 | A | 125 | A | 117 |
| 445 | A | 68 | A | 69 |
| 446 | A | 192 | | |
| 447 | A | 113 | A | 49 |
| 448 | A | 102 | B | 224 |
| 449 | A | 138 | B | 62 |
| 450 | A | 200 | A | 394 |
| 451 | A | 216 | A | 111 |
| 452 | A | 245 | A | 213 |
| 453 | A | 33 | A | 15 |
| 454 | A | 86 | B | 421 |
| 455 | A | 65 | A | 92 |
| 456 | A | 11 | A | 25 |
| 457 | A | 163 | A | 90 |

Unless otherwise defined, all technical and scientific terms used herein have the same meaning as commonly understood by one of ordinary skill in the art to which this disclosure belongs.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A compound of Formula (I)

(I)

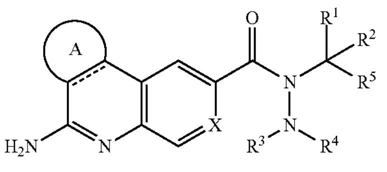

or a pharmaceutically acceptable salt thereof, wherein

 is a single or double bond;

ring A is $C_{5-7}$ cycloalkyl, phenyl, 5 to 7 membered heterocyclyl, or 5 or 6 membered heteroaryl; the cycloalkyl, phenyl, heterocyclyl, or heteroaryl of ring A is optionally substituted with one to four $R^6$, which may be the same or different;

X is N or $CR^7$;

$R^1$ is H, $C_{1-6}$ alkyl, $C_{1-6}$ haloalkyl, $C_{6-10}$ aryl, $C_{3-10}$ cycloalkyl, 3 to 10 membered heterocyclyl, or 5 to 10 membered heteroaryl; wherein the alkyl, haloalkyl, aryl, cycloalkyl, heterocyclyl, or heteroaryl of $R^1$ is each optionally substituted with one to four $Z^1$, which may be the same or different;

$R^2$ is H, —CN, $C_{1-5}$ alkyl, $C_{1-5}$ haloalkyl, $C_{2-6}$ alkynyl, cyclopropyl, cyclobutyl, or oxetanyl; wherein the alkyl, haloalkyl, alkoxyalkyl, alkynyl, cyclopropyl, or cyclobutyl of $R^2$ is each optionally substituted with one to four $Z^2$, which may be the same or different; each $Z^2$ is independently $C_{2-6}$ alkynyl, halo, —CN,—$OR^{2a}$, cyclopropyl, cyclobutyl, or oxetanyl; $R^{2a}$ is H, $C_{1-3}$ haloalkyl, $C_{3-6}$ cycloalkyl, or $C_{1-3}$ alkyl;

$R^5$ is H, $C_{1-3}$ alkyl, or $C_{1-3}$ haloalkyl;

or $R^1$ and $R^2$ together with the carbon to which they are attached form $C_{3-10}$ cycloalkyl, 3 to 10 membered heterocyclyl; the cycloalkyl or heterocyclyl formed from $R^1$ and $R^2$ is optionally substituted with one to four $Z^5$, which may be the same or different;

or $R^2$ and $R^5$ together with the carbon to which they are attached form cyclopropyl, cyclobutyl, or oxetanyl; the cyclopropyl, or cyclobutyl formed from $R^2$ and $R^5$ is optionally substituted with one to four halo;

$R^3$ is H, $C_{1-6}$ alkyl, $C_{1-6}$ haloalkyl, —$COR^{3a}$, —$COOR^{3a}$, —$CONR^{3a}R^{3b}$, —$SO_2R^{3a}$, —$SO_2NR^{3a}R^{3b}$, $C_{6-10}$ aryl, $C_{3-10}$ cycloalkyl, 3 to 10 membered heterocyclyl, or 5 to 10 membered heteroaryl; wherein the alkyl, aryl, cycloalkyl, heterocyclyl, or heteroaryl of $R^3$ is each optionally substituted with one to four $Z^3$, which may be the same or different, $R^4$ is H, $C_{1-6}$ alkyl, $C_{1-6}$ haloalkyl, $C_{6-10}$ aryl, $C_{3-10}$ cycloalkyl, 3 to 10 membered heterocyclyl, or 5 to 10 membered heteroaryl; wherein the alkyl, aryl, cycloalkyl, heterocyclyl, or heteroaryl of $R^4$ is each optionally substituted with one to four $Z^4$, which may be the same or different, or $R^3$ and $R^4$ together with the nitrogen to which they are attached form a 3 to 10 membered heterocyclyl, or 5 to 10 membered heteroaryl; wherein the heterocyclyl or heteroaryl formed from $R^3$ and $R^4$ is optionally substituted with one to four $Z^9$, which may be the same or different, wherein the heterocyclyl formed from $R^3$ and $R^4$ is a heterocyclyl having 0 to 2 additional heteroatoms each independently N, O, or S, wherein the heteroaryl formed from $R^3$ and $R^4$ is a heteroaryl having 0 to 2 additional heteroatoms each independently N, O, or S, or $R^2$ and $R^4$ together with the atoms to which they are attached form a 5 to 10 membered heterocyclyl; wherein the heterocyclyl formed from $R^2$ and $R^4$ is optionally substituted with one to four $Z^8$, which may be the same or different;

each $R^6$ is independently halo, —OH, —$OCH_3$, oxo, —CN, $C_{1-3}$ alkyl, $C_{1-3}$ haloalkyl, or cyclopropyl;

$R^7$ is H, halo, CN, halomethyl, —$CH_3$, or —$OCH_3$;

each $Z^1$, $Z^3$, $Z^4$, $Z^5$, $Z^8$, or $Z^9$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, 3 to 10 membered heterocyclyl, $C_{6-10}$ aryl, 5 to 10 membered heteroaryl, oxo, —$NO_2$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12}$)$_2$($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —N$R^{12a}$S(O)$_2$N($R^{12b}$)($R^{12c}$), —N$R^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$$R^{12a}$, —S(O)$_2$N($R^{12a}$)($R^{12b}$), —S(O)(N$R^{12a}$)$R^{12b}$, or —Si($R^{12a}$)$_3$; wherein the alkyl, haloalkyl, alkenyl, alkynyl, cycloalkyl, heterocyclyl, aryl, or heteroaryl of each $Z^1$, $Z^3$, $Z^4$, $Z^5$, $Z^8$, or $Z^9$ is each optionally substituted with one to four $Z^{1a}$, which may be the same or different;

each $Z^{1a}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, 3 to 10 membered heterocyclyl, $C_{6-10}$ aryl, 5 to 10 membered heteroaryl, oxo, —$NO_2$, —CN, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$)$^+$, —N($R^{12a}$)—C(O)$R^{12b}$, —N($R^{12a}$)C(O)O($R^{12b}$), —N($R^{12a}$)C(O)N($R^{12b}$)($R^{12c}$), —N($R^{12a}$)S(O)$_2$($R^{12b}$), —N($R^{12a}$)S(O)$_2$—N($R^{12b}$)($R^{12c}$), —N($R^{12a}$)S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$$R^{12a}$, —S(O)$_2$N($R^{12a}$)($R^{12b}$), —S(O)(N$R^{12a}$)$R^{12b}$, or —Si($R^{12a}$)$_3$; wherein the alkyl, haloalkyl, alkenyl, alkynyl, cycloalkyl, heterocyclyl, aryl, or heteroaryl of $Z^{1a}$ is each optionally substituted with one to four $Z^{1b}$, which may be the same or different;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH (heterocyclyl), —NH($C_{6-10}$ aryl), —NH (heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$; wherein the alkyl, cycloalkyl, heterocyclyl, aryl, or heteroaryl of $Z^{1b}$ is optionally substituted with one to three $C_{1-9}$ alkyl, $C_{1-8}$ haloalkyl, halogen, —OH, —$NH_2$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$, wherein the heteroaryl of $Z^{1b}$ is 5 to 10 membered heteroaryl, the heterocyclyl of $Z^{1b}$ is 3 to 10 membered heterocyclyl; and each $R^{3a}$, $R^{3b}$, $R^{12a}$, $R^{12b}$, or $R^{12c}$ is independently H, $C_{1-6}$ alkyl, $C_{3-10}$ cycloalkyl, 3 to 10 membered heterocyclyl, $C_{6-10}$ aryl, or 5 to 10 heteroaryl, wherein the alkyl, cycloalkyl, heterocyclyl, aryl, or heteroaryl of each $R^{3a}$, $R^{3b}$, $R^{12a}$, $R^{12b}$, or $R^{12c}$ is each optionally substituted with one to four $Z^{1b}$, which may be the same or different;

wherein each heteroaryl or heterocyclyl of the compound of Formula (I) unless otherwise specified has one to three heteroatoms each independently N, O, or S.

2. The compound of claim 1, or a pharmaceutically acceptable salt thereof, wherein X is N.

3. The compound of claim 1, or a pharmaceutically acceptable salt thereof, wherein X is $CR^7$; and $R^7$ is H, halo, CN,—$CH_3$, or halomethyl.

4. The compound of claim 1, or a pharmaceutically acceptable salt thereof, having the structure of Formula (la 1)

(Ia-1)

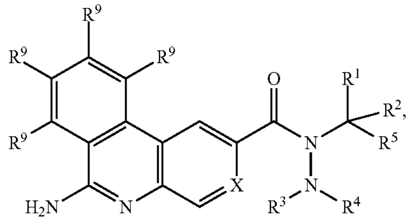

(Ia-2)

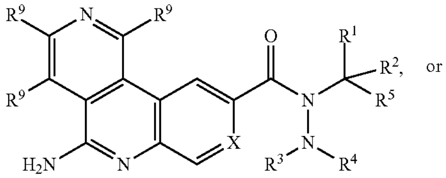

or (Ia-3)

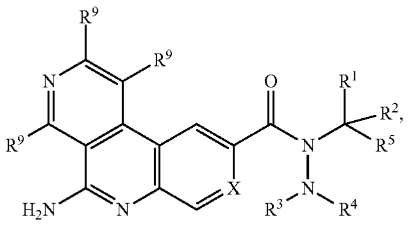

wherein each $R^9$ is independently H or $R^6$.

5. The compound of claim 1, or a pharmaceutically acceptable salt thereof, having the structure (Ib-1)

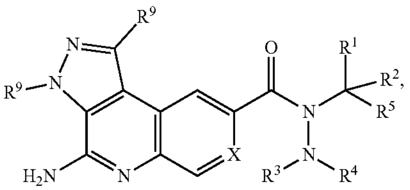

(Ib-2)

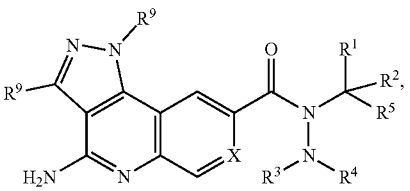

(Ib-3)

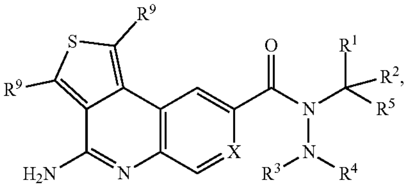

-continued (Ib-4)

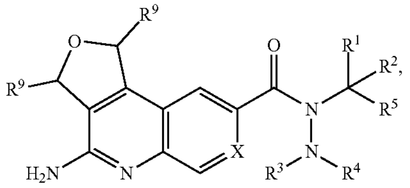

(Ib-5)

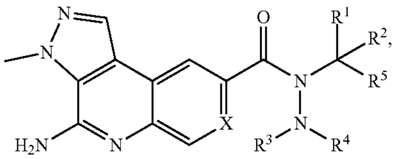

(Ib-6)

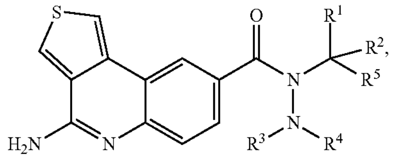

(Ib-7)

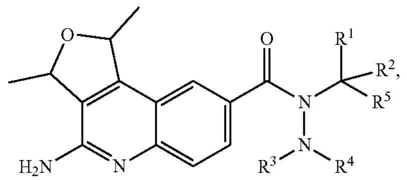

(Ib-8)

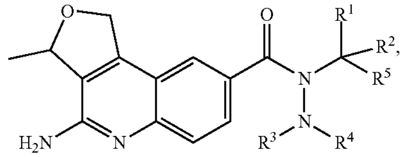

(Ib-9)

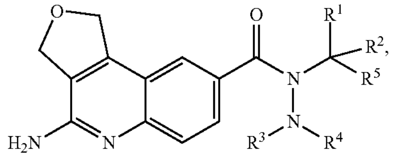

(Ib-10)

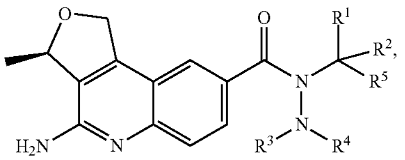

or (Ib-11)

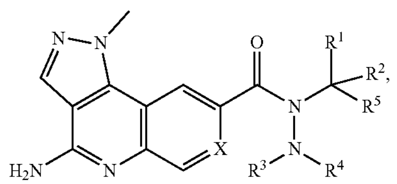

wherein each $R^9$ is independently H or $R^6$.

6. The compound of claim 1, or a pharmaceutically acceptable salt thereof, wherein each $R^6$ is independently halo, —OH, —CN, $C_{1-3}$ alkyl, or $C_{1-3}$ haloalkyl.

7. The compound of claim 1, or a pharmaceutically acceptable salt thereof, wherein $R^5$ is H; and $R^2$ is H, $C_{1-3}$ alkyl, or $C_{1-3}$ haloalkyl.

8. The compound of claim 1, or a pharmaceutically acceptable salt thereof, wherein $R^1$ is 5-10 membered heteroaryl including one to three heteroatoms each independently N, O, or S; the heteroaryl of $R^1$ is optionally substituted with one to three $Z^1$, which may be the same or different.

9. The compound of claim 1, or a pharmaceutically acceptable salt thereof, wherein $R^1$ is

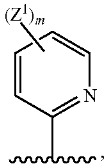,
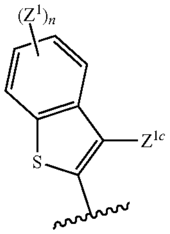,
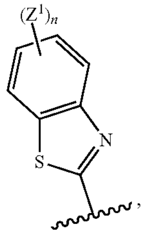,
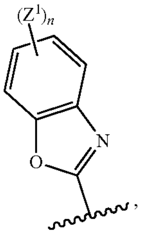,
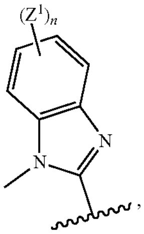,
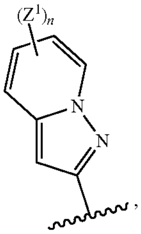,
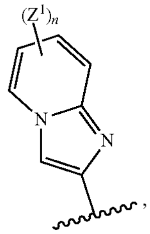,
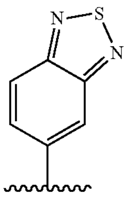,
or
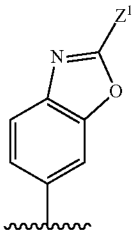;

m is 0, 1, or 2;

n is 0, 1, or 2; and $Z^{1c}$ is H or $Z^1$.

10. The compound of claim 1, or a pharmaceutically acceptable salt thereof, wherein each $Z^1$ is independently halo, —CN, $C_{1-6}$ alkyl, $C_{3-6}$ cycloalkyl, $C_{1-6}$ haloalkyl, $C_{1-6}$ alkoxy, or $C_{1-6}$ haloalkoxy.

11. The compound of claim 1, or a pharmaceutically acceptable salt thereof, wherein $R^1$ is

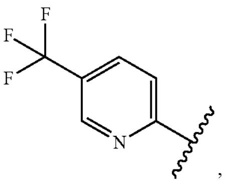,
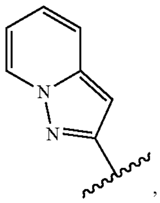,

-continued

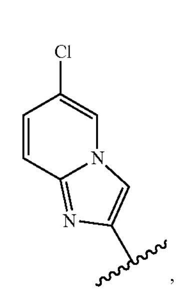,
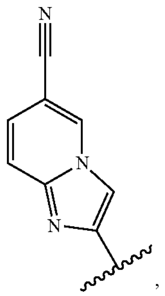,
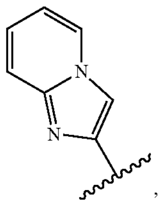,
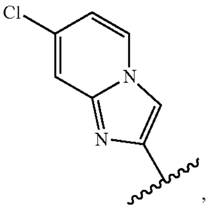,
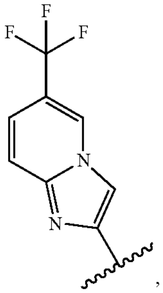,
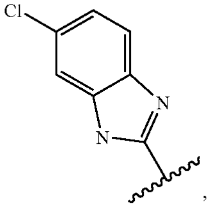,
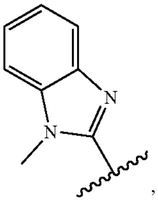,
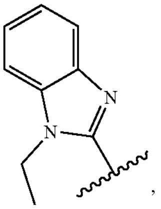,
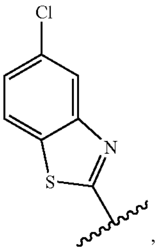,
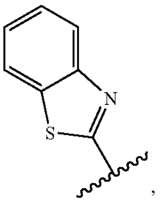,
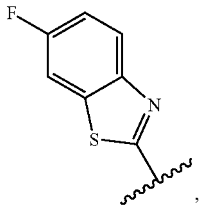,
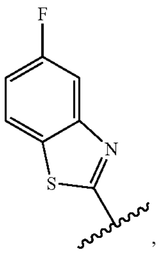, -continued

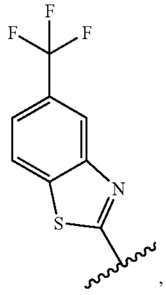

, or

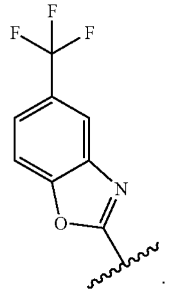

.

12. The compound of claim 1, or a pharmaceutically acceptable salt thereof, having the structure of formula (Ib-12)

(Ib-12)

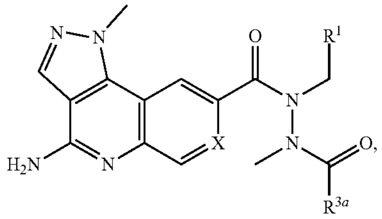

$R^{3a}$ is $C_{1-6}$ alkyl, $C_{3-8}$ cycloalkyl, $C_{6-10}$ aryl, or heteroaryl, wherein the alkyl, cycloalkyl, aryl, or heteroaryl of $R^{3a}$ is each optionally substituted with one to four $Z^{1b}$, each $Z^{1b}$ is independently halo, —CN, $C_{1-6}$ alkyl, $C_{1-6}$ haloalkyl, $C_{1-6}$ alkoxy, or $C_{1-6}$ haloalkoxy.

13. The compound of claim 1, or a pharmaceutically acceptable salt thereof, wherein each $R^3$ is —$COCH_3$, —$COC_2H_5$, —$COOC_2H_5$,

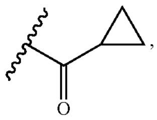

, or

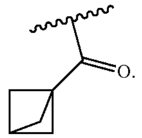

14. The compound of claim 1, or a pharmaceutically acceptable salt thereof, wherein

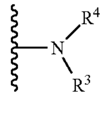

is

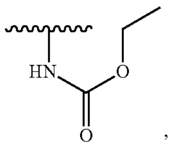

,

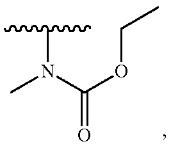

,

-continued

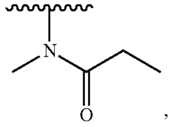

,

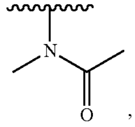

,

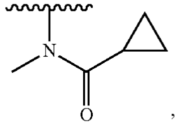

,

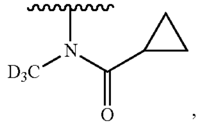

, or

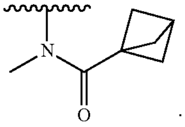

.

15. The compound of claim 1, or a pharmaceutically acceptable salt thereof, having the structure of Formula (Ib-13)

(Ib-13)

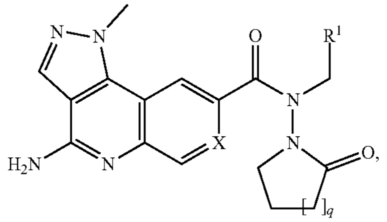

wherein q is 1 or 2.

16. A compound having the structure:

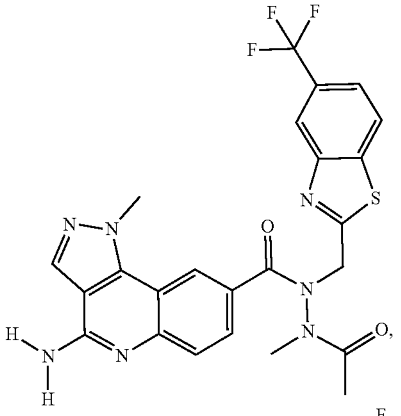

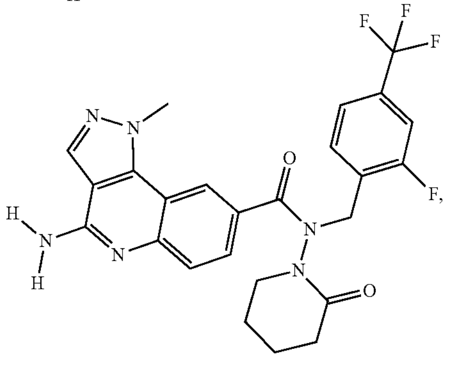

-continued
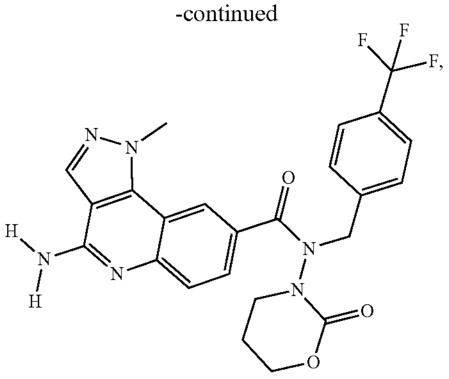
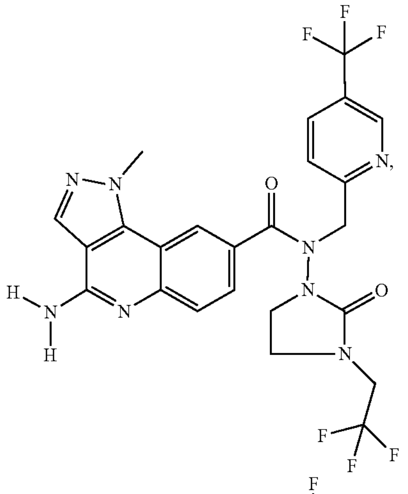
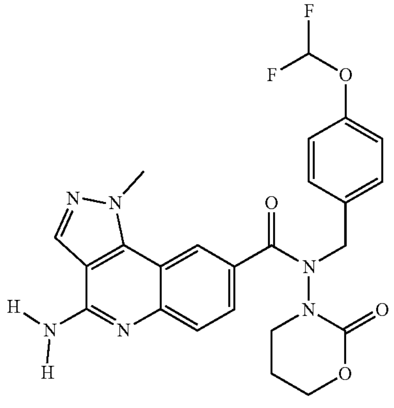
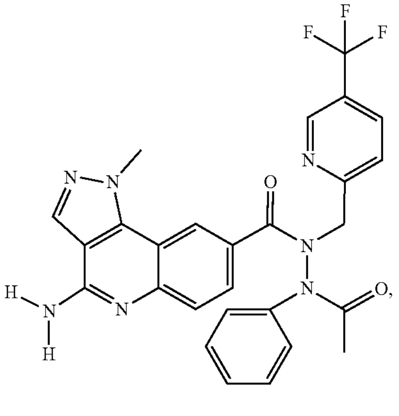
-continued
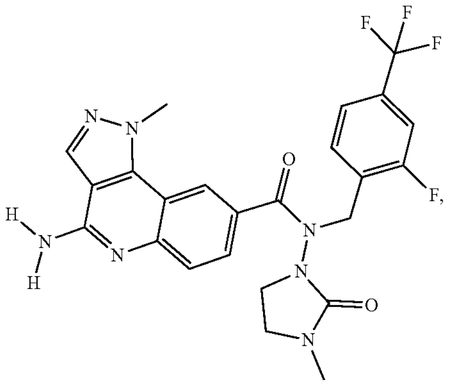
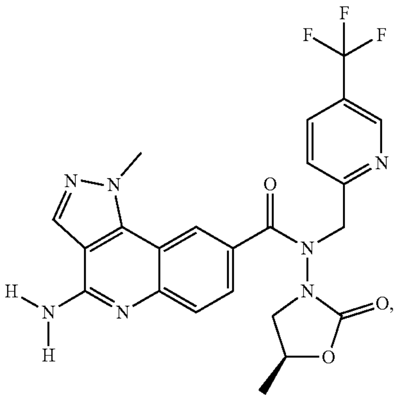
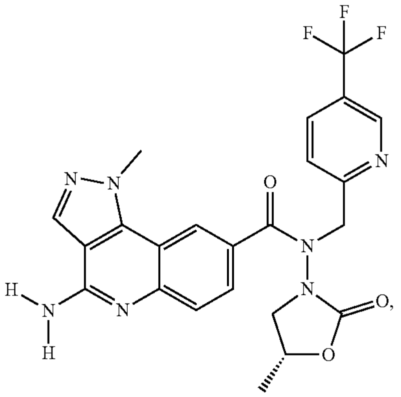
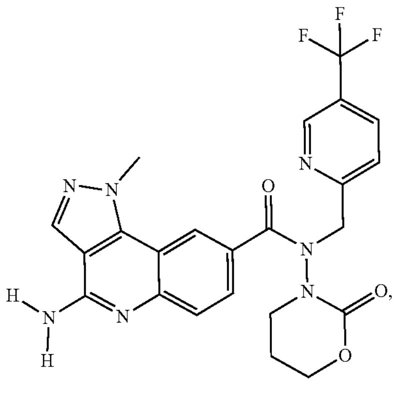

-continued
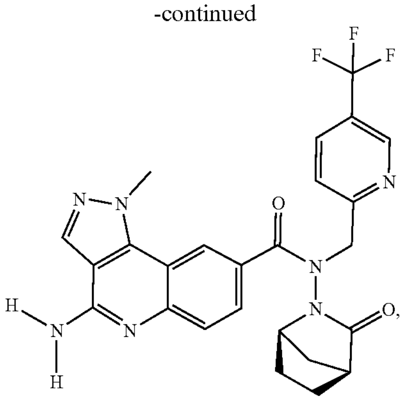
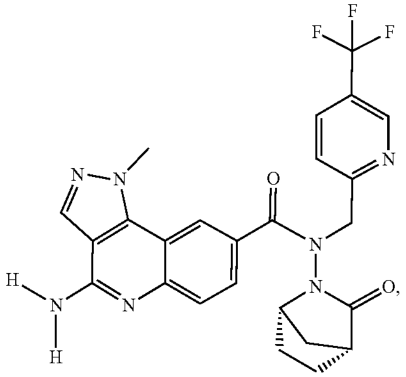
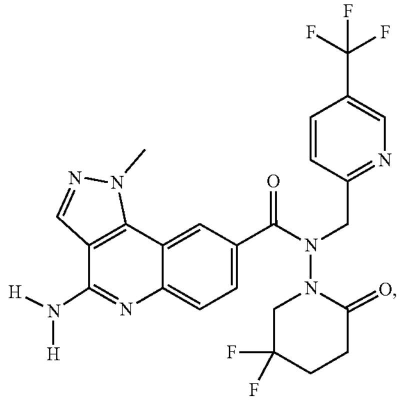
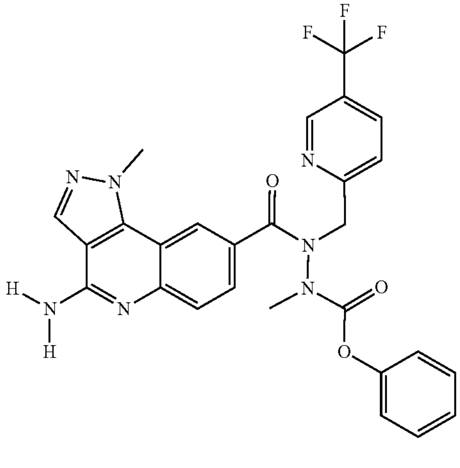
,
-continued
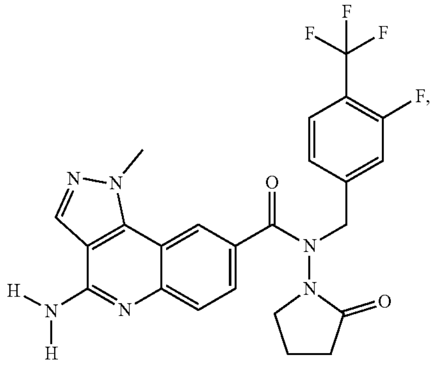
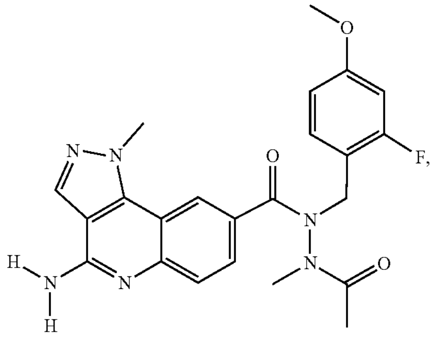
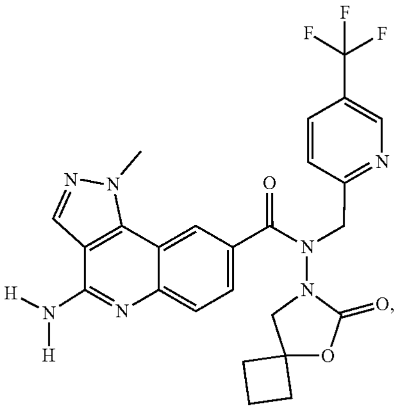
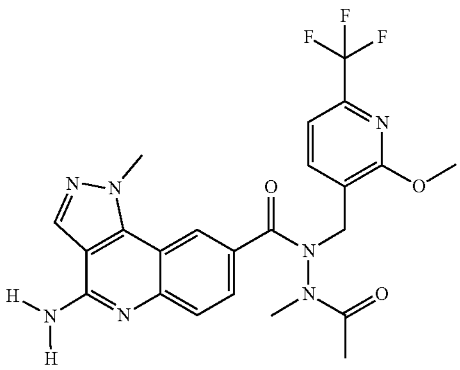
, -continued
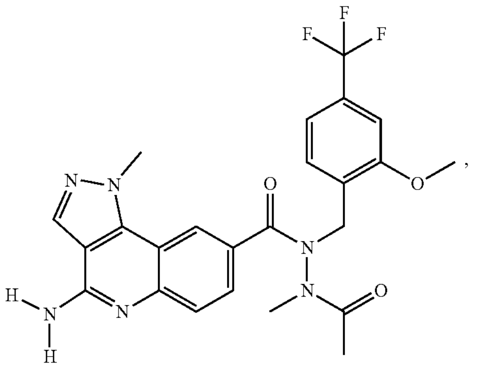
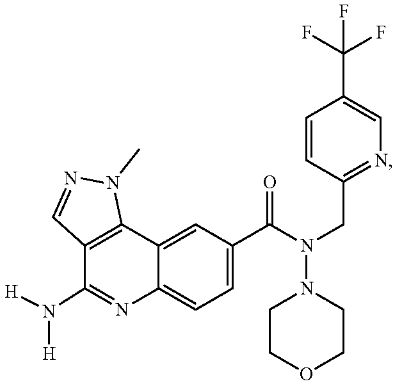
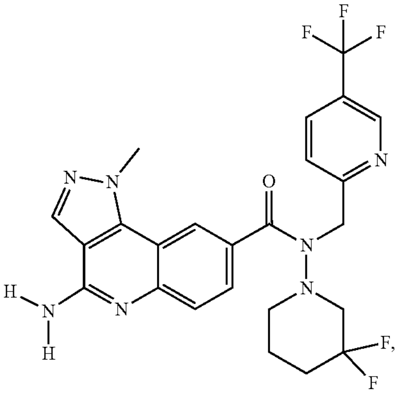
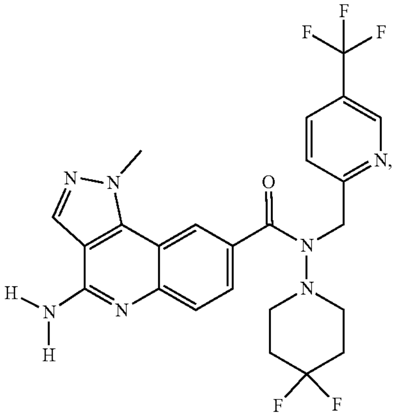
-continued
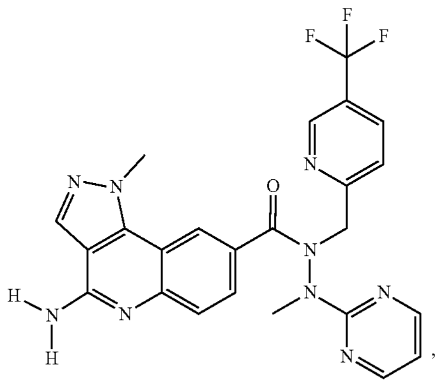
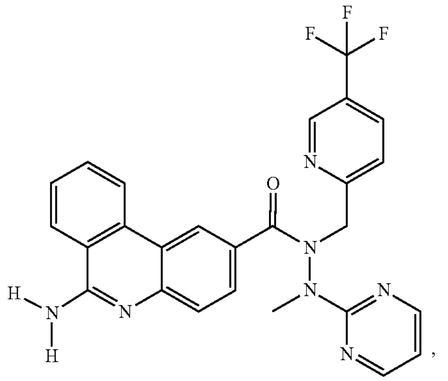
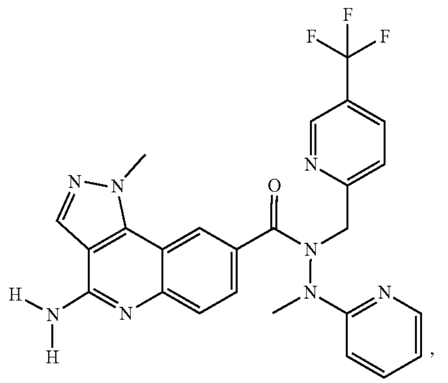
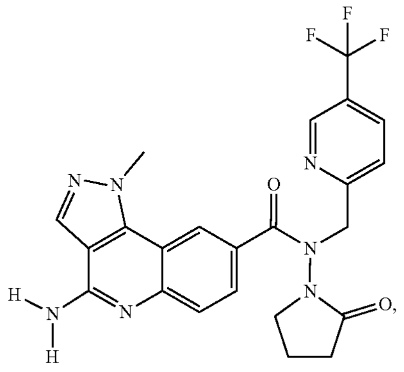

-continued
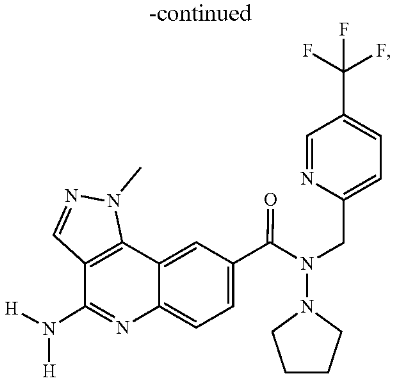
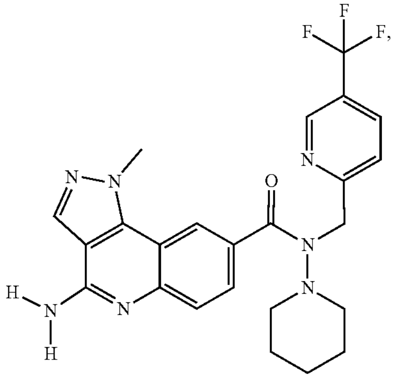
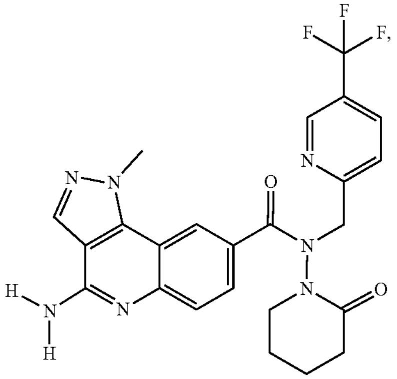
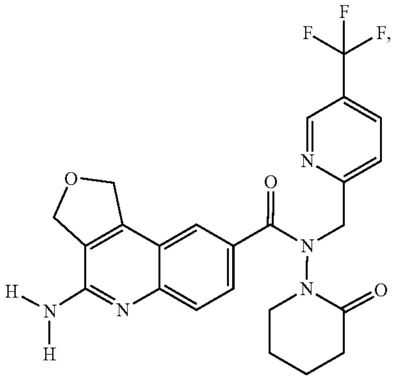
-continued
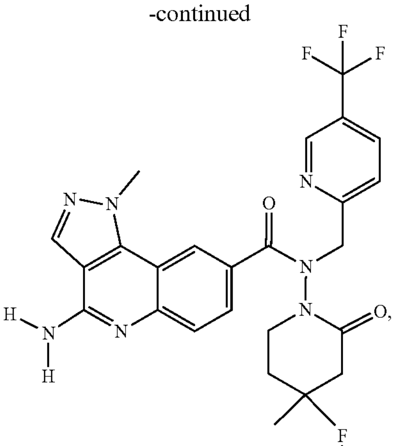
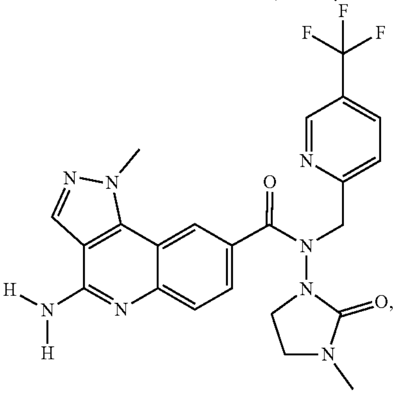
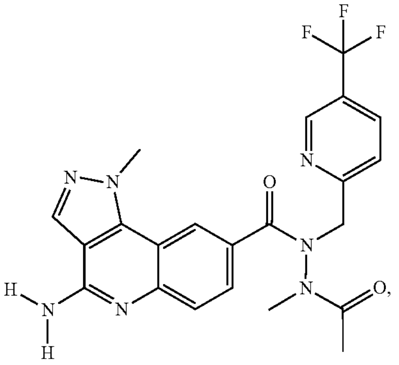
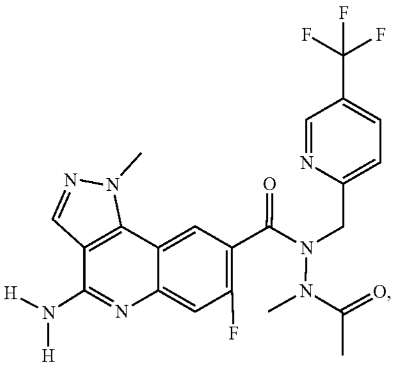

-continued
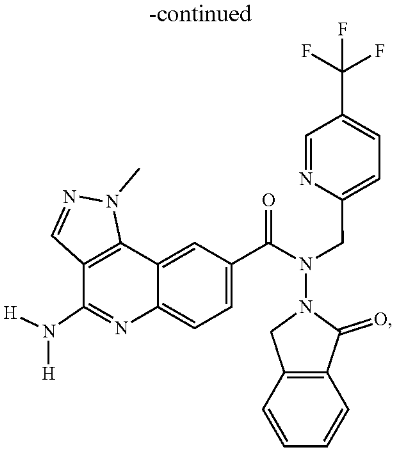
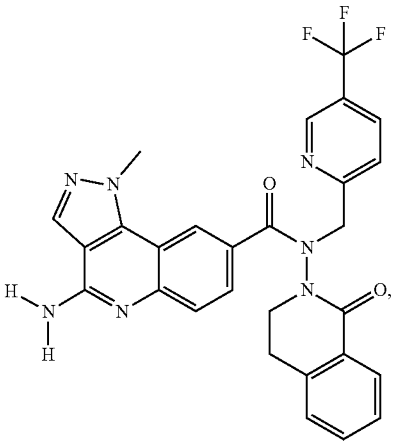
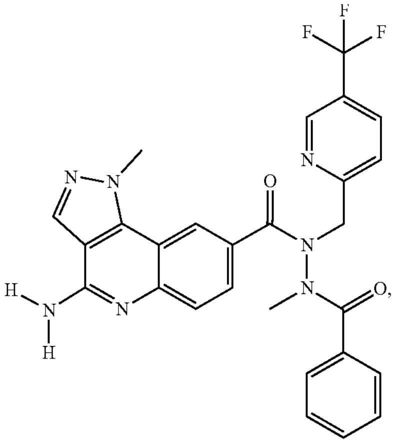
-continued
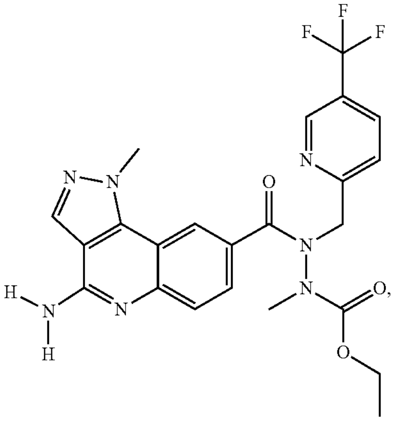
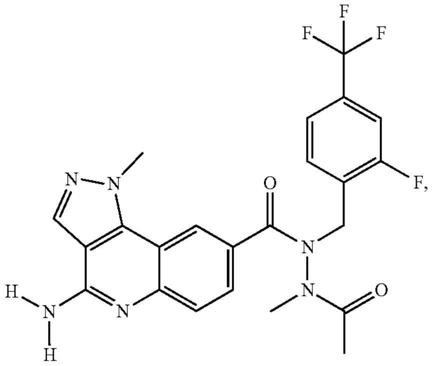
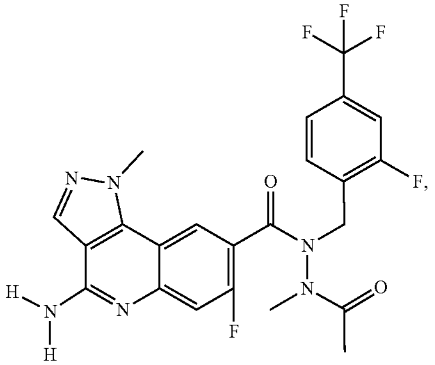
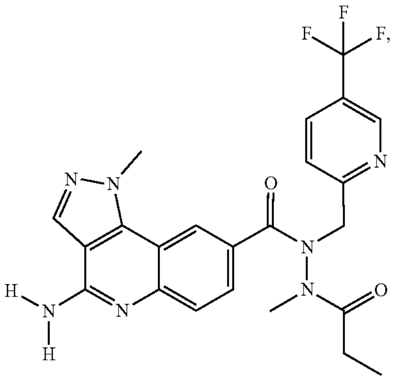

-continued
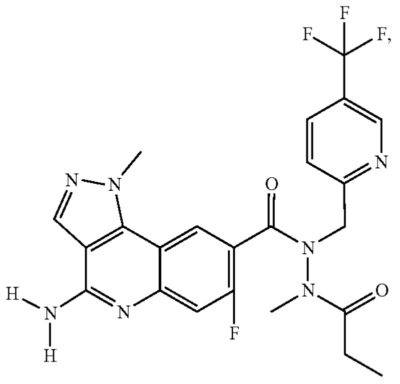
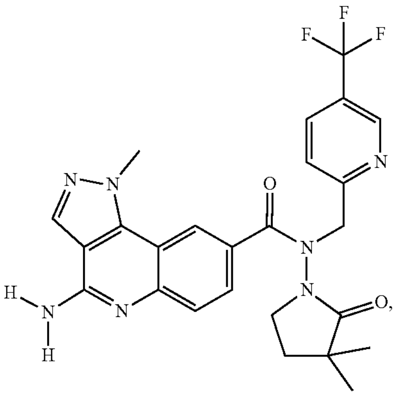
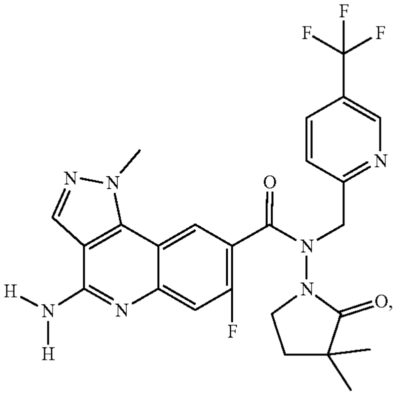
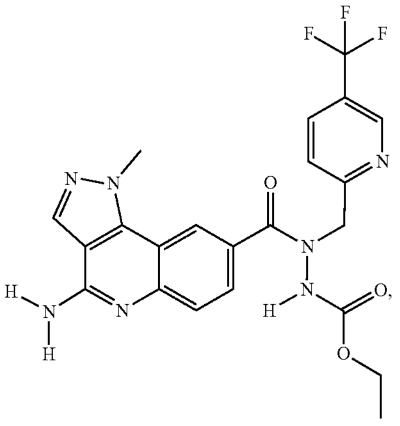
-continued
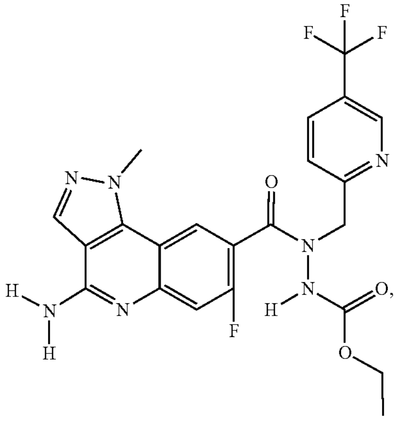
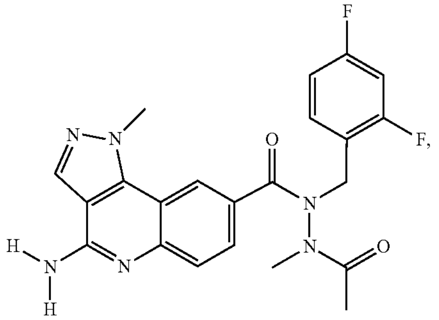
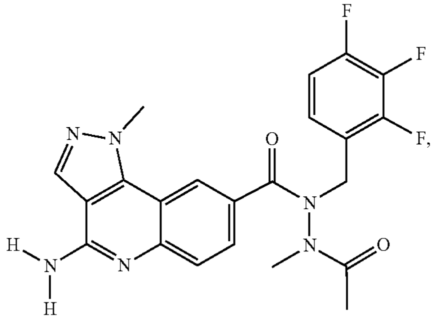
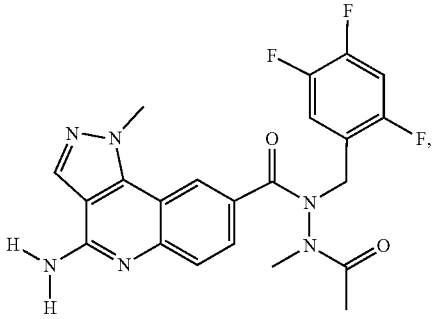

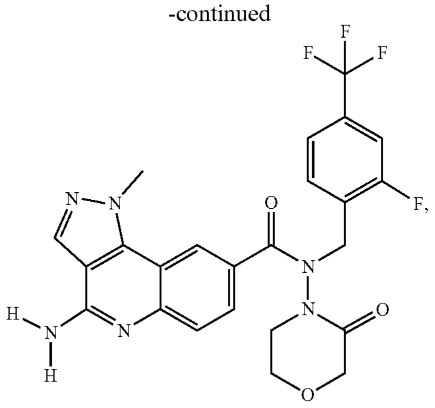
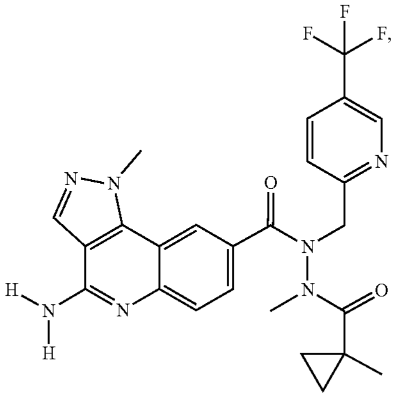
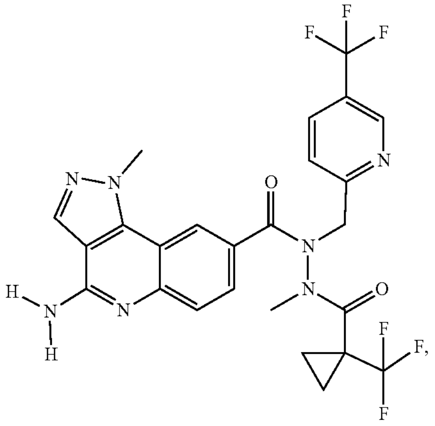
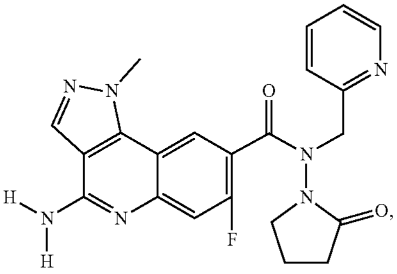
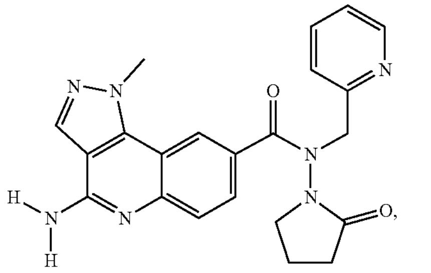
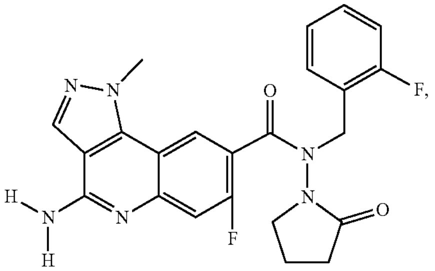
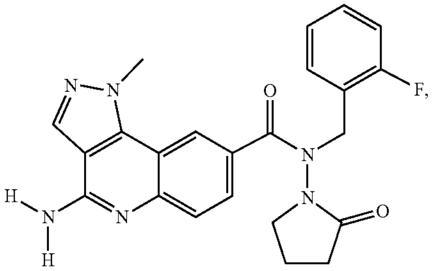
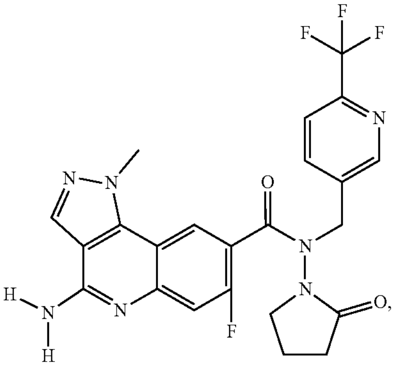
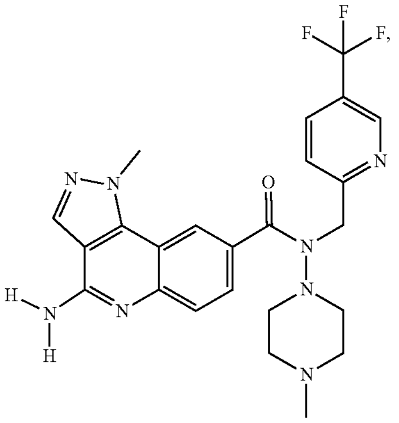

-continued
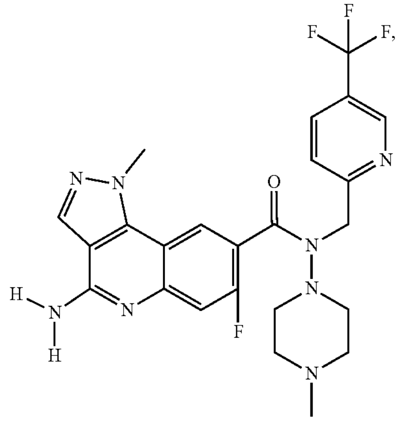
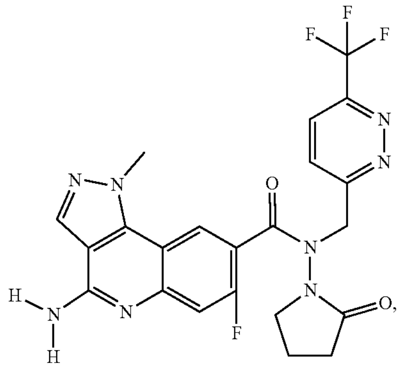
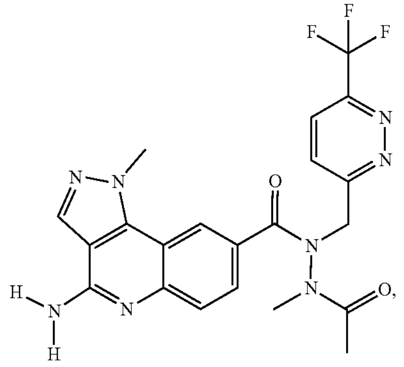
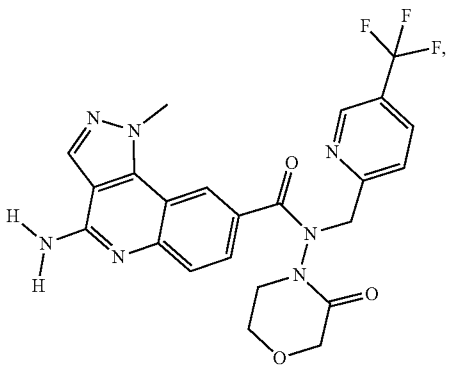
-continued
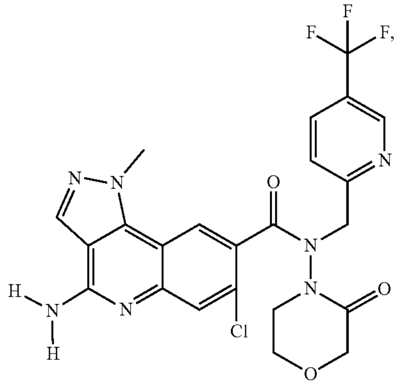
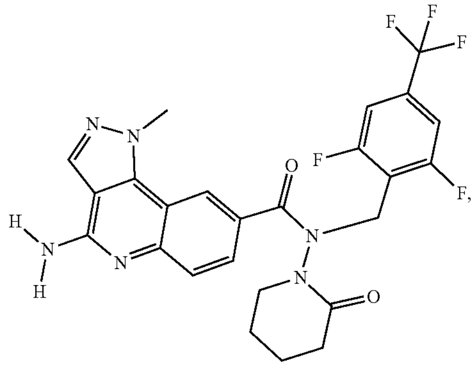
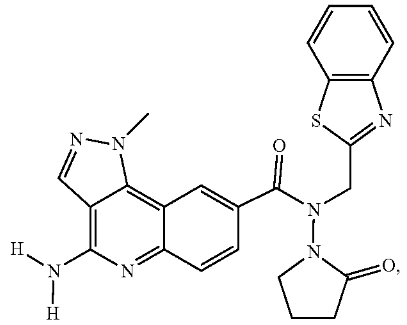
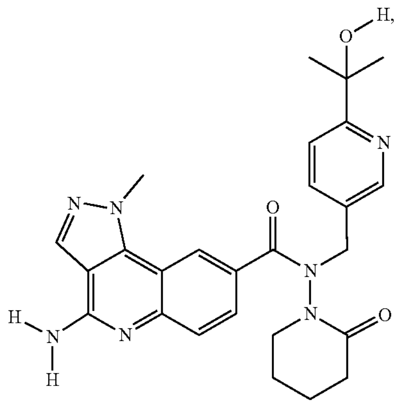

-continued
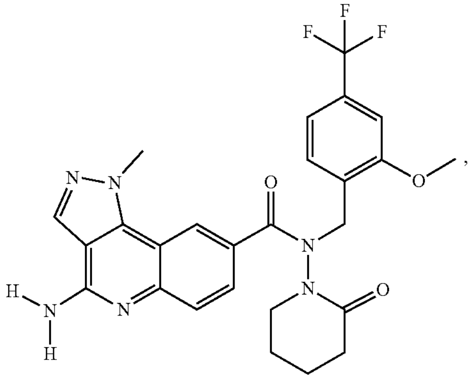
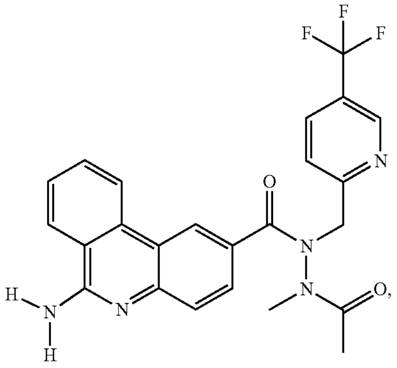
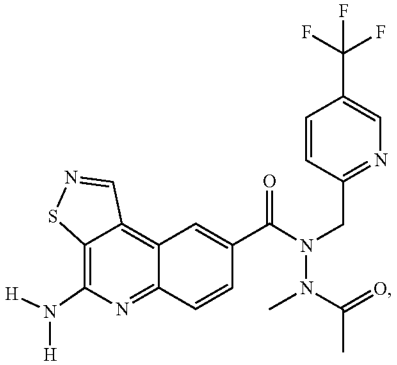
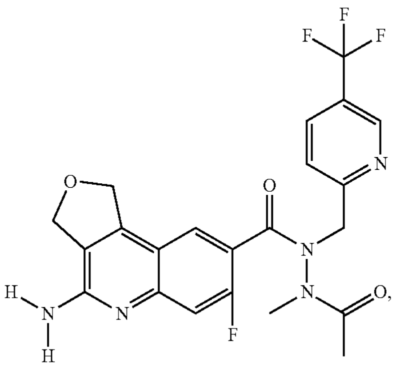
-continued
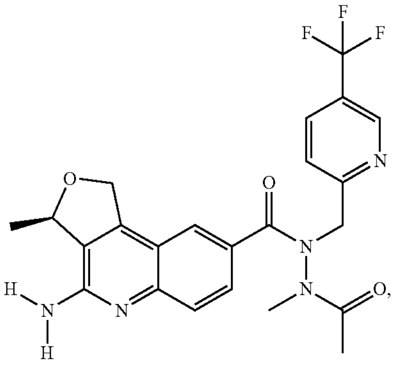
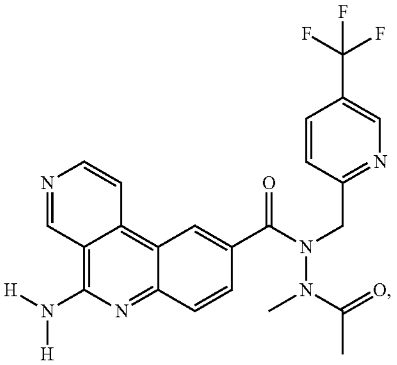
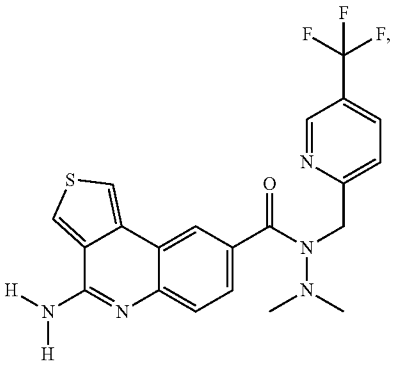
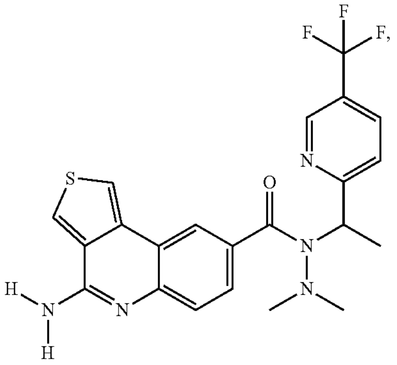

-continued
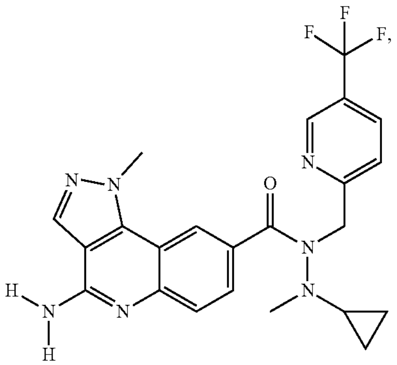
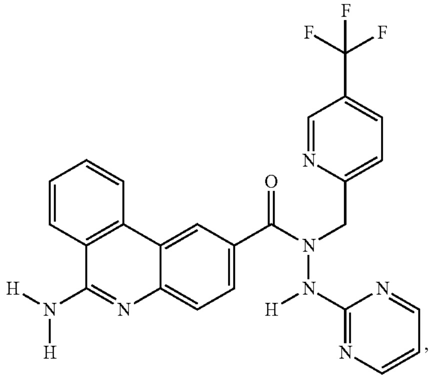
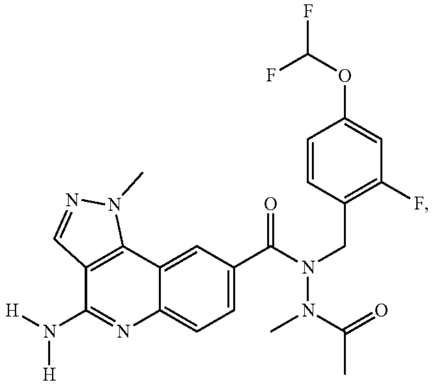
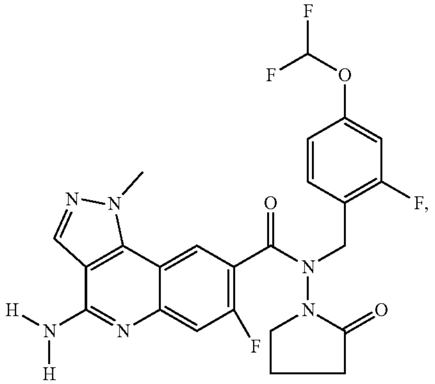
-continued
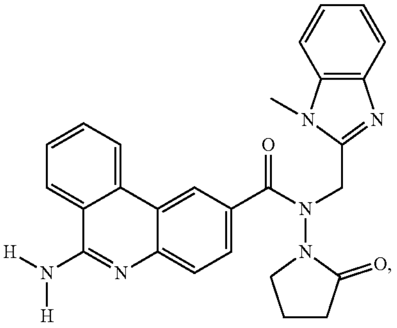
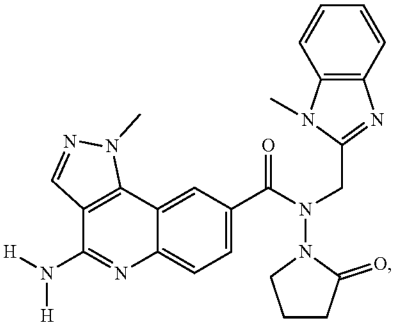
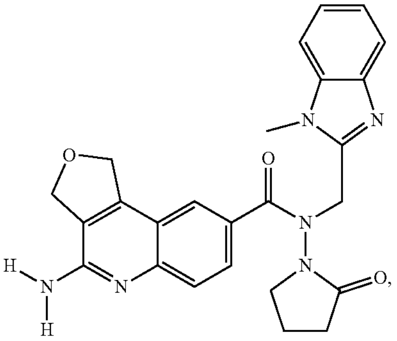
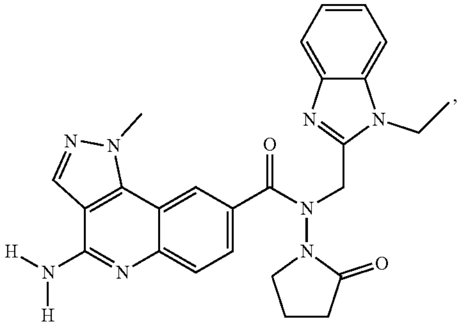
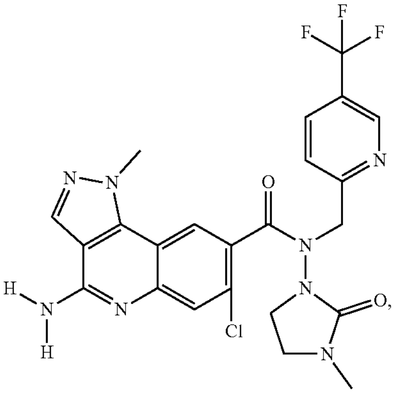

-continued
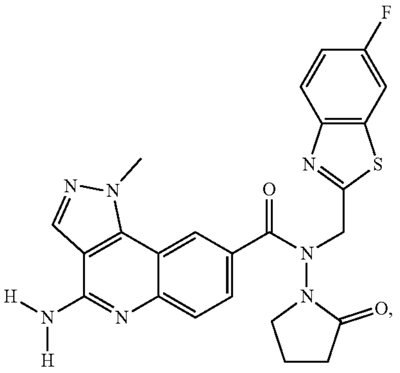
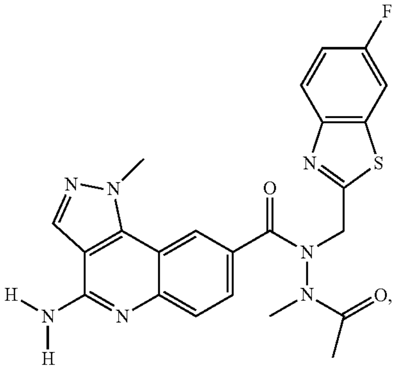
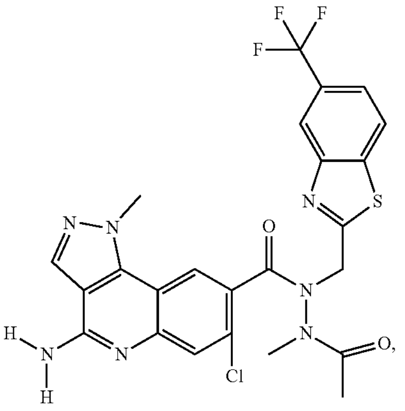
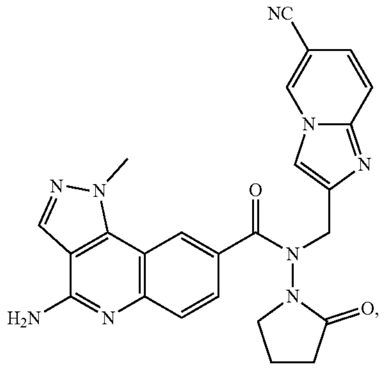
-continued
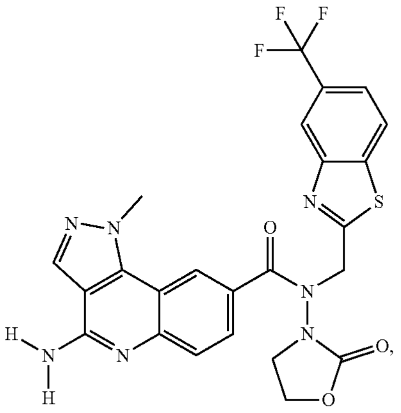
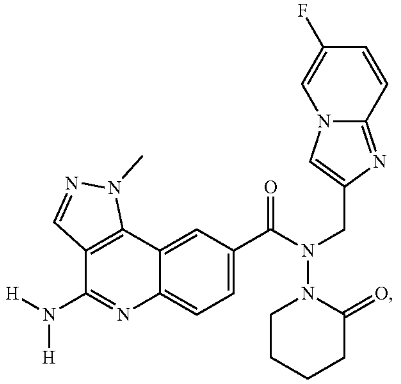
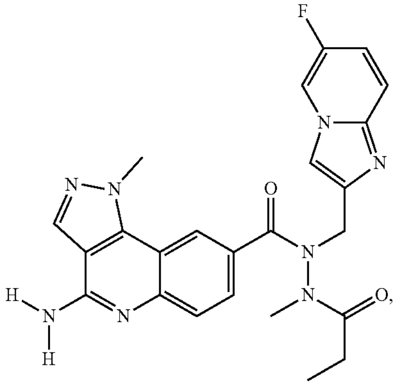
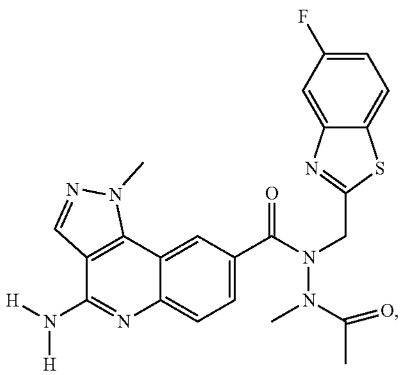

-continued
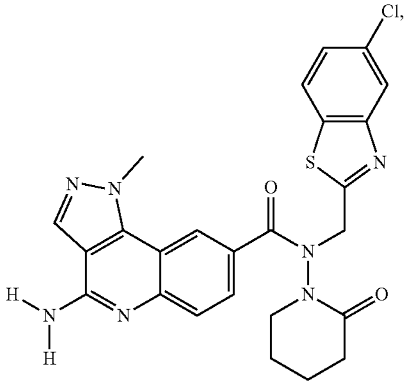
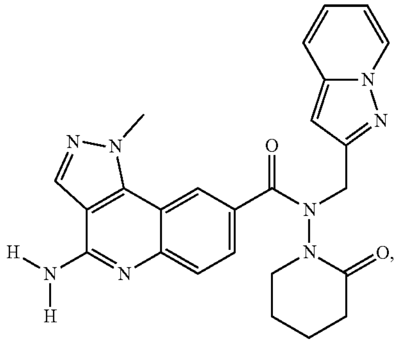
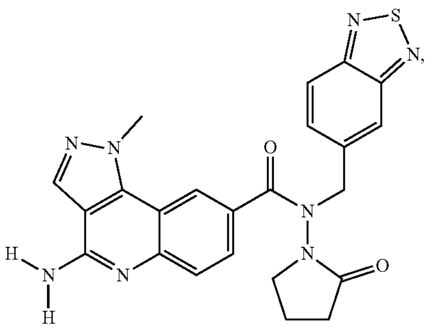
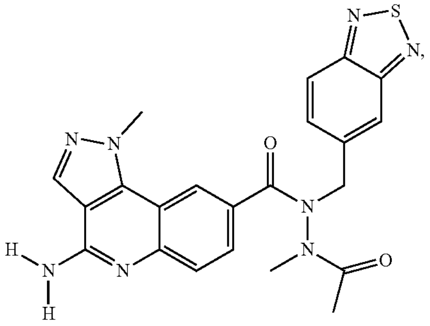
-continued
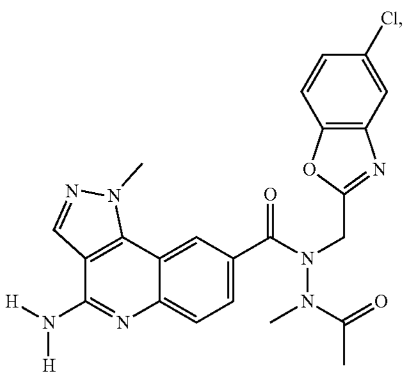
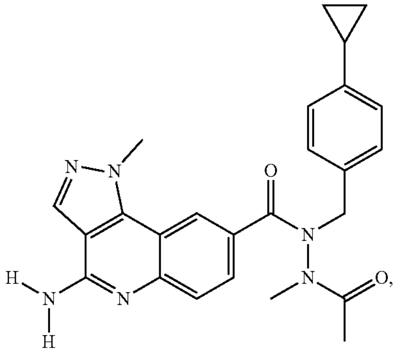
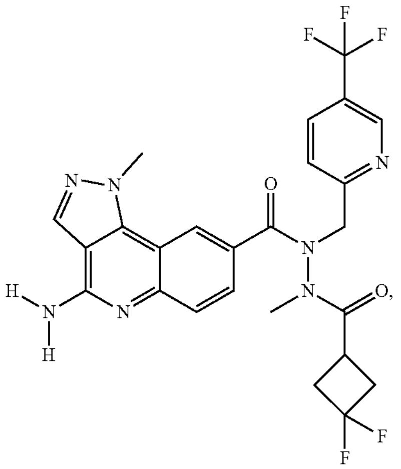
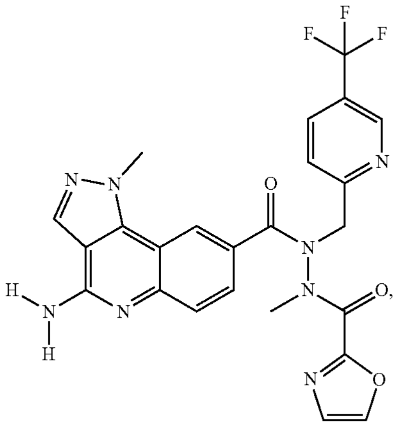

-continued
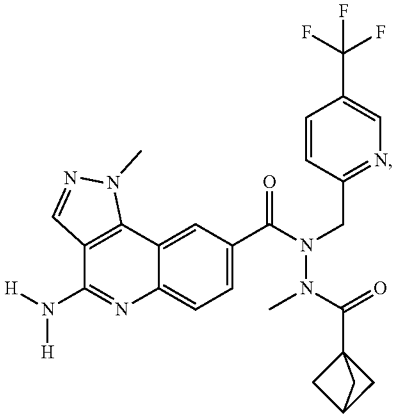
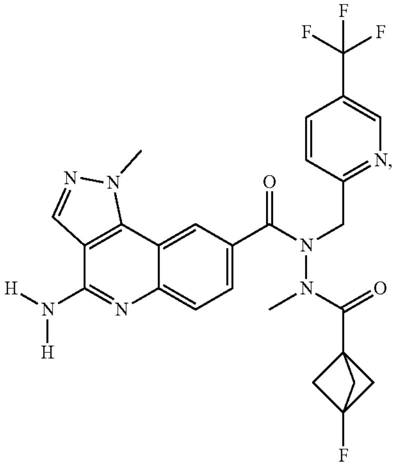
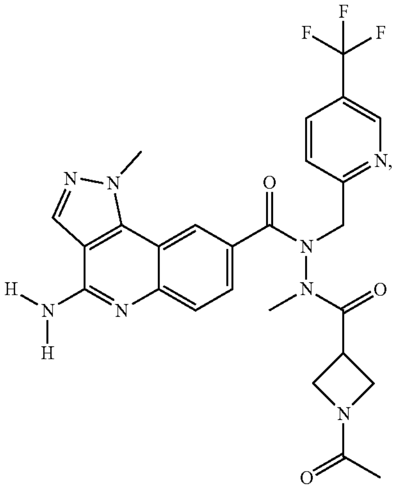
-continued
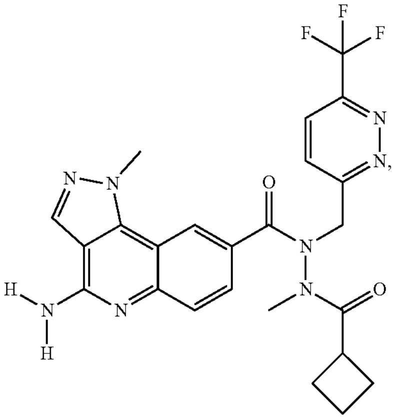
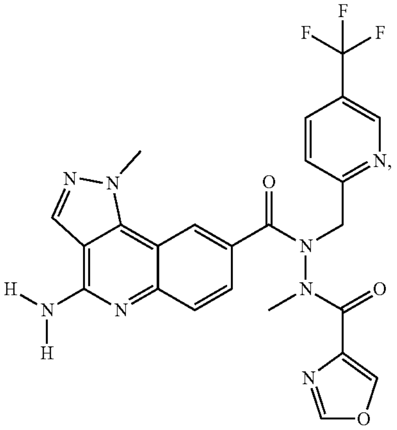
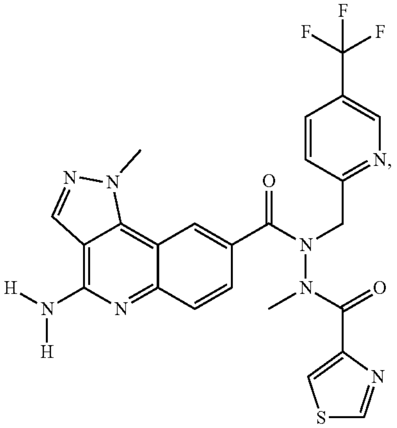
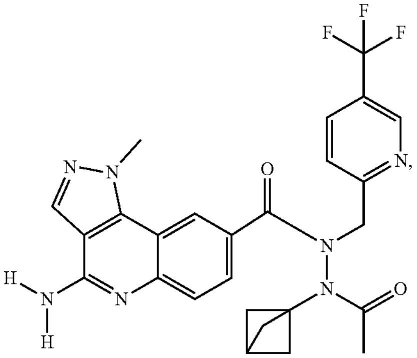

-continued
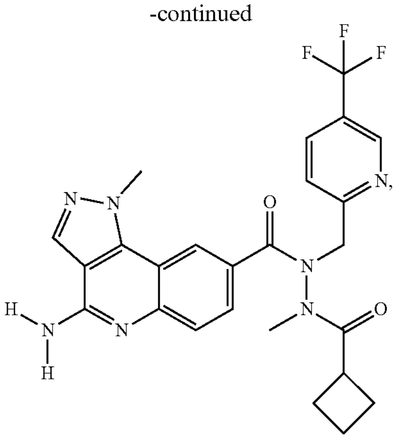
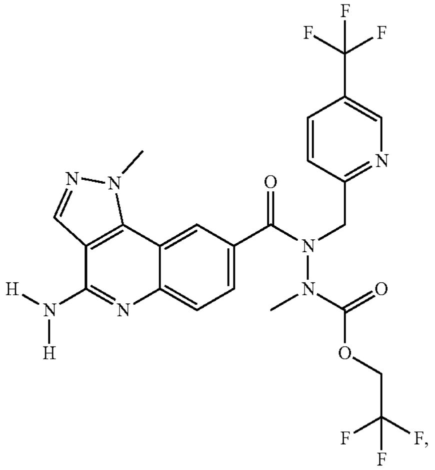
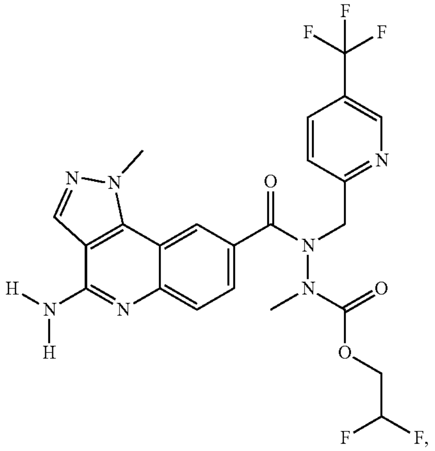
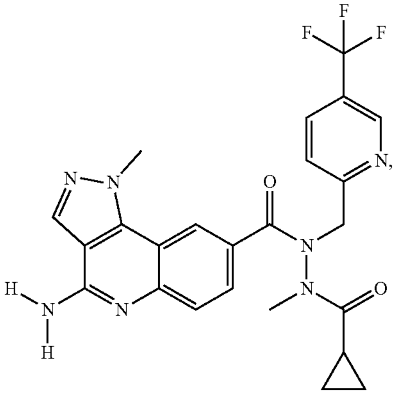
-continued
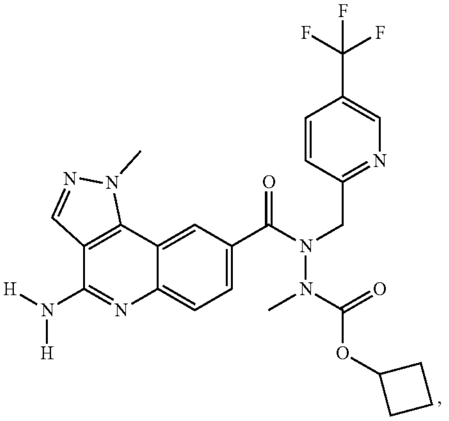
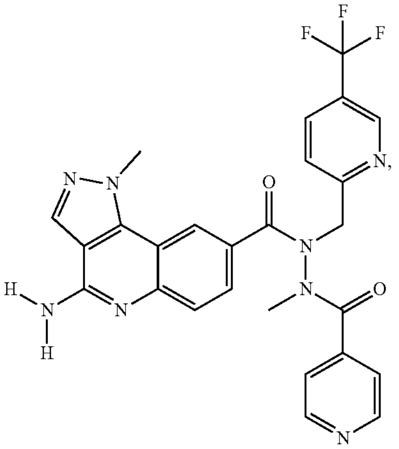
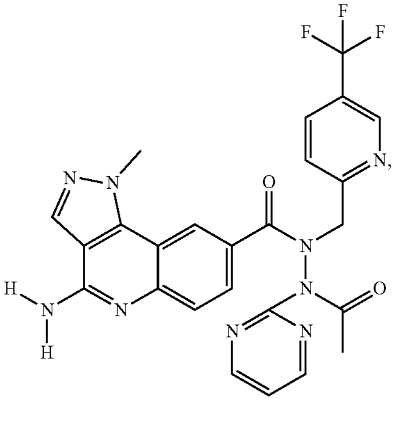
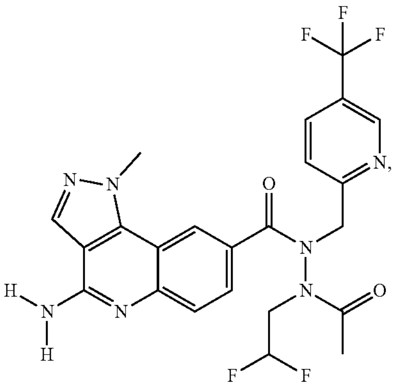

-continued
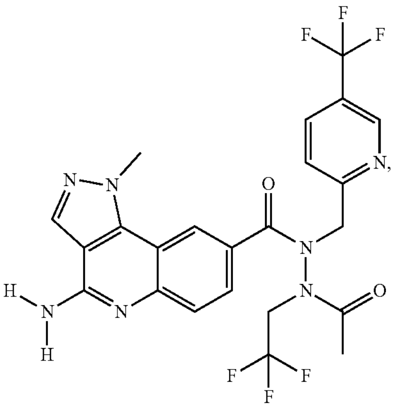
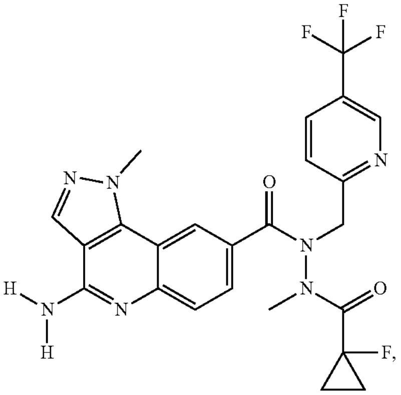
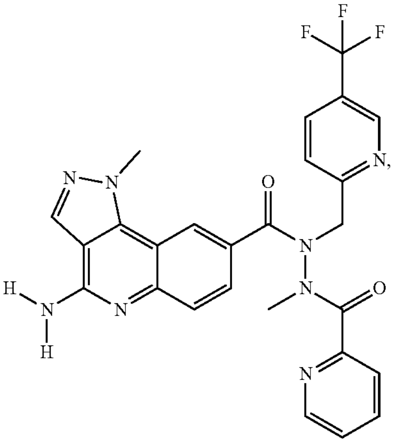
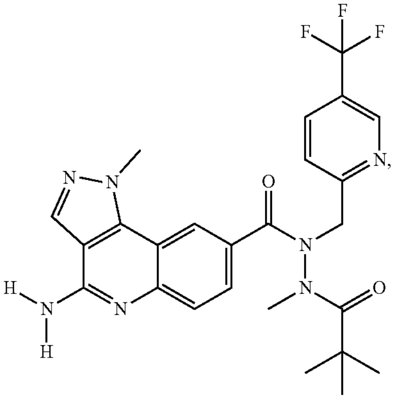
-continued
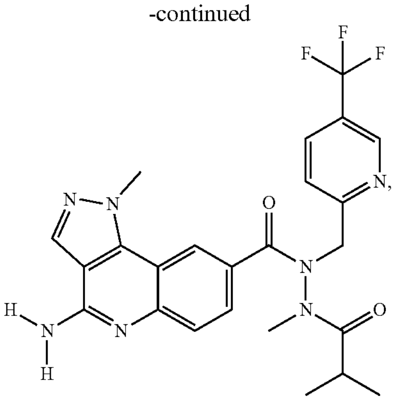
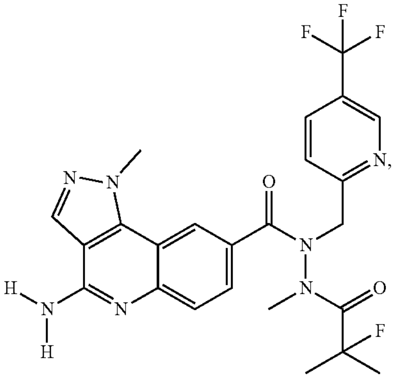
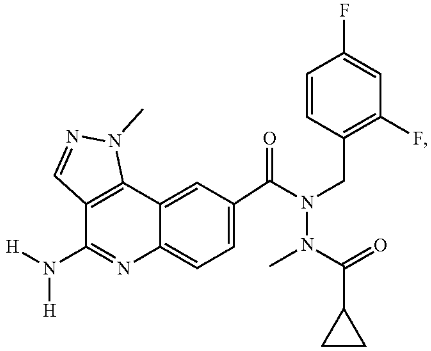
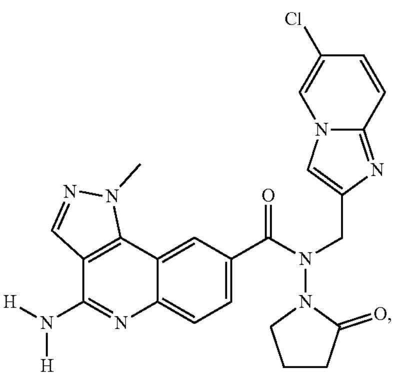

-continued
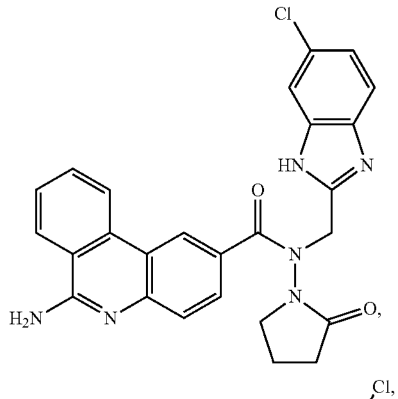
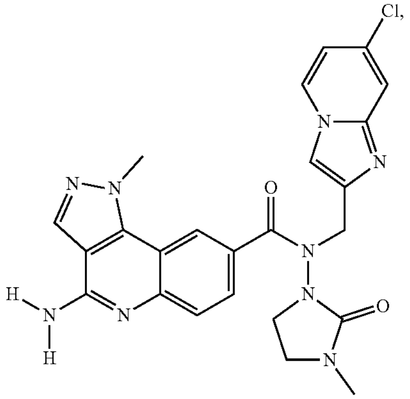
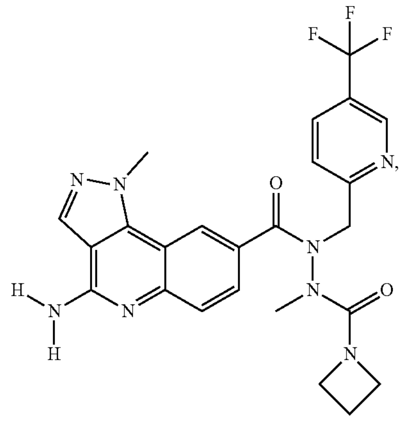
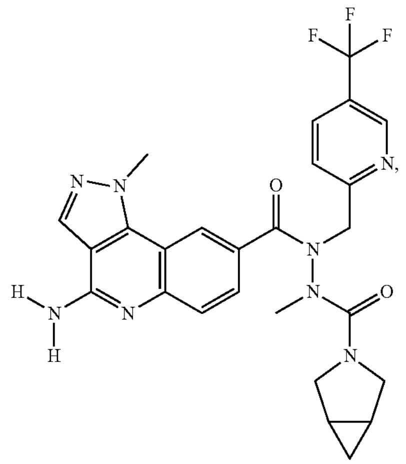
-continued
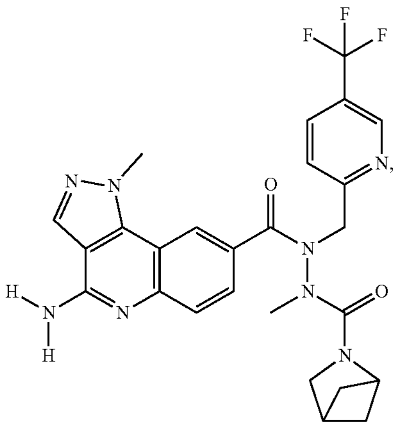
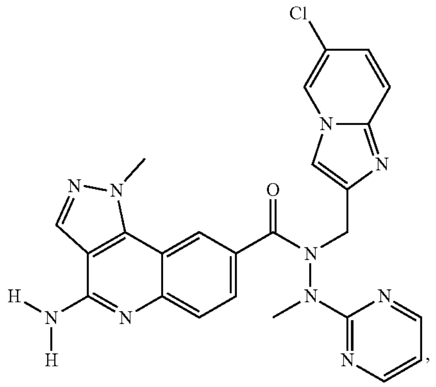
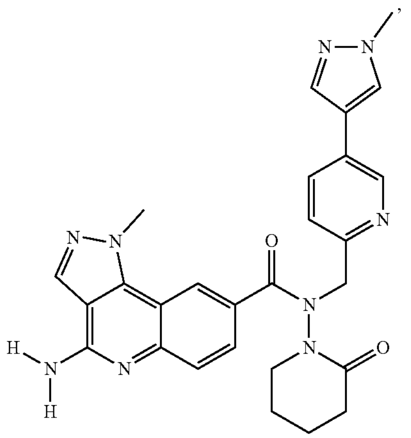
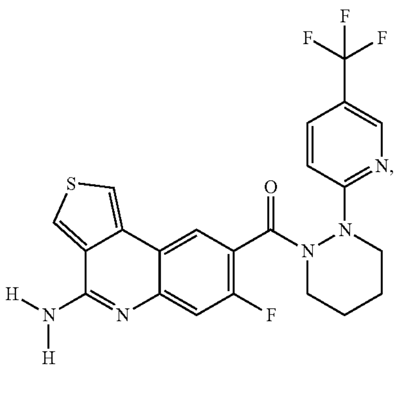

-continued
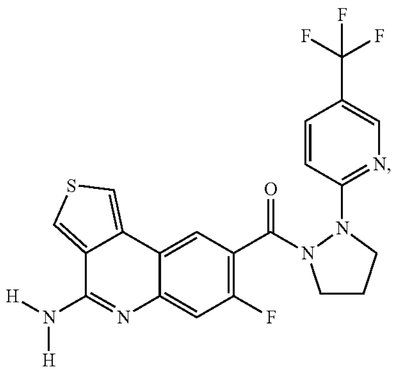
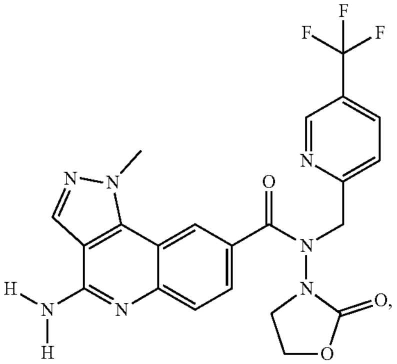
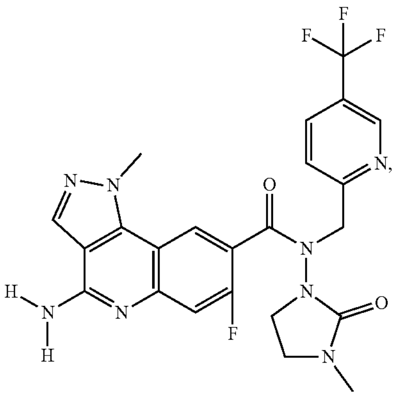
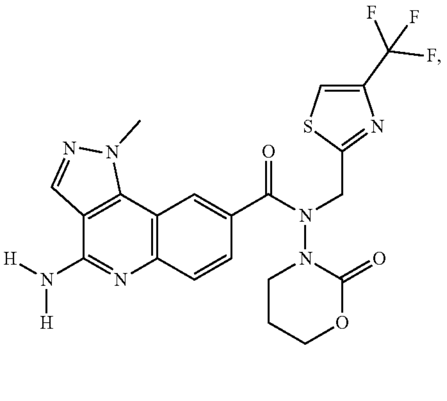
-continued
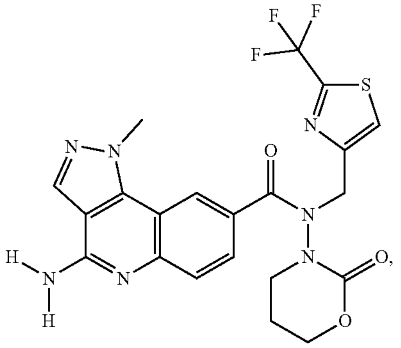
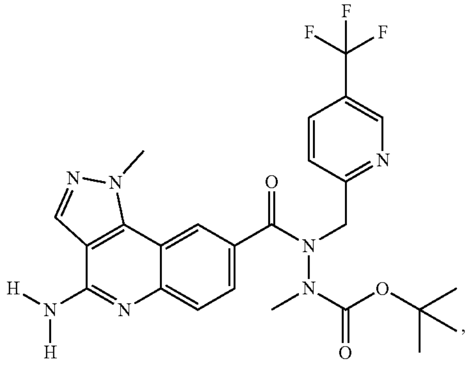
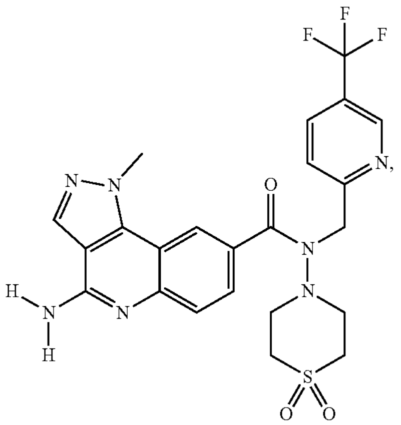
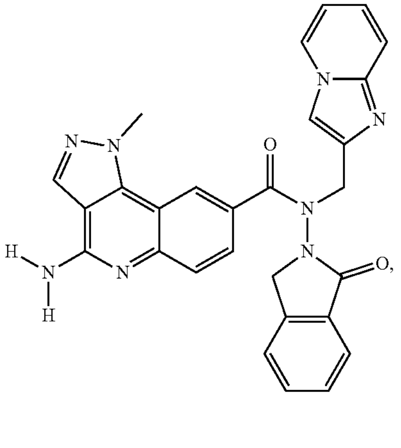

-continued
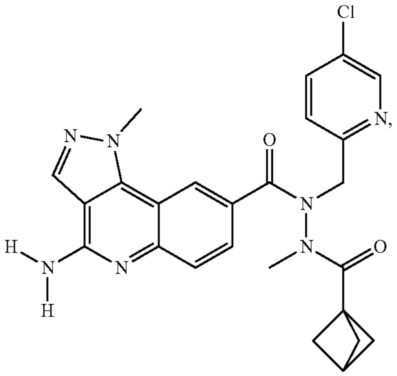
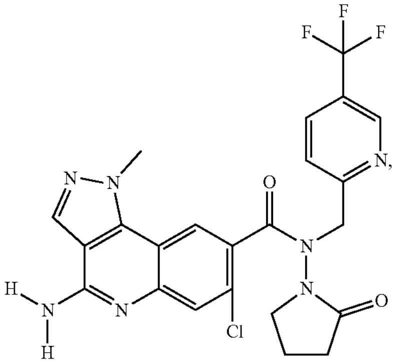
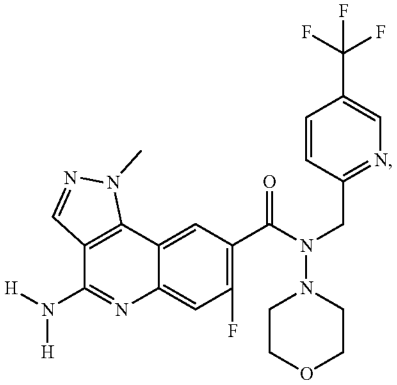
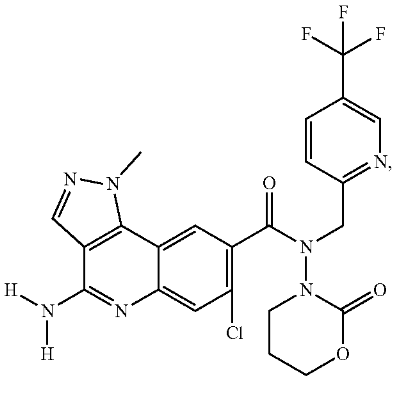
-continued
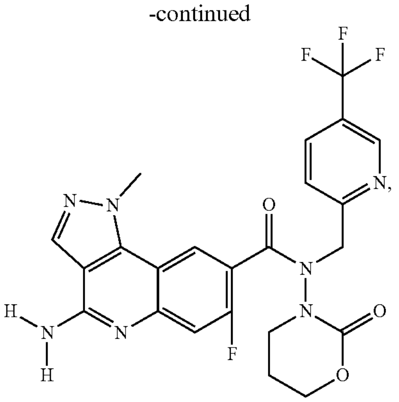
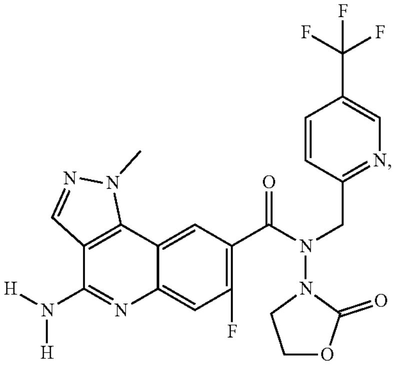
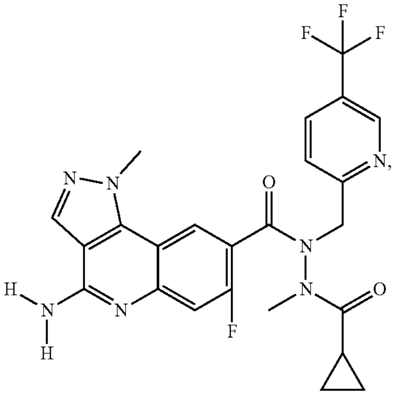
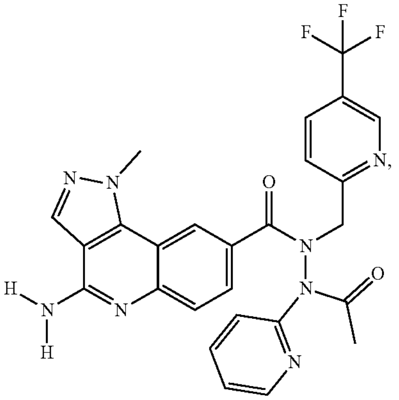

-continued
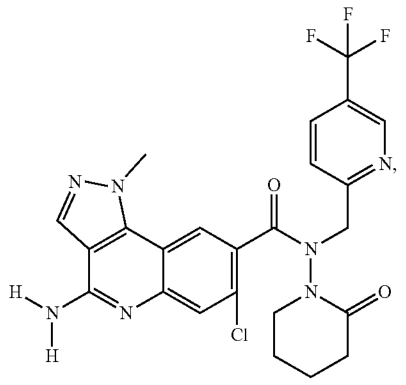
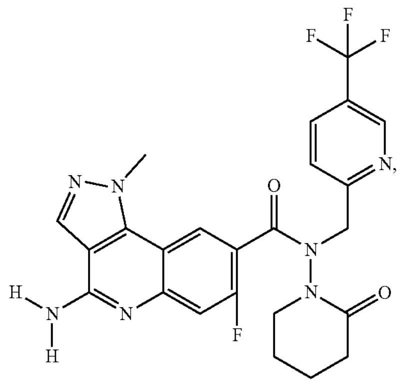
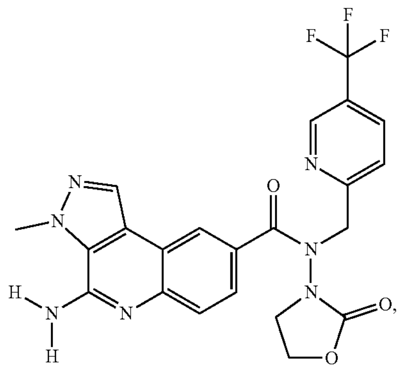
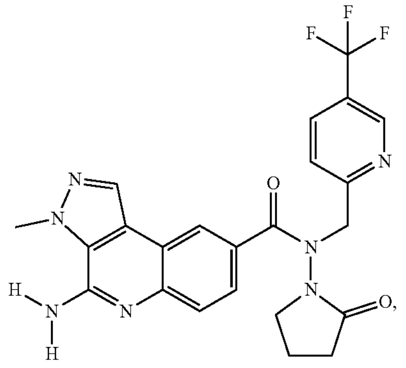
-continued
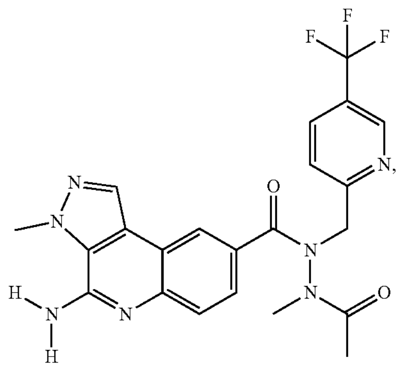
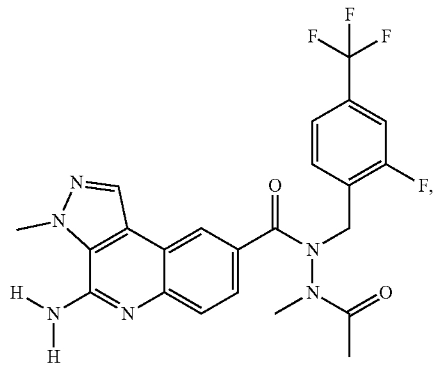
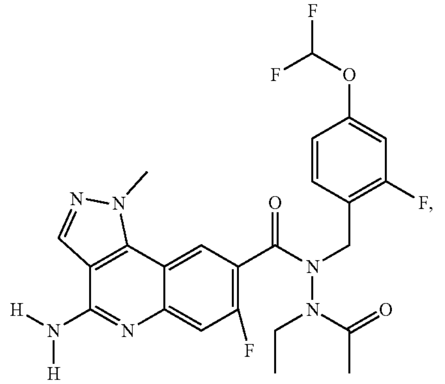
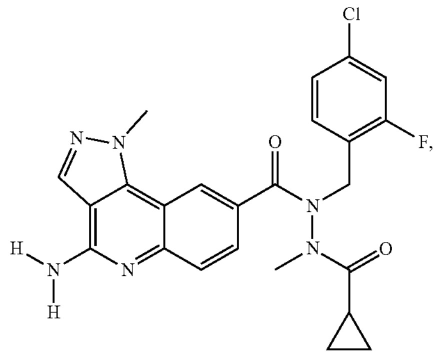

-continued
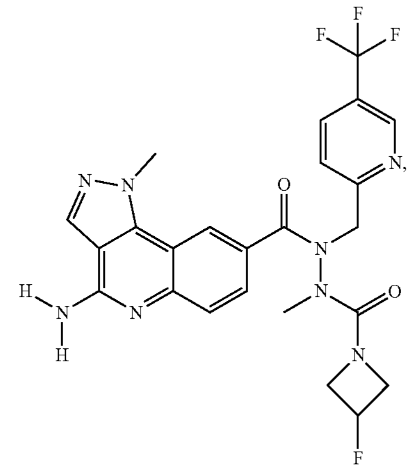
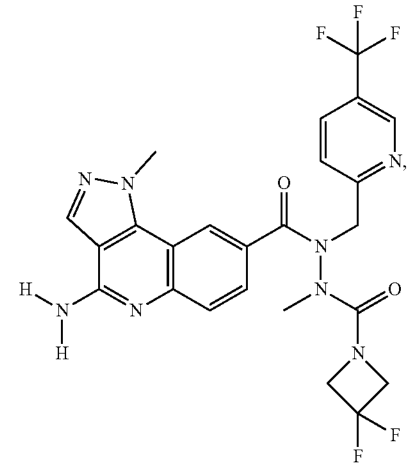
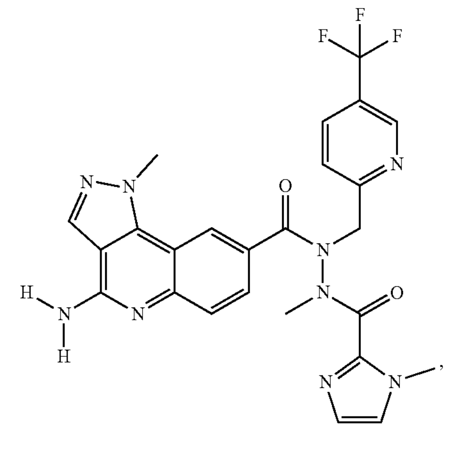
-continued
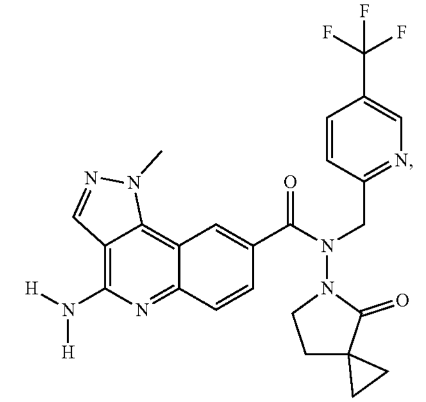
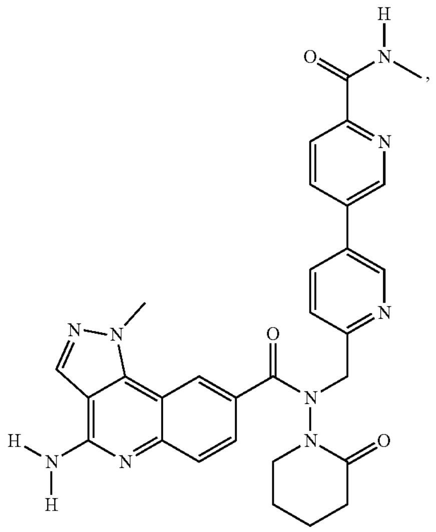
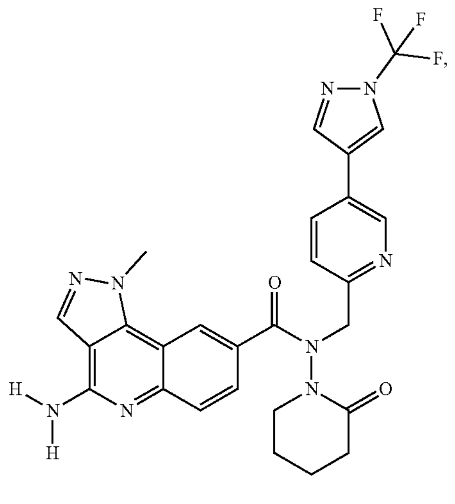

-continued
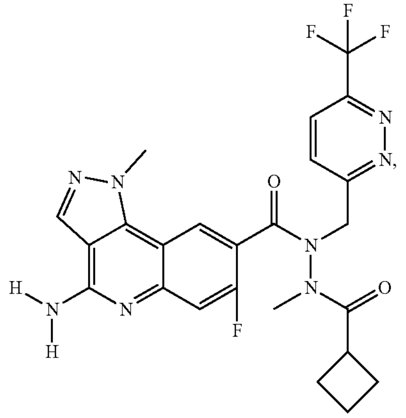
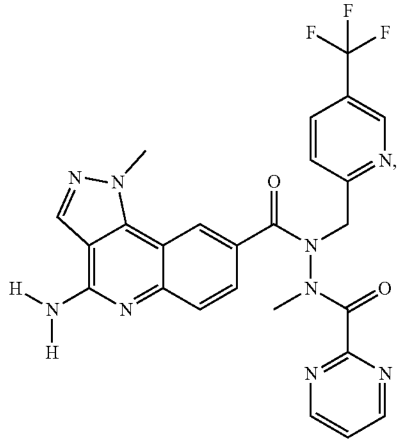
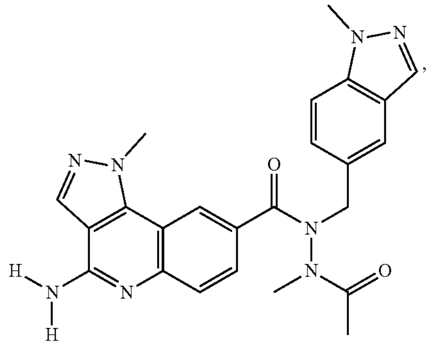
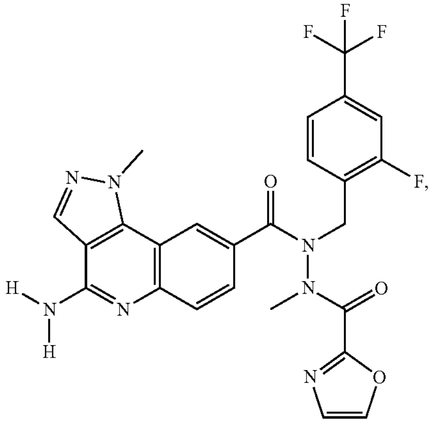
-continued
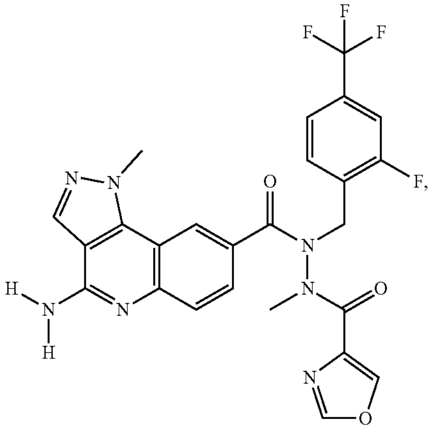
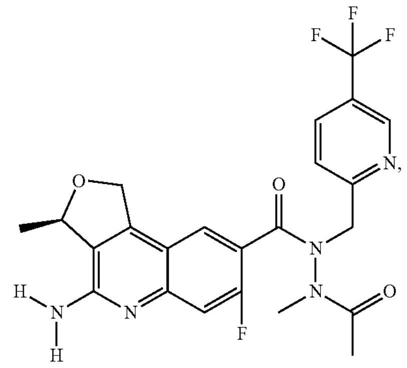
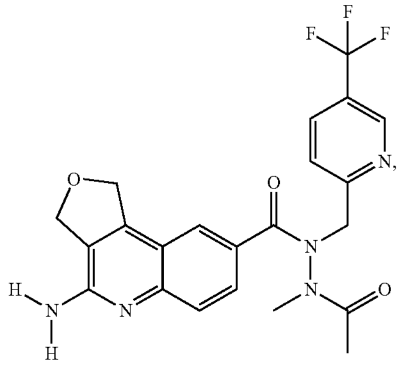
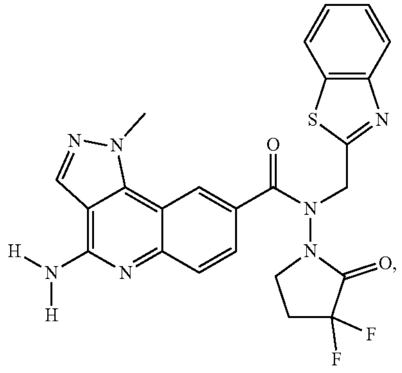

-continued
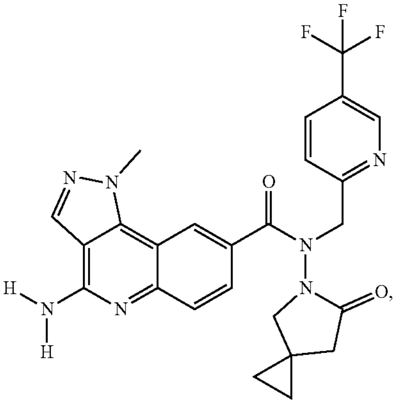
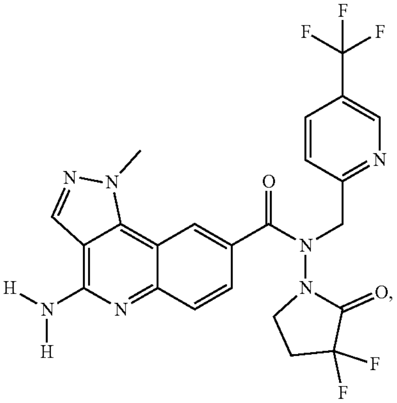
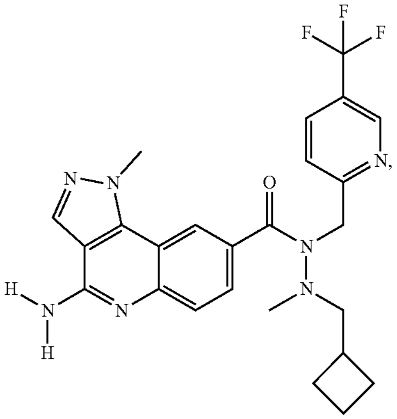
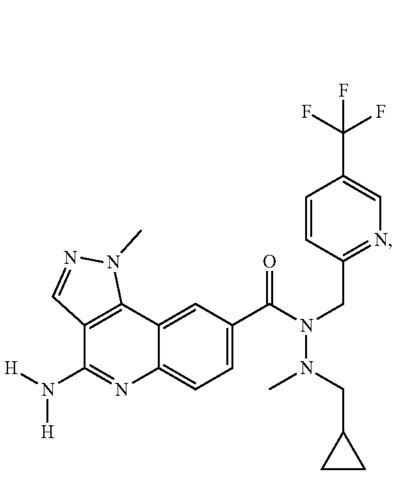
-continued
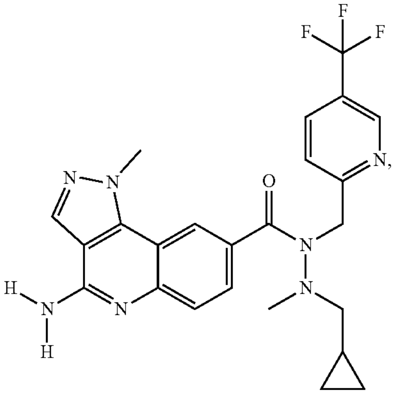
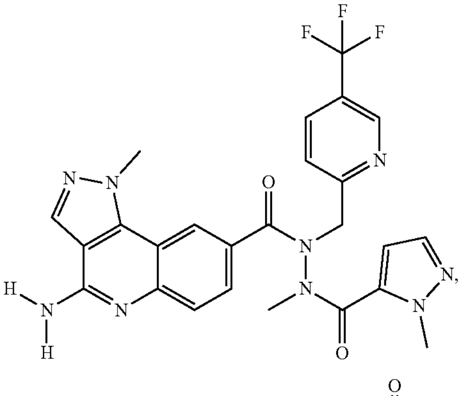
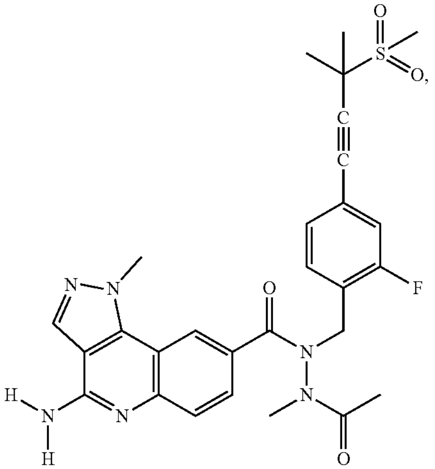
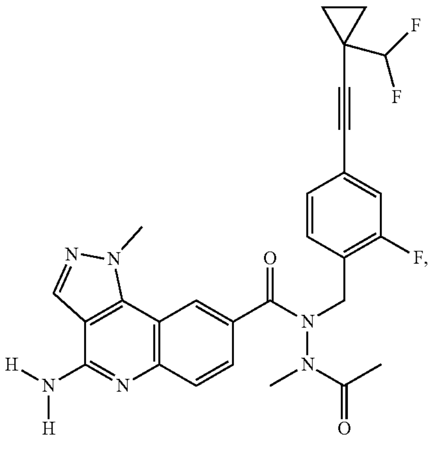

-continued
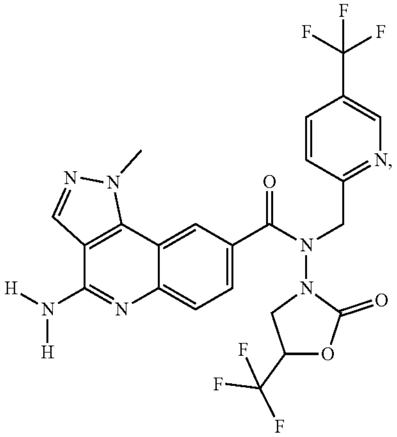
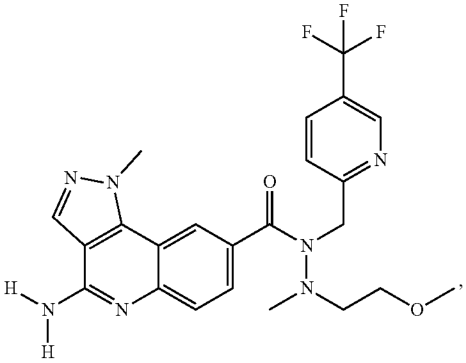
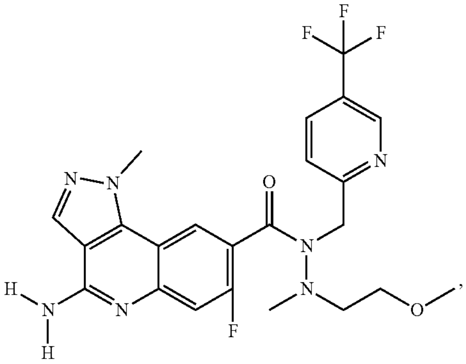
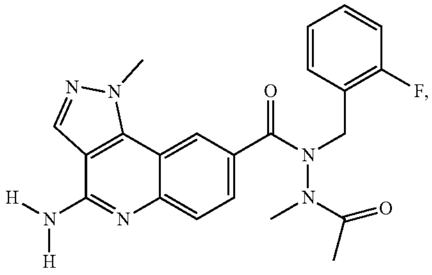
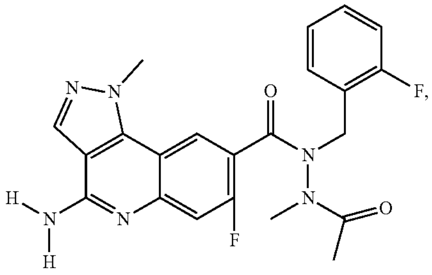
-continued
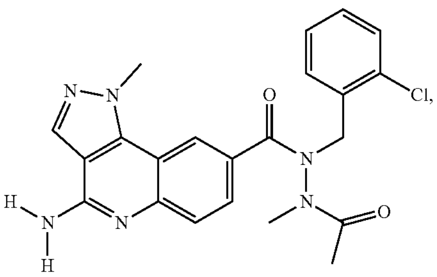
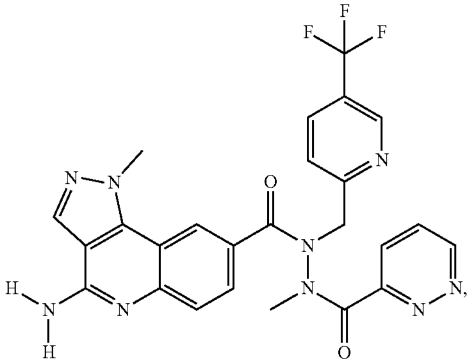
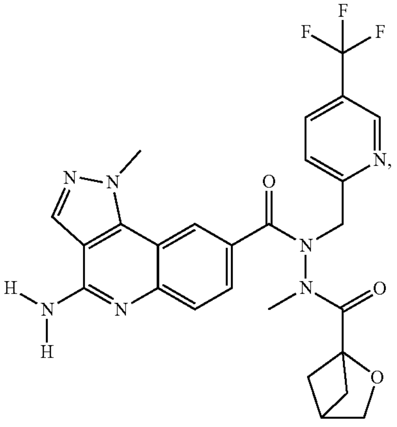
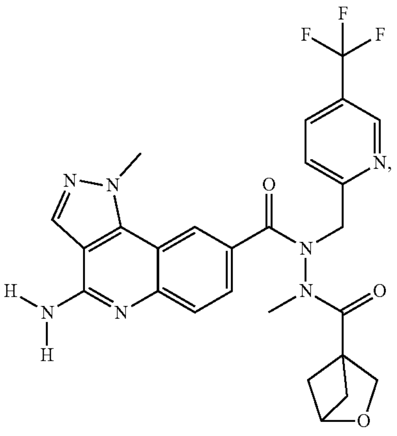

-continued
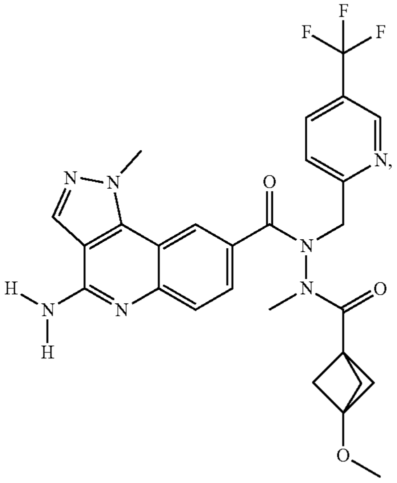
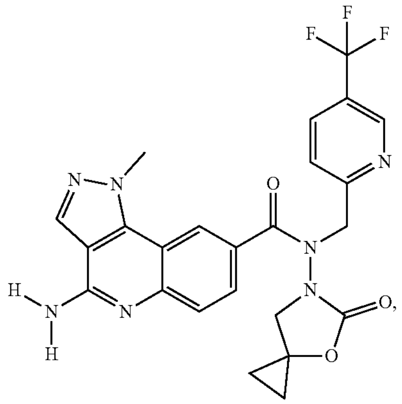
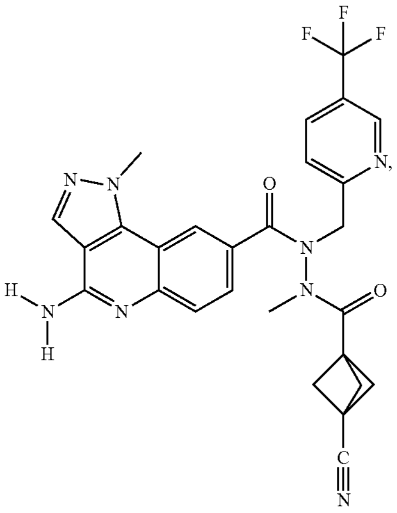
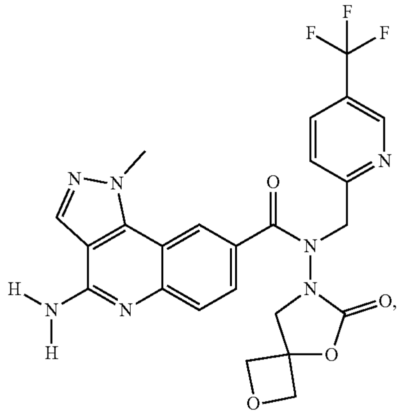
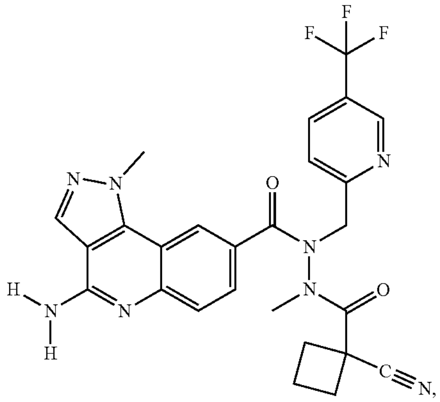
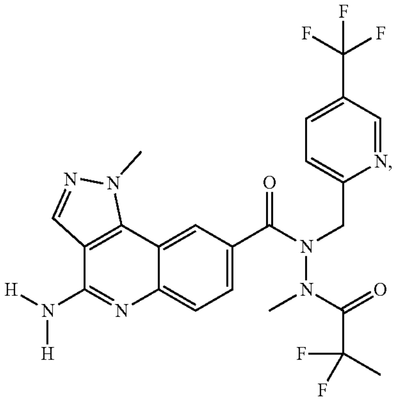
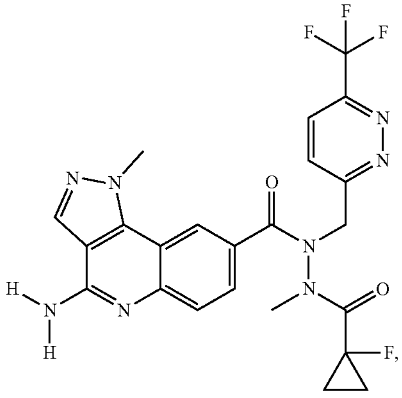

-continued
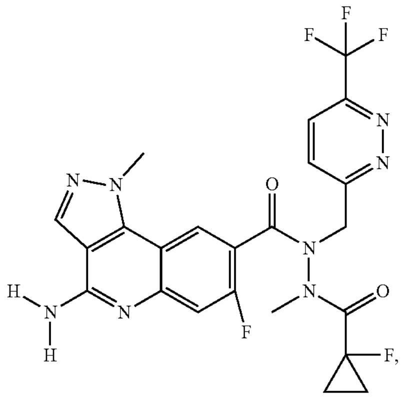
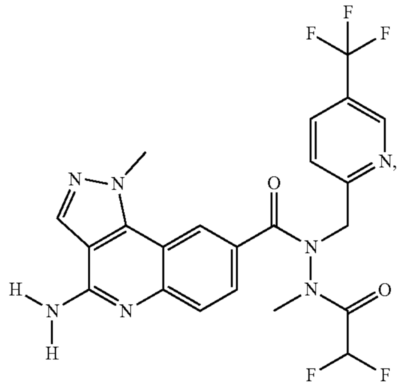
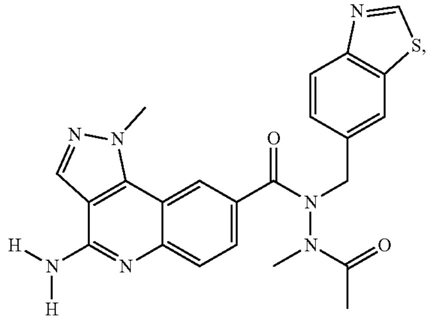
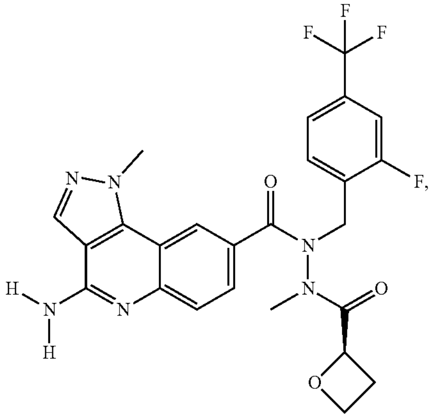
-continued
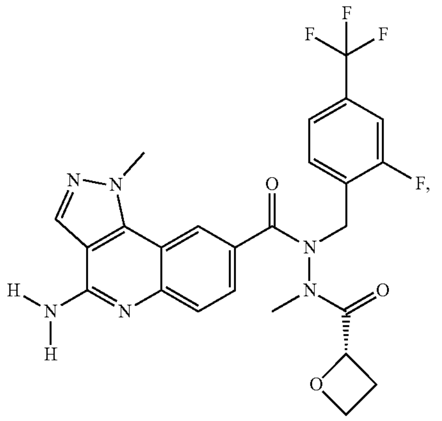
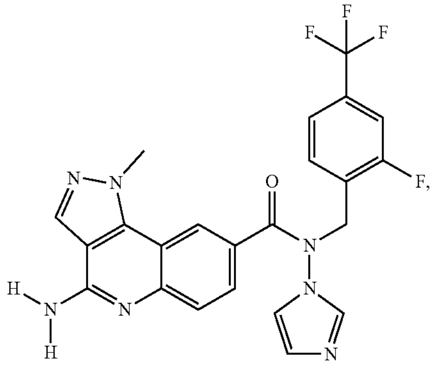
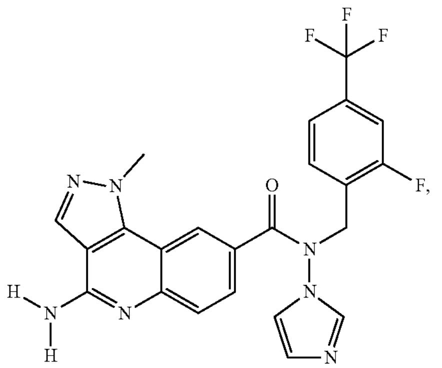
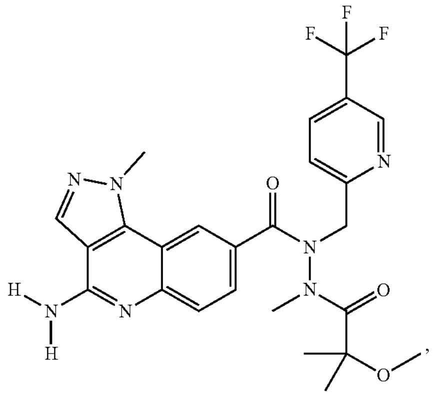

-continued
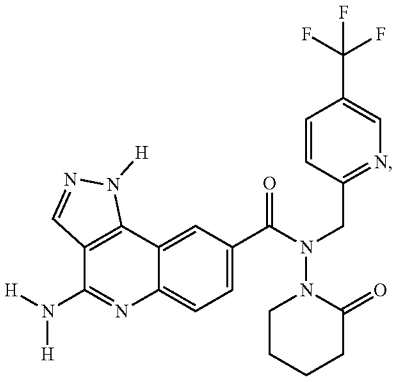
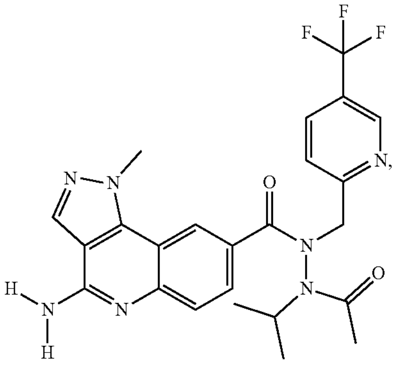
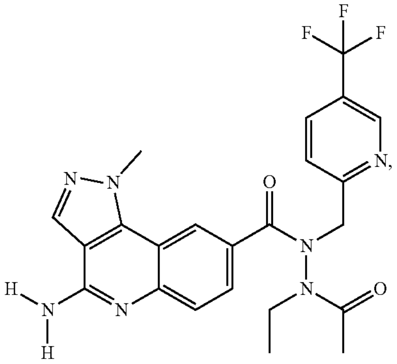
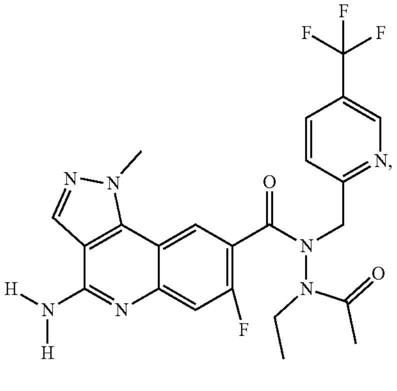
-continued
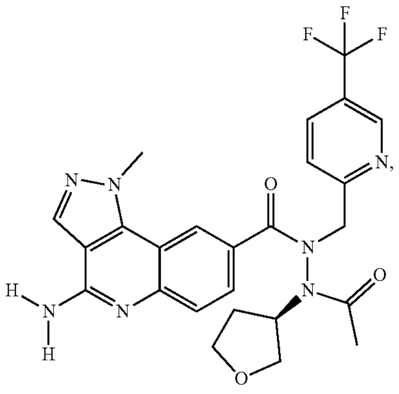
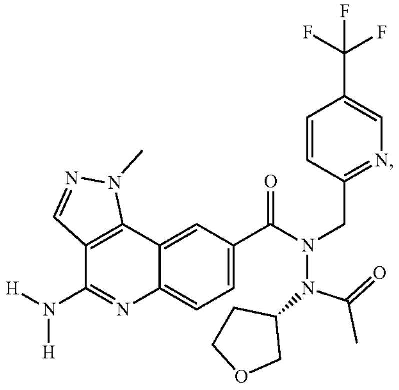
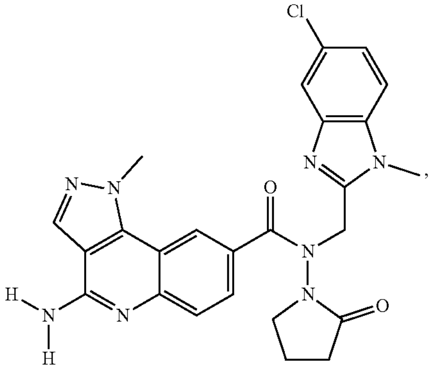
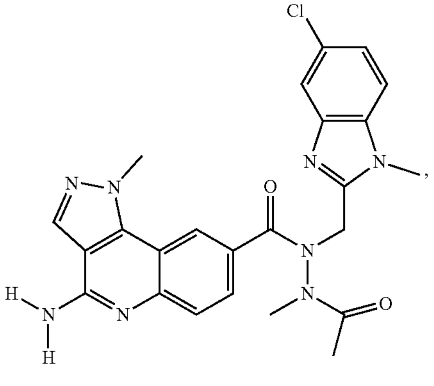

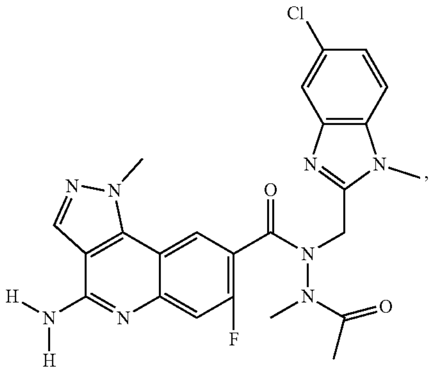
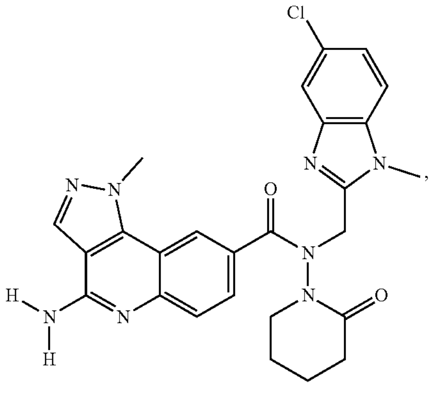
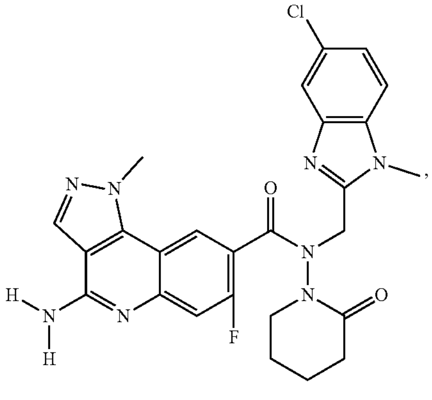
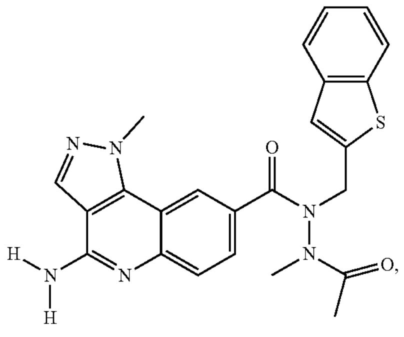
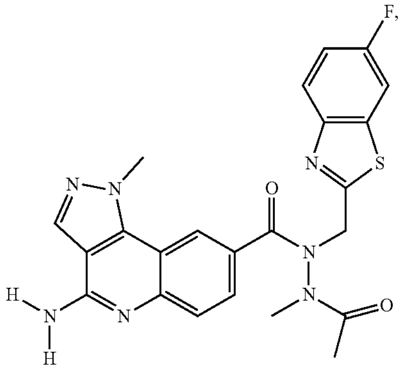
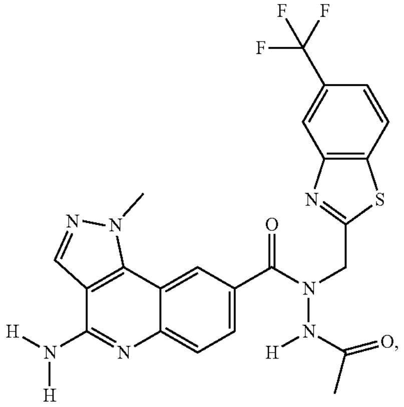
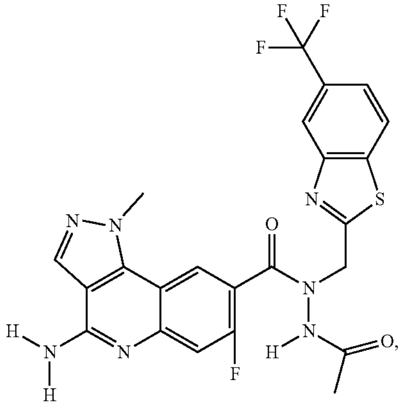
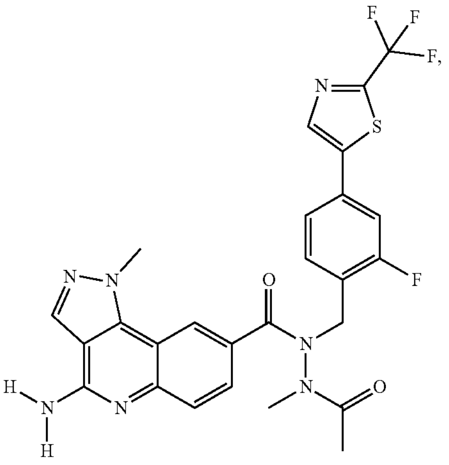

-continued
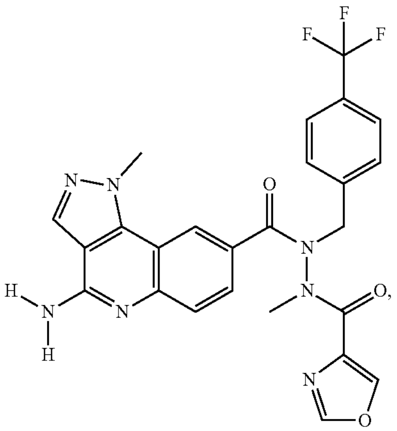
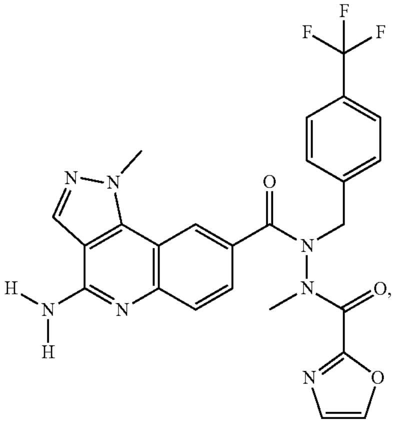
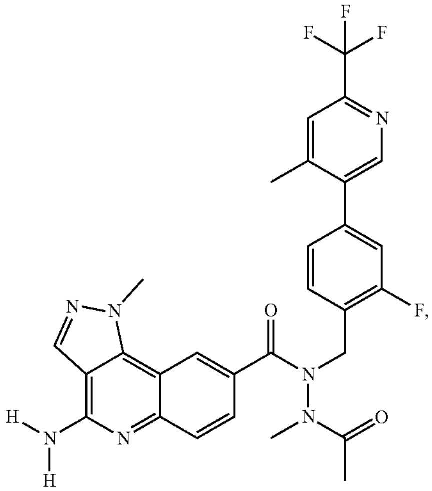
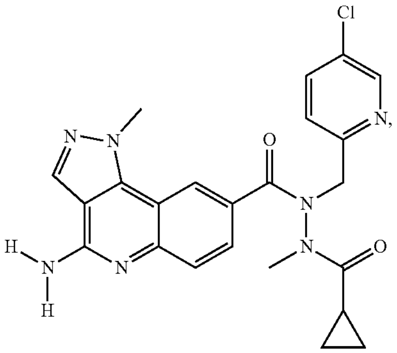
-continued
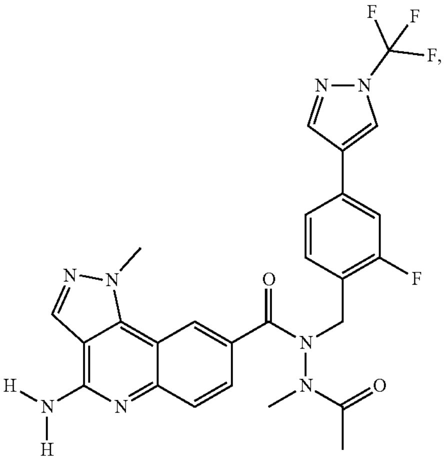
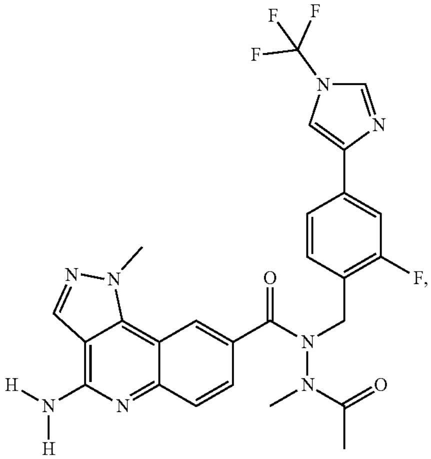
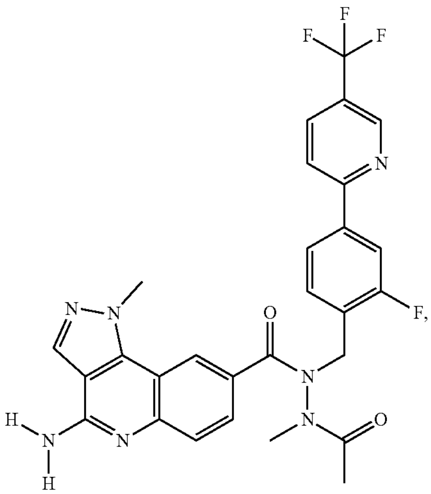

-continued
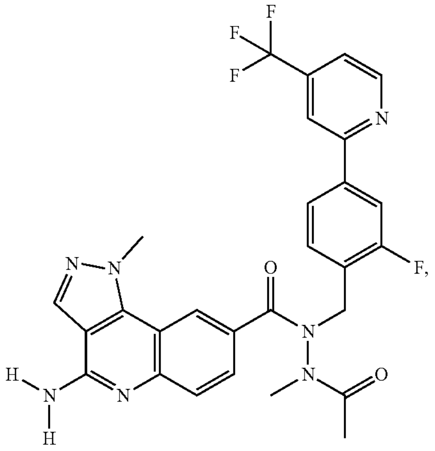
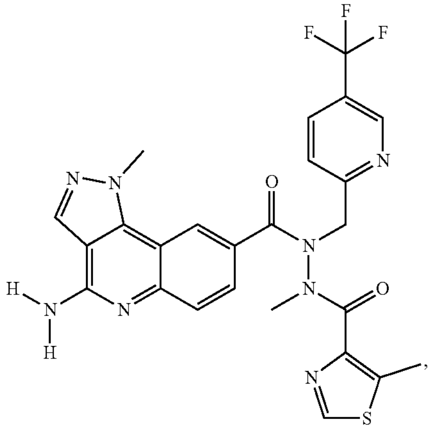
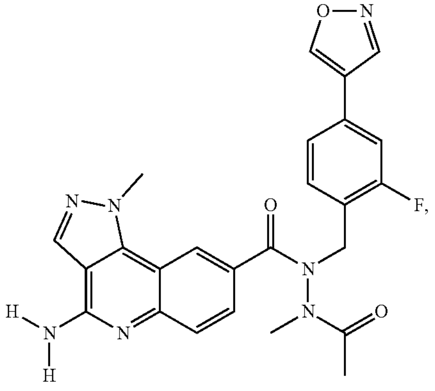
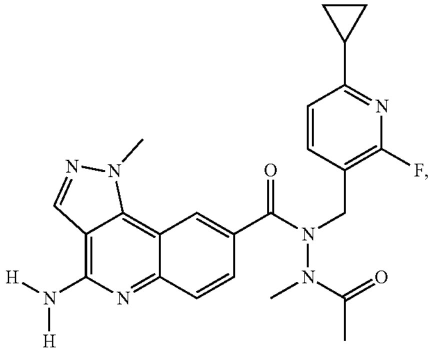
-continued
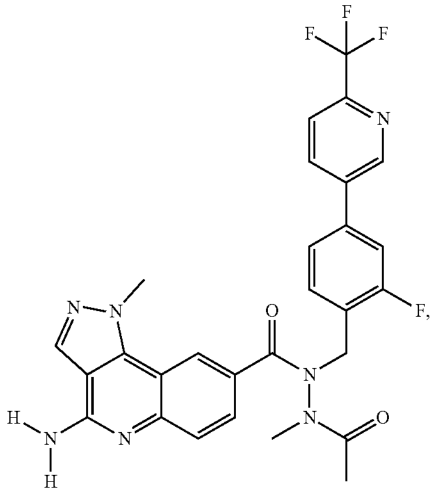
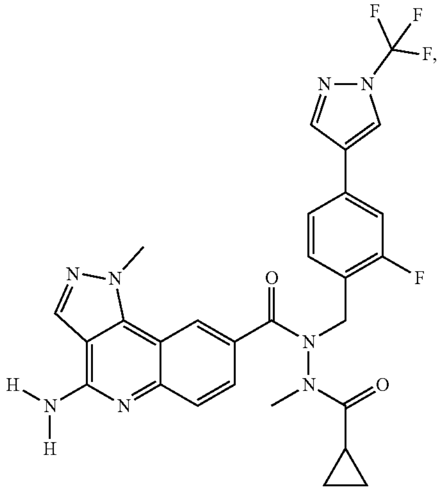
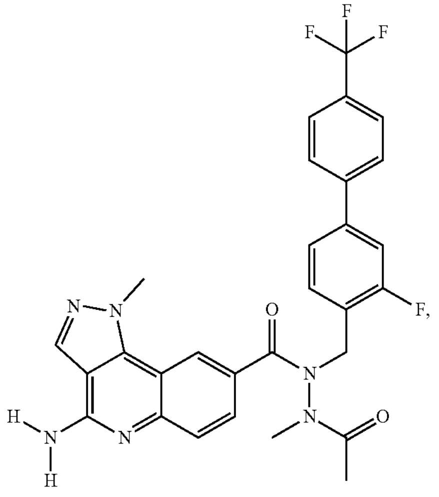

-continued
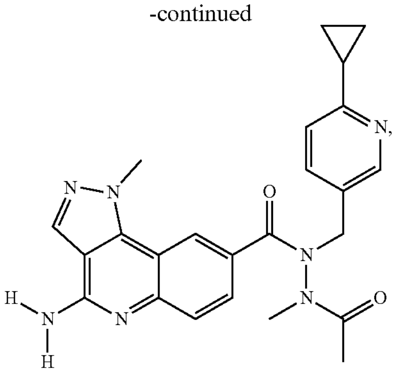
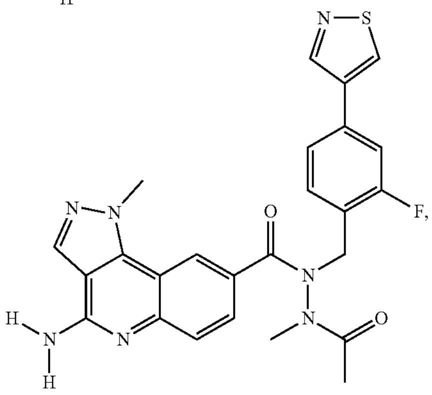
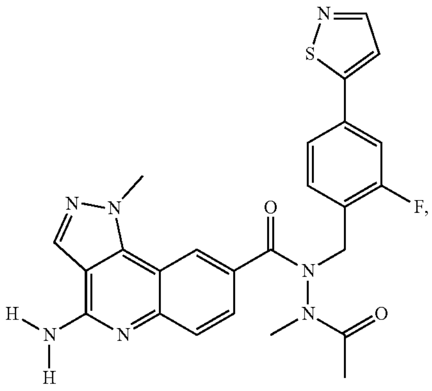
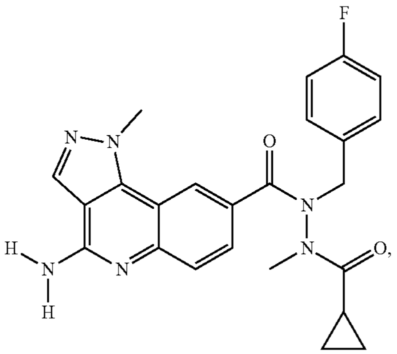
-continued
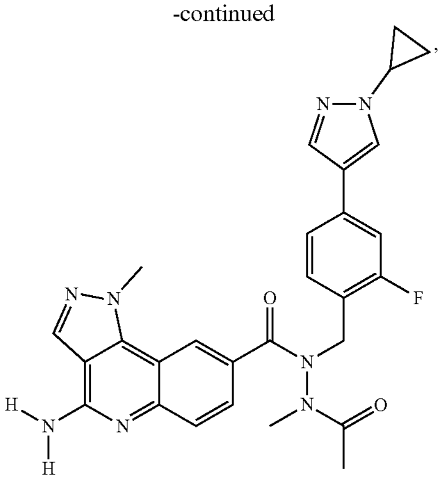
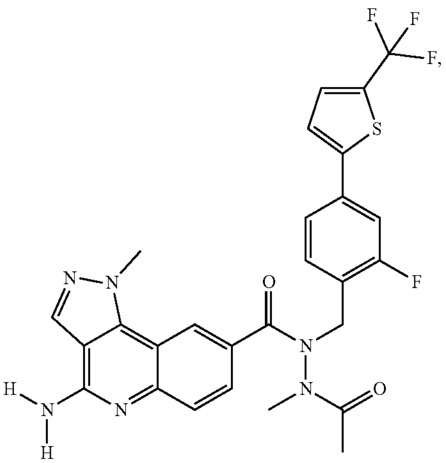
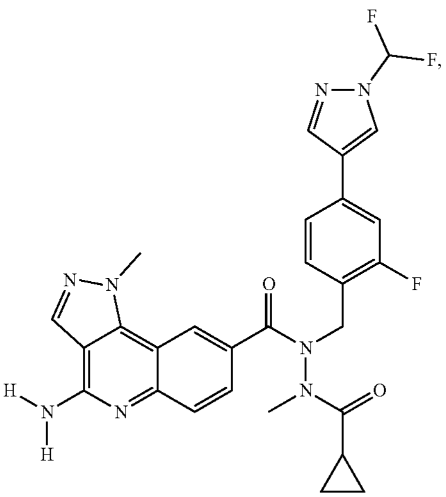

-continued
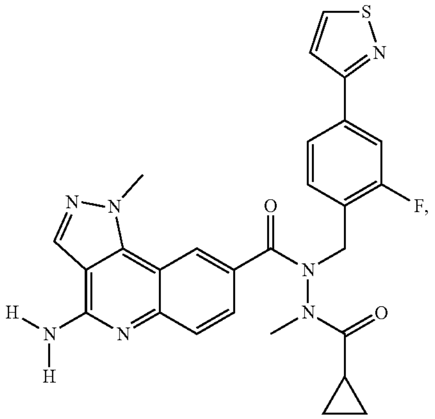
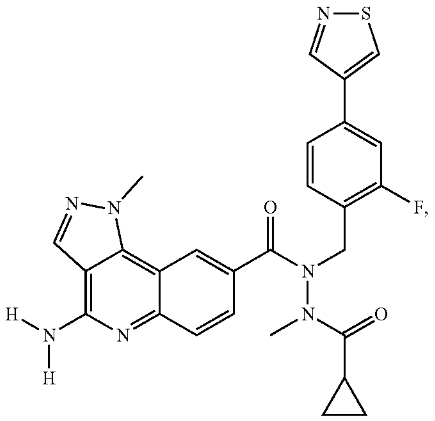
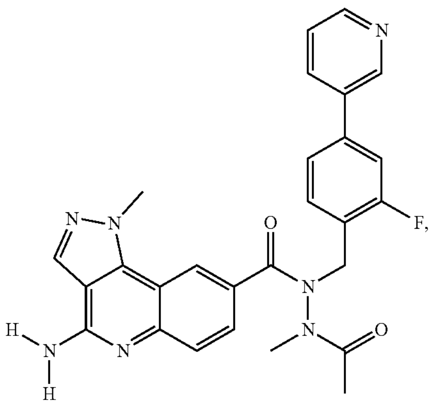
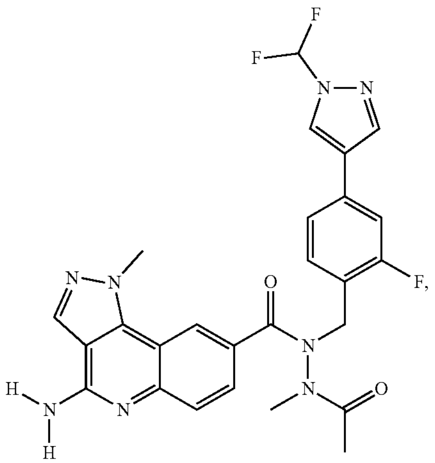
-continued
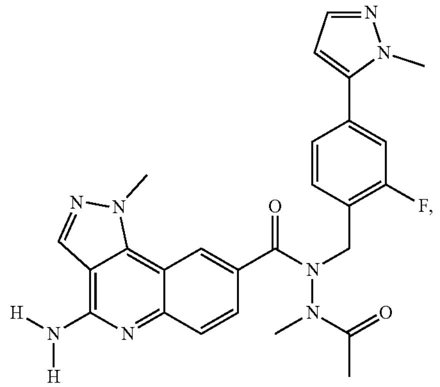
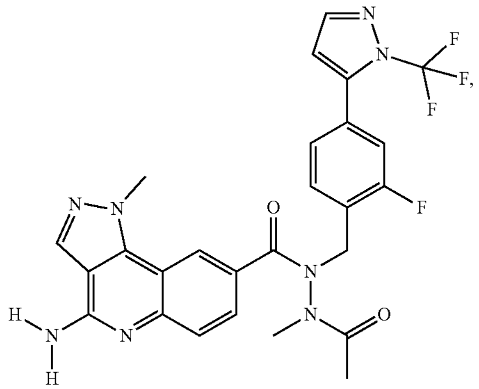
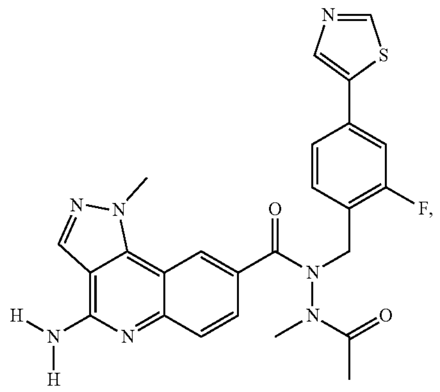
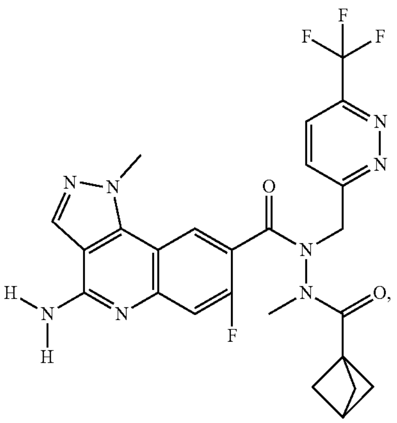

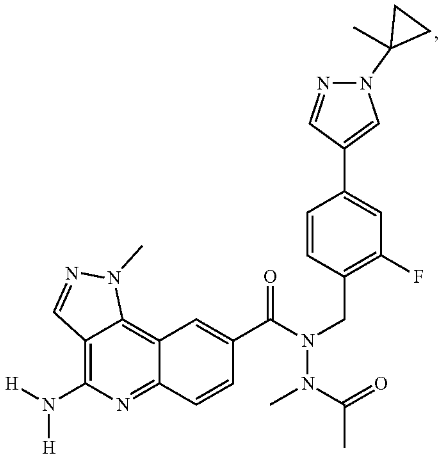
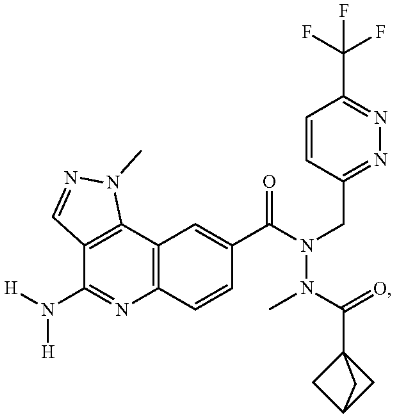
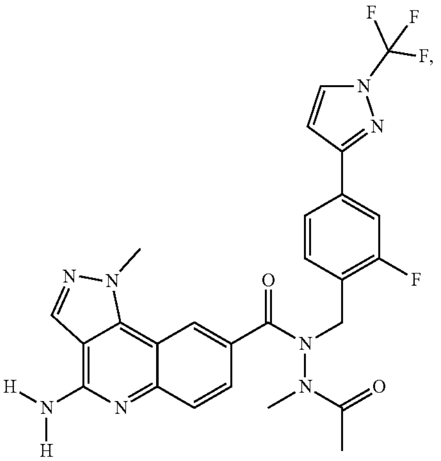
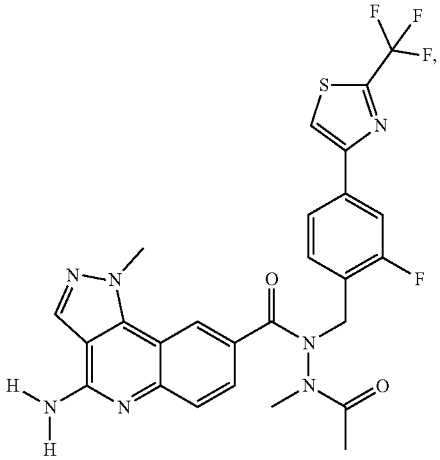
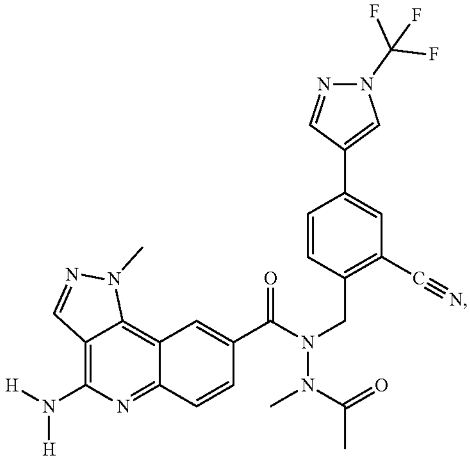
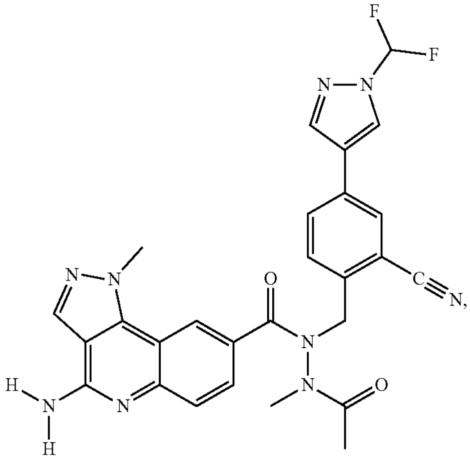

-continued
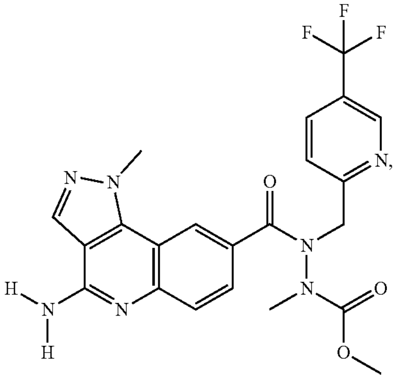
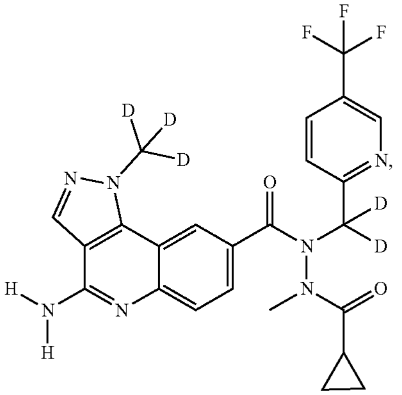
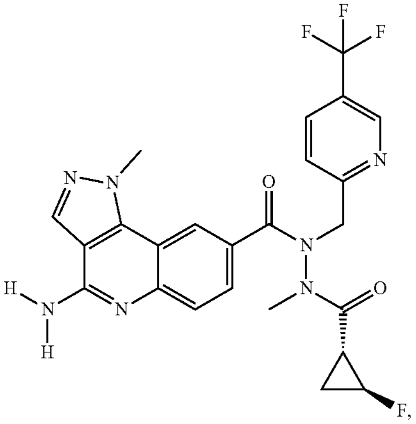
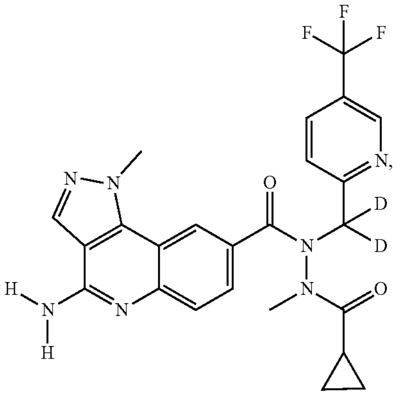
-continued
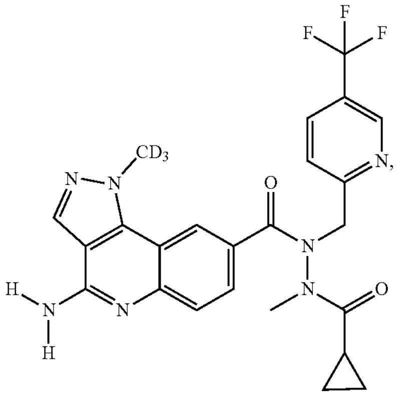
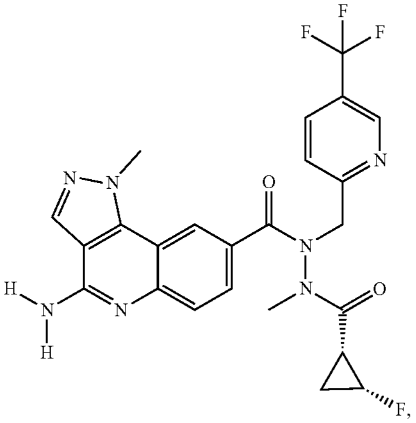
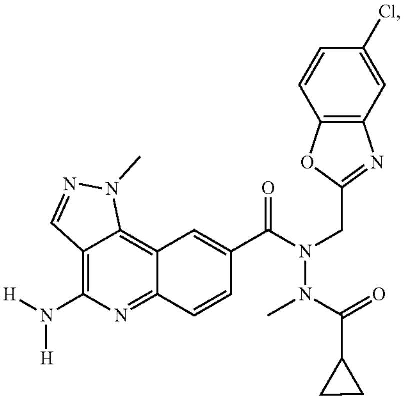
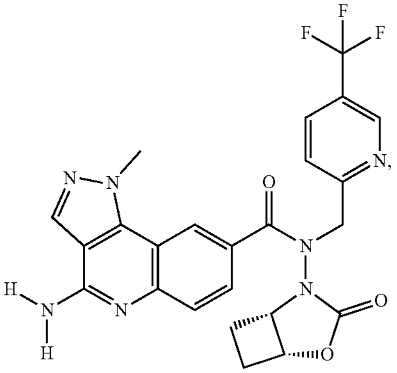

-continued
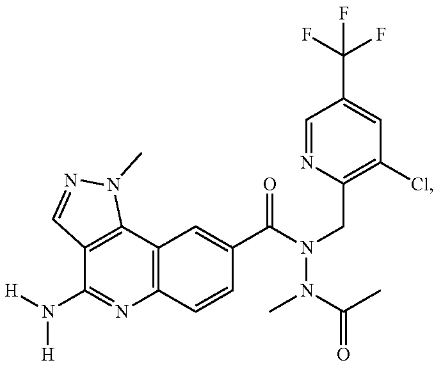
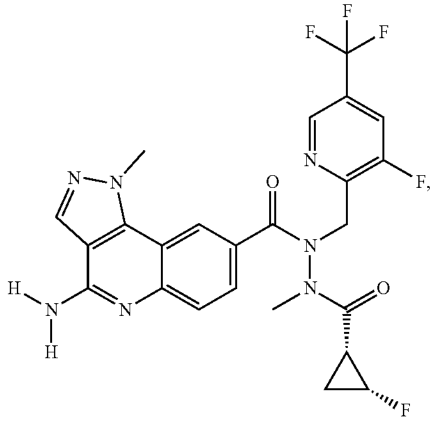
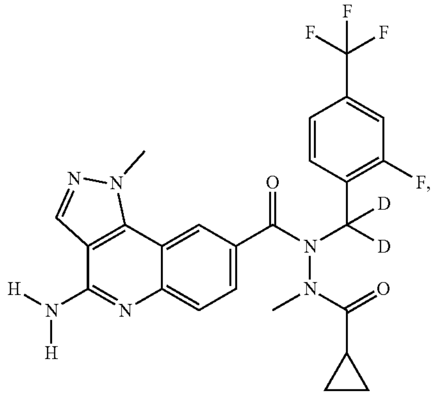
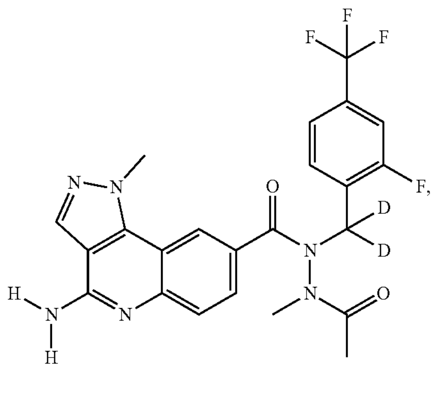
-continued
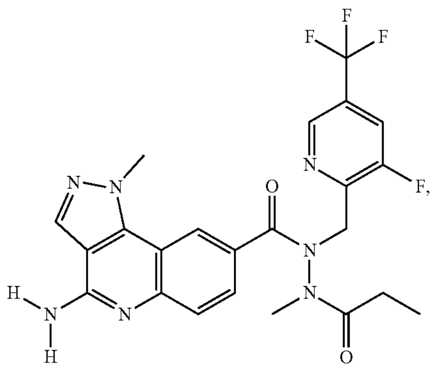
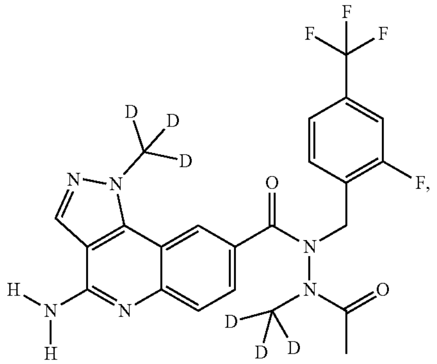
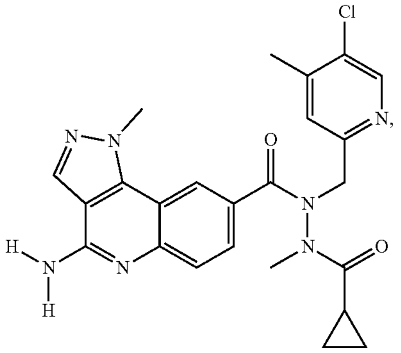
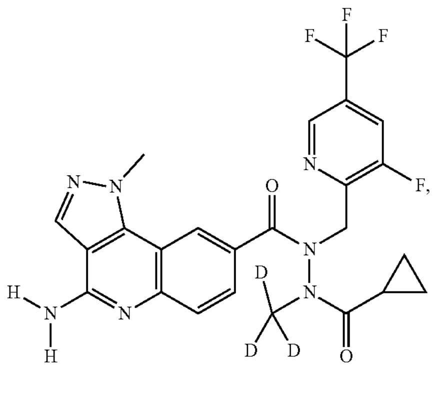

-continued
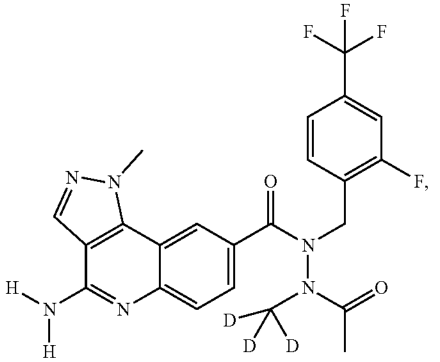
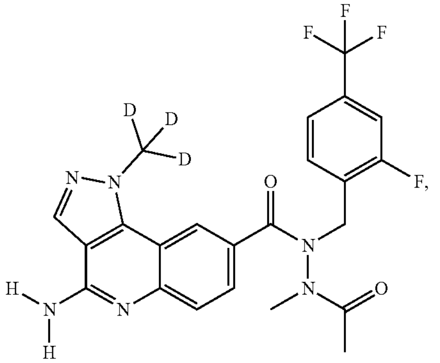
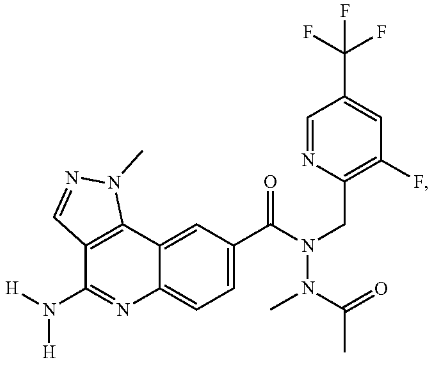
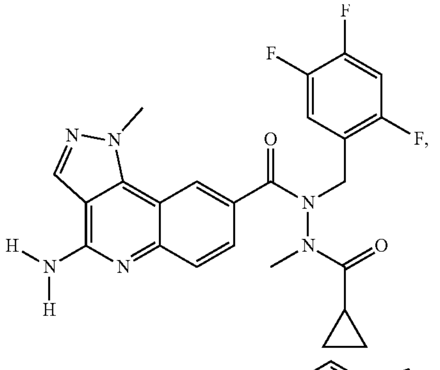
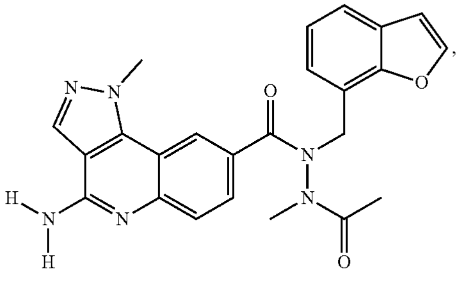
-continued
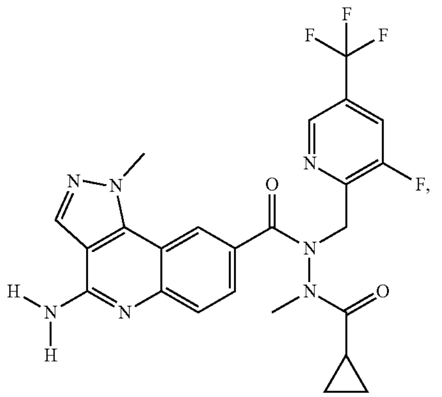
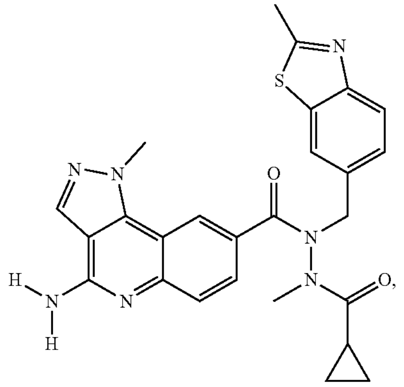
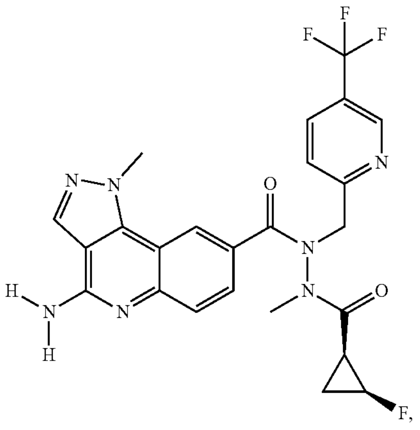
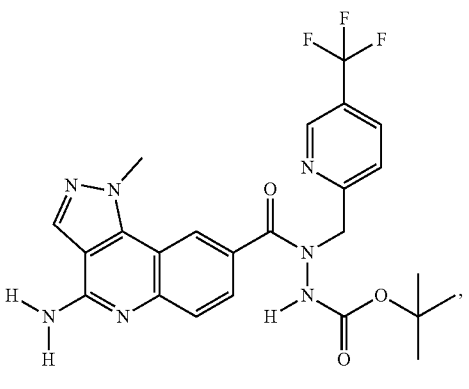

-continued
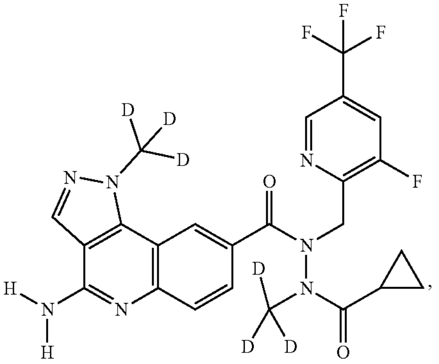
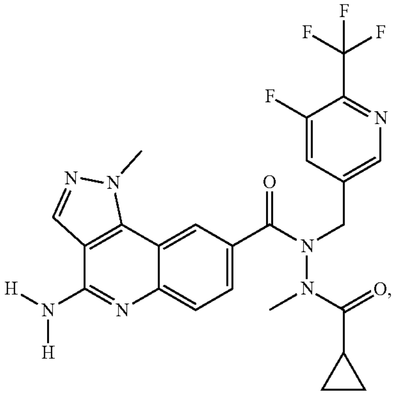
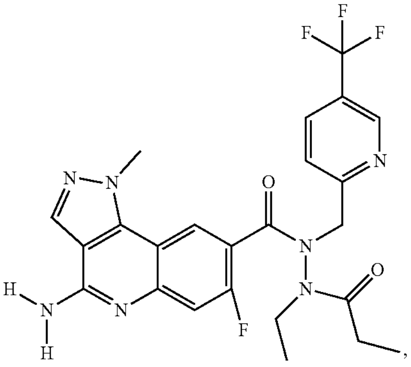
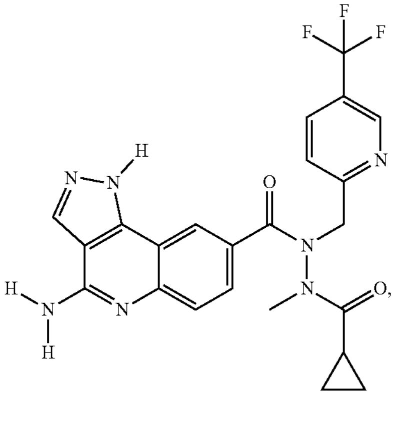
-continued
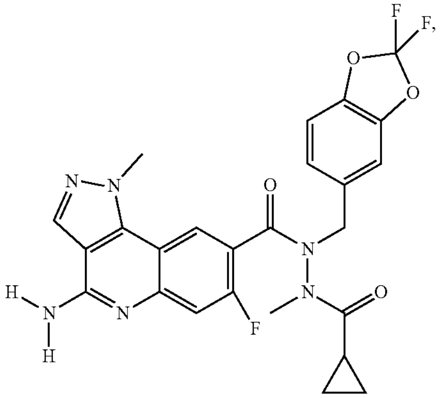
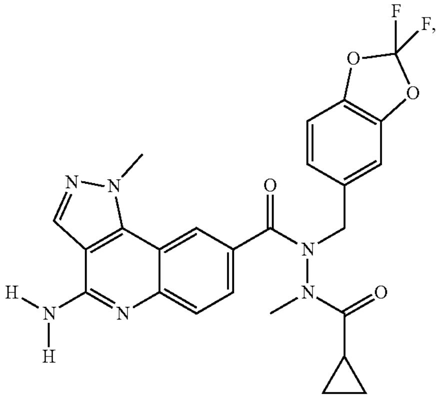
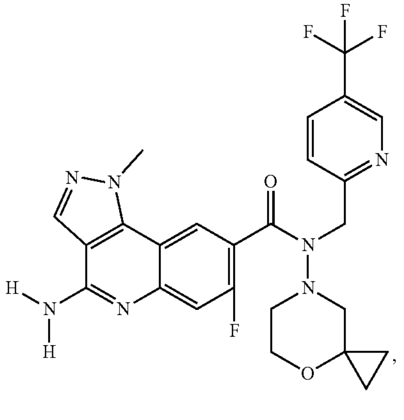
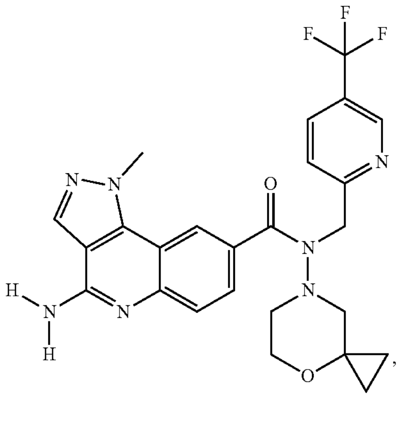

-continued
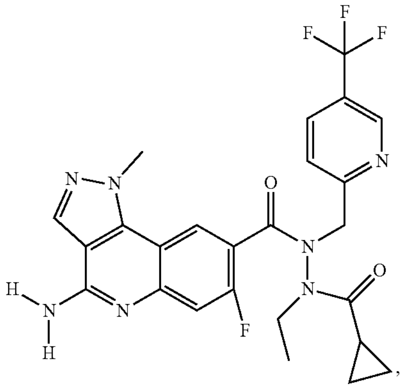
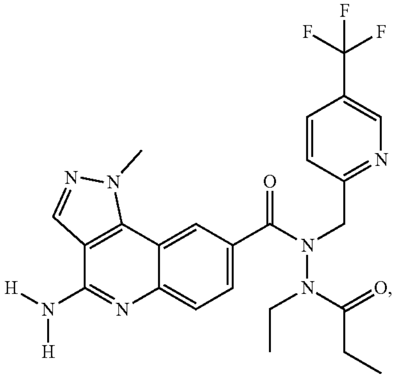
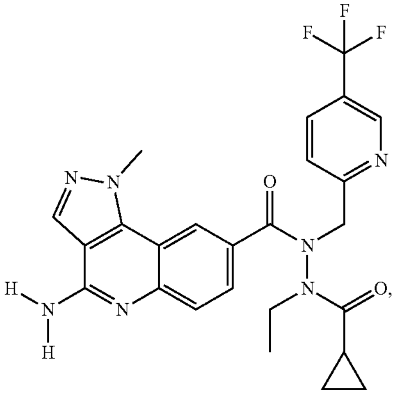
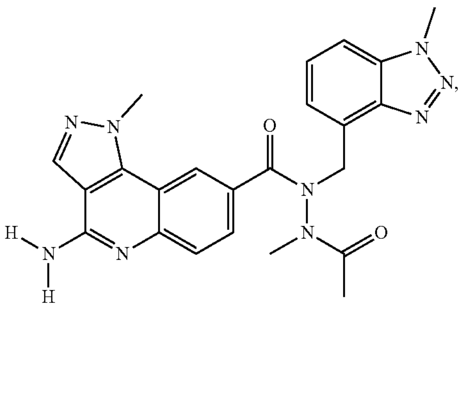
-continued
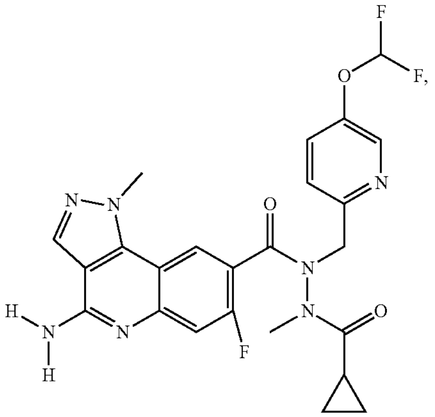
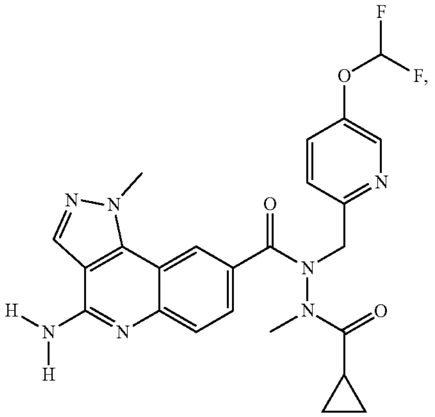
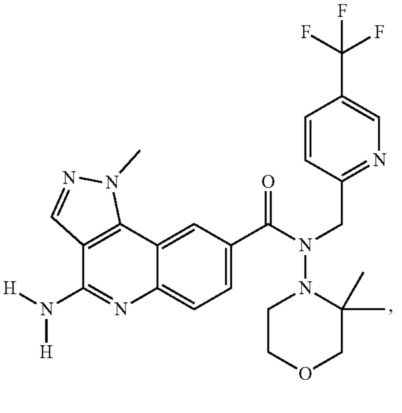
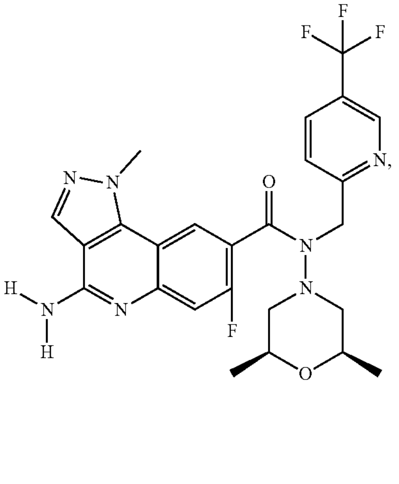

-continued
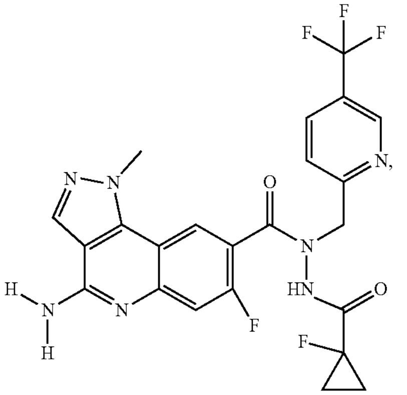
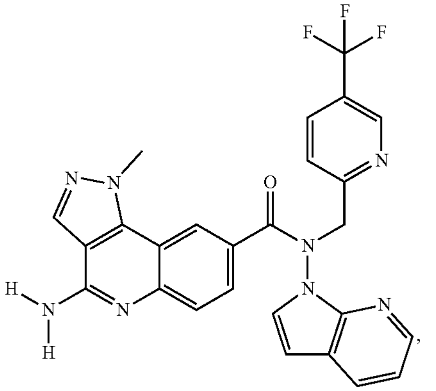
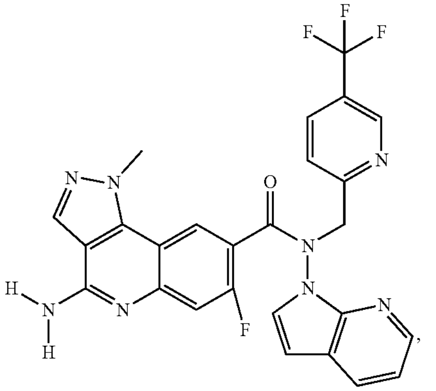
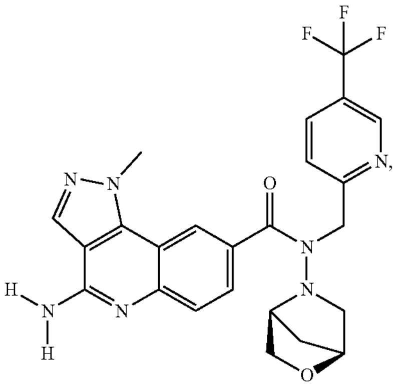
-continued
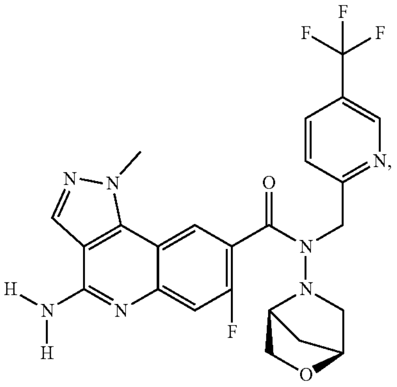
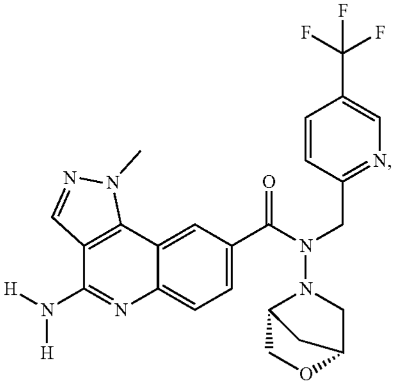
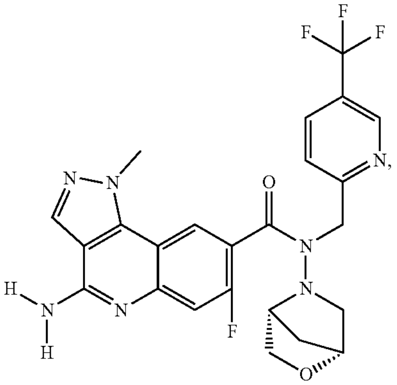
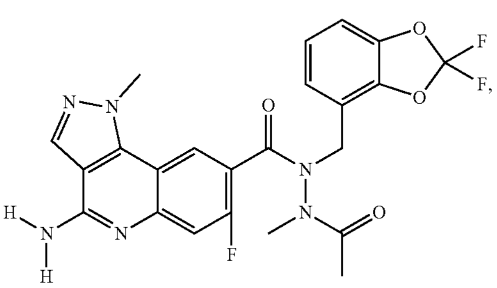

-continued
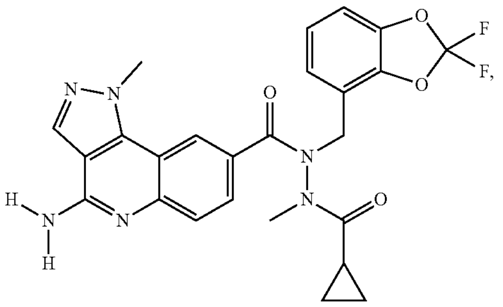
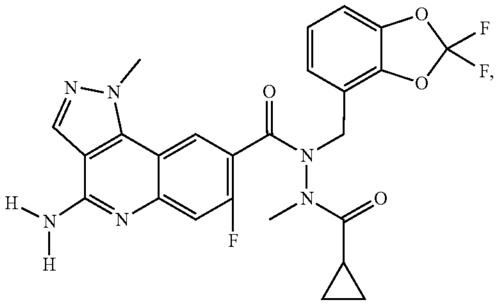
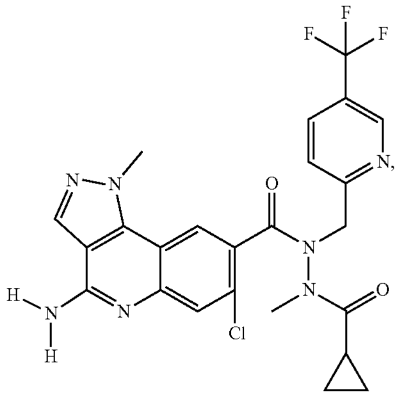
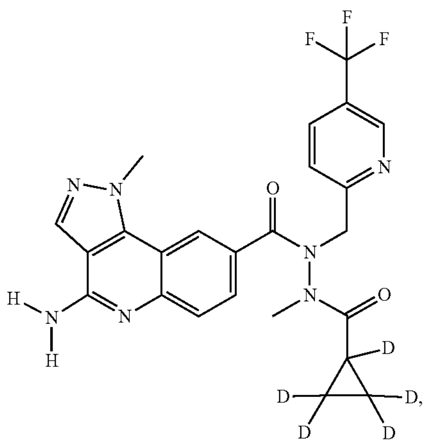
-continued
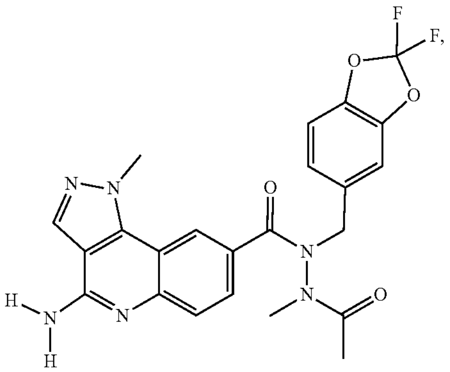
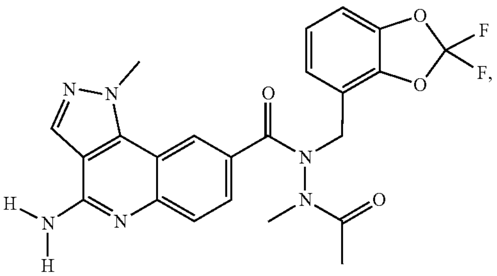
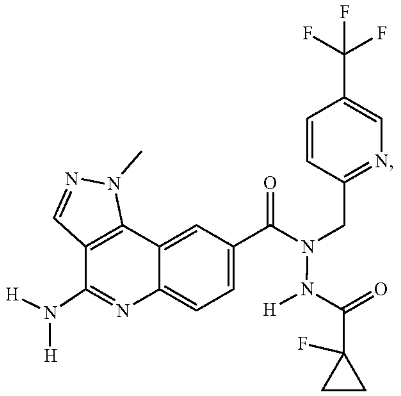
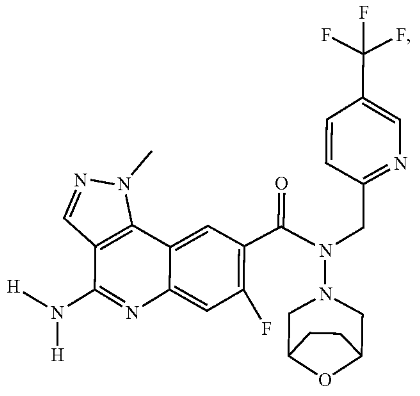

-continued
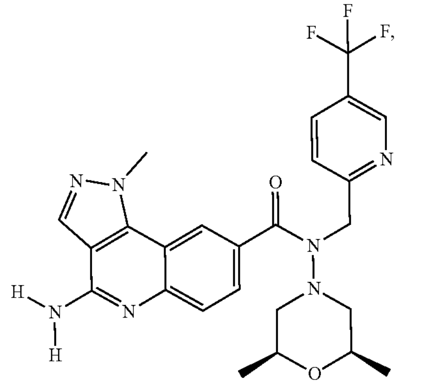
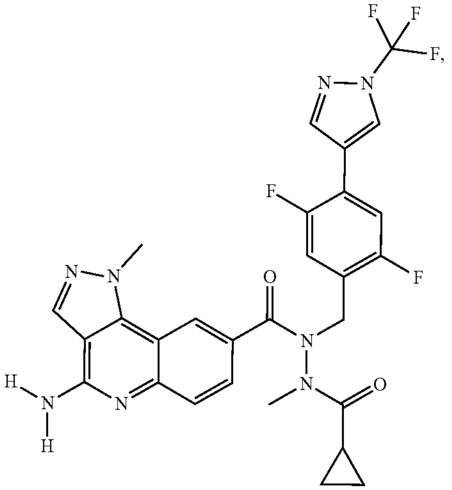
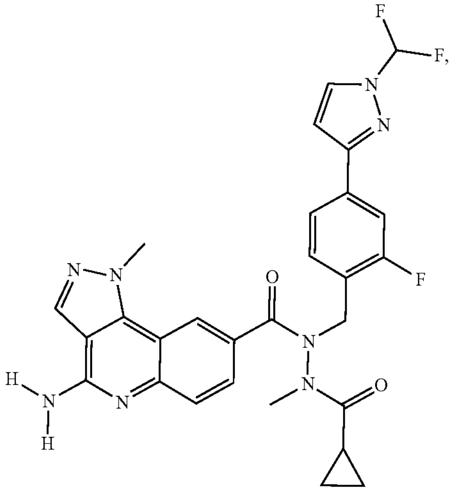
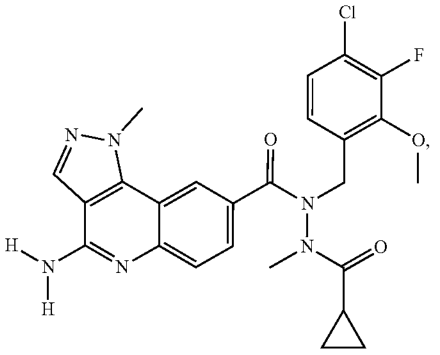
-continued
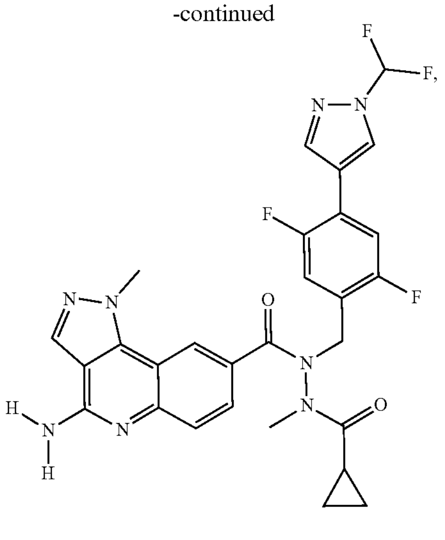
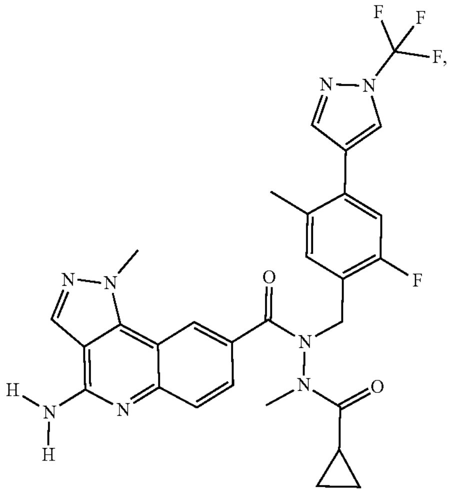
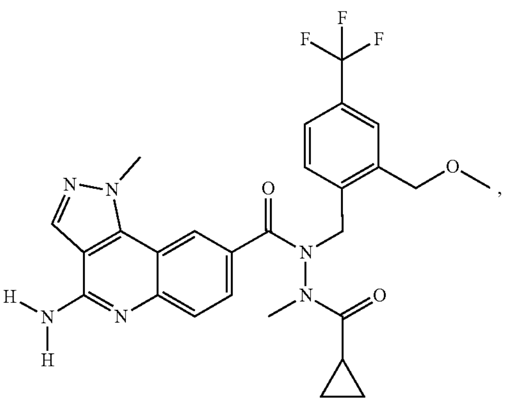

-continued
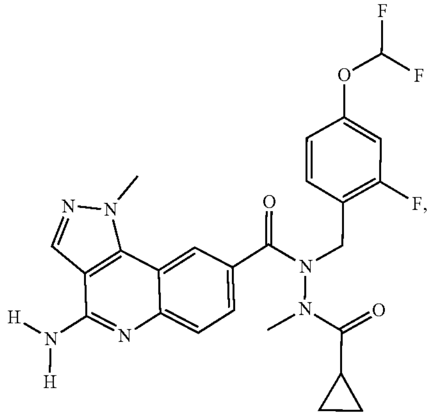
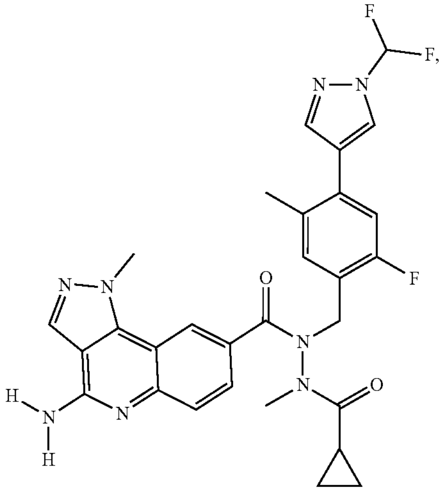
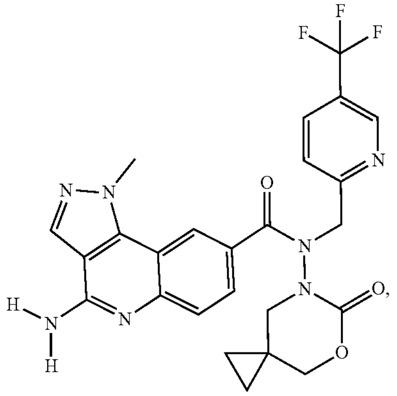
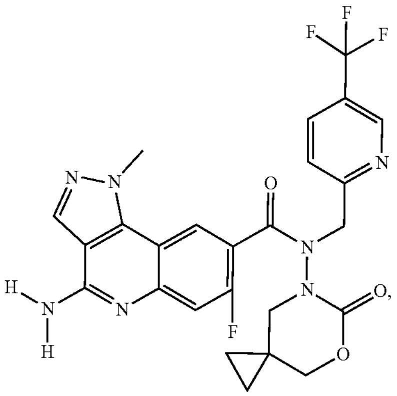
-continued
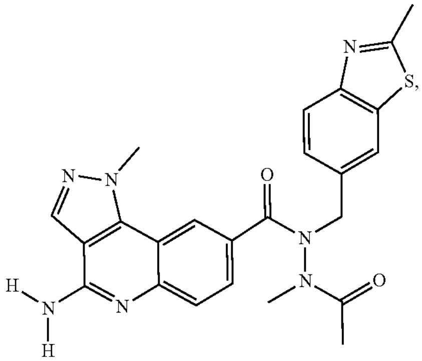
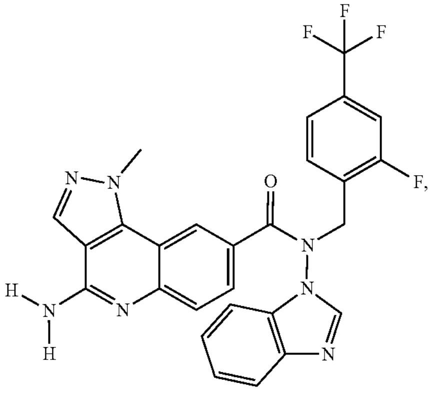
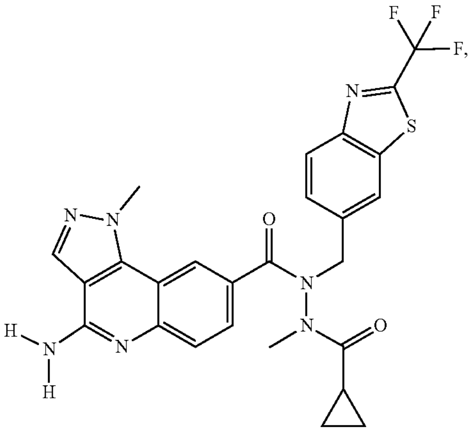
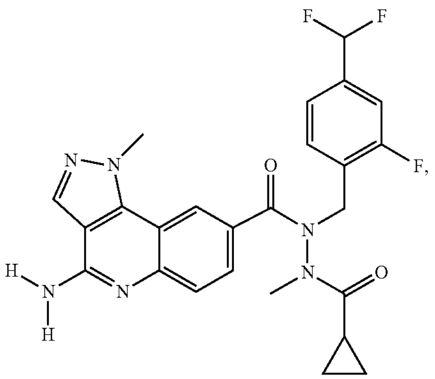

-continued
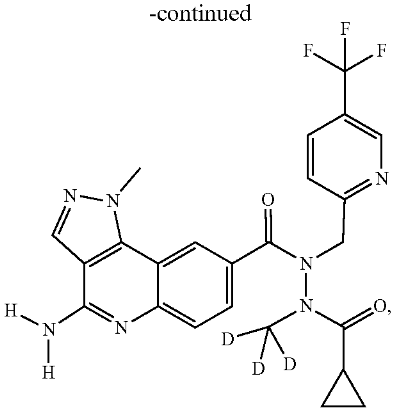
,
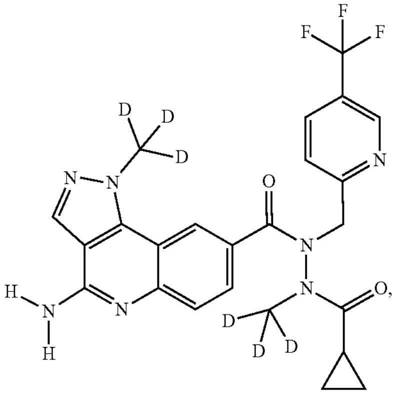
,
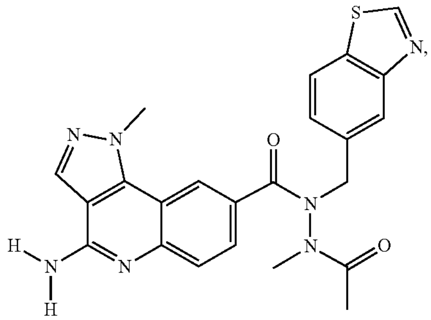
,
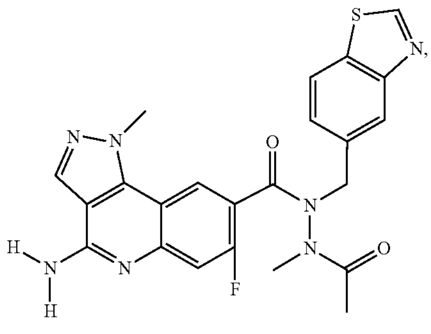
,
-continued
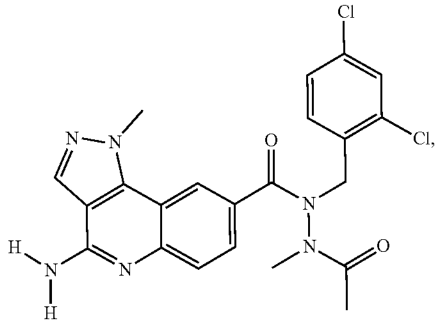
,
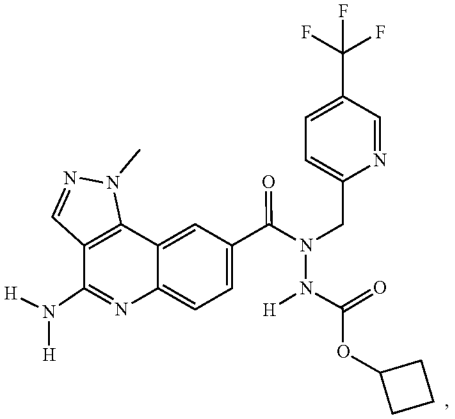
,
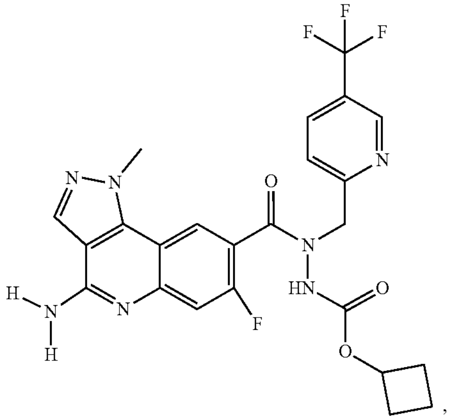
,
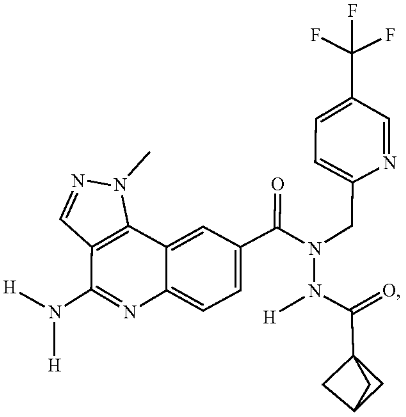
, -continued
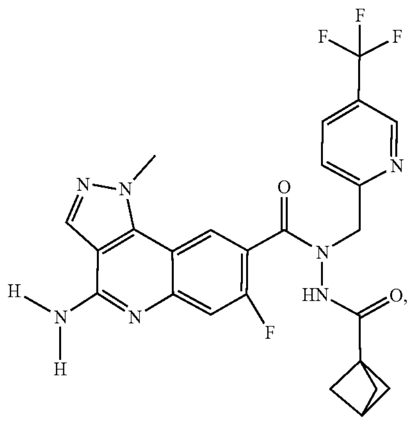
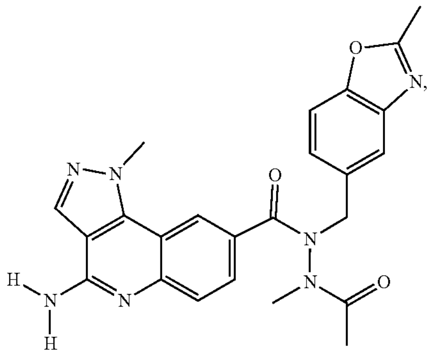
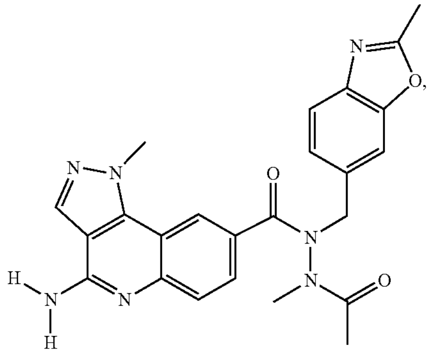
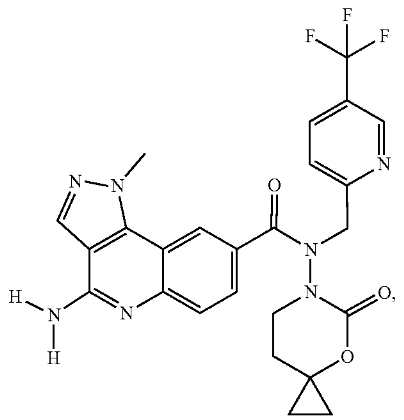
-continued
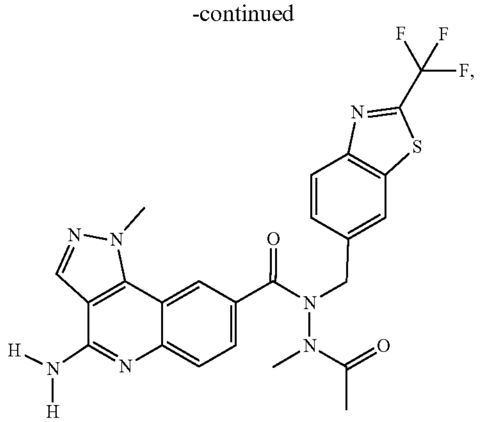
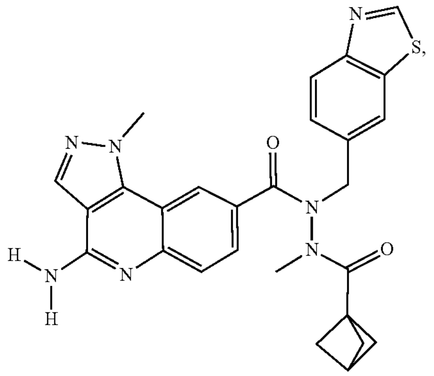
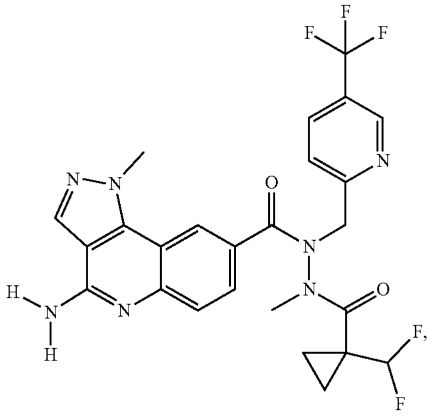
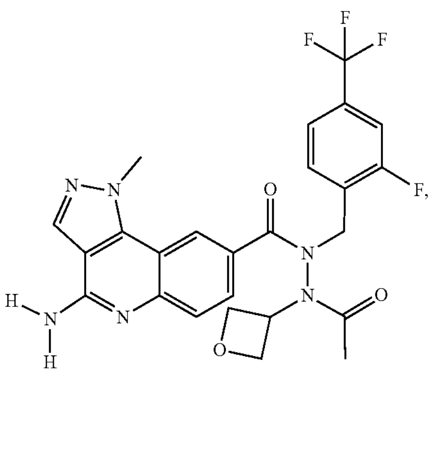

-continued
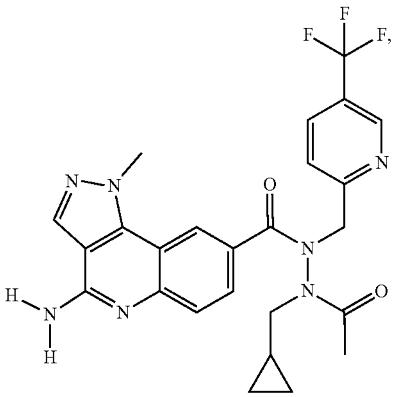
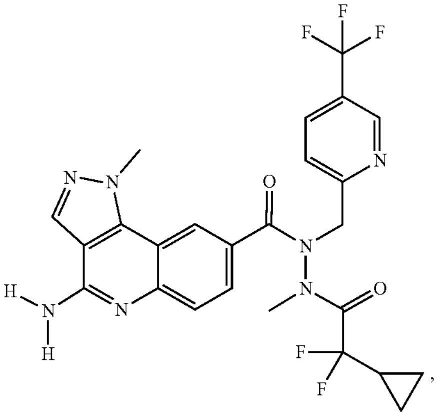
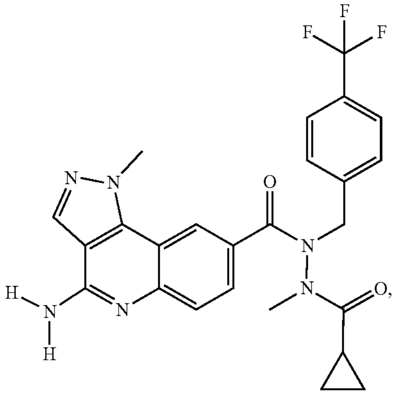
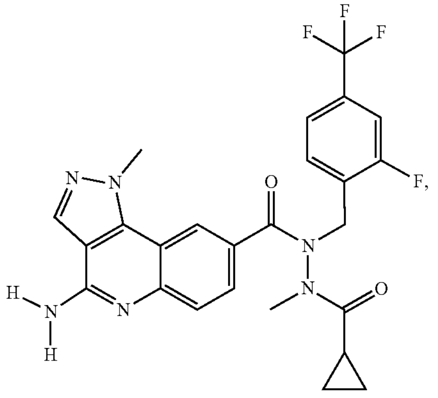
-continued
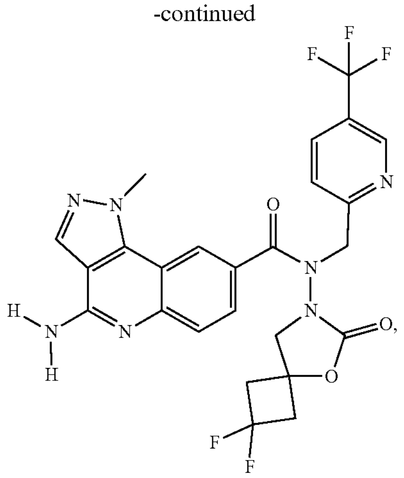
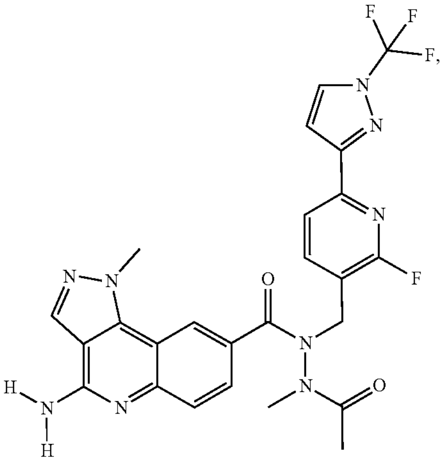
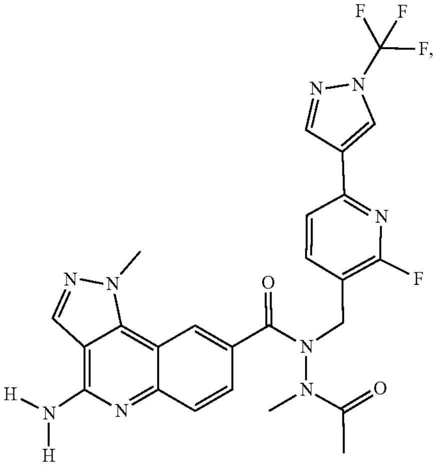

-continued
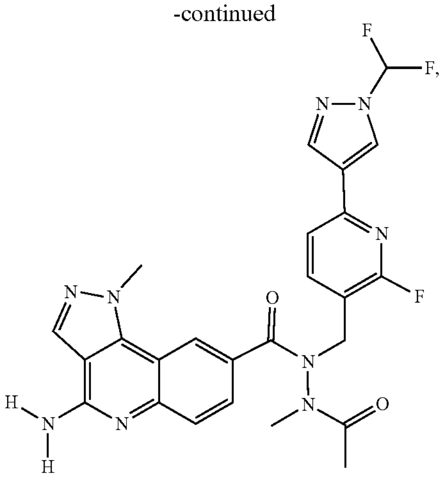
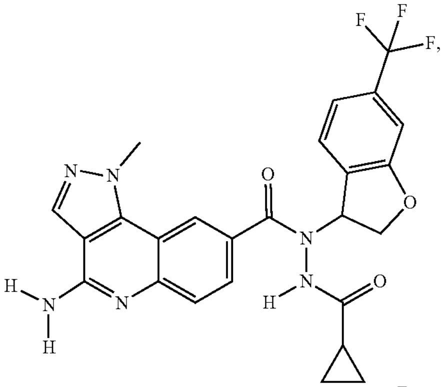
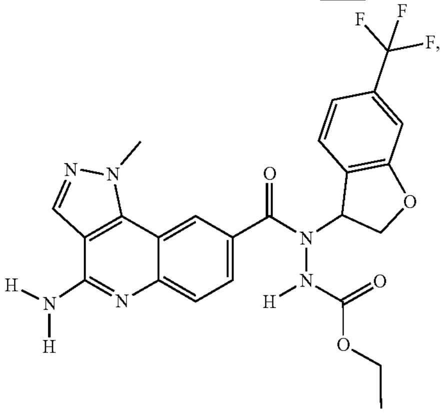
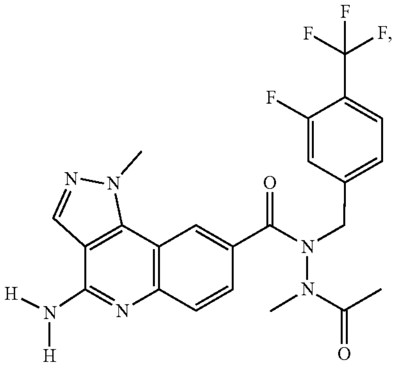
-continued
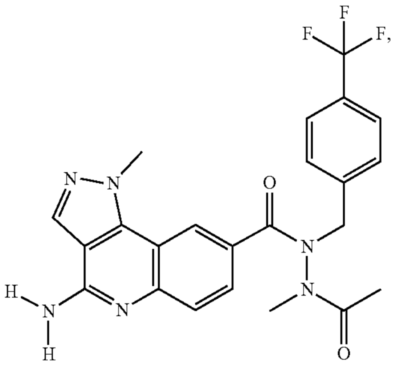
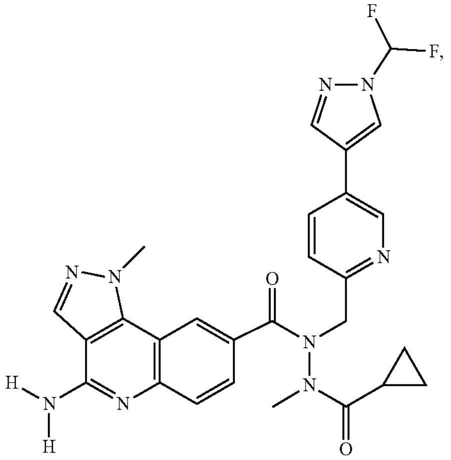
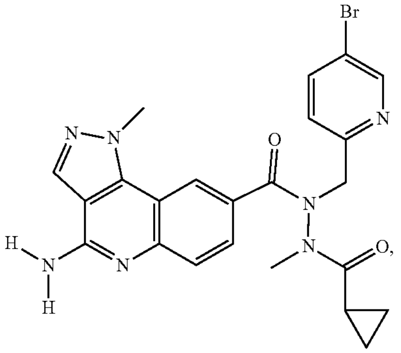
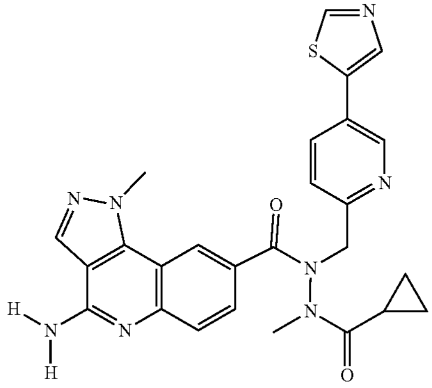
, -continued
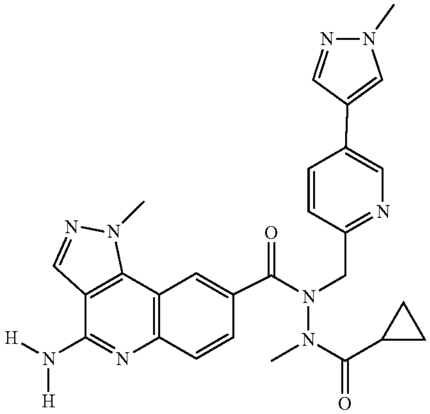
,
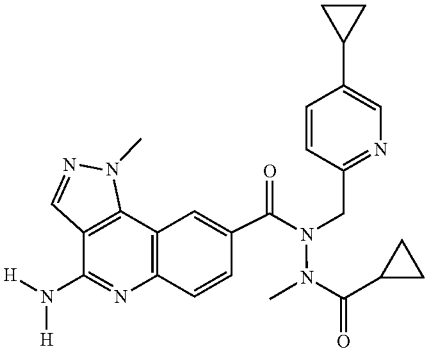
,
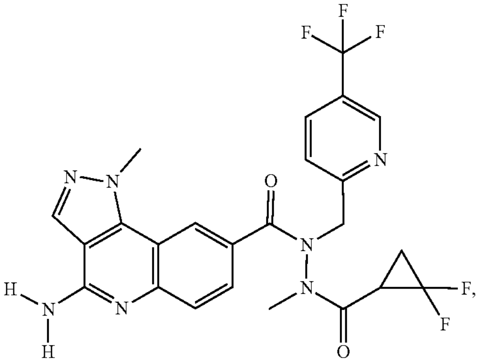
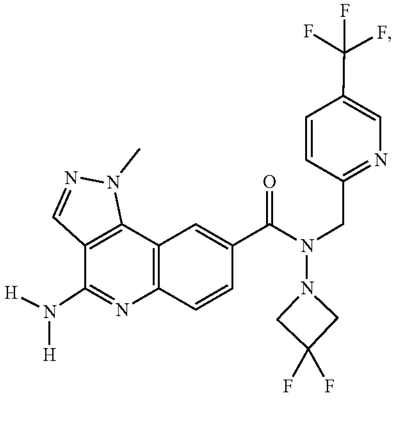
-continued
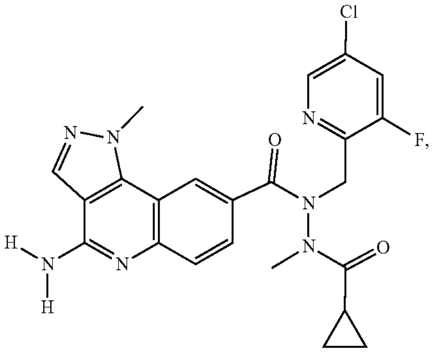
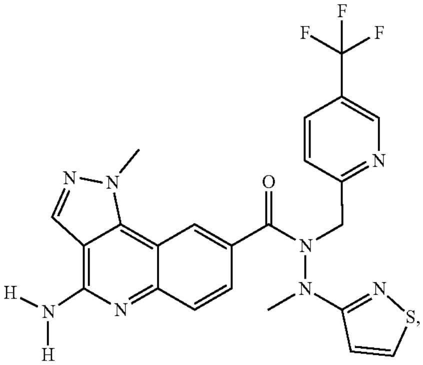
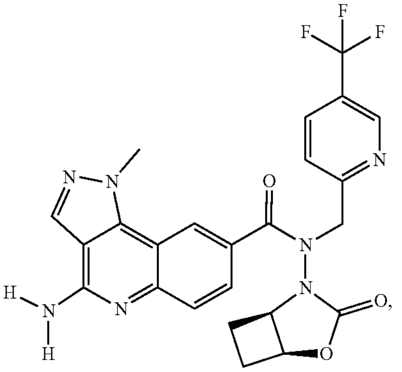
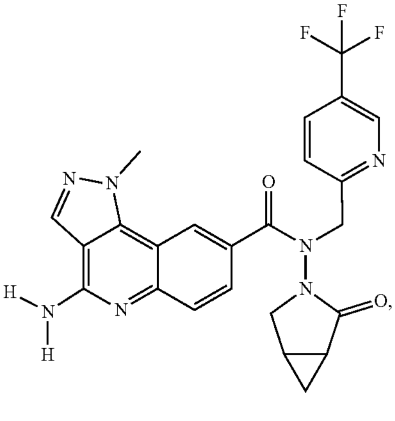

-continued
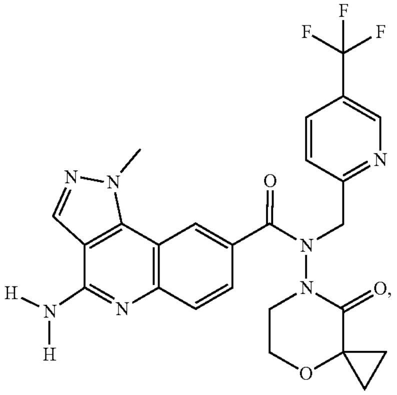
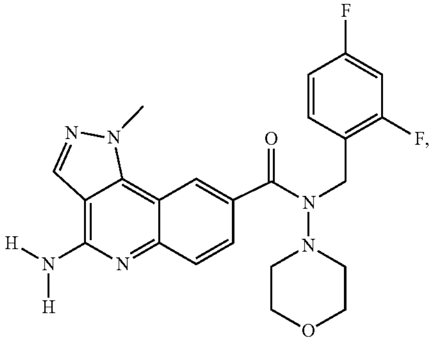
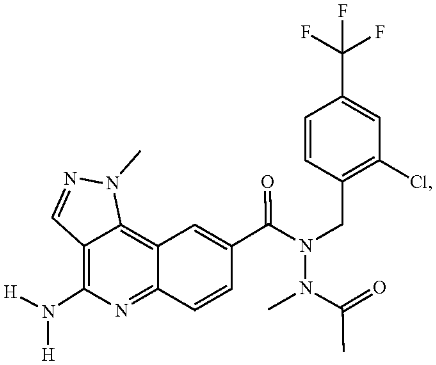
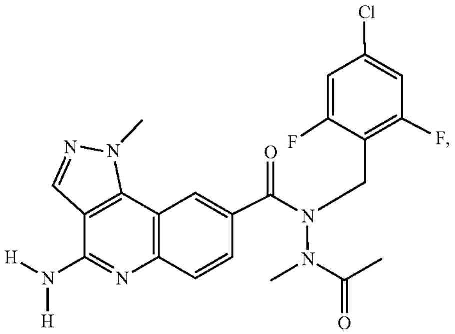
-continued
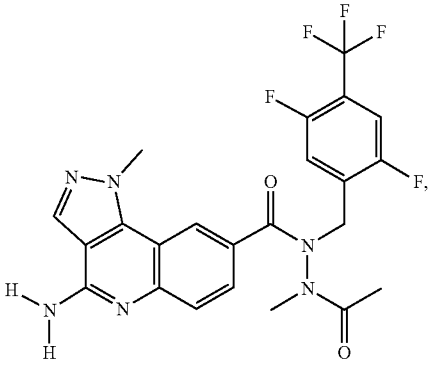
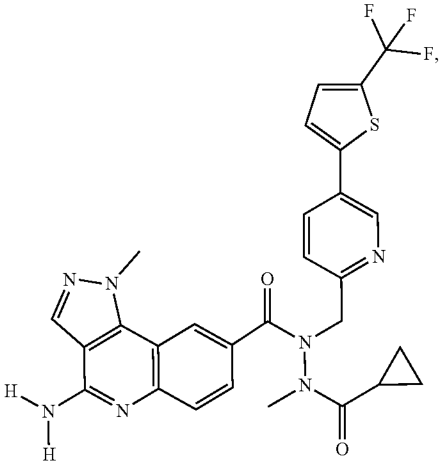
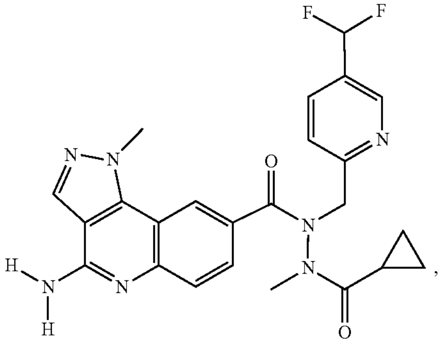
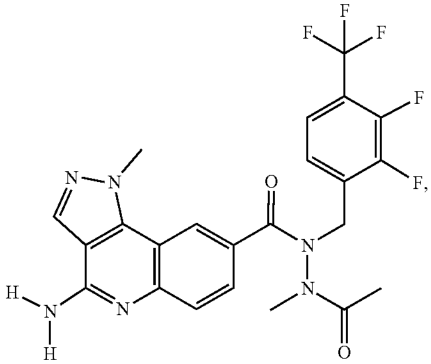

-continued
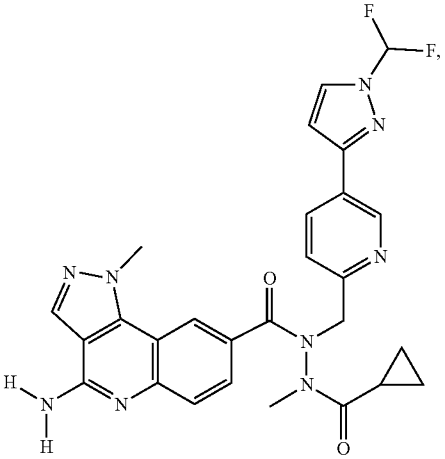
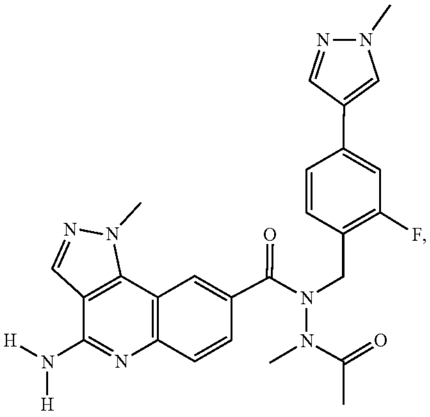
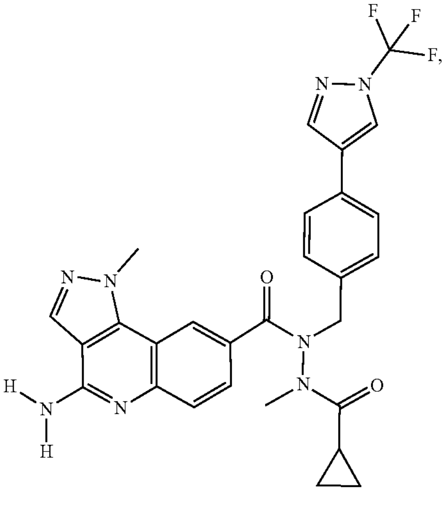
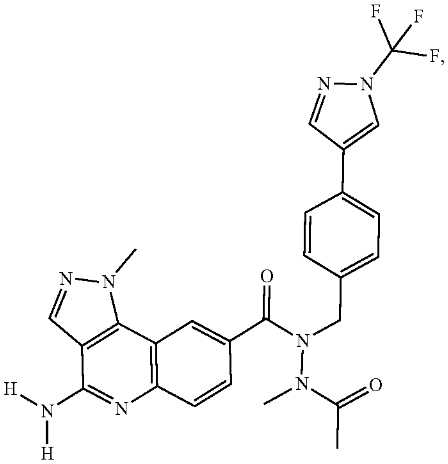
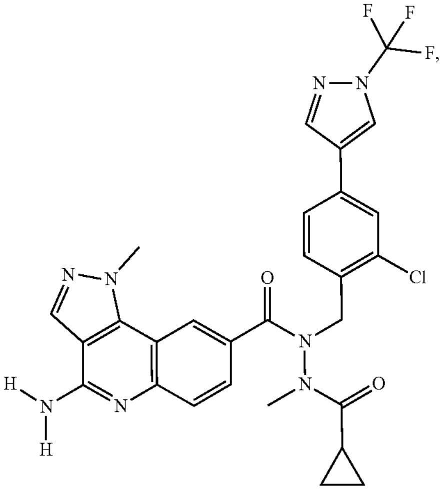
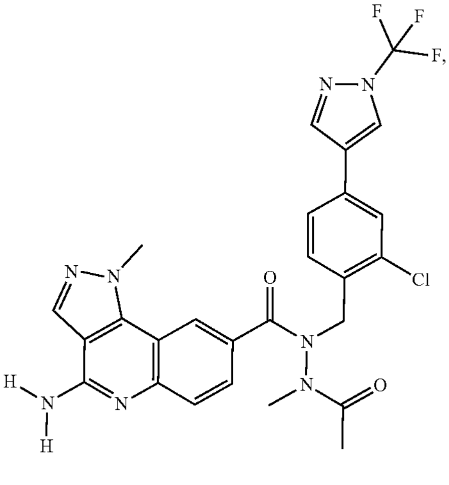

-continued
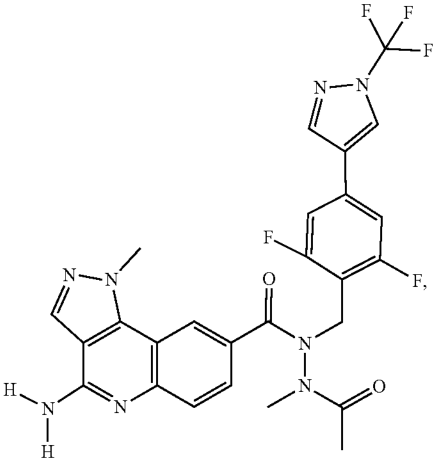
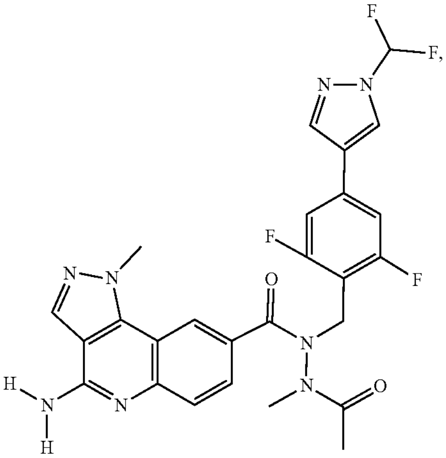
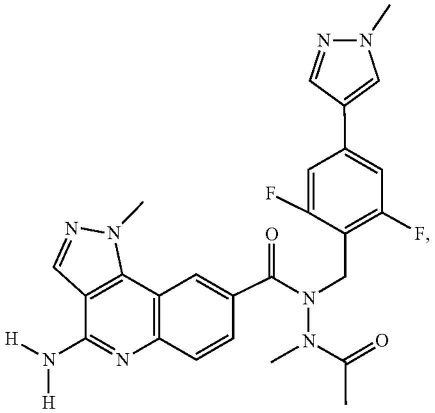
-continued
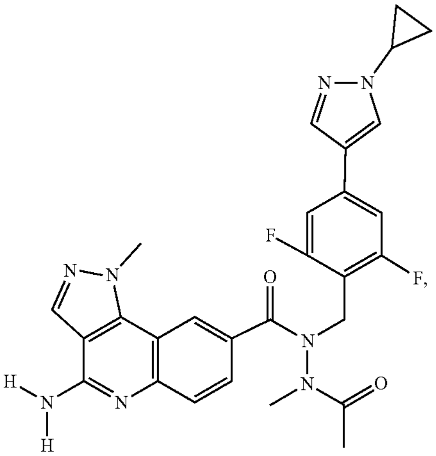
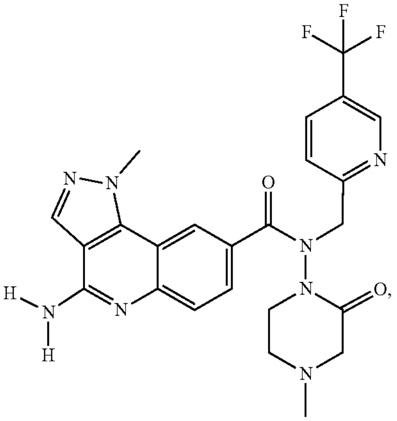
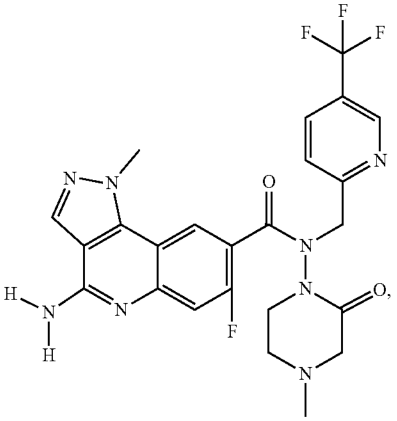

-continued
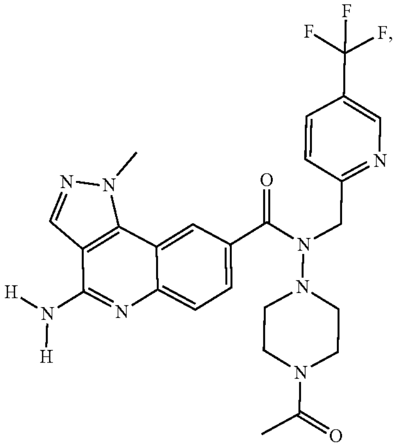
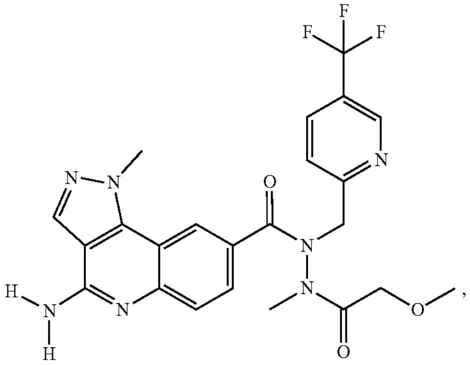
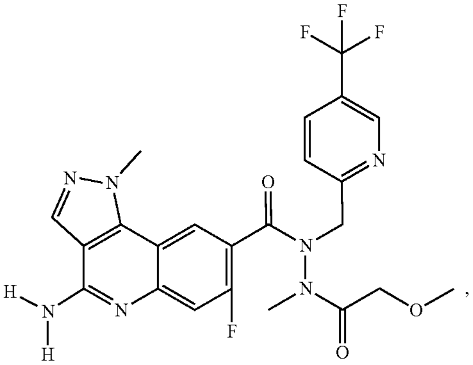
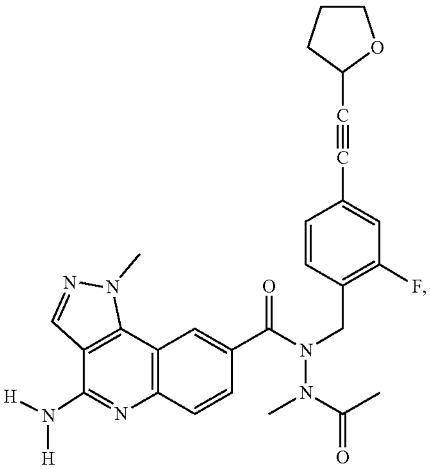
-continued
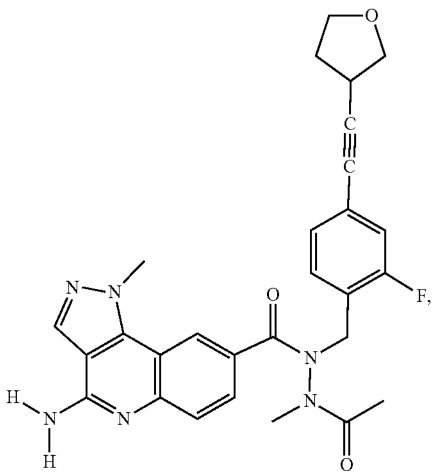
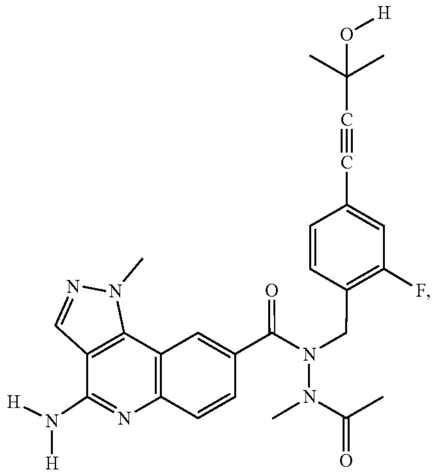
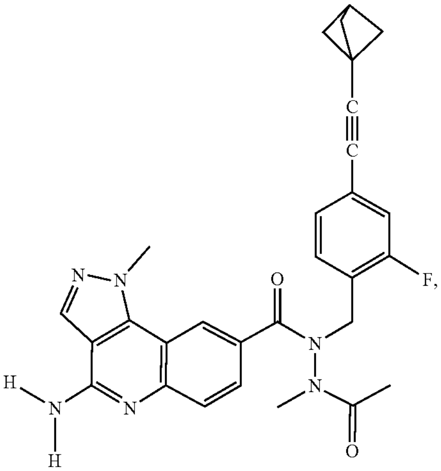

-continued
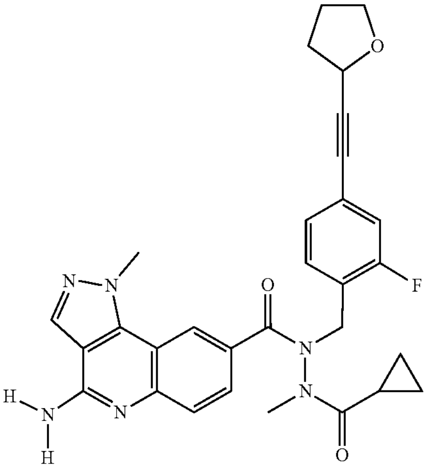
,
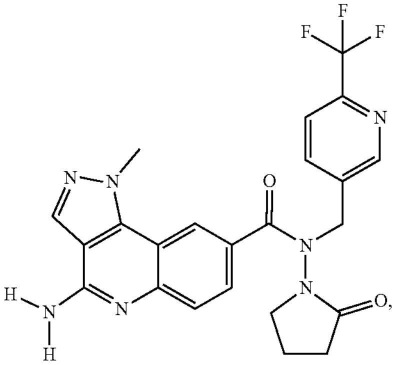
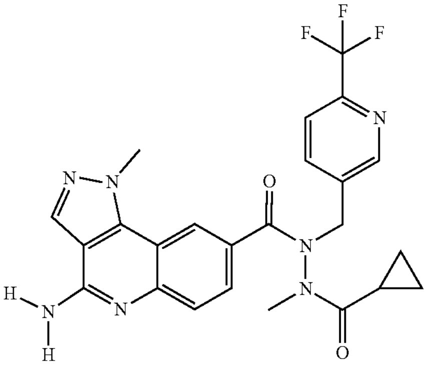
,
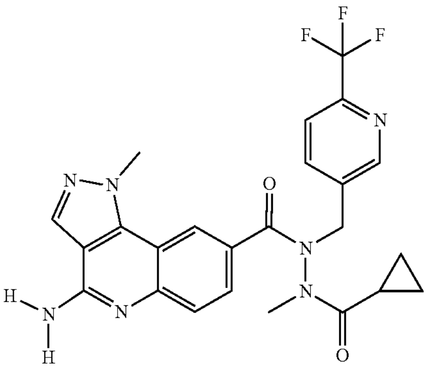
,
-continued
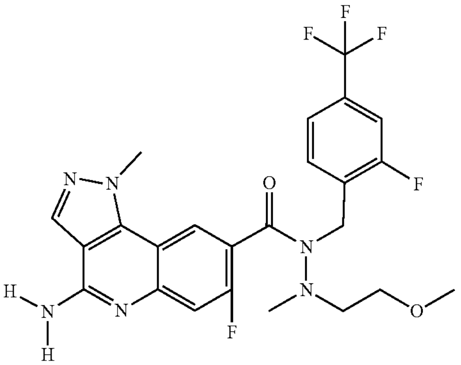
,
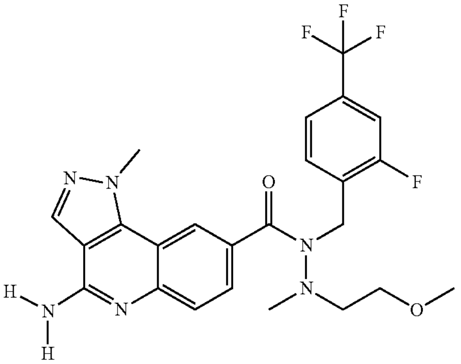
,
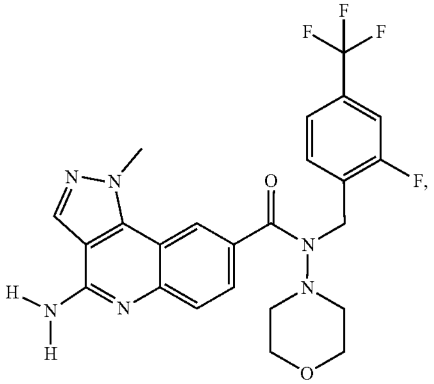
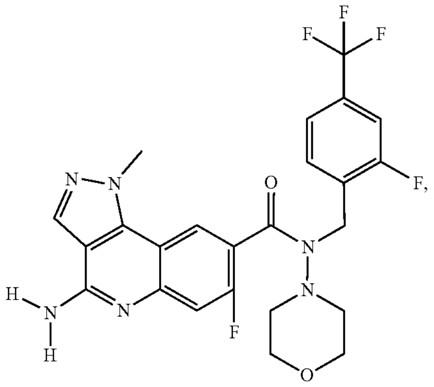

-continued
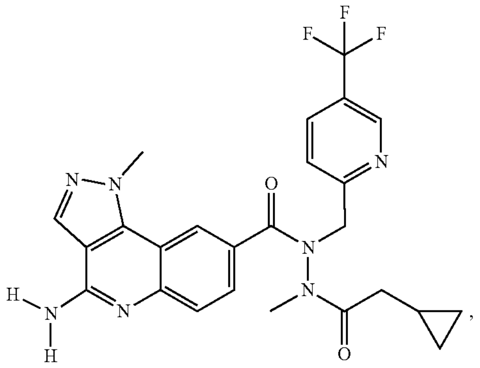
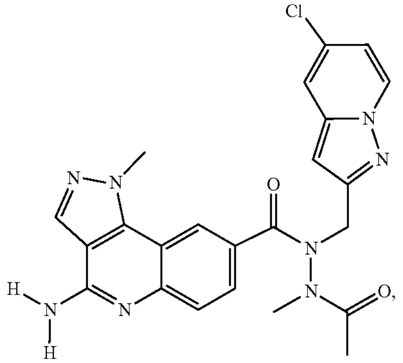
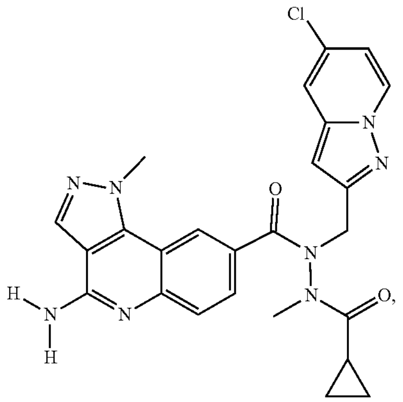
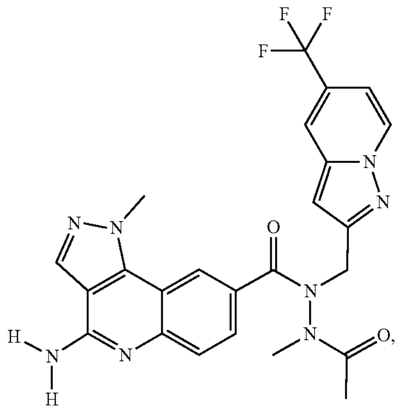
-continued
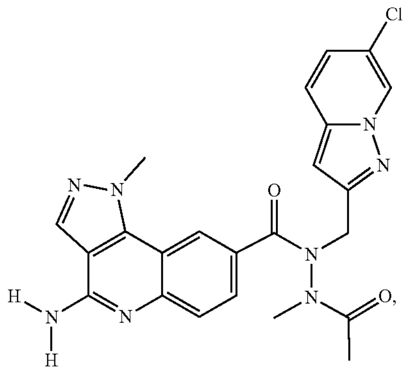
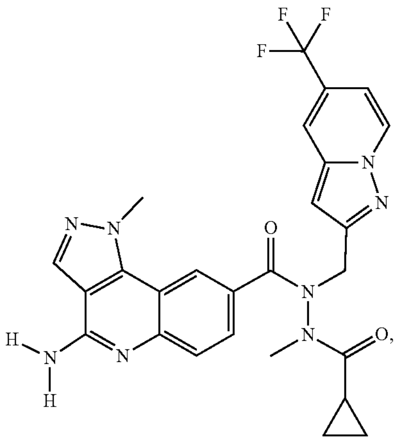
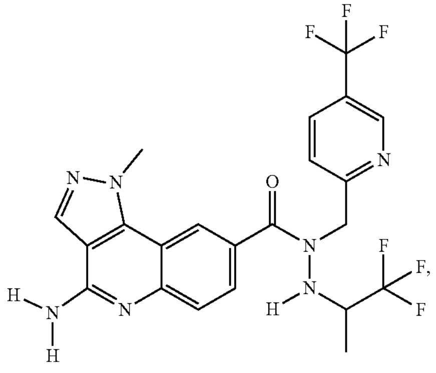

-continued
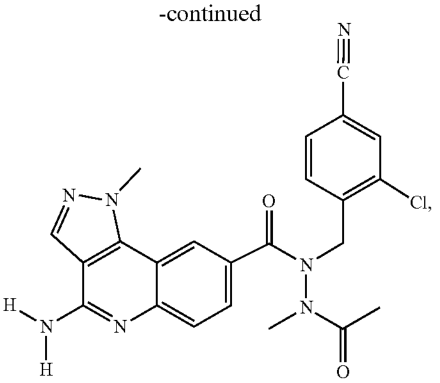
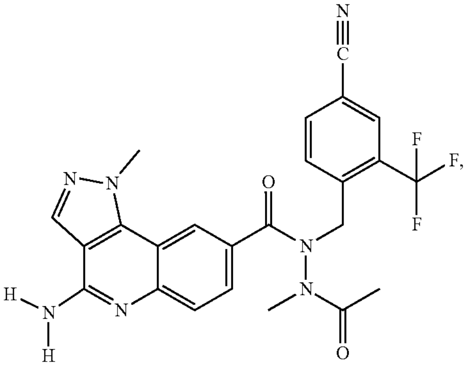
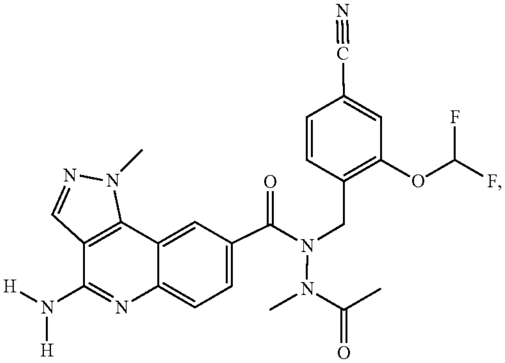
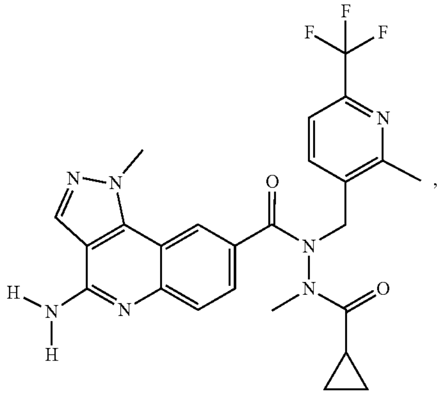
-continued
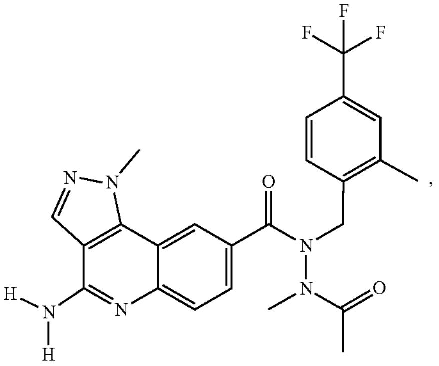
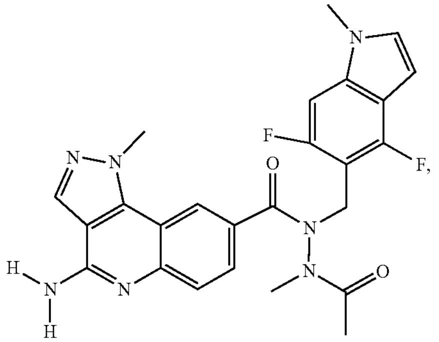
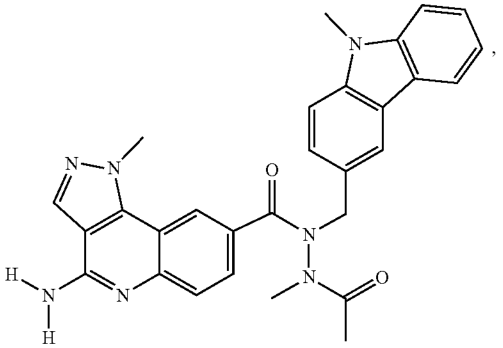
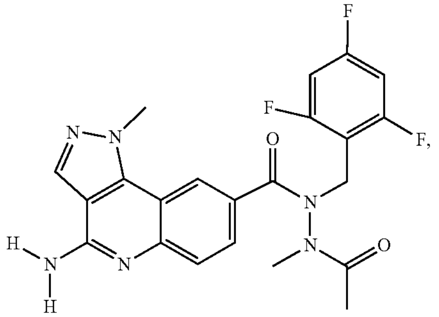
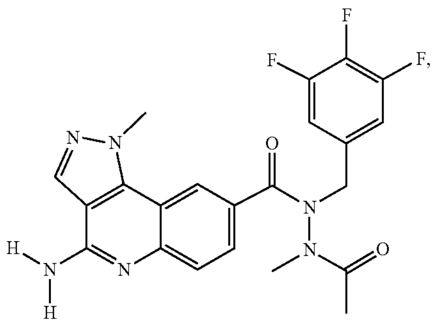

-continued
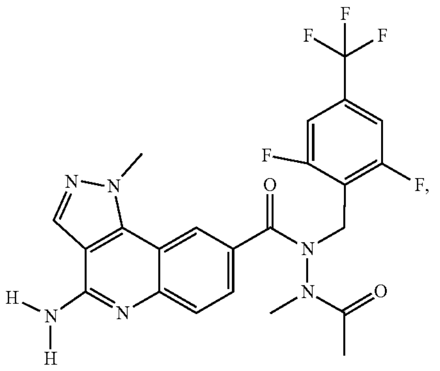
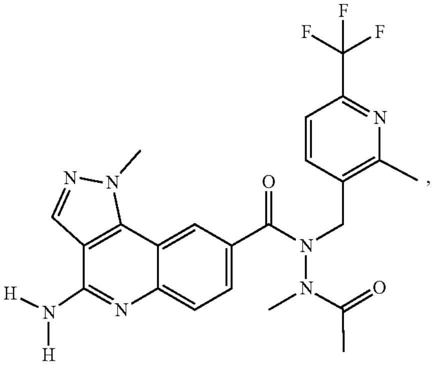
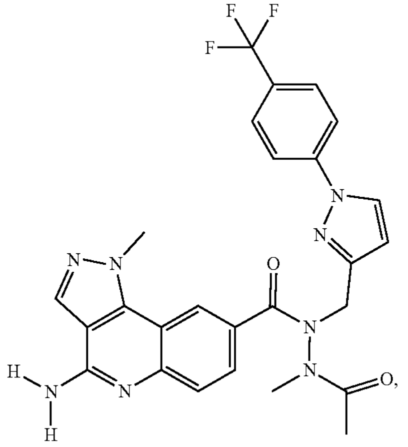
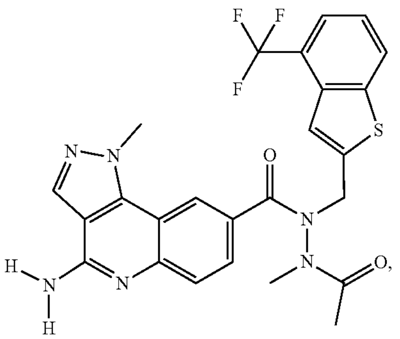
-continued
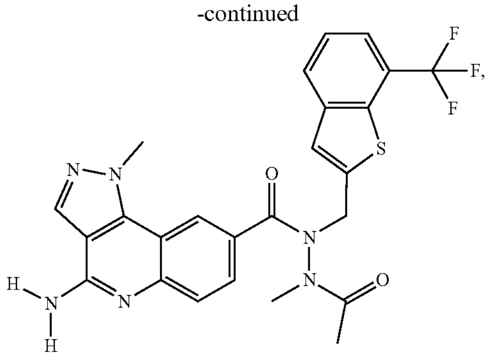
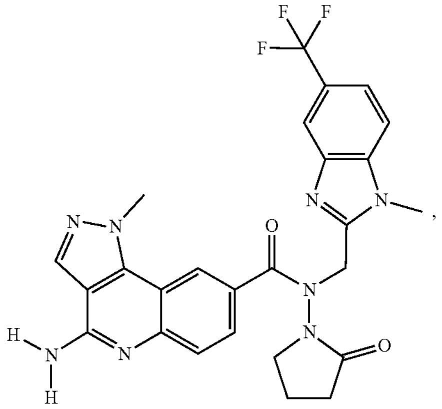
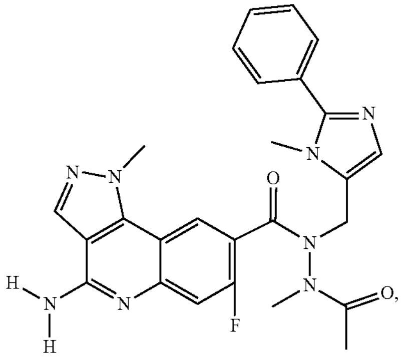
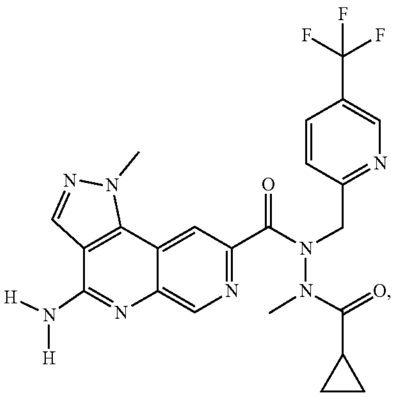

-continued
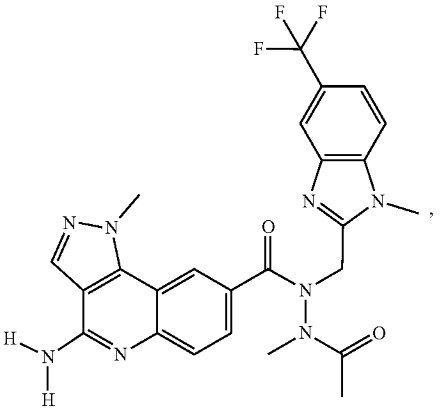
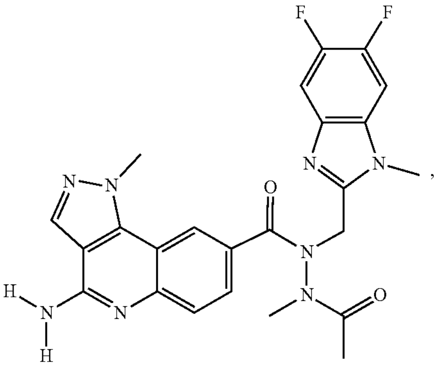
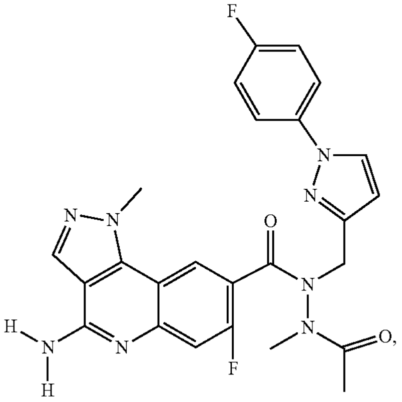
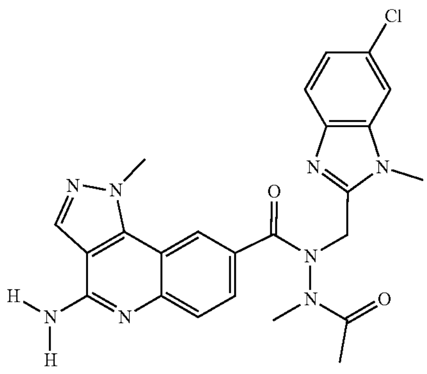
-continued
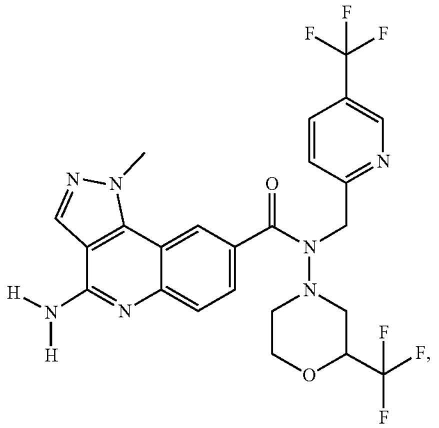
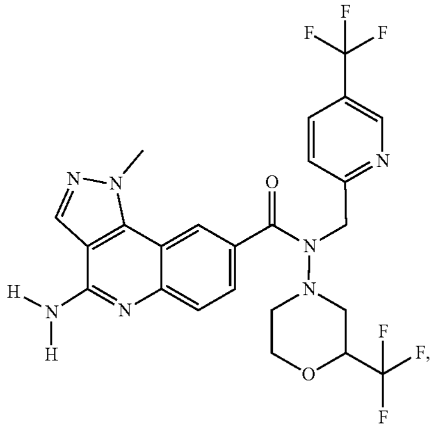
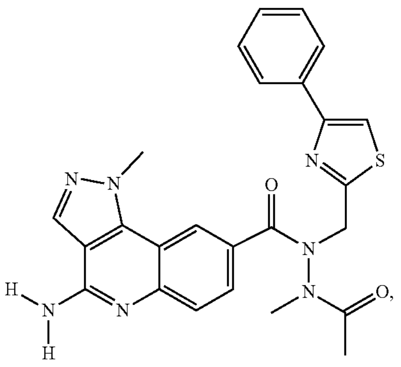
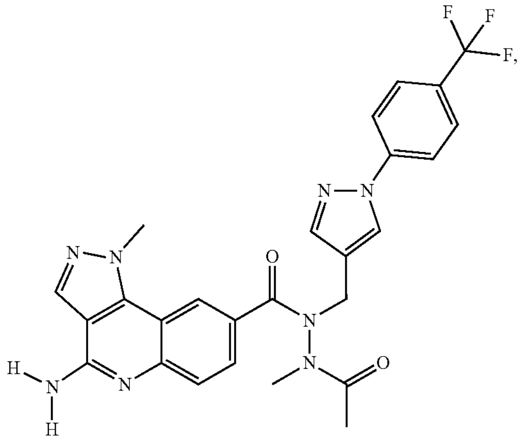

-continued
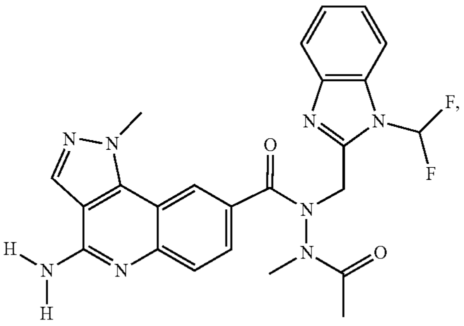
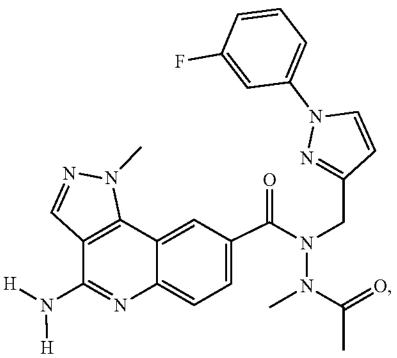
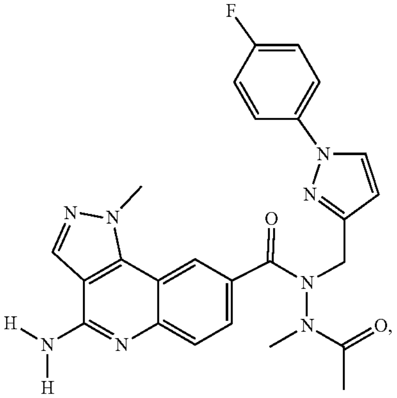
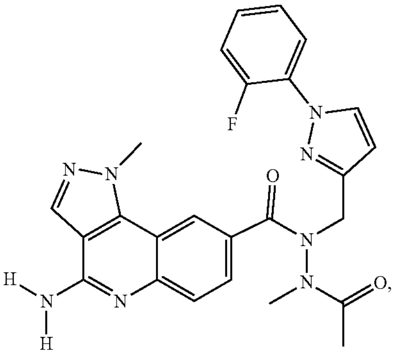
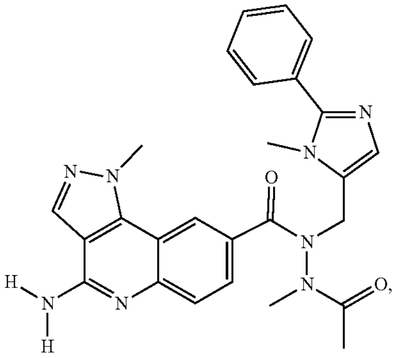
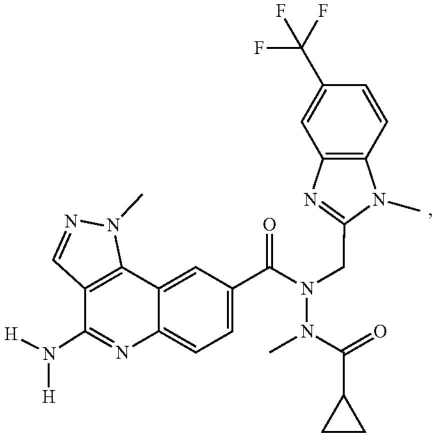
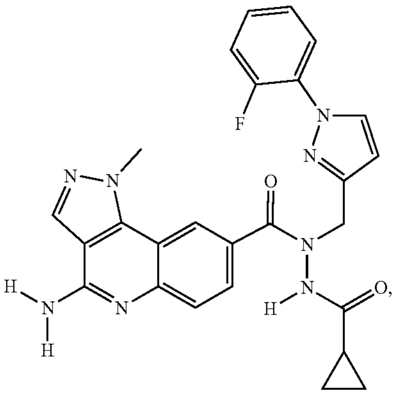
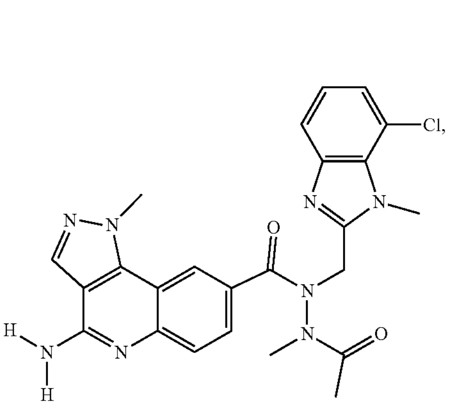

-continued
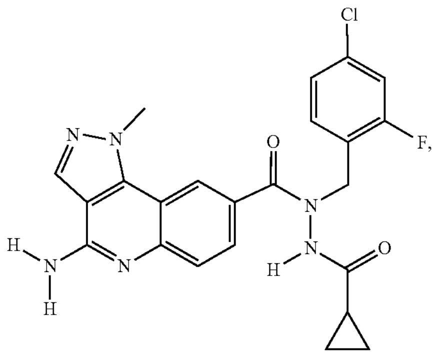
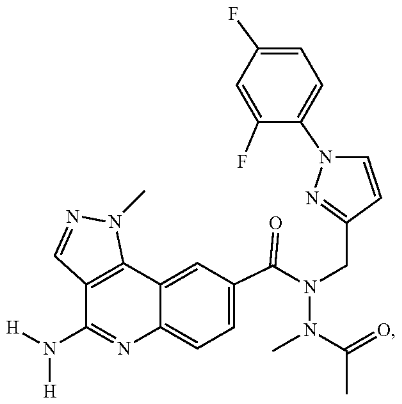
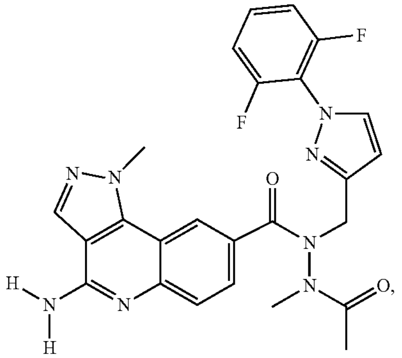
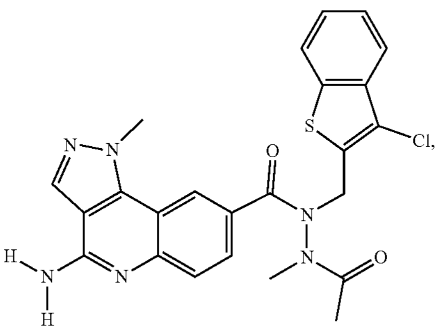
-continued
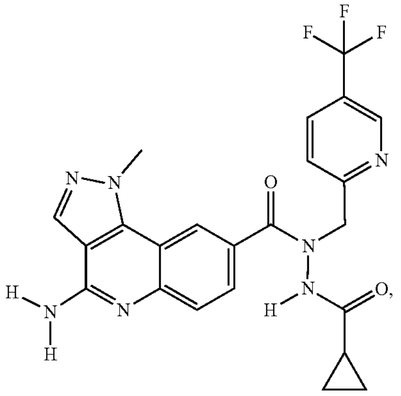
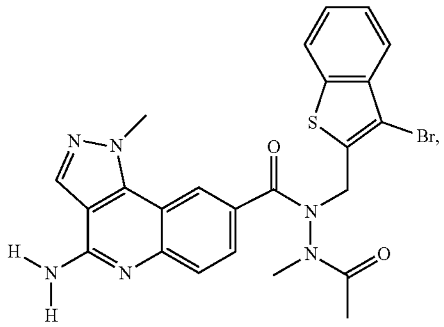
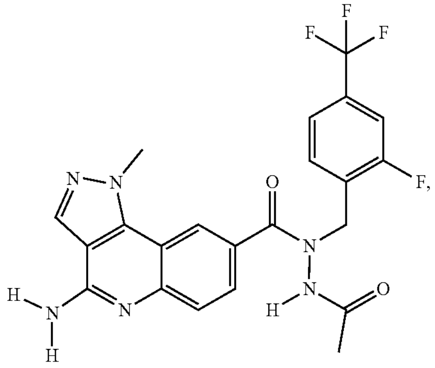
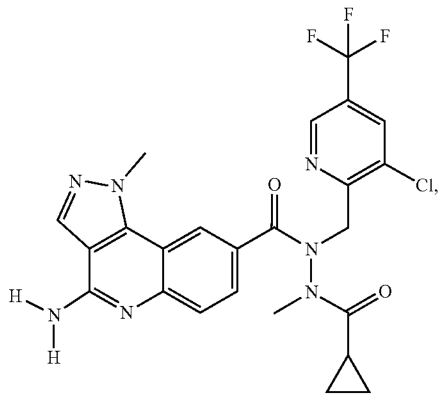

-continued
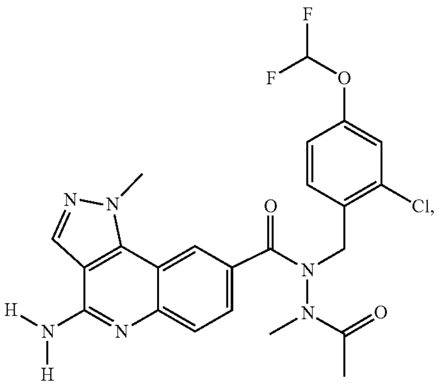
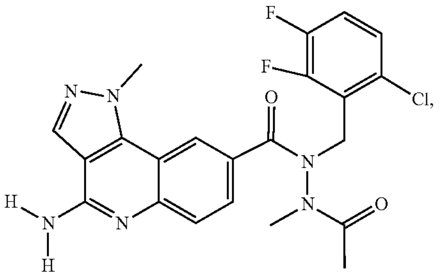
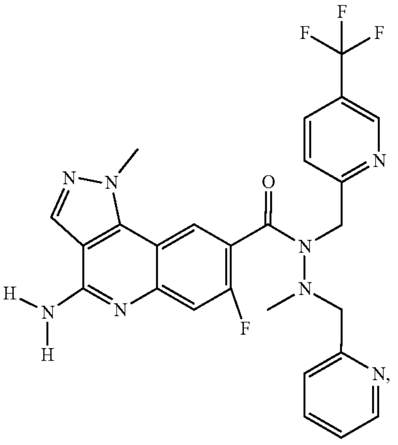
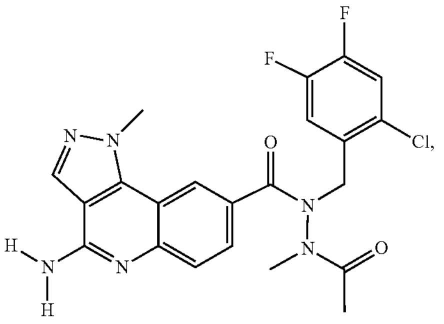
-continued
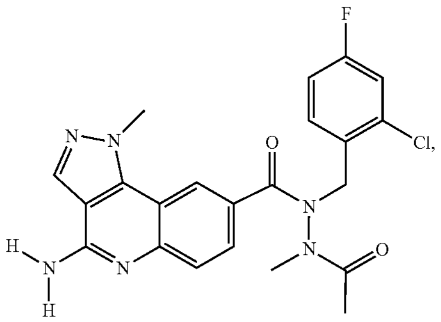
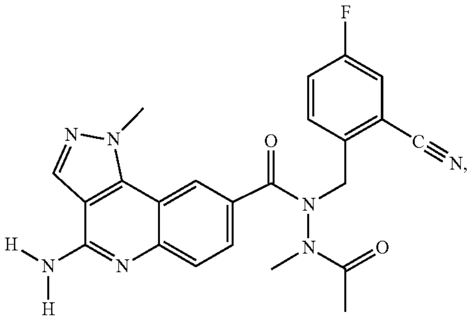
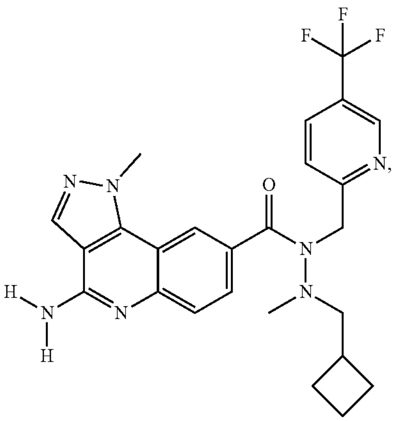

-continued
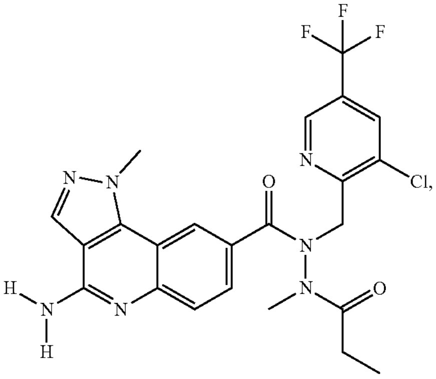
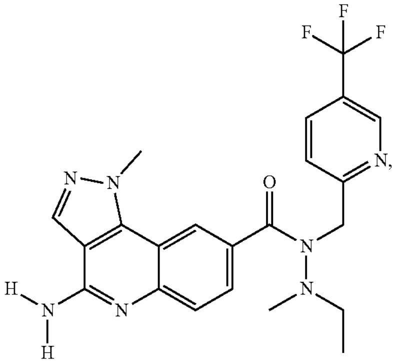
-continued
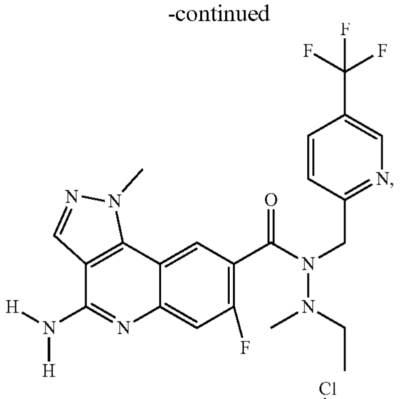
or
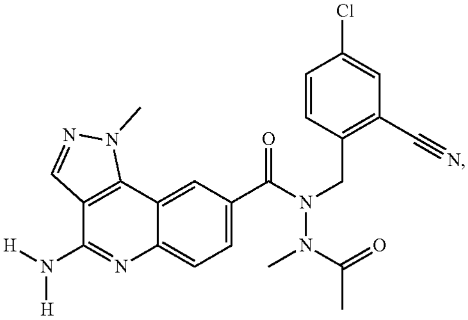
or a pharmaceutically acceptable salt thereof.
17. A pharmaceutical composition comprising a therapeutically effective amount of the compound of claim 1, or pharmaceutically acceptable salt thereof, and a pharmaceutically acceptable excipient.
* * * * *